(12) United States Patent
Duffey et al.

(10) Patent No.: US 9,962,386 B2
(45) Date of Patent: May 8, 2018

(54) HETEROARYL COMPOUNDS USEFUL AS INHIBITORS OF SUMO ACTIVATING ENZYME

(71) Applicant: Millennium Pharmaceuticals, Inc., Cambridge, MA (US)

(72) Inventors: Matthew O. Duffey, Chicago, IL (US); Dylan England, Milford, MA (US); Brian Scott Freeze, Boston, MA (US); Zhigen Hu, Newton Center, MA (US); Steven Langston, Andover, MA (US); Charles McIntyre, Cambridge, MA (US); Hirotake Mizutani, Arlington, MA (US); Koji Ono, Kanagawa (JP); He Xu, Needham, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days. days.

(21) Appl. No.: 15/488,795

(22) Filed: Apr. 17, 2017

(65) Prior Publication Data
US 2017/0216290 A1    Aug. 3, 2017

Related U.S. Application Data

(62) Division of application No. 14/788,675, filed on Jun. 30, 2015.
(Continued)

(51) Int. Cl.
| C07D 405/06 | (2006.01) |
| A61K 31/34 | (2006.01) |
| A61K 31/506 | (2006.01) |
| C07D 409/14 | (2006.01) |
| C07D 409/06 | (2006.01) |

(Continued)

(52) U.S. Cl.
CPC ............ *A61K 31/506* (2013.01); *A61K 31/34* (2013.01); *A61K 31/505* (2013.01); *C07D 405/06* (2013.01); *C07D 409/06* (2013.01); *C07D 409/14* (2013.01); *C07D 471/04* (2013.01); *C07D 487/04* (2013.01); *C07D 491/052* (2013.01); *C07D 493/04* (2013.01); *C07D 495/04* (2013.01); *C07D 498/04* (2013.01); *C07D 513/04* (2013.01); *C07F 9/5352* (2013.01); *C07F 9/5442* (2013.01); *C07F 9/65522* (2013.01); *C07F 9/65586* (2013.01)

(58) Field of Classification Search
CPC .. C07D 405/06; C07D 409/06; C07D 409/14; C07D 471/04; C07D 487/04; C07D 491/052; C07D 493/04; C07D 495/04; C07D 498/04; C07D 513/04; A61K 31/34; A61K 31/381; A61K 31/443; A61K 31/4436

USPC ............ 546/256, 281.4, 283.4; 514/333, 336
See application file for complete search history.

(56) References Cited

U.S. PATENT DOCUMENTS

| 5,194,446 A | 3/1993 | Lo et al. |
| 7,078,525 B2 | 7/2006 | Guzi et al. |

(Continued)

FOREIGN PATENT DOCUMENTS

| JP | 2005008581 A | 1/2005 |
| WO | WO 97/05132 A1 | 2/1997 |

(Continued)

OTHER PUBLICATIONS

Brownell et al., "Substrate-Assisted Inhibition of Ubiquitin-Like Protein-Activating Enzymes: The NEDD8 E1 Inhibitor MLN4924 Forms A NEDD8-AMP Mimetic In Situ," *Mol. Cell* 37:102-111, Elsevier, The Netherlands (2010).

(Continued)

*Primary Examiner* — Deepak Rao
(74) *Attorney, Agent, or Firm* — Sterne, Kessler, Goldstein & Fox P.L.L.C.

(57) ABSTRACT

Disclosed are chemical entities which are compounds of formula (I):

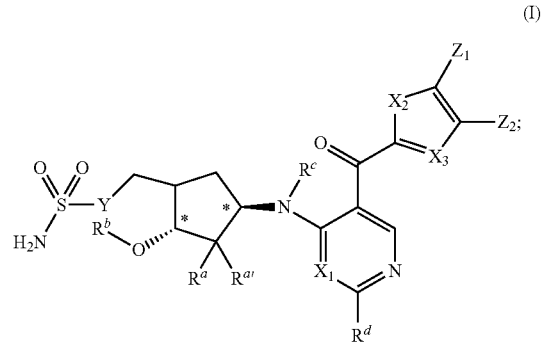

or pharmaceutically acceptable salts thereof; wherein Y, $R^a$, $R^{a'}$, $R^b$, $R^c$, $X_1$, $X_2$, $X_3$, $R^d$, $Z_1$, and $Z_2$ have the values described herein and stereochemical configurations depicted at asterisked positions indicate absolute stereochemistry. Chemical entities according to the disclosure can be useful as inhibitors of Sumo Activating Enzyme (SAE). Further provided are pharmaceutical compositions comprising a compound of the disclosure and methods of using the compositions in the treatment of proliferative, inflammatory, cardiovascular, and neurodegenerative diseases or disorders.

39 Claims, 17 Drawing Sheets

Related U.S. Application Data

(60) Provisional application No. 62/019,756, filed on Jul. 1, 2014, provisional application No. 62/185,678, filed on Jun. 28, 2015.

(51) Int. Cl.

| | | |
|---|---|---|
| *C07D 471/04* | (2006.01) | |
| *C07D 495/04* | (2006.01) | |
| *C07D 487/04* | (2006.01) | |
| *C07D 491/052* | (2006.01) | |
| *C07D 513/04* | (2006.01) | |
| *C07D 498/04* | (2006.01) | |
| *C07D 493/04* | (2006.01) | |
| *A61K 31/505* | (2006.01) | |
| *C07F 9/535* | (2006.01) | |
| *C07F 9/54* | (2006.01) | |
| *C07F 9/6558* | (2006.01) | |
| *C07F 9/655* | (2006.01) | |

(56) References Cited

U.S. PATENT DOCUMENTS

| | | |
|---|---|---|
| 7,196,092 B2 | 3/2007 | Guzi et al. |
| 7,563,798 B2 | 7/2009 | Guzi et al. |
| 7,642,266 B2 | 1/2010 | Guzi et al. |
| 8,008,307 B2 | 8/2011 | Claiborne et al. |
| 8,207,177 B2 | 6/2012 | Langston et al. |
| 8,481,550 B2 | 7/2013 | Claiborne et al. |
| 8,809,356 B2 | 8/2014 | McCarron et al. |
| 8,901,136 B2 | 12/2014 | Critchley et al. |
| 9,150,525 B2 | 10/2015 | Claiborne et al. |
| 9,290,500 B2 | 3/2016 | Afroze et al. |
| 2004/0102451 A1 | 5/2004 | Guzi et al. |
| 2006/0166926 A1 | 7/2006 | Wilde et al. |
| 2007/0082901 A1 | 4/2007 | Guzi et al. |
| 2007/0191293 A1 | 8/2007 | Langston et al. |
| 2008/0051404 A1 | 2/2008 | Claiborne et al. |
| 2011/0021544 A1 | 1/2011 | Armitage et al. |
| 2012/0077814 A1 | 3/2012 | Wang et al. |
| 2012/0258927 A1 | 10/2012 | Langston et al. |
| 2013/0217682 A1 | 8/2013 | Afroze et al. |
| 2015/0011572 A1 | 1/2015 | McCarron et al. |
| 2016/0039761 A1 | 2/2016 | Claiborne et al. |

FOREIGN PATENT DOCUMENTS

| | | |
|---|---|---|
| WO | WO 2003/073989 A2 | 9/2003 |
| WO | WO 2004/009609 A2 | 1/2004 |
| WO | WO 2004/009610 A2 | 1/2004 |
| WO | WO 2004/022559 A1 | 3/2004 |
| WO | WO 2004/026229 A2 | 4/2004 |
| WO | WO 2004/043955 A1 | 5/2004 |
| WO | WO 2004/087707 A1 | 10/2004 |
| WO | WO 2005/037845 A1 | 4/2005 |
| WO | WO 2005/051949 A1 | 6/2005 |
| WO | WO 2006/002284 A1 | 1/2006 |
| WO | WO 2006/084281 A1 | 8/2006 |
| WO | WO 2007/044401 A2 | 4/2007 |
| WO | WO 2007/092213 A2 | 8/2007 |
| WO | WO 2008/154642 A2 | 12/2008 |
| WO | WO 2009/082691 A1 | 7/2009 |
| WO | WO 2010/022121 A1 | 2/2010 |
| WO | WO 2010/022125 A1 | 2/2010 |
| WO | WO 2010/022126 A1 | 2/2010 |
| WO | WO 2010/022128 A1 | 2/2010 |
| WO | WO 2010/039548 A2 | 4/2010 |
| WO | WO 2010/086040 A1 | 8/2010 |
| WO | WO 2010/088518 A2 | 8/2010 |
| WO | WO 2010/132110 A1 | 11/2010 |
| WO | WO 2011/022440 A2 | 2/2011 |
| WO | WO 2011/100131 A1 | 8/2011 |
| WO | WO 2011/103441 A1 | 8/2011 |
| WO | WO 2011/109059 A1 | 9/2011 |
| WO | WO 2012/016217 A1 | 2/2012 |
| WO | WO 2013/066729 A1 | 5/2013 |
| WO | WO 2013/151975 A1 | 10/2013 |
| WO | WO 2015/002994 A2 | 1/2015 |
| WO | WO 2015/048547 A2 | 4/2015 |
| WO | WO 2015/061247 A2 | 4/2015 |
| WO | WO 2015/110999 A1 | 7/2015 |

OTHER PUBLICATIONS

Extended European Search Report for European patent Application No. 12825411.7 dated Mar. 25, 2015,(5 pages).
International Search Report and Written Opinion PCT/US07/017463 dated Nov. 23, 2007 corresponding to U.S. Appl. No. 11/890,338.
International Search Report and Written Opinion for PCT/US15/38712 dated Sep. 29, 2015.
PCT Notification of Transmittal of the International Search Report and the Written Opinion of the International Searching Authority, or the Declaration for International Application No. PCT/US2013/026113 dated Apr. 11, 2013.
Supplementary European Search Report of European Application No. EP 13748707, dated Jun. 9, 2015.
Pearce et al., "Failure modes in anticancer drug discovery and development, Cancer Drug Design and Discovery," Edited by Stephen Neidle, Chapter 18, pp. 424-435, Elsevier, The Netherlands, (2008).
Gura, "Systems for Identifying New Drugs Are Often Faulty," Cancer Models, *Science* 278(5340): 1041-1042, AAAS, The United States (Nov. 1997).
Johnson et al. "Relationships between drug activity in NCI preclinical in vitro and in vivo models and early clinical trials," British Journal of Cancer 84(10):1424-1431, Cancer Research Campaign, England (2001).
Simone, Oncology: Introduction, Cecil Textbook of Medicine, 20th Edition, vol. 1, pp. 1004-1010, W.B. Saunders Company, United states (1996).
Xu et al.. "The ubiquitin-activating enzyme E1 as a therapeutic target for the treatment of leukemia and multiple myeloma," *Blood* 115(11): 2251-2259, The American Society of Hematology, United States (Mar. 2010).
He, X., et al., "Characterization of the Loss of SUMO Pathway Function on Cancer Cells and Tumor Proliferation," PLoS One 10(4):e0123882, Public Library of Science, United States (Apr. 2015).
He, X., et al., "Probing the roles of SUMOylation in cancer cell biology by using a selective SAE inhibitor," Nature Chemical Biology 13:1164-1171, Nature Publishing Group, United States (2017).

HETEROARYL COMPOUNDS USEFUL AS INHIBITORS OF SUMO ACTIVATING ENZYME

This application claims the benefit of U.S. patent application Ser. No. 14/788,675, filed Jun. 30, 2015, U.S. Provisional Patent Application No. 62/019,756, filed Jul. 1, 2014, and U.S. Provisional Patent Application No. 62/185,678, filed Jun. 28, 2015, all of which are incorporated by reference in their entirety.

INTRODUCTION

Small ubiquitin-like modifier (SUMO) is a member of the ubiquitin-like protein (Ubl) family that is covalently conjugated to cellular proteins in a manner similar to Ub-conjugation (Kerscher, O., Felberbaum, R., and Hochstrasser, M. 2006. Modification of proteins by ubiquitin and ubiquitin-like proteins. *Annu Rev Cell Dev Biol.* 22:159-80). Mammalian cells express three major isoforms: SUMO1, SUMO2 and SUMO3. SUMO2 and SUMO3 share ~95% amino acid sequence homology but have ~45% sequence homology with SUMO1 (Kamitani, T., Kito, K., Nguyen, H. P., Fukuda-Kamitani, T., and Yeh, E. T. 1998. Characterization of a second member of the sentrin family of ubiquitin-like proteins. *J Biol Chem.* 273(18): 11349-53). SUMO proteins can be conjugated to a single lysine residue of a protein (monosumoylation) or to a second SUMO protein that is already conjugated to a protein forming a SUMO chain (polysumoylation). Only SUMO2/3 can form such chains because they possess internal consensus SUMO modification sites (Tatham, M. H., Jaffray, E., Vaughan, O. A., Desterro, J. M., Botting, C. H., Naismith, J. H., Hay, R. T. 2001. Polymeric chains of SUMO-2 and SUMO-3 are conjugated to protein substrates by SAE1/SAE2 and Ubc9. *J Biol Chem.* 276(38):35368-74). An additional isoform, SUMO4, is found in kidney, lymph node and spleen cells, but it is not known whether SUMO4 can be conjugated to cellular proteins.

SUMO1, SUMO2 and SUMO3 are activated in an ATP-dependent manner by the SUMO-activating enzyme (SAE). SAE is a heterodimer that consists of SAE1 (SUMO-activating enzyme subunit 1) and SAE2 (UBA2). SAE, like other E1 activating enzymes, uses ATP to adenylate the C-terminal glycine residue of SUMO. In a second step, a thioester intermediate is then formed between the C-terminal glycine of SUMO and a cysteine residue in SAE2. Next, SUMO is transferred from the E1 to the cysteine residue of the SUMO conjugating enzyme (E2), UBC9. Unlike the Ub pathway that contains many E2 enzymes, Ubc9 is currently the only known conjugating enzyme for SUMO and functions with SUMO1, SUMO2 and SUMO3 proteins. SUMO proteins are then conjugated to the target protein, either directly or in conjunction with an E3 ligase, through isopeptide bond formation with the epsilon amino group of a lysine side chain on a target protein. Several SUMO E3 ligases, including PIAS (protein inhibitor of activated signal transducer and activator of transcription protein) proteins and Ran-binding protein 2 (RanBP2), and polycomb 2 (Pc2), have been identified (Johnson, E. S., and Gupta, A. A. 2001. An E3-like factor that promotes SUMO conjugation to the yeast septins. *Cell.* 106(6):735-44; Pichler, A., Gast, A., Seeler, J. S., Dejean, A.; Melchior, F. 2002. The nucleoporin RanBP2 has SUMO1 E3 ligase activity. *Cell.* 108(1):109-20; Kagey, M. H., Melhuish, T. A., and Wotton, D. 2003. The polycomb protein Pc2 is a SUMO E3. *Cell.* 113(1): 127-37). Once attached to cellular targets, SUMO modulates the function, subcellular localization, complex formation and/or stability of substrate proteins (Müller, S., Hoege, C., Pyrowolakis, G., and Jentsch, S. 2001. SUMO, ubiquitin's mysterious cousin. *Nat Rev Mol Cell Biol.* 2(3):202-10). SUMO-conjugation is reversible through the action of de-sumoylating enzymes called SENPs (Hay, R. T. 2007. SUMO-specific proteases: a twist in the tail. *Trends Cell Biol.* 17(8):370-6) and the SUMO proteins can then participate in additional conjugation cycles.

SAE-initiated SUMO-conjugation plays a major role in regulating diverse cellular processes, including cell cycle regulation, transcriptional regulation, cellular protein targeting, maintenance of genome integrity, chromosome segregation, and protein stability (Hay, R. T. 2005. SUMO: a history of modification. *Mol Cell.* 18(1):1-12; Gill, G. 2004. SUMO and ubiquitin in the nucleus: different functions, similar mechanisms? *Genes Dev.* 18(17):2046-59). For example, SUMO-conjugation causes changes in the subcellular localization of RanGAP1 by targeting it to the nuclear pore complex (Mahajan, R., Delphin, C., Guan, T., Gerace, L., and Melchior, F. 1997. A small ubiquitin-related polypeptide involved in targeting RanGAP1 to nuclear pore complex protein RanBP2. *Cell.* 88(1):97-1070). Sumoylation counteracts ubiquitination and subsequently blocks the degradation of IκB, thereby negatively regulating NF-κB activation (Desterro, J. M., Rodriguez, M. S., Hay, R. T. 1998. SUMO-1 modification of IkappaBalpha inhibits NF-kappaB activation. *Mol Cell.* 2(2):233-9). Sumoylation has been reported to play an important role in transcription exhibiting both repressive and stimulatory effects. Many of the transcriptional nodes that are modulated play important roles in cancer. For example, sumoylation stimulates the transcriptional activities of transcription factors such as p53 and HSF2 (Rodriguez, M. S., Desterro, J. M., Lain, S., Midgley, C. A., Lane, D. P., and Hay, R. T. 1999. SUMO-1 modification activates the transcriptional response of p53. *EMBO J.* 18(22):6455-61; Goodson, M. L., Hong, Y., Rogers, R., Matunis, M. J., Park-Sarge, O. K., Sarge, K. D. 2001. Sumo-1 modification regulates the DNA binding activity of heat shock transcription factor 2, a promyelocytic leukemia nuclear body associated transcription factor. *J Biol Chem.* 276(21):18513-8). In contrast, SUMO-conjugation represses the transcriptional activities of transcription factors such as LEF (Sachdev, S., Bruhn, L., Sieber, H., Pichler, A., Melchior, F., Grosschedl, R. 2001. PIASy, a nuclear matrix-associated SUMO E3 ligase, represses LEF1 activity by sequestration into nuclear bodies. *Genes Dev.* 15(23): 3088-103) and c-Myb (Bies, J., Markus, J., and Wolff, L. 2002. Covalent attachment of the SUMO-1 protein to the negative regulatory domain of the c-Myb transcription factor modifies its stability and transactivation capacity. *J Biol Chem.* 277(11):8999-9009). Thus, SUMO-conjugation controls gene expression and growth control pathways that are important for cancer cell survival.

Altered expression of SAE pathway components have been noted in a variety of cancer types: (Moschos, S. J., Jukic, D. M., Athanassiou, C., Bhargava, R., Dacic, S., Wang, X., Kuan, S. F., Fayewicz, S. L., Galambos, C., Acquafondata, M., Dhir, R., and Becker, D. 2010. Expression analysis of Ubc9, the single small ubiquitin-like modifier (SUMO) E2 conjugating enzyme, in normal and malignant tissues. *Hum Pathol.* 41(9):1286-980); including multiple myeloma (Driscoll, J. J., Pelluru, D., Lefkimmiatis, K., Fulciniti, M., Prabhala, R. H., Greipp, P. R., Barlogie, B., Tai, Y. T., Anderson, K. C., Shaughnessy, J. D. Jr., Annunziata, C. M., and Munshi, N. C. 2010. The sumoylation pathway is dysregulated in multiple myeloma and is associated with adverse patient outcome. *Blood.* 115(14):2827-34); and breast cancer (Chen, S. F., Gong, C., Luo, M., Yao, H. R., Zeng, Y. J., and Su, F. X. 2011. Ubc9 expression predicts chemoresistance in breast cancer. *Chin J Cancer.* 30(9):638-44), In addition, preclinical studies indicate that Myc-driven cancers may be especially sensitive to SAE inhibition (Kessler, J. D., Kahle, K. T., Sun, T., Meerbrey, K. L., Schlabach, M. R., Schmitt, E. M., Skinner, S. O., Xu, Q., Li, M. Z., Hartman, Z. C., Rao, M., Yu, P., Dominguez-Vidana, R., Liang, A. C., Solimini, N. L., Bernardi, R. J., Yu, B., Hsu, T., Golding, I., Luo, J., Osborne, C. K., Creighton, C. J., Hilsenbeck, S. G., Schiff, R., Shaw, C. A., Elledge, S. J., and Westbrook, T. F. 2012. A SUMOylation-dependent transcriptional subprogram is required for Myc-driven tumorigenesis. *Science.* 335(6066):348-53; Hoellein, A., Fallahi, M., Schoeffmann, S., Steidle, S., Schaub, F. X., Rudelius, M., Laitinen, I., Nilsson, L., Goga, A., Peschel, C., Nilsson, J. A., Cleveland, J. L., and Keller, U. 2014. Myc-induced SUMOylation is a therapeutic vulnerability for B-cell lymphoma. *Blood.* 124(13):2081-90). Since SUMO-conjugation regulates essential cellular functions that contribute to the growth and survival of tumor cells, targeting SAE could represent an approach to treat proliferative disorders such as cancer.

SAE inhibitors may also be applicable for the treatment of other diseases and conditions outside of oncology. For example, SUMO modifies proteins that play important roles in neurodegenerative diseases (Steffan, J. S., Agrawal, N., Pallos, J., Rockabrand, E., Trotman, L. C., Slepko, N., Illes, K., Lukacsovich, T., Zhu, Y. Z., Cattaneo, E., Pandolfi, P. P., Thompson, L. M., Marsh, J. L. 2004. SUMO modification of Huntington and Huntington's disease pathology. *Science.* 304(5667):100-4); Dorval, V., and Fraser, P. E. 2006. Small ubiquitin-like modifier (SUMO) modification of natively unfolded proteins tau and alpha-synuclein. *J Biol Chem.* 281(15):9919-24; Ballatore, C., Lee, V. M., and Trojanowski, J. Q. 2007. Tau-mediated neurodegeneration in Alzheimer's disease and related disorders. *Nat Rev Neurosci.* 8(9):663-72). Sumoylation also has been reported to play important role in pathogenic viral infection, inflammation and cardiac function (Lee, H. R., Kim, D. J., Lee, J. M., Choi, C. Y., Ahn, B. Y., Hayward, G. S., and Ahn, J. H. 2004. Ability of the human cytomegalovirus IE1 protein to modulate sumoylation of PML correlates with its functional activities in transcriptional regulation and infectivity in cultured fibroblast cells. *J Virol.* 78(12):6527-42; Liu, B., and Shuai, K. 2009. Summon SUMO to wrestle with inflammation. *Mol Cell.* 35(6):731-2; Wang, J., and Schwartz, R. J. 2010. Sumoylation and regulation of cardiac gene expression. *Circ Res.* 107(1): 19-29).

It would be beneficial therefore to provide new SAE inhibitors that possess good therapeutic properties, especially for the treatment of proliferative, inflammatory, cardiovascular and neurodegenerative disorders.

This application provides chemical entities which are inhibitors of SAE and accordingly are useful for the treatment of proliferative, inflammatory, cardiovascular and neurodegenerative disorders. The chemical entities of the present disclosure are represented by Formula (I):

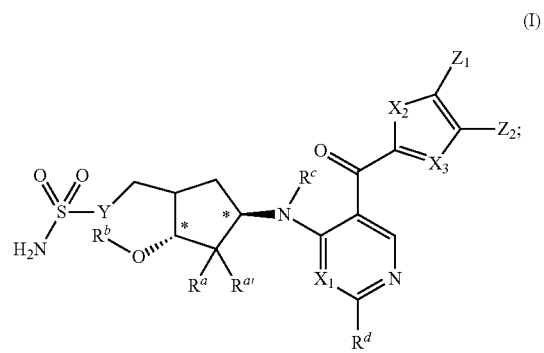

or a pharmaceutically acceptable salt thereof,
wherein:
stereochemical configurations depicted at asterisked positions indicate absolute stereochemistry;
Y is —O—, —CH$_2$—, or —N(H)—;
R$^a$ is hydrogen, fluoro, —NH$_2$, or hydroxyl;
R$^{a'}$ is hydrogen or fluoro, provided that when R$^a$ is —NH$_2$ or hydroxyl, R$^{a'}$ is hydrogen;
R$^b$ is hydrogen or, together with the oxygen to which it is attached, forms a prodrug;
R$^c$ is hydrogen or C$_{1-4}$ alkyl;
R$^d$ is hydrogen, halogen, —CF$_3$, or C$_{1-4}$ alkyl;
X$_1$ is C(H), C(F), or N;
X$_2$ is S or O;
X$_3$ is C(R$^{x3}$) or N;
R$^{x3}$ is hydrogen, methyl, or halogen;
Z$_1$ is hydrogen, halogen, cyano, R$^{z3}$, —S—R$^{z3}$, —S(O)—R$^{z3}$, or —S(O)$_2$—R$^{z3}$;
R$^{z3}$ is an optionally substituted phenyl, an optionally substituted 5- to 7-membered cycloaliphatic, an optionally substituted 5- to 7-membered heterocyclyl, or an optionally substituted C$_{1-4}$ aliphatic;
wherein Z$_1$ is not hydrogen, halogen, methyl, or cyano if Z$_2$ is hydrogen or methyl; and
(a) Z$_2$ is a ring system having an optionally substituted 5- to 7-membered heterocyclyl with 1-2 heteroatoms or an optionally substituted 5- to 7-membered cycloaliphatic fused to
(i) an optionally substituted 5-membered heteroaryl or an optionally substituted 6-membered aryl or heteroaryl to form a bicyclic group; or
(ii) an optionally substituted 9-membered heteroaryl or an optionally substituted 10-membered aryl or heteroaryl to form a tricyclic group;
OR
(b) Z$_2$ is L-R$^e$ wherein L is -L$_1$-, —V$_1$-L$_2$-, or -L$_1$-V$_1$-L$_2$-;
L$_1$ is a C$_{1-3}$ alkylene chain wherein 1 or 2 saturated carbon atoms are optionally substituted by (R$^f$)(R$^{f'}$) and in which there are optionally one or two degrees of unsaturation;
each R$^f$ is independently hydrogen; hydroxyl; —N(R$^h$)(R$^{h'}$); C$_{1-4}$ aliphatic optionally substituted with hydroxyl, —OCH$_3$, or cyclopropyl; —O—C$_{1-4}$ aliphatic optionally substituted with hydroxyl, —OCH$_3$, or cyclopropyl; or, together with R$^{f'}$ and the carbon atom to which they are attached, form =CH$_2$, or a 3- to 6-membered carbocycle or 4- to 6-membered heterocycle comprising a heteroatom chosen from N (which may be protonated or C$_{1-4}$ alkylated), O, or S, the heteroatom optionally located immediately adjacent to the quaternary carbon of the heterocycle;

each $R^{f'}$ is independently hydrogen; $C_{1-4}$ aliphatic optionally substituted with hydroxyl, —$OCH_3$, or cyclopropyl; —O—$C_{1-4}$ aliphatic optionally substituted with hydroxyl, —$OCH_3$, or cyclopropyl; or, together with $R^f$ and the carbon atom to which they are attached, form =$CH_2$, or a 3- to 6-membered carbocycle or 4- to 6-membered heterocycle comprising a heteroatom chosen from N (which may be protonated or $C_{1-4}$ alkylated), O, or S, the heteroatom optionally located immediately adjacent to the quaternary carbon of the heterocycle; wherein if $R^f$ is hydroxyl, $R^{f'}$ is not —O—$C_{1-4}$ aliphatic optionally substituted with hydroxyl, —$OCH_3$, or cyclopropyl;

$R^h$ and $R^{h'}$ are each independently hydrogen or $C_{1-4}$ alkyl;

$V_1$ is —S—, —O—, —S(O)—, —S(O)$_2$—, —C(O)— or —N($R^g$)—;

$L_2$ is a $C_{0-2}$ alkylene chain wherein one saturated carbon atom is optionally substituted by ($R^f$)($R^{f'}$);

$R^g$ is hydrogen or $C_{1-4}$ alkyl; and either (i) $R^e$ is hydrogen, hydroxyl, halogen, —$CF_3$, or an optionally substituted $C_{1-4}$ aliphatic, with the proviso that $R^e$ is not hydrogen if $R^f$ and $R^{f'}$ are present and form a ring;

OR (ii) $R^e$ is a ring chosen from optionally substituted 6-membered aryl, optionally substituted 5- to 6-membered heteroaryl, optionally substituted 3- to 7-membered cycloaliphatic, or optionally substituted 4- to 7-membered heterocyclyl, which is optionally fused to a second optionally substituted 6-membered aryl, optionally substituted 5- to 6-membered heteroaryl, optionally substituted 3- to 7-membered cycloaliphatic, or optionally substituted 4- to 7-membered heterocyclyl;

OR $Z_2$ is hydrogen.

DETAILED DESCRIPTION

Figure 1:
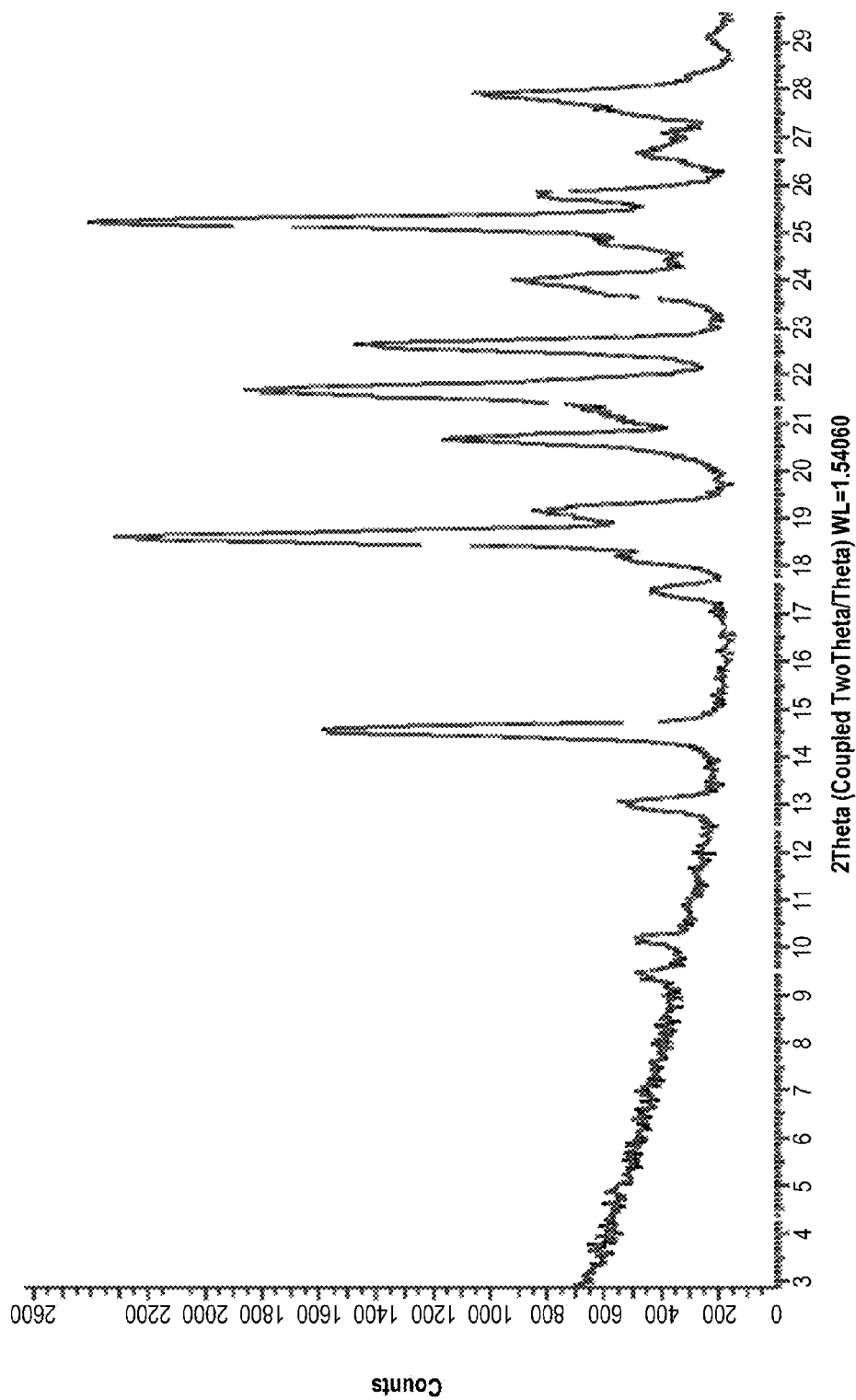
FIG. 1 is an XRPD pattern of compound I-257b Form 1.

Chemical entities of the present disclosure include those described generally for formula (I), above, and are further illustrated by the classes, subclasses, and species disclosed herein. It will be appreciated that preferred subsets described for each variable herein can be used for any of the structural subsets as well. As used herein, the following definitions shall apply unless otherwise indicated.

As described herein, chemical entities of the present disclosure may be optionally substituted with one or more substituents, such as are disclosed generally above, or as exemplified by particular classes, subclasses, and species disclosed herein. It will be appreciated that the phrase "optionally substituted" is used interchangeably with the phrase "substituted or unsubstituted." In general, the term "substituted," whether preceded by the term "optionally" or not, means that a hydrogen radical of the designated moiety is replaced with the radical of a specified substituent, provided that the substitution results in a stable or chemically feasible chemical entity. The term "substitutable," when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this disclosure are, for instance, those that result in the formation of stable or chemically feasible chemical entities.

A stable chemical entity or chemically feasible chemical entity is one in which the chemical structure is not substantially altered when kept at a temperature from about −80° C. to about +40° C., in the absence of moisture or other chemically reactive conditions, for at least a week, or a chemical entity which maintains its integrity long enough to be useful for therapeutic or prophylactic administration to a patient.

The phrase "one or more substituents," as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single chemical entity.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group," as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle," "cycloaliphatic," "cycloalkyl," or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-5, 1-4, 1-3, or 1-2 carbon atoms.

The term "alkyl," used alone or as part of a larger moiety, refers to an optionally substituted straight or branched chain saturated hydrocarbon group having 1-12, 1-10, 1-8, 1-6, 1-5, 1-4, 1-3, or 1-2 carbon atoms.

The term "alkenyl," used alone or as part of a larger moiety, refers to an optionally substituted straight or branched chain hydrocarbon group having at least one double bond and having 2-12, 2-10, 2-8, 2-6, 2-5, 2-4, or 2-3 carbon atoms.

The term "alkynyl," used alone or as part of a larger moiety, refers to an optionally substituted straight or branched chain hydrocarbon group having at least one triple bond and having 2-12, 2-10, 2-8, 2-6, 2-5, 2-4, or 2-3 carbon atoms.

The terms "cycloaliphatic," "carbocycle," "carbocyclyl," "carbocyclo," or "carbocyclic," used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic," "carbocycle," "carbocyclyl," "carbocyclo," or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl, and cycloheptenyl.

The terms "haloaliphatic," "haloalkyl," "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" and "ar-," used alone or as part of a larger moiety, e.g., "aralkyl," "aralkoxy," or "aryloxyalkyl," refer to an optionally substituted $C_{6-14}$ aromatic hydrocarbon moiety comprising one to three aromatic rings. In at least one embodiment, the aryl group is a $C_{6-10}$ aryl group. Aryl groups include, without limitation, optionally substituted phenyl, naphthyl, or anthracenyl. The terms "aryl" and "ar-," as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group," "aryl ring," and "aromatic ring."

An "aralkyl" or "arylalkyl" group comprises an aryl group covalently attached to an alkyl group, either of which independently is optionally substituted. In at least one embodiment, the aralkyl group is $C_{6-10}$ aryl $C_{1-6}$ alkyl, including, without limitation, benzyl, phenethyl, and naphthylmethyl.

The terms "heteroaryl" and "heteroar-," used alone or as part of a larger moiety, e.g., "heteroaralkyl," or "heteroaralkoxy," refer to groups having 5 to 14 ring atoms, such as 5, 6, 9, or 10 ring atoms; having 6, 10, or 14 pi electrons shared in a cyclic array; and having, in addition to carbon atoms, from one to five heteroatoms. A heteroaryl group may be mono-, bi-, tri-, or polycyclic, for instance mono-, bi-, or tricyclic, such as mono- or bicyclic. In the context of "heteroar" entities, the term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-," as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, for instance one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, for instance mono-, bi-, or tricyclic, and such as mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, such as from 1 to 6, from 1 to 5, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein, and include double and/or triple bonds between carbons in the alkylene chain.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted." In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR$^\circ$, —S(O)R$^\circ$, —SO$_2$R$^\circ$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R$^\circ$, —NR$^+$CO$_2$R$^+$, —NR$^+$SO$_2$R$^\circ$, —NR$^+$SO$_2$N(R$^+$)$_2$, —O—C(O)R$^+$, —O—CO$_2$R$^+$, —OC(O)N(R$^+$)$_2$, —C(O)R$^+$, —C(S)R$^\circ$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R$^\circ$)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl. Each R$^\circ$ is, independently, an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted." Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R$^\circ$=N—NHSO$_2$R$^\circ$ or =N—R* where R$^\circ$ is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide chemical entity. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R$^+$ (or any other variable similarly defined in the specification or claims herein) that are bound to different atoms and are taken together with both of those atoms to form a ring, for example where a phenyl group is substituted with two occurrences of

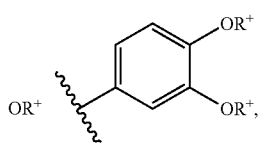

these two occurrences of R+ are taken together with the oxygen atoms to which they are bound to form a fused 6-membered oxygen containing ring:

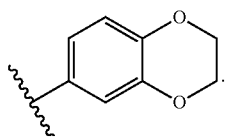 [SMILES: *c1ccc2c(c1)OCCO2]

It will be appreciated that a variety of other rings (e.g., spiro and bridged rings) can be formed when two independent occurrences of R+ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present chemical entities are within the scope of the present disclosure. Unless otherwise stated, all tautomeric forms of the chemical entities disclosed herein are within the scope of the present disclosure. Additionally, unless otherwise stated, structures depicted herein are also meant to include chemical entities that differ only in the presence of one or more isotopically enriched atoms. For example, chemical entities having the present structures where there is a replacement of hydrogen by deuterium or tritium, or a replacement of a carbon by a $^{13}C$- or $^{14}C$-enriched carbon are within the scope of this disclosure. Such chemical entities are useful, as a nonlimiting example, as analytical tools or probes in biological assays.

It is to be understood that, when a disclosed chemical entity has at least one chiral center, the present disclosure encompasses one enantiomer of inhibitor free from the corresponding optical isomer, a racemic mixture of the inhibitor, and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95%, 99%, or 99.5%.

The enantiomers of the present disclosure may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed chemical entity has at least two chiral centers, the present disclosure encompasses a diastereomer free of other diastereomers, a pair of diastereomers free from other diasteromeric pairs, mixtures of diastereomers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diastereomeric pair(s) relative to other diastereomers or diastereomeric pair(s) for the chemical entity, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of chemical entities disclosed herein are provided the examples herein.

For the avoidance of doubt, for chemical entities described herein, where the chemical entity is a single diastereomer and the absolute configuration of the chiral centers is known the name of the chemical entity reflects the assigned configuration at each stereochemical center; for example chemical entity I-43: {(1R,2S,4R)-4-[(5-{[4-(3-chlorobenzyl)-2-thienyl]carbonyl}pyrimidin-4-yl)amino]-2-hydroxycyclopentyl}methyl sulfamate. Where the chemical entity is a single diastereomer and the absolute configuration is known at some of the chiral centers but is unknown at one chiral center, the name reflects the two possibilities separated by an "or"; for example chemical entity I-1a: [(1R,2R,3S,4R)-4-{[5-({4-[(1S)-1-(6-bromopyridin-2-yl)-1-hydroxyethyl]-2-thienyl}carbonyl)pyrimidin-4-yl]amino}-2,3-dihydroxycyclopentyl]methyl sulfamate or [(1R,2R,3S,4R)-4-{[5-({4-[(1R)-1-(6-bromopyridin-2-yl)-1-hydroxyethyl]-2-thienyl}carbonyl)pyrimidin-4-yl]amino}-2,3-dihydroxycyclopentyl]methyl sulfamate. Where the chemical entity is a mixture of two or more diastereomers the name reflects the two or more possibilities by using "and" between the names of the individual diastereomers that make up the mixture; for example chemical entity I-1: [(1R,2R,3S,4R)-4-{[5-({4-[(1S)-1-(6-bromopyridin-2-yl)-1-hydroxyethyl]-2-thienyl}carbonyl)pyrimidin-4-yl]amino}-2,3-dihydroxycyclopentyl]methyl sulfamate and [(1R,2R,3S,4R)-4-{[5-({4-[(1R)-1-(6-bromopyridin-2-yl)-1-hydroxyethyl]-2-thienyl}carbonyl)pyrimidin-4-yl]amino}-2,3-dihydroxycyclopentyl]methyl sulfamate.

In some embodiments, the chemical entity of formula (I) is represented by formula (I-a):

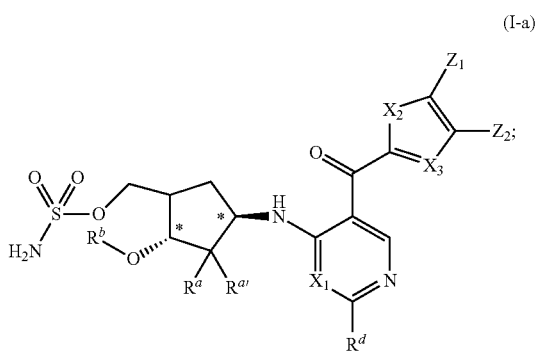

(I-a)

or a pharmaceutically acceptable salt thereof,
wherein $R^a$, $R^{a'}$, $R^b$, $X_1$, $X_2$, $X_3$, $R^d$, $Z_1$, and $Z_2$ have the values described herein and stereochemical configurations depicted at asterisked positions indicate absolute stereochemistry.

In some embodiments, the chemical entity of formula (I) is represented by formula (II):

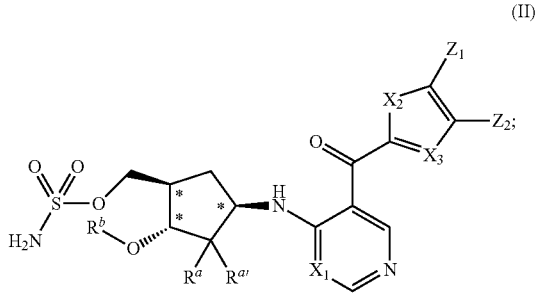

(II)

wherein $R^a$, $R^{a'}$, $R^b$, $X_1$, $X_2$, $X_3$, $Z_1$, and $Z_2$ have the values described herein and stereochemical configurations depicted at asterisked positions indicate absolute stereochemistry.

In some embodiments, the chemical entity of formula (I) is represented by formula (II-a) or (II-b):

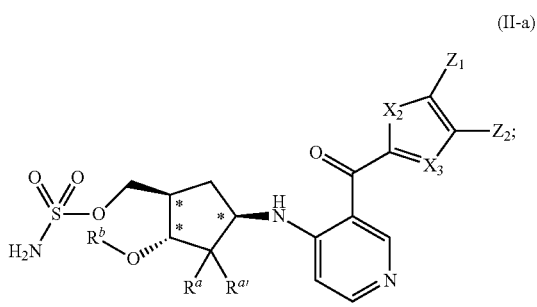

(II-a)

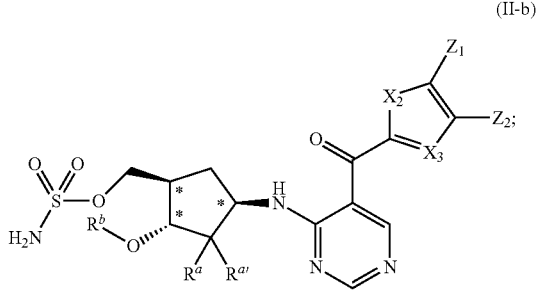

(II-b)

or a pharmaceutically acceptable salt thereof,
wherein $R^a$, $R^{a'}$, $R^b$, $X_2$, $X_3$, $Z_1$, and $Z_2$ have the values described herein and stereochemical configurations depicted at asterisked positions indicate absolute stereochemistry. In some embodiments, the chemical entity of formula (I) is represented by formula (II-a) wherein $R^a$, $R^{a'}$, $R^b$, $X_2$, $X_3$, $Z_1$, and $Z_2$ have the values described herein and stereochemical configurations depicted at asterisked positions indicate absolute stereochemistry. In some embodiments, the chemical entity of formula (I) is represented by formula (II-b) wherein $R^a$, $R^{a'}$, $R^b$, $X_2$, $X_3$, $Z_1$, and $Z_2$ have the values described herein and stereochemical configurations depicted at asterisked positions indicate absolute stereochemistry.

In some embodiments, the chemical entity of formula (I) is represented by formula (III-a) or (III-b):

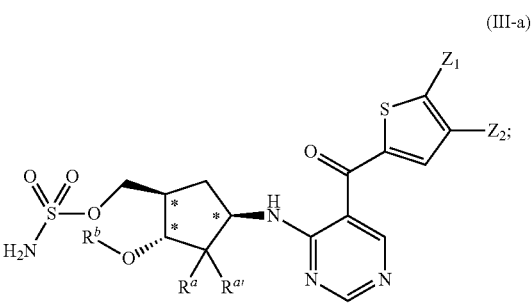

(III-a)

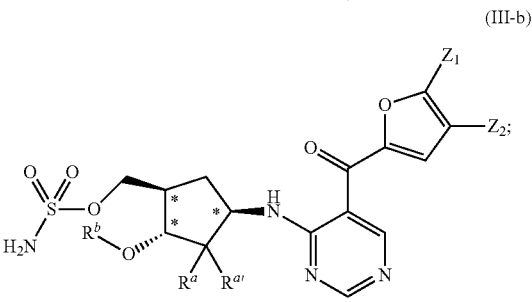

(III-b)

or a pharmaceutically acceptable salt thereof,
wherein $R^a$, $R^{a'}$, $R^b$, $Z_1$, and $Z_2$ have the values described herein and stereochemical configurations depicted at asterisked positions indicate absolute stereochemistry. In some embodiments, the chemical entity of formula (I) is represented by formula (III-a) wherein $R^a$, $R^{a'}$, $R^b$, $Z_1$, and $Z_2$ have the values described herein and stereochemical configurations depicted at asterisked positions indicate absolute stereochemistry. In some embodiments, the chemical entity of formula (I) is represented by formula (III-b) wherein $R^a$, $R^{a'}$, $R^b$, $Z_1$, and $Z_2$ have the values described herein and stereochemical configurations depicted at asterisked positions indicate absolute stereochemistry.

In some embodiments, the chemical entity of formula (I) is represented by formula (IV-a) or (IV-b):

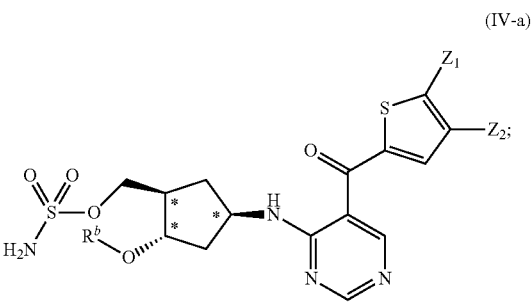

(IV-a)

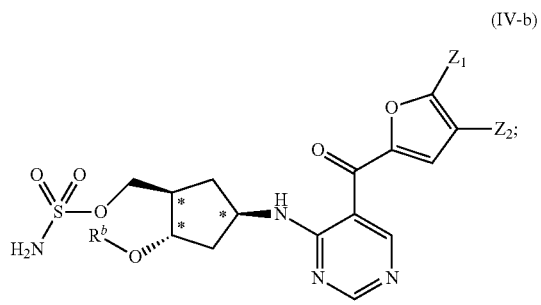

(IV-b)

or a pharmaceutically acceptable salt thereof, wherein $R^b$, $Z_1$, and $Z_2$ have the values described herein and stereochemical configurations depicted at asterisked positions indicate absolute stereochemistry. In some embodiments, the chemical entity of formula (I) is represented by formula (IV-a) wherein $R^b$, $Z_1$, and $Z_2$ have the values described herein and stereochemical configurations depicted at asterisked positions indicate absolute stereochemistry. In some embodiments, the chemical entity of formula (I) is represented by formula (IV-b) wherein $R^b$, $Z_1$, and $Z_2$ have the values described herein and stereochemical configurations depicted at asterisked positions indicate absolute stereochemistry.

In some embodiments, the chemical entity of formula (I) is represented by formula (V):

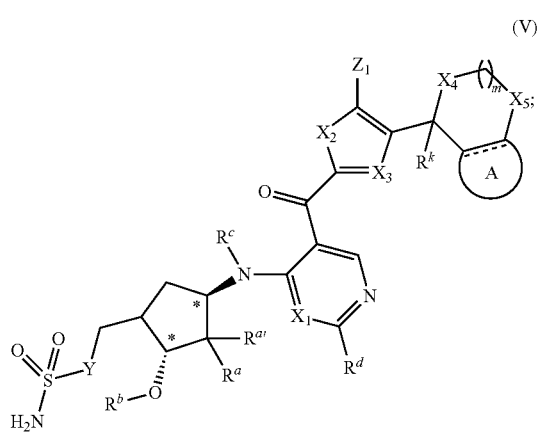

(V)

or a pharmaceutically acceptable salt thereof, wherein dashed lines indicate single or double bonds and Y, $R^a$, $R^{a'}$, $R^b$, $R^c$, $X_1$, $X_2$, $X_3$, $R^d$, $Z_1$, $R^k$, $X_4$, $X_5$, m, and Ring A have the values described herein and stereochemical configurations depicted at asterisked positions indicate absolute stereochemistry.

In some embodiments, the chemical entity of formula (I) is represented by formula (V-a) or (V-b):

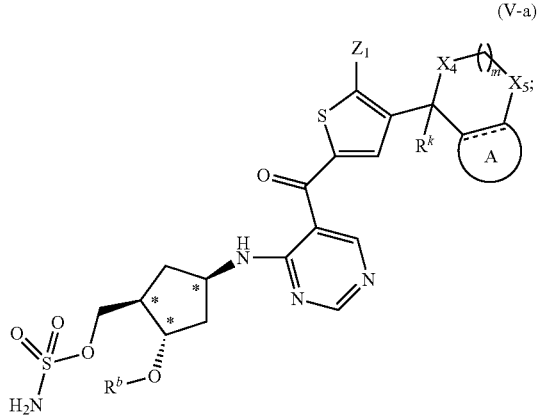

(V-a)

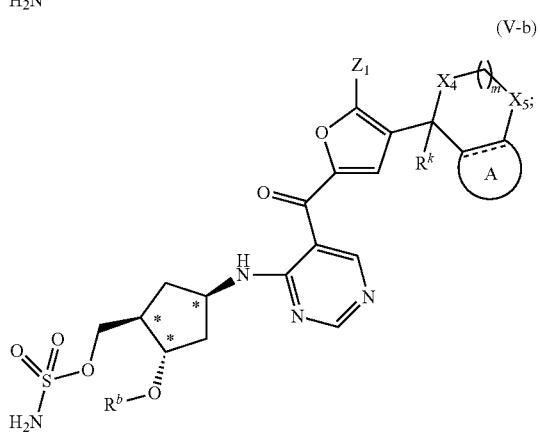

(V-b)

or a pharmaceutically acceptable salt thereof;
wherein dashed lines indicate single or double bonds and $R^b$, $Z_1$, $R^k$, $X_4$, $X_5$, m, and Ring A have the values described herein and stereochemical configurations depicted at asterisked positions indicate absolute stereochemistry. In some embodiments, the chemical entity of formula (I) is represented by formula (V-a) wherein $R^b$, $Z_1$, $R^k$, $X_4$, $X_5$, m, and Ring A have the values described herein and stereochemical configurations depicted at asterisked positions indicate absolute stereochemistry. In some embodiments, the chemical entity of formula (I) is represented by formula (V-b) wherein $R^b$, $Z_1$, $R^k$, $X_4$, $X_5$, m, and Ring A have the values described herein and stereochemical configurations depicted at asterisked positions indicate absolute stereochemistry.

In some embodiments, the chemical entity of formula (I) is represented by formula (VI):

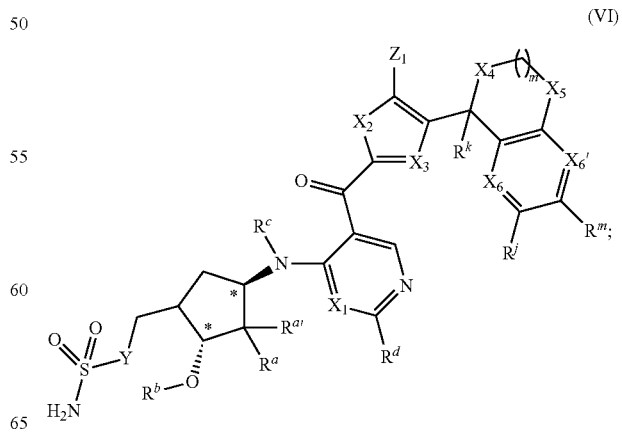

(VI)

or a pharmaceutically acceptable salt thereof, wherein Y, $R^a$, $R^{a'}$, $R^b$, $R^c$, $X_1$, $X_2$, $X_3$, $R^d$, $Z_1$, $R^k$, $X_4$, $X_5$, m, $X_6$, $X_6'$, $R^j$, and $R^m$ have the values described herein and stereochemical configurations depicted at asterisked positions indicate absolute stereochemistry.

In some embodiments, the chemical entity of formula (I) is represented by formula (VI-a) or (VI-b):

(VI-a)

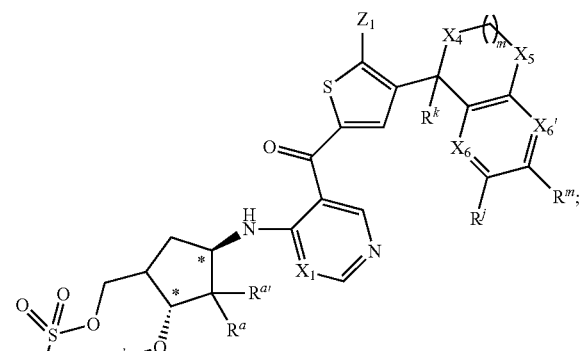

(VII)

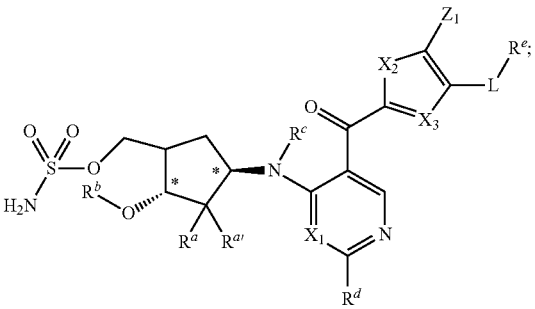

wherein $R^a$, $R^{a'}$, $R^b$, $R^c$, $X_1$, $R^d$, $Z_1$, $X_2$, $X_3$, L, and $R^e$ have the values described herein and stereochemical configurations depicted at asterisked positions indicate absolute stereochemistry.

In some embodiments, the chemical entity of formula (I) is represented by formula (VII-a) or (VII-b):

(VII-a)

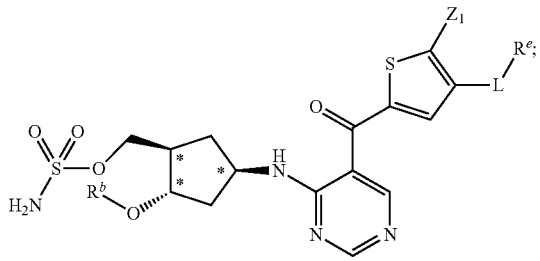

(VI-b)

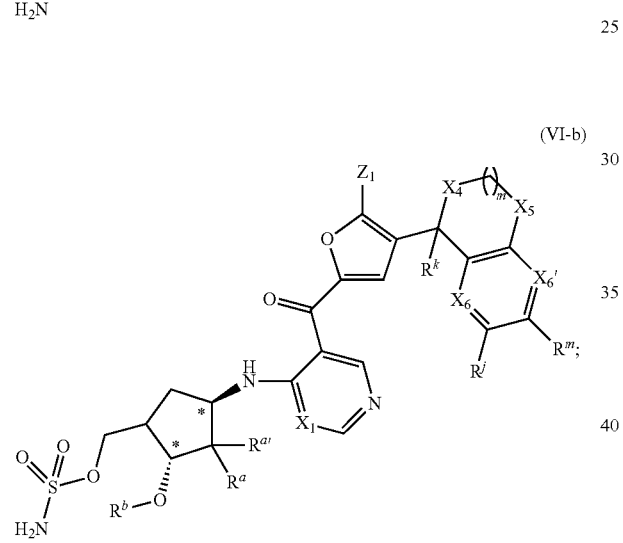

(VII-b)

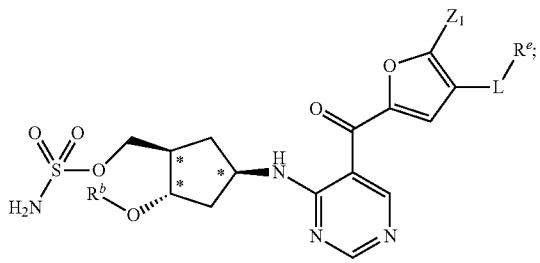

or a pharmaceutically acceptable salt thereof;

wherein $R^a$, $R^{a'}$, $R^b$, $X_1$, $Z_1$, $R^k$, $X_4$, $X_5$, m, $X_6$, $X_6'$, $R^j$, and $R^m$ have the values described herein and stereochemical configurations depicted at asterisked positions indicate absolute stereochemistry. In some embodiments, the chemical entity of formula (I) is represented by formula (VI-a) wherein $R^a$, $R^{a'}$, $R^b$, $X_1$, $Z_1$, $R^k$, $X_4$, $X_5$, m, $X_6$, $X_6'$, $R^j$, and $R^m$ have the values described herein and stereochemical configurations depicted at asterisked positions indicate absolute stereochemistry. In some embodiments, the chemical entity of formula (I) is represented by formula (VI-b) wherein $R^a$, $R^{a'}$, $R^b$, $X_1$, $Z_1$, $R^k$, $X_4$, $X_5$, m, $X_6$, $X_6'$, $R^j$, and $R^m$ have the values described herein and stereochemical configurations depicted at asterisked positions indicate absolute stereochemistry.

In some embodiments, the chemical entity of formula (I) is represented by formula (VII):

or a pharmaceutically acceptable salt thereof, wherein $R^b$, $Z_1$, L, and $R^e$ have the values described herein and stereochemical configurations depicted at asterisked positions indicate absolute stereochemistry. In some embodiments, the chemical entity of formula (I) is represented by formula (VII-a) wherein $R^b$, $Z_1$, L, and $R^e$ have the values described herein and stereochemical configurations depicted at asterisked positions indicate absolute stereochemistry. In some embodiments, the chemical entity of formula (I) is represented by formula (VII-b) wherein $R^b$, $Z_1$, L, and $R^e$ have the values described herein and stereochemical configurations depicted at asterisked positions indicate absolute stereochemistry.

In some embodiments, the chemical entity of formula (I) is represented by formula (VIII):

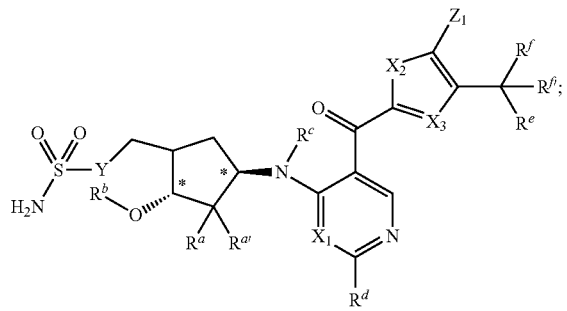

(VIII)

or a pharmaceutically acceptable salt thereof;
wherein Y, $R^a$, $R^{a'}$, $R^b$, $R^c$, $X_1$, $X_2$, $X_3$, $R^d$, $Z_1$, $R^f$, $R^{f'}$, and $R^e$ have the values described herein and stereochemical configurations depicted at asterisked positions indicate absolute stereochemistry.

In some embodiments, the chemical entity of formula (I) is represented by formula (VIII-a) or (VIII-b):

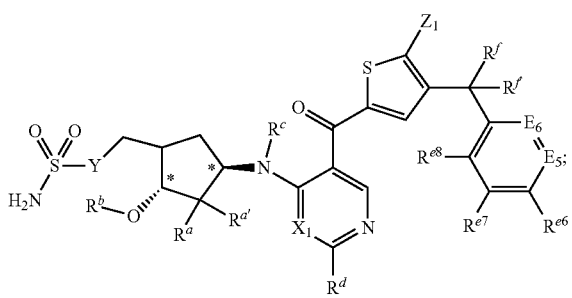

(VIII-a)

(VIII-b)

or a pharmaceutically acceptable salt thereof;
wherein Y, $R^a$, $R^{a'}$, $R^b$, $X_1$, $R^c$, $R^d$, $Z_1$, $R^f$, $R^{f'}$, $E_5$, $E_6$, $R^{e6}$, $R^{e7}$, and $R^{e8}$ have the values described herein and stereochemical configurations depicted at asterisked positions indicate absolute stereochemistry. In some embodiments, the chemical entity of formula (I) is represented by formula (VIII-a) wherein Y, $R^a$, $R^{a'}$, $R^b$, $X_1$, $R^c$, $R^d$, $Z_1$, $R^f$, $R^{f'}$, $E_5$, $E_6$, $R^{e6}$, $R^{e7}$, and $R^{e8}$ have the values described herein and stereochemical configurations depicted at asterisked positions indicate absolute stereochemistry. In some embodiments, the chemical entity of formula (I) is represented by formula (VIII-b) wherein Y, $R^a$, $R^{a'}$, $R^b$, $X_1$, $R^c$, $R^d$, $Z_1$, $R^f$, $R^{f'}$, $E_5$, $E_6$, $R^{e6}$, $R^{e7}$, and $R^{e8}$ have the values described herein and stereochemical configurations depicted at asterisked positions indicate absolute stereochemistry.

In some embodiments, the chemical entity of formula (I) is represented by formula (IX):

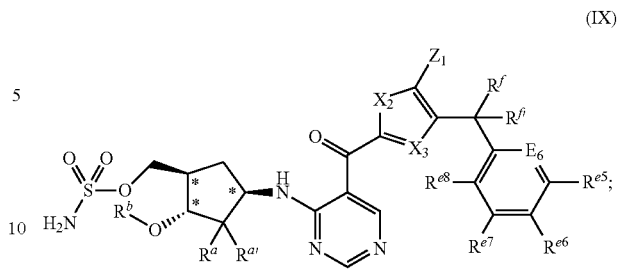

(IX)

or a pharmaceutically acceptable salt thereof;
wherein $R^a$, $R^{a'}$, $R^b$, $X_2$, $X_3$, $Z_1$, $R^f$, $R^{f'}$, $R^{e5}$, $E_6$, $R^{e6}$, $R^{e7}$, and $R^{e8}$ have the values described herein and stereochemical configurations depicted at asterisked positions indicate absolute stereochemistry.

In some embodiments, the chemical entity of formula (I) is represented by formula (IX-a) or (IX-b):

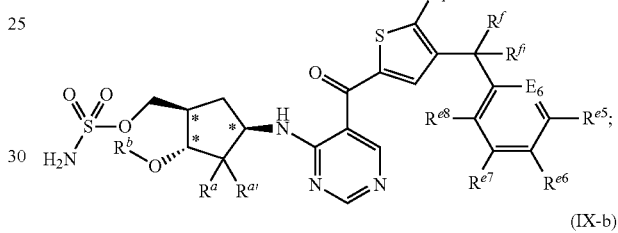

(IX-a)

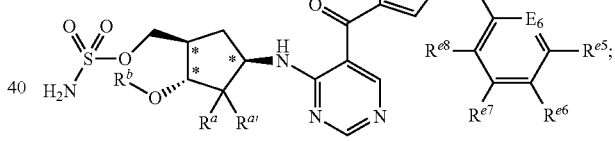

(IX-b)

or a pharmaceutically acceptable salt thereof;
wherein $R^a$, $R^{a'}$, $R^b$, $Z_1$, $R^f$, $R^{f'}$, $R^{e5}$, $E_6$, $R^{e6}$, $R^{e7}$, and $R^{e8}$ have the values described herein and stereochemical configurations depicted at asterisked positions indicate absolute stereochemistry. In some embodiments, the chemical entity of formula (I) is represented by formula (IX-a) wherein $R^a$, $R^{a'}$, $R^b$, $Z_1$, $R^f$, $R^{f'}$, $R^e$, $E_6$, $R^{e6}$, $R^{e7}$, and $R^{e8}$ have the values described herein and stereochemical configurations depicted at asterisked positions indicate absolute stereochemistry. In some embodiments, the chemical entity of formula (I) is represented by formula (IX-b) wherein $R^a$, $R^{a'}$, $R^b$, $Z_1$, $R^f$, $R^{f'}$, $R^{e5}$, $E_6$, $R^{e6}$, $R^{e7}$, and $R^{e8}$ have the values described herein and stereochemical configurations depicted at asterisked positions indicate absolute stereochemistry.

The following values are described for any of formulas (I), (I-a), (II), (II-a), (II-b), (III-a), (III-b), (IV-a), (IV-b), (V), (V-a), (V-b), (VI), (VI-a), (VI-b), (VII), (VII-a), (VII-b), (VIII), (VIII-a), (VIII-b), (IX), (IX-a), or (IX-b).

In some embodiments, Y is —O—, —CH$_2$—, or —N(H)—. In some embodiments, Y is —O—. In some embodiments, Y is —CH$_2$—. In some embodiments, Y is —N(H)—.

In some embodiments, $R^a$ is hydrogen, fluoro, —NH$_2$, or —OH. In some embodiments, $R^a$ is hydrogen, fluoro or —OH. In some embodiments, $R^a$ is hydrogen or —OH. In some embodiments, $R^a$ is hydrogen. In some embodiments, $R^a$ is —OH.

In some embodiments, $R^{a'}$ is hydrogen or fluoro; provided that when $R^a$ is —NH$_2$ or —OH, $R^{a'}$ is hydrogen. In some embodiments, $R^{a'}$ is hydrogen.

In some embodiments, $R^a$ is hydrogen and $R^{a'}$ is hydrogen. In some embodiments, $R^a$ is fluoro and $R^{a'}$ is fluoro. In some embodiments, $R^a$ is —NH$_2$ and $R^{a'}$ is hydrogen. In some embodiments, $R^a$ is hydrogen and $R^{a'}$ is fluoro. In some embodiments, $R^a$ is —OH and $R^{a'}$ is hydrogen. In some embodiments, $R^a$ is fluoro or hydrogen and $R^{a'}$ is fluoro.

In some embodiments, $R^c$ is hydrogen or $C_{1-4}$ alkyl. In some embodiments, $R^c$ is hydrogen or methyl. In some embodiments, $R^c$ is hydrogen.

In some embodiments, $R^d$ is hydrogen, halogen, —CF$_3$, or $C_{1-4}$ alkyl. In some embodiments, $R^d$ is hydrogen, fluoro, chloro, or methyl. In some embodiments, $R^d$ is hydrogen.

In some embodiments, $X_1$ is C(H), C(F) or N. In some embodiments, $X_1$ is C(H) or N. In some embodiments, $X_1$ is C(H). In some embodiments, $X_1$ is N.

In some embodiments, $X_2$ is S or O. In some embodiments, $X_2$ is S. In some embodiments, $X_2$ is O.

In some embodiments, $X_3$ is C($R^{x3}$) or N, wherein $R^{x3}$ has the values described herein. In some embodiments, $X_3$ is C($R^{x3}$), wherein $R^{x3}$ has the values described herein. In some embodiments, $X_3$ is N. In some embodiments, $X_3$ is C(H).

In some embodiments, $R^{x3}$ is hydrogen, methyl, or halogen. In some embodiments, $R^{x3}$ is hydrogen, methyl, fluoro, or chloro. In some embodiments, $R^{x3}$ is hydrogen or methyl. In some embodiments, $R^{x3}$ is hydrogen.

In some embodiments, $Z_1$ is hydrogen, halogen, cyano, $R^{z3}$, —S—$R^{z3}$, —S(O)—$R^{z3}$, or —S(O)$_2$—$R^{z3}$, wherein $R^{z3}$ has the values described herein, and wherein $Z_1$ is not hydrogen, halogen, methyl, or cyano if $Z_2$ is hydrogen or methyl.

In some embodiments, $Z_1$ is hydrogen; halogen; cyano; phenyl optionally substituted with one or more independently selected halogens; 5- to 7-membered cycloaliphatic or heterocyclyl optionally fused to a 6-membered aryl, wherein the 5- to 7-membered cycloaliphatic or heterocyclyl optionally fused to a 6-membered aryl is optionally substituted with one or more independently selected halogens; $C_{1-4}$ fluoroaliphatic; or a $C_{1-4}$ aliphatic group optionally substituted with one or more hydroxyl, $C_{1-4}$ alkoxy, phenyl optionally substituted with one more independently selected halogens, 5- or 6-membered cycloaliphatic, 5- or 6-membered heterocyclyl, or —N($R^{z5}$)$_2$; wherein each $R^{z5}$ independently has the values described herein; and wherein $Z_1$ is not hydrogen, halogen, methyl, or cyano if $Z_2$ is hydrogen or methyl. In some embodiments, $Z_1$ is phenyl, halophenyl, or 5- to 7-membered cycloaliphatic or heterocyclyl optionally fused to a 6-membered aryl, wherein the 5- to 7-membered cycloaliphatic or heterocyclyl optionally fused to a 6-membered aryl is optionally substituted with one or more halogen. In some embodiments, $Z_1$ is a $C_{1-4}$ aliphatic group (i) substituted with one or more phenyl, halophenyl, 5- or 6-membered cycloaliphatic or heterocyclyl, and (ii) optionally substituted with one or more hydroxyl, —OC$_{1-4}$ aliphatic, halogen, $C_{1-4}$ aliphatic, acetyl, —OCH$_3$, —CH$_2$OCH$_3$, cyano, —N($R^{z5}$)$_2$, —CH$_2$NH$_2$, —CO$_2$H, or —CF$_3$, wherein each $R^{z5}$ independently has the values described herein.

In some embodiments, $Z_1$ is hydrogen; halogen; cyano; or $C_{1-4}$ aliphatic optionally substituted with one or more hydroxyl, $C_{1-4}$ alkoxy, —N($R^{z5}$)$_2$, or phenyl optionally substituted with one more independently selected halogens wherein each $R^{z5}$ independently has the values described herein; wherein $Z_1$ is not hydrogen, halogen, methyl, or cyano if $Z_2$ is hydrogen or methyl. In some embodiments, $Z_1$ is hydrogen, chloro, or methyl, and $Z_2$ is not hydrogen or methyl. In some embodiments, $Z_1$ is hydrogen, and $Z_2$ is not hydrogen or methyl. In some embodiments, $Z_1$ is chloro, and $Z_2$ is not hydrogen or methyl. In some embodiments, $Z_1$ is methyl, and $Z_2$ is not hydrogen or methyl.

In some embodiments, $R^{z3}$ is an optionally substituted phenyl, an optionally substituted 5- to 7-membered cycloaliphatic, an optionally substituted 5- to 7-membered heterocyclyl, or an optionally substituted $C_{1-4}$ aliphatic. In some embodiments, $R^{z3}$ is a phenyl, 5- to 7-membered cycloaliphatic, 5- to 7-membered heterocyclyl, or $C_{1-4}$ aliphatic, any of which are optionally substituted with n occurrences of $R^2$, wherein n and $R^2$ have the values described herein. In some embodiments, $R^{z3}$ is a phenyl, 5- to 7-membered cycloaliphatic, 5- to 7-membered heterocyclyl, or $C_{1-4}$ aliphatic, any of which may be substituted with one or more independently selected $R^{z4}$, wherein each $R^{z4}$ independently has the values described herein. In some embodiments, $R^{z3}$ is a phenyl, 5- to 7-membered cycloaliphatic, 5- to 7-membered heterocyclyl, or $C_{1-4}$ aliphatic, any of which are optionally substituted with one to three independently selected $R^{z4}$, wherein each $R^{z4}$ independently has the values described herein. In some embodiments, $R^{z3}$ is a phenyl, 5- to 7-membered cycloaliphatic, 5- to 7-membered heterocyclyl, or $C_{1-4}$ aliphatic, any of which may be substituted with one to two independently selected $R^{z4}$, wherein each $R^{z4}$ independently has the values described herein. In some embodiments, $R^{z3}$ is a phenyl, 5- to 7-membered cycloaliphatic, 5- to 7-membered heterocyclyl, or $C_{1-4}$ aliphatic, any of which may be substituted with one $R^{z4}$, wherein $R^{z4}$ has the values described herein. In some embodiments, $R^{z3}$ is a phenyl, 5- to 7-membered cycloaliphatic, or $C_{1-4}$ aliphatic, any of which may be substituted with one to three $R^{z4}$, wherein each $R^{z4}$ independently has the values described herein. In some embodiments, $R^{z3}$ is a phenyl, 5- to 7-membered cycloaliphatic, or $C_{1-4}$ aliphatic, any of which may be substituted with one $R^{z4}$, wherein $R^{z4}$ has the values described herein.

In some embodiments, each occurrence of $R^{z4}$ is independently hydroxyl, halogen, cyano, $C_{1-4}$ aliphatic, $C_{1-4}$ fluoroaliphatic, $C_{1-4}$ alkoxy, $C_{1-4}$ fluoroalkoxy, —N($R^{z5}$)$_2$, —C(O)$R^{z6}$, —C(O)$_2R^{z5}$, 5- or 6-membered cycloaliphatic or heterocyclyl, or a phenyl optionally substituted with one or more independently selected halogens, wherein each $R^{z5}$ independently has the values described herein and $R^{z6}$ has the values described herein. In some embodiments, each occurrence of $R^{z4}$ is independently halogen, cyano, $C_{1-4}$ aliphatic, or $C_{1-4}$ fluoroaliphatic. In some embodiments, each occurrence of $R^{z4}$ is independently chloro, bromo, fluoro, iodo, methyl, ethyl, propyl, tert-butyl, methoxy, ethoxy, isopropoxy, tert-butoxy, difluoromethyl, trifluoromethyl, difluoromethoxy, trifluoromethoxy, trifluoromethylthio, dimethylamino, diethylamino, ethyne, cyclopropyl, or phenyl. In some embodiments, each occurrence of $R^{z4}$ is independently chloro, bromo, fluoro, iodo, methyl, ethyl, difluoromethoxy, trifluoromethoxy, ethyne, cyclopropyl, or phenyl. In some embodiments, each occurrence of $R^{z4}$ is independently chloro, bromo, fluoro, methyl, ethyl, or trifluoromethyl. In some embodiments, each occurrence of $R^{z4}$ is independently chloro, bromo, iodo, or methyl.

In some embodiments, each $R^{z5}$ is independently hydrogen or $C_{1-4}$ alkyl. In some embodiments, each $R^{z5}$ is independently hydrogen or methyl. In some embodiments, $R^{z5}$ is hydrogen. In some embodiments, $R^{z5}$ is methyl. In some embodiments, each $R^{z5}$ is independently methyl or ethyl.

In some embodiments, $R^{z6}$ is $C_{1-4}$ alkyl. In some embodiments, $R^{z6}$ is methyl. In some embodiments, $R^{z6}$ is methyl or ethyl.

In some embodiments, (a) $Z_2$ is a ring system having an optionally substituted 5- to 7-membered heterocyclyl with 1-2 heteroatoms or an optionally substituted 5- to 7-membered cycloaliphatic fused to
  (i) an optionally substituted 5-membered heteroaryl or an optionally substituted 6-membered aryl or heteroaryl to form a bicyclic group; or
  (ii) an optionally substituted 9-membered heteroaryl or an optionally substituted 10-membered aryl or heteroaryl to form a tricyclic group;
OR (b) $Z_2$ is L-$R^e$ wherein L and $R^e$ have the values described herein;
OR (c) $Z_2$ is hydrogen.

In some embodiments, (a) $Z_2$ is a ring system having a 5- to 7-membered heterocyclyl with 1-2 heteroatoms or a 5- to 7-membered cycloaliphatic fused to
  (i) a 5-membered heteroaryl or a 6-membered aryl or heteroaryl to form a bicyclic group; or
  (ii) a 9-membered heteroaryl or a 10-membered aryl or heteroaryl to form a tricyclic group;
wherein the ring system is optionally substituted by n occurrences of $R^2$, wherein n and $R^2$ have the values described herein;
OR
  (b) $Z_2$ is L-$R^e$ wherein L is -$L_1$-, —$V_1$-$L_2$-, or -$L_1$-$V_1$-$L_2$-; $R^e$ is either:
    (i) hydrogen, hydroxyl, halogen, —$CF_3$, or $C_{1-4}$ aliphatic optionally substituted with one or more hydroxyl, halogen, or $C_{1-4}$ aliphatic, with the proviso that $R^e$ is not hydrogen if $R^f$ and $R^{f'}$ are present and form a ring;
    OR (ii) a ring chosen from 3- to 7-membered cycloaliphatic or 4- to 7-membered heterocyclyl, which is optionally fused to a second 6-membered aryl, 5- to 6-membered heteroaryl, 3- to 7-membered cycloaliphatic, or 4- to 7-membered heterocyclyl, wherein the $R^e$ ring or rings are optionally substituted by n occurrences of $R^2$, wherein n and $R^2$ have the values described herein;
  $L_1$ is a $C_{1-3}$ alkylene chain wherein 1 or 2 saturated carbon atoms are optionally substituted by ($R^f$)($R^{f'}$) and in which there are optionally one or two degrees of unsaturation;
  $V_1$ is —S—, —O—, —S(O)—, —S(O)$_2$—, —C(O)— or —N($R^g$)—, wherein $R^g$ has the values described herein;
  $L_2$ is a $C_{0-2}$ alkylene chain wherein one saturated carbon atom is optionally substituted by ($R^f$)($R^{f'}$);
  wherein $R^f$ and $R^{f'}$ have the values described herein.

In some embodiments, (a) $Z_2$ is a ring system having a 5- to 7-membered heterocyclyl with 1-2 heteroatoms or a 5- to 7-membered cycloaliphatic fused to
  (i) a 5-membered heteroaryl or a 6-membered aryl or heteroaryl to form a bicyclic group; or
  (ii) a 9-membered heteroaryl or a 10-membered aryl or heteroaryl to form a tricyclic group;
  wherein the ring system is optionally substituted by 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, —S—$C_{1-4}$ aliphatic, —S—$C_{1-4}$ fluoroaliphatic, —N($R^{z7}$)$_2$, —C(O)$R^{z8}$, —S(O)$R^{z8}$, —S(O)$_2R^{z8}$, —C(O)$_2R^{z7}$, —C(O)N($R^{z7}$)$_2$, —S(O)$_2$N($R^{z7}$)$_2$, —OC(O)N($R^{z7}$)$_2$, —N($R^{z7}$)C(O)$R^{z8}$, —N($R^{z7}$)SO$_2R^{z8}$, —N($R^{z7}$)C(O)O$R^{z8}$, $T_2$-$R^{z9}$, a 5- to 6-membered heteroaryl, a 6-membered aryl, a 3- to 6-membered cycloaliphatic, or a 4- to 6-membered heterocyclyl; and the ring system is optionally substituted at one saturated carbon with oxo, a spirocyclic 3- to 6-membered carbocycle, or 4- to 6-membered heterocycle;
  each occurrence of $R^{z7}$ is independently hydrogen or $C_{1-4}$ alkyl;
  each occurrence of $R^{z8}$ is independently $C_{1-4}$ alkyl;
  $T_2$ is a $C_1$-$C_2$ alkylene chain; and
  $R^{z9}$ is cyano, —NO$_2$, —N($R^{z7}$)$_2$, —O$R^{z7}$, —C(O)$R^{z8}$, —C(O)$_2R^{z7}$, or —C(O)N($R^{z7}$)$_2$;
OR
  (b) $Z_2$ is L-$R^e$ wherein either:
    (i) $R^e$ is hydrogen, hydroxyl, halogen, —$CF_3$, or $C_{1-4}$ aliphatic optionally substituted with one or more hydroxyl, halogen, or $C_{1-4}$ aliphatic, with the proviso that $R^e$ is not hydrogen if $R^f$ and $R^{f'}$ are present and form a ring;
    OR (ii) $R^e$ is a ring chosen from 6-membered aryl, 5- to 6-membered heteroaryl, 3- to 7-membered cycloaliphatic, or 4- to 7-membered heterocyclyl, which is optionally fused to a second 6-membered aryl, 5- to 6-membered heteroaryl, 3- to 7-membered cycloaliphatic, or 4- to 7-membered heterocyclyl, $R^e$ being optionally substituted by 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, —S—$C_{1-4}$ aliphatic, —S—$C_{1-4}$ fluoroaliphatic, —N($R^{z7}$)$_2$, —C(O)$R^{z8}$, —S(O)$R^{z8}$, —S(O)$_2R^{z8}$, —C(O)$_2R^{z7}$, —C(O)N($R^{z7}$)$_2$, —S(O)$_2$N($R^{z7}$)$_2$, —OC(O)N($R^{z7}$)$_2$, —N($R^{z7}$)C(O)$R^{z8}$, —N($R^{z7}$)SO$_2R^{z8}$, —N($R^{z7}$)C(O)O$R^{z8}$, $T_2$-$R^{z9}$, a 5- to 6-membered heteroaryl, a 6-membered aryl, a 3- to 6-membered cycloaliphatic, or a 4- to 6-membered heterocyclyl; and which is optionally substituted at one saturated carbon with oxo, a spirocyclic 3- to 6-membered carbocycle, or a spirocyclic 4- to 6-membered heterocycle;
  each occurrence of $R^{z7}$ is independently hydrogen or $C_{1-4}$ alkyl;
  each occurrence of $R^{z8}$ is independently $C_{1-4}$ alkyl;
  $T_2$ is a $C_1$-$C_2$ alkylene chain; and
  $R^{z9}$ is cyano, —NO$_2$, —N($R^{z7}$)$_2$, —O$R^{z7}$, —C(O)$R^{z8}$, —C(O)$_2R^{z7}$, or —C(O)N($R^{z7}$)$_2$.

In some embodiments, (a) $Z_2$ is a ring system having a 5- to 7-membered heterocyclyl with 1-2 heteroatoms or a 5- to 7-membered cycloaliphatic fused to
  (i) a 5-membered heteroaryl or a 6-membered aryl or heteroaryl to form a bicyclic group; or
  (ii) a 9-membered heteroaryl or a 10-membered aryl or heteroaryl to form a tricyclic group;
wherein the ring system is optionally substituted by n occurrences of $R^2$, wherein n and $R^2$ have the values described herein.

In some embodiments, $Z_2$ is a ring system having a 5- to 7-membered heterocyclyl with 1-2 heteroatoms or a 5- to 7-membered cycloaliphatic fused to
  (i) a 5-membered heteroaryl or a 6-membered aryl or heteroaryl to form a bicyclic group; or
  (ii) a 9-membered heteroaryl or a 10-membered aryl or heteroaryl to form a tricyclic group;
wherein the ring system is optionally substituted by 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, —S—$C_{1-4}$ aliphatic, —S—$C_{1-4}$ fluoroaliphatic, —N($R^{z7}$)$_2$, —C(O)$R^{z8}$, —S(O)$R^{z8}$, —S(O)$_2R^{z8}$, —C(O)$_2R^{z7}$, —C(O)N($R^{z7}$)$_2$, —S(O)$_2$N($R^{z7}$)$_2$, —OC(O)N($R^{z7}$)$_2$, —N($R^{z7}$)C(O)$R^{z8}$, —N($R^{z7}$)SO$_2R^{z8}$, —N($R^{z7}$)C(O)O$R^{z8}$, $T_2$-$R^{z9}$, a 5- to 6-membered heteroaryl, a 6-membered aryl, a 3- to 6-membered cycloaliphatic, or a 4- to 6-membered heterocyclyl; and the ring system is optionally substituted at one saturated carbon with oxo, a spirocyclic 3- to 6-membered carbocycle, or 4- to 6-membered heterocycle; wherein each $R^{z7}$ independently has the values described herein and $R^{z8}$, $T_2$, and $R^{z9}$ have the values described herein.

In some embodiments, $Z_2$ is a ring system having a 5- to 7-membered heterocyclyl with 1-2 heteroatoms or a 5- to 7-membered cycloaliphatic fused to a 5-membered heteroaryl or a 6-membered aryl or heteroaryl to form a bicyclic group; wherein the ring system is optionally substituted by 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, —S—$C_{1-4}$ aliphatic, —S—$C_{1-4}$ fluoroaliphatic, —N($R^{z7}$)$_2$, —C(O)$R^{z8}$, —S(O)$R^{z8}$, —S(O)$_2R^{z8}$, —C(O)$_2R^{z7}$, —C(O)N($R^{z7}$)$_2$, —S(O)$_2$N($R^{z7}$)$_2$, —OC(O)N($R^{z7}$)$_2$, —N($R^{z7}$)C(O)$R^{z8}$, —N($R^{z7}$)SO$_2R^{z8}$, —N($R^{z7}$)C(O)O$R^{z8}$, $T_2$-$R^{z9}$, a 5- to 6-membered heteroaryl, a 6-membered aryl, a 3- to 6-membered cycloaliphatic, or a 4- to 6-membered heterocyclyl; and the ring system is optionally substituted at one saturated carbon with oxo, a spirocyclic 3- to 6-membered carbocycle, or a spirocyclic 4- to 6-membered heterocycle; wherein each $R^{z7}$ independently has the values described herein and $R^{z8}$, $T_2$, $R^{z9}$ have the values described herein.

In some embodiments, $Z_2$ is a 6-membered heterocyclyl, the heterocyclyl containing 1 N or O atom, fused to a 6-membered aryl or heteroaryl ring to form a bicyclic group, wherein the ring system is optionally substituted by 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, —S—$C_{1-4}$ aliphatic, —S—$C_{1-4}$ fluoroaliphatic, —N($R^{z7}$)$_2$, —C(O)$R^{z8}$, —S(O)$R^{z8}$, —S(O)$_2R^{z8}$, —C(O)$_2R^{z7}$, —C(O)N($R^{z7}$)$_2$, —S(O)$_2$N($R^{z7}$)$_2$, —OC(O)N($R^{z7}$)$_2$, —N($R^{z7}$)C(O)$R^{z8}$, —N($R^{z7}$)SO$_2R^{z8}$, —N($R^{z7}$)C(O)O$R^{z8}$, $T_2$-$R^{z9}$, a 5- to 6-membered heteroaryl, a 6-membered aryl, a 3- to 6-membered cycloaliphatic, or a 4- to 6-membered heterocyclyl; and the ring system is optionally substituted at one saturated carbon with oxo, a spirocyclic 3- to 6-membered carbocycle, or 4- to 6-membered heterocycle; wherein each $R^{z7}$ independently has the values described herein and $R^{z8}$, $T_2$, and $R^{z9}$ have the values described herein.

In some embodiments, $R^{z7}$ is hydrogen or $C_{1-4}$ alkyl. In some embodiments, $R^{z7}$ is hydrogen or methyl. In some embodiments, $R^{z7}$ is hydrogen. In some embodiments, $R^{z7}$ is methyl. In some embodiments, $R^{z7}$ is methyl or ethyl.

In some embodiments, $R^{z8}$ is $C_{1-4}$ alkyl. In some embodiments, $R^{z8}$ is methyl. In some embodiments, $R^{z8}$ is methyl or ethyl.

In some embodiments, $T_2$ is an optionally substituted $C_{1-2}$ alkylene chain. In some embodiments, $T_2$ is a $C_1$-$C_2$ alkylene chain optionally substituted with 0-3 independent occurrences of $R^{t2}$, wherein $R^{t2}$ has the values described herein. In some embodiments, $T_2$ is a $C_{1-2}$ alkylene chain. In some embodiments, $T_2$ is —CH$_2$—CH$_2$—. In some embodiments, $T_2$ is —C(CH$_3$)$_2$—. In some embodiments, $T_2$ is —CH$_2$—.

In some embodiments, each occurrence of $R^{t2}$ is independently $C_{1-4}$ alkyl. In some embodiments, each occurrence of $R^{t2}$ is independently methyl or ethyl. In some embodiments, $R^{t2}$ is methyl.

In some embodiments, $R^{z9}$ is cyano, —N($R^{z7}$)$_2$, —O$R^{z7}$, —C(O)$R^{z8}$, —C(O)$_2R^{z7}$, or —C(O)N($R^{z7}$)$_2$, wherein $R^{z7}$ and $R^{z8}$ have the values described herein.

In some embodiments, $Z_2$ is

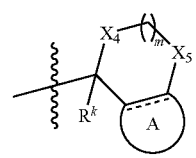

(a-i)

wherein $X_4$, $X_5$, $R^k$, m, and Ring A have the values described herein.

In some embodiments, $R^k$ is hydrogen or methyl. In some embodiments, $R^k$ is deuterium. In some embodiments, $R^k$ is hydrogen.

In some embodiments, $X_4$ is S, O, or N($R^{n4}$), wherein $R^{n4}$ has the values described herein. In some embodiments, $X_4$ is O or N($R^{n4}$), wherein $R^{n4}$ has the values described herein. In some embodiments, $X_4$ is N($R^{n4}$), wherein $R^{n4}$ has the values described herein. In some embodiments, $X_4$ is O or N(H). In some embodiments, $X_4$ is O. In some embodiments, $X_4$ is N(H).

In some embodiments, $R^{n4}$ is hydrogen or $C_{1-4}$ alkyl. In some embodiments, $R^{n4}$ is hydrogen or methyl. In some embodiments, $R^{n4}$ is hydrogen.

In some embodiments, $X_5$ is O, C(O), or C($R^{x5}$)($R^{x5'}$), wherein $R^{x5}$ and $R^{x5'}$ have the values described herein. In some embodiments, $X_5$ is O. In some embodiments, $X_5$ is C($R^{x5}$)($R^{x5'}$). In some embodiments, $X_5$ is CD$_2$. In some embodiments, $X_5$ is O, C(O), or C($R^{x5}$)($R^{x5'}$), wherein $X_5$ is not O if $X_4$ is N($R^{n4}$) or S. In some embodiments, $X_5$ is CH$_2$.

In some embodiments, $R^{x5}$ is hydrogen, halogen, hydroxyl, or $C_{1-4}$ alkyl, or $R^{x5}$ and $R^{x5'}$, taken together with the carbon atom to which they are attached, form a spirocyclic 3-6 membered carbocycle or a spirocyclic 4-6 membered heterocycle comprising one heteroatom chosen from O, N, or S. In some embodiments, $R^{x5}$ is hydrogen, fluoro, hydroxyl, or $C_{1-4}$ alkyl, or $R^{x5}$ and $R^{x5'}$, taken together with the carbon atom to which they are attached, form a spirocyclic 3-6 membered carbocycle or a spirocyclic 4-6 membered heterocycle comprising one heteroatom chosen from O, N, or S. In some embodiments, $R^{x5}$ is hydrogen, fluoro, hydroxyl, or $C_{1-4}$ alkyl. In some embodiments, $R^{x5}$ is hydrogen, fluoro, chloro, hydroxyl, or methyl. In some embodiments, $R^{x5}$ is hydrogen or methyl. In some embodiments, $R^{x5}$ is hydrogen.

In some embodiments, $R^{x5'}$ is hydrogen, halogen or $C_{1-4}$ alkyl, or $R^{x5}$ and $R^{x5'}$, taken together with the carbon atom to which they are attached, form a spirocyclic 3-6 membered carbocycle or a spirocyclic 4-6 membered heterocycle comprising one heteroatom chosen from O, N, or S, wherein $R^{x5'}$ is not halogen if $R^{x5}$ is hydroxyl. In some embodiments, $R^{x5'}$ is hydrogen, fluoro, or $C_{1-4}$ alkyl, or $R^{x5}$ and $R^{x5'}$, taken together with the carbon atom to which they are attached, form a spirocyclic 3-6 membered carbocycle or a spirocyclic 4-6 membered heterocycle comprising one heteroatom chosen from O, N, or S, wherein $R^{x5'}$ is not halogen if $R^{x5}$ is hydroxyl. In some embodiments, $R^{x5'}$ is hydrogen, fluoro, or $C_{1-4}$ alkyl, wherein $R^{x5'}$ is not fluoro if $R^{x5}$ is hydroxyl. In some embodiments, $R^{x5'}$ is hydrogen, fluoro, chloro, or methyl, wherein $R^{x5'}$ is not fluoro if $R^{x5}$ is hydroxyl. In some embodiments, $R^{x5'}$ is hydrogen.

In some embodiments, $R^{x5}$ is hydrogen, halogen, hydroxyl, or $C_{1-4}$ alkyl and $R^{x5'}$ is hydrogen. In some embodiments, $R^{x5}$ is hydrogen, fluoro, chloro, hydroxyl, or methyl and $R^{x5'}$ is hydrogen. In some embodiments, $R^{x5}$ is hydrogen or methyl and $R^{x5'}$ is hydrogen. In some embodiments, $R^{x5}$ is hydrogen and $R^{x5'}$ is hydrogen. In some embodiments, $R^{x5}$ is fluoro and $R^{x5'}$ is fluoro. In some embodiments, $R^{x5}$ is methyl and $R^{x5'}$ is methyl. In some embodiments, $R^{x5}$ and $R^{x5'}$, taken together with the carbon atom to which they are attached, a spirocyclic 3-6 membered carbocycle or a spirocyclic 4-6 membered heterocycle comprising one heteroatom chosen from O, N, or S. In some embodiments, $R^{x5}$ and $R^{x5'}$, taken together with the carbon atom to which they are attached, form a spirocyclic 3-6 membered carbocycle. In some embodiments, $R^{x5}$ and $R^{x5'}$, taken together with the carbon atom to which they are attached, form a cyclopropyl ring. In some embodiments, $R^{x5}$ and $R^{x5'}$, are independently hydrogen or fluoro; or, together with the carbon to which they are attached, form a cyclopropyl ring.

In some embodiments, Ring A is a fused 5-membered heteroaryl or 6-membered aryl or heteroaryl, and is optionally substituted with 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, —S—$C_{1-4}$ aliphatic, —S—$C_{1-4}$ fluoroaliphatic, —N($R^{z7}$)$_2$, —C(O)$R^{z8}$, —S(O)$R^{z8}$, —S(O)$_2R^{z8}$, —C(O)$_2R^{z7}$, —C(O)N($R^{z7}$)$_2$, —S(O)$_2$N($R^{z7}$)$_2$, —OC(O)N($R^{z7}$)$_2$, —N($R^{z7}$)C(O)$R^{z8}$, —N($R^{z7}$)SO$_2R^{z8}$, —N($R^{z7}$)C(O)O$R^{z8}$, $T_2$-$R^{z9}$, a 5- to 6-membered heteroaryl, a 6-membered aryl, a 3- to 6-membered cycloaliphatic, or a 4- to 6-membered heterocyclyl, wherein $R^{z7}$, $R^{z8}$, $T_2$, and $R^{z9}$ have the values described herein. In some embodiments, Ring A is a fused 6-membered aryl or heteroaryl having one heteroatom and is optionally substituted with 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, —S—$C_{1-4}$ aliphatic, —S—$C_{1-4}$ fluoroaliphatic, —N($R^{z7}$)$_2$, —C(O)$R^{z8}$, —S(O)$R^{z8}$, —S(O)$_2R^{z8}$, —C(O)$_2R^{z7}$, —C(O)N($R^{z7}$)$_2$, —S(O)$_2$N($R^{z7}$)$_2$, —OC(O)N($R^{z7}$)$_2$, —N($R^{z7}$)C(O)$R^{z8}$, —N($R^{z7}$)SO$_2R^{z8}$, —N($R^{z7}$)C(O)O$R^{z8}$, $T_2$-$R^{z9}$, a 5- to 6-membered heteroaryl, a 6-membered aryl, a 3- to 6-membered cycloaliphatic, or a 4- to 6-membered heterocyclyl, wherein $R^{z7}$, $R^{z8}$, $T_2$, and $R^{z9}$ have the values described herein.

In some embodiments, Ring A is a fused 5-membered heteroaryl or 6-membered aryl or heteroaryl, and is optionally substituted with 1-3 independent occurrences of chloro, bromo, fluoro, iodo, methyl, ethyl, propyl, isopropyl, tert-butyl, methoxy, ethoxy, isopropoxy, tert-butoxy, difluoromethyl, trifluoromethyl, difluoromethoxy, trifluoromethoxy, trifluoromethylthio, dimethylamino, diethylamino, cyano, ethyne, cyclopropyl, or phenyl. In some embodiments, Ring A is a fused 6-membered aryl or heteroaryl, and is optionally substituted with 1-3 independent occurrences of chloro, bromo, fluoro, iodo, methyl, ethyl, propyl, isopropyl, tert-butyl, methoxy, ethoxy, isopropoxy, tert-butoxy, difluoromethyl, trifluoromethyl, difluoromethoxy, trifluoromethoxy, trifluoromethylthio, dimethylamino, diethylamino, cyano, ethyne, cyclopropyl, or phenyl.

In some embodiments, Ring A is a fused phenyl or pyridyl, and is optionally substituted with 1-3 independent occurrences of chloro, bromo, fluoro, iodo, methyl, ethyl, propyl, isopropyl, tert-butyl, methoxy, ethoxy, isopropoxy, tert-butoxy, difluoromethyl, trifluoromethyl, difluoromethoxy, trifluoromethoxy, trifluoromethylthio, dimethylamino, diethylamino, cyano, ethyne, cyclopropyl, or phenyl. In some embodiments, Ring A is a fused 6-membered aryl or heteroaryl, and is optionally substituted with 1-3 independent occurrences of chloro, bromo, fluoro, iodo, methyl, ethyl, propyl, isopropyl, tert-butyl, methoxy, ethoxy, isopropoxy, tert-butoxy, difluoromethyl, trifluoromethyl, difluoromethoxy, trifluoromethoxy, trifluoromethylthio, dimethylamino, cyano, diethylamino, ethyne, cyclopropyl, or phenyl.

In some embodiments, $Z_2$ is

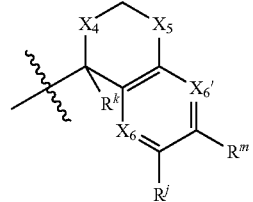

(a-ii)

wherein $X_4$, $X_5$, $X_6$, $X_6'$, $R^m$, and $R^j$ have the values described herein.

In some embodiments, $Z_2$ is

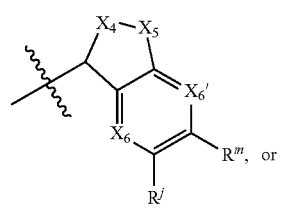

(a-iii)

In some embodiments, $Z_2$ is

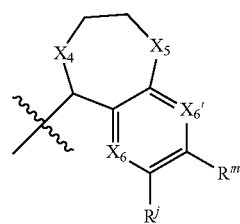

(a-iv)

wherein $X_4$, $X_5$, $X_6$, $X_6'$, $R^m$, and $R^j$ have the values described herein. In some embodiments, $Z_2$ is (a-iii), wherein $X_4$, $X_5$, $X_6$, $X_6'$, $R^m$, and $R^j$ have the values described herein. In some embodiments, $Z_2$ is (a-iv), wherein $X_4$, $X_5$, $X_6$, $X_6'$, $R^m$, and $R^j$ have the values described herein.

In some embodiments, $Z_2$ is

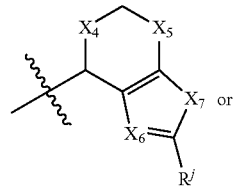

(a-v)

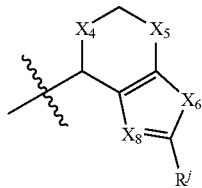
(a-vi)

wherein $X_4, X_5, X_6, X_7, X_8$, and $R^j$ have the values described herein. In some embodiments, $Z_2$ is (a-v), wherein $X_4, X_5, X_6, X_7, X_8$, and $R^j$ have the values described herein. In some embodiments, $Z_2$ is (a-vi), wherein $X_4, X_5, X_6, X_7, X_8$, and $R^j$ have the values described herein. In some embodiments, $X_7$ is O or S.

In some embodiments, $X_8$ is S or N(H).

In some embodiments, $Z_2$ is

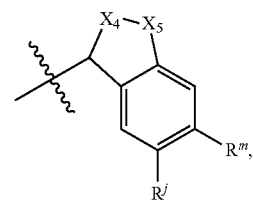
(a-vii)

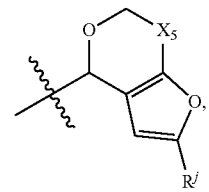
(a-viii)

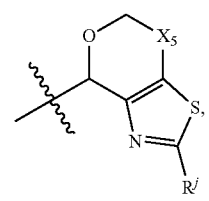
(a-ix)

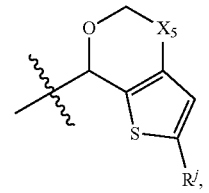
(a-x)

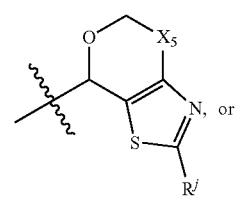
(a-xi)

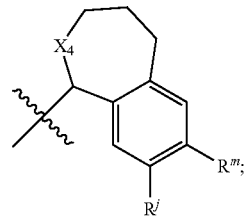
(a-xii)

wherein $X_4, X_5, R^m$, and $R^j$ have the values described herein. In some embodiments, $Z_2$ is (a-vii), wherein $X_4, X_5, R^m$, and $R^j$ have the values described herein. In some embodiments, $Z_2$ is (a-viii), wherein $X_5$ and $R^j$ have the values described herein. In some embodiments, $Z_2$ is (a-ix), wherein $X_5$ and $R^j$ have the values described herein. In some embodiments, $Z_2$ is (a-x), wherein $X_5$ and $R^j$ have the values described herein. In some embodiments, $Z_2$ is (a-xi), wherein $X_5$ and $R^j$ have the values described herein. In some embodiments, $Z_2$ is (a-xii), wherein $X_4, R^m$, and $R^j$ have the values described herein. In some embodiments, $Z_2$ is

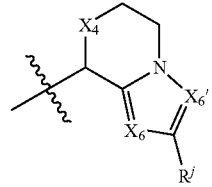
(a-xiii)

wherein $X_4$, $X_6$, $X_6'$, and $R^j$ have the values described herein.

In some embodiments, $X_6$ is N or $C(R^{x6})$, wherein $R^{x6}$ has the values described herein. In some embodiments, $X_6$ is N or C(H). In some embodiments, $X_6$ is N. In some embodiments, $X_6$ is $C(R^{x6})$, wherein $R^{x6}$ has the values described herein. In some embodiments, $X_6$ is C(H).

In some embodiments, $R^{x6}$ is hydrogen, halogen, hydroxyl, cyano, $C_{1-4}$ aliphatic, $C_{1-4}$ fluoroaliphatic, $C_{1-4}$ alkoxy, $C_{1-4}$ fluoroalkoxy, —$N(R^{z7})_2$, —$C(O)_2R^{z7}$, —$C(O)N(R^{z7})_2$, —$S(O)_2N(R^{z7})_2$, —$CH_2$—$OR^{z7}$, —$CH_2NR^{z7}$, a 3- to 6-membered cycloaliphatic, or a 4- to 6-membered heterocyclyl, wherein each $R^{z7}$ independently has the values described herein. In some embodiments, $R^{x6}$ is hydrogen, chloro, bromo, fluoro, iodo, methyl, ethyl, propyl, tert-butyl, methoxy, ethoxy, isopropoxy, tert-butoxy, difluoromethyl, trifluoromethyl, difluoromethoxy, trifluoromethoxy, trifluoromethylthio, dimethylamino, diethylamino, ethyne, or cyclopropyl. In some embodiments, $R^{x6}$ is hydrogen, chloro, fluoro, bromo, iodo, methyl, ethyl, isopropyl, cyano, cyclopropyl, $CF_3$, —$OCH_3$, —$OCH_2CH_3$, or —C≡CH. In some embodiments, $R^{x6}$ is hydrogen, fluoro, chloro, bromo, iodo, or methyl. In some embodiments, $R^{x6}$ is hydrogen, fluoro, chloro, or methyl. In some embodiments, $R^{x6}$ is hydrogen, fluoro, or chloro. In some embodiments, $R^{x6}$ is hydrogen.

In some embodiments, $X_6'$ is N or $C(R^{x6'})$, wherein $R^{x6'}$ has the values described herein. In some embodiments, $X_6'$ is N or $C(R^{x6})$, wherein $R^{x6}$ has the values described herein. In some embodiments, $X_6'$ is N or C(H). In some embodiments, $X_6'$ is N. In some embodiments, $X_6'$ is $C(R^{x6'})$, wherein $R^{x6'}$ has the values described herein. In some embodiments, $X_6'$ is C(H).

In some embodiments, $R^{x6'}$ is hydrogen, halogen, hydroxyl, cyano, $C_{1-4}$ aliphatic, $C_{1-4}$ fluoroaliphatic, $C_{1-4}$ alkoxy, $C_{1-4}$ fluoroalkoxy, —N($R^{z7}$)$_2$, —C(O)$_2$$R^{z7}$, —C(O)N($R^{z7}$)$_2$, —S(O)$_2$N($R^{z7}$)$_2$, —CH$_2$—O$R^{z7}$, —CH$_2$N$R^{z7}$, a 3- to 6-membered cycloaliphatic, or a 4- to 6-membered heterocyclyl, wherein each $R^{z7}$ independently has the values described herein. In some embodiments, $R^{x6'}$ is hydrogen, chloro, bromo, fluoro, iodo, methyl, ethyl, propyl, tert-butyl, methoxy, ethoxy, isopropoxy, tert-butoxy, difluoromethyl, trifluoromethyl, difluoromethoxy, trifluoromethoxy, trifluoromethylthio, dimethylamino, diethylamino, ethyne, or cyclopropyl. In some embodiments, $R^{x6'}$ is hydrogen, chloro, fluoro, bromo, iodo, methyl, ethyl, isopropyl, cyano, cyclopropyl, CF$_3$, —OCH$_3$, —OCH$_2$CH$_3$, or —C≡CH. In some embodiments, $R^{x6'}$ is hydrogen, fluoro, chloro, bromo, iodo, or methyl. In some embodiments, $R^{x6'}$ is hydrogen, fluoro, chloro, bromo, iodo, or methyl. In some embodiments, $R^{x6'}$ is hydrogen, fluoro, chloro, or methyl. In some embodiments, $R^{x6'}$ is hydrogen, fluoro, or chloro. In some embodiments, $R^{x6'}$ is hydrogen.

In some embodiments, $R^j$ is hydrogen, halogen, hydroxyl, cyano, $C_{1-4}$ aliphatic, $C_{1-4}$ fluoroaliphatic, $C_{1-4}$ alkoxy, $C_{1-4}$ fluoroalkoxy, —N($R^{z7}$)$_2$, —C(O)$_2$$R^{z7}$, —C(O)N($R^{z7}$)$_2$, —S(O)$_2$N($R^{z7}$)$_2$, —CH$_2$—O$R^{z7}$, —CH$_2$N$R^{z7}$, a 3- to 6-membered cycloaliphatic, or a 4- to 6-membered heterocyclyl, wherein each $R^{z7}$ independently has the values described herein. In some embodiments, $R^j$ is hydrogen, chloro, bromo, fluoro, iodo, methyl, ethyl, propyl, tert-butyl, methoxy, ethoxy, isopropoxy, tert-butoxy, difluoromethyl, trifluoromethyl, difluoromethoxy, trifluoromethoxy, trifluoromethylthio, dimethylamino, diethylamino, ethyne, or cyclopropyl. In some embodiments, $R^j$ is hydrogen, chloro, fluoro, bromo, iodo, methyl, ethyl, isopropyl, cyano, cyclopropyl, CF$_3$, —OCH$_3$, —OCH$_2$CH$_3$, or —C≡CH. In some embodiments, $R^j$ is methyl, ethyl, isopropyl, hydrogen, fluoro, chloro, bromo, cyclopropyl, —C≡CH or —CF$_3$. In some embodiments, $R^j$ is hydrogen, fluoro, chloro, bromo, iodo, or methyl. In some embodiments, $R^j$ is hydrogen, fluoro, chloro, or methyl. In some embodiments, $R^j$ is fluoro, chloro, or methyl. In some embodiments, $R^j$ is hydrogen, fluoro, or chloro. In some embodiments, $R^j$ is hydrogen. In some embodiments, $R^j$ is fluoro or chloro. In some embodiments, $R^j$ is methyl. In some embodiments, $R^j$ is fluoro. In some embodiments, $R^j$ is chloro.

In some embodiments, $R^m$ is hydrogen, halogen, hydroxyl, cyano, $C_{1-4}$ aliphatic, $C_{1-4}$ fluoroaliphatic, $C_{1-4}$ alkoxy, $C_{1-4}$ fluoroalkoxy, —N($R^{z7}$)$_2$, —C(O)$_2$$R^{z7}$, —C(O)N($R^{z7}$)$_2$, —S(O)$_2$N($R^{z7}$)$_2$, —CH$_2$—O$R^{z7}$, —CH$_2$N$R^{z7}$, a 3- to 6-membered cycloaliphatic, or a 4- to 6-membered heterocyclyl, wherein each $R^{z7}$ independently has the values described herein. In some embodiments, $R^m$ is hydrogen, chloro, bromo, fluoro, iodo, methyl, ethyl, propyl, tert-butyl, methoxy, ethoxy, isopropoxy, tert-butoxy, difluoromethyl, trifluoromethyl, difluoromethoxy, trifluoromethoxy, trifluoromethylthio, dimethylamino, diethylamino, ethyne, or cyclopropyl. In some embodiments, $R^m$ is hydrogen, fluoro, chloro, fluoro, bromo, iodo, methyl, ethyl, isopropyl, cyano, cyclopropyl, CF$_3$, —OCH$_3$, —OCH$_2$CH$_3$, or —C≡CH. In some embodiments, $R^m$ is hydrogen, fluoro, chloro, bromo, iodo, or methyl. In some embodiments, $R^m$ is hydrogen, fluoro, chloro, or methyl. In some embodiments, $R^m$ is hydrogen, fluoro, or chloro. In some embodiments, $R^m$ is hydrogen.

In some embodiments, each $R^{x6}$, $R^{x6'}$, $R^j$ and $R^m$ is independently hydrogen, halogen, hydroxyl, cyano, $C_{1-4}$ aliphatic, $C_{1-4}$ fluoroaliphatic, $C_{1-4}$ alkoxy, $C_{1-4}$ fluoroalkoxy, —N($R^{z7}$)$_2$, —C(O)$_2$$R^{z7}$, —C(O)N($R^{z7}$)$_2$, —S(O)$_2$N($R^{z7}$)$_2$, —CH$_2$—O$R^{z7}$, —CH$_2$N$R^{z7}$, 3- to 6-membered cycloaliphatic, or a 4- to 6-membered heterocyclyl, wherein each $R^{z7}$ independently has the values described herein and at least one of $R^{x6}$, $R^{x6'}$, $R^j$ and $R^m$ is hydrogen. In some embodiments, each of $R^{x6}$, $R^{x6'}$, $R^j$, and $R^m$ is independently hydrogen, chloro, fluoro, bromo, iodo, methyl, ethyl, isopropyl, cyano, cyclopropyl, CF$_3$, —OCH$_3$, —OCH$_2$CH$_3$, or —C≡CH; wherein at least one of $R^{x6}$, $R^{x7}$, $R^j$ and $R^m$ is hydrogen. In some embodiments, each $R^{x6}$, $R^{x6'}$, $R^j$ and $R^m$ is independently hydrogen, halogen, hydroxyl, cyano, $C_{1-4}$ aliphatic, $C_{1-4}$ fluoroaliphatic, $C_{1-4}$ alkoxy, $C_{1-4}$ fluoroalkoxy, —N($R^{z7}$)$_2$, —C(O)$_2$$R^{z7}$, —C(O)N($R^{z7}$)$_2$, —S(O)$_2$N($R^{z7}$)$_2$, —CH$_2$—O$R^{z7}$, —CH$_2$N$R^{z7}$, 3- to 6-membered cycloaliphatic, or a 4- to 6-membered heterocyclyl, wherein each $R^{z7}$ independently has the values described herein and at least one of $R^{x6}$, $R^{x6'}$, $R^j$ and $R^m$ is hydrogen. In some embodiments, each of $R^{x6}$, $R^{x6'}$, $R^j$, and $R^m$ is independently hydrogen, chloro, fluoro, bromo, iodo, methyl, ethyl, isopropyl, cyano, cyclopropyl, CF$_3$, —OCH$_3$, —OCH$_2$CH$_3$, or —C≡CH; wherein at least two of $R^{x6}$, $R^{x7}$, $R^j$ and $R^m$ are hydrogen. In some embodiments, each $R^{x6}$, $R^{x6'}$, $R^j$ and $R^m$ is independently hydrogen, halogen, hydroxyl, cyano, $C_{1-4}$ aliphatic, $C_{1-4}$ fluoroaliphatic, $C_{1-4}$ alkoxy, $C_{1-4}$ fluoroalkoxy, —N($R^{z7}$)$_2$, —C(O)$_2$$R^{z7}$, —C(O)N($R^{z7}$)$_2$, —S(O)$_2$N($R^{z7}$)$_2$, —CH$_2$—O$R^{z7}$, —CH$_2$N$R^{z7}$, 3- to 6-membered cycloaliphatic, or a 4- to 6-membered heterocyclyl, wherein each $R^{z7}$ independently has the values described herein and at least one of $R^{x6}$, $R^{x6'}$, $R^j$ and $R^m$ is hydrogen. In some embodiments, each of $R^{x6}$, $R^{x6'}$, $R^j$, and $R^m$ is independently hydrogen, chloro, fluoro, bromo, iodo, methyl, ethyl, isopropyl, cyano, cyclopropyl, CF$_3$, —OCH$_3$, —OCH$_2$CH$_3$, or —C≡CH; wherein at least two of $R^{x6}$, $R^{x7}$, $R^j$ and $R^m$ are hydrogen.

In some embodiments, $R^{x6}$ is hydrogen; $R^{x6'}$ is hydrogen; and $R^j$ and $R^m$ are independently hydrogen, halogen, hydroxyl, cyano, $C_{1-4}$ aliphatic, $C_{1-4}$ fluoroaliphatic, $C_{1-4}$ alkoxy, $C_{1-4}$ fluoroalkoxy, —N($R^{z7}$)$_2$, —C(O)$_2$$R^{z7}$, —C(O)N($R^{z7}$)$_2$, —S(O)$_2$N($R^{z7}$)$_2$, —CH$_2$—O$R^{z7}$, —CH$_2$N$R^{z7}$, 3- to 6-membered cycloaliphatic, or a 4- to 6-membered heterocyclyl, wherein each $R^{z7}$ independently has the values described herein. In some embodiments, $R^{x6}$ is hydrogen; $R^{x6'}$ is hydrogen; and $R^j$ and $R^m$ are independently hydrogen, chloro, fluoro, bromo, iodo, methyl, ethyl, isopropyl, cyano, cyclopropyl, CF$_3$, —OCH$_3$, —OCH$_2$CH$_3$, or —C≡CH. In some embodiments, $R^{x6}$ is hydrogen; $R^{x6'}$ is hydrogen; $R^m$ is hydrogen; and $R^j$ is methyl, ethyl, isopropyl, hydrogen, fluoro, chloro, bromo, cyclopropyl, —C≡CH or —CF$_3$. In some embodiments, $R^{x6}$ is hydrogen; $R^{x6'}$ is hydrogen; $R^m$ is hydrogen; and $R^j$ is hydrogen, fluoro, chloro, or methyl.

In some embodiments, m is 0-2. In some embodiments, m is 1-2. In some embodiments, m is 0-1. In some embodiments, m is 0. In some embodiments, m is 1. In some embodiments, m is 2.

In some embodiments, $Z_2$ is L-$R^e$.

In some embodiments, L is -$L_1$-, —$V_1$-$L_2$-, or -$L_1$-$V_1$-$L_2$-, wherein $L_1$, $V_1$, and $L_2$ have the values described herein. In some embodiments, L is —C($R^f$)($R^{f'}$)—, —S—, —S(O)—, —S(O)$_2$—, —C(O)—, —C(=CH$_2$)—, —C($R^f$)($R^{f'}$)—C(=CH$_2$)—, —C($R^f$)($R^{f'}$)—C≡C—, —C($R^f$)($R^{f'}$)—O—, —C($R^f$)($R^{f'}$)—S—, —C($R^f$)($R^{f'}$)—N($R^g$)—, —C($R^f$)($R^{f'}$)—N($R^g$)—CH$_2$—, —C($R^f$)($R^{f'}$)—CH$_2$—, —C($R^f$)($R^{f'}$)—CH$_2$—CH$_2$—, or —C(O)—C($R^f$)($R^{f'}$)—, wherein $R^f$, $R^{f'}$, and $R^g$ have the values described herein. In some embodiments, L is —C($R^f$)($R^{f'}$)—, —S—, —C(=O)—, —C($R^f$)($R^{f'}$)—O—, —C($R^f$)($R^{f'}$)—S—, —C($R^f$)($R^{f'}$)—N($R^g$)—, —C($R^f$)($R^{f'}$)—CH$_2$— or —C($R^f$)($R^{f'}$)—C≡C—, wherein $R^f$, $R^{f'}$, and $R^g$ have the values described herein.

In some embodiments, L is —CH$_2$—, —CH(OH)—, —C(OH)(CH$_3$)—, —CH(NH$_2$)—, —C(CH$_3$)(NH$_2$)—, —CH$_2$—CH$_2$—, —S(O)—,

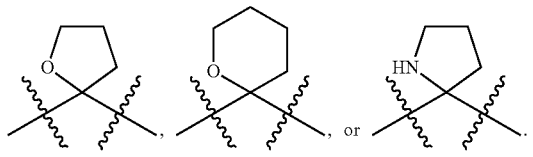 [SMILES: *C1(*)CCCO1 ; *C1(*)CCCCO1 ; *C1(*)CCCN1]
, or .

In some embodiments, L is —CH(OH)— or —C(OH)(CH$_3$)—. In some embodiments, L is —CH(NH$_2$)— or —C(CH$_3$)(NH$_2$)—. In some embodiments, L is —CH(OH)— or —CH(NH$_2$)—. In some embodiments, L is —C(CH$_3$)(OH)— or —C(CH$_3$)(NH$_2$)—. In some embodiments, L is

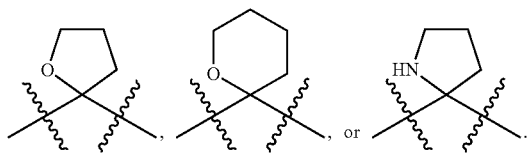 [SMILES: *C1(*)CCCO1 ; *C1(*)CCCCO1 ; *C1(*)CCCN1]
, or .

In some embodiments, L is —CH$_2$—. In some embodiments, L is —CH(OH)—. In some embodiments, L is —C(OH)(CH$_3$)—. In some embodiments, L is —CH(NH$_2$)—. In some embodiments, L is —C(CH$_3$)(NH$_2$)—. In some embodiments, L is —CH$_2$—CH$_2$—. In some embodiments, L is —S(O)—. In some embodiments, L is

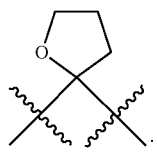
.

In some embodiments, L is

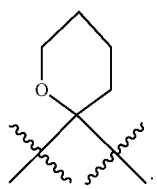
.

In some embodiments, L is

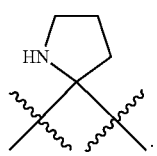
.

In some embodiments, L$_1$ is a C$_{1-3}$ alkylene chain wherein 1 or 2 saturated carbon atoms are optionally substituted by (R$^f$)(R$^{f'}$) and in which there are optionally one or two degrees of unsaturation, wherein R$^f$ and R$^{f'}$ have the values described herein. In some embodiments, L$_1$ is —C(R$^f$)(R$^{f'}$)—, wherein R$^f$ and R$^{f'}$ have the values described herein. In some embodiments, L$_1$ is —CH$_2$—. In some embodiments, L$_1$ is

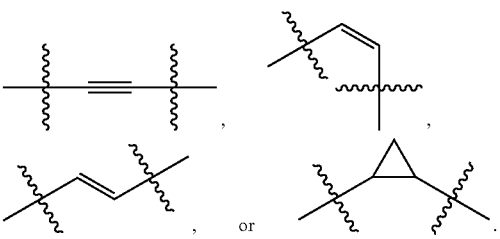
, or .

In some embodiments, each R$^f$ is independently hydrogen; hydroxyl; —N(R$^h$)(R$^{h'}$); C$_{1-4}$ aliphatic optionally substituted with hydroxyl, —OCH$_3$, or cyclopropyl; —O—C$_{1-4}$ aliphatic optionally substituted with hydroxyl, —OCH$_3$, or cyclopropyl; or, together with R$^{f'}$ and the carbon atom to which they are attached, form C═CH$_2$, a 3- to 6-membered carbocycle, or a 4- to 6-membered heterocycle comprising a heteroatom chosen from N (which may be protonated or C$_{1-4}$ alkylated), O, or S, the heteroatom optionally located immediately adjacent to the quaternary carbon of the heterocycle. In some embodiments, each R$^f$ is independently hydrogen, hydroxyl, N(R$^h$)(R$^{h'}$), —OCH$_3$, cyclopropyl, or C$_{1-4}$ aliphatic optionally substituted with hydroxyl or —OCH$_3$, wherein R$^h$ and R$^{h'}$ have the values described herein, or, together with the carbon atom to which they are attached, R$^f$ and R$^{f'}$ form a 4- to 6-membered heterocycle comprising a heteroatom chosen from N (which may be protonated or C$_{1-4}$ alkylated), O, or S, the heteroatom optionally located immediately adjacent to the quaternary carbon of the heterocycle. In some embodiments, each R$^f$ is independently hydrogen, hydroxyl, N(R$^h$)(R$^{h'}$), —OCH$_3$, cyclopropyl, or C$_{1-4}$ aliphatic optionally substituted with hydroxyl or —OCH$_3$, or, together with the carbon atom to which they are attached, R$^f$ and R$^{f'}$ form

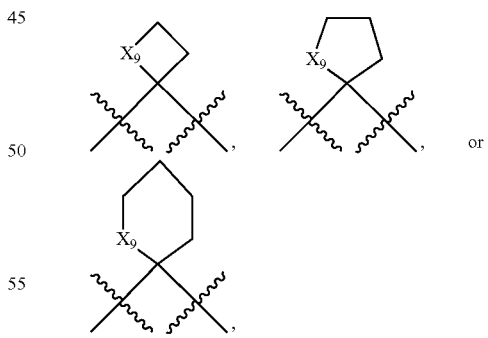
, , or , wherein X$_9$ has the values described herein. In some embodiments, each R$^f$ is independently hydrogen, hydroxyl, N(R$^h$)(R$^{h'}$), C$_{1-4}$ alkoxy, cyclopropyl, or C$_{1-4}$ alkyl optionally substituted with hydroxyl or —OCH$_3$. In some embodiments, each R$^f$ is independently hydrogen, C$_{1-4}$ alkyl, or cyclopropyl. In some embodiments, each R$^f$ is independently hydrogen, methyl, ethyl, or isopropyl. In some embodiments, each R$^f$ is independently hydrogen or methyl. In some embodiments, each R$^f$ is hydrogen.

In some embodiments, each $R^{f'}$ is independently hydrogen; $C_{1-4}$ aliphatic optionally substituted with hydroxyl, —OCH$_3$, or cyclopropyl; —O—$C_{1-4}$ aliphatic optionally substituted with hydroxyl, —OCH$_3$, or cyclopropyl; or, together with $R^f$ and the carbon atom to which they are attached, form C=CH$_2$, a 3- to 6-membered carbocycle, or a 4- to 6-membered heterocycle comprising a heteroatom chosen from N (which may be protonated or $C_{1-4}$ alkylated), O, or S, the heteroatom optionally located immediately adjacent to the quaternary carbon of the heterocycle; wherein if $R^f$ is hydroxyl, $R^{f'}$ is not —O—$C_{1-4}$ aliphatic optionally substituted with hydroxyl, —OCH$_3$, or cyclopropyl. In some embodiments, each $R^{f'}$ is independently hydrogen, cyclopropyl, or $C_{1-4}$ aliphatic optionally substituted with hydroxyl or —OCH$_3$, or, together with the carbon atom to which they are attached, $R^f$ and $R^{f'}$ form a 4- to 6-membered heterocycle comprising a heteroatom chosen from N (which may be protonated or $C_{1-4}$ alkylated), O, or S, the heteroatom optionally located immediately adjacent to the quaternary carbon of the heterocycle; or, together with the carbon atom to which they are attached, $R^f$ and $R^{f'}$ form

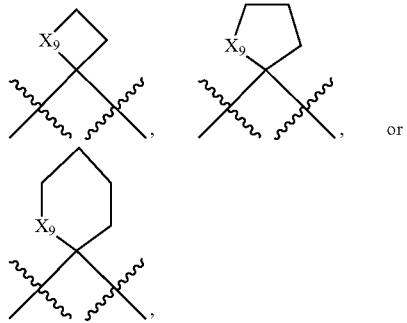

wherein $X_9$ has the values described herein. In some embodiments, each $R^{f'}$ is independently hydrogen, cyclopropyl, or $C_{1-4}$ alkyl optionally substituted with hydroxyl or —OCH$_3$. In some embodiments, each $R^{f'}$ is independently hydrogen, $C_{1-4}$ alkyl, or cyclopropyl. In some embodiments, each $R^{f'}$ is independently hydrogen, methyl, ethyl, or isopropyl. In some embodiments, each $R^{f'}$ is independently hydrogen or methyl. In some embodiments, each $R^{f'}$ is independently hydrogen or methyl. In some embodiments, each $R^{f'}$ is hydrogen.

In some embodiments, each $R^f$ is independently hydrogen, hydroxyl, N($R^h$)($R^{h'}$), —OCH$_3$, cyclopropyl, or $C_{1-4}$ aliphatic optionally substituted with hydroxyl or —OCH$_3$; and each $R^{f'}$ is independently hydrogen, cyclopropyl, or $C_{1-4}$ aliphatic optionally substituted with hydroxyl or —OCH$_3$; wherein at least one of $R^f$ and $R^{f'}$ comprises at least one heteroatom; or, together with the carbon atom to which they are attached, $R^f$ and $R^{f'}$ form a 4- to 6-membered heterocycle comprising a heteroatom chosen from N (which may be protonated or $C_{1-4}$ alkylated), O, or S, the heteroatom optionally located immediately adjacent to the quaternary carbon of the heterocycle. In some embodiments, together with the carbon atom to which they are attached, $R^f$ and $R^{f'}$ form

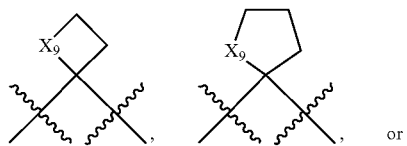

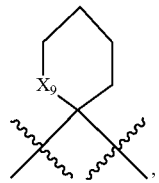

wherein $X_9$ has the values described herein. In some embodiments, together with the carbon atom to which they are attached, $R^f$ and $R^{f'}$ form

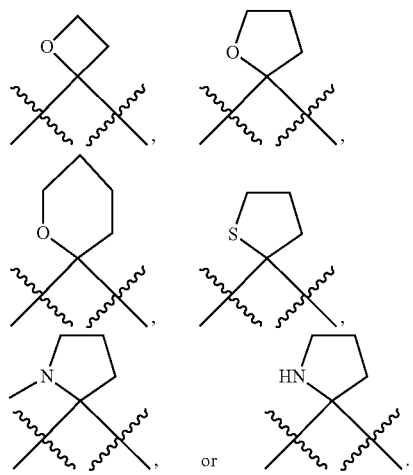

In some embodiments, together with the carbon atom to which they are attached, $R^f$ and $R^{f'}$ form

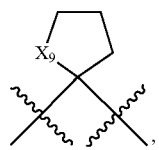

wherein $X_9$ has the values described herein. In some embodiments, each $R^f$ is independently hydrogen, hydroxyl, N($R^h$)($R^{h'}$), $C_{1-4}$ alkoxy, cyclopropyl, or $C_{1-4}$ alkyl optionally substituted with hydroxyl or —OCH$_3$; and each $R^{f'}$ is independently hydrogen, cyclopropyl, or $C_{1-4}$ alkyl optionally substituted with hydroxyl or —OCH$_3$. In some embodiments, each $R^f$ and $R^{f'}$ is independently hydrogen, $C_{1-4}$ alkyl, or cyclopropyl; or are taken together to form =CH$_2$. In some embodiments, each $R^f$ and $R^{f'}$ is independently hydrogen, methyl, ethyl, or isopropyl. In some embodiments, each $R^f$ and $R^{f'}$ is independently hydrogen or methyl.

In some embodiments, $R^h$ and $R^{h'}$ are each independently hydrogen or $C_{1-4}$ alkyl. In some embodiments, $R^h$ and $R^{h'}$ are each independently hydrogen or methyl. In some embodiments, $R^h$ and $R^{h'}$ are each hydrogen. In some embodiments, $R^h$ is hydrogen or $C_{1-4}$ alkyl. In some embodiments, $R^h$ is hydrogen or methyl. In some embodiments, $R^h$ is hydrogen. In some embodiments, $R^h$ is hydrogen or $C_{1-4}$ alkyl and $R^{h'}$ is hydrogen. In some embodiments, $R^h$ is hydrogen or methyl and $R^{h'}$ is hydrogen. In some embodiments, $R^h$ is methyl and $R^{h'}$ is methyl.

In some embodiments, $X_9$ is O, N($R^h$), or S, wherein $R^h$ has the values described herein. In some embodiments, $X_9$ is O, N(H), N(CH₃), or S. In some embodiments, X₉ is O. In some embodiments, X₉ is N(H). In some embodiments, X₉ is N(CH₃). In some embodiments, X₉ is S.

In some embodiments, V₁ is —S—, —O—, —S(O)—, —S(O)₂—, —C(O)— or —N(R$^g$)—, wherein R$^g$ has the values described herein. In some embodiments, V₁ is —C(O)— or —N(R$^g$)—, wherein R$^g$ has the values described herein. In some embodiments, V₁ is —S—, —S(O)—, or —S(O)₂—. In some embodiments, V₁ is —O—.

In some embodiments, R$^g$ is hydrogen or C$_{1-4}$ alkyl. In some embodiments, R$^g$ is hydrogen, methyl, ethyl, or isopropyl. In some embodiments, R$^g$ is hydrogen or methyl. In some embodiments, R$^g$ is hydrogen. In some embodiments, R$^g$ is methyl.

In some embodiments, L₂ is a C$_{0-2}$ alkylene chain wherein one saturated carbon atom is optionally substituted by (R$^f$)(R$^{f'}$), wherein R$^f$ and R$^{f'}$ have the values described herein. In some embodiments, L₂ is —C(R$^f$)(R$^{f'}$)—. In some embodiments, L₂ is —CH₂—. In some embodiments, L₂ is —CH₂—CH₂—. In some embodiments, L₂ is absent.

In some embodiments, R$^e$ is either (i) hydrogen, hydroxyl, halogen, —CF₃, or an optionally substituted C$_{1-4}$ aliphatic, with the proviso that R$^e$ is not hydrogen if R$^f$ and R$^{f'}$ are present and form a ring; OR (ii) R$^e$ is a ring chosen from optionally substituted 6-membered aryl, optionally substituted 5- to 6-membered heteroaryl, optionally substituted 3- to 7-membered cycloaliphatic, or optionally substituted 4- to 7-membered heterocyclyl, which is optionally fused to a second optionally substituted 6-membered aryl, optionally substituted 5- to 6-membered heteroaryl, optionally substituted 3- to 7-membered cycloaliphatic, or optionally substituted 4- to 7-membered heterocyclyl. In some embodiments, R$^e$ is hydrogen, hydroxyl, halogen, —CF₃, or C$_{1-4}$ alkyl optionally substituted with one or more hydroxyl, halogen, or C$_{1-4}$ alkyl, with the proviso that R$^e$ is not hydrogen if R$^f$ and R$^{f'}$ are present and form a ring. In some embodiments, R$^e$ is hydroxyl, halogen, —CF₃, or C$_{1-4}$ alkyl optionally substituted with one or more hydroxyl, halogen, or C$_{1-4}$ alkyl.

In some embodiments, R$^e$ is an optionally substituted ring chosen from 3- to 7-membered cycloaliphatic or 4- to 7-membered heterocyclyl, which is optionally fused to a second 6-membered aryl, 5- to 6-membered heteroaryl, 3- to 7-membered cycloaliphatic, or 4- to 7-membered heterocyclyl, which is optionally substituted. In some embodiments, R$^e$ is a ring chosen from 3- to 7-membered cycloaliphatic or 4- to 7-membered heterocyclyl, which is optionally fused to a second 6-membered aryl, 5- to 6-membered heteroaryl, 3- to 7-membered cycloaliphatic, or 4- to 7-membered heterocyclyl, wherein the R$^e$ ring or rings are optionally substituted by n occurrences of R², wherein n and R² have the values described herein.

In some embodiments, R$^e$ is a ring chosen from 3- to 7-membered cycloaliphatic or 4- to 7-membered heterocyclyl, which is optionally fused to a second 6-membered aryl, 5- to 6-membered heteroaryl, 3- to 7-membered cycloaliphatic, or 4- to 7-membered heterocyclyl, wherein the R$^e$ ring or rings are optionally substituted by 1-3 independent occurrences of halogen, hydroxyl, cyano, C$_{1-4}$ aliphatic, C$_{1-4}$ fluoroaliphatic, C$_{1-4}$ alkoxy, C$_{1-4}$ fluoroalkoxy, S—C$_{1-4}$ aliphatic, S—C$_{1-4}$ fluoroaliphatic, —N(R$^{z7}$)₂, —C(O)R$^{z8}$, —S(O)R$^{z8}$, —S(O)₂R$^{z8}$, —C(O)₂R$^{z7}$, —C(O)N(R$^{z7}$)₂, —S(O)₂N(R$^{z7}$)₂, —OC(O)N(R$^{z7}$)₂, —N(R$^{z7}$)C(O)R$^{z8}$, —N(R$^{z7}$)SO₂R$^{z8}$, —N(R$^{z7}$)C(O)OR$^{z8}$, T₂-R$^{z9}$, a 5- to 6-membered heteroaryl, a 6-membered aryl, a 3- to 6-membered cycloaliphatic, or a 4- to 6-membered heterocyclyl; and which is optionally substituted at one saturated carbon with oxo, a spirocyclic 3- to 6-membered carbocycle, or a 4- to 6-membered heterocycle, wherein each R$^{z7}$ independently has the values described herein and R$^{z8}$, T₂, and R$^{z9}$ have the values described herein. In some embodiments, R$^e$ is R$^R$ which is optionally substituted by 1-3 independent occurrences of halogen, hydroxyl, cyano, C$_{1-4}$ aliphatic, C$_{1-4}$ fluoroaliphatic, C$_{1-4}$ alkoxy, C$_{1-4}$ fluoroalkoxy, S—C$_{1-4}$ aliphatic, S—C$_{1-4}$ fluoroaliphatic, —N(R$^{z7}$)₂, —C(O)R$^{z8}$, —S(O)R$^{z8}$, —S(O)₂R$^{z8}$, —C(O)₂R$^{z7}$, —C(O)N(R$^{z7}$)₂, —S(O)₂N(R$^{z7}$)₂, —OC(O)N(R$^{z7}$)₂, —N(R$^{z7}$)C(O)R$^{z8}$, —N(R$^{z7}$)SO₂R$^{z8}$, —N(R$^{z7}$)C(O)OR$^{z8}$, T₂-R$^{z9}$, a 5- to 6-membered heteroaryl, a 6-membered aryl, a 3- to 6-membered cycloaliphatic, or a 4- to 6-membered heterocyclyl; and which is optionally substituted at one saturated carbon with oxo, a spirocyclic 3- to 6-membered carbocycle, or a 4- to 6-membered heterocycle, wherein each R$^{z7}$ independently has the values described herein and R$^R$, R$^{z8}$, T₂, and R$^{z9}$ have the values described herein.

In some embodiments, R$^e$ is a 5- to 7-membered cycloaliphatic ring or a 5- to 7-membered heterocyclyl having only one heteroatom, wherein the ring is optionally substituted. In some embodiments, R$^e$ is a 5- to 7-membered cycloaliphatic ring or a 5- to 7-membered heterocyclyl having only one heteroatom, wherein the ring is optionally substituted by n occurrences of R², wherein n and R² have the values described herein. In some embodiments, R$^e$ is a 5- to 7-membered cycloaliphatic ring or a 5- to 7-membered heterocyclyl having only one heteroatom, wherein the ring is optionally substituted by 1-3 independent occurrences of halogen, hydroxyl, cyano, C$_{1-4}$ aliphatic, C$_{1-4}$ fluoroaliphatic, C$_{1-4}$ alkoxy, C$_{1-4}$ fluoroalkoxy, S—C$_{1-4}$ aliphatic, S—C$_{1-4}$ fluoroaliphatic, —N(R$^{z7}$)₂, —C(O)R$^{z8}$, —S(O)R$^{z8}$, —S(O)₂R$^{z8}$, —C(O)₂R$^{z7}$, —C(O)N(R$^{z7}$)₂, —S(O)₂N(R$^{z7}$)₂, —OC(O)N(R$^{z7}$)₂, —N(R$^{z7}$)C(O)R$^{z8}$, —N(R$^{z7}$)SO₂R$^{z8}$, —N(R$^{z7}$)C(O)OR$^{z8}$, T₂-R$^{z9}$, a 5- to 6-membered heteroaryl, a 6-membered aryl, a 3- to 6-membered cycloaliphatic, or a 4- to 6-membered heterocyclyl; and which is optionally substituted at one saturated carbon with oxo, a spirocyclic 3- to 6-membered carbocycle, or a 4- to 6-membered heterocycle, wherein each R$^{z7}$ independently has the values described herein and R$^{z8}$, T₂, and R$^{z9}$ have the values described herein.

In some embodiments, R$^e$ is

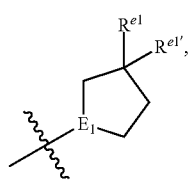

(b-i)

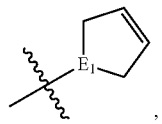

(b-ii)

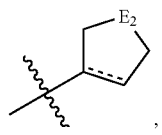

(b-iii)

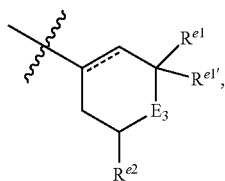
(b-iv)

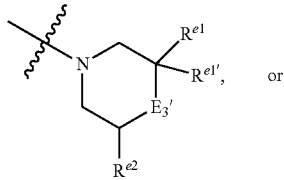
(b-v)

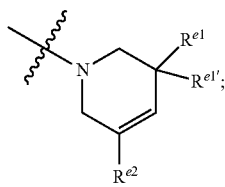
(b-vi)

wherein $E_1$, $E_2$, $E_3$, $E_3'$, $R^{e1}$, $R^{e1'}$, and $R^{e2}$ have the values described herein and dashes indicate single or double bonds. In some embodiments, $R^e$ is (b-i) wherein $E_1$, $R^{e1}$, and $R^{e1'}$ have the values described herein. In some embodiments, $R^e$ is (b-ii) wherein $E_1$ has the values described herein. In some embodiments, $R^e$ is (b-iii) wherein $E_2$ has the values described herein and dashes indicate single or double bonds. In some embodiments, $R^e$ is (b-iv) wherein $E_3$, $R^{e1}$, $R^{e1'}$, and $R^{e2}$ have the values described herein and dashes indicate single or double bonds. In some embodiments, $R^e$ is (b-v) wherein $E_3'$, $R^{e1}$, $R^{e1'}$, and $R^{e2}$ have the values described herein. In some embodiments, $R^e$ is (b-vi) wherein $R^{e1}$, $R^{e1'}$, and $R^{e2}$ have the values described herein. In some embodiments, $E_1$ is N or C(H). In some embodiments, $E_2$ is O, S, or $CH_2$. In some embodiments, $E_3$ is O, S, $N(R^{e3})$, or $C(H)(R^{e3})$, wherein $R^{e3}$ has the values described herein. In some embodiments, $E_3'$ is O, $N(R^{e3})$ or $C(H)(R^{e3})$, wherein $R^{e3}$ has the values described herein. In some embodiments, $R^{e1}$ and $R^{e1'}$ are each independently hydrogen or fluoro. In some embodiments, $R^{e2}$ is hydrogen or methyl. In some embodiments, $R^{e3}$ is hydrogen or methyl.

In some embodiments, $R^e$ is a 6-membered aryl or 5- to 6-membered heteroaryl, which is optionally fused to a second 6-membered aryl, 5- to 6-membered heteroaryl, 3- to 7-membered cycloaliphatic, or 4- to 7-membered heterocyclyl, wherein the $R^e$ ring or rings are optionally substituted. In some embodiments, $R^e$ is a 6-membered aryl or 5- to 6-membered heteroaryl, which is optionally fused to a second 6-membered aryl, 5- to 6-membered heteroaryl, 3- to 7-membered cycloaliphatic, or 4- to 7-membered heterocyclyl, wherein the $R^e$ ring or rings are optionally substituted with n occurrences of $R^2$, wherein n and $R^2$ have the values described herein. In some embodiments, $R^e$ is a 6-membered aryl or 5- to 6-membered heteroaryl, which is optionally fused to a second 6-membered aryl, 5- to 6-membered heteroaryl, 3- to 7-membered cycloaliphatic, or 4- to 7-membered heterocyclyl, wherein the $R^e$ ring or rings are optionally substituted with 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, $-N(R^{z7})_2$, $-C(O)_2R^{z7}$, $-C(O)N(R^{z7})_2$, $-S(O)_2N(R^{z7})_2$, $-CH_2-OR^{z7}$, $-CH_2NR^{z7}$ or a 3- to 6-membered cycloaliphatic or 4- to 6-membered heterocyclyl, wherein each $R^{z7}$ independently has the values described herein. In some embodiments, $R^e$ is a 6-membered aryl or 5- to 6-membered heteroaryl, which is optionally substituted with 1-3 independent occurrences of chloro, fluoro, bromo, iodo, methyl, ethyl, cyano, cyclopropyl, $CF_3$, $-OCH_3$, $-OCH_2CH_3$, or $-C\equiv CH$.

In some embodiments, $R^e$ is

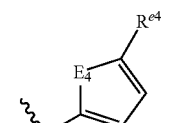
(b-vii)

or

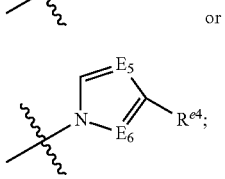
(b-viii)

wherein $E_4$, $E_5$, $E_6$, and $R^{e4}$ have the values described herein. In some embodiments, $R^e$ is (b-vii), wherein $E_4$ and $R^{e4}$ have the values described herein. In some embodiments, $R^e$ is (b-viii), wherein $E_5$, $E_6$, and $R^{e4}$ have the values described herein. In some embodiments, $R^e$ is

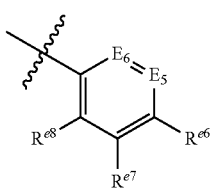
(b-ix)

wherein $E_5$, $E_6$, $R^{e6}$, $R^{e7}$, and $R^{e8}$ have the values described herein.

In some embodiments, $E_4$ is S, O, or $N(R^{n4})$, wherein $R^{n4}$ has the values described herein. In some embodiments, $E_4$ is S or O. In some embodiments, $E_4$ is S. In some embodiments, $E_4$ is O.

In some embodiments, $R^{e4}$ is hydrogen, methyl, chloro, fluoro, bromo, iodo, cyano, or $-CF_3$. In some embodiments, $R^{e4}$ is hydrogen, methyl, chloro, fluoro, cyano, or $-CF_3$. In some embodiments, $R^{e4}$ is hydrogen, methyl, chloro, or fluoro. In some embodiments, $R^{e4}$ is hydrogen or methyl. In some embodiments, $R^{e4}$ is hydrogen.

In some embodiments, $E_5$ is N or $C(R^{e5})$, wherein $R^{e5}$ has the values described herein. In some embodiments, $E_5$ is $C(R^{e5})$, wherein $R^{e5}$ has the values described herein. In some embodiments, $E_5$ is N or C(H). In some embodiments, $E_5$ is C(H). In some embodiments, $E_5$ is N.

In some embodiments, $R^{e5}$ is hydrogen, halogen, methyl, $-SCH_3$, $-OCH_3$, $-CF_3$, $-OCF_3$, $-OCF_2H$, or $-C\equiv CH$. In some embodiments, $R^{e5}$ is hydrogen, halogen, methyl, $-OCH_3$, $-CF_3$, or $-C\equiv CH$. In some embodiments, $R^{e5}$ is hydrogen or halogen. In some embodiments, $R^{e5}$ is hydrogen, fluoro, or chloro. In some embodiments, $R^{e5}$ is hydrogen, methyl, fluoro, or chloro. In some embodiments, $R^{e5}$ is hydrogen.

In some embodiments, $E_6$ is N or C(H). In some embodiments, $E_6$ is N. In some embodiments, $E_6$ is C(H).

In some embodiments, $R^{e6}$ is hydrogen, halogen, methyl, —$SCH_3$, —$OCH_3$, —$CF_3$, —$OCF_3$, —$OCF_2H$, or —C≡CH. In some embodiments, $R^{e6}$ is hydrogen, halogen, methyl, —$OCH_3$, —$CF_3$, or —C≡CH. In some embodiments, $R^{e6}$ is hydrogen or halogen. In some embodiments, $R^{e6}$ is hydrogen, fluoro, or chloro. In some embodiments, $R^{e6}$ is hydrogen, methyl, fluoro, or chloro. In some embodiments, $R^{e6}$ is hydrogen.

In some embodiments, $R^{e7}$ is hydrogen, halogen, methyl, —$SCH_3$, —$OCH_3$, —$CF_3$, —$OCF_3$, —$OCF_2H$, or —C≡CH. In some embodiments, $R^{e7}$ is hydrogen, halogen, methyl, —$OCH_3$, —$CF_3$, or —C≡CH. In some embodiments, $R^{e7}$ is hydrogen or halogen. In some embodiments, $R^{e7}$ is hydrogen, fluoro, or chloro. In some embodiments, $R^{e7}$ is hydrogen, methyl, fluoro, or chloro. In some embodiments, $R^{e7}$ is hydrogen.

In some embodiments, $R^{e8}$ is hydrogen, halogen, methyl, —$SCH_3$, —$OCH_3$, —$CF_3$, —$OCF_3$, —$OCF_2H$, or —C≡CH. In some embodiments, $R^{e8}$ is hydrogen, halogen, methyl, —$OCH_3$, —$CF_3$, or —C≡CH. In some embodiments, $R^{e8}$ is hydrogen or halogen. In some embodiments, $R^{e8}$ is hydrogen, fluoro, or chloro. In some embodiments, $R^{e8}$ is hydrogen, methyl, fluoro, or chloro. In some embodiments, $R^{e8}$ is hydrogen.

In some embodiments, each of $R^{e5}$, $R^{e6}$, $R^{e7}$, and $R^{e8}$ is independently hydrogen, halogen, methyl, —$OCH_3$, —$CF_3$, or —C≡CH; wherein at least one of $R^{e5}$, $R^{e6}$, $R^{e7}$, and $R^{e8}$ is hydrogen. In some embodiments, each of $R^{e5}$, $R^{e6}$, $R^{e7}$, and $R^{e8}$ is independently hydrogen, halogen, methyl, —$OCH_3$, —$CF_3$, or —C≡CH; wherein at least two of $R^{e5}$, $R^{e6}$, $R^{e7}$, and $R^{e8}$ are hydrogen.

In some embodiments, $R^{e6}$ is hydrogen, fluoro, or chloro; $R^{e7}$ is hydrogen, fluoro, or chloro; and $R^{e8}$ is hydrogen, halogen, methyl, —$OCH_3$, or cyano; wherein at least one of $R^{e6}$, $R^{e7}$, and $R^{e8}$ is hydrogen. In some embodiments, $R^{e6}$ is hydrogen, fluoro, or chloro; $R^{e7}$ is hydrogen, fluoro, or chloro; and $R^{e8}$ is hydrogen, halogen, methyl, —$OCH_3$, or cyano; wherein at least two of $R^{e6}$, $R^{e7}$, and $R^{e8}$ are hydrogen.

In some embodiments, $R^R$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydronaphthyridinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, dihydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiomorpholinyl, quinuclidinyl, phenanthridinyl, tetrahydronaphthyl, oxodihydropyridyl, indolinyl, benzodioxanyl, chromanyl, oxetanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, azabicyclooctanyl, oxabicyclooctanyl, bicyclononyl, bicyclooctanyl, or adamantyl. In some embodiments, $R^R$ is furanyl, thienyl, phenyl, naphthyl, pyridyl, benzothienyl, benzofuranyl, cyclohexyl, or cyclohexenyl.

In some embodiments, $Z_2$ is hydrogen. In some embodiments, $Z_2$ is chloro and $Z_1$ is not hydrogen, halogen, methyl, or cyano.

In some embodiments, $R^b$ is hydrogen or, together with the oxygen to which it is attached, forms a prodrug. In some embodiments, $R^b$ is hydrogen or —C(O)—$R^{bx}$, wherein $R^{bx}$ has the values described herein. In some embodiments, $R^b$ is hydrogen. In some embodiments, $R^b$ is —C(O)—$R^{bx}$, wherein $R^{bx}$ has the values described herein.

In some embodiments, $R^{bx}$ is $C_{1-4}$ alkyl, —CH($R^{by}$)—$NH_2$, pyrrolidinyl, or -$L_b$-$OPO_3H_2$, wherein $L_b$ and $R^{by}$ have the values described herein. In some embodiments, $R^{bx}$ is —CH($R^{by}$)—$NH_2$ wherein $R^{by}$ has the values described herein. In some embodiments, $R^{bx}$ is -$L_b$-$OPO_3H_2$, wherein $L_b$ has the values described herein. In some embodiments, $R^{bx}$ is $C_{1-4}$ alkyl.

In some embodiments, $R^{by}$ is $C_{1-4}$ alkyl optionally substituted with hydroxyl, phenyl, phenolyl, imidazolyl, carboxyl, amino, guanidino, —$SCH_3$, —C(O)$NH_2$, or indolyl. In some embodiments, $R^{by}$ is $C_{1-4}$ alkyl optionally substituted with hydroxyl, phenyl, carboxyl, amino, or —C(O)$NH_2$. In some embodiments, $R^{by}$ is $C_{1-4}$ alkyl. In some embodiments, $R^{by}$ is methyl, ethyl, isopropyl, propyl, butyl, or isobutyl. In some embodiments, $R^{by}$ is methyl, ethyl, isopropyl, or isobutyl. In some embodiments, $R^{by}$ is methyl. In some embodiments, $R^{by}$ is ethyl. In some embodiments, $R^{by}$ is isopropyl. In some embodiments, $R^{by}$ is isobutyl.

In some embodiments, $L_b$ is a bivalent linker chosen from $C_{1-4}$ alkylene or —$(CH_2)_{n1}$-phenylene-$(CH_2)_{n2}$— where n1 is 0 or 1 and n2 is 1 or 2. In some embodiments, $L_b$ is $C_{1-4}$ alkylene. In some embodiments, $L_b$ is $C_{1-4}$ methylene. In some embodiments, $L_b$ is $C_{1-4}$ ethylene. In some embodiments, $L_b$ is —$(CH_2)_{n1}$-phenylene-$(CH_2)_{n2}$— where n1 is 0 or 1 and n2 is 1 or 2. In some embodiments, $L_b$ is -phenylene-$(CH_2)$— where n2 is 1 or 2. In some embodiments, $L_b$ is —$CH_2$-phenylene-$(CH_2)_{n2}$— where n2 is 1 or 2. In some embodiments, $L_b$ is —$(CH_2)_{n1}$-phenylene-$CH_2$— where n1 is 0 or 1. In some embodiments, $L_b$ is —$(CH_2)_{n1}$-phenylene-$(CH_2)_{n2}$— where n1 is 0 or 1 and n2 is 2.

In some embodiments, at least one, at least two, at least three, at least four, at least five, at least six, or all of the following is/are true: Y is —O—; $R^a$ is hydroxyl; $R^{a'}$ is hydrogen; $R^c$ is hydrogen; $X_1$ is N; $R^d$ is hydrogen; or $X_3$ is C(H). In some embodiments, at least one, at least two, at least three, at least four, at least five, at least six, or all of the following is/are true: Y is —O—; $R^a$ is hydrogen; $R^{a'}$ is hydrogen; $R^c$ is hydrogen; $X_1$ is N; $R^d$ is hydrogen; or $X_3$ is C(H).

In some embodiments, n is 1-5. In some embodiments, n is 1-4. In some embodiments, n is 1-3. In some embodiments, n is 1-2. In some embodiments, n is 1.

In some embodiments, each occurrence of $R^2$ is independently —$R^{2a}$, -$T_3$-$R^{2d}$, -$T_3$-$R^{2a}$, or —$V_2$-$T_3$-$R^{2d}$, wherein $R^{2a}$, $T_3$, $R^{2d}$, $V_2$ and $T_3$ have the values described herein. In some embodiments, each occurrence of $R^2$ is independently —$R^{2a}$ or $T_3$-$R^{2a}$, wherein $R^{2a}$ and $T_3$ have the values described herein. In some embodiments, each occurrence of $R^2$ is independently —$R^{2a}$, wherein $R^{2a}$ has the values described herein. In some embodiments, each occurrence of $R^2$ is independently halogen, —$R^{2c}$, —N($R^{2b}$)$_2$, —$OR^{2b}$, —$SR^{2c}$, $C_{1-6}$ aliphatic or $C_{1-6}$ fluoroaliphatic, wherein $R^{2b}$ and $R^{2c}$ have the values described herein.

In some embodiments, each occurrence of $R^{2a}$ is independently halogen, —CN, —$NO_2$, —$R^{2c}$, —N($R^{2b}$)$_2$, —$OR^{2b}$, —$SR^{2c}$, —S(O)$R^{2c}$, —S(O)$_2R^{2c}$, —C(O)$R^{2b}$, —C(O)$OR^{2b}$, —C(O)N($R^{2b}$)$_2$, —S(O)$_2$N($R^{2b}$)$_2$, —OC(O)N($R^{2b}$)$_2$, —N($R^{2e}$)C(O)$R^{2c}$, —N($R^{2e}$)$SO_2R^{2c}$, —N($R^{2e}$)C(O)

$OR^{2b}$, $-N(R^{2e})C(O)N(R^{2b})_2$, $-N(R^{2e})SO_2N(R^{2b})_2$, or $-Si(R^{2c})_3$, or a $C_{1-6}$ aliphatic or $C_{1-6}$ haloaliphatic, wherein $R^{2b}$, $R^{2c}$, and $R^{2e}$ have the values described herein.

In some embodiments, each occurrence of $R^{2b}$ is independently hydrogen or a group selected from $C_{1-6}$ aliphatic, $C_{1-6}$ haloaliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur, or two occurrences of $R^{2b}$, taken together with a nitrogen atom to which they are bound, form a 4- to -7-membered heterocyclyl having 0-1 additional heteroatoms selected from nitrogen, oxygen, and sulfur.

In some embodiments, each occurrence of $R^{2c}$ is independently a group selected from $C_1$-$C_6$ aliphatic, $C_1$-$C_6$ haloaliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur.

In some embodiments, each occurrence of $R^{2d}$ is independently hydrogen or a group selected from 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur.

In some embodiments, each occurrence of $R^{2e}$ is independently hydrogen or a $C_{1-6}$ aliphatic group.

In some embodiments, each occurrence of $V_2$ is independently $-N(R^{2e})-$, $-O-$, $-S-$, $-S(O)-$, $-S(O)_2-$, $-C(O)-$, $-C(O)O-$, $-C(O)N(R^{2e})-$, $-S(O)_2N(R^{2e})-$, $-OC(O)N(R^{2e})-$, $-N(R^{2e})C(O)-$, $-N(R^{2e})SO_2-$, $-N(R^{2e})C(O)O-$, $-N(R^{2e})C(O)N(R^{2e})-$, $-N(R^{2e})SO_2N(R^{2e})-$, $-OC(O)-$, or $-C(O)N(R^{2e})-O-$, wherein $R^{2e}$ has the values described herein.

In some embodiments, each occurrence of $T_3$ is a $C_{1-6}$ alkylene chain wherein the alkylene chain optionally is interrupted by $-N(R^4)-$, $-O-$, $-S-$, $-S(O)-$, $-S(O)_2-$, $-C(O)-$, $-C(O)O-$, $-C(O)N(R^4)-$, $-S(O)_2N(R^4)-$, $-OC(O)N(R^4)-$, $-N(R^4)C(O)-$, $-N(R^4)SO_2-$, $-N(R^4)C(O)O-$, $-N(R^4)C(O)N(R^4)-$, $-N(R^4)S(O)_2N(R^4)-$, $-OC(O)-$, or $-C(O)N(R^4)-O-$ or wherein $T_3$ or a portion thereof optionally forms part of a 3- to 7-membered cycloaliphatic or 4- to 7-membered heterocyclyl, wherein $R^4$ is hydrogen or a $C_{1-4}$ aliphatic group.

In some embodiments, the chemical entity of formula (I) is represented by formula (X-a):

(X-a)

or a pharmaceutically acceptable salt thereof, wherein:
stereochemical configurations depicted at asterisked positions indicate absolute stereochemistry;
$R^a$ is hydrogen and $R^{a'}$ is hydrogen; $R^a$ is hydrogen and $R^{a'}$ is fluoro; $R^a$ is fluoro and $R^{a'}$ is fluoro; or $R^a$ is OH and $R^{a'}$ is hydrogen;
$Z_1$ is hydrogen, halogen, cyano, $R^{z3}$, $-S-R^{z3}$, $-S(O)-R^{z3}$, or $-S(O)_2-R^{z3}$;
$R^{z3}$ is a phenyl, 5- to 7-membered cycloaliphatic, 5- to 7-membered heterocyclyl, or $C_{1-4}$ aliphatic, any of which may be substituted with one or more independently selected $R^{z4}$;
$R^{z4}$ is hydroxyl, halogen, cyano, $C_{1-4}$ aliphatic, $C_{1-4}$ fluoroaliphatic, $C_{1-4}$ alkoxy, $C_{1-4}$ fluoroalkoxy, $-N(R^{z5})_2$, $-C(O)R^{z6}$, $-C(O)_2R^{z5}$, 5- or 6-membered cycloaliphatic or heterocyclyl, or a phenyl optionally substituted with one or more independently selected halogens;
each $R^{z5}$ is independently hydrogen or $C_{1-4}$ alkyl;
$R^{z6}$ is $C_{1-4}$ alkyl;
$X_4$ is O or $N(R^{n4})$;
$R^{n4}$ is hydrogen or $C_{1-4}$ alkyl;
$X_6$ is N or $C(R^{x6})$;
each of $R^{x6}$, $R^{x6'}$, $R^j$ and $R^m$ is independently hydrogen, halogen, hydroxyl, cyano, $C_{1-4}$ aliphatic, $C_{1-4}$ fluoroaliphatic, $C_{1-4}$ alkoxy, $C_{1-4}$ fluoroalkoxy, $-N(R^{z7})_2$, $-C(O)_2R^{z7}$, $-C(O)N(R^{z7})_2$, $-S(O)_2N(R^{z7})_2$, $-CH_2-OR^{z7}$, $-CH_2NR^{z7}$, a 3- to 6-membered cycloaliphatic, or a 4- to 6-membered heterocyclyl, wherein at least one of $R^{x6}$, $R^{x6'}$, $R^j$ and $R^m$ is hydrogen; and
each $R^{z7}$ is independently hydrogen or $C_{1-4}$ alkyl.

In some such embodiments described directly above:
$Z_1$ is hydrogen, halogen, cyano, or $C_{1-4}$ aliphatic optionally substituted with one or more hydroxyl, $C_{1-4}$ alkoxy, $-N(R^{z5})_2$, or phenyl optionally substituted with one more independently selected halogens;
$X_4$ is O or N(H);
$X_6$ is N or C(H);
$R^{x6'}$ is hydrogen;
$R^m$ is hydrogen, fluoro or chloro; and
$R^j$ is methyl, ethyl, isopropyl, hydrogen, fluoro, chloro, bromo, cyclopropyl, $-C\equiv CH$ or $-CF_3$.

In some embodiments, the chemical entity of formula (I) is:
[(1R,2S,4R)-4-{[5-({4-[7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate;
[(1R,2S,4R)-4-{[5-({5-chloro-4-[7-chloro-1,2,3,4-tetrahydroisoquinolin-1-yl]-2-thienyl}carbonyl)pyrimidin-4-yl]amino}-2-hydroxycyclopentyl]methyl sulfamate;
[(1R,2S,4R)-4-{[5-({4-[7-chloro-1,2,3,4-tetrahydroisoquinolin-1-yl]-2-thienyl}carbonyl)pyrimidin-4-yl]amino}-2-hydroxycyclopentyl]methyl sulfamate;
[(1R,2R,3S,4R)-4-{[5-({5-chloro-4-[7-chloro-1,2,3,4-tetrahydroisoquinolin-1-yl]-2-thienyl}carbonyl)pyrimidin-4-yl]amino}-2,3-dihydroxycyclopentyl]methyl sulfamate;
[(1R,2S,4R)-4-{[5-({4-[7-chloro-3,4-dihydro-1H-isochromen-1-yl]-5-methyl-2-thienyl}carbonyl)pyrimidin-4-yl]amino}-2-hydroxycyclopentyl]methyl sulfamate;
[(1R,2S,4R)-4-{[5-({4-[3,4-dihydro-1H-isochromen-1-yl]-5-methyl-2-thienyl}carbonyl)pyrimidin-4-yl]amino}-2-hydroxycyclopentyl]methyl sulfamate;
[(1R,2S,4R)-4-{[5-({5-chloro-4-[7-chloro-3,4-dihydro-1H-isochromen-1-yl]-2-thienyl}carbonyl)pyrimidin-4-yl]amino}-2-hydroxycyclopentyl]methyl sulfamate;

[(1R,2S,4R)-4-{[5-({4-[7-chloro-3,4-dihydro-1H-isochromen-1-yl]-2-thienyl}carbonyl)pyrimidin-4-yl]amino}-2-hydroxycyclopentyl]methyl sulfamate;

or a pharmaceutically acceptable salt thereof.

In some embodiments, the chemical entity of formula (I) is:

[(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate;

[(1R,2S,4R)-4-{[5-({5-chloro-4-[7-chloro-1,2,3,4-tetrahydroisoquinolin-1-yl]-2-thienyl}carbonyl)pyrimidin-4-yl]amino}-2-hydroxycyclopentyl]methyl sulfamate;

[(1R,2S,4R)-4-{[5-({4-[7-chloro-1,2,3,4-tetrahydroisoquinolin-1-yl]-2-thienyl}carbonyl)pyrimidin-4-yl]amino}-2-hydroxycyclopentyl]methyl sulfamate;

[(1R,2R,3S,4R)-4-{[5-({5-chloro-4-[7-chloro-1,2,3,4-tetrahydroisoquinolin-1-yl]-2-thienyl}carbonyl)pyrimidin-4-yl]amino}-2,3-dihydroxycyclopentyl]methyl sulfamate;

[(1R,2S,4R)-4-{[5-({4-[(1R)-7-chloro-3,4-dihydro-1H-isochromen-1-yl]-5-methyl-2-thienyl}carbonyl)pyrimidin-4-yl]amino}-2-hydroxycyclopentyl]methyl sulfamate;

[(1R,2S,4R)-4-{[5-({4-[(1R)-3,4-dihydro-1H-isochromen-1-yl]-5-methyl-2-thienyl}carbonyl)pyrimidin-4-yl]amino}-2-hydroxycyclopentyl]methyl sulfamate;

[(1R,2S,4R)-4-{[5-({5-chloro-4-[7-chloro-3,4-dihydro-1H-isochromen-1-yl]-2-thienyl}carbonyl)pyrimidin-4-yl]amino}-2-hydroxycyclopentyl]methyl sulfamate;

[(1R,2S,4R)-4-{[5-({4-[7-chloro-3,4-dihydro-1H-isochromen-1-yl]-2-thienyl}carbonyl)pyrimidin-4-yl]amino}-2-hydroxycyclopentyl]methyl sulfamate;

or a pharmaceutically acceptable salt thereof.

In some embodiments, a chemical entity is provided which is

I-16a [(1R,2S,4R)-4-{[5-({4-[(S)-(3-bromophenyl)(hydroxy)methyl]-5-chloro-2-thienyl}carbonyl)pyrimidin-4-yl]amino}-2-hydroxycyclopentyl]methyl sulfamate or [(1R,2S,4R)-4-{[5-({4-[(R)-(3-bromophenyl)(hydroxy)methyl]-5-chloro-2-thienyl}carbonyl)pyrimidin-4-yl]amino}-2-hydroxycyclopentyl]methyl sulfamate;

I-18b [(1R,2S,4R)-4-{[5-({4-[(R)-amino(6-bromopyridin-2-yl)methyl]-5-chloro-2-thienyl}carbonyl)pyrimidin-4-yl]amino}-2-hydroxycyclopentyl]methyl sulfamate or [(1R,2S,4R)-4-{[5-({4-[(S)-amino(6-bromopyridin-2-yl)methyl]-5-chloro-2-thienyl}carbonyl)pyrimidin-4-yl]amino}-2-hydroxycyclopentyl]methyl sulfamate;

I-22b [(1R,2S,4R)-4-{[5-({4-[(R)-amino(3-bromophenyl)methyl]-5-chloro-2-thienyl}carbonyl)pyrimidin-4-yl]amino}-2-hydroxycyclopentyl]methyl sulfamate or [(1R,2S,4R)-4-{[5-({4-[(S)-amino(3-bromophenyl)methyl]-5-chloro-2-thienyl}carbonyl)pyrimidin-4-yl]amino}-2-hydroxycyclopentyl]methyl sulfamate;

I-248a [(1R,2S,4R)-4-{[5-({4-[(1S)-7-bromo-1,2,3,4-tetrahydroisoquinolin-1-yl]-5-methyl-2-thienyl}carbonyl)pyrimidin-4-yl]amino}-2-hydroxycyclopentyl]methyl sulfamate or [(1R,2S,4R)-4-{[5-({4-[(1R)-7-bromo-1,2,3,4-tetrahydroisoquinolin-1-yl]-5-methyl-2-thienyl}carbonyl)pyrimidin-4-yl]amino}-2-hydroxycyclopentyl]methyl sulfamate;

I-24a [(1R,2R,3S,4R)-4-{[5-({4-[(R)-amino(3-bromophenyl)methyl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(S)-amino(3-bromophenyl)methyl]-5-chloro-2-thienyl}carbonyl)pyrimidin-4-yl]amino}-2,3-dihydroxycyclopentyl]methyl sulfamate;

I-251a [(1R,2S,4R)-4-{[5-({4-[(1R)-7-bromo-1,2,3,4-tetrahydroisoquinolin-1-yl]-5-chloro-2-thienyl}carbonyl)pyrimidin-4-yl]amino}-2-hydroxycyclopentyl]methyl sulfamate or [(1R,2S,4R)-4-{[5-({4-[(1S)-7-bromo-1,2,3,4-tetrahydroisoquinolin-1-yl]-5-chloro-2-thienyl}carbonyl)pyrimidin-4-yl]amino}-2-hydroxycyclopentyl]methyl sulfamate;

I-252b [(1R,2S,4R)-4-{[5-({4-[(1R)-7-ethynyl-3,4-dihydro-1H-isochromen-1-yl]-5-methyl-2-thienyl}carbonyl)pyrimidin-4-yl]amino}-2-hydroxycyclopentyl]methyl sulfamate or [(1R,2S,4R)-4-{[5-({4-[(1S)-7-ethynyl-3,4-dihydro-1H-isochromen-1-yl]-5-methyl-2-thienyl}carbonyl)pyrimidin-4-yl]amino}-2-hydroxycyclopentyl]methyl sulfamate;

I-253a [(1R,2S,4R)-4-{[5-({5-chloro-4-[(8S)-2-chloro-5,6,7,8-tetrahydro-1,7-naphthyridin-8-yl]-2-thienyl}carbonyl)pyrimidin-4-yl]amino}-2-hydroxycyclopentyl]methyl sulfamate or [(1R,2S,4R)-4-{[5-({5-chloro-4-[(8R)-2-chloro-5,6,7,8-tetrahydro-1,7-naphthyridin-8-yl]-2-thienyl}carbonyl)pyrimidin-4-yl]amino}-2-hydroxycyclopentyl]methyl sulfamate;

I-254b [(1R,2S,4R)-4-{[5-({4-[(1R)-3,4-dihydro-1H-isochromen-1-yl]-2-thienyl}carbonyl)pyrimidin-4-yl]amino}-2-hydroxycyclopentyl]methyl sulfamate or [(1R,2S,4R)-4-{[5-({4-[(1S)-3,4-dihydro-1H-isochromen-1-yl]-2-thienyl}carbonyl)pyrimidin-4-yl]amino}-2-hydroxycyclopentyl]methyl sulfamate;

I-255b [(1R,2S,4R)-4-{[5-({5-chloro-4-[(1R)-7-chloro-1,2,3,4-tetrahydroisoquinolin-1-yl]-2-thienyl}carbonyl)pyrimidin-4-yl]amino}-2-hydroxycyclopentyl]methyl sulfamate or [(1R,2S,4R)-4-{[5-({5-chloro-4-[(1S)-7-chloro-1,2,3,4-tetrahydroisoquinolin-1-yl]-2-thienyl}carbonyl)pyrimidin-4-yl]amino}-2-hydroxycyclopentyl]methyl sulfamate;

I-256b [(1R,2S,4R)-4-{[5-({4-[(1R)-3,4-Dihydro-1H-isochromen-1-yl]-5-methyl-2-thienyl}carbonyl)pyrimidin-4-yl]amino}-2-hydroxycyclopentyl]methyl sulfamate;

I-257b [(1R,2S,4R)-4-{[5-({4-[(1R)-7-Chloro-3,4-dihydro-1H-isochromen-1-yl]-5-methyl-2-thienyl}carbonyl)pyrimidin-4-yl]amino}-2-hydroxycyclopentyl]methyl sulfamate;

I-258a [(1R,2S,4R)-2-hydroxy-4-{[5-({5-methyl-4-[(1R)-7-(trifluoromethyl)-3,4-dihydro-1H-isochromen-1-yl]-2-thienyl}carbonyl)pyrimidin-4-yl]amino}cyclopentyl]methyl sulfamate or [(1R,2S,4R)-2-hydroxy-4-{[5-({5-methyl-4-[(1S)-7-(trifluoromethyl)-3,4-dihydro-1H-isochromen-1-yl]-2-thienyl}carbonyl)pyrimidin-4-yl]amino}cyclopentyl]methyl sulfamate;

I-259a [(1R,2R,3S,4R)-4-{[5-({4-[(1R)-7-bromo-1,2,3,4-tetrahydroisoquinolin-1-yl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(1S)-7-bromo-1,2,3,4-tetrahydroisoquinolin-1-yl]-5-chloro-2-thienyl}carbonyl)pyrimidin-4-yl]amino}-2,3-dihydroxycyclopentyl]methyl sulfamate;

I-261b [(1R,2S,4R)-4-{[5-({4-[(1R)-7-chloro-3,4-dihydro-1H-isochromen-1-yl]-2-thienyl}carbonyl)pyrimidin-4-yl]amino}-2-hydroxycyclopentyl]methyl sulfamate or [(1R,2S,4R)-4-{[5-({4-[(1S)-7-chloro-3,4-dihydro-1H-isochromen-1-yl]-2-thienyl}carbonyl)pyrimidin-4-yl]amino}-2-hydroxycyclopentyl]methyl sulfamate;

I-263a [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate;

I-264b [(1R,2R,3R,4R)-4-{[5-({4-[(1S)-7-chloro-3,4-dihydro-1H-isochromen-1-yl]-5-methyl-2-thienyl}carbonyl)pyrimidin-4-yl]amino}-3-fluoro-2-hydroxycyclopentyl]methyl sulfamate or [(1R,2R,3R,4R)-

4-{[5-({4-[(1R)-7-chloro-3,4-dihydro-1H-isochromen-1-yl]-5-methyl-2-thienyl}carbonyl)pyrimidin-4-yl]amino}-3-fluoro-2-hydroxycyclopentyl]methyl sulfamate;

I-266b [(1R,2S,4R)-4-{[5-({5-chloro-4-[(8S)-5,8-dihydro-6H-pyrano[3,4-b]pyridin-8-yl]-2-thienyl}carbonyl)pyrimidin-4-yl]amino}-2-hydroxycyclopentyl]methyl sulfamate or [(1R,2S,4R)-4-{[5-({5-chloro-4-[(8R)-5,8-dihydro-6H-pyrano[3,4-b]pyridin-8-yl]-2-thienyl}carbonyl)pyrimidin-4-yl]amino}-2-hydroxycyclopentyl]methyl sulfamate;

I-268b [(1R,2S,4R)-4-{[5-({4-[(1R)-7-bromo-3,4-dihydro-1H-isochromen-1-yl]-2-thienyl}carbonyl)pyrimidin-4-yl]amino}-2-hydroxycyclopentyl]methyl sulfamate or [(1R,2S,4R)-4-{[5-({4-[(1S)-7-bromo-3,4-dihydro-1H-isochromen-1-yl]-2-thienyl}carbonyl)pyrimidin-4-yl]amino}-2-hydroxycyclopentyl]methyl sulfamate;

I-269a [(1R,2S,4R)-4-{[5-({4-[(7S)-4,7-dihydro-5H-thieno[2,3-c]pyran-7-yl]-5-methyl-2-thienyl}carbonyl)pyrimidin-4-yl]amino}-2-hydroxycyclopentyl]methyl sulfamate or [(1R,2S,4R)-4-{[5-({4-[(7R)-4,7-dihydro-5H-thieno[2,3-c]pyran-7-yl]-5-methyl-2-thienyl}carbonyl)pyrimidin-4-yl]amino}-2-hydroxycyclopentyl]methyl sulfamate;

I-270b {(1R,2S,4R)-4-[(5-{4-[(1R)-7-chloro-3,4-dihydro-1H-isochromen-1-yl]-5-methyl-2-furoyl}pyrimidin-4-yl)amino]-2-hydroxycyclopentyl}methyl sulfamate or {(1R,2S,4R)-4-[(5-{4-[(1S)-7-chloro-3,4-dihydro-1H-isochromen-1-yl]-5-methyl-2-furoyl}pyrimidin-4-yl)amino]-2-hydroxycyclopentyl}methyl sulfamate;

I-271a [(1R,2R,3R,4R)-4-{[5-({4-[(1R)-3,4-dihydro-1H-isochromen-1-yl]-5-methyl-2-thienyl}carbonyl)pyrimidin-4-yl]amino}-3-fluoro-2-hydroxycyclopentyl]methyl sulfamate or [(1R,2R,3R,4R)-4-{[5-({4-[(1S)-3,4-dihydro-1H-isochromen-1-yl]-5-methyl-2-thienyl}carbonyl)pyrimidin-4-yl]amino}-3-fluoro-2-hydroxycyclopentyl]methyl sulfamate;

I-277a [(1R,2S,4R)-4-{[5-({4-[(1R)-7-cyclopropyl-3,4-dihydro-1H-isochromen-1-yl]-5-methyl-2-thienyl}carbonyl)pyrimidin-4-yl]amino}-2-hydroxycyclopentyl]methyl sulfamate or [(1R,2S,4R)-4-{[5-({4-[(1S)-7-cyclopropyl-3,4-dihydro-1H-isochromen-1-yl]-5-methyl-2-thienyl}carbonyl)pyrimidin-4-yl]amino}-2-hydroxycyclopentyl]methyl sulfamate;

I-282b [(1R,2S,4R)-4-{[5-({5-chloro-4-[(1R)-7-chloro-3,4-dihydro-1H-isochromen-1-yl]-2-thienyl}carbonyl)pyrimidin-4-yl]amino}-2-hydroxycyclopentyl]methyl sulfamate or [(1R,2S,4R)-4-{[5-({5-chloro-4-[(1S)-7-chloro-3,4-dihydro-1H-isochromen-1-yl]-2-thienyl}carbonyl)pyrimidin-4-yl]amino}-2-hydroxycyclopentyl]methyl sulfamate;

I-285a [(1R,2S,4R)-4-{[5-({4-[(8S)-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate or [(1R,2S,4R)-4-{[5-({4-[(8R)-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate;

I-6a [(1R,2S,4R)-4-{[5-({4-[(R)-amino(3-chlorophenyl)methyl]-5-methyl-2-thienyl}carbonyl)pyrimidin-4-yl]amino}-2-hydroxycyclopentyl]methyl sulfamate or [(1R,2S,4R)-4-{[5-({4-[(S)-amino(3-chlorophenyl)methyl]-5-methyl-2-thienyl}carbonyl)pyrimidin-4-yl]amino}-2-hydroxycyclopentyl]methyl sulfamate;

I-9a [(1R,2S,4R)-4-{[5-({5-chloro-4-[(R)-(3-chlorophenyl)(hydroxy)methyl]-2-thienyl}carbonyl)pyrimidin-4-yl]amino}-2-hydroxycyclopentyl]methyl sulfamate or [(1R,2S,4R)-4-{[5-({5-chloro-4-[(S)-(3-chlorophenyl)(hydroxy)methyl]-2-thienyl}carbonyl)pyrimidin-4-yl]amino}-2-hydroxycyclopentyl]methyl sulfamate;

or a pharmaceutically acceptable salt thereof.

In some embodiments, the chemical entity of formula (I) is represented by formula (X-b):

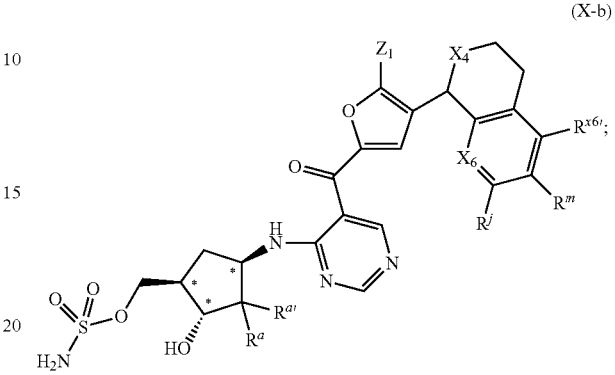

(X-b)

or a pharmaceutically acceptable salt thereof,
wherein:
stereochemical configurations depicted at asterisked positions indicate absolute stereochemistry;
$R^a$ is hydrogen and $R^{a'}$ is hydrogen; $R^a$ is hydrogen and $R^{a'}$ is fluoro; $R^a$ is fluoro and $R^{a'}$ is fluoro; or $R^a$ is OH and $R^{a'}$ is hydrogen;
$Z_1$ is hydrogen, halogen, cyano, $R^{z3}$, —S—$R^{z3}$, —S(O)—$R^{z3}$, or —S(O)$_2$—$R^{z3}$;
$R^{z3}$ is a phenyl, 5- to 7-membered cycloaliphatic, 5- to 7-membered heterocyclyl, or $C_{1-4}$ aliphatic, any of which may be substituted with one or more independently selected $R^{z4}$;
$R^{z4}$ is hydroxyl, halogen, cyano, $C_{1-4}$ aliphatic, $C_{1-4}$ fluoroaliphatic, $C_{1-4}$ alkoxy, $C_{1-4}$ fluoroalkoxy, —N($R^{z5}$)$_2$, —C(O)$R^{z6}$, —C(O)$_2R^{z5}$, 5- or 6-membered cycloaliphatic or heterocyclyl, or a phenyl optionally substituted with one or more independently selected halogens;
each $R^{z5}$ is independently hydrogen or $C_{1-4}$ alkyl;
$R^{z6}$ is $C_{1-4}$ alkyl;
$X_4$ is O or N($R^{n4}$);
$R^{n4}$ is hydrogen or $C_{1-4}$ alkyl;
$X_6$ is N or C($R^{x6}$);
each of $R^{x6}$, $R^{x6'}$, $R^j$ and $R^m$ is independently hydrogen, halogen, hydroxyl, cyano, $C_{1-4}$ aliphatic, $C_{1-4}$ fluoroaliphatic, $C_{1-4}$ alkoxy, $C_{1-4}$ fluoroalkoxy, —N($R^{z7}$)$_2$, —C(O)$_2R^{z7}$, —C(O)N($R^{z7}$)$_2$, —S(O)$_2$N($R^{z7}$)$_2$, —CH$_2$—O$R^{z7}$, —CH$_2$N($R^{z7}$)$_2$, a 3- to 6-membered cycloaliphatic, or a 4- to 6-membered heterocyclyl, wherein at least one of $R^{x6}$, $R^{x6'}$, $R^j$ and $R^m$ is hydrogen; and
each $R^{z7}$ is independently hydrogen or $C_{1-4}$ alkyl.

In some such embodiments described directly above:
$Z_1$ is hydrogen, halogen, cyano, or $C_{1-4}$ aliphatic optionally substituted with one or more hydroxyl, $C_{1-4}$ alkoxy, —N($R^{z5}$)$_2$, or phenyl optionally substituted with one more independently selected halogens;
$X_4$ is O or N(H);
$X_6$ is N or C(H);
$R^{x6'}$ is hydrogen;
$R^m$ is hydrogen, fluoro or chloro; and
$R^j$ is methyl, ethyl, isopropyl, hydrogen, fluoro, chloro, bromo, cyclopropyl, —C≡CH or —CF$_3$.

Representative examples of the chemical entities of formula (I) are shown below in Table 1.

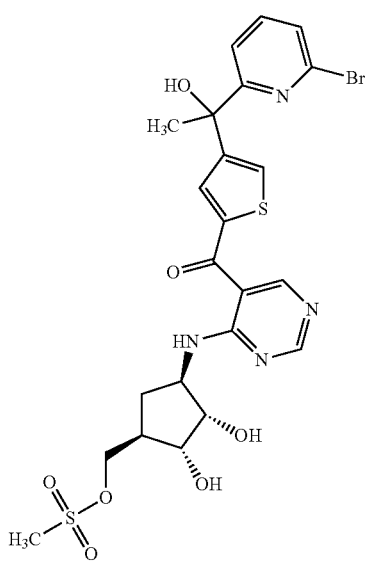
I-1
I-1a
I-1b
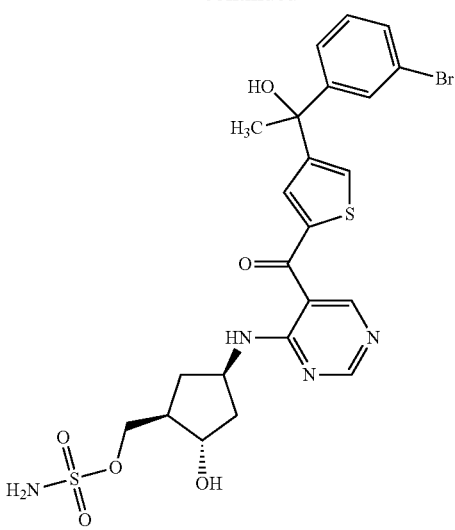
I-3
I-3a
I-3b
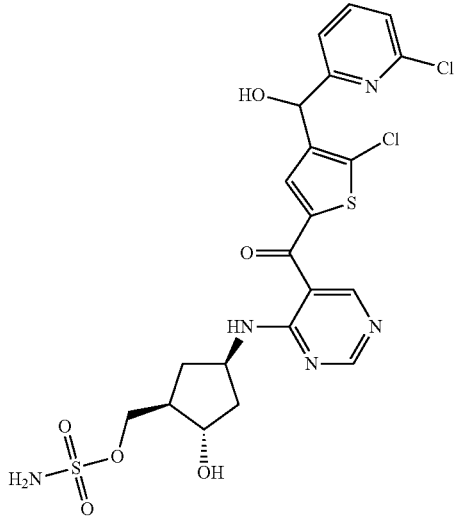
I-2
I-2a
I-2b
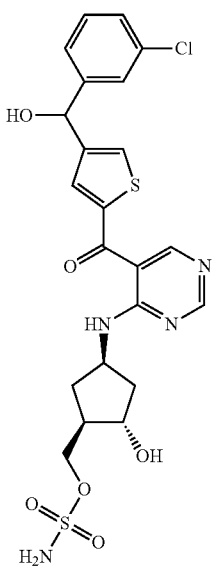
I-4
I-4a
I-4b

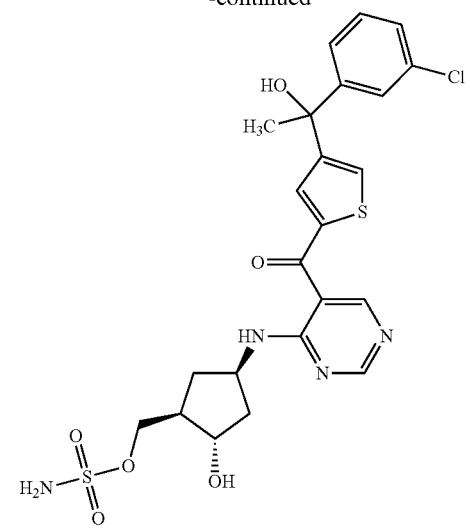
I-5
I-5a
I-5b
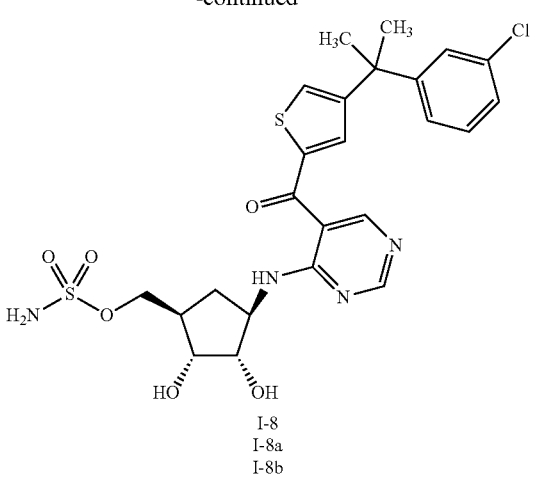
I-8
I-8a
I-8b
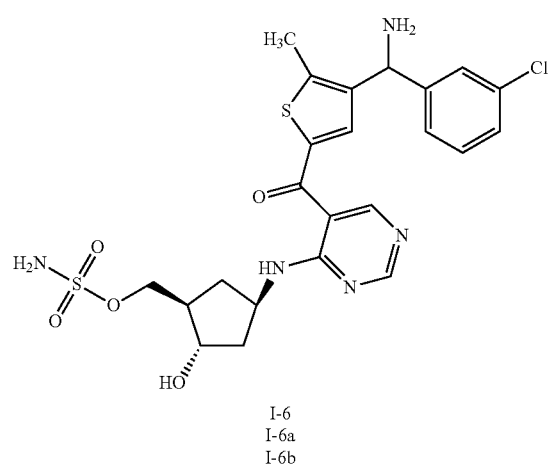
I-6
I-6a
I-6b
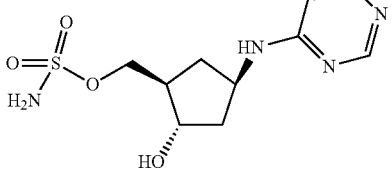
I-9
I-9a
I-9b
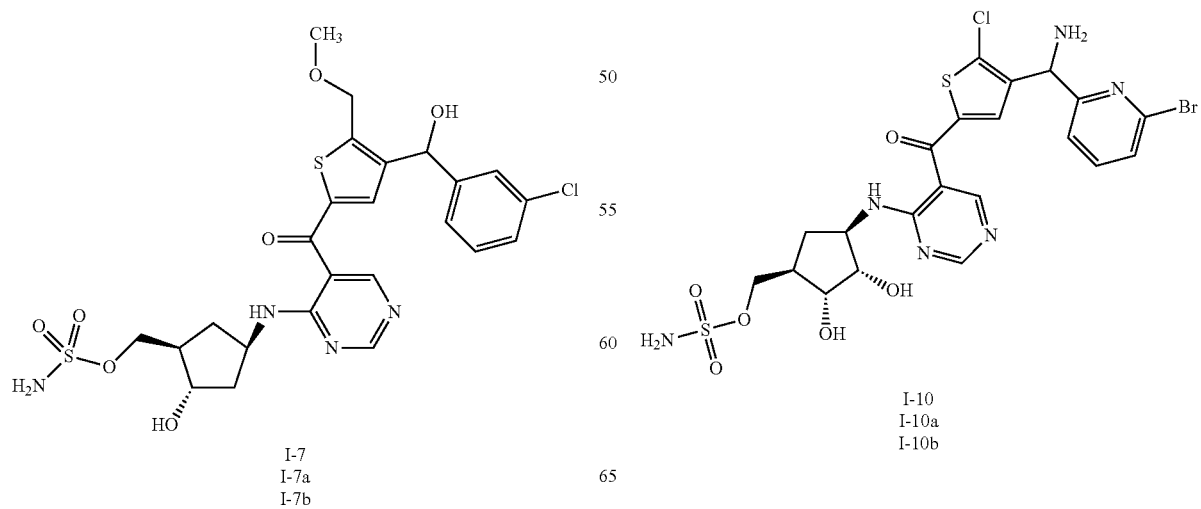
I-7
I-7a
I-7b
I-10
I-10a
I-10b

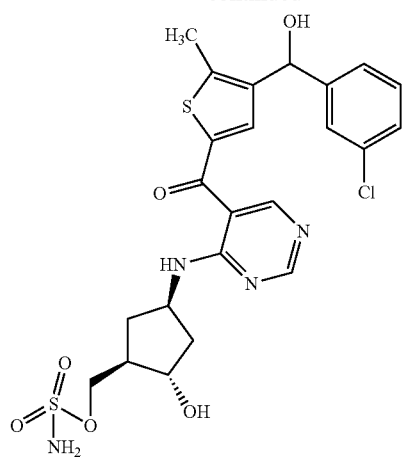
I-11
I-11a
I-11b
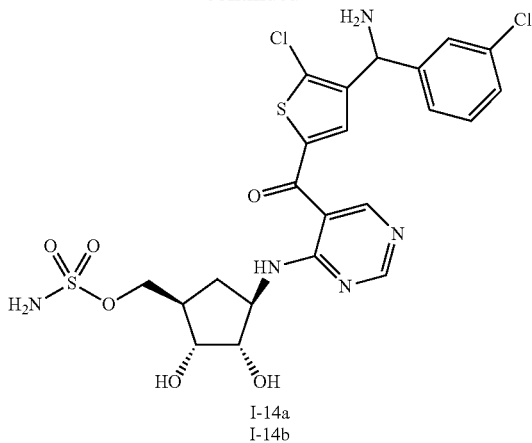
I-14a
I-14b
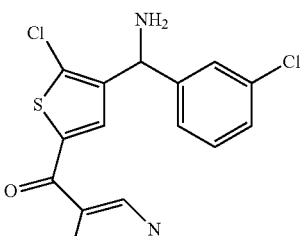
I-12
I-12a
I-12b
I-15
I-15a
I-15b
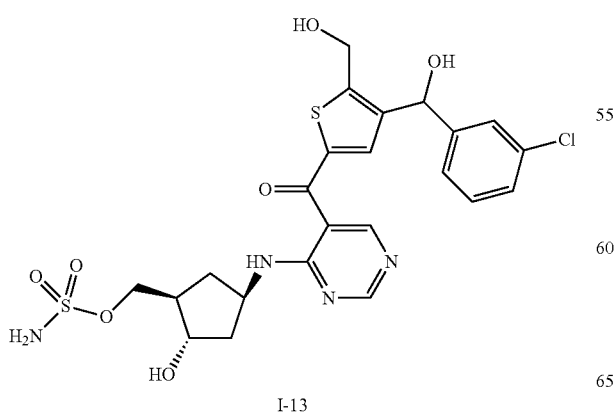
I-13
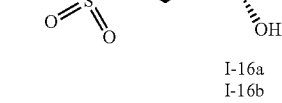
I-16a
I-16b 55
-continued
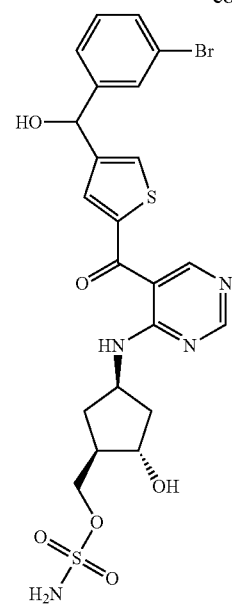
I-17
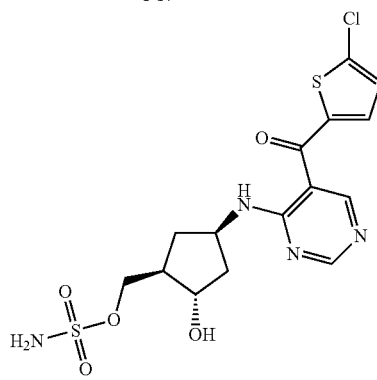
I-18
I-18a
I-18b
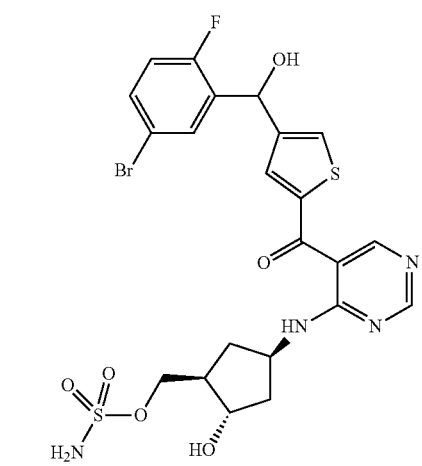
I-19
I-19a
I-19b
56
-continued
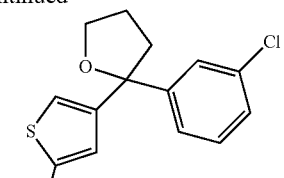
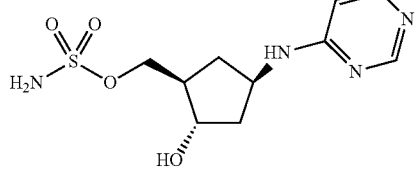
I-20a
I-20b
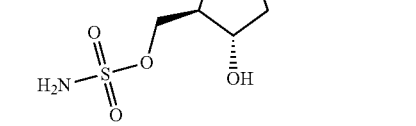
I-21
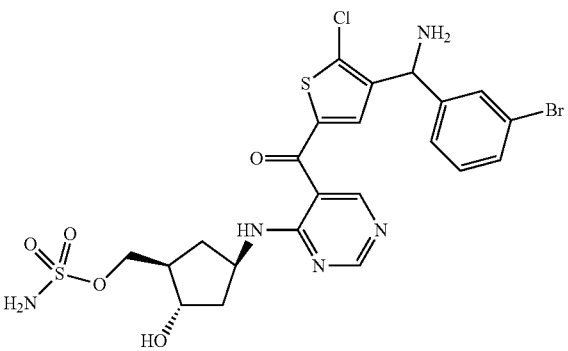
I-22
I-22a
I-22b

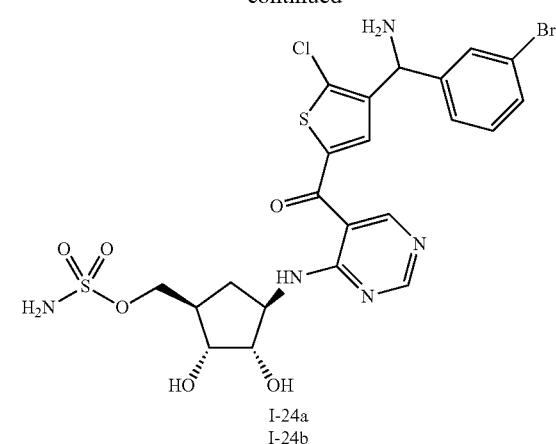
I-24a
I-24b
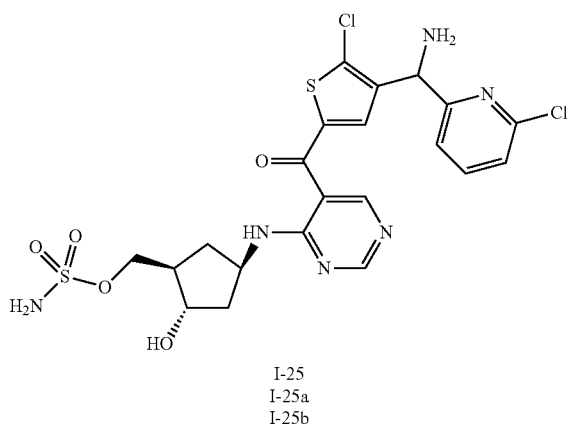
I-25
I-25a
I-25b
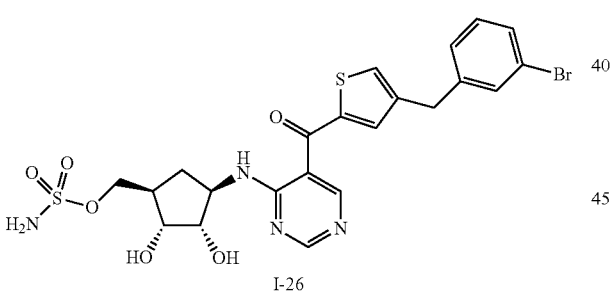
I-26
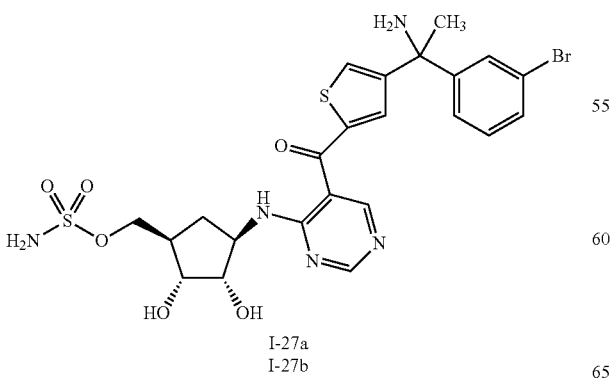
I-27a
I-27b
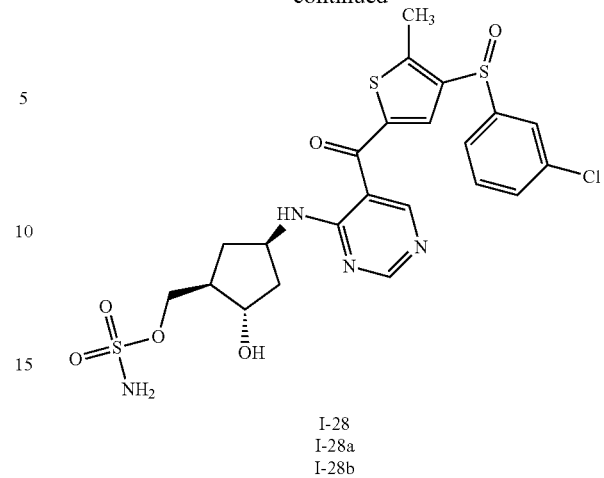
I-28
I-28a
I-28b
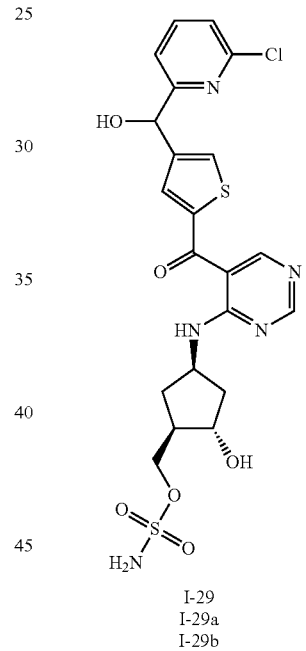
I-29
I-29a
I-29b
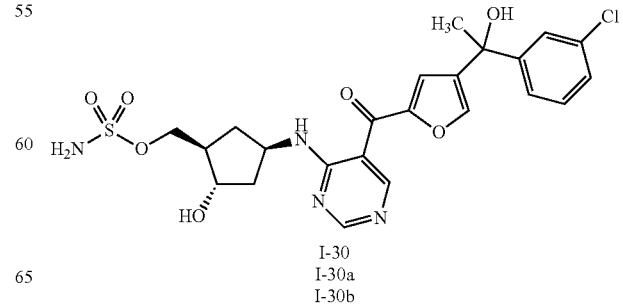
I-30
I-30a
I-30b

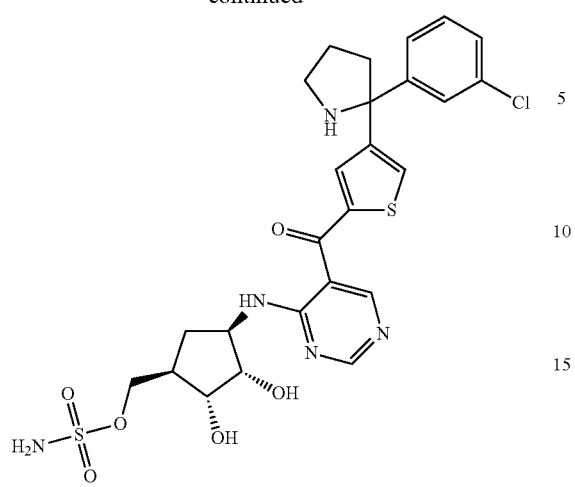
I-31
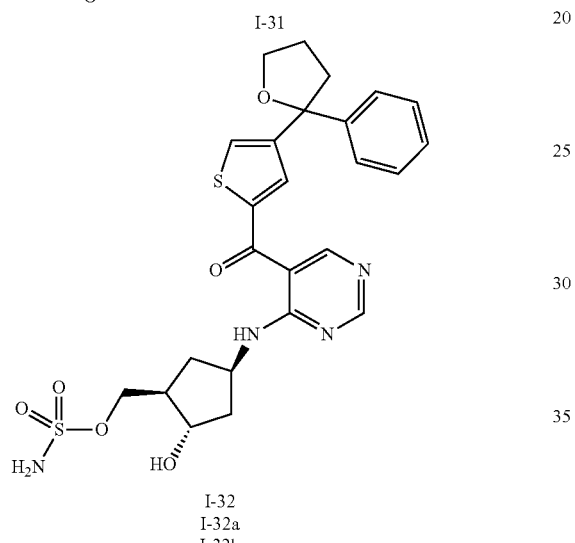
I-32
I-32a
I-32b
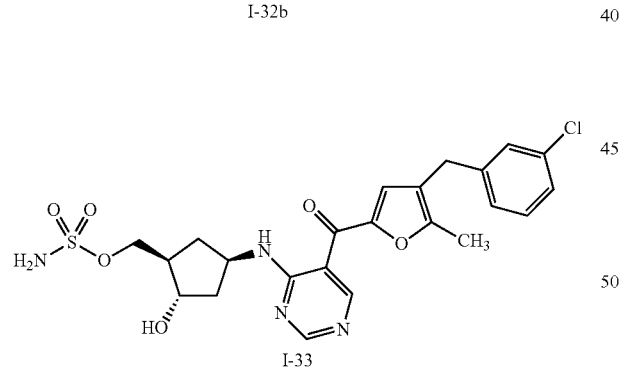
I-33
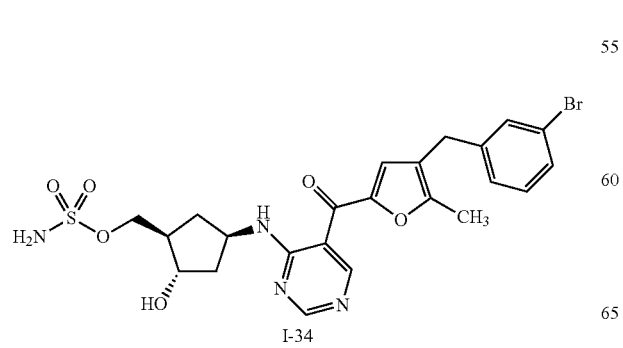
I-34
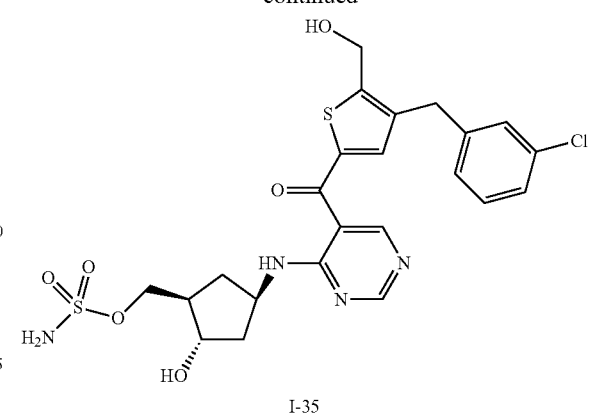
I-35
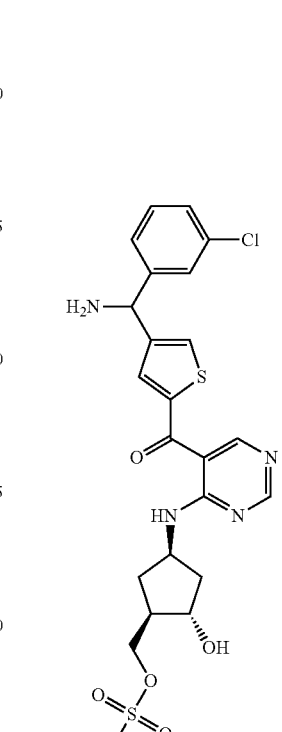
I-36
I-36a
I-36b
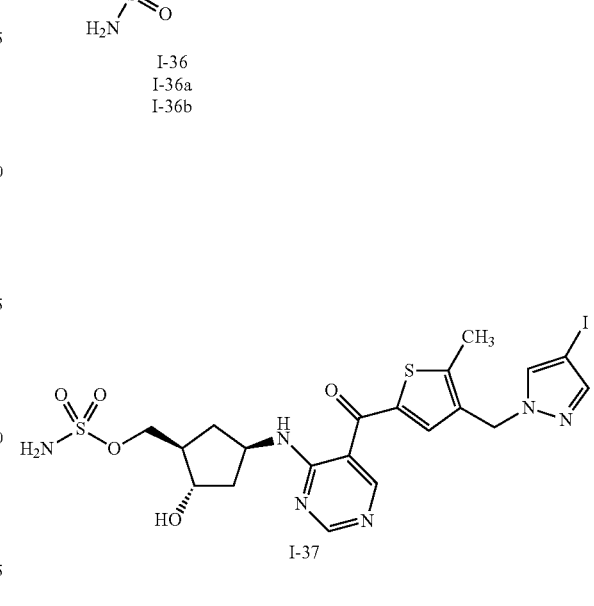
I-37

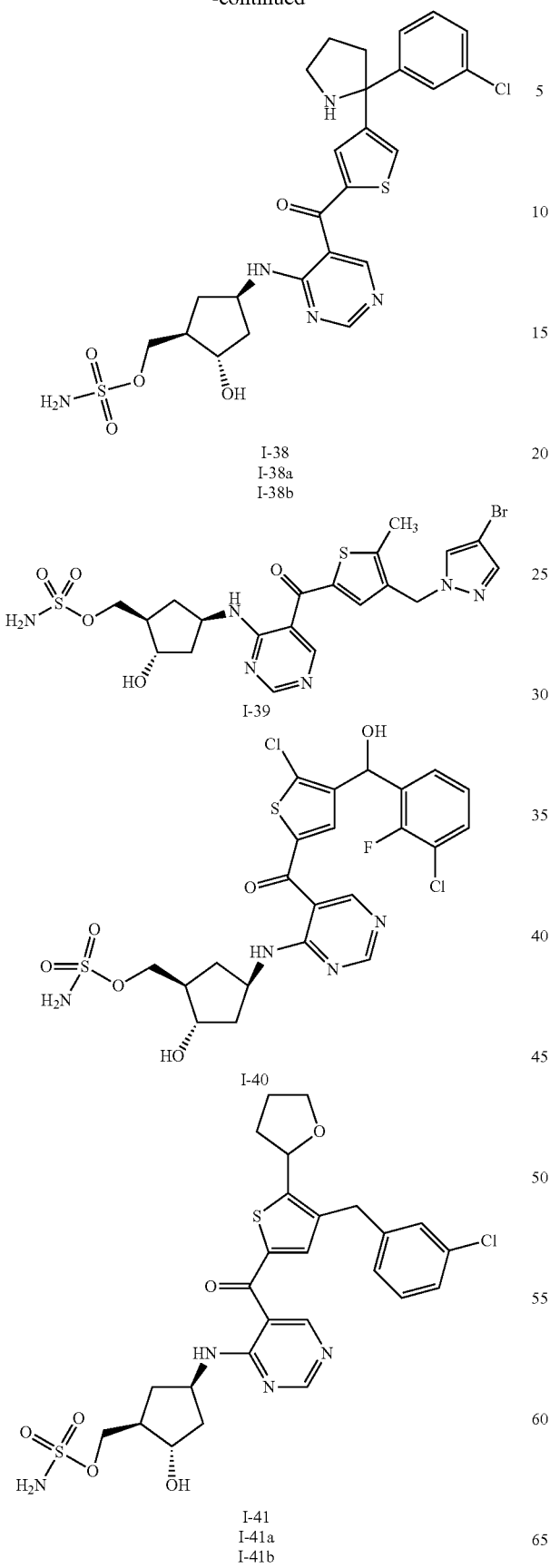
I-38
I-38a
I-38b
I-39
I-40
I-41
I-41a
I-41b
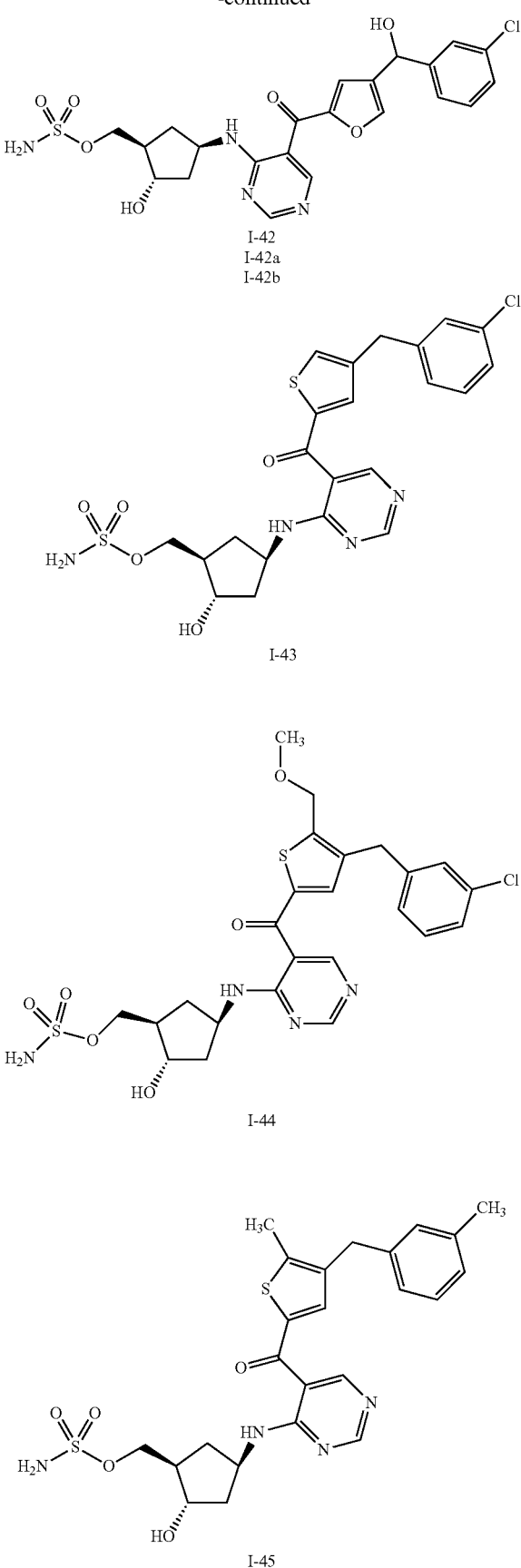
I-42
I-42a
I-42b
I-43
I-44
I-45

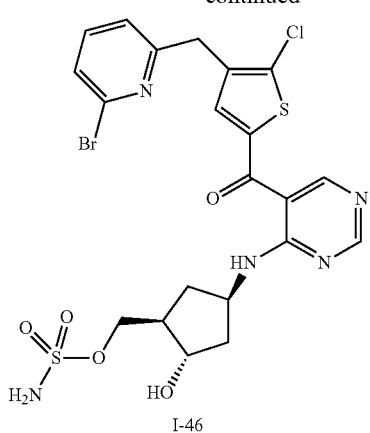
I-46
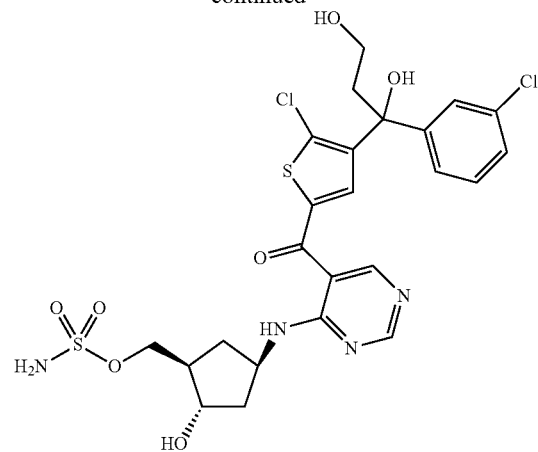
I-49
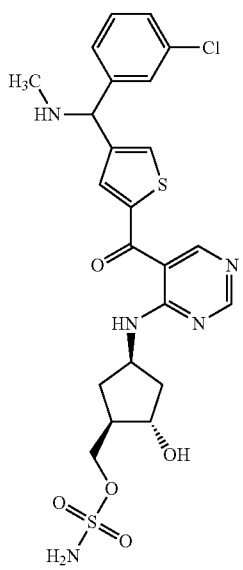
I-47
I-47a
I-47b
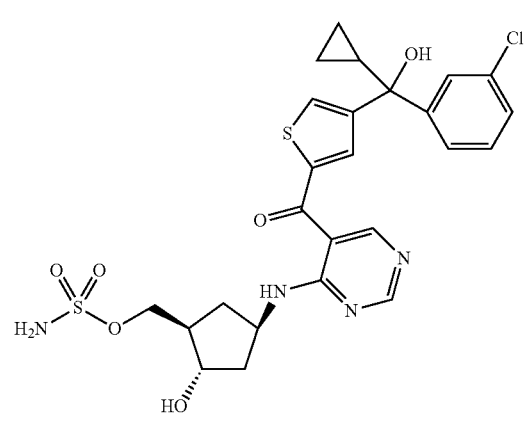
I-50
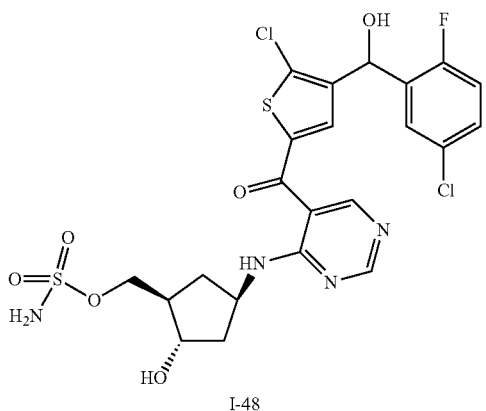
I-48
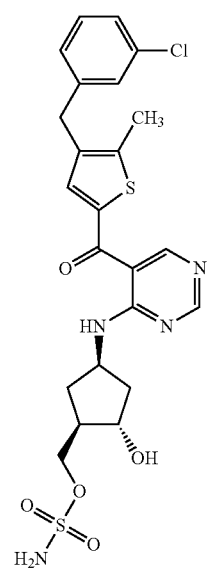
I-51

65
-continued
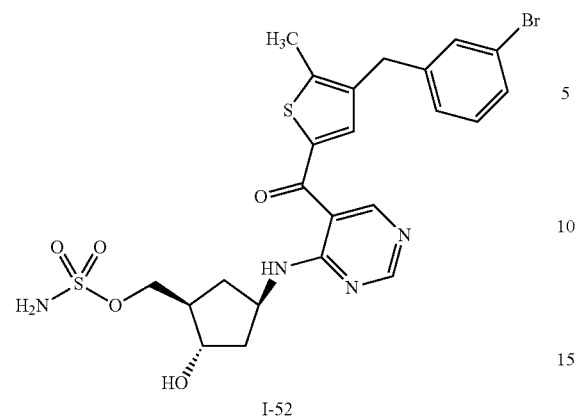
I-52
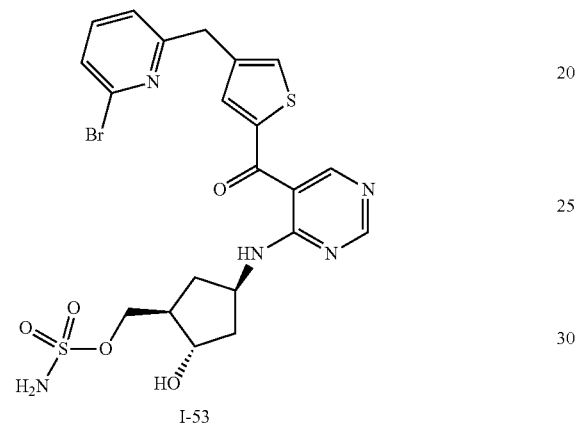
I-53
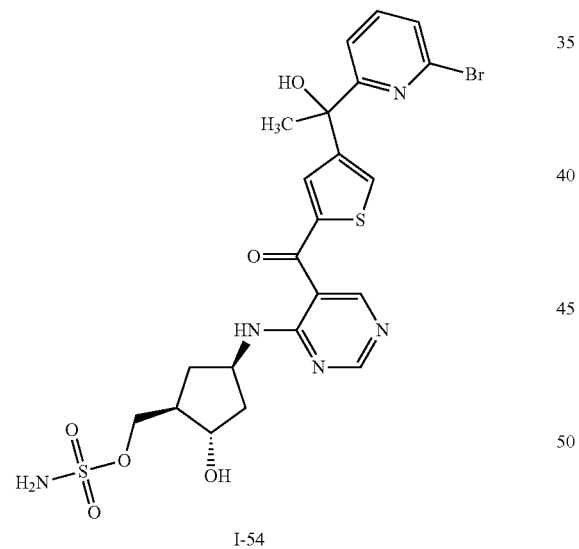
I-54
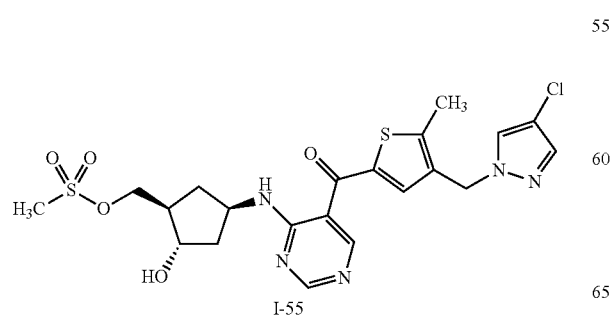
I-55
66
-continued
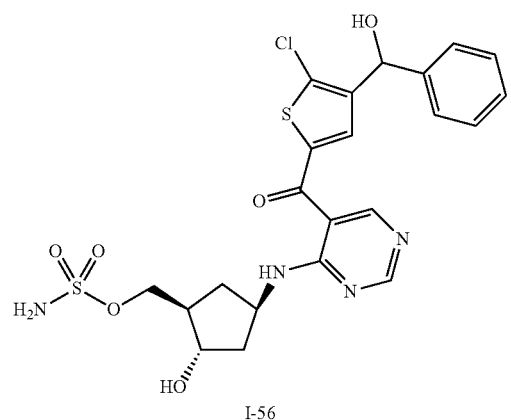
I-56
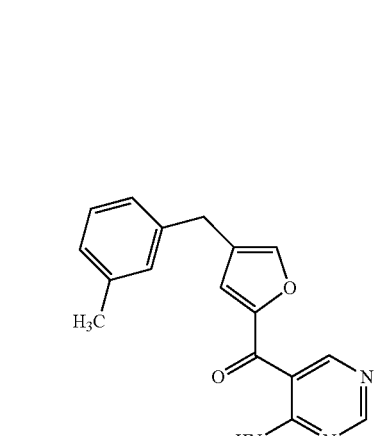
I-57
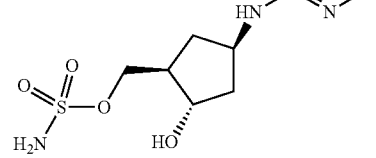
I-58
I-58a
I-58b -continued
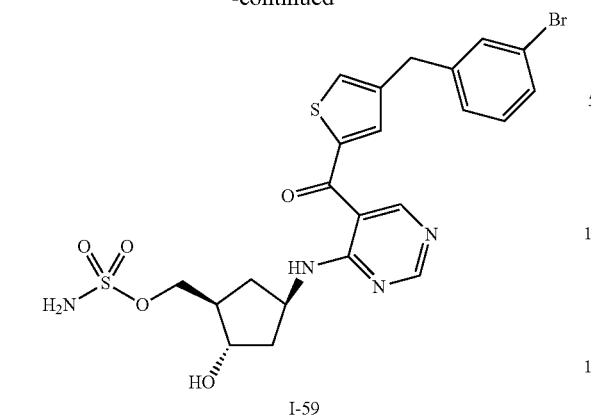
I-59
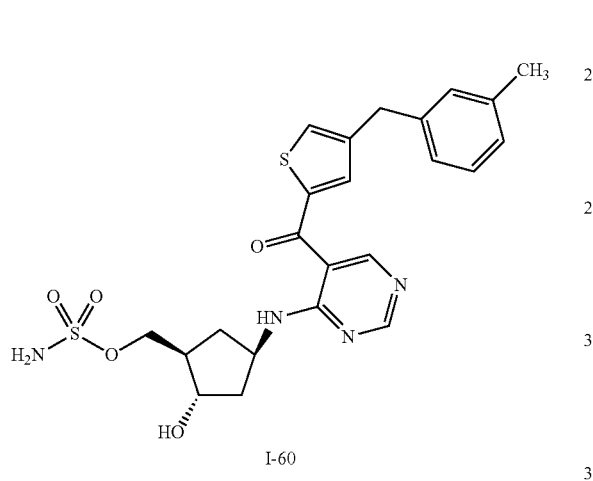
I-60
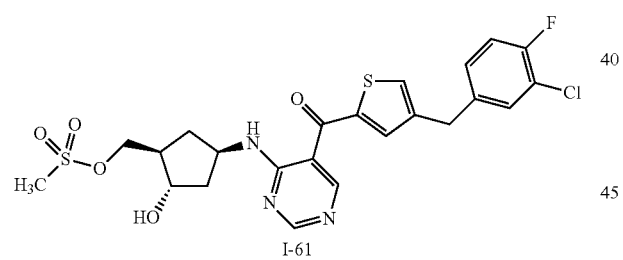
I-61
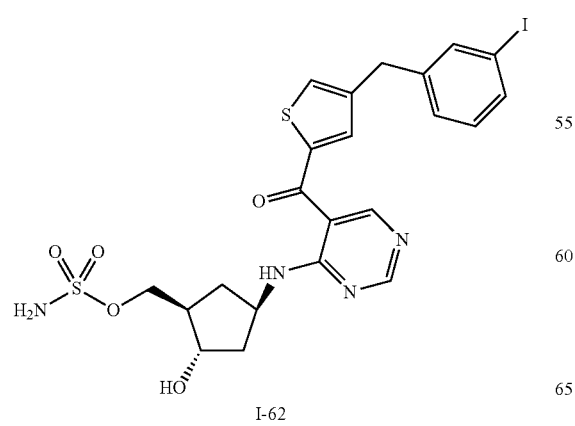
I-62
-continued
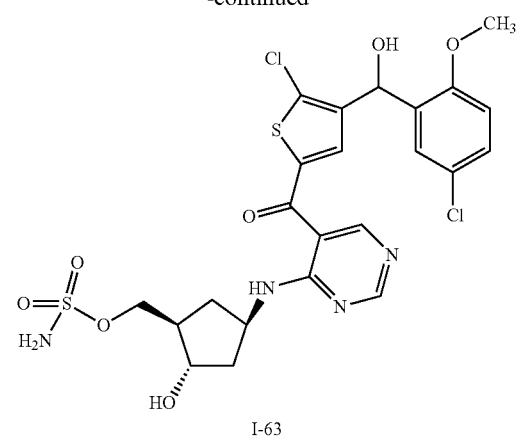
I-63
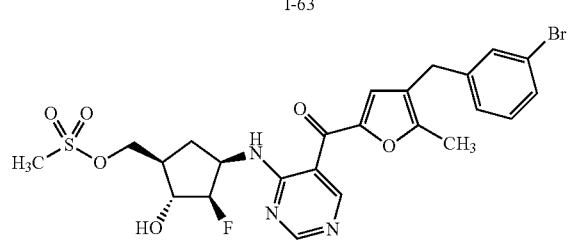
I-64
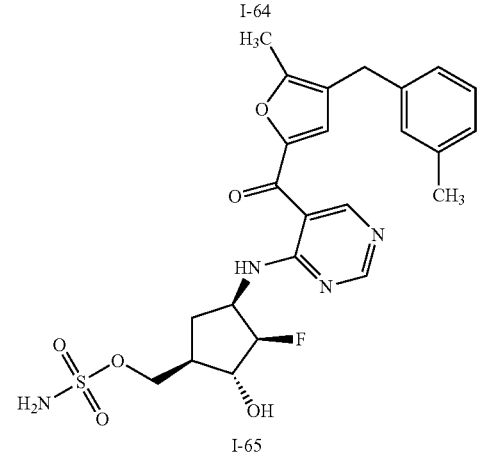
I-65
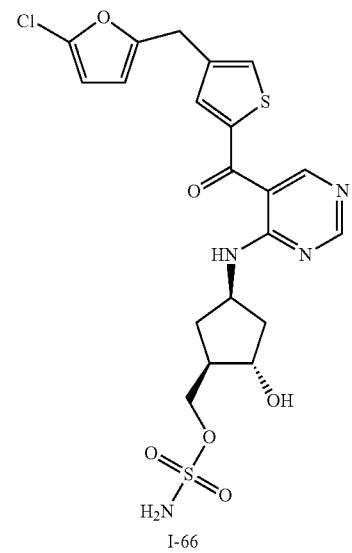
I-66

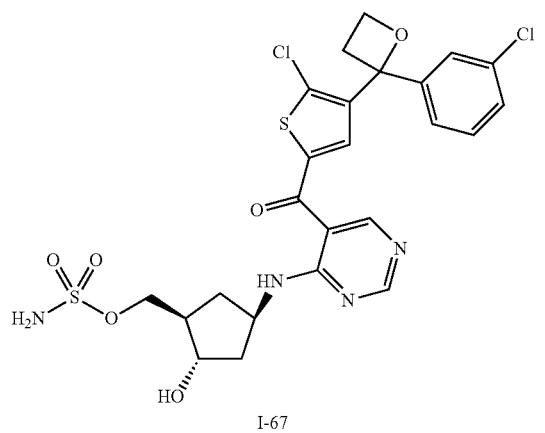
I-67
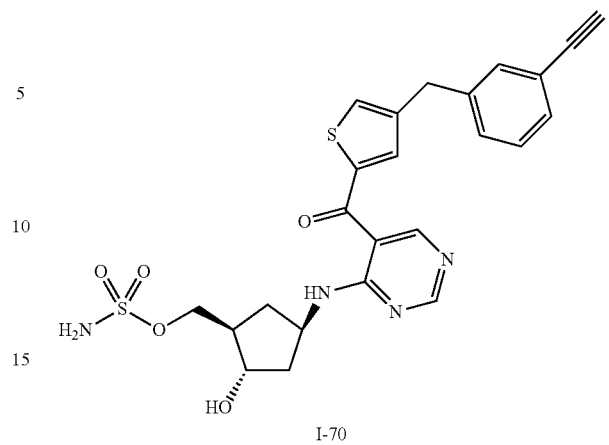
I-70
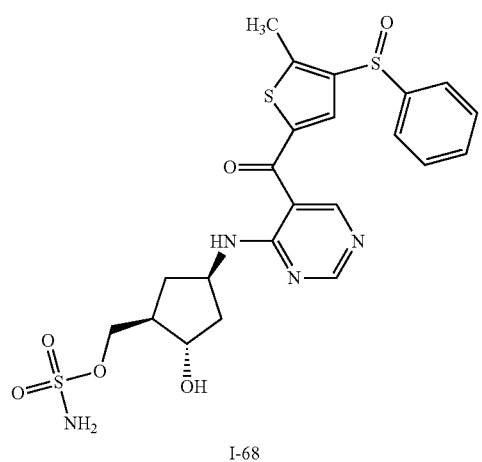
I-68
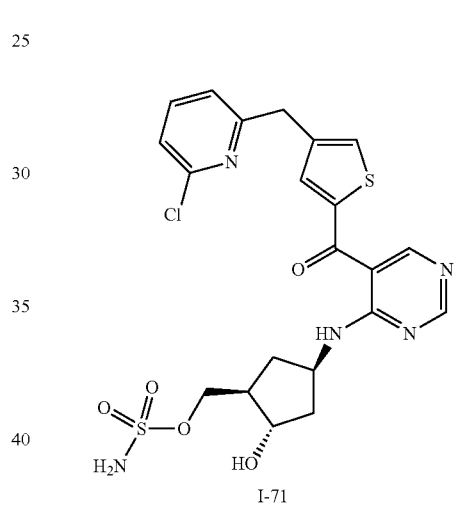
I-71
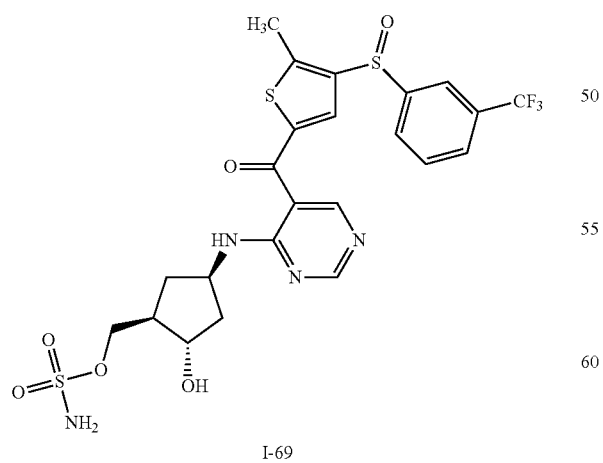
I-69
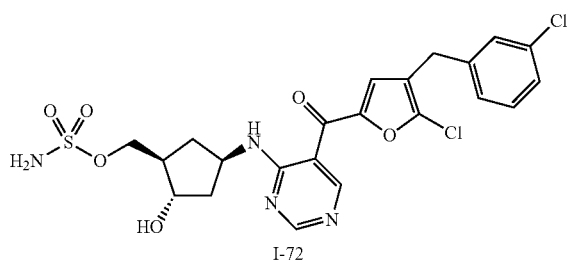
I-72

I-73a
I-73b
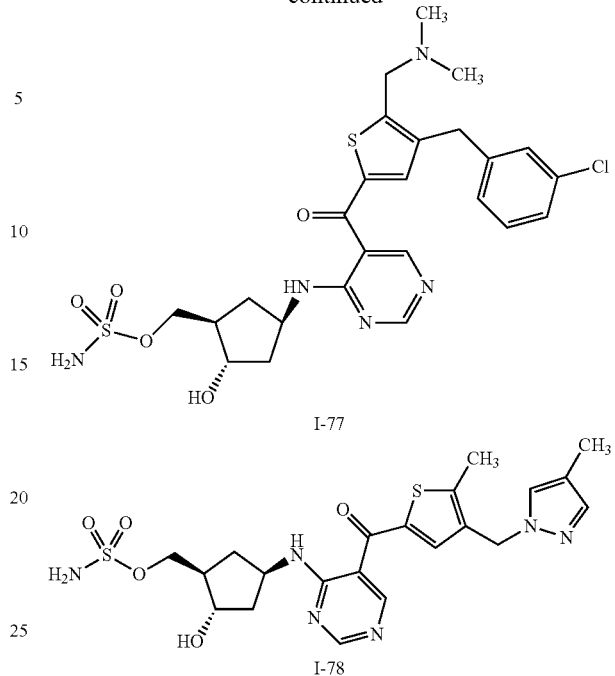
I-77
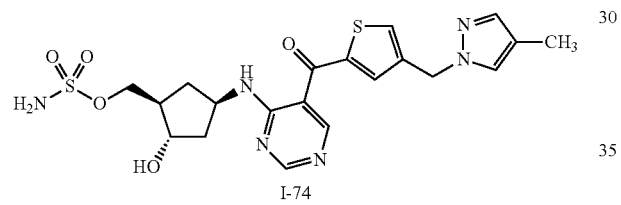
I-74
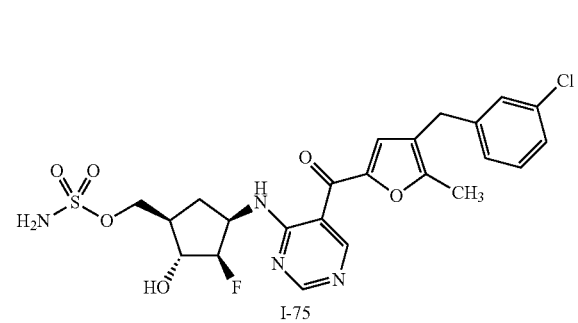
I-78
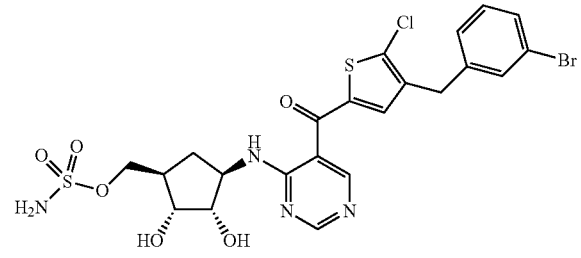
I-75
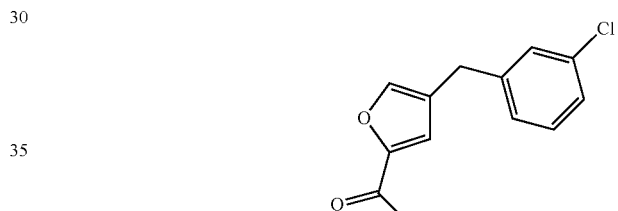
I-79
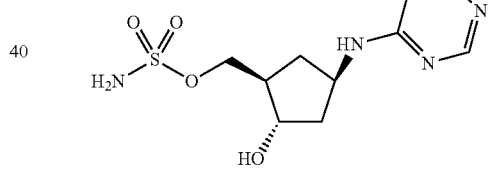
I-76
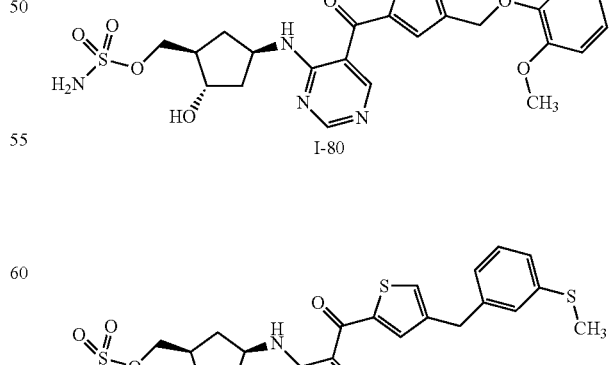
I-80
I-81

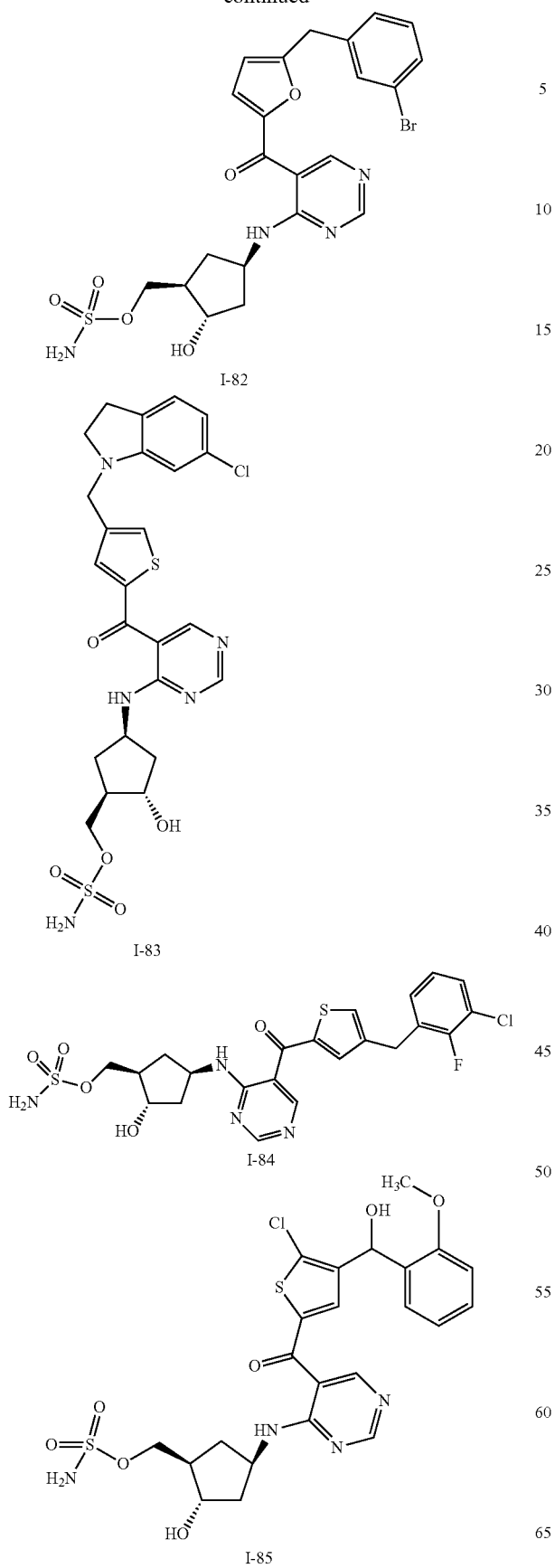
I-82
I-83
I-84
I-85
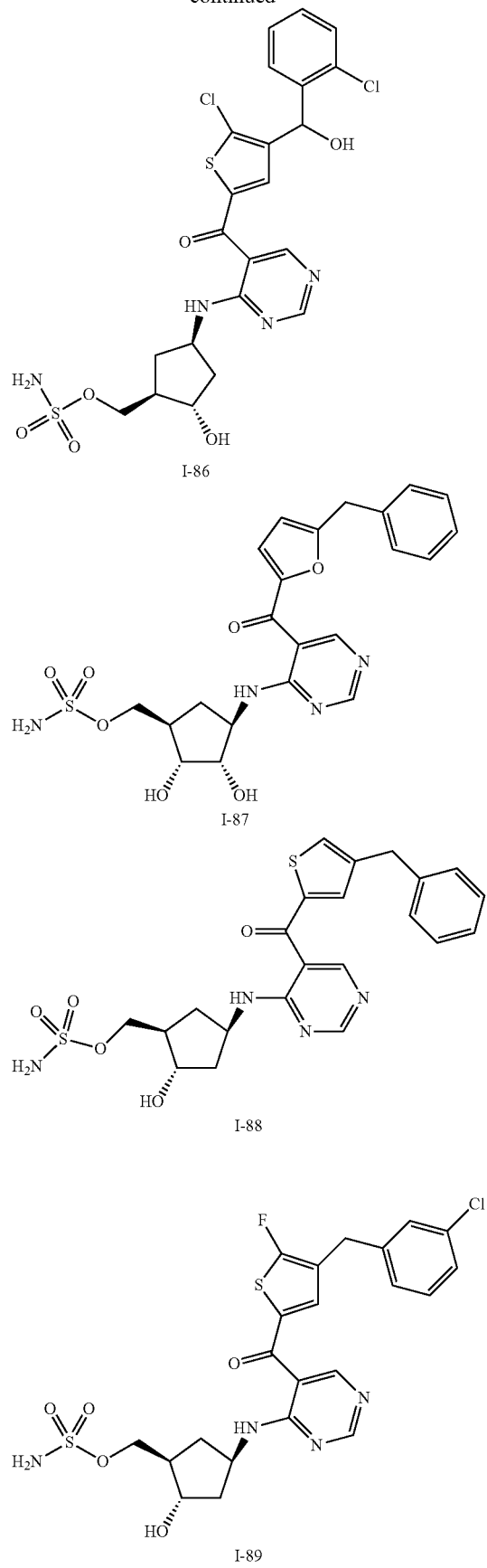
I-86
I-87
I-88
I-89

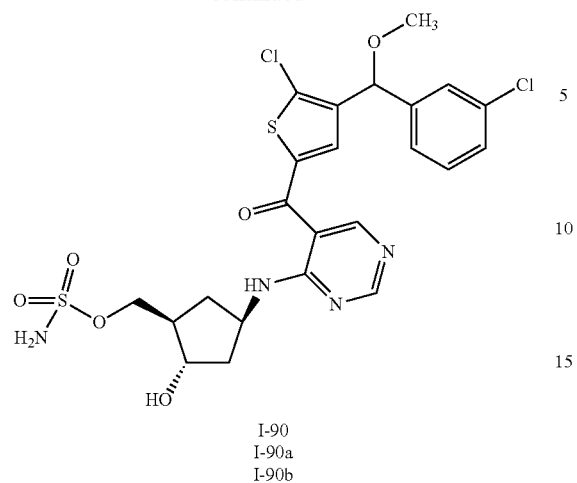
I-90
I-90a
I-90b
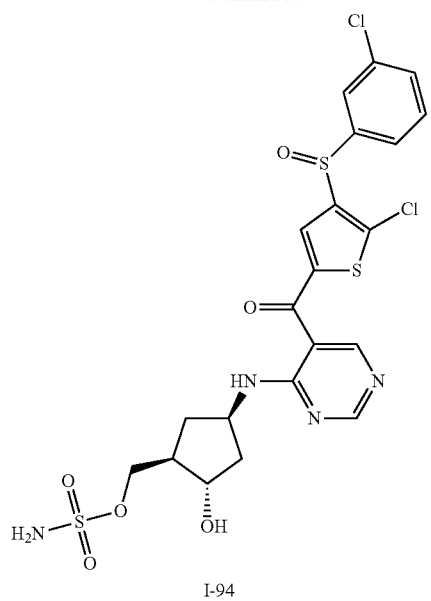
I-94
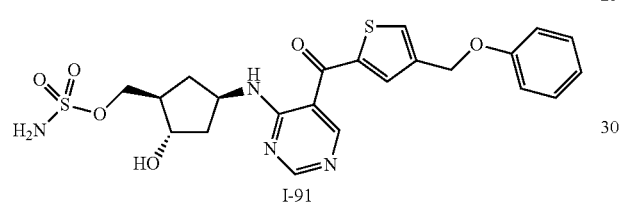
I-91
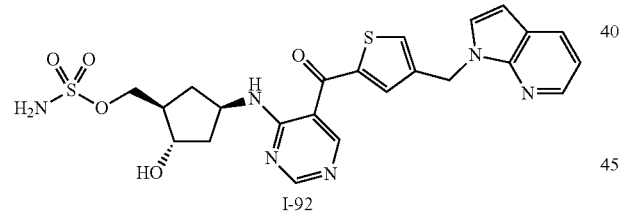
I-92
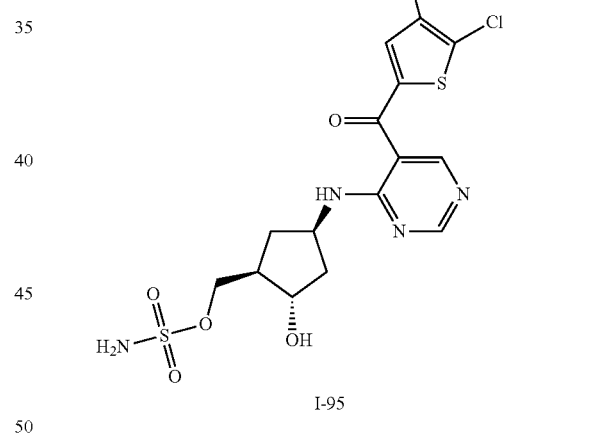
I-95
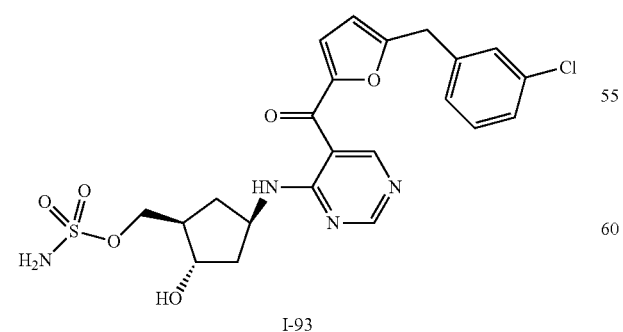
I-93
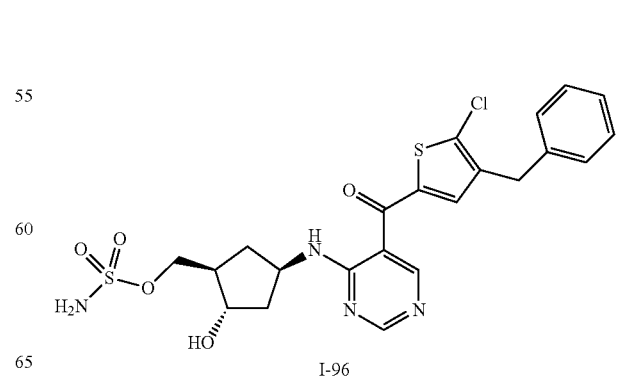
I-96

77
-continued
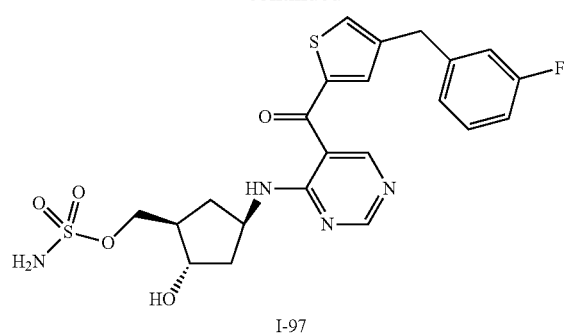
I-97
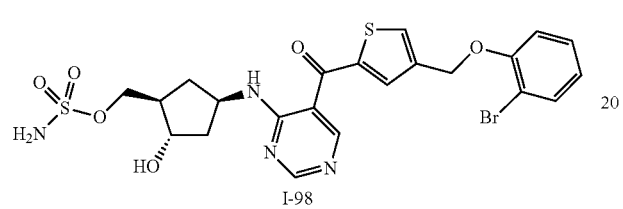
I-98
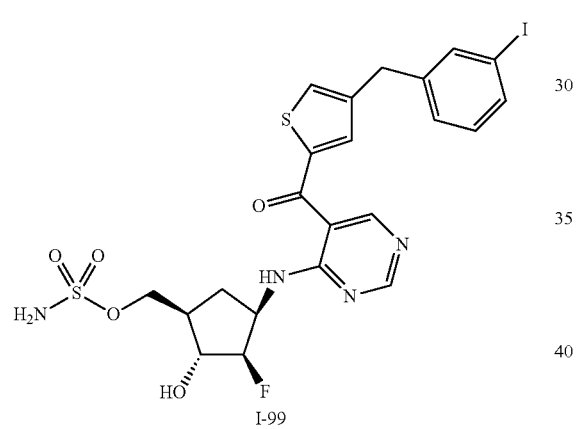
I-99
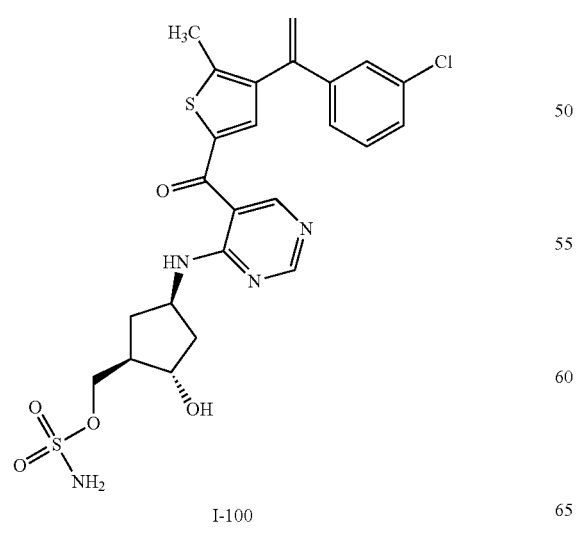
I-100
78
-continued
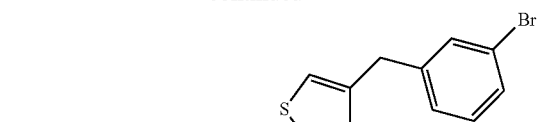
I-101
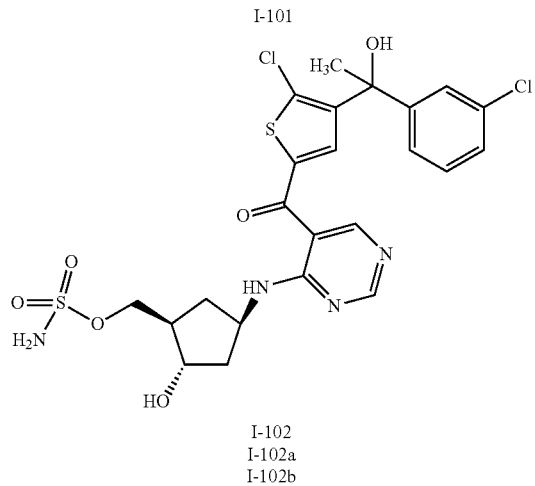
I-102
I-102a
I-102b
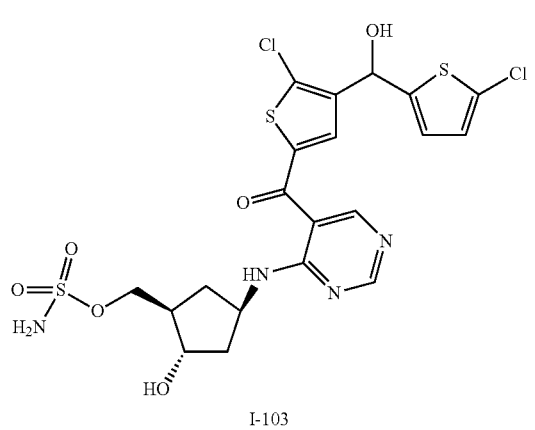
I-103
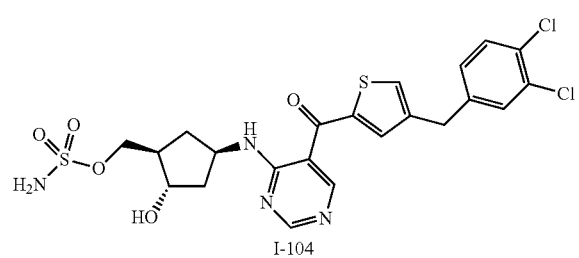
I-104

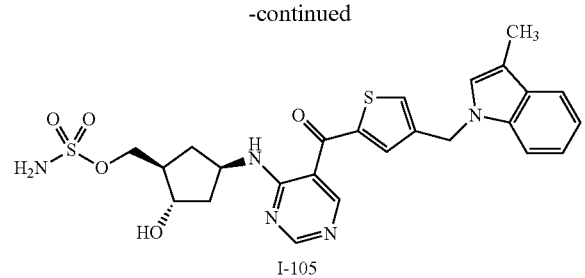
I-105
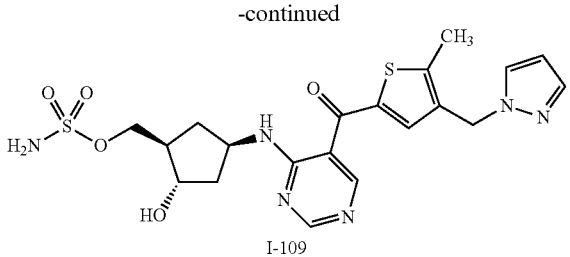
I-109
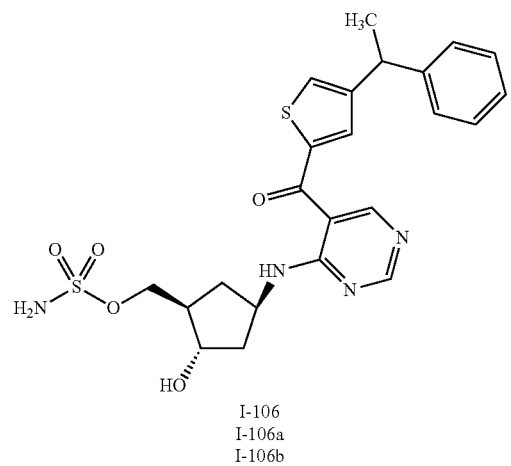
I-106
I-106a
I-106b
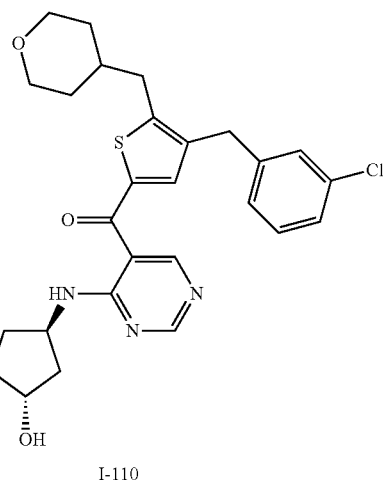
I-110
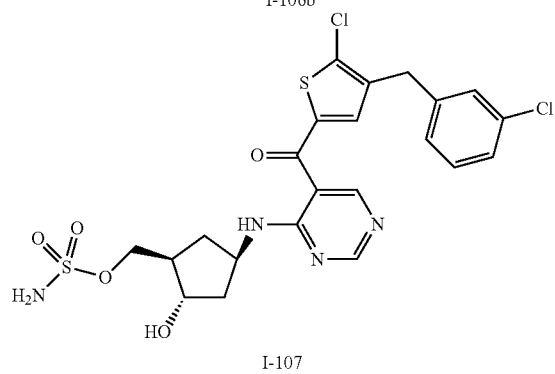
I-107
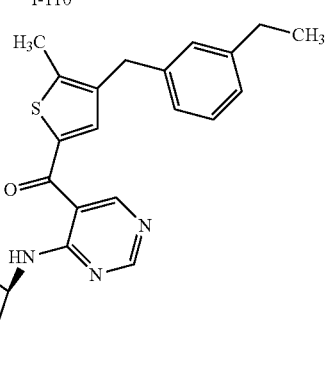
I-111
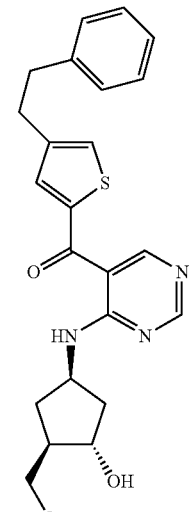
I-108
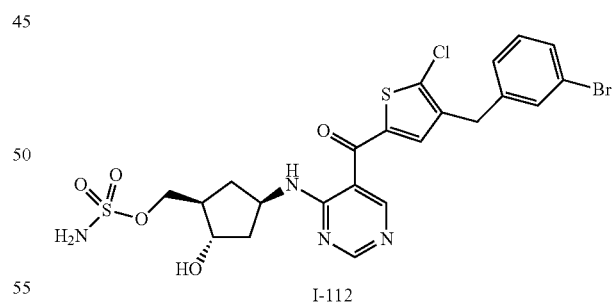
I-112
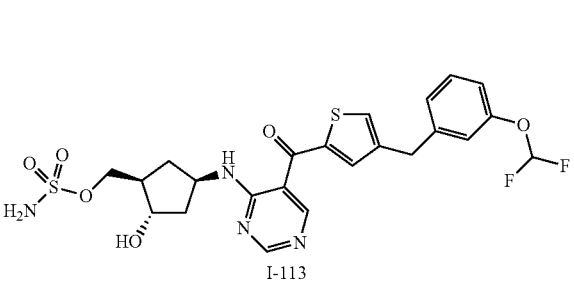
I-113

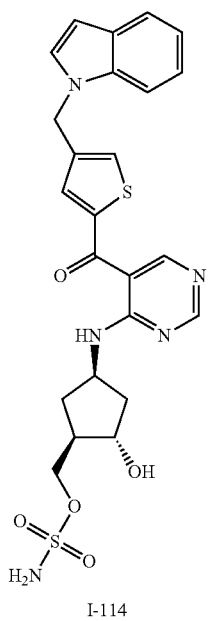
I-114
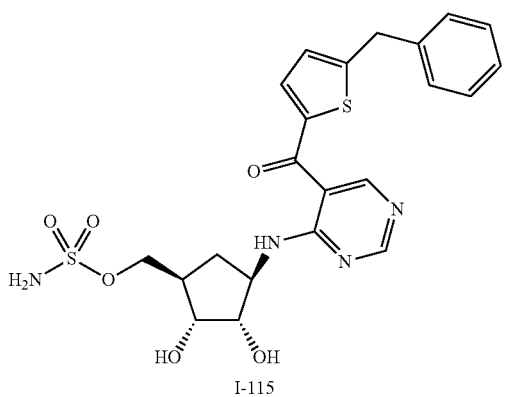
I-115
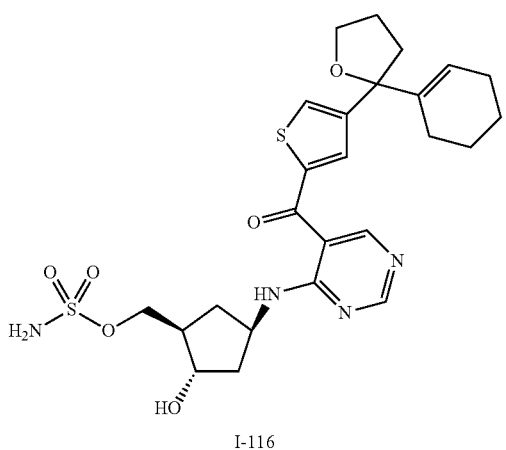
I-116
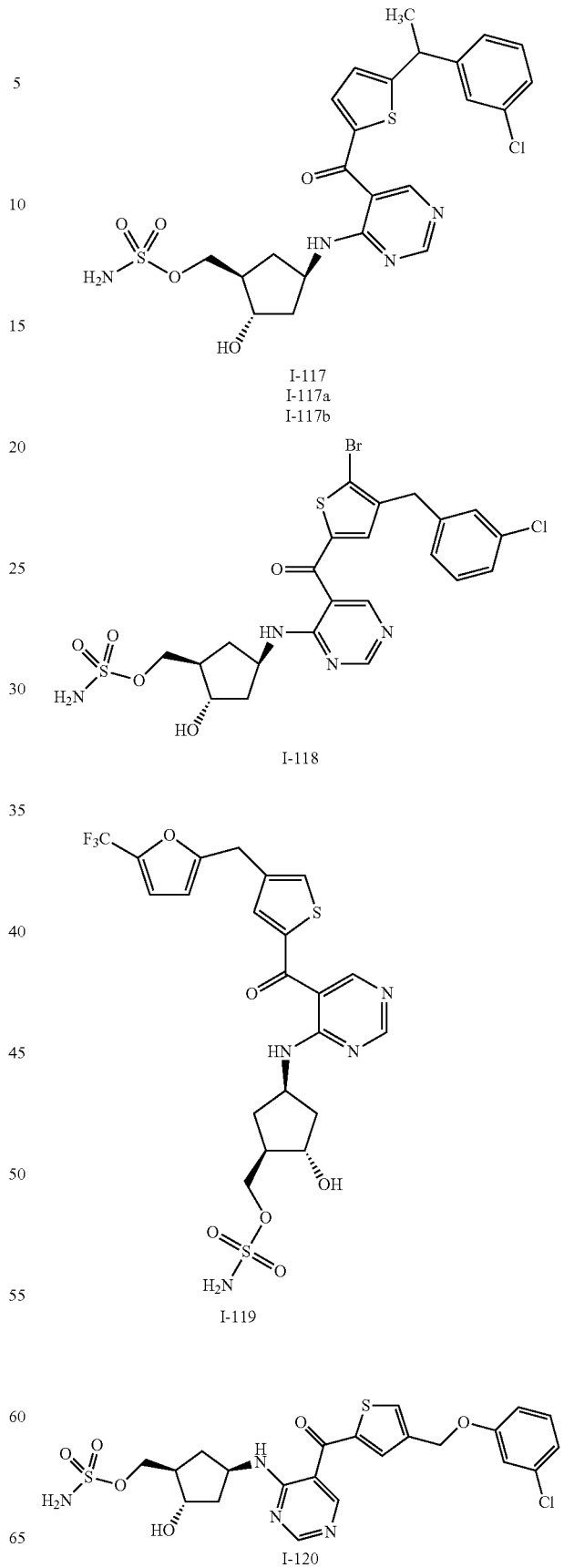
I-117
I-117a
I-117b
I-118
I-119
I-120

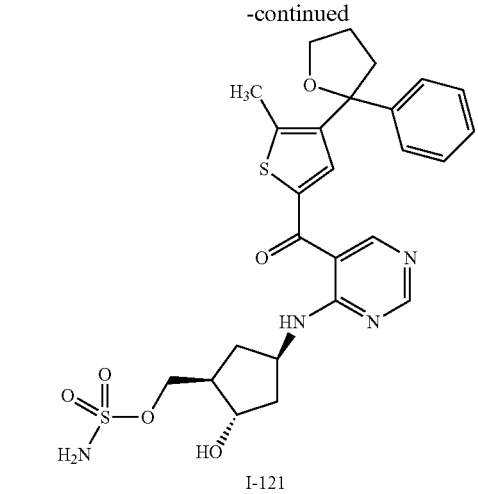
I-121
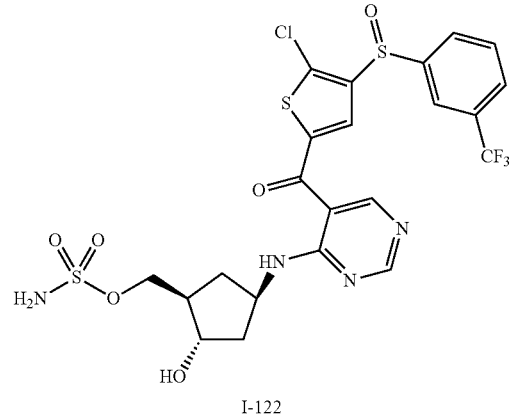
I-122
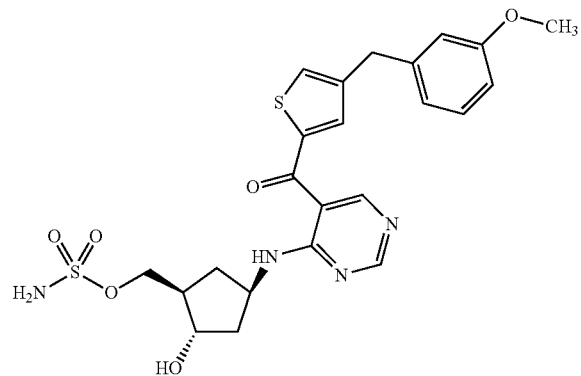
I-123
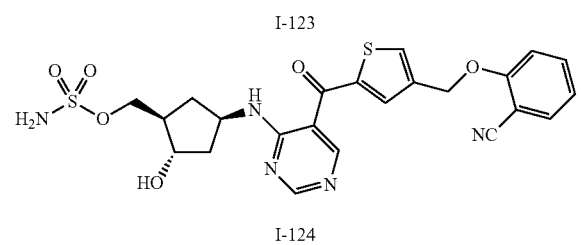
I-124
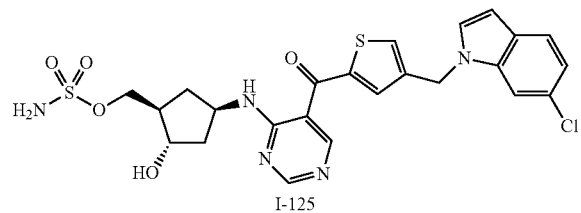
I-125
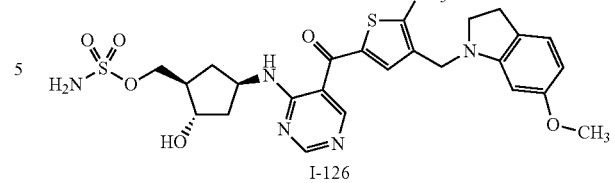
I-126
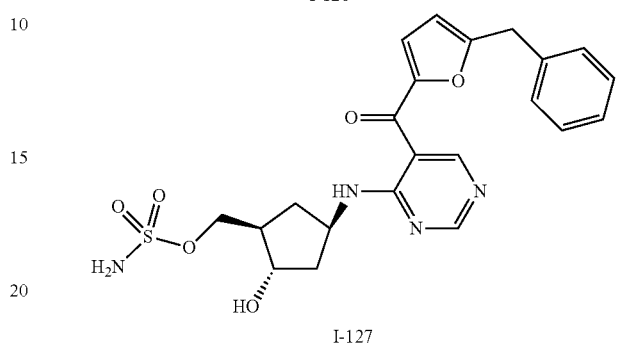
I-127
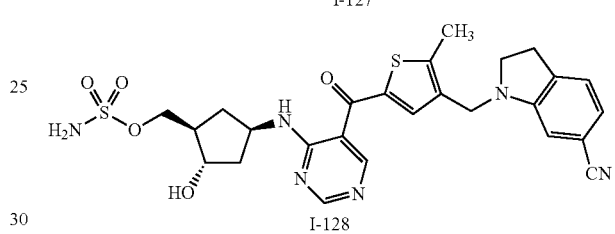
I-128
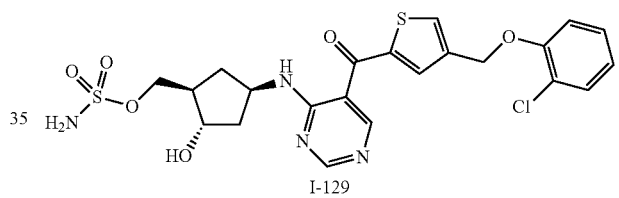
I-129
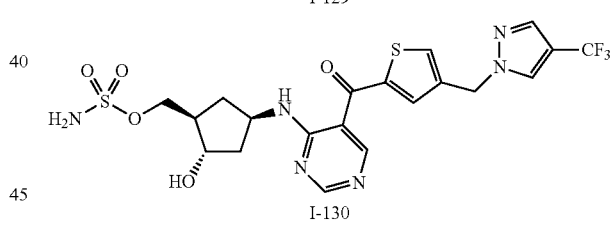
I-130
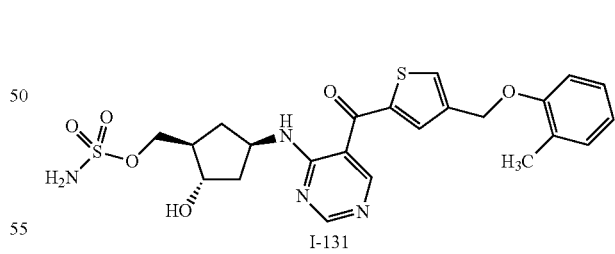
I-131
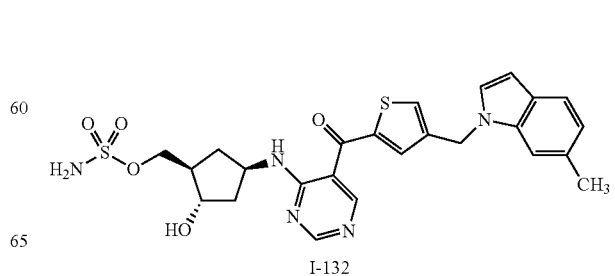
I-132

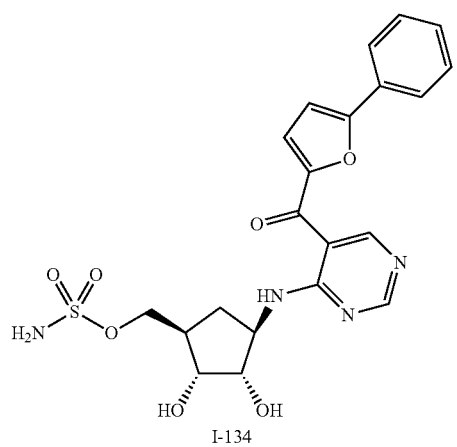
I-134
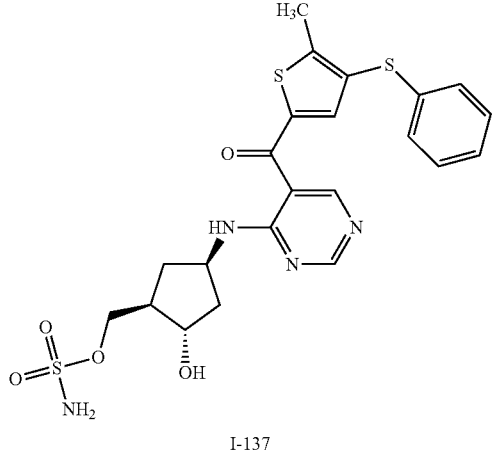
I-137
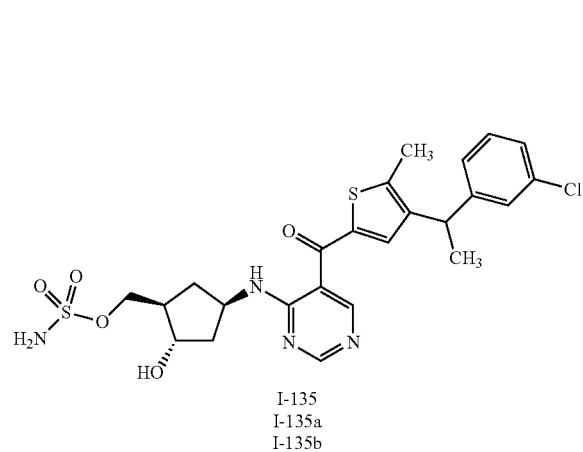
I-135
I-135a
I-135b
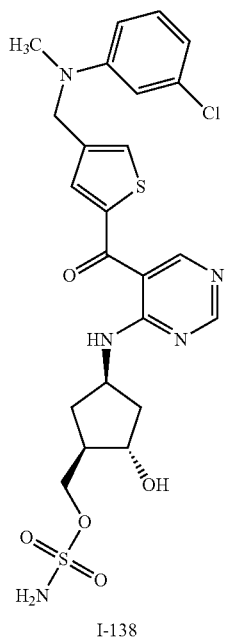
I-138
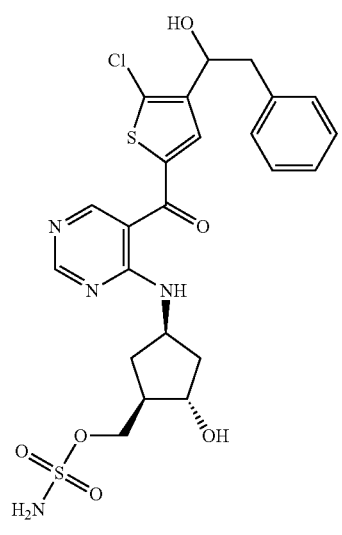
I-136
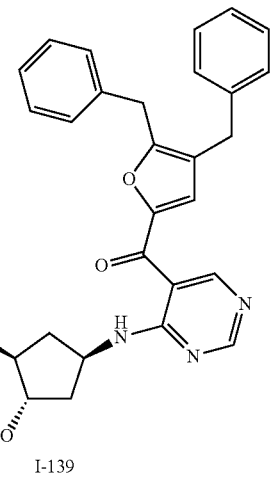
I-139

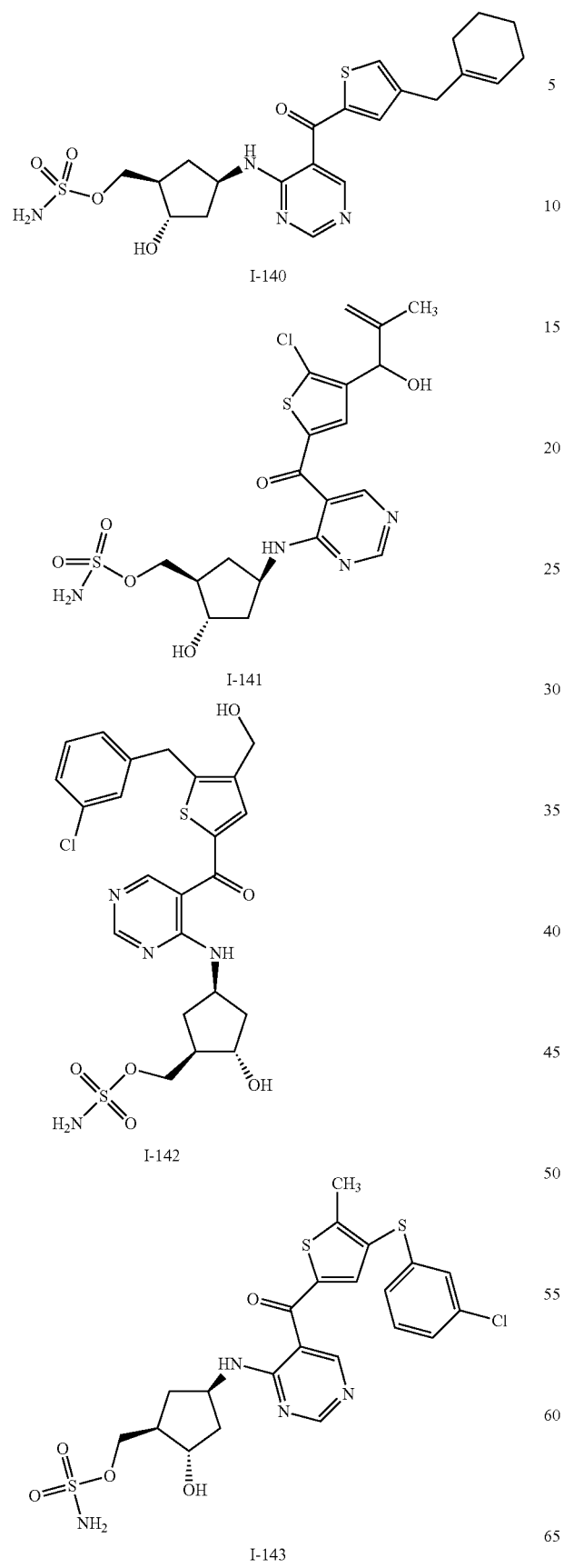
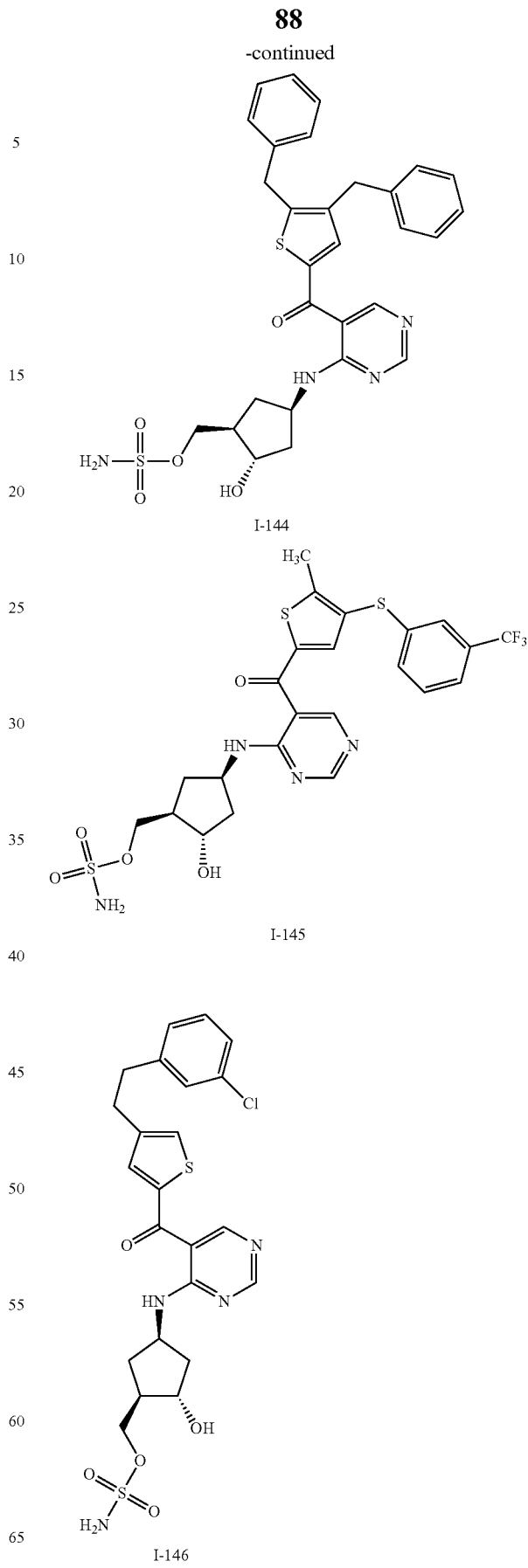

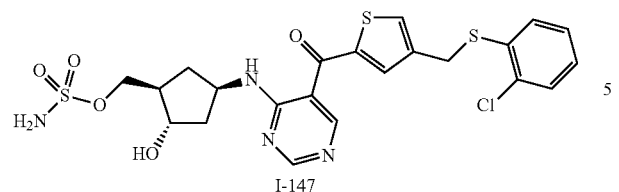
I-147
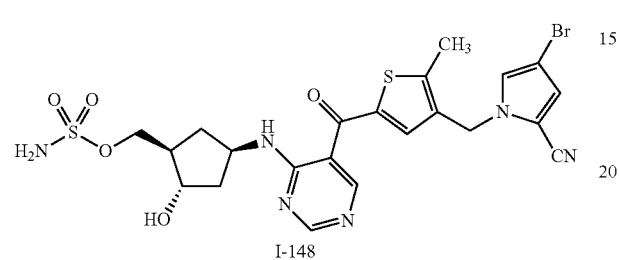
I-148
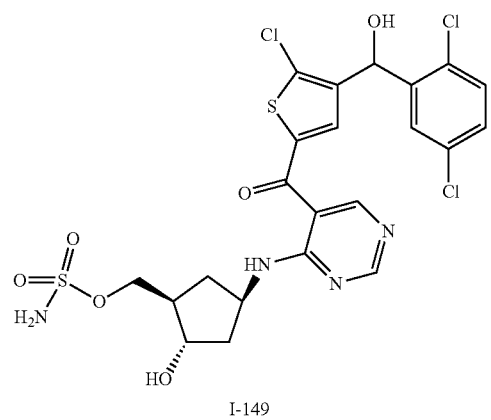
I-149
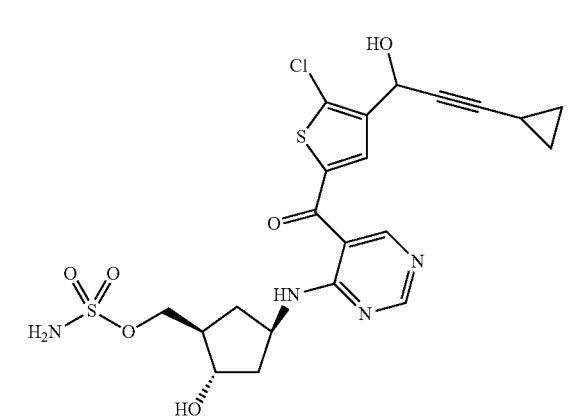
I-150
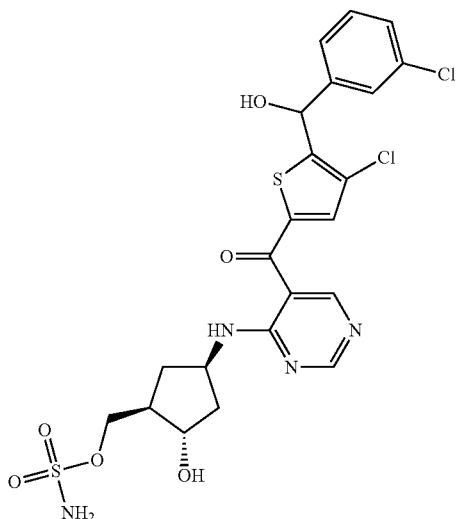
I-151
I-151a
I-151b
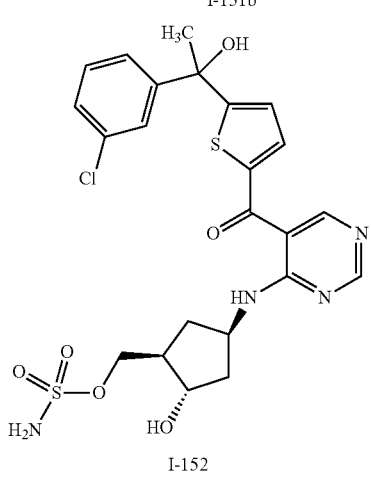
I-152
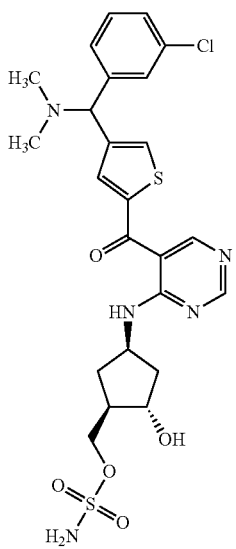
I-153
I-153a
I-153b

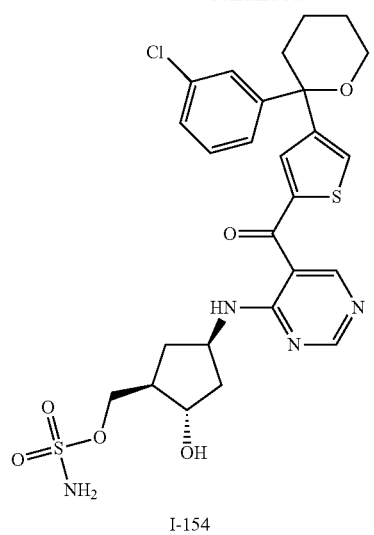
I-154
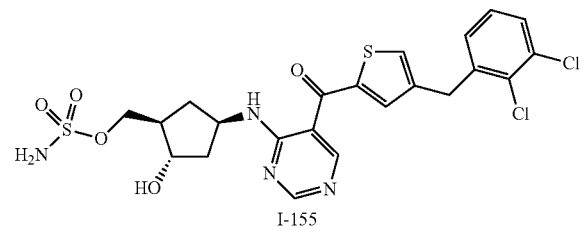
I-155
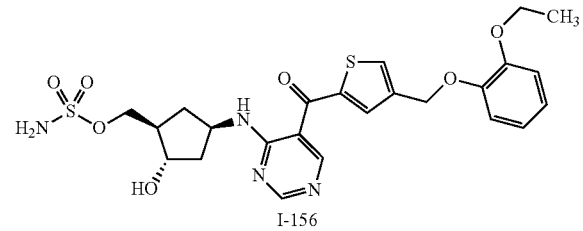
I-156
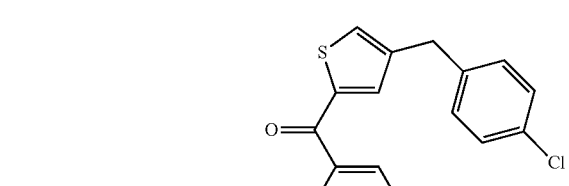
I-157
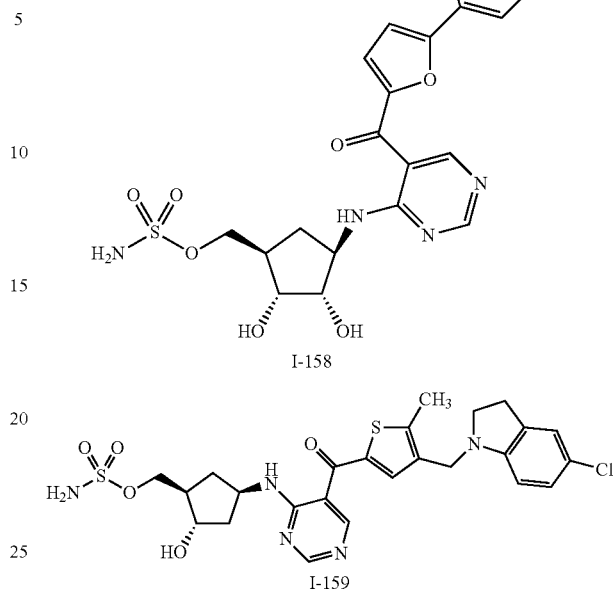
I-158
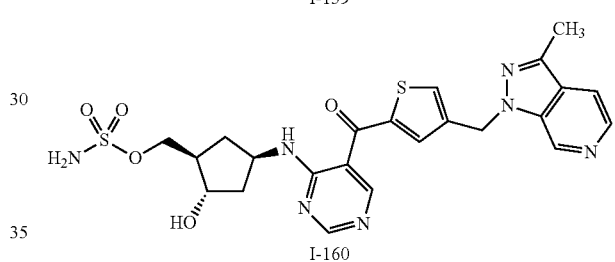
I-159
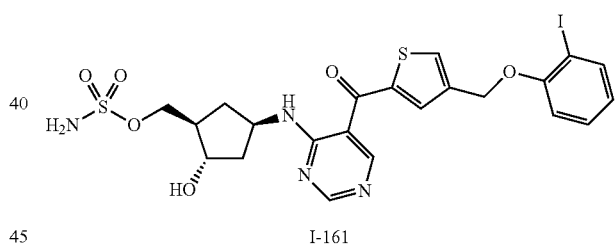
I-160
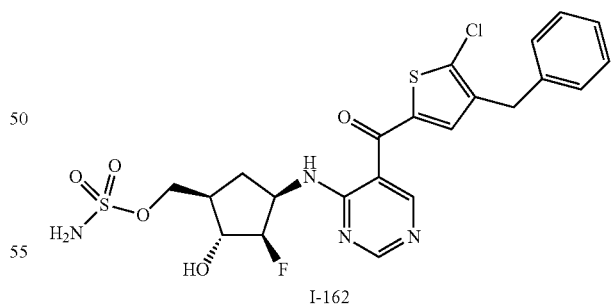
I-161
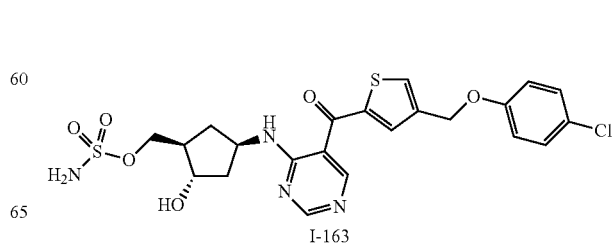
I-162
I-163

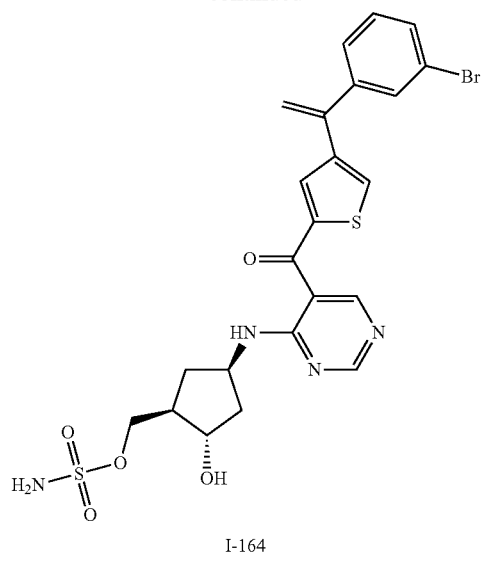
I-164
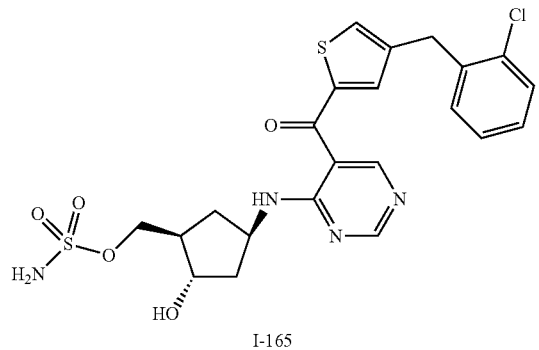
I-165
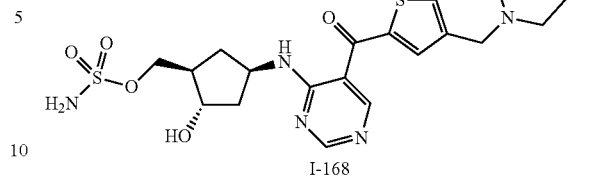
I-168

I-169
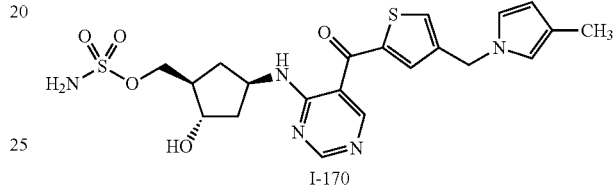
I-170
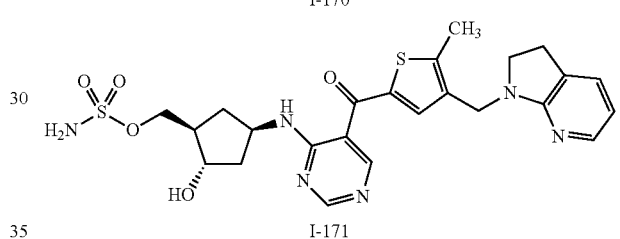
I-171
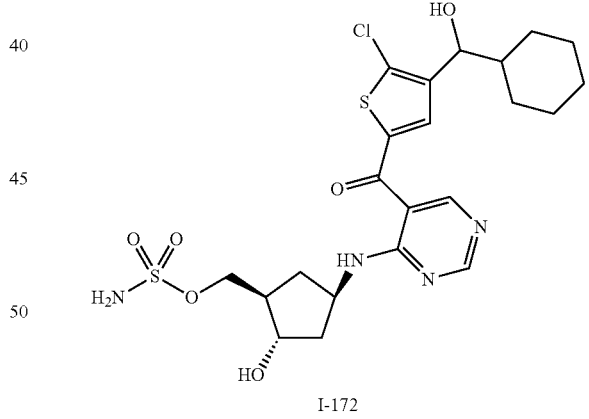
I-166
I-172
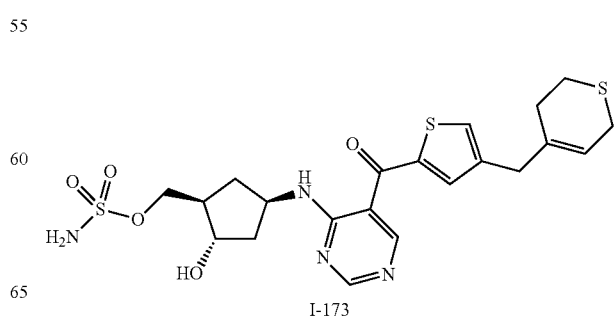
I-167
I-173

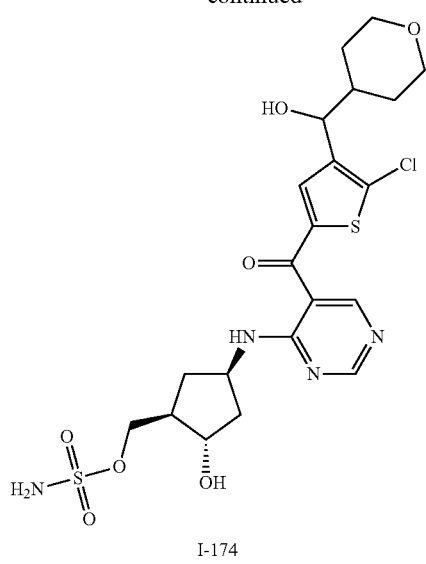
I-174
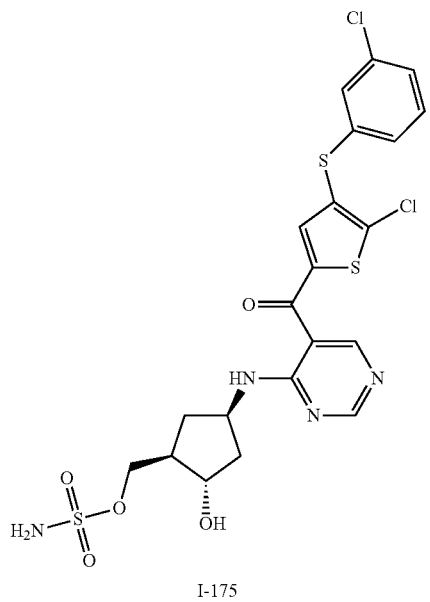
I-175
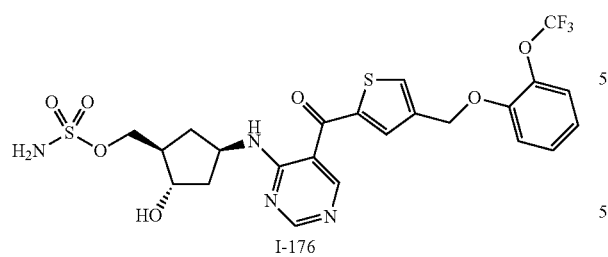
I-176
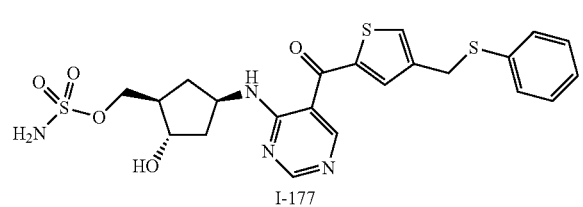
I-177
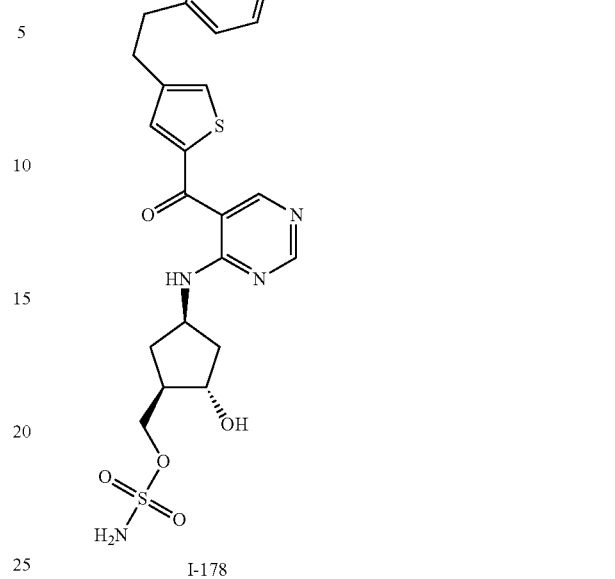
I-178
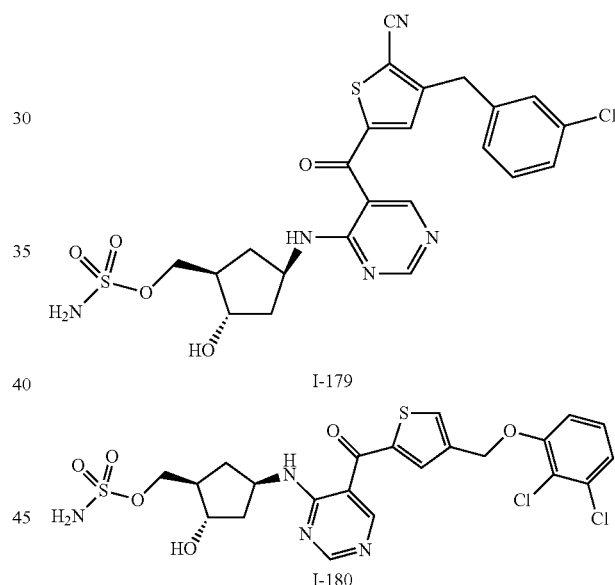
I-179
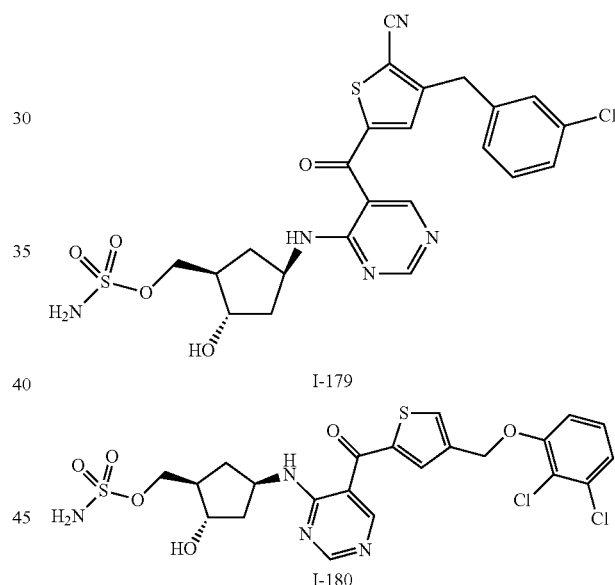
I-180
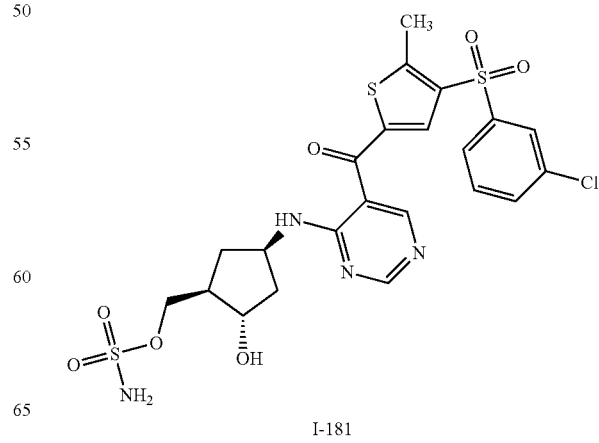
I-181

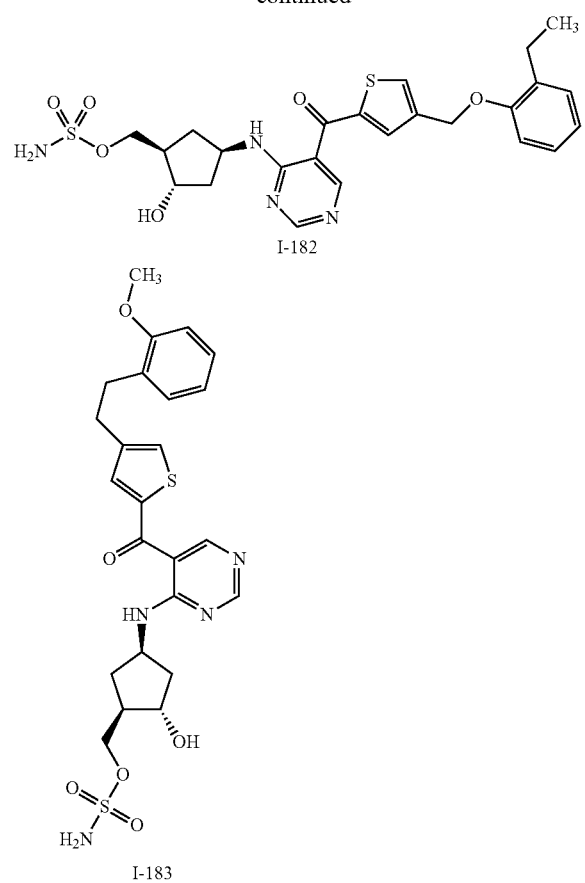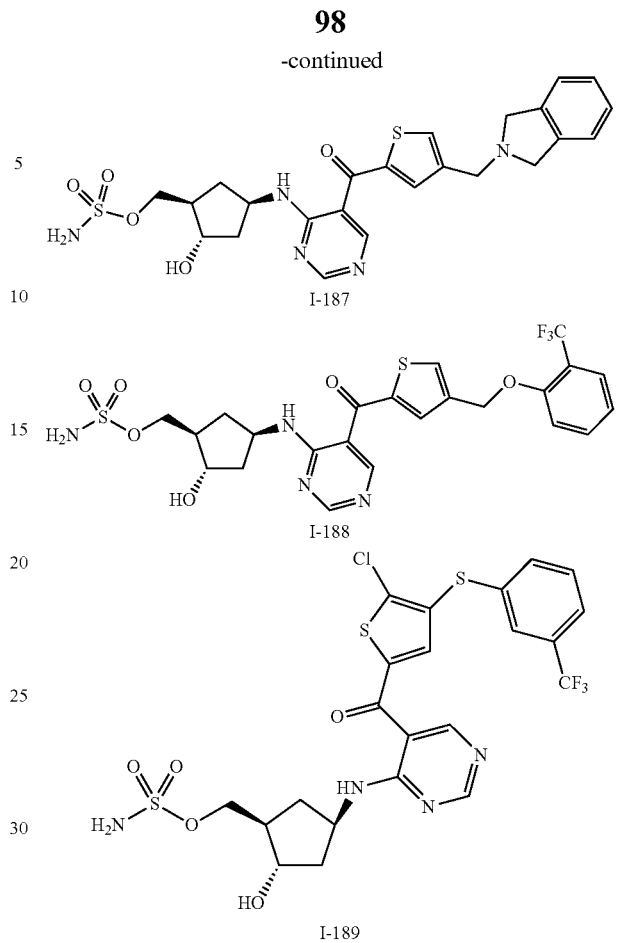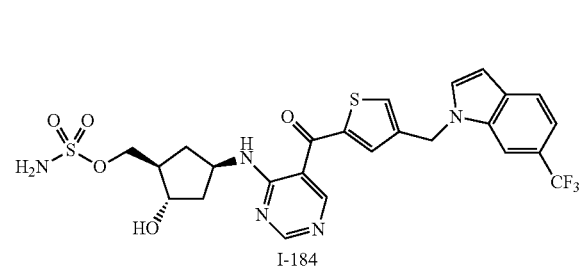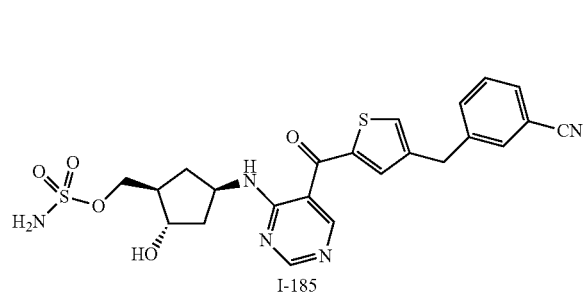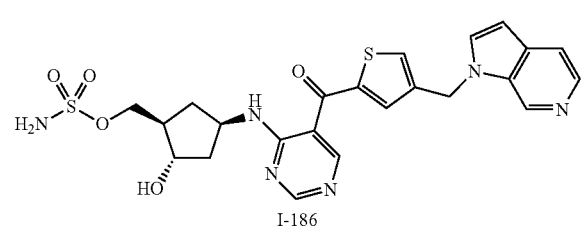

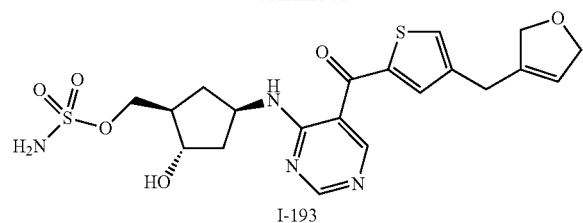
I-193
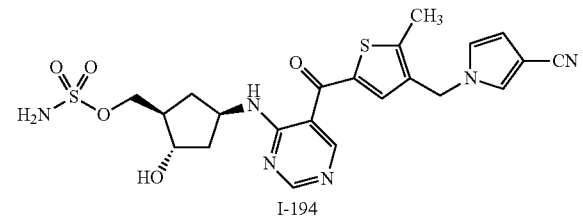
I-194
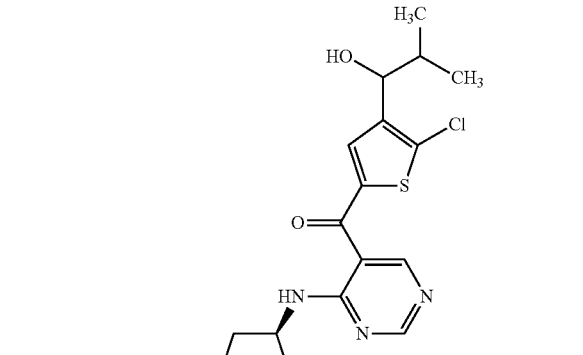
I-195
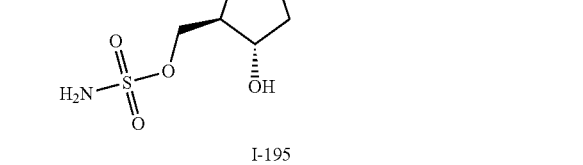
I-196
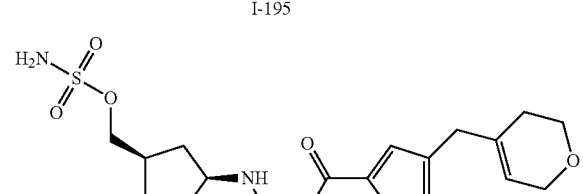
I-197
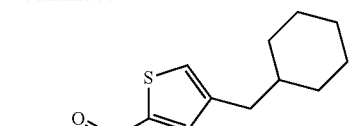
I-199
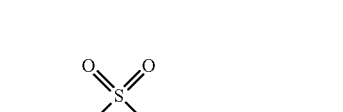
I-200
I-201
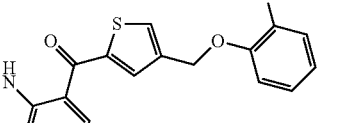
I-202

-continued
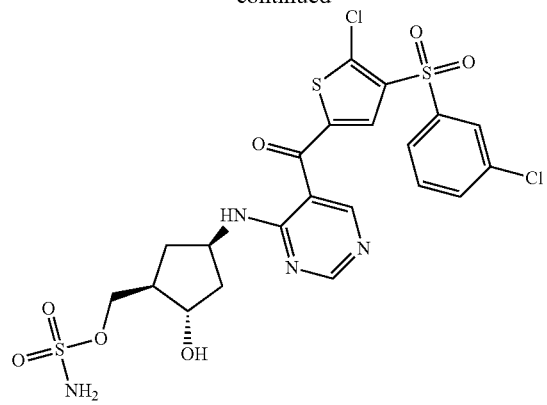
I-203
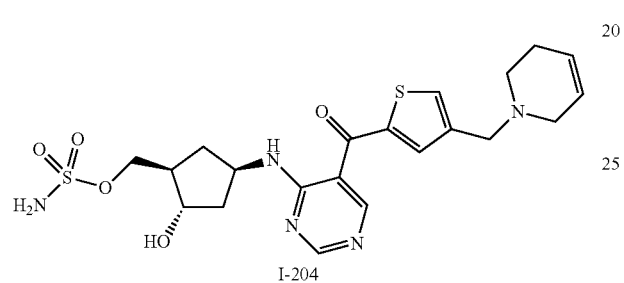
I-204
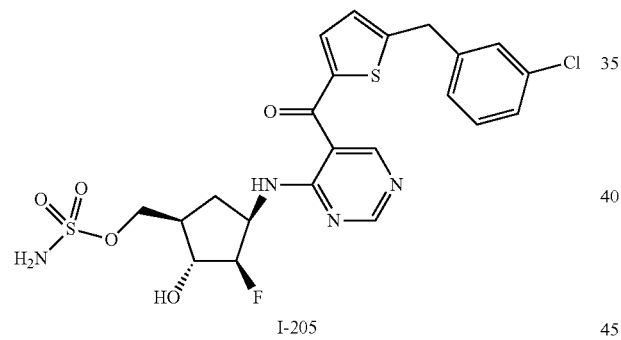
I-205
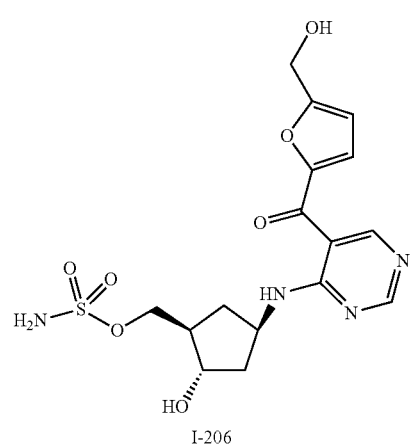
I-206
-continued
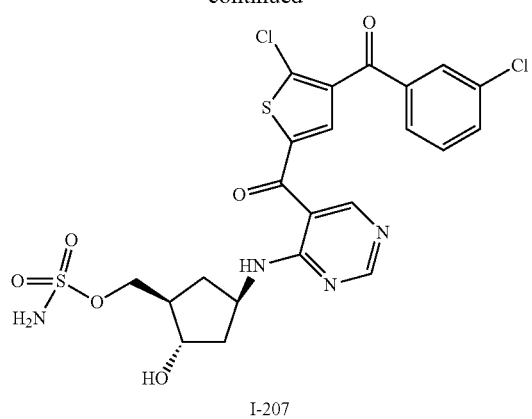
I-207
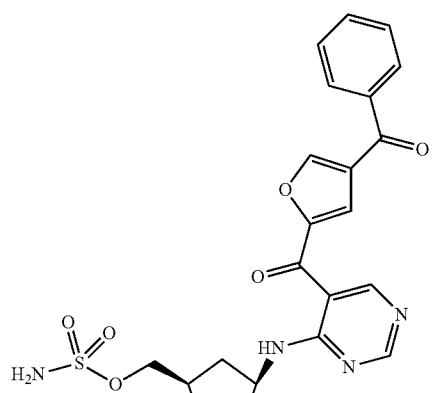
I-208
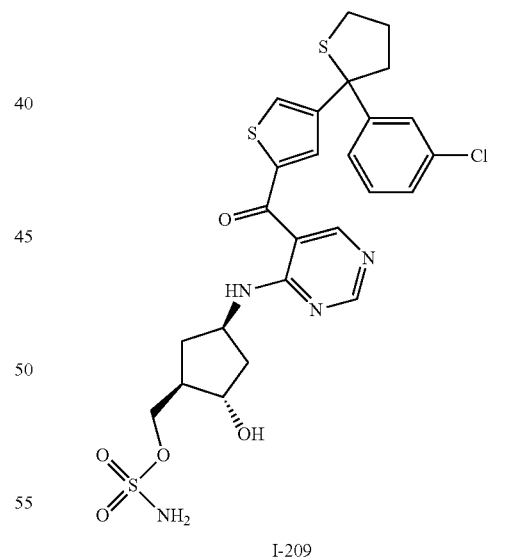
I-209
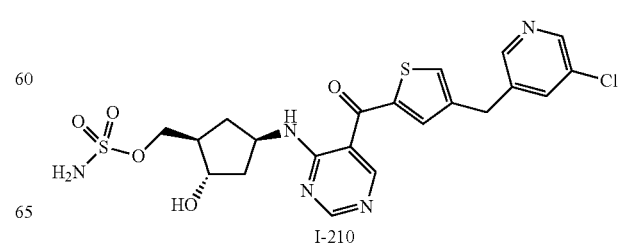
I-210

103
-continued
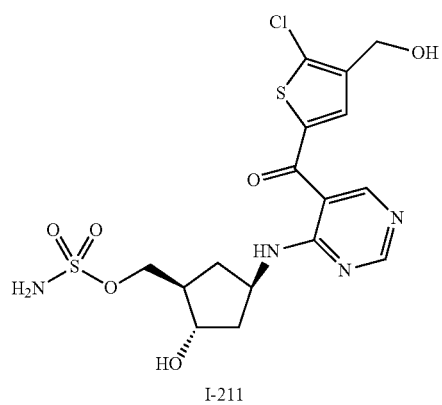
I-211
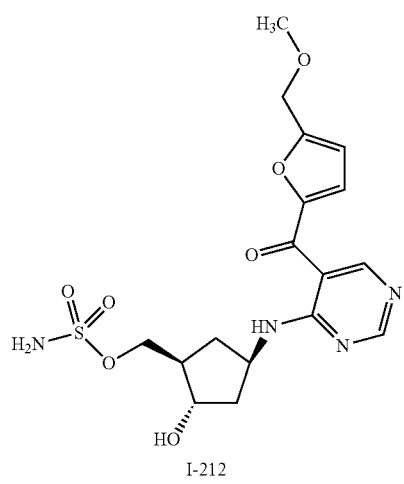
I-212
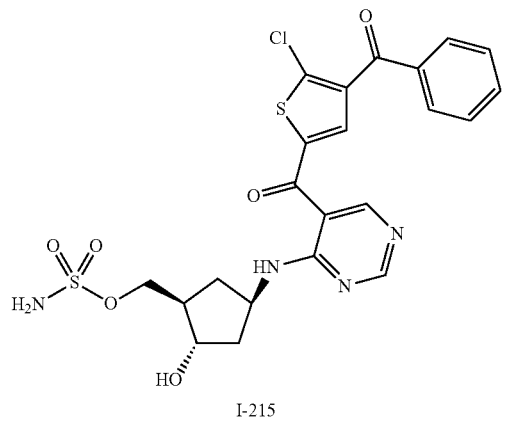
I-215
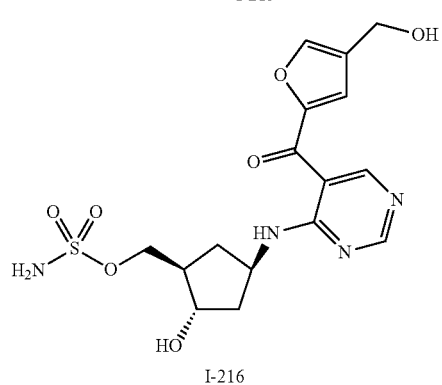
I-216
104
-continued
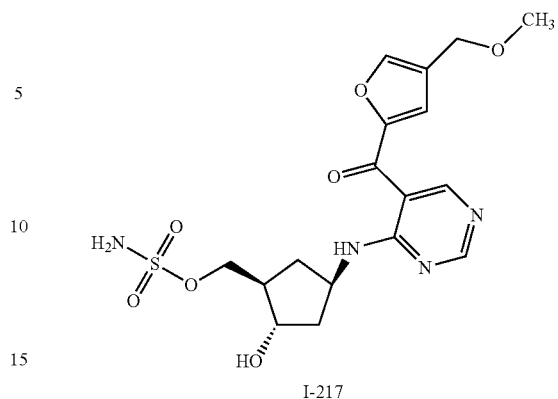
I-217
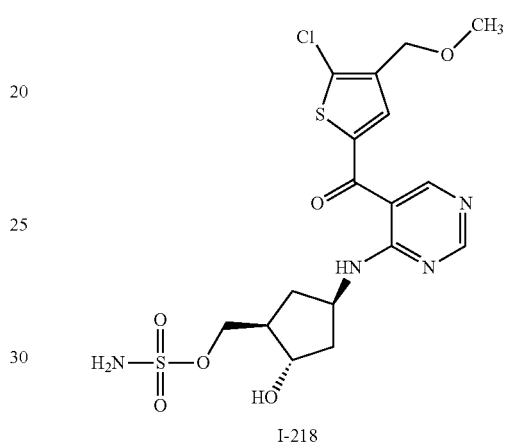
I-218
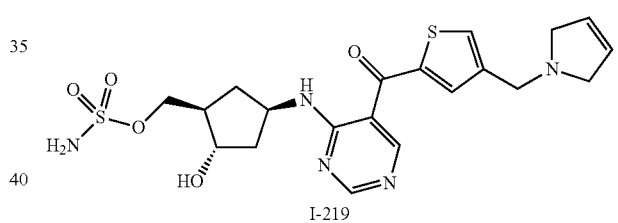
I-219
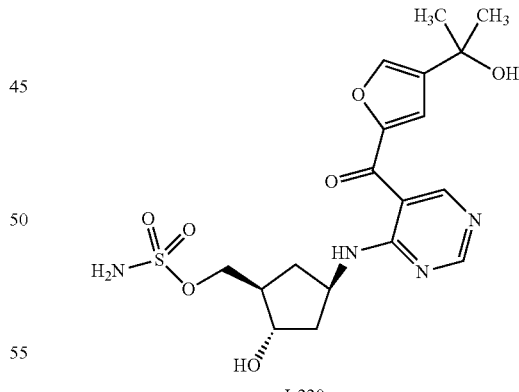
I-220
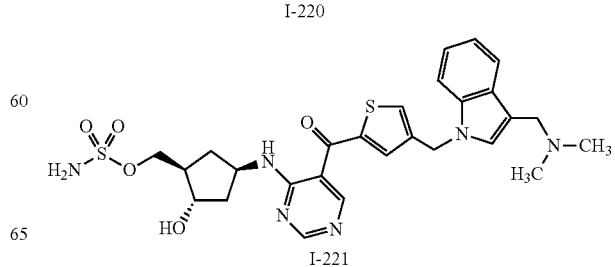
I-221

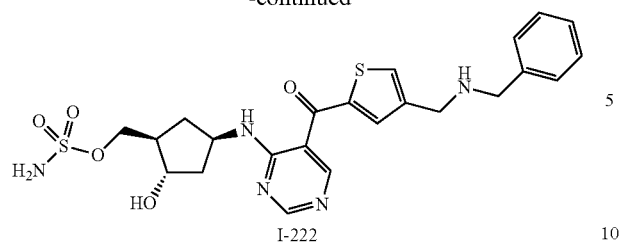
I-222
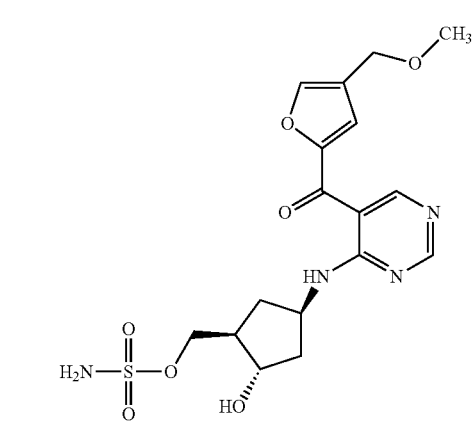
I-223
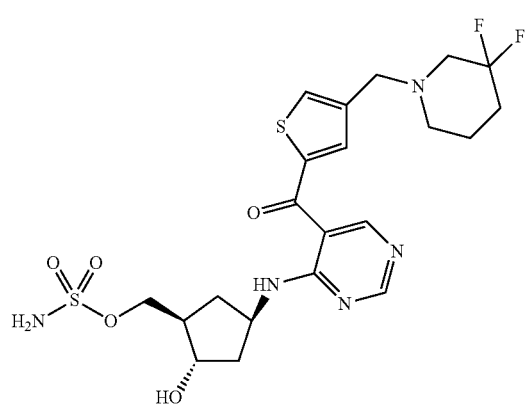
I-224
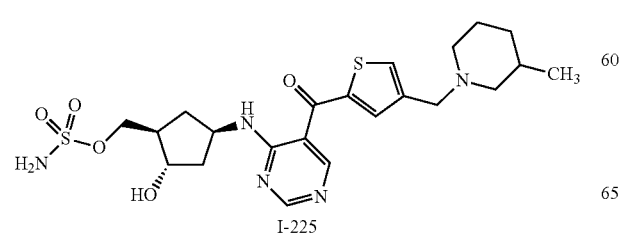
I-225
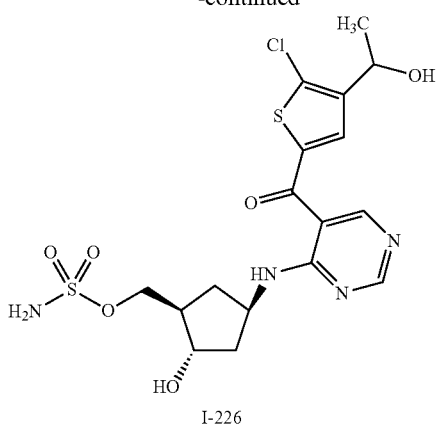
I-226
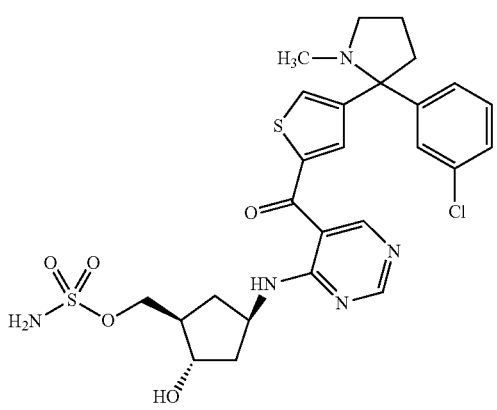
I-227
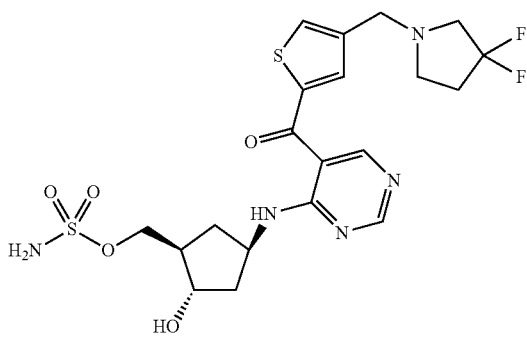
I-228
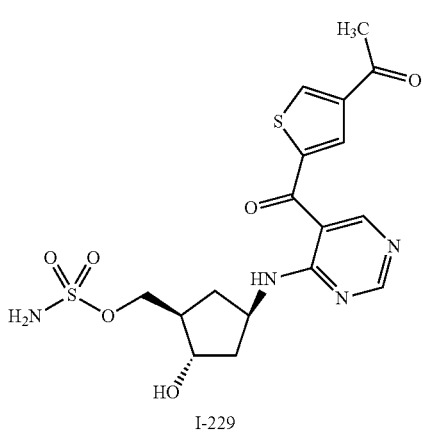
I-229

107
-continued
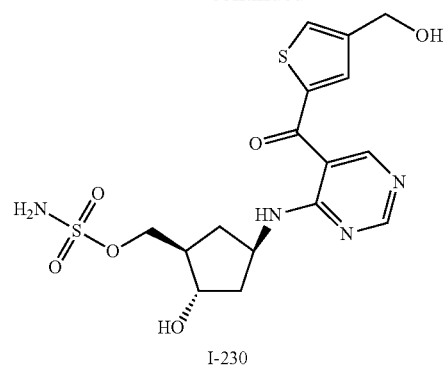
I-230
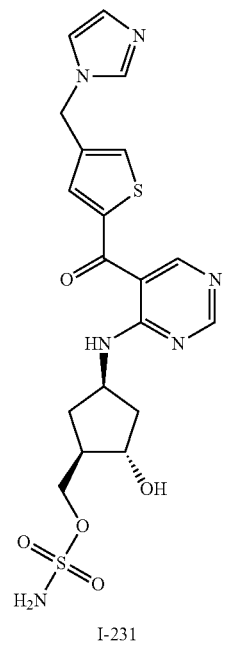
I-231
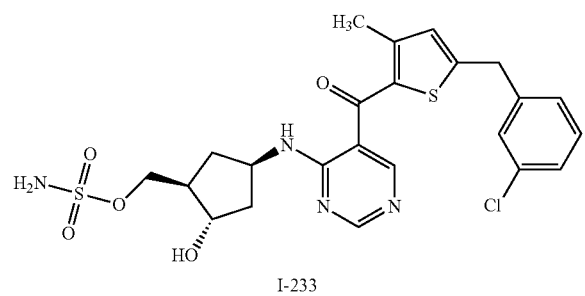
I-233
108
-continued
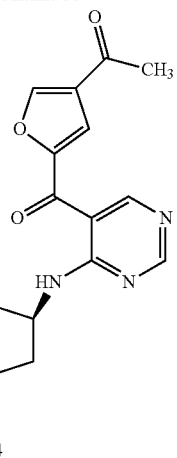
I-234
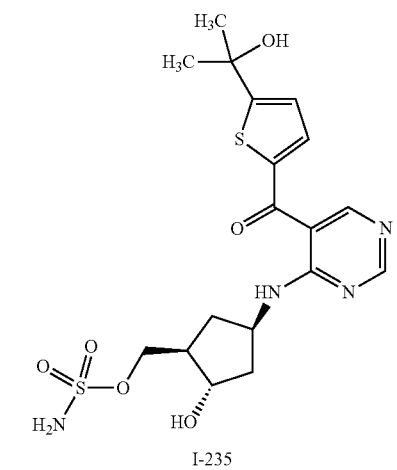
I-235
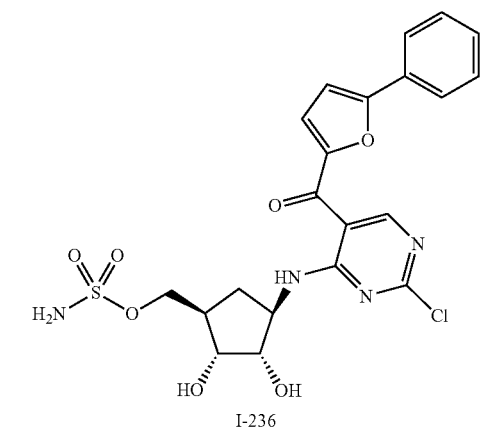
I-236
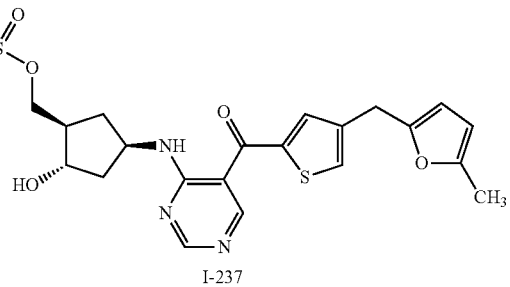
I-237

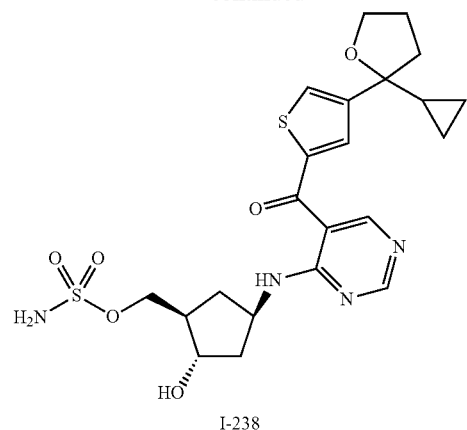
I-238
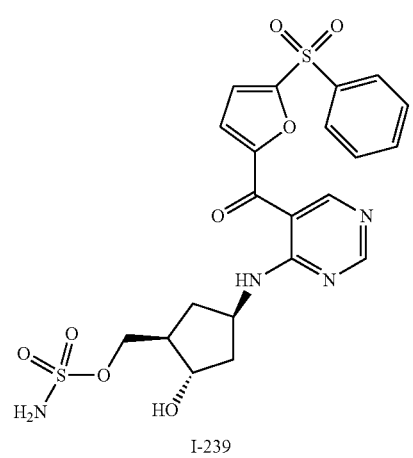
I-239
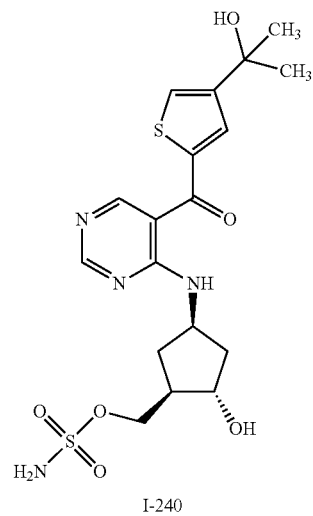
I-240
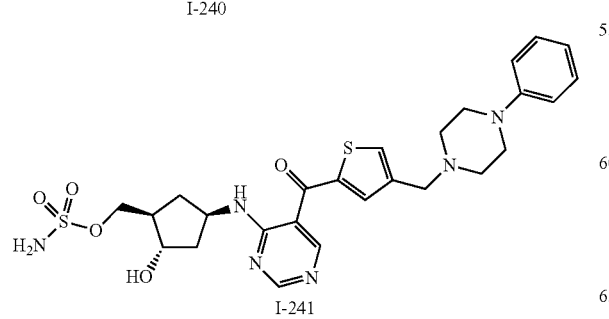
I-241
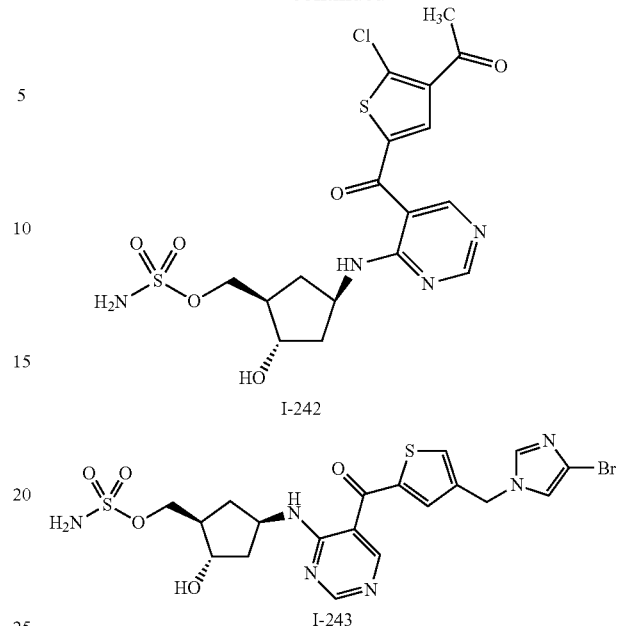
I-242
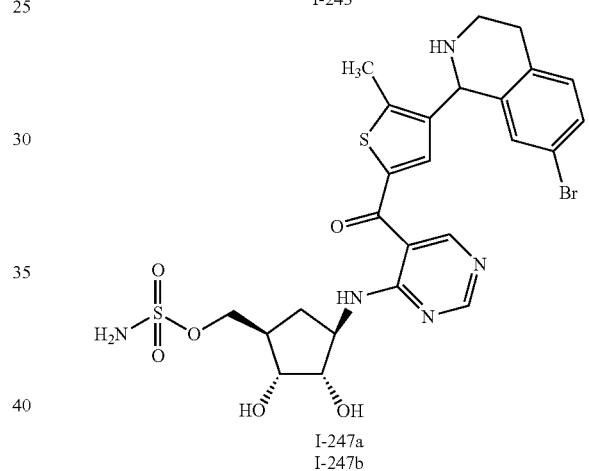
I-243
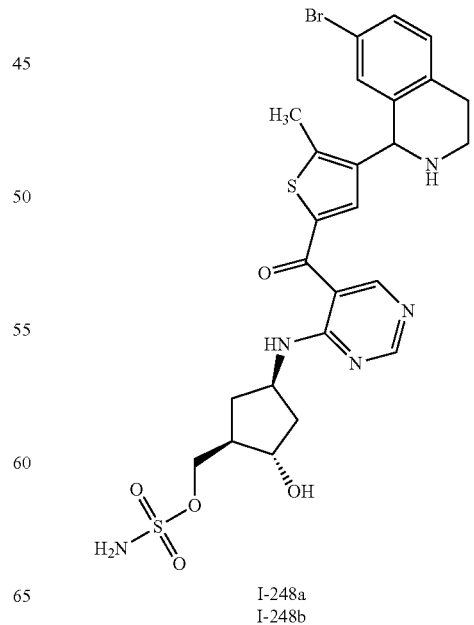
I-247a
I-247b
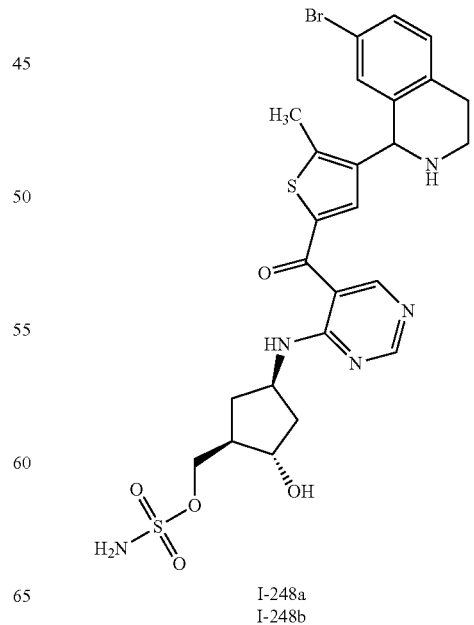
I-248a
I-248b

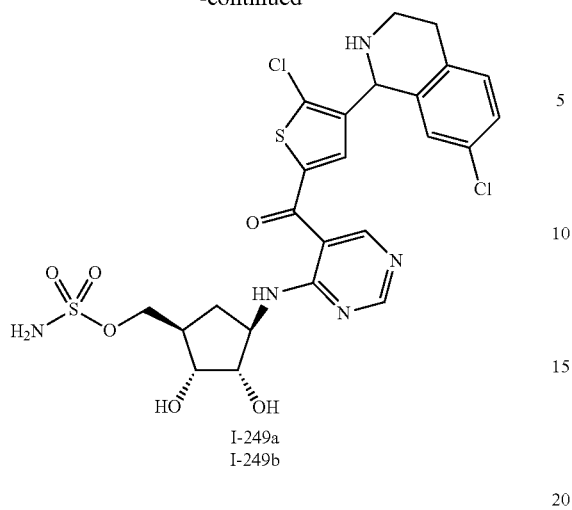
I-249a
I-249b
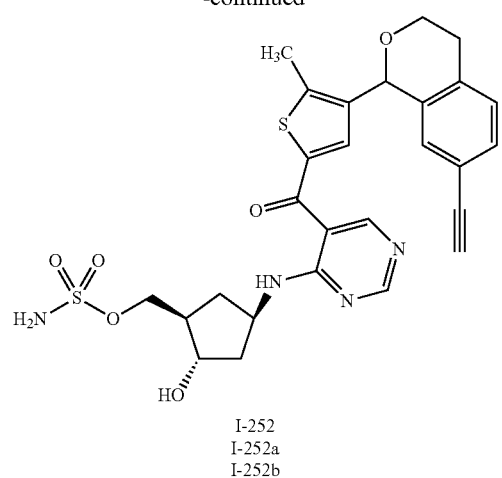
I-252
I-252a
I-252b
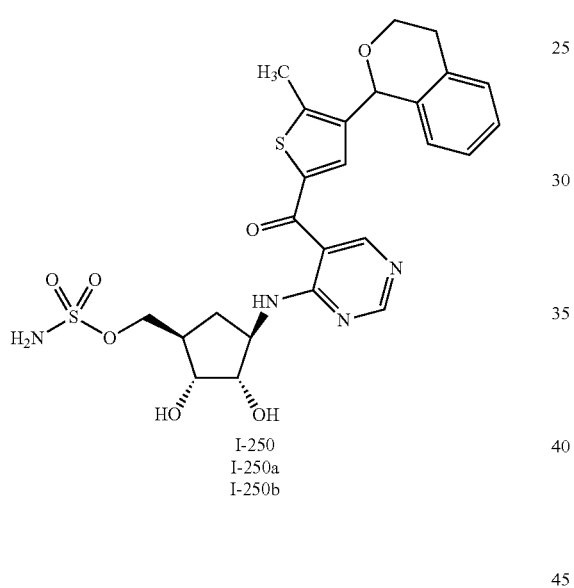
I-250
I-250a
I-250b
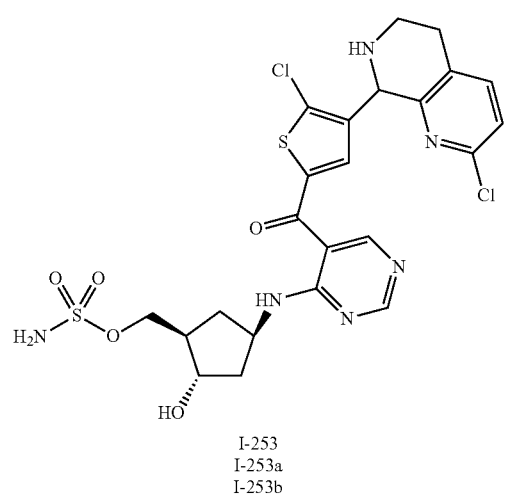
I-253
I-253a
I-253b
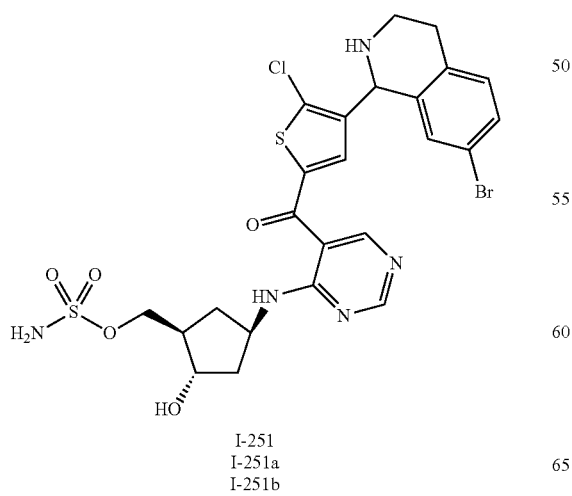
I-251
I-251a
I-251b
I-254
I-254a
I-254b

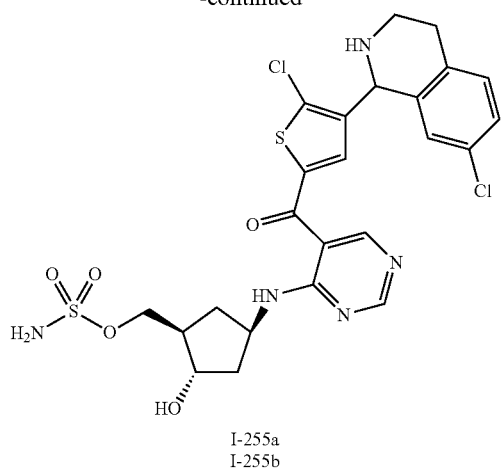
I-255a
I-255b
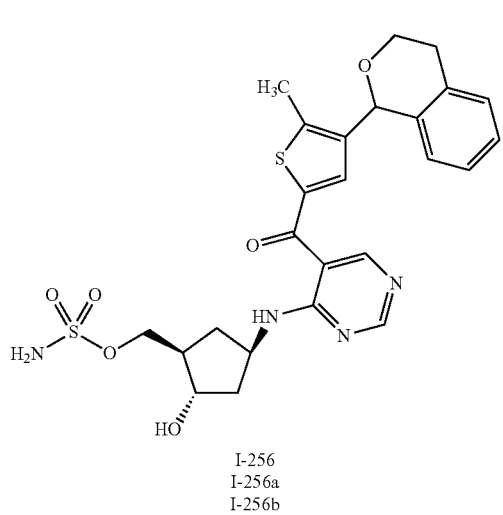
I-256
I-256a
I-256b
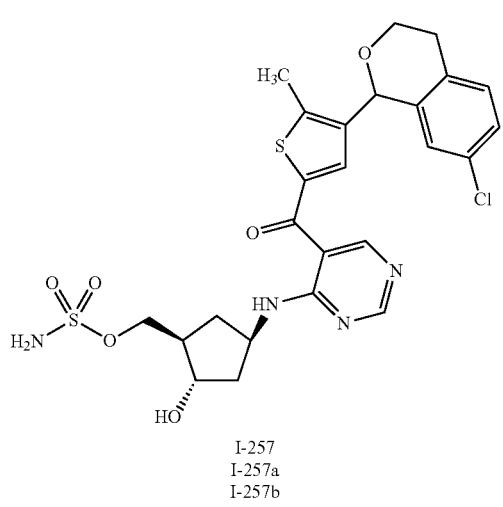
I-257
I-257a
I-257b
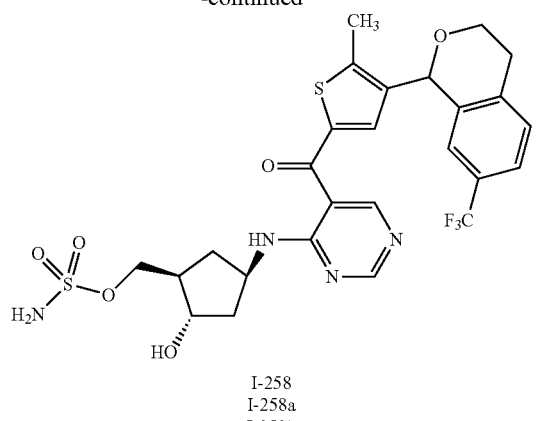
I-258
I-258a
I-258b
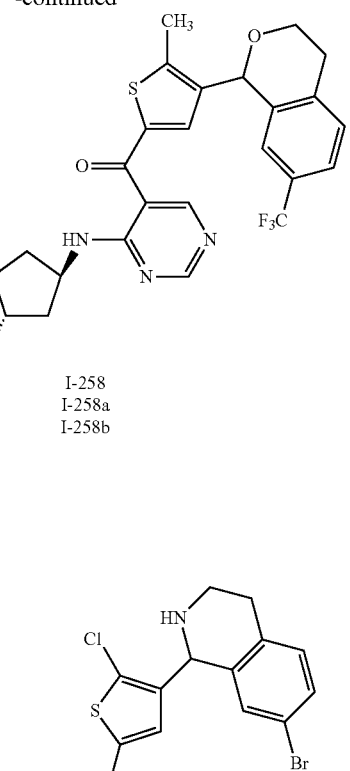
I-259
I-259a
I-259b
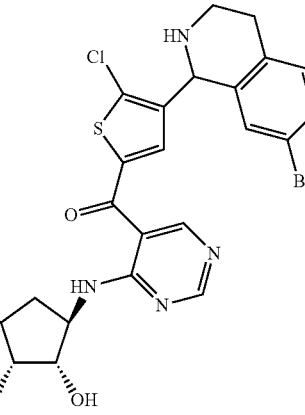
I-260
I-260a
I-260b

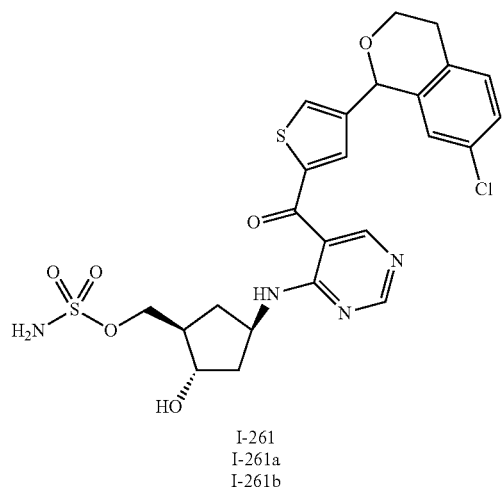
I-261
I-261a
I-261b
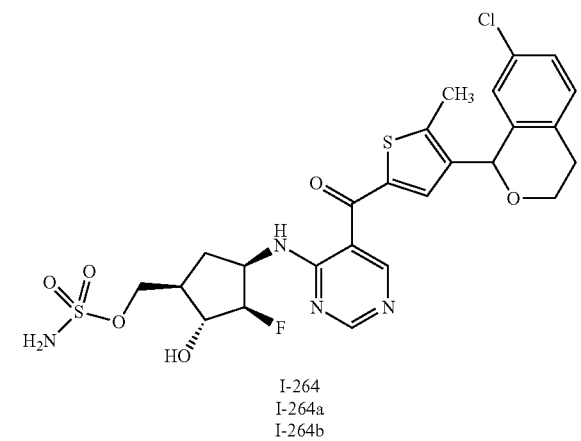
I-264
I-264a
I-264b
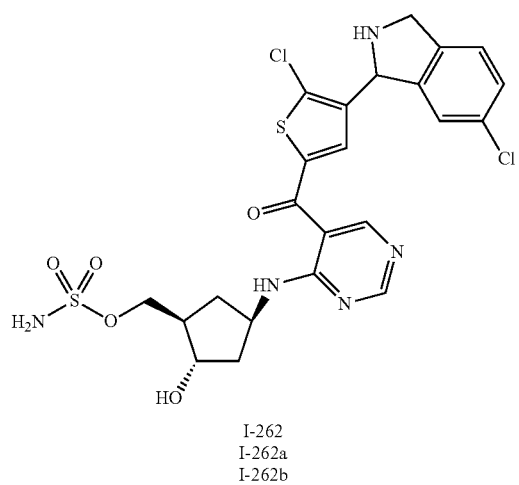
I-262
I-262a
I-262b
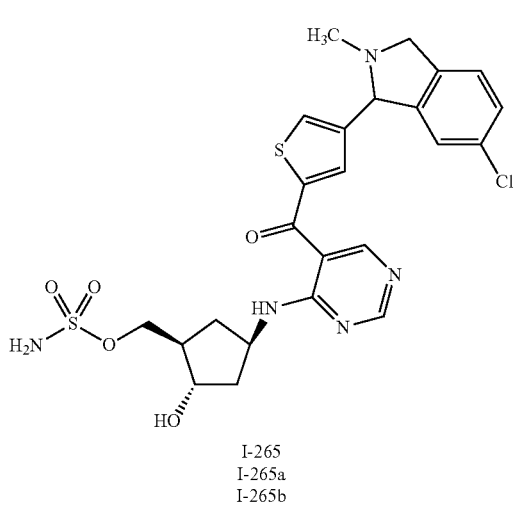
I-265
I-265a
I-265b
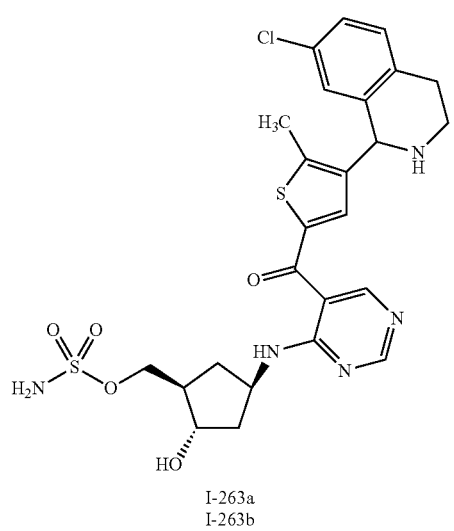
I-263a
I-263b
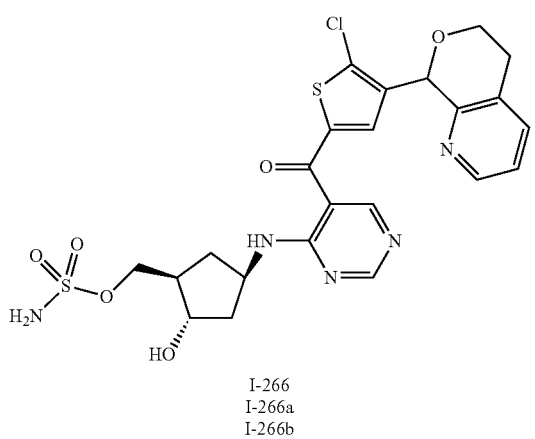
I-266
I-266a
I-266b

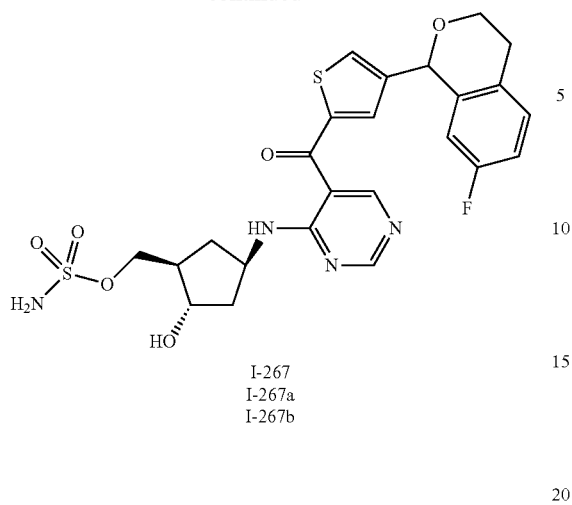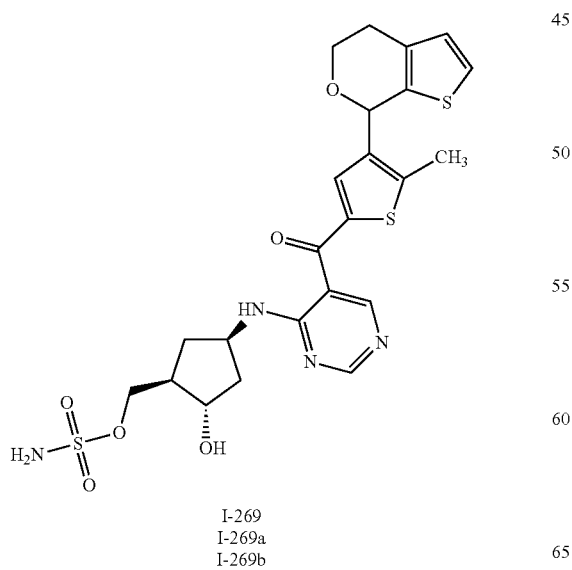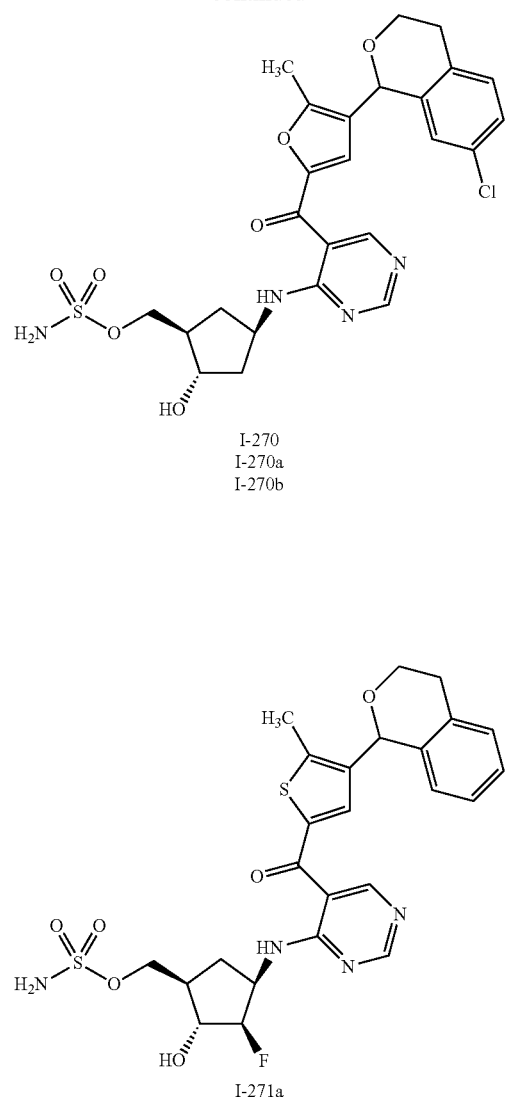

-continued
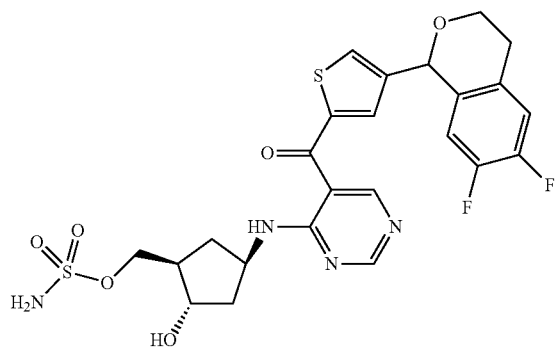
I-273 a
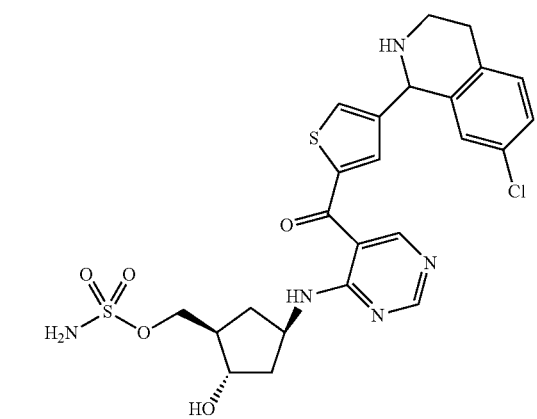
I-274
I-274a
I-274b
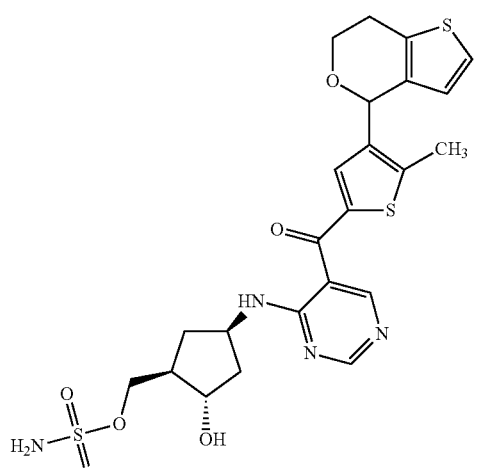
I-275
-continued
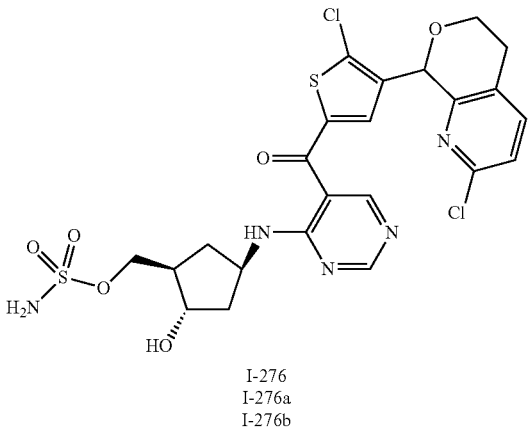
I-276
I-276a
I-276b
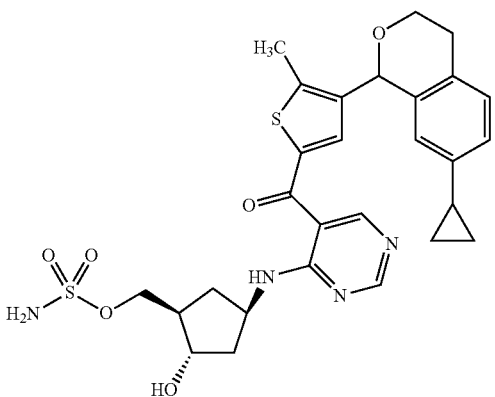
I-277
I-277a
I-277b
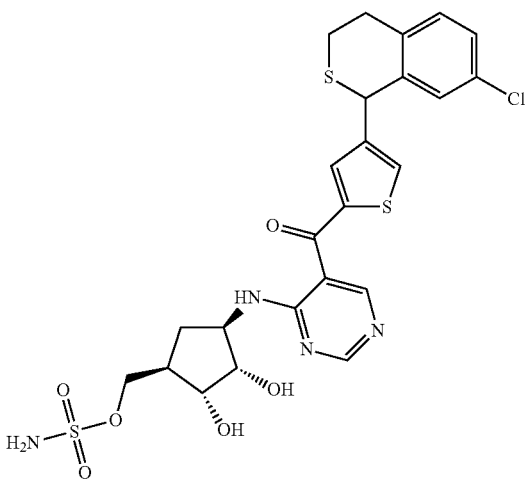
I-278
I-278a
I-278b

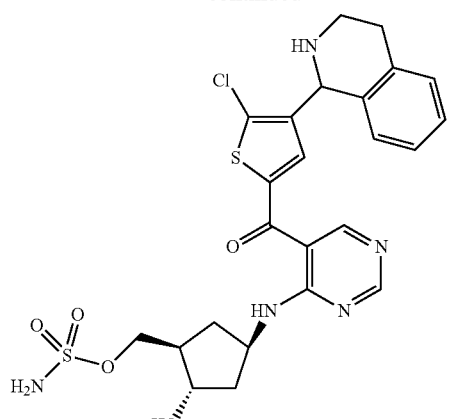
I-279
I-279a
I-279b
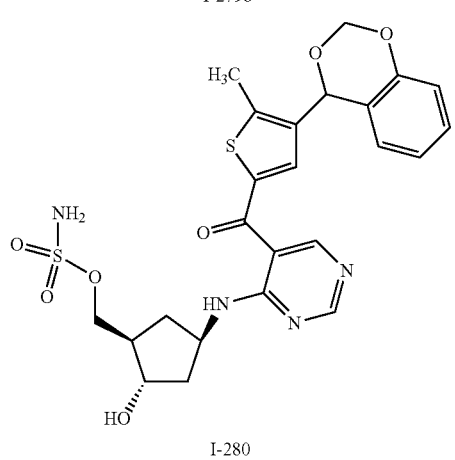
I-280
I-280a
I-280b
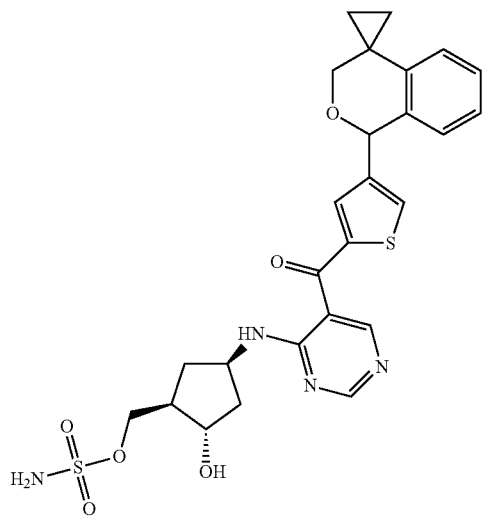
I-281
I-281a
I-281b
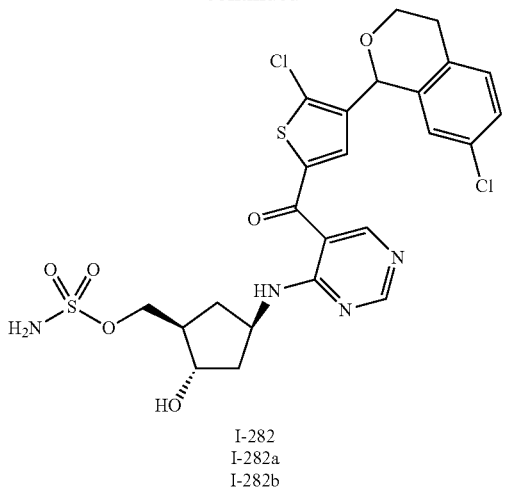
I-282
I-282a
I-282b
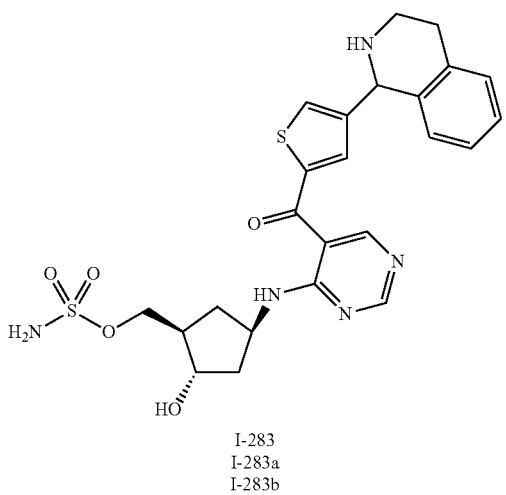
I-283
I-283a
I-283b
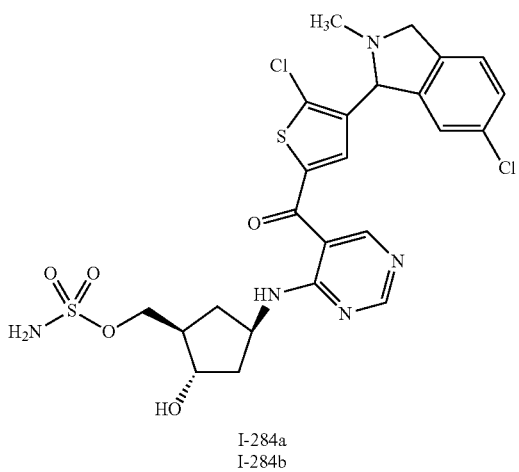
I-284a
I-284b

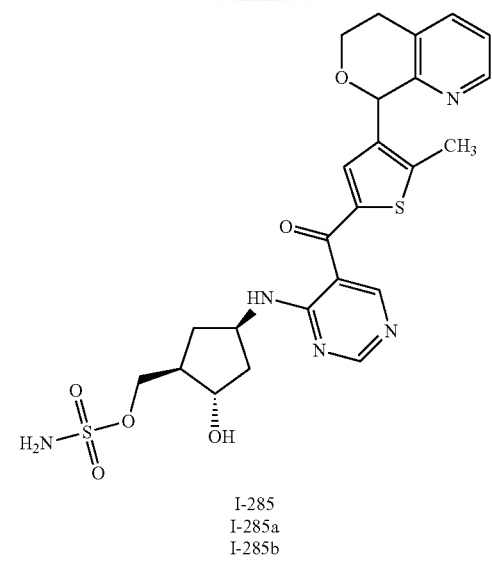
I-285
I-285a
I-285b
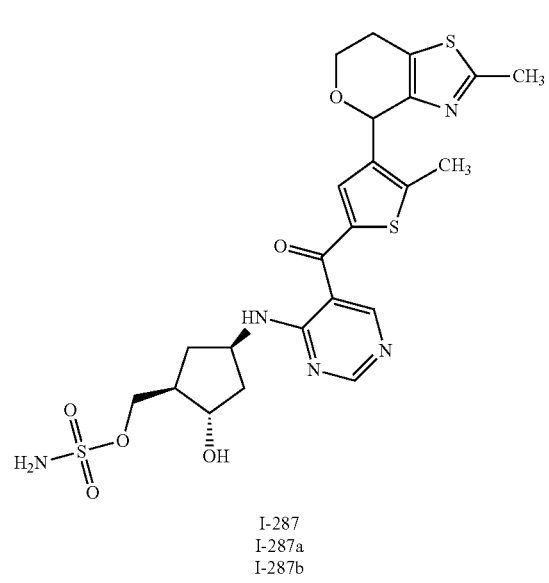
I-286
I-286a
I-286b
I-287
I-287a
I-287b
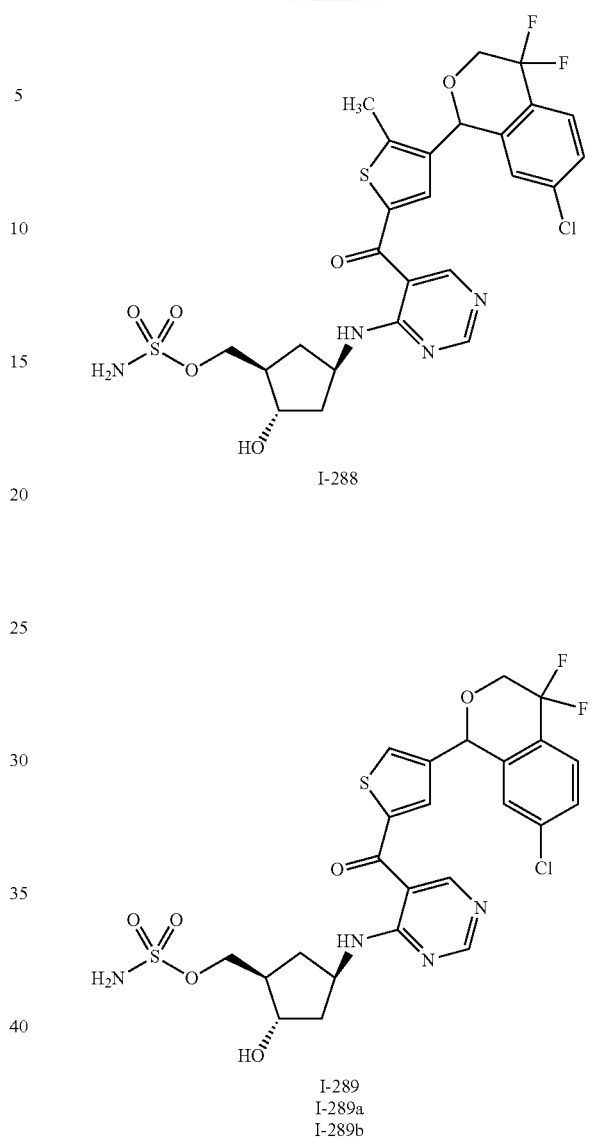
I-288
I-289
I-289a
I-289b
I-290a
I-290b

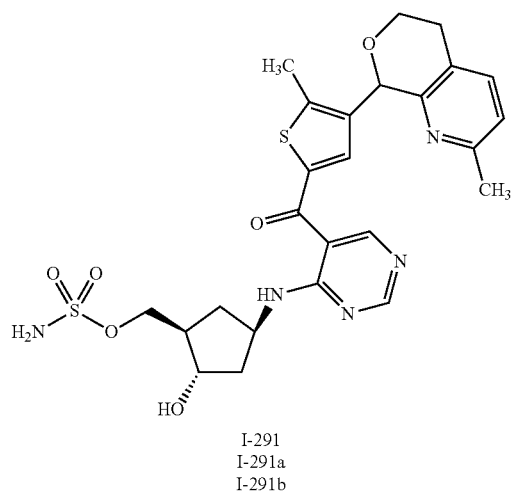
I-291
I-291a
I-291b
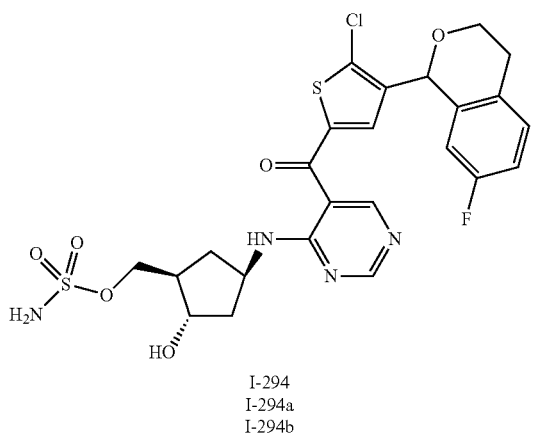
I-294
I-294a
I-294b
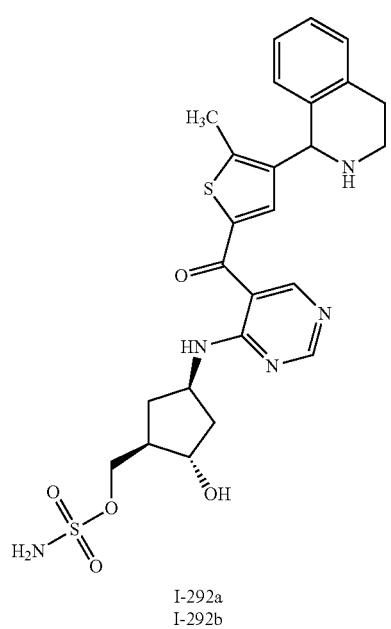
I-292a
I-292b
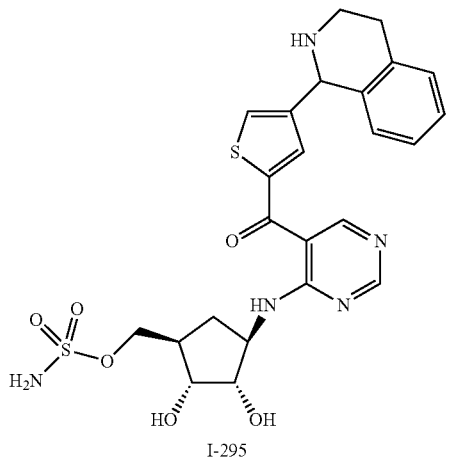
I-295
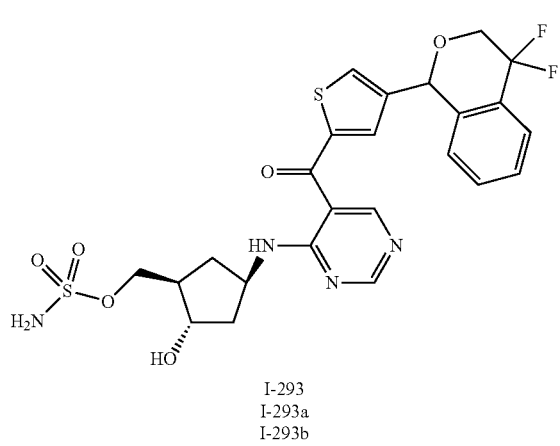
I-293
I-293a
I-293b
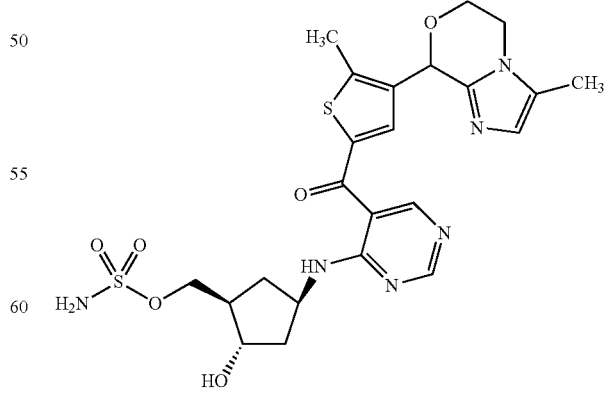
I-296

127
-continued
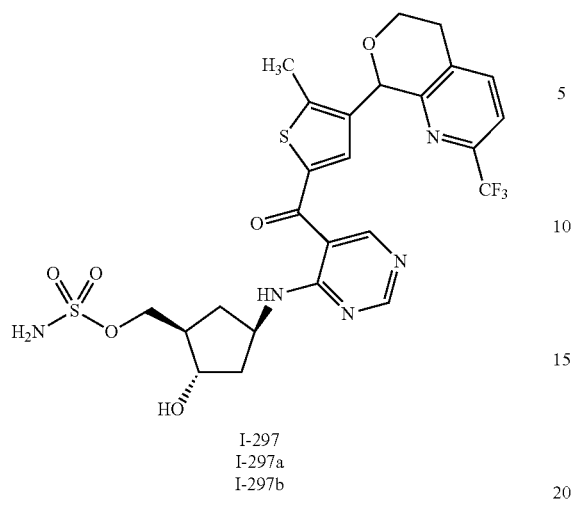
I-297
I-297a
I-297b
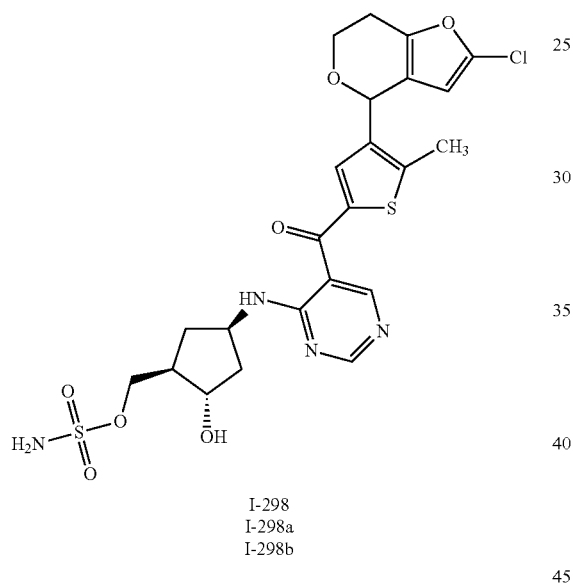
I-298
I-298a
I-298b
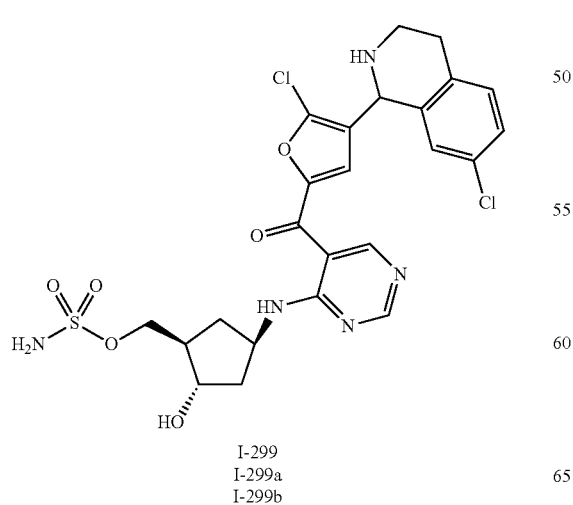
I-299
I-299a
I-299b
128
-continued
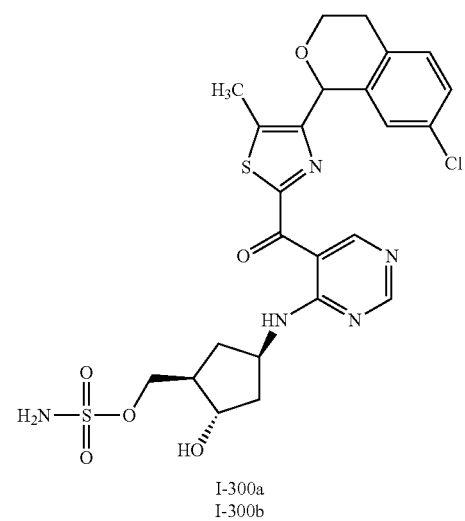
I-300a
I-300b
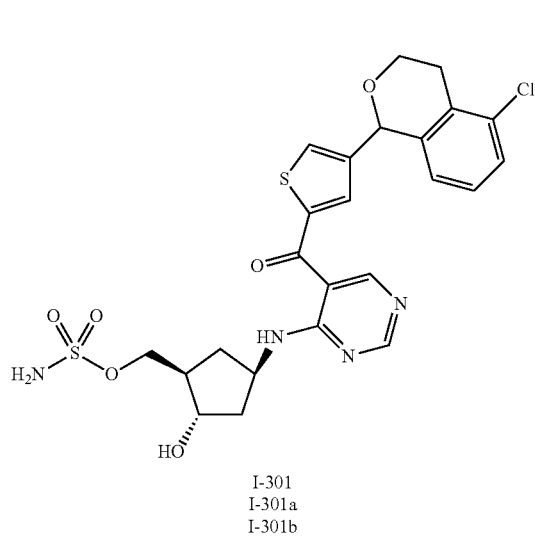
I-301
I-301a
I-301b
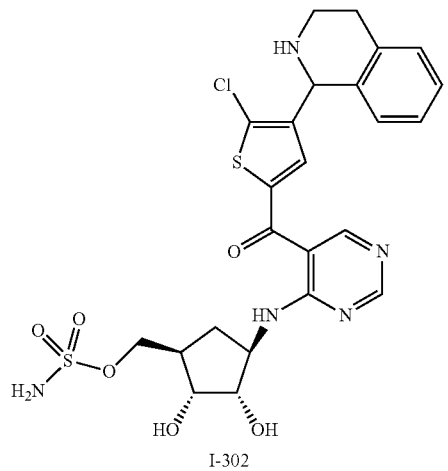
I-302

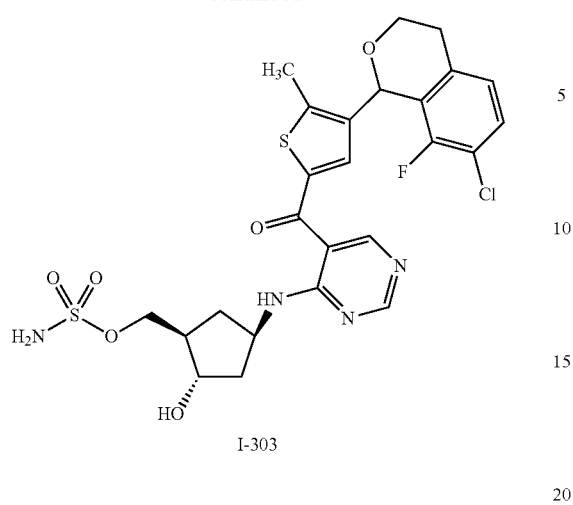
I-303
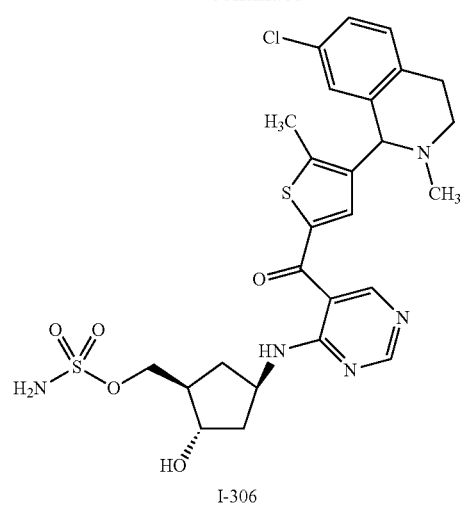
I-306
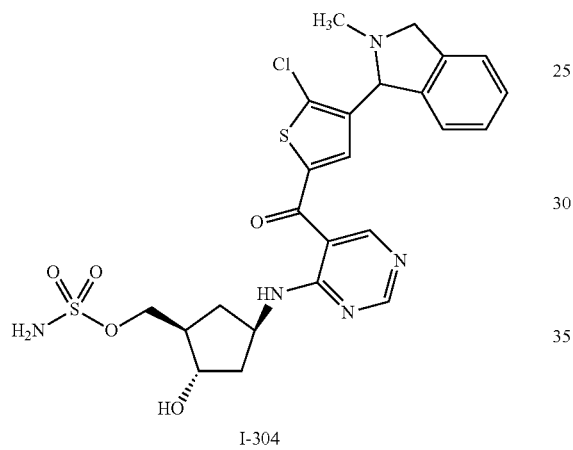
I-304
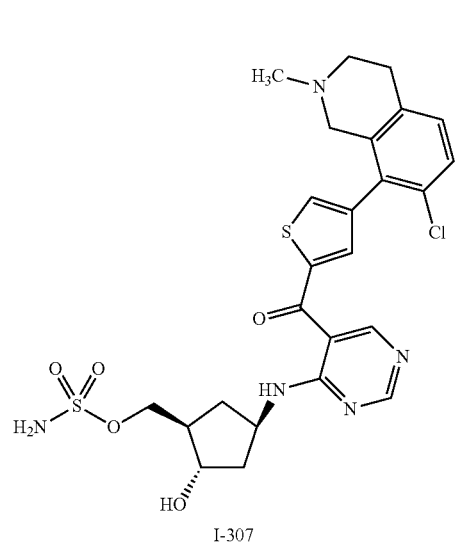
I-307
I-307a
I-307b
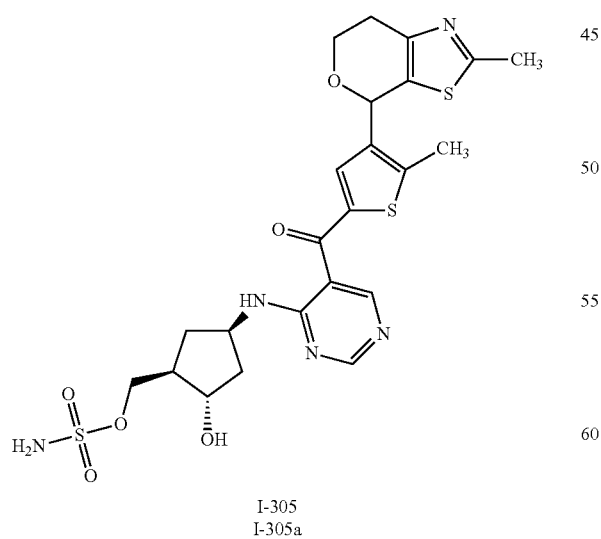
I-305
I-305a
I-305b
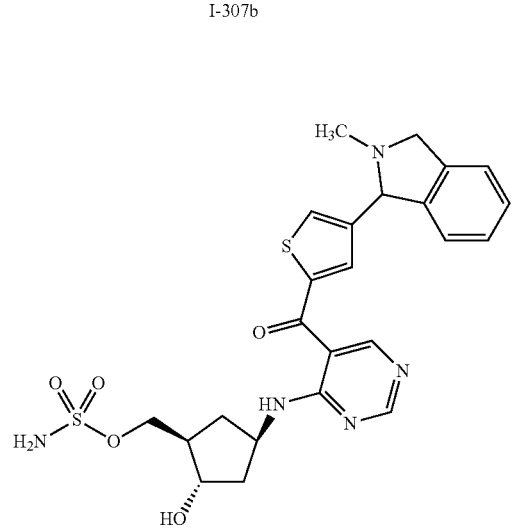
I-308

131
-continued
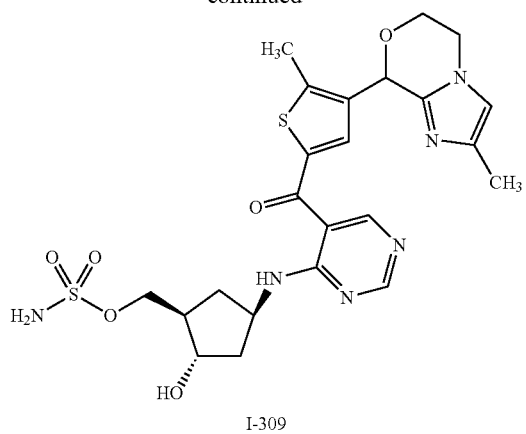
I-309
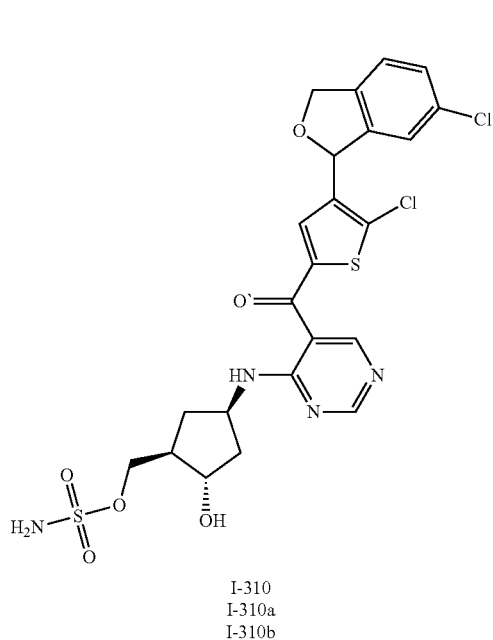
I-310
I-310a
I-310b
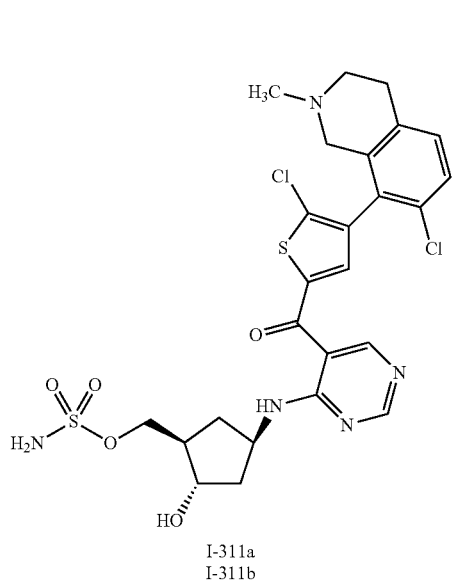
I-311a
I-311b
132
-continued
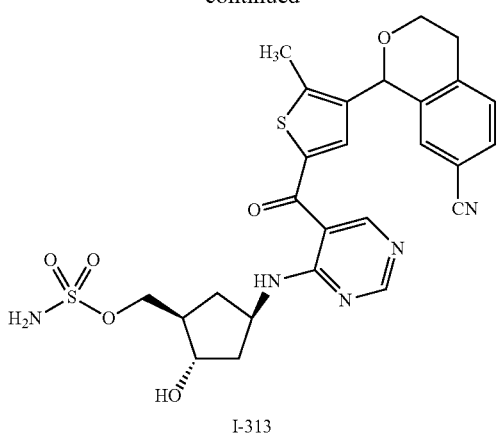
I-313
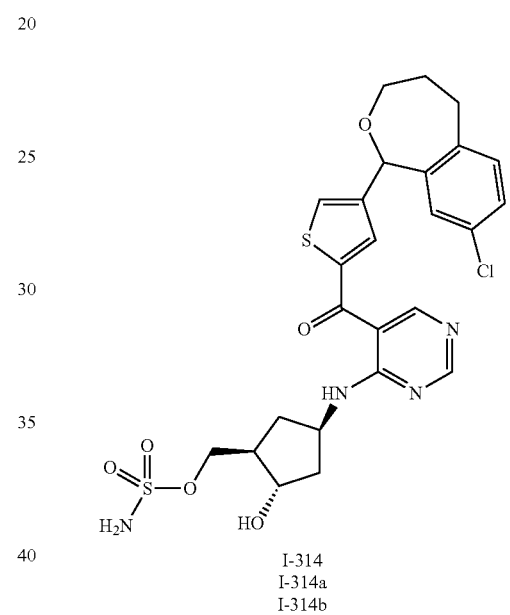
I-314
I-314a
I-314b
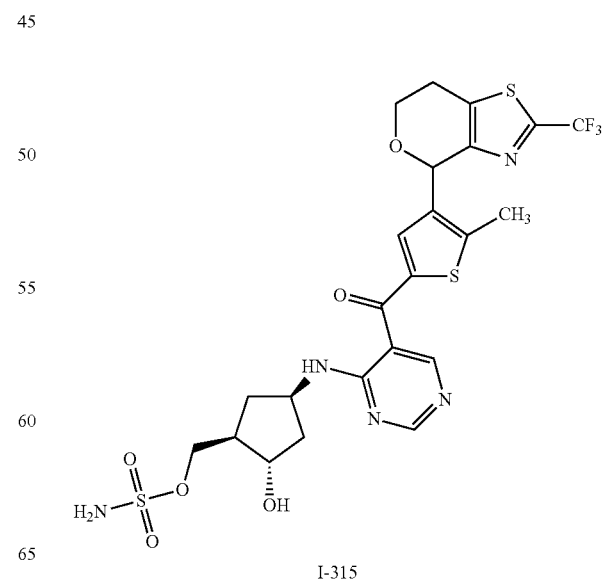
I-315

133
-continued
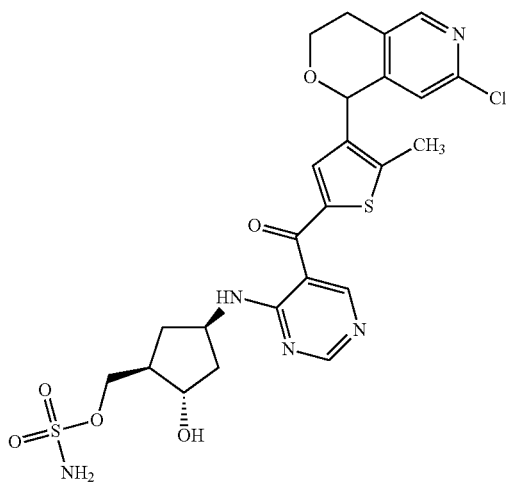
I-316
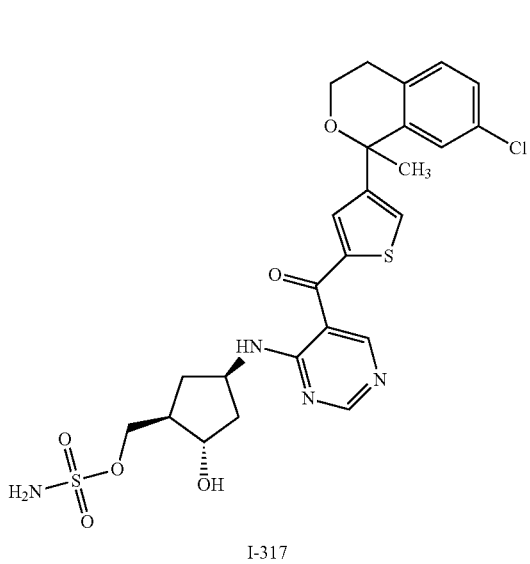
I-317
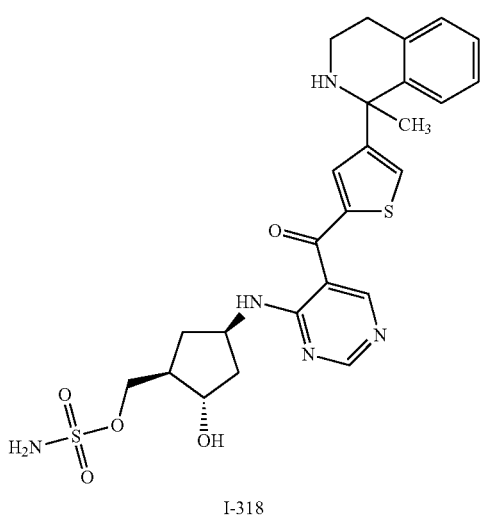
I-318
134
-continued
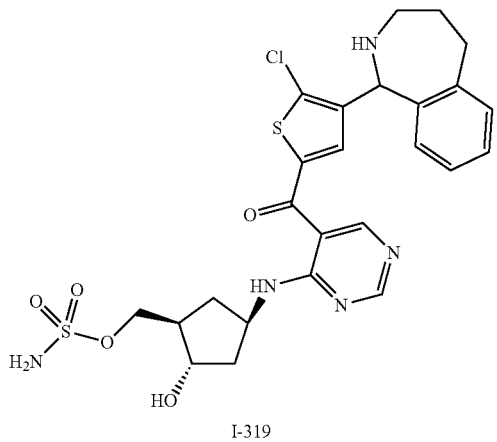
I-319
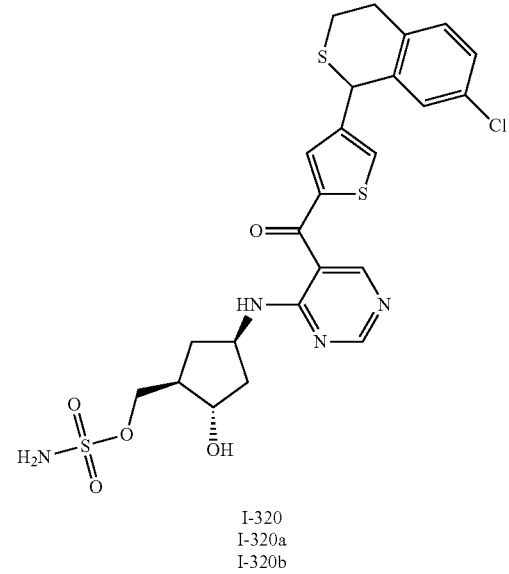
I-320
I-320a
I-320b
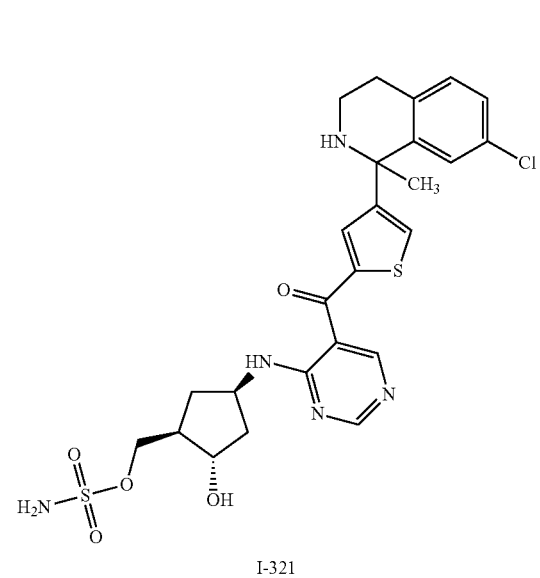
I-321

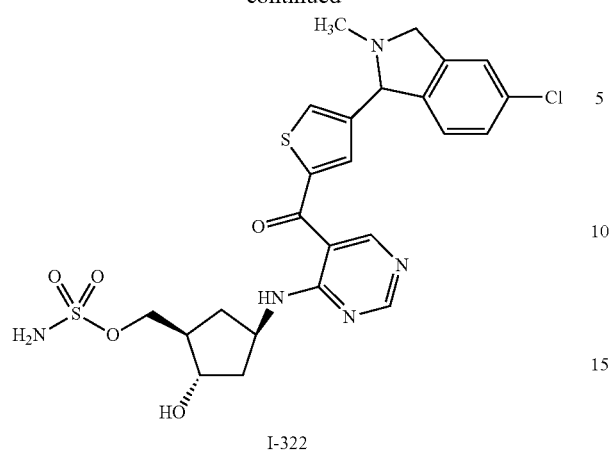
I-322
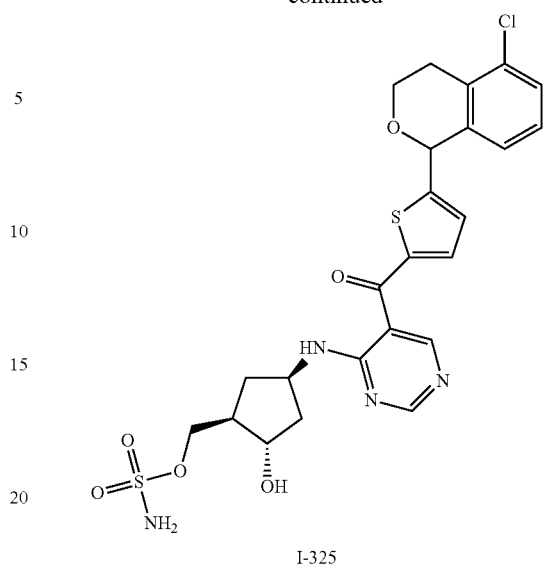
I-325
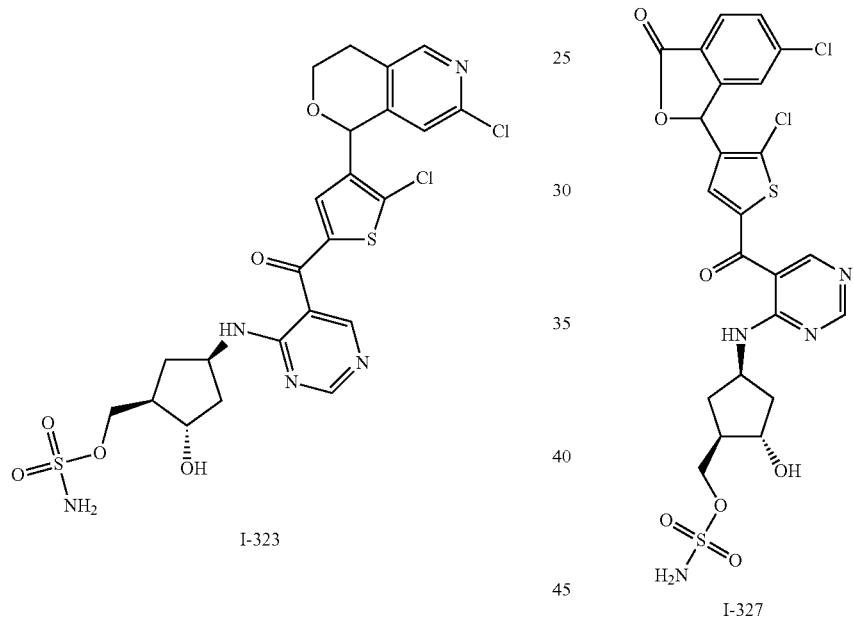
I-323
I-327
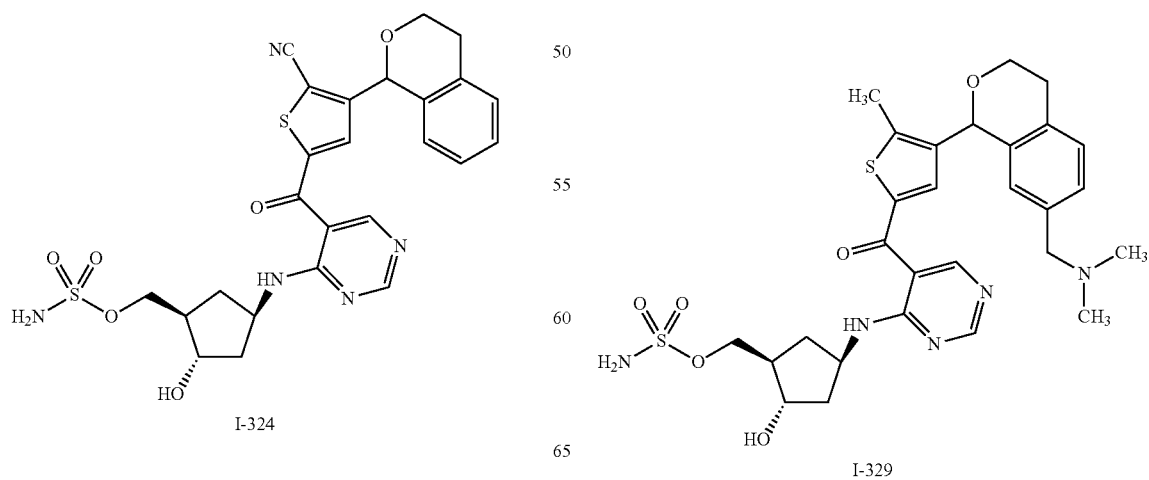
I-324
I-329

137
-continued
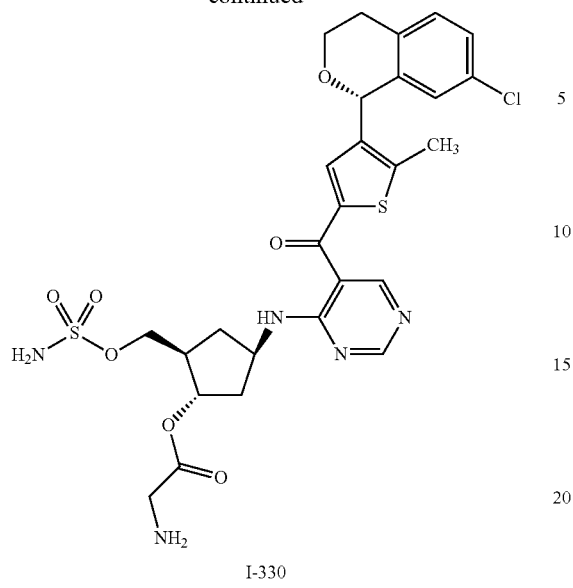
I-330
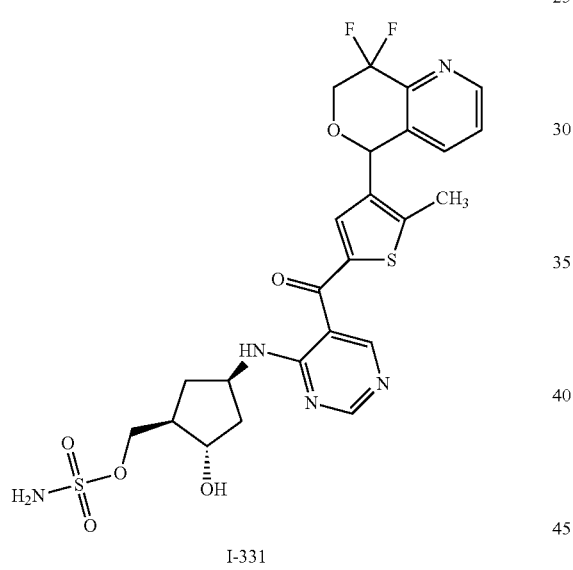
I-331
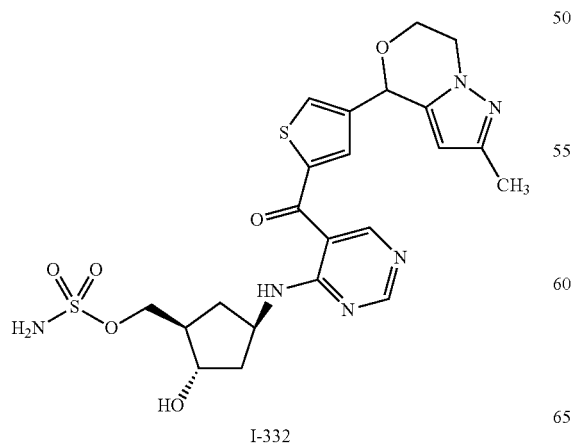
I-332
138
-continued
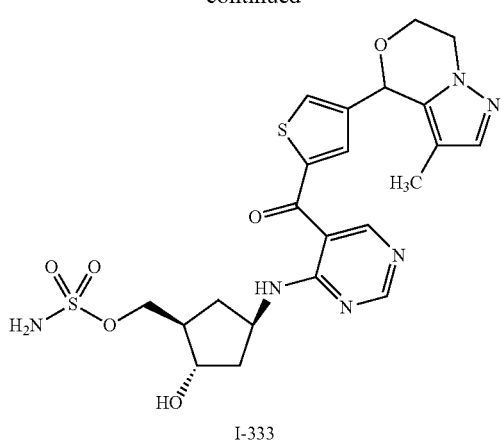
I-333
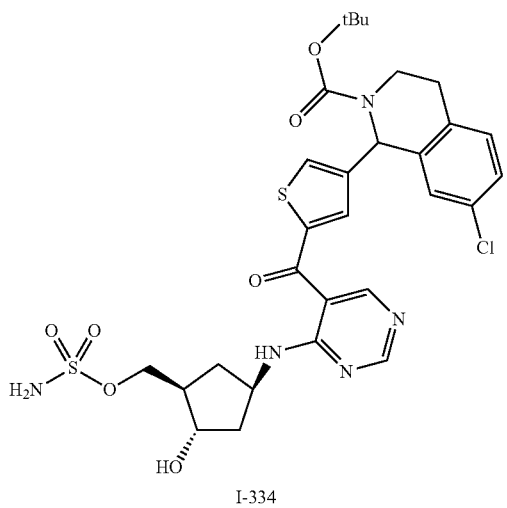
I-334
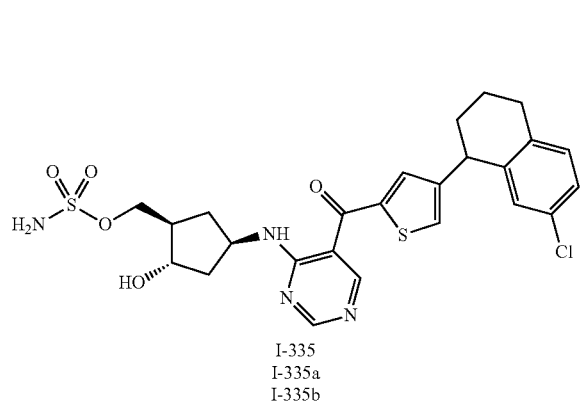
I-335
I-335a
I-335b

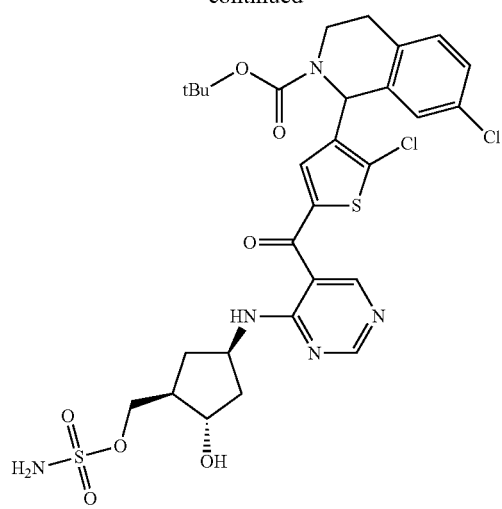
I-336
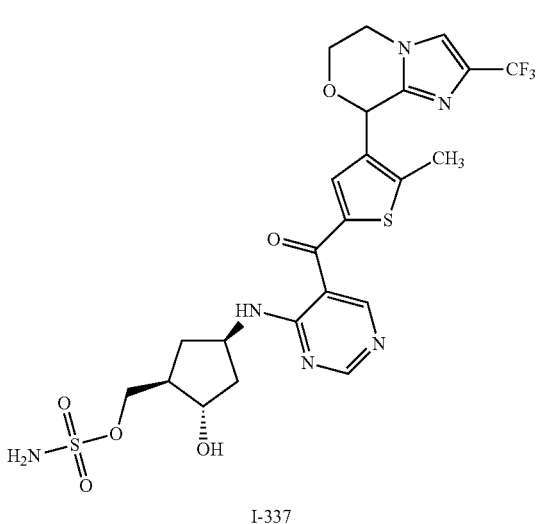
I-337
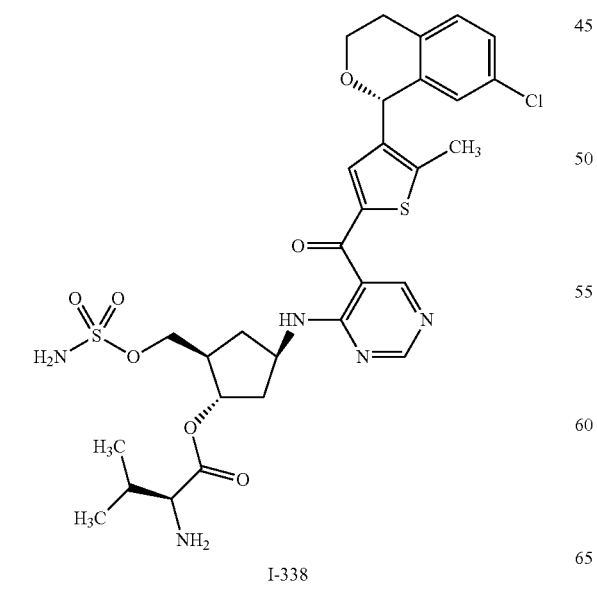
I-338
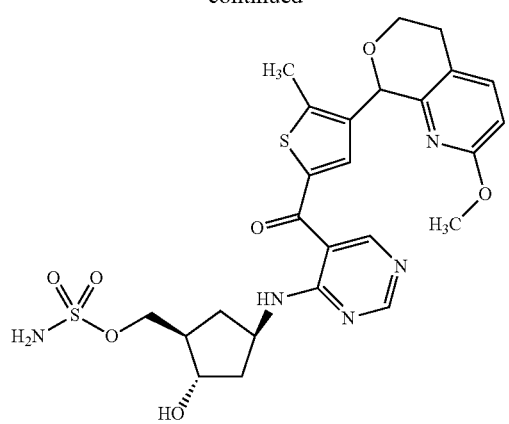
I-339
I-339a
I-339b
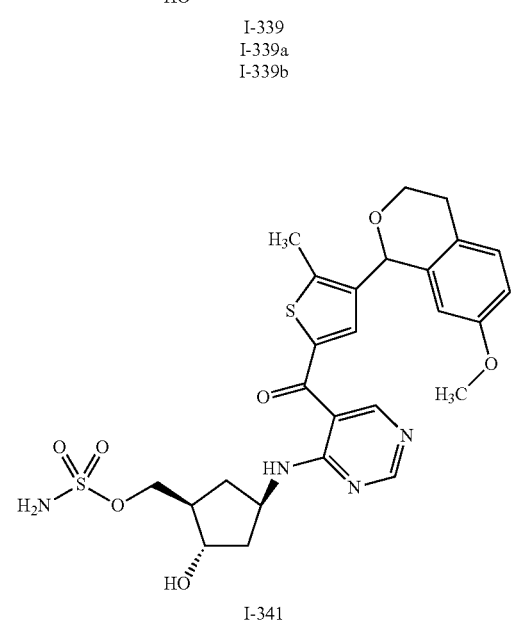
I-341
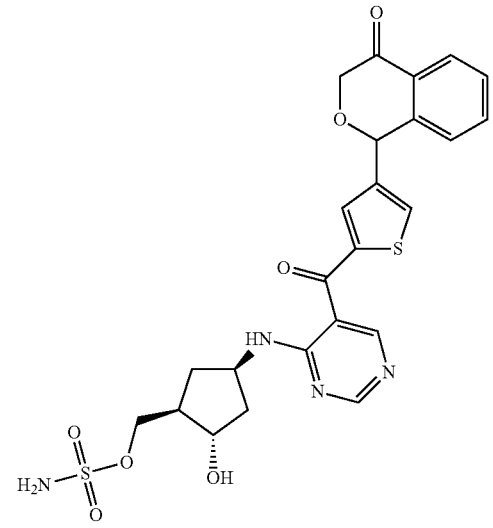
I-342

141
-continued
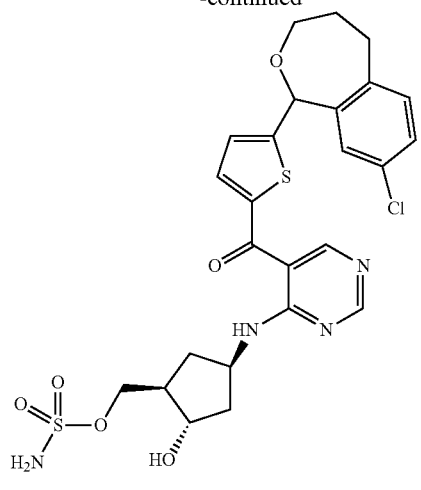
I-343a
I-343b
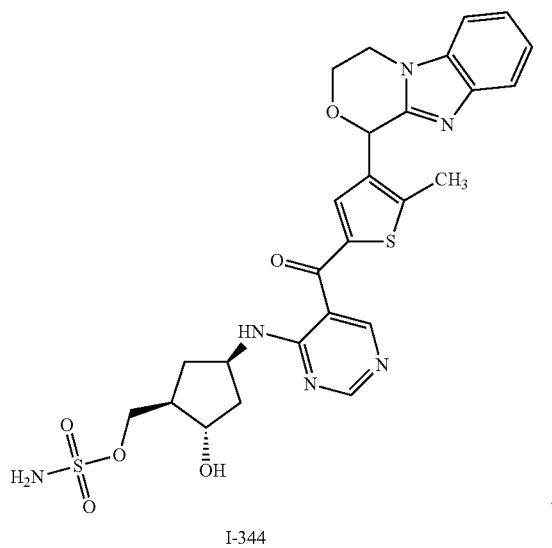
I-344
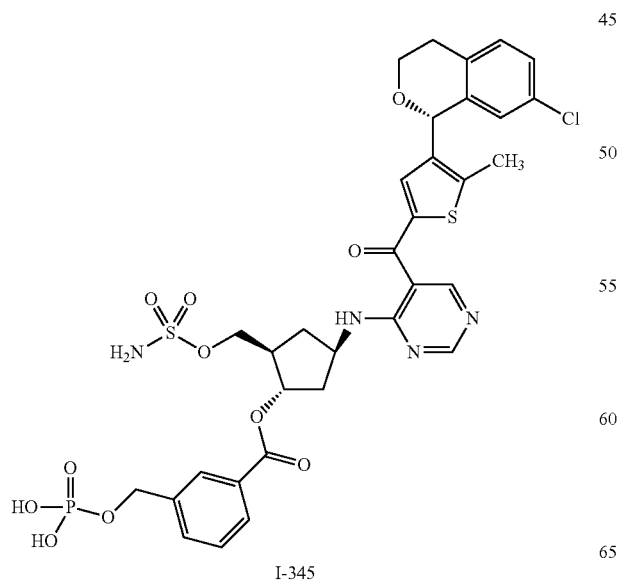
I-345
142
-continued
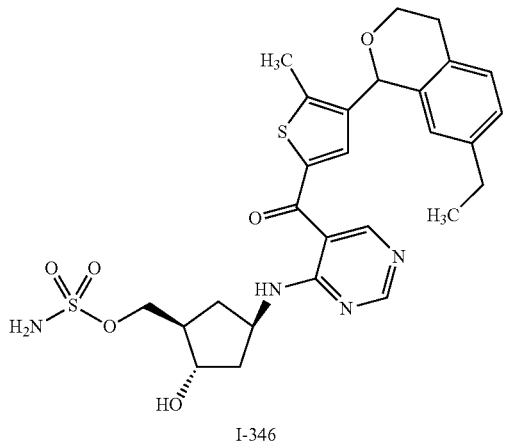
I-346
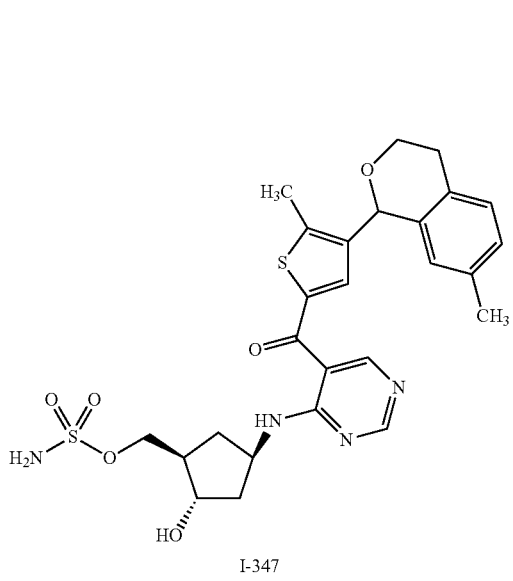
I-347
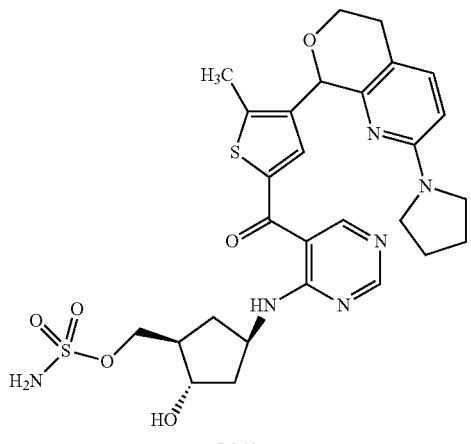
I-348

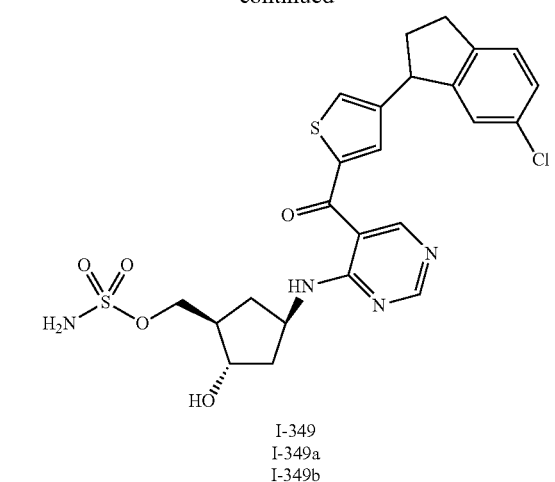
I-349
I-349a
I-349b
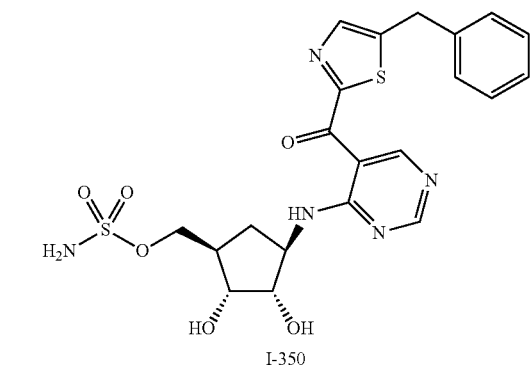
I-350
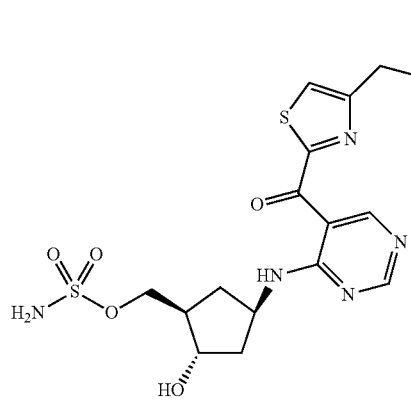
I-351
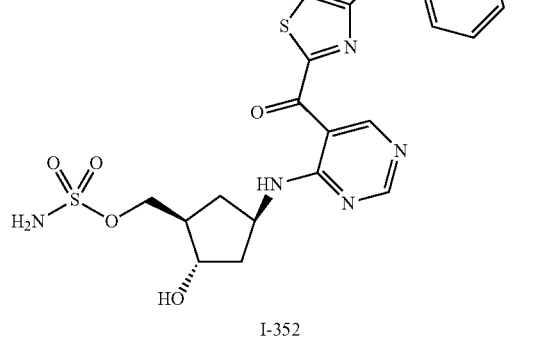
I-352
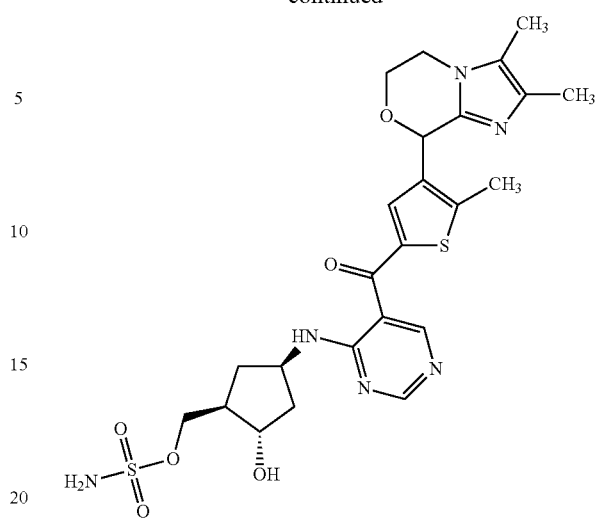
I-356
I-356a
I-356b
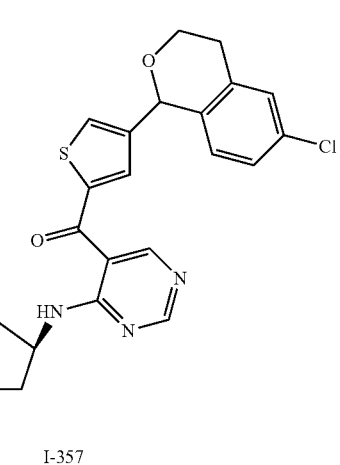
I-357
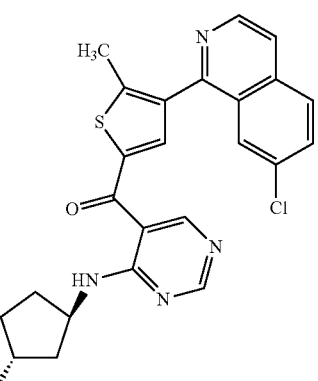
I-358

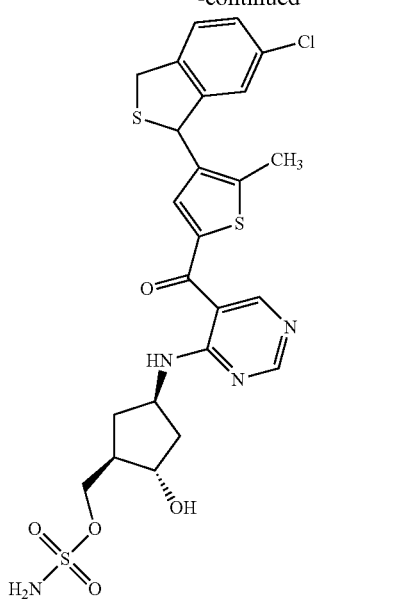
I-359a
I-359b
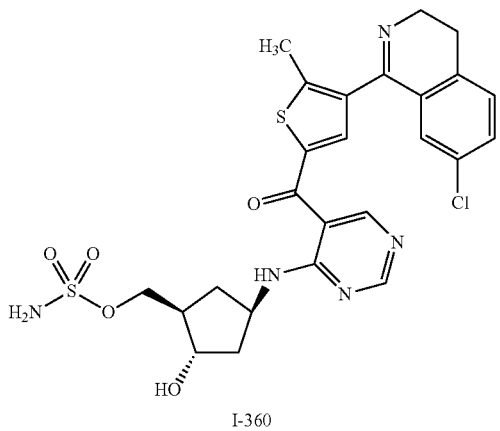
I-360
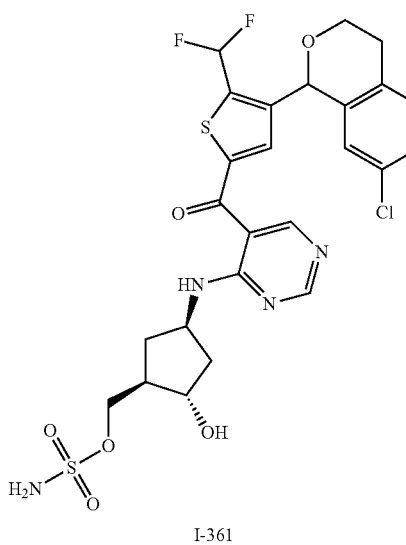
I-361
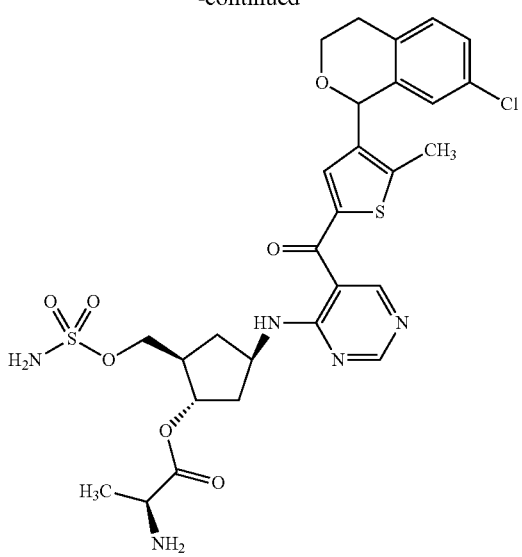
I-362
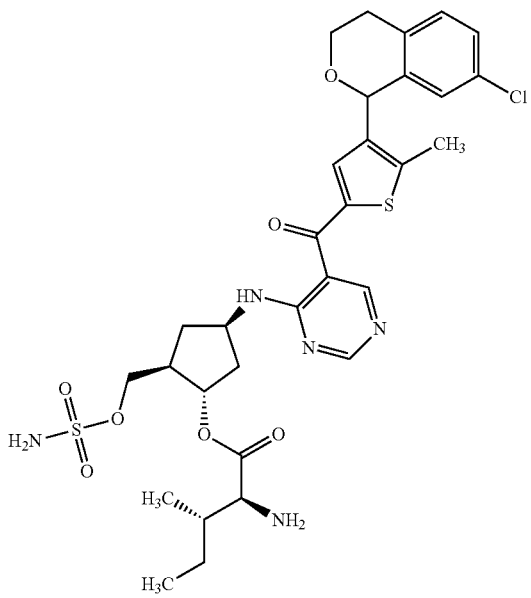
I-363

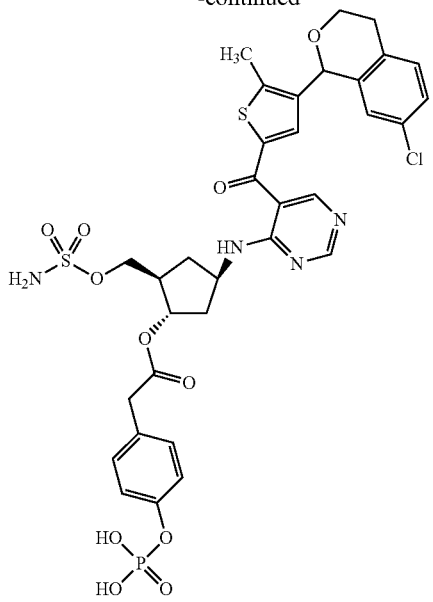

I-364

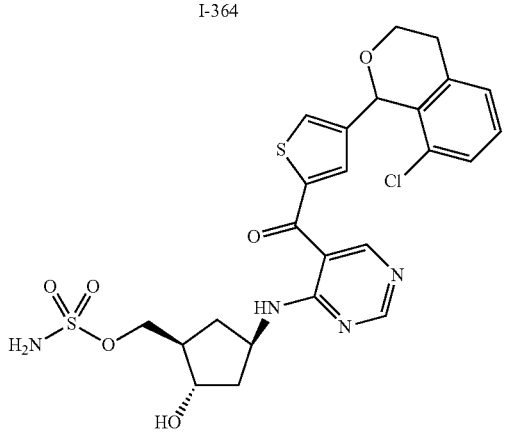

I-365

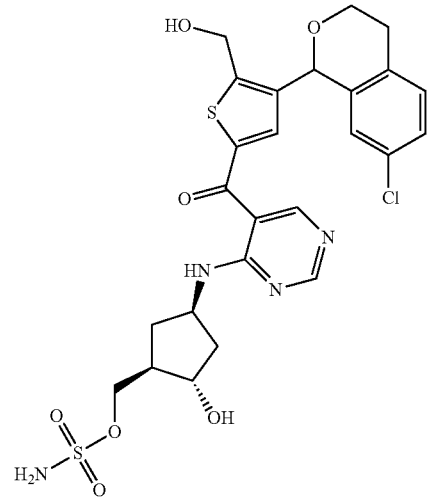

I-366

The chemical entities in Table 1 may also be identified by the following chemical names:

| Compound No. | Name |
|---|---|
| I-1 | [(1R,2R,3S,4R)-4-{[5-({4-[(1S)-1-(6-bromopyridin-2-yl)-1-hydroxyethyl]-2-thienyl}carbonyl)pyrimidin-4-yl]amino}-2,3-dihydroxycyclopentyl]methyl sulfamate and [(1R,2R,3S,4R)-4-{[5-({4-[(1R)-1-(6-bromopyridin-2-yl)-1-hydroxyethyl]-2-thienyl}carbonyl)pyrimidin-4-yl]amino}-2,3-dihydroxycyclopentyl]methyl sulfamate |
| I-1a | [(1R,2R,3S,4R)-4-{[5-({4-[(1S)-1-(6-bromopyridin-2-yl)-1-hydroxyethyl]-2-thienyl}carbonyl)pyrimidin-4-yl]amino}-2,3-dihydroxycyclopentyl]methyl sulfamate or [(1R,2R,3S,4R)-4-{[5-({4-[(1R)-1-(6-bromopyridin-2-yl)-1-hydroxyethyl]-2-thienyl}carbonyl)pyrimidin-4-yl]amino}-2,3-dihydroxycyclopentyl]methyl sulfamate |
| I-1b | [(1R,2R,3S,4R)-4-{[5-({4-[(1S)-1-(6-bromopyridin-2-yl)-1-hydroxyethyl]-2-thienyl}carbonyl)pyrimidin-4-yl]amino}-2,3-dihydroxycyclopentyl]methyl sulfamate or [(1R,2R,3S,4R)-4-{[5-({4-[(1R)-1-(6-bromopyridin-2-yl)-1-hydroxyethyl]-2-thienyl}carbonyl)pyrimidin-4-yl]amino}-2,3-dihydroxycyclopentyl]methyl sulfamate |
| I-2 | [(1R,2S,4R)-4-{[5-({5-chloro-4-[(S)-(6-chloropyridin-2-yl)(hydroxy)methyl]-2-thienyl}carbonyl)pyrimidin-4-yl]amino}-2-hydroxycyclopentyl]methyl sulfamate and [(1R,2S,4R)-4-{[5-({5-chloro-4-[(R)-(6-chloropyridin-2-yl)(hydroxy)methyl]-2-thienyl}carbonyl)pyrimidin-4-yl]amino}-2-hydroxycyclopentyl]methyl sulfamate |

-continued

| Compound No. | Name |
|---|---|
| I-2a | [(1R,2S,4R)-4-{[5-({5-chloro-4-[(S)-(6-chloropyridin-2-yl)(hydroxy)methyl]-2-thienyl}carbonyl)pyrimidin-4-yl]amino}-2-hydroxycyclopentyl]methyl sulfamate or [(1R,2S,4R)-4-{[5-({5-chloro-4-[(R)-(6-chloropyridin-2-yl)(hydroxy)methyl]-2-thienyl}carbonyl)pyrimidin-4-yl]amino}-2-hydroxycyclopentyl]methyl sulfamate |
| I-2b | [(1R,2S,4R)-4-{[5-({5-chloro-4-[(S)-(6-chloropyridin-2-yl)(hydroxy)methyl]-2-thienyl}carbonyl)pyrimidin-4-yl]amino}-2-hydroxycyclopentyl]methyl sulfamate or [(1R,2S,4R)-4-{[5-({5-chloro-4-[(R)-(6-chloropyridin-2-yl)(hydroxy)methyl]-2-thienyl}carbonyl)pyrimidin-4-yl]amino}-2-hydroxycyclopentyl]methyl sulfamate |
| I-3 | [(1R,2S,4R)-4-{[5-({4-[(1R)-1-(3-bromophenyl)-1-hydroxyethyl]-2-thienyl}carbonyl)pyrimidin-4-yl]amino}-2-hydroxycyclopentyl]methyl sulfamate and [(1R,2S,4R)-4-{[5-({4-[(1S)-1-(3-bromophenyl)-1-hydroxyethyl]-2-thienyl}carbonyl)pyrimidin-4-yl]amino}-2-hydroxycyclopentyl]methyl sulfamate |
| I-3a | [(1R,2S,4R)-4-{[5-({4-[(1R)-1-(3-bromophenyl)-1-hydroxyethyl]-2-thienyl}carbonyl)pyrimidin-4-yl]amino}-2-hydroxycyclopentyl]methyl sulfamate or [(1R,2S,4R)-4-{[5-({4-[(1S)-1-(3-bromophenyl)-1-hydroxyethyl]-2-thienyl}carbonyl)pyrimidin-4-yl]amino}-2-hydroxycyclopentyl]methyl sulfamate |
| I-3b | [(1R,2S,4R)-4-{[5-({4-[(1R)-1-(3-bromophenyl)-1-hydroxyethyl]-2-thienyl}carbonyl)pyrimidin-4-yl]amino}-2-hydroxycyclopentyl]methyl sulfamate or [(1R,2S,4R)-4-{[5-({4-[(1S)-1-(3-bromophenyl)-1-hydroxyethyl]-2-thienyl}carbonyl)pyrimidin-4-yl]amino}-2-hydroxycyclopentyl]methyl sulfamate |
| I-4 | [(1R,2S,4R)-4-{[5-({4-[(R)-(3-chlorophenyl)(hydroxy)methyl]-2-thienyl}carbonyl)pyrimidin-4-yl]amino}-2-hydroxycyclopentyl]methyl sulfamate and [(1R,2S,4R)-4-{[5-({4-[(S)-(3-chlorophenyl)(hydroxy)methyl]-2-thienyl}carbonyl)pyrimidin-4-yl]amino}-2-hydroxycyclopentyl]methyl sulfamate |
| I-4a | [(1R,2S,4R)-4-{[5-({4-[(R)-(3-chlorophenyl)(hydroxy)methyl]-2-thienyl}carbonyl)pyrimidin-4-yl]amino}-2-hydroxycyclopentyl]methyl sulfamate or [(1R,2S,4R)-4-{[5-({4-[(S)-(3-chlorophenyl)(hydroxy)methyl]-2-thienyl}carbonyl)pyrimidin-4-yl]amino}-2-hydroxycyclopentyl]methyl sulfamate |
| I-4b | [(1R,2S,4R)-4-{[5-({4-[(R)-(3-chlorophenyl)(hydroxy)methyl]-2-thienyl}carbonyl)pyrimidin-4-yl]amino}-2-hydroxycyclopentyl]methyl sulfamate or [(1R,2S,4R)-4-{[5-({4-[(S)-(3-chlorophenyl)(hydroxy)methyl]-2-thienyl}carbonyl)pyrimidin-4-yl]amino}-2-hydroxycyclopentyl]methyl sulfamate |
| I-5 | [(1R,2S,4R)-4-{[5-({4-[(1R)-1-(3-chlorophenyl)-1-hydroxyethyl]-2-thienyl}carbonyl)pyrimidin-4-yl]amino}-2-hydroxycyclopentyl]methyl sulfamate and [(1R,2S,4R)-4-{[5-({4-[(1S)-1-(3-chlorophenyl)-1-hydroxyethyl]-2-thienyl}carbonyl)pyrimidin-4-yl]amino}-2-hydroxycyclopentyl]methyl sulfamate |
| I-5a | [(1R,2S,4R)-4-{[5-({4-[(1R)-1-(3-chlorophenyl)-1-hydroxyethyl]-2-thienyl}carbonyl)pyrimidin-4-yl]amino}-2-hydroxycyclopentyl]methyl sulfamate or [(1R,2S,4R)-4-{[5-({4-[(1S)-1-(3-chlorophenyl)-1-hydroxyethyl]-2-thienyl}carbonyl)pyrimidin-4-yl]amino}-2-hydroxycyclopentyl]methyl sulfamate |
| I-5b | [(1R,2S,4R)-4-{[5-({4-[(1R)-1-(3-chlorophenyl)-1-hydroxyethyl]-2-thienyl}carbonyl)pyrimidin-4-yl]amino}-2-hydroxycyclopentyl]methyl sulfamate or [(1R,2S,4R)-4-{[5-({4-[(1S)-1-(3-chlorophenyl)-1-hydroxyethyl]-2-thienyl}carbonyl)pyrimidin-4-yl]amino}-2-hydroxycyclopentyl]methyl sulfamate |
| I-6 | [(1R,2S,4R)-4-{[5-({4-[(R)-amino(3-chlorophenyl)methyl]-5-methyl-2-thienyl}carbonyl)pyrimidin-4-yl]amino}-2-hydroxycyclopentyl]methyl sulfamate and [(1R,2S,4R)-4-{[5-({4-[(S)-amino(3-chlorophenyl)methyl]-5-methyl-2-thienyl}carbonyl)pyrimidin-4-yl]amino}-2-hydroxycyclopentyl]methyl sulfamate |
| I-6a | [(1R,2S,4R)-4-{[5-({4-[(R)-amino(3-chlorophenyl)methyl]-5-methyl-2-thienyl}carbonyl)pyrimidin-4-yl]amino}-2-hydroxycyclopentyl]methyl sulfamate or [(1R,2S,4R)-4-{[5-({4-[(S)-amino(3-chlorophenyl)methyl]-5-methyl-2-thienyl}carbonyl)pyrimidin-4-yl]amino}-2-hydroxycyclopentyl]methyl sulfamate |
| I-6b | [(1R,2S,4R)-4-{[5-({4-[(R)-amino(3-chlorophenyl)methyl]-5-methyl-2-thienyl}carbonyl)pyrimidin-4-yl]amino}-2-hydroxycyclopentyl]methyl sulfamate or [(1R,2S,4R)-4-{[5-({4-[(S)-amino(3-chlorophenyl)methyl]-5-methyl-2-thienyl}carbonyl)pyrimidin-4-yl]amino}-2-hydroxycyclopentyl]methyl sulfamate |
| I-7 | [(1R,2S,4R)-4-{[5-({4-[(R)-(3-chlorophenyl)(hydroxy)methyl]-5-(methoxymethyl)-2-thienyl}carbonyl)pyrimidin-4-yl]amino}-2-hydroxycyclopentyl]methyl sulfamate and [(1R,2S,4R)-4-{[5-({4-[(S)-(3-chlorophenyl)(hydroxy)methyl]-5-(methoxymethyl)-2-thienyl}carbonyl)pyrimidin-4-yl]amino}-2-hydroxycyclopentyl]methyl sulfamate |

-continued

| Compound No. | Name |
|---|---|
| I-7a | [(1R,2S,4R)-4-{[5-({4-[(R)-(3-chlorophenyl)(hydroxy)methyl]-5-(methoxymethyl)-2-thienyl}carbonyl)pyrimidin-4-yl]amino}-2-hydroxycyclopentyl]methyl sulfamate<br>or<br>[(1R,2S,4R)-4-{[5-({4-[(S)-(3-chlorophenyl)(hydroxy)methyl]-5-(methoxymethyl)-2-thienyl}carbonyl)pyrimidin-4-yl]amino}-2-hydroxycyclopentyl]methyl sulfamate |
| I-7b | [(1R,2S,4R)-4-{[5-({4-[(R)-(3-chlorophenyl)(hydroxy)methyl]-5-(methoxymethyl)-2-thienyl}carbonyl)pyrimidin-4-yl]amino}-2-hydroxycyclopentyl]methyl sulfamate<br>or<br>[(1R,2S,4R)-4-{[5-({4-[(S)-(3-chlorophenyl)(hydroxy)methyl]-5-(methoxymethyl)-2-thienyl}carbonyl)pyrimidin-4-yl]amino}-2-hydroxycyclopentyl]methyl sulfamate |
| I-8 | [(1R,2R,3S,4R)-4-{[5-({4-[(1S)-1-amino-1-(3-chlorophenyl)ethyl]-2-thienyl}carbonyl)pyrimidin-4-yl]amino}-2,3-dihydroxycyclopentyl]methyl sulfamate<br>and<br>[(1R,2R,3S,4R)-4-{[5-({4-[(1R)-1-amino-1-(3-chlorophenyl)ethyl]-2-thienyl}carbonyl)pyrimidin-4-yl]amino}-2,3-dihydroxycyclopentyl]methyl sulfamate |
| I-8a | [(1R,2R,3S,4R)-4-{[5-({4-[(1S)-1-amino-1-(3-chlorophenyl)ethyl]-2-thienyl}carbonyl)pyrimidin-4-yl]amino}-2,3-dihydroxycyclopentyl]methyl sulfamate<br>or<br>[(1R,2R,3S,4R)-4-{[5-({4-[(1R)-1-amino-1-(3-chlorophenyl)ethyl]-2-thienyl}carbonyl)pyrimidin-4-yl]amino}-2,3-dihydroxycyclopentyl]methyl sulfamate |
| I-8b | [(1R,2R,3S,4R)-4-{[5-({4-[(1S)-1-amino-1-(3-chlorophenyl)ethyl]-2-thienyl}carbonyl)pyrimidin-4-yl]amino}-2,3-dihydroxycyclopentyl]methyl sulfamate<br>or<br>[(1R,2R,3S,4R)-4-{[5-({4-[(1R)-1-amino-1-(3-chlorophenyl)ethyl]-2-thienyl}carbonyl)pyrimidin-4-yl]amino}-2,3-dihydroxycyclopentyl]methyl sulfamate |
| I-9 | [(1R,2S,4R)-4-{[5-({5-chloro-4-[(R)-(3-chlorophenyl)(hydroxy)methyl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(S)-(3-chlorophenyl)(hydroxy)methyl]-2-thienyl}carbonyl)pyrimidin-4-yl]amino}-2-hydroxycyclopentyl]methyl sulfamate |
| I-9a | [(1R,2S,4R)-4-{[5-({5-chloro-4-[(R)-(3-chlorophenyl)(hydroxy)methyl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(S)-(3-chlorophenyl)(hydroxy)methyl]-2-thienyl}carbonyl)pyrimidin-4-yl]amino}-2-hydroxycyclopentyl]methyl sulfamate |
| I-9b | [(1R,2S,4R)-4-{[5-({5-chloro-4-[(R)-(3-chlorophenyl)(hydroxy)methyl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(S)-(3-chlorophenyl)(hydroxy)methyl]-2-thienyl}carbonyl)pyrimidin-4-yl]amino}-2-hydroxycyclopentyl]methyl sulfamate |
| I-10 | [(1R,2R,3S,4R)-4-{[5-({4-[(R)-amino(6-bromopyridin-2-yl)methyl]-5-chloro-2-thienyl}carbonyl)pyrimidin-4-yl]amino}-2,3-dihydroxycyclopentyl]methyl sulfamate<br>and<br>[(1R,2R,3S,4R)-4-{[5-({4-[(S)-amino(6-bromopyridin-2-yl)methyl]-5-chloro-2-thienyl}carbonyl)pyrimidin-4-yl]amino}-2,3-dihydroxycyclopentyl]methyl sulfamate |
| I-10a | [(1R,2R,3S,4R)-4-{[5-({4-[(R)-amino(6-bromopyridin-2-yl)methyl]-5-chloro-2-thienyl}carbonyl)pyrimidin-4-yl]amino}-2,3-dihydroxycyclopentyl]methyl sulfamate<br>or<br>[(1R,2R,3S,4R)-4-{[5-({4-[(S)-amino(6-bromopyridin-2-yl)methyl]-5-chloro-2-thienyl}carbonyl)pyrimidin-4-yl]amino}-2,3-dihydroxycyclopentyl]methyl sulfamate |
| I-10b | [(1R,2R,3S,4R)-4-{[5-({4-[(R)-amino(6-bromopyridin-2-yl)methyl]-5-chloro-2-thienyl}carbonyl)pyrimidin-4-yl]amino}-2,3-dihydroxycyclopentyl]methyl sulfamate<br>or<br>[(1R,2R,3S,4R)-4-{[5-({4-[(S)-amino(6-bromopyridin-2-yl)methyl]-5-chloro-2-thienyl}carbonyl)pyrimidin-4-yl]amino}-2,3-dihydroxycyclopentyl]methyl sulfamate |
| I-11 | [(1R,2S,4R)-4-{[5-({4-[(R)-(3-chlorophenyl)(hydroxy)methyl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(S)-(3-chlorophenyl)(hydroxy)methyl]-5-methyl-2-thienyl}carbonyl)pyrimidin-4-yl]amino}-2-hydroxycyclopentyl]methyl sulfamate |
| I-11a | [(1R,2S,4R)-4-{[5-({4-[(R)-(3-chlorophenyl)(hydroxy)methyl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(S)-(3-chlorophenyl)(hydroxy)methyl]-5-methyl-2-thienyl}carbonyl)pyrimidin-4-yl]amino}-2-hydroxycyclopentyl]methyl sulfamate |
| I-11b | [(1R,2S,4R)-4-{[5-({4-[(R)-(3-chlorophenyl)(hydroxy)methyl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(S)-(3-chlorophenyl)(hydroxy)methyl]-5-methyl-2-thienyl}carbonyl)pyrimidin-4-yl]amino}-2-hydroxycyclopentyl]methyl sulfamate |
| I-12 | [(1R,2S,4R)-4-{[5-({4-[(1S)-1-amino-1-(3-chlorophenyl)ethyl]-2-thienyl}carbonyl)pyrimidin-4-yl]amino}-2-hydroxycyclopentyl]methyl sulfamate<br>and<br>[(1R,2S,4R)-4-{[5-({4-[(1R)-1-amino-1-(3-chlorophenyl)ethyl]-2-thienyl}carbonyl)pyrimidin-4-yl]amino}-2-hydroxycyclopentyl]methyl sulfamate |

-continued

| Compound No. | Name |
|---|---|
| I-12a | [(1R,2S,4R)-4-{[5-({4-[(1S)-1-amino-1-(3-chlorophenyl)ethyl]-2-thienyl}carbonyl)pyrimidin-4-yl]amino}-2-hydroxycyclopentyl]methyl sulfamate or [(1R,2S,4R)-4-{[5-({4-[(1R)-1-amino-1-(3-chlorophenyl)ethyl]-2-thienyl}carbonyl)pyrimidin-4-yl]amino}-2-hydroxycyclopentyl]methyl sulfamate |
| I-12b | [(1R,2S,4R)-4-{[5-({4-[(1S)-1-amino-1-(3-chlorophenyl)ethyl]-2-thienyl}carbonyl)pyrimidin-4-yl]amino}-2-hydroxycyclopentyl]methyl sulfamate or [(1R,2S,4R)-4-{[5-({4-[(1R)-1-amino-1-(3-chlorophenyl)ethyl]-2-thienyl}carbonyl)pyrimidin-4-yl]amino}-2-hydroxycyclopentyl]methyl sulfamate |
| I-13 | [(1R,2S,4R)-4-{[5-({4-[(R)-(3-chlorophenyl)(hydroxy)methyl]-5-(hydroxymethyl)-2-thienyl}carbonyl)pyrimidin-4-yl]amino}-2-hydroxycyclopentyl]methyl sulfamate and [(1R,2S,4R)-4-{[5-({4-[(S)-(3-chlorophenyl)(hydroxy)methyl]-5-(hydroxymethyl)-2-thienyl}carbonyl)pyrimidin-4-yl]amino}-2-hydroxycyclopentyl]methyl sulfamate |
| I-14a | [(1R,2R,3S,4R)-4-{[5-({4-[(R)-amino(3-chlorophenyl)methyl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(S)-amino(3-chlorophenyl)methyl]-5-chloro-2-thienyl}carbonyl)pyrimidin-4-yl]amino}-2,3-dihydroxycyclopentyl]methyl sulfamate |
| I-14b | [(1R,2R,3S,4R)-4-{[5-({4-[(R)-amino(3-chlorophenyl)methyl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(S)-amino(3-chlorophenyl)methyl]-5-chloro-2-thienyl}carbonyl)pyrimidin-4-yl]amino}-2,3-dihydroxycyclopentyl]methyl sulfamate |
| I-15 | [(1R,2S,4R)-4-{[5-({4-[(R)-amino(3-chlorophenyl)methyl]-5-chloro-2-thienyl}carbonyl)pyrimidin-4-yl]amino}-2-hydroxycyclopentyl]methyl sulfamate and [(1R,2S,4R)-4-{[5-({4-[(S)-amino(3-chlorophenyl)methyl]-5-chloro-2-thienyl}carbonyl)pyrimidin-4-yl]amino}-2-hydroxycyclopentyl]methyl sulfamate |
| I-15a | [(1R,2S,4R)-4-{[5-({4-[(R)-amino(3-chlorophenyl)methyl]-5-chloro-2-thienyl}carbonyl)pyrimidin-4-yl]amino}-2-hydroxycyclopentyl]methyl sulfamate or [(1R,2S,4R)-4-{[5-({4-[(S)-amino(3-chlorophenyl)methyl]-5-chloro-2-thienyl}carbonyl)pyrimidin-4-yl]amino}-2-hydroxycyclopentyl]methyl sulfamate |
| I-15b | [(1R,2S,4R)-4-{[5-({4-[(R)-amino(3-chlorophenyl)methyl]-5-chloro-2-thienyl}carbonyl)pyrimidin-4-yl]amino}-2-hydroxycyclopentyl]methyl sulfamate or [(1R,2S,4R)-4-{[5-({4-[(S)-amino(3-chlorophenyl)methyl]-5-chloro-2-thienyl}carbonyl)pyrimidin-4-yl]amino}-2-hydroxycyclopentyl]methyl sulfamate |
| I-16a | [(1R,2S,4R)-4-{[5-({4-[(S)-(3-bromophenyl)(hydroxy)methyl]-5-chloro-2-thienyl}carbonyl)pyrimidin-4-yl]amino}-2-hydroxycyclopentyl]methyl sulfamate or [(1R,2S,4R)-4-{[5-({4-[(R)-(3-bromophenyl)(hydroxy)methyl]-5-chloro-2-thienyl}carbonyl)pyrimidin-4-yl]amino}-2-hydroxycyclopentyl]methyl sulfamate |
| I-16b | [(1R,2S,4R)-4-{[5-({4-[(S)-(3-bromophenyl)(hydroxy)methyl]-5-chloro-2-thienyl}carbonyl)pyrimidin-4-yl]amino}-2-hydroxycyclopentyl]methyl sulfamate or [(1R,2S,4R)-4-{[5-({4-[(R)-(3-bromophenyl)(hydroxy)methyl]-5-chloro-2-thienyl}carbonyl)pyrimidin-4-yl]amino}-2-hydroxycyclopentyl]methyl sulfamate |
| I-17 | [(1R,2S,4R)-4-{[5-({4-[(R)-(3-bromophenyl)(hydroxy)methyl]-2-thienyl}carbonyl)pyrimidin-4-yl]amino}-2-hydroxycyclopentyl]methyl sulfamate and [(1R,2S,4R)-4-{[5-({4-[(S)-(3-bromophenyl)(hydroxy)methyl]-2-thienyl}carbonyl)pyrimidin-4-yl]amino}-2-hydroxycyclopentyl]methyl sulfamate |
| I-18 | [(1R,2S,4R)-4-{[5-({4-[(R)-amino(6-bromopyridin-2-yl)methyl]-5-chloro-2-thienyl}carbonyl)pyrimidin-4-yl]amino}-2-hydroxycyclopentyl]methyl sulfamate and [(1R,2S,4R)-4-{[5-({4-[(S)-amino(6-bromopyridin-2-yl)methyl]-5-chloro-2-thienyl}carbonyl)pyrimidin-4-yl]amino}-2-hydroxycyclopentyl]methyl sulfamate |
| I-18a | [(1R,2S,4R)-4-{[5-({4-[(R)-amino(6-bromopyridin-2-yl)methyl]-5-chloro-2-thienyl}carbonyl)pyrimidin-4-yl]amino}-2-hydroxycyclopentyl]methyl sulfamate or [(1R,2S,4R)-4-{[5-({4-[(S)-amino(6-bromopyridin-2-yl)methyl]-5-chloro-2-thienyl}carbonyl)pyrimidin-4-yl]amino}-2-hydroxycyclopentyl]methyl sulfamate |
| I-18b | [(1R,2S,4R)-4-{[5-({4-[(R)-amino(6-bromopyridin-2-yl)methyl]-5-chloro-2-thienyl}carbonyl)pyrimidin-4-yl]amino}-2-hydroxycyclopentyl]methyl sulfamate or [(1R,2S,4R)-4-{[5-({4-[(S)-amino(6-bromopyridin-2-yl)methyl]-5-chloro-2-thienyl}carbonyl)pyrimidin-4-yl]amino}-2-hydroxycyclopentyl]methyl sulfamate |
| I-19 | [(1R,2S,4R)-4-{[5-({4-[(R)-(5-bromo-2-fluorophenyl)(hydroxy)methyl]-2-thienyl}carbonyl)pyrimidin-4-yl]amino}-2-hydroxycyclopentyl]methyl sulfamate and [(1R,2S,4R)-4-{[5-({4-[(S)-(5-bromo-2-fluorophenyl)(hydroxy)methyl]-2-thienyl}carbonyl)pyrimidin-4-yl]amino}-2-hydroxycyclopentyl]methyl sulfamate |

| Compound No. | Name |
|---|---|
| I-19a | [(1R,2S,4R)-4-{[5-({4-[(R)-(5-bromo-2-fluorophenyl)(hydroxy)methyl]-2-thienyl}carbonyl)pyrimidin-4-yl]amino}-2-hydroxycyclopentyl]methyl sulfamate or [(1R,2S,4R)-4-{[5-({4-[(S)-(5-bromo-2-fluorophenyl)(hydroxy)methyl]-2-thienyl}carbonyl)pyrimidin-4-yl]amino}-2-hydroxycyclopentyl]methyl sulfamate |
| I-19b | [(1R,2S,4R)-4-{[5-({4-[(R)-(5-bromo-2-fluorophenyl)(hydroxy)methyl]-2-thienyl}carbonyl)pyrimidin-4-yl]amino}-2-hydroxycyclopentyl]methyl sulfamate or [(1R,2S,4R)-4-{[5-({4-[(S)-(5-bromo-2-fluorophenyl)(hydroxy)methyl]-2-thienyl}carbonyl)pyrimidin-4-yl]amino}-2-hydroxycyclopentyl]methyl sulfamate |
| I-20a | [(1R,2S,4R)-4-{[5-({4-[(2S)-2-(3-chlorophenyl)tetrahydrofuran-2-yl]-2-thienyl}carbonyl)pyrimidin-4-yl]amino}-2-hydroxycyclopentyl]methyl sulfamate or [(1R,2S,4R)-4-{[5-({4-[(2R)-2-(3-chlorophenyl)tetrahydrofuran-2-yl]-2-thienyl}carbonyl)pyrimidin-4-yl]amino}-2-hydroxycyclopentyl]methyl sulfamate |
| I-20b | [(1R,2S,4R)-4-{[5-({4-[(2S)-2-(3-chlorophenyl)tetrahydrofuran-2-yl]-2-thienyl}carbonyl)pyrimidin-4-yl]amino}-2-hydroxycyclopentyl]methyl sulfamate or [(1R,2S,4R)-4-{[5-({4-[(2R)-2-(3-chlorophenyl)tetrahydrofuran-2-yl]-2-thienyl}carbonyl)pyrimidin-4-yl]amino}-2-hydroxycyclopentyl]methyl sulfamate |
| I-21 | [(1R,2S,4R)-4-{[5-({4-[(S)-(5-chloro-2-furyl)(hydroxy)methyl]-2-thienyl}carbonyl)pyrimidin-4-yl]amino}-2-hydroxycyclopentyl]methyl sulfamate and [(1R,2S,4R)-4-{[5-({4-[(R)-(5-chloro-2-furyl)(hydroxy)methyl]-2-thienyl}carbonyl)pyrimidin-4-yl]amino}-2-hydroxycyclopentyl]methyl sulfamate |
| I-22 | [(1R,2S,4R)-4-{[5-({4-[(R)-amino(3-bromophenyl)methyl]-5-chloro-2-thienyl}carbonyl)pyrimidin-4-yl]amino}-2-hydroxycyclopentyl]methyl sulfamate and [(1R,2S,4R)-4-{[5-({4-[(S)-amino(3-bromophenyl)methyl]-5-chloro-2-thienyl}carbonyl)pyrimidin-4-yl]amino}-2-hydroxycyclopentyl]methyl sulfamate |
| I-22a | [(1R,2S,4R)-4-{[5-({4-[(R)-amino(3-bromophenyl)methyl]-5-chloro-2-thienyl}carbonyl)pyrimidin-4-yl]amino}-2-hydroxycyclopentyl]methyl sulfamate or [(1R,2S,4R)-4-{[5-({4-[(S)-amino(3-bromophenyl)methyl]-5-chloro-2-thienyl}carbonyl)pyrimidin-4-yl]amino}-2-hydroxycyclopentyl]methyl sulfamate |
| I-22b | [(1R,2S,4R)-4-{[5-({4-[(R)-amino(3-bromophenyl)methyl]-5-chloro-2-thienyl}carbonyl)pyrimidin-4-yl]amino}-2-hydroxycyclopentyl]methyl sulfamate or [(1R,2S,4R)-4-{[5-({4-[(S)-amino(3-bromophenyl)methyl]-5-chloro-2-thienyl}carbonyl)pyrimidin-4-yl]amino}-2-hydroxycyclopentyl]methyl sulfamate |
| I-24a | [(1R,2R,3S,4R)-4-{[5-({4-[(R)-amino(3-bromophenyl)methyl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(S)-amino(3-bromophenyl)methyl]-5-chloro-2-thienyl}carbonyl)pyrimidin-4-yl]amino}-2,3-dihydroxycyclopentyl]methyl sulfamate |
| I-24b | [(1R,2R,3S,4R)-4-{[5-({4-[(R)-amino(3-bromophenyl)methyl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(S)-amino(3-bromophenyl)methyl]-5-chloro-2-thienyl}carbonyl)pyrimidin-4-yl]amino}-2,3-dihydroxycyclopentyl]methyl sulfamate |
| I-25 | [(1R,2S,4R)-4-{[5-({4-[(S)-amino(6-chloropyridin-2-yl)methyl]-5-chloro-2-thienyl}carbonyl)pyrimidin-4-yl]amino}-2-hydroxycyclopentyl]methyl sulfamate and [(1R,2S,4R)-4-{[5-({4-[(R)-amino(6-chloropyridin-2-yl)methyl]-5-chloro-2-thienyl}carbonyl)pyrimidin-4-yl]amino}-2-hydroxycyclopentyl]methyl sulfamate |
| I-25a | [(1R,2S,4R)-4-{[5-({4-[(S)-amino(6-chloropyridin-2-yl)methyl]-5-chloro-2-thienyl}carbonyl)pyrimidin-4-yl]amino}-2-hydroxycyclopentyl]methyl sulfamate or [(1R,2S,4R)-4-{[5-({4-[(R)-amino(6-chloropyridin-2-yl)methyl]-5-chloro-2-thienyl}carbonyl)pyrimidin-4-yl]amino}-2-hydroxycyclopentyl]methyl sulfamate |
| I-25b | [(1R,2S,4R)-4-{[5-({4-[(S)-amino(6-chloropyridin-2-yl)methyl]-5-chloro-2-thienyl}carbonyl)pyrimidin-4-yl]amino}-2-hydroxycyclopentyl]methyl sulfamate or [(1R,2S,4R)-4-{[5-({4-[(R)-amino(6-chloropyridin-2-yl)methyl]-5-chloro-2-thienyl}carbonyl)pyrimidin-4-yl]amino}-2-hydroxycyclopentyl]methyl sulfamate |
| I-26 | {(1R,2R,3S,4R)-4-[(5-{4-(3-bromobenzyl)-2-thienyl]carbonyl}pyrimidin-4-yl)amino]-2,3-dihydroxycyclopentyl}methyl sulfamate |
| I-27a | [(1R,2R,3S,4R)-4-{[5-({4-[(1S)-1-amino-1-(3-bromophenyl)ethyl]-2-thienyl}carbonyl)pyrimidin-4-yl]amino}-2,3-dihydroxycyclopentyl]methyl sulfamate or [(1R,2R,3S,4R)-4-{[5-({4-[(1R)-1-amino-1-(3-bromophenyl)ethyl]-2-thienyl}carbonyl)pyrimidin-4-yl]amino}-2,3-dihydroxycyclopentyl]methyl sulfamate |

| Compound No. | Name |
|---|---|
| I-27b | [(1R,2R,3S,4R)-4-{[5-({4-[(1S)-1-amino-1-(3-bromophenyl)ethyl]-2-thienyl}carbonyl)pyrimidin-4-yl]amino}-2,3-dihydroxycyclopentyl]methyl sulfamate or [(1R,2R,3S,4R)-4-{[5-({4-[(1R)-1-amino-1-(3-bromophenyl)ethyl]-2-thienyl}carbonyl)pyrimidin-4-yl]amino}-2,3-dihydroxycyclopentyl]methyl sulfamate |
| I-28 | [(1R,2S,4R)-4-{[5-({4-[(R)-(3-chlorophenyl)sulfinyl]-5-methyl-2-thienyl}carbonyl)pyrimidin-4-yl]amino}-2-hydroxycyclopentyl]methyl sulfamate and [(1R,2S,4R)-4-{[5-({4-[(S)-(3-chlorophenyl)sulfinyl]-5-methyl-2-thienyl}carbonyl)pyrimidin-4-yl]amino}-2-hydroxycyclopentyl]methyl sulfamate |
| I-28a | [(1R,2S,4R)-4-{[5-({4-[(R)-(3-chlorophenyl)sulfinyl]-5-methyl-2-thienyl}carbonyl)pyrimidin-4-yl]amino}-2-hydroxycyclopentyl]methyl sulfamate or [(1R,2S,4R)-4-{[5-({4-[(S)-(3-chlorophenyl)sulfinyl]-5-methyl-2-thienyl}carbonyl)pyrimidin-4-yl]amino}-2-hydroxycyclopentyl]methyl sulfamate |
| I-28b | [(1R,2S,4R)-4-{[5-({4-[(R)-(3-chlorophenyl)sulfinyl]-5-methyl-2-thienyl}carbonyl)pyrimidin-4-yl]amino}-2-hydroxycyclopentyl]methyl sulfamate or [(1R,2S,4R)-4-{[5-({4-[(S)-(3-chlorophenyl)sulfinyl]-5-methyl-2-thienyl}carbonyl)pyrimidin-4-yl]amino}-2-hydroxycyclopentyl]methyl sulfamate |
| I-29 | [(1R,2S,4R)-4-{[5-({4-[(S)-(6-chloropyridin-2-yl)(hydroxy)methyl]-2-thienyl}carbonyl)pyrimidin-4-yl]amino}-2-hydroxycyclopentyl]methyl sulfamate and [(1R,2S,4R)-4-{[5-({4-[(R)-(6-chloropyridin-2-yl)(hydroxy)methyl]-2-thienyl}carbonyl)pyrimidin-4-yl]amino}-2-hydroxycyclopentyl]methyl sulfamate |
| I-29a | [(1R,2S,4R)-4-{[5-({4-[(S)-(6-chloropyridin-2-yl)(hydroxy)methyl]-2-thienyl}carbonyl)pyrimidin-4-yl]amino}-2-hydroxycyclopentyl]methyl sulfamate or [(1R,2S,4R)-4-{[5-({4-[(R)-(6-chloropyridin-2-yl)(hydroxy)methyl]-2-thienyl}carbonyl)pyrimidin-4-yl]amino}-2-hydroxycyclopentyl]methyl sulfamate |
| I-29b | [(1R,2S,4R)-4-{[5-({4-[(S)-(6-chloropyridin-2-yl)(hydroxy)methyl]-2-thienyl}carbonyl)pyrimidin-4-yl]amino}-2-hydroxycyclopentyl]methyl sulfamate or [(1R,2S,4R)-4-{[5-({4-[(R)-(6-chloropyridin-2-yl)(hydroxy)methyl]-2-thienyl}carbonyl)pyrimidin-4-yl]amino}-2-hydroxycyclopentyl]methyl sulfamate |
| I-30 | {(1R,2S,4R)-4-[(5-{4-[(1S)-1-(3-chlorophenyl)-1-hydroxyethyl]-2-furoyl}pyrimidin-4-yl)amino]-2-hydroxycyclopentyl}methyl sulfamate and {(1R,2S,4R)-4-[(5-{4-[(1R)-1-(3-chlorophenyl)-1-hydroxyethyl]-2-furoyl}pyrimidin-4-yl)amino]-2-hydroxycyclopentyl}methyl sulfamate |
| I-30a | {(1R,2S,4R)-4-[(5-{4-[(1S)-1-(3-chlorophenyl)-1-hydroxyethyl]-2-furoyl}pyrimidin-4-yl)amino]-2-hydroxycyclopentyl}methyl sulfamate or {(1R,2S,4R)-4-[(5-{4-[(1R)-1-(3-chlorophenyl)-1-hydroxyethyl]-2-furoyl}pyrimidin-4-yl)amino]-2-hydroxycyclopentyl}methyl sulfamate |
| I-30b | {(1R,2S,4R)-4-[(5-{4-[(1S)-1-(3-chlorophenyl)-1-hydroxyethyl]-2-furoyl}pyrimidin-4-yl)amino]-2-hydroxycyclopentyl}methyl sulfamate or {(1R,2S,4R)-4-[(5-{4-[(1R)-1-(3-chlorophenyl)-1-hydroxyethyl]-2-furoyl}pyrimidin-4-yl)amino]-2-hydroxycyclopentyl}methyl sulfamate |
| I-31 | [(1R,2R,3S,4R)-4-{[5-({4-[(2S)-2-(3-chlorophenyl)pyrrolidin-2-yl]-2-thienyl}carbonyl)pyrimidin-4-yl]amino}-2,3-dihydroxycyclopentyl]methyl sulfamate and [(1R,2R,3S,4R)-4-{[5-({4-[(2R)-2-(3-chlorophenyl)pyrrolidin-2-yl]-2-thienyl}carbonyl)pyrimidin-4-yl]amino}-2,3-dihydroxycyclopentyl]methyl sulfamate |
| I-32 | [(1R,2S,4R)-2-hydroxy-4-{[5-({4-[(2S)-2-phenyltetrahydrofuran-2-yl]-2-thienyl}carbonyl)pyrimidin-4-yl]amino}cyclopentyl]methyl sulfamate and [(1R,2S,4R)-2-hydroxy-4-{[5-({4-[(2R)-2-phenyltetrahydrofuran-2-yl]-2-thienyl}carbonyl)pyrimidin-4-yl]amino}cyclopentyl]methyl sulfamate |
| I-32a | [(1R,2S,4R)-2-hydroxy-4-{[5-({4-[(2S)-2-phenyltetrahydrofuran-2-yl]-2-thienyl}carbonyl)pyrimidin-4-yl]amino}cyclopentyl]methyl sulfamate or [(1R,2S,4R)-2-hydroxy-4-{[5-({4-[(2R)-2-phenyltetrahydrofuran-2-yl]-2-thienyl}carbonyl)pyrimidin-4-yl]amino}cyclopentyl]methyl sulfamate |
| I-32b | [(1R,2S,4R)-2-hydroxy-4-{[5-({4-[(2S)-2-phenyltetrahydrofuran-2-yl]-2-thienyl}carbonyl)pyrimidin-4-yl]amino}cyclopentyl]methyl sulfamate or [(1R,2S,4R)-2-hydroxy-4-{[5-({4-[(2R)-2-phenyltetrahydrofuran-2-yl]-2-thienyl}carbonyl)pyrimidin-4-yl]amino}cyclopentyl]methyl sulfamate |
| I-33 | [(1R,2S,4R)-4-({5-[4-(3-chlorobenzyl)-5-methyl-2-furoyl]pyrimidin-4-yl}amino)-2-hydroxycyclopentyl]methyl sulfamate |
| I-34 | [(1R,2S,4R)-4-({5-[4-(3-bromobenzyl)-5-methyl-2-furoyl]pyrimidin-4-yl}amino)-2-hydroxycyclopentyl]methyl sulfamate |
| I-35 | {(1R,2S,4R)-4-[(5-{[4-(3-chlorobenzyl)-5-(hydroxymethyl)-2-thienyl]carbonyl}pyrimidin-4-yl)amino]-2-hydroxycyclopentyl}methyl sulfamate |

-continued

| Compound No. | Name |
|---|---|
| I-36 | [(1R,2S,4R)-4-{[5-({4-[(R)-amino(3-chlorophenyl)methyl]-2-thienyl}carbonyl)pyrimidin-4-yl]amino}-2-hydroxycyclopentyl]methyl sulfamate and |
| | [(1R,2S,4R)-4-{[5-({4-[(S)-amino(3-chlorophenyl)methyl]-2-thienyl}carbonyl)pyrimidin-4-yl]amino}-2-hydroxycyclopentyl]methyl sulfamate |
| I-36a | [(1R,2S,4R)-4-{[5-({4-[(R)-amino(3-chlorophenyl)methyl]-2-thienyl}carbonyl)pyrimidin-4-yl]amino}-2-hydroxycyclopentyl]methyl sulfamate or |
| | [(1R,2S,4R)-4-{[5-({4-[(S)-amino(3-chlorophenyl)methyl]-2-thienyl}carbonyl)pyrimidin-4-yl]amino}-2-hydroxycyclopentyl]methyl sulfamate |
| I-36b | [(1R,2S,4R)-4-{[5-({4-[(R)-amino(3-chlorophenyl)methyl]-2-thienyl}carbonyl)pyrimidin-4-yl]amino}-2-hydroxycyclopentyl]methyl sulfamate or |
| | [(1R,2S,4R)-4-{[5-({4-[(S)-amino(3-chlorophenyl)methyl]-2-thienyl}carbonyl)pyrimidin-4-yl]amino}-2-hydroxycyclopentyl]methyl sulfamate |
| I-37 | [(1R,2S,4R)-2-hydroxy-4-{[5-({4-[(4-iodo-1H-pyrazol-1-yl)methyl]-5-methyl-2-thienyl}carbonyl)pyrimidin-4-yl]amino}cyclopentyl]methyl sulfamate |
| I-38 | [(1R,2S,4R)-4-{[5-({4-[(2S)-2-(3-chlorophenyl)pyrrolidin-2-yl]-2-thienyl}carbonyl)pyrimidin-4-yl]amino}-2-hydroxycyclopentyl]methyl sulfamate and |
| | [(1R,2S,4R)-4-{[5-({4-[(2R)-2-(3-chlorophenyl)pyrrolidin-2-yl]-2-thienyl}carbonyl)pyrimidin-4-yl]amino}-2-hydroxycyclopentyl]methyl sulfamate |
| I-38a | [(1R,2S,4R)-4-{[5-({4-[(2S)-2-(3-chlorophenyl)pyrrolidin-2-yl]-2-thienyl}carbonyl)pyrimidin-4-yl]amino}-2-hydroxycyclopentyl]methyl sulfamate or |
| | [(1R,2S,4R)-4-{[5-({4-[(2R)-2-(3-chlorophenyl)pyrrolidin-2-yl]-2-thienyl}carbonyl)pyrimidin-4-yl]amino}-2-hydroxycyclopentyl]methyl sulfamate |
| I-38b | [(1R,2S,4R)-4-{[5-({4-[(2S)-2-(3-chlorophenyl)pyrrolidin-2-yl]-2-thienyl}carbonyl)pyrimidin-4-yl]amino}-2-hydroxycyclopentyl]methyl sulfamate or |
| | [(1R,2S,4R)-4-{[5-({4-[(2R)-2-(3-chlorophenyl)pyrrolidin-2-yl]-2-thienyl}carbonyl)pyrimidin-4-yl]amino}-2-hydroxycyclopentyl]methyl sulfamate |
| I-39 | [(1R,2S,4R)-4-{[5-({4-[(4-bromo-1H-pyrazol-1-yl)methyl]-5-methyl-2-thienyl}carbonyl)pyrimidin-4-yl]amino}-2-hydroxycyclopentyl]methyl sulfamate |
| I-40 | [(1R,2S,4R)-4-{[5-({5-chloro-4-[(R)-(3-chloro-2-fluorophenyl)(hydroxy)methyl]-2-thienyl}carbonyl)pyrimidin-4-yl]amino}-2-hydroxycyclopentyl]methyl sulfamate and |
| | [(1R,2S,4R)-4-{[5-({5-chloro-4-[(S)-(3-chloro-2-fluorophenyl)(hydroxy)methyl]-2-thienyl}carbonyl)pyrimidin-4-yl]amino}-2-hydroxycyclopentyl]methyl sulfamate |
| I-41 | [(1R,2S,4R)-4-{[5-({4-(3-chlorobenzyl)-5-[(2S)-tetrahydrofuran-2-yl]-2-thienyl}carbonyl)pyrimidin-4-yl]amino}-2-hydroxycyclopentyl]methyl sulfamate and |
| | [(1R,2S,4R)-4-{[5-({4-(3-chlorobenzyl)-5-[(2R)-tetrahydrofuran-2-yl]-2-thienyl}carbonyl)pyrimidin-4-yl]amino}-2-hydroxycyclopentyl]methyl sulfamate |
| I-41a | [(1R,2S,4R)-4-{[5-({4-(3-chlorobenzyl)-5-[(2S)-tetrahydrofuran-2-yl]-2-thienyl}carbonyl)pyrimidin-4-yl]amino}-2-hydroxycyclopentyl]methyl sulfamate or |
| | [(1R,2S,4R)-4-{[5-({4-(3-chlorobenzyl)-5-[(2R)-tetrahydrofuran-2-yl]-2-thienyl}carbonyl)pyrimidin-4-yl]amino}-2-hydroxycyclopentyl]methyl sulfamate |
| I-41b | [(1R,2S,4R)-4-{[5-({4-(3-chlorobenzyl)-5-[(2S)-tetrahydrofuran-2-yl]-2-thienyl}carbonyl)pyrimidin-4-yl]amino}-2-hydroxycyclopentyl]methyl sulfamate or |
| | [(1R,2S,4R)-4-{[5-({4-(3-chlorobenzyl)-5-[(2R)-tetrahydrofuran-2-yl]-2-thienyl}carbonyl)pyrimidin-4-yl]amino}-2-hydroxycyclopentyl]methyl sulfamate |
| I-42 | {(1R,2S,4R)-4-[(5-{4-[(R)-(3-chlorophenyl)(hydroxy)methyl]-2-furoyl}pyrimidin-4-yl)amino]-2-hydroxycyclopentyl}methyl sulfamate and |
| | {(1R,2S,4R)-4-[(5-{4-[(S)-(3-chlorophenyl)(hydroxy)methyl]-2-furoyl}pyrimidin-4-yl)amino]-2-hydroxycyclopentyl}methyl sulfamate |
| I-42a | {(1R,2S,4R)-4-[(5-{4-[(R)-(3-chlorophenyl)(hydroxy)methyl]-2-furoyl}pyrimidin-4-yl)amino]-2-hydroxycyclopentyl}methyl sulfamate or |
| | {(1R,2S,4R)-4-[(5-{4-[(S)-(3-chlorophenyl)(hydroxy)methyl]-2-furoyl}pyrimidin-4-yl)amino]-2-hydroxycyclopentyl}methyl sulfamate |
| I-42b | {(1R,2S,4R)-4-[(5-{4-[(R)-(3-chlorophenyl)(hydroxy)methyl]-2-furoyl}pyrimidin-4-yl)amino]-2-hydroxycyclopentyl}methyl sulfamate or |
| | {(1R,2S,4R)-4-[(5-{4-[(S)-(3-chlorophenyl)(hydroxy)methyl]-2-furoyl}pyrimidin-4-yl)amino]-2-hydroxycyclopentyl}methyl sulfamate |
| I-43 | {(1R,2S,4R)-4-[(5-{[4-(3-chlorobenzyl)-2-thienyl]carbonyl}pyrimidin-4-yl)amino]-2-hydroxycyclopentyl}methyl sulfamate |
| I-44 | {(1R,2S,4R)-4-[(5-{[4-(3-chlorobenzyl)-5-(methoxymethyl)-2-thienyl]carbonyl}pyrimidin-4-yl)amino]-2-hydroxycyclopentyl}methyl sulfamate |
| I-45 | {(1R,2S,4R)-2-hydroxy-4-[(5-{[5-methyl-4-(3-methylbenzyl)-2-thienyl]carbonyl}pyrimidin-4-yl)amino]cyclopentyl}methyl sulfamate |

| Compound No. | Name |
|---|---|
| I-46 | [(1R,2S,4R)-4-{[5-({4-[(6-bromopyridin-2-yl)methyl]-5-chloro-2-thienyl}carbonyl)pyrimidin-4-yl]amino}-2-hydroxycyclopentyl]methyl sulfamate |
| I-47 | [(1R,2S,4R)-4-{[5-({4-[(R)-(3-chlorophenyl)(methylamino)methyl]-2-thienyl}carbonyl)pyrimidin-4-yl]amino}-2-hydroxycyclopentyl]methyl sulfamate and [(1R,2S,4R)-4-{[5-({4-[(S)-(3-chlorophenyl)(methylamino)methyl]-2-thienyl}carbonyl)pyrimidin-4-yl]amino}-2-hydroxycyclopentyl]methyl sulfamate |
| I-47a | [(1R,2S,4R)-4-{[5-({4-[(R)-(3-chlorophenyl)(methylamino)methyl]-2-thienyl}carbonyl)pyrimidin-4-yl]amino}-2-hydroxycyclopentyl]methyl sulfamate or [(1R,2S,4R)-4-{[5-({4-[(S)-(3-chlorophenyl)(methylamino)methyl]-2-thienyl}carbonyl)pyrimidin-4-yl]amino}-2-hydroxycyclopentyl]methyl sulfamate |
| I-47b | [(1R,2S,4R)-4-{[5-({4-[(R)-(3-chlorophenyl)(methylamino)methyl]-2-thienyl}carbonyl)pyrimidin-4-yl]amino}-2-hydroxycyclopentyl]methyl sulfamate or [(1R,2S,4R)-4-{[5-({4-[(S)-(3-chlorophenyl)(methylamino)methyl]-2-thienyl}carbonyl)pyrimidin-4-yl]amino}-2-hydroxycyclopentyl]methyl sulfamate |
| I-48 | [(1R,2S,4R)-4-{[5-({5-chloro-4-[(R)-(5-chloro-2-fluorophenyl)(hydroxy)methyl]-2-thienyl}carbonyl)pyrimidin-4-yl]amino}-2-hydroxycyclopentyl]methyl sulfamate and [(1R,2S,4R)-4-{[5-({5-chloro-4-[(S)-(5-chloro-2-fluorophenyl)(hydroxy)methyl]-2-thienyl}carbonyl)pyrimidin-4-yl]amino}-2-hydroxycyclopentyl]methyl sulfamate |
| I-49 | [(1R,2S,4R)-4-{[5-({5-chloro-4-[(1R)-1-(3-chlorophenyl)-1,3-dihydroxypropyl]-2-thienyl}carbonyl)pyrimidin-4-yl]amino}-2-hydroxycyclopentyl]methyl sulfamate and [(1R,2S,4R)-4-{[5-({5-chloro-4-[(1S)-1-(3-chlorophenyl)-1,3-dihydroxypropyl]-2-thienyl}carbonyl)pyrimidin-4-yl]amino}-2-hydroxycyclopentyl]methyl sulfamate |
| I-50 | [(1R,2S,4R)-4-{[5-({4-[(S)-(3-chlorophenyl)(cyclopropyl)hydroxymethyl]-2-thienyl}carbonyl)pyrimidin-4-yl]amino}-2-hydroxycyclopentyl]methyl sulfamate and [(1R,2S,4R)-4-{[5-({4-[(R)-(3-chlorophenyl)(cyclopropyl)hydroxymethyl]-2-thienyl}carbonyl)pyrimidin-4-yl]amino}-2-hydroxycyclopentyl]methyl sulfamate |
| I-51 | {(1R,2S,4R)-4-[(5-{[4-(3-chlorobenzyl)-5-methyl-2-thienyl]carbonyl}pyrimidin-4-yl)amino]-2-hydroxycyclopentyl}methyl sulfamate |
| I-52 | {(1R,2S,4R)-4-[(5-{[4-(3-bromobenzyl)-5-methyl-2-thienyl]carbonyl}pyrimidin-4-yl)amino]-2-hydroxycyclopentyl}methyl sulfamate |
| I-53 | [(1R,2S,4R)-4-{[5-({4-[(6-bromopyridin-2-yl)methyl]-2-thienyl}carbonyl)pyrimidin-4-yl]amino}-2-hydroxycyclopentyl]methyl sulfamate |
| I-54 | [(1R,2S,4R)-4-{[5-({4-[(1S)-1-(6-bromopyridin-2-yl)-1-hydroxyethyl]-2-thienyl}carbonyl)pyrimidin-4-yl]amino}-2-hydroxycyclopentyl]methyl sulfamate and [(1R,2S,4R)-4-{[5-({4-[(1R)-1-(6-bromopyridin-2-yl)-1-hydroxyethyl]-2-thienyl}carbonyl)pyrimidin-4-yl]amino}-2-hydroxycyclopentyl]methyl sulfamate |
| I-55 | [(1R,2S,4R)-4-{[5-({4-[(4-chloro-1H-pyrazol-1-yl)methyl]-5-methyl-2-thienyl}carbonyl)pyrimidin-4-yl]amino}-2-hydroxycyclopentyl]methyl sulfamate |
| I-56 | [(1R,2S,4R)-4-{[5-({5-chloro-4-[(R)-hydroxy(phenyl)methyl]-2-thienyl}carbonyl)pyrimidin-4-yl]amino}-2-hydroxycyclopentyl]methyl sulfamate and [(1R,2S,4R)-4-{[5-({5-chloro-4-[(S)-hydroxy(phenyl)methyl]-2-thienyl}carbonyl)pyrimidin-4-yl]amino}-2-hydroxycyclopentyl]methyl sulfamate |
| I-57 | [(1R,2S,4R)-2-hydroxy-4-({5-[4-(3-methylbenzyl)-2-furoyl]pyrimidin-4-yl}amino)cyclopentyl]methyl sulfamate |
| I-58 | {(1R,2S,4R)-2-hydroxy-4-[(5-{4-[(1S)-1-hydroxy-1-phenylethyl]-2-furoyl}pyrimidin-4-yl)amino]cyclopentyl}methyl sulfamate and {(1R,2S,4R)-2-hydroxy-4-[(5-{4-[(1R)-1-hydroxy-1-phenylethyl]-2-furoyl}pyrimidin-4-yl)amino]cyclopentyl}methyl sulfamate |
| I-58a | {(1R,2S,4R)-2-hydroxy-4-[(5-{4-[(1S)-1-hydroxy-1-phenylethyl]-2-furoyl}pyrimidin-4-yl)amino]cyclopentyl}methyl sulfamate or {(1R,2S,4R)-2-hydroxy-4-[(5-{4-[(1R)-1-hydroxy-1-phenylethyl]-2-furoyl}pyrimidin-4-yl)amino]cyclopentyl}methyl sulfamate |
| I-58b | {(1R,2S,4R)-2-hydroxy-4-[(5-{4-[(1S)-1-hydroxy-1-phenylethyl]-2-furoyl}pyrimidin-4-yl)amino]cyclopentyl}methyl sulfamate or {(1R,2S,4R)-2-hydroxy-4-[(5-{4-[(1R)-1-hydroxy-1-phenylethyl]-2-furoyl}pyrimidin-4-yl)amino]cyclopentyl}methyl sulfamate |
| I-59 | {(1R,2S,4R)-4-[(5-{[4-(3-bromobenzyl)-2-thienyl]carbonyl}pyrimidin-4-yl)amino]-2-hydroxycyclopentyl}methyl sulfamate |
| I-60 | {(1R,2S,4R)-2-hydroxy-4-[(5-{[4-(3-methylbenzyl)-2-thienyl]carbonyl}pyrimidin-4-yl)amino]cyclopentyl}methyl sulfamate |
| I-61 | {(1R,2S,4R)-4-[(5-{[4-(3-chloro-4-fluorobenzyl)-2-thienyl]carbonyl}pyrimidin-4-yl)amino]-2-hydroxycyclopentyl}methyl sulfamate |
| I-62 | {(1R,2S,4R)-4-[(5-{[4-(3-iodobenzyl)-2-thienyl]carbonyl}pyrimidin-4-yl)amino]-2-hydroxycyclopentyl}methyl sulfamate |

-continued

| Compound No. | Name |
|---|---|
| I-63 | [(1R,2S,4R)-4-{[5-({5-chloro-4-[(R)-(5-chloro-2-methoxyphenyl)(hydroxy)methyl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(S)-(5-chloro-2-methoxyphenyl)(hydroxy)methyl]-2-thienyl}carbonyl)pyrimidin-4-yl]amino}-2-hydroxycyclopentyl]methyl sulfamate |
| I-64 | [(1R,2R,3R,4R)-4-({5-[4-(3-bromobenzyl)-5-methyl-2-furoyl]pyrimidin-4-yl}amino)-3-fluoro-2-hydroxycyclopentyl]methyl sulfamate |
| I-65 | [(1R,2R,3R,4R)-3-fluoro-2-hydroxy-4-({5-[5-methyl-4-(3-methylbenzyl)-2-furoyl]pyrimidin-4-yl}amino)cyclopentyl]methyl sulfamate |
| I-66 | [(1R,2S,4R)-4-{[5-({4-[(5-chloro-2-furyl)methyl]-2-thienyl}carbonyl)pyrimidin-4-yl]amino}-2-hydroxycyclopentyl]methyl sulfamate |
| I-67 | [(1R,2S,4R)-4-{[5-({5-chloro-4-[(2R)-2-(3-chlorophenyl)oxetan-2-yl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(2S)-2-(3-chlorophenyl)oxetan-2-yl]-2-thienyl}carbonyl)pyrimidin-4-yl]amino}-2-hydroxycyclopentyl]methyl sulfamate |
| I-68 | [(1R,2S,4R)-2-hydroxy-4-{[5-({5-methyl-4-[(R)-phenylsulfinyl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(S)-phenylsulfinyl]-2-thienyl}carbonyl)pyrimidin-4-yl]amino}cyclopentyl]methyl sulfamate |
| I-69 | [(1R,2S,4R)-2-hydroxy-4-({5-[(5-methyl-4-{(R)-[3-(trifluoromethyl)phenyl]sulfinyl}-2-thienyl)carbonyl]pyrimidin-4-yl}amino)cyclopentyl]methyl sulfamate<br>and<br>[(1R,2S,4R)-2-hydroxy-4-({5-[(5-methyl-4-{(S)-[3-(trifluoromethyl)phenyl]sulfinyl}-2-thienyl)carbonyl]pyrimidin-4-yl}amino)cyclopentyl]methyl sulfamate |
| I-70 | {(1R,2S,4R)-4-[(5-{[4-(3-ethynylbenzyl)-2-thienyl]carbonyl}pyrimidin-4-yl)amino]-2-hydroxycyclopentyl}methyl sulfamate |
| I-71 | [(1R,2S,4R)-4-{[5-({4-[(6-chloropyridin-2-yl)methyl]-2-thienyl}carbonyl)pyrimidin-4-yl]amino}-2-hydroxycyclopentyl]methyl sulfamate |
| I-72 | [(1R,2S,4R)-4-({5-[5-chloro-4-(3-chlorobenzyl)-2-furoyl]pyrimidin-4-yl}amino)-2-hydroxycyclopentyl]methyl sulfamate |
| I-73a | [(1R,2S,4R)-4-{[5-({4-[(R)-(3-bromophenyl)(methoxy)methyl]-2-thienyl}carbonyl)pyrimidin-4-yl]amino}-2-hydroxycyclopentyl]methyl sulfamate<br>or<br>[(1R,2S,4R)-4-{[5-({4-[(S)-(3-bromophenyl)(methoxy)methyl]-2-thienyl}carbonyl)pyrimidin-4-yl]amino}-2-hydroxycyclopentyl]methyl sulfamate |
| I-73b | [(1R,2S,4R)-4-{[5-({4-[(R)-(3-bromophenyl)(methoxy)methyl]-2-thienyl}carbonyl)pyrimidin-4-yl]amino}-2-hydroxycyclopentyl]methyl sulfamate<br>or<br>[(1R,2S,4R)-4-{[5-({4-[(S)-(3-bromophenyl)(methoxy)methyl]-2-thienyl}carbonyl)pyrimidin-4-yl]amino}-2-hydroxycyclopentyl]methyl sulfamate |
| I-74 | [(1R,2S,4R)-2-hydroxy-4-{[5-({4-[(4-methyl-1H-pyrazol-1-yl)methyl]-2-thienyl}carbonyl)pyrimidin-4-yl]amino}cyclopentyl]methyl sulfamate |
| I-75 | [(1R,2R,3R,4R)-4-({5-[4-(3-chlorobenzyl)-5-methyl-2-furoyl]pyrimidin-4-yl}amino)-3-fluoro-2-hydroxycyclopentyl]methyl sulfamate |
| I-76 | {(1R,2R,3S,4R)-4-[(5-{[4-(3-bromobenzyl)-5-chloro-2-thienyl]carbonyl}pyrimidin-4-yl)amino]-2,3-dihydroxycyclopentyl}methyl sulfamate |
| I-77 | [(1R,2S,4R)-4-{[5-({4-(3-chlorobenzyl)-5-[(dimethylamino)methyl]-2-thienyl}carbonyl)pyrimidin-4-yl]amino}-2-hydroxycyclopentyl]methyl sulfamate |
| I-78 | [(1R,2S,4R)-2-hydroxy-4-{[5-({5-methyl-4-[(4-methyl-1H-pyrazol-1-yl)methyl]-2-thienyl}carbonyl)pyrimidin-4-yl]amino}cyclopentyl]methyl sulfamate |
| I-79 | [(1R,2S,4R)-4-({5-[4-(3-chlorobenzyl)-2-furoyl]pyrimidin-4-yl}amino)-2-hydroxycyclopentyl]methyl sulfamate |
| I-80 | [(1R,2S,4R)-2-hydroxy-4-{[5-({4-[(2-methoxyphenoxy)methyl]-2-thienyl}carbonyl)pyrimidin-4-yl]amino}cyclopentyl]methyl sulfamate |
| I-81 | [(1R,2S,4R)-2-hydroxy-4-{[5-({4-[3-(methylsulfanyl)benzyl]-2-thienyl}carbonyl)pyrimidin-4-yl]amino}cyclopentyl]methyl sulfamate |
| I-82 | [(1R,2S,4R)-4-({5-[5-(3-bromobenzyl)-2-furoyl]pyrimidin-4-yl}amino)-2-hydroxycyclopentyl]methyl sulfamate |
| I-83 | [(1R,2S,4R)-4-{[5-({4-[(6-chloro-2,3-dihydro-1H-indol-1-yl)methyl]-2-thienyl}carbonyl)pyrimidin-4-yl]amino}-2-hydroxycyclopentyl]methyl sulfamate |
| I-84 | {(1R,2S,4R)-4-[(5-{[4-(3-chloro-2-fluorobenzyl)-2-thienyl]carbonyl}pyrimidin-4-yl)amino]-2-hydroxycyclopentyl}methyl sulfamate |
| I-85 | [(1R,2S,4R)-4-{[5-({5-chloro-4-[(R)-hydroxy(2-methoxyphenyl)methyl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(S)-hydroxy(2-methoxyphenyl)methyl]-2-thienyl}carbonyl)pyrimidin-4-yl]amino}-2-hydroxycyclopentyl]methyl sulfamate |
| I-86 | [(1R,2S,4R)-4-{[5-({5-chloro-4-[(S)-(2-chlorophenyl)(hydroxy)methyl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(R)-(2-chlorophenyl)(hydroxy)methyl]-2-thienyl}carbonyl)pyrimidin-4-yl]amino}-2-hydroxycyclopentyl]methyl sulfamate |
| I-87 | [(1R,2R,3S,4R)-4-{[5-(5-benzyl-2-furoyl)pyrimidin-4-yl]amino}-2,3-dihydroxycyclopentyl]methyl sulfamate |

-continued

| Compound No. | Name |
|---|---|
| I-88 | [(1R,2S,4R)-4-({5-[(4-benzyl-2-thienyl)carbonyl]pyrimidin-4-yl}amino)-2-hydroxycyclopentyl]methyl sulfamate |
| I-89 | {(1R,2S,4R)-4-[(5-{[4-(3-chlorobenzyl)-5-fluoro-2-thienyl]carbonyl}pyrimidin-4-yl)amino]-2-hydroxycyclopentyl}methyl sulfamate |
| I-90 | [(1R,2S,4R)-4-{[5-({5-chloro-4-[(R)-(3-chlorophenyl)(methoxy)methyl]-2-thienyl}carbonyl)pyrimidin-4-yl]amino}-2-hydroxycyclopentyl]methyl sulfamate and [(1R,2S,4R)-4-{[5-({5-chloro-4-[(S)-(3-chlorophenyl)(methoxy)methyl]-2-thienyl}carbonyl)pyrimidin-4-yl]amino}-2-hydroxycyclopentyl]methyl sulfamate |
| I-90a | [(1R,2S,4R)-4-{[5-({5-chloro-4-[(R)-(3-chlorophenyl)(methoxy)methyl]-2-thienyl}carbonyl)pyrimidin-4-yl]amino}-2-hydroxycyclopentyl]methyl sulfamate or [(1R,2S,4R)-4-{[5-({5-chloro-4-[(S)-(3-chlorophenyl)(methoxy)methyl]-2-thienyl}carbonyl)pyrimidin-4-yl]amino}-2-hydroxycyclopentyl]methyl sulfamate |
| I-90b | [(1R,2S,4R)-4-{[5-({5-chloro-4-[(R)-(3-chlorophenyl)(methoxy)methyl]-2-thienyl}carbonyl)pyrimidin-4-yl]amino}-2-hydroxycyclopentyl]methyl sulfamate or [(1R,2S,4R)-4-{[5-({5-chloro-4-[(S)-(3-chlorophenyl)(methoxy)methyl]-2-thienyl}carbonyl)pyrimidin-4-yl]amino}-2-hydroxycyclopentyl]methyl sulfamate |
| I-91 | {(1R,2S,4R)-2-hydroxy-4-[(5-{[4-(phenoxymethyl)-2-thienyl]carbonyl}pyrimidin-4-yl)amino]cyclopentyl}methyl sulfamate |
| I-92 | {(1R,2S,4R)-2-hydroxy-4-[(5-{[4-(1H-pyrrolo[2,3-b]pyridin-1-ylmethyl)-2-thienyl]carbonyl}pyrimidin-4-yl)amino]cyclopentyl}methyl sulfamate |
| I-93 | [(1R,2S,4R)-4-({5-[5-(3-chlorobenzyl)-2-furoyl]pyrimidin-4-yl}amino)-2-hydroxycyclopentyl]methyl sulfamate |
| I-94 | [(1R,2S,4R)-4-{[5-({5-chloro-4-[(R)-(3-chlorophenyl)sulfinyl]-2-thienyl}carbonyl)pyrimidin-4-yl]amino}-2-hydroxycyclopentyl]methyl sulfamate and [(1R,2S,4R)-4-{[5-({5-chloro-4-[(S)-(3-chlorophenyl)sulfinyl]-2-thienyl}carbonyl)pyrimidin-4-yl]amino}-2-hydroxycyclopentyl]methyl sulfamate |
| I-95 | [(1R,2S,4R)-4-{[5-({5-chloro-4-[(R)-(3-chlorophenyl)(methylamino)methyl]-2-thienyl}carbonyl)pyrimidin-4-yl]amino}-2-hydroxycyclopentyl]methyl sulfamate and [(1R,2S,4R)-4-{[5-({5-chloro-4-[(S)-(3-chlorophenyl)(methylamino)methyl]-2-thienyl}carbonyl)pyrimidin-4-yl]amino}-2-hydroxycyclopentyl]methyl sulfamate |
| I-96 | [(1R,2S,4R)-4-({5-[(4-benzyl-5-chloro-2-thienyl)carbonyl]pyrimidin-4-yl}amino)-2-hydroxycyclopentyl]methyl sulfamate |
| I-97 | {(1R,2S,4R)-4-[(5-{[4-(3-fluorobenzyl)-2-thienyl]carbonyl}pyrimidin-4-yl)amino]-2-hydroxycyclopentyl}methyl sulfamate |
| I-98 | [(1R,2S,4R)-4-{[5-({4-[(2-bromophenoxy)methyl]-2-thienyl}carbonyl)pyrimidin-4-yl]amino}-2-hydroxycyclopentyl]methyl sulfamate |
| I-99 | {(1R,2R,3R,4R)-3-fluoro-2-hydroxy-4-[(5-{[4-(3-iodobenzyl)-2-thienyl]carbonyl}pyrimidin-4-yl)amino]cyclopentyl}methyl sulfamate |
| I-100 | [(1R,2S,4R)-4-{[5-({4-[1-(3-chlorophenyl)vinyl]-5-methyl-2-thienyl}carbonyl)pyrimidin-4-yl]amino}-2-hydroxycyclopentyl]methyl sulfamate |
| I-101 | {(1R,2R,3R,4R)-4-[(5-{[4-(3-bromobenzyl)-2-thienyl]carbonyl}pyrimidin-4-yl)amino]-3-fluoro-2-hydroxycyclopentyl}methyl sulfamate |
| I-102 | [(1R,2S,4R)-4-{[5-({5-chloro-4-[(1R)-1-(3-chlorophenyl)-1-hydroxyethyl]-2-thienyl}carbonyl)pyrimidin-4-yl]amino}-2-hydroxycyclopentyl]methyl sulfamate and [(1R,2S,4R)-4-{[5-({5-chloro-4-[(1S)-1-(3-chlorophenyl)-1-hydroxyethyl]-2-thienyl}carbonyl)pyrimidin-4-yl]amino}-2-hydroxycyclopentyl]methyl sulfamate |
| I-102a | [(1R,2S,4R)-4-{[5-({5-chloro-4-[(1R)-1-(3-chlorophenyl)-1-hydroxyethyl]-2-thienyl}carbonyl)pyrimidin-4-yl]amino}-2-hydroxycyclopentyl]methyl sulfamate or [(1R,2S,4R)-4-{[5-({5-chloro-4-[(1S)-1-(3-chlorophenyl)-1-hydroxyethyl]-2-thienyl}carbonyl)pyrimidin-4-yl]amino}-2-hydroxycyclopentyl]methyl sulfamate |
| I-102b | [(1R,2S,4R)-4-{[5-({5-chloro-4-[(1R)-1-(3-chlorophenyl)-1-hydroxyethyl]-2-thienyl}carbonyl)pyrimidin-4-yl]amino}-2-hydroxycyclopentyl]methyl sulfamate or [(1R,2S,4R)-4-{[5-({5-chloro-4-[(1S)-1-(3-chlorophenyl)-1-hydroxyethyl]-2-thienyl}carbonyl)pyrimidin-4-yl]amino}-2-hydroxycyclopentyl]methyl sulfamate |
| I-103 | [(1R,2S,4R)-4-{[5-({5-chloro-4-[(S)-(5-chloro-2-thienyl)(hydroxy)methyl]-2-thienyl}carbonyl)pyrimidin-4-yl]amino}-2-hydroxycyclopentyl]methyl sulfamate and [(1R,2S,4R)-4-{[5-({5-chloro-4-[(R)-(5-chloro-2-thienyl)(hydroxy)methyl]-2-thienyl}carbonyl)pyrimidin-4-yl]amino}-2-hydroxycyclopentyl]methyl sulfamate |
| I-104 | {(1R,2S,4R)-4-[(5-{[4-(3,4-dichlorobenzyl)-2-thienyl]carbonyl}pyrimidin-4-yl)amino]-2-hydroxycyclopentyl}methyl sulfamate |
| I-105 | [(1R,2S,4R)-2-hydroxy-4-{[5-({4-[(3-methyl-1H-indol-1-yl)methyl]-2-thienyl}carbonyl)pyrimidin-4-yl]amino}cyclopentyl]methyl sulfamate |
| I-106 | [(1R,2S,4R)-2-hydroxy-4-{[5-({4-[(1R)-1-phenylethyl]-2-thienyl}carbonyl)pyrimidin-4-yl]amino}cyclopentyl]methyl sulfamate and [(1R,2S,4R)-2-hydroxy-4-{[5-({4-[(1S)-1-phenylethyl]-2-thienyl}carbonyl)pyrimidin-4-yl]amino}cyclopentyl]methyl sulfamate |

-continued

| Compound No. | Name |
|---|---|
| I-106a | [(1R,2S,4R)-2-hydroxy-4-{[5-({4-[(1R)-1-phenylethyl]-2-thienyl}carbonyl)pyrimidin-4-yl]amino}cyclopentyl]methyl sulfamate<br>or<br>[(1R,2S,4R)-2-hydroxy-4-{[5-({4-[(1S)-1-phenylethyl]-2-thienyl}carbonyl)pyrimidin-4-yl]amino}cyclopentyl]methyl sulfamate |
| I-106b | [(1R,2S,4R)-2-hydroxy-4-{[5-({4-[(1R)-1-phenylethyl]-2-thienyl}carbonyl)pyrimidin-4-yl]amino}cyclopentyl]methyl sulfamate<br>or<br>[(1R,2S,4R)-2-hydroxy-4-{[5-({4-[(1S)-1-phenylethyl]-2-thienyl}carbonyl)pyrimidin-4-yl]amino}cyclopentyl]methyl sulfamate |
| I-107 | {(1R,2S,4R)-4-[(5-{[5-chloro-4-(3-chlorobenzyl)-2-thienyl]carbonyl}pyrimidin-4-yl)amino]-2-hydroxycyclopentyl}methyl sulfamate |
| I-108 | {(1R,2S,4R)-2-hydroxy-4-[(5-{[4-(2-phenylethyl)-2-thienyl]carbonyl}pyrimidin-4-yl)amino]cyclopentyl}methyl sulfamate |
| I-109 | {(1R,2S,4R)-2-hydroxy-4-[(5-{[5-methyl-4-(1H-pyrazol-1-ylmethyl)-2-thienyl]carbonyl}pyrimidin-4-yl)amino]cyclopentyl}methyl sulfamate |
| I-110 | {(1R,2S,4R)-4-[(5-{[4-(3-chlorobenzyl)-5-(tetrahydro-2H-pyran-4-ylmethyl)-2-thienyl]carbonyl}pyrimidin-4-yl)amino]-2-hydroxycyclopentyl}methyl sulfamate |
| I-111 | {(1R,2S,4R)-4-[(5-{[4-(3-ethylbenzyl)-5-methyl-2-thienyl]carbonyl}pyrimidin-4-yl)amino]-2-hydroxycyclopentyl}methyl sulfamate |
| I-112 | {(1R,2S,4R)-4-[(5-{[4-(3-bromobenzyl)-5-chloro-2-thienyl]carbonyl}pyrimidin-4-yl)amino]-2-hydroxycyclopentyl}methyl sulfamate |
| I-113 | [(1R,2S,4R)-4-{[5-({4-[3-(difluoromethoxy)benzyl]-2-thienyl}carbonyl)pyrimidin-4-yl]amino}-2-hydroxycyclopentyl]methyl sulfamate |
| I-114 | {(1R,2S,4R)-2-hydroxy-4-[(5-{[4-(1H-indol-1-ylmethyl)-2-thienyl]carbonyl}pyrimidin-4-yl)amino]cyclopentyl}methyl sulfamate |
| I-115 | [(1R,2R,3S,4R)-4-({5-[(5-benzyl-2-thienyl)carbonyl]pyrimidin-4-yl}amino)-2,3-dihydroxycyclopentyl]methyl sulfamate |
| I-116 | [(1R,2S,4R)-4-{[5-({4-[(2S)-2-(cyclohex-1-en-1-yl)tetrahydrofuran-2-yl]-2-thienyl}carbonyl)pyrimidin-4-yl]amino}-2-hydroxycyclopentyl]methyl sulfamate<br>and<br>[(1R,2S,4R)-4-{[5-({4-[(2R)-2-(cyclohex-1-en-1-yl)tetrahydrofuran-2-yl]-2-thienyl}carbonyl)pyrimidin-4-yl]amino}-2-hydroxycyclopentyl]methyl sulfamate |
| I-117 | [(1R,2S,4R)-4-{[5-({4-[(1S)-1-(3-chlorophenyl)ethyl]-2-thienyl}carbonyl)pyrimidin-4-yl]amino}-2-hydroxycyclopentyl]methyl sulfamate<br>and<br>[(1R,2S,4R)-4-{[5-({4-[(1R)-1-(3-chlorophenyl)ethyl]-2-thienyl}carbonyl)pyrimidin-4-yl]amino}-2-hydroxycyclopentyl]methyl sulfamate |
| I-117a | [(1R,2S,4R)-4-{[5-({4-[(1S)-1-(3-chlorophenyl)ethyl]-2-thienyl}carbonyl)pyrimidin-4-yl]amino}-2-hydroxycyclopentyl]methyl sulfamate<br>or<br>[(1R,2S,4R)-4-{[5-({4-[(1R)-1-(3-chlorophenyl)ethyl]-2-thienyl}carbonyl)pyrimidin-4-yl]amino}-2-hydroxycyclopentyl]methyl sulfamate |
| I-117b | [(1R,2S,4R)-4-{[5-({4-[(1S)-1-(3-chlorophenyl)ethyl]-2-thienyl}carbonyl)pyrimidin-4-yl]amino}-2-hydroxycyclopentyl]methyl sulfamate<br>or<br>[(1R,2S,4R)-4-{[5-({4-[(1R)-1-(3-chlorophenyl)ethyl]-2-thienyl}carbonyl)pyrimidin-4-yl]amino}-2-hydroxycyclopentyl]methyl sulfamate |
| I-118 | {(1R,2S,4R)-4-[(5-{[5-bromo-4-(3-chlorobenzyl)-2-thienyl]carbonyl}pyrimidin-4-yl)amino]-2-hydroxycyclopentyl}methyl sulfamate |
| I-119 | [(1R,2S,4R)-2-hydroxy-4-({5-[(4-{[5-(trifluoromethyl)-2-furyl]methyl}-2-thienyl)carbonyl]pyrimidin-4-yl}amino)cyclopentyl]methyl sulfamate |
| I-120 | [(1R,2S,4R)-4-{[5-({4-[(3-chlorophenoxy)methyl]-2-thienyl}carbonyl)pyrimidin-4-yl]amino}-2-hydroxycyclopentyl]methyl sulfamate |
| I-121 | [(1R,2S,4R)-2-hydroxy-4-{[5-({5-methyl-4-[(2S)-2-phenyltetrahydrofuran-2-yl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(2R)-2-phenyltetrahydrofuran-2-yl]-2-thienyl}carbonyl)pyrimidin-4-yl]amino}cyclopentyl]methyl sulfamate |
| I-122 | [(1R,2S,4R)-4-({5-[(5-chloro-4-{(R)-[3-(trifluoromethyl)phenyl]sulfinyl}-2-thienyl)carbonyl]pyrimidin-4-yl}amino)-2-hydroxycyclopentyl]methyl sulfamate<br>and<br>[(1R,2S,4R)-4-({5-[(5-chloro-4-{(S)-[3-(trifluoromethyl)phenyl]sulfinyl}-2-thienyl)carbonyl]pyrimidin-4-yl}amino)-2-hydroxycyclopentyl]methyl sulfamate |
| I-123 | {(1R,2S,4R)-2-hydroxy-4-[(5-{[4-(3-methoxybenzyl)-2-thienyl]carbonyl}pyrimidin-4-yl)amino]cyclopentyl}methyl sulfamate |
| I-124 | [(1R,2S,4R)-4-{[5-({4-[(2-cyanophenoxy)methyl]-2-thienyl}carbonyl)pyrimidin-4-yl]amino}-2-hydroxycyclopentyl]methyl sulfamate |
| I-125 | [(1R,2S,4R)-4-{[5-({4-[(6-chloro-1H-indol-1-yl)methyl]-2-thienyl}carbonyl)pyrimidin-4-yl]amino}-2-hydroxycyclopentyl]methyl sulfamate |
| I-126 | [(1R,2S,4R)-2-hydroxy-4-{[5-({4-[(6-methoxy-2,3-dihydro-1H-indol-1-yl)methyl]-5-methyl-2-thienyl}carbonyl)pyrimidin-4-yl]amino}cyclopentyl]methyl sulfamate |
| I-127 | [(1R,2S,4R)-4-{[5-(5-benzyl-2-furoyl)pyrimidin-4-yl]amino}-2-hydroxycyclopentyl]methyl sulfamate |
| I-128 | [(1R,2S,4R)-4-{[5-({4-[(6-cyano-2,3-dihydro-1H-indol-1-yl)methyl]-5-methyl-2-thienyl}carbonyl)pyrimidin-4-yl]amino}-2-hydroxycyclopentyl]methyl sulfamate |

-continued

| Compound No. | Name |
|---|---|
| I-129 | [(1R,2S,4R)-4-{[5-({4-[(2-chlorophenoxy)methyl]-2-thienyl}carbonyl)pyrimidin-4-yl]amino}-2-hydroxycyclopentyl]methyl sulfamate |
| I-130 | [(1R,2S,4R)-2-hydroxy-4-({5-[(4-{[4-(trifluoromethyl)-1H-pyrazol-1-yl]methyl}-2-thienyl)carbonyl]pyrimidin-4-yl}amino)cyclopentyl]methyl sulfamate |
| I-131 | [(1R,2S,4R)-2-hydroxy-4-{[5-({4-[(2-methylphenoxy)methyl]-2-thienyl}carbonyl)pyrimidin-4-yl]amino}cyclopentyl]methyl sulfamate |
| I-132 | [(1R,2S,4R)-2-hydroxy-4-{[5-({4-[(6-methyl-1H-indol-1-yl)methyl]-2-thienyl}carbonyl)pyrimidin-4-yl]amino}cyclopentyl]methyl sulfamate |
| I-134 | [(1R,2R,3S,4R)-2,3-dihydroxy-4-{[5-(5-phenyl-2-furoyl)pyrimidin-4-yl]amino}cyclopentyl]methyl sulfamate |
| I-135 | [(1R,2S,4R)-4-{[5-({4-[(1R)-1-(3-chlorophenyl)ethyl]-5-methyl-2-thienyl}carbonyl)pyrimidin-4-yl]amino}-2-hydroxycyclopentyl]methyl sulfamate and [(1R,2S,4R)-4-{[5-({4-[(1S)-1-(3-chlorophenyl)ethyl]-5-methyl-2-thienyl}carbonyl)pyrimidin-4-yl]amino}-2-hydroxycyclopentyl]methyl sulfamate |
| I-135a | [(1R,2S,4R)-4-{[5-({4-[(1R)-1-(3-chlorophenyl)ethyl]-5-methyl-2-thienyl}carbonyl)pyrimidin-4-yl]amino}-2-hydroxycyclopentyl]methyl sulfamate or [(1R,2S,4R)-4-{[5-({4-[(1S)-1-(3-chlorophenyl)ethyl]-5-methyl-2-thienyl}carbonyl)pyrimidin-4-yl]amino}-2-hydroxycyclopentyl]methyl sulfamate |
| I-135b | [(1R,2S,4R)-4-{[5-({4-[(1R)-1-(3-chlorophenyl)ethyl]-5-methyl-2-thienyl}carbonyl)pyrimidin-4-yl]amino}-2-hydroxycyclopentyl]methyl sulfamate or [(1R,2S,4R)-4-{[5-({4-[(1S)-1-(3-chlorophenyl)ethyl]-5-methyl-2-thienyl}carbonyl)pyrimidin-4-yl]amino}-2-hydroxycyclopentyl]methyl sulfamate |
| I-136 | [(1R,2S,4R)-4-{[5-({5-chloro-4-[(1R)-1-hydroxy-2-phenylethyl]-2-thienyl}carbonyl)pyrimidin-4-yl]amino}-2-hydroxycyclopentyl]methyl sulfamate and [(1R,2S,4R)-4-{[5-({5-chloro-4-[(1S)-1-hydroxy-2-phenylethyl]-2-thienyl}carbonyl)pyrimidin-4-yl]amino}-2-hydroxycyclopentyl]methyl sulfamate |
| I-137 | {(1R,2S,4R)-2-hydroxy-4-[(5-{[5-methyl-4-(phenylsulfanyl)-2-thienyl]carbonyl}pyrimidin-4-yl)amino]cyclopentyl}methyl sulfamate |
| I-138 | [(1R,2S,4R)-4-({5-[(4-{[(3-chlorophenyl)(methyl)amino]methyl}-2-thienyl)carbonyl]pyrimidin-4-yl}amino)-2-hydroxycyclopentyl]methyl sulfamate |
| I-139 | [(1R,2S,4R)-4-{[5-(4,5-dibenzyl-2-furoyl)pyrimidin-4-yl]amino}-2-hydroxycyclopentyl]methyl sulfamate |
| I-140 | {(1R,2S,4R)-4-[(5-{[4-(cyclohex-1-en-1-ylmethyl)-2-thienyl]carbonyl}pyrimidin-4-yl)amino]-2-hydroxycyclopentyl}methyl sulfamate |
| I-141 | [(1R,2S,4R)-4-{[5-({5-chloro-4-[(1S)-1-hydroxy-2-methylprop-2-en-1-yl]-2-thienyl}carbonyl)pyrimidin-4-yl]amino}-2-hydroxycyclopentyl]methyl sulfamate and [(1R,2S,4R)-4-{[5-({5-chloro-4-[(1R)-1-hydroxy-2-methylprop-2-en-1-yl]-2-thienyl}carbonyl)pyrimidin-4-yl]amino}-2-hydroxycyclopentyl]methyl sulfamate |
| I-142 | {(1R,2S,4R)-4-[(5-{[5-(3-chlorobenzyl)-4-(hydroxymethyl)-2-thienyl]carbonyl}pyrimidin-4-yl)amino]-2-hydroxycyclopentyl}methyl sulfamate |
| I-143 | [(1R,2S,4R)-4-{[5-({4-[(3-chlorophenyl)sulfanyl]-5-methyl-2-thienyl}carbonyl)pyrimidin-4-yl]amino}-2-hydroxycyclopentyl]methyl sulfamate |
| I-144 | [(1R,2S,4R)-4-({5-[(4,5-dibenzyl-2-thienyl)carbonyl]pyrimidin-4-yl}amino)-2-hydroxycyclopentyl]methyl sulfamate |
| I-145 | [(1R,2S,4R)-2-hydroxy-4-({5-[(5-methyl-4-{[3-(trifluoromethyl)phenyl]sulfanyl}-2-thienyl)carbonyl]pyrimidin-4-yl}amino)cyclopentyl]methyl sulfamate |
| I-146 | [(1R,2S,4R)-4-{[5-({4-[2-(3-chlorophenyl)ethyl]-2-thienyl}carbonyl)pyrimidin-4-yl]amino}-2-hydroxycyclopentyl]methyl sulfamate |
| I-147 | [(1R,2S,4R)-4-({5-[(4-{[(2-chlorophenyl)sulfanyl]methyl}-2-thienyl)carbonyl]pyrimidin-4-yl}amino)-2-hydroxycyclopentyl]methyl sulfamate |
| I-148 | [(1R,2S,4R)-4-{[5-({4-[(4-bromo-2-cyano-1H-pyrrol-1-yl)methyl]-5-methyl-2-thienyl}carbonyl)pyrimidin-4-yl]amino}-2-hydroxycyclopentyl]methyl sulfamate |
| I-149 | [(1R,2S,4R)-4-{[5-({5-chloro-4-[(R)-(2,5-dichlorophenyl)(hydroxy)methyl]-2-thienyl}carbonyl)pyrimidin-4-yl]amino}-2-hydroxycyclopentyl]methyl sulfamate and [(1R,2S,4R)-4-{[5-({5-chloro-4-[(S)-(2,5-dichlorophenyl)(hydroxy)methyl]-2-thienyl}carbonyl)pyrimidin-4-yl]amino}-2-hydroxycyclopentyl]methyl sulfamate |
| I-150 | [(1R,2S,4R)-4-{[5-({5-chloro-4-[(1R)-3-cyclopropyl-1-hydroxyprop-2-yn-1-yl]-2-thienyl}carbonyl)pyrimidin-4-yl]amino}-2-hydroxycyclopentyl]methyl sulfamate and [(1R,2S,4R)-4-{[5-({5-chloro-4-[(1S)-3-cyclopropyl-1-hydroxyprop-2-yn-1-yl]-2-thienyl}carbonyl)pyrimidin-4-yl]amino}-2-hydroxycyclopentyl]methyl sulfamate |
| I-151 | [(1R,2S,4R)-4-{[5-({4-chloro-5-[(R)-(3-chlorophenyl)(hydroxy)methyl]-2-thienyl}carbonyl)pyrimidin-4-yl]amino}-2-hydroxycyclopentyl]methyl sulfamate and [(1R,2S,4R)-4-{[5-({4-chloro-5-[(S)-(3-chlorophenyl)(hydroxy)methyl]-2-thienyl}carbonyl)pyrimidin-4-yl]amino}-2-hydroxycyclopentyl]methyl sulfamate |

-continued

| Compound No. | Name |
|---|---|
| I-151a | [(1R,2S,4R)-4-{[5-({4-chloro-5-[(R)-(3-chlorophenyl)(hydroxy)methyl]-2-thienyl}carbonyl)pyrimidin-4-yl]amino}-2-hydroxycyclopentyl]methyl sulfamate or [(1R,2S,4R)-4-{[5-({4-chloro-5-[(S)-(3-chlorophenyl)(hydroxy)methyl]-2-thienyl}carbonyl)pyrimidin-4-yl]amino}-2-hydroxycyclopentyl]methyl sulfamate |
| I-151b | [(1R,2S,4R)-4-{[5-({4-chloro-5-[(R)-(3-chlorophenyl)(hydroxy)methyl]-2-thienyl}carbonyl)pyrimidin-4-yl]amino}-2-hydroxycyclopentyl]methyl sulfamate or [(1R,2S,4R)-4-{[5-({4-chloro-5-[(S)-(3-chlorophenyl)(hydroxy)methyl]-2-thienyl}carbonyl)pyrimidin-4-yl]amino}-2-hydroxycyclopentyl]methyl sulfamate |
| I-152 | [(1R,2S,4R)-4-{[5-({5-[(1R)-1-(3-chlorophenyl)-1-hydroxyethyl]-2-thienyl}carbonyl)pyrimidin-4-yl]amino}-2-hydroxycyclopentyl]methyl sulfamate and [(1R,2S,4R)-4-{[5-({5-[(1S)-1-(3-chlorophenyl)-1-hydroxyethyl]-2-thienyl}carbonyl)pyrimidin-4-yl]amino}-2-hydroxycyclopentyl]methyl sulfamate |
| I-153 | [(1R,2S,4R)-4-{[5-({4-[(R)-(3-chlorophenyl)(dimethylamino)methyl]-2-thienyl}carbonyl)pyrimidin-4-yl]amino}-2-hydroxycyclopentyl]methyl sulfamate and [(1R,2S,4R)-4-{[5-({4-[(S)-(3-chlorophenyl)(dimethylamino)methyl]-2-thienyl}carbonyl)pyrimidin-4-yl]amino}-2-hydroxycyclopentyl]methyl sulfamate |
| I-153a | [(1R,2S,4R)-4-{[5-({4-[(R)-(3-chlorophenyl)(dimethylamino)methyl]-2-thienyl}carbonyl)pyrimidin-4-yl]amino}-2-hydroxycyclopentyl]methyl sulfamate or [(1R,2S,4R)-4-{[5-({4-[(S)-(3-chlorophenyl)(dimethylamino)methyl]-2-thienyl}carbonyl)pyrimidin-4-yl]amino}-2-hydroxycyclopentyl]methyl sulfamate |
| I-153b | [(1R,2S,4R)-4-{[5-({4-[(R)-(3-chlorophenyl)(dimethylamino)methyl]-2-thienyl}carbonyl)pyrimidin-4-yl]amino}-2-hydroxycyclopentyl]methyl sulfamate or [(1R,2S,4R)-4-{[5-({4-[(S)-(3-chlorophenyl)(dimethylamino)methyl]-2-thienyl}carbonyl)pyrimidin-4-yl]amino}-2-hydroxycyclopentyl]methyl sulfamate |
| I-154 | [(1R,2S,4R)-4-{[5-({4-[(2R)-2-(3-chlorophenyl)tetrahydro-2H-pyran-2-yl]-2-thienyl}carbonyl)pyrimidin-4-yl]amino}-2-hydroxycyclopentyl]methyl sulfamate and [(1R,2S,4R)-4-{[5-({4-[(2S)-2-(3-chlorophenyl)tetrahydro-2H-pyran-2-yl]-2-thienyl}carbonyl)pyrimidin-4-yl]amino}-2-hydroxycyclopentyl]methyl sulfamate |
| I-155 | {(1R,2S,4R)-4-[(5-{[4-(2,3-dichlorobenzyl)-2-thienyl]carbonyl}pyrimidin-4-yl)amino]-2-hydroxycyclopentyl}methyl sulfamate |
| I-156 | [(1R,2S,4R)-4-{[5-({4-[(2-ethoxyphenoxy)methyl]-2-thienyl}carbonyl)pyrimidin-4-yl]amino}-2-hydroxycyclopentyl]methyl sulfamate |
| I-157 | {(1R,2S,4R)-4-[(5-{[4-(4-chlorobenzyl)-2-thienyl]carbonyl}pyrimidin-4-yl)amino]-2-hydroxycyclopentyl}methyl sulfamate |
| I-158 | [(1R,2R,3S,4R)-4-({5-[5-(2-chlorophenyl)-2-furoyl]pyrimidin-4-yl}amino)-2,3-dihydroxycyclopentyl]methyl sulfamate |
| I-159 | [(1R,2S,4R)-4-{[5-({4-[(5-chloro-2,3-dihydro-1H-indol-1-yl)methyl]-5-methyl-2-thienyl}carbonyl)pyrimidin-4-yl]amino}-2-hydroxycyclopentyl]methyl sulfamate |
| I-160 | [(1R,2S,4R)-2-hydroxy-4-{[5-({4-[(3-methyl-1H-pyrazolo[3,4-c]pyridin-1-yl)methyl]-2-thienyl}carbonyl)pyrimidin-4-yl]amino}cyclopentyl]methyl sulfamate |
| I-161 | [(1R,2S,4R)-2-hydroxy-4-{[5-({4-[(2-iodophenoxy)methyl]-2-thienyl}carbonyl)pyrimidin-4-yl]amino}cyclopentyl]methyl sulfamate |
| I-162 | [(1R,2R,3R,4R)-4-({5-[(4-benzyl-5-chloro-2-thienyl)carbonyl]pyrimidin-4-yl}amino)-3-fluoro-2-hydroxycyclopentyl]methyl sulfamate |
| I-163 | [(1R,2S,4R)-4-{[5-({4-[(4-chlorophenoxy)methyl]-2-thienyl}carbonyl)pyrimidin-4-yl]amino}-2-hydroxycyclopentyl]methyl sulfamate |
| I-164 | [(1R,2S,4R)-4-{[5-({4-[1-(3-bromophenyl)vinyl]-2-thienyl}carbonyl)pyrimidin-4-yl]amino}-2-hydroxycyclopentyl]methyl sulfamate |
| I-165 | {(1R,2S,4R)-4-[(5-{[4-(2-chlorobenzyl)-2-thienyl]carbonyl}pyrimidin-4-yl)amino]-2-hydroxycyclopentyl}methyl sulfamate |
| I-166 | [(1R,2S,4R)-4-{[5-({4-[(2S)-2-cyclohexyltetrahydrofuran-2-yl]-2-thienyl}carbonyl)pyrimidin-4-yl]amino}-2-hydroxycyclopentyl]methyl sulfamate and [(1R,2S,4R)-4-{[5-({4-[(2R)-2-cyclohexyltetrahydrofuran-2-yl]-2-thienyl}carbonyl)pyrimidin-4-yl]amino}-2-hydroxycyclopentyl]methyl sulfamate |
| I-167 | {(1R,2S,4R)-4-[(5-{[4-(3,4-dihydroisoquinolin-2(1H)-ylmethyl)-2-thienyl]carbonyl}pyrimidin-4-yl)amino]-2-hydroxycyclopentyl}methyl sulfamate |
| I-168 | {(1R,2S,4R)-4-[(5-{[4-(6,7-dihydrothieno[3,2-c]pyridin-5(4H)-ylmethyl)-2-thienyl]carbonyl}pyrimidin-4-yl)amino]-2-hydroxycyclopentyl}methyl sulfamate |
| I-169 | [(1R,2S,4R)-4-{[5-({4-[(6-cyano-1H-indol-1-yl)methyl]-2-thienyl}carbonyl)pyrimidin-4-yl]amino}-2-hydroxycyclopentyl]methyl sulfamate |
| I-170 | [(1R,2S,4R)-2-hydroxy-4-{[5-({4-[(3-methyl-1H-pyrrol-1-yl)methyl]-2-thienyl}carbonyl)pyrimidin-4-yl]amino}cyclopentyl]methyl sulfamate |
| I-171 | {(1R,2S,4R)-4-[(5-{[4-(2,3-dihydro-1H-pyrrolo[2,3-b]pyridin-1-ylmethyl)-5-methyl-2-thienyl]carbonyl}pyrimidin-4-yl)amino]-2-hydroxycyclopentyl}methyl sulfamate |

-continued

| Compound No. | Name |
|---|---|
| I-172 | [(1R,2S,4R)-4-{[5-({5-chloro-4-[(R)-cyclohexyl(hydroxy)methyl]-2-thienyl}carbonyl)pyrimidin-4-yl]amino}-2-hydroxycyclopentyl]methyl sulfamate and [(1R,2S,4R)-4-{[5-({5-chloro-4-[(S)-cyclohexyl(hydroxy)methyl]-2-thienyl}carbonyl)pyrimidin-4-yl]amino}-2-hydroxycyclopentyl]methyl sulfamate |
| I-173 | {(1R,2S,4R)-4-[(5-{[4-(3,6-dihydro-2H-thiopyran-4-ylmethyl)-2-thienyl]carbonyl}pyrimidin-4-yl)amino]-2-hydroxycyclopentyl}methyl sulfamate |
| I-174 | [(1R,2S,4R)-4-{[5-({5-chloro-4-[(R)-hydroxy(tetrahydro-2H-pyran-4-yl)methyl]-2-thienyl}carbonyl)pyrimidin-4-yl]amino}-2-hydroxycyclopentyl]methyl sulfamate and [(1R,2S,4R)-4-{[5-({5-chloro-4-[(S)-hydroxy(tetrahydro-2H-pyran-4-yl)methyl]-2-thienyl}carbonyl)pyrimidin-4-yl]amino}-2-hydroxycyclopentyl]methyl sulfamate |
| I-175 | [(1R,2S,4R)-4-{[5-({5-chloro-4-[(3-chlorophenyl)sulfanyl]-2-thienyl}carbonyl)pyrimidin-4-yl]amino}-2-hydroxycyclopentyl]methyl sulfamate |
| I-176 | [(1R,2S,4R)-2-hydroxy-4-({5-[(4-{[2-(trifluoromethoxy)phenoxy]methyl}-2-thienyl)carbonyl]pyrimidin-4-yl}amino)cyclopentyl]methyl sulfamate |
| I-177 | [(1R,2S,4R)-2-hydroxy-4-{[5-({4-[(phenylsulfanyl)methyl]-2-thienyl}carbonyl)pyrimidin-4-yl]amino}cyclopentyl]methyl sulfamate |
| I-178 | [(1R,2S,4R)-4-{[5-({4-[2-(4-chlorophenyl)ethyl]-2-thienyl}carbonyl)pyrimidin-4-yl]amino}-2-hydroxycyclopentyl]methyl sulfamate |
| I-179 | {(1R,2S,4R)-4-[(5-{[4-(3-chlorobenzyl)-5-cyano-2-thienyl]carbonyl}pyrimidin-4-yl)amino]-2-hydroxycyclopentyl}methyl sulfamate |
| I-180 | [(1R,2S,4R)-4-{[5-({4-[(2,3-dichlorophenoxy)methyl]-2-thienyl}carbonyl)pyrimidin-4-yl]amino}-2-hydroxycyclopentyl]methyl sulfamate |
| I-181 | [(1R,2S,4R)-4-{[5-[4-[(3-chlorophenyl)sulfonyl]-5-methyl-2-thienyl}carbonyl)pyrimidin-4-yl]amino}-2-hydroxycyclopentyl]methyl sulfamate |
| I-182 | [(1R,2S,4R)-4-{[5-({4-[(2-ethylphenoxy)methyl]-2-thienyl}carbonyl)pyrimidin-4-yl]amino}-2-hydroxycyclopentyl]methyl sulfamate |
| I-183 | [(1R,2S,4R)-2-hydroxy-4-{[5-({4-[2-(2-methoxyphenyl)ethyl]-2-thienyl}carbonyl)pyrimidin-4-yl]amino}cyclopentyl]methyl sulfamate |
| I-184 | [(1R,2S,4R)-2-hydroxy-4-({5-[(4-{[6-(trifluoromethyl)-1H-indol-1-yl]methyl}-2-thienyl)carbonyl]pyrimidin-4-yl}amino)cyclopentyl]methyl sulfamate |
| I-185 | {(1R,2S,4R)-4-[(5-{[4-(3-cyanobenzyl)-2-thienyl]carbonyl}pyrimidin-4-yl)amino]-2-hydroxycyclopentyl}methyl sulfamate |
| I-186 | {(1R,2S,4R)-2-hydroxy-4-[(5-{[4-(1H-pyrrolo[2,3-c]pyridin-1-ylmethyl)-2-thienyl]carbonyl}pyrimidin-4-yl)amino]cyclopentyl}methyl sulfamate |
| I-187 | {(1R,2S,4R)-4-[(5-{[4-(1,3-dihydro-2H-isoindol-2-ylmethyl)-2-thienyl]carbonyl}pyrimidin-4-yl)amino]-2-hydroxycyclopentyl}methyl sulfamate |
| I-188 | [(1R,2S,4R)-2-hydroxy-4-({5-[(4-{[2-(trifluoromethyl)phenoxy]methyl}-2-thienyl)carbonyl]pyrimidin-4-yl}amino)cyclopentyl]methyl sulfamate |
| I-189 | [(1R,2S,4R)-4-({5-[(5-chloro-4-{[3-(trifluoromethyl)phenyl]sulfanyl}-2-thienyl)carbonyl]pyrimidin-4-yl}amino)-2-hydroxycyclopentyl]methyl sulfamate |
| I-190 | {(1R,2S,4R)-4-[(5-{[4-(5,6-dihydroimidazo[1,2-a]pyrazin-7(8H)-ylmethyl)-2-thienyl]carbonyl}pyrimidin-4-yl)amino]-2-hydroxycyclopentyl}methyl sulfamate |
| I-191 | [(1R,2S,4R)-2-hydroxy-4-{[5-({4-[(2-isopropylphenoxy)methyl]-2-thienyl}carbonyl)pyrimidin-4-yl]amino}cyclopentyl]methyl sulfamate |
| I-192 | {(1R,2S,4R)-4-[(5-{[4-(1H-benzimidazol-1-ylmethyl)-2-thienyl]carbonyl}pyrimidin-4-yl)amino]-2-hydroxycyclopentyl}methyl sulfamate |
| I-193 | {(1R,2S,4R)-4-[(5-{[4-(2,5-dihydrofuran-3-ylmethyl)-2-thienyl]carbonyl}pyrimidin-4-yl)amino]-2-hydroxycyclopentyl}methyl sulfamate |
| I-194 | [(1R,2S,4R)-4-{[5-({4-[(3-cyano-1H-pyrrol-1-yl)methyl]-5-methyl-2-thienyl}carbonyl)pyrimidin-4-yl]amino}-2-hydroxycyclopentyl]methyl sulfamate |
| I-195 | [(1R,2S,4R)-4-{[5-({5-chloro-4-[(1R)-1-hydroxy-2-methylpropyl]-2-thienyl}carbonyl)pyrimidin-4-yl]amino}-2-hydroxycyclopentyl]methyl sulfamate and [(1R,2S,4R)-4-{[5-({5-chloro-4-[(1S)-1-hydroxy-2-methylpropyl]-2-thienyl}carbonyl)pyrimidin-4-yl]amino}-2-hydroxycyclopentyl]methyl sulfamate |
| I-196 | {(1R,2S,4R)-4-[(5-{[4-(3,6-dihydro-2H-pyran-4-ylmethyl)-2-thienyl]carbonyl}pyrimidin-4-yl)amino]-2-hydroxycyclopentyl}methyl sulfamate |
| I-197 | {(1R,2S,4R)-2-hydroxy-4-[(5-{4-[(1S)-1-hydroxy-2-methylprop-2-en-1-yl]-2-furoyl}pyrimidin-4-yl)amino]cyclopentyl}methyl sulfamate and {(1R,2S,4R)-2-hydroxy-4-[(5-{4-[(1R)-1-hydroxy-2-methylprop-2-en-1-yl]-2-furoyl}pyrimidin-4-yl)amino]cyclopentyl}methyl sulfamate |
| I-199 | {(1R,2S,4R)-4-[(5-{[4-(cyclohexylmethyl)-2-thienyl]carbonyl}pyrimidin-4-yl)amino]-2-hydroxycyclopentyl}methyl sulfamate |
| I-200 | {(1R,2S,4R)-2-hydroxy-4-[(5-{[4-(phenylsulfonyl)-2-thienyl]carbonyl}pyrimidin-4-yl)amino]cyclopentyl}methyl sulfamate |
| I-201 | [(1R,2S,4R)-2-hydroxy-4-{[5-({4-[(2-isopropoxyphenoxy)methyl]-2-thienyl}carbonyl)pyrimidin-4-yl]amino}cyclopentyl]methyl sulfamate |
| I-202 | {(1R,2R,3S,4R)-2,3-dihydroxy-4-[(5-{[5-(2-hydroxypropan-2-yl)-2-thienyl]carbonyl}pyrimidin-4-yl)amino]cyclopentyl}methyl sulfamate |
| I-203 | [(1R,2S,4R)-4-{[5-({5-chloro-4-[(3-chlorophenyl)sulfonyl]-2-thienyl}carbonyl)pyrimidin-4-yl]amino}-2-hydroxycyclopentyl]methyl sulfamate |
| I-204 | {(1R,2S,4R)-4-[(5-{[4-(3,6-dihydropyridin-1(2H)-ylmethyl)-2-thienyl]carbonyl}pyrimidin-4-yl)amino]-2-hydroxycyclopentyl}methyl sulfamate |

| Compound No. | Name |
|---|---|
| I-205 | {(1R,2R,3R,4R)-4-[(5-{[5-(3-chlorobenzyl)-2-thienyl]carbonyl}pyrimidin-4-yl)amino]-3-fluoro-2-hydroxycyclopentyl}methyl sulfamate |
| I-206 | [(1R,2S,4R)-2-hydroxy-4-({5-[5-(hydroxymethyl)-2-furoyl]pyrimidin-4-yl}amino)cyclopentyl]methyl sulfamate |
| I-207 | {(1R,2S,4R)-4-[(5-{[5-chloro-4-(3-chlorobenzoyl)-2-thienyl]carbonyl}pyrimidin-4-yl)amino]-2-hydroxycyclopentyl}methyl sulfamate |
| I-208 | [(1R,2S,4R)-4-{[5-(4-benzoyl-2-furoyl)pyrimidin-4-yl]amino}-2-hydroxycyclopentyl]methyl sulfamate |
| I-209 | {(1R,2S,4R)-4-[(5-{[(2S)-2-(3-chlorophenyl)-2,3,4,5-tetrahydro-2,3'-bithiophen-5'-yl]carbonyl}pyrimidin-4-yl)amino]-2-hydroxycyclopentyl}methyl sulfamate and {(1R,2S,4R)-4-[(5-{[(2R)-2-(3-chlorophenyl)-2,3,4,5-tetrahydro-2,3'-bithiophen-5'-yl]carbonyl}pyrimidin-4-yl)amino]-2-hydroxycyclopentyl}methyl sulfamate |
| I-210 | [(1R,2S,4R)-4-{[5-({4-[(5-chloropyridin-3-yl)methyl]-2-thienyl}carbonyl)pyrimidin-4-yl]amino}-2-hydroxycyclopentyl]methyl sulfamate |
| I-211 | {(1R,2S,4R)-4-[(5-{[5-chloro-4-(hydroxymethyl)-2-thienyl]carbonyl}pyrimidin-4-yl)amino]-2-hydroxycyclopentyl}methyl sulfamate |
| I-212 | [(1R,2S,4R)-2-hydroxy-4-({5-[5-(methoxymethyl)-2-furoyl]pyrimidin-4-yl}amino)cyclopentyl]methyl sulfamate |
| I-215 | [(1R,2S,4R)-4-({5-[(4-benzoyl-5-chloro-2-thienyl)carbonyl]pyrimidin-4-yl}amino)-2-hydroxycyclopentyl]methyl sulfamate |
| I-216 | [(1R,2S,4R)-2-hydroxy-4-({5-[4-(hydroxymethyl)-2-furoyl]pyrimidin-4-yl}amino)cyclopentyl]methyl sulfamate |
| I-217 | {(1R,2S,4R)-2-hydroxy-4-[(5-{[4-(methoxymethyl)-2-thienyl]carbonyl}pyrimidin-4-yl)amino]cyclopentyl}methyl sulfamate |
| I-218 | {(1R,2S,4R)-4-[(5-{[5-chloro-4-(methoxymethyl)-2-thienyl]carbonyl}pyrimidin-4-yl)amino]-2-hydroxycyclopentyl}methyl sulfamate |
| I-219 | {(1R,2S,4R)-4-[(5-{[4-(2,5-dihydro-1H-pyrrol-1-ylmethyl)-2-thienyl]carbonyl}pyrimidin-4-yl)amino]-2-hydroxycyclopentyl}methyl sulfamate |
| I-220 | [(1R,2S,4R)-2-hydroxy-4-({5-[4-(2-hydroxypropan-2-yl)-2-furoyl]pyrimidin-4-yl}amino)cyclopentyl]methyl sulfamate |
| I-221 | {(1R,2S,4R)-4-[(5-{[4-({3-[(dimethylamino)methyl]-1H-indol-1-yl}methyl)-2-thienyl]carbonyl}pyrimidin-4-yl)amino]-2-hydroxycyclopentyl}methyl sulfamate |
| I-222 | [(1R,2S,4R)-4-{[5-({4-[(benzylamino)methyl]-2-thienyl}carbonyl)pyrimidin-4-yl]amino}-2-hydroxycyclopentyl]methyl sulfamate |
| I-223 | [(1R,2S,4R)-2-hydroxy-4-({5-[4-(methoxymethyl)-2-furoyl]pyrimidin-4-yl}amino)cyclopentyl]methyl sulfamate |
| I-224 | [(1R,2S,4R)-4-{[5-({4-[(3,3-difluoropiperidin-1-yl)methyl]-2-thienyl}carbonyl)pyrimidin-4-yl]amino}-2-hydroxycyclopentyl]methyl sulfamate |
| I-225 | [(1R,2S,4R)-2-hydroxy-4-({5-[(4-{[(3R)-3-methylpiperidin-1-yl]methyl}-2-thienyl)carbonyl]pyrimidin-4-yl}amino)cyclopentyl]methyl sulfamate and [(1R,2S,4R)-2-hydroxy-4-({5-[(4-{[(3S)-3-methylpiperidin-1-yl]methyl}-2-thienyl)carbonyl]pyrimidin-4-yl}amino)cyclopentyl]methyl sulfamate |
| I-226 | [(1R,2S,4R)-4-{[5-({5-chloro-4-[(1S)-1-hydroxyethyl]-2-thienyl}carbonyl)pyrimidin-4-yl]amino}-2-hydroxycyclopentyl]methyl sulfamate and [(1R,2S,4R)-4-{[5-({5-chloro-4-[(1R)-1-hydroxyethyl]-2-thienyl}carbonyl)pyrimidin-4-yl]amino}-2-hydroxycyclopentyl]methyl sulfamate |
| I-227 | [(1R,2S,4R)-4-{[5-({4-[(2S)-2-(3-chlorophenyl)-1-methylpyrrolidin-2-yl]-2-thienyl}carbonyl)pyrimidin-4-yl]amino}-2-hydroxycyclopentyl]methyl sulfamate and [(1R,2S,4R)-4-{[5-({4-[(2R)-2-(3-chlorophenyl)-1-methylpyrrolidin-2-yl]-2-thienyl}carbonyl)pyrimidin-4-yl]amino}-2-hydroxycyclopentyl]methyl sulfamate |
| I-228 | [(1R,2S,4R)-4-{[5-({4-[(3,3-difluoropyrrolidin-1-yl)methyl]-2-thienyl}carbonyl)pyrimidin-4-yl]amino}-2-hydroxycyclopentyl]methyl sulfamate |
| I-229 | [(1R,2S,4R)-4-({5-[(4-acetyl-2-thienyl)carbonyl]pyrimidin-4-yl}amino)-2-hydroxycyclopentyl]methyl sulfamate |
| I-230 | {(1R,2S,4R)-2-hydroxy-4-[(5-{[4-(hydroxymethyl)-2-thienyl]carbonyl}pyrimidin-4-yl)amino]cyclopentyl}methyl sulfamate |
| I-231 | {(1R,2S,4R)-2-hydroxy-4-[(5-{[4-(1H-imidazol-1-ylmethyl)-2-thienyl]carbonyl}pyrimidin-4-yl)amino]cyclopentyl}methyl sulfamate |
| I-233 | {(1R,2S,4R)-4-[(5-{[5-(3-chlorobenzyl)-3-methyl-2-thienyl]carbonyl}pyrimidin-4-yl)amino]-2-hydroxycyclopentyl}methyl sulfamate |
| I-234 | [(1R,2S,4R)-4-{[5-(4-acetyl-2-furoyl)pyrimidin-4-yl]amino}-2-hydroxycyclopentyl]methyl sulfamate |
| I-235 | {(1R,2S,4R)-2-hydroxy-4-[(5-{[5-(2-hydroxypropan-2-yl)-2-thienyl]carbonyl}pyrimidin-4-yl)amino]cyclopentyl}methyl sulfamate |
| I-236 | [(1R,2R,3S,4R)-4-{[2-chloro-5-(5-phenyl-2-furoyl)pyrimidin-4-yl]amino}-2,3-dihydroxycyclopentyl]methyl sulfamate |
| I-237 | [(1R,2S,4R)-2-hydroxy-4-{[5-({4-[(5-methyl-2-furyl)methyl]-2-thienyl}carbonyl)pyrimidin-4-yl]amino}cyclopentyl]methyl sulfamate |

-continued

| Compound No. | Name |
|---|---|
| I-238 | [(1R,2S,4R)-4-{[5-({4-[(2S)-2-cyclopropyltetrahydrofuran-2-yl]-2-thienyl}carbonyl)pyrimidin-4-yl]amino}-2-hydroxycyclopentyl]methyl sulfamate and [(1R,2S,4R)-4-{[5-({4-[(2R)-2-cyclopropyltetrahydrofuran-2-yl]-2-thienyl}carbonyl)pyrimidin-4-yl]amino}-2-hydroxycyclopentyl]methyl sulfamate |
| I-239 | [(1R,2S,4R)-2-hydroxy-4-({5-[5-(phenylsulfonyl)-2-furoyl]pyrimidin-4-yl}amino)cyclopentyl]methyl sulfamate |
| I-240 | {(1R,2S,4R)-2-hydroxy-4-[(5-{4-(2-hydroxypropan-2-yl)-2-thienyl]carbonyl}pyrimidin-4-yl)amino]cyclopentyl}methyl sulfamate |
| I-241 | [(1R,2S,4R)-2-hydroxy-4-{[5-({4-[(4-phenylpiperazin-1-yl)methyl]-2-thienyl}carbonyl)pyrimidin-4-yl]amino}cyclopentyl]methyl sulfamate |
| I-242 | [(1R,2S,4R)-4-({5-[(4-acetyl-5-chloro-2-thienyl)carbonyl]pyrimidin-4-yl}amino)-2-hydroxycyclopentyl]methyl sulfamate |
| I-243 | [(1R,2S,4R)-4-{[5-({4-[(4-bromo-1H-imidazol-1-yl)methyl]-2-thienyl}carbonyl)pyrimidin-4-yl]amino}-2-hydroxycyclopentyl]methyl sulfamate |
| I-247a | [(1R,2R,3S,4R)-4-{[5-({4-[(1R)-7-bromo-1,2,3,4-tetrahydroisoquinolin-1-yl]-5-methyl-2-thienyl}carbonyl)pyrimidin-4-yl]amino}-2,3-dihydroxycyclopentyl]methyl sulfamate or [(1R,2R,3S,4R)-4-{[5-({4-[(1S)-7-bromo-1,2,3,4-tetrahydroisoquinolin-1-yl]-5-methyl-2-thienyl}carbonyl)pyrimidin-4-yl]amino}-2,3-dihydroxycyclopentyl]methyl sulfamate |
| I-247b | [(1R,2R,3S,4R)-4-{[5-({4-[(1R)-7-bromo-1,2,3,4-tetrahydroisoquinolin-1-yl]-5-methyl-2-thienyl}carbonyl)pyrimidin-4-yl]amino}-2,3-dihydroxycyclopentyl]methyl sulfamate or [(1R,2R,3S,4R)-4-{[5-({4-[(1S)-7-bromo-1,2,3,4-tetrahydroisoquinolin-1-yl]-5-methyl-2-thienyl}carbonyl)pyrimidin-4-yl]amino}-2,3-dihydroxycyclopentyl]methyl sulfamate |
| I-248a | [(1R,2S,4R)-4-{[5-({4-[(1S)-7-bromo-1,2,3,4-tetrahydroisoquinolin-1-yl]-5-methyl-2-thienyl}carbonyl)pyrimidin-4-yl]amino}-2-hydroxycyclopentyl]methyl sulfamate or [(1R,2S,4R)-4-{[5-({4-[(1R)-7-bromo-1,2,3,4-tetrahydroisoquinolin-1-yl]-5-methyl-2-thienyl}carbonyl)pyrimidin-4-yl]amino}-2-hydroxycyclopentyl]methyl sulfamate |
| I-248b | [(1R,2S,4R)-4-{[5-({4-[(1S)-7-bromo-1,2,3,4-tetrahydroisoquinolin-1-yl]-5-methyl-2-thienyl}carbonyl)pyrimidin-4-yl]amino}-2-hydroxycyclopentyl]methyl sulfamate or [(1R,2S,4R)-4-{[5-({4-[(1R)-7-bromo-1,2,3,4-tetrahydroisoquinolin-1-yl]-5-methyl-2-thienyl}carbonyl)pyrimidin-4-yl]amino}-2-hydroxycyclopentyl]methyl sulfamate |
| I-249a | [(1R,2R,3S,4R)-4-{[5-({5-chloro-4-[(1R)-7-chloro-1,2,3,4-tetrahydroisoquinolin-1-yl]-2-thienyl}carbonyl)pyrimidin-4-yl]amino}-2,3-dihydroxycyclopentyl]methyl sulfamate or [(1R,2R,3S,4R)-4-{[5-({5-chloro-4-[(1S)-7-chloro-1,2,3,4-tetrahydroisoquinolin-1-yl]-2-thienyl}carbonyl)pyrimidin-4-yl]amino}-2,3-dihydroxycyclopentyl]methyl sulfamate |
| I-249b | [(1R,2R,3S,4R)-4-{[5-({5-chloro-4-[(1R)-7-chloro-1,2,3,4-tetrahydroisoquinolin-1-yl]-2-thienyl}carbonyl)pyrimidin-4-yl]amino}-2,3-dihydroxycyclopentyl]methyl sulfamate or [(1R,2R,3S,4R)-4-{[5-({5-chloro-4-[(1S)-7-chloro-1,2,3,4-tetrahydroisoquinolin-1-yl]-2-thienyl}carbonyl)pyrimidin-4-yl]amino}-2,3-dihydroxycyclopentyl]methyl sulfamate |
| I-250 | [(1R,2R,3S,4R)-4-{[5-({4-[(1R)-3,4-dihydro-1H-isochromen-1-yl]-5-methyl-2-thienyl}carbonyl)pyrimidin-4-yl]amino}-2,3-dihydroxycyclopentyl]methyl sulfamate and [(1R,2R,3S,4R)-4-{[5-({4-[(1S)-3,4-dihydro-1H-isochromen-1-yl]-5-methyl-2-thienyl}carbonyl)pyrimidin-4-yl]amino}-2,3-dihydroxycyclopentyl]methyl sulfamate |
| I-250a | [(1R,2R,3S,4R)-4-{[5-({4-[(1R)-3,4-dihydro-1H-isochromen-1-yl]-5-methyl-2-thienyl}carbonyl)pyrimidin-4-yl]amino}-2,3-dihydroxycyclopentyl]methyl sulfamate or [(1R,2R,3S,4R)-4-{[5-({4-[(1S)-3,4-dihydro-1H-isochromen-1-yl]-5-methyl-2-thienyl}carbonyl)pyrimidin-4-yl]amino}-2,3-dihydroxycyclopentyl]methyl sulfamate |
| I-250b | [(1R,2R,3S,4R)-4-{[5-({4-[(1R)-3,4-dihydro-1H-isochromen-1-yl]-5-methyl-2-thienyl}carbonyl)pyrimidin-4-yl]amino}-2,3-dihydroxycyclopentyl]methyl sulfamate or [(1R,2R,3S,4R)-4-{[5-({4-[(1S)-3,4-dihydro-1H-isochromen-1-yl]-5-methyl-2-thienyl}carbonyl)pyrimidin-4-yl]amino}-2,3-dihydroxycyclopentyl]methyl sulfamate |
| I-251 | [(1R,2S,4R)-4-{[5-({4-[(1R)-7-bromo-1,2,3,4-tetrahydroisoquinolin-1-yl]-5-chloro-2-thienyl}carbonyl)pyrimidin-4-yl]amino}-2-hydroxycyclopentyl]methyl sulfamate and [(1R,2S,4R)-4-{[5-({4-[(1S)-7-bromo-1,2,3,4-tetrahydroisoquinolin-1-yl]-5-chloro-2-thienyl}carbonyl)pyrimidin-4-yl]amino}-2-hydroxycyclopentyl]methyl sulfamate |
| I-251a | [(1R,2S,4R)-4-{[5-({4-[(1R)-7-bromo-1,2,3,4-tetrahydroisoquinolin-1-yl]-5-chloro-2-thienyl}carbonyl)pyrimidin-4-yl]amino}-2-hydroxycyclopentyl]methyl sulfamate or [(1R,2S,4R)-4-{[5-({4-[(1S)-7-bromo-1,2,3,4-tetrahydroisoquinolin-1-yl]-5-chloro-2-thienyl}carbonyl)pyrimidin-4-yl]amino}-2-hydroxycyclopentyl]methyl sulfamate |
| I-251b | [(1R,2S,4R)-4-{[5-({4-[(1R)-7-bromo-1,2,3,4-tetrahydroisoquinolin-1-yl]-5-chloro-2-thienyl}carbonyl)pyrimidin-4-yl]amino}-2-hydroxycyclopentyl]methyl sulfamate or [(1R,2S,4R)-4-{[5-({4-[(1S)-7-bromo-1,2,3,4-tetrahydroisoquinolin-1-yl]-5-chloro-2-thienyl}carbonyl)pyrimidin-4-yl]amino}-2-hydroxycyclopentyl]methyl sulfamate |

-continued

| Compound No. | Name |
|---|---|
| I-252 | [(1R,2S,4R)-4-{[5-({4-[(1R)-7-ethynyl-3,4-dihydro-1H-isochromen-1-yl]-5-methyl-2-thienyl}carbonyl)pyrimidin-4-yl]amino}-2-hydroxycyclopentyl]methyl sulfamate and<br>[(1R,2S,4R)-4-{[5-({4-[(1S)-7-ethynyl-3,4-dihydro-1H-isochromen-1-yl]-5-methyl-2-thienyl}carbonyl)pyrimidin-4-yl]amino}-2-hydroxycyclopentyl]methyl sulfamate |
| I-252a | [(1R,2S,4R)-4-{[5-({4-[(1R)-7-ethynyl-3,4-dihydro-1H-isochromen-1-yl]-5-methyl-2-thienyl}carbonyl)pyrimidin-4-yl]amino}-2-hydroxycyclopentyl]methyl sulfamate or<br>[(1R,2S,4R)-4-{[5-({4-[(1S)-7-ethynyl-3,4-dihydro-1H-isochromen-1-yl]-5-methyl-2-thienyl}carbonyl)pyrimidin-4-yl]amino}-2-hydroxycyclopentyl]methyl sulfamate |
| I-252b | [(1R,2S,4R)-4-{[5-({4-[(1R)-7-ethynyl-3,4-dihydro-1H-isochromen-1-yl]-5-methyl-2-thienyl}carbonyl)pyrimidin-4-yl]amino}-2-hydroxycyclopentyl]methyl sulfamate or<br>[(1R,2S,4R)-4-{[5-({4-[(1S)-7-ethynyl-3,4-dihydro-1H-isochromen-1-yl]-5-methyl-2-thienyl}carbonyl)pyrimidin-4-yl]amino}-2-hydroxycyclopentyl]methyl sulfamate |
| I-253 | [(1R,2S,4R)-4-{[5-({5-chloro-4-[(8S)-2-chloro-5,6,7,8-tetrahydro-1,7-naphthyridin-8-yl]-2-thienyl}carbonyl)pyrimidin-4-yl]amino}-2-hydroxycyclopentyl]methyl sulfamate and<br>[(1R,2S,4R)-4-{[5-({5-chloro-4-[(8R)-2-chloro-5,6,7,8-tetrahydro-1,7-naphthyridin-8-yl]-2-thienyl}carbonyl)pyrimidin-4-yl]amino}-2-hydroxycyclopentyl]methyl sulfamate |
| I-253a | [(1R,2S,4R)-4-{[5-({5-chloro-4-[(8S)-2-chloro-5,6,7,8-tetrahydro-1,7-naphthyridin-8-yl]-2-thienyl}carbonyl)pyrimidin-4-yl]amino}-2-hydroxycyclopentyl]methyl sulfamate or<br>[(1R,2S,4R)-4-{[5-({5-chloro-4-[(8R)-2-chloro-5,6,7,8-tetrahydro-1,7-naphthyridin-8-yl]-2-thienyl}carbonyl)pyrimidin-4-yl]amino}-2-hydroxycyclopentyl]methyl sulfamate |
| I-253b | [(1R,2S,4R)-4-{[5-({5-chloro-4-[(8S)-2-chloro-5,6,7,8-tetrahydro-1,7-naphthyridin-8-yl]-2-thienyl}carbonyl)pyrimidin-4-yl]amino}-2-hydroxycyclopentyl]methyl sulfamate or<br>[(1R,2S,4R)-4-{[5-({5-chloro-4-[(8R)-2-chloro-5,6,7,8-tetrahydro-1,7-naphthyridin-8-yl]-2-thienyl}carbonyl)pyrimidin-4-yl]amino}-2-hydroxycyclopentyl]methyl sulfamate |
| I-254 | [(1R,2S,4R)-4-{[5-({4-[(1R)-3,4-dihydro-1H-isochromen-1-yl]-2-thienyl}carbonyl)pyrimidin-4-yl]amino}-2-hydroxycyclopentyl]methyl sulfamate and<br>[(1R,2S,4R)-4-{[5-({4-[(1S)-3,4-dihydro-1H-isochromen-1-yl]-2-thienyl}carbonyl)pyrimidin-4-yl]amino}-2-hydroxycyclopentyl]methyl sulfamate |
| I-254a | [(1R,2S,4R)-4-{[5-({4-[(1R)-3,4-dihydro-1H-isochromen-1-yl]-2-thienyl}carbonyl)pyrimidin-4-yl]amino}-2-hydroxycyclopentyl]methyl sulfamate or<br>[(1R,2S,4R)-4-{[5-({4-[(1S)-3,4-dihydro-1H-isochromen-1-yl]-2-thienyl}carbonyl)pyrimidin-4-yl]amino}-2-hydroxycyclopentyl]methyl sulfamate |
| I-254b | [(1R,2S,4R)-4-{[5-({4-[(1R)-3,4-dihydro-1H-isochromen-1-yl]-2-thienyl}carbonyl)pyrimidin-4-yl]amino}-2-hydroxycyclopentyl]methyl sulfamate or<br>[(1R,2S,4R)-4-{[5-({4-[(1S)-3,4-dihydro-1H-isochromen-1-yl]-2-thienyl}carbonyl)pyrimidin-4-yl]amino}-2-hydroxycyclopentyl]methyl sulfamate |
| I-255a | [(1R,2S,4R)-4-{[5-({5-chloro-4-[(1R)-7-chloro-1,2,3,4-tetrahydroisoquinolin-1-yl]-2-thienyl}carbonyl)pyrimidin-4-yl]amino}-2-hydroxycyclopentyl]methyl sulfamate or<br>[(1R,2S,4R)-4-{[5-({5-chloro-4-[(1S)-7-chloro-1,2,3,4-tetrahydroisoquinolin-1-yl]-2-thienyl}carbonyl)pyrimidin-4-yl]amino}-2-hydroxycyclopentyl]methyl sulfamate |
| I-255b | [(1R,2S,4R)-4-{[5-({5-chloro-4-[(1R)-7-chloro-1,2,3,4-tetrahydroisoquinolin-1-yl]-2-thienyl}carbonyl)pyrimidin-4-yl]amino}-2-hydroxycyclopentyl]methyl sulfamate or<br>[(1R,2S,4R)-4-{[5-({5-chloro-4-[(1S)-7-chloro-1,2,3,4-tetrahydroisoquinolin-1-yl]-2-thienyl}carbonyl)pyrimidin-4-yl]amino}-2-hydroxycyclopentyl]methyl sulfamate |
| I-256 | [(1R,2S,4R)-4-{[5-({4-[(1R)-3,4-dihydro-1H-isochromen-1-yl]-5-methyl-2-thienyl}carbonyl)pyrimidin-4-yl]amino}-2-hydroxycyclopentyl]methyl sulfamate and<br>[(1R,2S,4R)-4-{[5-({4-[(1S)-3,4-dihydro-1H-isochromen-1-yl]-5-methyl-2-thienyl}carbonyl)pyrimidin-4-yl]amino}-2-hydroxycyclopentyl]methyl sulfamate |
| I-256a | [(1R,2S,4R)-4-{[5-({4-[(1S)-3,4-dihydro-1H-isochromen-1-yl]-5-methyl-2-thienyl}carbonyl)pyrimidin-4-yl]amino}-2-hydroxycyclopentyl]methyl sulfamate |
| I-256b | [(1R,2S,4R)-4-{[5-({4-[(1R)-3,4-dihydro-1H-isochromen-1-yl]-5-methyl-2-thienyl}carbonyl)pyrimidin-4-yl]amino}-2-hydroxycyclopentyl]methyl sulfamate |
| I-257 | [(1R,2S,4R)-4-{[5-({4-[(1R)-7-chloro-3,4-dihydro-1H-isochromen-1-yl]-5-methyl-2-thienyl}carbonyl)pyrimidin-4-yl]amino}-2-hydroxycyclopentyl]methyl sulfamate and<br>[(1R,2S,4R)-4-{[5-({4-[(1S)-7-chloro-3,4-dihydro-1H-isochromen-1-yl]-5-ethyl-2-thienyl}carbonyl)pyrimidin-4-yl]amino}-2-hydroxycyclopentyl]methyl sulfamate |
| I-257a | [(1R,2S,4R)-4-{[5-({4-[(1S)-7-chloro-3,4-dihydro-1H-isochromen-1-yl]-5-methyl-2-thienyl}carbonyl)pyrimidin-4-yl]amino}-2-hydroxycyclopentyl]methyl sulfamate |
| I-257b | [(1R,2S,4R)-4-{[5-({4-[(1R)-7-chloro-3,4-dihydro-1H-isochromen-1-yl]-5-methyl-2-thienyl}carbonyl)pyrimidin-4-yl]amino}-2-hydroxycyclopentyl]methyl sulfamate |
| I-258 | [(1R,2S,4R)-2-hydroxy-4-{[5-({5-methyl-4-[(1R)-7-(trifluoromethyl)-3,4-dihydro-1H-isochromen-1-yl]-2-thienyl}carbonyl)pyrimidin-4-yl]amino}cyclopentyl]methyl sulfamate |

-continued

| Compound No. | Name |
|---|---|
| | and [(1R,2S,4R)-2-hydroxy-4-{[5-({5-methyl-4-[(1S)-7-(trifluoromethyl)-3,4-dihydro-1H-isochromen-1-yl]-2-thienyl}carbonyl)pyrimidin-4-yl]amino}cyclopentyl]methyl sulfamate |
| I-258a | [(1R,2S,4R)-2-hydroxy-4-{[5-({5-methyl-4-[(1R)-7-(trifluoromethyl)-3,4-dihydro-1H-isochromen-1-yl]-2-thienyl}carbonyl)pyrimidin-4-yl]amino}cyclopentyl]methyl sulfamate or [(1R,2S,4R)-2-hydroxy-4-{[5-({5-methyl-4-[(1S)-7-(trifluoromethyl)-3,4-dihydro-1H-isochromen-1-yl]-2-thienyl}carbonyl)pyrimidin-4-yl]amino}cyclopentyl]methyl sulfamate |
| I-258b | [(1R,2S,4R)-2-hydroxy-4-{[5-({5-methyl-4-[(1R)-7-(trifluoromethyl)-3,4-dihydro-1H-isochromen-1-yl]-2-thienyl}carbonyl)pyrimidin-4-yl]amino}cyclopentyl]methyl sulfamate or [(1R,2S,4R)-2-hydroxy-4-{[5-({5-methyl-4-[(1S)-7-(trifluoromethyl)-3,4-dihydro-1H-isochromen-1-yl]-2-thienyl}carbonyl)pyrimidin-4-yl]amino}cyclopentyl]methyl sulfamate |
| I-259 | [(1R,2R,3S,4R)-4-{[5-({4-[(1R)-7-bromo-1,2,3,4-tetrahydroisoquinolin-1-yl]-5-chloro-2-thienyl}carbonyl)pyrimidin-4-yl]amino}-2,3-dihydroxycyclopentyl]methyl sulfamate and [(1R,2R,3S,4R)-4-{[5-({4-[(1S)-7-bromo-1,2,3,4-tetrahydroisoquinolin-1-yl]-5-chloro-2-thienyl}carbonyl)pyrimidin-4-yl]amino}-2,3-dihydroxycyclopentyl]methyl sulfamate |
| I-259a | [(1R,2R,3S,4R)-4-{[5-({4-[(1R)-7-bromo-1,2,3,4-tetrahydroisoquinolin-1-yl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(1S)-7-bromo-1,2,3,4-tetrahydroisoquinolin-1-yl]-5-chloro-2-thienyl}carbonyl)pyrimidin-4-yl]amino}-2,3-dihydroxycyclopentyl]methyl sulfamate |
| I-259b | [(1R,2R,3S,4R)-4-{[5-({4-[(1R)-7-bromo-1,2,3,4-tetrahydroisoquinolin-1-yl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(1S)-7-bromo-1,2,3,4-tetrahydroisoquinolin-1-yl]-5-chloro-2-thienyl}carbonyl)pyrimidin-4-yl]amino}-2,3-dihydroxycyclopentyl]methyl sulfamate |
| I-260 | [(1R,2S,4R)-4-{[5-({4-[(8R)-2-chloro-5,5-difluoro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate and [(1R,2S,4R)-4-{[5-({4-[(8S)-2-chloro-5,5-difluoro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate |
| I-260a | [(1R,2S,4R)-4-{[5-({4-[(8R)-2-chloro-5,5-difluoro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate or [(1R,2S,4R)-4-{[5-({4-[(8S)-2-chloro-5,5-difluoro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate |
| I-260b | [(1R,2S,4R)-4-{[5-({4-[(8R)-2-chloro-5,5-difluoro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate or [(1R,2S,4R)-4-{[5-({4-[(8S)-2-chloro-5,5-difluoro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate |
| I-261 | [(1R,2S,4R)-4-{[5-({4-[(1R)-7-chloro-3,4-dihydro-1H-isochromen-1-yl]-2-thienyl}carbonyl)pyrimidin-4-yl]amino}-2-hydroxycyclopentyl]methyl sulfamate and [(1R,2S,4R)-4-{[5-({4-[(1S)-7-chloro-3,4-dihydro-1H-isochromen-1-yl]-2-thienyl}carbonyl)pyrimidin-4-yl]amino}-2-hydroxycyclopentyl]methyl sulfamate |
| I-261a | [(1R,2S,4R)-4-{[5-({4-[(1R)-7-chloro-3,4-dihydro-1H-isochromen-1-yl]-2-thienyl}carbonyl)pyrimidin-4-yl]amino}-2-hydroxycyclopentyl]methyl sulfamate or [(1R,2S,4R)-4-{[5-({4-[(1S)-7-chloro-3,4-dihydro-1H-isochromen-1-yl]-2-thienyl}carbonyl)pyrimidin-4-yl]amino}-2-hydroxycyclopentyl]methyl sulfamate |
| I-261b | [(1R,2S,4R)-4-{[5-({4-[(1R)-7-chloro-3,4-dihydro-1H-isochromen-1-yl]-2-thienyl}carbonyl)pyrimidin-4-yl]amino}-2-hydroxycyclopentyl]methyl sulfamate or [(1R,2S,4R)-4-{[5-({4-[(1S)-7-chloro-3,4-dihydro-1H-isochromen-1-yl]-2-thienyl}carbonyl)pyrimidin-4-yl]amino}-2-hydroxycyclopentyl]methyl sulfamate |
| I-262 | [(1R,2S,4R)-4-{[5-({5-chloro-4-[(1R)-6-chloro-2,3-dihydro-1H-isoindol-1-yl]-2-thienyl}carbonyl)pyrimidin-4-yl]amino}-2-hydroxycyclopentyl]methyl sulfamate and [(1R,2S,4R)-4-{[5-({5-chloro-4-[(1S)-6-chloro-2,3-dihydro-1H-isoindol-1-yl]-2-thienyl}carbonyl)pyrimidin-4-yl]amino}-2-hydroxycyclopentyl]methyl sulfamate |

-continued

| Compound No. | Name |
|---|---|
| I-262a | [(1R,2S,4R)-4-{[5-({5-chloro-4-[(1R)-6-chloro-2,3-dihydro-1H-isoindol-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-6-chloro-2,3-dihydro-1H-isoindol-1-yl]-2-thienyl}carbonyl)pyrimidin-4-yl]amino}-2-hydroxycyclopentyl]methyl sulfamate |
| I-262b | [(1R,2S,4R)-4-{[5-({5-chloro-4-[(1R)-6-chloro-2,3-dihydro-1H-isoindol-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-6-chloro-2,3-dihydro-1H-isoindol-1-yl]-2-thienyl}carbonyl)pyrimidin-4-yl]amino}-2-hydroxycyclopentyl]methyl sulfamate |
| I-263a | [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate |
| I-263b | [(1R,2S,4R)-4-{[5-({4-[(1S)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate |
| I-264 | [(1R,2R,3R,4R)-4-{[5-({4-[(1S)-7-chloro-3,4-dihydro-1H-isochromen-1-yl]-5-methyl-2-thienyl}carbonyl)pyrimidin-4-yl]amino}-3-fluoro-2-hydroxycyclopentyl]methyl sulfamate<br>and<br>[(1R,2R,3R,4R)-4-{[5-({4-[(1R)-7-chloro-3,4-dihydro-1H-isochromen-1-yl]-5-methyl-2-thienyl}carbonyl)pyrimidin-4-yl]amino}-3-fluoro-2-hydroxycyclopentyl]methyl sulfamate |
| I-264a | [(1R,2R,3R,4R)-4-{[5-({4-[(1S)-7-chloro-3,4-dihydro-1H-isochromen-1-yl]-5-methyl-2-thienyl}carbonyl)pyrimidin-4-yl]amino}-3-fluoro-2-hydroxycyclopentyl]methyl sulfamate<br>or<br>[(1R,2R,3R,4R)-4-{[5-({4-[(1R)-7-chloro-3,4-dihydro-1H-isochromen-1-yl]-5-methyl-2-thienyl}carbonyl)pyrimidin-4-yl]amino}-3-fluoro-2-hydroxycyclopentyl]methyl sulfamate |
| I-264b | [(1R,2R,3R,4R)-4-{[5-({4-[(1S)-7-chloro-3,4-dihydro-1H-isochromen-1-yl]-5-methyl-2-thienyl}carbonyl)pyrimidin-4-yl]amino}-3-fluoro-2-hydroxycyclopentyl]methyl sulfamate<br>or<br>[(1R,2R,3R,4R)-4-{[5-({4-[(1R)-7-chloro-3,4-dihydro-1H-isochromen-1-yl]-5-methyl-2-thienyl}carbonyl)pyrimidin-4-yl]amino}-3-fluoro-2-hydroxycyclopentyl]methyl sulfamate |
| I-265 | [(1R,2S,4R)-4-{[5-({4-[(1R)-6-chloro-2-methyl-2,3-dihydro-1H-isoindol-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-6-chloro-2-methyl-2,3-dihydro-1H-isoindol-1-yl]-2-thienyl}carbonyl)pyrimidin-4-yl]amino}-2-hydroxycyclopentyl]methyl sulfamate |
| I-265a | [(1R,2S,4R)-4-{[5-({4-[(1R)-6-chloro-2-methyl-2,3-dihydro-1H-isoindol-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-6-chloro-2-methyl-2,3-dihydro-1H-isoindol-1-yl]-2-thienyl}carbonyl)pyrimidin-4-yl]amino}-2-hydroxycyclopentyl]methyl sulfamate |
| I-265b | [(1R,2S,4R)-4-{[5-({4-[(1R)-6-chloro-2-methyl-2,3-dihydro-1H-isoindol-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-6-chloro-2-methyl-2,3-dihydro-1H-isoindol-1-yl]-2-thienyl}carbonyl)pyrimidin-4-yl]amino}-2-hydroxycyclopentyl]methyl sulfamate |
| I-266 | [(1R,2S,4R)-4-{[5-({5-chloro-4-[(8S)-5,8-dihydro-6H-pyrano[3,4-b]pyridin-8-yl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(8R)-5,8-dihydro-6H-pyrano[3,4-b]pyridin-8-yl]-2-thienyl}carbonyl)pyrimidin-4-yl]amino}-2-hydroxycyclopentyl]methyl sulfamate |
| I-266a | [(1R,2S,4R)-4-{[5-({5-chloro-4-[(8S)-5,8-dihydro-6H-pyrano[3,4-b]pyridin-8-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(8R)-5,8-dihydro-6H-pyrano[3,4-b]pyridin-8-yl]-2-thienyl}carbonyl)pyrimidin-4-yl]amino}-2-hydroxycyclopentyl]methyl sulfamate |
| I-266b | [(1R,2S,4R)-4-{[5-({5-chloro-4-[(8S)-5,8-dihydro-6H-pyrano[3,4-b]pyridin-8-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(8R)-5,8-dihydro-6H-pyrano[3,4-b]pyridin-8-yl]-2-thienyl}carbonyl)pyrimidin-4-yl]amino}-2-hydroxycyclopentyl]methyl sulfamate |
| I-267 | [(1R,2S,4R)-4-{[5-({4-[(1R)-7-fluoro-3,4-dihydro-1H-isochromen-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-7-fluoro-3,4-dihydro-1H-isochromen-1-yl]-2-thienyl}carbonyl)pyrimidin-4-yl]amino}-2-hydroxycyclopentyl]methyl sulfamate |
| I-267a | [(1R,2S,4R)-4-{[5-({4-[(1R)-7-fluoro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-7-fluoro-3,4-dihydro-1H-isochromen-1-yl]-2-thienyl}carbonyl)pyrimidin-4-yl]amino}-2-hydroxycyclopentyl]methyl sulfamate |

-continued

| Compound No. | Name |
|---|---|
| I-267b | [(1R,2S,4R)-4-{[5-({4-[(1R)-7-fluoro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-7-fluoro-3,4-dihydro-1H-isochromen-1-yl]-2-thienyl}carbonyl)pyrimidin-4-yl]amino}-2-hydroxycyclopentyl]methyl sulfamate |
| I-268 | [(1R,2S,4R)-4-{[5-({4-[(1R)-7-bromo-3,4-dihydro-1H-isochromen-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-7-bromo-3,4-dihydro-1H-isochromen-1-yl]-2-thienyl}carbonyl)pyrimidin-4-yl]amino}-2-hydroxycyclopentyl]methyl sulfamate |
| I-268a | [(1R,2S,4R)-4-{[5-({4-[(1R)-7-bromo-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-7-bromo-3,4-dihydro-1H-isochromen-1-yl]-2-thienyl}carbonyl)pyrimidin-4-yl]amino}-2-hydroxycyclopentyl]methyl sulfamate |
| I-268b | [(1R,2S,4R)-4-{[5-({4-[(1R)-7-bromo-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-7-bromo-3,4-dihydro-1H-isochromen-1-yl]-2-thienyl}carbonyl)pyrimidin-4-yl]amino}-2-hydroxycyclopentyl]methyl sulfamate |
| I-269 | [(1R,2S,4R)-4-{[5-({4-[(7S)-4,7-dihydro-5H-thieno[2,3-c]pyran-7-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(7R)-4,7-dihydro-5H-thieno[2,3-c]pyran-7-yl]-5-methyl-2-thienyl}carbonyl)pyrimidin-4-yl]amino}-2-hydroxycyclopentyl]methyl sulfamate |
| I-269a | [(1R,2S,4R)-4-{[5-({4-[(7S)-4,7-dihydro-5H-thieno[2,3-c]pyran-7-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(7R)-4,7-dihydro-5H-thieno[2,3-c]pyran-7-yl]-5-methyl-2-thienyl}carbonyl)pyrimidin-4-yl]amino}-2-hydroxycyclopentyl]methyl sulfamate |
| I-269b | [(1R,2S,4R)-4-{[5-({4-[(7S)-4,7-dihydro-5H-thieno[2,3-c]pyran-7-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(7R)-4,7-dihydro-5H-thieno[2,3-c]pyran-7-yl]-5-methyl-2-thienyl}carbonyl)pyrimidin-4-yl]amino}-2-hydroxycyclopentyl]methyl sulfamate |
| I-270 | {(1R,2S,4R)-4-[(5-{4-[(1R)-7-chloro-3,4-dihydro-1H-isochromen-1-yl]-5-methyl-2-furoyl}pyrimidin-4-yl)amino]-2-hydroxycyclopentyl}methyl sulfamate<br>and<br>{(1R,2S,4R)-4-[(5-{4-[(1S)-7-chloro-3,4-dihydro-1H-isochromen-1-yl]-5-methyl-2-furoyl}pyrimidin-4-yl)amino]-2-hydroxycyclopentyl}methyl sulfamate |
| I-270a | {(1R,2S,4R)-4-[(5-{4-[(1R)-7-chloro-3,4-dihydro-1H-isochromen-1-yl]-5-methyl-2-furoyl}pyrimidin-4-yl)amino]-2-hydroxycyclopentyl}methyl sulfamate<br>or<br>{(1R,2S,4R)-4-[(5-{4-[(1S)-7-chloro-3,4-dihydro-1H-isochromen-1-yl]-5-methyl-2-furoyl}pyrimidin-4-yl)amino]-2-hydroxycyclopentyl}methyl sulfamate |
| I-270b | {(1R,2S,4R)-4-[(5-{4-[(1R)-7-chloro-3,4-dihydro-1H-isochromen-1-yl]-5-methyl-2-furoyl}pyrimidin-4-yl)amino]-2-hydroxycyclopentyl}methyl sulfamate<br>or<br>{(1R,2S,4R)-4-[(5-{4-[(1S)-7-chloro-3,4-dihydro-1H-isochromen-1-yl]-5-methyl-2-furoyl}pyrimidin-4-yl)amino]-2-hydroxycyclopentyl}methyl sulfamate |
| I-271a | [(1R,2R,3R,4R)-4-{[5-({4-[(1R)-3,4-dihydro-1H-isochromen-1-yl]-5-methyl-2-thienyl}carbonyl)pyrimidin-4-yl]amino}-3-fluoro-2-hydroxycyclopentyl]methyl sulfamate<br>or<br>[(1R,2R,3R,4R)-4-{[5-({4-[(1S)-3,4-dihydro-1H-isochromen-1-yl]-5-methyl-2-thienyl}carbonyl)pyrimidin-4-yl]amino}-3-fluoro-2-hydroxycyclopentyl]methyl sulfamate |
| I-272a | {(1R,2S,4R)-4-[(5-{4-[(1R)-3,4-dihydro-1H-isochromen-1-yl]-5-methyl-2-furoyl}pyrimidin-4-yl)amino]-2-hydroxycyclopentyl}methyl sulfamate<br>or<br>{(1R,2S,4R)-4-[(5-{4-[(1S)-3,4-dihydro-1H-isochromen-1-yl]-5-methyl-2-furoyl}pyrimidin-4-yl)amino]-2-hydroxycyclopentyl}methyl sulfamate |
| I-272b | {(1R,2S,4R)-4-[(5-{4-[(1R)-3,4-dihydro-1H-isochromen-1-yl]-5-methyl-2-furoyl}pyrimidin-4-yl)amino]-2-hydroxycyclopentyl}methyl sulfamate<br>or<br>{(1R,2S,4R)-4-[(5-{4-[(1S)-3,4-dihydro-1H-isochromen-1-yl]-5-methyl-2-furoyl}pyrimidin-4-yl)amino]-2-hydroxycyclopentyl}methyl sulfamate |
| I-273 | [(1R,2S,4R)-4-{[5-({4-[(1R)-6,7-difluoro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-6,7-difluoro-3,4-dihydro-1H-isochromen-1-yl]-2-thienyl}carbonyl)pyrimidin-4-yl]amino}-2-hydroxycyclopentyl]methyl sulfamate |

| Compound No. | Name |
|---|---|
| I-274 | [(1R,2S,4R)-4-{[5-({4-[(1R)-7-chloro-1,2,3,4-tetrahydroisoquinolin-1-yl]-2-thienyl}carbonyl)pyrimidin-4-yl]amino}-2-hydroxycyclopentyl]methyl sulfamate and [(1R,2S,4R)-4-{[5-({4-[(1S)-7-chloro-1,2,3,4-tetrahydroisoquinolin-1-yl]-2-thienyl}carbonyl)pyrimidin-4-yl]amino}-2-hydroxycyclopentyl]methyl sulfamate |
| I-274a | [(1R,2S,4R)-4-{[5-({4-[(1R)-7-chloro-1,2,3,4-tetrahydroisoquinolin-1-yl]-2-thienyl}carbonyl)pyrimidin-4-yl]amino}-2-hydroxycyclopentyl]methyl sulfamate or [(1R,2S,4R)-4-{[5-({4-[(1S)-7-chloro-1,2,3,4-tetrahydroisoquinolin-1-yl]-2-thienyl}carbonyl)pyrimidin-4-yl]amino}-2-hydroxycyclopentyl]methyl sulfamate |
| I-274b | [(1R,2S,4R)-4-{[5-({4-[(1R)-7-chloro-1,2,3,4-tetrahydroisoquinolin-1-yl]-2-thienyl}carbonyl)pyrimidin-4-yl]amino}-2-hydroxycyclopentyl]methyl sulfamate or [(1R,2S,4R)-4-{[5-({4-[(1S)-7-chloro-1,2,3,4-tetrahydroisoquinolin-1-yl]-2-thienyl}carbonyl)pyrimidin-4-yl]amino}-2-hydroxycyclopentyl]methyl sulfamate |
| I-275 | [(1R,2S,4R)-4-{[5-({4-[(4S)-6,7-dihydro-4H-thieno[3,2-c]pyran-4-yl]-5-methyl-2-thienyl}carbonyl)pyrimidin-4-yl]amino}-2-hydroxycyclopentyl]methyl sulfamate and [(1R,2S,4R)-4-{[5-({4-[(4R)-6,7-dihydro-4H-thieno[3,2-c]pyran-4-yl]-5-methyl-2-thienyl}carbonyl)pyrimidin-4-yl]amino}-2-hydroxycyclopentyl]methyl sulfamate |
| I-276 | [(1R,2S,4R)-4-{[5-({5-chloro-4-[(8S)-2-chloro-5,8-dihydro-6H-pyrano[3,4-b]pyridin-8-yl]-2-thienyl}carbonyl)pyrimidin-4-yl]amino}-2-hydroxycyclopentyl]methyl sulfamate and [(1R,2S,4R)-4-{[5-({5-chloro-4-[(8R)-2-chloro-5,8-dihydro-6H-pyrano[3,4-b]pyridin-8-yl]-2-thienyl}carbonyl)pyrimidin-4-yl]amino}-2-hydroxycyclopentyl]methyl sulfamate |
| I-276a | [(1R,2S,4R)-4-{[5-({5-chloro-4-[(8S)-2-chloro-5,8-dihydro-6H-pyrano[3,4-b]pyridin-8-yl]-2-thienyl}carbonyl)pyrimidin-4-yl]amino}-2-hydroxycyclopentyl]methyl sulfamate or [(1R,2S,4R)-4-{[5-({5-chloro-4-[(8R)-2-chloro-5,8-dihydro-6H-pyrano[3,4-b]pyridin-8-yl]-2-thienyl}carbonyl)pyrimidin-4-yl]amino}-2-hydroxycyclopentyl]methyl sulfamate |
| I-276b | [(1R,2S,4R)-4-{[5-({5-chloro-4-[(8S)-2-chloro-5,8-dihydro-6H-pyrano[3,4-b]pyridin-8-yl]-2-thienyl}carbonyl)pyrimidin-4-yl]amino}-2-hydroxycyclopentyl]methyl sulfamate or [(1R,2S,4R)-4-{[5-({5-chloro-4-[(8R)-2-chloro-5,8-dihydro-6H-pyrano[3,4-b]pyridin-8-yl]-2-thienyl}carbonyl)pyrimidin-4-yl]amino}-2-hydroxycyclopentyl]methyl sulfamate |
| I-277 | [(1R,2S,4R)-4-{[5-({4-[(1R)-7-cyclopropyl-3,4-dihydro-1H-isochromen-1-yl]-5-methyl-2-thienyl}carbonyl)pyrimidin-4-yl]amino}-2-hydroxycyclopentyl]methyl sulfamate and [(1R,2S,4R)-4-{[5-({4-[(1S)-7-cyclopropyl-3,4-dihydro-1H-isochromen-1-yl]-5-methyl-2-thienyl}carbonyl)pyrimidin-4-yl]amino}-2-hydroxycyclopentyl]methyl sulfamate |
| I-277a | [(1R,2S,4R)-4-{[5-({4-[(1R)-7-cyclopropyl-3,4-dihydro-1H-isochromen-1-yl]-5-methyl-2-thienyl}carbonyl)pyrimidin-4-yl]amino}-2-hydroxycyclopentyl]methyl sulfamate or [(1R,2S,4R)-4-{[5-({4-[(1S)-7-cyclopropyl-3,4-dihydro-1H-isochromen-1-yl]-5-methyl-2-thienyl}carbonyl)pyrimidin-4-yl]amino}-2-hydroxycyclopentyl]methyl sulfamate |
| I-277b | [(1R,2S,4R)-4-{[5-({4-[(1R)-7-cyclopropyl-3,4-dihydro-1H-isochromen-1-yl]-5-methyl-2-thienyl}carbonyl)pyrimidin-4-yl]amino}-2-hydroxycyclopentyl]methyl sulfamate or [(1R,2S,4R)-4-{[5-({4-[(1S)-7-cyclopropyl-3,4-dihydro-1H-isochromen-1-yl]-5-methyl-2-thienyl}carbonyl)pyrimidin-4-yl]amino}-2-hydroxycyclopentyl]methyl sulfamate |
| I-278 | [(1R,2R,3S,4R)-4-{[5-({4-[(1R)-7-chloro-3,4-dihydro-1H-isothiochromen-1-yl]-2-thienyl}carbonyl)pyrimidin-4-yl]amino}-2,3-dihydroxycyclopentyl]methyl sulfamate and [(1R,2R,3S,4R)-4-{[5-({4-[(1S)-7-chloro-3,4-dihydro-1H-isothiochromen-1-yl]-2-thienyl}carbonyl)pyrimidin-4-yl]amino}-2,3-dihydroxycyclopentyl]methyl sulfamate |
| I-278a | [(1R,2R,3S,4R)-4-{[5-({4-[(1R)-7-chloro-3,4-dihydro-1H-isothiochromen-1-yl]-2-thienyl}carbonyl)pyrimidin-4-yl]amino}-2,3-dihydroxycyclopentyl]methyl sulfamate or [(1R,2R,3S,4R)-4-{[5-({4-[(1S)-7-chloro-3,4-dihydro-1H-isothiochromen-1-yl]-2-thienyl}carbonyl)pyrimidin-4-yl]amino}-2,3-dihydroxycyclopentyl]methyl sulfamate |
| I-278b | [(1R,2R,3S,4R)-4-{[5-({4-[(1R)-7-chloro-3,4-dihydro-1H-isothiochromen-1-yl]-2-thienyl}carbonyl)pyrimidin-4-yl]amino}-2,3-dihydroxycyclopentyl]methyl sulfamate or [(1R,2R,3S,4R)-4-{[5-({4-[(1S)-7-chloro-3,4-dihydro-1H-isothiochromen-1-yl]-2-thienyl}carbonyl)pyrimidin-4-yl]amino}-2,3-dihydroxycyclopentyl]methyl sulfamate |
| I-279 | [(1R,2S,4R)-4-{[5-({5-chloro-4-[(1S)-1,2,3,4-tetrahydroisoquinolin-1-yl]-2-thienyl}carbonyl)pyrimidin-4-yl]amino}-2-hydroxycyclopentyl]methyl sulfamate and [(1R,2S,4R)-4-{[5-({5-chloro-4-[(1R)-1,2,3,4-tetrahydroisoquinolin-1-yl]-2-thienyl}carbonyl)pyrimidin-4-yl]amino}-2-hydroxycyclopentyl]methyl sulfamate |

| Compound No. | Name |
|---|---|
| I-279a | [(1R,2S,4R)-4-{[5-({5-chloro-4-[(1S)-1,2,3,4-tetrahydroisoquinolin-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1R)-1,2,3,4-tetrahydroisoquinolin-1-yl]-2-thienyl}carbonyl)pyrimidin-4-yl]amino}-2-hydroxycyclopentyl]methyl sulfamate |
| I-279b | [(1R,2S,4R)-4-{[5-({5-chloro-4-[(1S)-1,2,3,4-tetrahydroisoquinolin-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1R)-1,2,3,4-tetrahydroisoquinolin-1-yl]-2-thienyl}carbonyl)pyrimidin-4-yl]amino}-2-hydroxycyclopentyl]methyl sulfamate |
| I-280 | [(1R,2S,4R)-4-{[5-({4-[(4R)-4H-1,3-benzodioxin-4-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(4S)-4H-1,3-benzodioxin-4-yl]-5-methyl-2-thienyl}carbonyl)pyrimidin-4-yl]amino}-2-hydroxycyclopentyl]methyl sulfamate |
| I-280a | [(1R,2S,4R)-4-{[5-({4-[(4R)-4H-1,3-benzodioxin-4-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(4S)-4H-1,3-benzodioxin-4-yl]-5-methyl-2-thienyl}carbonyl)pyrimidin-4-yl]amino}-2-hydroxycyclopentyl]methyl sulfamate |
| I-280b | [(1R,2S,4R)-4-{[5-({4-[(4R)-4H-1,3-benzodioxin-4-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(4S)-4H-1,3-benzodioxin-4-yl]-5-methyl-2-thienyl}carbonyl)pyrimidin-4-yl]amino}-2-hydroxycyclopentyl]methyl sulfamate |
| I-281 | [(1R,2S,4R)-2-hydroxy-4-{[5-({4-[(1'R)-1'H-spiro[cyclopropane-1,4'-isochromen]-1'-yl]-2-thienyl}carbonyl)pyrimidin-4-yl]amino}cyclopentyl]methyl sulfamate<br>and<br>[(1R,2S,4R)-2-hydroxy-4-{[5-({4-[(1'S)-1'H-spiro[cyclopropane-1,4'-isochromen]-1'-yl]-2-thienyl}carbonyl)pyrimidin-4-yl]amino}cyclopentyl]methyl sulfamate |
| I-281a | [(1R,2S,4R)-2-hydroxy-4-{[5-({4-[(1'R)-1'H-spiro[cyclopropane-1,4'-isochromen]-1'-yl]-2-thienyl}carbonyl)pyrimidin-4-yl]amino}cyclopentyl]methyl sulfamate<br>or<br>[(1R,2S,4R)-2-hydroxy-4-{[5-({4-[(1'S)-1'H-spiro[cyclopropane-1,4'-isochromen]-1'-yl]-2-thienyl}carbonyl)pyrimidin-4-yl]amino}cyclopentyl]methyl sulfamate |
| I-281b | [(1R,2S,4R)-2-hydroxy-4-{[5-({4-[(1'R)-1'H-spiro[cyclopropane-1,4'-isochromen]-1'-yl]-2-thienyl}carbonyl)pyrimidin-4-yl]amino}cyclopentyl]methyl sulfamate<br>or<br>[(1R,2S,4R)-2-hydroxy-4-{[5-({4-[(1'S)-1'H-spiro[cyclopropane-1,4'-isochromen]-1'-yl]-2-thienyl}carbonyl)pyrimidin-4-yl]amino}cyclopentyl]methyl sulfamate |
| I-282 | [(1R,2S,4R)-4-{[5-({5-chloro-4-[(1R)-7-chloro-3,4-dihydro-1H-isochromen-1-yl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(1S)-7-chloro-3,4-dihydro-1H-isochromen-1-yl]-2-thienyl}carbonyl)pyrimidin-4-yl]amino}-2-hydroxycyclopentyl]methyl sulfamate |
| I-282a | [(1R,2S,4R)-4-{[5-({5-chloro-4-[(1R)-7-chloro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-7-chloro-3,4-dihydro-1H-isochromen-1-yl]-2-thienyl}carbonyl)pyrimidin-4-yl]amino}-2-hydroxycyclopentyl]methyl sulfamate |
| I-282b | [(1R,2S,4R)-4-{[5-({5-chloro-4-[(1R)-7-chloro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-7-chloro-3,4-dihydro-1H-isochromen-1-yl]-2-thienyl}carbonyl)pyrimidin-4-yl]amino}-2-hydroxycyclopentyl]methyl sulfamate |
| I-283 | [(1R,2S,4R)-2-hydroxy-4-{[5-({4-[(1R)-1,2,3,4-tetrahydroisoquinolin-1-yl]-2-thienyl}carbonyl)pyrimidin-4-yl]amino}cyclopentyl]methyl sulfamate<br>and<br>[(1R,2S,4R)-2-hydroxy-4-{[5-({4-[(1S)-1,2,3,4-tetrahydroisoquinolin-1-yl]-2-thienyl}carbonyl)pyrimidin-4-yl]amino}cyclopentyl]methyl sulfamate |
| I-283a | [(1R,2S,4R)-2-hydroxy-4-{[5-({4-[(1R)-1,2,3,4-tetrahydroisoquinolin-1-yl]-2-thienyl}carbonyl)pyrimidin-4-yl]amino}cyclopentyl]methyl sulfamate<br>or<br>[(1R,2S,4R)-2-hydroxy-4-{[5-({4-[(1S)-1,2,3,4-tetrahydroisoquinolin-1-yl]-2-thienyl}carbonyl)pyrimidin-4-yl]amino}cyclopentyl]methyl sulfamate |
| I-283b | [(1R,2S,4R)-2-hydroxy-4-{[5-({4-[(1R)-1,2,3,4-tetrahydroisoquinolin-1-yl]-2-thienyl}carbonyl)pyrimidin-4-yl]amino}cyclopentyl]methyl sulfamate<br>or<br>[(1R,2S,4R)-2-hydroxy-4-{[5-({4-[(1S)-1,2,3,4-tetrahydroisoquinolin-1-yl]-2-thienyl}carbonyl)pyrimidin-4-yl]amino}cyclopentyl]methyl sulfamate |
| I-284a | [(1R,2S,4R)-4-{[5-({5-chloro-4-[(1R)-6-chloro-2-methyl-2,3-dihydro-1H-isoindol-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-6-chloro-2-methyl-2,3-dihydro-1H-isoindol-1-yl]-2-thienyl}carbonyl)pyrimidin-4-yl]amino}-2-hydroxycyclopentyl]methyl sulfamate |

-continued

| Compound No. | Name |
|---|---|
| I-284b | [(1R,2S,4R)-4-{[5-({5-chloro-4-[(1R)-6-chloro-2-methyl-2,3-dihydro-1H-isoindol-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-6-chloro-2-methyl-2,3-dihydro-1H-isoindol-1-yl]-2-thienyl}carbonyl)pyrimidin-4-yl]amino}-2-hydroxycyclopentyl]methyl sulfamate |
| I-285 | [(1R,2S,4R)-4-{[5-({4-[(8S)-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(8R)-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate |
| I-285a | [(1R,2S,4R)-4-{[5-({4-[(8S)-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(8R)-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate |
| I-285b | [(1R,2S,4R)-4-{[5-({4-[(8S)-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(8R)-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate |
| I-286 | [(1R,2S,4R)-4-{[5-({4-[(8S)-2-chloro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(8R)-2-chloro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate |
| I-286a | [(1R,2S,4R)-4-{[5-({4-[(8S)-2-chloro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(8R)-2-chloro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate |
| I-286b | [(1R,2S,4R)-4-{[5-({4-[(8S)-2-chloro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(8R)-2-chloro-5,8-dihydro-6H-pyrano[3,4-b]pyridin-8-yl]-5-methyl-2-thienyl}carbonyl)pyrimidin-4-yl]amino}-2-hydroxycyclopentyl]methyl sulfamate |
| I-287 | [(1R,2S,4R)-2-hydroxy-4-{[5-({5-methyl-4-[(4S)-2-methyl-6,7-dihydro-4H-pyrano[3,4-d][1,3]thiazol-4-yl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(4R)-2-methyl-6,7-dihydro-4H-pyrano[3,4-d][1,3]thiazol-4-yl]-2-thienyl}carbonyl)pyrimidin-4-yl]amino}cyclopentyl]methyl sulfamate |
| I-287a | [(1R,2S,4R)-2-hydroxy-4-{[5-({5-methyl-4-[(4S)-2-methyl-6,7-dihydro-4H-pyrano[3,4-d][1,3]thiazol-4-yl]-2-thienyl}carbonyl)pyrimidin-4-yl]amino}cyclopentyl]methyl sulfamate<br>or<br>[(1R,2S,4R)-2-hydroxy-4-{[5-({5-methyl-4-[(4R)-2-methyl-6,7-dihydro-4H-pyrano[3,4-d][1,3]thiazol-4-yl]-2-thienyl}carbonyl)pyrimidin-4-yl]amino}cyclopentyl]methyl sulfamate |
| I-287b | [(1R,2S,4R)-2-hydroxy-4-{[5-({5-methyl-4-[(4S)-2-methyl-6,7-dihydro-4H-pyrano[3,4-d][1,3]thiazol-4-yl]-2-thienyl}carbonyl)pyrimidin-4-yl]amino}cyclopentyl]methyl sulfamate<br>or<br>[(1R,2S,4R)-2-hydroxy-4-{[5-({5-methyl-4-[(4R)-2-methyl-6,7-dihydro-4H-pyrano[3,4-d][1,3]thiazol-4-yl]-2-thienyl}carbonyl)pyrimidin-4-yl]amino}cyclopentyl]methyl sulfamate |
| I-288 | [(1R,2S,4R)-4-{[5-({4-[(1R)-7-chloro-4,4-difluoro-3,4-dihydro-1H-isochromen-1-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(1S)-7-chloro-4,4-difluoro-3,4-dihydro-1H-isochromen-1-yl]-5-methyl-2-thienyl}carbonyl)pyrimidin-4-yl]amino}-2-hydroxycyclopentyl]methyl sulfamate |
| I-289 | [(1R,2S,4R)-4-{[5-({4-[(1R)-7-chloro-4,4-difluoro-3,4-dihydro-1H-isochromen-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-7-chloro-4,4-difluoro-3,4-dihydro-1H-isochromen-1-yl]-2-thienyl}carbonyl)pyrimidin-4-yl]amino}-2-hydroxycyclopentyl]methyl sulfamate |
| I-289a | [(1R,2S,4R)-4-{[5-({4-[(1R)-7-chloro-4,4-difluoro-3,4-dihydro-1H-isochromen-1-yl]-2-thienyl}carbonyl)pyrimidin-4-yl]amino}-2-hydroxycyclopentyl]methyl sulfamate |

| Compound No. | Name |
|---|---|
| I-289b | or<br>[(1R,2S,4R)-4-{[5-({4-[(1S)-7-chloro-4,4-difluoro-3,4-dihydro-1H-isochromen-1-yl]-2-thienyl}carbonyl)pyrimidin-4-yl]amino}-2-hydroxycyclopentyl]methyl sulfamate<br>[(1R,2S,4R)-4-{[5-({4-[(1R)-7-chloro-4,4-difluoro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-7-chloro-4,4-difluoro-3,4-dihydro-1H-isochromen-1-yl]-2-thienyl}carbonyl)pyrimidin-4-yl]amino}-2-hydroxycyclopentyl]methyl sulfamate |
| I-290a | [(1R,2S,4R)-4-{[5-({5-chloro-4-[(1R)-6,7-difluoro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-6,7-difluoro-3,4-dihydro-1H-isochromen-1-yl]-2-thienyl}carbonyl)pyrimidin-4-yl]amino}-2-hydroxycyclopentyl]methyl sulfamate |
| I-290b | [(1R,2S,4R)-4-{[5-({5-chloro-4-[(1R)-6,7-difluoro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-6,7-difluoro-3,4-dihydro-1H-isochromen-1-yl]-2-thienyl}carbonyl)pyrimidin-4-yl]amino}-2-hydroxycyclopentyl]methyl sulfamate |
| I-291 | [(1R,2S,4R)-2-hydroxy-4-{[5-({5-methyl-4-[(8S)-2-methyl-5,8-dihydro-6H-pyrano[3,4-b]pyridin-8-yl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(8R)-2-methyl-5,8-dihydro-6H-pyrano[3,4-b]pyridin-8-yl]-2-thienyl}carbonyl)pyrimidin-4-yl]amino}cyclopentyl]methyl sulfamate |
| I-291a | [(1R,2S,4R)-2-hydroxy-4-{[5-({5-methyl-4-[(8S)-2-methyl-5,8-dihydro-6H-pyrano[3,4-b]pyridin-8-yl]-2-thienyl}carbonyl)pyrimidin-4-yl]amino}cyclopentyl]methyl sulfamate<br>or<br>[(1R,2S,4R)-2-hydroxy-4-{[5-({5-methyl-4-[(8R)-2-methyl-5,8-dihydro-6H-pyrano[3,4-b]pyridin-8-yl]-2-thienyl}carbonyl)pyrimidin-4-yl]amino}cyclopentyl]methyl sulfamate |
| I-291b | [(1R,2S,4R)-2-hydroxy-4-{[5-({5-methyl-4-[(8S)-2-methyl-5,8-dihydro-6H-pyrano[3,4-b]pyridin-8-yl]-2-thienyl}carbonyl)pyrimidin-4-yl]amino}cyclopentyl]methyl sulfamate<br>or<br>[(1R,2S,4R)-2-hydroxy-4-{[5-({5-methyl-4-[(8R)-2-methyl-5,8-dihydro-6H-pyrano[3,4-b]pyridin-8-yl]-2-thienyl}carbonyl)pyrimidin-4-yl]amino}cyclopentyl]methyl sulfamate |
| I-292a | [(1R,2S,4R)-2-hydroxy-4-{[5-({5-methyl-4-[(1S)-1,2,3,4-tetrahydroisoquinolin-1-yl]-2-thienyl}carbonyl)pyrimidin-4-yl]amino}cyclopentyl]methyl sulfamate<br>or<br>[(1R,2S,4R)-2-hydroxy-4-{[5-({5-methyl-4-[(1R)-1,2,3,4-tetrahydroisoquinolin-1-yl]-2-thienyl}carbonyl)pyrimidin-4-yl]amino}cyclopentyl]methyl sulfamate |
| I-292b | [(1R,2S,4R)-2-hydroxy-4-{[5-({5-methyl-4-[(1S)-1,2,3,4-tetrahydroisoquinolin-1-yl]-2-thienyl}carbonyl)pyrimidin-4-yl]amino}cyclopentyl]methyl sulfamate<br>or<br>[(1R,2S,4R)-2-hydroxy-4-{[5-({5-methyl-4-[(1R)-1,2,3,4-tetrahydroisoquinolin-1-yl]-2-thienyl}carbonyl)pyrimidin-4-yl]amino}cyclopentyl]methyl sulfamate |
| I-293 | [(1R,2S,4R)-4-{[5-({4-[(1R)-4,4-difluoro-3,4-dihydro-1H-isochromen-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-4,4-difluoro-3,4-dihydro-1H-isochromen-1-yl]-2-thienyl}carbonyl)pyrimidin-4-yl]amino}-2-hydroxycyclopentyl]methyl sulfamate |
| I-293a | [(1R,2S,4R)-4-{[5-({4-[(1R)-4,4-difluoro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-4,4-difluoro-3,4-dihydro-1H-isochromen-1-yl]-2-thienyl}carbonyl)pyrimidin-4-yl]amino}-2-hydroxycyclopentyl]methyl sulfamate |
| I-293b | [(1R,2S,4R)-4-{[5-({4-[(1R)-4,4-difluoro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-4,4-difluoro-3,4-dihydro-1H-isochromen-1-yl]-2-thienyl}carbonyl)pyrimidin-4-yl]amino}-2-hydroxycyclopentyl]methyl sulfamate |
| I-294 | [(1R,2S,4R)-4-{[5-({5-chloro-4-[(1R)-7-fluoro-3,4-dihydro-1H-isochromen-1-yl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(1S)-7-fluoro-3,4-dihydro-1H-isochromen-1-yl]-2-thienyl}carbonyl)pyrimidin-4-yl]amino}-2-hydroxycyclopentyl]methyl sulfamate |
| I-294a | [(1R,2S,4R)-4-{[5-({5-chloro-4-[(1R)-7-fluoro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-7-fluoro-3,4-dihydro-1H-isochromen-1-yl]-2-thienyl}carbonyl)pyrimidin-4-yl]amino}-2-hydroxycyclopentyl]methyl sulfamate |
| I-294b | [(1R,2S,4R)-4-{[5-({5-chloro-4-[(1R)-7-fluoro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-7-fluoro-3,4-dihydro-1H-isochromen-1-yl]-2-thienyl}carbonyl)pyrimidin-4-yl]amino}-2-hydroxycyclopentyl]methyl sulfamate |

| Compound No. | Name |
| --- | --- |
| I-295 | [(1R,2R,3S,4R)-2,3-dihydroxy-4-{[5-({4-[(1S)-1,2,3,4-tetrahydroisoquinolin-1-yl]-2-thienyl}carbonyl)pyrimidin-4-yl]amino}cyclopentyl]methyl sulfamate<br>and<br>[(1R,2R,3S,4R)-2,3-dihydroxy-4-{[5-({4-[(1R)-1,2,3,4-tetrahydroisoquinolin-1-yl]-2-thienyl}carbonyl)pyrimidin-4-yl]amino}cyclopentyl]methyl sulfamate |
| I-296 | [(1R,2S,4R)-2-hydroxy-4-{[5-({5-methyl-4-[(8S)-3-methyl-5,6-dihydro-8H-imidazo[2,1-c][1,4]oxazin-8-yl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(8R)-3-methyl-5,6-dihydro-8H-imidazo[2,1-c][1,4]oxazin-8-yl]-2-thienyl}carbonyl)pyrimidin-4-yl]amino}cyclopentyl]methyl sulfamate |
| I-297 | [(1R,2S,4R)-2-hydroxy-4-{[5-({5-methyl-4-[(8S)-2-(trifluoromethyl)-5,8-dihydro-6H-pyrano[3,4-b]pyridin-8-yl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(8R)-2-(trifluoromethyl)-5,8-dihydro-6H-pyrano[3,4-b]pyridin-8-yl]-2-thienyl}carbonyl)pyrimidin-4-yl]amino}cyclopentyl]methyl sulfamate |
| I-297a | [(1R,2S,4R)-2-hydroxy-4-{[5-({5-methyl-4-[(8S)-2-(trifluoromethyl)-5,8-dihydro-6H-pyrano[3,4-b]pyridin-8-yl]-2-thienyl}carbonyl)pyrimidin-4-yl]amino}cyclopentyl]methyl sulfamate<br>or<br>[(1R,2S,4R)-2-hydroxy-4-{[5-({5-methyl-4-[(8R)-2-(trifluoromethyl)-5,8-dihydro-6H-pyrano[3,4-b]pyridin-8-yl]-2-thienyl}carbonyl)pyrimidin-4-yl]amino}cyclopentyl]methyl sulfamate |
| I-297b | [(1R,2S,4R)-2-hydroxy-4-{[5-({5-methyl-4-[(8S)-2-(trifluoromethyl)-5,8-dihydro-6H-pyrano[3,4-b]pyridin-8-yl]-2-thienyl}carbonyl)pyrimidin-4-yl]amino}cyclopentyl]methyl sulfamate<br>or<br>[(1R,2S,4R)-2-hydroxy-4-{[5-({5-methyl-4-[(8R)-2-(trifluoromethyl)-5,8-dihydro-6H-pyrano[3,4-b]pyridin-8-yl]-2-thienyl}carbonyl)pyrimidin-4-yl]amino}cyclopentyl]methyl sulfamate |
| I-298 | [(1R,2S,4R)-4-{[5-({4-[(4R)-2-chloro-6,7-dihydro-4H-furo[3,2-c]pyran-4-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(4S)-2-chloro-6,7-dihydro-4H-furo[3,2-c]pyran-4-yl]-5-methyl-2-thienyl}carbonyl)pyrimidin-4-yl]amino}-2-hydroxycyclopentyl]methyl sulfamate |
| I-298a | [(1R,2S,4R)-4-{[5-({4-[(4R)-2-chloro-6,7-dihydro-4H-furo[3,2-c]pyran-4-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(4S)-2-chloro-6,7-dihydro-4H-furo[3,2-c]pyran-4-yl]-5-methyl-2-thienyl}carbonyl)pyrimidin-4-yl]amino}-2-hydroxycyclopentyl]methyl sulfamate |
| I-298b | [(1R,2S,4R)-4-{[5-({4-[(4R)-2-chloro-6,7-dihydro-4H-furo[3,2-c]pyran-4-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(4S)-2-chloro-6,7-dihydro-4H-furo[3,2-c]pyran-4-yl]-5-methyl-2-thienyl}carbonyl)pyrimidin-4-yl]amino}-2-hydroxycyclopentyl]methyl sulfamate |
| I-299 | {(1R,2S,4R)-4-[(5-{5-chloro-4-[(1R)-7-chloro-1,2,3,4-tetrahydroisoquinolin-1-yl]-2-furoyl}pyrimidin-4-yl)amino]-2-hydroxycyclopentyl}methyl sulfamate<br>and<br>{(1R,2S,4R)-4-[(5-{5-chloro-4-[(1S)-7-chloro-1,2,3,4-tetrahydroisoquinolin-1-yl]-2-furoyl}pyrimidin-4-yl)amino]-2-hydroxycyclopentyl}methyl sulfamate |
| I-299a | {(1R,2S,4R)-4-[(5-{5-chloro-4-[(1R)-7-chloro-1,2,3,4-tetrahydroisoquinolin-1-yl]-2-furoyl}pyrimidin-4-yl)amino]-2-hydroxycyclopentyl}methyl sulfamate<br>or<br>{(1R,2S,4R)-4-[(5-{5-chloro-4-[(1S)-7-chloro-1,2,3,4-tetrahydroisoquinolin-1-yl]-2-furoyl}pyrimidin-4-yl)amino]-2-hydroxycyclopentyl}methyl sulfamate |
| I-299b | {(1R,2S,4R)-4-[(5-{5-chloro-4-[(1R)-7-chloro-1,2,3,4-tetrahydroisoquinolin-1-yl]-2-furoyl}pyrimidin-4-yl)amino]-2-hydroxycyclopentyl}methyl sulfamate<br>or<br>{(1R,2S,4R)-4-[(5-{5-chloro-4-[(1S)-7-chloro-1,2,3,4-tetrahydroisoquinolin-1-yl]-2-furoyl}pyrimidin-4-yl)amino]-2-hydroxycyclopentyl}methyl sulfamate |
| I-300a | [(1R,2S,4R)-4-{[5-({4-[(1R)-7-chloro-3,4-dihydro-1H-isochromen-1-yl]-5-methyl-1,3-thiazol-2-yl}carbonyl)pyrimidin-4-yl]amino}-2-hydroxycyclopentyl]methyl sulfamate<br>or<br>[(1R,2S,4R)-4-{[5-({4-[(1S)-7-chloro-3,4-dihydro-1H-isochromen-1-yl]-5-methyl-1,3-thiazol-2-yl}carbonyl)pyrimidin-4-yl]amino}-2-hydroxycyclopentyl]methyl sulfamate |
| I-300b | [(1R,2S,4R)-4-{[5-({4-[(1R)-7-chloro-3,4-dihydro-1H-isochromen-1-yl]-5-methyl-1,3-thiazol-2-yl}carbonyl)pyrimidin-4-yl]amino}-2-hydroxycyclopentyl]methyl sulfamate<br>or<br>[(1R,2S,4R)-4-{[5-({4-[(1S)-7-chloro-3,4-dihydro-1H-isochromen-1-yl]-5-methyl-1,3-thiazol-2-yl}carbonyl)pyrimidin-4-yl]amino}-2-hydroxycyclopentyl]methyl sulfamate |

| Compound No. | Name |
|---|---|
| I-301 | [(1R,2S,4R)-4-{[5-({4-[(1R)-5-chloro-3,4-dihydro-1H-isochromen-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-5-chloro-3,4-dihydro-1H-isochromen-1-yl]-2-thienyl}carbonyl)pyrimidin-4-yl]amino}-2-hydroxycyclopentyl]methyl sulfamate |
| I-301a | [(1R,2S,4R)-4-{[5-({4-[(1R)-5-chloro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-5-chloro-3,4-dihydro-1H-isochromen-1-yl]-2-thienyl}carbonyl)pyrimidin-4-yl]amino}-2-hydroxycyclopentyl]methyl sulfamate |
| I-301b | [(1R,2S,4R)-4-{[5-({4-[(1R)-5-chloro-3,4-dihydro-1H-isochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-5-chloro-3,4-dihydro-1H-isochromen-1-yl]-2-thienyl}carbonyl)pyrimidin-4-yl]amino}-2-hydroxycyclopentyl]methyl sulfamate |
| I-302 | [(1R,2R,3S,4R)-4-{[5-({5-chloro-4-[(1S)-1,2,3,4-tetrahydroisoquinolin-1-yl]-2-thienyl}carbonyl)pyrimidin-4-yl]amino}-2,3-dihydroxycyclopentyl]methyl sulfamate<br>and<br>[(1R,2R,3S,4R)-4-{[5-({5-chloro-4-[(1R)-1,2,3,4-tetrahydroisoquinolin-1-yl]-2-thienyl}carbonyl)pyrimidin-4-yl]amino}-2,3-dihydroxycyclopentyl]methyl sulfamate |
| I-303 | [(1R,2S,4R)-4-{[5-({4-[(1R)-7-chloro-8-fluoro-3,4-dihydro-1H-isochromen-1-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(1S)-7-chloro-8-fluoro-3,4-dihydro-1H-isochromen-1-yl]-5-methyl-2-thienyl}carbonyl)pyrimidin-4-yl]amino}-2-hydroxycyclopentyl]methyl sulfamate |
| I-304 | [(1R,2S,4R)-4-{[5-({5-chloro-4-[(1R)-2-methyl-2,3-dihydro-1H-isoindol-1-yl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(1S)-2-methyl-2,3-dihydro-1H-isoindol-1-yl]-2-thienyl}carbonyl)pyrimidin-4-yl]amino}-2-hydroxycyclopentyl]methyl sulfamate |
| I-305 | [(1R,2S,4R)-2-hydroxy-4-{[5-({5-methyl-4-[(4S)-2-methyl-6,7-dihydro-4H-pyrano[4,3-d][1,3]thiazol-4-yl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(4R)-2-methyl-6,7-dihydro-4H-pyrano[4,3-d][1,3]thiazol-4-yl]-2-thienyl}carbonyl)pyrimidin-4-yl]amino}cyclopentyl]methyl sulfamate |
| I-305a | [(1R,2S,4R)-2-hydroxy-4-{[5-({5-methyl-4-[(4S)-2-methyl-6,7-dihydro-4H-pyrano[4,3-d][1,3]thiazol-4-yl]-2-thienyl}carbonyl)pyrimidin-4-yl]amino}cyclopentyl]methyl sulfamate<br>or<br>[(1R,2S,4R)-2-hydroxy-4-{[5-({5-methyl-4-[(4R)-2-methyl-6,7-dihydro-4H-pyrano[4,3-d][1,3]thiazol-4-yl]-2-thienyl}carbonyl)pyrimidin-4-yl]amino}cyclopentyl]methyl sulfamate |
| I-305b | [(1R,2S,4R)-2-hydroxy-4-{[5-({5-methyl-4-[(4S)-2-methyl-6,7-dihydro-4H-pyrano[4,3-d][1,3]thiazol-4-yl]-2-thienyl}carbonyl)pyrimidin-4-yl]amino}cyclopentyl]methyl sulfamate<br>or<br>[(1R,2S,4R)-2-hydroxy-4-{[5-({5-methyl-4-[(4R)-2-methyl-6,7-dihydro-4H-pyrano[4,3-d][1,3]thiazol-4-yl]-2-thienyl}carbonyl)pyrimidin-4-yl]amino}cyclopentyl]methyl sulfamate |
| I-306 | [(1R,2S,4R)-4-{[5-({4-[(1S)-7-chloro-2-methyl-1,2,3,4-tetrahydroisoquinolin-1-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(1R)-7-chloro-2-methyl-1,2,3,4-tetrahydroisoquinolin-1-yl]-5-methyl-2-thienyl}carbonyl)pyrimidin-4-yl]amino}-2-hydroxycyclopentyl]methyl sulfamate |
| I-307 | [(1R,2S,4R)-4-{[5-({4-[(1R)-7-chloro-2-methyl-1,2,3,4-tetrahydroisoquinolin-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-7-chloro-2-methyl-1,2,3,4-tetrahydroisoquinolin-1-yl]-2-thienyl}carbonyl)pyrimidin-4-yl]amino}-2-hydroxycyclopentyl]methyl sulfamate |
| I-307a | [(1R,2S,4R)-4-{[5-({4-[(1R)-7-chloro-2-methyl-1,2,3,4-tetrahydroisoquinolin-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-7-chloro-2-methyl-1,2,3,4-tetrahydroisoquinolin-1-yl]-2-thienyl}carbonyl)pyrimidin-4-yl]amino}-2-hydroxycyclopentyl]methyl sulfamate |
| I-307b | [(1R,2S,4R)-4-{[5-({4-[(1R)-7-chloro-2-methyl-1,2,3,4-tetrahydroisoquinolin-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-7-chloro-2-methyl-1,2,3,4-tetrahydroisoquinolin-1-yl]-2-thienyl}carbonyl)pyrimidin-4-yl]amino}-2-hydroxycyclopentyl]methyl sulfamate |

| Compound No. | Name |
|---|---|
| I-308 | [(1R,2S,4R)-2-hydroxy-4-{[5-({4-[(1R)-2-methyl-2,3-dihydro-1H-isoindol-1-yl]-2-thienyl}carbonyl)pyrimidin-4-yl]amino}cyclopentyl]methyl sulfamate<br>and<br>[(1R,2S,4R)-2-hydroxy-4-{[5-({4-[(1S)-2-methyl-2,3-dihydro-1H-isoindol-1-yl]-2-thienyl}carbonyl)pyrimidin-4-yl]amino}cyclopentyl]methyl sulfamate |
| I-309 | [(1R,2S,4R)-2-hydroxy-4-{[5-({5-methyl-4-[(8S)-2-methyl-5,6-dihydro-8H-imidazo[2,1-c][1,4]oxazin-8-yl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(8R)-2-methyl-5,6-dihydro-8H-imidazo[2,1-c][1,4]oxazin-8-yl]-2-thienyl}carbonyl)pyrimidin-4-yl]amino}cyclopentyl]methyl sulfamate |
| I-310 | [(1R,2S,4R)-4-{[5-({5-chloro-4-[(1R)-6-chloro-1,3-dihydro-2-benzofuran-1-yl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(1S)-6-chloro-1,3-dihydro-2-benzofuran-1-yl]-2-thienyl}carbonyl)pyrimidin-4-yl]amino}-2-hydroxycyclopentyl]methyl sulfamate |
| I-310a | [(1R,2S,4R)-4-{[5-({5-chloro-4-[(1R)-6-chloro-1,3-dihydro-2-benzofuran-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-6-chloro-1,3-dihydro-2-benzofuran-1-yl]-2-thienyl}carbonyl)pyrimidin-4-yl]amino}-2-hydroxycyclopentyl]methyl sulfamate |
| I-310b | [(1R,2S,4R)-4-{[5-({5-chloro-4-[(1R)-6-chloro-1,3-dihydro-2-benzofuran-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-6-chloro-1,3-dihydro-2-benzofuran-1-yl]-2-thienyl}carbonyl)pyrimidin-4-yl]amino}-2-hydroxycyclopentyl]methyl sulfamate |
| I-311a | [(1R,2S,4R)-4-{[5-({5-chloro-4-[(1R)-7-chloro-2-methyl-1,2,3,4-tetrahydroisoquinolin-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-7-chloro-2-methyl-1,2,3,4-tetrahydroisoquinolin-1-yl]-2-thienyl}carbonyl)pyrimidin-4-yl]amino}-2-hydroxycyclopentyl]methyl sulfamate |
| I-311b | [(1R,2S,4R)-4-{[5-({5-chloro-4-[(1R)-7-chloro-2-methyl-1,2,3,4-tetrahydroisoquinolin-1-yl]-2-thienyl}carbonyl)pyrimidin-4-yl]amino}-2-hydroxycyclopentyl]methyl sulfamate<br>or<br>[(1R,2S,4R)-4-{[5-({5-chloro-4-[(1S)-7-chloro-2-methyl-1,2,3,4-tetrahydroisoquinolin-1-yl]-2-thienyl}carbonyl)pyrimidin-4-yl]amino}-2-hydroxycyclopentyl]methyl sulfamate |
| I-313 | [(1R,2S,4R)-4-{[5-({4-[(1R)-7-cyano-3,4-dihydro-1H-isochromen-1-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(1S)-7-cyano-3,4-dihydro-1H-isochromen-1-yl]-5-methyl-2-thienyl}carbonyl)pyrimidin-4-yl]amino}-2-hydroxycyclopentyl]methyl sulfamate |
| I-314 | [(1R,2S,4R)-4-{[5-({4-[(1R)-8-chloro-1,3,4,5-tetrahydro-2-benzoxepin-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-8-chloro-1,3,4,5-tetrahydro-2-benzoxepin-1-yl]-2-thienyl}carbonyl)pyrimidin-4-yl]amino}-2-hydroxycyclopentyl]methyl sulfamate |
| I-314a | [(1R,2S,4R)-4-{[5-({4-[(1R)-8-chloro-1,3,4,5-tetrahydro-2-benzoxepin-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-8-chloro-1,3,4,5-tetrahydro-2-benzoxepin-1-yl]-2-thienyl}carbonyl)pyrimidin-4-yl]amino}-2-hydroxycyclopentyl]methyl sulfamate |
| I-314b | [(1R,2S,4R)-4-{[5-({4-[(1R)-8-chloro-1,3,4,5-tetrahydro-2-benzoxepin-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-8-chloro-1,3,4,5-tetrahydro-2-benzoxepin-1-yl]-2-thienyl}carbonyl)pyrimidin-4-yl]amino}-2-hydroxycyclopentyl]methyl sulfamate |
| I-315 | [(1R,2S,4R)-2-hydroxy-4-{[5-({5-methyl-4-[(4S)-2-(trifluoromethyl)-6,7-dihydro-4H-pyrano[3,4-d][1,3]thiazol-4-yl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(4R)-2-(trifluoromethyl)-6,7-dihydro-4H-pyrano[3,4-d][1,3]thiazol-4-yl]-2-thienyl}carbonyl)pyrimidin-4-yl]amino}cyclopentyl]methyl sulfamate |
| I-316 | [(1R,2S,4R)-4-{[5-({4-[(1R)-7-chloro-3,4-dihydro-1H-pyrano[4,3-c]pyridin-1-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(1S)-7-chloro-3,4-dihydro-1H-pyrano[4,3-c]pyridin-1-yl]-5-methyl-2-thienyl}carbonyl)pyrimidin-4-yl]amino}-2-hydroxycyclopentyl]methyl sulfamate |

-continued

| Compound No. | Name |
|---|---|
| I-317 | [(1R,2S,4R)-4-{[5-({4-[(1R)-7-chloro-1-methyl-3,4-dihydro-1H-isochromen-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-7-chloro-1-methyl-3,4-dihydro-1H-isochromen-1-yl]-2-thienyl}carbonyl)pyrimidin-4-yl]amino}-2-hydroxycyclopentyl]methyl sulfamate |
| I-318 | [(1R,2S,4R)-2-hydroxy-4-{[5-({4-[(1R)-1-methyl-1,2,3,4-tetrahydroisoquinolin-1-yl]-2-thienyl}carbonyl)pyrimidin-4-yl]amino}cyclopentyl]methyl sulfamate<br>and<br>[(1R,2S,4R)-2-hydroxy-4-{[5-({4-[(1S)-1-methyl-1,2,3,4-tetrahydroisoquinolin-1-yl]-2-thienyl}carbonyl)pyrimidin-4-yl]amino}cyclopentyl]methyl sulfamate |
| I-319 | [(1R,2S,4R)-4-{[5-({5-chloro-4-[(1R)-2,3,4,5-tetrahydro-1H-2-benzazepin-1-yl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(1S)-2,3,4,5-tetrahydro-1H-2-benzazepin-1-yl]-2-thienyl}carbonyl)pyrimidin-4-yl]amino}-2-hydroxycyclopentyl]methyl sulfamate |
| I-320 | [(1R,2S,4R)-4-{[5-({4-[(1R)-7-chloro-3,4-dihydro-1H-isothiochromen-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-7-chloro-3,4-dihydro-1H-isothiochromen-1-yl]-2-thienyl}carbonyl)pyrimidin-4-yl]amino}-2-hydroxycyclopentyl]methyl sulfamate |
| I-320a | [(1R,2S,4R)-4-{[5-({4-[(1R)-7-chloro-3,4-dihydro-1H-isothiochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-7-chloro-3,4-dihydro-1H-isothiochromen-1-yl]-2-thienyl}carbonyl)pyrimidin-4-yl]amino}-2-hydroxycyclopentyl]methyl sulfamate |
| I-320b | [(1R,2S,4R)-4-{[5-({4-[(1R)-7-chloro-3,4-dihydro-1H-isothiochromen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-7-chloro-3,4-dihydro-1H-isothiochromen-1-yl]-2-thienyl}carbonyl)pyrimidin-4-yl]amino}-2-hydroxycyclopentyl]methyl sulfamate |
| I-321 | [(1R,2S,4R)-4-{[5-({4-[(1R)-7-chloro-1-methyl-1,2,3,4-tetrahydroisoquinolin-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-7-chloro-1-methyl-1,2,3,4-tetrahydroisoquinolin-1-yl]-2-thienyl}carbonyl)pyrimidin-4-yl]amino}-2-hydroxycyclopentyl]methyl sulfamate |
| I-322 | [(1R,2S,4R)-4-{[5-({4-[(1R)-5-chloro-2-methyl-2,3-dihydro-1H-isoindol-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-5-chloro-2-methyl-2,3-dihydro-1H-isoindol-1-yl]-2-thienyl}carbonyl)pyrimidin-4-yl]amino}-2-hydroxycyclopentyl]methyl sulfamate |
| I-323 | [(1R,2S,4R)-4-{[5-({5-chloro-4-[(1R)-7-chloro-3,4-dihydro-1H-pyrano[4,3-c]pyridin-1-yl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(1S)-7-chloro-3,4-dihydro-1H-pyrano[4,3-c]pyridin-1-yl]-2-thienyl}carbonyl)pyrimidin-4-yl]amino}-2-hydroxycyclopentyl]methyl sulfamate |
| I-324 | [(1R,2S,4R)-4-{[5-({5-cyano-4-[(1R)-3,4-dihydro-1H-isochromen-1-yl]-2-thienyl}carbonyl)pyrimidin-4-yl]amino}-2-hydroxycyclopentyl]methyl sulfamate<br>and<br>[(1R,2S,4R)-4-{[5-({5-cyano-4-[(1S)-3,4-dihydro-1H-isochromen-1-yl]-2-thienyl}carbonyl)pyrimidin-4-yl]amino}-2-hydroxycyclopentyl]methyl sulfamate |
| I-325 | [(1R,2S,4R)-4-{[5-({5-[(1R)-5-chloro-3,4-dihydro-1H-isochromen-1-yl]-2-thienyl}carbonyl)pyrimidin-4-yl]amino}-2-hydroxycyclopentyl]methyl sulfamate<br>and<br>[(1R,2S,4R)-4-{[5-({5-[(1S)-5-chloro-3,4-dihydro-1H-isochromen-1-yl]-2-thienyl}carbonyl)pyrimidin-4-yl]amino}-2-hydroxycyclopentyl]methyl sulfamate |
| I-327 | [(1R,2S,4R)-4-{[5-({5-chloro-4-[(1R)-6-chloro-3-oxo-1,3-dihydro-2-benzofuran-1-yl]-2-thienyl}carbonyl)pyrimidin-4-yl]amino}-2-hydroxycyclopentyl]methyl sulfamate<br>and<br>[(1R,2S,4R)-4-{[5-({5-chloro-4-[(1S)-6-chloro-3-oxo-1,3-dihydro-2-benzofuran-1-yl]-2-thienyl}carbonyl)pyrimidin-4-yl]amino}-2-hydroxycyclopentyl]methyl sulfamate |
| I-329 | [(1R,2S,4R)-4-({5-[(4-{(1R)-7-[(dimethylamino)methyl]-3,4-dihydro-1H-isochromen-1-yl}-5-methyl-2-thienyl)carbonyl]pyrimidin-4-yl}amino)-2-hydroxycyclopentyl]methyl sulfamate<br>and<br>[(1R,2S,4R)-4-({5-[(4-{(1S)-7-[(dimethylamino)methyl]-3,4-dihydro-1H-isochromen-1-yl}-5-methyl-2-thienyl)carbonyl]pyrimidin-4-yl}amino)-2-hydroxycyclopentyl]methyl sulfamate |
| I-330 | (1S,2R,4R)-4-{[5-({4-[(1R)-7-chloro-3,4-dihydro-1H-isochromen-1-yl]-5-methyl-2-thienyl}carbonyl)pyrimidin-4-yl]amino}-2-[(sulfamoyloxy)methyl]cyclopentyl aminoacetate |

-continued

| Compound No. | Name |
|---|---|
| I-331 | [(1R,2S,4R)-4-{[5-({4-[(5R)-8,8-difluoro-7,8-dihydro-5H-pyrano[4,3-b]pyridin-5-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(5S)-8,8-difluoro-7,8-dihydro-5H-pyrano[4,3-b]pyridin-5-yl]-5-methyl-2-thienyl}carbonyl)pyrimidin-4-yl]amino}-2-hydroxycyclopentyl]methyl sulfamate |
| I-332 | [(1R,2S,4R)-2-hydroxy-4-{[5-({4-[(4S)-2-methyl-6,7-dihydro-4H-pyrazolo[5,1-c][1,4]oxazin-4-yl]-2-thienyl}carbonyl)pyrimidin-4-yl]amino}cyclopentyl]methyl sulfamate<br>and<br>[(1R,2S,4R)-2-hydroxy-4-{[5-({4-[(4R)-2-methyl-6,7-dihydro-4H-pyrazolo[5,1-c][1,4]oxazin-4-yl]-2-thienyl}carbonyl)pyrimidin-4-yl]amino}cyclopentyl]methyl sulfamate |
| I-333 | [(1R,2S,4R)-2-hydroxy-4-{[5-({4-[(4S)-3-methyl-6,7-dihydro-4H-pyrazolo[5,1-c][1,4]oxazin-4-yl]-2-thienyl}carbonyl)pyrimidin-4-yl]amino}cyclopentyl]methyl sulfamate<br>and<br>[(1R,2S,4R)-2-hydroxy-4-{[5-({4-[(4R)-3-methyl-6,7-dihydro-4H-pyrazolo[5,1-c][1,4]oxazin-4-yl]-2-thienyl}carbonyl)pyrimidin-4-yl]amino}cyclopentyl]methyl sulfamate |
| I-334 | tert-butyl (1R)-7-chloro-1-(5-{[4-({(1R,3S,4R)-3-hydroxy-4-[(sulfamoyloxy)methyl]cyclopentyl}amino)pyrimidin-5-yl]carbonyl}-3-thienyl)-3,4-dihydroisoquinoline-2(1H)-carboxylate<br>and<br>tert-butyl (1S)-7-chloro-1-(5-{[4-({(1R,3S,4R)-3-hydroxy-4-[(sulfamoyloxy)methyl]cyclopentyl}amino)pyrimidin-5-yl]carbonyl}-3-thienyl)-3,4-dihydroisoquinoline-2(1H)-carboxylate |
| I-335 | [(1R,2S,4R)-4-{[5-({4-[(1R)-7-chloro-1,2,3,4-tetrahydronaphthalen-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-7-chloro-1,2,3,4-tetrahydronaphthalen-1-yl]-2-thienyl}carbonyl)pyrimidin-4-yl]amino}-2-hydroxycyclopentyl]methyl sulfamate |
| I-335a | [(1R,2S,4R)-4-{[5-({4-[(1R)-7-chloro-1,2,3,4-tetrahydronaphthalen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-7-chloro-1,2,3,4-tetrahydronaphthalen-1-yl]-2-thienyl}carbonyl)pyrimidin-4-yl]amino}-2-hydroxycyclopentyl]methyl sulfamate |
| I-335b | [(1R,2S,4R)-4-{[5-({4-[(1R)-7-chloro-1,2,3,4-tetrahydronaphthalen-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-7-chloro-1,2,3,4-tetrahydronaphthalen-1-yl]-2-thienyl}carbonyl)pyrimidin-4-yl]amino}-2-hydroxycyclopentyl]methyl sulfamate |
| I-336 | tert-butyl (1R)-7-chloro-1-(2-chloro-5-{[4-({(1R,3S,4R)-3-hydroxy-4-[(sulfamoyloxy)methyl]cyclopentyl}amino)pyrimidin-5-yl]carbonyl}-3-thienyl)-3,4-dihydroisoquinoline-2(1H)-carboxylate<br>and<br>tert-butyl (1S)-7-chloro-1-(2-chloro-5-{[4-({(1R,3S,4R)-3-hydroxy-4-[(sulfamoyloxy)methyl]cyclopentyl}amino)pyrimidin-5-yl]carbonyl}-3-thienyl)-3,4-dihydroisoquinoline-2(1H)-carboxylate |
| I-337 | [(1R,2S,4R)-2-hydroxy-4-{[5-({5-methyl-4-[(8S)-2-(trifluoromethyl)-5,6-dihydro-8H-imidazo[2,1-c][1,4]oxazin-8-yl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(8R)-2-(trifluoromethyl)-5,6-dihydro-8H-imidazo[2,1-c][1,4]oxazin-8-yl]-2-thienyl}carbonyl)pyrimidin-4-yl]amino}cyclopentyl]methyl sulfamate |
| I-338 | (1S,2R,4R)-4-{[5-({4-[(1R)-7-chloro-3,4-dihydro-1H-isochromen-1-yl]-5-methyl-2-thienyl}carbonyl)pyrimidin-4-yl]amino}-2-[(sulfamoyloxy)methyl]cyclopentyl (2S)-2-amino-3-methylbutanoate |
| I-339 | [(1R,2S,4R)-2-hydroxy-4-{[5-({4-[(8S)-2-methoxy-5,8-dihydro-6H-pyrano[3,4-b]pyridin-8-yl]-5-methyl-2-thienyl}carbonyl)pyrimidin-4-yl]amino}cyclopentyl]methyl sulfamate<br>and<br>[(1R,2S,4R)-2-hydroxy-4-{[5-({4-[(8R)-2-methoxy-5,8-dihydro-6H-pyrano[3,4-b]pyridin-8-yl]-5-methyl-2-thienyl}carbonyl)pyrimidin-4-yl]amino}cyclopentyl]methyl sulfamate |
| I-339a | [(1R,2S,4R)-2-hydroxy-4-{[5-({4-[(8S)-2-methoxy-5,8-dihydro-6H-pyrano[3,4-b]pyridin-8-yl]-5-methyl-2-thienyl}carbonyl)pyrimidin-4-yl]amino}cyclopentyl]methyl sulfamate<br>or<br>[(1R,2S,4R)-2-hydroxy-4-{[5-({4-[(8R)-2-methoxy-5,8-dihydro-6H-pyrano[3,4-b]pyridin-8-yl]-5-methyl-2-thienyl}carbonyl)pyrimidin-4-yl]amino}cyclopentyl]methyl sulfamate |

-continued

| Compound No. | Name |
|---|---|
| I-339b | [(1R,2S,4R)-2-hydroxy-4-{[5-({4-[(8S)-2-methoxy-5,8-dihydro-6H-pyrano[3,4-b]pyridin-8-yl]-5-methyl-2-thienyl}carbonyl)pyrimidin-4-yl]amino}cyclopentyl]methyl sulfamate<br>or<br>[(1R,2S,4R)-2-hydroxy-4-{[5-({4-[(8R)-2-methoxy-5,8-dihydro-6H-pyrano[3,4-b]pyridin-8-yl]-5-methyl-2-thienyl}carbonyl)pyrimidin-4-yl]amino}cyclopentyl]methyl sulfamate |
| I-341 | [(1R,2S,4R)-2-hydroxy-4-{[5-({4-[(1R)-7-methoxy-3,4-dihydro-1H-isochromen-1-yl]-5-methyl-2-thienyl}carbonyl)pyrimidin-4-yl]amino}cyclopentyl]methyl sulfamate<br>and<br>[(1R,2S,4R)-2-hydroxy-4-{[5-({4-[(1S)-7-methoxy-3,4-dihydro-1H-isochromen-1-yl]-5-methyl-2-thienyl}carbonyl)pyrimidin-4-yl]amino}cyclopentyl]methyl sulfamate |
| I-342 | [(1R,2S,4R)-2-hydroxy-4-{[5-({4-[(1R)-4-oxo-3,4-dihydro-1H-isochromen-1-yl]-2-thienyl}carbonyl)pyrimidin-4-yl]amino}cyclopentyl]methyl sulfamate<br>and<br>[(1R,2S,4R)-2-hydroxy-4-{[5-({4-[(1S)-4-oxo-3,4-dihydro-1H-isochromen-1-yl]-2-thienyl}carbonyl)pyrimidin-4-yl]amino}cyclopentyl]methyl sulfamate |
| I-343a | [(1R,2S,4R)-4-{[5-({5-[(1R)-8-chloro-1,3,4,5-tetrahydro-2-benzoxepin-1-yl]-2-thienyl}carbonyl)pyrimidin-4-yl]amino}-2-hydroxycyclopentyl]methyl sulfamate<br>or<br>[(1R,2S,4R)-4-{[5-({5-[(1S)-8-chloro-1,3,4,5-tetrahydro-2-benzoxepin-1-yl]-2-thienyl}carbonyl)pyrimidin-4-yl]amino}-2-hydroxycyclopentyl]methyl sulfamate |
| I-343b | [(1R,2S,4R)-4-{[5-({5-[(1R)-8-chloro-1,3,4,5-tetrahydro-2-benzoxepin-1-yl]-2-thienyl}carbonyl)pyrimidin-4-yl]amino}-2-hydroxycyclopentyl]methyl sulfamate<br>or<br>[(1R,2S,4R)-4-{[5-({5-[(1S)-8-chloro-1,3,4,5-tetrahydro-2-benzoxepin-1-yl]-2-thienyl}carbonyl)pyrimidin-4-yl]amino}-2-hydroxycyclopentyl]methyl sulfamate |
| I-344 | [(1R,2S,4R)-4-{[5-({4-[(1S)-3,4-dihydro-1H-[1,4]oxazino[4,3-a]benzimidazol-1-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(1R)-3,4-dihydro-1H-[1,4]oxazino[4,3-a]benzimidazol-1-yl]-5-methyl-2-thienyl}carbonyl)pyrimidin-4-yl]amino}-2-hydroxycyclopentyl]methyl sulfamate |
| I-345 | (1S,2R,4R)-4-{[5-({4-[(1R)-7-chloro-3,4-dihydro-1H-isochromen-1-yl]-5-methyl-2-thienyl}carbonyl)pyrimidin-4-yl]amino}-2-[(sulfamoyloxy)methyl]cyclopentyl 3-[(phosphonooxy)methyl]benzoate |
| I-346 | [(1R,2S,4R)-4-{[5-({4-[(1R)-7-ethyl-3,4-dihydro-1H-isochromen-1-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(1S)-7-ethyl-3,4-dihydro-1H-isochromen-1-yl]-5-methyl-2-thienyl}carbonyl)pyrimidin-4-yl]amino}-2-hydroxycyclopentyl]methyl sulfamate |
| I-347 | [(1R,2S,4R)-2-hydroxy-4-{[5-({5-methyl-4-[(1R)-7-methyl-3,4-dihydro-1H-isochromen-1-yl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(1S)-7-methyl-3,4-dihydro-1H-isochromen-1-yl]-2-thienyl}carbonyl)pyrimidin-4-yl]amino}cyclopentyl]methyl sulfamate |
| I-348 | [(1R,2S,4R)-2-hydroxy-4-{[5-({5-methyl-4-[(8R)-2-(pyrrolidin-1-yl)-5,8-dihydro-6H-pyrano[3,4-b]pyridin-8-yl]-2-thienyl}carbonyl)pyrimidin-4-yl]amino}cyclopentyl]methyl sulfamate<br>and<br>[(1R,2S,4R)-2-hydroxy-4-{[5-({5-methyl-4-[(8S)-2-(pyrrolidin-1-yl)-5,8-dihydro-6H-pyrano[3,4-b]pyridin-8-yl]-2-thienyl}carbonyl)pyrimidin-4-yl]amino}cyclopentyl]methyl sulfamate |
| I-349 | [(1R,2S,4R)-4-{[5-({4-[(1R)-6-chloro-2,3-dihydro-1H-inden-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-6-chloro-2,3-dihydro-1H-inden-1-yl]-2-thienyl}carbonyl)pyrimidin-4-yl]amino}-2-hydroxycyclopentyl]methyl sulfamate |
| I-349a | [(1R,2S,4R)-4-{[5-({4-[(1R)-6-chloro-2,3-dihydro-1H-inden-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-6-chloro-2,3-dihydro-1H-inden-1-yl]-2-thienyl}carbonyl)pyrimidin-4-yl]amino}-2-hydroxycyclopentyl]methyl sulfamate |
| I-349b | [(1R,2S,4R)-4-{[5-({4-[(1R)-6-chloro-2,3-dihydro-1H-inden-1-yl]-2-thienyl}carbonyl)pyrimidin-4-yl]amino}-2-hydroxycyclopentyl]methyl sulfamate<br>or<br>[(1R,2S,4R)-4-{[5-({4-[(1S)-6-chloro-2,3-dihydro-1H-inden-1-yl]-2-thienyl}carbonyl)pyrimidin-4-yl]amino}-2-hydroxycyclopentyl]methyl sulfamate |
| I-350 | [(1R,2R,3S,4R)-4-({5-[(5-benzyl-1,3-thiazol-2-yl)carbonyl]pyrimidin-4-yl}amino)-2,3-dihydroxycyclopentyl]methyl sulfamate |
| I-351 | {(1R,2S,4R)-2-hydroxy-4-[(5-{[4-(3-methylbenzyl)-1,3-thiazol-2-yl]carbonyl}pyrimidin-4-yl)amino]cyclopentyl}methyl sulfamate |

-continued

| Compound No. | Name |
| --- | --- |
| I-352 | {(1R,2R,3S,4R)-4-[(5-{[4-(3-chlorobenzyl)-5-methyl-1,3-thiazol-2-yl]carbonyl}pyrimidin-4-yl)amino]-2,3-dihydroxycyclopentyl}methyl sulfamate |
| I-353 | {(1R,2S,4R)-4-[(5-{[4-(3-chlorobenzyl)-5-methyl-1,3-thiazol-2-yl]carbonyl}pyrimidin-4-yl)amino]-2-hydroxycyclopentyl}methyl sulfamate |
| I-354 | {(1R,2R,3S,4R)-4-[(5-{[4-(3-bromobenzyl)-5-methyl-1,3-thiazol-2-yl]carbonyl}pyrimidin-4-yl)amino]-2,3-dihydroxycyclopentyl}methyl sulfamate |
| I-355 | [(1R,2S,4R)-4-{[5-({4-[(R)-(3-chlorophenyl)(hydroxy)methyl]-5-methyl-1,3-thiazol-2-yl}carbonyl)pyrimidin-4-yl]amino}-2-hydroxycyclopentyl]methyl sulfamate<br>and<br>[(1R,2S,4R)-4-{[5-({4-[(S)-(3-chlorophenyl)(hydroxy)methyl]-5-methyl-1,3-thiazol-2-yl}carbonyl)pyrimidin-4-yl]amino}-2-hydroxycyclopentyl]methyl sulfamate |
| I-355a | [(1R,2S,4R)-4-{[5-({4-[(R)-(3-chlorophenyl)(hydroxy)methyl]-5-methyl-1,3-thiazol-2-yl}carbonyl)pyrimidin-4-yl]amino}-2-hydroxycyclopentyl]methyl sulfamate<br>or<br>[(1R,2S,4R)-4-{[5-({4-[(S)-(3-chlorophenyl)(hydroxy)methyl]-5-methyl-1,3-thiazol-2-yl}carbonyl)pyrimidin-4-yl]amino}-2-hydroxycyclopentyl]methyl sulfamate |
| I-355b | [(1R,2S,4R)-4-{[5-({4-[(R)-(3-chlorophenyl)(hydroxy)methyl]-5-methyl-1,3-thiazol-2-yl}carbonyl)pyrimidin-4-yl]amino}-2-hydroxycyclopentyl]methyl sulfamate<br>or<br>[(1R,2S,4R)-4-{[5-({4-[(S)-(3-chlorophenyl)(hydroxy)methyl]-5-methyl-1,3-thiazol-2-yl}carbonyl)pyrimidin-4-yl]amino}-2-hydroxycyclopentyl]methyl sulfamate |
| I-356 | [(1R,2S,4R)-4-{[5-({4-[(8R)-2,3-dimethyl-5,6-dihydro-8H-imidazo[2,1-c][1,4]oxazin-8-yl]-5-methyl-2-thienyl}carbonyl)pyrimidin-4-yl]amino}-2-hydroxycyclopentyl]methyl sulfamate<br>and<br>[(1R,2S,4R)-4-{[5-({4-[(8S)-2,3-dimethyl-5,6-dihydro-8H-imidazo[2,1-c][1,4]oxazin-8-yl]-5-methyl-2-thienyl}carbonyl)pyrimidin-4-yl]amino}-2-hydroxycyclopentyl]methyl sulfamate |
| I-356a | [(1R,2S,4R)-4-{[5-({4-[(8R)-2,3-dimethyl-5,6-dihydro-8H-imidazo[2,1-c][1,4]oxazin-8-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(8S)-2,3-dimethyl-5,6-dihydro-8H-imidazo[2,1-c][1,4]oxazin-8-yl]-5-methyl-2-thienyl}carbonyl)pyrimidin-4-yl]amino}-2-hydroxycyclopentyl]methyl sulfamate |
| I-356b | [(1R,2S,4R)-4-{[5-({4-[(8R)-2,3-dimethyl-5,6-dihydro-8H-imidazo[2,1-c][1,4]oxazin-8-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(8S)-2,3-dimethyl-5,6-dihydro-8H-imidazo[2,1-c][1,4]oxazin-8-yl]-5-methyl-2-thienyl}carbonyl)pyrimidin-4-yl]amino}-2-hydroxycyclopentyl]methyl sulfamate |
| I-357 | [(1R,2S,4R)-4-{[5-({4-[(1R)-6-chloro-3,4-dihydro-1H-isochromen-1-yl]-2-thienyl}carbonyl)pyrimidin-4-yl]amino}-2-hydroxycyclopentyl]methyl sulfamate<br>and<br>[(1R,2S,4R)-4-{[5-({4-[(1S)-6-chloro-3,4-dihydro-1H-isochromen-1-yl]-2-thienyl}carbonyl)pyrimidin-4-yl]amino}-2-hydroxycyclopentyl]methyl sulfamate |
| I-358 | {(1R,2S,4R)-4-[(5-{[4-(7-chloroisoquinolin-1-yl)-5-methyl-2-thienyl]carbonyl}pyrimidin-4-yl)amino]-2-hydroxycyclopentyl}methyl sulfamate |
| I-359a | [(1R,2S,4R)-4-{[5-({4-[(1R)-6-chloro-1,3-dihydro-2-benzothiophen-1-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(1S)-6-chloro-1,3-dihydro-2-benzothiophen-1-yl]-5-methyl-2-thienyl}carbonyl)pyrimidin-4-yl]amino}-2-hydroxycyclopentyl]methyl sulfamate |
| I-359b | [(1R,2S,4R)-4-{[5-({4-[(1R)-6-chloro-1,3-dihydro-2-benzothiophen-1-yl]-5-methyl-2-thienyl}carbonyl)pyrimidin-4-yl]amino}-2-hydroxycyclopentyl]methyl sulfamate<br>or<br>[(1R,2S,4R)-4-{[5-({4-[(1S)-6-chloro-1,3-dihydro-2-benzothiophen-1-yl]-5-methyl-2-thienyl}carbonyl)pyrimidin-4-yl]amino}-2-hydroxycyclopentyl]methyl sulfamate |
| I-360 | {(1R,2S,4R)-4-[(5-{[4-(7-chloro-3,4-dihydroisoquinolin-1-yl)-5-methyl-2-thienyl]carbonyl}pyrimidin-4-yl)amino]-2-hydroxycyclopentyl}methyl sulfamate |
| I-361 | [(1R,2S,4R)-4-{[5-({4-[(1R)-7-chloro-3,4-dihydro-1H-isochromen-1-yl]-5-(difluoromethyl)-2-thienyl}carbonyl)pyrimidin-4-yl]amino}-2-hydroxycyclopentyl]methyl sulfamate<br>and<br>[(1R,2S,4R)-4-{[5-({4-[(1S)-7-chloro-3,4-dihydro-1H-isochromen-1-yl]-5-(difluoromethyl)-2-thienyl}carbonyl)pyrimidin-4-yl]amino}-2-hydroxycyclopentyl]methyl sulfamate |
| I-362 | (1S,2R,4R)-4-{[5-({4-[(1R)-7-chloro-3,4-dihydro-1H-isochromen-1-yl]-5-methyl-2-thienyl}carbonyl)pyrimidin-4-yl]amino}-2-[(sulfamoyloxy)methyl]cyclopentyl (2S)-2-aminopropanoate |
| I-363 | (1S,2R,4R)-4-{[5-({4-[(1R)-7-chloro-3,4-dihydro-1H-isochromen-1-yl]-5-methyl-2-thienyl}carbonyl)pyrimidin-4-yl]amino}-2-[(sulfamoyloxy)methyl]cyclopentyl (2S,3S)-2-amino-3-methylpentanoate |

-continued

| Compound No. | Name |
|---|---|
| I-364 | (1S,2R,4R)-4-{[5-({4-[(1R)-7-chloro-3,4-dihydro-1H-isochromen-1-yl]-5-methyl-2-thienyl}carbonyl)pyrimidin-4-yl]amino}-2-[(sulfamoyloxy)methyl]cyclopentyl [4-(phosphonooxy)phenyl]acetate |
| I-365 | [(1R,2S,4R)-4-{[5-({4-[(1R)-8-chloro-3,4-dihydro-1H-isochromen-1-yl]-2-thienyl}carbonyl)pyrimidin-4-yl]amino}-2-hydroxycyclopentyl]methyl sulfamate and [(1R,2S,4R)-4-{[5-({4-[(1S)-8-chloro-3,4-dihydro-1H-isochromen-1-yl]-2-thienyl}carbonyl)pyrimidin-4-yl]amino}-2-hydroxycyclopentyl]methyl sulfamate |
| I-366 | [(1R,2S,4R)-4-{[5-({4-[(1R)-7-chloro-3,4-dihydro-1H-isochromen-1-yl]-5-(hydroxymethyl)-2-thienyl}carbonyl)pyrimidin-4-yl](methyl)amino}-2-hydroxycyclopentyl]methyl sulfamate and [(1R,2S,4R)-4-{[5-({4-[(1S)-7-chloro-3,4-dihydro-1H-isochromen-1-yl]-5-(hydroxymethyl)-2-thienyl}carbonyl)pyrimidin-4-yl](methyl)amino}-2-hydroxycyclopentyl]methyl sulfamate |

It will be appreciated that the chemical entities of this disclosure may be derivatized at functional groups to provide prodrug derivatives which are capable of conversion back to the parent chemical entities in vivo. Examples of such prodrugs include the physiologically acceptable and metabolically labile derivatives. More specifically, the prodrug of the chemical entity of this disclosure is an ether or ester of the —OH group of the chemical entity. Prodrugs according to this disclosure include those in which $R^b$ is —C(O)—$R^{bx}$, wherein $R^{bx}$ has the values described herein, as discussed above. Furthermore, various approaches for providing prodrugs are known to those skilled in the art, as described in, e.g., Li et al., "Prodrugs of Nucleoside Analogues for Improved Oral Absorption and Tissue Targeting," J. Pharm. Sci. 97, 1109-34 (2008); Rautio et al., "Prodrugs: design and clinical applications," Nat. Rev. Drug Discovery 7, 255-270 (2008); and Rautio, Prodrugs and Targeted Delivery, Wiley-VCH (2011) (ISBN-10: 3527326030).

As used herein, "crystalline" refers to a solid in which the constituent atoms, molecules, or ions are packed in a regularly ordered, repeating three-dimensional pattern having a highly regular chemical structure. In particular, a crystalline compound or salt might be produced as one or more crystalline forms. For the purposes of this application, the terms "crystalline form" and "polymorph" are synonymous; the terms distinguish between crystals that have different properties (e.g., different XRPD patterns, different DSC scan results). Pseudopolymorphs are typically different solvates of a material, and thus the properties of pseudopolymorphs differ from one another. Thus, each distinct polymorph and pseudopolymorph is considered to be a distinct crystalline form herein.

"Substantially crystalline" refers to compounds or salts that are at least a particular weight percent crystalline. In some embodiments, the compound or salt is substantially crystalline. Examples of a crystalline form or substantially crystalline form include a single crystalline form or a mixture of different crystalline forms. Particular weight percentages include 50%, 60%, 70%, 75%, 80%, 85%, 87%, 88%, 89%, 90%, 91%, 92%, 93%, 94%, 95%, 96%, 97%, 98%, 99%, 99.5% and 99.9%. In some embodiments, substantially crystalline refers to compounds or salts that are at least 70% crystalline. In some embodiments, substantially crystalline refers to compounds or salts that are at least 80% crystalline. In some embodiments, substantially crystalline refers to compounds or salts that are at least 85% crystalline. In some embodiments, substantially crystalline refers to compounds or salts that are at least 90% crystalline. In some embodiments, substantially crystalline refers to compounds or salts that are at least 95% crystalline.

The term "hydrate" includes, for example, hemihydrates, monohydrates, sesquihydrates, dihydrates, and trihydrates. In some embodiments, a hydrate, such as a sesquihydrate, may be prepared by crystallization of a chemical entity disclosed herein from ethanol/distilled water. In some embodiments, a hydrate may be prepared by crystallization of a chemical entity disclosed herein from aqueous 50 mM citrate buffer at about pH 4.5.

The term "seeding" refers to the addition of crystalline material to a solution or mixture to initiate crystallization.

Some embodiments are directed to compounds or salts wherein at least a particular percentage by weight of the compound or salt is crystalline. Some embodiments are directed to a compound or salt wherein at least a particular percentage by weight of the compound or salt is crystalline. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%. When a particular percentage by weight of the compound or salt is crystalline, the remainder of the compound or salt is the amorphous form of the compound or salt. When a particular percentage by weight of the compound or salt is a designated crystalline form, the remainder of the compound or salt is some combination of the amorphous form of the compound or salt, and one or more crystalline forms of the compound or salt excluding the designated crystalline form.

When a crystalline form of a compound or salt is identified using one or more temperatures from a DSC profile (e.g., onset of endothermic transition, melt, etc.), each of the temperature values is understood to mean the given value ±2° C.

When a crystalline form of a compound or salt is identified using one or more peaks from a raman pattern expressed as $cm^{-1}$, it is understood to mean the given value ±0.2 $cm^{-1}$, unless otherwise expressed.

Solid State Forms of I-257b.

Provided herein is an assortment of characterizing information, which is sufficient, but not all of which is necessary, to describe crystalline Form 1 anhydrous compound I-257 ("I-257b Form 1").

FIG. 1 shows an X-ray powder diffraction (XRPD) pattern of Form 1 of compound I-257b obtained using CuKα radiation. Peaks identified in FIG. 1 include those listed in the table below.

| Angle (2 Theta) ° | Relative Intensity |
| --- | --- |
| 7.0 | 2.7% |
| 9.4 | 5.6% |
| 10.2 | 7.5% |
| 13.0 | 13.4% |
| 14.5 | 62.5% |
| 17.5 | 10.5% |
| 18.2 | 15.4% |
| 18.6 | 96.8% |
| 19.1 | 29.0% |
| 20.7 | 41.5% |
| 21.4 | 23.8% |
| 21.7 | 74.8% |
| 22.6 | 53.9% |
| 24.0 | 30.0% |
| 24.8 | 19.1% |
| 25.2 | 100.0% |
| 25.8 | 27.2% |
| 26.7 | 12.6% |
| 27.0 | 5.9% |
| 27.9 | 38.0% |
| 29.1 | 2.7% |

In some embodiments, I-257b Form 1 is characterized by an XRPD pattern having a peak at 2θ angle 25.2°. In some embodiments, I-257b Form 1 is characterized by an XRPD pattern having peaks at 2θ angles of 25.2° and 18.6°. In some embodiments, I-257b Form 1 is characterized by an XRPD pattern having peaks at 2θ angles of 25.2°, 21.7°, 18.6°, and 14.5°. In some embodiments, I-257b Form 1 is characterized by an XRPD pattern having peaks at 2θ angles of 25.2°, 21.7°, 18.6°, 14.5°, 22.6°, 20.7° and 27.9°. In some embodiments, I-257b Form 1 is characterized by an XRPD pattern having peaks at 2θ angles of 25.2°, 21.7°, 18.6°, 14.5°, 22.6°, 20.7°, 27.9°, 24.0°, 19.1°, 25.8° and 21.4°. In some embodiments, the 2θ angles given above have an error tolerance of ±0.10. In some embodiments, the 2θ angles given above have an error tolerance of ±0.2°. In some embodiments, the 2θ angles given above have an error tolerance of ±0.3°. In some embodiments, I-257b Form 1 is characterized by an XRPD pattern substantially as shown in FIG. 1.

In some embodiments, I-257b Form 1 is characterized by an XRPD pattern having a reference peak with a 2θ angle of 14.5±0.3°, and having peaks at 2θ angles of 4.1°, 7.2°, and 10.7° relative to the reference peak. The term "reference peak" refers to a peak in the XRPD diffractogram that one skilled in the art considers as informing the polymorphic form of the material, i.e., differentiated from instrument noise. By "relative" it is meant that the observed 2θ angle of each peak will be the sum of the 2θ angle of the reference peak and the relative 2θ angle of that peak. For example, if the reference peak has a 2θ angle of 14.2°, the relative peaks will have 2θ angles of 18.3°, 21.4°, and 24.9°; if the reference peak has a 2θ angle of 14.3°, the relative peaks will have 2θ angles of 18.4°, 21.5°, and 25.0°; if the reference peak has a 2θ angle of 14.4°, the relative peaks will have 2θ angles of 18.5°, 21.6°, and 25.1°; etc. In some embodiments, I-257b Form 1 is characterized by an XRPD pattern having a reference peak with a 2θ angle of 14.5±0.3°, and having peaks at 2θ angles of 4.10, 6.2°, 7.2°, 8.1°, 10.7°, and 13.4° relative to the reference peak. In some embodiments, I-257b Form 1 is characterized by an XRPD pattern having a reference peak with a 2θ angle of 14.5±0.3°, and having peaks at 2θ angles of 4.10, 4.6°, 6.2°, 6.9°, 7.2°, 8.1°, 9.5°, 10.7°, 11.3°, and 13.4° relative to the reference peak. Any of the peaks that one skilled in the art considers as informing the polymorphic form of the material can serve as the reference peak and the relative peaks can then be calculated. For example, if the reference peak has a 2θ angle of 25.2°, then the relative peaks will have 2θ angles of −3.5, −6.6°, and −10.7° relative to the reference peak.

In some embodiments, the chemical entity according to the disclosure is or comprises substantially crystalline I-257b Form 1. In some embodiments, the chemical entity according to the disclosure comprises at least 70% by weight crystalline I-257b Form 1. In some embodiments, the chemical entity according to the disclosure comprises at least 80% by weight crystalline I-257b Form 1. In some embodiments, the chemical entity according to the disclosure comprises at least 90% by weight crystalline I-257b Form 1. In some embodiments, the chemical entity according to the disclosure comprises at least 95% by weight crystalline I-257b Form 1.

Figure 8:
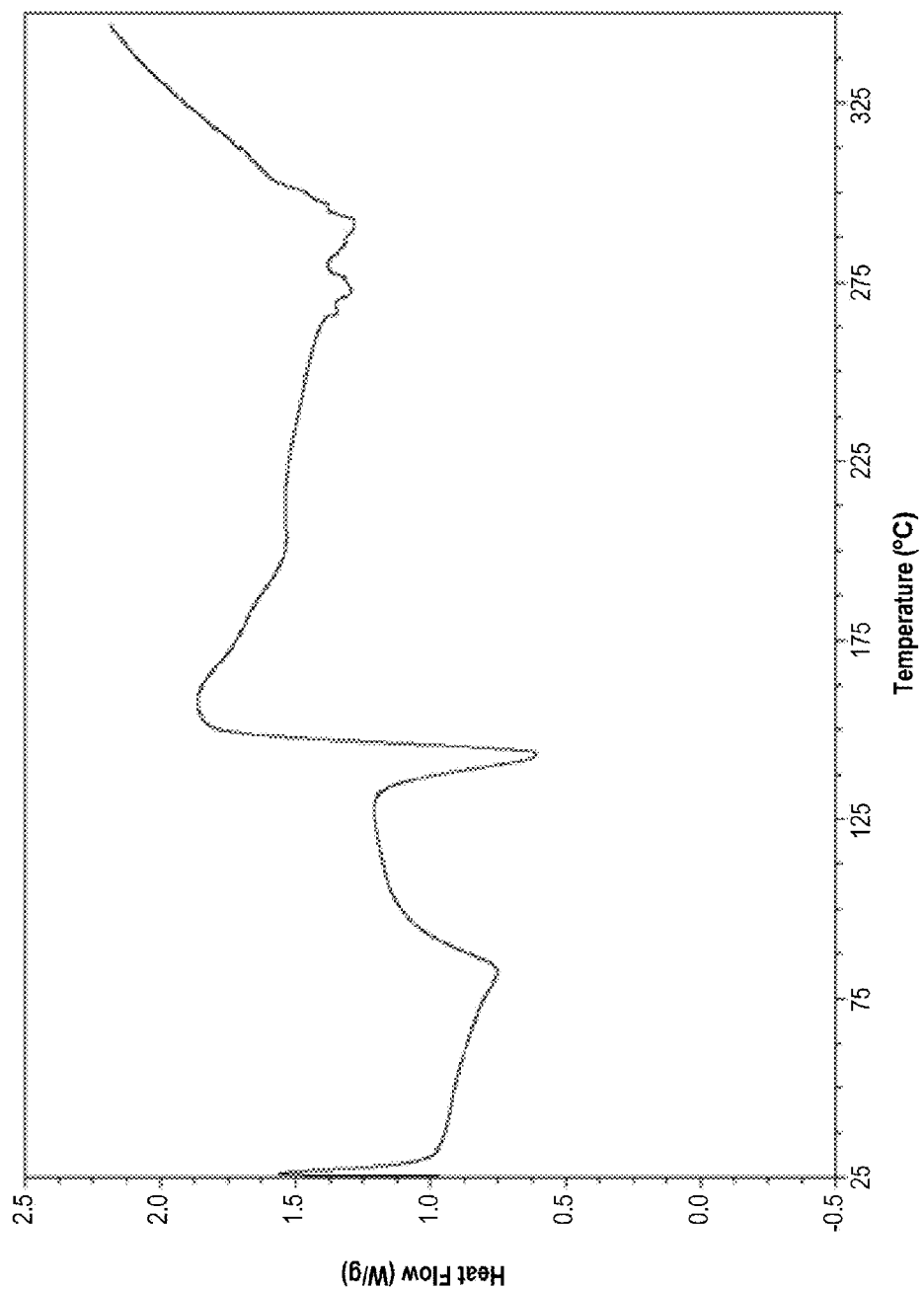
FIG. 8 shows a differential scanning calorimetry (DSC) thermogram for I-257b Form 1.

FIG. 8 shows a differential scanning calorimetry (DSC) profile of I-257b Form 1. The DSC thermogram plots the heat flow as a function of temperature from a sample, the temperature rate change being about 10° C./min. In some embodiments, I-257b Form 1 is characterized by a DSC profile substantially as shown in FIG. 8. FIG. 8 shows an endotherm event with onset of about 57.8° C. and peak at about 83.2° C. FIG. 8 also shows an endotherm event with onset of about 135.0° C. and peak at about 143.8° C. In some embodiments, I-257b Form 1 is characterized by a DSC profile having an endotherm event with onset of about 57.8° C. In some embodiments, I-257b Form 1 is characterized by a DSC profile having an endotherm event with peak at about 83.2° C. In some embodiments, I-257b Form 1 is characterized by a DSC profile having an endotherm event with onset of about 135.0° C. In some embodiments, I-257b Form 1 is characterized by a DSC profile having an endotherm event with peak at about 143.8° C.

Figure 9:
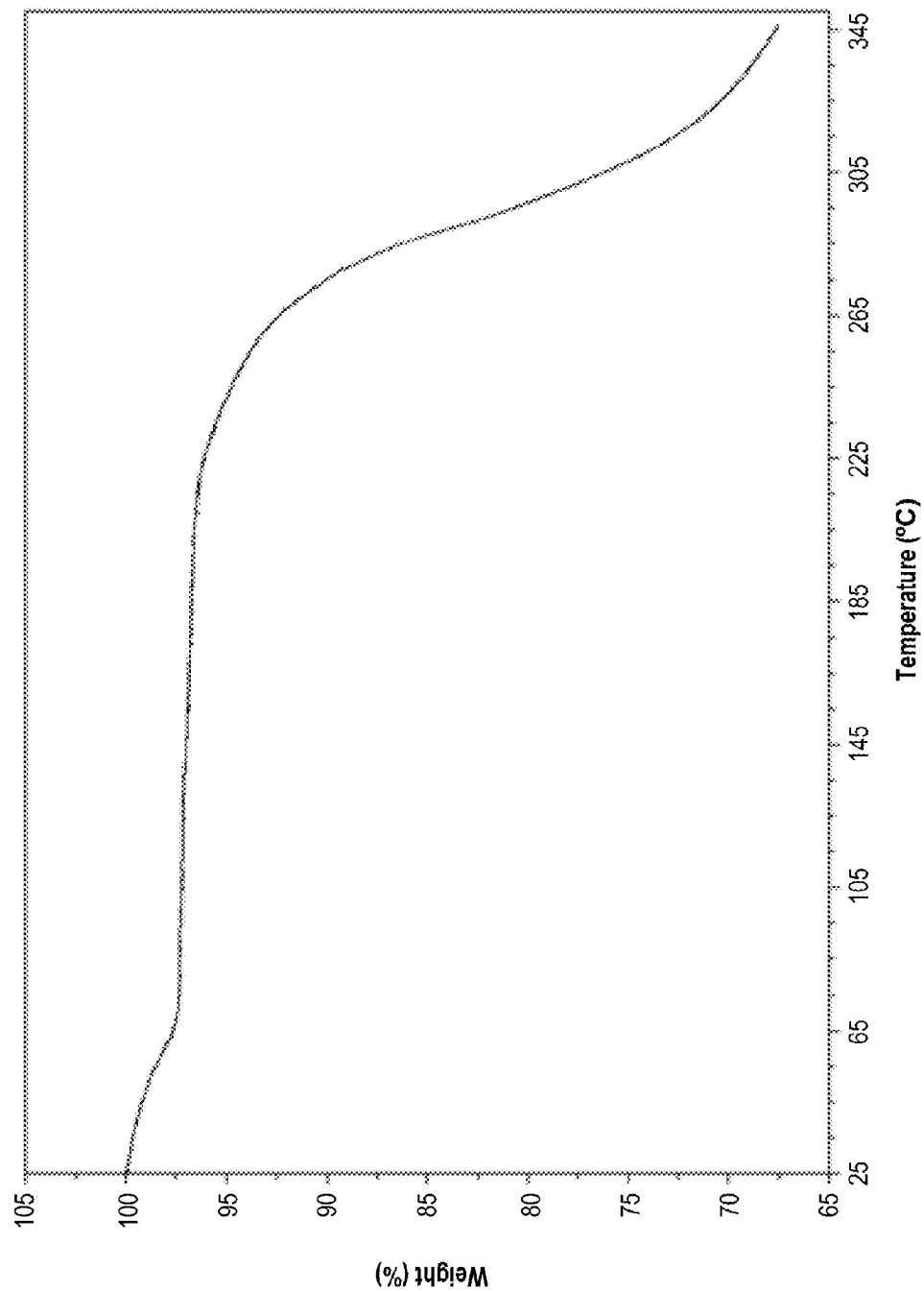
FIG. 9 shows a thermogravimetric analysis (TGA) thermogram for I-257b Form 1.

FIG. 9 shows a thermal gravimetric analysis (TGA) profile of I-257b Form 1. The TGA thermogram plots the percent loss of weight of the sample as a function of temperature, the temperature rate change being about 10° C./min. FIG. 9 shows approximately 2.7% weight loss to 79.5° C. In some embodiments, I-257b Form 1 is characterized by a TGA profile substantially as shown in FIG. 9. In some embodiments, I-257b Form 1 is characterized by a TGA profile having about 2.7% weight loss to 79.5° C.

Figure 10:
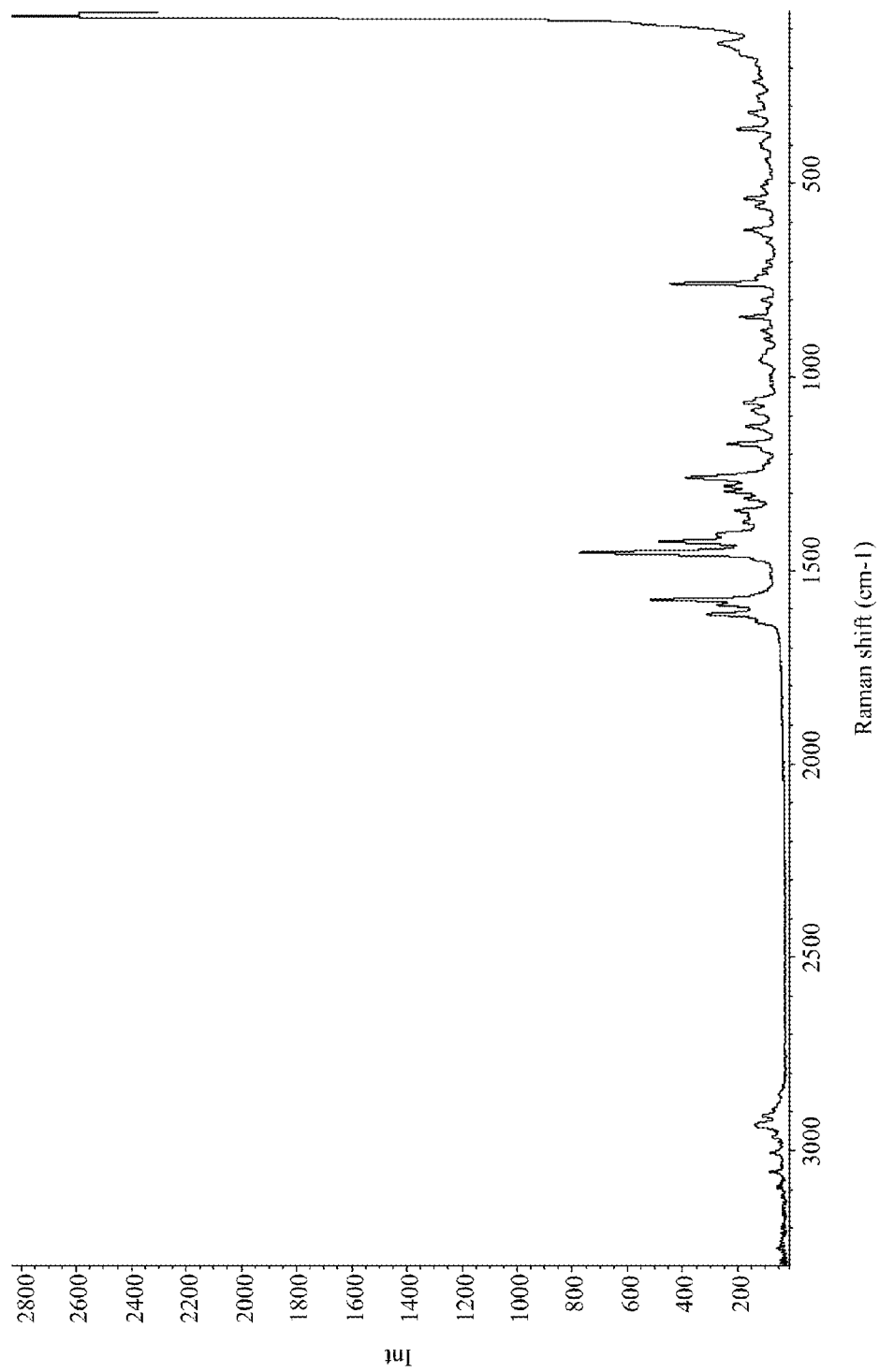
FIG. 10 shows a raman pattern for I-257b Form 1 including data in the region of 500 cm$^{-1}$ to 3000 cm$^{-1}$.
Figure 11:
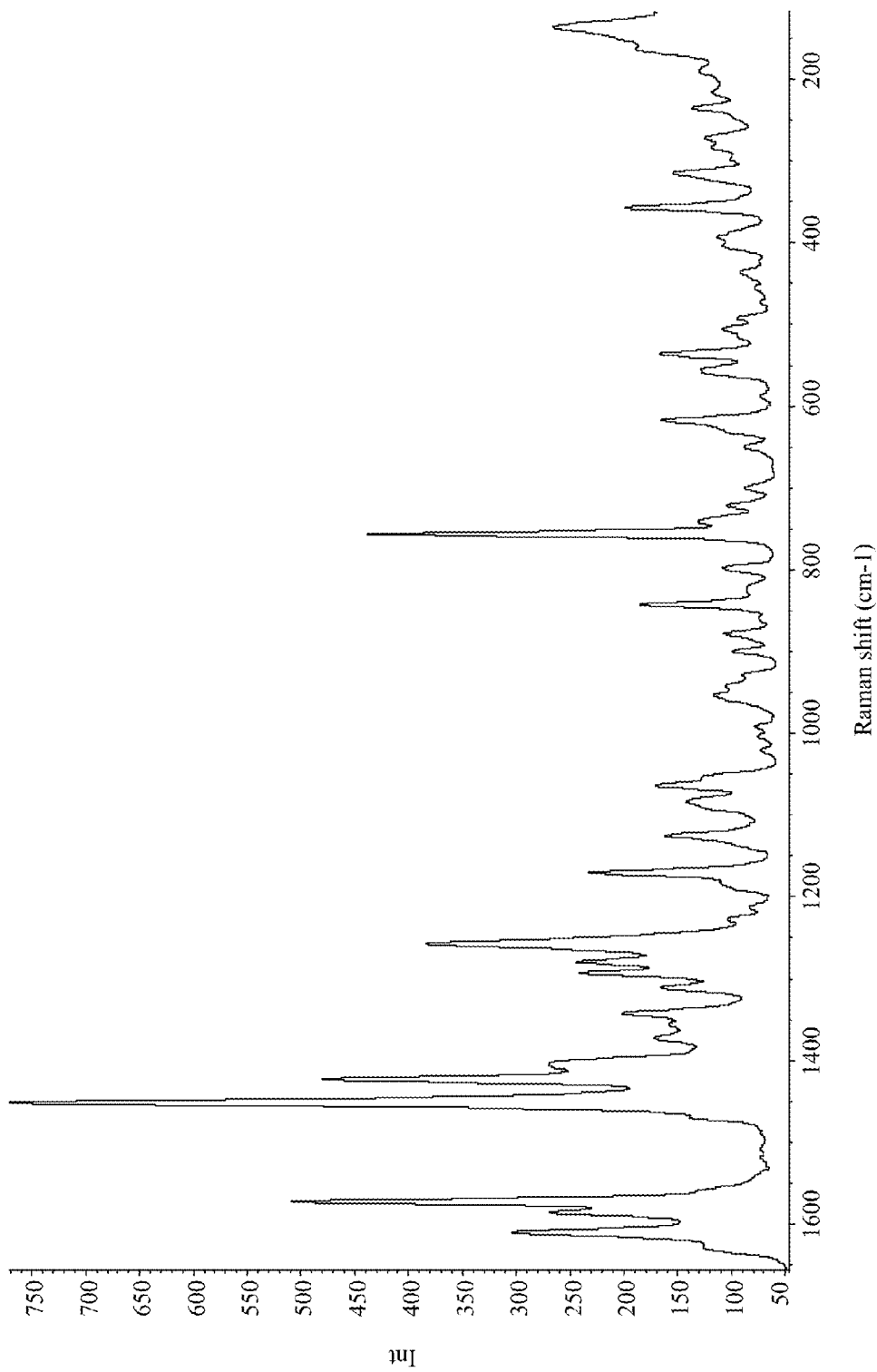
FIG. 11 shows a raman pattern for I-257b Form 1 including data in the region of 200 cm$^{-1}$ to 1600 cm$^{-1}$.

FIG. 10 shows a raman pattern of I-257b Form 1 including data in the region of 500 $cm^{-1}$ to 3000 $cm^{-1}$. In some embodiments, I-257b Form 1 is characterized by a raman pattern substantially as shown in FIG. 10. FIG. 11 shows a raman pattern of I-257b Form 1 including data in the region of 200 $cm^{-1}$ to 1600 $cm^{-1}$. In some embodiments, I-257b Form 1 is characterized by a raman pattern substantially as shown in FIG. 11.

In some embodiments, I-257b Form 1 is characterized by a raman pattern with a peak at 1450 $cm^{-1}$. In some embodiments, I-257b Form 1 is characterized by a raman pattern with a peak at 1572 $cm^{-1}$. In some embodiments, I-257b Form 1 is characterized by a raman pattern with a peak at 1422 $cm^{-1}$. In some embodiments, I-257b Form 1 is characterized by a raman pattern with a peak at 754 $cm^{-1}$. In some embodiments, I-257b Form 1 is characterized by a raman pattern with a peaks at 1450, 1572, 1422, and 754 $cm^{-1}$. In some embodiments, I-257b Form 1 is characterized by a raman pattern with a peaks at 1450, 1572, and 1422 $cm^{-1}$. In some embodiments, I-257b Form 1 is characterized by a raman pattern with a peaks at 1450 and 1572 $cm^{-1}$.

In some embodiments, I-257b Form 1 is characterized by at least one of the following features (I-i)-(I-v):

(I-i) an XRPD pattern having peaks at 2θ angles of 25.2°, 21.7°, 18.6°, and 14.5°;
(I-ii) a DSC profile substantially as shown in FIG. 8;
(I-iii) a TGA profile substantially as shown in FIG. 9;
(I-iv) a raman pattern substantially as shown in FIG. 10;
(I-v) a raman pattern substantially as shown in FIG. 11.

In some embodiments, I-257b Form 1 is characterized by at least two of the features (I-i)-(I-v). In some embodiments, I-257b Form 1 is characterized by at least three of the features (I-i)-(I-v). In some embodiments, I-257b Form 1 is characterized by at least four of the features (I-i)-(I-v). In some embodiments, I-257b Form 1 is characterized by all five of the features (I-i)-(I-v).

Solid State Forms of I-263a.

Provided herein is an assortment of characterizing information, which is sufficient, but not all of which is necessary, to describe crystalline Form 1 anhydrous compound I-263a ("I-263a Form 1").

Figure 2:
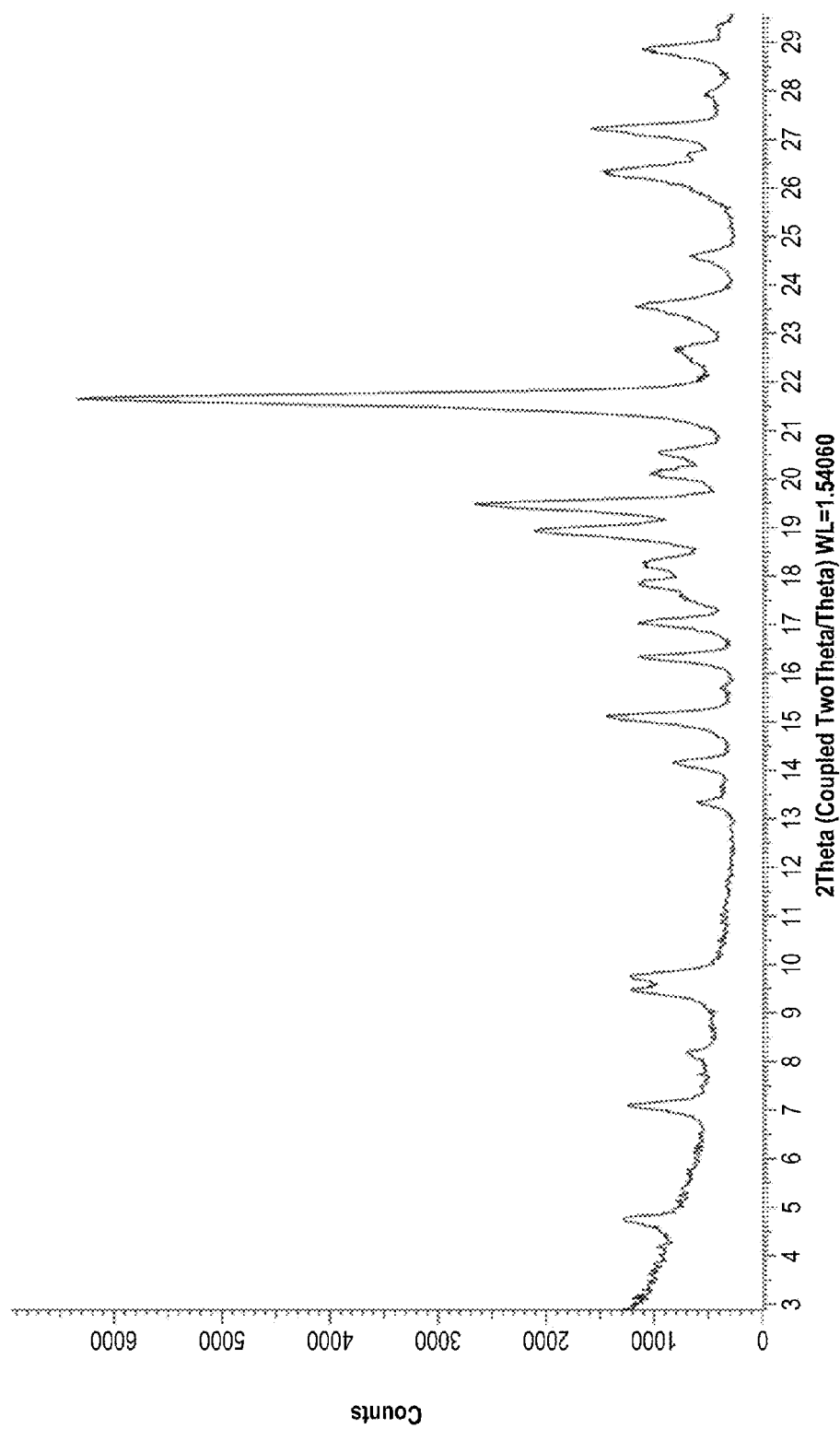
FIG. 2 is an XRPD pattern of compound I-263a Form 1.

FIG. 2 shows an X-ray powder diffraction (XRPD) pattern of Form 1 of compound I-263a obtained using CuKα radiation. Peaks identified in FIG. 2 include those listed in the table below.

| Angle (2 Theta) | Relative Intensity |
|---|---|
| 4.7 | 8.1% |
| 7.1 | 11.7% |
| 9.5 | 10.8% |
| 9.7 | 13.1% |
| 13.3 | 5.5% |
| 14.1 | 9.0% |
| 15.1 | 18.5% |
| 16.3 | 13.7% |
| 17.0 | 13.6% |
| 17.7 | 6.6% |
| 17.9 | 12.6% |
| 18.2 | 12.0% |
| 18.9 | 29.4% |
| 19.5 | 37.2% |
| 20.1 | 10.1% |
| 20.5 | 9.2% |
| 21.6 | 100.0% |
| 22.6 | 7.2% |
| 23.5 | 14.6% |
| 24.6 | 6.1% |
| 26.3 | 19.6% |
| 27.2 | 21.2% |
| 28.8 | 13.6% |

In some embodiments, I-263a Form 1 is characterized by an XRPD pattern having a peak at 2θ angle 21.6°. In some embodiments, I-263a Form 1 is characterized by an XRPD pattern having peaks at 2θ angles of 21.6° and 19.5°. In some embodiments, I-263a Form 1 is characterized by an XRPD pattern having peaks at 2θ angles of 21.6°, 19.5°, 18.9°, and 27.2°. In some embodiments, I-263a Form 1 is characterized by an XRPD pattern having peaks at 2θ angles of 21.6°, 19.5°, 18.9°, 27.2°, 26.3°, 15.1°, and 23.5°. In some embodiments, I-263a Form 1 is characterized by an XRPD pattern having peaks at 2θ angles of 21.6°, 19.5°, 18.9°, 27.2°, 26.3°, 15.1°, 23.5°, 16.3°, 17.0°, 28.8°, and 9.7°. In some embodiments, the 2θ angles given above have an error tolerance of ±0.10. In some embodiments, the 2θ angles given above have an error tolerance of ±0.2°. In some embodiments, the 2θ angles given above have an error tolerance of ±0.3°. In some embodiments, I-263a Form 1 is characterized by an XRPD pattern substantially as shown in FIG. 2.

In some embodiments, I-263a Form 1 is characterized by an XRPD pattern having a reference peak with a 2θ angle of 18.9±0.3°, and having peaks at 2θ angles of 0.6°, 2.7°, and 8.3° relative to the reference peak. The term "reference peak" refers to a peak in the XRPD diffractogram that one skilled in the art considers as informing the polymorphic form of the material, i.e., differentiated from instrument noise. By "relative" it is meant that the observed 2θ angle of each peak will be the sum of the 2θ angle of the reference peak and the relative 2θ angle of that peak. For example, if the reference peak has a 2θ angle of 18.6°, the relative peaks will have 2θ angles of 19.2°, 21.3°, and 26.9°; if the reference peak has a 2θ angle of 18.7°, the relative peaks will have 2θ angles of 19.3°, 21.4°, and 27.0°; if the reference peak has a 2θ angle of 18.8°, the relative peaks will have 2θ angles of 19.4°, 21.5°, and 27.1°; etc. In some embodiments, I-263a Form 1 is characterized by an XRPD pattern having a reference peak with a 2θ angle of 18.9±0.3°, and having peaks at 2θ angles of −3.8°, 0.6°, 2.7°, 4.6°, 7.4°, and 8.3° relative to the reference peak. In some embodiments, I-263a Form 1 is characterized by an XRPD pattern having a reference peak with a 2θ angle of 18.9±0.3°, and having peaks at 2θ angles of −9.2°, −3.8°, −2.6°, −1.9°, 0.6°, 2.7°, 4.6°, 7.4°, and 8.3° and 9.9° relative to the reference peak. Any of the peaks that one skilled in the art considers as informing the polymorphic form of the material can serve as the reference peak and the relative peaks can then be calculated. For example, if the reference peak has a 2θ angle of 21.6°, then the relative peaks will have 2θ angles of −2.7°, −2.10, and 5.6° relative to the reference peak.

In some embodiments, the chemical entity according to the disclosure is or comprises substantially crystalline I-263a Form 1. In some embodiments, the chemical entity according to the disclosure comprises at least 70% by weight crystalline I-263a Form 1. In some embodiments, the chemical entity according to the disclosure comprises at least 80% by weight crystalline I-263a Form 1. In some embodiments, the chemical entity according to the disclosure comprises at least 90% by weight crystalline I-263a Form 1. In some embodiments, the chemical entity according to the disclosure comprises at least 95% by weight crystalline I-263a Form 1.

Figure 4:
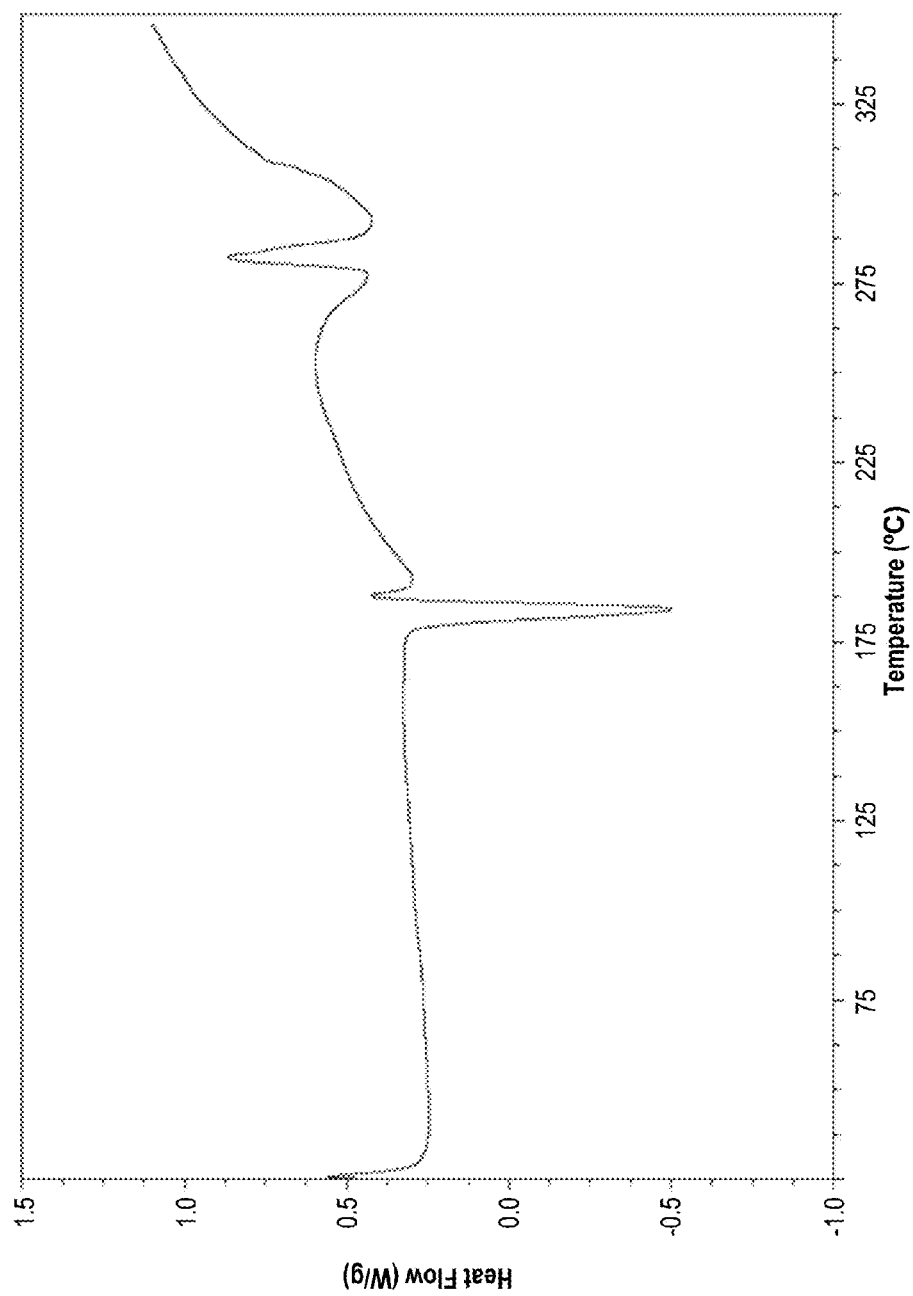
FIG. 4 shows a differential scanning calorimetry (DSC) thermogram for I-263a Form 1.

FIG. 4 shows a differential scanning calorimetry (DSC) profile of I-263a Form 1. The DSC thermogram plots the heat flow as a function of temperature from a sample, the temperature rate change being about 10° C./min. In some embodiments, I-263a Form 1 is characterized by a DSC profile substantially as shown in FIG. 4. FIG. 4 shows an endotherm event with onset of about 179.4° C. and peak at about 184.0° C. FIG. 4 also shows an exotherm event with onset of about 279.0° C. and peak at about 282.4° C. In some embodiments, I-263a Form 1 is characterized by a DSC profile having an endotherm event with onset of about 179.4° C. In some embodiments, I-263a Form 1 is characterized by a DSC profile having an endotherm event with peak at about 184.0° C. In some embodiments, I-263a Form 1 is characterized by a DSC profile having an exotherm event with onset of about 279.0° C. In some embodiments, I-263a Form 1 is characterized by a DSC profile having an exotherm event with peak at about 282.4° C.

Figure 5:
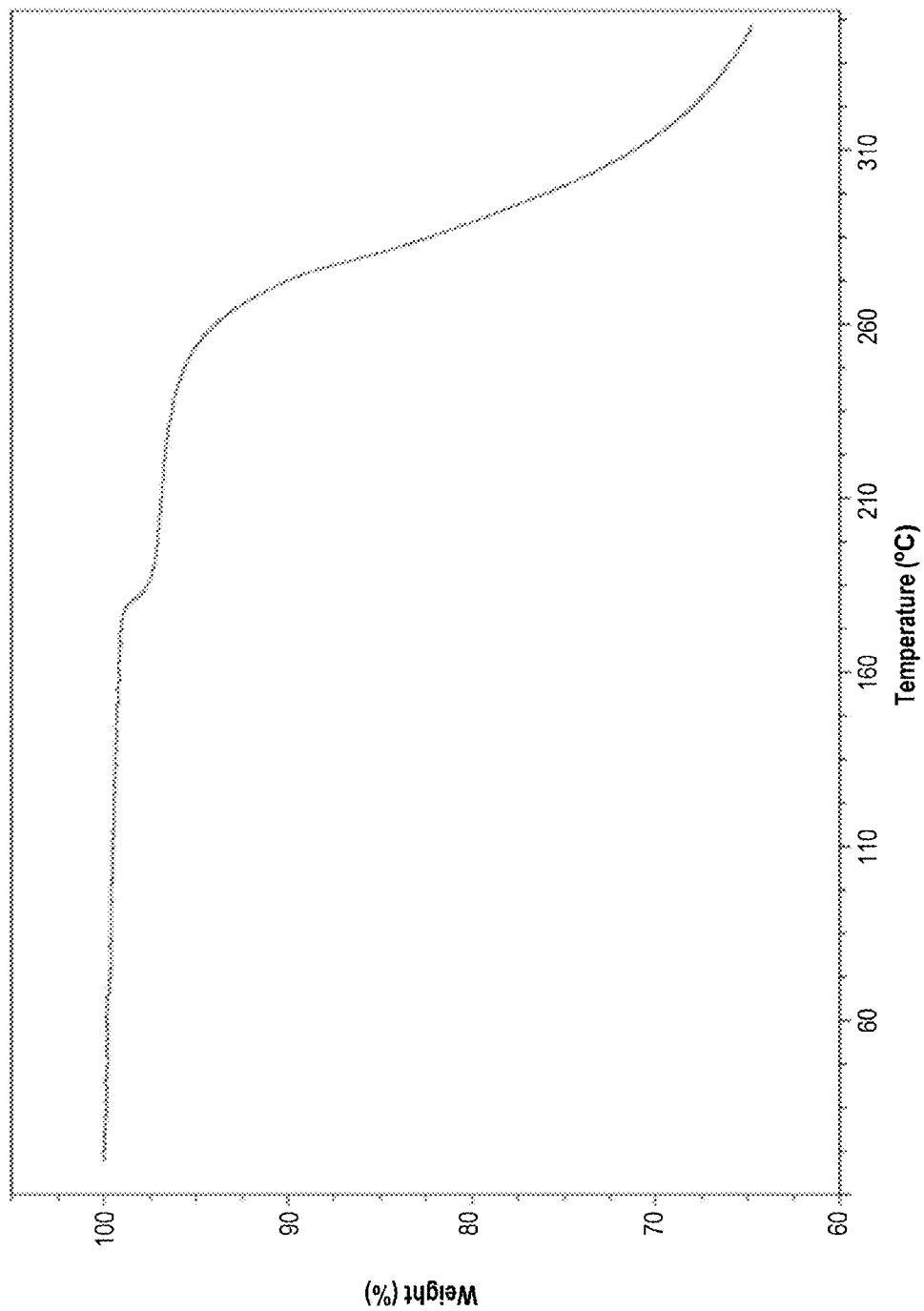
FIG. 5 shows a thermogravimetric analysis (TGA) thermogram for I-263a Form 1.

FIG. 5 shows a thermal gravimetric analysis (TGA) profile of I-263a Form 1. The TGA thermogram plots the percent loss of weight of the sample as a function of temperature, the temperature rate change being about 10° C./min. FIG. 5 shows approximately 0.9% weight loss to 170.4° C. In some embodiments, I-263a Form 1 is characterized by a TGA profile substantially as shown in FIG. 5. In some embodiments, I-263a Form 1 is characterized by a TGA profile having about 0.9% weight loss to 170.4° C.

Figure 6:
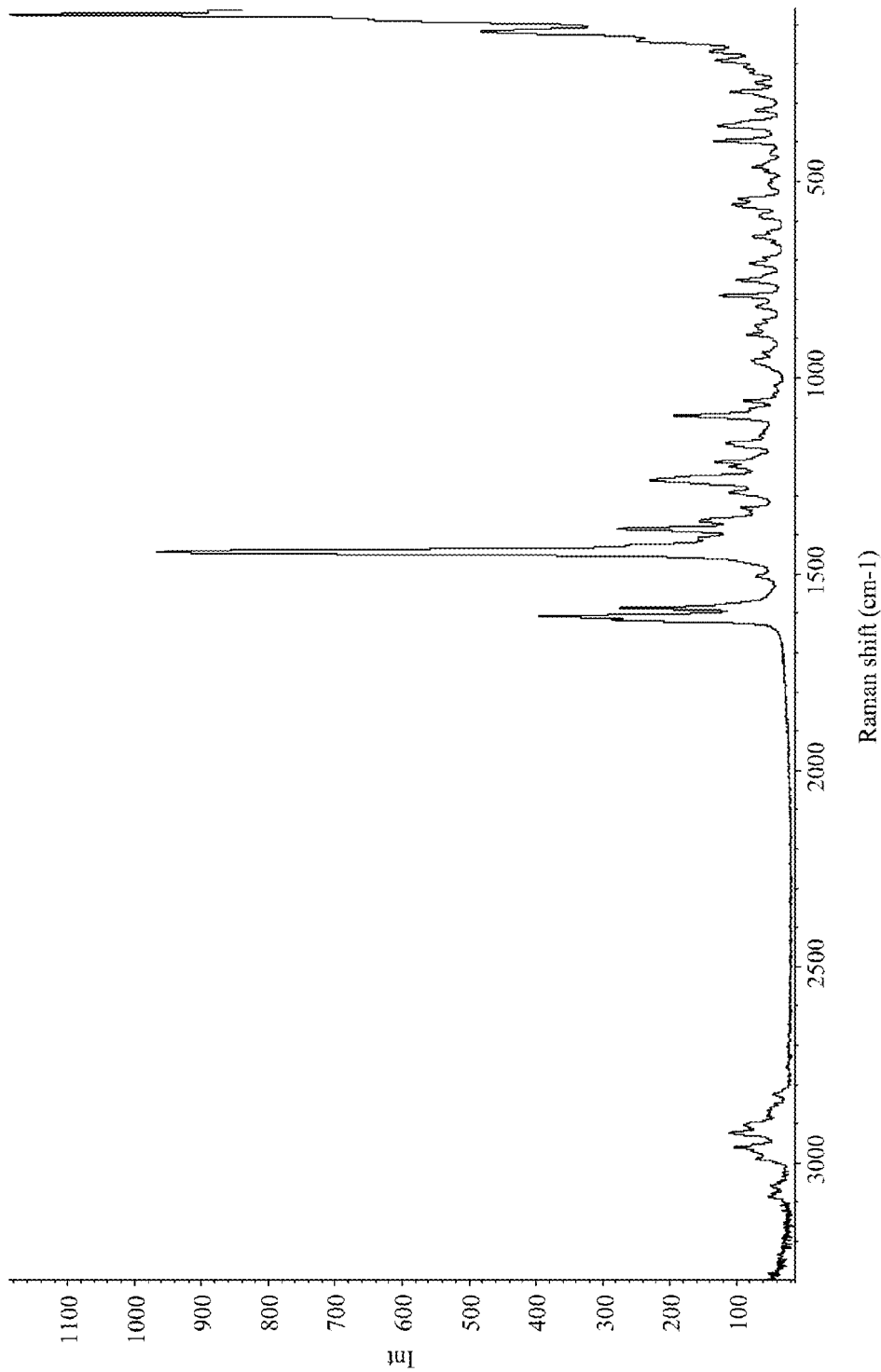
FIG. 6 shows a raman pattern for I-263a Form 1 including data in the region of 500 cm$^{-1}$ to 3000 cm$^{-1}$.
Figure 7:
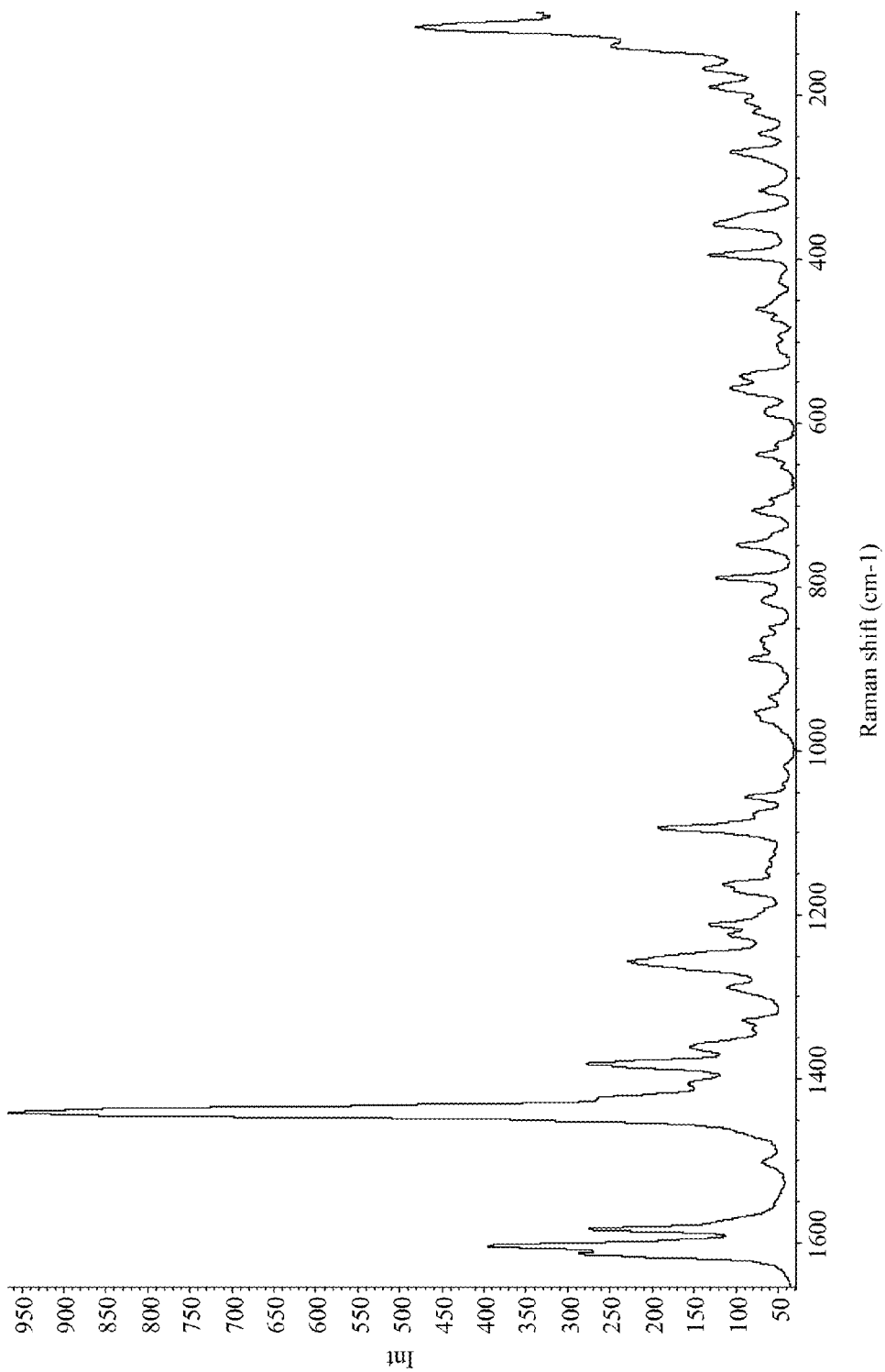
FIG. 7 shows a raman pattern for I-263a Form 1 including data in the region of 200 cm$^{-1}$ to 1600 cm$^{-1}$.

FIG. 6 shows a raman pattern of I-263a Form 1 including data in the region of 500 cm$^{-1}$ to 3000 cm$^{-1}$. In some embodiments, I-263a Form 1 is characterized by a raman pattern substantially as shown in FIG. 6. FIG. 7 shows a raman pattern of I-263a Form 1 including data in the region of 200 cm$^{-1}$ to 1600 cm$^{-1}$. In some embodiments, I-263a Form 1 is characterized by a raman pattern substantially as shown in FIG. 7.

In some embodiments, I-263a Form 1 is characterized by a raman pattern with a peak at 1441 cm$^{-1}$. In some embodiments, I-263a Form 1 is characterized by a raman pattern with a peak at 1604 cm$^{-1}$. In some embodiments, I-263a Form 1 is characterized by a raman pattern with a peak at 1583 cm$^{-1}$. In some embodiments, I-263a Form 1 is characterized by a raman pattern with a peak at 1381 cm$^{-1}$. In some embodiments, I-263a Form 1 is characterized by a raman pattern with a peaks at 1441, 1604, 1583, and 1381 cm$^{-1}$. In some embodiments, I-263a Form 1 is characterized by a raman pattern with a peaks at 1441, 1604, and 1583 cm$^{-1}$. In some embodiments, I-263a Form 1 is characterized by a raman pattern with a peaks at 1441 and 1604 cm$^{-1}$.

In some embodiments, I-263a Form 1 is characterized by at least one of the following features (I-i)-(I-v):

(I-i) an XRPD pattern having peaks at 2θ angles of 21.6°, 19.5°, 18.9°, and 27.2°;
(I-ii) a DSC profile substantially as shown in FIG. 4;
(I-iii) a TGA profile substantially as shown in FIG. 5;
(I-iv) a raman pattern substantially as shown in FIG. 6;
(I-v) a raman pattern substantially as shown in FIG. 7.

In some embodiments, I-263a Form 1 is characterized by at least two of the features (I-i)-(I-v). In some embodiments, I-263a Form 1 is characterized by at least three of the features (I-i)-(I-v). In some embodiments, I-263a Form 1 is characterized by at least four of the features (I-i)-(I-v). In some embodiments, I-263a Form 1 is characterized by all five of the features (I-i)-(I-v).

In some embodiments, the chemical entity I-263a is a hydrate. In some embodiments, the chemical entity I-263a is a sesquihydrate. In some embodiments, the chemical entity I-263a is a hydrate comprising between 2 and 3 equivalents of H$_2$O.

I-263a Form 2.

Provided herein is an assortment of characterizing information, which is sufficient, but not all of which is necessary, to describe crystalline Form 2 sesquihydrate compound I-263a ("I-263a Form 2"). I-263a Form 2 may be prepared by crystallization of I-263a from a solvent system containing water (e.g., distilled water) and an organic solvent such as methanol, ethanol, isopropyl alcohol, acetonitrile, formamide, or 1,4-dioxane.

Figure 14:
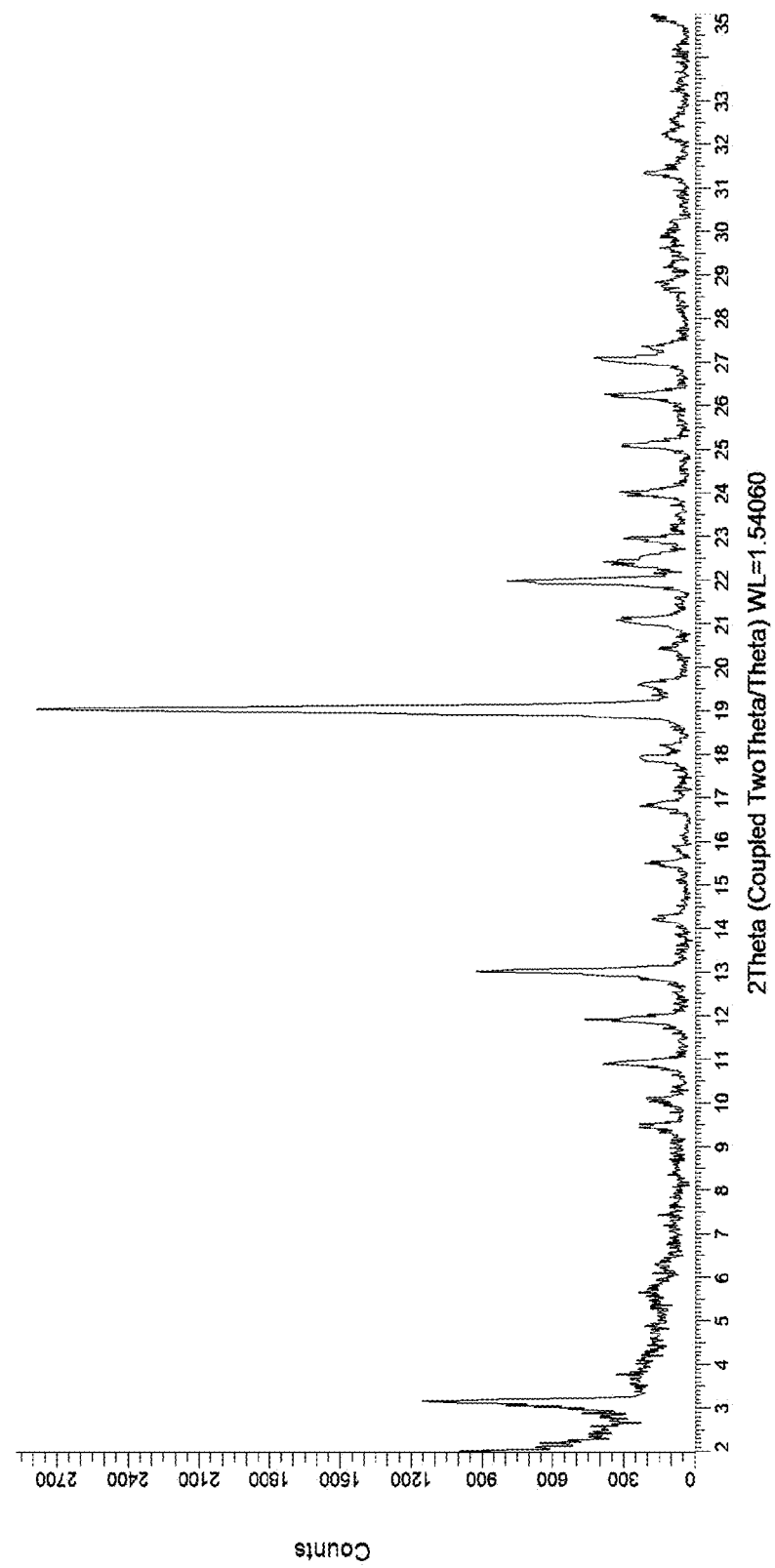
FIG. 14 is an XRPD pattern of compound I-263a Form 2.

FIG. 14 shows an X-ray powder diffraction (XRPD) pattern of I-263a Form 2 of obtained using CuKα radiation. Peaks identified in FIG. 14 include those listed in the table below.

| Angle (2 Theta) | Relative Intensity |
|---|---|
| 3.1 | 21.4% |
| 9.4 | 6.2% |
| 10.1 | 4.4% |
| 10.9 | 12.7% |
| 11.9 | 11.2% |
| 13.0 | 32.8% |
| 14.2 | 4.0% |
| 15.5 | 5.9% |
| 16.8 | 6.0% |
| 17.9 | 7.3% |
| 19.0 | 100.0% |
| 19.5 | 4.4% |
| 20.4 | 4.2% |
| 21.1 | 10.2% |
| 22.0 | 28.3% |
| 22.4 | 12.2% |
| 22.9 | 6.0% |
| 24.0 | 9.4% |
| 25.1 | 10.2% |
| 26.2 | 11.6% |
| 27.1 | 14.0% |
| 31.4 | 6.3% |

In some embodiments, I-263a Form 2 is characterized by an XRPD pattern having a peak at 2θ angle 19.0°. In some embodiments, I-263a Form 2 is characterized by an XRPD pattern having peaks at 2θ angles of 19.0° and 13.0°. In some embodiments, I-263a Form 2 is characterized by an XRPD pattern having peaks at 2θ angles of 19.0°, 13.00, 22.0° and 3.1°. In some embodiments, I-263a Form 2 is characterized by an XRPD pattern having peaks at 2θ angles of 19.0°, 13.0°, 22.0°, 3.1°, 27.1°, 10.9° and 22.4°. In some embodiments, I-263a Form 2 is characterized by an XRPD pattern having peaks at 2θ angles of 19.0°, 13.0°, 22.0°, 3.1°, 27.10, 10.9°, 22.4°, 26.2°, 11.9°, 25.1° and 21.1°. In some embodiments, the 2θ angles given above have an error tolerance of ±0.10. In some embodiments, the 2θ angles given above have an error tolerance of ±0.2°. In some embodiments, the 2θ angles given above have an error tolerance of ±0.3°. In some embodiments, I-263a Form 2 is characterized by an XRPD pattern substantially as shown in FIG. 14.

In some embodiments, I-263a Form 2 is characterized by an XRPD pattern having a reference peak with a 2θ angle of 3.1±0.3°, and having peaks at 2θ angles of 9.90, 15.9° and 18.9° relative to the reference peak. The term "reference peak" refers to a peak in the XRPD diffractogram that one skilled in the art considers as informing the polymorphic form of the material, i.e., differentiated from instrument noise. By "relative" it is meant that the observed 2θ angle of each peak will be the sum of the 2θ angle of the reference peak and the relative 2θ angle of that peak. For example, if the reference peak has a 2θ angle of 2.8°, the relative peaks will have 2θ angles of 12.7°, 18.7° and 21.7°; if the reference peak has a 2θ angle of 2.9°, the relative peaks will have 2θ angles of 12.8°, 18.8° and 21.8°; if the reference peak has a 2θ angle of 3.0°, the relative peaks will have 2θ angles of 12.9°, 18.9° and 21.9°; etc. In some embodiments, I-263a Form 2 is characterized by an XRPD pattern having a reference peak with a 2θ angle of 3.1±0.3°, and having peaks at 2θ angles of 7.8°, 9.9°, 15.9°, 18.9°, 19.3° and 24.0° relative to the reference peak. In some embodiments, I-263a Form 2 is characterized by an XRPD pattern having a reference peak with a 2θ angle of 3.1±0.3°, and having peaks at 2θ angles of 7.8°, 8.8°, 9.9°, 15.9°, 18.0°, 18.9°, 19.3°, 22.0°, 23.1° and 24.0° relative to the reference peak. Any of the peaks that one skilled in the art considers as informing the polymorphic form of the material can serve as the reference peak and the relative peaks can then be calculated. For example, if the reference peak has a 2θ angle of 19.0°, then the relative peaks will have 2θ angles of −15.9°, −6.0° and 3.0° relative to the reference peak.

Karl Fischer measurements of I-263a Form 2 show a water content of about 4.8%. A thermal gravimetric analysis (TGA) profile of I-263a Form 2 can show that the percent loss of weight of the sample as a function of temperature, the temperature rate change being about 10° C./min, is approximately 5% weight loss to 50.7° C. The TGA profile can also show that the percent loss of weight of the sample as a function of temperature, the temperature rate change being about 10° C./min, is approximately 10.1% weight loss to 252.8° C. A differential scanning calorimetry (DSC) profile of I-263a Form 2 can show the following regarding the heat flow as a function of temperature from a sample of I-263a Form 2, the temperature rate change being about 10° C./min. In some embodiments, I-263a Form 2 is characterized by an endotherm event with a peak at about 47.7° C. In some embodiments, I-263a Form 2 is characterized by an endotherm event with a peak at about 60.7° C. In some embodiments, I-263a Form 2 is characterized by an endotherm event with a peak at about 73.8° C. In some embodiments, I-263a Form 2 is characterized by an exotherm event with a peak at about 132.9° C. In some embodiments, I-263a Form 2 is characterized by an exotherm event with a peak at about 149.3° C.

In some embodiments, I-263a Form 2 is characterized by at least one of the following features (I-i)-(I-iv):
(I-i) an XRPD pattern having peaks at 2θ angles of 3.1°, 13.0°, 19.0°, and 22.0° as shown in FIG. 14;
(I-ii) a DSC profile characterized by at least two of an endotherm event with a peak at about 47.7° C., an endotherm event with a peak at about 60.7° C., an endotherm event with a peak at about 73.8° C., an exotherm event with a peak at about 132.9° C., and an exotherm event with a peak at about 149.3° C.;
(I-iii) a TGA profile characterized by at least one of approximately 5% weight loss to 50.7° C. and approximately 10.1% weight loss to 252.8° C.
(I-iv) a water content of about 4.8% according to Karl Fischer measurements.

In some embodiments, I-263a Form 2 is characterized by at least two of the features (I-i)-(I-iv). In some embodiments, I-263a Form 2 is characterized by at least three of the features (I-i)-(I-iv). In some embodiments, I-263a Form 2 is characterized by all four of the features (I-i)-(I-iv).

I-263a Form 3.

Provided herein is an assortment of characterizing information, which is sufficient, but not all of which is necessary, to describe crystalline Form 3 hydrate compound I-263a ("I-263a Form 3"). I-263a Form 3 may be prepared by crystallization of I-263a from aqueous 50 mM citrate buffer at about pH 4.5.

Figure 15:
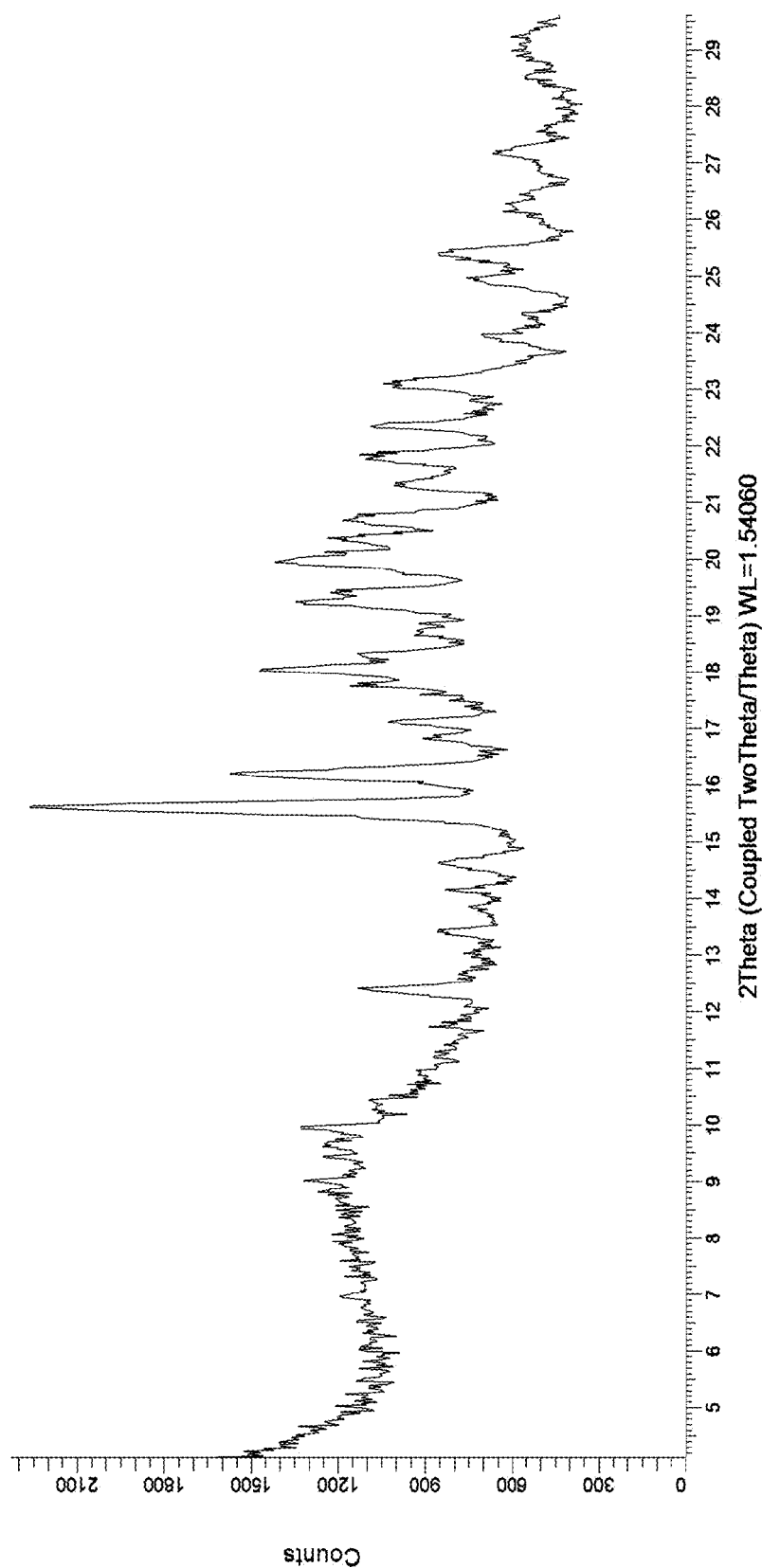
FIG. 15 is an XRPD pattern of compound I-263a Form 3.

FIG. 15 shows an X-ray powder diffraction (XRPD) pattern of I-263a Form 3 of obtained using CuKα radiation. Peaks identified in FIG. 15 include those listed in the table below.

| Angle (2 Theta) | Relative Intensity |
| --- | --- |
| 9.0 | 14.0% |
| 9.9 | 19.8% |
| 12.4 | 23.2% |
| 14.6 | 14.9% |
| 15.6 | 100.0% |
| 16.2 | 55.0% |
| 17.1 | 18.8% |
| 17.8 | 24.1% |
| 18.0 | 44.1% |
| 18.3 | 21.9% |
| 19.2 | 35.0% |
| 19.4 | 27.0% |
| 20.0 | 39.3% |
| 20.3 | 26.7% |
| 20.7 | 26.3% |
| 21.3 | 18.4% |
| 21.8 | 25.6% |
| 22.3 | 29.2% |
| 23.1 | 31.4% |
| 23.9 | 15.4% |
| 24.9 | 17.9% |
| 25.4 | 25.6% |
| 27.2 | 13.2% |

In some embodiments, I-263a Form 3 is characterized by an XRPD pattern having a peak at 2θ angle 15.6°. In some embodiments, I-263a Form 3 is characterized by an XRPD pattern having peaks at 2θ angles of 15.6° and 16.2°. In some embodiments, I-263a Form 3 is characterized by an XRPD pattern having peaks at 2θ angles of 15.6°, 16.2°, 18.0° and 20.0°. In some embodiments, I-263a Form 3 is characterized by an XRPD pattern having peaks at 2θ angles of 15.6°, 16.2°, 18.0°, 19.2°, 20.0°, 22.3°, and 23.1°. In some embodiments, I-263a Form 3 is characterized by an XRPD pattern having peaks at 2θ angles of 15.6°, 16.2°, 18.0°, 19.2°, 20.0°, 22.3°, 23.1°, 20.3°, 20.7°, 21.8°, and 25.4°. In some embodiments, the 2θ angles given above have an error tolerance of ±0.10. In some embodiments, the 2θ angles given above have an error tolerance of ±0.2°. In some embodiments, the 2θ angles given above have an error tolerance of ±0.3°. In some embodiments, I-263a Form 3 is characterized by an XRPD pattern substantially as shown in FIG. 14.

In some embodiments, I-263a Form 3 is characterized by an XRPD pattern having a reference peak with a 2θ angle of 15.6±0.3°, and having peaks at 2θ angles of 0.6°, 2.4° and 4.4° relative to the reference peak. The term "reference peak" refers to a peak in the XRPD diffractogram that one skilled in the art considers as informing the polymorphic form of the material, i.e., differentiated from instrument noise. By "relative" it is meant that the observed 2θ angle of each peak will be the sum of the 2θ angle of the reference peak and the relative 2θ angle of that peak. For example, if the reference peak has a 2θ angle of 15.3°, the relative peaks will have 2θ angles of 15.9°, 17.7° and 19.7°; if the reference peak has a 2θ angle of 15.4°, the relative peaks will have 2θ angles of 16.0°, 17.8° and 19.8°; if the reference peak has a 2θ angle of 15.5°, the relative peaks will have 2θ angles of 16.10, 17.9° and 19.9°; etc. In some embodiments, I-263a Form 3 is characterized by an XRPD pattern having a reference peak with a 2θ angle of 15.6±0.3°, and having peaks at 2θ angles of 0.6°, 2.4°, 3.6°, 4.4°, 6.7°, and 7.5° relative to the reference peak. In some embodiments, I-263a Form 3 is characterized by an XRPD pattern having a reference peak with a 2θ angle of 15.6±0.3°, and having peaks at 2θ angles of 0.6°, 2.4°, 3.6°, 4.4°, 4.7°, 5.1°, 6.2°, 6.7°, 7.5°, and 9.8° relative to the reference peak. Any of the peaks that one skilled in the art considers as informing the polymorphic form of the material can serve as the reference peak and the relative peaks can then be calculated. For example, if the reference peak has a 2θ angle of 18.0°, then the relative peaks will have 2θ angles of −2.4°, −1.8° and 2.0° relative to the reference peak.

Figure 16:
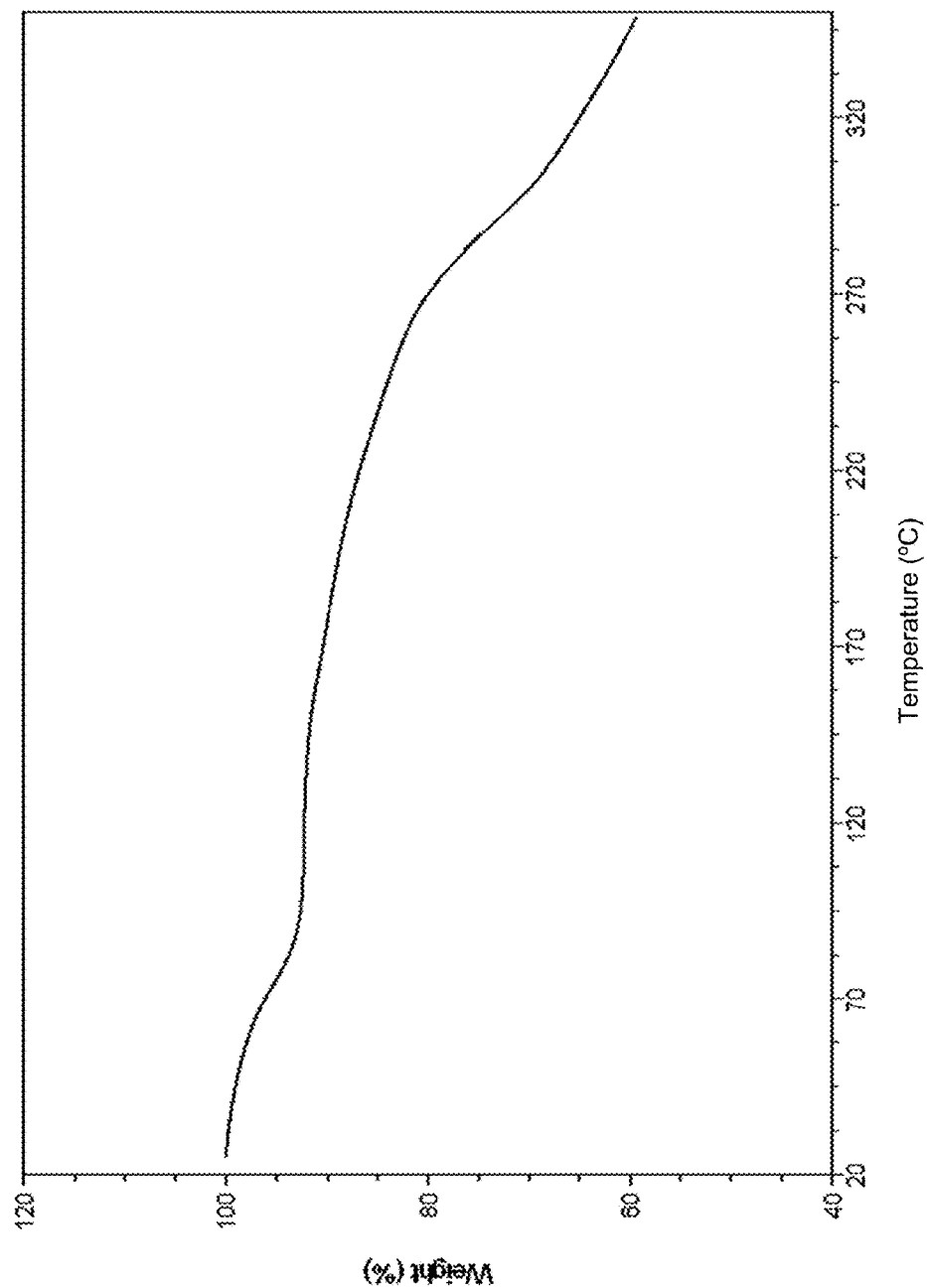
FIG. 16 shows a thermogravimetric analysis (TGA) thermogram for I-263a Form 3.

FIG. 16 shows a thermal gravimetric analysis (TGA) profile of I-263a Form 3. The TGA thermogram plots the percent loss of weight of the sample as a function of temperature, the temperature rate change being about 10° C./min. FIG. 16 shows approximately 7.6% weight loss to 110.3° C. FIG. 16 also shows approximately 15.2% weight loss to 237.8° C. In some embodiments, I-263a Form 3 is characterized by a TGA profile substantially as shown in FIG. 16. In some embodiments, I-263a Form 3 is characterized by a TGA profile showing approximately 7.6% weight loss to 110.3° C. In some embodiments, I-263a Form 3 is characterized by a TGA profile showing approximately 15.2% weight loss to 237.8° C. The weight loss of approximately 7.6% to 110.3° C. shown in the TGA profile is consistent with a water content of about 2 to about 3 molar equivalents of $H_2O$.

Figure 17:
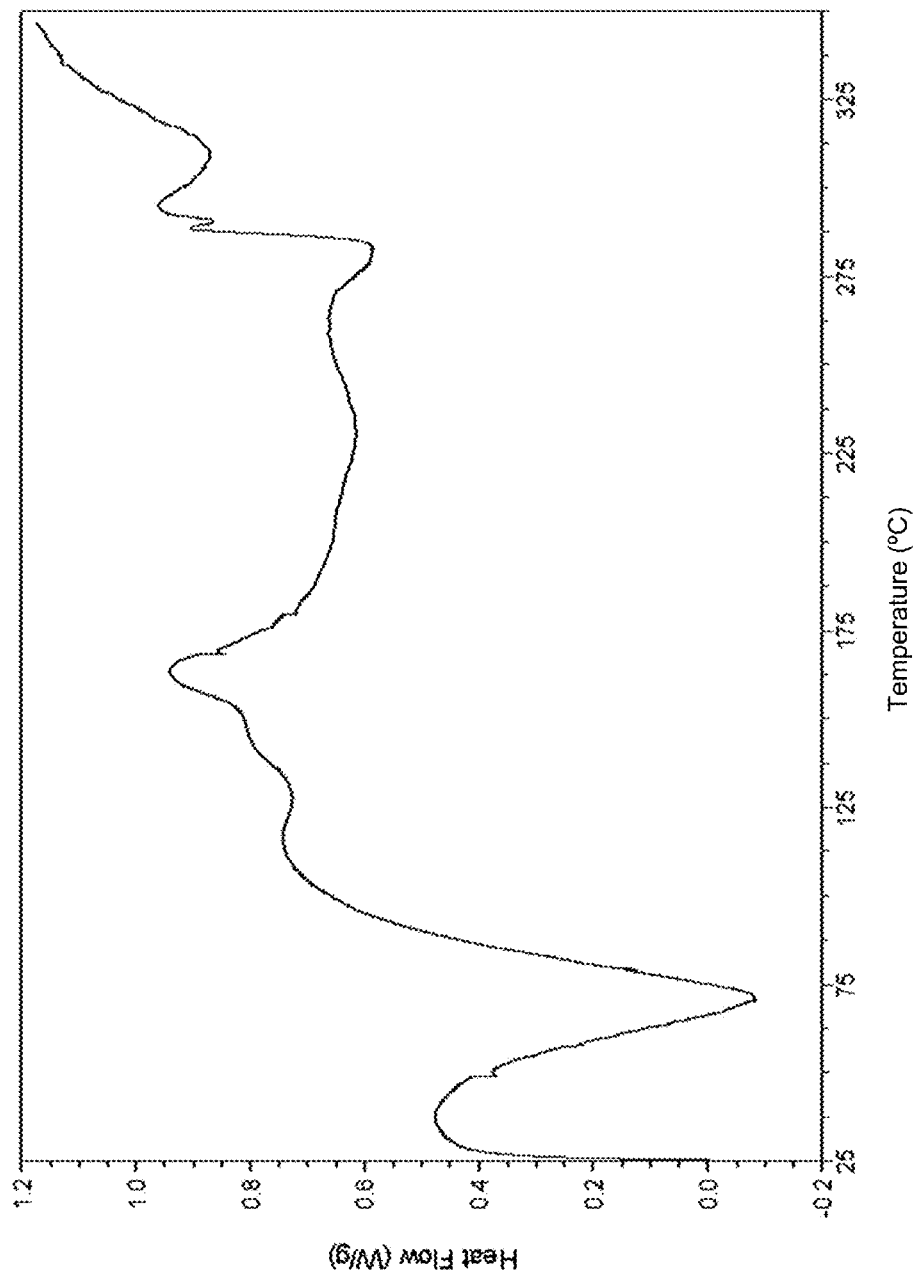
FIG. 17 shows a differential scanning calorimetry (DSC) thermogram for I-263a Form 3.

FIG. 17 shows a differential scanning calorimetry (DSC) profile of I-263a Form 3. The DSC thermogram plots the heat flow as a function of temperature from a sample, the temperature rate change being about 10° C./min. In some embodiments, I-263a Form 3 is characterized by a DSC profile substantially as shown in FIG. 17. FIG. 17 shows an endotherm event with onset of about 50.1° C. and peak at about 72.3° C. FIG. 4 also shows an exotherm event with onset of about 148.0° C. and peak at about 164.3° C. In some embodiments, I-263a Form 3 is characterized by a DSC profile having an endotherm event with onset of about 50.1° C. In some embodiments, I-263a Form 3 is characterized by a DSC profile having an endotherm event with peak at about 72.3° C. In some embodiments, I-263a Form 3 is characterized by a DSC profile having an exotherm event with onset of about 148.0° C. In some embodiments, I-263a Form 3 is characterized by a DSC profile having an exotherm event with peak at about 164.3° C.

In some embodiments, I-263a Form 3 of compound I-101 is characterized by at least one of the following features (I-i)-(I-iii):

(I-i) an XRPD pattern having peaks at 2θ angles of 15.6°, 16.2°, 18.0°, and 20.0° as shown in FIG. 15;
(I-ii) a DSC profile substantially as shown in FIG. 17;
(I-iii) a TGA profile substantially as shown in FIG. 16.

In some embodiments, I-263a Form 3 is characterized by at least two of the features (I-i)-(I-iii). In some embodiments, I-263a Form 3 is characterized by all three of the features (I-i)-(I-iii).

Solid State Forms of I-256b.

Provided herein is an assortment of characterizing information, which is sufficient, but not all of which is necessary, to describe crystalline Form 1 anhydrous compound I-256b ("I-256b Form 1").

Figure 3:
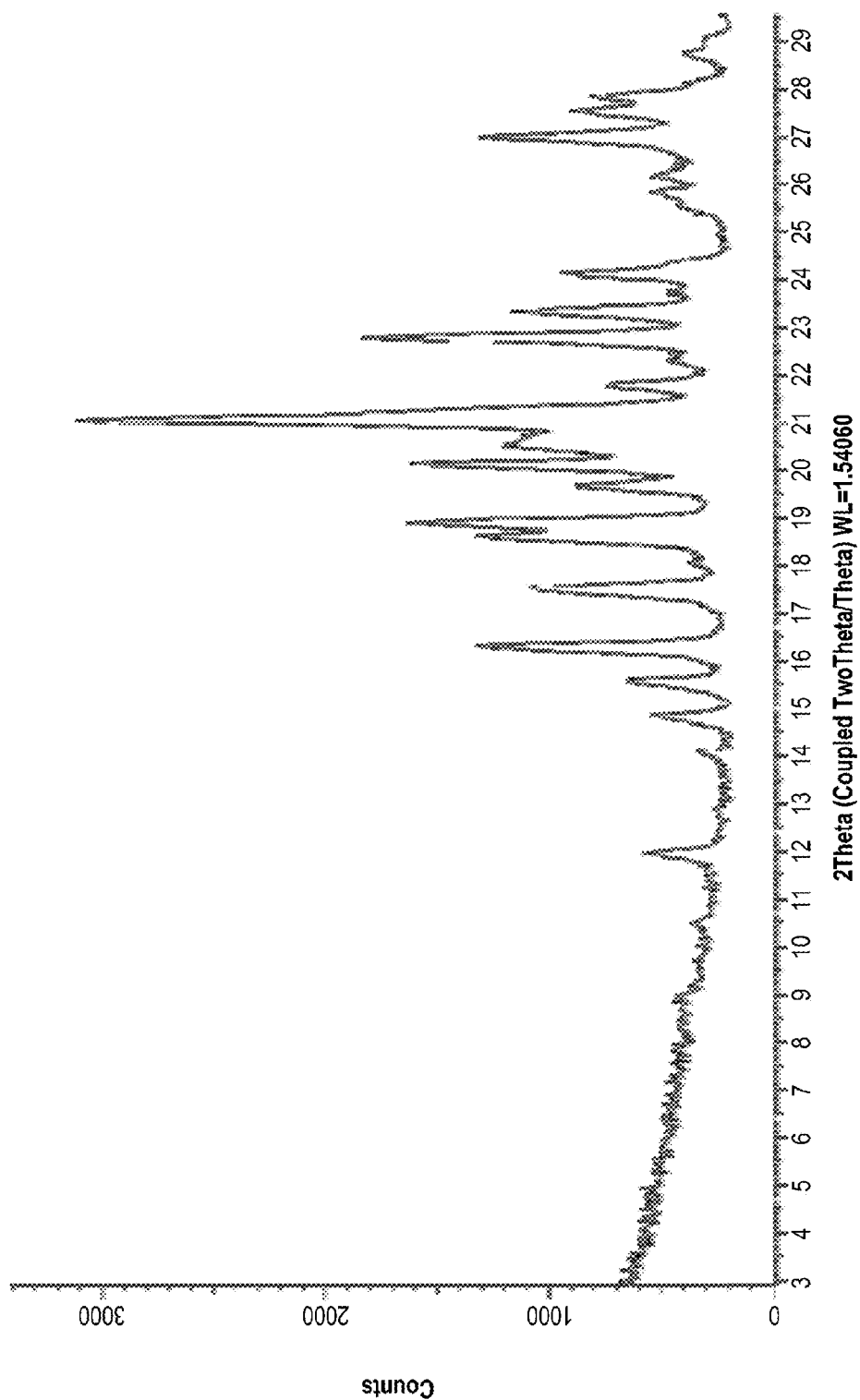
FIG. 3 is an XRPD pattern of compound I-256b Form 1.

FIG. 3 shows an X-ray powder diffraction (XRPD) pattern of Form 1 of compound I-256b obtained using CuKα radiation. Peaks identified in FIG. 3 include those listed in the table below.

| Angle (2 Theta) | Relative Intensity |
|---|---|
| 11.9 | 10.1% |
| 14.8 | 9.9% |
| 15.5 | 15.4% |
| 16.3 | 37.4% |
| 17.5 | 28.3% |
| 18.7 | 34.8% |
| 18.9 | 44.0% |
| 19.7 | 20.2% |
| 20.1 | 45.9% |
| 20.6 | 30.0% |
| 21.1 | 100.0% |
| 21.8 | 15.1% |
| 22.8 | 55.5% |
| 23.3 | 32.1% |
| 24.1 | 23.8% |
| 25.8 | 10.2% |
| 26.2 | 10.3% |
| 27.0 | 38.3% |
| 27.5 | 23.6% |
| 27.8 | 19.6% |
| 28.8 | 5.4% |

In some embodiments, I-256b Form 1 is characterized by an XRPD pattern having a peak at 2θ angle 21.1°. In some embodiments, I-256b Form 1 is characterized by an XRPD pattern having peaks at 2θ angles of 21.1° and 22.8°. In some embodiments, I-256b Form 1 is characterized by an XRPD pattern having peaks at 2θ angles of 21.1°, 22.8°, 20.1°, and 18.9°. In some embodiments, I-256b Form 1 is characterized by an XRPD pattern having peaks at 2θ angles of 21.1°, 22.8°, 20.1°, 18.9°, 27.0°, 16.3°, and 18.7°. In some embodiments, I-256b Form 1 is characterized by an XRPD pattern having peaks at 2θ angles of 21.1°, 22.8°, 20.1°, 18.9°, 27.0°, 16.3°, 18.7°, 23.3°, 17.5°, 24.1°, and 27.5°. In some embodiments, the 2θ angles given above have an error tolerance of ±0.10. In some embodiments, the 2θ angles given above have an error tolerance of ±0.2°. In some embodiments, the 2θ angles given above have an error tolerance of ±0.3°. In some embodiments, I-256b Form 1 is characterized by an XRPD pattern substantially as shown in FIG. 3.

In some embodiments, I-256b Form 1 is characterized by an XRPD pattern having a reference peak with a 2θ angle of 18.9±0.3°, and having peaks at 2θ angles of 1.2°, 2.2°, and 3.9° relative to the reference peak. The term "reference peak" refers to a peak in the XRPD diffractogram that one skilled in the art considers as informing the polymorphic form of the material, i.e., differentiated from instrument noise. By "relative" it is meant that the observed 2θ angle of each peak will be the sum of the 2θ angle of the reference peak and the relative 2θ angle of that peak. For example, if the reference peak has a 2θ angle of 18.6°, the relative peaks will have 2θ angles of 19.8°, 20.8°, and 22.5°; if the reference peak has a 2θ angle of 18.7°, the relative peaks will have 2θ angles of 19.9°, 20.9°, and 22.6°; if the reference peak has a 2θ angle of 18.8°, the relative peaks will have 2θ angles of 20.0°, 21.0°, and 22.7°; etc. In some embodiments, I-256b Form 1 is characterized by an XRPD pattern having a reference peak with a 2θ angle of 18.9±0.3°, and having peaks at 2θ angles of −2.6°, −0.2°, 1.2°, 2.2°, 3.9°, and 8.10 relative to the reference peak. In some embodiments, I-256b Form 1 is characterized by an XRPD pattern having a reference peak with a 2θ angle of ±0.3°, and having peaks at 2θ angles of −2.6°, −1.4°, −0.2°, 1.2°, 2.2°, 3.9°, 4.4°, 5.2°, 8.1°, and 8.6° relative to the reference peak. Any of the peaks that one skilled in the art considers as informing the polymorphic form of the material can serve as the reference peak and the relative peaks can then be calculated. For example, if the reference peak has a 2θ angle of 21.1°, then the relative peaks will have 2θ angles of −2.2°, −1.0°, and 1.7° relative to the reference peak.

In some embodiments, the chemical entity according to the disclosure is or comprises substantially crystalline I-256b Form 1. In some embodiments, the chemical entity according to the disclosure comprises at least 70% by weight crystalline I-256b Form 1. In some embodiments, the chemical entity according to the disclosure comprises at least 80% by weight crystalline I-256b Form 1. In some embodiments, the chemical entity according to the disclosure comprises at least 90% by weight crystalline I-256b Form 1. In some embodiments, the chemical entity according to the disclosure comprises at least 95% by weight crystalline I-256b Form 1.

Figure 12:
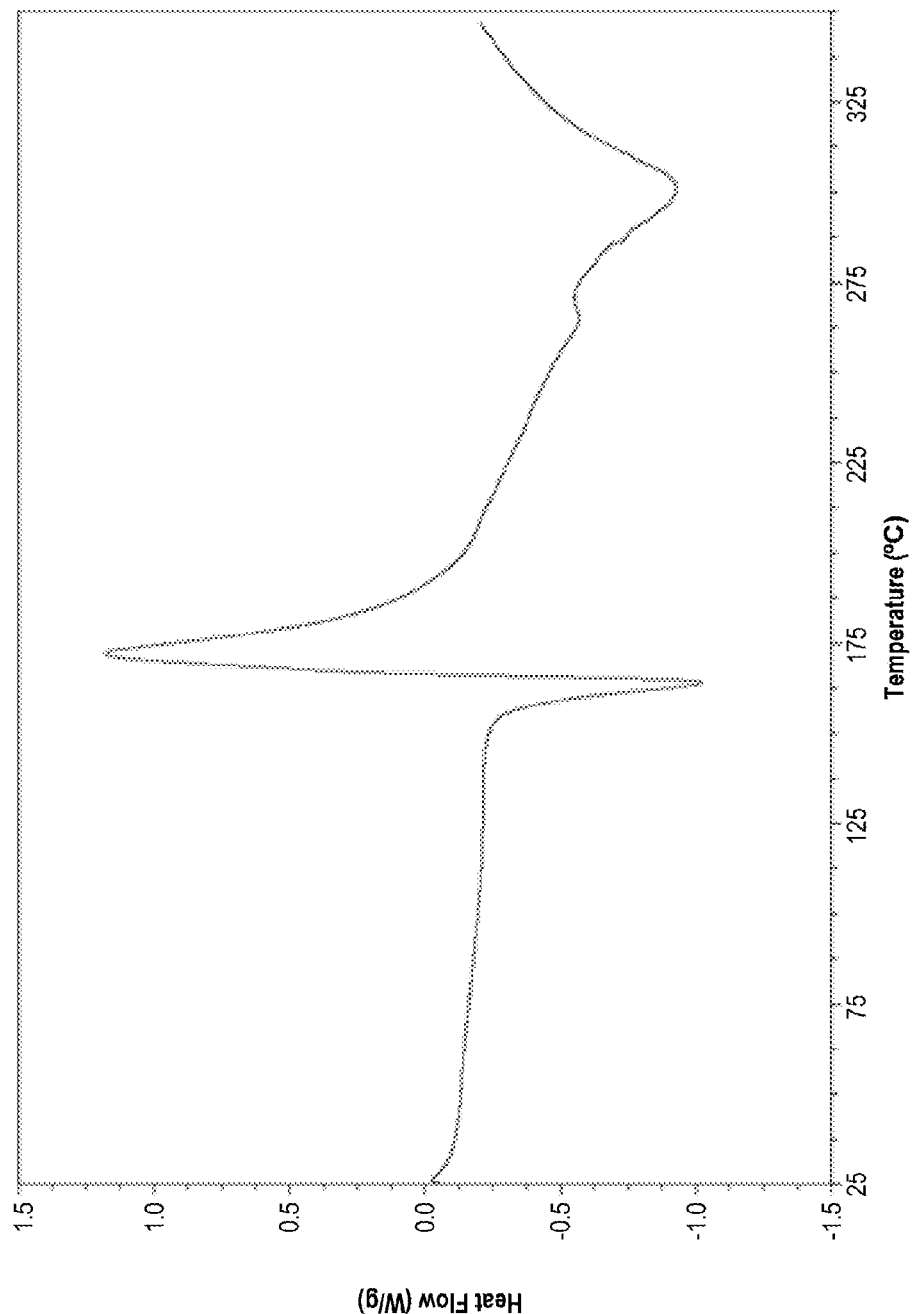
FIG. 12 shows a differential scanning calorimetry (DSC) thermogram for I-256b Form 1.

FIG. 12 shows a differential scanning calorimetry (DSC) profile of I-256b Form 1. The DSC thermogram plots the heat flow as a function of temperature from a sample, the temperature rate change being about 10° C./min. In some embodiments, I-256b Form 1 is characterized by a DSC profile substantially as shown in FIG. 12. FIG. 12 shows an endotherm event with onset of about 157.7° C. and peak at about 163.9° C. FIG. 12 also shows an exotherm event with onset of about 167.1° C. and peak at about 172.6° C. In some embodiments, I-256b Form 1 is characterized by a DSC profile having an endotherm event with onset of about 157.7° C. In some embodiments, I-256b Form 1 is characterized by a DSC profile having an endotherm event with peak at about 163.9° C. In some embodiments, I-256b Form 1 is characterized by a DSC profile having an exotherm event with onset of about 167.1° C. In some embodiments, I-256b Form 1 is characterized by a DSC profile having an exotherm event with peak at about 172.6° C.

Figure 13:
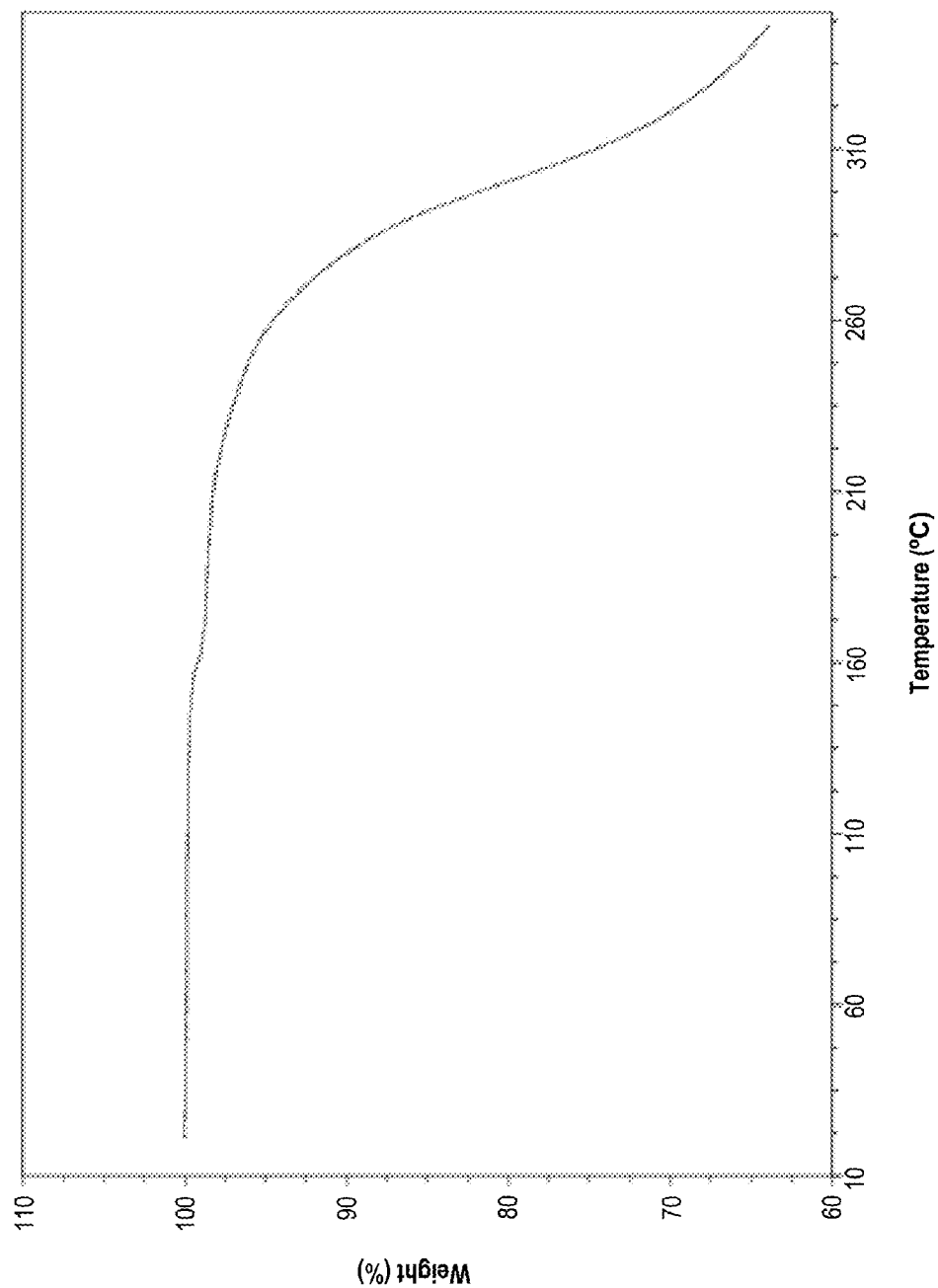
FIG. 13 shows a thermogravimetric analysis (TGA) thermogram for I-256b Form 1.

FIG. 13 shows a thermal gravimetric analysis (TGA) profile of I-256b Form 1. The TGA thermogram plots the percent loss of weight of the sample as a function of temperature, the temperature rate change being about 10° C./min. FIG. 13 shows approximately 0.3% weight loss to 141.3° C. In some embodiments, I-256b Form 1 is characterized by a TGA profile substantially as shown in FIG. 13. In some embodiments, I-256b Form 1 is characterized by a TGA profile having about 0.3% weight loss to 141.3° C.

In some embodiments, I-256b Form 1 is characterized by at least one of the following features (I-i)-(I-iii):

(I-i) an XRPD pattern having peaks at 2θ angles of 21.1°, 22.8°, 20.1°, and 18.9°;
(I-ii) a DSC profile substantially as shown in FIG. 12;
(I-iii) a TGA profile substantially as shown in FIG. 13.

In some embodiments, I-256b Form 1 is characterized by at least two of the features (I-i)-(I-iii). In some embodiments, I-256b Form 1 is characterized by at least three of the features (I-i)-(I-v). In some embodiments, I-256b Form 1 is characterized by at least four of the features (I-i)-(I-v). In some embodiments, I-256b Form 1 is characterized by all three of the features (I-i)-(I-iii).

As discussed above, the present disclosure provides chemical entities that are useful as inhibitors of SAE, and thus the present chemical entities can be useful for treating proliferative, inflammatory, cardiovascular and neurodegenerative disorders.

The chemical entities and pharmaceutical compositions of the present disclosure can be useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors (hematologic malignancies). The term "cancer" encompasses diseases of skin, tissues, organs, bone, cartilage, blood, and vessels. The term "cancer" further encompasses primary and metastatic cancers.

In some embodiments, therefore, the present disclosure provides the chemical entity of formula (I), or a pharmaceutically acceptable salt thereof, for use in treating cancer. In some embodiments, the present disclosure provides a pharmaceutical composition (as described herein) for the treatment of cancer comprising the chemical entity of formula (I), or a pharmaceutically acceptable salt thereof. In some embodiments, the present disclosure provides the use of the chemical entity of formula (I), or a pharmaceutically acceptable salt thereof, for the preparation of a pharmaceutical composition (as described herein) for the treatment of cancer. In some embodiments, the present disclosure provides the use of an effective amount of the chemical entity of formula (I), or a pharmaceutically acceptable salt thereof, for the treatment of cancer. In some embodiments, the present disclosure provides the chemical entity of formula (I), or a pharmaceutically acceptable salt thereof, for the preparation of a medicament for use in treating cancer.

Non-limiting examples of solid tumors that can be treated with the disclosed inhibitors include pancreatic cancer; bladder cancer including invasive bladder cancer; colorectal cancer; thyroid cancer, gastric cancer, breast cancer, including metastatic breast cancer; prostate cancer, including androgen-dependent and androgen-independent prostate cancer; renal cancer, including, e.g., metastatic renal cell carcinoma; liver cancer including e.g. hepatocellular cancer and intrahepatic bile duct; lung and bronchus cancer, including non-small cell lung cancer (NSCLC), squamous lung cancer, brochioloalveolar carcinoma (BAC), adenocarcinoma of the lung, and small cell lung cancer (SCLC); ovarian cancer, including, e.g., progressive epithelial or primary peritoneal cancer; cervical cancer; uterine cancer including e.g. uterine corpus and uterine cervix; endometrial cancer; gastric cancer; esophageal cancer; head and neck cancer, including, e.g., squamous cell carcinoma of the head and neck, nasopharyngeal cancer, oral cavity and pharynx; melanoma; neuroendocrine cancer, including metastatic neuroendocrine tumors; brain cancer, including, e.g., glioma/glioblastoma, anaplastic oligodendroglioma, adult glioblastoma multiforme, and adult anaplastic astrocytoma; neuroendocrine, including metastatic neuroendocrine tumors; bone cancer; and soft tissue sarcoma.

Non-limiting examples of hematologic malignancies that can be treated with the disclosed inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma including diffuse large B-cell lymphoma (DLBCL); T-cell lymphoma; multiple myeloma (MM); amyloidosis; Waldenstrom's macroglobulinemia; myelodysplastic syndromes (MDS), including refractory anemia (RA), refractory anemia with ringed sideblasts (RARS), (refractory anemia with excess blasts (RAEB), and RAEB in transformation (RAEB-T); small lymphocytic lymphoma (SLL); marginal zone lymphoma; smoldering multiple myeloma; and myeloproliferative syndromes.

In some embodiments, chemical entities of the present disclosure are suitable for the treatment of breast cancer, lung cancer, ovarian cancer, multiple myeloma, acute myeloid leukemia or acute lymphoblastic leukemia. In some embodiments, chemical entities of the present disclosure are suitable for the treatment of NHL. In some embodiments, chemical entities of the present disclosure are suitable for the treatment of indolent NHL. In some embodiments, chemical entities of the present disclosure are suitable for the treatment of follicular lymphoma, small lymphocytic lymphoma, mantle cell lymphoma or marginal zone lymphoma. In some embodiments, chemical entities of the present disclosure are suitable for the treatment of diffuse large B-cell lymphoma (DLBCL) or chronic lymphocytic lymphoma (CLL). In some embodiments, chemical entities of the present disclosure are suitable for the treatment of multiple myeloma. In some embodiments, chemical entities of the present disclosure are suitable for the treatment of ALL, AML, or MDS.

In other embodiments, chemical entities of the present disclosure are suitable for the treatment of inflammatory, cardiovascular and neurodegenerative disorders including, but not limited to, allergies/anaphylaxis, acute and/or chronic inflammation, rheumatoid arthritis, autoimmunity disorders, thrombosis, hypertension, cardiac hypertrophy, heart failure, Huntington's disease and Alzheimers.

Accordingly, in another aspect of the present disclosure, pharmaceutical compositions are provided, wherein these compositions comprise any of the chemical entities as described herein, and optionally comprise a pharmaceutically acceptable carrier, adjuvant or vehicle. In certain embodiments, these compositions optionally further comprise one or more additional therapeutic agents.

It will also be appreciated that certain of the chemical entities of present disclosure can exist in free form for treatment, or where appropriate, as a pharmaceutically acceptable derivative thereof. According to the present disclosure, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a chemical entity as otherwise described herein, or a metabolite or residue thereof.

As used herein, the term "pharmaceutically acceptable salt" refers to those salts which are, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt or salt of an ester of a compound of this disclosure that, upon administration to a recipient, is capable of providing, either directly or indirectly, a compound of this disclosure or an inhibitorily active metabolite or residue thereof. As used herein, the term "inhibitorily active metabolite or residue thereof" means that a metabolite or residue thereof is also an inhibitor of SAE.

Pharmaceutically acceptable salts are well known in the art. For example, S. M. Berge et al., describe pharmaceutically acceptable salts in detail in *J. Pharmaceutical Sciences*, 1977, 66, 1-19. The chemical entities of this disclosure include pharmaceutically acceptable salts, such as those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. The present disclosure also envisions the quaternization of any basic nitrogen-containing groups of the chemical entities disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present disclosure additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the chemical entities of the present disclosure, such as by producing any undesirable biological effect or otherwise interacting in a deleterious manner with any other component(s) of the pharmaceutically acceptable composition, its use is contemplated to be within the scope of the present disclosure. Some examples of materials which can serve as pharmaceutically acceptable carriers include, but are not limited to, ion exchangers; alumina; aluminum stearate; lecithin; serum proteins, such as human serum albumin; buffer substances such as phosphates (including but not limited to phosphate buffer solutions), glycine, sorbic acid, or potassium sorbate; partial glyceride mixtures of saturated vegetable fatty acids; water; salts or electrolytes, such as protamine sulfate, disodium hydrogen phosphate, potassium hydrogen phosphate, sodium chloride, and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and non-toxic compatible lubricants such as sodium lauryl sulfate and magnesium stearate. Additionally, coloring agents; releasing agents; coating agents; sweetening, flavoring and perfuming agents; preservatives; and antioxidants can also be present in the composition, according to the judgment of the formulator. In some embodiments, pharmaceutically acceptable compositions of the disclosure comprise a compound of Formula (I) (5 mg/mL); β-Cyclodextrin Sulfobutyl Ethers, Sodium Salts (Captisol®) (Ligand Pharmaceuticals Inc) (10% w/v); the composition being adjusted to a pH of 2+/−0.2 using 25 mM HCl and $H_3PO_4$; and Water for injection (q.s. to a fill volume, e.g., 5 mL or 10 mL). In some embodiments, pharmaceutically acceptable compositions of the disclosure comprise a compound of Formula (I) (10 mg/mL); β-Cyclodextrin Sulfobutyl Ethers, Sodium Salts (Captisol®) (Ligand Pharmaceuticals Inc) (10% w/v); the composition being adjusted to a pH of 2+/−0.2 using 50 mM $H_3PO_4$; and Water for injection (q.s. to a fill volume, e.g 10 mL).

In yet another aspect, a method for treating a proliferative, inflammatory, cardiovascular or neurodegenerative disorder is provided comprising administering an effective amount of a chemical entity, or a pharmaceutical composition to a subject in need thereof. In certain embodiments of the present disclosure an "effective amount" of the chemical entity or pharmaceutical composition is that amount effective for treating a proliferative, inflammatory, infectious, neurological or cardiovascular disorder, or is that amount effective for treating cancer. In other embodiments, an "effective amount" of a chemical entity is an amount which inhibits binding of SAE.

The chemical entities and compositions, according to the method of the present disclosure, may be administered using any amount and any route of administration effective for treating the disease. The exact amount required will vary from subject to subject, depending on the species, age, and general condition of the subject, the severity of the infection, the particular agent, its mode of administration, and the like. The chemical entities of the present disclosure are frequently formulated in dosage unit form for ease of administration and uniformity of dosage. The expression "dosage unit form" as used herein refers to a physically discrete unit of agent appropriate for the patient to be treated. It will be understood, however, that the total daily usage of the chemical entities and compositions of the present disclosure will be decided by the attending physician within the scope of sound medical judgment. The specific effective dose level for any particular patient or organism will depend upon a variety of factors including the disease being treated and the severity of the disease; the activity of the specific chemical entity employed; the specific composition employed; the age, body weight, general health, sex and diet of the patient; the time of administration, route of administration, and rate of excretion of the specific chemical entity employed; the duration of the treatment; drugs used in combination or coincidental with the specific chemical entity employed, and like factors well known in the medical arts. The term "patient," as used herein, means an animal, for instance a mammal, such as a human.

The pharmaceutically acceptable compositions of the present disclosure can be administered to humans and other animals orally, rectally, parenterally, intracisternally, intravaginally, intraperitoneally, topically (as by powders, ointments, lotions, salves, or drops), bucally, as an oral or nasal spray, or the like, depending on the severity of the infection being treated. In certain embodiments, the chemical entities of the present disclosure may be administered orally or parenterally at dosage levels of about 0.01 mg/kg to about 50 mg/kg, for instance from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active chemical entities, the liquid dosage forms may contain inert diluents commonly used in the art such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (for instance, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a chemical entity of the present disclosure, it is often desirable to slow the absorption of the chemical entity from subcutaneous or intramuscular injection. This may be accomplished by the use of a liquid suspension of crystalline or amorphous material with poor water solubility. The rate of absorption of the chemical entity then depends upon its rate of dissolution that, in turn, may depend upon crystal size and crystalline form. Alternatively, delayed absorption of a parenterally administered chemical entity form is accomplished by dissolving or suspending the chemical entity in an oil vehicle. Injectable depot forms are made by forming microencapsule matrices of the chemical entity in biodegradable polymers such as polylactide-polyglycolide. Depending upon the ratio of chemical entity to polymer and the nature of the particular polymer employed, the rate of chemical entity release can be controlled. Examples of other biodegradable polymers include poly(orthoesters) and poly(anhydrides). Depot injectable formulations are also prepared by entrapping the chemical entity in liposomes or microemulsions that are compatible with body tissues.

Compositions for rectal or vaginal administration are, for instance, suppositories which can be prepared by mixing the chemical entities of the present disclosure with suitable non-irritating excipients or carriers such as cocoa butter, polyethylene glycol or a suppository wax which are solid at ambient temperature but liquid at body temperature and therefore melt in the rectum or vaginal cavity and release the active chemical entity.

Solid dosage forms for oral administration include capsules, tablets, pills, powders, and granules. In such solid dosage forms, the active chemical entity is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or for instance, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active chemical entities can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active chemical entity may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or for instance, in a certain part of the intestinal tract, optionally, in a delayed manner. Examples of embedding compositions that can be used include polymeric substances and waxes.

Dosage forms for topical or transdermal administration of a chemical entity of the present disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of the present disclosure. Additionally, the present disclosure contemplates the use of transdermal patches, which have the added advantage of providing controlled delivery of a chemical entity to the body. Such dosage forms can be made by dissolving or dispensing the chemical entity in the proper medium. Absorption enhancers can also be used to increase the flux of the chemical entity across the skin. The rate can be controlled by either providing a rate controlling membrane or by dispersing the chemical entity in a polymer matrix or gel.

In some embodiments, a chemical entity of the present disclosure or a pharmaceutical composition thereof is administered in conjunction with an anticancer agent. As used herein, the term "anticancer agent" refers to any agent that is administered to a subject with cancer for purposes of treating the cancer. Combination therapy includes administration of the therapeutic agents concurrently or sequentially. Alternatively, the therapeutic agents can be combined into one composition which is administered to the patient.

In one embodiment, the chemical entities of the present disclosure are used in combination with other therapeutic agents. In some embodiments, the additional therapeutic agent is selected from other inhibitors of SAE. In other embodiments, a chemical entity of the present disclosure is administered in conjunction with a therapeutic agent selected from the group consisting of cytotoxic agents, radiotherapy, and immunotherapy. In some embodiments, the chemical entities of the present disclosure can be used in combination with a chemotherapeutic regimen for the treatment of relapsed/refractory non-Hodgkin's lymphoma including DLBCL and CLL. Chemotherapeutic regimens include, but are not limited to R-ICE (rituximab, ifosfamide, carboplatin and etoposide), R-DHAP (rituximab, dexamethasone, high-dose cytarabine and cisplatin), and R-GDP (rituximab, gemcitabine, cisplatin and dexamethasone). It is understood that other combinations may be undertaken while remaining within the scope of the invention.

Those additional agents may be administered separately from a provided combination therapy, as part of a multiple dosage regimen. Alternatively, those agents may be part of a single dosage form, mixed together with a chemical entity of the present disclosure. If administered as part of a combination therapy, the two therapeutic agents may be submitted simultaneously, sequentially, or intermittently. Combination therapy can be used for any of the therapeutic indications described herein. In some embodiments, the combination therapy is for the treatment of a proliferative disorder (e.g., cancer) in a patient. In some embodiments, the proliferative disorder is breast cancer, lung cancer, ovarian cancer, multiple myeloma, acute myeloid leukemia or acute lymphoblastic leukemia.

Another aspect of the present disclosure relates to inhibiting SAE activity in a biological sample or a patient, which method comprises administering to the patient, or contacting said biological sample with a chemical entity of formula (I), or a composition comprising said chemical entity. The term "biological sample," as used herein, generally includes in vivo, in vitro, and ex vivo materials, and also includes, without limitation, cell cultures or extracts thereof, biopsied material obtained from a mammal or extracts thereof, and blood, saliva, urine, feces, semen, tears, or other body fluids or extracts thereof.

Still another aspect of the present disclosure is to provide a kit comprising separate containers in a single package, wherein a compound disclosed herein or a pharmaceutical composition and/or salt thereof is provided in combination with one or more pharmaceutically acceptable carriers for use in treating one or more disorders, symptoms and diseases where SAE plays a role.

General Synthetic Methods and Intermediates

The chemical entities of the present disclosure can be prepared by one of ordinary skill in the art in light of the present disclosure and knowledge in the art, and/or by reference to the schemes shown below and the synthetic examples. Exemplary synthetic routes are set forth in Schemes below and in the Examples.

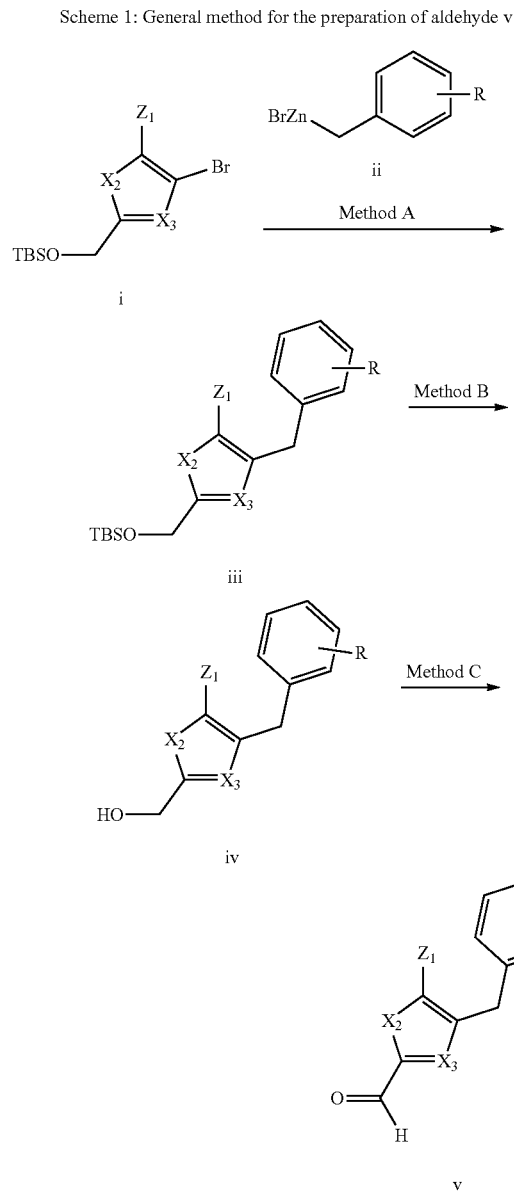

Scheme 1: General method for the preparation of aldehyde v

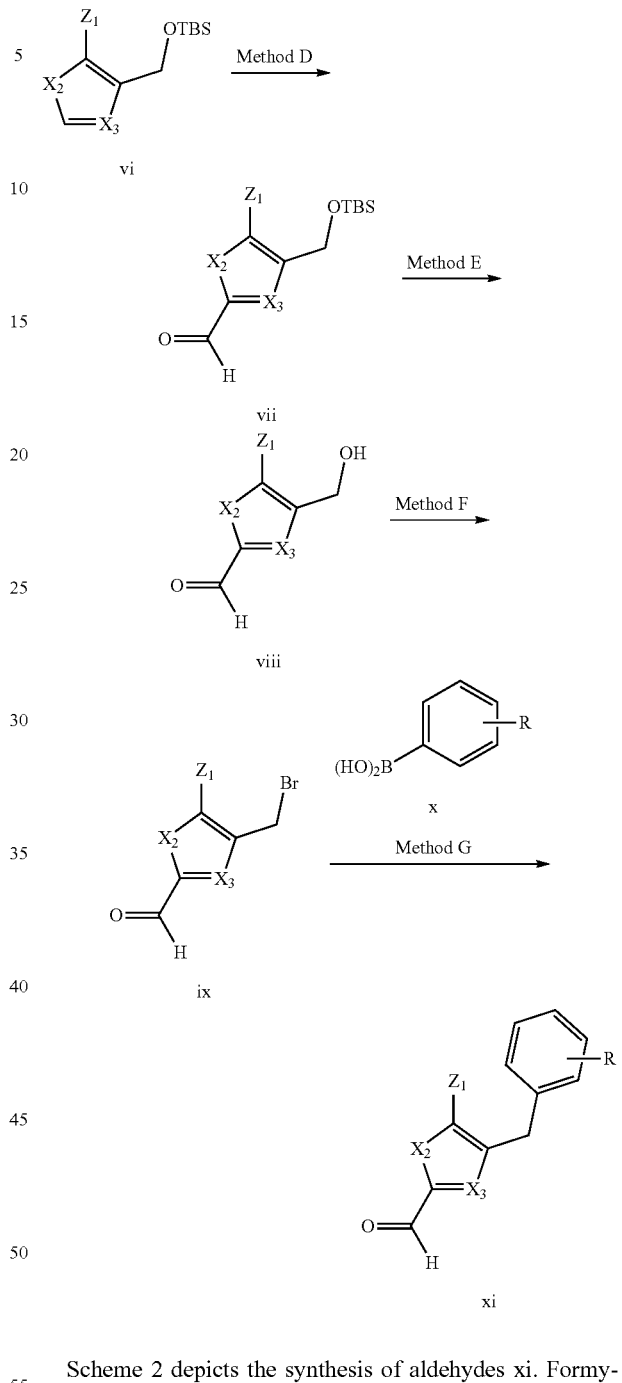

Scheme 2: General method for the preparation of aldehyde xi

Scheme 1 depicts the synthesis of aldehydes v. Conversion of i to the compound iii is accomplished by a palladium mediated coupling reaction with an organozinc reagent ii in suitable solvent, such as 1,4-dioxane or THF at elevated temperature or microwave irradiation (Method A). Deprotection of TBS group of iii is effected by treatment with TBAF or acid, such as aq. HCl or TFA (Method B). Further treatment with an oxidation reagent, such as $MnO_2$ or Dess-Martin periodinane, in DCM affords the aldehyde v (method C).

Scheme 2 depicts the synthesis of aldehydes xi. Formylation of the appropriate heteroaryl vi in the presence of alkyl lithium, such as n-BuLi or t-BuLi, and DMF in THF at cold temperature gives aldehydes vii (Method D), that are then deprotected with TBAF or acid, such as aq. HCl or TFA, to afford compounds of formula viii (Method E). Formation of the methylene bromide is achieved using a suitable reagent, for example $PPh_3$ and $CBr_4$ in DCM to afford halides of formula ix (Method F). Halides ix can be subjected to a coupling reaction with boronic acid derivatives x under suitable conditions, for example $Pd(PPh_3)_4$, $K_2CO_3$ in a suitable solvent, such as a dioxane-water mixture at elevated temperature or microwave irradiation, to give compounds of formula xi (Method G).

Scheme 3: General method for the preparation of aldehyde xiv

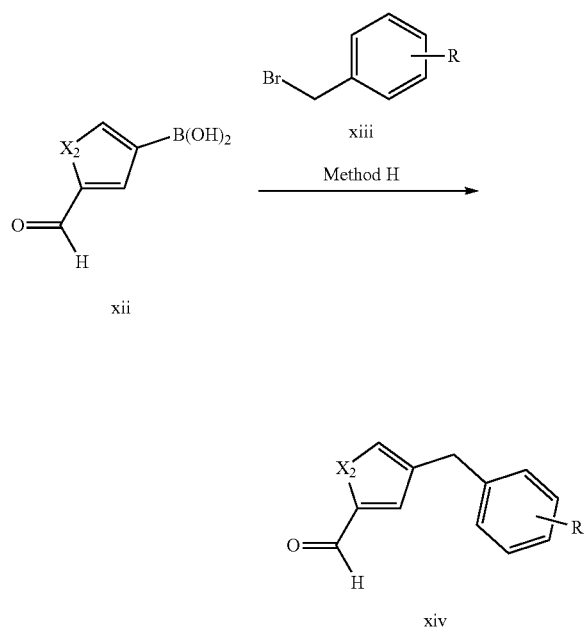

Scheme 4 depicts the synthesis of aldehydes xvii. Lithiation of appropriate heteroaryl bromides xv using alkyl lithium, such as n-BuLi or t-BuLi, and addition of suitable aldehydes or ketones gives the alcohols xvi (Method I). Protection of the alcohol, such as with a TIPS or TBS group followed by cleavage of the acetal group using acidic conditions, such as aq. HCl/THF or Dowex resin, in suitable solvent, such as acetone, gives the aldehydes xvii (Method J). Alternatively, silyl ethers xviii are lithiated in an analogous fashion and reacted with suitable aldehydes or ketones to give alcohols xix. Protection followed by selective deprotection of the primary silyl ether with mild acidic conditions, such as 1% HCl in ethanol followed by an oxidation using Dess-Martin periodinane or $MnO_2$ in suitable solvent, such as DCM, gives the aldehydes xvii (Method K).

Scheme 5: General method for the preparation of isochroman substituted aldehyde xxiii

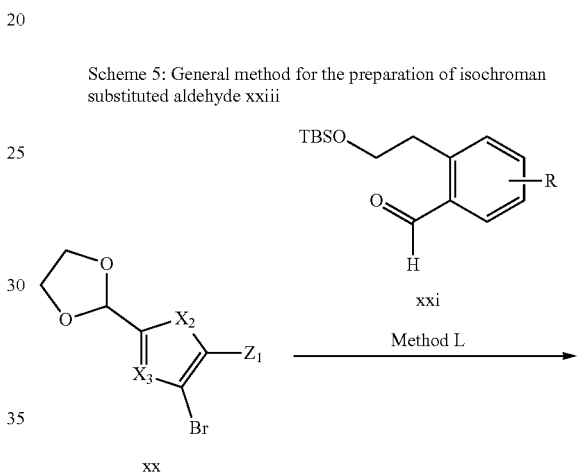

Scheme 3 depicts the synthesis of aldehydes xiv. The appropriate boronic acid derivatives xii can be coupled with alkyl or aryl halides, such as benzyl bromide under standard Suzuki coupling conditions, such as $Pd(PPh_3)_4$, $Na_2CO_3$, dioxane/water, elevated temperature or microwave irradiation to give compounds of formula xiv (Method H).

Scheme 4: General method for the preparation of aldehyde xvii

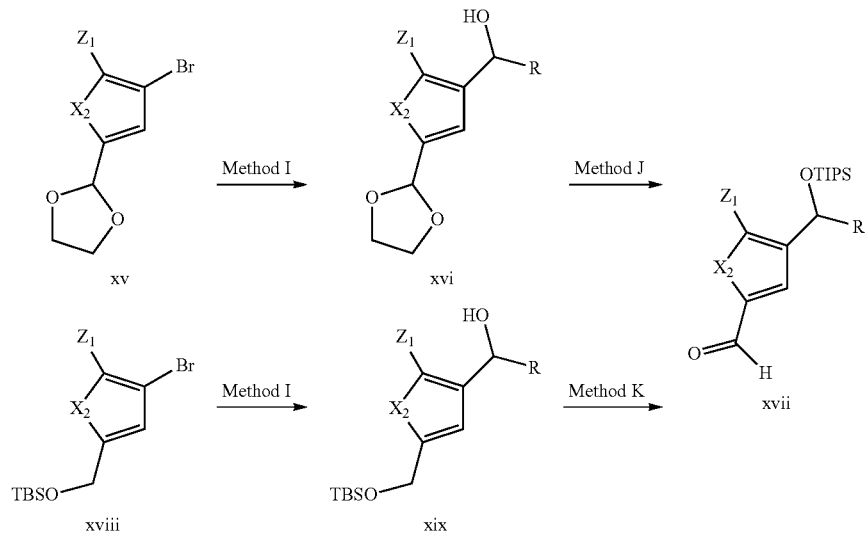

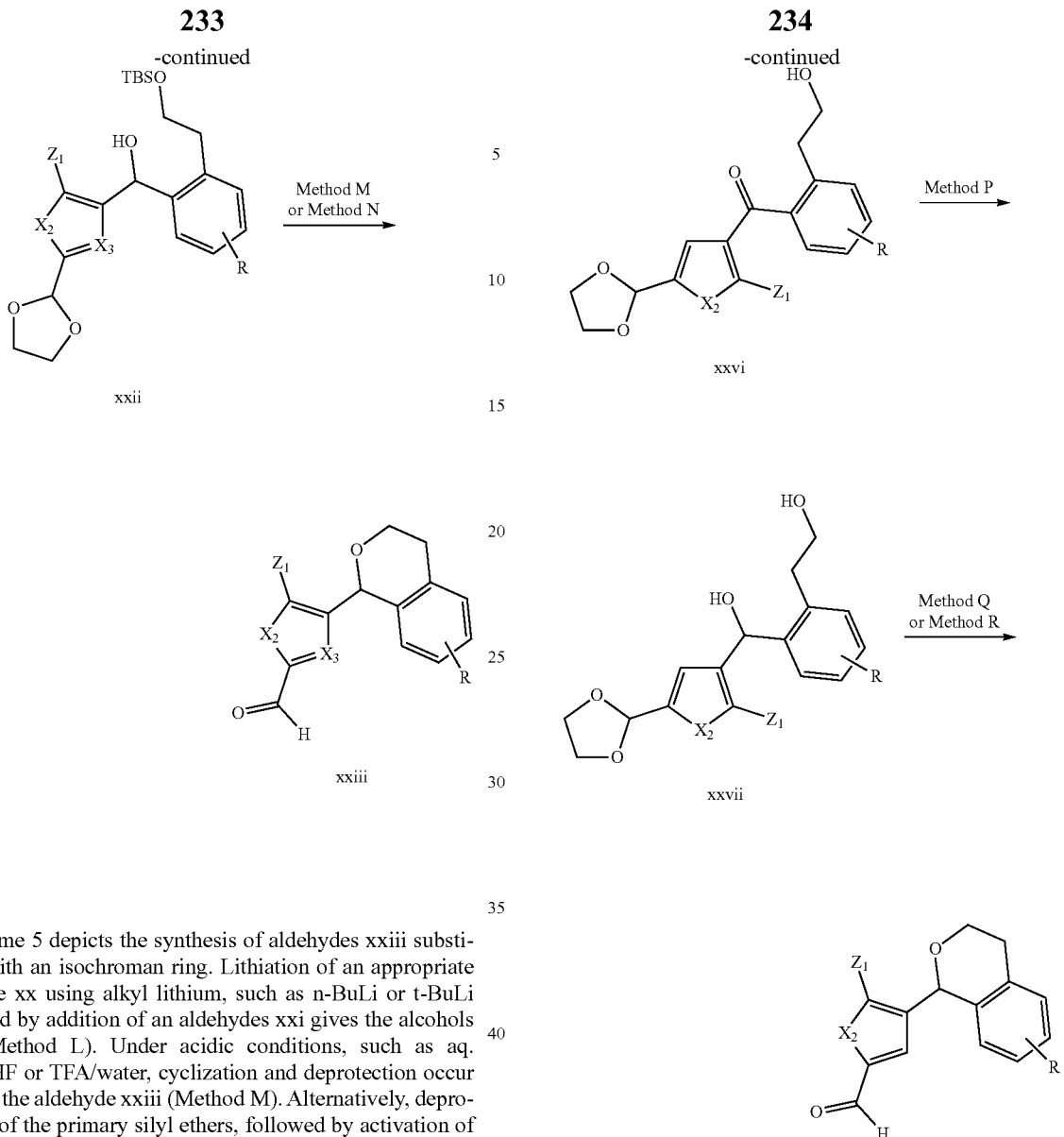

Scheme 5 depicts the synthesis of aldehydes xxiii substituted with an isochroman ring. Lithiation of an appropriate bromide xx using alkyl lithium, such as n-BuLi or t-BuLi followed by addition of an aldehydes xxi gives the alcohols xxii (Method L). Under acidic conditions, such as aq. HCl/THF or TFA/water, cyclization and deprotection occur to form the aldehyde xxiii (Method M). Alternatively, deprotection of the primary silyl ethers, followed by activation of the primary alcohols, such as conversion to the iodide or mesylate, facilitates cyclization using $Ag_2O$ or base such as NaH in suitable solvent, such as $Et_2O$ or DMF. Deprotection of the acetals yields aldehydes xxiii (Method N).

Scheme 6: General method for the preparation of isochroman substituted aldehydes xxviii

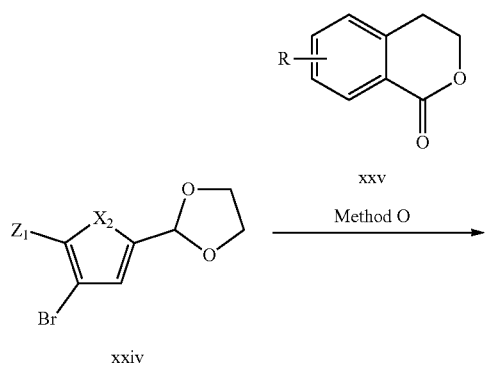

Scheme 3b depicts an alternative synthesis of aldehydes xxviii substituted with an isochroman ring. Lithiation of an appropriate bromide using alkyl lithium, such as n-BuLi or t-BuLi, at cold temperature followed by addition of lactones xxv gives the ketones xxvi (Method O). Reduction of the ketone by reducing agent, such as $NaBH_4$ in a suitable solvent, such as THF, provides alcohols xxvii (Method P). Under acidic conditions, such as aq. HCl/THF or TFA/water cyclization and deprotection occur to form the aldehyde xxviii (Method Q). Alternatively, activation of the primary alcohols, such as conversion to the iodide or mesylate facilitates cyclization using $Ag_2O$ or base such as NaH in suitable solvent, such as $Et_2O$ or DMF. Deprotection of the acetals under acidic condition, such as aq. HCl/THF or TFA/water yields aldehydes xxviii (Method R).

Scheme 7: General method for the preparation of tetrahydroisoquinoline substituted aldehyde xxxii

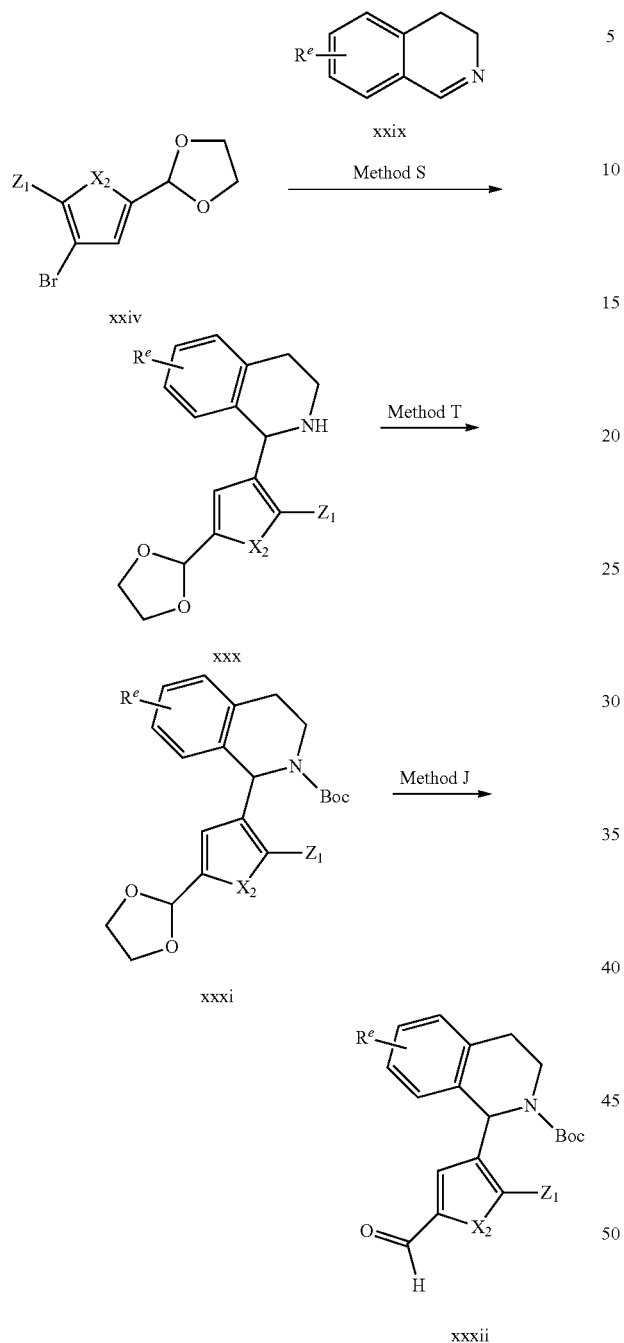

Scheme 8: General method for the preparation of pyrrolidine substituted aldehyde xxxv

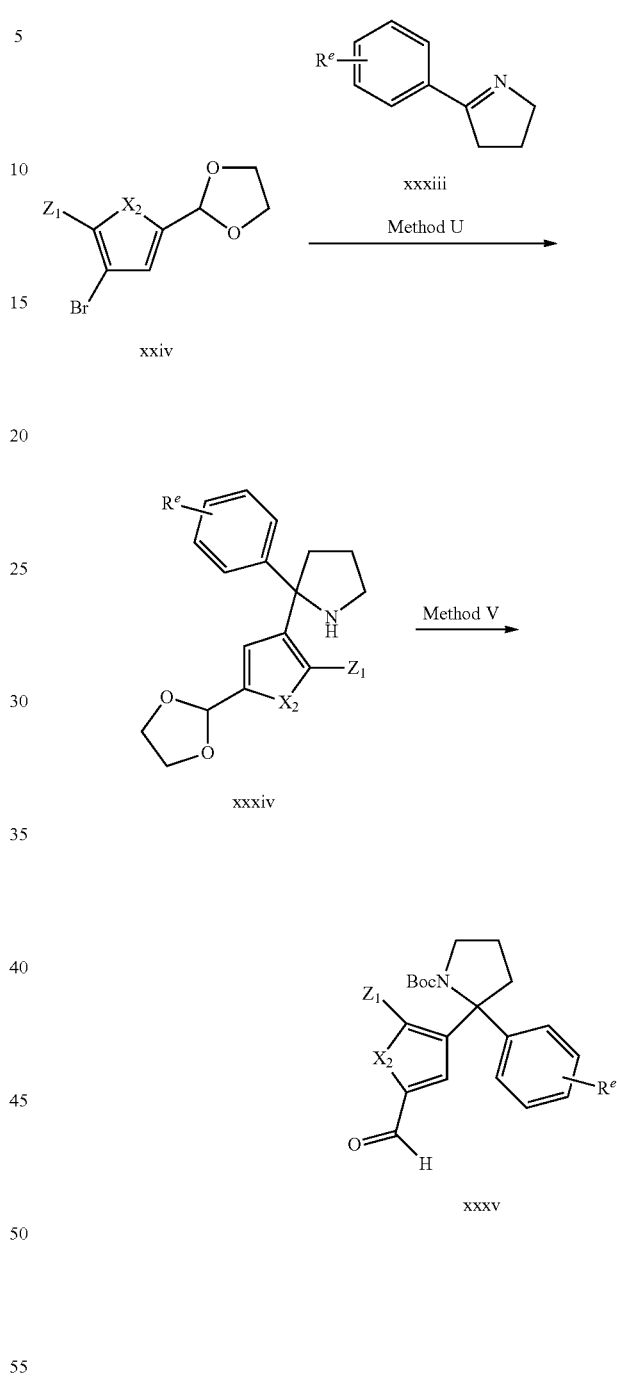

Scheme 4 depicts the synthesis of aldehydes xxxii, substituted with a tetrahydroisoquinoline ring. Lithiation of an appropriate heteroaryl bromide using alkyl lithium, such as n-BuLi or t-BuLi at cold temperature and addition of dihydroisoquinolines (imine) xxix in the presence of Lewis acid, such as BF$_3$·Et$_2$O complex, gives the tetrahydroisoquinolines xxx (Method S). Protection of amines under general conditions, such as (Boc)$_2$O/DMAP in acetonitrile, affords carbamates xxxi (Method T). Cleavage of the acetal group using acidic conditions, such as aq. HCl/THF or Dowex resin in suitable solvent, such as acetone, gives the aldehydes xxxii (Method J).

Scheme 8 depicts the synthesis of aldehydes substituted with a pyrrolidine ring. Lithiation of an appropriate bromides using alkyl lithium, such as n-BuLi or t-BuLi, at cold temperature and addition of a dihydropyrrolidines (imine) xxxiii gives the pyrrolidine intermediates xxxiv (Method U). Acetals xxxiv are treated under acidic conditions, such as aq. HCl/acetone or Dowex/acetone followed by protection of amines under usual conditions, such as (Boc)$_2$O, DMAP in suitable solvent, such as acetonitrile, gives the aldehydes xxxv (Method V).

Scheme 9: General method for the preparation of thiophene and furan aldehydes xxxviii Scheme 10: General method for the preparation of aldehydes xlv

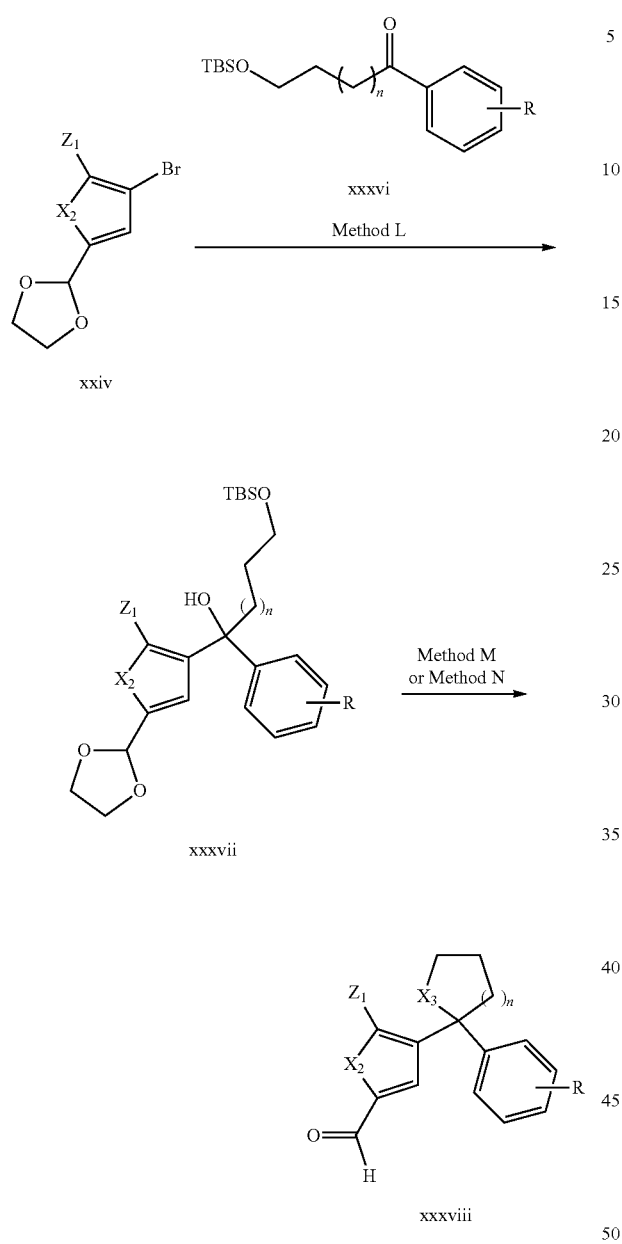

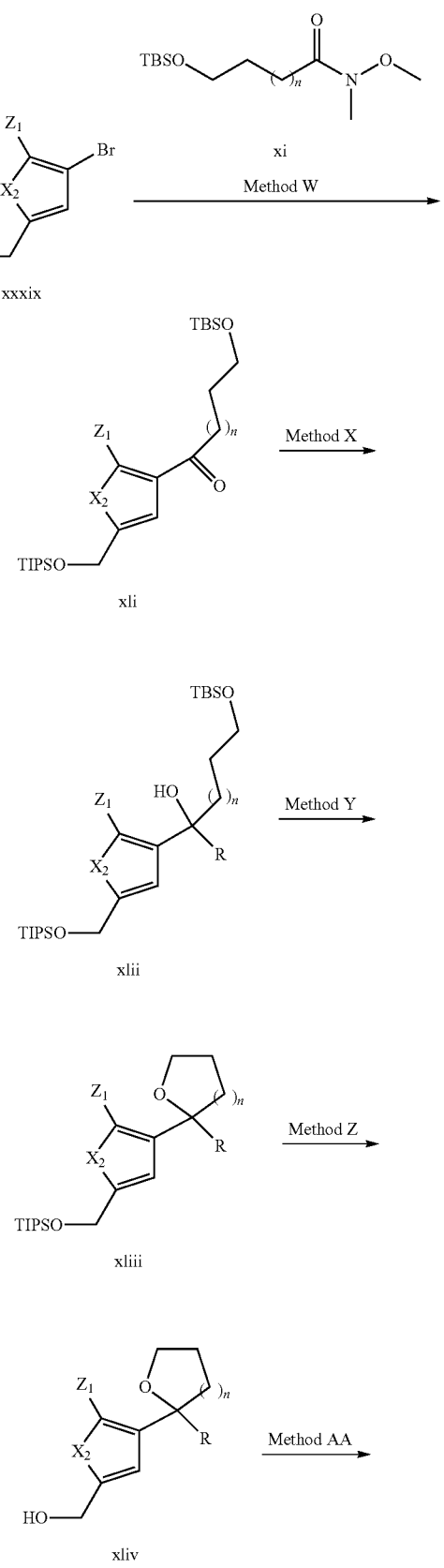

Scheme 9 depicts the synthesis of aldehydes xxxviii. Alcohols xxxvii can be prepared by appropriate bromides xxiv and phenyl ketone derivatives xxxvi under an analogous reaction condition described in scheme 5 (Method L). Under acidic conditions, such as aq. HCl/THF or TFA/water, cyclization and deprotection occur to form the aldehydes xxxviii (Method M). Alternatively, deprotection of the primary silyl ethers, followed by activation of the primary alcohols, such as conversion to the iodide or mesylate, facilitates cyclization using $Ag_2O$ or base such as NaH in suitable solvent, such as $Et_2O$ or DMF. Deprotection of the acetals under acidic conditions, such as aq. HCl/acetone or Dowex/acetone, yields aldehydes xxxviii (Method N). Alternatively, a trityl sulfur group instead of the TBS ether group provides corresponding aldehyde xxxviii.

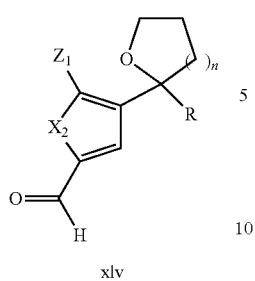

xlv

Scheme 10 depicts the synthesis of aldehydes xlv. Lithiation of appropriate bromides xxxix using alkyl lithium, such as n-BuLi or t-BuLi, at cold temperature and addition of Weinreb amides xl gives corresponding ketones xli (Method W). Subjecting the ketones xli to alkylation with appropriate Grignard reagents or alkyl lithium reagents in suitable solvent, such as THF, at cold temperature gives alcohols xlii (Method X). Deprotection of TBS group followed by internal cyclization under acidic conditions, such as 1% HCl in ethanol, affords tetrahydrofuran derivatives xliii (Method Y) and then deprotection of TIPS group using TBAF or acid, such as aq. HCl/THF or TFA/water (Method Z), followed by oxidation by MnO$_2$ or Dess-Martin periodinane in suitable solvent, such as DCM, provides the aldehydes xlv (Method AA).

Scheme 11: General method for the preparation of aldehydes xlviii

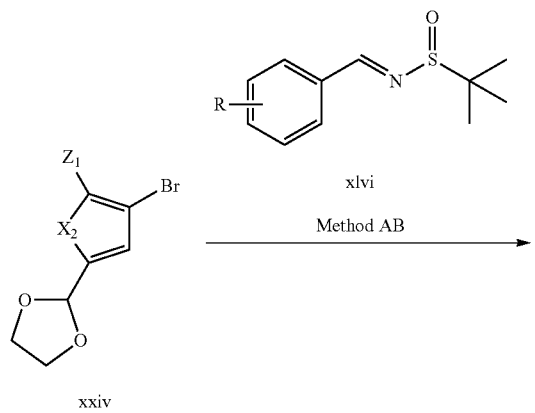

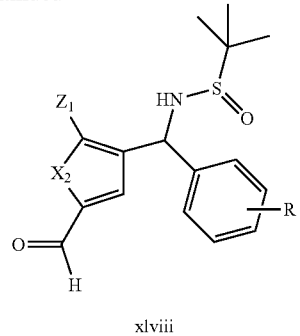

xlviii

Scheme 11 depicts the synthesis of aldehydes xlviii. Lithiation of appropriate bromides xxiv using alkyl lithium, such as n-BuLi or t-BuLi, at cold temperature and addition of sulfonamides xlvi gives the compounds of formula xlvii (Method AB). Deprotection of the acetal group under conditions analogous to those described in Scheme 5 gives the aldehydes xlviii (Method J).

Scheme 12: General method for the preparation of aldehyde liii

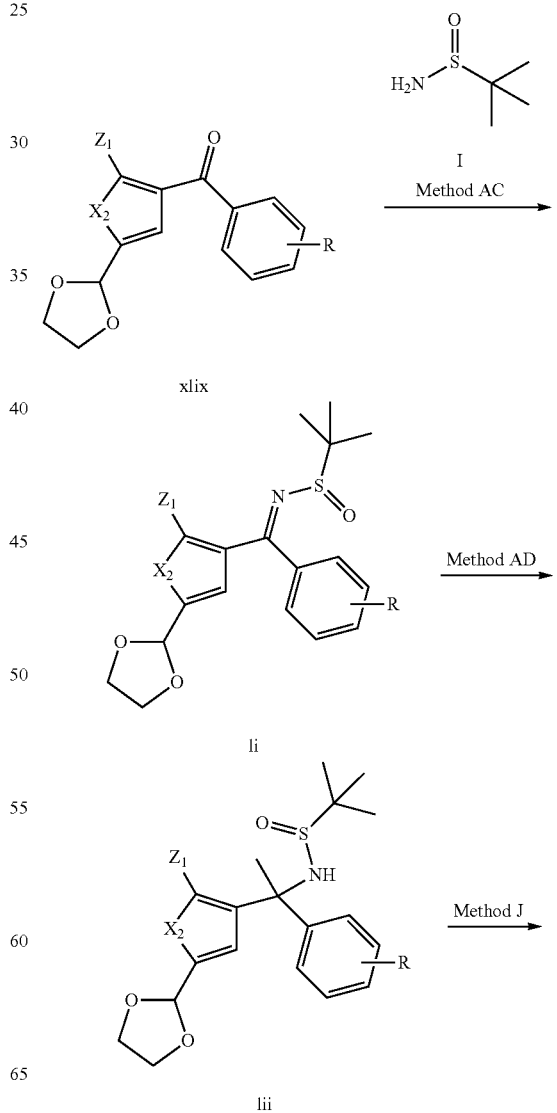

241

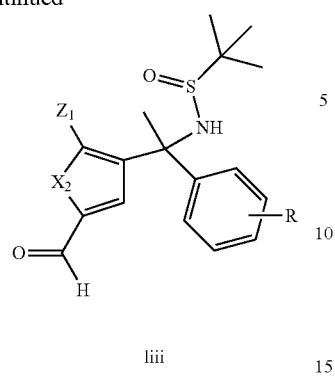

liii

Scheme 12 depicts the synthesis of aldehydes liii. Condensation of an appropriate ketone xlix and 2-methylpropane-2-sulfinamide 1 using Lewis acid, such as Ti(OEt)$_4$ in suitable solvent, such as THF, gives the intermediates li. The compounds li are treated with MeLi at cold temperature to afford compounds of formula lii, and deprotection of acetal group under conditions analogous to those described in Scheme 5 gives the aldehydes liii (Method J).

Scheme 13: General method for the preparation of diaryl ketones lvii

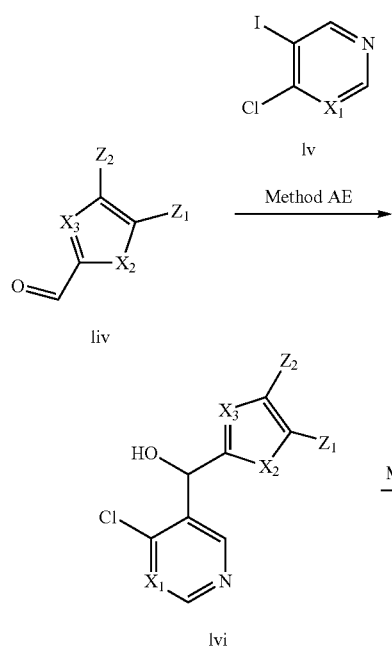

242

Scheme 13 depicts the synthesis of diaryl ketone intermediates lvii. Lithiation of bis-halogenated pyrimidines or pyridines Iv can be followed by addition of the aldehydes liv to give diaryl alcohols lvi (Method AE). Oxidation for example with MnO$_2$ or Dess-Martin periodinane provides diarylketones lvii (Method AF).

Scheme 14: General method for the preparation of diaryl ketones lix

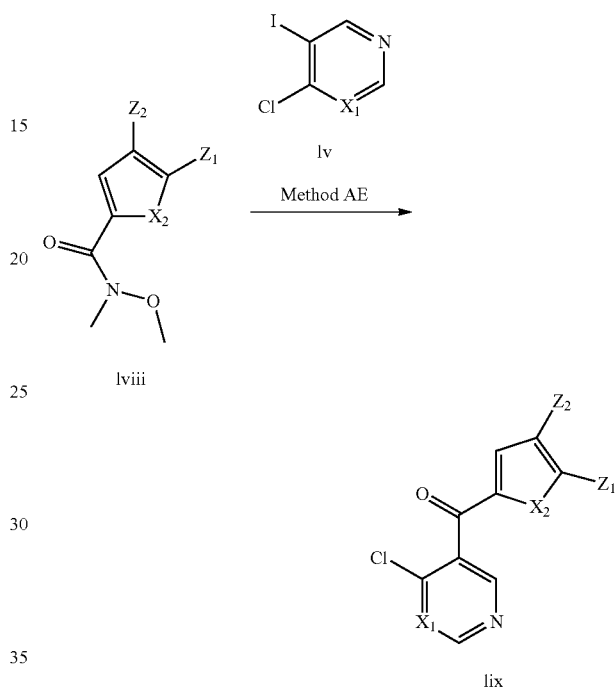

Scheme 14 depicts that the diarylketones lix can also be accessed by reaction of Weinreb amides lviii with bis-halogenated pyrimidines or pyridines Iv (method AE).

Scheme 15: General method for the synthesis of keto arylamines lxi and lxii

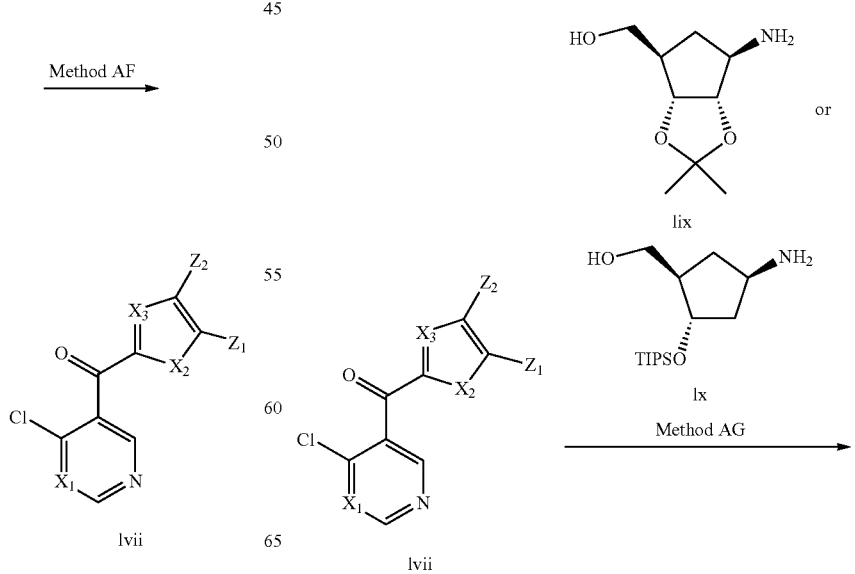

Scheme 15 shows a synthetic route for the preparation of compounds of formula lxi and lxii. Diaryl ketones lvii can be treated with an appropriate amines, such as (1R,2S,3R,4R)-1-amino-2,3-(isopropylidenyl)dihydroxy-4-hydroxymethyl cyclopentane lix (prepared according to Claiborne, C. F. et al; PCT Application Publication WO 2008/019124) or lx in the presence of a suitable base, such as K$_2$CO$_3$, DIEA or TEA in a polar solvent, such as iPrOH, PrOH, nBuOH or DMF (Method AG).

Alternative amines can be used in this reaction (Method AG, scheme 15) such as those shown by the general formula lxiii and represented by lxiv through lxix in Diagram A below. Salts of the amine, such as the hydrochloride, can usually be used in this reaction with the appropriate equivalents of base. For amine lxiv see: Ober, M. et al. *J. Am. Chem. Soc.* 2005, 127, 18143-18149; for lxv see: Armitage, I. et al. US Patent Application Publication 2009/0036678; for lxvi, lxvii, lxix see: Biggadike, K. at al. *J. Chem. Soc. Perkin Trans.* 1988, 3, 549-554; Borthwick, A. D. et al. *J Med. Chem.* 1990, 33, 179-186.

Scheme 16: General method for the preparation of ketoaryl intermediates lxxiv

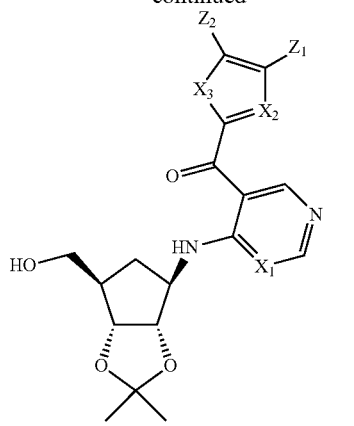

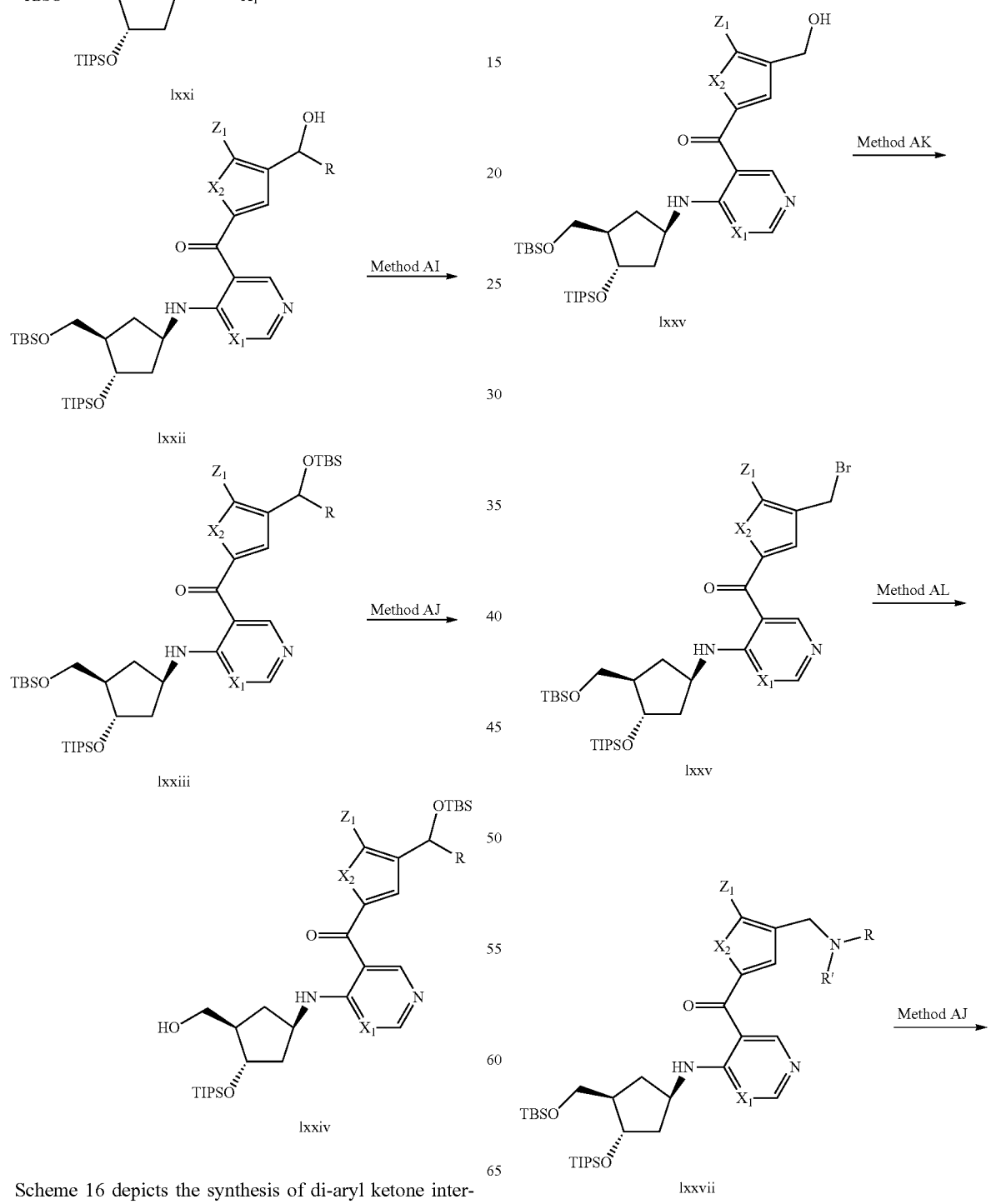

dized to the aldehydes lxxi (Method AF). The aldehydes lxxi can be reacted with appropriate Grignard reagents or organolithium reagents to give compounds of formula lxxii (Method AH). A suitable protection, such as TBS or TIPS group under general conditions (Method AI) and deprotection of the primary TBS ether under mild acidic conditions, such as 1% aq. HCl in ethanol, at cold temperature gives compounds of formula lxxiv (Method AJ).

Scheme 17: General method for the preparation of ketoaryl intermediates lxxviii

Scheme 16 depicts the synthesis of di-aryl ketone intermediates lxxiv. The alcohol intermediates lxx can be oxi-

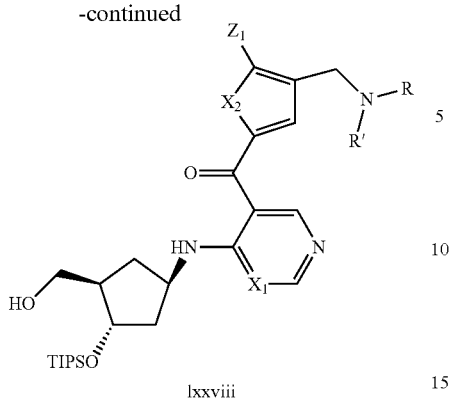

lxxviii

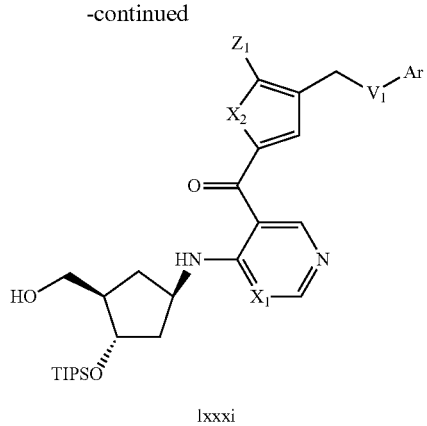

lxxxi

Scheme 17 depicts the synthesis of keto aryl intermediates lxxviii. The alcohol intermediates lxxv are activated, for example by conversion to the bromide or chloride under standard conditions, such as $PPh_3$ with $CBr_4$ or $CCl_4$ in suitable solvent, such as DCM, to give intermediate alkyl halides lxxvi (Method AK) and reacted with an appropriate amines in the presence of base, such as DIEA or $Et_3N$ to give amine derivatives lxxvii (Method AL). Additional nucleophiles may also be employed. For example, the bromide may be reacted with an alcohol or alkoxide to give ethers. The nitrogen nucleophile may be part of an aromatic ring, for example a pyrrole, imidazole, or indole. A suitable protection/deprotection strategy such as that shown at method AJ in scheme 16 gives the intermediates lxxviii.

Scheme 18 depicts the synthesis of keto aryl intermediates lxxxi where $V_1$ is S or O. The alcohol is activated, for example by conversion to the bromide or chloride, and reacted with appropriate alcohol or thiol derivatives, such as optionally substituted phenols or benzenethiols, to give ether or thio ether intermediates lxxxi.

Scheme 19: General method for the preparation of sulfamate derivatives of the keto arylamines Scheme 18: General method for the preparation of ketoaryl intermediates lxxxi

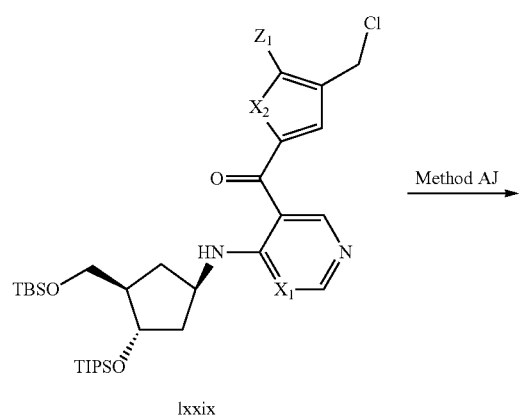

lxxix

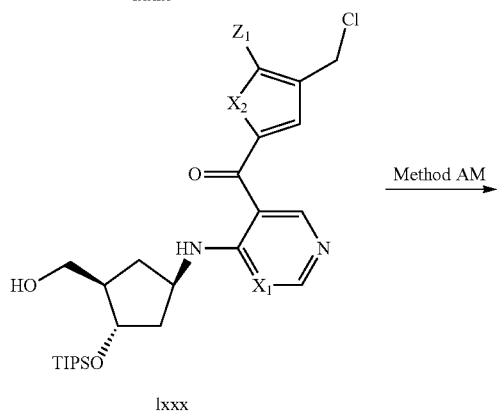

lxxx

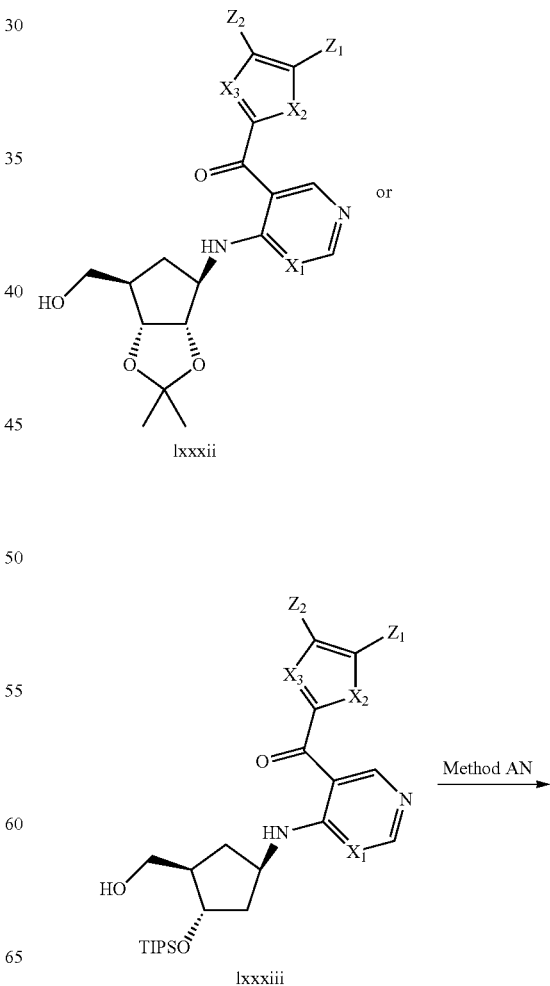

lxxxii lxxxiii

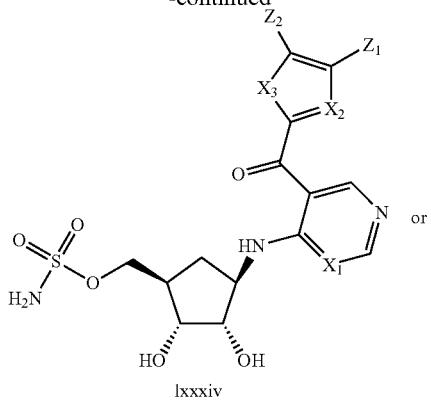

lxxxiv lxxxv

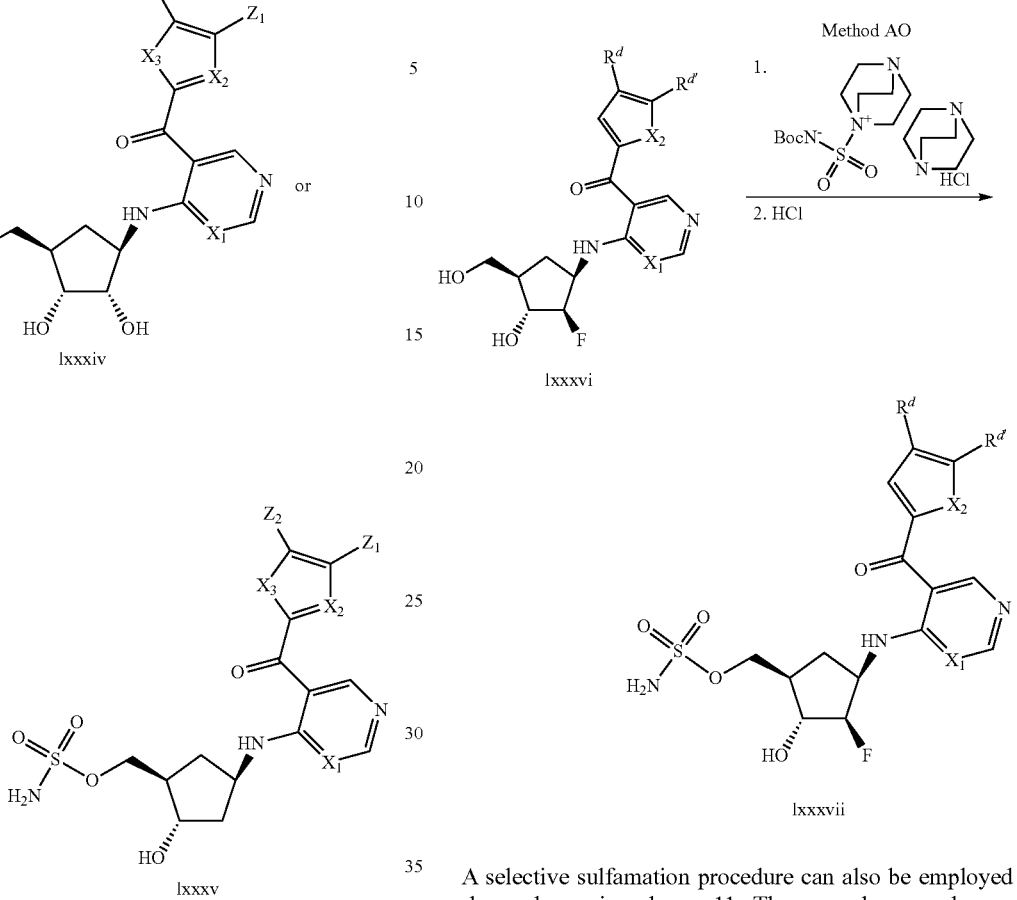

Scheme 20: Procedure for selective sulfamation lxxxvi lxxxvii

A selective sulfamation procedure can also be employed such as shown in scheme 11. The procedure employs a modified Burgess reagent (Armitage, I. et al. *Org. Lett.* 2012, 14, 2626-2629) followed by treatment with acid to deprotect the sulfamate (Method AO).

Preparation of Exemplary Chemical Entities

Definitions

Scheme 19 illustrates the syntheses of compounds with general structure lxxxiv and lxxxv. A two-step sequence consisting of sulfamation and deprotection completes the synthesis of ketopyrimidines (ketopyridines) lxxxiv and lxxxv. The acetonide can be removed under acidic conditions, such as aq. HCl/THF or TFA/water, and the silyl group can be removed under acidic conditions, such as aq. HCl/THF $H_3PO_4$/acetonitrile or TFA/water, or by using an appropriate fluoride source, such as TBAF or TASF. If using a bis protected diol such as lxix the silyl group (TBS) can be selectively removed from the primary alcohol (e.g. mild acidic conditions at reduced temperature, such as 1% HCl in EtOH at 4° C.) prior to sulfamation. When using amines with unprotected alcohols, such as lxiv through lxviii, a suitable protecting group strategy can be employed to give the desired sulfamate. For example, protection of the free alcohols can be accomplished by prolonged treatment with TBSCl in DMF, which is then subjected to selective deprotection of the primary silyl group with mild acid at reduced temperature. Subsequent sulfamation and deprotection provides the desired sulfamate.

AA LCMS method using ammonium acetate
ACN acetonitrile
aq aqueous
Boc tert-butoxycarbonyl
BPR back pressure regulator
C Celsius
CBS Corey-Bakshi-Shibata
DCM methylene chloride
DEA diethylamine
DIAD diisopropyl azodicarboxylate
DIBAl-H diisobutylaluminum hydride
DIEA diisopropylethylamine
DMA dimethylacetamide
DMAP N,N-dimethyl-4-aminopyridine
DME dimethyl ether
DMF dimethylformamide
DMSO dimethyl sulfoxide
EtOAc ethyl acetate
FA LCMS method using formic acid
FR flow rate
h hour(s)
HPLC high performance liquid chromatography
$IC_{50}$ inhibitory concentration 50%

KHMDS potassium hexamethyldisilazide
LAH lithium aluminium hydride
LCMS liquid chromatography mass spectrometry
LC liquid chromatography
m/z mass to charge
min minute(s)
NBS N-bromosuccinimide
NCS N-chlorosuccinimide
NMM N-methylmorpholine
NMP N-methylpyrrolidone
NMR nuclear magnetic resonance
PPh₃ Triphenylphosphine
PPTS pyridinium p-toluenesulfonate
psi pounds per square inch
PTSA p-toluenesulfonic acid
Rf retention factor
rt room temperature
SFC supercritical fluid chromatography
STAB sodium triacetoxyborohydride
TAS-F tris(dimethylamino)sulfonium difluorotrimethylsilicate
TBAF tetra-n-butylammonium fluoride
TBS tert-butyldimethylsilyl
TEA triethylamine
TEMPO 2,2,6,6-Tetramethylpiperidin-1-yl)oxyl
TFA trifluoroacetic acid
THF tetrahydrofuran
TIPS triisopropylsilyl
TLC thin layer chromatography
TMS trimethylsilyl Analytical Methods NMR conditions: $^1$H NMR spectra are run on a 400 MHz Bruker unless otherwise stated.

LCMS Conditions:

LCMS spectra are recorded on a Hewlett-Packard HP 1100 or Agilent 1100 Series LC system connected to a Micromass mass spectromteter using reverse phase C18 columns. Various gradients and run times are selected in order to best characterize the compounds. Mobile phases are based on ACN/water gradients and contain either 0.1% formic acid (methods indicated FA) or 10 mM ammonium acetate (methods indicated AA). One example of a solvent gradient that is used is 100% mobile phase A (mobile phase A=99% water+1% ACN+0.1% formic acid) to 100% mobile phase B (mobile phase B=95% ACN+5% water+0.1% formic acid) at a flow rate of 1 mL/min for a 16.5 min e.

One of ordinary skill in the art will recognize that modifications of the gradient, column length, and flow rate are possible and that some conditions may be more suitable for compound characterization than others, depending on the chemical species being analyzed.

Example 1: 2-(4-Bromo-5-methyl-2-thienyl)-1,3-dioxolane Int-1

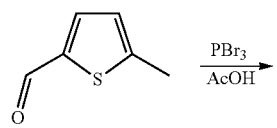

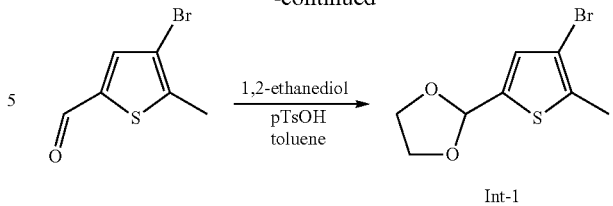

Step 1: 4-Bromo-5-methyl-2-thiophenecarbaldehyde

A 1000 mL round bottom flask was charged with 5-methyl-2-thiophenecarboxaldehyde (15 g, 120 mmol) and acetic acid (200 mL, 4000 mmol). Added pyridinium tribromide (48.5 g, 137 mmol). Heated in a 40° C. oil bath for 24 h. Reaction mixture was cooled to rt and poured into water (1 L). Layers were separated, and the aqueous layer was extracted three times with EtOAc. Combined organics were washed with saturated NaHCO₃ and then brine. The organic layer was dried over anhydrous magnesium sulfate, filtered, and concentrated. Subjected to ISCO chromatography eluting with a hexane/EtOAc gradient to afford the title compound as a white solid (yield=11.44 g). $^1$H NMR (400 MHz, Acetone-d6) δ 9.87 (s, 1H), 7.88 (s, 1H), 2.52 (s, 3H).

Step 2: 2-(4-Bromo-5-methyl-2-thienyl)-1,3-dioxolane

To a round bottom flask was added 4-bromo-5-methyl-2-thiophenecarbaldehyde (4.23 g, 20.6 mmol), 1,2-ethanediol (7.80 mL, 1.40E2 mmol), p-toluenesulfonic acid monohydrate (0.39 g, 2.1 mmol), and 100 ml toluene. The resulting reaction mixture was heated at reflux with a Dean-Stark trap overnight. The mixture was cooled to rt. EtOAc was added and the mixture was washed with saturated aqueous NaHCO₃ and water. The organic layer was dried over Na₂SO₄, filtered, and concentrated. The residue was chromatographed (hexanes/EtOAc=9/1 as eluent) to give 4.2 g of the title compound. $^1$H NMR (400 MHz, Chloroform-d) δ 6.99 (s, 1H), 6.02 (s, 1H), 4.15-4.09 (m, 2H), 4.06-3.99 (m, 2H), 2.40 (s, 3H).

Example 2: 2-(4-Bromo-5-chloro-2-thienyl)-1,3-dioxolane Int-2

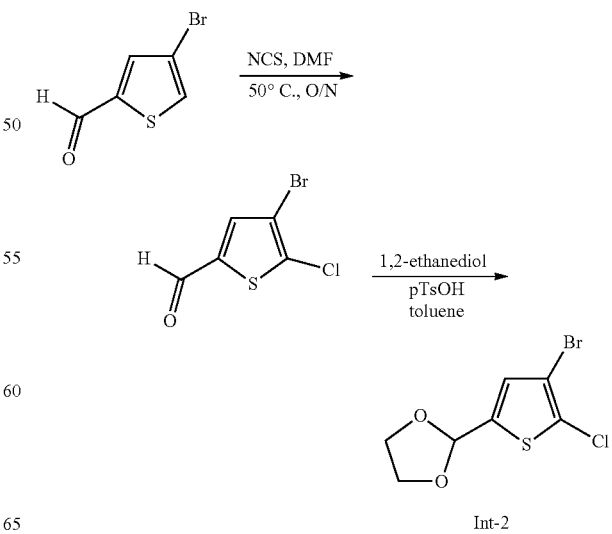

Step 1: 4-bromo-5-chlorothiophene-2-carbaldehyde

To a solution of 4-bromothiophene-2-carbaldehyde (20 g, 100 mmol) in DMF (49 mL, 630 mmol) was added N-chlorosuccinimide (21 g, 160 mmol), in portions. The reaction mixture was stirred at 50° C. overnight. The resulting solution was cooled to rt and then poured onto 500 mL of ice water (a light pink precipitate formed). The precipitate was collected via vacuum filtration and then dried in a vacuum oven to give 19.35 g of the title compound as a light tan solid. $^1$H NMR (400 MHz, Chloroform-d) δ 9.79 (s, 1H), 7.62 (s, 1H).

Step 2: 2-(4-Bromo-5-chloro-2-thienyl)-1,3-dioxolane

To a solution of 4-bromo-5-chlorothiophene-2-carbaldehyde (19.35 g, 85.81 mmol) in toluene (300 mL, 2000 mmol) was added 1,2-ethanediol (23.9 mL, 429 mmol) and p-toluenesulfonic acid monohydrate (0.816 g, 4.29 mmol). The reaction mixture was fitted with a Dean-Stark trap, stirred at reflux overnight under argon gas. The reaction was quenched with water (300 mL), extracted with EtOAc (3×150 mL), washed with brine, dried over magnesium sulfate, filtered and concentrated to give ~28 g of crude product as a brown oil. The product was purified by flash chromatography (330 g column, DCM loaded) with 0-10% EtOAc in hexanes over 20 min to give 21.25 g of the title compound as an amber oil. $^1$H NMR (400 MHz, Chloroform-d) δ 6.99 (d, J=0.5 Hz, 1H), 6.02 (s, 1H), 4.15-4.07 (m, 2H), 4.07-3.99 (m, 2H).

The compound listed in the table below was prepared in an analogous fashion to that described above starting from the corresponding starting materials:

| Starting material | Product (Int #) | NMR Data |
|---|---|---|
| (furan-Br with CHO) | Int-3 (chloro-furan-Br with dioxolane) | $^1$H NMR (400 MHz, Chloroform-d) δ 6.53 (s, 1H), 5.87 (s, 1H), 4.17-4.07 (m, 2H), 4.07-3.97 (m, 2H). |

Example 3: [(4-Bromo-2-thienyl)methoxy](triisopropyl)silane Int-4

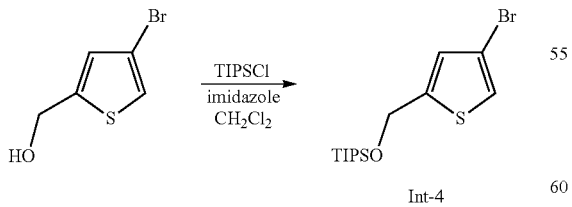

To a solution of (4-bromo-2-thienyl)methanol (9.11 g, 47.2 mmol) in DCM (200 mL, 4000 mmol) was added 1H-imidazole (4.82 g, 70.8 mmol) followed by triisopropylsilyl chloride (12.5 mL, 59.0 mmol) at rt, and the reaction was stirred overnight. The reaction was quenched by addition of water (150 mL) and extracted with DCM (50 mL×2). The combined organic layers were dried over Na$_2$SO$_4$, filtered, and concentrated in vacuo. Crude residue was loaded onto the column as a solution in hexanes. Chromatography was performed (330 g column, 0-5% EtOAc: hexanes over 40 min) to afford the title compound. yield=15.6 g. $^1$H NMR (400 MHz, Chloroform-d) δ 7.14 (s, 1H), 6.84 (s, 1H), 4.95 (s, 2H), 1.26-1.04 (m, 21H).

The compound listed in the table below was prepared in an analogous fashion to that described above, using TBSCl instead of TIPSCl:

| Starting material | Product (Int #) | NMR Data |
|---|---|---|
| 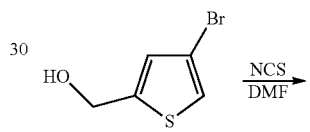 | Int-5 (TBSO-thienyl-Br) | $^1$H NMR (400 MHz, Chloroform-d) δ 7.02 (d, J = 1.4 Hz, 1H), 6.73-6.70 (m, 1H), 4.72 (d, J = 0.9 Hz, 2H), 0.82 (s, 9H), −0.00 (s, 6H). |

Example 4: [(4-Bromo-5-chloro-2-thienyl)methoxy](tert-butyl)dimethylsilane Int-6

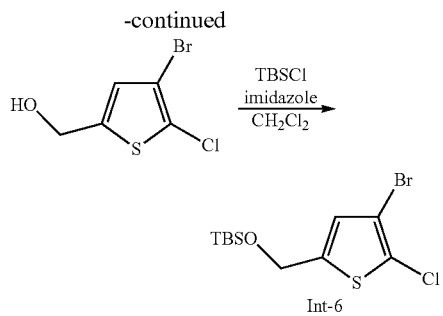

Step 1: (4-Bromo-5-chloro-2-thienyl)methanol

To a solution of (4-bromo-2-thienyl)methanol (5.00 g, 25.9 mmol) in DMF (10.0 mL) was added N-chlorosuccinimide (4.15 g, 31.1 mmol), and the reaction was heated at 60° C. for 3 h. Reaction was allowed to cool to rt and stirred for 14 h. The reaction was concentrated in vacuo. To the residue was added Et$_2$O and the suspension was filtered. The filtrate was concentrated and then purified by ISCO silica gel column chromatography (120 g, eluting with 15% EtOAc in hexanes, 70 mL/min flow) to give 4.08 g of the title compound as a colorless solid. $^1$H NMR (400 MHz, Chloroform-d) δ 6.84 (s, 1H), 4.76 (d, J=6.0 Hz, 2H), 1.86 (t, J=6.1 Hz, 1H).

Step 2: [(4-Bromo-5-chloro-2-thienyl)methoxy](tert-butyl)dimethylsilane

To a solution of (4-bromo-5-chloro-2-thienyl)methanol (3.50 g, 15.4 mmol) in DCM (48.3 mL) was added 1H-imidazole (1.57 g, 23.1 mmol) followed by TBSCl (2.55 g, 16.9 mmol) at rt, and the mixture was stirred for 2 h. The reaction was quenched by addition of water (100 mL) and extracted with hexane (100 mL×2). The combined organic layers were dried over Na$_2$SO$_4$, filtered, and concentrated in vacuo. The residue as purified by ISCO silica gel column chromatography (120 g, eluting with 0% EtOAc in hexane for 3 min then gradient to 5% EtOAc in hexane over 10 min, 50 mL/min flow) to give 5.01 g of the title compound as colorless solid. $^1$H NMR (400 MHz, Chloroform-d) δ 6.60 (t, J=1.0 Hz, 1H), 4.65 (d, J=1.1 Hz, 2H), 0.82 (s, 9H), −0.00 (s, 6H).

Example 5: 3-Bromo-2-methyl-5-[(trityloxy)methyl]furan Int-7

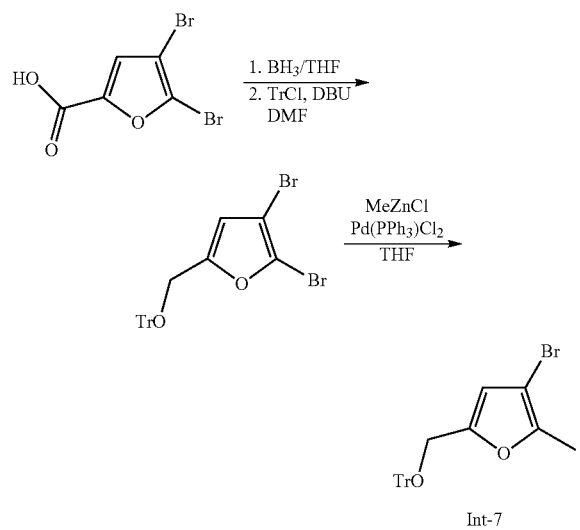

Step 1: (4,5-Dibromo-2-furyl)methanol

To a solution of 4,5-dibromo-2-furoic acid (10.0 g, 37.0 mmol) in THF (174.8 mL, 2154 mmol) was slowly added 1.0 M of borane in THF (52.4 mL, 52.4 mmol) as gas evolved. Toward the end of the addition of borane the reaction mixture progressed from a clear solution to a white cloudy mixture. When bubbling ceased a reflux condenser was attached and the resulting reaction mixture was heated at 80° C. overnight. Over the first hour of heating, cloudy mixture progressed to a clear, pink solution. Reaction was cooled to rt and quenched via addition of saturated aqueous NaHCO$_3$ (care, gas evolution). Reaction mixture was transferred to a separatory funnel and diluted with Et$_2$O (200 mL). Layers were separated, and the aqueous layer was extracted 1×Et$_2$O (40 mL). Combined organic layers were dried over Na$_2$SO$_4$, filtered, and concentrated in vacuo. Chromatography was performed (220 g column, 0-30% EtOAc:hexanes as eluent) to afford the title compound. Yield=7.25 g. $^1$H NMR (400 MHz, Chloroform-d) δ 6.41 (s, 1H), 4.59 (s, 2H).

Step 2: 2,3-Dibromo-5-[(trityloxy)methyl]furan

To a solution of (4,5-dibromo-2-furyl)methanol (10.5 g, 41.0 mmol) and 1,8-diazabicyclo[5.4.0]undec-7-ene (18.4 mL, 123 mmol) in DMF (41.0 mL, 5.30E2 mmol) was added triphenylmethyl chloride (28.6 g, 102 mmol). The resulting mixture was stirred at rt overnight. Reaction mixture was partitioned between water (200 mL) and EtOAc (500 mL). Layers were separated, and the aqueous layer was extracted 2×EtOAc (100 mL each). Combined organic layers were dried over Na$_2$SO$_4$, filtered, and concentrated in vacuo. Crude residue was adsorbed to Celite (75 mL) for dry-loading onto the column. Chromatography was performed (330 g column, 0-8% EtOAc:hexanes as eluent) to afford the title compound. yield=19.5 g. $^1$H NMR (400 MHz, Chloroform-d) δ 7.55-7.45 (m, 6H), 7.39-7.24 (m, 9H), 6.32 (s, 1H), 4.07 (d, J=0.6 Hz, 2H).

Step 3: 3-Bromo-2-methyl-5-[(trityloxy)methyl]furan

To a solution of 2,3-dibromo-5-[(trityloxy)methyl]furan (9.5 g, 19 mmol) in THF (110 mL, 1400 mmol) was added 2.00 M of methylzinc chloride in THF (38.14 mL, 76.27 mmol) and the mixture was purged with vacuum/argonargon. Bis(triphenylphosphine)palladium(II) chloride (1.338 g, 1.907 mmol) was then added and the resulting mixture was stirred overnight at rt. Reaction mixture was filtered through Celite, and the filtrate was then concentrated in vacuo. The crude residue was adsorbed to Celite (100 mL) for dry-loading onto the column. Chromatography was performed (0-5% EtOAc:hexanes as eluent, 220 g column) afforded the title compound. Yield=5.06 g. $^1$H NMR (400 MHz, Chloroform-d) δ 7.55-7.45 (m, 6H), 7.37-7.30 (m, 6H), 7.28-7.23 (m, 3H), 6.23 (s, 1H), 4.02 (s, 2H), 2.31 (s, 3H).

Example 6: 4-Bromo-2-({[tert-butyl(dimethyl)silyl]oxy}methyl)-5-methyl-1,3-thiazole Int-8

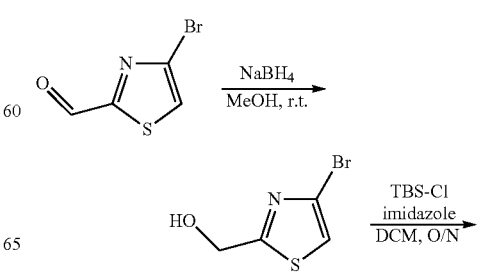

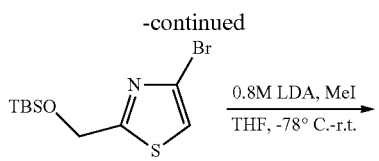

Step 1: (4-Bromo-thiazol-2-yl)-methanol

To a solution of 4-bromo-2-formylthiazole (4.00 g, 20.8 mmol) in methanol (60.0 mL, 1480 mmol) was slowly added sodium tetrahydroborate (0.946 g, 25.0 mmol), and the reaction was stirred at rt for 20 min. The reaction was concentrated in vacuo, diluted with EtOAc, and washed with water 2× and then brine 1×. Organic layer was dried over Na$_2$SO$_4$, filtered and concentrated in vacuo. The residue was purified via column chromatograpy (40 g column, 20%-50% EtOAc in hexanes over 30 min) to give a light yellow oil. Yield=3.28 g. $^1$H NMR (400 MHz, Chloroform-d) δ 7.22 (s, 1H), 4.95 (d, J=6.2 Hz, 2H), 2.76 (t, J=6.2 Hz, 1H). LCMS (FA): 196.0 m/z (M+1).

Step 2: 4-Bromo-2-({[tert-butyl(dimethyl)silyl]oxy}methyl)-1,3-thiazole (4-Bromo-thiazol-2-yl)-methanol (3.28 g, 16.9 mmol), DCM (32.8 mL, 512 mmol), tert-butyldimethylsilyl chloride (3.18 g, 21.1 mmol), 1H-imidazole (2.88 g, 42.2 mmol) and N,N-dimethylaminopyridine (103 mg, 0.845 mmol) were combined in a 250 mL round-bottom flask at rt and stirred overnight. The reaction was diluted with EtOAc and water, and the organic layer was washed 1× water, 2× saturated NH$_4$Cl and 1× brine. The organic layer was then dried over Na$_2$SO$_4$, filtered and concentrated in vacuo. The residue was purified via column chromatography (40 g ISCO, 4% EtOAc in hexanes isocratic) to give the title compound as a clear colorless oil. Yield=5.09 g. $^1$H NMR (400 MHz, Chloroform-d) δ 7.17 (s, 1H), 4.94 (s, 2H), 0.95 (s, 9H), 0.13 (s, 6H).

Step 3: 4-Bromo-2-({[tert-butyl(dimethyl)silyl]oxy}methyl)-5-methyl-1,3-thiazole A solution of 4-bromo-2-({[tert-butyl(dimethyl)silyl]oxy}methyl)-1,3-thiazole (0.500 g, 1.62 mmol) in THF (1.50 mL, 18.5 mmol) was cooled to −78° C. 0.8 M of lithium diisopropylamide in THF (2.25 mL, 1.80 mmol) was added dropwise at −78° C. The reaction became a yellow color upon addition. The reaction was allowed to stir for 30 min under an atmosphere of argon at −78° C. Methyl iodide (0.500 mL, 8.03 mmol) was added, and the reaction was stirred at −78° C. for 30 min then allowed to warm to rt. The reaction was quenched with saturated NH$_4$Cl and diluted with EtOAc. The organic layer was washed 2× with saturated NH$_4$Cl and 1× brine and then dried over Na$_2$SO$_4$, filtered and concentrated in vacuo. The material was purified via column chromatography (24 g ISCO 1% EtOAc in hexanes isocratic) to give a clear colorless oil. Yield=452 mg. $^1$H NMR (400 MHz, Methanol-d4) δ 4.85 (s, 2H), 2.38 (s, 3H), 0.96 (s, 9H), 0.15 (s, 6H). LCMS (FA): 324.4 m/z (M+1).

Example 7: [2-(2-Bromo-4-chloro-3-fluorophonyl)ethoxy](tert-butyl)dimethylsilane Int-9

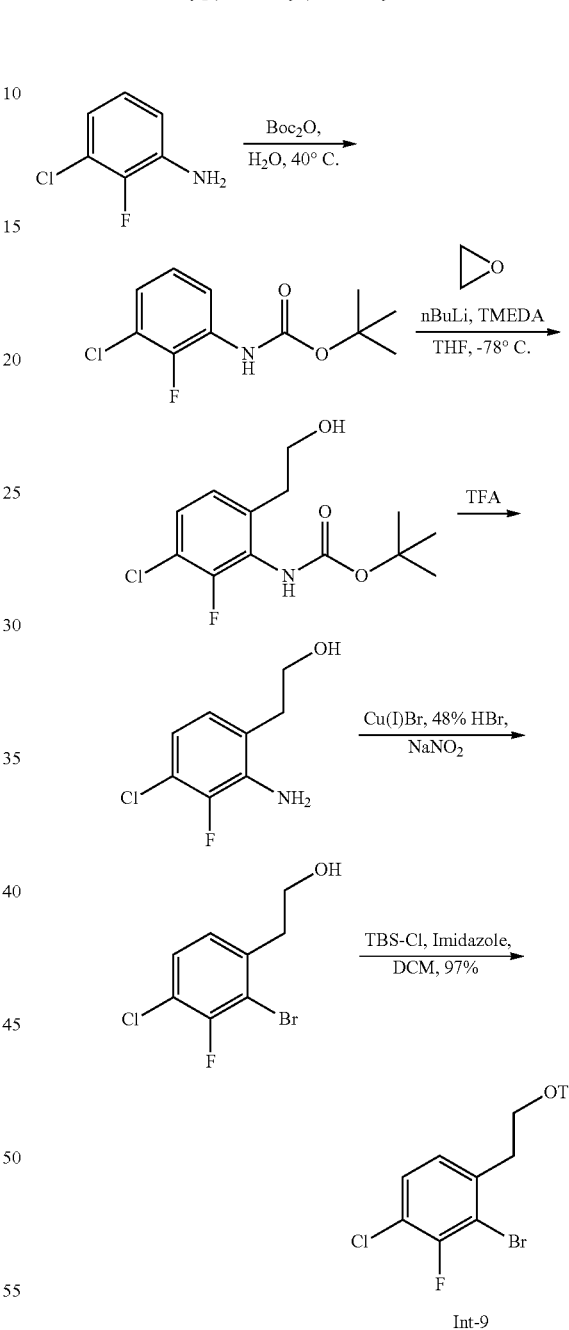

Step 1: tert-Butyl (3-chloro-2-fluorophenyl)carbamate

2-Fluoro-3-chloroaniline (3.00 g, 0.0206 mol), di-tert-butyldicarbonate (9.44 g, 0.0433 mol), THF (46.3 mL, 0.571 mol), N,N-dimethylaminopyridine (252 mg, 0.00206 mol) were combined in a 250 mL round-bottom flask with vigorous stirring and heated at rt overnight. The reaction was diluted with EtOAc, and then washed with brine, dried over Na₂SO₄, filtered and concentrated in vacuo. The residue was purified via column chromatography (0.5% EtOAC in hexanes isocratic eluent, 80 g ISCO column, 50 mL/min) to give 3.40 g (67%) of the product as a clear colorless oil. ¹H NMR (400 MHz, Chloroform-d) δ 8.06-7.97 (m, 1H), 7.07-6.98 (m, 2H), 6.70 (s, 1H), 1.53 (s, 9H)

Step 2: tert-Butyl [3-chloro-2-fluoro-6-(2-hydroxyethyl)phenyl]carbamate

A solution of tert-butyl (3-chloro-2-fluorophenyl)carbamate (1.58 g, 6.43 mmol) was dissolved in THF (20.0 mL, 246 mmol) was cooled to −78° C. under an atmosphere of argon. N,N,N',N'-tetramethylethylenediamine (2.27 mL, 15.0 mmol) was added followed by 1.40 M of sec-butyllithium in cyclohexane (10.4 mL, 14.5 mmol) and the solution turned a light yellow color. The reaction was warmed to 0° C. and then immediately cooled back to −78° C. Separately, ethylene oxide (1.61 mL, 32.2 mmol) was condensed at 0° C. and transferred via cannula to the reaction. The reaction was stirred at −78° C. for 30 min then warmed to rt. The reaction was quenched with saturated NH₄Cl, extracted 2× with EtOAc. The combined organics were washed with brine, dried over Na₂SO₄, filtered and concentrated in vacuo. The residue was purified via column chromatography (80 g ISCO, 10%-50% EtOAc in hexanes) to give 0.852 g (45%) of the product as an off-white solid. ¹H NMR (400 MHz, Chloroform-d) δ 7.25-7.19 (m, 1H), 6.96 (dd, J=8.4, 1.4 Hz, 1H), 6.81 (s, 1H), 3.90 (q, J=5.7 Hz, 2H), 2.87 (t, J=5.8 Hz, 2H), 1.96 (t, J=4.4 Hz, 1H), 1.50 (s, 9H).

Step 3: 2-(2-Amino-4-chloro-3-fluorophenyl)ethanol

Tert-butyl [3-chloro-2-fluoro-6-(2-hydroxyethyl)phenyl] carbamate (0.752 g, 2.60 mmol) was weighed into a 50 mL round-bottom flask. To the flask was added TFA (4.00 mL, 51.9 mmol), at which point gas evolved. Once gas evolution ceased, the reaction was quenched with saturated NaHCO₃ and extracted 2× with DCM. The combined organics were dried over Na₂SO₄, filtered and concentrated in vacuo. The residue was loaded onto a 40 g Gold ISCO column eluting with 50% EtOAc in hexanes isocratic to give 0.421 g (86%) of the product as a white solid. ¹H NMR (400 MHz, Chloroform-d) δ 6.80-6.72 (m, 2H), 3.92 (t, J=5.9 Hz, 2H), 2.81 (t, J=5.9 Hz, 2H).

Step 4: 2-(2-Bromo-4-chloro-3-fluorophenyl)ethanol

A 100 mL round bottom flask was charged with [2-(2-amino-4-chloro-3-fluorophenyl)ethanol (0.420 g, 2.22 mmol) and 8.90 M of hydrobromic acid in water (3.61 mL, 32.2 mmol), and the mixture was cooled in an ice bath. To this was added an ice-cooled solution of sodium nitrite (0.153 g, 2.22 mmol) in ~1 mL water dropwise. A brown solution resulted. In a separate flask, copper(I) bromide (0.318 g, 2.22 mmol) and 8.90 M of hydrobromic acid in water (0.723 mL, 6.43 mmol) were combined and cooled in an ice bath. The second solution was added to the first via rapid, dropwise addition and the mixture was warmed to rt. Reaction was quenched with water, and the aqueous mixture was extracted 3× with DCM. The combined organics were washed with brine, dried over Na₂SO₄, filtered and concentrated in vacuo. The residue was purified via column chromatography (24 g Gold ISCO, 30% EtOAc in hexanes isocratic 25 mL/min) to give 0.442 g (79%) of the product as yellow oil. ¹H NMR (400 MHz, DMSO-d6) δ 7.58-7.51 (m, 1H), 7.24 (dd, J=8.4, 1.5 Hz, 1H), 4.77 (t, J=5.3 Hz, 1H), 3.65-3.55 (m, 2H), 2.89 (t, J=6.8 Hz, 2H).

Step 5: [2-(2-Bromo-4-chloro-3-fluorophenyl) ethoxy](tert-butyl)dimethylsilane

To a solution of 2-(2-bromo-4-chloro-3-fluorophenyl) ethanol (0.442 g, 1.74 mmol) in DCM (4.78 mL, 74.6 mmol) was added 1H-imidazole (0.308 g, 4.52 mmol) followed by tert-butyldimethylsilyl chloride (0.309 g, 2.05 mmol). The reaction was stirred for 30 min at rt. The reaction was quenched with water, the layers were separated, and the aqueous layer was extracted 2× with DCM. The combined organic layers were washed with brine, dried over Na₂SO₄, filtered and concentrated in vacuo. The residue was purified via column chromatography (40 g ISCO, 0-10% EtOAc in hexanes over 20 min) to give 0.620 g (97%) of a clear colorless oil. ¹H NMR (400 MHz, Chloroform-d) δ 7.29-7.23 (m, 1H), 7.02 (dd, J=8.3, 1.4 Hz, 1H), 3.81 (t, J=6.7 Hz, 2H), 2.98 (t, J=6.6 Hz, 2H), 0.86 (s, 9H), −0.02 (s, 6H).

Example 8: 5-(2-{[tert-Butyl(dimethyl)silyl] oxy}ethyl)-2-chloropyridine Int-10

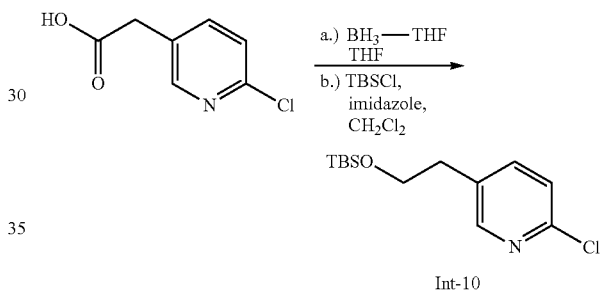

Int-10

This compound was prepared in an analogous fashion to that described in Example 11, Step 1, beginning with (2-chloropyridyl)-5-acetic acid. ¹H NMR (400 MHz, DMSO-d6) δ 8.33 (d, J=2.2 Hz, 1H), 7.80 (dd, J=8.2, 2.5 Hz, 1H), 7.50 (d, J=8.2 Hz, 1H), 3.85 (t, J=6.2 Hz, 2H), 2.83 (t, J=6.2 Hz, 2H), 0.87 (s, 9H), −0.00 (s, 6H).

Example 9: 1-(2-Bromo-4-chlorophenyl)-N-methylmethanamine Int-11

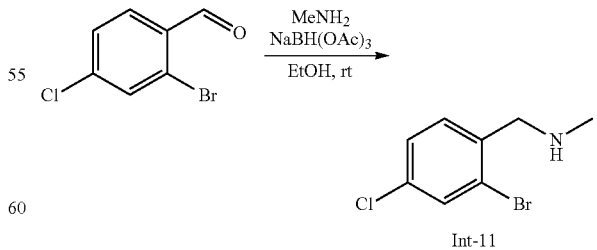

Int-11

To a solution of 2-bromo-4-chlorobenzaldehyde (3.00 g, 13.7 mmol) in ethanol (10.0 mL, 171 mmol) was added 8.4 M of methylamine in ethanol (3.27 mL, 27.3 mmol) and the mixture was stirred for 4 h at rt. The mixture was cooled at 0° C. and sodium triacetoxyborohydride (3.04 g, 14.4 mmol) was added portion wise. The reaction was stirred for 1 h. The reaction was concentrated in vacuo, and then 1N NaOH (200 mL) was added to the residue and the mixture was extracted with DCM (200 mL×3). The combined organic layers were dried over $Na_2SO_4$, filtered, and concentrated in vacuo. The residue was purified by ISCO silica gel column chromatography (40 g, eluting with 5% MeOH in DCM for 5 min then gradient to 10% MeOH in DCM over 15 min, 40 mL/min flow) to give 2.5 g of the title compound. $^1$H NMR (400 MHz, DMSO-d6) δ 7.71 (d, J=2.1 Hz, 1H), 7.51 (d, J=8.3 Hz, 1H), 7.46 (dd, J=8.3, 2.1 Hz, 1H), 2.29 (s, 3H), 2.22 (s, 1H).

The compound listed in the table below was prepared in an analogous fashion to that described above starting from the corresponding starting materials:

| Starting material | Product (Int #) |
|---|---|
| 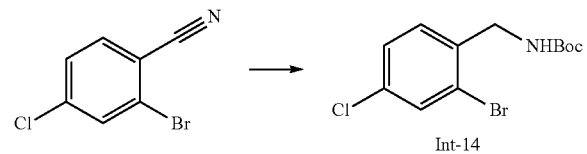 [SMILES: N#Cc1ccc(Cl)cc1Br ; CC(C)(C)OC(=O)NCc1ccc(Cl)cc1Br] | |

Example 10: tert-Butyl (2-bromo-4-chlorobenzyl)carbamate Int-14

In a microwave vial, a solution of 2-bromo-4-chlorobenzonitrile (1.0 g, 4.6 mmol) in toluene (6.00 mL, 56.3 mmol) was purged with argon and sealed with a septum. To the solution was added 1,1,3,3-tetramethyldisiloxane (0.816 mL, 4.62 mmol) followed by titanium tetraisopropoxide (1.36 mL, 4.62 mmol) at rt, and the mixture was stirred at 60° C. for 24 h. The reaction was cooled to rt and quenched by addition of 1N HCl. The mixture was washed with EtOAc (×2). The water layer was basified by addition of 3N NaOH until pH ~10 and extracted with DCM (×3). The combined organic layers were dried over $Na_2SO_4$, filtered, and concentrated in vacuo. The residue was dissolved in $CH_3CN$ (3.00 mL, 57.4 mmol) and di-tert-butyldicarbonate (1.01 g, 4.62 mmol) was added. Some colorless precipitates were observed. To the mixture was added triethylamine (0.9658 mL, 6.930 mmol) and the suspension turned to a clear solution. After 30 min, the mixture was concentrated in vacuo and the residue was purified by ISCO silica gel column chromatography (24 g, eluting with 5% EtOAc in Hexane, 40 mL/min flow) to give the title compound as colorless solid. Yield 404 mg (27%).

Example 11: 2-(2-{[tert-Butyl(dimethyl)silyl]oxy}ethyl)-5-chlorobenzaldehyde Int-15

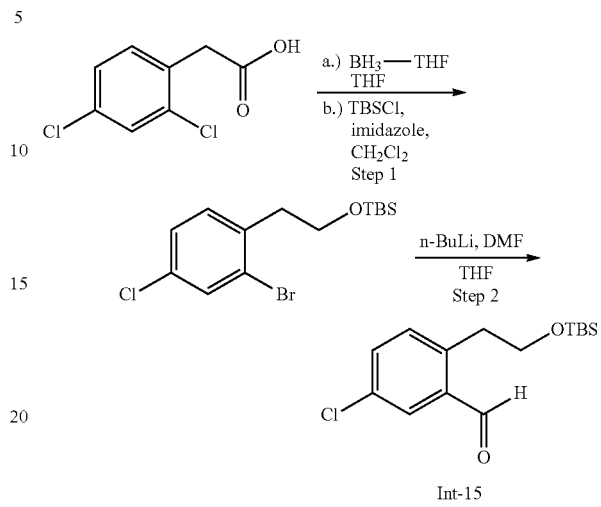

Step 1: [2-(2-Bromo-4-chlorophenyl)ethoxy](tert-butyl)dimethylsilane

To a solution of (2-bromo-4-chlorophenyl)acetic acid (25.0 g, 100 mmol in THF (400 mL, 5000 mmol) was added slowly 1.0 M of borane in THF (120.2 mL, 120.2 mmol) at rt. When bubbling ceased the resulting reaction mixture was heated at 60° C. overnight. Reaction was quenched via slow careful addition of 1.0 M of HCl in water (300 mL, 300 mmol). THF was removed in vacuo and the resulting residue was partitioned between $Et_2O$ and water. Layers were separated, and the aqueous layer was extracted 2×$Et_2O$. The combined organic solvents were dried, filtered and concentrated in vacuo. Crude yield: 23.1 g.

To a solution of the crude alcohol produced above (23.5 g, 99.8 mmol) in DCM (435.2 mL, 6789 mmol) was added 1H-imidazole (11.89 g, 174.6 mmol) followed by tert-butyldimethylsilyl chloride (22.56 g, 149.7 mmol) at rt, and the reaction was stirred for 24 h. The reaction was quenched by addition of water (250 mL) and extracted with DCM (3×). The combined organic layers were dried over MgSO4, filtered, and concentrated in vacuo. The residue was purified by ISCO silica gel column chromatography (750 g, Hexanes then 0-10% EtOAc/Hexanes over 50 min) to afford the title compound. Yield: 23.9 g (69%—2 steps). $^1$H NMR (400 MHz, Chloroform-d) δ 7.57 (d, J=1.3 Hz, 1H), 7.23 (d, J=1.9 Hz, 2H), 3.83 (t, J=6.7 Hz, 2H), 2.96 (t, J=6.7 Hz, 2H), 0.89 (s, 9H), −0.00 (s, 6H).

Step 2: Reaction Conditions A (as Depicted in Example 11): 2-(2-{[tert-Butyl(dimethyl)silyl]oxy}-ethyl)-5-chlorobenzaldehyde A solution of [2-(2-bromo-4-chlorophenyl)ethoxy](tert-butyl)dimethylsilane (15.5 g, 44.3 mmol) in THF (197 mL, 2430 mmol) was cooled to −78° C., at which point was added 2.50 M of n-BuLi in hexane (24.8 mL, 62.0 mmol). After stirring for 5 min, DMF (5.15 mL, 66.5 mmol) was added, and the reaction mixture was stirred at −78° C. for 10 min. The reaction was quenched by adding saturated aq. $NH_4Cl$ (150 mL) and then was warmed to rt. Reaction mixture was further diluted with water (60 mL, enough for complete dissolution of white solid). THF was removed in vacuo. Aqueous residue was diluted with Et$_2$O (300 mL), the layers were separated, and the aqueous layer was extracted 2×Et$_2$O (70 mL each). Combined organic layers were dried over Na$_2$SO$_4$, filtered, and concentrated in vacuo. Crude residue was loaded onto the column as a solution in hexane. Chromatography was performed (330 g column, 0-20% EtOAc:hexanes over 50 min) to afford the title compound. Yield=12.7 g (96%). $^1$H NMR (400 MHz, Chloroform-d) δ 10.25 (s, 1H), 7.83 (d, J=2.3 Hz, 1H), 7.50-7.45 (m, 1H), 3.83 (t, J=6.2 Hz, 2H), 3.20 (t, J=6.2 Hz, 2H), 0.81 (s, 9H), −0.09 (s, 6H).

Alternative Conditions for Step 2: Reaction Conditions B (e.g., Entry 8, Below): 3-(2-{[tert-Butyl(dimethyl)silyl]oxy}ethyl)-6-chloropyridine-2-carbaldehyde To a 0° C. cooled solution of N,N-dimethylaminoethanol (4.430 mL, 44.08 mmol) in hexane (25.0 mL, 191 mmol) was added a 2.5 M solution of n-BuLi in hexane (36.7 mL, 91.7 mmol), dropwise over 30 min via syringe. The reaction mixture was stirred at 0° C. then cooled to −78° C. To the resulting mixture was added a solution of 5-(2-{[tert-butyl(dimethyl)silyl]oxy}ethyl)-2-chloropyridine (4.00 g, 14.7 mmol) in hexane (25.0 mL, 191 mmol), dropwise over 15 min, via syringe. The reaction mixture was stirred at −78° C. for 1 hour followed by addition of a solution of DMF (5.13 mL, 66.2 mmol) in THF (26 mL, 320 mmol), dropwise over 15 min, via syringe. The resulting solution was stirred at −78° C. for 1 hour then quenched with saturated aqueous NH$_4$Cl and extracted with EtOAc. The combined organic layers were washed with brine, dried over magnesium sulfate, filtered and concentrated to give 6.655 g of crude product as a brown oil. The crude material was purified by ISCO silica gel chromatography eluting with 0-5% EtOAc in hexanes to give 2.439 g of the title compound (55%). $^1$H NMR (400 MHz, Chloroform-d) δ 10.15 (s, 1H), 7.77 (d, J=8.1 Hz, 1H), 7.50 (d, J=8.1 Hz, 1H), 7.33 (s, 1H), 3.91 (t, J=5.9 Hz, 2H), 3.32 (t, J=5.9 Hz, 2H), 0.89 (s, 9H), −0.00 (s, 6H); LCMS (FA) M+1 300.1.

The compounds listed in the table below were prepared in an analogous fashion to that described above starting from the appropriate starting materials:

| Entry | Starting material | Reaction conditions for Step 2 | Product (Int #) | NMR Data |
|---|---|---|---|---|
| 1 | HO-CH$_2$C(O)-(2-Br,4-CF$_3$-phenyl) | A | TBSO-CH$_2$CH$_2$-(2-CHO,4-CF$_3$-phenyl) Int-16 | $^1$H NMR (400 MHz, DMSO-d6) δ 10.31 (s, 1H), 8.12 (d, J = 1.4 Hz, 1H), 7.96 (dd, J = 8.1, 1.6 Hz, 1H), 7.65 (d, J = 8.0 Hz, 1H), 3.82 (t, J = 6.1 Hz, 2H), 3.34-3.26 (m, 2H), 0.74 (s, 9H), −0.15 (s, 6H). |
| 2 | HO-CH$_2$C(O)-(2-Cl,6-Br-phenyl) | A | TBSO-CH$_2$CH$_2$-(2-Cl,6-CHO-phenyl) Int-17 | $^1$H NMR (400 MHz, Chloroform-d) δ 10.47 (s, 1H), 7.91 (dd, J = 7.7, 1.3 Hz, 1H), 7.71 (dd, J = 7.9, 1.3 Hz, 1H), 7.47-7.38 (m, 1H), 4.00-3.94 (m, 2H), 3.58-3.50 (m, 2H), 0.89 (s, 9H), −0.00 (s, 6H). |
| 3 | HO-CH$_2$-C(cyclopropyl)-C(O)-(2-Br-phenyl) | A | TBSO-CH$_2$-C(cyclopropyl)-(2-CHO-phenyl) Int-18 | $^1$H NMR (400 MHz, Chloroform-d) δ 10.75 (d, J = 0.7 Hz, 1H), 7.90 (dd, J = 7.8, 1.0 Hz, 1H), 7.55-7.45 (m, 2H), 7.39-7.32 (m, 1H), 3.65 (s, 2H), 1.04-0.99 (m, 2H), 0.90-0.85 (m, 2H), 0.78 (s, 9H), −0.16 (s, 6H). |
| 4 | H-C(O)-CH$_2$-(2-Br-phenyl) | A | TBSO-CH$_2$CH$_2$-(2-CHO-phenyl) Int-19 | $^1$H NMR (400 MHz, Chloroform-d) δ 10.38 (s, 1H), 7.94 (dd, J = 7.7, 1.2 Hz, 1H), 7.63-7.56 (m, 1H), 7.50-7.44 (m, 1H), 7.40 (d, J = 7.6 Hz, 1H), 3.94 (t, J = 6.4 Hz, 2H), 3.34 (t, = 6.4 Hz, 2H), 0.91 (s, 9H), −0.00 (s, 6H). |

-continued

| Entry | Starting material | Reaction conditions for Step 2 | Product (Int #) | NMR Data |
|---|---|---|---|---|
| 5 | methyl (2-methylthiazol-4-yl)acetate | A | Int-20 | ¹H NMR (400 MHz, Chloroform-d) δ 10.08 (s, 1H), 4.07-3.99 (m, 2H), 3.31 (t, J = 5.9 Hz, 2H), 2.82 (s, 3H), 0.88 (s, 9H), 0.00 (s, 6H). |
| 6 | 2-(2-bromo-4-fluorophenyl)acetic acid | A | Int-21 | N/A |
| 7 | 2-(2-bromo-4,5-difluorophenyl)acetic acid | A | Int-22 | N/A |
| 8 | 2-(6-chloropyridin-3-yl)acetic acid | B | Int-23 | ¹H NMR (400 MHz, Chloroform-d) δ 10.15 (s, 1H), 7.77 (d, J = 8.1 Hz, 1H), 7.50 (d, J = 8.1 Hz, 1H), (s, 1H), 3.91 (t, J = 5.9 Hz, 2H), 3.32 (t, J = 5.9 Hz, 2H), 0.89 (s, 9H), −0.00 (s, 6H) |

Example 12: 3-(2-{[tert-Butyl(dimethyl)silyl]oxy}ethyl)pyridine-2-carbaldehyde Int-24

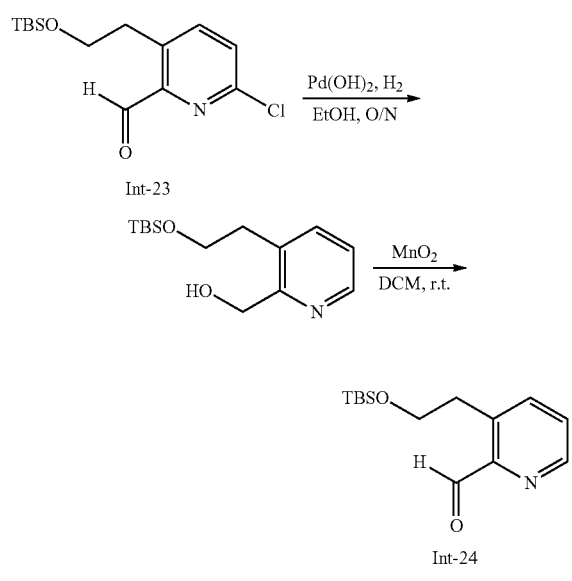

Step 1: [3-(2-{[tert-Butyl(dimethyl)silyl]oxy}ethyl)pyridin-2-yl]methanol

To a solution of 3-(2-{[tert-butyl(dimethyl)silyl]oxy}ethyl)-6-chloropyridine-2-carbaldehyde (Int-23, 2.299 g, 7.667 mmol) in ethanol (75.4 mL, 1290 mmol) was added NaHCO₃ (2.576 g, 30.67 mmol) and Pearlman's catalyst (palladium hydroxide on carbon)(10:90, palladium hydroxide:methane, 0.538 g, 0.383 mmol). The resulting mixture was purged with hydrogen gas, and then stirred at rt under a balloon of hydrogen gas for 15 h. The reaction mixture was filtered over a pad of Celite and the filtrate was concentrated to give crude product as a grey residue. The crude material was purified by ISCO silica gel chromatography eluting with 0-5% MeOH in DCM to give 1.955 g of the title compound (95%) as a clear oil. ¹H NMR (400 MHz, Chloroform-d) δ 8.54-8.49 (m, 1H), 7.66-7.54 (m, 1H), 7.31-7.22 (m, 1H), 4.84 (s, 2H), 3.87 (t, J=6.4 Hz, 2H), 2.81 (t, J=6.4 Hz, 2H), 0.88 (s, 9H), −0.00 (s, 6H); LCMS (FA) M+1 268.2

Step 2: 3-(2-{[tert-Butyl(dimethyl)silyl]oxy}ethyl)pyridine-2-carbaldehyde

To a solution of [3-(2-{[tert-butyl(dimethyl)silyl]oxy}ethyl)pyridin-2-yl]methanol (1.995 g, 7.460 mmol) in DCM (71.5 mL, 1120 mmol) was added MnO₂ (6.49 g, 74.7 mmol). The reaction mixture was stirred at rt for 20 h then filtered over a pad of Celite. The resulting filtrate was concentrated to give 2.421 g of crude product. The crude material was purified by ISCO silica gel chromatography eluting with 0-20% EtOAc in hexanes to give 1.308 g of the title compound (66%) as a clear oil. $^1$H NMR (400 MHz, Chloroform-d) δ 10.28 (d, J=0.5 Hz, 1H), 8.83-8.64 (m, 1H), 7.91-7.72 (m, 1H), 7.55-7.44 (m, 1H), 3.95 (t, J=6.1 Hz, 2H), 3.37 (t, J=6.1 Hz, 2H), 0.90 (s, 9H), −0.00 (s, 6H); LCMS (FA) M+1 266.2.

Example 13: 2-(3-{[tert-Butyl(dimethyl)silyl]oxy}propyl)-5-chlorobenzaldehyde Int-25

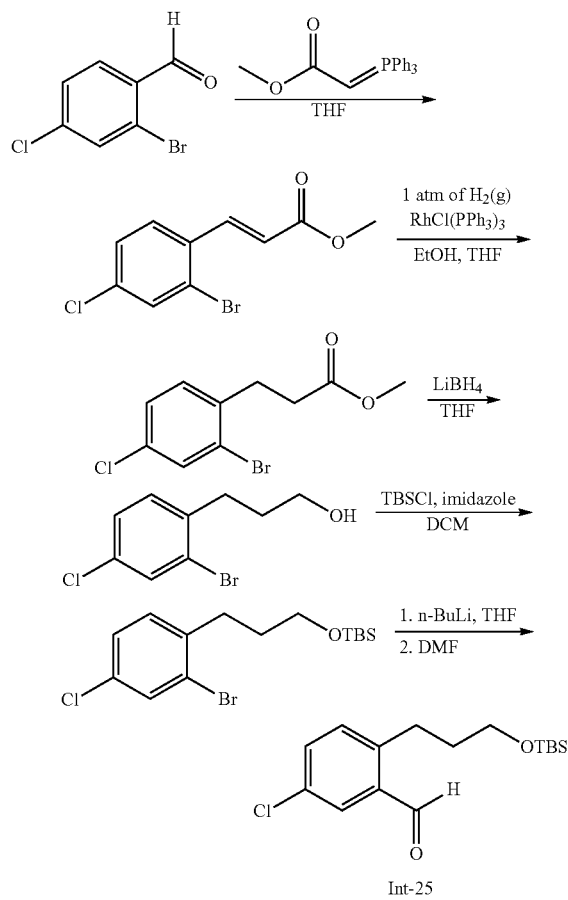

Int-25

Step 1: Methyl (2E)-3-(2-bromo-4-chlorophenyl)acrylate

To a flask was added 2-bromo-4-chlorobenzaldehyde (3.00 g, 0.0137 mol) dissolved in THF (40 mL, 0.5 mol). The solution was cooled to 0° C. and (carbomethoxymethylene)triphenylphosphorane (5.26 g, 0.0157 mol) was added. The resulting mixture was stirred at 0° C. for 30 min and overnight at RT. Celite was then added to the reaction followed by concentration to dryness. The residue was solid loaded and purified by ISCO silica gel chromatography (80 g column, eluting with 0-30-50% EtOAc/Hex. over 25 min) to give 3.15 g (84%) of the title compound as a 2:1 mixture of trans and cis. LCMS (FA): m/z=275.2 (M+H).

Step 2: Methyl 3-(2-bromo-4-chlorophenyl)propanoate

Into a 1-neck round-bottom flask was added methyl (2E)-3-(2-bromo-4-chlorophenyl)acrylate (1.78 g, 6.46 mmol) dissolved in ethanol (20.0 mL, 342 mmol) and THF (10.0 mL, 123 mmol). Tris(triphenylphosphine)rhodium(I) chloride (0.598 g, 0.646 mmol) was added and the mixture was purged with a H$_2$ gas balloon (3×). The resulting mixture was then stirred at rt over the weekend under a balloon of H$_2$ gas. The balloon was removed and the mixture was flushed with argon. Celite was then added to the reaction mixture and concentrated to dryness. The residue was solid loaded and purified by ISCO silica gel chromatography (40 g column, eluting with 0-30-50% EtOAc/Hex. over 20 min) to give 1.62 g (90%) of the title compound. $^1$H NMR (400 MHz, Chloroform-d) δ 7.55 (d, J=1.9 Hz, 1H), 7.24-7.17 (m, 2H), 3.68 (s, 3H), 3.04 (t, J=7.7 Hz, 2H), 2.63 (t, J=7.7 Hz, 2H).

Steps 3 and 4: 2-(3-{[tert-Butyl(dimethyl)silyl]oxy}propyl)-5-chlorobenzaldehyde These steps were performed in analogous fashion to Example 11, using LiBH$_4$ instead of BH3/THF in Step 1, and using Reaction Conditions A in Step 2. $^1$H NMR (400 MHz, Chloroform-d) δ 10.27 (s, 1H), 7.81 (d, J=2.3 Hz, 1H), 7.46 (dd, J=8.2, 2.3 Hz, 1H), 7.25-7.22 (m, 1H), 3.64 (t, J=6.0 Hz, 2H), 3.11-3.04 (m, 2H), 1.86-1.76 (m, 2H), 0.91 (d, J=2.6 Hz, 9H), 0.06 (s, 6H).

Example 14: 3-(2-{[tert-Butyl(dimethyl)silyl]oxy}ethyl)-6-(trifluoromethyl)pyridine-2-carbaldehyde Int-26

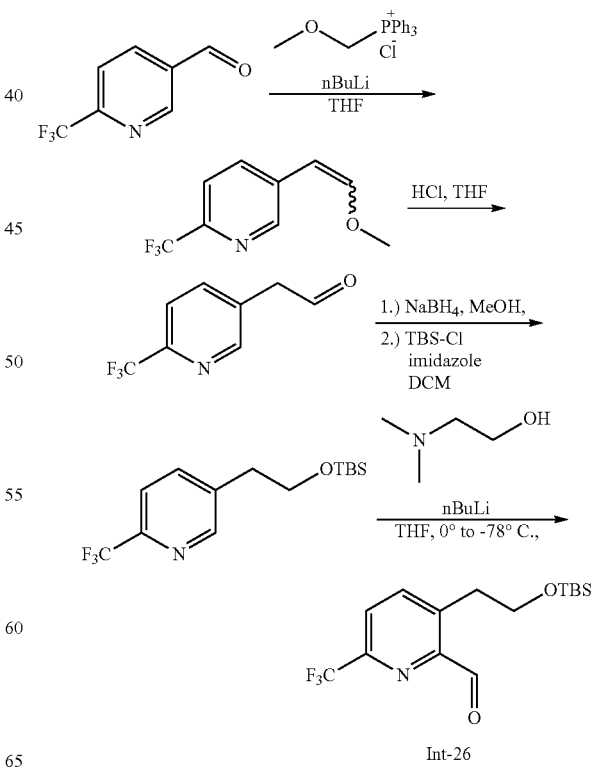

Int-26

Step 1: 5-[(E)-2-Methoxyvinyl]-2-(trifluoromethyl) pyridine and 5-[(Z)-2-methoxyvinyl]-2-(trifluoromethyl)pyridine (Methoxymethyl)triphenylphosphonium chloride (11.7 g, 34.3 mmol) was placed in a 250 ml two-neck round bottom flask under an atmosphere of argon. THF (1.00e2 ml, 1230 mmol) was added and the suspension was cooled at −78° C. 2.5 M of n-BuLi in hexane (12.8 ml, 32.0 mmol) was added drop wise. The reaction turned an orange color but remained a suspension. The reaction was warmed at 0° C. and turned a dark orange color and presented as a solution which was stirred at 0° C. for 30 min under an atmosphere of argon. 5-formyl-2-(trifluoromethyl)pyridine (4.00 g, 22.8 mmol) in THF (10.0 ml, 123 mmol) was added dropwise quickly to the solution at 0° C. The reaction was stirred for 30 min at 0° C. under an atmosphere of argon. The reaction was warmed to rt and quenched. TLC (10% EtOAc in hexanes) showed no starting material remaining with a major spot just above it. The reaction was quenched with water and saturated NH$_4$Cl. The reaction was extracted 3× with DCM. The combined organics were washed with brine, dried over Na$_2$SO$_4$, filtered and concentrated in vacuo. The residue was loaded with DCM onto a 220 g gold isco column (10% EtOAc in hexanes isocratic 100 ml/min) to give the product as a 1:1 mixture of the title products as a yellow oil. LCMS (FA) 203.9 (m+1).

Step 2: [6-(Trifluoromethyl)pyridin-3-yl]acetaldehyde

To a solution of 5-[(Z)-2-methoxyvinyl]-2-(trifluoromethyl)pyridine (1.30 g, 6.4 mmol) and 5-[(E)-2-methoxyvinyl]-2-(trifluoromethyl)pyridine (1.30 g, 6.4 mmol) in THF (100 mL, 1000 mmol) was added 1N HCl. The reaction was stirred overnight. The reaction was basified by addition of saturated NaHCO$_3$ and the mixture was extraction with EtOAc (×3). The combined organic layers were dried over Na$_2$SO$_4$, filtered, and concentrated in vacuo. The residue was purified via column chromatography (80 g ISCO, 30% EtOAc in hexanes isocratic) to give the title compound as a yellow oil. $^1$H NMR (400 MHz, Chloroform-d) δ 9.85 (s, 1H), 8.59 (s, 1H), 7.79-7.66 (m, 2H), 3.88 (s, 2H).

Steps 3 and 4: 3-(2-{[tert-Butyl(dimethyl)silyl]oxy}ethyl)-6-(trifluoromethyl)pyridine-2-carbaldehyde These steps were performed in analogous fashion to Example 11, using NaBH$_4$ instead of BH$_3$/THF in Step 1, and using Reaction Conditions B in Step 2. LCMS (FA) 335.2 (M+1)

Example 15: 2-(2-{[tert-Butyl(dimethyl)silyl]oxy}ethyl)thiophene-3-carbaldehyde Int-27

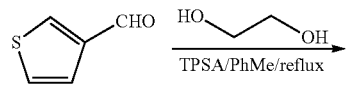

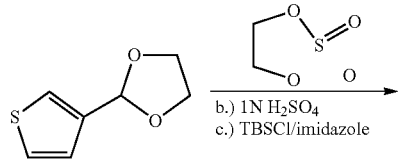

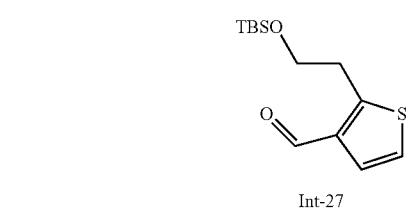

Step 1: 3-Thiophenecarboxaldehyde ethylene acetal

3-Thiophenecarboxaldehyde (5.8341 g, 52.020 mmol) and 1,2-ethanediol (9.6863 g, 156.06 mmol) were added to toluene (180 mL, 1700 mmol), then toluenesulfonic acid (0.35832 g, 2.0808 mmol) was added to the solution. The reaction was stirred at reflux for 24 hrs. The reaction mixture was then cooled to rt and washed with 3×40 ml water. The organic layer was concentrated to yield 7.34 g (90%) of the title compound as a crude oil. $^1$H NMR (400 MHz, Chloroform-d) δ 7.44 (ddd, J=3.0, 1.2, 0.6 Hz, 1H), 7.34 (dd, J=5.0, 3.0 Hz, 1H), 7.18 (dd, J=5.0, 1.2 Hz, 1H), 5.93 (s, 1H), 4.15-4.10 (m, 2H), 4.07-4.01 (m, 2H).

Step 2: 2-(2-{[tert-Butyl(dimethyl)silyl]oxy}ethyl) thiophene-3-carbaldehyde A solution of 3-thiophenecarboxaldehyde ethylene acetal (4.33 g, 27.7 mmol) in THF (130.0 mL, 1603 mmol) was cooled to −78° C., at which point 2.50 M of n-BuLi in hexane (17.74 mL, 44.35 mmol) was added. A solution of ethylenesulfate (3.7846 g, 30.492 mmol) in THF (10.0 mL, 123 mmol) was added solution and the reaction was stirred for 30 min at −78° C. The reaction was concentrated to ~20% of the original volume in vacuo, and then a solution of 6 ml 98% H$_2$SO$_4$ in 30 ml water was added to the mixture. This mixture was then stirred at 75° C. overnight. The solution was added slowly to 150 ml saturated NaHCO$_3$ aqueous solution to neutralize and then extracted with 3×50 ml DCM. The combined organic layers were concentrated to dryness, and the residue was dissolved into DCM (100 mL, 2000 mmol), to which were added 1H-imidazole (3.774 g, 55.44 mmol) and tert-butyldimethylsilyl chloride (5.013 g, 33.26 mmol). The reaction was stirred for 30 min, and poured into 60 ml water. The aqueous was extracted with 2×40 mL DCM. The combined organic layers were concentrated in vacuo and purified by flash column (80 g, eluent was 0-25% EtOAc in hexane over 15 min) to afford 3.102 g (41%) of the title compound. $^1$H NMR (400 MHz, Chloroform-d) δ 10.04 (s, 1H), 7.43 (d, J=5.4 Hz, 1H), 7.15 (dd, J=5.4, 0.5 Hz, 1H), 3.89 (t, J=6.0 Hz, 2H), 3.40 (t, J=6.0 Hz, 2H), 0.88 (s, 9H), −0.00 (s, 6H).

Example 16: 1-(2-{[tert-Butyl(dimethyl)silyl]
oxy}ethyl)-4-methyl-1H-imidazole-2-carbaldehyde
(Int-28) and 1-(2-{[tert-Butyl(dimethyl)silyl]
oxy}ethyl)-5-methyl-1H-imidazole-2-carbaldehyde
(Int-29)

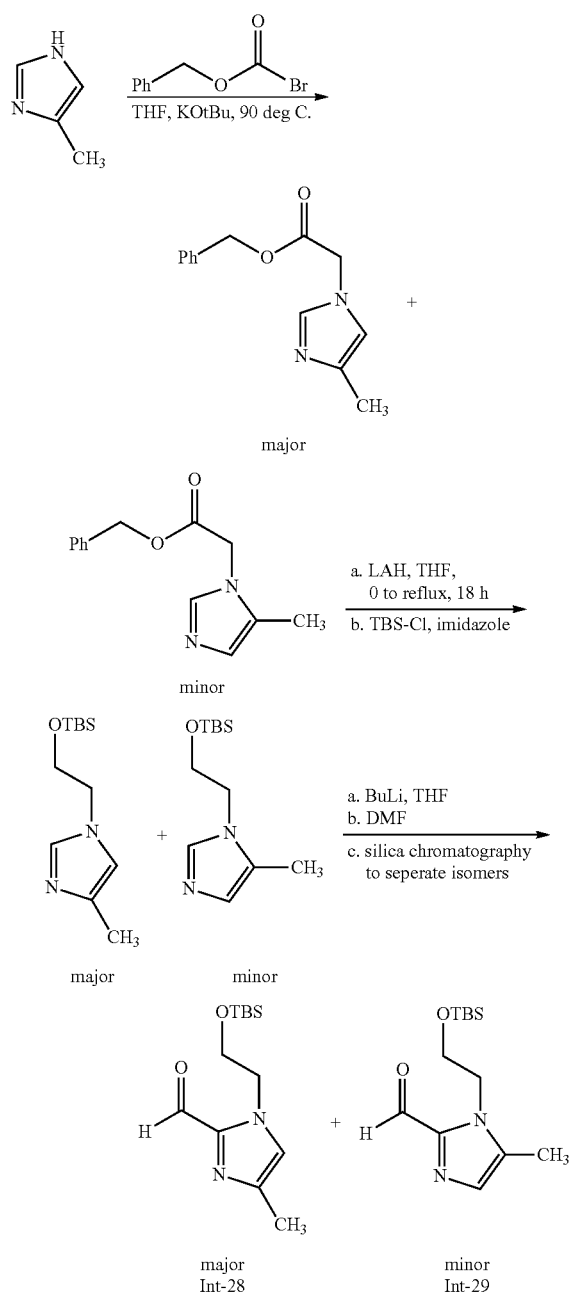

Step 1: Benzyl (4-methyl-1H-imidazol-1-yl)acetate
and Benzyl (5-methyl-1H-imidazol-1-yl)acetate An oven-dried 500 mL 2-neck round bottom flask under nitrogen was charged with 4-methylimidazole (2.00 g, 24.4 mmol) and 2-methyltetrahydrofuran (10 mL), then placed in a 70° C. oil bath. Added 1.00 M of potassium tert-butoxide in THF (26.8 mL, 26.8 mmol) in a stream. Added benzyl 2-bromoacetate (4.25 mL, 26.8 mmol) in a single portion. After 30 min quenched by adding ice. Poured into saturated NaHCO$_3$; extracted three times with EtOAc; washed combined organic portions with brine; dried with anhydrous sodium sulfate; filtered, and concentrated in vacuo. An oil remained. Residue was subjected to ISCO chromatography eluting with a DCM/MeOH gradient to afford a brown oil (2.06 g). LCMS indicates this substance is a mixture of the title compounds. Used as is in next step. LCMS: (AA) M+1 231.1

Steps 2 and 3: 1-(2-{[tert-Butyl(dimethyl)silyl]
oxy}ethyl)-4-methyl-1H-imidazole-2-carbaldehyde
and 1-(2-{[tert-Butyl(dimethyl)silyl]oxy}ethyl)-5-methyl-1H-imidazole-2-carbaldehyde These steps were performed in analogous fashion to Example 11, using lithium tetrahydroaluminate instead of BH$_3$/THF in Step 1, and using Reaction Conditions A in Step 2. Major isomer: $^1$H NMR (400 MHz, Chloroform-d) δ 9.74 (s, 1H), 6.98 (s, 1H), 4.48-4.43 (m, 2H), 3.88-3.84 (m, 2H), 2.29 (s, 3H), 0.83 (s, 9H), −0.09 (s, 6H).

Example 17: 1-(2-{[tert-Butyl(dimethyl)silyl]
oxy}ethyl)-4-(trifluoromethyl)-1H-imidazole-2-carbaldehyde Int-30

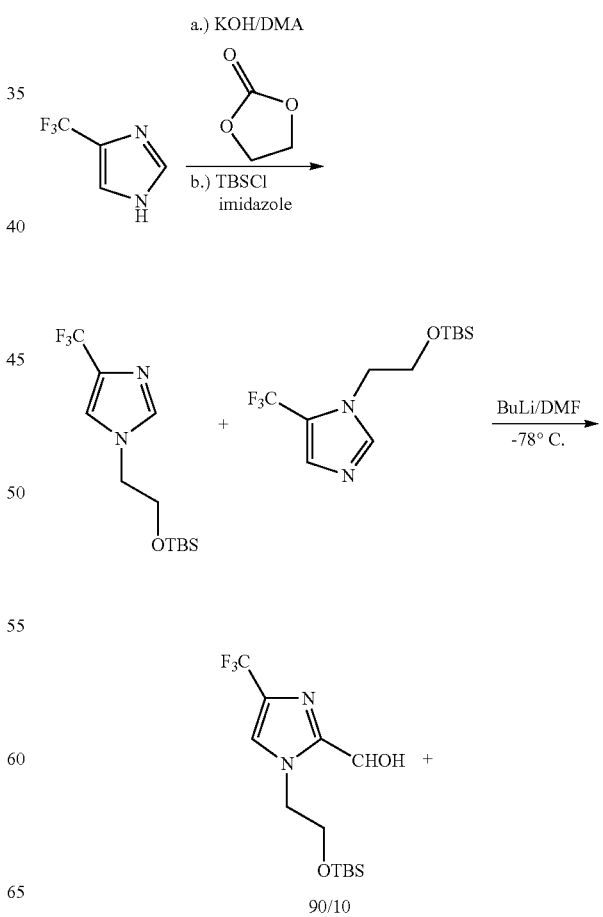

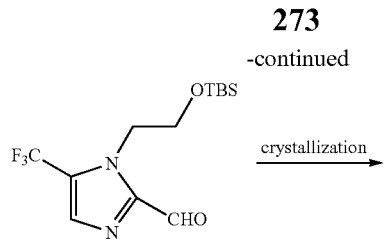

Int-30

Step 1: 1-(2-{[tert-Butyl(dimethyl)silyl]oxy}ethyl)-4-(trifluoromethyl)-1H-imidazole (A) and 1-(2-{[tert-Butyl(dimethyl)silyl]oxy}ethyl)-5-(trifluoromethyl)-1H-imidazole To a solution of 4-(trifluoromethyl)-1H-imidazole (6.233 g, 45.80 mmol) in N,N-dimethylacetamide (30.0 mL, 323 mmol) was added ethylene carbonate (4.840 g, 54.97 mmol) and potassium hydroxide (0.2570 g, 4.580 mmol). The reaction was heated at 160° C. for 2 hrs, and then cooled to 0° C. To the cooled mixture were added DCM (80.0 mL, 1250 mmol) and 1H-imidazole (6.237 g, 91.61 mmol), and then tert-butyldimethylsilyl chloride (8.975 g, 59.55 mmol) was added slowly to the solution. The reaction was stirred at rt for an additional 2 h. The mixture was then poured into 150 ml water, and extracted with 2×50 ml DCM. Concentrated the organic layers in vacuo, and purified by flash column (80 g). The products contained regio isomers (A/B=90/10 by NMR) which couldn't be separated by chromatography. Total recovery of mixture: 9.70 g (72%) as an oil. The product was used as is in the next step.

Step 2: 1-(2-{[tert-Butyl(dimethyl)silyl]oxy}ethyl)-4-(trifluoromethyl)-1H-imidazole-2-carbaldehyde The 90:10 mixture of 1-(2-{[tert-butyl(dimethyl)silyl]oxy}ethyl)-4-(trifluoromethyl)-1H-imidazole (9.50 g, 32.3 mmol) and 1-(2-{[tert-butyl(dimethyl)silyl]oxy}ethyl)-5-(trifluoromethyl)-1H-imidazole (0.95 g, 3.2 mmol) isolated above was dissolved into THF (150.0 mL, 1849 mmol), and the solution was cooled to −78° C. 2.50 M of n-BuLi in hexane (20.65 mL, 51.63 mmol) was added to the solution at −78° C. over 15 min, and then DMF (7.784 g, 106.5 mmol) was added to the solution. The reaction was stirred for 30 min, at which point acetic acid (3.670 mL, 64.54 mmol) was added and the mixture was allowed to warm to rt. The solution was poured into 200 ml water and extracted 3×150 ml EtOAc. The organic layers were combined and concentrated, and then purified by ISCO column (80 g, eluent was 0-35% EtOAc in hexane over 15 min) to afford 7.35 g crude product which contained a 90:10 mixture of regioisomers. The crude product was the crystallized from 30% DCM in hexane to afford 3.452 g (33%) of the title compound as a single regioisomer. $^1$H NMR (400 MHz, Chloroform-d) δ 9.92 (d, J=0.9 Hz, 1H), 7.63 (s, 1H), 4.69-4.57 (m, 2H), 4.04-3.91 (m, 2H), 0.90 (s, 9H), −0.00 (s, 6H). LCMS (AA) M+1 323

Example 18: 2-(2-{[tert-Butyl(dimethyl)silyl]oxy}ethyl)-5-chloro-3-furaldehyde Int-31

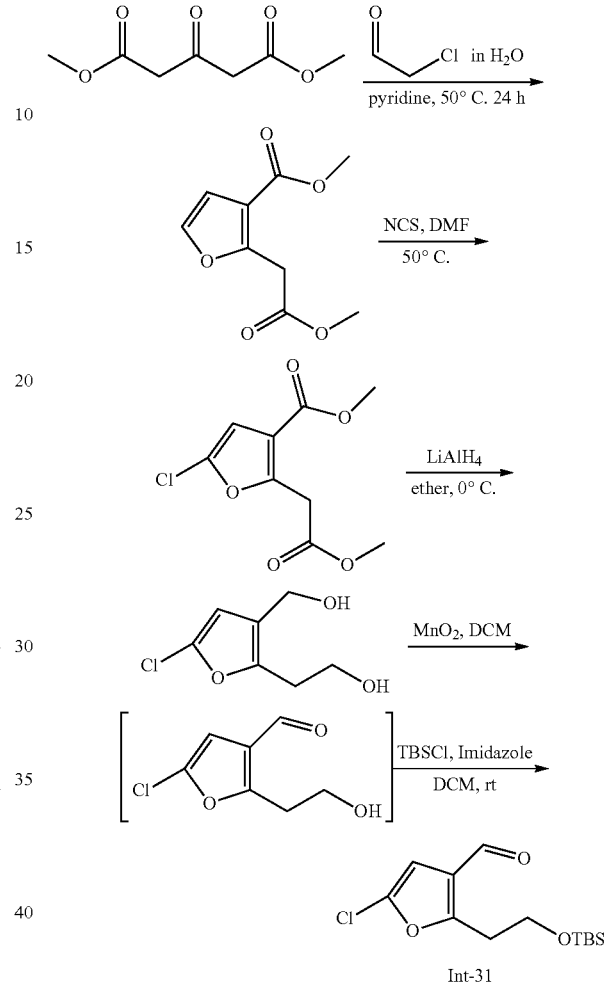

Step 1: Methyl 3-(methoxycarbonyl)-2-furanacetate (Methyl 3-(methoxycarbonyl)-2-furanacetate was prepared according to the procedure reported in M. Tada, et al. Chem Pharm. Bull. 42(10), 2167-2169, 1994. A solution of 50% chloroacetaldehyde in water (4.64 mL, 36.5 mmol) was added dropwise to a solution of dimethyl 1,3-acetonedicarboxylate (5.00 g, 28.7 mmol) in pyridine (10.0 mL, 124 mmol) with stirring at rt. A slight exotherm was observed. The orange solution was then heated at 50° C. under argon for 18 h. The reaction was cooled to rt and partitioned between water and EtOAc. The organic layer was washed sequentially with 1N HCl, saturated aqueous NaHCO$_3$, 1N NaOH and brine. The organic layer was then dried over Na$_2$SO$_4$, filtered, and concentrated. The crude residue was purified by silica gel column chromatography (0 to 25% EtOAc in hexane) to give 3.386 g (60%) of product as a colorless oil. $^1$H NMR (400 MHz, Chloroform-d) δ 7.34 (d, J=2.0 Hz, 1H), 6.70 (d, J=1.9 Hz, 1H), 4.08 (s, 2H), 3.83 (s, 3H), 3.73 (s, 3H); LCMS (AA): (M+H) 199.1

Step 2: Methyl 5-chloro-2-(2-methoxy-2-oxoethyl)-3-furoate

In a 100 mL round bottom flask equipped with reflux condenser, a solution of methyl 3-(methoxycarbonyl)-2-furanacetate (2.3280 g, 11.747 mmol) and N-chlorosuccinimide (1.57 g, 11.7 mmol) in DMF (23.6 mL) was stirred at 50° C. for 2 h. N-chlorosuccinimide (1.57 g, 11.7 mmol) was added and the reaction was stirred at 50° C. for 1.5 h. The reaction was quenched with water, extracted with EtOAc, washed with saturated Na$_2$SO$_3$, brine, dried over Na$_2$SO$_4$, filtered, and concentrated. The crude residue was purified by silica gel column chromatography (0 to 15% EtOAc in hexane) to obtain 2.062 g (75%) of product as a colorless oil. $^1$H NMR (400 MHz, Chloroform-d) δ 6.48 (s, 1H), 4.04 (s, 2H), 3.82 (s, 3H), 3.74 (s, 3H); LCMS (AA): (M+H) 233.0/235.0

Step 3: 2-[5-Chloro-3-(hydroxymethyl)-2-furyl]ethanol

To a solution of methyl 5-chloro-2-(2-methoxy-2-oxoethyl)-3-furoate (2.048 g, 8.804 mmol) in ether (7.931 mL) at 0° C. under argon was added 1.0 M of lithium tetrahydroaluminate in THF (26.50 mL, 26.50 mmol). The reaction was stirred for 3 h at rt. Then the reaction was cooled to 0° C. and quenched with water and 1N HCl. The layers were separated, and the aqueous layer was extracted with EtOAc (2×), and the combined extracts were washed with brine, dried over Na$_2$SO$_4$, filtered, and concentrated. The crude residue was purified by silica gel column chromatography (0 to 10% MeOH in DCM, monitored by TLC with UV and KMnO4 stain) to obtain 1.009 g (65%) of product as a brown oil. $^1$H NMR (400 MHz, Chloroform-d) δ 6.14 (s, 1H), 4.42 (s, 2H), 3.83 (t, J=5.6 Hz, 2H), 2.89 (t, J=5.7 Hz, 2H), 2.22 (s, 2H); LCMS (AA): (M−OH) 159.0

Step 4: 2-(2-{[tert-Butyl(dimethyl)silyl]oxy}ethyl)-5-chloro-3-furaldehyde

To a solution of 2-[5-chloro-3-(hydroxymethyl)-2-furyl]ethanol (0.796 g, 4.51 mmol) in DCM (167 mL) was added MnO$_2$ (3.92 g, 45.1 mmol) at rt, and the mixture was stirred for 2 h. MnO$_2$ (3.92 g, 45.1 mmol) was added and the mixture was stirred at rt for 2.5 h. The mixture was filtered through a pad of Celite and the filter cake was washed with EtOAc. The filtrate was transferred to a 500 mL round bottom flask, and the volume of solvent was reduced until ~100 mL remained to provide a solution of 5-chloro-2-(2-hydroxyethyl)-3-furaldehyde. LCMS (AA): (M+H) 175.0/177.0 To this solution of 5-chloro-2-(2-hydroxyethyl)-3-furaldehyde was added 1H-imidazole (0.614 g, 9.01 mmol), followed by tert-butyldimethylsilyl chloride (1.02 g, 6.76 mmol). The resulting mixture was stirred at rt under argon for several min, and then stored in the refrigerator for 17 h. The reaction mixture was diluted with water and extracted with EtOAc (2×). The combined organic layers were washed with water and brine, dried over Na$_2$SO$_4$, filtered, and concentrated. The crude oil was purified by silica gel column chromatography (0 to 10% EtOAc in hexane) to obtain 513 mg (39%) of 2-(2-{[tert-butyl(dimethyl)silyl]oxy}ethyl)-5-chloro-3-furaldehyde as a colorless oil. $^1$H NMR (400 MHz, Chloroform-d) δ 9.85 (s, 1H), 6.49 (s, 1H), 3.89 (t, J=6.0 Hz, 2H), 3.11 (t, J=6.0 Hz, 2H), 0.83 (s, 9H), −0.03 (s, 6H); LCMS (AA): (M+H) 289.1/291.1

Example 19: 5-Chloro-2-{2-[(4-methoxybenzyl)sulfanyl]ethyl}benzaldehyde Int-32

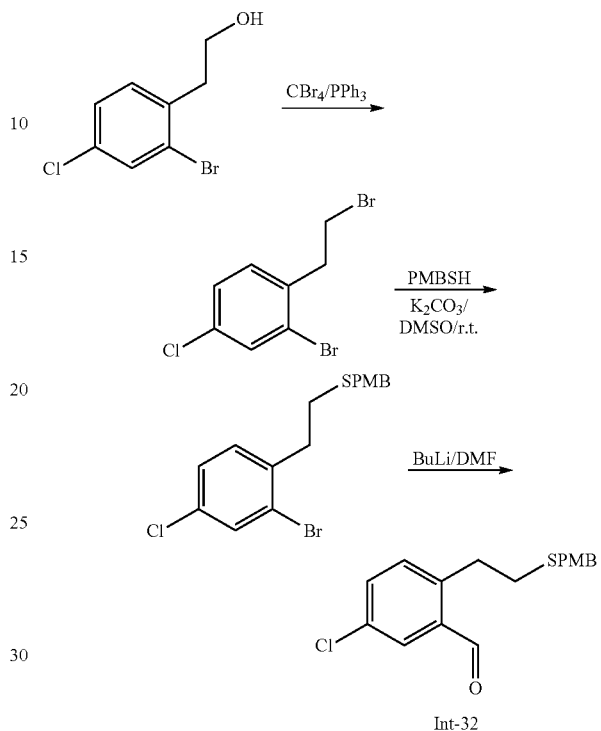

Step 1: 2-Bromo-1-(2-bromoethyl)-4-chlorobenzene 2-(2-bromo-4-chlorophenyl)ethanol (1.97 g, 8.36 mmol) and carbon tetrabromide (3.61 g, 10.9 mmol) were dissolved into DCM (30.0 mL, 468 mmol), then triphenylphosphine (3.29 g, 12.5 mmol) was added at rt. The reaction was stirred at rt for 2 hrs. To the reaction mixture was added 100 mL hexane with stirring, at which point a precipitate formed that was removed by filtration. The filtrate was concentrated and purified by flash column (80 g column, 100% hexane as eluent) to provide 1.92 g (77%) of the title compound. $^1$H NMR (400 MHz, Chloroform-d) δ 7.55-7.41 (s, 1H), 7.23-7.15 (d, J=8.2 Hz, 1H), 7.13 (d, J=8.2 Hz, 1H), 3.49 (t, J=7.3 Hz, 2H), 3.18 (t, J=7.3 Hz, 2H).

Step 2: 2-Bromo-4-chloro-1-{2-[(4-methoxybenzyl)sulfanyl]ethyl}benzene4-({[2-(2-bromo-4-chlorophenyl)ethyl]sulfanyl}methyl)phenyl methyl ether To a solution of 2-bromo-1-(2-bromoethyl)-4-chlorobenzene (2.47 g, 8.28 mmol) and p-methoxy-α-toluenethiol (1.3262 mL, 9.5190 mmol) in dimethyl sulfoxide (6.00 mL, 84.5 mmol) was added potassium carbonate (2.2880 g, 16.555 mmol) and the reaction was stirred at rt for 72 h. The reaction was quenched by pouring into 40 ml water, the layers were separated, and the aqueous layer was extracted 2×15 ml DCM. The combined organic layers were concentrated and purified by flash column (80 g, eluent 0-15% EtOAc in hexane for 15 min) to give 1.95 g (64%) of title compound. $^1$H NMR (400 MHz, Chloroform-d) δ 7.48 (s, 1H), 7.23-7.13 (m, 3H), 7.06 (d, J=8.2 Hz, 1H), 6.80 (d, J=8.5 Hz, 2H), 3.75 (s, 3H), 3.64 (s, 2H), 2.93-2.79 (t, J=7.3 Hz, 2H), 2.65-2.51 (t, J=7.3 Hz, 2H).

Step 3: 5-Chloro-2-{2-[(4-methoxybenzyl)sulfanyl]ethyl}benzaldehyde

A solution of 2-bromo-4-chloro-1-{2-[(4-methoxybenzyl)sulfanyl]ethyl}benzene4-({[2-(2-bromo-4-chlorophenyl)ethyl]sulfanyl}methyl)phenyl methyl ether (1.102 g, 2.964 mmol) in THF (40.0 mL, 493 mmol) was cooled to −78° C. 2.50 M of n-BuLi in hexane (2.016 mL, 5.040 mmol) was added and the mixture was stirred at −78° C. for 10 min. DMF (1.148 mL, 14.82 mmol) was then added and the mixture was stirred at −78° C. for 5 min. The mixture warmed to rt over 10 min and then the solution was poured into 30 ml brine. The layers were separated, and the aqueous layer was extracted 3×40 ml EtOAc. The combined organic layers were concentrated and the residue was chromatographed (hexane/EtOAc=3/1 as eluent) to give 0.4572 g (48%) of the title compound. $^1$H NMR (400 MHz, Chloroform-d) δ 10.17 (s, 1H), 7.79 (s, 1H), 7.48 (d, J=8.1 Hz, 1H), 7.21 (t, J=7.6 Hz, 3H), 6.86 (d, J=7.9 Hz, 2H), 3.84-3.78 (s, 3H), 3.69 (s, 2H), 3.22 (t, J=7.3 Hz, 2H), 2.67 (t, J=7.3 Hz, 2H).

Example 20: 2-(Trifluoromethyl)-5-{2-[(triisopropylsilyl)oxy]ethyl}-1,3-thiazole-4-carbaldehyde Int-33

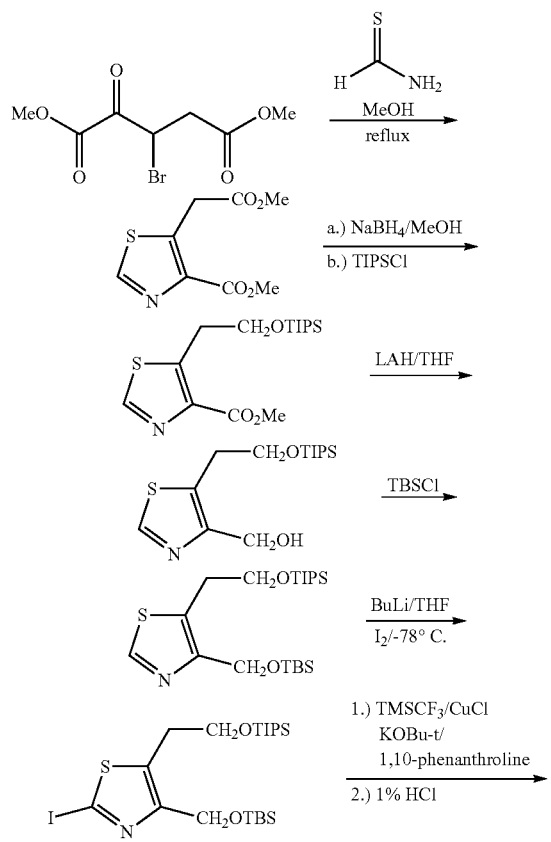

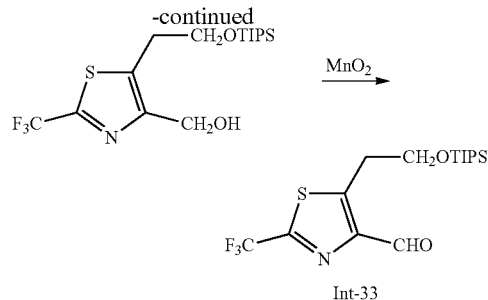

Step 1: Methyl 5-(2-methoxy-2-oxoethyl)-1,3-thiazole-4-carboxylate

To a solution of dimethyl 3-bromo-2-oxopentanedioate (7.52 g, 29.7 mmol) in methanol (100 mL, 2000 mmol) was added methanethioamide (2.72 g, 44.6 mmol). The reaction was stirred at reflux for 2 hrs. The reaction mixture was concentrated in vacuo, then 25 ml THF was added to the residue. 40 ml hexane was added to the solution with stirring, at which point mixture was filtered and the filtrate was concentrated and purified by flash column (80 g, eluent was 30-90% EtOAc in hexane for 20 min) to afford 4.18 g (65%) of title compound. $^1$H NMR (400 MHz, Chloroform-d) δ 8.73 (s, 1H), 4.37 (s, 2H), 3.95 (s, 3H), 3.77 (s, 3H).

Step 2: Methyl 5-{2-[(triisopropylsilyl)oxy]ethyl}-1,3-thiazole-4-carboxylate

To a 0° C. solution of methyl 5-(2-methoxy-2-oxoethyl)-1,3-thiazole-4-carboxylate (1.45 g, 7.75 mmol) and 2,6-lutidine (1.347 mL, 11.63 mmol) in DCM (60.0 mL, 936 mmol) was added triisopropylsilyl triflate (2.293 mL, 8.531 mmol) and the mixture was stirred at rt overnight. The reaction was quenched by addition of saturated NH$_4$Cl (50 mL), and then the resulting mixture was extracted with DCM (70 mL×3). The combined organic layers were washed with brine, dried over Na$_2$SO$_4$, filtered, and concentrated in vacuo. The residue was purified by ISCO silica gel column chromatography (eluent was 0-50% EtOAc in hexane) to afford 1.553 g (51%) of the title compound. $^1$H NMR (400 MHz, Chloroform-d) δ 8.66 (s, 1H), 3.96 (s, 3H), 3.95 (t, 2H), 3.57-3.52 (t, 2H).

Step 3: (5-{2-[(Triisopropylsilyl)oxy]ethyl}-1,3-thiazol-4-yl)methanol

To a solution of methyl 5-{2-[(triisopropylsilyl)oxy]ethyl}-1,3-thiazole-4-carboxylate (1.70 g, 4.95 mmol) in THF (60.0 mL, 7.40E2 mmol) was added lithium tetrahydroaluminate (0.2817 g, 7.422 mmol) slowly at 0° C. The reaction was stirred at 0° C. for 30 min, and then allowed to warm to rt with stirring for 2 hrs. The solution was poured slowly into a mixture of 80 ml water and 5 ml acetic acid with stirring. The layers were separated, and the aqueous layer was extracted with 3×70 ml EtOAc. The organic layer was concentrated and purified by flash column (40 g, eluent was 0-90% EtOAc in hexane) to afford the title compound (0.8090 g, 52%). $^1$H NMR (400 MHz, Chloroform-d) δ 8.62 (s, 1H), 3.95 (m, J=10.1, 4.2 Hz, 5H), 3.51 (t, J=5.6 Hz, 2H), 1.08-0.94 (m, 21H).

Step 4: 4-({[tert-Butyl(dimethyl)silyl]oxy}methyl)-5-{2-[(triisopropylsilyl)oxy]ethyl}-1,3-thiazole To a round bottom flask was added (5-{2-[(triisopropylsilyl)oxy]ethyl}-1,3-thiazol-4-yl)methanol (0.8090 g, 2.564 mmol), 1H-imidazole (0.5236 g, 7.691 mmol), 60 ml DCM, and tert-butyldimethylsilyl chloride (0.6183 g, 4.102 mmol). The resulting reaction mixture was stirred at rt for 4 hrs. The mixture was concentrated in vacuo, and the residue was suspended in EtOAc. The mixture was filtered through Celite and the filtrate was concentrated in vacuo. The residue was chromatographed (40 g column, 0-30% EtOAc in hexane) to provide 0.8043 g (73%) of the title compound as an oil. $^1$H NMR (400 MHz, Chloroform-d) δ 8.48 (s, 1H), 4.74 (s, 2H), 3.80 (t, J=6.2 Hz, 2H), 3.04 (t, J=6.2 Hz, 2H), 0.98-0.93 (m, 21H), 0.81 (s, 9H), 0.00 (s, 6H).

Step 5: 4-({[tert-Butyl(dimethyl)silyl]oxy}methyl)-2-iodo-5-{2-[(triisopropylsilyl)oxy]ethyl}-1,3-thiazole A solution of 4-({[tert-butyl(dimethyl)silyl]oxy}methyl)-5-{2-[(triisopropylsilyl)oxy]ethyl}-1,3-thiazole (0.4320 g, 1.005 mmol) into THF (20.0 mL, 246 mmol) was cooled to −78° C. 2.50 M of n-BuLi in hexane (1.206 mL, 3.015 mmol) was added followed by a solution of iodine (0.3316 g, 1.307 mmol) in 2 ml THF and the reaction was stirred for 30 min at −78° C. A solution of acetic acid (0.1811 g, 3.015 mmol) in 1 ml THF was added to the reaction, and then the solvent was removed in vacuo. The residue was purified by flash column (24 g column, eluent was 0-10% EtOAc in hexane) to provide 0.4210 g (75%) of the title compound. $^1$H NMR (400 MHz, Chloroform-d) δ 4.70 (s, 2H), 3.76 (t, J=6.0 Hz, 2H), 3.02 (t, J=6.0 Hz, 2H), 1.00-0.95 (m, 21H), 0.81 (s, 9H), −0.00 (s, 6H).

Step 6: [2-(Trifluoromethyl)-5-{2-[(triisopropylsilyl)oxy]ethyl}-1,3-thiazol-4-yl]methanol Potassium tert-butoxide (0.4258 g, 3.794 mmol), o-phenanthroline (0.6837 g, 3.794 mmol) and cuprous monochloride (0.3756 g, 3.794 mmol) were added to a 100 ml flask which was dried by heat gun. The flask was sealed with a rubber stopper and purged with vacuum and then backfilled with argon. DMF (8.00 mL, 103 mmol) was added to the flask and the mixture was stirred at rt for 30 min, at which point (trifluoromethyl)trimethylsilane (0.5929 mL, 3.794 mmol) was added and the reaction was stirred for 30 min at rt. Next, a solution of 4-({[tert-butyl(dimethyl)silyl]oxy}methyl)-2-iodo-5-{2-[(triisopropylsilyl)oxy]ethyl}-1,3-thiazole (0.4217 g, 0.7588 mmol) in 2 ml DMF was added to the mixture, and the reaction was stirred at 50° C. for 1 hr. The reaction was poured into 100 ml water, the layers were separated, and the aqueous layer was extracted 3×50 ml DCM. The combined organic layers were concentrated in vacuo. The resulting residue was dissolved into 30 ml 1% HCl methanol solution, and the reaction was stirred at rt for 30 min. The solution was then poured into 60 ml saturated NaCl, the layers were separated, and the aqueous layer was extracted 3×40 ml DCM. The combined organic layers were concentrated in vacuo and the resulting residue was purified by flash column (24 g column, eluent was 0-20% EtOAc in hexane) to provide 0.1732 g (60%) of the title compound. $^1$H NMR (400 MHz, Chloroform-d) δ 4.67 (d, J=5.7 Hz, 2H), 3.82 (t, J=5.7 Hz, 2H), 3.04 (t, J=5.7 Hz, 2H), 1.04-0.84 (m, 21H). LCMS (AA) M+1 384.

Step 7: 2-(Trifluoromethyl)-5-{2-[(triisopropylsilyl)oxy]ethyl}-1,3-thiazole-4-carbaldehyde To a solution of [2-(trifluoromethyl)-5-{2-[(triisopropylsilyl)oxy]ethyl}-1,3-thiazol-4-yl]methanol (0.2297 g, 0.5989 mmol) was in DCM (40.0 mL, 624 mmol) was added MnO$_2$ (0.6248 g, 7.187 mmol) and the resulting mixture was stirred at rt overnight. Reaction was not complete, so MnO$_2$ (0.2083 g, 2.396 mmol) was added and the reaction was stirred for an additional 8 hrs at rt. The mixture was filtered, and the filtrate was concentrated in vacuo to provide the title compound (137 mg). $^1$H NMR (400 MHz, Chloroform-d) δ 10.11 (s, 1H), 3.89 (t, J=5.4 Hz, 2H), 3.48 (t, J=5.3 Hz, 2H), 1.06-0.93 (m, 21H).

Example 21: 5-({[tert-Butyl(dimethyl)silyl]oxy}methyl)thiophene-3-carbaldehyde Int-34

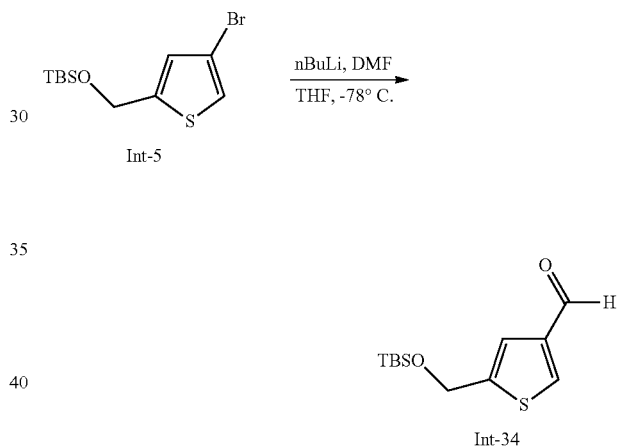

A heat-gun dried 250 mL round bottom flask was charged with 2.50 M of n-BuLi in hexane (8.590 mL, 21.48 mmol) and THF (30.0 mL, 3.70E2 mmol) and cooled to −78° C. Int-5 (6.00 g, 19.5 mmol) was next added (neat) and the solution was stirred for 5 min at −78° C. To the mixture was then added DMF (2.268 mL, 29.28 mmol) quickly dropwise and the reaction was stirred for 10 min at −78° C. The reaction was quenched by addition of water (80 mL) and extracted with EtOAc (80 mL×3). The combined organic layers were washed with brine, dried over Na$_2$SO$_4$, filtered, and concentrated in vacuo. Crude residue was loaded onto the column as a solution in hexane. Chromatography was performed (220 g column, 0-10% EtOAc:hexanes as eluent) to afford 1 minor peak and then the major title product peak. Yield=1.95 g. $^1$H NMR (400 MHz, Chloroform-d) δ 9.72 (s, 1H), 7.90 (d, J=1.2 Hz, 1H), 7.20 (s, 1H), 4.78-4.73 (m, 2H), 0.82 (s, 9H), −0.00 (s, 6H).

The compounds listed in the table below were prepared in an analogous fashion to that described above starting from the corresponding starting materials:

| Entry | Starting material | Product (Int #) | NMR Data |
|---|---|---|---|
| 1 | Int-6 | 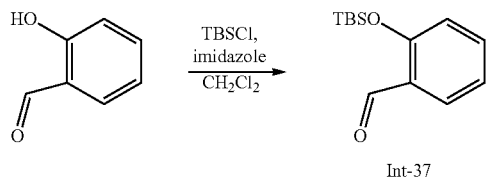<br>Int-35 | ¹H NMR (400 MHz, Chloroform-d) δ 9.86 (s, 1H), 6.99 (s, 1H), 4.67 (d, J = 1.0 Hz, 2H), 0.82 (s, 9H), −0.00 (s, 6H). |
| 2 | Int-1 | Int-36 | ¹H NMR (400 MHz, DMSO-d6) δ 9.95 (s, 1H), 7.43 (s, 1H), 6.00 (s, 1H), 4.06-3.99 (m, 2H), 3.99-3.91 (m, 2H), 2.76 (s, 3H). |

Example 22: 2-{[tert-Butyl(dimethyl)silyl]oxy}benzaldehyde Int-37

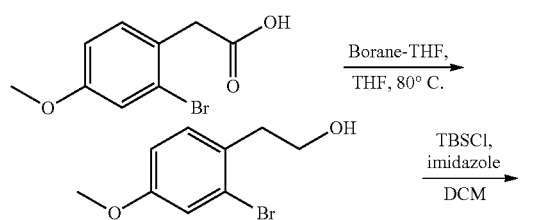

Int-37

To a solution of 2-hydroxybenzaldehyde (2.62 mL, 24.6 mmol) in DCM (30 mL, 400 mmol) were added 1H-imidazole (5.02 g, 73.7 mmol) and tert-butyldimethylsilyl chloride (5.55 g, 36.8 mmol). The thick slurry was then stirred overnight at RT. Quenched with water (20 mL) and diluted with additional DCM (40 mL). Layers were separated, and the aqueous layer was extracted 2×DCM (40 mL each). Combined organic layers were dried over Na₂SO₄, filtered, and concentrated in vacuo. Crude residue was adsorbed to Celite (50 mL) for dry-loading. Chromatography was performed (80 g column, 0-5% EtOAc:hexanes) to afford one major peak. Yield=5.2 g. ¹H NMR (400 MHz, Chloroform-d) δ 10.41 (s, 1H), 7.75 (dd, J=7.8, 1.8 Hz, 1H), 7.46-7.34 (m, 1H), 6.97 (t, J=7.5 Hz, 1H), 6.82 (d, J=8.3 Hz, 1H), 0.96 (s, 9H), 0.22 (s, 6H).

Example 23: [2-(2-Bromo-4-methoxyphenyl)ethoxy](tert-butyl)dimethylsilane Int-38

-continued

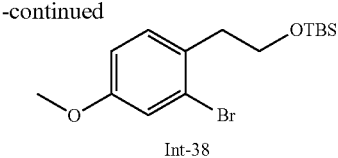

Int-38

This sequence was performed in an analogous fashion to that described in Step 1 of Example 11, beginning with 2-bromo-4-methoxyphenylacetic acid as starting material. ¹H NMR (400 MHz, Chloroform-d) δ 7.17 (d, J=8.5 Hz, 1H), 7.10 (d, J=2.6 Hz, 1H), 6.80 (dd, J=8.5, 2.6 Hz, 1H), 3.82-3.76 (m, 5H), 2.92 (t, J=7.1 Hz, 2H), 0.88 (s, 9H), −0.00 (s, 6H).

Example 24: 4,4-Difluoro-3,4-dihydro-1H-isochromen-1-one Int-39

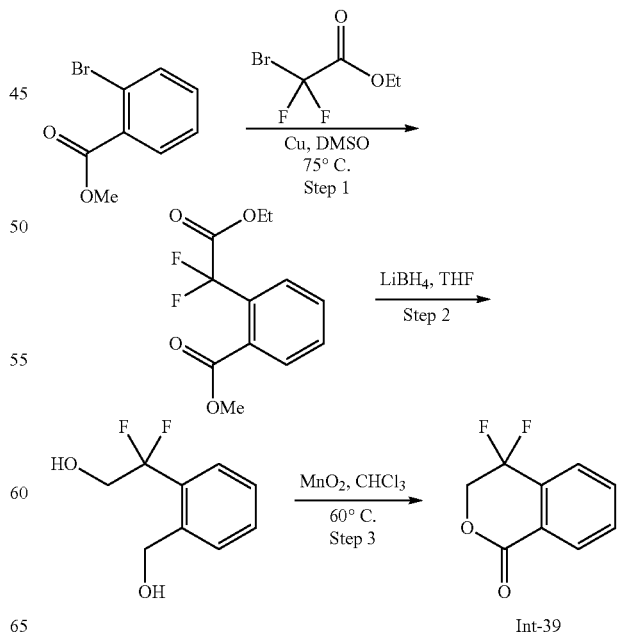

Step 1: Methyl 2-(2-ethoxy-1,1-difluoro-2-oxoethyl)benzoate

To a solution of methyl 2-iodobenzoate (1.12 mL, 7.63 mmol) in dimethyl sulfoxide (33.4 mL, 4.70E2 mmol) was added ethyl bromodifluoroacetate (1.475 mL, 11.45 mmol) followed by activated copper (1.455 g, 22.90 mmol) at rt. After the reaction vessel was purged with argon, the reaction was heated at 75° C. for 14 h. After cooling to room temp, the reaction was quenched by addition of 1N $KH_2PO_4$ solution (200 mL) and the mixture was stirred for 30 min. Mixture was transferred to a separatory funnel and diluted with EtOAc (600 mL) The lower, aqueous layer contained a blue suspended solid, and the upper, organic layer contained a yellow suspended solid. Layers were separated and the EtOAc layer (containing the yellow solid) was filtered. The filtrate was washed 2× water and 1× brine, then dried over $Na_2SO_4$, filtered, and concentrated in vacuo. Crude residue was loaded onto the column as a solution in hexane, with a small amount of DCM for complete solubility. Chromatography was performed (80 g column, 0-25% EtOAc:hexanes over 35 min) to afford 2 very minor byproduct peaks and then the major title compound peak. Yield=1.75 g. $^1$H NMR (400 MHz, Chloroform-d) δ 8.03 (d, J=7.7 Hz, 1H), 7.88 (d, J=7.8 Hz, 1H), 7.69 (t, J=7.6 Hz, 1H), 7.61 (t, J=7.6 Hz, 1H), 4.37 (q, J=7.2 Hz, 2H), 3.90 (s, 3H), 1.34 (t, J=7.1 Hz, 3H).

Step 2: 2,2-Difluoro-2-[2-(hydroxymethyl)phenyl]ethanol

To a solution of methyl 2-(2-ethoxy-1,1-difluoro-2-oxoethyl)benzoate (1.75 g, 6.78 mmol) in THF (79.2 mL, 977 mmol) was added 2.00 M of lithium borohydride in THF (10.2 mL, 20.3 mmol) and the mixture was stirred in the fridge (~4° C.) overnight. The reaction was carefully quenched by addition of saturated $NaHCO_3$ (30 mL). Reaction mixture was then diluted with and EtOAc (80 mL). Layers were separated, and the aqueous layer was extracted 2×EtOAc (40 mL each). The combined organic layers were dried over $Na_2SO_4$, filtered, and concentrated in vacuo. Crude residue was loaded onto the column as a solution in DCM. Chromatography was performed (40 g column, 0-50% EtOAc:hexanes over 25 min) to afford one major compound. Yield=909 mg. $^1$H NMR (400 MHz, Chloroform-d) δ 7.57 (d, J=7.9 Hz, 2H), 7.51 (t, J=7.4 Hz, 1H), 7.43 (t, J=7.5 Hz, 1H), 4.87 (s, 2H), 4.10 (t, J=13.4 Hz, 2H), 2.36 (s, 1H), 2.07 (s, 1H). LC/MS (FA): M+Na=211.

Step 3: 4,4-Difluoro-3,4-dihydro-1H-isochromen-1-one

To a solution of 2,2-difluoro-2-[2-(hydroxymethyl)phenyl]ethanol (0.905 g, 4.81 mmol) in chloroform (60.13 mL, 751.6 mmol) was added $MnO_2$ (5.284 g, 60.78 mmol) at rt, and the mixture was stirred for 18 h at 50° C. After cooling to room temp, the reaction was filtered through a Celite pad and the residual solid was rinsed with EtOAc several times. The filtrate was concentrated in vacuo to afford the title compound Yield=642 mg. $^1$H NMR (400 MHz, Chloroform-d) δ 8.21 (d, J=7.7 Hz, 1H), 7.86-7.77 (m, 2H), 7.73 (t, J=7.4 Hz, 1H), 4.71 (t, J=10.7 Hz, 2H). LC/MS (FA): M+H=185.

The compounds listed in the table below were prepared in an analogous fashion to that described above starting from the appropriate starting materials:

| Entry | Starting material | Product (Int #) | NMR Data |
|---|---|---|---|
| 1 | ![Br, Cl, OMe benzoate] | Int-40 (difluoro chloro isochromanone) | $^1$H NMR (400 MHz, DMSO-d6) δ 8.08-8.05 (m, 1H), 8.02 (dd, J = 8.3, 2.2 Hz, 1H), 7.91 (d, J = 8.3 Hz, 1H), 5.00 (t, J = 11.6 Hz, 2H) |
| 2 | ![Br pyridine aldehyde] | Int-41 (difluoro pyrano-pyridinone) | $^1$H NMR (400 MHz, Chloroform-d) δ 9.03 (dd, J = 4.8, 1.7 Hz, 1H), 8.51 (dq, J = 8.0, 1.3 Hz), 7.77-7.65 (m, 1H), 4.80 (t, J = 11.0 Hz, 2H) |

Example 25: 7-Chloro-3,4-dihydro-1H-pyrano[4,3-c]pyridin-1-one Int-42

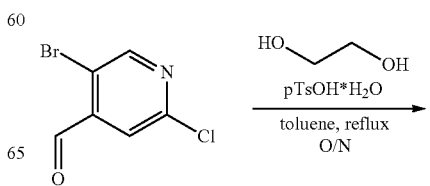

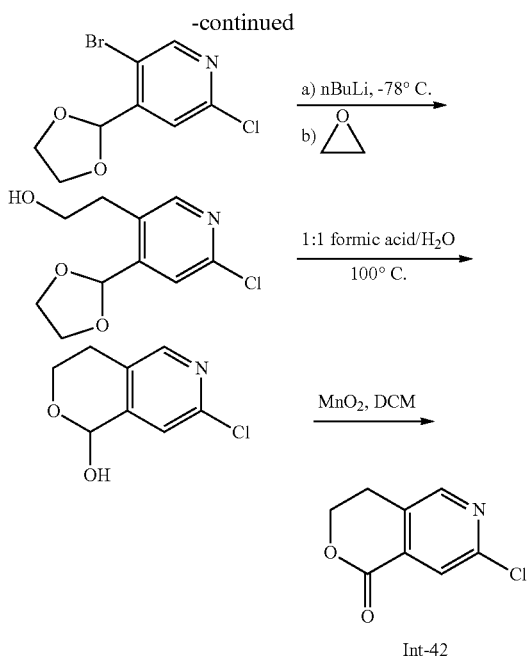

Step 1: 5-Bromo-2-chloro-4-(1,3-dioxolan-2-yl)pyridine

To a solution of 5-bromo-2-chloropyridine-4-carboxaldehyde (5.235 g, 23.75 mmol) and 1,2-ethanediol (6.62 mL, 119 mmol) in toluene (36.0 mL) was added p-toluenesulfonic acid monohydrate (0.226 g, 1.19 mmol). The reaction flask was fitted with a Dean-Stark trap (which was fitted with a reflux condenser), and the reaction mixture was stirred at reflux under argon for 17 h. The reaction was cooled to rt, diluted with EtOAc, and transferred to a separatory funnel. The mixture was washed with saturated NaHCO$_3$ (2×) and brine, then dried over Na$_2$SO$_4$, filtered, and concentrated. The dark brown oil was purified by silica gel column chromatography (0 to 15% EtOAc in hexanes) to give 6.00 g (96%) of product as a white solid. $^1$H NMR (400 MHz, DMSO-d6) δ 8.65 (s, 1H), 7.58 (s, 1H), 5.95 (s, 1H), 4.13-3.97 (m, 4H); LCMS: (AA) M+1 264.0/266.0

Step 2: 2-[6-Chloro-4-(1,3-dioxolan-2-yl)pyridin-3-yl]ethanol 5-bromo-2-chloro-4-(1,3-dioxolan-2-yl)pyridine (5.60 g, 21.2 mmol) was dissolved in THF (35.29 mL) under argon, and the resulting yellow solution was cooled to −78° C. To the mixture was added dropwise 2.50 M of n-BuLi in hexanes (11.85 mL, 29.64 mmol), keeping the internal temperature less than −70° C. The resulting brown mixture was stirred for 1 hour at −78° C., at which point 2.50 M of ethylene oxide in THF (12.70 mL, 31.76 mmol) was added dropwise via syringe. The reaction was stirred for 5 min, and then boron trifluoride etherate (4.829 mL, 38.11 mmol) was added dropwise, keeping the temperature below −70° C. The reaction was stirred at −78° C. for 1 hour. The reaction was quenched by addition of saturated NaHCO$_3$ (26 mL) and brine (26 mL), and the reaction was allowed to warm up to rt. The layers were separated, and the aqueous layer was extracted with EtOAc (2×). The combined organics were washed with brine, dried over Na$_2$SO$_4$, filtered, and concentrated. The yellow oil was purified by silica gel column chromatography (0 to 100% EtOAc in hexane) to afford 0.973 g (20%) of the title compound as an orange solid. $^1$H NMR (400 MHz, DMSO-d6) δ 8.30 (s, 1H), 7.44 (s, 1H), 6.01 (s, 1H), 4.75 (t, J=5.2 Hz, 1H), 4.09-3.95 (m, 4H), 3.64-3.56 (m, 2H), 2.85 (t, J=6.6 Hz, 2H); LCMS: (AA) M+1 230.0/232.0

Step 3: 7-Chloro-3,4-dihydro-1H-pyrano[4,3-c]pyridin-1-ol

A solution of 2-[6-chloro-4-(1,3-dioxolan-2-yl)pyridin-3-yl]ethanol (972.0 mg, 4.232 mmol) in formic acid (14.53 mL, 385.1 mmol) and water (14.49 mL, 804.1 mmol) was stirred at 100° C. for 3 h. The reaction was cooled to rt, diluted with EtOAc, transferred to separatory funnel and washed with saturated NaHCO$_3$ (2×) and brine. The organic layer was then dried over Na$_2$SO$_4$, filtered, and concentrated to afford 719 mg (82%) crude title compound as a beige solid, which was used in the next step without purification. $^1$H NMR (400 MHz, DMSO-d6) δ 8.26 (s, 1H), 7.31 (s, 1H), 7.09 (d, J=6.3 Hz, 1H), 5.76 (d, J=6.3 Hz, 1H), 4.06-3.97 (m, 1H), 3.89-3.82 (m, 1H), 2.79-2.71 (m, 2H); LCMS: (AA) M+1 186.1/188.1

Step 4: 7-Chloro-3,4-dihydro-1H-pyrano[4,3-c]pyridin-1-one

To a solution of 7-chloro-3,4-dihydro-1H-pyrano[4,3-c]pyridin-1-ol (708.0 mg, 3.814 mmol) in DCM (141.3 mL) was added MnO$_2$ (3.32 g, 38.1 mmol), and the mixture was stirred at rt for 23 h. The reaction was filtered through a pad of Celite, and the filter cake was washed with EtOAc. The filtrate was concentrated in vacuo to give 572 mg (82%) of the title compound as a yellow solid. $^1$H NMR (400 MHz, DMSO-d6) δ 8.62-8.58 (m, 1H), 7.83 (s, 1H), 4.59 (t, J=6.0 Hz, 2H), 3.10 (t, J=6.0 Hz, 2H); LCMS: (AA) M+1 184.0/186.0

Example 26: 7-Bromo-3,4-dihydro-1H-isochromen-1-one Int-43

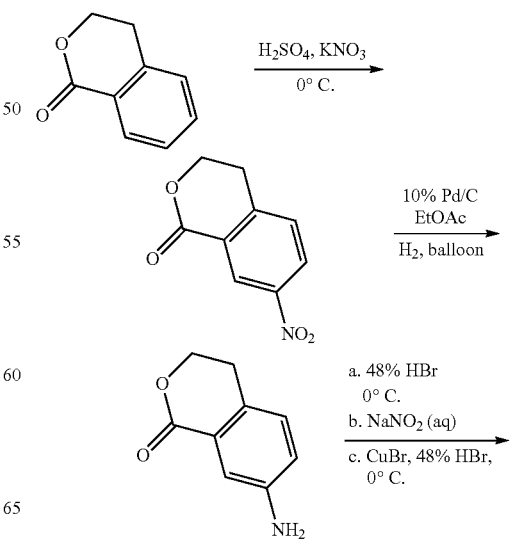

-continued

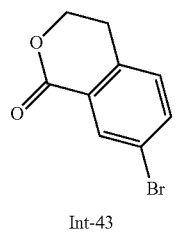

Int-43

Step 1: 7-Nitro-3,4-dihydro-1H-isochromen-1-one

A 3-neck 1 L round bottom flask was charged with 18.4 M sulfuric acid in water (55.6 mL, 1020 mmol) and cooled to 0° C. Isochroman-1-one (20.00 g, 135.0 mmol) was added dropwise over 30 min, keeping the internal temperature less than +5° C. A solution of potassium nitrate (13.8 g, 136 mmol) in 18.4 M sulfuric acid in water (77.8 mL, 1430 mmol) was added dropwise over 100 min, keeping the internal temperature less than or equal to 0° C. The mixture was warmed to rt and poured onto ice and water to afford a white precipitate. This heterogeneous mixture was stirred at rt, and then the white solid product was isolated by vacuum filtration. The filter cake was allowed dry by pulling vacuum through it over the weekend, and then purified by ISCO chromatography eluting with a hexanes/EtOAc gradient to afford the title compound as a white solid, 18 g (70%). $^1$H NMR (400 MHz, Chloroform-d) δ 8.28-8.19 (m, 1H), 7.70-7.60 (m, 1H), 7.20-7.11 (m, 1H), 4.60-4.46 (m, 2H), 3.08-2.96 (m, 2H).

Step 2: 7-Amino-3,4-dihydro-1H-isochromen-1-one

A 1 L round bottom flask was charged with 7-nitro-3,4-dihydro-1H-isochromen-1-one (12.24 g, 63.37 mmol) and EtOAc (250 mL). To this solution was added 10% palladium on carbon (1.00 g), and the reaction mixture was stirred under balloon pressure of hydrogen for 18 h. The mixture was filtered through Celite, and the filtrate was concentrated in vacuo to afford a white solid which was used as is in the following step.

Step 3: 7-Bromo-3,4-dihydro-1H-isochromen-1-one

A 1 L round bottom flask was charged with 7-amino-3,4-dihydro-1H-isochromen-1-one (13.40 g, 82.12 mmol) and 8.90 M of hydrobromic acid in water (134 mL, 1190 mmol), and the resulting mixture was cooled in an ice bath. To this white suspension was added an ice cooled solution of sodium nitrite (5.66 g, 82.1 mmol) in ~2 mL water dropwise keeping the internal temperature less than +5° C. In a separate flask, copper(I) bromide (11.8 g, 82.1 mmol) and 8.90 M hydrobromic acid in water (26.8 mL, 238 mmol) were combined and cooled in an ice bath, at which point this solution was rapidly added to the first solution. The reaction mixture was allowed to warm to rt, and then ~1 L water was added. The resulting tan precipitate was isolated by vacuum filtration and dried under vacuum overnight. The solid was then subjected to ISCO chromatography eluting with a hexanes/EtOAc gradient to afford a pale brown solid, 12.91 g (69%). $^1$H NMR (400 MHz, Chloroform-d) δ 8.29-8.17 (m, 1H), 7.73-7.57 (m, 1H), 7.19-7.11 (m, 1H), 4.61-4.44 (m, 2H), 3.09-2.95 (m, 2H).

Example 27:
4,5-Dihydro-7H-thieno[2,3-c]pyran-7-one Int-44

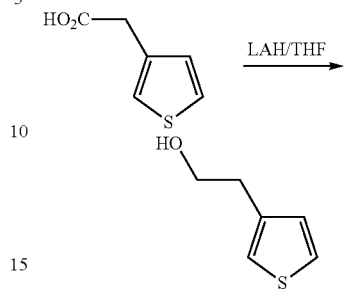

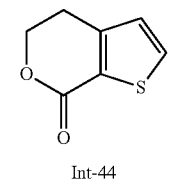

Int-44

Step 1: 2-(3-Thienyl)ethanol

A solution of thiophene-3-acetic acid (4.982 g, 35.04 mmol) in THF (120 mL, 1500 mmol) was cooled to 0° C., and lithium tetrahydroaluminate (1.596 g, 42.05 mmol) was added slowly over 15 min. The reaction was allowed to warm to rt and stirred for 2 hrs. The reaction was quenched via addition of water (5 mL) and EtOAc (10 ml). The mixture was filtered, and the filter cake was washed with 30 ml EtOAc. The filtrate was concentrated in vacuo to afford the title compound (3.59 g). $^1$H NMR (400 MHz, Chloroform-d) δ 7.31 (dd, J=4.9, 3.0 Hz, 1H), 7.11-7.05 (m, 1H), 7.05-6.97 (m, 1H), 3.87 (t, J=6.4 Hz, 2H), 2.92 (t, J=6.4 Hz, 2H), 1.71 (s, 1H).

Step 2: 4,5-Dihydro-7H-thieno[2,3-c]pyran-7-one

A solution of 2-(3-thienyl)ethanol (2.18 g, 17.0 mmol) in DCM (60.0 mL, 936 mmol) was cooled to 0° C., then triphosgene (3.2801 g, 11.054 mmol) was added and the reaction was stirred for 15 min at 0° C. N,N-diisopropylethylamine (4.4431 mL, 25.508 mmol) was added dropwise to the solution over 15 min, and the resulting mixture was warmed to rt and stirred for 1 hr. The solution was poured into 80 ml 1N HCl solution, the layers were separated, and the aqueous layer was extracted 2×60 ml DCM. The combined organic layers were concentrated in vacuo to afford crude intermediate chloroformate (3.18 g), which was dissolved into toluene (50.0 mL, 469 mmol) and cooled to 0° C. Aluminum trichloride (3.4013 g, 25.508 mmol) was added to this solution at 0° C. and the resulting mixture was warmed to rt and stirred for 1 hr. The reaction was quenched via addition of a solution of sodium potassium tartrate tetrahydrate (28.796 g, 102.03 mmol) in 150 ml water. The layers were separated, and the aqueous layer was extracted 3×60 ml EtOAc. The combined organic layers were concentrated in vacuo and purified by flash column (80 g column, eluent was 0-70% EtOAc) to afford the title compound as brown solid (1.124 g, 43%). $^1$H NMR (400 MHz, Chloroform-d) δ 7.67 (d, J=5.0 Hz, 1H), 7.02 (d, J=5.0 Hz, 1H), 4.66-4.50 (m, 2H), 3.04 (t, J=6.2 Hz, 2H).

Example 28: 4-{[tert-Butyl(dimethyl)silyl]oxy}-3,4-dihydro-1H-isochromen-1-one Int-45

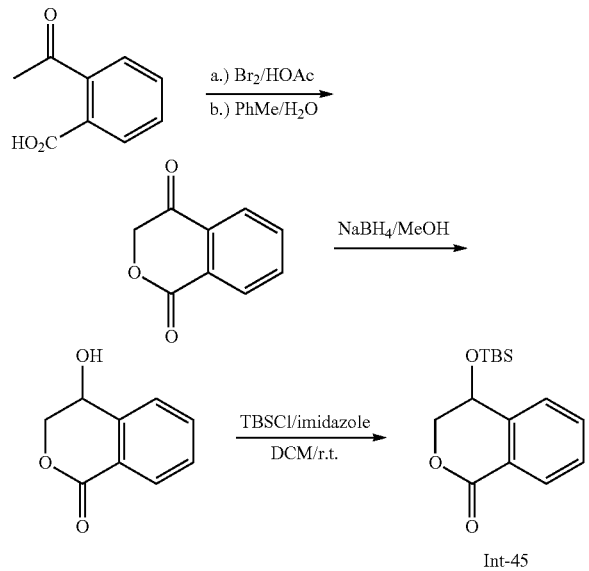

Int-45

Step 1: 1H-Isochromene-1,4(3H)-dione

To a solution of 2-acetylbenzoic acid (8.458 g, 51.52 mmol) in acetic acid (50.0 mL, 879 mmol) was added 30 ml of 33% HBr in acetic acid. Bromine (8.646 g, 54.10 mmol) was next added to the solution, and the reaction was heated to 40° C. with stirring for 30 min. The reaction mixture was poured into 300 ml water, the layers were separated, and the aqueous layer was extracted with 3×100 ml DCM. Combined the organic layers and concentrated in vacuo to yield crude intermediate, which was dissolved in 25 ml acetic acid, 130 ml toluene and 30 ml water. The resulting mixture was stirred at reflux overnight. The reaction was cooled to rt, and the layers were separated. The organic layer was concentrated in vacuo and purified by flash column (120 g column, eluent 0-55% EtOAc in hexane) to afford 5.24 g (63%) of title compound. $^1$H NMR (400 MHz, Chloroform-d) δ 8.36-8.28 (m, 1H), 8.17-8.07 (m, 1H), 7.95-7.79 (m, 2H), 5.16 (s, 2H).

Step 2: 4-Hydroxy-3,4-dihydro-1H-isochromen-1-one

A solution of 1H-isochromene-1,4(3H)-dione (3.05 g, 18.8 mmol) in methanol (60.0 mL, 1480 mmol), was cooled to 0° C., and sodium tetrahydroborate (1.067 g, 28.22 mmol) was added. The reaction was allowed to warm to rt and stirred for 60 min. The mixture was poured into 200 ml water, the layers were separated, and the aqueous layer was extracted 3×60 ml DCM. The combined organic layers were dried over MgSO4, filtered, and concentrated in vacuo to yield 2.69 g (87%) the title compound. LCMS (AA) M+1 165

Step 3: 4-{[tert-Butyl(dimethyl)silyl]oxy}-3,4-dihydro-H-isochromen-1-one

To a round bottom flask was added 4-hydroxy-3,4-dihydro-1H-isochromen-1-one (0.3052 g, 1.859 mmol), 1H-imidazole (0.5063 g, 7.437 mmol), 60 ml DCM, and tert-butyldimethylsilyl chloride (0.8406 g, 5.578 mmol). The resulting reaction mixture was stirred at rt for 4 hrs. The mixture was concentrated in vacuo, and the residue was suspended in EtOAc. The mixture was filtered through Celite and the filtrate was concentrated in vacuo. The residue was chromatographed (100% hexanes as eluent) to provide the title compound (0.5812 g, 90%) as an oil. $^1$H NMR (400 MHz, Chloroform-d) δ 7.97 (dd, J=8.1, 1.3 Hz, 1H), 7.57-7.51 (m, 1H), 7.39-7.31 (m, 2H), 4.91 (dd, J=8.5, 4.4 Hz, 1H), 4.33 (dd, J=10.8, 4.4 Hz, 1H), 4.18 (dd, J=10.8, 8.5 Hz, 1H), 0.84 (s, 9H), 0.07 (d, J=8.8 Hz, 6H).

Example 29: 2-Methyl-6,7-dihydro-4H-pyrano[3,4-d][1,3]thiazol-4-one Int-46

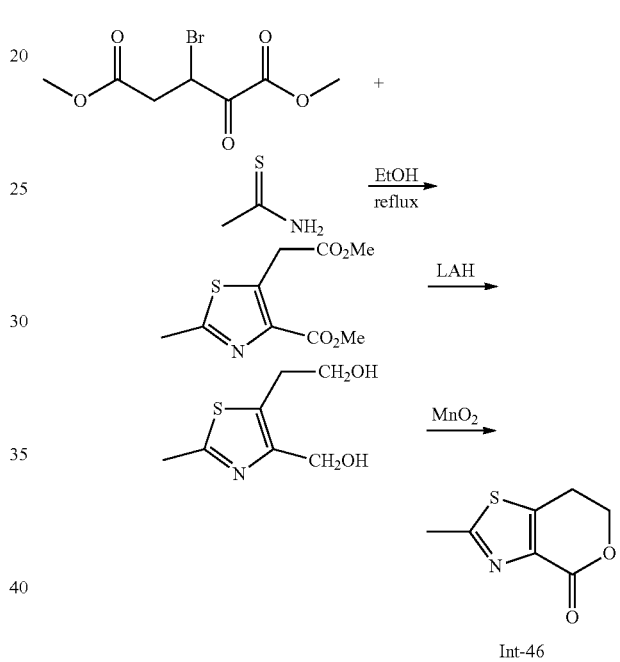

Int-46

Step 1: Methyl 5-(2-methoxy-2-oxoethyl)-2-methyl-1,3-thiazole-4-carboxylate

To a solution of methyl 3-bromo-2-oxopentanedioate (23 g, 73 mmol) in methanol (250.0 mL, 6172 mmol) was added ethanethioamide (10.65 g, 141.8 mmol). The mixture was stirred at reflux for 2 hrs, and then cooled to rt. The volatiles were removed in vacuo and the residue was suspended in 25 ml THF and 40 ml hexane with stirring. The solid (ethanethioamide) was filtered and the filtrate was concentrated and purified by flash column (120 g column, eluent was 0-70% EtOAc in hexane) to provide 10.01 g (60%) of the title compound. $^1$H NMR (400 MHz, Chloroform-d) δ 4.27 (s, 2H), 3.90 (s, 3H), 3.72 (d, J=2.2 Hz, 3H), 2.69 (s, 3H).

Step 2: 2-[4-(Hydroxymethyl)-2-methyl-1,3-thiazol-5-yl]ethanol

To a solution of ethyl 5-(2-methoxy-2-oxoethyl)-2-methyl-1,3-thiazole-4-carboxylate (1.79 g, 7.81 mmol) in THF (50.0 mL, 616 mmol) was added lithium tetrahydroaluminate (0.5927 g, 15.62 mmol) and the mixture was stirred for 20 min. Reaction was quenched by addition of 2 ml water, the solid was filtered and the filter cake was washed with 30 ml methanol. The filtrate was concentrated and purified by flash column (40 g column, eluent 0-20% methanol in EtOAc) to provide 0.7121 g (53%) of the title compound. $^1$H NMR (400 MHz, Chloroform-d) δ 4.61 (s, 2H), 3.79 (t, J=5.8 Hz, 2H), 3.03 (t, J=5.8 Hz, 2H), 2.63 (s, 3H).

Step 3: 2-Methyl-6,7-dihydro-4H-pyrano[3,4-d][1,3]thiazol-4-one

To a solution of 2-[4-(hydroxymethyl)-2-methyl-1,3-thiazol-5-yl]ethanol (0.09262 g, 0.5346 mmol) in DCM (10.0 mL, 156 mmol) was added MnO$_2$ (1.859 g, 21.39 mmol) and the reaction was stirred at rt overnight. The solid was filtered, and the filtrate was concentrated in vacuo and purified by flash column (24 g column, eluent was 0-60% EtOAc in hexanes) to provide 0.0244 g (27%) of the title compound. $^1$H NMR (400 MHz, Chloroform-d) δ 4.54 (t, J=6.1 Hz, 2H), 3.13 (t, J=6.1 Hz, 2H), 2.67 (s, 3H).

Example 30: 2-Methyl-6,7-dihydro-4H-pyrazolo[5,1-c][1,4]oxazin-4-one Int-47

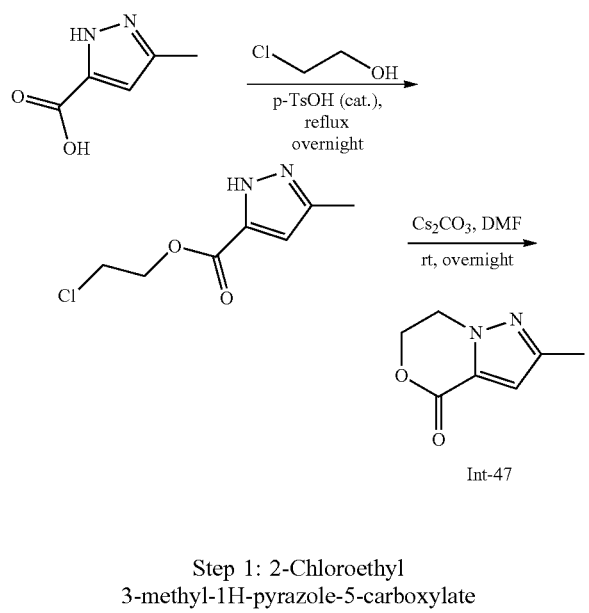

Step 1: 2-Chloroethyl 3-methyl-1H-pyrazole-5-carboxylate

To a solution of 3-methyl-5-pyrazolecarboxylic acid (1.00 g, 7.93 mmol) in 2-chloroethanol (7.97 mL) was added p-toluenesulfonic acid monohydrate (603 mg, 3.17 mmol) and the reaction mixture was heated to 115° C. with stirring overnight. The mixture was cooled to rt and the solvent was removed in vacuo. The residue was diluted with EtOAc and saturated aqueous NaHCO$_3$. The layers were separated and the aqueous phase was extracted with EtOAc. The combined organic layers were dried over Na$_2$SO$_4$, filtered and concentrated in vacuo. The crude product was purified by silica gel column chromatography (0 to 80% EtOAc in hexanes) to give 728 mg (49%) of the title product as a colorless solid. $^1$H NMR (400 MHz, Chloroform-d) δ 10.56 (s, 1H), 6.64 (s, 1H), 4.56 (t, J=5.9 Hz, 2H), 3.79 (t, J=5.9 Hz, 2H), 2.37 (s, 3H); LCMS (FA): m/z=189.0 (M+H).

Step 2: 2-Methyl-6,7-dihydro-4H-pyrazolo[5,1-c][1,4]oxazin-4-one

To a solution of 2-chloroethyl 5-methyl-1H-pyrazole-3-carboxylate (690 mg, 3.66 mmol) in DMF (2.34 mL) was added Cs$_2$CO$_3$ (1.79 g, 5.49 mmol) and the reaction was stirred at rt overnight. The reaction mixture was filtered through a Celite pad and the filtrate was concentrated in vacuo. The resulting residue was purified by silica gel column chromatography (0 to 100% EtOAc in hexanes) to provide 299 mg (54%) of the title product as a colorless solid. $^1$H NMR (400 MHz, Chloroform-d) δ 6.77 (s, 1H), 4.71-4.66 (m, 2H), 4.42-4.36 (m, 2H), 2.34 (s, 3H); LCMS (FA): m/z=153.1 (M+H).

The compound listed in the table below was prepared in an analogous fashion to that described above starting from the corresponding starting materials:

| Starting material | Product (Int #) | NMR Data |
|---|---|---|
| ![sm] | Int-48 | $^1$H NMR (400 MHz, Chloroform-d) δ 7.40 (s, 1H), 4.70-4.60 (m, 1H), 4.40-4.30 (m, 1H), 2.30 (s, 3H). |

Example 31: 5-(2-{[tert-Butyl(dimethyl)silyl]oxy}-1,1-difluoroethyl)-2-chloropyridine Int-49

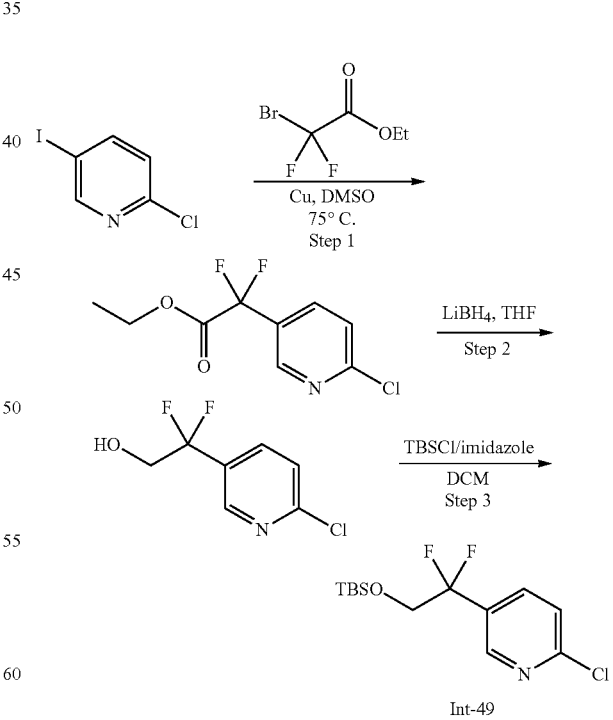

Steps 1 and 2 were performed in an analogous fashion to that described in Example 24, steps 1 and 2. Step 3 was performed in an analogous fashion to that described in Example 4, step 2. $^1$H NMR (400 MHz, Chloroform-d) δ

8.54 (d, J=1.7 Hz, 1H), 7.78 (dd, J=8.3, 2.5 Hz, 1H), 7.40 (d, J=8.3 Hz, 1H), 3.98 (t, J=11.8 Hz, 2H), 0.84 (s, 9H), 0.02 (s, 6H).

Example 32: 7-Chloro-3,4-dihydroisoquinoline Int-50

To a solution of 7-chloro-1,2,3,4-tetrahydro-isoquinoline (1.15 g, 6.86 mmol) in DCM (70.0 mL, 1090 mmol) was added MnO$_2$ (5.96 g, 68.6 mmol) at rt, and the mixture was stirred for 16 h. The reaction was filtered through a Celite pad and the residual solid was rinsed with DCM several times. The filtrate was concentrated in vacuo and the residue was purified by ISCO silica gel column chromatography (40 g, eluting with 50% EtOAc in DCM, 50 mL/min flow) to give 915 mg of the title compound as colorless solid. $^1$H NMR (400 MHz, DMSO-d6) δ 8.35 (t, J=2.1 Hz, 1H), 7.52 (d, J=2.2 Hz, 1H), 7.46 (dd, J=8.0, 2.3 Hz, 1H), 7.28 (d, J=8.0 Hz, 1H), 3.70-3.63 (m, 2H), 2.71-2.65 (m, 2H).

The compounds listed in the table below was prepared in an analogous fashion to that described above starting from the corresponding starting materials:

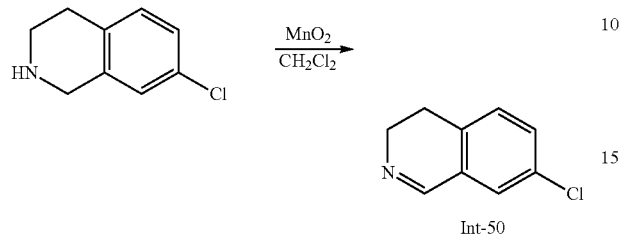

| Starting material | Product (Int #) | NMR Data |
|---|---|---|
| HN—◯—Br | N═◯—Br (Int-51) | $^1$H NMR (400 MHz, Chloroform-d) δ 8.30 (t, J = 2.1 Hz, 1H), 7.50 (dd, J = 8.0, 2.0 Hz, 1H), 7.44 (d, J = 2.0 Hz, 1H), 7.07 (d, J = 8.0 Hz, 1H), 3.87-3.73 (m, 2H), 2.80-2.64 (m, 2H). |
| HN—◯ (benzazepine) | N═◯ (Int-52) | $^1$H NMR (400 MHz, Chloroform-d) δ 8.52 (s, 1H), 7.38-7.31 (m, 3H), 7.26-7.22 (m, 1H), 3.64 (t, J = 5.6 Hz, 2H), 2.79 (t, J = 6.9 Hz, 2H), 2.35-2.24 (m, 2H). |

Example 33: rac-4-{1-Phenyl-1-[(trimethylsilyl)oxy]ethyl}-2-furaldehyde Int-53

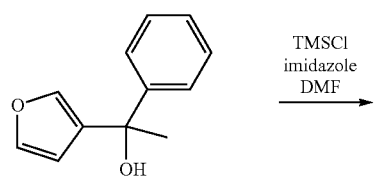

Step 1: rac-1-(3-Furyl)-1-phenylethoxy](trimethyl)silane 1-(3-Furyl)-1-phenylethanol (1.53 g, 8.13 mmol) was dissolved in DMF (8.62 mL) and the solution was cooled to 0° C. Imidazole (1.66 g, 24.4 mmol) and TMSCl (1.55 mL, 12.2 mmol) were added. The reaction was allowed to warm to rt and stirred for 1 hour. The reaction was quenched by adding saturated aqueous NaHCO$_3$ and extracted with EtOAc. The combined organic layers were washed with water and brine, dried over Na$_2$SO$_4$, filtered and concentrated in vacuo. The residue was purified by ISCO column chromatography (0%-5% EtOAc in hexanes as eluent) to afford 2.11 g (99%) of the title product as a colorless oil. $^1$H NMR (400 MHz, Chloroform-d) δ 7.45-7.38 (m, 2H), 7.34-7.27 (m, 4H), 7.24-7.17 (m, 1H), 6.22-6.16 (m, 1H), 1.86 (s, 3H), 0.04 (s, 9H).

Step 2: rac-4-{1-Phenyl-1-[(trimethylsilyl)oxy]ethyl}-2-furaldehyde

[1-(3-Furyl)-1-phenylethoxy](trimethyl)silane (1.32 g, 5.07 mmol) was dissolved in THF (23.3 mL), and then cooled at –78° C. 1.40 M of sec-BuLi in cyclohexane (4.71 mL, 6.59 mmol) was added to the solution at –78° C. After 30 min, DMF (1.18 mL, 15.2 mmol) was added to the solution and the resulting mixture was stirred for 10 min. The reaction was quenched by adding saturated aqueous NH₄Cl, warmed to rt and extracted with EtOAc. The combined organic layers were washed with brine, dried over Na₂SO₄, filtered and concentrated in vacuo. The residue was purified by ISCO column chromatography (0%-10% EtOAc in hexanes as eluent) to give 1.02 g (70%) of the title compound as a colorless oil. ¹H NMR (400 MHz, Chloroform-d) δ 9.56 (s, 1H), 7.58-7.54 (m, 1H), 7.42-7.37 (m, 2H), 7.35-7.29 (m, 2H), 7.25-7.22 (m, 1H), 7.04-7.02 (m, 1H), 1.92 (s, 3H), 0.04 (s, 9H).

The compounds listed in the table below was prepared in an analogous fashion to that described above starting from the corresponding starting materials:

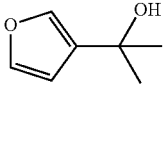

| Starting material | Product/Int-No. | Characterization Data |
|---|---|---|
| (furan-CH(OH)-CMe₂-) | Int-54 | ¹H NMR (400 MHz, Chloroform-d) δ 9.62 (s, 1H), 7.53 (s, 1H), 7.19 (d, J = 0.8 Hz, 1H), 1.56 (s, 6H), 0.10 (s, 9H). ¹H NMR |

Example 34: rac-4-[{[tert-Butyl(dimethyl)silyl]oxy}(3-chlorophenyl)methyl]-2-furaldehyde Int-55

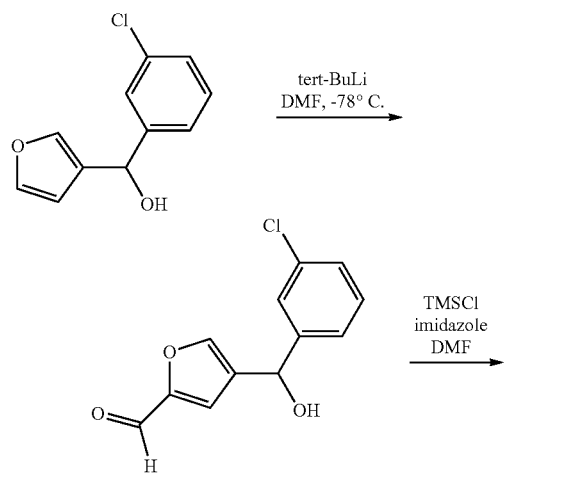

Step 1: rac-4-[(3-Chlorophenyl)(hydroxy)methyl]-2-furaldehyde

To a solution of rac-(3-chlorophenyl)(3-furyl)methanol (2.00 g, 9.58 mmol) in Et₂O (40.0 mL) was added 1.70 M of tert-BuLi in pentane (14.1 mL, 24.0 mmol) at −78° C. After stirring at −78° C. for 30 min, DMF (1.11 mL, 14.4 mmol) was added to the mixture. Then, the reaction mixture was warmed to 0° C. and stirred for 1 hour. The reaction mixture was poured into saturated aqueous NH₄Cl at rt and extracted with EtOAc. The combined organic layers were washed with water and brine, dried over MgSO₄, filtered, and concentrated in vacuo. The residue was purified by ISCO column chromatography (10%-30% EtOAc in hexanes as eluent) to give 862 mg (38%) of the title compound as a pale yellow oil. ¹H NMR (400 MHz, Chloroform-d) δ 9.58 (d, J=0.6 Hz, 1H), 7.64-7.55 (m, 1H), 7.42-7.36 (m, 1H), 7.34-7.24 (m, 3H), 7.15-7.08 (m, 1H), 5.79 (s, 1H), 2.57-2.38 (br s, 1H).

Step 2: rac-4-[{[tert-Butyl(dimethyl)silyl]oxy}(3-chlorophenyl)methyl]-2-furaldehyde To a solution of rac-4-[(3-chlorophenyl)(hydroxy)methyl]-2-furaldehyde (550 mg, 2.32 mmol) in DMF (10.0 mL) were added imidazole (396 mg, 5.81 mmol) and TBSCl (420 mg, 2.78 mmol) at rt. After overnight, the reaction mixture was poured into saturated aqueous NaHCO₃ and extracted with EtOAc. The extract was washed with water and brine, dried over MgSO₄, filtered, and concentrated in vacuo. The residue was purified by ISCO column chromatography (0%-10% EtOAc in hexanes as eluent) to give 478 mg (59%) of the title compound as a pale yellow oil. ¹H NMR (400 MHz, Chloroform-d) δ 9.57 (d, J=0.6 Hz, 1H), 7.53 (d, J=0.8 Hz, 1H), 7.35 (t, J=1.7 Hz, 1H), 7.31-7.21 (m, 3H), 7.07-7.03 (m, 1H), 5.69 (s, 1H), 0.91 (s, 9H), 0.06 (s, 3H), −0.01 (s, 3H).

Example 35: rac-4-{1-(3-Chlorophenyl)-1-[(trimethylsilyl)oxy]ethyl}-2-furaldehyde Int-56

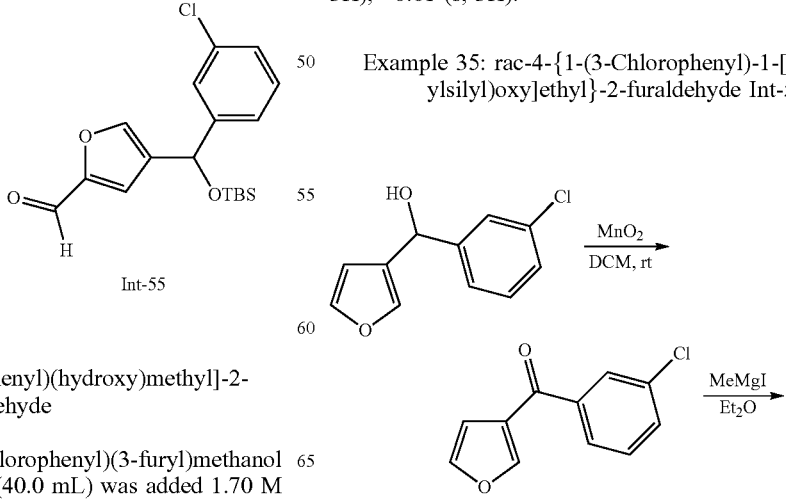

-continued

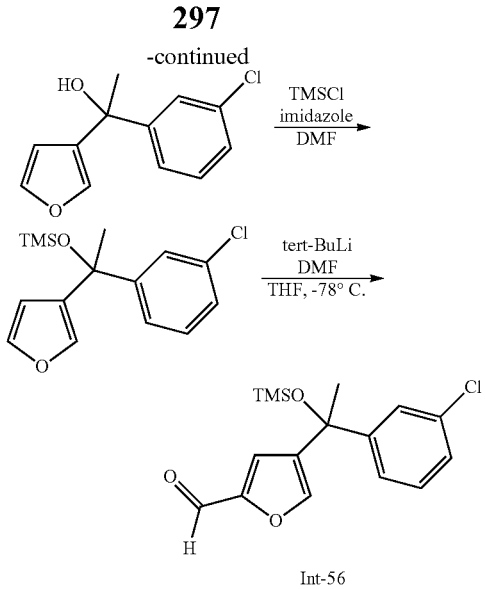

Int-56

Step 1: (3-Chlorophenyl)(3-furyl)methanone

To a solution of rac-(3-chlorophenyl)(3-furyl)methanol (1.81 g, 8.68 mmol) in DCM (30.0 mL) was added $MnO_2$ (11.3 g, 130 mmol) at rt. After stirring overnight, the reaction mixture was filtered through a Celite pad, and washed with DCM. The filtrate was concentrated in vacuo. The residue was purified by ISCO column chromatography (0%-5% EtOAc in hexanes as eluent) to give 1.60 g (90%) of the title compound as a white powder. $^1$H NMR (400 MHz, Chloroform-d) δ 7.93 (dd, J=1.4, 0.8 Hz, 1H), 7.83 (t, J=1.7 Hz, 1H), 7.73 (dt, J=7.7, 1.3 Hz, 1H), 7.56 (ddd, J=8.0, 2.1, 1.1 Hz, 1H), 7.54-7.51 (m, 1H), 7.44 (t, J=7.7 Hz, 1H), 6.90 (dd, J=1.9, 0.8 Hz, 1H).

Step 2: rac-1-(3-Chlorophenyl)-1-(3-furyl)ethanol

To a solution of (3-chlorophenyl)(3-furyl)methanone (1.60 g, 7.74 mmol) in $Et_2O$ (30 mL) was added 3.0 M of MeMgI in $Et_2O$ (3.87 mL, 11.6 mmol) at 0° C. After stirring at 0° C. for 1 hour, the reaction mixture was poured into saturated aqueous $NH_4Cl$ at rt and extracted with EtOAc. The extract was washed with brine, dried over $MgSO_4$, filtered, and concentrated in vacuo. The residue was purified by ISCO column chromatography (10%-30% EtOAc in hexanes as eluent) to give 1.48 g (86%) of the title compound as a pale red oil. $^1$H NMR (400 MHz, Chloroform-d) δ 7.50-7.47 (m, 1H), 7.39-7.37 (m, 1H), 7.35-7.30 (m, 2H), 7.29-7.21 (m, 2H), 6.35-6.24 (m, 1H), 2.15-2.07 (br s, 1H), 1.85 (s, 3H).

Step 3: rac-[1-(3-Chlorophenyl)-1-(3-furyl)ethoxy](trimethyl)silane

To a solution of rac-1-(3-chlorophenyl)-1-(3-furyl)ethanol (1.48 g, 6.65 mmol) in DMF (20.0 mL) were added imidazole (1.13 g, 16.6 mmol) and TMSCl (1.01 mL, 7.98 mmol) at rt. After stirring overnight, the reaction mixture was poured into saturated aqueous $NaHCO_3$ at rt and extracted with EtOAc. The combined organic layers were washed with brine, dried over $MgSO_4$, filtered, and concentrated in vacuo. The residue was purified by ISCO column chromatography (100% hexanes as eluent) to give 1.65 g (84%) of the title compound as a colorless oil. $^1$H NMR (400 MHz, Chloroform-d) δ 7.43-7.40 (m, 1H), 7.37-7.34 (m, 1H), 7.34-7.31 (m, 1H), 7.27-7.16 (m, 3H), 6.20-6.12 (m, 1H), 1.84 (s, 3H), 0.05 (s, 9H).

Step 4: rac-4-{1-(3-Chlorophenyl)-1-[(trimethylsilyl)oxy]ethyl}-2-furaldehyde To a solution of rac-[1-(3-chlorophenyl)-1-(3-furyl)ethoxy](trimethyl)silane (1.64 g, 5.56 mmol) in $Et_2O$ (20.0 mL) was added 1.70 M of tert-BuLi in pentane (4.91 mL, 8.34 mmol) at −78° C. After stirring at −78° C. for 30 min, DMF (0.65 mL, 8.34 mmol) was added to the mixture. Then, the reaction mixture was allowed to warm to 0° C. and stirred for 1 hour. The reaction mixture was poured into saturated aqueous $NH_4Cl$ at rt and extracted with EtOAc. The extract was washed with brine, dried over $MgSO_4$, filtered, and concentrated in vacuo. The residue was purified by ISCO column chromatography (0%-5% EtOAc in hexanes as eluent) to give 549 mg (31%) of the title compound as a pale yellow oil. $^1$H NMR (400 MHz, Chloroform-d) δ 9.58 (s, 1H), 7.60-7.56 (m, 1H), 7.42-7.37 (m, 1H), 7.26-7.20 (m, 3H), 7.02 (d, J=0.9 Hz, 1H), 1.90 (s, 3H), 0.06 (s, 9H).

Example 36: 5-Benzyl-2-furaldehyde Int-57

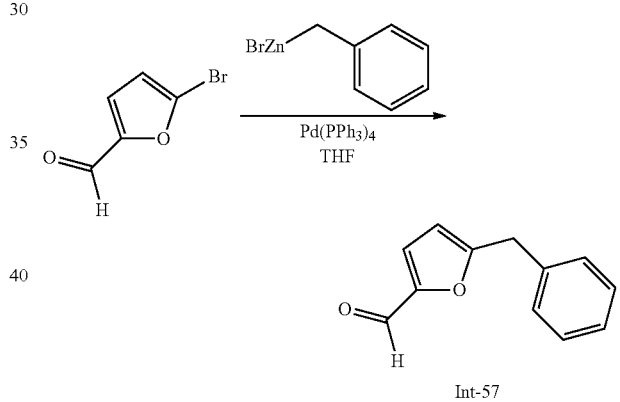

Int-57

Step 1: 5-Benzyl-2-furaldehyde

A solution of 5-bromo-2-furaldehyde (1.00 g, 5.72 mmol) and $Pd(PPh_3)_4$ (132 mg, 0.11 mmol) in THF (35.7 mL) was degassed with argon gas. 0.50 M of benzylzinc bromide in THF (14.3 mL, 7.14 mmol) was added, and the reaction mixture was then stirred at 70° C. for 2 h. The solution was concentrated to remove the solvent and diluted with EtOAc. The organic layer was washed with 1M HCl, saturated $NaHCO_3$, and brine. The resulting solution was dried over $MgSO_4$, filtered and then concentrated in vacuo. The crude material was purified by ISCO column chromatography (0%-30% EtOAc in hexanes as eluent) to give 554 mg of the title compound (52%) as an orange residue. $^1$H NMR (400 MHz, DMSO-$d_6$) δ 9.49 (s, 1H), 7.48 (d, J=3.5 Hz, 1H), 7.38-7.31 (m, 2H), 7.32-7.22 (m, 2H), 7.22-7.13 (m, 2H), 4.12 (s, 2H). LCMS (FA): m/z=187.2 (M+H).

The compound listed in the table below was prepared in an analogous fashion to that described above starting from the corresponding starting materials:

| Grignard reagent | Product/Int No. | Characterization Data |
|---|---|---|
| BrZn-CH2-C6H4-Cl (3-Cl) | Int-58 (5-(3-chlorobenzyl)-2-furaldehyde) | LCMS (FA): m/z = 221.3 (M + H). |

Example 37: 5-(3-Bromobenzyl)-2-furaldehyde Int-59

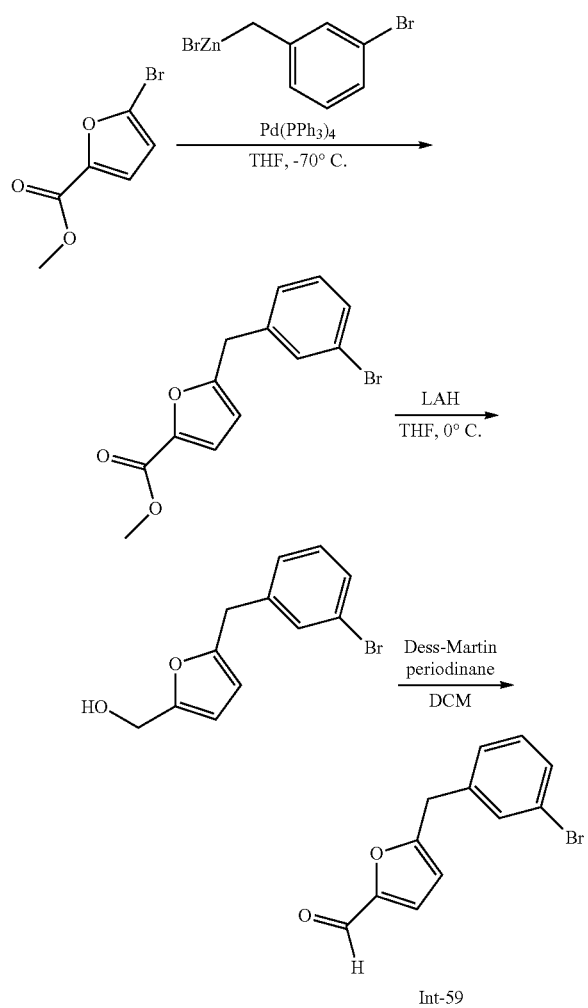

Int-59

Step 1: Methyl 5-(3-bromobenzyl)-2-furoate

A microwave reaction tube was charged with methyl 5-bromofuran-2-carboxylate (775 mg, 3.78 mmol) and Pd(PPh$_3$)$_4$ (218 mg, 0.19 mmol). The flask was sealed and purged with argon for 5 min, and then THF (10.0 mL) was added to the reaction vessel. 0.5 M of 3-bromobenzylzinc-bromide in THF (8.32 mL, 4.16 mmol) was then added to the solution and the reaction was heated at 70° C. for 1 day. The reaction was quenched with saturated NH$_4$Cl and extracted with EtOAc (×3). The combined organic layers were then washed with water, brine, dried using Na$_2$SO$_4$, filtered and concentrated. The residue was purified by ISCO column chromatography (0%-30% EtOAc in hexanes as eluent) to give 0.60 g (54%) of the title compound. $^1$H NMR (400 MHz, Chloroform-d) δ 7.40-7.36 (m, 2H), 7.20-7.16 (m, 2H), 7.10 (d, J=3.4 Hz, 1H), 6.11 (d, J=3.4 Hz, 1H), 4.01 (s, 2H), 3.88 (s, 3H).

Step 2: [5-(3-Bromobenzyl)-2-furyl]methanol

To a round bottom flask was added methyl 5-(3-bromobenzyl)-2-furoate (733 mg, 2.48 mmol) in THF (8.00 mL) and cooled at 0° C. 1.0 M of lithium tetrahydroaluminate in Et$_2$O (3.23 mL, 3.23 mmol) was then added slowly and the resulting mixture was stirred at 0° C. for 2 h. Added 1 mL of water slowly to quench reaction mixture, then added solid Na$_2$SO$_4$. The mixture was stirred at rt for 1 hour and then filtered through a pad of Celite. The filtrate was concentrated to dryness and no further purification was done to give 610 mg of crude title compound. $^1$H NMR (400 MHz, Chloroform-d) δ 7.39-7.37 (m, 1H), 7.32-7.28 (m, 1H), 7.25-7.21 (m, 2H), 7.18-7.15 (m, 1H), 6.22-6.17 (m, 1H), 5.98-5.91 (m, 1H), 4.56 (s, 2H), 3.94 (d, J=13.7 Hz, 2H).

Step 3: 5-(3-Bromobenzyl)-2-furaldehyde

Into a round bottom flask was added crude [5-(3-bromobenzyl)-2-furyl]methanol (609 mg, 2.28 mmol) dissolved in DCM (10.0 mL). Dess-Martin periodinane (1.16 g, 2.74 mmol) was added and the resulting reaction mixture was stirred at rt for 1 hour. The reaction was then quenched by the addition of saturated Na$_2$S$_2$O$_3$ and extracted with DCM (×3). The combined organic layers were then washed with water, brine, dried using Na$_2$SO$_4$, filtered and concentrated. The residue was purified by ISCO column chromatography (0%-50% EtOAc in hexanes as eluent) to give 167 mg (28%) of the title compound. $^1$H NMR (400 MHz, Chloroform-d) δ 9.56 (s, 1H), 7.43-7.37 (m, 2H), 7.23-7.14 (m, 3H), 6.22 (d, J=3.5 Hz, 1H), 4.03 (s, 2H).

Example 38: 5-Chloro-4-(3-chlorobenzyl)-2-furaldehyde Int-60

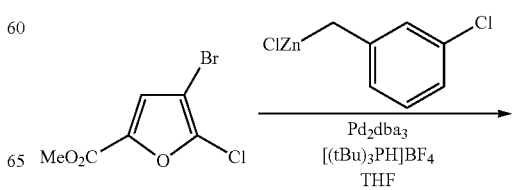

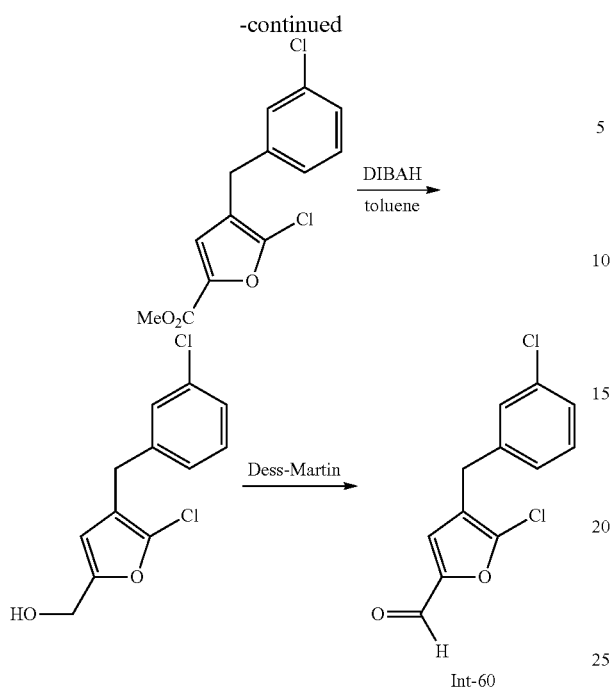

added 1.0 M of DIBAL-H in toluene (6.14 mL, 6.14 mmol) at −78° C. After stirring at −78° C. for 30 min, the reaction mixture was poured into saturated aqueous Rochelle's salt at rt and EtOAc was added to the mixture. The resulting mixture was vigorously stirred at rt for 1 hour. The layers were separated, and the organic layer was washed with brine, dried over MgSO$_4$, filtered, and concentrated in vacuo. The residue was purified by ISCO column chromatography (0%-30% EtOAc in hexanes as eluent) to give 528.2 mg (84%) of the title compound as a colorless oil. $^1$H NMR (400 MHz, Chloroform-d) δ 7.30-7.17 (m, 3H), 7.12-7.07 (m, 1H), 6.15 (s, 1H), 4.52 (d, J=0.5 Hz, 2H), 3.68 (s, 2H), 1.93-1.81 (br s, 1H).

Step 3: 5-Chloro-4-(3-chlorobenzyl)-2-furaldehyde

To a solution of [5-chloro-4-(3-chlorobenzyl)-2-furyl]methanol (510 mg, 1.98 mmol) in DCM (10.0 mL) was added MnO$_2$ (2.59 g, 29.8 mmol) at rt. After stirring at rt overnight, the mixture was filtered through a Celite pad and washed with DCM. The filtrate was concentrated in vacuo. The residue was purified by ISCO column chromatography (0%-30% EtOAc in hexanes as eluent) to give 332 mg (66%) of the title compound as a colorless oil. $^1$H NMR (400 MHz, Chloroform-d) δ 9.51 (s, 1H), 7.32-7.23 (m, 2H), 7.22-7.16 (m, 1H), 7.13-7.08 (m, 1H), 7.06 (s, 1H), 3.78 (s, 2H).

| Starting material | Product/Int No. | Characterization Data |
|---|---|---|
| ![MeO2C-furan-Br-Me] | ![Int-61] | $^1$H NMR (400 MHz, Chloroform-d) δ 9.46 (s, 1H), 7.26-7.18 (m, 2H), 7.14-7.11 (m, 1H), 7.03 (dt, J = 7.0, 1.7 Hz, 1H), 6.98 (s, 1H), 3.72 (s, 2H), 2.36 (s, 3H). |

Step 1: Methyl 5-chloro-4-(3-chlorobenzyl)-2-furoate

To a solution of methyl 4-bromo-5-chloro-2-furoate (1.20 g, 5.01 mmol) in THF (20.0 mL), degassed with nitrogen gas) were added Pd$_2$(dba)$_3$ (184 mg, 0.20 mmol) and tri-tert-butylphosphonium tetrafluoroborate (116 mg, 0.40 mmol) at rt. After stirring at rt for 10 min, 0.5 M of 3-chlorobenzylzinc chloride in THF (15.0 mL, 7.52 mmol) was added to the mixture. After stirring at rt for 4 h, the reaction mixture was poured into saturated aqueous NH$_4$Cl and extracted with EtOAc. The combined organic layers were washed with brine, dried over MgSO$_4$, filtered, and concentrated in vacuo. The residue was purified by ISCO column chromatography (0%-5% EtOAc in hexanes as eluent) to give 628 mg (44%) of the title compound as a yellow oil. $^1$H NMR (400 MHz, Chloroform-d) δ 7.29-7.21 (m, 2H), 7.20-7.16 (m, 1H), 7.11-7.06 (m, 1H), 7.01 (s, 1H), 3.89 (s, 3H), 3.74 (s, 2H).

Step 2: [5-Chloro-4-(3-chlorobenzyl)-2-furyl]methanol

To a solution of methyl 5-chloro-4-(3-chlorobenzyl)-2-furoate (700 mg, 2.46 mmol) in toluene (10.0 mL) was Example 39: 4-(3-Chlorobenzyl)-2-furaldehyde Int-62

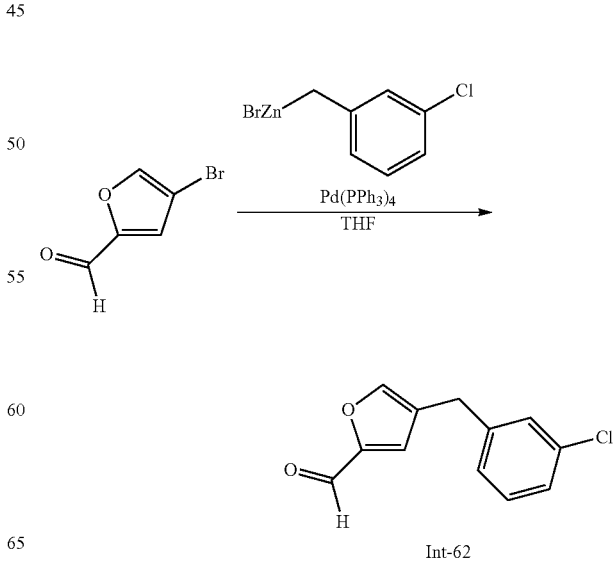

Step 1: 4-(3-Chlorobenzyl)-2-furaldehyde

A 20 mL of microwave vessel was charged with 4-bromo-2-furaldehyde (500 mg, 2.86 mmol), Pd$_2$(dba)$_3$ (52.3 mg, 0.06 mmol), and tri-tert-butylphosphonium tetrafluoroborate (33.2 mg, 0.11 mmol). THF (2.0 mL) was added to the mixture and the reaction vessel was purged with argon followed by sealing with a cap. After the mixture was stirred for 5 min at rt, 0.5 M of 3-chlorobenzylzinc chloride in THF (7.43 mL, 3.72 mmol) was added to the mixture and then the resulting mixture was heated at 50° C. for 1 hour. The reaction was cooled to rt and diluted with EtOAc. The organic layer was washed with water and brine. After drying over Na$_2$SO$_4$, the mixture was filtered through a glass frit funnel and the filtrate was concentrated in vacuo. The residue was purified by ISCO column chromatography (10% EtOAc in hexanes as eluent) to give 135 mg (20%) of the title compound.

Example 40: 4-(3-Bromobenzyl)-5-methyl-2-furaldehyde Int-63

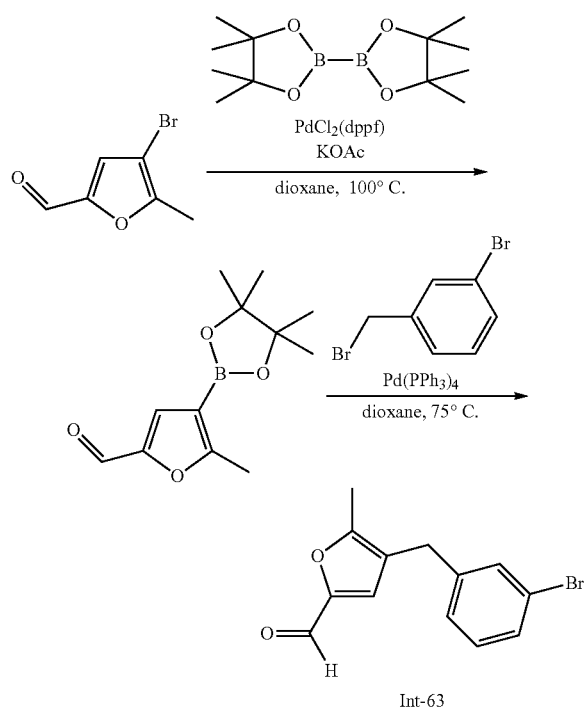

Step 1: 5-Methyl-4-(4,4,5,5-tetramethyl-1,3,2-dioxa-borolan-2-yl)-2-furaldehyde To a solution of 4-bromo-5-methyl-2-furaldehyde (880 mg, 4.66 mmol) in 1,4-dioxane (15.0 mL) were added bis(pinacolato)diborom (1.54 g, 6.05 mmol), potassium acetate (1.37 g, 13.9 mmol) and [1,1'-bis(diphenylphosphino)ferrocene]palladium(II)dichloride (192 mg, 0.23 mmol) at rt. After stirring at 100° C. overnight, the reaction mixture was poured into water at rt and extracted with EtOAc. The combined organic layers were washed with brine, dried over Na$_2$SO$_4$, filtered, and concentrated in vacuo. The residue was dissolved in EtOAc and then activated charcoal was added to the mixture, and stirred for 15 min at rt. The mixture was filtered through a Celite pad, and washed with EtOAc. The filtrate was concentrated in vacuo to give 1.94 g of crude title compound. LCMS (FA): m/z=237.2 (M+H).

Step 2: 4-(3-Bromobenzyl)-5-methyl-2-furaldehyde

To a solution of crude 5-methyl-4-(4,4,5,5-tetramethyl-1,3,2-dioxaborolan-2-yl)-2-furaldehyde (1.09 g, 4.66 mmol) in 1,4-dioxane (40.0 mL) and water (10.0 mL) were added 3-bromobenzyl bromide (1.28 g, 5.12 mmol), Pd(PPh$_3$)$_4$ (538 mg, 0.47 mmol) and Na$_2$CO$_3$ (1.48 g, 13.9 mmol) at rt. After stirring at 75° C. overnight, the reaction mixture was poured into water at rt and extracted with EtOAc. The extract was washed with brine, dried over MgSO$_4$, filtered, and concentrated in vacuo. The residue was purified by column chromatography (0%-20% EtOAc in hexanes as eluent) to give 291 mg (22%) of the title product as a brown oil. $^1$H NMR (400 MHz, Chloroform-d) δ 9.46 (s, 1H), 7.40-7.33 (m, 1H), 7.29 (t, J=1.6 Hz, 1H), 7.22-7.13 (m, 1H), 7.13-7.04 (m, 1H), 6.98 (s, 1H), 3.72 (s, 2H), 2.37 (s, 3H).

Example 41: 4-(3-Methylbenzyl)-2-furaldehyde Int-64

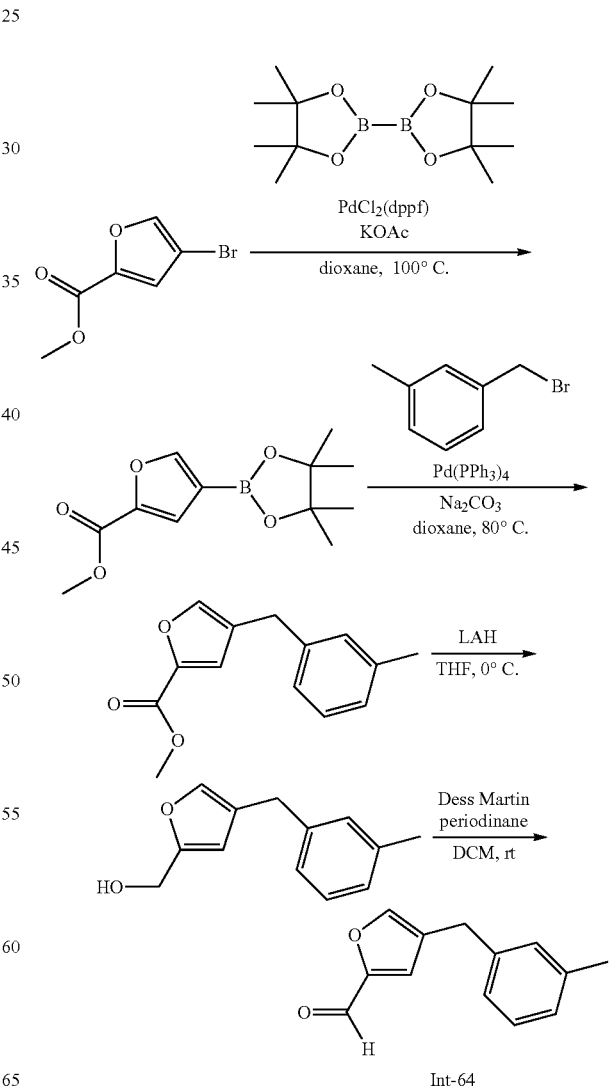

Step 1: Methyl 4-(4,4,5,5-tetramethyl-1,3,2-dioxaborolan-2-yl)-2-furoate

Methyl 4-bromofuran-2-carboxylate (1.00 g, 4.88 mmol), bis(pinacolato)diboron (1.61 g, 6.3 mmol), and potassium acetate (1.44 g, 14.6 mmol) were weighed into a microwave vial and 1,4-dioxane (15.0 mL) was added to the vial. The mixture was purged with argon and to this suspension was added [1,1'-bis(diphenylphosphino)ferrocene]palladium(II) dichloride (201 mg, 0.24 mmol). The reaction mixture was heated at 100° C. overnight in an oil bath. The reaction was quenched with water and extracted with EtOAc (3×). The combined organic layers were then washed with water, brine, dried using $Na_2SO_4$, filtered and concentrated. The residue was purified by ISCO basic alumina column chromatography (0%-10% MeOH in DCM as eluent) to give the title compound. LCMS (FA): m/z=253.1 (M+H).

Step 2: Methyl 4-(3-methylbenzyl)-2-furoate

1-Bromomethyl-3-methylbenzene (110 mg, 0.60 mmol) and methyl 4-(4,4,5,5-tetramethyl-1,3,2-dioxaborolan-2-yl)-2-furoate (600 mg, 2.38 mmol) were weighed into a microwave vial with a stirbar. 1,4-Dioxane (5.0 mL) and water (1.30 mL, 72.2 mmol) were added followed by $Na_2CO_3$ (189 mg, 1.78 mmol). The mixture was purged with argon and $Pd(PPh_3)_4$ (68.8 mg, 0.06 mmol) was added. The resulting reaction mixture was heated to 80° C. and stirred overnight. The reaction was quenched with water and extracted with EtOAc (×3). The combined organic layers were then washed with water, brine, dried using $Na_2SO_4$, filtered and concentrated. The residue was purified by ISCO column chromatography (0%-30% EtOAc in hexanes as eluent) to give 130 mg (95%) of the title compound. LCMS (FA): m/z=231.0 (M+H).

Step 3: [4-(3-Methylbenzyl)-2-furyl]methanol

To a round bottom flask was added methyl 4-(3-methylbenzyl)-2-furoate (283 mg, 1.23 mmol) in THF (4.0 mL) and cooled at 0° C. 1.0 M of lithium tetrahydroaluminate in $Et_2O$ (1.60 mL, 1.60 mmol) was then added slowly and the resulting mixture was stirred at 0° C. for 1 hour. Added 1 mL of water slowly to quench reaction mixture, then added solid $Na_2SO_4$. The mixture was stirred at rt for 1 hour and then filtered through a pad of Celite. The filtrate was concentrated to dryness and no further purification was done to give 230 mg (93%) of crude title compound. LCMS (FA): m/z=203.5 (M+H).

Step 4: 4-(3-Methylbenzyl)-2-furaldehyde

Into a 1-neck round-bottom flask was added crude [4-(3-methylbenzyl)-2-furyl]methanol (230 mg, 1.14 mmol) dissolved in DCM (5.0 mL). Dess-Martin periodinane (579 mg, 1.37 mmol) was then added and the resulting reaction mixture was stirred at rt for 1 hour. The reaction was quenched by the addition of saturated $Na_2S_2O_3$ and extracted with DCM (×3). The combined organic layers were then washed with saturated $NaHCO_3$, water, brine, dried using $Na_2SO_4$, filtered and concentrated. The residue was purified by ISCO column chromatography (0%-50% EtOAc in hexanes as eluent) to give 129 mg (57%) of the title compound. $^1$H NMR (400 MHz, Chloroform-d) δ 9.58 (s, 1H), 7.47 (s, 1H), 7.24-7.18 (m, 1H), 7.10-7.04 (m, 2H), 7.03-6.97 (m, 2H), 3.78 (s, 2H), 2.33 (s, 3H).

Example 42: 5-Methyl-4-(3-methylbenzyl)-2-furaldehyde Int-65

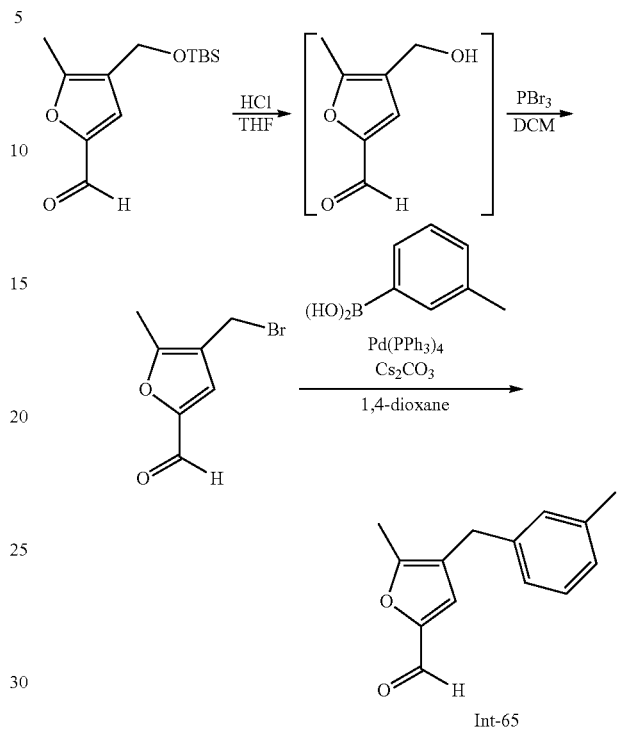

Step 1: 4-(Bromomethyl)-5-methyl-2-furaldehyde

To a round bottom flask was added 4-({[tert-butyl(dimethyl)silyl]oxy}methyl)-5-methyl-2-furaldehyde (0.56 g, 2.2 mmol), THF (3 mL), and 4 M HCl in 1,4-dioxane (2 mL). The resulting reaction mixture was stirred at rt 2 h. The mixture was concentrated in vacuo. To the residue was added DCM (5 mL) and $PBr_3$ (0.29 mL, 3.08 mmol) at rt and the mixture was stirred for 20 min. The reaction was quenched by addition of water and the resulting mixture was extracted with DCM. After concentration in vacuo, the residue was purified by ISCO column chromatography (30% EtOAc in hexanes as eluent) to give 0.19 g (42%) of the title compound. $^1$H NMR (400 MHz, Chloroform-d) δ 9.42 (s, 1H), 7.12 (s, 1H), 4.24 (s, 2H), 2.32 (s, 3H).

Step 2: 5-Methyl-4-(3-methylbenzyl)-2-furaldehyde 4-(Bromomethyl)-5-methyl-2-furaldehyde (0.52 g, 2.6 mmol) and m-tolylboronic acid (696 mg, 5.12 mmol) were weighed into a microwave vial with stir bar. 1,4-Dioxane (12.0 mL) and water (2.00 mL) were added to the reaction vessel. Then $Cs_2CO_3$ (2.92 g, 8.96 mmol) and $Pd(PPh_3)_4$ (444 mg, 0.38 mmol) was added and the reaction mixture was then heated to 130° C. in microwaver for 25 min. The mixture was filtered through Celite and the filtered was concentrated in vacuo. The residue was purified by ISCO column chromatography (30% EtOAc in hexanes as eluent) to give 268 mg (49%) of the title compound. LCMS (FA): m/z=215.2 (M+H)

Example 43: 4,5-Dibenzyl-2-furaldehyde Int-66

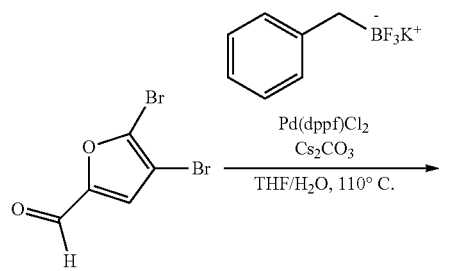

Int-66

Step 1: 4,5-Dibenzyl-2-furaldehyde

A sealable reaction vessel was charged with 4,5-dibromo-2-furaldehyde (1.00 g, 3.94 mmol), benzyltrifluoroborate potassium salt (1.95 g, 9.85 mmol), Cs$_2$CO$_3$ (3.89 g, 11.9 mmol), [1,1'-bis(diphenylphosphino)ferrocene]palladium(II)dichloride (648 mg, 0.79 mmol). The contents were dissolved in THF (48 mL) and water (4.7 mL, 260 mmol), and a stir bar was added. The vessel was sealed and the resulting solution was stirred at 80° C. overnight, and then the reaction was stirred for 8 h at 110° C. Reaction mixture was filtered through Celite pad, and the filtrate was partitioned between water (30 mL) and EtOAc (100 mL). Layers were separated, and the aqueous layer was extracted with EtOAc (100 mL×2). The combined organic layers were washed brine, then dried over Na$_2$SO$_4$, filtered, and concentrated in vacuo. Crude residue was purified by ISCO column chromatography (0%-15% EtOAc in hexanes as eluent) to afford 141 mg (13%) of the title compound. LCMS (FA): m/z=277.5 (M+H).

Example 44: 4-Benzyl-5-chlorothiophene-2-carbaldehyde. Int-67

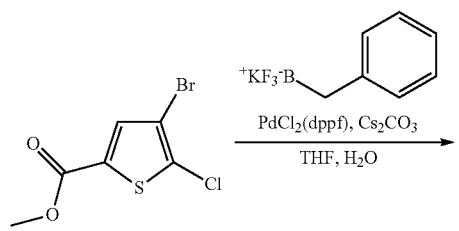

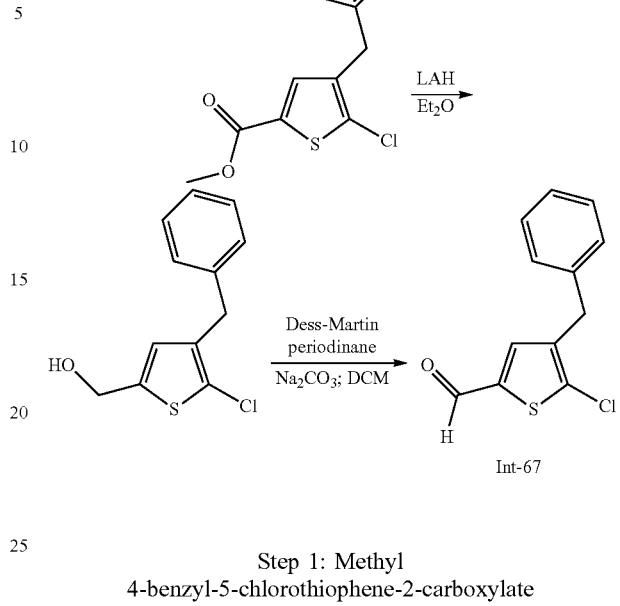

Int-67

Step 1: Methyl 4-benzyl-5-chlorothiophene-2-carboxylate

A microwave vial was charged with a stirbar, methyl 4-bromo-5-chlorothiophene-2-carboxylate (0.10 g, 0.39 mmol), Benzyltrifluoroborate potassium salt (94.0 mg, 0.47 mmol), Cs$_2$CO$_3$ (0.39 g, 1.18 mmol) and [1,1'-bis(diphenylphosphino)ferrocene]palladium(II)dichloride (64.4 mg, 78.3 umol). The mixture was sealed under an atmosphere of argon. THF (4.7 mL) and water (0.47 mL, 26 mmol) were then added and the resulting solution stirred at 75° C. for 16 h. The reaction was concentrated. The crude pdt was purified on ISCO column chromatography (0%-5% EtOAC/hexanes as eluent) to give the title compound (yield=74 mg). LCMS (FA): m/z=267.0 (M+1)

Step 2: (4-Benzyl-5-chloro-2-thienyl)methanol 1.0 M of lithium tetrahydroaluminate in THF (0.55 mL, 0.55 mmol) was added to an ice-bath cooled solution of methyl 4-benzyl-5-chlorothiophene-2-carboxylate (0.10 g, 0.37 mmol) in Et$_2$O (3.5 mL). The resulting solution was stirred at 0° C. for 45 min. The reaction was quenched with water (~1 mL) at 0° C. Na$_2$SO$_4$ dodecahydrate (~2 g) was added along with ~15 mL EtOAc and the mixture allowed to warm to rt and the mixture was stirred for 2 h. The mixture was filtered and the filter cake was washed with EtOAc. The filtrate was concentrated. Crude product was purified on ISCO column chromatography (0%-20% EtOAc/hexanes as eluent) to give the title compound (yield=80 mg). $^1$H NMR (400 MHz, Chloroform-d) δ 7.33-7.26 (m, 2H), 7.25-7.17 (m, 3H), 6.60 (s, 1H), 4.64 (s, 2H), 3.88 (s, 2H), 1.82 (s, 1H).

Step 3: 4-Benzyl-5-chlorothiophene-2-carbaldehyde (4-Benzyl-5-chloro-2-thienyl)methanol (0.21 g, 0.88 mmol) was dissolved in DCM (15.3 mL), then Dess-Martin periodinane (0.45 g, 1.1 mmol) was added to this solution. The reaction was allowed to stir at rt for 1 hour. The reaction was concentrated and the crude material purified on ISCO column chromatography (0%-10% EtOAC/hexanes as eluent) to give the title compound (yield=190 mg). $^1$H NMR (400 MHz, Chloroform-d) δ 9.68 (s, 1H), 7.38-7.30 (m, 3H), 7.29-7.23 (m, 1H), 7.23-7.17 (m, 2H), 3.96 (s, 2H).

Example 45:
4-(2-Hydroxypropan-2-yl)thiophene-2-carbaldehyde. Int-68

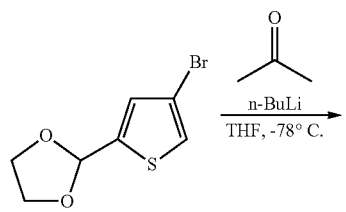

Step 1:
4-(2-Hydroxypropan-2-yl)thiophene-2-carbaldehyde

To a round bottom flask was added THF (50 mL) and 2.5 M n-BuLi in hexane (3.1 mL, 7.66 mmol) at −78° C. 2-(4-Bromothiophen-2-yl)-1,3-dioxolane (1.50 g, 6.38 mmol) in 5 mL THF was added and the mixture was stirred for 30 seconds. To the mixture was added acetone (2.00 mL, 27.2 mmol) and the reaction was stirred at −78° C. for 10 min. The reaction was quenched by addition of saturated NH₄Cl was added and the reaction was warmed to rt. The mixture was extracted with EtOAc (×2) and the combined organic layers were washed with brine, dried under MgSO₄, filtered, and concentrated in vacuo. To the residue was added 40 ml of acetone and 3 g of Dowex 50WX2-200 ion-exchange resin and the mixture was stirred for 2 h at rt. The mixture was filtered and the filtrate was concentrated in vacuo. The residue was purified by column chromatography (50% EtOAc in hexanes as eluent) to give 0.76 g (70%) of the title compound. LCMS (FA): m/z=171.1 (M+1).

The compounds listed in the table below were prepared using similar methods to that described above starting from the listed starting materials.

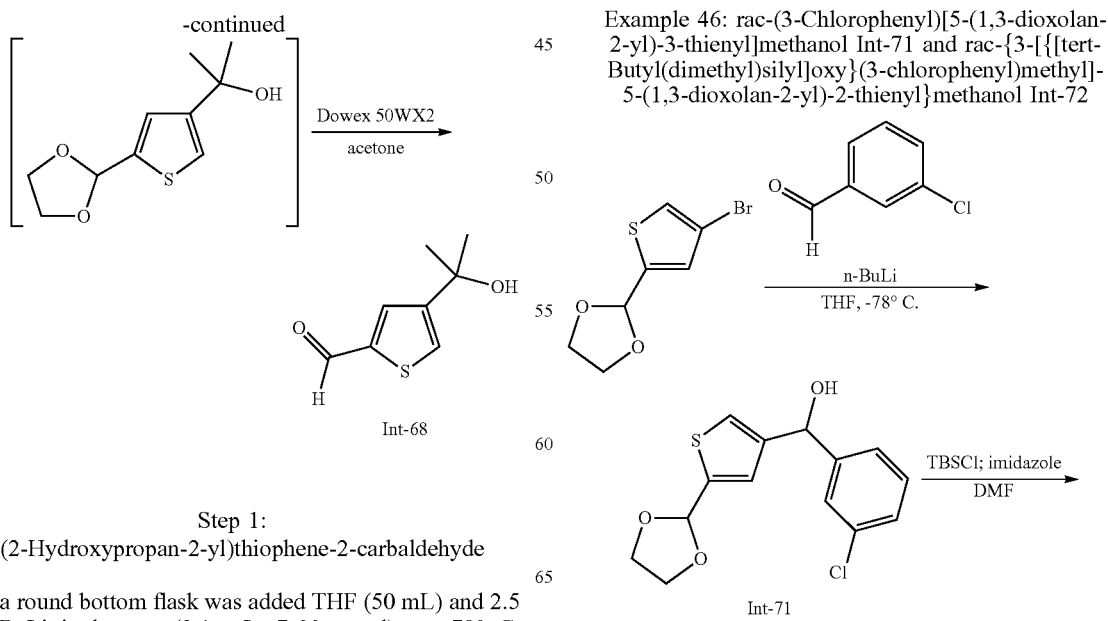

| Starting ketone | Product/Int No. | Characterization Data |
|---|---|---|
| (3-chloroacetophenone) | Int-69 | ¹H NMR (400 MHz, Chloroform-d) δ 9.80 (d, J = 1.2 Hz, 1H), 7.62 (dt, J = 2.7, 1.5 Hz, 2H), 7.47-7.44 (m, 1H), 7.30-7.23 (m, 3H), 2.68-2.30 (br s, 1H), 1.94 (s, 3H). ¹H NMR |
| 1-(6-bromopyridin-2-yl)ethanone | Int-70 | ¹H NMR (400 MHz, Chloroform-d) δ 9.85 (d, J = 1.2 Hz, 1H), 7.73 (d, J = 1.5 Hz, 1H), 7.69 (t, J = 1.4 Hz, 1H), 7.56 (t, J = 7.8 Hz, 1H), 7.43 (dd, J = 7.8, 0.7 Hz, 1H), 7.28 (dd, J = 7.7, 0.7 Hz, 1H), 2.05-1.95 (br s, 1H), 1.92 (s, 3H). ¹H NMR |

Example 46: rac-(3-Chlorophenyl)[5-(1,3-dioxolan-2-yl)-3-thienyl]methanol Int-71 and rac-{3-[{[tert-Butyl(dimethyl)silyl]oxy}(3-chlorophenyl)methyl]-5-(1,3-dioxolan-2-yl)-2-thienyl}methanol Int-72

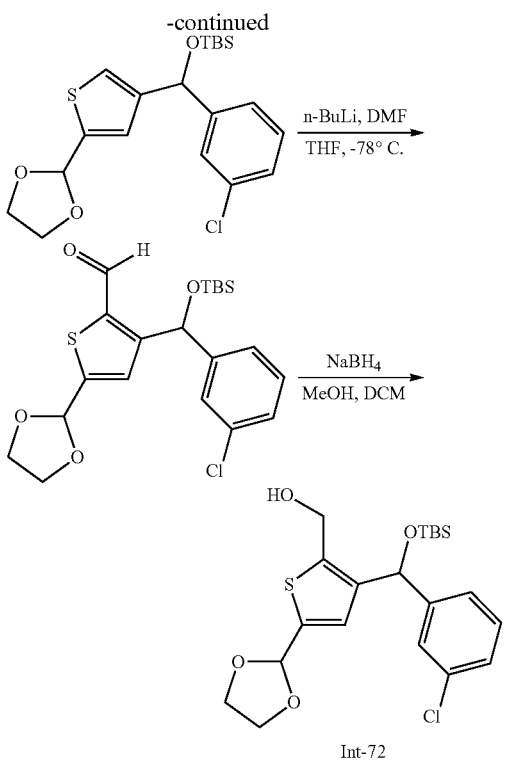

Int-72

Step 1: rac-(3-Chlorophenyl)[5-(1,3-dioxolan-2-yl)-3-thienyl]methanol

To a −78° C. cooled solution of 2.50 M of n-BuLi in hexane (4.08 mL, 10.2 mmol) in THF (40 mL) was added a solution of 2-(4-bromothiophen-2-yl)-1,3-dioxolane (2.00 g, 8.50 mmol) in THF (4 mL) dropwise. Immediately after addition was complete 3-chlorobenzaldehyde (0.97 mL, 8.50 mmol) was added dropwise (~2 min) as a solution in THF (4 mL). The resulting mixture was allowed to stir 30 min at −78° C. The reaction was quenched with water before warming all the way to rt. The mixture was extracted with EtOAc (2×) and the combined organic layers were dried over MgSO$_4$, filtered, and concentrated. The crude product was purified by ISCO column chromatography eluting with 0%-30% EtOAc in hexanes to give 1.7 g (67%) of the title compound. $^1$H NMR (400 MHz, Chloroform-d) δ 7.42 (s, 1H), 7.35-7.24 (m, 4H), 7.21 (s, 1H), 7.06 (s, 1H), 6.04 (s, 1H), 5.82 (d, J=3.6 Hz, 1H), 4.21-3.94 (m, 4H).

Step 2: rac-tert-Butyl{(3-chlorophenyl)[5-(1,3-dioxolan-2-yl)-3-thienyl]methoxy}dimethylsilane To a solution of (3-chlorophenyl)[5-(1,3-dioxolan-2-yl)-3-thienyl]methanol (3.02 g, 10.2 mmol) in DMF (106 mL) was added TBSCl (4.60 g, 30.5 mmol) and 1H-imidazole (2.08 g, 30.5 mmol). The reaction mixture was stirred at 50° C. for 4 h. The mixture was quenched with water and extracted with EtOAc. The combined organic layers were washed with 10% aqueous LiCl, dried over magnesium sulfate, filtered and concentrated in vacuo. The crude material was purified by ISCO column chromatography eluting with 0%-10% EtOAc in hexanes to give 4.15 g (99%) of the title compound as a clear oil. LCMS (FA): m/z=411.4 (M+1).

Step 3: rac-3-[{[tert-Butyl(dimethyl)silyl]oxy}(3-chlorophenyl)methyl]-5-(1,3-dioxolan-2-yl)thiophene-2-carbaldehyde To a −78° C. cooled solution of 2.50 M of n-BuLi in hexane (0.46 mL, 1.14 mmol) and THF (3.00 mL) was a solution of tert-butyl{(3-chlorophenyl)[5-(1,3-dioxolan-2-yl)-3-thienyl]methoxy}dimethylsilane (234 mg, 0.57 mmol) in THF (2.0 mL). The reaction mixture was stirred at −78° C. for 15 min. A solution of DMF (88.2 uL, 1.14 mmol) in THF (1.0 mL) was added dropwise and then stirred for an additional 1 hour. The reaction mixture was quenched with water and extracted with EtOAc. The combined organic layers were dried over MgSO$_4$, filtered and concentrated in vacuo. The crude material was purified by ISCO column chromatography eluting with 0%-10% EtOAc in hexanes to give 141 mg (56%) of the title compound. $^1$H NMR (400 MHz, DMSO-d6) δ 10.41 (s, 1H), 7.53 (s, 1H), 7.48-7.39 (m, 3H), 7.41-7.32 (m, 2H), 6.58 (s, 1H), 6.11 (s, 1H), 4.09-3.92 (m, 4H), 0.90 (s, 9H), 0.08--0.04 (m, 6H). LCMS (FA): m/z=439.5 (M+1).

Step 4: rac-{3-[{[tert-Butyl(dimethyl)silyl]oxy}(3-chlorophenyl)methyl]-5-(1,3-dioxolan-2-yl)-2-thienyl}methanol To a 0° C. cooled solution of 3-[{[tert-butyl(dimethyl)silyl]oxy}(3-chlorophenyl)methyl]-5-(1,3-dioxolan-2-yl)thiophene-2-carbaldehyde (141 mg, 0.32 mmol) in MeOH (1.5 mL) and DCM (1.5 mL) was added NaBH$_4$ (18.2 mg, 0.48 mmol). The reaction mixture was stirred at rt overnight and then concentrated to remove the solvent. The resulting residue was diluted with water and extracted with EtOAc. The combined organic layers were dried over MgSO$_4$, filtered and concentrated in vacuo. The crude material was purified by ISCO column chromatography eluting with 0%-25% EtOAc in hexanes to give 100 mg (71%) of the title compound. LCMS (FA): m/z=441.5 (M+1).

Example 47: rac-4-[{[tert-Butyl(dimethyl)silyl]oxy}(3-chlorophenyl)methyl]-5-(methoxymethyl)thiophene-2-carbaldehyde Int-73

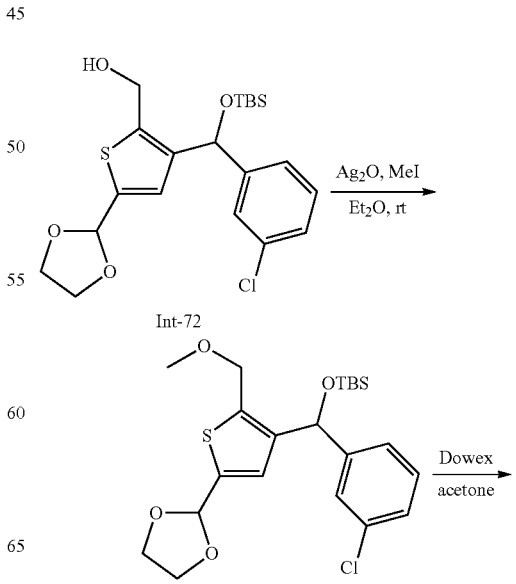

313

-continued

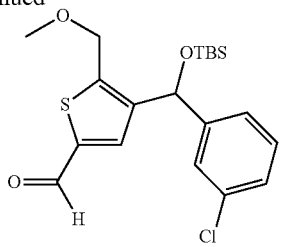

Int-73

Step 1: rac-tert-Butyl{(3-chlorophenyl)[5-(1,3-di-oxolan-2-yl)-2-(methoxymethyl)-3-thienyl]methoxy}dimethylsilane To a solution of Int-72 (480 mg, 1.09 mmol) in Et$_2$O (10 mL) was added Ag$_2$O (630 mg, 2.72 mmol) and MeI (2.71 mL, 43.5 mmol). The resulting mixture was stirred at rt for 5 days, and then filtered over a pad of Celite. The filtrate was concentrated in vacuo. The crude material was purified by ISCO column chromatography eluting with 0%-10% EtOAc in hexanes to give 371 mg (75%) of the title compound as a clear oil. $^1$H NMR (400 MHz, DMSO-d6) δ 7.52-7.32 (m, 4H), 7.16-6.91 (m, 1H), 6.41-6.12 (m, 1H), 6.04-5.99 (m, 1H), 4.74-4.51 (m, 2H), 4.17-3.92 (m, 4H), 3.40-3.35 (m, 3H), 0.94 (s, 9H), 0.12--0.03 (m, 6H); LCMS (FA) M+1 455.5

Step 2: rac-4-[{[tert-Butyl(dimethyl)silyl]oxy}(3-chlorophenyl)methyl]-5-(methoxymethyl)thiophene-2-carbaldehyde To a solution of tert-butyl{(3-chlorophenyl)[5-(1,3-dioxolan-2-yl)-2-(methoxymethyl)-3-thienyl]methoxy}dimethylsilane (371 mg, 0.82 mmol) in acetone (10.8 mL) was added 380 mg of DOWEX 50WX2-200 (H). The resulting mixture was stirred at rt for 2 h and then filtered. The filtrate was concentrated in vacuo and the crude material was purified by ISCO column chromatography eluting with 0%-10% EtOAc in hexanes to give 283 mg (84%) of the title compound as a clear oil. $^1$H NMR (400 MHz, DMSO-d6) δ 10.41-9.84 (m, 1H), 8.02-7.22 (m, 5H), 6.61-6.03 (m, 1H), 4.82-4.61 (m, 2H), 3.40-3.28 (m, 3H), 0.95-0.83 (m, 9H), 0.09--0.04 (m, 6H). LCMS (FA): m/z=411.4 (M+1).

Example 48: rac-4-[{[tert-Butyl(dimethyl)silyl]oxy}(3-chlorophenyl)methyl]-5-({[tert-butyl(dimethyl)silyl]oxy}methyl)thiophene-2-carbaldehyde Int-74

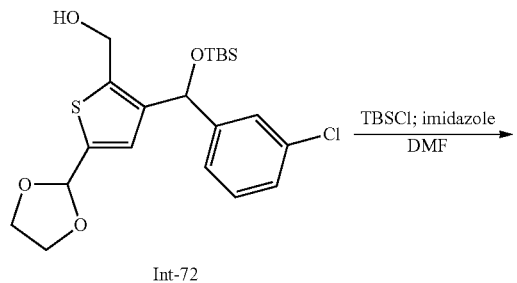

Int-72

314

-continued

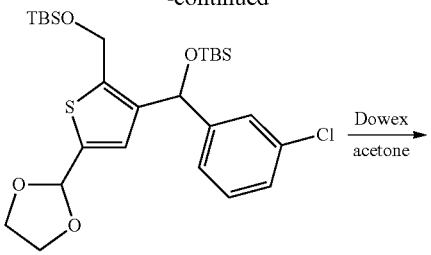

Int-74

Step 1: rac-tert-Butyl({3-[{[tert-butyl(dimethyl)silyl]oxy}(3-chlorophenyl)methyl]-5-(1,3-dioxolan-2-yl)-2-thienyl}methoxy)dimethylsilane To a solution of Int-72 (648 mg, 1.47 mmol) in DMF (15 mL) was added TBSCl (664 mg, 4.41 mmol) and 1H-imidazole (300 mg, 4.41 mmol). The reaction mixture was stirred at rt for 17 h then quenched with water and extracted with EtOAc. The combined organic layers were dried over MgSO$_4$, washed with 10% aqueous LiCl, filtered and concentrated in vacuo and the crude material was purified by ISCO column chromatography eluting with 0%-5% EtOAc in hexanes to give 373 mg (46%) of the title compound. LCMS (FA): m/z=555.6 (M+1).

Step 2: rac-4-[{[tert-Butyl(dimethyl)silyl]oxy}(3-chlorophenyl)methyl]-5-({[tert-butyl(dimethyl)silyl]oxy}methyl)thiophene-2-carbaldehyde To a solution of tert-butyl({3-[{[tert-butyl(dimethyl)silyl]oxy}(3-chlorophenyl)methyl]-5-(1,3-dioxolan-2-yl)-2-thienyl}methoxy)dimethylsilane (373 mg, 0.67 mmol) in acetone (8.9 mL) was added 380 mg of DOWEX 50WX2-200 (H). The resulting mixture was stirred at rt for 2 h and then filtered. The filtrate was concentrated in vacuo and the crude material was purified by ISCO column chromatography eluting with 0%-10% EtOAc in hexanes to give 289 mg (84%) of the title compound as a clear oil. $^1$H NMR (400 MHz, DMSO-d6) δ 9.76 (s, 1H), 7.88 (s, 1H), 7.40-7.24 (m, 4H), 5.98 (s, 1H), 4.86 (s, 2H), 0.83 (d, J=0.9 Hz, 16H), 0.04--0.02 (m, 6H), -0.03--0.11 (m, 6H). LCMS (FA): m/z=511.6 (M+1).

Example 49: rac-4-{(5-Chloro-2-furyl)[(triisopropylsilyl)oxy]methyl}thiophene-2-carbaldehyde Int-75

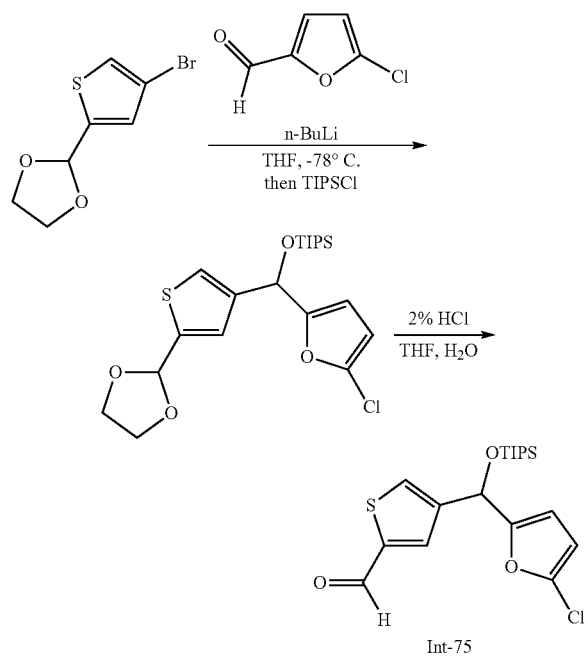

Int-75

Step 1: rac-{(5-Chloro-2-furyl)[5-(1,3-dioxolan-2-yl)-3-thienyl]methoxy}(triisopropyl)silane 2.50 M of n-BuLi in hexane (2.68 mL, 6.69 mmol) was added dropwise via syringe into THF (40 mL) at −78° C. 2-(4-Bromothiophen-2-yl)-1,3-dioxolane (1.05 g, 4.46 mmol) was added to the solution at −78° C., and then 5-chloro-2-furaldehyde (582 mg, 4.46 mmol) was added to the solution at once at −78° C. The reaction was stirred at −78° C. for 15 min. To the mixture was TIPSCl (1.72 g, 8.92 mmol) was added to this solution and the resulting mixture was warmed to rt followed by refluxing for 4 h. The solution was poured into 60 ml water and the mixture was extracted with EtOAc (50 ml×2). The combined organic layers were concentrated in vacuo. The residue was purified by ISCO column chromatography (0%-30% EtOAc in hexanes as eluent) to give 1.51 g (76%) of the title compound as a colorless oil. $^1$H NMR (400 MHz, Chloroform-d) δ 7.31 (s, 1H), 7.12 (s, 1H), 6.12 (d, 1H), 6.07 (s, 1H), 6.06 (d, J=3.3 Hz, 1H), 5.83 (s, 1H), 4.20-4.11 (m, 2H), 4.07-3.98 (m, 2H), 1.07 (s, 21H).

Step 2: rac-4-{(5-Chloro-2-furyl)[(triisopropylsilyl)oxy]methyl}thiophene-2-carbaldehyde To a solution of {(5-chloro-2-furyl)[5-(1,3-dioxolan-2-yl)-3-thienyl]methoxy}(triisopropyl)silane (1.96 g, 4.43 mmol) in THF (20.0 mL) was added water (1.00 mL, 55.5 mmol) followed by 20 ml 2% HCl in THF solution at rt. The reaction was stirred for 15 min at same temperature. The solution was poured into the solution of 30 ml saturated NaHCO$_3$ solution and 30 ml water solution. The mixture was extracted with EtOAc (50 ml×2). The combined organic layers were concentrated in vacuo and the residue was purified by ISCO column chromatography (0%-30% EtOAc in hexanes as eluent) to give 1.18 g (67%) of the title compound as a white solid. $^1$H NMR (400 MHz, Chloroform-d) δ 9.80 (s, 1H), 7.66 (d, J=3.3 Hz, 1H), 7.65-7.62 (s, 1H), 6.09 (s, 1H), 6.00 (d, J=3.3 Hz, 1H), 5.80 (s, 1H), 1.03-0.89 (m, 21H).

Example 50: rac-Bromo[1-(3-chlorophenyl)ethyl]zinc. Int-76

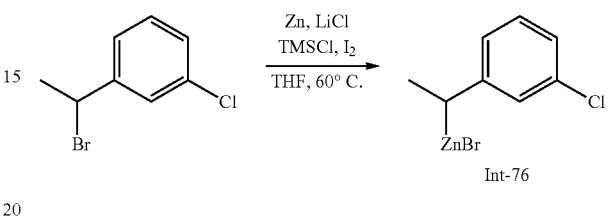

Int-76

Step 1: rac-Bromo[1-(3-chlorophenyl)ethyl]zinc

Lithium chloride (0.39 g, 9.11 mmol) was added to an oven-dried 50 mL 2-neck round bottom flask under an atmosphere of argon. The vessel was evacuated under high vacuum and heated with a heat gun for 10 min and backfilled with argon after cooling to rt. Zinc powder (0.596 g, 9.11 mmol) was added. The vessel was heated with a heat gun under high vac for 10 min and backfilled with argon after cooling to rt. THF (4.6 mL) was added followed by 1,2-dibromoethane (20 uL, 0.2 mmol). The reaction was heated at 60° C. for 20 min. TMSCl (5.78 uL, 45.6 umol) and iodine (5.78 mg, 22.8 umol) in THF (0.5 mL) were added to the vessel via syringe and the reaction was heated for 20 min at 60° C. 1-(1-Bromoethyl)-3-chlorobenzene (1.00 g, 4.56 mmol) was added and the reaction was heated at 50° C. for 2 h. TLC showed no starting material remaining and a new less polar spot. An additional 5 mL of THF was added. This solution of Int-76 in the next reaction without further purification.

Example 51: tert-Butyl{[4-(3-chlorobenzyl)-2-thienyl]methoxy}dimethylsilane Int-77, and 4-(3-chlorobenzyl)thiophene-2-carbaldehyde Int-78

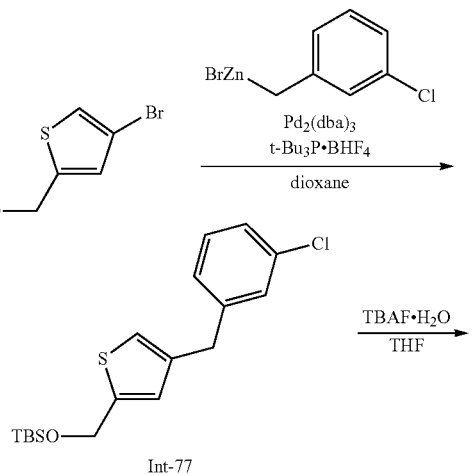

Int-77

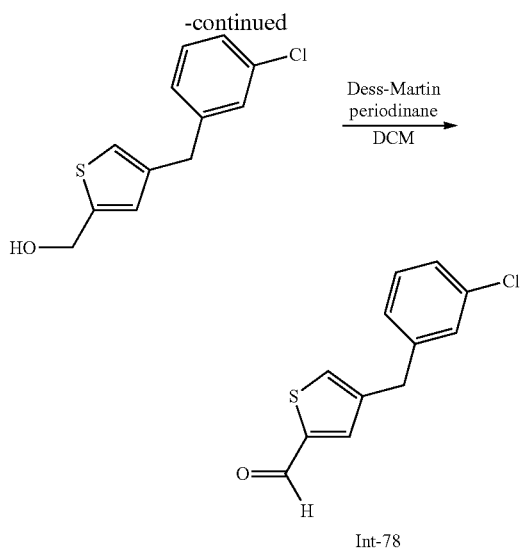

Int-78

Step 1: tert-Butyl{[4-(3-chlorobenzyl)-2-thienyl]methoxy}dimethylsilane

A 20 mL of microwave vessel was charged with ((4-bromothiophen-2-yl)methoxy)(tert-butyl)dimethylsilane (425 mg, 1.38 mmol), Pd$_2$(dba)$_3$ (25.3 mg, 0.03 mmol), and tri-tert-butylphosphonium tetrafluoroborate (16.1 mg, 0.06 mmol). To the mixture was added THF (18.2 mL) and the reaction vessel was purged with argon followed by sealing with a cap. After the mixture was stirred for 5 min at rt, 0.5 M of 3-chlorobenzylzinc chloride in THF solution (3.18 mL, 1.59 mmol) was added to the mixture. The reaction was heated at 50° C. for 1 hour. The reaction was cooled to rt and diluted with EtOAc. The organic layer was filtered through a Celite pad and the filtrate was washed with water followed by brine. The EtOAc layer was filtered and the filtrate was concentrated in vacuo. The residue was purified by ISCO column chromatography (5% EtOAc in hexanes as eluent) to give 475 mg (92%) of the title compound as colorless oil. $^1$H NMR (400 MHz, DMSO-d$_6$) δ 7.35-7.17 (m, 4H), 7.12 (s, 1H), 6.80 (s, 1H), 4.77 (s, 2H), 3.88 (s, 2H), 0.86 (s, 9H), 0.04 (s, 6H).

Step 2: [4-(3-Chlorobenzyl)-2-thienyl]methanol

To a solution of tert-butyl{[4-(3-chlorobenzyl)-2-thienyl]methoxy}dimethylsilane (1.68 g, 4.76 mmol) in THF (15.0 mL) was added TBAF hydrate (1.87 g, 7.14 mmol) at rt and the reaction was stirred overnight. The mixture was concentrated in vacuo and the residue was purified by ISCO column chromatography (40% EtOAc in hexanes as eluent) to give 0.82 g (72%) of the title compound. $^1$H NMR (400 MHz, Chloroform-d) δ 7.14-7.06 (m, 3H), 7.02-6.94 (m, 1H), 6.82-6.77 (m, 1H), 6.69 (s, 1H), 4.66 (s, 2H), 3.79 (s, 2H).

Step 3: 4-(3-Chlorobenzyl)thiophene-2-carbaldehyde

To a solution of [4-(3-chlorobenzyl)-2-thienyl]methanol (0.82 g, 3.4 mmol) in DCM (30.0 mL) was added Dess-Martin periodinane (1.53 g, 3.61 mmol) at rt and the reaction was stirred for 2 h. The mixture was filtered through Celite pad and the filtrate was concentrated in vacuo. The residue was purified by ISCO column chromatography (10% EtOAc in hexanes as eluent) to give 0.80 g (98%) of the title compound. $^1$H NMR (400 MHz, Chloroform-d) d 9.82 (s, 1H), 7.55 (s, 1H), 7.38 (s, 1H), 7.28-7.17 (m, 3H), 7.09 (dt, J=7.2, 1.6 Hz, 1H), 3.96 (s, 2H).

The compounds listed in the table below were prepared in a similar fashion to that described above starting from the listed starting materials. The following alternative conditions can be employed in the described reaction steps. Step 1: Pd(PPh$_3$)$_4$, THF at 70° C. instead of Pd$_2$(dba)$_3$ with tri-tert-butylphosphonium tetrafluoroborate, THF at 50° C.

| Step 1 zinc reagent | Step 1 condition | Product/Int No. | Characterization Data |
|---|---|---|---|
| BrZn—CH$_2$—C$_6$H$_4$—Br (3-bromobenzyl) | Pd(PPh$_3$)$_4$ THF; 70° C. | Int-79 | $^1$H NMR (400 MHz, Chloroform-d) δ 9.86 (d, J = 1.1 Hz, 1H), 7.55 (d, J = 1.2 Hz, 1H), 7.41-7.37 (m, 2H), 7.35 (s, 1H), 7.20 (t, J = 7.7 Hz, 1H), 7.13 (d, J = 7.7 Hz, 1H), 3.97 (s, 2H). LCMS (FA): m/z = 282.9 (M + 1). |
| BrZn—CH$_2$—C$_6$H$_4$—CH$_3$ (3-methylbenzyl) | Pd(PPh$_3$)$_4$ THF; 70° C. | Int-80 | $^1$H NMR (400 MHz, Chloroform-d) δ 9.84 (d, J = 1.1 Hz, 1H), 7.56 (d, J = 1.2 Hz, 1H), 7.38 (s, 1H), 7.21 (t, J = 7.5 Hz, 1H), 7.06 (d, J = 7.5 Hz, 1H), 7.03-6.97 (m, 2H), 3.95 (s, 2H), 2.33 (s, 3H). LCMS (FA): m/z = 217.1 (M + 1). |

Example 52: rac-4-(1-Phenylethyl)thiophene-2-carbaldehyde. Int-81

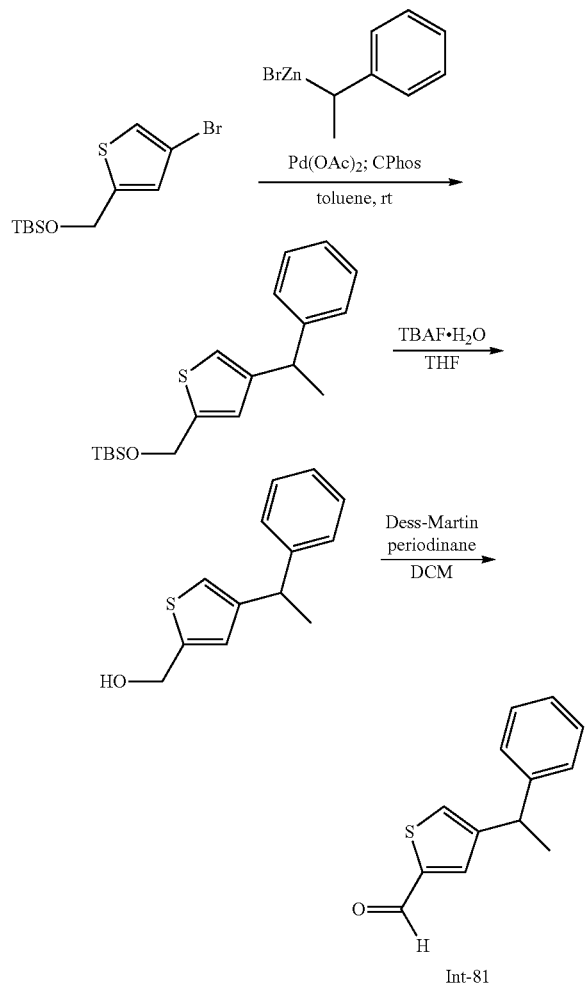

Step 1: rac-tert-Butyl(dimethyl){[4-(1-phenylethyl)-2-thienyl]methoxy}silane ((4-Bromothiophen-2-yl)methoxy)(tert-butyl)dimethylsilane (135 mg, 0.439 mmol), Pd(OAc)$_2$ (7.1 mg, 0.032 mmol) and 2-dicyclohexylphosphino-2',6'-bis(N,N-dimethylamino)biphenyl (21.2 mg, 48.6 umol) were added to a microwave reaction vial. The vial was purged with argon and toluene (1.00 mL) was added. To the dark red solution at rt was added 0.5 M of alpha-methylbenzylzinc bromide in THF (1.32 mL, 0.66 mmol) dropwise over 30 min and the reaction was stirred for 1 hour. The reaction was quenched with 0.5 M HCl and diluted with water and EtOAc. The layers were separated and the aqueous layer was washed with brine, dried over Na$_2$SO$_4$, filtered and concentrated in vacuo. The residue was purified via ISCO column chromatography (2% isocratic EtOAc in hexanes as eluent) to give the title compound as clear colorless oil (yield=134 mg). $^1$H NMR (400 MHz, Chloroform-d) δ 7.32-7.26 (m, 2H), 7.22-7.18 (m, 3H), 6.86-6.84 (m, 1H), 6.69-6.66 (m, 1H), 4.78 (d, J=0.9 Hz, 2H), 4.08 (q, J=7.1 Hz, 1H), 1.60 (d, J=7.2 Hz, 3H), 0.90 (s, 9H), 0.07 (s, 6H).

Step 2: rac-[4-(1-Phenylethyl)-2-thienyl]methanol tert-Butyl(dimethyl){[4-(1-phenylethyl)-2-thienyl]methoxy}silane (134 mg, 0.40 mmol), THF (4.0 mL) and TBAF hydrate (225 mg, 0.81 mmol) were combined in a 100 mL round-bottom flask and the reaction was stirred for 10 min. The reaction was concentrated in vacuo and purified via ISCO column chromatography (20% EtOAc in hexanes isocratic as eluent) to give the title compound as colorless oil (yield=90 mg). $^1$H NMR (400 MHz, Chloroform-d) δ 7.34-7.26 (m, 2H), 7.24-7.14 (m, 3H), 6.92 (s, 1H), 6.78 (s, 1H), 4.74 (s, 2H), 4.09 (q, J=7.2 Hz, 1H), 1.61 (d, J=7.2 Hz, 3H).

Step 3: rac-4-(1-Phenylethyl)thiophene-2-carbaldehyde

To a solution of [4-(1-phenylethyl)-2-thienyl]methanol (132 mg, 0.61 mmol) in DCM (12 mL) was added Dess-Martin periodinane (385 mg, 0.91 mmol) at rt and the mixture was stirred for 30 min. The reaction was quenched by addition of saturated NaHCO$_3$ (50 mL) and extracted with DCM (50 mL×2). The combined organic layers were washed with brine, dried over Na$_2$SO$_4$, filtered, and concentrated in vacuo. The residue was purified by ISCO silica gel column chromatography (5% EtOAc in hexanes as eluent) to give the title compound as a colorless oil (yield=98 mg). $^1$H NMR (400 MHz, Chloroform-d) δ 9.83 (d, J=1.1 Hz, 1H), 7.55 (d, J=1.3 Hz, 1H), 7.44-7.39 (m, 1H), 7.32 (t, J=7.4 Hz, 2H), 7.25-7.16 (m, 3H), 4.17 (q, J=7.1 Hz, 1H), 1.66 (d, J=7.2 Hz, 3H).

The compound listed in the table below was prepared in an analogous fashion to that described above starting from the listed starting material:

| Step 1 zinc reagent | Product/Int No. | Characterization Data |
| --- | --- | --- |
| BrZn-CH(CH₃)-(3-chlorophenyl) (Int-40) | Int-82 | $^1$H NMR (400 MHz, Chloroform-d) δ 9.84 (d, J = 1.1 Hz, 1H), 7.53 (d, J = 1.3 Hz, 1H), 7.44-7.40 (m, 1H), 7.29-7.19 (m, 2H), 7.19-7.16 (m, 1H), 7.10-7.05 (m, 1H), 4.15 (q, J = 7.2 Hz, 1H), 1.65 (d, J = 7.2 Hz, 3H). |

Example 53: 4-(3-Chlorobenzyl)-5-fluorothiophene-2-carbaldehyde Int-83

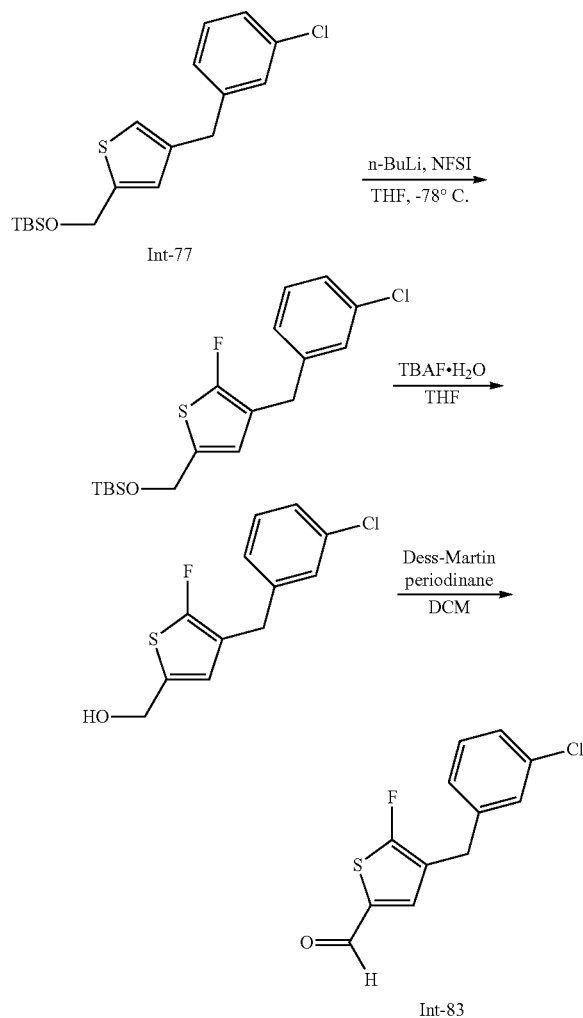

Step 1: tert-Butyl{[4-(3-chlorobenzyl)-5-fluoro-2-thienyl]methoxy}dimethylsilane tert-Butyl{[4-(3-chlorobenzyl)-2-thienyl]methoxy}dimethylsilane (Int-77, 380 mg, 1.08 mmol) in a 100 mL 2-neck round bottom flask was dissolved in THF (20.0 mL) under atmosphere of argon, and the solution was cooled at −78° C. To the solution was added dropwise 2.50 M of n-BuLi in hexane (0.65 mL, 1.62 mmol) and the light orange solution was stirred for 30 min at −78° C. To the solution was added dropwise a solution of N-fluoro-N-(phenylsulfonyl)benzenesulfonamide (509 mg, 1.62 mmol) in THF (4.0 mL) at −78° C., and the reaction was stirred for 30 min. The reaction was quenched by addition of saturated NH$_4$Cl (50 mL) and extracted with hexane (60 mL×3). The combined organic layers were dried over Na$_2$SO$_4$, filtered, and concentrated in vacuo. The residue was purified by ISCO column chromatography (0.5% EtOAc in hexanes as eluent) to give 283 mg (67%) of the title compound as colorless oil. $^1$H NMR (400 MHz, DMSO-d$_6$) δ 7.33 (t, J=7.9 Hz, 1H), 7.30-7.24 (m, 2H), 7.17 (d, J=7.5 Hz, 1H), 6.58 (d, J=4.0 Hz, 1H), 4.68 (d, J=2.1 Hz, 2H), 3.81 (s, 2H), 0.85 (s, 9H), 0.04 (s, 6H).

Step 2: [4-(3-Chlorobenzyl)-5-fluoro-2-thienyl]methanol tert-Butyl{[4-(3-chlorobenzyl)-5-fluoro-2-thienyl]methoxy}dimethylsilane (283 mg, 0.76 mmol) in THF (10.0 mL, 123 mmol) was added a solution of TBAF hydrate (320 mg, 1.14 mmol) in THF (2.0 mL) at rt, and the mixture was stirred for 30 min. The reaction was quenched by addition of water (80 mL) and extracted with EtOAc (80 mL×3). The combined organic layers were dried over Na$_2$SO$_4$, filtered, and concentrated in vacuo. The residue was purified by preparative HPLC (FA, 45% to 80% CH$_3$CN in water, UV: 232). The product fractions were combined and concentrated in vacuo to remove organic solvent. The residual water layer was added 20 mL of saturated NaHCO$_3$ and then the mixture was extracted with EtOAc (60 mL×3). The combined organic layers were washed with brine, dried over Na$_2$SO$_4$, filtered, and concentrated in vacuo to give 185 mg (95%) of the title compound as colorless oil. $^1$H NMR (400 MHz, DMSO-d$_6$) δ 7.37-7.30 (m, 1H), 7.30-7.24 (m, 2H), 7.18 (d, J=7.5 Hz, 1H), 6.54 (d, J=4.0 Hz, 1H), 5.46 (t, J=5.8 Hz, 1H), 4.48-4.41 (m, 2H), 3.80 (s, 2H).

Step 3: 4-(3-Chlorobenzyl)-5-fluorothiophene-2-carbaldehyde

To a solution of [4-(3-chlorobenzyl)-5-fluoro-2-thienyl]methanol (180 mg, 0.70 mmol) in DCM (10.0 mL, 156 mmol) was added Dess-Martin periodinane (446 mg, 1.05 mmol) at rt, and the reaction was stirred for 30 min. The reaction was quenched by addition of saturated NaHCO$_3$ (60 mL) and extracted with DCM (50 mL×3). The combined organic layers were dried over Na$_2$SO$_4$, filtered, and concentrated in vacuo. The residue was purified by ISCO silica gel column chromatography (5%-10% EtOAc in hexanes as eluent) to give 125 mg (70%) of the title compound as colorless oil. $^1$H NMR (400 MHz, DMSO-d$_6$) δ 9.76 (d, J=4.4 Hz, 1H), 7.79 (d, J=4.5 Hz, 1H), 7.40-7.34 (m, 2H), 7.31 (d, J=8.3 Hz, 1H), 7.23 (d, J=7.3 Hz, 1H), 3.95 (s, 2H).

Example 54: 4-(3-Chlorobenzyl)-5-methylthiophene-2-carbaldehyde. Int-84

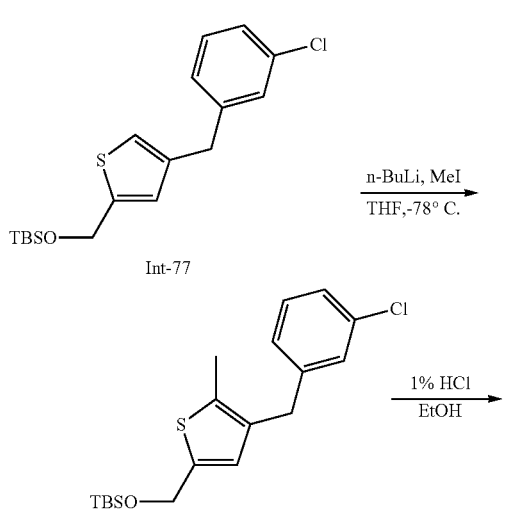

-continued

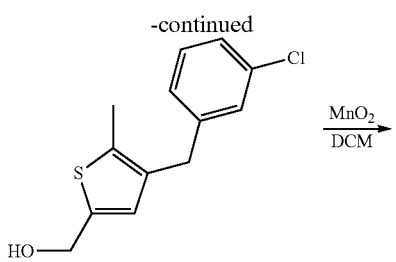

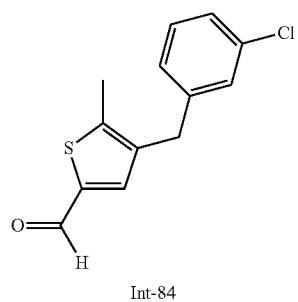

Int-84

Step 1: tert-Butyl{[4-(3-chlorobenzyl)-5-methyl-2-thienyl]methoxy}dimethylsilane Int-77 (0.67 g, 1.90 mmol) was dissolved into THF (10.0 mL), and then cooled down at −78° C. 2.50 M of n-BuLi in hexane (6.08 mL, 15.2 mmol) was added dropwise via syringe to this solution at −78° C. and the mixture was stirred for 30 min. To the mixture was added methyl iodide (1.18 mL, 19.0 mmol) and the reaction was stirred at −78° C. for 30 min. The reaction was quenched by addition of 30 ml water at −78° C. and the mixture was warmed at rt. The resulting mixture was extracted with DCM (30 ml×2). The organic layers were combined and concentrated in vacuo to yield 574 mg (82%) of the title compound. $^1$H NMR (400 MHz, Chloroform-d) δ 7.12-7.08 (m, 2H), 7.03 (s, 1H), 6.94 (d, J=7.1 Hz, 1H), 6.45 (s, 1H), 4.66 (s, 2H), 3.71 (s, 2H), 2.26 (s, 3H), 0.83 (s, 9H), −0.00 (s, 6H).

Step 2: [4-(3-Chlorobenzyl)-5-methyl-2-thienyl]methanol tert-Butyl{[4-(3-chlorobenzyl)-5-methyl-2-thienyl]methoxy}dimethylsilane (0.62 g, 1.69 mmol) was dissolved into 20 ml 1% HCl in EtOH solution and the mixture was stirred at rt for 30 min. The solution was poured into 30 ml saturated NaHCO$_3$ solution and the mixture was extracted with DCM (30 ml×2). The combined organics were concentrated in vacuo and the mixture was purified by ISCO column chromatography (0%-60% EtOAc in hexanes as eluent) to give 332.5 mg (78%) of the title compound. $^1$H NMR (400 MHz, Chloroform-d) δ 7.26-7.17 (m, 2H), 7.14 (s, 1H), 7.05 (dd, J=7.1, 1.7 Hz, 1H), 6.65 (s, 1H), 4.71 (s, 2H), 3.82 (s, 2H), 2.39 (s, 3H).

Step 3: 4-(3-Chlorobenzyl)-5-methylthiophene-2-carbaldehyde

To a solution of [4-(3-chlorobenzyl)-5-methyl-2-thienyl]methanol (324.2 mg, 1.28 mmol) in DCM (40.0 mL) was added MnO$_2$ (1.67 g, 19.2 mmol) and the mixture was stirred at rt for 6 h. The reaction mixture was filtered through a Celite pad and the filter cake was washed with DCM several times. The filtrate was concentrated in vacuo to yield 289.2 mg (90%) of the title compound. $^1$H NMR (400 MHz, Chloroform-d) δ 9.76 (s, 1H), 7.42 (s, 1H), 7.30-7.19 (m, 2H), 7.14 (s, 1H), 7.11-7.00 (m, 1H), 3.90 (s, 2H), 2.48 (s, 3H).

Example 55: 4-({[tert-Butyl(dimethyl)silyl]oxy}methyl)-5-methylthiophene-2-carbaldehyde Int-85, and 4-(3-bromobenzyl)-5-methylthiophene-2-carbaldehyde Int-86

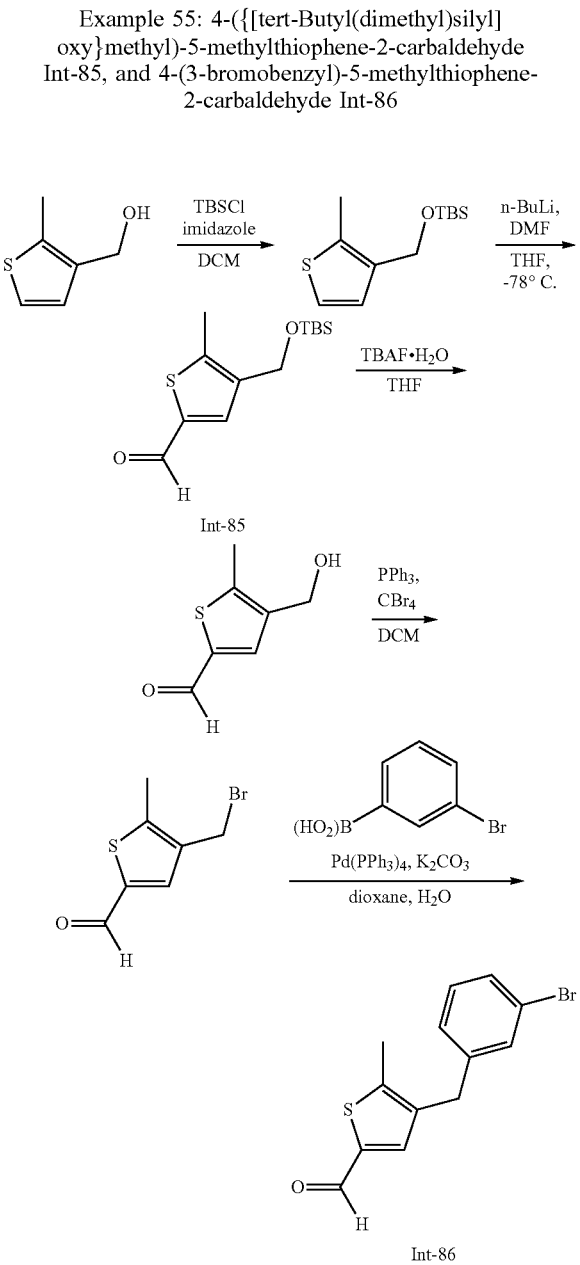

Step 1: tert-Butyl(dimethyl)[(2-methyl-3-thienyl)methoxy]silane

To a solution of (2-methyl-3-thienyl)methanol (2.6 g, 20.0 mmol) in DCM (64.2 mL) was added 1H-imidazole (2.07 g, 30.4 mmol) followed by TBSCl (3.21 g, 21.3 mmol) at rt, and the mixture was stirred for 6 h. The reaction was quenched by addition of water (50 mL) and then mixture was extracted with EtOAc (1×). The combined organic layers were dried over MgSO$_4$, filtered, and concentrated. The residue was purified on ISCO column chromatography (0%-25% EtOAc in hexanes as eluent) to give 4.44 g (90%) of the title compound as colorless oil. $^1$H NMR (400 MHz, Chloroform-d) δ 7.00 (d, J=5.2 Hz, 1H), 6.96 (d, J=5.2 Hz, 1H), 4.63 (s, 2H), 2.40 (s, 3H), 0.92 (s, 9H), 0.07 (s, 6H).

Step 2: 4-({[tert-Butyl(dimethyl)silyl]oxy}methyl)-5-methylthiophene-2-carbaldehyde tert-Butyl(dimethyl)[(2-methyl-3-thienyl)methoxy]silane (1.0 g, 4.10 mmol) was weighed into a 250 mL 2-neck round bottom flask and the reaction vessel was purged with argon. The content was dissolved in THF (20.0 mL) and the solution was cooled at −78° C. To this solution was added dropwise 2.50 M of n-BuLi in hexane (1.73 mL, 4.33 mmol) and the mixture was stirred for 30 min. Then DMF (0.48 mL, 6.19 mmol) was added dropwise to the mixture at −78° C. The reaction was stirred for 30 min. The reaction was quenched by addition of saturated NH$_4$Cl (80 mL) and extracted with EtOAc (80 mL×3). The combined organic layers were dried over Na$_2$SO$_4$, filtered, and concentrated in vacuo. The residue was purified by ISCO column chromatography (5% EtOAc in hexanes as eluent) to give 888 mg of the title compound as colorless oil. $^1$H NMR (400 MHz, Chloroform-d) δ 9.79 (s, 1H), 7.64 (s, 1H), 4.62 (s, 2H), 2.47 (s, 3H), 1.55 (s, 2H), 0.93 (s, 9H), 0.10 (s, 6H).

Step 5: 4-(3-Bromobenzyl)-5-methylthiophene-2-carbaldehyde

A microwave reaction vial was charged with 4-(bromomethyl)-5-methylthiophene-2-carbaldehyde (95.0 mg, 0.43 mmol), 3-bromophenylboronic acid (87.1 mg, 0.43 mmol), K$_2$CO$_3$ (0.18 g, 1.30 mmol), and Pd(PPh$_3$)$_4$ (25.0 mg, 0.02 mmol). The contents were dissolved in 1,4-dioxane (2.0 mL) followed by addition of water (0.5 mL), and the vial was sealed with cap under atmosphere of argon. The reaction was heated at 80° C. for 1 hour. The reaction was cooled at rt and transferred into a separatory funnel with EtOAc and water. The mixture was extracted with EtOAc (×3) and the combined organic layers were dried over Na$_2$SO$_4$, filtered, and concentrated in vacuo. The residue was purified by ISCO column chromatography (10% EtOAc in hexanes as eluent) to give 92 mg of the title compound as light yellow oil. LCMS (FA): m/z=296.9 (M+H).

The compound listed in the table below was prepared in an analogous fashion to that described above starting from the listed starting material:

| Step 5 boronic acid | Compound Name/Int No. | Characterization Data |
|---|---|---|
| (HO)$_2$B-[3-ethylphenyl] | Int-87 | $^1$H NMR (400 MHz, Chloroform-d) δ 9.73 (s, 1H), 7.41 (s, 1H), 7.22 (t, J = 7.6 Hz, 1H), 7.07 (d, J = 7.6 Hz, 1H), 7.01-6.92 (m, 2H), 3.88 (s, 2H), 2.62 (q, J = 7.6 Hz, 2H), 2.47 (s, 3H), 1.22 (t, J = 7.6 Hz, 3H). LCMS (FA): m/z = 245.1 (M + 1). |

Step 3: 4-(Hydroxymethyl)-5-methylthiophene-2-carbaldehyde

To a solution of 4-({[tert-butyl(dimethyl)silyl]oxy}methyl)-5-methylthiophene-2-carbaldehyde (850.0 mg, 3.143 mmol) in THF (20.0 mL) was added TBAF monohydrate (966 mg, 3.46 mmol) at rt, and the mixture was stirred for 30 min. The reaction was quenched by addition of water (60 mL) and extracted with EtOAc (60 mL×3). The combined organic layers were washed with brine, dried over Na$_2$SO$_4$, filtered, and concentrated in vacuo. The residue was purified by ISCO silica gel column chromatography (50% EtOAc in hexanes as eluent) to give 395 mg (81%) of the title compound as colorless oil. LCMS (FA): m/z=156.9 (M+H).

Step 4: 4-(Bromomethyl)-5-methylthiophene-2-carbaldehyde 4-(hydroxymethyl)-5-methylthiophene-2-carbaldehyde (316 mg, 2.02 mmol) in DCM (31.6 mL) was added PPh$_3$ (689.8 mg, 2.63 mmol) followed by CBr$_4$ (805 mg, 2.43 mmol) at rt, and the mixture was stirred for 1 hour. The reaction was concentrated in vacuo and the residue was purified by ISCO column chromatography (0%-30% EtOAc in hexanes as eluent) to give 365 mg (82%) of the title compound as light yellow solid. $^1$H NMR (400 MHz, Chloroform-d) δ 9.79 (s, 1H), 7.66 (s, 1H), 4.44 (s, 2H), 2.54 (s, 3H).

Example 56: rac-4-{(3-Bromophenyl)[(triisopropylsilyl)oxy]methyl}thiophene-2-carbaldehyde Int-88

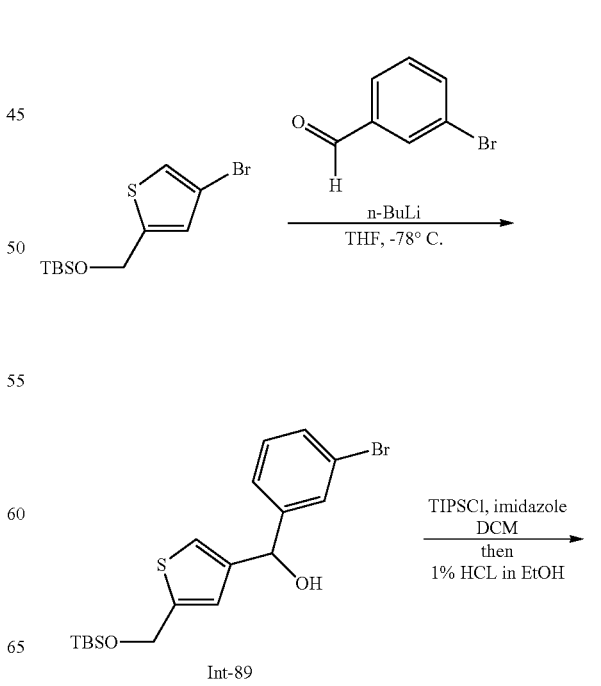

Int-89

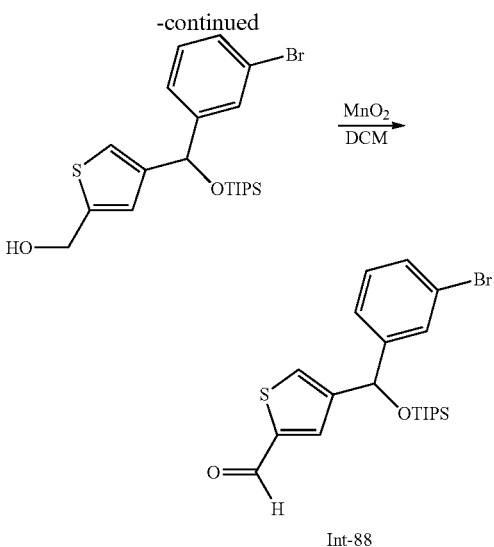

Int-88

Step 1: rac-(3-Bromophenyl)[5-({[tert-butyl(dimethyl)silyl]oxy}methyl)-3-thienyl]methanol. Int-89

2.50 M of n-BuLi in hexane (5.99 mL, 15.0 mmol) was dissolved into THF (75.0 mL) at −78° C., then ((4-bromothiophen-2-yl)methoxy)(tert-butyl)dimethylsilane (3.83 g, 12.5 mmol) was added to this solution at −78° C. and the mixture was stirred for 2 min. 3-Bromobenzaldehyde (2.42 g, 13.1 mmol) was added to the solution at −78° C. and the reaction was stirred at −78° C. for 15 min. The solution was poured into 100 ml of 5 g acetic acid in water solution and the resulting mixture was extracted with DCM (70 ml×2). The combined organic layers were concentrated in vacuo. The residue was purified by ISCO column chromatography (0%-15% EtOAc in hexanes as eluent) to give 4.05 g (79%) of the title compound. $^1$H NMR (400 MHz, Chloroform-d) δ 7.47 (s, 1H), 7.33 (d, J=7.3, 1H), 7.22 (d, J=7.7 Hz, 1H), 7.13 (t, J=7.8 Hz, 1H), 7.04-6.98 (s, 1H), 6.69 (s, 1H), 5.69 (s, 1H), 4.72 (s, 2H), 0.83 (s, 9H), 0.01 (s, 6H).

Step 2: rac-(4-{(3-Bromophenyl)[(triisopropylsilyl)oxy]methyl}-2-thienyl)methanol rac-(3-Bromophenyl)[5-({[tert-butyl(dimethyl)silyl]oxy}methyl)-3-thienyl]methanol (1.32 g, 3.19 mmol) and 1H-imidazole (3.26 g, 47.9 mmol) was dissolved in DCM (20.0 mL), then TIPSCl (6.16 g, 31.9 mmol) was added to this solution at rt. The solvent was removed by evaporation. The neat reaction mixture was heated at 80° C. for 2 h. The reaction was quenched by addition of 30 ml water and the mixture was extracted with DCM (10 ml×2). The combined organic layers were concentrated in vacuo and the residue was purified by ISCO column chromatography (0%-8% EtOAc in hexanes as eluent) provide the disilylated intermediate. The mixture was dissolved in 30 mL of 1% HCl in EtOH solution and the resulting mixture was stirred for 15 min at rt. The reaction was quenched by addition of saturated NaHCO$_3$ (30 mL) and the mixture was extracted with DCM (30 mL×2). The combined organic layers were washed with brine, dried over Na$_2$SO$_4$, filtered, and concentrated in vacuo. The residue was purified by ISCO column chromatography (0%-30% EtOAc in hexanes as eluent) to give 0.50 g (34%) of the title compound. LCMS (FA): m/z=455.0 (M+1).

Step 3: rac-4-{(3-Bromophenyl)[(triisopropylsilyl)oxy]methyl}thiophene-2-carbaldehyde rac-(4-{(3-Bromophenyl)[(triisopropylsilyl)oxy]methyl}-2-thienyl)methanol (0.50 g, 1.10 mmol) was dissolved into DCM (30.0 mL), then MnO$_2$ (1.43 g, 16.5 mmol) was added to this solution. The reaction was stirred at rt overnight. The mixture was filtered through a Celite pad and washed with DCM. The filtrate was concentrated in vacuo and the residue was purified by ISCO column chromatography (0%-20% EtOAc in hexanes as eluent) to give 201.3 mg (40%) of the title compound as a white solid. $^1$H NMR (400 MHz, Chloroform-d) δ 9.85 (d, J=1.3 Hz, 1H), 7.69-7.66 (m, 1H), 7.65-7.59 (m, 1H), 7.59-7.54 (m, 1H), 7.42-7.37 (m, 1H), 7.35 (d, J=7.8 Hz, 1H), 7.22 (t, J=7.8 Hz, 1H), 5.87 (s, 1H), 1.19-0.95 (m, 21H).

The compounds listed in the table below were prepared in an analogous fashion to that described above starting from the listed starting material:

| Step 1 aldehyde | Compound Name/No. | Characterization Data |
|---|---|---|
| ![aldehyde with F and Br] | Int-90 | $^1$H NMR (400 MHz, Chloroform-d) δ 9.84 (d, J = 1.1 Hz, 1H), 7.76 (dd, J = 6.3, 2.5 Hz, 1H), 7.72-7.68 (m, 2H), 7.34 (ddd, J = 8.6, 4.6, 2.6 Hz, 1H), 6.94-6.87 (m, 1H), 6.20 (s, 1H), 1.22-1.07 (m, 3H), 1.04-0.95 (m, 18H). $^1$H NMR |
| ![aldehyde with Cl] | Int-91 | $^1$H NMR (400 MHz, Chloroform-d) δ 9.82 (d, J = 1.2 Hz, 1H), 7.65 (q, J = 1.3 Hz, 1H), 7.60 (d, J = 1.4 Hz, 1H), 7.40 (s, 1H), 7.30-7.26 (m, 2H), 7.23 (ddt, J = 6.6, 4.5, 2.6 Hz, 1H), 5.86 (s, 1H), 1.16-1.05 (m, 3H), 1.04-0.96 (m, 18H). $^1$H NMR |

Example 57: 5-{2-[(Trimethylsilyl)oxy]propan-2-yl}thiophene-2-carbaldehyde. Int-92

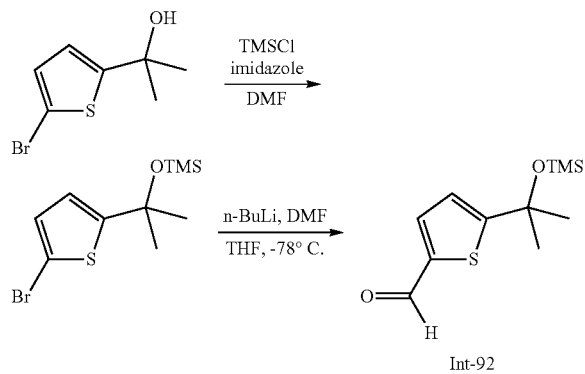

Step 1: {[2-(5-Bromo-2-thienyl)propan-2-yl]oxy}(trimethyl)silane

To a solution of 2-(5-bromo-2-thienyl)propan-2-ol (821 mg, 3.71 mmol) in DMF (14.0 mL) was added 1H-imidazole (758 mg, 11.1 mmol) and TMSCl (0.71 mL, 5.57 mmol) at rt and the reaction was stirred overnight. The reaction mixture was then poured into saturated aqueous NaHCO$_3$ at rt and extracted with EtOAc (3×). The combined organic layers were washed with water, brine, dried using Na$_2$SO$_4$, filtered and concentrated. The residue was purified by ISCO column chromatography (0%-5% EtOAc in hexanes as eluent) to give 835 mg (77%) of the title compound. $^1$H NMR (400 MHz, Chloroform-d) δ 6.84 (d, J=3.8 Hz, 1H), 6.57 (d, J=3.8 Hz, 1H), 1.61 (s, 6H), 0.11 (s, 9H).

Step 2: 5-{2-[(Trimethylsilyl)oxy]propan-2-yl}thiophene-2-carbaldehyde

Into a round-bottom flask cooled at −78° C. was added 2.50 M of n-BuLi in hexane (1.25 mL, 3.13 mmol). To the n-BuLi solution was added quickly dropwise a solution of {[2-(5-bromo-2-thienyl)propan-2-yl]oxy}(trimethyl)silane (835 mg, 2.85 mmol) in THF (9.0 mL) and the mixture was stirred for 5 min at −78° C. To the mixture was added quickly dropwise a solution of DMF (0.33 mL, 4.27 mmol) in THF (2.0 mL) and the reaction was stirred for 30 min. The reaction was then quenched with water and extracted with EtOAc (3×). The combined organic layers were then washed with water, brine, dried using Na$_2$SO$_4$, filtered and concentrated. The residue was purified by ISCO column chromatography (0%-5% EtOAc in hexanes as eluent) to give 494 mg (72%) of the title compound. $^1$H NMR (400 MHz, Chloroform-d) δ 9.84 (s, 1H), 7.60 (d, J=3.9 Hz, 1H), 6.94 (d, J=3.9 Hz, 1H), 1.66 (s, 6H), 0.14 (s, 9H).

Example 58: rac-5-{1-(3-Chlorophenyl)-1-[(trimethylsilyl)oxy]ethyl}thiophene-2-carbaldehyde Int-93

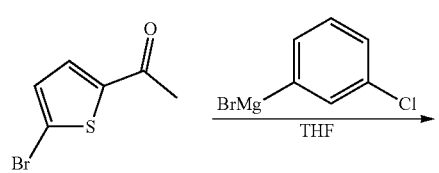

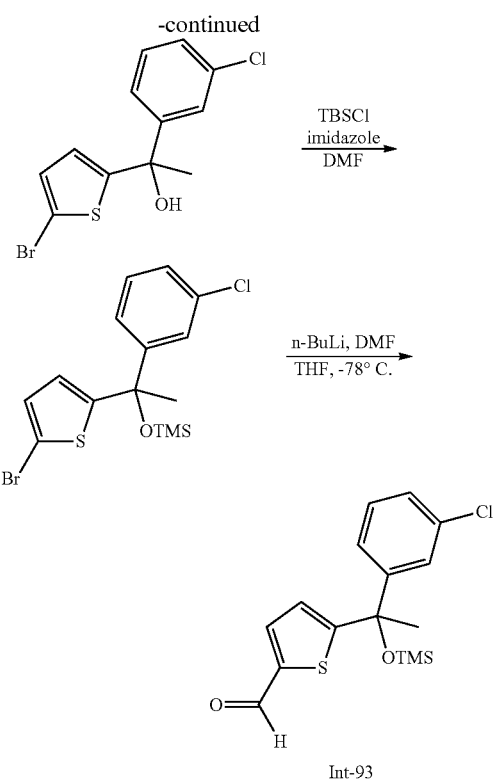

Step 1: rac-1-(5-Bromo-2-thienyl)-1-(3-chlorophenyl)ethanol

Into a round-bottom flask was added 2-bromo-5-acetylthiophene (1.00 g, 4.88 mmol) dissolved in THF (10.0 mL). The mixture was cooled to 0° C. and a 0.5 M solution of 3-chlorophenylmagnesium bromide in THF (19.5 mL, 9.75 mmol) was added dropwise over 30 min. The mixture was then stirred at 0° C. for 1 hour, warmed to rt and stirred overnight. The reaction was quenched with saturated NH$_4$Cl and extracted with EtOAc (3×). The combined organic layers were then washed with water, brine, dried using Na$_2$SO$_4$, filtered and concentrated. The residue was purified by ISCO column chromatography (0%-30% EtOAc in hexanes as eluent) to give 1.20 g (78%) of the title compound. $^1$H NMR (400 MHz, Chloroform-d) δ 7.51-7.48 (m, 1H), 7.36-7.32 (m, 1H), 7.28-7.26 (m, 2H), 6.88 (d, J=3.8 Hz, 1H), 6.65 (d, J=3.8 Hz, 1H), 2.36 (s, 1H), 1.96 (s, 3H).

Step 2: rac-[1-(5-Bromo-2-thienyl)-1-(3-chlorophenyl)ethoxy](trimethyl)silane To a solution of rac-1-(5-bromo-2-thienyl)-1-(3-chlorophenyl)ethanol (590 mg, 1.86 mmol) in DMF (7.0 mL) was added 1H-imidazole (379 mg, 5.57 mmol) and TMSCl (0.35 mL, 2.79 mmol) at rt. The reaction was then stirred at rt for 2 h. The reaction mixture was poured into a saturated aqueous NaHCO$_3$ solution and extracted with EtOAc (3×). The organic layers were then washed with water, brine, dried using Na$_2$SO$_4$, filtered and concentrated. The residue was purified by ISCO column chromatography (0%-5% EtOAc in hexanes as eluent) to give 523 mg (72%) of the title compound. $^1$H NMR (400 MHz, Chloroform-d) δ 7.44-7.41 (m, 1H), 7.29-7.26 (m, 1H), 7.23-7.20 (m, 2H), 6.84 (d, J=3.8 Hz, 1H), 6.58 (d, J=3.8 Hz, 1H), 1.95 (s, 3H), 0.08 (s, 9H).

Step 3: rac-5-{1-(3-Chlorophenyl)-1-[(trimethylsilyl)oxy]ethyl}thiophene-2-carbaldehyde Into a round-bottom flask cooled at −78° C. 2.50 M of n-BuLi in hexane (0.59 mL, 1.48 mmol) was added. To the n-BuLi solution was added quickly dropwise a solution of rac-[1-(5-bromo-2-thienyl)-1-(3-chlorophenyl)ethoxy](trimethyl)silane (523 mg, 1.34 mmol) in THF (4.00 mL) and the mixture was stirred for 5 min at −78° C. To the mixture was added quickly dropwise a solution of DMF (0.16 mL, 2.01 mmol) in THF (1.00 mL) and the reaction was stirred for 10 min. The reaction was quenched with water and extracted with EtOAc (3×). The combined organic layers were then washed with water, brine, dried using Na$_2$SO$_4$, filtered and concentrated. The residue was purified by ISCO column chromatography (0%-30% EtOAc in hexanes as eluent) to give 362 mg (80%) of the title compound. $^1$H NMR (400 MHz, Chloroform-d) δ 9.83 (s, 1H), 7.57 (d, J=3.9 Hz, 1H), 7.45-7.42 (m, 1H), 7.33-7.28 (m, 1H), 7.25-7.21 (m, 2H), 6.87 (d, J=3.9 Hz, 1H), 2.03 (s, 3H), 0.08 (s, 9H).

Example 59: 3-(3-Chlorobenzyl)thiophene-2-carbaldehyde Int-94 and 4-(3-Chlorobenzyl)-5-(methoxymethyl)thiophene-2-carbaldehyde Int-95

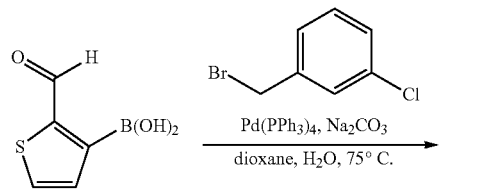

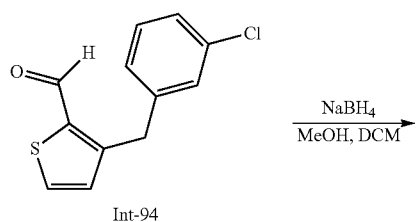

Int-94

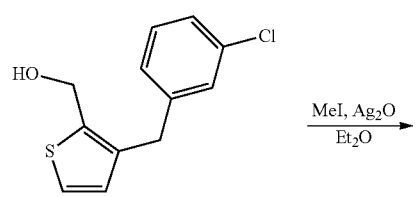

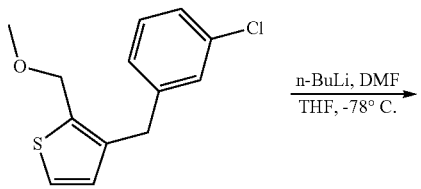

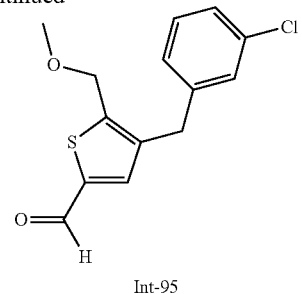

Int-95

Step 1: 3-(3-Chlorobenzyl)thiophene-2-carbaldehyde

To a degassed solution of 2-formyl-3-thiopheneboronic acid (3.05 g, 19.5 mmol), 1-(bromomethyl)-3-chlorobenzene (2.82 mL, 21.5 mmol), and Na$_2$CO$_3$ (6.21 g, 58.6 mmol) in 1,4-dioxane (60 mL) and water (15 mL, 830 mmol) was added Pd(PPh$_3$)$_4$ (2.26 g, 1.95 mmol). The reaction mixture was stirred 75° C. for 15 h and then quenched with water and extracted with EtOAc. The combined organic layers were dried over MgSO$_4$, washed with brine, filtered and concentrated in vacuo and the crude material was purified by ISCO column chromatography eluting with 0%-10% EtOAc in hexanes to give 3.86 g (84%) of the title compound as a tan oil. $^1$H NMR (400 MHz, DMSO-d6) δ 10.18 (d, J=1.0 Hz, 1H), 8.03 (d, J=4.9 Hz, 1H), 7.43-7.20 (m, 4H), 7.15 (d, J=5.0 Hz, 1H), 4.38 (s, 2H). LCMS (FA): m/z=237.3 (M+1).

Step 2: [3-(3-Chlorobenzyl)-2-thienyl]methanol

To a 0° C. stirred solution of 3-(3-chlorobenzyl)thiophene-2-carbaldehyde (3.54 g, 15.0 mmol) in MeOH (50 mL) and DCM (50 mL, 800 mmol) was added NaBH$_4$ (848 mg, 22.4 mmol). The reaction mixture was stirred at 0° C. for 15 h, then quenched with water and concentrated to remove the solvent. The resulting aqueous layer was extracted with EtOAc, washed with brine, dried over MgSO$_4$, filtered and concentrated in vacuo and the crude material was purified by ISCO column chromatography eluting with 0%-10% EtOAc in hexanes to give 3.34 g (94%) of the title compound as a clear oil. $^1$H NMR (400 MHz, DMSO-d6) δ 7.37-7.11 (m, 5H), 6.82 (d, J=5.1 Hz, 1H), 5.42 (t, J=5.5 Hz, 1H), 4.62 (d, J=5.5 Hz, 2H), 3.91 (s, 2H).

Step 3: [3-(3-Chlorobenzyl)-2-thienyl]methyl methyl ether3-(3-chlorobenzyl)-2-(methoxymethyl)thiophene To a solution of [3-(3-chlorobenzyl)-2-thienyl]methanol (979 mg, 4.10 mmol) in Et$_2$O (26 mL) was added MeI (10.2 mL, 164 mmol) and Ag$_2$O (2.38 g, 10.2 mmol). The reaction was stirred at rt for 16 h and then filtered over a pad of Celite. The resulting filtrate was concentrated in vacuo and the crude material was purified by ISCO column chromatography eluting with 0%-10% EtOAc in hexanes to give 450 mg (44%) of the title compound. $^1$H NMR (400 MHz, Chloroform-d) δ 7.24-7.16 (m, 4H), 7.04-6.99 (m, 1H), 6.82-6.78 (m, 1H), 4.57 (s, 2H), 3.96 (s, 2H), 3.40 (s, 3H).

Step 4: 4-(3-Chlorobenzyl)-5-(methoxymethyl)thiophene-2-carbaldehyde

To a −78° C. cooled solution of [3-(3-chlorobenzyl)-2-thienyl]methyl methyl ether3-(3-chlorobenzyl)-2-(methoxymethyl)thiophene (541 mg, 2.14 mmol) in THF (15.0 mL) was added a 2.50 M solution of n-BuLi in hexane (1.71 mL, 4.28 mmol), dropwise, via syringe. The resulting mixture was stirred for 30 min followed by addition of DMF (1.66 mL, 21.4 mmol), dropwise, via syringe. The reaction was allowed to stir at −78° C. for an additional 30 min and then quenched with saturated aqueous NaHCO$_3$ and extracted with EtOAc. The combined organic layers were dried over MgSO$_4$, washed with brine, filtered and concentrated in vacuo and the crude material was purified by ISCO column chromatography eluting with 0%-15% EtOAc in hexanes to give 305 mg (51%) of the title compound as a light brown oil. $^1$H NMR (400 MHz, Chloroform-d) δ 9.82 (s, 1H), 7.46 (s, 1H), 7.35-7.20 (m, 3H), 7.17 (s, 1H), 7.06 (d, J=6.6 Hz, 1H), 4.60 (s, 2H), 3.96 (s, 2H), 3.45 (s, 3H). LCMS (FA): m/z=281.4 (M+1).

The compound listed in the table below was prepared in an analogous fashion to that described above starting from the listed starting material:

| Step 3 reaction reagents | Compound Name/No. | Characterization Data |
|---|---|---|
| TBSCl, imidazole DMF | 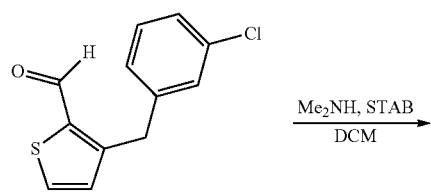<br>Int-96 | $^1$H NMR (400 MHz, DMSO-d$_6$) δ 9.78 (s, 1H), 7.74 (s, 1H), 7.38-7.25 (m, 3H), 7.21 (d, J = 7.4 Hz, 1H), 4.91 (s, 2H), 3.94 (s, 2H), 0.89 (s, 9H), 0.08 (s, 6H). $^1$H NMR |

Example 60: 4-(3-Chlorobenzyl)-5-[(dimethylamino)methyl]thiophene-2-carbaldehyde Int-97

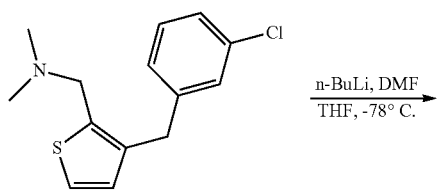

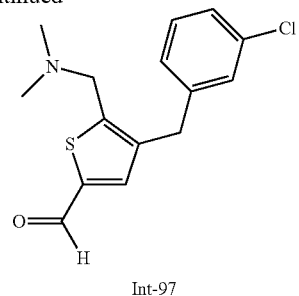

Int-97

Step 1: 1-[3-(3-Chlorobenzyl)-2-thienyl]-N,N-dimethylmethanamine

To a solution of Int-94 (415 mg, 1.75 mmol) in MeOH (12.3 mL) was added a 2.0 M solution of Me$_2$NH in MeOH (1.75 mL, 3.51 mmol) and sodium triacetoxyborohydride (743 mg, 3.51 mmol). The reaction mixture was stirred at rt for 24 h and then concentrated to remove the solvent. The residue was diluted in water and extracted with EtOAc. The combined organic layers were dried over MgSO$_4$, filtered and concentrated in vacuo and the crude material was purified by ISCO column chromatography eluting with 0%-50% EtOAc in hexanes to give 357 mg (77%) of the title compound as a clear oil. $^1$H NMR (400 MHz, DMSO-d6) δ 7.37-7.28 (m, 2H), 7.27-7.20 (m, 2H), 7.15 (d, J=7.6 Hz, 1H), 6.83 (d, J=5.1 Hz, 1H), 3.93 (s, 2H), 3.54 (s, 2H), 2.16 (s, 6H). LCMS (FA): m/z=266.3 (M+1).

Step 2: 4-(3-Chlorobenzyl)-5-[(dimethylamino)methyl]thiophene-2-carbaldehyde To a −78° C. cooled solution of 1-[3-(3-chlorobenzyl)-2-thienyl]-N,N-dimethylmethanamine (357 mg, 1.34 mmol) in THF (12.6 mL) was added a 2.50 M solution of n-BuLi in hexane (1.07 mL, 2.69 mmol), dropwise, via syringe. The reaction was allowed to stir at −78° C. for 20 min followed by addition of a solution of DMF (0.21 mL, 2.69 mmol) in THF (3 mL), dropwise, via syringe. After 30 min, the reaction mixture was quenched with water and extracted with EtOAc. The combined organic layers were dried over MgSO$_4$, filtered and concentrated in vacuo and the crude material was purified by ISCO column chromatography eluting with 0%-5% MeOH in DCM to give 270 mg (69%) of the title compound as a light yellow oil. LCMS (FA): m/z=295.9 (M+1).

Example 61: 4-Benzylthiophene-2-carbaldehyde Int-98

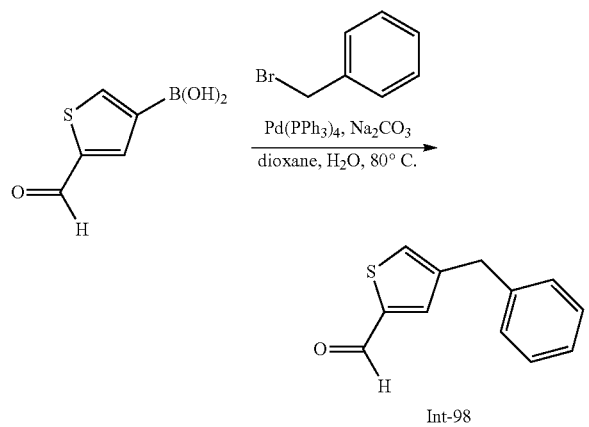

Step 1: 4-Benzylthiophene-2-carbaldehyde

To a degassed solution of 2-formyl-4-thiopheneboronic acid (509 mg, 3.26 mmol), benzyl bromide (558 mg, 3.26 mmol), and $Na_2CO_3$ (692 mg, 6.53 mmol) in 1,4-dioxane (24.4 mL) was added $Pd(PPh_3)_4$ (377 mg, 0.33 mmol). The reaction mixture was stirred at 80° C. for 3 h then quenched with water and extracted with EtOAc. The combined organic layers were dried over $Mg_2SO_4$, filtered and concentrated in vacuo the crude material was purified by ISCO column chromatography eluting with 0%-10% EtOAc in hexanes to give 377 mg (57%) of the title compound as a light yellow oil. $^1$H NMR (400 MHz, DMSO-d6) δ 9.86 (d, J=1.2 Hz, 1H), 7.84 (d, J=6.1 Hz, 2H), 7.38-7.18 (m, 5H), 4.00 (s, 2H). LCMS (FA): m/z=203.0 (M+1).

The compounds listed in the table below were prepared in an analogous fashion to that described above starting from the appropriate starting materials. The following alternative conditions could be employed in the described reaction steps. Condition A: $Pd(PPh_3)_4$, $Na_2CO_3$, dioxane, water, 80° C., B: $Pd(PPh_3)_4$, $K_2CO_3$, dioxane, water, 80° C., C: $PdCl_2$(dppf), $Cs_2CO_3$, dioxane, water, 60° C., D: $Pd(PPh_3)_4$, $Cs_2CO_3$, dioxane, water, 75° C., E: $PdCl_2$(dppf), $Cs_2CO_3$, THF, water, 70° C.

| Alkyl bromide | Reaction Condition | Compound Name/No. | Characterization Data |
| --- | --- | --- | --- |
| 3-fluorobenzyl bromide | A | Int-99 | $^1$H NMR (400 MHz, DMSO-d$_6$) δ 9.86 (d, J = 1.3 Hz, 1H), 7.89-7.84 (m, 2H), 7.35 (td, J = 8.1, 6.3 Hz, 1H), 7.15-7.09 (m, 2H), 7.04 (td, J = 8.6, 8.2, 2.5 Hz, 1H), 4.02 (s, 2H). $^1$H NMR |
| 3-bromobenzyl bromide | A | Int-79 | $^1$H NMR (400 MHz, Chloroform-d) δ 9.86 (d, J = 1.2 Hz, 1H), 7.55 (d, J = 1.2 Hz, 1H), 7.42-7.32 (m, 3H), 7.20 (t, J = 7.7 Hz, 1H), 7.13 (d, J = 7.7 Hz, 1H), 3.97 (s, 2H). $^1$H NMR |
| 3-chlorobenzyl bromide | A | Int-78 | $^1$H NMR (400 MHz, DMSO-d$_6$) δ 9.86 (d, J = 1.0 Hz, 1H), 7.87 (s, 2H), 7.39-7.31 (m, 2H), 7.31-7.22 (m, 2H), 4.01 (s, 2H). $^1$H NMR |
| 2-chlorobenzyl bromide | A | Int-100 | $^1$H NMR (400 MHz, DMSO-d$_6$) δ 9.86 (d, J = 1.3 Hz, 1H), 7.86-7.78 (m, 2H), 7.49-7.38 (m, 2H), 7.36-7.26 (m, 2H), 4.10 (s, 2H). $^1$H NMR |

-continued

| Alkyl bromide | Reaction Condition | Compound Name/No. | Characterization Data |
|---|---|---|---|
| 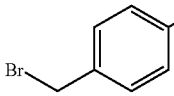 | A | 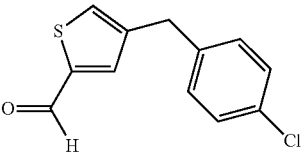<br>Int-101 | ¹H NMR (400 MHz, DMSO-d₆) δ 9.86 (d, J = 1.2 Hz, 1H), 7.83 (d, J = 2.0 Hz, 2H), 7.42-7.33 (m, 2H), 7.32-7.25 (m, 2H), 3.99 (s, 2H). ¹H NMR |
| 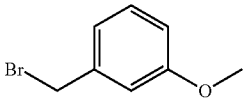 | B | 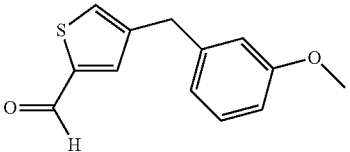<br>Int-102 | ¹H NMR (400 MHz, Chloroform-d) δ 9.84 (d, J = 0.9 Hz, 1H), 7.56 (s, 1H), 7.39 (s, 1H), 7.26-7.21 (m, 1H), 6.83-6.75 (m, 2H), 6.73 (s, 1H), 3.97 (s, 2H), 3.79 (s, 3H). LCMS (FA): m/z = 233.1 (M + 1). |
| 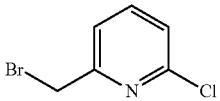 | C | 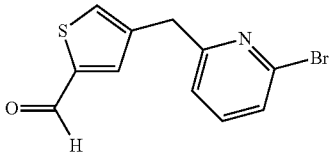<br>Int-103 | ¹H NMR (400 MHz, Chloroform-d) δ 9.87 (d, J = 1.1 Hz, 1H), 7.67 (d, J = 1.1 Hz, 1H), 7.60 (t, J = 7.7 Hz, 1H), 7.52 (s, 1H), 7.22 (d, J = 8.0 Hz, 1H), 7.06 (d, J = 7.5 Hz, 1H), 4.15 (s, 2H). ¹H NMR |
| 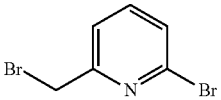 | D | 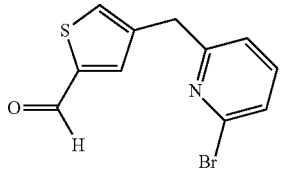<br>Int-104 | ¹H NMR (400 MHz, Chloroform-d) δ 9.87 (d, J = 1.0 Hz, 1H), 7.66 (d, J = 1.1 Hz, 1H), 7.52 (s, 1H), 7.48 (d, J = 7.7 Hz, 1H), 7.37 (d, J = 7.9 Hz, 1H), 7.09 (d, J = 7.5 Hz, 1H), 4.15 (s, 2H). ¹H NMR |
| 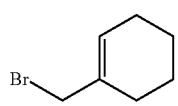 | E | 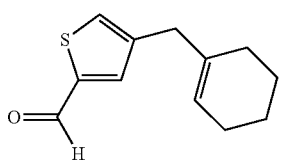<br>Int-105 | ¹H NMR (400 MHz, Chloroform-d) δ 9.87 (d, J = 1.1 Hz, 1H), 7.58 (d, J = 1.1 Hz, 1H), 7.38 (s, 1H), 5.51-5.46 (m, 1H), 3.25 (s, 2H), 2.08-1.97 (m, 2H), 1.92-1.82 (m, 2H), 1.68-1.49 (m, 4H). LCMS (FA): m/z = 207.1 (M + 1). |

Example 62:
5-Bromo-4-(3-chlorobenzyl)thiophene-2-carbaldehyde Int-106

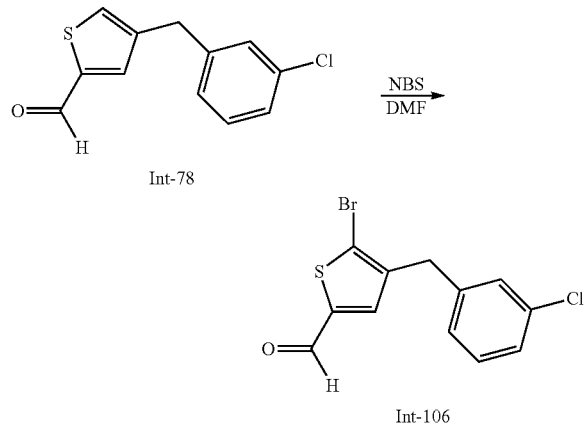

Step 1:
5-Bromo-4-(3-chlorobenzyl)thiophene-2-carbaldehyde

To a solution of Int-78 (637 mg, 2.69 mmol) and NBS (718 mg, 4.04 mmol) in DMF (27 mL). The reaction mixture was stirred at 50° C. for 15 h and then quenched with water and extracted with EtOAc. The combined organic layers were washed with 10% aqueous LiCl, dried over $MgSO_4$, filtered and concentrated in vacuo and the crude material was purified by ISCO column chromatography eluting with 0%-25% EtOAc in hexanes to give 289 mg (34%) of title compound as a clear oil. LCMS (FA): m/z=317.0 (M+1).

The compounds listed in the table below were prepared in an analogous fashion to that described above starting from the appropriate starting materials. The following alternative conditions could be employed in the described reaction steps. Step 1: NCS instead of NBS halogenation.

| Starting material | Step 1 reagent | Compound Name/No. | Characterization Data |
| --- | --- | --- | --- |
| Int-78 | NCS | Int-107 | $^1$H NMR (400 MHz, DMSO-$d_6$) δ 9.78 (s, 1H), 7.89 (s, 1H), 7.40-7.29 (m, 3H), 7.24-7.19 (m, 1H), 4.00 (s, 2H). $^1$H NMR |
| Int-79 | NCS | Int-108 | $^1$H NMR (400 MHz, Chloroform-d) δ 9.71 (s, 1H), 7.42-7.32 (m, 3H), 7.20 (t, J = 7.8 Hz, 1H), 7.13 (d, J = 7.8 Hz, 1H), 3.93 (s, 2H). LCMS (FA): m/z = 317.1 (M + 1). |
| Int-103 | NCS | Int-109 | LCMS (FA): m/z = 318.1 (M + 1). |

341

Example 63: 2-[5-Bromo-4-(3-chlorobenzyl)-2-thienyl]-1,3-dioxolane Int-10 and 4-(3-Chlorobenzyl)-5-(tetrahydro-2H-pyran-4-ylmethyl)thiophene-2-carbaldehyde Int-111

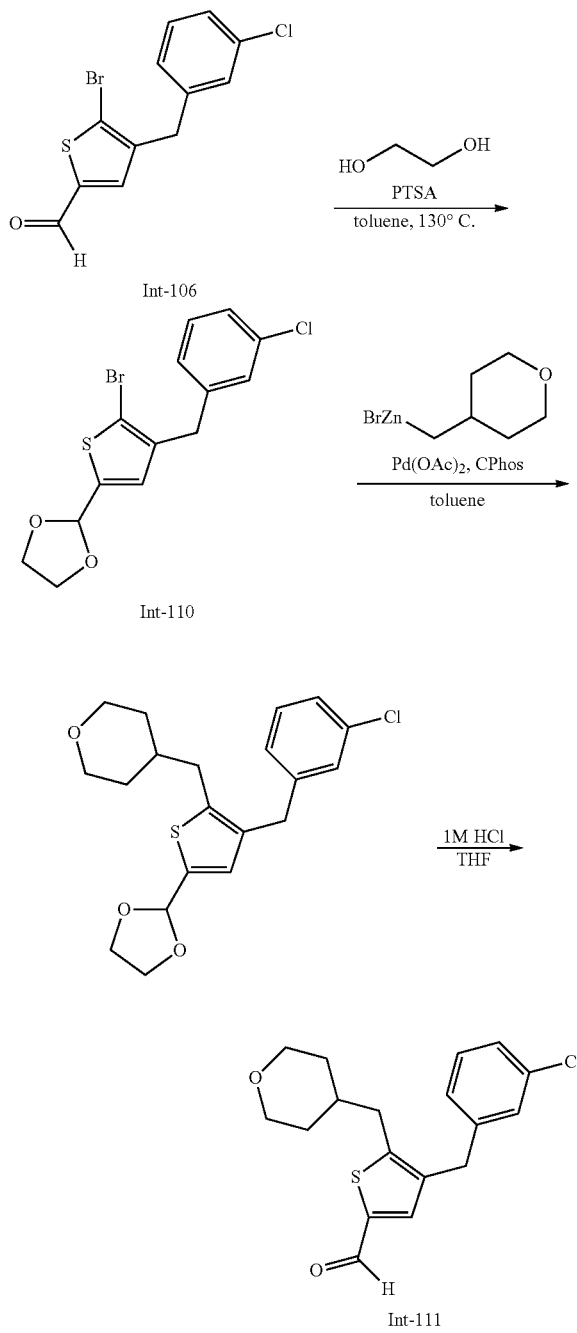

Step 1: 2-[5-Bromo-4-(3-chlorobenzyl)-2-thienyl]-1,3-dioxolane

A 1 L round bottom flask under nitrogen was charged with Int-106 (1.70 g, 5.39 mmol), toluene (20 mL), 1,2-ethanediol (1.50 mL, 26.9 mmol), and p-toluenesulfonic acid monohydrate (51.2 mg, 0.27 mmol). Attached a Dean-Stark Trap and a condenser and heated to reflux overnight. The reaction mixture was allowed to cool to rt and quenched with water. The solution was extracted with EtOAc (25 mL×3).

342

The combined organic layers were washed with brine, dried with anhydrous $Na_2SO_4$, filtered, and concentrated in vacuo. The residue was subjected to ISCO column chromatography (0%-30% EtOAc in hexanes as eluent) to give 1.8 g (93%) of the title compound as an amber oil. $^1$H NMR (400 MHz, Chloroform-d) δ 7.23-7.15 (m, 3H), 7.09-7.04 (m, 1H), 6.75 (s, 1H), 5.95 (s, 1H), 4.11-4.03 (m, 2H), 4.01-3.93 (m, 2H), 3.85 (s, 2H).

Step 2: 4-{[3-(3-Chlorobenzyl)-5-(1,3-dioxolan-2-yl)-2-thienyl]methyl}tetrahydro-2H-pyran A 100 mL 2-neck round bottom flask was charged with zinc powder (548 mg, 8.38 mmol) and the reaction vessel was purged with argon. DMA (6 mL) was added into the flask and iodine (36 mg, 0.14 mmol) was added to the suspension. The resulting mixture was stirred until the red color of iodine had faded. To the mixture was added 4-bromomethyltetrahydropyran (1 g, 6 mmol) and the mixture was allowed to stir for 12 h at 70° C. After cooling to rt, the gray solution was passed through Acrodisc R filter and this 1.0M solution was carried on the next reaction without purification.

A 20 mL of microwave vessel was charged with 2-[5-bromo-4-(3-chlorobenzyl)-2-thienyl]-1,3-dioxolane (500 mg, 1 mmol)), Pd(OAc)$_2$ (15.6 mg, 0.07 mmol) and 2-dicyclohexylphosphino-2',6'-bis(N,N-dimethylamino)biphenyl (60.7 mg, 0.14 mmol). To the mixture was added toluene (4.26 mL) followed by the addition of 1.0M [(tetrahydro-2H-pyran-4-yl)methyl]zinc(II) bromide in DMA solution (2.78 mL, 2.78 mmol) dropwise over 30 min. Upon addition of the solution turned a deep red color and the reaction vessel was purged with argon followed by sealing with a cap. The reaction mixture was stirred for 16 h at rt. The reaction mixture was quenched with 0.5M HCl and diluted with water and EtOAc. The combined organic layers were washed with brine, dried over $Na_2SO_4$, filtered and concentrated in vacuo. The residue was purified by ISCO column chromatography (0%-40% EtOAc in hexanes as eluent) to give 186 mg (40%) of the title compound as an orange color oil. $^1$H NMR (400 MHz, Chloroform-d) δ 7.20-7.16 (m, 2H), 7.09 (s, 1H), 6.99 (d, J=6.7 Hz, 1H), 6.79 (s, 1H), 5.95 (s, 1H), 4.15-4.09 (m, 2H), 4.01-3.96 (m, 2H), 3.92 (dd, J=12.0, 5.0 Hz, 2H), 3.82 (s, 2H), 3.29 (t, 2H), 2.66 (d, J=7.1 Hz, 2H), 1.65-1.58 (m, 2H), 1.56 (s, 1H), 1.30-1.23 (m, 2H).

Step 3: 4-(3-Chlorobenzyl)-5-(tetrahydro-2H-pyran-4-ylmethyl)thiophene-2-carbaldehyde To a solution of 4-{[3-(3-Chlorobenzyl)-5-(1,3-dioxolan-2-yl)-2-thienyl]methyl}tetrahydro-2H-pyran (170 mg, 0.45 mmol) in THF (3.0 mL) was added 1.0 M of HCl in water (1.21 mL) at rt. After 2 h, the reaction mixture was basified with saturated NaHCO$_3$, extracted with EtOAc (50 mL×2). The combined organic layers were dried over Na$_2$SO$_4$, concentrated in vacuo and purified by ISCO column chromatography (0%-40% EtOAc in hexanes as eluent) to give 128 mg (85%) of the title compound as a pale yellow oil. $^1$H NMR (400 MHz, Chloroform-d) δ 9.81 (s, 1H), 7.46 (s, 1H), 7.31 (d, J=6.9 Hz, 1H), 7.28 (s, 1H), 7.16 (s, 1H), 7.07 (d, J=6.7 Hz, 1H), 3.99 (dd, J=11.4, 3.7 Hz, 2H), 3.95 (s, 2H), 3.37 (t, J=11.1 Hz, 2H), 2.80 (d, J=7.2 Hz, 2H), 2.10 (s, 1H), 1.67 (d, J=13.1 Hz, 2H), 1.37 (dd, J=12.5, 4.1 Hz, 2H).

Example 64: rac-4-(3-Chlorobenzyl)-5-(tetrahydrofuran-2-yl)thiophene-2-carbaldehyde. Int-112

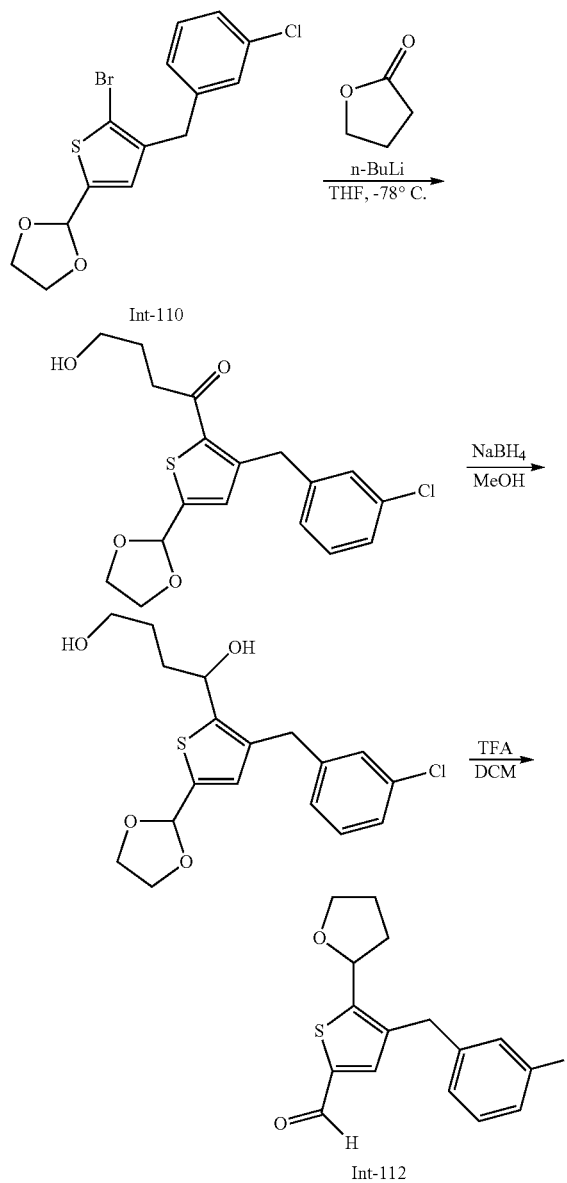

Int-112

Step 1: 1-[3-(3-Chlorobenzyl)-5-(1,3-dioxolan-2-yl)-2-thienyl]-4-hydroxybutan-1-one To a stirred solution of Int-110 (120 mg, 0.33 mmol) in dry Et$_2$O (3 mL) 1.6 M of n-BuLi in hexane (0.25 mL, 0.40 mmol) was added dropwise at −78° C. The solution was stirred for 30 min at −78° C. The solution of γ-butyrolactone (40 mg, 0.5 mmol) in Et$_2$O (0.5 mL) was added slowly and stirred for 15 min at −78° C. The solution was allowed to rt and stirred 1 hour. The solution was quenched with saturated NH$_4$Cl aq. (5 mL) solution and was extracted with EtOAc (2×20 ml). The combined organic layers were dried over Na$_2$SO$_4$, filtered and concentrated in vacuo. The residue was purified by ISCO column chromatography (0%-80% EtOAc in hexanes as eluent) to give 75 mg (61%) of the title compound. $^1$H NMR (400 MHz, Chloroform-d) δ 7.32 (s, 1H), 7.25-7.23 (m, 2H), 7.18-7.11 (m, 1H), 6.95 (s, 1H), 6.07 (s, 1H), 4.38 (s, 2H), 4.18-4.15 (m, 2H), 4.11-4.04 (m, 2H), 3.77 (t, J=5.3 Hz, 2H), 3.06 (t, J=6.9 Hz, 2H), 2.04 (q, J=6.5 Hz, 2H).

Step 2: rac-1-[3-(3-Chlorobenzyl)-5-(1,3-dioxolan-2-yl)-2-thienyl]butane-1,4-diol To a solution of 1-[3-(3-chlorobenzyl)-5-(1,3-dioxolan-2-yl)-2-thienyl]-4-hydroxybutan-1-one (50 mg, 0.1 mmol) in MeOH (5 mL) was added NaBH$_4$ (6.19 mg, 0.16 mmol) at 0° C. and the reaction was stirred for 2 h at 0° C. The reaction mixture was quenched by addition of saturated NaHCO$_3$ (5 mL) and extracted with EtOAc (10 mL×3). The combined organic layers were dried over Na$_2$SO$_4$, filtered, and concentrated in vacuo. The residue was purified by ISCO column chromatography (0%-100% EtOAc in hexanes as eluent) to give 40 mg (80%) of the title compound. LCMS (FA): m/z=369.5 (M+1).

Step 3: rac-4-(3-Chlorobenzyl)-5-(tetrahydrofuran-2-yl)thiophene-2-carbaldehyde rac-1-[3-(3-chlorobenzyl)-5-(1,3-dioxolan-2-yl)-2-thienyl]butane-1,4-diol (815 mg, 2.21 mmol) was dissolved into DCM (5.1 mL), then TFA (18 mL, 230 mmol) was added to this solution with stirring at rt. The reaction mixture was stirred at rt for 2 h, and quenched with water, and extracted with DCM (10 mL×2). The combined organic layers were dried over Na$_2$SO$_4$, filtered and concentrated. The residue was purified by ISCO column chromatography (0%-35% EtOAc in hexanes as eluent) to give 681 mg (92%) of the title compound as a pink oil. $^1$H NMR (400 MHz, Chloroform-d) δ 9.89 (s, 1H), 7.54 (s, 1H), 7.42-7.33 (m, 3H), 7.15 (dd, J=6.4, 2.0 Hz, 1H), 5.31 (t, J=7.0 Hz, 1H), 4.29-4.21 (m, 2H), 4.06-4.00 (m, 2H), 2.46-2.37 (m, 1H), 2.28-2.09 (m, 2H), 1.98-1.88 (m, 1H).

Example 65: 3-(3-Chlorobenzyl)-5-formylthiophene-2-carbonitrile Int-113

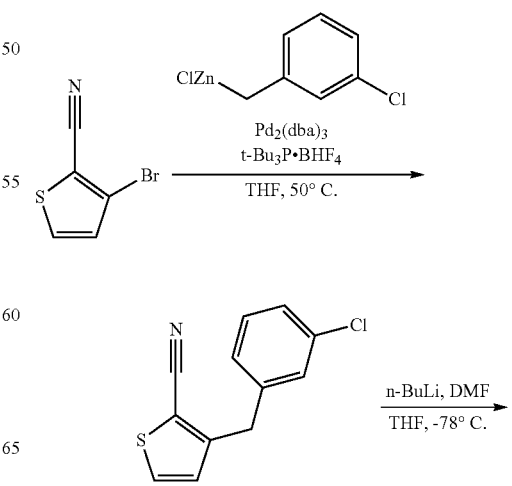

345

-continued

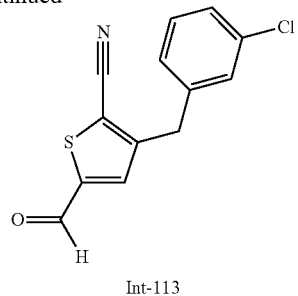

Int-113

Step 1: 3-(3-Chlorobenzyl)thiophene-2-carbonitrile

To a solution of 3-bromothiophene-2-carbonitrile (419 mg, 2.23 mmol) in THF (10.0 mL) was added Pd$_2$(dba)$_3$ (41 mg, 0.05 mmol), tri-t-butylphosphonium tetrafluoroborate (25 mg, 0.09 mmol). The reaction mixture was stirred at 50° C. for 24 h then quenched with water and extracted with EtOAc. The combined organic layers were washed with brine, dried over magnesium sulfate, filtered and concentrated in vacuo. The crude material was purified by ISCO column chromatography (0%-10% EtOAc in hexanes as eluent) to give 225 mg (43%) of the title compound as a clear oil. $^1$H NMR (400 MHz, Methanol-d4) δ 7.83-7.73 (m, 1H), 7.38-7.13 (m, 4H), 7.12-7.02 (m, 1H), 4.15 (s, 2H)

Step 2: 3-(3-Chlorobenzyl)-5-formylthiophene-2-carbonitrile

To a −78° C. cooled solution of 3-(3-chlorobenzyl)thiophene-2-carbonitrile (150 mg, 0.64 mmol) in THF (6.04 mL) was added a 2.50 M solution of n-BuLi in hexane (0.39 mL, 0.96 mmol) dropwise, via syringe. The reaction mixture was allowed to stir for 20 min followed by addition of a solution of DMF (0.10 mL, 1.28 mmol) in THF (2 mL), dropwise, via syringe. The resulting mixture was stirred for an additional 1 hour then quenched with water and extracted with EtOAc. The combined organic layers were washed with brine, dried over magnesium sulfate, filtered and concentrated in vacuo. The crude material was purified by ISCO column chromatography (0%-10% EtOAc in hexanes as eluent) to give 84 mg (50%) of the title compound as a white solid. $^1$H NMR (400 MHz, Methanol-d4) δ 10.76 (s, 1H), 8.81 (s, 1H), 8.29-8.13 (m, 3H), 8.07 (d, J=7.4 Hz, 1H), 4.14 (s, 2H).

Example 66:
4-(3-Iodobenzyl)thiophene-2-carbaldehyde. Int-114

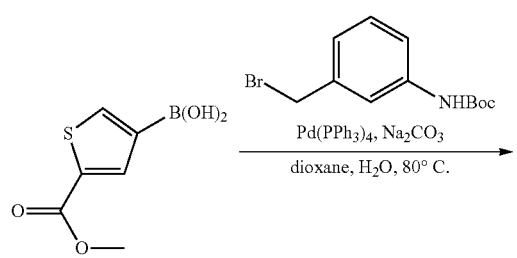

346

-continued

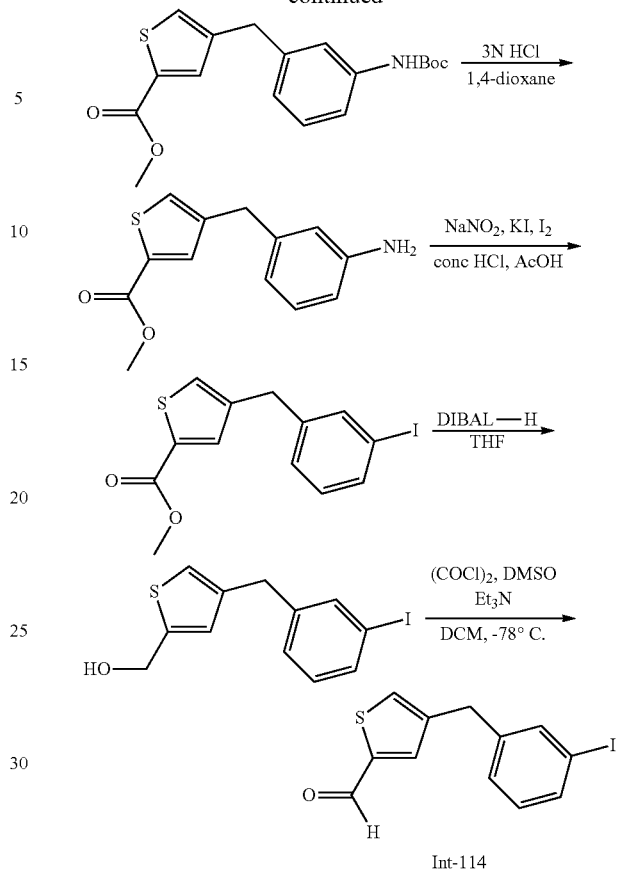

Int-114

Step 1: Methyl 4-{3-[(tert-butoxycarbonyl)amino]benzyl}thiophene-2-carboxylate A threaded 250 mL round bottom flask was charged with 5-(methoxycarbonyl)thiophene-3-boronic acid (1.9 g, 10 mmol), tert-butyl [3-(bromomethyl)phenyl]carbamate (3.00 g, 10.5 mmol), Na$_2$CO$_3$ (3.33 g, 31.4 mmol), 1,4-dioxane (89.2 mL), and water (22.8 mL). The mixture was degassed with nitrogen for 15 min. To the mixture was added Pd(PPh$_3$)$_4$ (1.21 g, 1.05 mmol) and the reaction vessel was sealed. The reaction was heated in an 85° C. oil bath for 18 h. The mixture was concentrated in vacuo to remove dioxane followed by addition of water. The resulting mixture was extracted three times with EtOAc and then the combined organic portions were washed with brine, dried with MgSO$_4$, filtered, and concentrated in vacuo. Residue was subjected to ISCO chromatography eluting with a hexane/EtOAc gradient to give the title compound as a yellow solid, 2.25 g, (62%). $^1$H NMR (400 MHz, Chloroform-d) δ 7.61-7.56 (m, 1H), 7.25-7.17 (m, 3H), 7.17-7.15 (m, 1H), 6.88-6.82 (m, 1H), 6.44 (s, 1H), 3.92-3.91 (m, 2H), 3.85 (s, 3H), 1.51 (s, 9H).

Step 2: Methyl 4-(3-aminobenzyl)thiophene-2-carboxylate

A 100 mL round bottom flask was charged with methyl 4-{3-[(tert-butoxycarbonyl)amino]benzyl}thiophene-2-carboxylate (3.28 g, 9.44 mmol) and EtOAc (20 mL) and the solution was cooled in an ice bath. To the solution was added 4 M HCl in 1,4-dioxane (20 mL) and the mixture was stirred at rt for 18 h. The reaction was poured into saturated NaHCO₃ and then the mixture was extracted three times with EtOAc, washed combined organic portions with brine, dried with MgSO₄, filtered, and concentrated in vacuo. Residue was subjected to ISCO chromatography eluting with a hexanes/EtOAc gradient to give the title compound as yellow oil, 2.20 g, (94%). ¹H NMR (400 MHz, Chloroform-d) δ 7.65-7.56 (m, 1H), 7.18-7.15 (m, 1H), 7.12-7.05 (m, 1H), 6.62-6.57 (m, 1H), 6.57-6.53 (m, 1H), 6.51-6.47 (m, 1H), 3.89-3.80 (m, 5H), 3.62 (s, 2H).

Step 3: Methyl 4-(3-iodobenzyl)thiophene-2-carboxylate

A 50 mL round bottom flask was charged with methyl 4-(3-aminobenzyl)thiophene-2-carboxylate (2.20 g, 8.90 mmol), acetic acid (4.4 mL), and 12 M HCl in water (1.8 mL). To this mixture was added dropwise a solution of sodium nitrite (0.65 g, 9.4 mmol) in water (3.1 mL) keeping the internal temperature below 10° C. and the mixture was stirred for 20 min with cooling. To the mixture was added dropwise a solution of KI (1.77 g, 10.6 mmol) and I₂ (1.32 g, 5.21 mmol) in water (1.8 mL), and the reaction was stirred for 30 min. The resulting mixture was transferred to a separatory funnel and 10% sodium bisulfite solution was added. The mixture was extracted three times with EtOAc and the combined organic portions were washed with brine, dried organic layer with MgSO₄, filtered, and concentrated in vacuo. Residue was subjected to ISCO chromatography eluting with a hexanes/EtOAc gradient to give the title compound as colorless oil, 1.35 g (42%). ¹H NMR (400 MHz, Chloroform-d) δ 7.59-7.53 (m, 3H), 7.18-7.12 (m, 2H), 7.07-7.01 (m, 1H), 3.89 (s, 2H), 3.86 (s, 3H).

Step 4: [4-(3-Iodobenzyl)-2-thienyl]methanol

A 500 mL round bottom flask under nitrogen was charged with methyl 4-(3-iodobenzyl)thiophene-2-carboxylate (1.35 g, 3.77 mmol) and THF (87 mL). The solution was cooled to −65° C. and then 1.0 M of DIBAL-H in toluene (15 mL) was added dropwise to the solution keeping the internal temperature below −60° C. The reaction was stirred 1 hour at −60° C. followed by stirring for 3 h at −40° C. The reaction was quenched by adding a 10% solution of Rochelle's Salt and the mixture was extracted three times with EtOAc. The combined organic portions were washed with brine, dried with MgSO₄, filtered, and concentrated in vacuo. Residue was subjected to ISCO chromatography eluting with a hexane/EtOAc gradient to give the title compound as a colorless oil, 1.24 g (94%). ¹H NMR (400 MHz, Chloroform-d) δ 7.58-7.52 (m, 2H), 7.18-7.13 (m, 1H), 7.06-7.00 (m, 1H), 6.90-6.86 (m, 1H), 6.80-6.76 (m, 1H), 4.80-4.70 (m, 2H), 3.85 (s, 2H).

Step 5: 4-(3-Iodobenzyl)thiophene-2-carbaldehyde

A 100 mL round bottom flask under nitrogen was charged with DCM (9.4 mL) and oxalyl chloride (0.35 mL, 4.13 mmol) and the solution was cooled to −60° C. To the solution was added dimethyl sulfoxide (0.64 mL, 9.01 mmol) dropwise and the mixture was stirred for 5 min. To the mixture was added a solution of [4-(3-iodobenzyl)-2-thienyl]methanol (1.24 g, 3.76 mmol) in DCM (4.8 mL) in a slow stream and the resulting mixture was stirred 10 min with cooling. To the reaction was added triethylamine (2.62 mL, 18.8 mmol) at −60° C. and the mixture was warmed slowly to rt. The resulting mixture was poured into saturated NaHCO₃ and extracted three times with DCM. The combined organic portions were washed with brine, dried with MgSO₄, filtered, and concentrated in vacuo. Residue was subjected to ISCO chromatography eluting with a hexane/EtOAc gradient to give the title compound as pale, 1.22 g (99%). ¹H NMR (400 MHz, Chloroform-d) δ 9.94-9.78 (m, 1H), 7.62-7.52 (m, 3H), 7.40-7.36 (m, 1H), 7.18-7.13 (m, 1H), 7.09-7.03 (m, 1H), 3.94 (s, 2H).

Example 67: 5-Benzyl-thiophene-2-carbaldehyde. Int-115

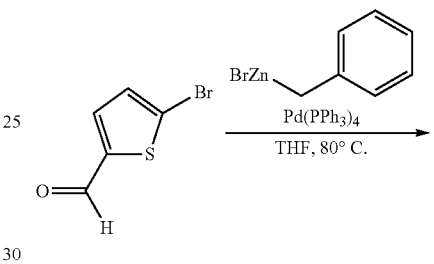

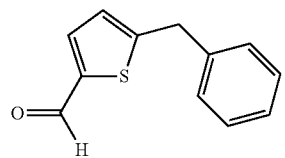

Int-115

Step 1: 5-Benzyl-thiophene-2-carbaldehyde

5-Bromo-2-thiophenecarboxaldehyde (500 mg, 2.62 mmol) and Pd(PPh₃)₄ (75.6 mg, 0.07 mmol) were weighed into a microwave tube and THF (5 mL) was added to the tube. The solution was stirred for 15 min under atmosphere of argon. To the mixture was added 0.50 M of benzylzinc bromide in THF (7.85 mL, 3.93 mmol), and the mixture was heated at 70° C. for 1 hour. The reaction was cooled to rt and concentrated in vacuo. To the residue was added EtOAc (100 mL) and the organic layer was washed with 1N HCl (50 mL) followed by saturated NaHCO₃ (50 mL) and then brine (50 mL). The organic layer was dried over Na₂SO₄, filtered, and concentrated in vacuo. The residue was purified by ISCO column chromatography (10% EtOAc in hexanes as eluent) to give 319 mg (54%) of the title compound as a yellow oil. LCMS (AA): m/z=203.4 (M+H).

The compound listed in the table below was prepared in an analogous fashion to that described above starting from the listed starting material:

| Step 1 zinc reagent | Compound Name/No. | Characterization Data |
|---|---|---|
| 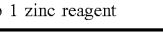 | 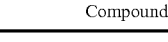  Int-116 | ¹H NMR (400 MHz, DMSO-d₆) δ 9.82 (s, 1H), 7.88 (d, J = 3.8 Hz, 1H), 7.40 (q, J = 1.6 Hz, 1H), 7.36 (d, J = 7.4 Hz, 1H), 7.32 (dt, J = 8.0, 1.5 Hz, 1H), 7.28 (dd, J = 7.3, 1.6 Hz, 1H), 7.16 (d, J = 3.8 Hz, 1H), 4.27 (s, 2H). LCMS (FA): m/z = 237.4 (M + H) |

Example 68: 4-[1-(3-Chlorophenyl)ethyl]-5-methyl-thiophene-2-carbaldehyde Int-117

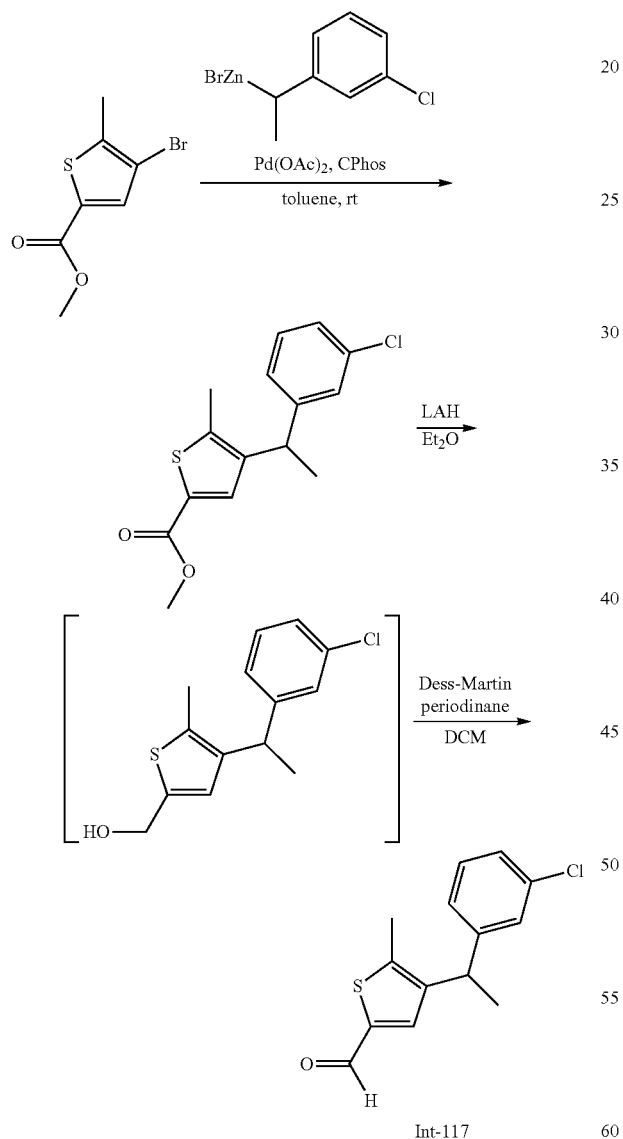

Step 1: rac-Methyl 4-[1-(3-chlorophenyl)ethyl]-5-methylthiophene-2-carboxylate

Methyl 4-bromo-5-methylthiophene-2-carboxylate (400 mg, 2.0 mmol), Pd(OAc)₂ (14.6 mg, 0.07 mmol) and 2-di-cyclohexylphosphino-2',6'-bis(N,N-dimethylamino)biphenyl (56.7 mg, 0.13 mmol) were added to a microwave reaction vial. The vial was purged with argon and toluene (4.2 mL) was added. To the dark red solution at 0° C., 0.50 M of bromo[1-(3-chlorophenyl)ethyl]zinc in THF (4.0 mL, 2.00 mmol) was added dropwise over 10 min. The reaction was allowed to warm to rt and stir for 14 h. The reaction was quenched with 1 M HCl and diluted with water and EtOAc. The layers were separated and the aqueous layer was extracted with EtOAc (2×). The combined org layers were dried over MgSO₄, filtered and concentrated in vacuo. Residue was subjected to ISCO chromatography eluting with a hexane/EtOAc gradient to afford the title compound (yield=442 mg). ¹H NMR (400 MHz, Chloroform-d) δ 7.63 (s, 1H), 7.24-7.14 (m, 2H), 7.14-7.11 (m, 1H), 7.03 (d, J=7.3 Hz, 1H), 4.09 (q, J=7.2 Hz, 1H), 3.85 (s, 3H), 2.32 (s, 3H). LCMS (FA): m/z=295.2 (M+H).

Step 2: rac-4-[1-(3-Chlorophenyl)ethyl]-5-methylthiophene-2-carbaldehyde 1.0 M of lithium tetrahydroaluminate in THF (1.46 mL, 1.46 mmol) was added to an ice-bath cooled solution of methyl 4-[1-(3-chlorophenyl)ethyl]-5-methylthiophene-2-carboxylate (0.43 g, 1.40 mmol) in Et₂O (8.5 mL). The resulting solution was stirred at 0° C. for 15 min. The reaction was quenched with water (~1 mL) at 0° C. Na₂SO₄ decahydrate (~1 g) was added along with 20 mL EtOAc and the mixture allowed to warm to rt. The mixture was stirred for 2 h, filtered and the filter cake was washed with EtOAc. The filtrate was concentrated to yield 0.37 g (95%) of alcohol product. This compound was dissolved in DCM (20 mL), and then Dess-Martin periodinane (0.71 g, 1.70 mmol) was added to the solution. The reaction was allowed to stir at rt for 30 min. The reaction was concentrated and the crude material purified on ISCO chromatography eluting with a hexane/EtOAc gradient to afford the title compound (yield=227 mg).

Example 69: rac-4-{(3-Chlorophenyl)[(triisopropylsilyl)oxy]methyl}-5-methylthiophene-2-carbaldehyde. Int-118

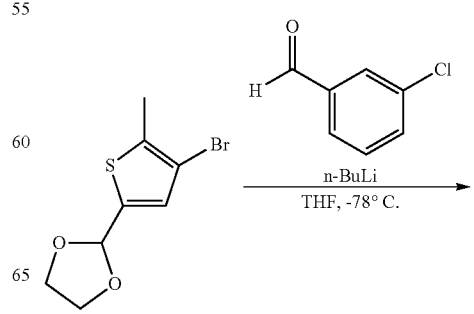

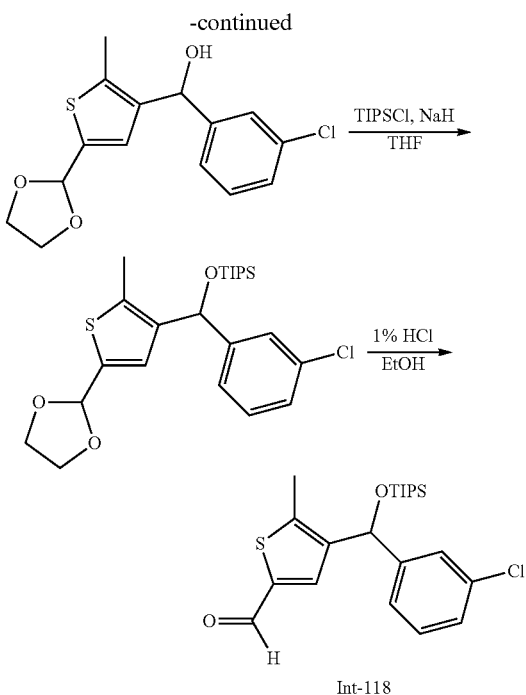

Int-118

Step 1: rac-(3-Chlorophenyl)[5-(1,3-dioxolan-2-yl)-2-methyl-3-thienyl]methanol

A 100 mL 2-neck round bottom flask was charged with THF (60 mL) then the flask was purged with argon, and was cooled at −78° C. To the THF, 2.50 M of n-BuLi in hexane (5.40 mL, 13.5 mmol) was added dropwise via syringe and the mixture was stirred for 10 min at −78° C. 2-(4-bromo-5-methyl-2-thienyl)-1,3-dioxolane (2.69 g, 10.8 mmol) was added dropwise at −78° C. The solution was stirred for 30 min at −78° C. 3-chlorobenzaldehyde (1.23 mL, 10.8 mmol) was added to the solution at once at −78° C. and stirred for 15 min. The reaction was quenched by addition of saturated NH$_4$Cl (50 mL) and extracted with EtOAc (50 mL×3). The combined organic layers were dried over Na$_2$SO$_4$, filtered, and concentrated in vacuo. The residue was purified by ISCO column chromatography (0%-50% EtOAc in hexanes as eluent) to give 2.3 g (68%) of the title compound. $^1$H NMR (400 MHz, Chloroform-d) δ 7.14-7.06 (m, 4H), 6.79 (s, 1H), 5.81 (s, 1H), 5.70 (s, 1H), 4.00-3.91 (m, 3H), 3.88-3.77 (m, 2H), 2.32 (s, 4H).

Step 2: rac-{(3-Chlorophenyl)[5-(1,3-dioxolan-2-yl)-2-methyl-3-thienyl]methoxy}(triisopropyl)silane rac-(3-chlorophenyl)[5-(1,3-dioxolan-2-yl)-2-methyl-3-thienyl]methanol (927 mg, 2.98 mmol) was dissolved in THF (30.6 mL), then 60% NaH in mineral oil (329 mg, 13.7 mmol) was added to this solution. The solution was stirred at 40° C. for 30 min. TIPSCl (1.45 mL, 6.86 mmol) was added and the reaction mixture stirred at rt overnight. The solution was poured into 30 mL saturated NH$_4$Cl solution. The solution was extracted with EtOAc (30 mL×2). The combined organic layers were dried over Na$_2$SO$_4$, filtered, concentrated in vacuo. The residue was purified by ISCO column chromatography (10%-25% EtOAc in hexanes as eluent) to give 1.39 g (100%) of the title compound. TH NMR (400 MHz, Chloroform-d) δ 7.17-7.02 (m, 4H), 6.96 (s, 1H), 5.87 (s, 1H), 5.72 (s, 1H), 4.00-3.94 (m, 2H), 3.90-3.85 (m, 2H), 2.33 (s, 3H), 1.00-0.93 (m, 21H).

Step 3: rac-4-{(3-Chlorophenyl)[(triisopropylsilyl)oxy]methyl}-5-methylthiophene-2-carbaldehyde rac-{(3-Chlorophenyl)[5-(1,3-dioxolan-2-yl)-2-methyl-3-thienyl]methoxy}(triisopropyl)silane (1.6 g, 3.4 mmol) was dissolved in 1% HCl in EtOH (20 mL) and the reaction was stirred at rt for 2 h. The reaction mixture was diluted with water, extracted with DCM (20 ml×2). The combined organic layers were dried over Na$_2$SO$_4$, filtered, concentrated in vacuo. The residue was purified by ISCO column chromatography (28%-30% EtOAc in hexanes as eluent) to give 1.4 g (97%) of the title compound. $^1$H NMR (400 MHz, Chloroform-d) δ 9.67 (s, 1H), 7.63 (s, 1H), 7.21-7.03 (m, 4H), 5.75 (s, 1H), 2.40 (s, 3H), 1.06-0.92 (m, 21H).

Example 70: rac-4-[(3-Chlorophenyl)(cyclopropyl)hydroxymethyl]thiophene-2-carbaldehyde Int-119

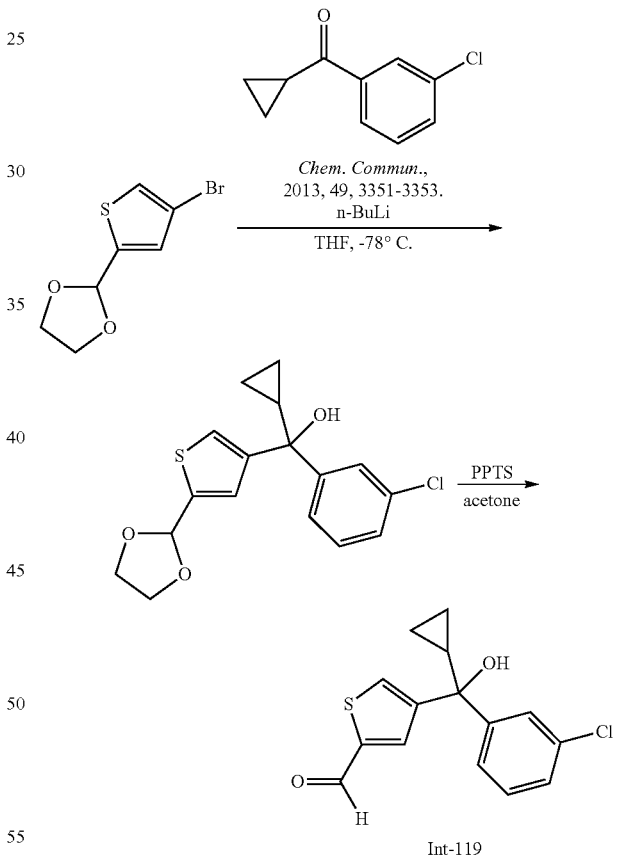

Int-119

Step 1: rac-(3-Chlorophenyl)(cyclopropyl)[5-(1,3-dioxolan-2-yl)-3-thienyl]methanol A 2-neck 250 mL round bottom flask under nitrogen was charged with THF (100 mL). To the solution was added 2.50 M of n-BuLi in hexane (9.2 mL, 23 mmol) at −78° C. followed by addition of a solution of 2-(4-bromothiophen-2-yl)-1,3-dioxolane (4.15 g, 17.7 mmol) in THF (10 mL). After 5 min, a solution of 3-chlorophenyl cyclopropyl ketone (3.35 g, 18.5 mmol) in THF (10 mL) was added to the mixture in a single portion, and the reaction was allowed to stir for 30 min. The reaction mixture was quenched by adding saturated NH$_4$Cl and the resulting mixture was warmed to rt. The mixture was extracted with EtOAc (×3) and the combined organic portions were washed with brine, dried with MgSO$_4$, filtered, and concentrated in vacuo. Residue was subjected to ISCO column chromatography eluting using a hexane/EtOAc gradient to give the title compound as pale solid, 3.72 g (63%). $^1$H NMR (400 MHz, Chloroform-d) δ 7.48-7.46 (m, 1H), 7.34-7.31 (m, 1H), 7.30-7.26 (m, 1H), 7.25-7.21 (m, 2H), 7.03-7.00 (m, 1H), 5.99 (s, 1H), 4.19-3.94 (m, 4H), 1.85 (s, 1H), 1.63-1.54 (m, 1H), 0.69-0.61 (m, 1H), 0.55-0.45 (m, 3H).

Step 2: rac-4-[(3-Chlorophenyl)(cyclopropyl)hydroxymethyl]thiophene-2-carbaldehyde A 100 mL round bottom flask under nitrogen was charged with rac-(3-chlorophenyl)(cyclopropyl) [5-(1,3-dioxolan-2-yl)-3-thienyl]methanol (250 mg, 0.74 mmol), acetone (5.45 mL), and water (1.34 mL). To the mixture was added PPTS (373 mg, 1.48 mmol) and the reaction was allowed to stir for 2 h at rt. The reaction was poured into water and extracted with EtOAc (×3). The combined organic portions were washed with brine, dried with MgSO$_4$, filtered, and concentrated in vacuo. Residue was subjected to ISCO chromatography eluting with a hexane/EtOAc gradient to give the title compound as colorless oil, 195 mg (90%). $^1$H NMR (400 MHz, Chloroform-d) δ 9.86-9.81 (m, 1H), 7.75-7.71 (m, 1H), 7.64-7.59 (m, 1H), 7.51-7.47 (m, 1H), 7.35-7.24 (m, 3H), 2.04 (s, 1H), 1.65-1.54 (m, 1H), 0.73-0.44 (m, 4H).

Example 71: 5-(3-Chlorobenzyl)-3-methylthiophene-2-carbaldehyde. Int-120

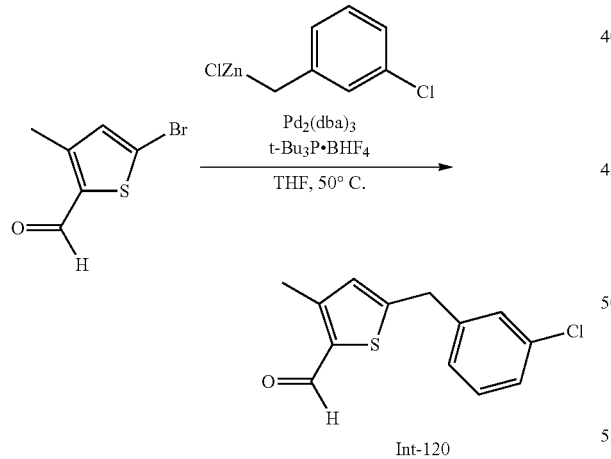

Step 1: 5-(3-Chlorobenzyl)-3-methylthiophene-2-carbaldehyde

A 20 mL of microwave vessel was charged with 5-bromo-3-methylthiophene-2-carbaldehyde (680 mg, 3.32 mmol), Pd$_2$dba$_3$ (60.8 mg, 66.3 umol), and tri-tert-butylphosphonium tetrafluoroborate (38.5 mg, 0.13 mmol). To the mixture was added THF (4.0 mL) and the reaction vessel was purged with argon followed by sealing with a cap. After the mixture was stirred for 5 min at rt, 0.5 M of 3-chlorobenzylzinc chloride in THF solution (8.62 mL, 4.31 mmol) was added to the mixture and then the resulting mixture was heated at 50° C. for 1 hour. The reaction was cooled to rt and diluted with EtOAc. The organic layer was washed with water (50 mL) followed by brine. After drying over Na$_2$SO$_4$, the mixture was filtered through a glass frit funnel and the filtrate was concentrated in vacuo. The residue was purified by ISCO column chromatography (0%-15% EtOAc in hexanes as eluent) to give 184 mg (22%) of the title compound. $^1$H NMR (400 MHz, Chloroform-d) δ 9.96 (s, 1H), 7.65 (s, 1H), 7.49-7.40 (m, 1H), 7.27 (t, 1H), 7.25 (d, J=4.6 Hz, 1H), 7.14 (d, J=4.5 Hz, 1H), 6.69 (s, 1H), 4.10 (s, 2H), 2.52 (s, 3H).

Example 72: rac-4-[2-(3-Chlorophenyl)pyrrolidin-2-yl]thiophene-2-carbaldehyde Int-121 and rac-tert-butyl 2-(3-Chlorophenyl)-2-(5-formyl-3-thienyl)pyrrolidine-1-carboxylate Int-122

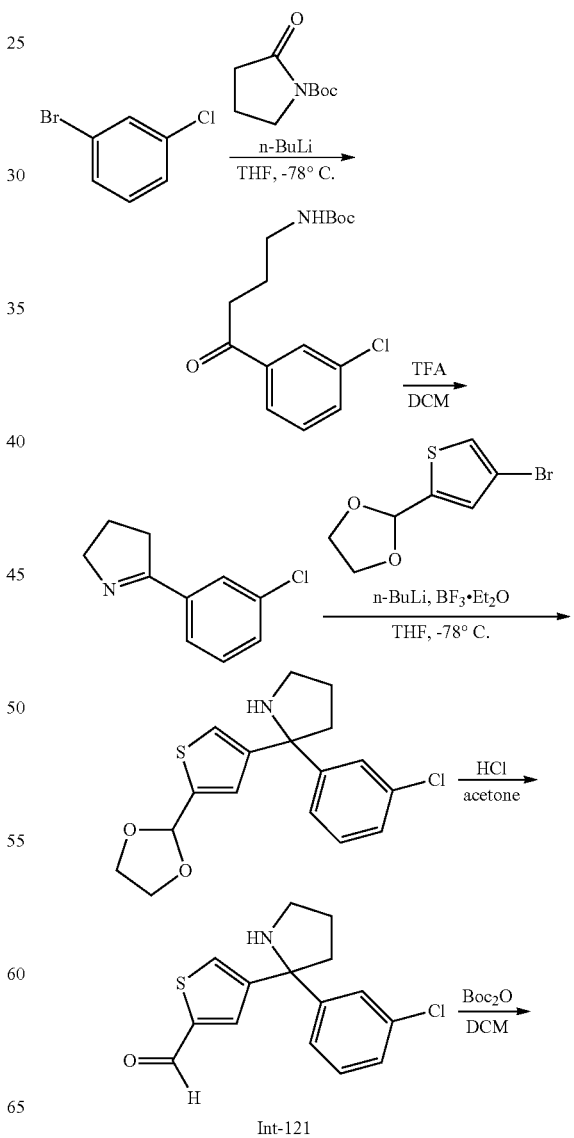

-continued

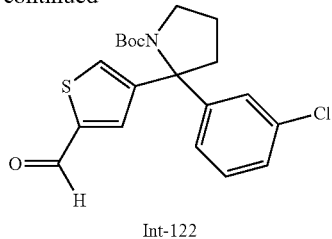

Int-122

Step 1: tert-Butyl [4-(3-chlorophenyl)-4-oxobutyl]carbamate

A 500 mL 2-neck round bottom flask under nitrogen was charged with THF (192.0 mL) and cooled at −78° C. To the solution was added 2.50 M of n-BuLi in hexane (30.6 mL, 76.6 mmol) followed by a solution of 3-chlorobromobenzene (11.3 g, 58.9 mmol) in THF (10 mL). To the mixture was added immediately a solution of 1-(tert-butoxycarbonyl)-2-pyrrolidine (12.0 g, 64.8 mmol) in THF (10 mL). After 15 min, the reaction was quenched by slow addition of saturated NaHCO$_3$ and the resulting mixture was warmed to rt. The mixture was extracted with EtOAc (×3) and the combined organics were washed with brine, dried with MgSO$_4$, filtered, and concentrated in vacuo. Residue was subjected to ISCO column chromatography eluting with a hexane/EtOAc gradient to give the title compound as yellow oil, 15.54 g (89%). $^1$H NMR (400 MHz, Chloroform-d) δ 7.94-7.90 (m, 1H), 7.85-7.79 (m, 1H), 7.56-7.50 (m, 1H), 7.43-7.37 (m, 1H), 4.62 (s, 1H), 3.26-3.17 (m, 2H), 3.05-2.97 (m, 2H), 1.99-1.88 (m, 2H), 1.43-1.41 (m, 9H).

Step 2: 5-(3-Chlorophenyl)-3,4-dihydro-2H-pyrrole

A 500 mL round bottom flask was charged with tert-butyl [4-(3-chlorophenyl)-4-oxobutyl]carbamate (15.6 g, 52.3 mmol) and DCM (26 mL). To the solution was added TFA (48.3 mL, 627.4 mmol). After 1 hour, the reaction was poured into water and the mixture was extracted with DCM (×3). The combined organics were washed with saturated NaHCO$_3$ then brine; dried with MgSO$_4$, filtered, and concentrated in vacuo. Residue was subjected to ISCO column chromatography eluting with a hexane/EtOAc to give the title compound as white solid, 4.93 g (53%). $^1$H NMR (400 MHz, Chloroform-d) δ 7.87-7.81 (m, 1H), 7.74-7.67 (m, 1H), 7.42-7.37 (m, 1H), 7.37-7.31 (m, 1H), 4.10-4.01 (m, 2H), 2.98-2.84 (m, 2H), 2.13-1.98 (m, 2H).

Step 3: rac-2-(3-Chlorophenyl)-2-[5-(1,3-dioxolan-2-yl)-3-thienyl]pyrrolidine To a solution of 5-(3-chlorophenyl)-3,4-dihydro-2H-pyrrole (5.90 g, 32.8 mmol) in THF (100 mL) was added boron trifluoride diethyl ether complex (4.5 mL, 36.1 mmol) at −78° C. and the mixture was stirred for 30 min. A separate reaction vessel was charged with THF (300 mL), cooled to −78° C., 2.50 M of n-BuLi in hexane (22.3 mL, 55.8 mmol) was added followed by a solution of 2-(4-bromothiophen-2-yl)-1,3-dioxolane (10.8 g, 46.0 mmol) in THF (10 mL) and the mixture was stirred for 5 min. To the mixture was added a previously prepared solution via cannula at −78° C., and the mixture was allowed to stir at −40° C. for 1 hour. The reaction was quenched by addition of saturated NaHCO$_3$, and the resulting mixture was extracted with EtOAc (×3). The combined organic layers were washed with brine, dried with MgSO$_4$, filtered, and concentrated in vacuo. Residue was subjected to ISCO column chromatography eluting with a hexane/EtOAc gradient to give the title compound as brown foam oil, 7.09 g (64%). LCMS (FA): m/z=336.1 (M+H).

Step 4: rac-4-[2-(3-Chlorophenyl)pyrrolidin-2-yl]thiophene-2-carbaldehyde

To a solution of rac-2-(3-chlorophenyl)-2-[5-(1,3-dioxolan-2-yl)-3-thienyl]pyrrolidine (7.09 g, 21.1 mmol) in acetone (100 mL) was added a solution of 12 M of HCl in water (2 mL) and the reaction was allowed to stir at rt 6 h. The reaction was poured into saturated NaHCO$_3$ and the mixture was extracted with DCM (×3). The combined organic portions were dried with MgSO$_4$, filtered, and concentrated in vacuo. Residue was subjected to ISCO column chromatography eluting with a hexane/EtOAc gradient to give the title compound as orange oil, 4.15 g (67%). $^1$H NMR (400 MHz, Chloroform-d) δ 9.81 (s, 1H), 7.64-7.58 (m, 2H), 7.52-7.46 (m, 1H), 7.34-7.29 (m, 1H), 7.25-7.22 (m, 1H), 7.22-7.18 (m, 1H), 3.18-3.01 (m, 2H), 2.50-2.27 (m, 2H), 2.01-1.80 (m, 3H).

Step 5: rac-tert-Butyl 2-(3-chlorophenyl)-2-(5-formyl-3-thienyl)pyrrolidine-1-carboxylate A 100 mL round bottom flask under nitrogen was charged with rac-4-[2-(3-chlorophenyl)pyrrolidin-2-yl]thiophene-2-carbaldehyde (4.15 g, 14.2 mmol), DCM (69.6 mLm), N,N-dimethylaminopyridine (0.08 mg, 0.7 mmol), and Boc$_2$O (4.66 g, 21.3 mmol). After 18 h at rt, the reaction was concentrated in vacuo. Residue was subjected to ISCO column chromatography eluting with a hexane/EtOAc gradient to give the title compound as white foam, 2.83 g (51%). $^1$H NMR (400 MHz, Chloroform-d) δ 9.93-9.85 (m, 1H), 7.83-7.68 (m, 1H), 7.68-7.50 (m, 1H), 7.36-7.11 (m, 4H), 3.92-3.80 (m, 2H), 2.77-2.45 (m, 2H), 2.03-1.79 (m, 2H), 1.55-1.27 (m, 9H).

Example 73: rac-4-[2-(3-Chlorophenyl)-1-methylpyrrolidin-2-yl]thiophene-2-carbaldehyde. Int-123

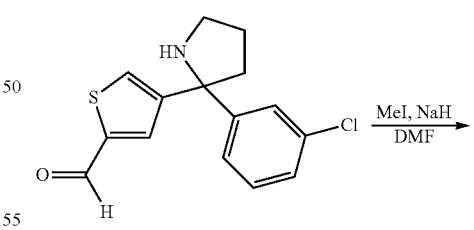

Int-121

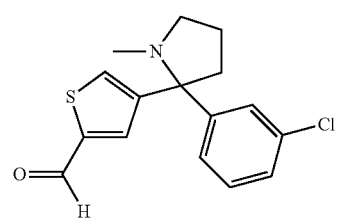

Int-123

Step 1: rac-4-[2-(3-Chlorophenyl)-1-methylpyrrolidin-2-yl]thiophene-2-carbaldehyde An oven-dried 100 mL round bottom flask under nitrogen was charged with DMF (10 mL) and 60% NaH in mineral oil (228 mg, 5.69 mmol) and the mixture was cooled at 0° C. To the mixture was added a solution of Int-121 (664 mg, 2.28 mmol) in DMF (5 mL) and the reaction was stirred for 30 min. To the mixture was added MeI (0.43 mL, 6.83 mmol) and the reaction was stirred for 1 hour at rt. The reaction mixture was poured onto ice and saturated NaHCO$_3$ was added to the mixture. The mixture was extracted EtOAc (×3), and the combined organic portions were washed with brine, dried with MgSO$_4$, filtered, and concentrated in vacuo. The residue was subjected to ISCO column chromatography eluting with a hexane/EtOAc gradient to give the title compound as a pale oil, 133 mg (20%). $^1$H NMR (400 MHz, Methanol-d4) δ 9.88-9.80 (m, 1H), 7.76-7.69 (m, 1H), 7.62-7.55 (m, 1H), 7.39-7.35 (m, 1H), 7.34-7.24 (m, 2H), 7.22-7.17 (m, 1H), 3.06-2.96 (m, 1H), 2.63-2.45 (m, 2H), 2.22-2.11 (m, 1H), 2.08 (s, 3H), 2.06-1.94 (m, 2H).

Example 74: 5-Methyl-4-(3-methylbenzyl)thiophene-2-carbaldehyde. Int-124

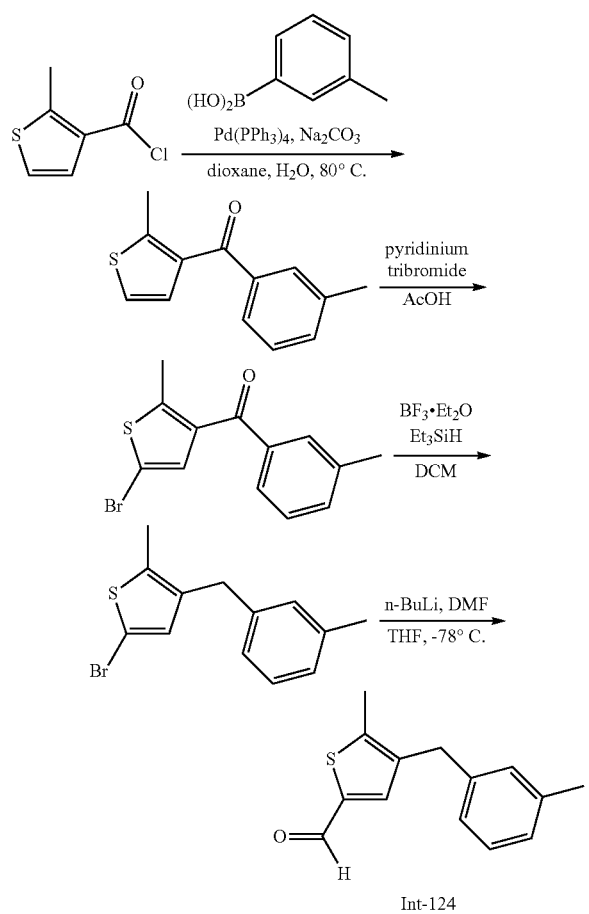

Int-124

Step 1: (3-Methylphenyl)(2-methyl-3-thienyl)methanone

A microwave tube was charged with m-tolylboronic acid (231 mg, 1.70 mmol), Cs$_2$CO$_3$ (830 mg, 2.55 mmol), and Pd(PPh$_3$)$_4$ (58.9 mg, 0.05 mmol). These contents were suspended with toluene (5 mL) followed by addition of 2-methylthiophene-3-carbonyl chloride (300 mg, 1.87 mmol) at rt. The reaction vessel was purged with argon and then sealed with cap. The reaction was heated at 100° C. with oil-bath for 30 min. The reaction was cooled to rt and transferred into a separatory funnel. The mixture was diluted with EtOAc (70 mL) and the organic layer was washed with water (50 mL) followed by brine. The EtOAc layer was dried over Na$_2$SO$_4$, filtered, and concentrated in vacuo. The residue was purified by ISCO column chromatography (3% EtOAc in Hexanes as eluent) to give 220 mg (60%) of the title compound as colorless oil. $^1$H NMR (400 MHz, Chloroform-d) δ 7.61 (s, 1H), 7.57 (d, J=7.0 Hz, 1H), 7.41-7.31 (m, 2H), 7.13 (d, J=5.3 Hz, 1H), 7.04 (d, J=5.3 Hz, 1H), 2.65 (s, 3H), 2.41 (s, 3H).

Step 2: (5-Bromo-2-methyl-3-thienyl)(3-methylphenyl)methanone

To a solution of (3-methylphenyl)(2-methyl-3-thienyl)methanone (410 mg, 1.90 mmol) in acetic acid (2.0 mL) was added pyridinium tribromide (1.52 g, 4.74 mmol) at rt, and the reaction was heated at 50° C. for 2 h. The reaction was cooled at rt and poured into water (100 mL). The mixture was extracted with EtOAc (100 mL×2). The combined organic layers were washed with saturated NaHCO$_3$ (100 mL) followed by Na$_2$S$_2$O$_3$ solution and then brine. The EtOAc layer was dried over Na$_2$SO$_4$, filtered, and concentrated in vacuo. The residue was purified by ISCO column chromatography (5% EtOAc in hexanes as eluent) to give 529 mg (85%) of the title compound as a light yellow sticky oil. $^1$H NMR (400 MHz, Chloroform-d) δ 7.58 (s, 1H), 7.54 (d, J=7.1 Hz, 1H), 7.42-7.32 (m, 2H), 7.08 (s, 1H), 2.57 (s, 3H), 2.42 (s, 3H).

Step 3: 5-Bromo-2-methyl-3-(3-methylbenzyl)thiophene (5-Bromo-2-methyl-3-thienyl)(3-methylphenyl)methanone (520 mg, 1.60 mmol) in a 100 mL round bottom flask was dissolved in CH$_3$CN (5.0 mL) and DCM (5.0 mL) under atmosphere of argon and the mixture was cooled to 0° C. To this solution was added triethylsilane (0.76 mL, 4.76 mmol) followed by boron trifluoride etherate (0.60 mL, 4.76 mmol), and the reaction was stirred for 14 h at 0° C. to room temp. The reaction was quenched by slow addition of K$_2$CO$_3$ aqueous solution (50 mL) and extracted with EtOAc (50 mL×3). The combined organic layers were washed with brine, dried over Na$_2$SO$_4$, filtered, and concentrated in vacuo. The residue was purified by ISCO column chromatography (100% hexane as eluent) to give 447 mg (90%) of the title compound as a colorless oil. $^1$H NMR (400 MHz, Chloroform-d) δ 7.17 (t, J=7.5 Hz, 1H), 7.02 (d, J=7.5 Hz, 1H), 6.97-6.88 (m, 2H), 6.66 (s, 1H), 3.77 (s, 2H), 2.33 (s, 2H), 2.32 (s, 3H).

Step 4: 5-Methyl-4-(3-methylbenzyl)thiophene-2-carbaldehyde

5-Bromo-2-methyl-3-(3-methylbenzyl)thiophene (235 mg, 0.75 mmol) was weighed into a 100 mL 2-neck round bottom flask and the reaction vessel was purged with argon. The content was dissolved in THF (12.0 mL) and the solution was cooled at −78° C. To the solution was added dropwise 2.50 M of n-BuLi in hexane (0.69 mL, 1.71 mmol) at −78° C., and the mixture was stirred for 30 min. To the mixture was added DMF (0.13 mL, 1.67 mmol) at −78° C., and the resulting mixture was stirred for 15 min. The reaction was quenched by addition of saturated NH₄Cl (50 mL) and extracted with EtOAc (50 mL×3). The combined organic layers were washed with brine, dried over Na₂SO₄, filtered, and concentrated in vacuo. The residue was purified by ISCO column chromatography (5% EtOAc in hexanes as eluent) to give 151 mg (87%) of the title compound as colorless oil. ¹H NMR (400 MHz, Chloroform-d) δ 9.73 (s, 1H), 7.41 (s, 1H), 7.20 (t, J=7.5 Hz, 1H), 7.05 (d, J=7.6 Hz, 1H), 6.94 (d, J=7.8 Hz, 2H), 3.86 (s, 2H), 2.47 (s, 3H), 2.33 (s, 3H).

Example 75: rac-5-Chloro-4-[2-(3-chlorophenyl) oxetan-2-yl]thiophene-2-carbaldehyde. Int-125

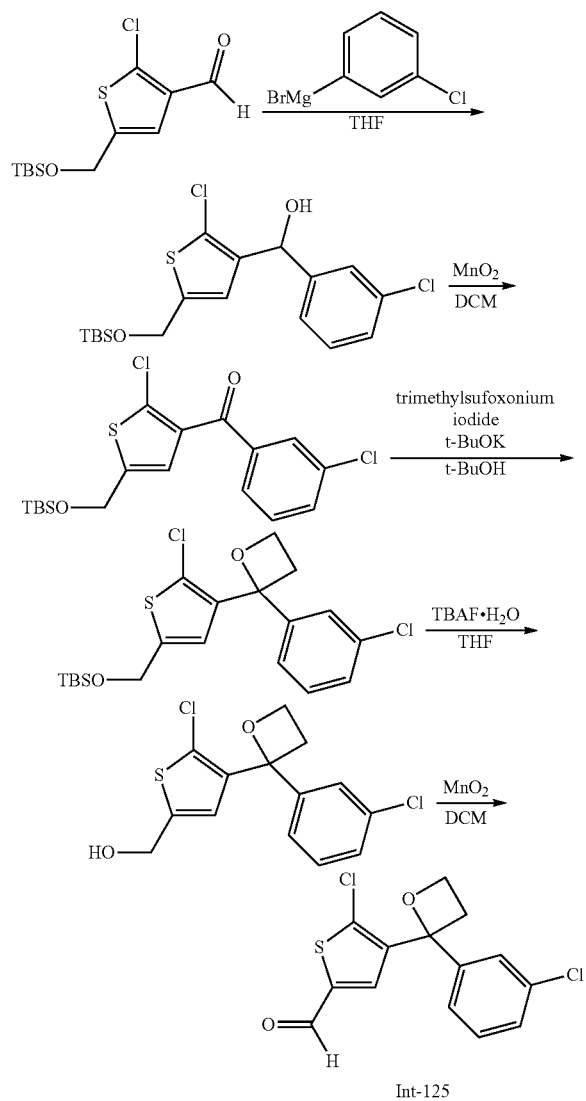

Int-125

Step 1: rac-[5-({[tert-Butyl(dimethyl)silyl] oxy}methyl)-2-chloro-3-thienyl](3-chlorophenyl) methanol To a solution of 5-({[tert-butyl(dimethyl)silyl] oxy}methyl)-2-chlorothiophene-3-carbaldehyde (1.00 g, 3.44 mmol) in THF (20.0 mL) and the solution was cooled at 0° C. To the solution was added dropwise 0.50 M of 3-chlorophenylmagnesium bromide in THF (8.25 mL, 4.13 mmol), and the reaction was stirred for 30 min at rt. The reaction was quenched by addition of saturated NH₄Cl (100 mL) and extracted with EtOAc (100 mL×3). The combined organic layers were washed with brine, dried over Na₂SO₄, filtered, and concentrated in vacuo. The residue was purified by ISCO column chromatography (10% EtOAc in hexanes as eluent) to give 1.35 g (97%) of the title compound as light yellow oil. ¹H NMR (400 MHz, Chloroform-d) δ 7.43 (s, 1H), 7.26 (d, J=4.1 Hz, 3H), 6.66 (s, 1H), 5.94 (s, 1H), 4.71 (d, J=0.9 Hz, 2H), 2.57-1.90 (br s, 1H), 0.90 (s, 9H), 0.07 (s, 6H).

Step 2: [5-({[tert-Butyl(dimethyl)silyl]oxy}methyl)-2-chloro-3-thienyl](3-chlorophenyl)methanone To a solution of rac-[5-({[tert-butyl(dimethyl)silyl] oxy}methyl)-2-chloro-3-thienyl](3-chlorophenyl)methanol (1.35 g, 3.35 mmol) in DCM (50.0 mL) was added MnO₂ (2.91 g, 33.5 mmol) at rt, and the reaction was stirred for 21 h. The reaction was filtered through a Celite pad and the residual filter cake was rinsed with DCM several times. The filtrate was concentrated in vacuo and the residue was purified by ISCO column chromatography (0%-5% EtOAc in hexanes as eluent) to give 742 mg (55%) of the title compound as colorless oil. ¹H NMR (400 MHz, Chloroform-d) δ 7.79 (t, J=1.8 Hz, 1H), 7.69 (dt, J=7.7, 1.3 Hz, 1H), 7.56 (ddd, J=8.0, 2.1, 1.1 Hz, 1H), 7.42 (t, J=7.8 Hz, 1H), 6.91 (s, 1H), 4.80 (d, J=1.0 Hz, 2H), 0.94 (s, 9H), 0.12 (s, 6H).

Step 3: rac-tert-Butyl({5-chloro-4-[2-(3-chlorophenyl)oxetan-2-yl]-2-thienyl}methoxy)dimethylsilane A 20 mL microwave reaction tube was charged with Trimethylsufoxonium iodide (576 mg, 2.62) and t-BuOK (294 mg, 2.62 mmol) and then the reaction tube was purged with argon followed by sealed with cap. To the reaction vessel was added t-BuOH (3.0 mL) and the mixture was stirred for 30 min at 50° C. To the white suspension was added a solution of [5-({[tert-butyl(dimethyl)silyl] oxy}methyl)-2-chloro-3-thienyl](3-chlorophenyl)methanone (300 mg, 0.75 mmol) in t-BuOH (4.5 mL, 47.0 mmol) at 50° C., and the resulting mixture was stirred for 44 h. The reaction was quenched by addition of water (60 mL) and extracted with EtOAc (50 mL×3). The combined organic layers were dried over Na₂SO₄, filtered, and concentrated in vacuo. The residue was purified by ISCO column chromatography (2% EtOAc in hexanes as eluent) to give 195 mg (61%) of the title compound as colorless oil. ¹H NMR (400 MHz, Chloroform-d) δ 7.50 (t, J=1.8 Hz, 1H), 7.35 (dt, J=7.5, 1.6 Hz, 1H), 7.29 (t, J=7.8 Hz, 1H), 7.24 (dt, J=7.8, 1.7 Hz, 1H), 6.78 (s, 1H), 4.74 (s, 2H), 4.69-4.63 (m, 2H), 3.54-3.44 (m, 1H), 3.14-3.03 (m, 1H), 0.91 (s, 9H), 0.09 (d, J=1.8 Hz, 6H).

Step 4: rac-{5-Chloro-4-[2-(3-chlorophenyl)oxetan-2-yl]-2-thienyl}methanol

To a solution of rac-tert-butyl({5-chloro-4-[2-(3-chlorophenyl)oxetan-2-yl]-2-thienyl}methoxy)dimethylsilane (290 mg, 0.68 mmol) in THF (10 mL) was added a solution of TBAF monohydrate (283 mg, 1.01 mmol) in THF (3.0 mL) at rt, and the mixture was stirred for 1 hour. The reaction was quenched by addition of water (50 mL) and extracted with EtOAc (60 mL×3). The combined organic layers were washed with brine, dried over Na₂SO₄, filtered, and concentrated in vacuo. The residue was purified by ISCO column chromatography (20%-30% EtOAc in hexanes as eluent) to give 207 mg (97%) of the title compound as colorless oil. ¹H NMR (400 MHz, Chloroform-d) δ 7.54 (t, J=1.7 Hz, 1H), 7.38 (dt, J=7.5, 1.6 Hz, 1H), 7.32 (t, J=7.6 Hz, 1H), 7.28-7.24 (m, 1H), 6.92 (s, 1H), 4.76-4.65 (m, 4H), 3.53 (dt, J=11.3, 7.8 Hz, 1H), 3.12 (dt, J=11.3, 7.4 Hz, 1H), 1.86 (t, J=6.0 Hz, 1H).

Step 5: rac-5-Chloro-4-[2-(3-chlorophenyl)oxetan-2-yl]thiophene-2-carbaldehyde

To a solution of rac-{5-chloro-4-[2-(3-chlorophenyl)oxetan-2-yl]-2-thienyl}methanol (205 mg, 0.65 mmol) in DCM (20.0 mL) was added MnO₂ (565 mg, 6.50 mmol) at rt, and the mixture was stirred for 14 h. The reaction was filtered through a Celite pad and the residual filter cake was rinsed with DCM several times. The filtrate was concentrated in vacuo and the residue was purified by ISCO column chromatography (10% EtOAc in hexanes as eluent) to give 188 mg (92%) of the title compound as a colorless oil. ¹H NMR (400 MHz, Chloroform-d) δ 9.76 (s, 1H), 7.74 (s, 1H), 7.51 (s, 1H), 7.37-7.27 (m, 3H), 4.70 (t, J=7.7 Hz, 2H), 3.44 (dt, J=11.4, 7.7 Hz, 1H), 3.20 (dt, J=11.4, 7.6 Hz, 1H).

Example 76: 4-({[tert-Butyl(dimethyl)silyl]oxy}methyl)-5-(3-chlorobenzyl)thiophene-2-carbaldehyde. Int-126

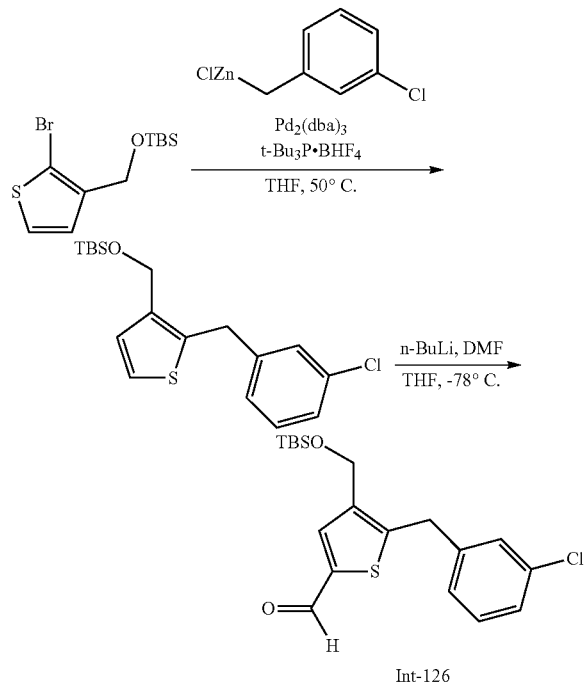

Int-126

Step 1: tert-Butyl{[2-(3-chlorobenzyl)-3-thienyl]methoxy}dimethylsilane

A 20 mL of microwave reaction tube was charged with [(2-bromo-3-thienyl)methoxy](tert-butyl)dimethylsilane (1.63 g, 5.30 mmol), Pd₂(dba)₃ (194 mg, 0.21 mmol), and tri-tert-butylphosphonium tetrafluoroborate (123 mg, 0.42 mmol). After addition of THF (11.2 mL), the reaction vessel was purged with argon followed by sealing with a cap. After the mixture was stirred for 5 min at rt, 0.5 M of 3-chlorobenzylzinc chloride in THF (12.2 mL, 6.10 mmol) was added to the mixture. The reaction was stirred at rt for 2 h, and then the resulting mixture was heated at 50° C. for 1 hour. The mixture was cooled to rt and diluted with EtOAc. The organic layer was washed with water (50 mL) and brine. After drying over Na₂SO₄, the mixture was filtered through a glass frit funnel and the filtrate was concentrated in vacuo. The residue was purified by ISCO column chromatography (10% EtOAc in hexanes as eluent) to give 1.4 g (76%) of the title compound. ¹H NMR (400 MHz, Chloroform-d) δ 7.17-7.10 (m, 3H), 7.04 (m, 2H), 6.94 (d, J=5.2 Hz, 1H), 4.57 (s, 2H), 4.05 (s, 2H), 0.85 (s, 9H), 0.00 (s, 6H).

Step 2: 4-({[tert-Butyl(dimethyl)silyl]oxy}methyl)-5-(3-chlorobenzyl)thiophene-2-carbaldehyde To a solution of tert-butyl{[2-(3-chlorobenzyl)-3-thienyl]methoxy}dimethylsilane (1.40 g, 3.97 mmol) in THF (30.0 mL) was added dropwise 2.5 M n-BuLi in hexane (2.1 mL, 5.16 mmol) at −78° C. and the mixture was stirred for 3 min. To the mixture was added DMF (0.49 mL, 6.34 mmol) at −78° C. and the reaction was allowed to stir for 10 min, and then warmed to rt for 10 min. The reaction mixture was added saturated NH₄Cl and extracted with EtOAc (×2). The combined organic layers were washed with brine, dried over MgSO₄, and concentrated in vacuo. The residue was purified by column chromatography (15% EtOAc in hexanes as eluent) to give 0.75 g (50%) of the title compound. ¹H NMR (400 MHz, Chloroform-d) δ 9.86 (s, 1H), 7.75 (s, 1H), 7.28 (t, J=7.5 Hz, 3H), 7.16 (d, J=6.3 Hz, 1H), 4.70 (s, 2H), 4.20 (s, 2H), 0.99 (s, 9H), 0.16 (s, 6H).

Example 77: 2-(4-Bromo-5-chloro-2-thienyl)-1,3-dioxolane Int-127 and rac-4-[{[tert-Butyl(dimethyl)silyl]oxy}(cyclohexyl)methyl]-5-chlorothiophene-2-carbaldehyde Int-128

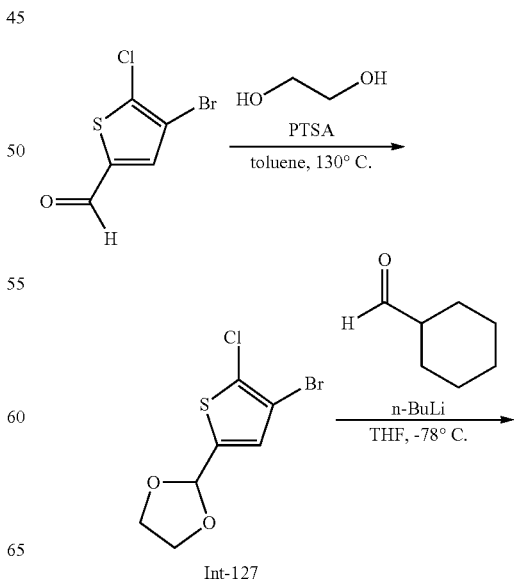

Int-127

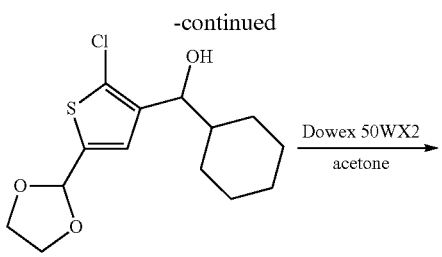

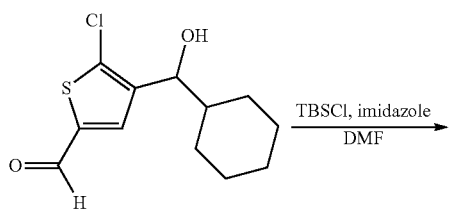

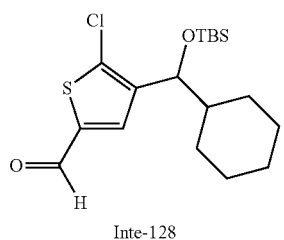

Inte-128

Step 1: 2-(4-Bromo-5-chloro-2-thienyl)-1,3-dioxolane

To a solution of 4-bromo-5-chlorothiophene-2-carbaldehyde (4.1 g, 18 mmol) in toluene (60 mL) was added 1,2-ethanediol (5.07 mL, 90.9 mmol) and p-toluenesulfonic acid monohydrate (0.17 g, 0.91 mmol) and then the mixture was heated to reflux with a Dean-Stark apparatus for 3 h. After cooling to rt, the reaction mixture was quenched by addition of saturated NaHCO$_3$ (100 mL) and water (50 mL). The resulting mixture was extracted with hexane (150 mL×3). The combined organic layers were dried over Na$_2$SO$_4$, filtered, and concentrated in vacuo. The residue was purified by ISCO silica gel column chromatography (10% EtOAc in hexanes as eluent) to give the title compound as colorless solid (yield=4.75 g). $^1$H NMR (400 MHz, DMSO-d$_6$) δ 7.30 (s, 1H), 6.03 (s, 1H), 4.07-3.99 (m, 2H), 3.99-3.91 (m, 2H).

Step 2: rac-[2-Chloro-5-(1,3-dioxolan-2-yl)-3-thienyl](cyclohexyl)methanol 2-(4-bromo-5-chloro-2-thienyl)-1,3-dioxolane (1.09 g, 4.04 mmol) was placed in a 50 mL 2-neck round bottom flask under an atmosphere of argon. THF (6.50 mL) was added and the reaction was cooled at −78° C. 2.50 M of n-BuLi in hexane (1.80 mL, 4.50 mmol) was added dropwise and the solution was stirred for 30 min. Concurrently, Cerium trichloride (1.00 g, 4.06 mmol) was placed in a two-neck round-bottom flask under an atmosphere of argon. THF (10.0 mL) was added and the slurry was cooled at −78° C. 2-(4-bromo-5-chloro-2-thienyl)-1,3-dioxolane lithiated species was added dropwise quickly to the above solution and the solution was stirred for 1 hour at −78° C. Cyclohexanecarboxaldehyde (0.60 mL, 4.80 mmol) in THF (2.0 mL) was added dropwise to the solution at −78° C. The reaction was stirred for 30 min at −78° C. The reaction was quenched with saturated NH$_4$Cl and the mixture was extracted with EtOAc. An emulsion formed and was filtered through a pad of Celite. The filtrate layers were separated and the organic was dried over MgSO$_4$, filtered and concentrated in vacuo. The residue was purified via ISCO column chromatography (10%-30% EtOAc in hexanes as eluent) to give an orange oil (yield=622 mg). LCMS (FA): m/z=303.1 (M+1)

Step 3: rac-5-Chloro-4-[cyclohexyl(hydroxy)methyl]thiophene-2-carbaldehyde

Dowex 50WX2-200 (H) (1 g) was added to a solution of rac-[2-chloro-5-(1,3-dioxolan-2-yl)-3-thienyl](cyclohexyl)methanol (0.62 g, 2.04 mmol) in acetone (40 mL) at rt. The reaction was allowed to stir at rt for 17 h. The reaction was filtered to remove solid resin and the filtrate was concentrated. The crude material was purified on ISCO silica gel (100% hexanes then 20% EtOAc/hexanes as eluent) to give the title compound as yellow oil (yield=338 mg). LCMS (FA): m/z=259.1 (M+1)

Step 4: rac-4-[{[tert-Butyl(dimethyl)silyl]oxy}(cyclohexyl)methyl]-5-chlorothiophene-2-carbaldehyde rac-5-Chloro-4-[cyclohexyl(hydroxy)methyl]thiophene-2-carbaldehyde (338 mg, 1.31 mmol), 1H-imidazole (267 mg, 3.92 mmol), N,N-dimethylaminopyridine (16.0 mg, 0.13 mmol), and DMF (10.0 mL) were combined in a 100 mL round bottom flask under an atmosphere of argon. The solution was cooled at 0° C. TBSCl (225 mg, 1.49 mmol) was added and the reaction was warmed to rt. After 5 h, 1H-imidazole (88.9 mg, 1.31 mmol) and TBSCl (98.4 mg, 0.65 mmol) were added and the reaction was stirred overnight. The reaction was quenched with saturated NH$_4$Cl, diluted with EtOAc and water. The layers were separated and the aqueous layer was extracted EtOAc. The combined organics were washed with 10% aqueous LiCl solution (×3), brine (×1), dried over Na$_2$SO$_4$, filtered and concentrated in vacuo. The residue was purified via ISCO column chromatography (10% EtOAc in hexanes as eluent) to give colorless oil (yield=386 mg). $^1$H NMR (400 MHz, Chloroform-d) δ 9.78 (s, 1H), 7.61 (s, 1H), 4.50 (d, J=7.1 Hz, 1H), 1.98-1.57 (m, 4H), 1.44-0.88 (m, 7H), 0.86 (s, 9H), 0.04 (s, 3H), −0.18 (s, 3H).

The compounds listed in the table below were prepared in an analogous fashion to that described above starting from the appropriate starting materials. The following alternative conditions could be employed in the described reaction steps. Step 4; Condition A: TMSCl/imidazole/DCM, B: TIPSCl/NaH/THF, C: TBSCl/imidazole/DMF.

| Step 2 aldehyde | Step 4 Condition | Compound Name/No. | Characterization Data |
|---|---|---|---|
| 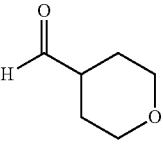 | A | 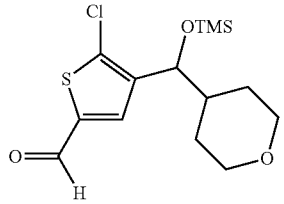<br>Int-129 | ¹H NMR (400 MHz, Chloroform-d) δ 9.78 (s, 1H), 7.64 (s, 1H), 4.51 (d, J = 7.2 Hz, 1H), 4.01 (dd, J = 11.5, 4.1 Hz, 1H), 3.94 (dd, J = 11.5, 3.4 Hz, 1H), 3.40-3.23 (m, 2H), 1.79 (dtq, J = 15.3, 7.5, 3.7 Hz, 2H), 1.49-1.33 (m, 2H), 1.25-1.16 (m, 1H), 0.03 (s, 9H). ¹H NMR |
| 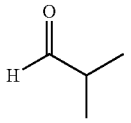 | A | 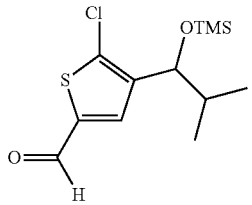<br>Int-130 | ¹H NMR (400 MHz, Chloroform-d) δ 9.78 (s, 1H), 7.64 (s, 1H), 4.46 (d, J = 7.0 Hz, 1H), 1.88 (dq, J = 13.5, 6.7 Hz, 1H), 0.96 (d, J = 6.6 Hz, 3H), 0.81 (d, J = 6.8 Hz, 3H), 0.02 (s, 9H). ¹H NMR |
| 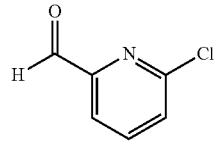 | B | 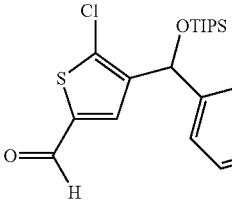<br>Int-131 | ¹H NMR (400 MHz, Chloroform-d) δ 9.73 (s, 1H), 7.71-7.65 (m, 2H), 7.60 (d, J = 7.6 Hz, 1H), 7.22-7.17 (m, 1H), 6.03 (s, 1H), 1.20-1.08 (m, 3H), 1.02-0.96 (m, 18H). ¹H NMR |
| 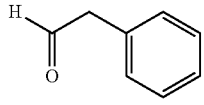 | B | 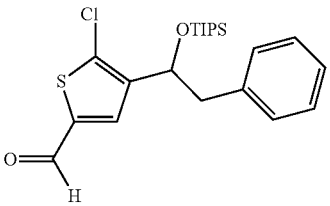<br>Int-132 | ¹H NMR (400 MHz, Chloroform-d) δ 9.62 (s, 1H), 7.41 (s, 1H), 7.15-7.07 (m, 3H), 6.94-6.87 (m, 2H), 5.07 (t, J = 6.1 Hz, 1H), 2.99 (dd, J = 13.2, 5.5 Hz, 1H), 2.89 (dd, J = 13.2, 6.8 Hz, 1H), 1.00-0.81 (m, 21H). ¹H NMR |
| 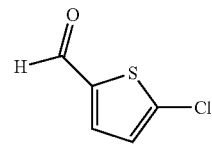 | C | 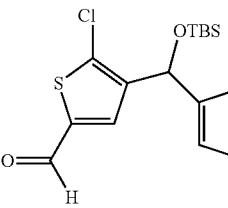<br>Int-133 | ¹H NMR (400 MHz, Chloroform-d) δ 9.75 (s, 1H), 7.70 (s, 1H), 6.71 (d, J = 3.8 Hz, 1H), 6.57 (dd, J = 3.8, 1.1 Hz, 1H), 6.01 (d, J = 0.9 Hz, 1H), 0.91 (s, 9H), 0.11-0.00 (m, 6H). ¹H NMR |

Example 78: rac-5-Chloro-4-[(3-chlorophenyl)(methoxy)methyl]thiophene-2-carbaldehyde Int-134

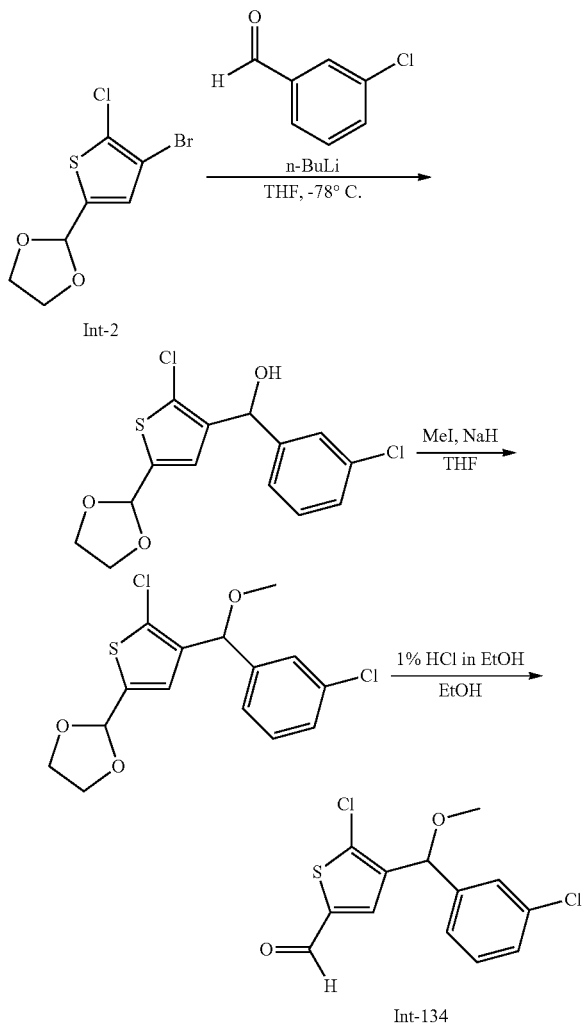

Step 1: rac-2-Chloro-5-(1,3-dioxolan-2-yl)-3-thienyl](3-chlorophenyl)methanol

A 100 mL 2-neck round bottom flask was charged with THF (20 mL) then the flask was purged with argon, and was cooled at −78° C. To the THF, 2.50 M of n-BuLi in hexane (1.86 mL, 4.64 mmol was added dropwise via syringe and the mixture was stirred for 10 min at −78° C. Int-2 (1.0 g, 3.7 mmol) was added dropwise at −78° C. The solution was stirred for 30 min at −78° C. 3-Chlorobenzaldehyde (422 uL, 3.71 mmol) was added to the solution at once at −78° C. and stirred for 15 min. The reaction was quenched by addition of saturated NH$_4$Cl (50 mL) and extracted with EtOAc (50 mL×3). The combined organic layers were dried over Na$_2$SO$_4$, filtered, and concentrated in vacuo. The residue was purified by ISCO column chromatography (0%-50% EtOAc in hexanes as eluent) to give 494 mg (40%) of the title compound. $^1$H NMR (400 MHz, Chloroform-d) δ 7.16-7.02 (m, 4H), 6.78 (s, 1H), 5.76 (s, 1H), 5.75 (s, 1H), 3.93-3.87 (m, 2H), 3.84-3.77 (m, 2H).

Step 2: rac-2-{5-Chloro-4-[(3-chlorophenyl)(methoxy)methyl]-2-thienyl}-1,3-dioxolane A 100 mL round bottom flask was charged with rac-[2-chloro-5-(1,3-dioxolan-2-yl)-3-thienyl](3-chlorophenyl)methanol (490 mg, 1.48 mmol). To the mixture THF (14.5 mL), and 60% NaH in mineral oil (213 mg, 4.44 mmol) were added at rt and the reaction mixture was purged with argon followed by the addition of MeI (276 uL, 4.44 mmol) and heated at 50° C. for 2 h. The solution was quenched with saturated NH$_4$Cl solution and was extracted with DCM (30 mL×2). The combined organic layers were dried over Na$_2$SO$_4$, filtered, and concentrated in vacuo. The residue was purified by ISCO column chromatography (0%-35% EtOAc in hexanes as eluent) to give 404 mg (79%) of the title compound. $^1$H NMR (400 MHz, Chloroform-d) δ 7.21-7.04 (m, 4H), 6.79 (s, 1H), 5.80 (s, 1H), 5.24 (s, 1H), 3.98-3.92 (m, 2H), 3.88-3.82 (m, 2H), 3.23 (s, 3H).

Step 3: rac-5-Chloro-4-[(3-chlorophenyl)(methoxy)methyl]thiophene-2-carbaldehyde rac-2-{5-Chloro-4-[(3-chlorophenyl)(methoxy)methyl]-2-thienyl}-1,3-dioxolane (1.0 g, 2.9 mmol) was dissolved in 1% HCl (20 mL) in EtOH. The reaction mixture was stirred at rt for 2 h. The reaction mixture was diluted with water, extracted with DCM (20 mL×2). The combined organic layers were dried over Na$_2$SO$_4$, filtered, concentrated in vacuo. The residue was purified by ISCO column chromatography (0%-50% EtOAc in hexanes as eluent) to give 0.8 g (90%) of the title compound. $^1$H NMR (400 MHz, Chloroform-d) δ 9.61 (s, 1H), 7.44 (s, 1H), 7.19-7.05 (m, 4H), 5.26 (s, 1H), 3.26 (s, 3H).

Example 79: N-[(E)-(3-Chlorophenyl)methylene]-2-methylpropane-2-sulfinamide Int-135 and rac-N-[(2-Chloro-5-formyl-3-thienyl)(3-chlorophenyl)methyl]-2-methylpropane-2-sulfinamide. Int-136

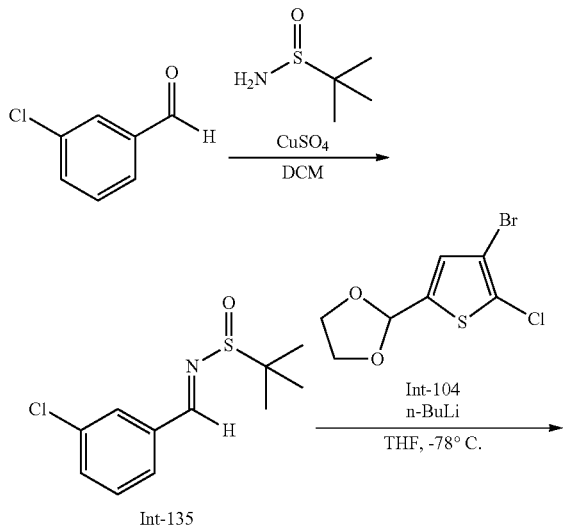

-continued

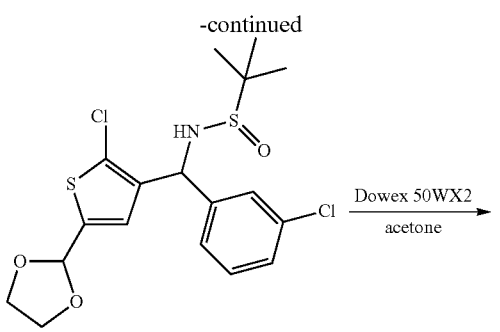

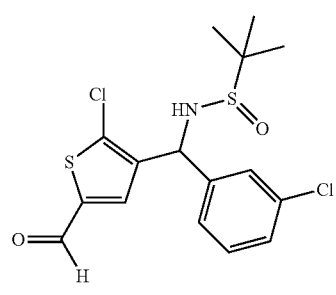

Int-136

Step 1: N-[(E)-(3-Chlorophenyl)methylene]-2-methylpropane-2-sulfinamide

Copper(II) sulfate (2.9 g, 18.0 mmol) and 3-chlorobenzaldehyde (1.3 g, 9.1 mmol) were added to a solution of 2-methyl-2-propanesulfinamide (1.0 g, 8.2 mmol) in DCM (16 mL) at rt. The resulting suspension was allowed to stir for 15 h. The reaction mixture was filtered through a pad of Celite and the filter cake was washed with DCM. The filtrate was concentrated and the crude mixture was purified on ISCO chromatography eluting with a hexane/EtOAc gradient to afford the title compound (yield=1.32 g). $^1$H NMR (400 MHz, Chloroform-d) δ 8.54 (s, 1H), 7.86 (t, J=1.7 Hz, 1H), 7.69 (dt, J=7.5, 1.2 Hz, 1H), 7.49 (ddd, J=8.0, 2.0, 1.2 Hz, 1H), 7.42 (t, J=7.8 Hz, 1H), 1.27 (s, 9H). LCMS (FA): m/z=244.3 (M+H).

Step 2: rac-N-{[2-Chloro-5-(1,3-dioxolan-2-yl)-3-thienyl](3-chlorophenyl)methyl}-2-methylpropane-2-sulfinamide A solution of 2-(4-bromo-5-chloro-2-thienyl)-1,3-dioxolane (900 mg, 3.30 mmol) in THF (30 mL) was cooled to −78° C. and 2.50 M of n-BuLi in hexane (1.66 mL, 4.15 mmol) was added dropwise. Immediately after a solution of N-[(E)-(3-chlorophenyl)methylene]-2-methylpropane-2-sulfinamide (0.97 g, 3.97 mmol) in THF (4 mL) was added quickly to the reaction mixture. The resulting solution was allowed to stir for 15 min at that temperature. After warming to ~0° C., the reaction was quenched by addition of water. The mixture was extracted with EtOAc (3×) and the combined organic extracts were dried over $Na_2SO_4$, filtered and concentrated. The crude product was purified on ISCO chromatography eluting with a hexane/EtOAc gradient to afford the title compound (yield=1.2 g). $^1$H NMR (400 MHz, Chloroform-d) δ 7.41 (d, J=17.9 Hz, 1H), 7.36-7.24 (m, 3H), 6.98 (d, J=10.3 Hz, 1H), 5.97 (d, J=6.8 Hz, 1H), 5.76 (dd, J=7.5, 2.6 Hz, 1H), 4.15-4.07 (m, 2H), 4.06-3.96 (m, 2H), 3.69-3.61 (m, 1H), 1.33-1.22 (m, 9H).

Step 3: rac-N-[(2-Chloro-5-formyl-3-thienyl)(3-chlorophenyl)methyl]-2-methylpropane-2-sulfinamide Dowex 50WX2-200 (H) (1 g) was added to a solution of N-{[2-chloro-5-(1,3-dioxolan-2-yl)-3-thienyl](3-chlorophenyl)methyl}-2-methylpropane-2-sulfinamide (0.90 g, 2.10 mmol) in acetone (20 mL) at rt. The reaction was allowed to stir for 1 hour. The reaction was filtered to remove solid resin and the crude material was purified on ISCO chromatography eluting with a hexane/EtOAc gradient to afford the title compound (yield=750 mg). $^1$H NMR (400 MHz, Chloroform-d) δ 9.75 (d, J=4.0 Hz, 1H), 7.63 (d, J=16.4 Hz, 1H), 7.38 (d, J=12.8 Hz, 1H), 7.34-7.27 (m, 3H), 5.78 (dd, J=15.0, 3.1 Hz, 1H), 3.80-3.70 (m, 1H), 1.27 (s, 9H).

The compounds listed in the table below were prepared in a similar fashion to that described above starting from the listed starting materials:

| Starting material | Compound Name/No. | Characterization Data |
|---|---|---|
| ![Br-benzaldehyde] | ![Int-137 structure] | LCMS (FA): m/z = 436.1 (M + H). |

Int-137

| Starting material | Compound Name/No. | Characterization Data |
|---|---|---|
| (6-chloropyridine-2-carbaldehyde structure) | Int-138 | $^1$H NMR (400 MHz, Chloroform-d) δ 9.73 (s, 1H), 7.63 (t, J = 7.8 Hz, 1H), 7.59 (s, 1H), 7.28 (d, J = 8.0 Hz, 1H), 7.13 (d, J = 7.6 Hz, 1H), 5.83 (d, J = 2.9 Hz, 1H), 5.38 (s, 1H), 1.27 (s, 9H). $^1$H NMR |
| (6-bromopyridine-2-carbaldehyde structure) | Int-139 | $^1$H NMR (400 MHz, Chloroform-d) δ 9.74 (s, 1H), 7.57 (s, 1H), 7.53 (t, J = 7.7 Hz, 1H), 7.43 (d, J = 7.8 Hz, 1H), 7.16 (d, J = 7.5 Hz, 1H), 5.82 (d, J = 3.6 Hz, 1H), 5.40 (d, J = 3.4 Hz, 1H), 1.27 (s, 9H). $^1$H NMR |

Example 80: rac-4-Chloro-5-{(3-chlorophenyl)[(trimethylsilyl)oxy]methyl}thiophene-2-carbaldehyde Int-140

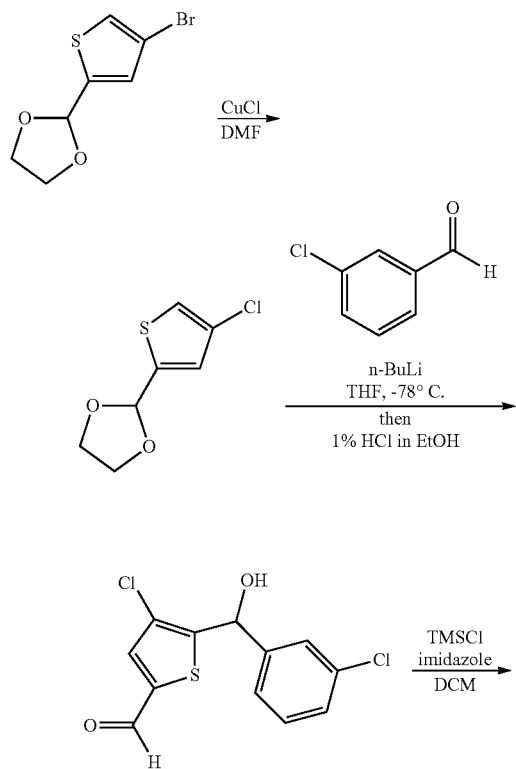

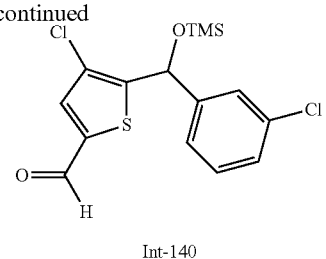

Int-140

Step 1: 2-(4-Chloro-2-thienyl)-1,3-dioxolane 2-(4-Bromothiophen-2-yl)-1,3-dioxolane (2.81 g, 12.0 mmol) was dissolved into DMF (3.0 mL) in a microwave tube, and then CuCl (1.66 g, 16.7 mmol) was added to this solution. The reaction was heated at 180° C. with stirring for 90 min. The solid was filtered, and the residual solid was washed with DCM. The filtrate was poured into 50 ml water, and the mixture was extracted with DCM (40 mL×2). The combined organic layers were concentrated in vacuo and the residue was purified by ISCO column chromatography (0%-30% EtOAc in hexanes as eluent) to give 1.40 g (61%) of the title compound as colorless oil. $^1$H NMR (400 MHz, Chloroform-d) δ 7.12 (s, 1H), 7.07 (s, 1H), 6.07 (s, 1H), 4.16-4.09 (m, 2H), 4.07-4.00 (m, 2H).

Step 2: rac-4-Chloro-5-[(3-chlorophenyl)(hydroxy)methyl]thiophene-2-carbaldehyde 2.50 M of n-BuLi in hexane (1.44 mL, 3.59 mmol) was added dropwise via syringe into THF (40 mL), and then cooled down at −78° C. 2-(4-Chloro-2-thienyl)-1,3-dioxolane (489 mg, 2.57 mmol) was added to this solution at −78°

C., then 3-chlorobenzaldehyde (433 mg, 3.08 mmol) was added to the solution at once at −78° C. The reaction was stirred at −78° C. for 15 min. The solution was poured into 60 ml saturated NH₄Cl solution and the mixture was extracted with EtOAc (50 ml×2). The combined the organic layers were concentrated in vacuo and the residues were dissolved into 30 ml 1% HCl in MeOH with 5 ml water. The mixture was stirred at rt for 30 min. The reaction mixture was poured into 30 ml saturated NaHCO₃ solution, and extracted with DCM (30 ml×3). The combined the organic layers were concentrated in vacuo and the residue was purified by ISCO column (0%-40% EtOAc in hexanes as eluent) to give 402 mg (55%) of the title compound. ¹H NMR (400 MHz, Chloroform-d) δ 9.75 (s, 1H), 7.53 (s, 1H), 7.49-7.40 (m, 1H), 7.40-7.25 (m, 3H), 6.12 (s, 1H), 3.81-3.23 (br s, 1H).

Step 3: rac-4-Chloro-5-{(3-chlorophenyl)[(trimethylsilyl)oxy]methyl}thiophene-2-carbaldehyde To a solution of rac-4-chloro-5-[(3-chlorophenyl)(hydroxy)methyl]thiophene-2-carbaldehyde (0.42 g, 1.47 mmol) in DCM (25.0 mL) was added TMSCl (0.24 mL, 1.91 mmol) followed by 1H-imidazole (0.20 g, 2.94 mmol), and the reaction was stirred at for 1 hour. The reaction mixture was poured into saturated aqueous NH₄Cl (50 mL) at rt and the mixture was extracted with DCM (×3). The combined organic layers were washed with water, brine, dried using MgSO₄, filtered and concentrated in vacuo. The residue was purified by ISCO column chromatography (0%-20% EtOAc in hexanes as eluent) to give 296 mg (56%) of the title compound. ¹H NMR (400 MHz, Chloroform-d) δ 9.68 (s, 1H), 7.38 (s, 1H), 7.30 (s, 1H), 7.23-7.18 (m, 1H), 7.17-7.06 (m, 2H), 5.89 (s, 1H), −0.01 (s, 9H).

Example 81: rac-4-{1-(3-Bromophenyl)-1-[(trimethylsilyl)oxy]ethyl}thiophene-2-carbaldehyde. Int-141

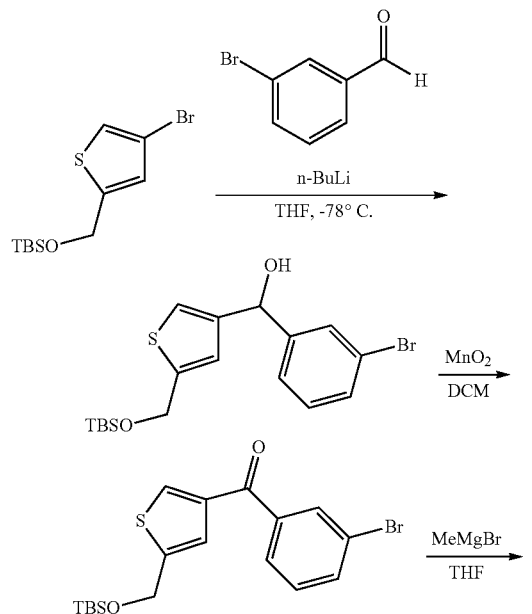

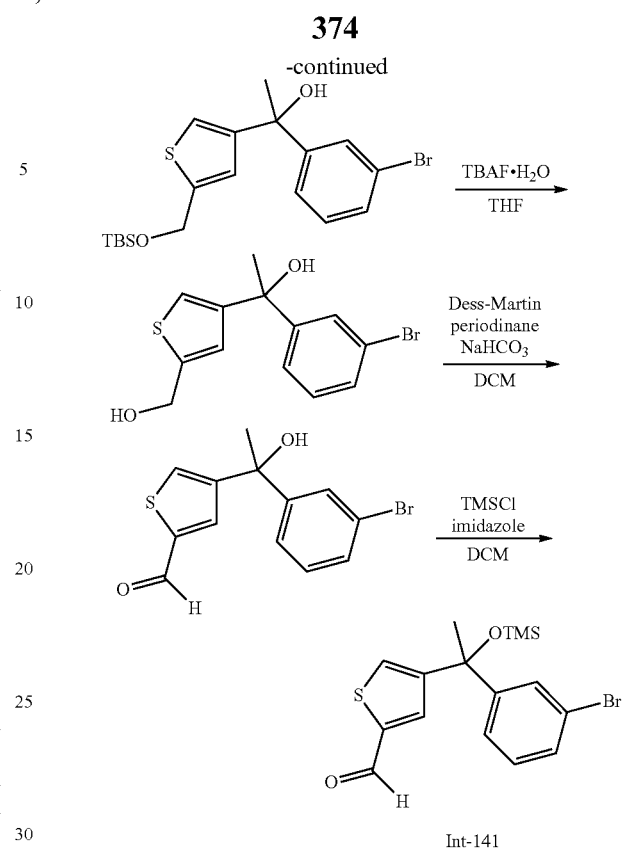

Int-141

Step 1: rac-(3-Bromophenyl)[5-({[tert-butyl(dimethyl)silyl]oxy}methyl)-3-thienyl]methanol Magnesium turnings (370 mg, 15.2 mmol) were weighed into a 100 mL round bottom flask and the reaction vessel was purged with argon followed by addition of THF (8.0 mL). A separate bottom flask was charged with [((4-bromothiophen-2-yl)methoxy)(tert-butyl)dimethylsilane (1.17 g, 3.81 mmol) and the substrate was dissolved in THF (8.0 mL). An aliquot of this solution (0.1 mL) was added into the magnesium suspension and the mixture was heated with a heat gun. The remainder of the solution was added dropwise into the magnesium suspension and the mixture was stirred for 2 h. This resulting mixture was cooled to at 0° C. with ice-bath. To the Grignard reagent solution was added dropwise a solution of 3-bromobenzaldehyde (704 mg, 3.81 mmol) in THF (40.0 mL) at 0° C., and the mixture was stirred for 30 min at rt. The reaction was quenched by addition of saturated NH₄Cl (50 mL) and the mixture was extracted with EtOAc (×3). The combined organic layers were washed with brine, dried over Na₂SO₄, filtered, and concentrated in vacuo. The residue was purified by ISCO column chromatography (10% EtOAc in hexanes as eluent) to give 1.28 g (82%) of the title compound as a light yellow oil. ¹H NMR (400 MHz, Chloroform-d) δ 7.56 (s, 1H), 7.41 (d, J=8.0 Hz, 1H), 7.30 (d, J=7.7 Hz, 1H), 7.21 (t, J=7.8 Hz, 1H), 7.08 (s, 1H), 6.77 (s, 1H), 5.78 (d, J=3.7 Hz, 1H), 4.80 (s, 2H), 2.18 (d, J=3.8 Hz, 1H), 0.91 (s, 9H), 0.08 (s, 6H).

Step 2: (3-Bromophenyl)[5-({[tert-butyl(dimethyl)silyl]oxy}methyl)-3-thienyl]methanone To a solution of rac-(3-bromophenyl)[5-({[tert-butyl(dimethyl)silyl]oxy}methyl)-3-thienyl]methanol (934 mg, 2.26 mmol) in DCM (20.0 mL) was added MnO₂ (1.96 g, 22.6 mmol). The mixture was stirred for 19 h at rt. The reaction was then filtered through a Celite pad and the residual solid was washed with DCM several times. The filtrate was concentrated in vacuo to obtain 881 mg (95%) of the title compound as white solid. $^1$H NMR (400 MHz, Chloroform-d) δ 7.95 (s, 1H), 7.82 (d, J=1.3 Hz, 1H), 7.75 (d, J=7.7 Hz, 1H), 7.73-7.66 (m, 1H), 7.40-7.32 (m, 2H), 4.92-4.86 (m, 2H), 0.94 (s, 9H), 0.13 (s, 6H).

Step 3: rac-1-(3-Bromophenyl)-1-[5-({[tert-butyl (dimethyl)silyl]oxy}methyl)-3-thienyl]ethanol A round-bottom flask was charged with 3-bromophenyl) [5-({[tert-butyl(dimethyl)silyl]oxy}methyl)-3-thienyl] methanone (125 mg, 0.30 mmol) and the content was dissolved in THF (2.8 mL). The solution was cooled to 0° C. and 3.0 M of methylmagnesium bromide in Et₂O (0.20 mL, 0.61 mmol) was added dropwise over 10 min. The reaction was then stirred at 0° C. for 1 hour. To the mixture was added 3.0 M of methylmagnesium bromide in Et₂O (1.5 mL, 4.58 mmol) and the resulting mixture was stirred for 1 hour. The reaction was quench reaction with saturated NH₄Cl and the mixture was extracted with EtOAc (×3). The combined organic layers were then washed with water, brine, dried using Na₂SO₄, filtered and concentrated. No further purification was done (100% yield assumed). $^1$H NMR (400 MHz, Chloroform-d) δ 7.61 (d, J=1.7 Hz, 1H), 7.37 (d, J=7.9 Hz, 1H), 7.32 (d, J=7.9 Hz, 1H), 7.18 (t, J=7.9 Hz, 1H), 7.08 (d, J=1.5 Hz, 1H), 6.75 (s, 1H), 4.81-4.77 (m, 2H), 1.88 (s, 3H), 0.90 (s, 9H), 0.07 (s, 6H).

Step 4: rac-1-(3-Bromophenyl)-1-[5-(hydroxymethyl)-3-thienyl]ethanol

To a solution of rac-1-(3-bromophenyl)-1-[5-({[tert-butyl (dimethyl)silyl]oxy}methyl)-3-thienyl]ethanol (0.92 g, 2.14 mmol) in THF (30.0 mL) was added TBAF hydrate (1.20 g, 4.28 mmol) was then added and the reaction was stirred at rt for 3 h. The reaction was quenched by addition of saturated NaHCO₃ and the mixture was extracted with EtOAc (×3). The combined organic layers were then washed with water, brine, dried using Na₂SO₄, filtered and concentrated. The residue was purified by ISCO column chromatography (0%-100% EtOAc in hexanes as eluent) to give 676 mg (100%) of the title compound. $^1$H NMR (400 MHz, Chloroform-d) δ 7.62 (s, 1H), 7.38 (d, J=7.8 Hz, 1H), 7.33 (d, J=7.9 Hz, 1H), 7.19 (t, J=7.9 Hz, 1H), 7.16-7.12 (m, 1H), 6.86 (s, 1H), 4.75 (s, 2H), 1.90 (s, 3H), 1.87-1.67 (br s, 2H).

Step 5: rac-4-[1-(3-Bromophenyl)-1-hydroxyethyl] thiophene-2-carbaldehyde

A round bottom flask was charged with rac-1-(3-bromophenyl)-1-[5-(hydroxymethyl)-3-thienyl]ethanol (676 mg, 2.16 mmol) and the content was dissolved in DCM (20.0 mL). To the solution was added NaHCO₃ (544 mg, 6.48 mmol) followed by Dess-Martin periodinane (1.10 g, 2.59 mmol) and the reaction was stirred at rt for 1 hour. The reaction was then quenched by the addition of saturated Na₂S₂O₃, extracted with DCM (×3). The combined organic layers were then washed with water, brine, dried using Na₂SO₄, filtered and concentrated. The residue was purified by ISCO column chromatography (0%-50% EtOAc in hexanes as eluent) to give 396 mg (59%) of the title compound. LCMS (FA): m/z=313.1 (M+1).

Step 6: rac-4-{1-(3-Bromophenyl)-1-[(trimethylsilyl)oxy]ethyl}thiophene-2-carbaldehyde To a solution of rac-4-[1-(3-bromophenyl)-1-hydroxyethyl]thiophene-2-carbaldehyde (396 mg, 1.27 mmol) in DMF (5.0 mL) was added 1H-imidazole (260 mg, 3.82 mmol) followed by TMSCl (0.24 mL, 1.91 mmol) at rt and the reaction was then stirred for 3 h. The reaction mixture was poured into saturated aqueous NaHCO₃ (50 mL) at rt and extracted with EtOAc (×3). The combined organic layers were washed with water, brine, dried using Na₂SO₄, filtered and concentrated in vacuo. The residue was purified by ISCO column chromatography (0%-10% EtOAc in hexanes as eluent) to give 334 mg (68%) of the title compound. $^1$H NMR (400 MHz, Chloroform-d) δ 9.82 (d, J=1.1 Hz, 1H), 7.60 (s, 1H), 7.55 (s, 1H), 7.52 (d, J=1.4 Hz, 1H), 7.37 (d, J=7.8 Hz, 1H), 7.27-7.23 (m, 1H), 7.17 (t, J=7.8 Hz, 1H), 1.94 (s, 3H), 0.03 (s, 9H).

Example 82: 5-{[tert-Butyl(dimethyl)silyl]oxy}-1-(3-chlorophenyl)pentan-1-one. Int-142

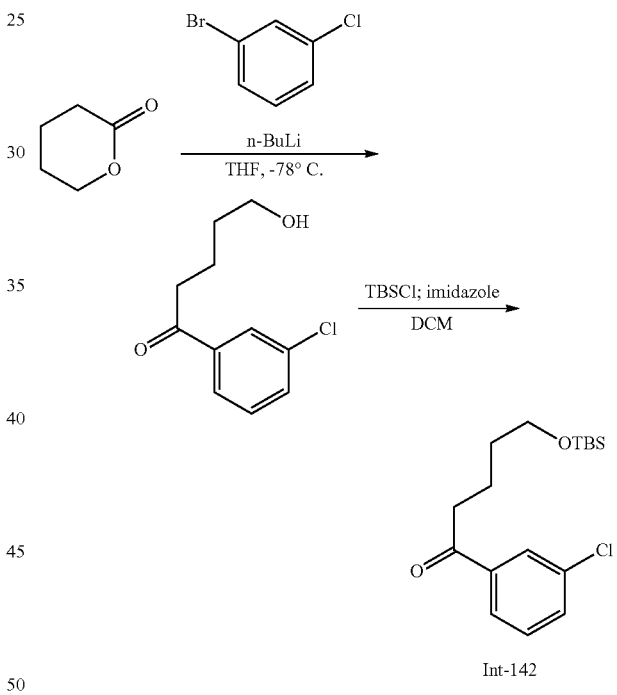

Step 1: 1-(3-Chlorophenyl)-5-hydroxypentan-1-one

A 100 mL 2-neck round bottom flask was charged with 3-chlorobromobenzene (3 mL, 20 mmol) then the flask was purged with argon. The content was dissolved in THF (50 mL), and the solution was cooled at −78° C. To the solution was added dropwise 2.50 M of n-BuLi in hexane (12.3 mL, 30.7 mmol) at −78° C. and the mixture was stirred for 30 min at same temperature. To the mixture was added dropwise a solution of δ-valerolactone (2.37 mL, 25.5 mmol) in THF (2.0 mL) at −78° C., and the reaction was stirred for 15 min followed by stirring at rt for 30 min. The reaction was quenched by addition of saturated NH₄Cl (15 mL) and extracted with EtOAc (50 mL×3). The combined organic layers were dried over Na₂SO₄, filtered, and concentrated in vacuo. The residue was purified by ISCO column chromatography (0%-50% EtOAc in hexanes as eluent) to give 5.0 g (90%) of the title compound as light yellow oil. ¹H NMR (400 MHz, Chloroform-d) δ 7.92 (s, 1H), 7.83 (d, J=7.8 Hz, 1H), 7.52 (d, J=8.6 Hz, 1H), 7.40 (t, J=7.9 Hz, 1H), 3.67 (t, J=6.3 Hz, 2H), 3.00 (t, J=7.1 Hz, 2H), 1.85-1.80 (m, 2H), 1.67-1.62 (m, 2H).

Step 2: 5-{[tert-Butyl(dimethyl)silyl]oxy}-1-(3-chlorophenyl)pentan-1-one

A 250 mL round bottom flask was charged with 1-(3-chlorophenyl)-5-hydroxypentan-1-one (5.0 g, 22 mmol), then the flask was purged with argon. The content was dissolved into DCM (100 mL), then 1H-imidazole (2.45 g, 36.0 mmol) was added followed by the addition of TBSCl (4.70 g, 31.2 mmol) at rt for 1 hour. The reaction was quenched by addition of water (15 mL) and extracted with DCM (50 mL×3). The combined organic layers were dried over Na₂SO₄, filtered, and concentrated in vacuo. The residue was purified by ISCO column chromatography (0%-30% EtOAc in hexanes as eluent) to give 7.0 g (90%) of the title compound as colorless oil. ¹H NMR (400 MHz, Chloroform-d) δ 7.92 (s, 1H), 7.83 (d, J=7.7 Hz, 1H), 7.52 (d, J=8.0 Hz, 1H), 7.40 (t, J=7.8 Hz, 1H), 3.66 (t, J=6.2 Hz, 2H), 2.98 (t, J=7.3 Hz, 2H), 1.86-1.74 (m, 2H), 1.65-1.53 (m, 3H), 0.89 (s, 9H), 0.05 (s, 6H).

The compound listed in the table below was prepared in an analogous fashion to that described above starting from the listed starting material:

| Starting material | Compound Name/No. | Characterization Data |
|---|---|---|
| 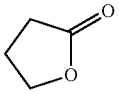 | 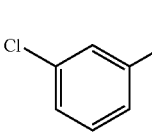 Int-143 | ¹H NMR (400 MHz, Chloroform-d) δ 7.93 (t, J = 1.7 Hz, 1H), 7.84 (d, J = 7.8 Hz, 1H), 7.55-7.49 (m, 1H), 7.39 (t, J = 7.9 Hz, 1H), 3.70 (t, J = 6.0 Hz, 2H), 3.03 (t, J = 7.2 Hz, 2H), 1.94 (p, J = 6.4 Hz, 2H), 0.88 (s, 9H), 0.04 (s, 6H). ¹H NMR |

Example 83: rac-2-(3-Chlorophenyl)-2,3,4,5-tetrahydro-2,3'-bithiophene-5'-carbaldehyde. Int-144

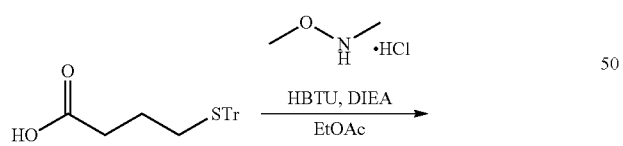

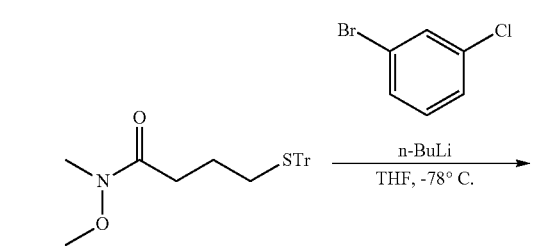

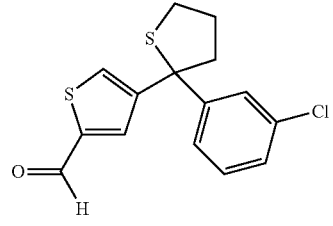

Int-144

Step 1:
N-Methoxy-N-methyl-4-(tritylsulfanyl)butanamide

To a solution of 4-(tritylsulfanyl)butanoic acid (5.91 g, 16.3 mmol) and N,O-dimethylhydroxylamine hydrochloride (2.06 g, 21.1 mmol) in DMF (96.4 mL) was added N,N-diisopropylethylamine (11.4 mL, 65.2 mmol) and O-(benzotriazol-1-yl)-N,N,N',N'-tetramethyluronium hexafluorophosphate (6.76 g, 17.8 mmol). The reaction was stirred at rt overnight. The reaction was partitioned between 50 mL water/50 mL brine and 250 mL EtOAc. The organic layer was separated and washed with saturated NaHCO$_3$ (3×110 mL), brine (100 mL), dried over Na$_2$SO$_4$, filtered, and concentrated to give 7.43 g of the title compound as yellow oil. $^1$H NMR (400 MHz, Chloroform-d) δ 7.43 (d, J=7.5 Hz, 5H), 7.36-7.18 (m, 10H), 3.65 (s, 3H), 3.15 (s, 3H), 2.40 (m, 2H), 2.25 (t, J=7.1 Hz, 2H), 1.74 (p, J=7.2 Hz, 2H); LCMS (FA): m/z=428.1 (M+H+Na)

Step 2:
1-(3-Chlorophenyl)-4-(tritylsulfanyl)butan-1-one

To a solution of N-methoxy-N-methyl-4-(tritylsulfanyl) butanamide (6.93 g, 13.9 mmol) in THF (36.2 mL) at 0° C. under argon was added 0.5 M of 3-chlorophenylmagnesium bromide in THF (33.4 mL, 16.7 mmol). The resulting reaction mixture was stirred at 0° C. for 15 min. Then the cold bath was removed and the reaction was stirred at rt for 60 min. The reaction was quenched with addition of saturated NH$_4$Cl. The mixture was diluted with water and extracted with EtOAc (2×). The combined organic layers were washed with brine, dried over Na$_2$SO$_4$, filtered, and concentrated in vacuo. The residue was purified by ISCO column chromatography (0%-6% EtOAc in hexane as eluent) to give 5.03 g (80%) of the title compound as white solid. $^1$H NMR (400 MHz, Chloroform-d) δ 7.85 (t, J=1.8 Hz, 1H), 7.78-7.73 (m, 1H), 7.54-7.50 (m, 1H), 7.44-7.36 (m, 7H), 7.30-7.23 (m, 10H, overlaps with CDCl3), 7.23-7.17 (m, 3H), 2.87 (t, J=7.2 Hz, 2H), 2.30 (t, J=7.0 Hz, 2H), 1.80 (p, J=7.0 Hz, 2H); LCMS (FA): m/z=479.1 (M+1+Na)

Step 3: rac-1-(3-Chlorophenyl)-1-[5-(1,3-dioxolan-2-yl)-3-thienyl]-4-(tritylsulfanyl)butan-1-ol An oven-dried 500 mL 3-neck flask equipped with septam, stir bar and 3-way stop cock with argon balloon was purged with argon. THF (55.6 mL) was added into the flask and cooled at −78° C. with dry-ice/acetone bath. 2.50 M of n-BuLi in hexane (5.34 mL, 13.3 mmol) was added, and the mixture was stirred 3 min. To the mixture was added by quick steady stream a solution of 2-(4-bromothiophen-2-yl)-1,3-dioxolane (3.14 g, 13.3 mmol) in THF (22.5 mL) and stirred for 3 min at −78° C. To the orange mixture was added dropwise a solution of 1-(3-chlorophenyl)-4-(tritylsulfanyl) butan-1-one (5.08 g, 11.1 mmol) in THF (15.0 mL) at −78° C., and the resulting orange solution was stirred for 10 min. The reaction was quenched by addition of water (30 mL) and extracted with EtOAc (100 mL×3). The combined organic layers were washed with brine, dried over Na$_2$SO$_4$, filtered, and concentrated in vacuo. The oil was purified by silica gel column chromatography (0-30% EtOAc in hexanes as eluent) to afford 4.01 g of the title compound as yellow foam (15% other isomer present, overall 50% yield). $^1$H NMR (400 MHz, Chloroform-d) δ 7.41-7.33 (m, 6H), 7.29-7.22 (m, 13H, overlaps with CDCl3), 7.22-7.16 (m, 5H), 7.11 (d, J=1.5 Hz, 1H), 6.95 (d, J=1.1 Hz, 1H), 5.97 (s, 1H), 4.16-4.05 (m, 2H), 4.03-3.94 (m, 2H), 2.20-2.13 (m, 2H), 2.11-2.05 (m, 2H), 1.48-1.35 (m, 1H), 1.20 (m, 1H).

Step 4: rac-2-(3-Chlorophenyl)-2,3,4,5-tetrahydro-2, 3'-bithiophene-5'-carbaldehyde To rac-1-(3-chlorophenyl)-1-[5-(1,3-dioxolan-2-yl)-3-thienyl]-4-(tritylsulfanyl)butan-1-ol (4.01 g, 6.54 mmol) was added slowly TFA (9.57 mL, 124 mmol), and the resulting orange-red solution was stirred at rt for 30 min. The reaction was quenched with 50 mL saturated NaHCO$_3$ and extracted with EtOAc. The organic layer was washed with saturated NaHCO$_3$ (2×50 mL). The aqueous phase was backwashed with EtOAc (50 mL). The combined organics were washed with water, brine, dried over Na$_2$SO$_4$, filtered and concentrated. The crude red granular oil was purified by ISCO column chromatography (0-15% EtOAc in hexanes as eluent) to give 1.61 g (73%) of the title compound as an orange oil. $^1$H NMR (400 MHz, Chloroform-d) δ 9.82 (d, J=1.1 Hz, 1H), 7.63-7.60 (m, 1H), 7.58 (d, J=1.5 Hz, 1H), 7.49-7.46 (m, 1H), 7.32-7.28 (m, 1H), 7.25-7.22 (m, 2H), 3.15 (t, J=6.9 Hz, 2H), 2.66-2.58 (m, 2H), 2.14-2.04 (m, 2H). LCMS (FA): m/z=309.0 (M+H).

Example 84: rac-4-[2-(3-Chlorophenyl)tetrahydro-2H-pyran-2-yl]thiophene-2-carbaldehyde. Int-145

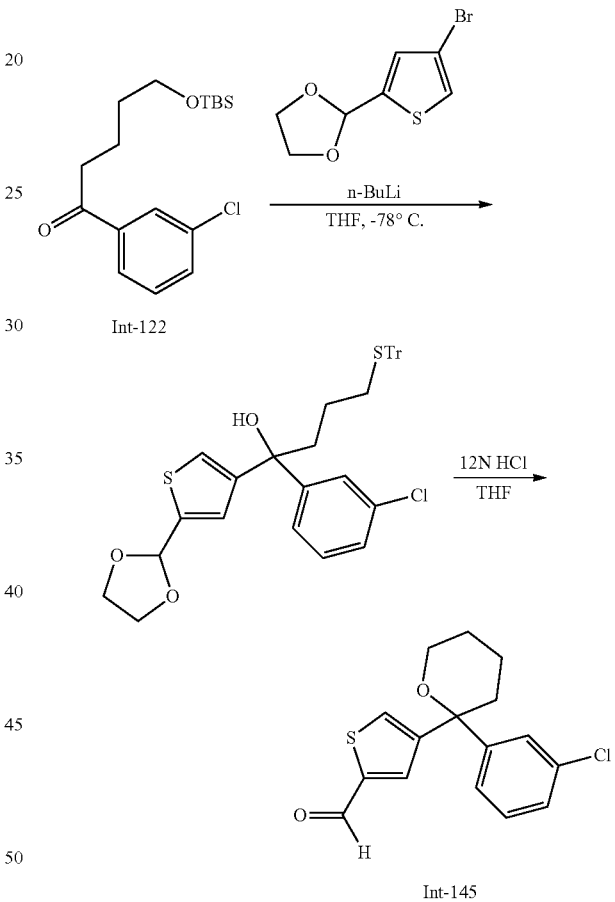

Step 1: rac-5-{[tert-Butyl(dimethyl)silyl]oxy}-1-(3-chlorophenyl)-1-[5-(1,3-dioxolan-2-yl)-3-thienyl] pentan-1-ol A 250 mL 2-neck round bottom flask was charged with THF (125 mL) then the flask was purged with argon, and was cooled at −78° C. To the THF, 2.50 M of n-BuLi in hexane (4.68 mL, 11.7 mmol) was added dropwise via syringe and the mixture was stirred for 10 min at −78° C. 2-(4-Bromothiophen-2-yl)-1,3-dioxolane (2.38 g, 10.1 mmol) was added dropwise at −78° C. The solution was stirred for 30 min at −78° C. Int-142 (2.55 g, 7.80 mmol) was added to the solution at once at −78° C. and stirred for 30 min. The reaction was quenched by addition of saturated NH$_4$Cl (50 mL) and extracted with EtOAc (75 mL×3). The combined organic layers were dried over Na$_2$SO$_4$, filtered, and concentrated in vacuo. The residue was purified by ISCO column chromatography (0%-40% EtOAc in hexanes as eluent) to give 3.1 g (82%) of the title compound. $^1$H NMR (400 MHz, Chloroform-d) δ 7.44 (s, 1H), 7.24-7.15 (m, 4H), 7.03 (s, 1H), 5.99 (s, 1H), 4.13-4.08 (m, 3H), 4.02-3.94 (m, 2H), 3.58 (t, J=6.2 Hz, 2H), 2.20 (t, J=8.0 Hz, 2H), 1.57-1.46 (m, 2H), 1.45-1.32 (m, 1H), 0.85 (s, 9H), 0.01 (s, 6H).

Step 2: rac-4-[2-(3-Chlorophenyl)tetrahydro-2H-pyran-2-yl]thiophene-2-carbaldehyde To a solution of rac-5-{[tert-butyl(dimethyl)silyl]oxy}-1-(3-chlorophenyl)-1-[5-(1,3-dioxolan-2-yl)-3-thienyl]pentan-1-ol (533 mg, 1.10 mmol) in THF (4.0 mL) was added 12 M of HCl (12.0 mL) was added and the reaction mixture was heated at 68° C. After 2 h, the reaction mixture was allowed to rt, and poured into a solution of Na$_2$CO$_3$ (9.75 g) in 100 mL of water. The aqueous layer was extracted with EtOAc (15 mL×2). The combined organic layers were dried over Na$_2$SO$_4$, concentrated in vacuo and purified by ISCO column chromatography (0%-100% EtOAc in hexanes as eluent) to give 233 mg (69%) of the title compound as an oil. $^1$H NMR (400 MHz, Chloroform-d) δ 9.84 (s, 1H), 7.64 (s, 1H), 7.54 (s, 1H), 7.42 (s, 1H), 7.27-7.18 (m, 3H), 3.80-3.63 (m, 2H), 2.24 (t, J=6.0 Hz, 2H), 1.79-1.69 (m, 2H), 1.68-1.59 (m, 2H).

Example 85: rac-5-Methyl-4-(2-phenyltetrahydrofuran-2-yl)thiophene-2-carbaldehyde. Int-146

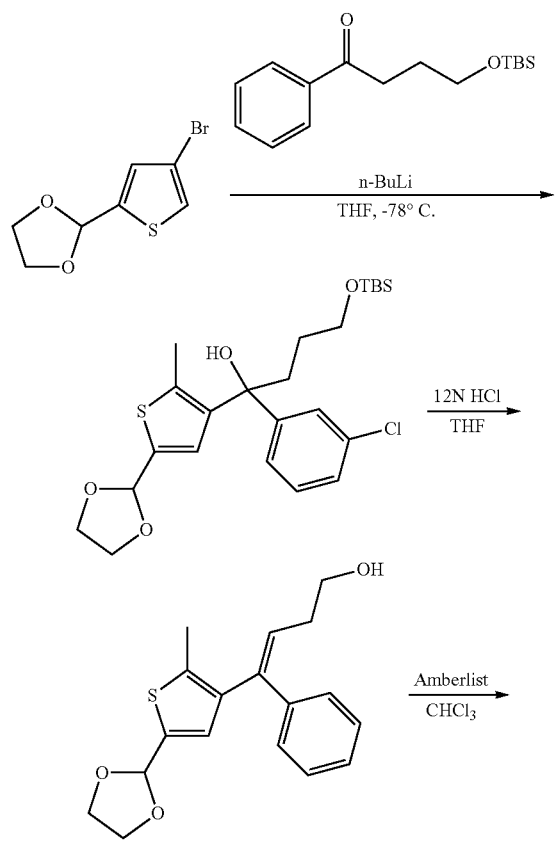

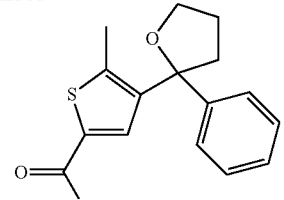

Int-146

Step 1: rac-4-{[tert-Butyl(dimethyl)silyl]oxy}-1-[5-(1,3-dioxolan-2-yl)-2-methyl-3-thienyl]-1-phenylbutan-1-ol To a round bottom flask was added THF (12.0 mL) and 2.50 M of n-BuLi in hexane (1.87 mL, 4.67 mmol). The solution was cooled at −78° C. and 2-(4-bromo-5-methyl-2-thienyl)-1,3-dioxolane (1.07 g, 4.31 mmol) in THF (5.0 mL) was added and the mixture was stirred for 10 minute. 4-{[tert-butyl(dimethyl)silyl]oxy}-1-phenylbutan-1-one (1.00 g, 3.59 mmol) in THF (5.0 mL) was then added quickly via syringe and the mixture was stirred at −78° C. for 1 hour. The reaction was quenched with saturated NH$_4$Cl and extracted with EtOAc (3×). The combined organic layers were then washed with water, brine, dried using Na$_2$SO$_4$, filtered and concentrated. The residue was purified by ISCO column chromatography (0%-50% EtOAc in hexanes as eluent) to give 1.27 g (79%) of the title compound. $^1$H NMR (400 MHz, Chloroform-d) δ 7.38-7.33 (m, 2H), 7.30-7.24 (m, 2H), 7.22-7.16 (m, 1H), 7.14 (s, 1H), 5.99 (s, 1H), 4.17-4.08 (m, 2H), 4.05-3.96 (m, 2H), 3.67-3.59 (m, 2H), 3.42 (s, 1H), 2.43-2.32 (m, 1H), 2.32-2.20 (m, 1H), 2.17 (s, 3H), 1.65-1.52 (m, 2H), 0.89 (s, 9H), 0.05 (s, 3H), 0.04 (s, 3H).

Step 2: rac-4-[(1Z)-4-Hydroxy-1-phenylbut-1-en-1-yl]-5-methylthiophene-2-carbaldehyde To a round bottom flask was added rac-4-{[tert-butyl(dimethyl)silyl]oxy}-1-[5-(1,3-dioxolan-2-yl)-2-methyl-3-thienyl]-1-phenylbutan-1-ol (1.27 g, 2.84 mmol) in THF (5.0 mL). 12 M of HCl in water (2.0 mL, 24 mmol) was added and the solution was heated to reflux for 1 hour. The reaction was then cooled to rt and quenched with saturated NaHCO$_3$ and extracted with EtOAc (3×). The combined organic layers were then washed with water, brine, dried using Na$_2$SO$_4$, filtered and concentrated. No purification was done to give crude title compound. LCMS (FA): m/z=273.3 (M+H)

Step 3: rac-5-Methyl-4-(2-phenyltetrahydrofuran-2-yl)thiophene-2-carbaldehyde rac-4-[(1Z)-4-Hydroxy-1-phenylbut-1-en-1-yl]-5-methylthiophene-2-carbaldehyde (773 mg, 2.84 mmol) was dissolved in chloroform (20.0 mL) and Amberlyst 15 ion-exchange resin (2 g) was added and the mixture was heated to 50° C. for 7 h. The reaction was then filtered to remove resin, rinsed with DCM and concentrated to dryness. The reaction was stopped before complete consumption of starting material to avoid decomposition of product. The residue was purified by ISCO column chromatography (0%-50% EtOAc in hexanes as eluent) to give 261 mg (34%, over 2 steps) of the title compound. ¹H NMR (400 MHz, Chloroform-d) δ 9.78 (s, 1H), 7.74 (s, 1H), 7.36-7.27 (m, 4H), 7.26-7.19 (m, 1H), 4.14-4.06 (m, 1H), 4.03-3.95 (m, 1H), 2.61-2.44 (m, 2H), 2.35 (s, 3H), 2.06-1.94 (m, 2H).

Example 86: rac-4-(2-Phenyltetrahydrofuran-2-yl) thiophene-2-carbaldehyde. Int-147

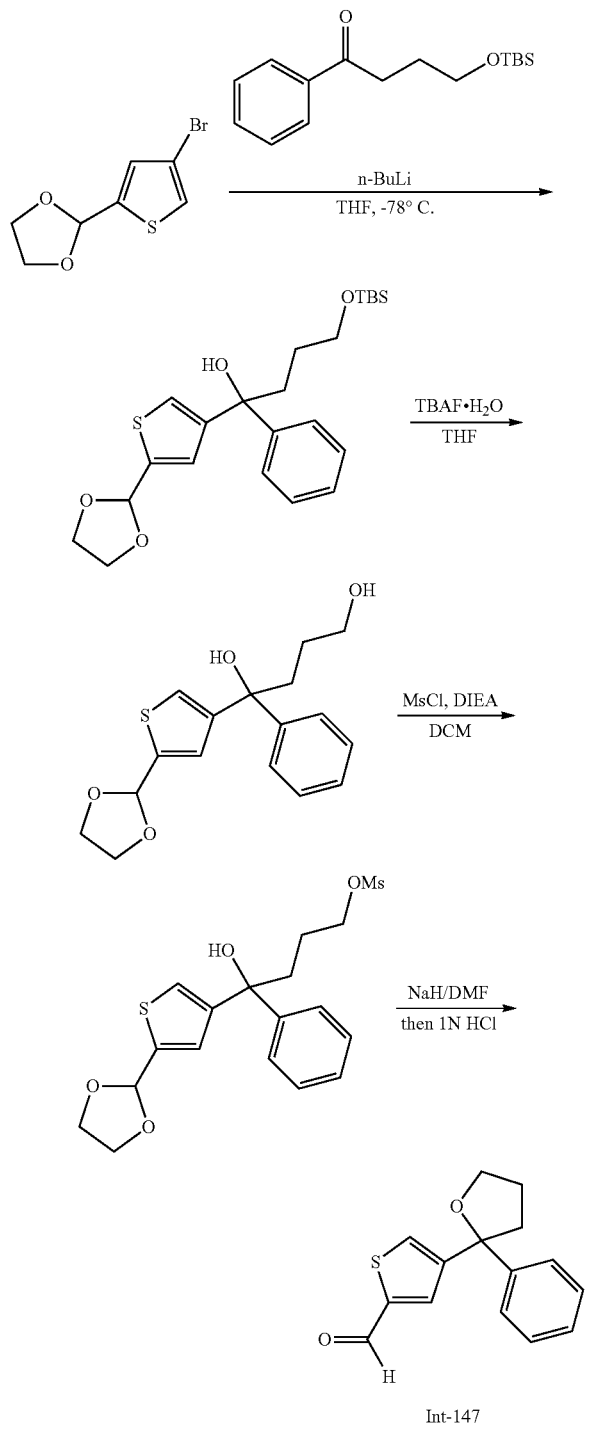

Int-147

Step 1: rac-4-{[tert-Butyl(dimethyl)silyl]oxy}-1-[5-(1,3-dioxolan-2-yl)-3-thienyl]-1-phenylbutan-1-ol To a round bottom flask was added THF (20.0 mL) and 2.50 M of n-BuLi in hexane (3.57 mL, 8.92 mmol). The mixture was cooled at −78° C. and 2-(4-bromothiophen-2-yl)-1,3-dioxolane (1.94 g, 8.23 mmol) in THF (10.0 mL) was added and the mixture was stirred for 10 min. 4-{[tert-butyl(dimethyl)silyl]oxy}-1-phenylbutan-1-one (1.91 g, 6.86 mmol) in THF (10.0 mL) was then added quickly via syringe and the mixture was stirred at −78° C. for 1 hour. The reaction was quenched with saturated NH₄Cl and extracted with EtOAc (×3). The combined organic layers were then washed with water, brine, dried using Na₂SO₄, filtered and concentrated. The residue was purified by ISCO column chromatography (0%-50% EtOAc in hexanes as eluent) to give 2.57 g (86%) of the title compound. ¹H NMR (400 MHz, Chloroform-d) δ 7.46-7.41 (m, 2H), 7.32-7.27 (m, 2H), 7.24-7.18 (m, 1H), 7.17 (d, J=1.4 Hz, 1H), 7.07 (d, J=1.1 Hz, 1H), 6.00 (s, 1H), 4.16-4.06 (m, 2H), 4.03-3.94 (m, 2H), 3.92 (s, 1H), 3.67-3.61 (m, 2H), 2.43-2.28 (m, 2H), 1.62-1.52 (m, 2H), 0.90 (s, 9H), 0.05 (s, 6H).

Step 2: rac-1-[5-(1,3-Dioxolan-2-yl)-3-thienyl]-1-phenylbutane-1,4-diol rac-4-{[tert-butyl(dimethyl)silyl]oxy}-1-[5-(1,3-dioxolan-2-yl)-3-thienyl]-1-phenylbutan-1-ol (2.56 g, 5.89 mmol) in THF (50.0 mL) was added TBAF hydrate (1.98 g, 7.07 mmol) at rt and the reaction was stirred overnight. To the reaction was added water and the mixture was extracted with EtOAc (3×). The combined organic layers were dried over Na₂SO₄, filtered, and concentrated in vacuo. The residue was purified by ISCO column chromatography (0%-100% EtOAc in hexanes as eluent) to give 1.68 g (89%) of the title compound. ¹H NMR (400 MHz, Chloroform-d) δ 7.45-7.39 (m, 2H), 7.35-7.28 (m, 2H), 7.26-7.20 (m, 1H), 7.18 (s, 1H), 7.06 (s, 1H), 5.99 (s, 1H), 4.15-4.06 (m, 2H), 4.03-3.94 (m, 2H), 3.69-3.62 (m, 2H), 3.13 (s, 1H), 2.43-2.30 (m, 2H), 1.71 (s, 1H), 1.66-1.49 (m, 2H).

Step 3: rac-4-[5-(1,3-Dioxolan-2-yl)-3-thienyl]-4-hydroxy-4-phenylbutyl methanesulfonate To a solution of rac-1-[5-(1,3-dioxolan-2-yl)-3-thienyl]-1-phenylbutane-1,4-diol (0.69 g, 2.14 mmol) in DCM (20 mL) cooled to 0° C. was added N,N-diisopropylethylamine (0.56 mL, 3.21 mmol) followed by methanesulfonyl chloride (182 uL, 2.36 mmol) and the reaction was stirred for 1 hour. The reaction was quenched by addition of water and extracted with DCM (3×). The combined organic layers were dried over Na₂SO₄, filtered, and concentrated in vacuo. No further purification was done to give crude title compound. LCMS (FA): m/z=399.2 (M+H)

Step 4: rac-4-(2-Phenyltetrahydrofuran-2-yl)thiophene-2-carbaldehyde

To a solution of rac-4-[5-(1,3-dioxolan-2-yl)-3-thienyl]-4-hydroxy-4-phenylbutyl methanesulfonate (853 mg, 2.14 mmol) in THF (15.0 mL) and DMF (5.0 mL) was added 60% NaH in mineral oil (128 mg, 3.21 mmol) and the reaction was stirred for 2 h. The reaction was quenched by addition of water and extracted with EtOAc (3×). The combined organic layers were dried over Na₂SO₄, filtered, and concentrated in vacuo. The crude product was then dissolved in acetone (15.0 mL) and to the solution was added water (7.0 mL) followed by 1.0 M of HCl (0.6 mL, 0.6 mmol) at rt. The resulting solution was then stirred for 30 min. The reaction was quenched by addition of saturated NaHCO$_3$ and extracted with EtOAc (3×). The combined organic layers were dried over Na$_2$SO$_4$, filtered, and concentrated in vacuo. The residue was purified by ISCO column chromatography (0%-30% EtOAc in hexanes as eluent) to give 414 mg (75%) of the title compound. $^1$H NMR (400 MHz, Chloroform-d) δ 9.83 (d, J=1.2 Hz, 1H), 7.68 (d, J=1.5 Hz, 1H), 7.56-7.54 (m, 1H), 7.45-7.41 (m, 2H), 7.37-7.31 (m, 2H), 7.28-7.23 (m, 1H), 4.12-4.01 (m, 2H), 2.56-2.49 (m, 2H), 2.09-1.94 (m, 2H).

Example 87: (1S)-1-(3-Chlorophenyl)-1-[5-(1,3-dioxolan-2-yl)-3-thienyl]butane-1,4-diol or 1R)-1-(3-chlorophenyl)-1-[5-(1,3-dioxolan-2-yl)-3-thienyl]butane-1,4-diol (Peak 1) Int-148, and (1S)-1-(3-chlorophenyl)-1-[5-(1,3-dioxolan-2-yl)-3-thienyl]butane-1,4-diol or (1R)-1-(3-chlorophenyl)-1-[5-(1,3-dioxolan-2-yl)-3-thienyl]butane-1,4-diol (Peak 2) Int-149

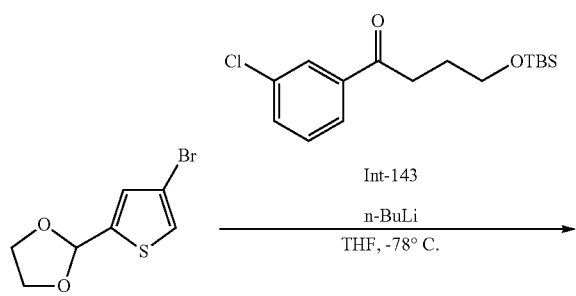

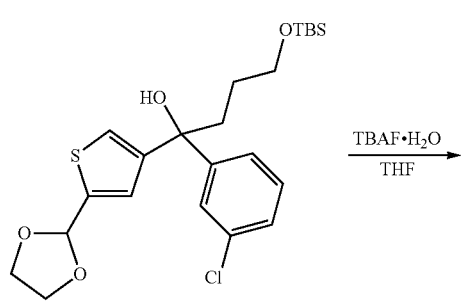

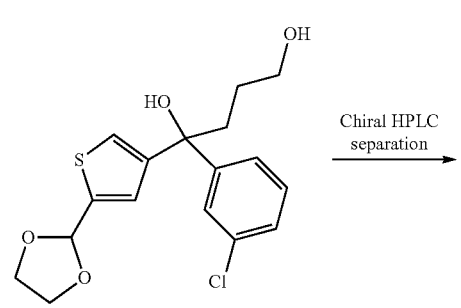

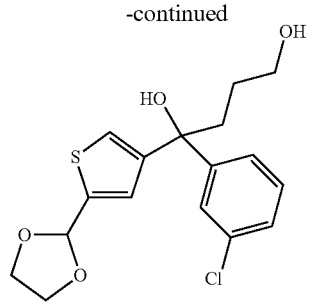

Int-148

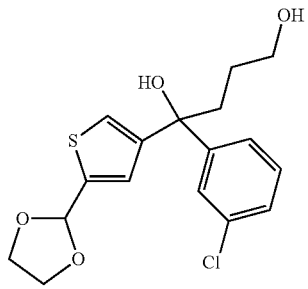

Int-149

Step 1: rac-4-{[tert-Butyl(dimethyl)silyl]oxy}-1-(3-chlorophenyl)-1-[5-(1,3-dioxolan-2-yl)-3-thienyl]butan-1-ol THF (20.0 mL) was added into a 250 mL 2-neck flask under atmosphere of argon and cooled at −78° C. 2.50 M of n-BuLi in hexane (1.92 mL, 4.79 mmol) was added into the THF. To the mixture was added quick dropwise a solution of 2-(4-bromothiophen-2-yl)-1,3-dioxolane (1.13 g, 4.79 mmol) in THF (8.0 mL) and the mixture was stirred for 3 min at −78° C. To the mixture was added dropwise a solution of Int-143 (1.25 g, 3.99 mmol) in THF (5 mL, 60 mmol) at −78° C., and the reaction was stirred for 10 min. The reaction was quenched by addition of water (100 mL) and extracted with EtOAc (100 mL×3). The combined organic layers were washed with brine, dried over Na$_2$SO$_4$, filtered, and concentrated in vacuo. The residue was purified by ISCO column chromatography (10%-30% EtOAc in hexanes as eluent) to give 1.44 g of the title compound (71%) colorless oil. $^1$H NMR (400 MHz, DMSO-d$_6$) δ 7.46-7.42 (m, 1H), 7.36 (d, J=1.4 Hz, 1H), 7.35-7.29 (m, 2H), 7.27-7.21 (m, 1H), 7.08 (d, J=1.3 Hz, 1H), 5.92 (s, 1H), 5.73 (s, 1H), 4.02-3.93 (m, 2H), 3.93-3.84 (m, 2H), 3.52 (tt, J=10.0, 5.1 Hz, 2H), 2.22-2.08 (m, 2H), 1.53-1.38 (m, 1H), 1.32-1.19 (m, 1H), 0.83 (s, 9H), −0.02 (s, 3H), −0.03 (s, 3H).

Step 2: rac-1-(3-Chlorophenyl)-1-[5-(1,3-dioxolan-2-yl)-3-thienyl]butane-1,4-diol To a solution of rac-4-{[tert-butyl(dimethyl)silyl]oxy}-1-(3-chlorophenyl)-1-[5-(1,3-dioxolan-2-yl)-3-thienyl]butan-1-ol (1.43 g, 2.80 mmol) in THF (40.0 mL) was added TBAF monohydrate (941 mg, 3.37 mmol) at rt, and the reaction was stirred for 15 min. The reaction was concentrated in vacuo. To the residue was added water and then the mixture was extracted with EtOAc (×3). The combined organic layers were dried over Na$_2$SO$_4$, filtered, and concentrated in vacuo. The residue was purified by ISCO column chromatography (20% EtOAc in DCM as eluent) to give 935 mg (89%) of the title compound as colorless oil. ¹H NMR (400 MHz, DMSO-d₆) δ 7.48-7.44 (m, 1H), 7.38 (d, J=1.4 Hz, 1H), 7.36-7.29 (m, 2H), 7.24 (dt, J=6.7, 2.1 Hz, 1H), 7.09 (d, J=1.3 Hz, 1H), 5.92 (s, 1H), 5.74 (s, 1H), 4.40 (t, J=5.2 Hz, 1H), 4.01-3.94 (m, 2H), 3.94-3.83 (m, 2H), 3.41-3.30 (m, 2H), 2.14 (tq, J=13.9, 6.9, 5.4 Hz, 2H), 1.48-1.35 (m, 1H), 1.28-1.14 (m, 1H).

Step 3: (1S)-1-(3-Chlorophenyl)-1-[5-(1,3-dioxolan-2-yl)-3-thienyl]butane-1,4-diol and (1R)-1-(3-chlorophenyl)-1-[5-(1,3-dioxolan-2-yl)-3-thienyl]butane-1,4-diol rac-1-(3-chlorophenyl)-1-[5-(1,3-dioxolan-2-yl)-3-thienyl]butane-1,4-diol was separated to enantiomers by chiral HPLC (chiral column IB 4.6×50 mm, 70/10/20/0.1 Hexane/IPA/EtOH/DEA 1.3 mL/min) to yield Peak 1: 381 mg (41%)>98% ee and Peak 2: 398 mg (43%)>98% ee.

Peak 1: (1S)-1-(3-Chlorophenyl)-1-[5-(1,3-dioxolan-2-yl)-3-thienyl]butane-1,4-diol or (1R)-1-(3-Chlorophenyl)-1-[5-(1,3-dioxolan-2-yl)-3-thienyl]butane-1,4-diol ¹H NMR (400 MHz, DMSO-d₆) δ 7.48-7.44 (m, 1H), 7.37 (d, J=1.4 Hz, 1H), 7.36-7.28 (m, 2H), 7.24 (dt, J=6.8, 2.1 Hz, 1H), 7.09 (d, J=1.3 Hz, 1H), 5.93 (s, 1H), 5.73 (s, 1H), 4.39 (t, J=5.2 Hz, 1H), 4.03-3.94 (m, 2H), 3.94-3.84 (m, 2H), 3.40-3.32 (m, 2H), 2.14 (tq, J=13.8, 6.8, 5.4 Hz, 2H), 1.49-1.35 (m, 1H), 1.29-1.16 (m, 1H).

Peak 2: (1S)-1-(3-Chlorophenyl)-1-[5-(1,3-dioxolan-2-yl)-3-thienyl]butane-1,4-diol or (1R)-1-(3-Chlorophenyl)-1-[5-(1,3-dioxolan-2-yl)-3-thienyl]butane-1,4-diol ¹H NMR (400 MHz, DMSO-d₆) δ 7.48-7.43 (m, 1H), 7.37 (d, J=1.3 Hz, 1H), 7.36-7.27 (m, 2H), 7.24 (dt, J=6.8, 2.1 Hz, 1H), 7.09 (d, J=1.2 Hz, 1H), 5.93 (s, 1H), 5.73 (s, 1H), 4.39 (t, J=5.2 Hz, 1H), 4.04-3.94 (m, 2H), 3.94-3.84 (m, 2H), 3.40-3.32 (m, 2H), 2.14 (tq, J=13.7, 6.8, 5.3 Hz, 2H), 1.49-1.35 (m, 1H), 1.29-1.15 (m, 1H).

Example 88: 4-[(2S)-2-(3-Chlorophenyl)tetrahydrofuran-2-yl]thiophene-2-carbaldehyde or 4-[(2R)-2-(3-Chlorophenyl)tetrahydrofuran-2-yl]thiophene-2-carbaldehyde. Int-150

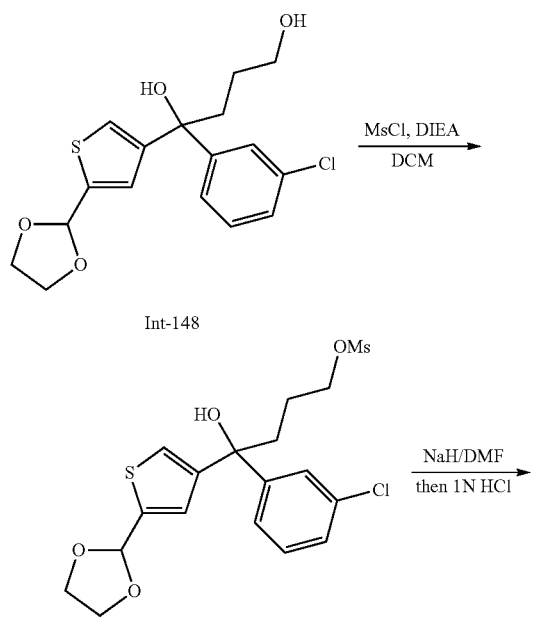

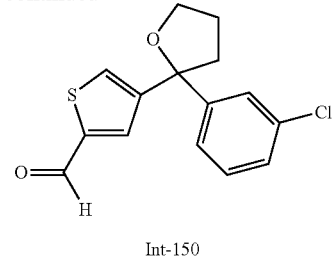

Int-150

Step 1: (4S)-4-(3-Chlorophenyl)-4-[5-(1,3-dioxolan-2-yl)-3-thienyl]-4-hydroxybutyl methanesulfonate or (4R)-4-(3-Chlorophenyl)-4-[5-(1,3-dioxolan-2-yl)-3-thienyl]-4-hydroxybutyl methanesulfonate (Peak 1)

To a solution of (1S or 1R)-1-(3-chlorophenyl)-1-[5-(1,3-dioxolan-2-yl)-3-thienyl]butane-1,4-diol (Int-148, 375 mg, 1.06 mmol) (Peak 1) in DCM (10.0 mL) was added N,N-diisopropylethylamine (0.28 mL, 1.59 mmol) followed by methanesulfonyl chloride (0.09 mL, 1.16 mmol) at rt, and the reaction was stirred for 1 hour. The reaction was quenched by addition of water (50 mL) and extracted with DCM (50 mL×3). The combined organic layers were dried over Na₂SO₄, filtered, and concentrated in vacuo. The residue was purified by ISCO silica gel column chromatography (24 g, eluting with 5% EtOAc in DCM for 3 min then gradient to 20% EtOAc in DCM over 15 min, 40 mL/min flow) to give 372 mg (81%) of the title compound as a colorless oil. LCMS (AA): m/z=433.0 (M+H).

Step 2: 4-[(2S)-2-(3-Chlorophenyl)tetrahydrofuran-2-yl]thiophene-2-carbaldehyde or 4-[(2R)-2-(3-Chlorophenyl)tetrahydrofuran-2-yl]thiophene-2-carbaldehyde To a solution of (4S or 4R)-4-(3-chlorophenyl)-4-[5-(1,3-dioxolan-2-yl)-3-thienyl]-4-hydroxybutyl methanesulfonate (368 mg, 0.85 mmol) in DMF (5.5 mL) was added 60% NaH in mineral oil (51.0 mg, 1.28 mmol) and the reaction was stirred for 1 hour. The reaction was quenched by addition of water (50 mL) and extracted with EtOAc (50 mL×3). The combined organic layers were dried over Na₂SO₄, filtered, and concentrated in vacuo. The residue was dissolved in acetone (6.0 mL, 81.7 mmol). To the solution was added water (3.0 mL) followed by 1.0 M of HCl in water (0.30 mL, 0.30 mmol) at rt, and the mixture was stirred for 1 hour. The reaction was quenched by addition of saturated NaHCO₃ (50 mL) and extracted with EtOAc (50 mL×3). The combined organic layers were washed with brine, dried over Na₂SO₄, filtered, and concentrated in vacuo. The residue was purified by ISCO column chromatography (0%-5% EtOAc in DCM as eluent) to give 128 mg (51%) of the title compound as a colorless oil. ¹H NMR (400 MHz, DMSO-d₆) δ 9.85 (d, J=1.3 Hz, 1H), 8.01 (t, J=1.4 Hz, 1H), 7.95 (d, J=1.6 Hz, 1H), 7.50 (t, J=1.8 Hz, 1H), 7.42 (dt, J=7.7, 1.5 Hz, 1H), 7.37 (t, J=7.7 Hz, 1H), 7.33-7.28 (m, 1H), 4.00-3.93 (m, 2H), 2.70-2.61 (m, 1H), 2.40 (dt, J=12.6, 7.5 Hz, 1H), 1.98-1.82 (m, 2H).

The compound listed in the table below was prepared in an analogous fashion to that described above starting from the listed starting material:

| Starting material | Compound Name/No. | Characterization Data |
|---|---|---|
| 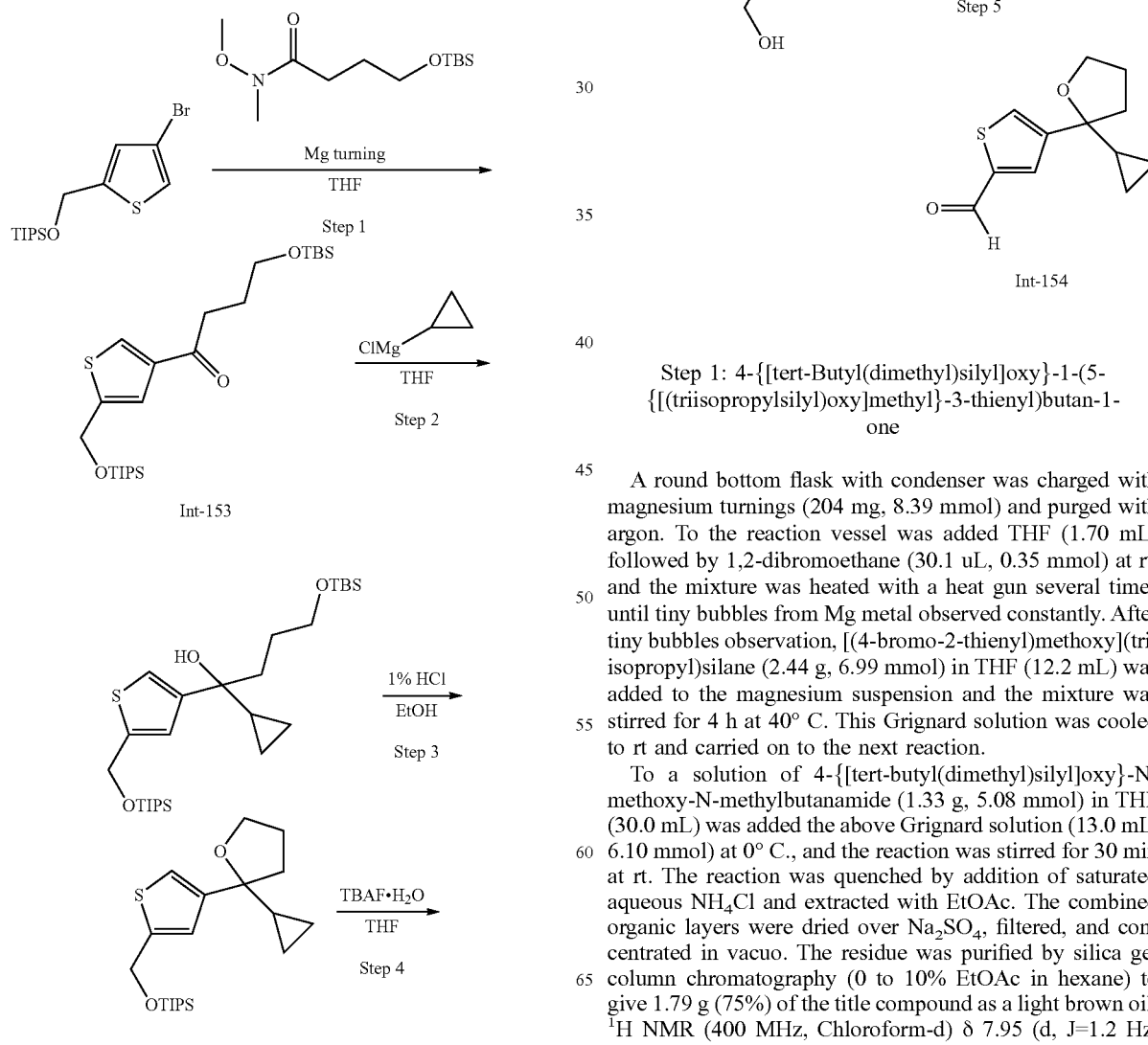 Int-151 | Peak 2 Int-152 | $^1$H NMR (400 MHz, DMSO-d$_6$) δ 9.85 (d, J = 1.3 Hz, 1H), 8.01 (t, J = 1.4 Hz, 1H), 7.95 (d, J = 1.6 Hz, 1H), 7.50 (t, J = 1.8 Hz, 1H), 7.42 (dt, J = 7.7, 1.5 Hz, 1H), 7.37 (t, J = 7.7 Hz, 1H), 7.33-7.28 (m, 1H), 4.02-3.91 (m, 2H), 2.70-2.60 (m, 1H), 2.40 (dt, J = 12.6, 7.5 Hz, 1H), 1.97-1.82 (m, 2H). LCMS (AA): m/z = 293.0 (M + H). |

Example 89: 4-{[tert-Butyl(dimethyl)silyl]oxy}-1-(5-{[(triisopropylsilyl)oxy]methyl}-3-thienyl)butan-1-one Int-153, and rac-4-(2-Cyclopropyltetrahydrofuran-2-yl)thiophene-2-carbaldehyde Int-154

Step 1: 4-{[tert-Butyl(dimethyl)silyl]oxy}-1-(5-{[(triisopropylsilyl)oxy]methyl}-3-thienyl)butan-1-one A round bottom flask with condenser was charged with magnesium turnings (204 mg, 8.39 mmol) and purged with argon. To the reaction vessel was added THF (1.70 mL) followed by 1,2-dibromoethane (30.1 uL, 0.35 mmol) at rt, and the mixture was heated with a heat gun several times until tiny bubbles from Mg metal observed constantly. After tiny bubbles observation, [(4-bromo-2-thienyl)methoxy](triisopropyl)silane (2.44 g, 6.99 mmol) in THF (12.2 mL) was added to the magnesium suspension and the mixture was stirred for 4 h at 40° C. This Grignard solution was cooled to rt and carried on to the next reaction.

To a solution of 4-{[tert-butyl(dimethyl)silyl]oxy}-N-methoxy-N-methylbutanamide (1.33 g, 5.08 mmol) in THF (30.0 mL) was added the above Grignard solution (13.0 mL, 6.10 mmol) at 0° C., and the reaction was stirred for 30 min at rt. The reaction was quenched by addition of saturated aqueous NH$_4$Cl and extracted with EtOAc. The combined organic layers were dried over Na$_2$SO$_4$, filtered, and concentrated in vacuo. The residue was purified by silica gel column chromatography (0 to 10% EtOAc in hexane) to give 1.79 g (75%) of the title compound as a light brown oil.
$^1$H NMR (400 MHz, Chloroform-d) δ 7.95 (d, J=1.2 Hz, 1H), 7.32 (s, 1H), 4.94 (s, 2H), 3.68 (t, J=6.0 Hz, 2H), 2.93 (t, J=7.3 Hz, 2H), 1.98-1.87 (m, 2H), 1.23-1.02 (m, 21H), 0.89 (s, 9H), 0.04 (s, 6H).

Step 2: rac-4-{[tert-Butyl(dimethyl)silyl]oxy}-1-cyclopropyl-1-(5-{[(triisopropylsilyl)oxy]methyl}-3-thienyl)butan-1-ol To a solution of 4-{[tert-butyl(dimethyl)silyl]oxy}-1-(5-{[(triisopropylsilyl)oxy]methyl}-3-thienyl)butan-1-one (202 mg, 0.43 mmol) in THF (1.8 mL) was added 0.5 M of cyclopropylmagnesium bromide in THF (2.41 mL, 1.21 mmol) at 0° C., and then the reaction was allowed to warm to rt. After 1 h, the reaction was quenched by addition of saturated aqueous NH$_4$Cl and extracted with EtOAc. The combined organic layers were washed with brine, dried over Na$_2$SO$_4$, filtered, and concentrated in vacuo. The residue was purified by silica gel column chromatography (0 to 5% EtOAc in hexane) to afford 186 mg (84%) of the title compound as a colorless oil. $^1$H NMR (400 MHz, Chloroform-d) δ 7.01 (s, 1H), 6.80 (s, 1H), 4.88 (s, 2H), 3.64-3.49 (m, 2H), 2.79 (s, 1H), 2.04-1.91 (m, 1H), 1.91-1.78 (m, 1H), 1.59-1.51 (m, 2H), 1.18-0.97 (m, 22H), 0.85 (s, 9H), 0.43-0.33 (m, 2H), 0.34-0.24 (m, 2H), 0.04 (s, 6H).

Step 3: rac-{[4-(2-Cyclopropyltetrahydrofuran-2-yl)-2-thienyl]methoxy}(triisopropyl)silane To a solution of rac-4-{[tert-butyl(dimethyl)silyl]oxy}-1-cyclopropyl-1-(5-{[(triisopropylsilyl)oxy]methyl}-3-thienyl)butan-1-ol (186 mg, 0.36 mmol) in EtOH (3.1 mL) was added 1% HCl in EtOH (3.11 mL, 0.38 mmol) at rt and the reaction was stirred for 30 min. The reaction was quenched by addition of saturated aqueous NaHCO$_3$ and concentrated in vacuo to remove EtOH. To the residue was added water and the mixture was extracted with EtOAc. The combined organic layers were dried over Na$_2$SO$_4$, filtered, and concentrated in vacuo. The residue was purified by silica gel column chromatography (0 to 5% EtOAc in hexane) to give 103 mg (75%) of the title compound as a colorless oil. $^1$H NMR (400 MHz, DMSO-d$_6$) δ 7.13 (s, 1H), 6.93 (s, 1H), 4.90 (s, 2H), 3.75 (t, J=6.7 Hz, 2H), 2.18-2.04 (m, 1H), 2.01-1.83 (m, 2H), 1.81-1.66 (m, 1H), 1.30-0.95 (m, 22H), 0.43-0.22 (m, 4H).

Step 4: rac-[4-(2-Cyclopropyltetrahydrofuran-2-yl)-2-thienyl]methanol

To a solution of rac-{[4-(2-cyclopropyltetrahydrofuran-2-yl)-2-thienyl]methoxy}(triisopropyl)silane (99.9 mg, 0.26 mmol) in THF (5.46 mL) was added TBAF hydrate (88.0 mg, 0.32 mmol) at rt and the reaction was stirred for 1 h. The reaction was concentrated in vacuo and the residue was purified by silica gel column chromatography (0 to 30% EtOAc in hexane) to give 54.5 mg (93%) of the title compound as a colorless oil. $^1$H NMR (400 MHz, Chloroform-d) δ 7.09 (s, 1H), 6.97 (s, 1H), 4.81 (d, J=6.0 Hz, 2H), 3.96-3.85 (m, 2H), 2.23-2.12 (m, 1H), 2.11-1.81 (m, 3H), 1.74 (t, J=6.0 Hz, 1H), 1.27-1.19 (m, 1H), 0.50-0.35 (m, 4H).

Step 5: rac-4-(2-Cyclopropyltetrahydrofuran-2-yl)thiophene-2-carbaldehyde

To a solution of rac-[4-(2-cyclopropyltetrahydrofuran-2-yl)-2-thienyl]methanol (54.5 mg, 0.24 mmol) in DCM (9.0 mL) was added Mn$_2$O (211 mg, 2.43 mmol) at rt, and the reaction was stirred overnight. The reaction was filtered through a Celite pad and the residual solid was rinsed with DCM several times. The filtrate was concentrated in vacuo and purified by silica gel column chromatography (0 to 20% EtOAc in hexane) to give 53.3 mg (98%) of the title compound as a colorless oil. $^1$H NMR (400 MHz, Chloroform-d) δ 9.91 (s, 1H), 7.74 (s, 1H), 7.60 (s, 1H), 3.99-3.84 (m, 2H), 2.23-1.97 (m, 3H), 1.95-1.80 (m, 1H), 1.31-1.20 (m, 1H), 0.57-0.35 (m, 4H).

The compound listed in the table below was prepared using similar methods to that described above starting from the listed starting material.

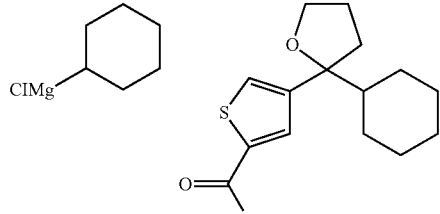

| Step 2 Grignard reagent | Compound Name/No. | Characterization Data |
|---|---|---|
| ClMg-cyclohexyl | Int-155 | $^1$H NMR (400 MHz, Chloroform-d) δ 9.89 (d, J = 1.1 Hz, 1H), 7.65 (d, J = 1.3 Hz, 1H), 7.52-7.47 (m, 1H), 3.91 (q, J = 7.5, 7.1 Hz, 1H), 3.83-3.74 (m, 1H), 2.15 (ddd, J = 12.1, 8.0, 4.0 Hz, 1H), 2.10-2.00 (m, 1H), 1.98-1.80 (m, 2H), 1.80-1.51 (m, 5H), 1.34-1.11 (m, 3H), 1.09-0.85 (m, 3H), 0.77 (qd, J = 12.7, 3.4 Hz, 1H). |

Example 90: rac-4-[2-(Cyclohex-1-en-1-yl)tetrahydrofuran-2-yl]thiophene-2-carbaldehyde. Int-156

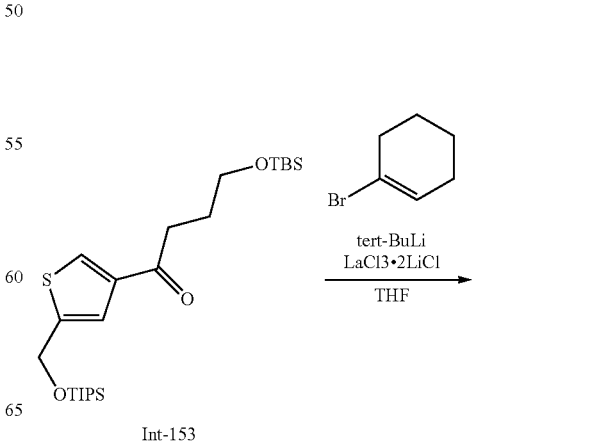

Int-153

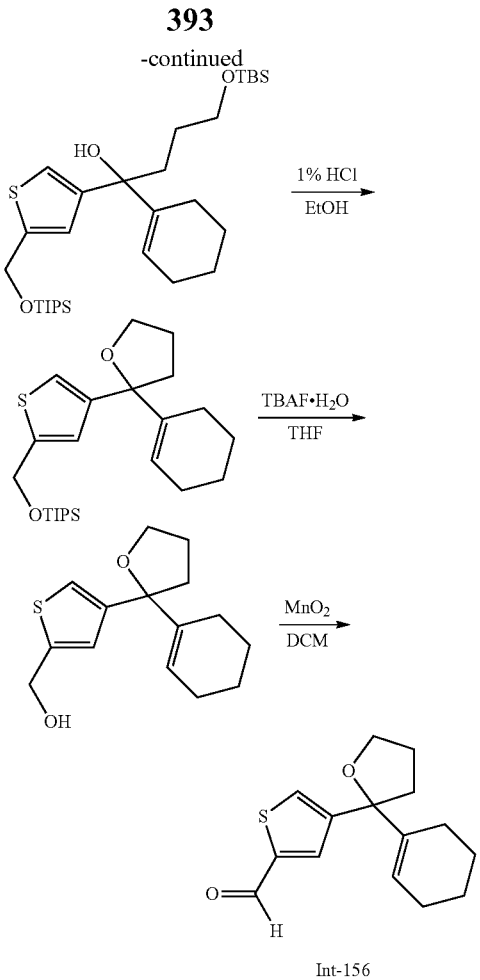

Int-156

Step 1: rac-4-{[tert-Butyl(dimethyl)silyl]oxy}-1-(cyclohex-1-en-1-yl)-1-(5-{[(triisopropylsilyl)oxy]methyl}-3-thienyl)butan-1-ol To a solution of 1-bromo-1-cyclohexene (880 uL, 7.85 mmol) in THF (15 mL) was added 1.70 M of tert-BuLi in pentane (9.24 mL, 15.7 mmol) at −78° C., and the reaction was stirred for 1 hour at same temperature. To a separate flask, 4-{[tert-butyl(dimethyl)silyl]oxy}-1-(5-{[(triisopropylsilyl)oxy]methyl}-3-thienyl)butan-1-one (Int-xxx) (616 mg, 1.31 mmol) was added followed by 0.6 M of lanthanum (III) chloride bis(lithium chloride) complex in THF (1.09 mL, 0.65 mmol) and the reaction mixture was stirred for 1 hour. The resulting lithiated cyclohexene solution was added to the ketone at 0° C. After stirring for 30 min at rt, the reaction was quenched by adding saturated aqueous NH$_4$Cl and extracted with EtOAc. The combined organic layers were dried over Na$_2$SO$_4$ and concentrated in vacuo. The residue was purified by silica gel column chromatography (0 to 10% EtOAc in hexane) to give 662 mg (91%) of the title compound as colorless oil. $^1$H NMR (400 MHz, Chloroform-d) δ 7.00 (s, 1H), 6.78 (s, 1H), 5.90-5.84 (m, 1H), 4.84 (s, 2H), 3.59 (t, J=5.9 Hz, 2H), 2.80 (s, 1H), 2.07-1.98 (m, 4H), 1.99-1.88 (m, 2H), 1.87-1.79 (m, 2H), 1.55-1.44 (m, 4H), 1.17-0.93 (m, 21H), 0.84 (s, 9H), 0.05 (s, 6H).

Step 2: rac-({4-[2-(Cyclohex-1-en-1-yl)tetrahydrofuran-2-yl]-2-thienyl}methoxy)(triisopropyl)silane To a solution of rac-4-{[tert-butyl(dimethyl)silyl]oxy}-1-(cyclohex-1-en-1-yl)-1-(5-{[(triisopropylsilyl)oxy]methyl}-3-thienyl)butan-1-ol (662 mg, 1.20 mmol) in EtOH (10.3 mL) was added 1% HCl in EtOH (10.3 mL, 1.24 mmol) at rt and the reaction was stirred for 30 min. The reaction was quenched by addition of saturated aqueous NaHCO$_3$ and concentrated in vacuo to remove EtOH. To the residue was added water and the mixture was extracted with EtOAc. The combined organic layers were dried over Na$_2$SO$_4$, filtered, and concentrated in vacuo. The residue was purified by silica gel column chromatography (0 to 5% EtOAc in hexane) to afford 291 mg (58%) of the title compound as colorless oil. $^1$H NMR (400 MHz, Chloroform-d) δ 6.96 (s, 1H), 6.74 (s, 1H), 5.76-5.70 (m, 1H), 4.88 (s, 2H), 3.88 (t, J=7.1 Hz, 2H), 2.21-2.07 (m, 2H), 2.07-1.98 (m, 2H), 1.95-1.79 (m, 4H), 1.53-1.46 (m, 4H), 1.19-0.98 (m, 21H).

Step 3: rac-{4-[2-(Cyclohex-1-en-1-yl)tetrahydrofuran-2-yl]-2-thienyl}methanol

To a solution of rac-({4-[2-(cyclohex-1-en-1-yl)tetrahydrofuran-2-yl]-2-thienyl}methoxy)(triisopropyl)silane (339 mg, 0.81 mmol) in THF (17 mL) was added TBAF hydrate (270 mg, 0.97 mmol) at rt. After 1 hour, the reaction was concentrated in vacuo and the residue was purified by silica gel column chromatography (0 to 30% EtOAc in hexane) to give 193 mg (91%) of the title compound as colorless oil. $^1$H NMR (400 MHz, Chloroform-d) δ 7.07 (s, 1H), 6.90 (s, 1H), 5.84-5.76 (m, 1H), 4.79 (d, J=5.7 Hz, 2H), 3.93 (t, J=7.2 Hz, 2H), 2.27-2.11 (m, 2H), 2.11-2.04 (m, 2H), 2.02-1.84 (m, 4H), 1.76 (t, J=6.0 Hz, 1H), 1.63-1.52 (m, 4H).

Step 4: rac-4-[2-(Cyclohex-1-en-1-yl)tetrahydrofuran-2-yl]thiophene-2-carbaldehyde To a solution of rac-{4-[2-(cyclohex-1-en-1-yl)tetrahydrofuran-2-yl]-2-thienyl}methanol (192 mg, 0.73 mmol) in DCM (26.9 mL) was added MnO$_2$ (634 mg, 7.29 mmol) at rt, and the reaction was stirred overnight. The reaction was filtered through a Celite pad and the residual solid was rinsed with DCM several times. The filtrate was concentrated in vacuo and the residue was purified by silica gel column chromatography (0 to 20% EtOAc in hexane) to give 176 mg (92%) of the title compound as colorless oil. $^1$H NMR (400 MHz, Chloroform-d) δ 9.89 (s, 1H), 7.68 (s, 1H), 7.62-7.53 (m, 1H), 5.87-5.76 (m, 1H), 3.95 (t, J=7.0 Hz, 2H), 2.37-2.27 (m, 1H), 2.19-2.06 (m, 3H), 2.06-1.83 (m, 4H), 1.64-1.52 (m, 4H).

Example 91: rac-N-[(3-Chlorophenyl)(5-formyl-2-methyl-3-thienyl)methyl]-2-methylpropane-2-sulfinamide. Int-157

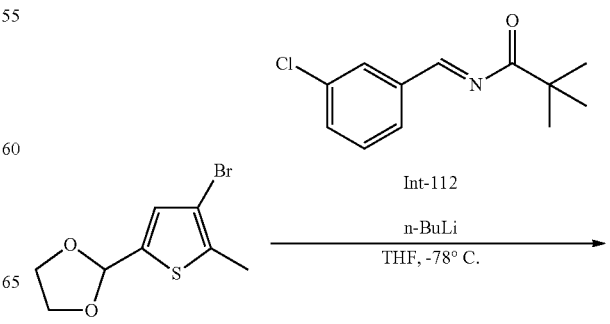

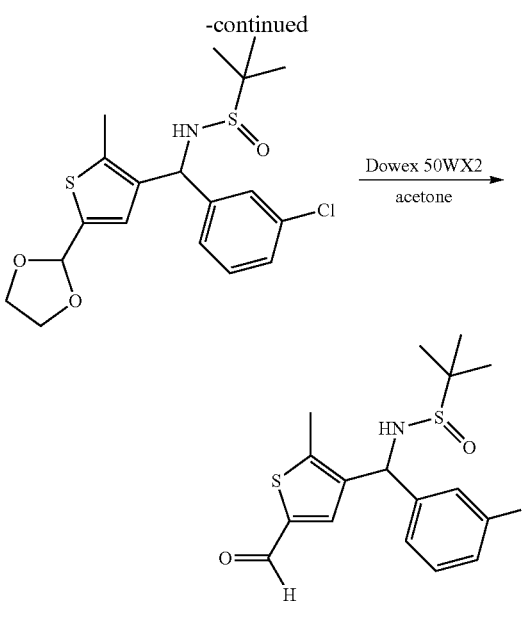

Step 1: rac-N-{(3-Chlorophenyl)[5-(1,3-dioxolan-2-yl)-2-methyl-3-thienyl]methyl}-2-methylpropane-2-sulfinamide A solution of 2-(4-Bromo-5-methyl-2-thienyl)-1,3-dioxolane (3.1 g, 12.0 mmol) in THF (6 mL) was added dropwise to a solution of 2.50 M of n-BuLi in hexane (5.91 mL, 14.8 mmol) in THF (60 mL) at −78° C. Immediately after addition was complete, N-[(E)-(3-chlorophenyl)methylene]-2-methylpropane-2-sulfinamide (3.0 g, 12.0 mmol) was added dropwise as a solution in THF (6 mL). The resulting mixture was allowed to stir 30 min at −78° C. and then allowed to warm to near rt. The reaction was quenched with water and the resulting mixture was extracted with EtOAc (2×). The combined organic layers were dried over $Na_2SO_4$, filtered, and concentrated. Residue was subjected to ISCO chromatography eluting with a hexane/EtOAc gradient to afford the title compound (yield=3.8 g). $^1$H NMR (400 MHz, Chloroform-d) δ 7.39 and 7.33 (each s, each 0.5H), 7.29-7.20 (m, 3H), 6.95 and 6.89 (each s, each 0.5H), 5.96 and 5.93 (each s, each 0.5H), 5.61 (d, J=1.8 Hz, 0.5H), 5.60 (d, J=2.7 Hz, 0.5H), 4.13-4.05 (m, 2H), 4.03-3.92 (m, 2H), 3.64 (d, J=2.5 Hz, 0.5H), 3.49 (s, 0.5H), 2.49 and 2.47 (each s, each 1.5H), 1.25 and 1.24 (each s, each 4.5H).

Step 2: rac-N-[(3-Chlorophenyl)(5-formyl-2-methyl-3-thienyl)methyl]-2-methylpropane-2-sulfinamide Dowex 50WX2-200 (H) (3.80 g) was added to a solution of rac-N-{(3-chlorophenyl)[5-(1,3-dioxolan-2-yl)-2-methyl-3-thienyl]methyl}-2-methylpropane-2-sulfinamide (3.80 g, 9.20 mmol) in acetone (80 mL) at rt. The reaction was allowed to stir for 1 hour. The reaction was filtered to remove solid resin and the crude material was purified on ISCO chromatography eluting with a hexane/EtOAc gradient to afford the title compound (yield=3.26 g). $^1$H NMR (400 MHz, Chloroform-d) δ 9.79 and 9.77 (each s, each 0.5H), 7.65 and 7.57 (each s, each 0.5H), 7.42-7.39 (m, 0.5H), 7.37-7.34 (m, 0.5H), 7.34-7.25 (m, 3H), 5.67 and 5.66 (each s, each 0.5H), 3.75 (d, J=2.2 Hz, 0.5H), 3.58 (d, J=2.5 Hz, 0.5H), 2.59 and 2.58 (each s, each 1.5H), 1.29 and 1.29 (each s, each 4.5H).

Example 92: rac-N-[1-(3-Chlorophenyl)-1-(5-formyl-3-thienyl)ethyl]-2-methylpropane-2-sulfinamide. Int-158

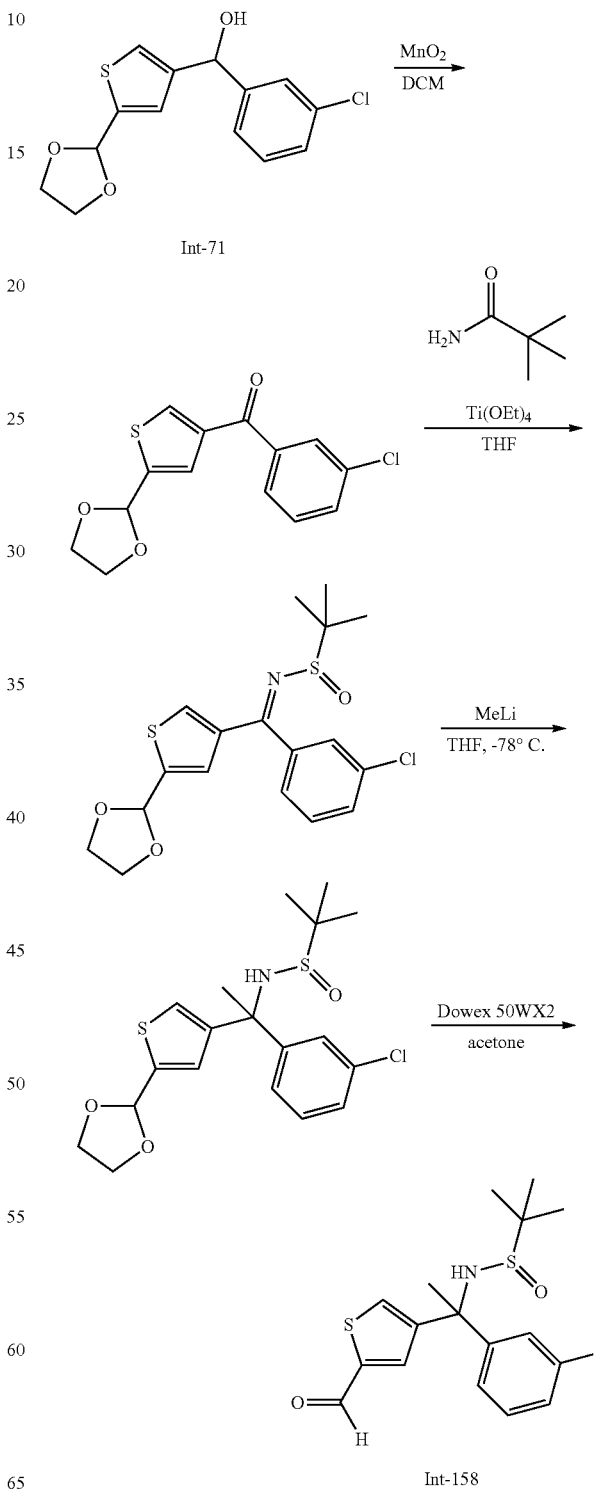

Step 1: (3-Chlorophenyl)[5-(1,3-dioxolan-2-yl)-3-thienyl]methanone

To a solution of Int-71 (1.8 g, 6.10 mmol) in DCM (54.5 mL) was added MnO₂ (5.80 g, 66.7 mmol). The mixture was stirred at rt for 14 h. The reaction was then filtered through a Celite pad and the residual solid was washed with DCM several times. The filtrate was concentrated in vacuo to yield 1.7 g of the title compound. ¹H NMR (400 MHz, Chloroform-d) δ 7.93 (d, J=1.4 Hz, 1H), 7.80 (t, J=1.8 Hz, 1H), 7.70 (dt, J=7.7, 1.3 Hz, 1H), 7.64-7.61 (m, 1H), 7.56 (ddd, J=8.0, 2.1, 1.1 Hz, 1H), 7.43 (t, J=7.8 Hz, 1H), 6.11 (s, 1H), 4.20-4.11 (m, 2H), 4.10-4.01 (m, 2H).

Step 2: N-{(E)-(3-Chlorophenyl)[5-(1,3-dioxolan-2-yl)-3-thienyl]methylene}-2-methylpropane-2-sulfinamide (3-Chlorophenyl)[5-(1,3-dioxolan-2-yl)-3-thienyl]methanone (1.70 g, 5.77 mmol) was added to a solution of Ti(OEt)₄ (5.30 g, 23.2 mmol) in THF (23 mL) under an atmosphere of argon. 2-methyl-2-propanesulfinamide (1.10 g, 9.08 mmol) was then added and the solution heated at 74° C. for 3 h. Additional 2-methyl-2-propanesulfinamide (0.46 g, 3.80 mmol) was added and the solution stirred at 80° C. for an additional 5 h. The reaction was allowed to cool to rt, and the mixture was poured into an equal volume of brine while rapidly stirring. The resulting suspension was filtered through a medium frit filter, and the filter cake was washed with EtOAc. The filtrate was transferred to a separatory funnel where the organic layer was washed with brine. The combined aqueous layers were extracted with EtOAc (1×). The combined organic layers were dried over MgSO₄, filtered, and concentrated in vacuo. The crude product was purified on ISCO chromatography eluting with a hexane/EtOAc gradient to afford the title compound as a white solid (yield=2.1 g). ¹H NMR (400 MHz, Chloroform-d) δ 7.63 (s, 1H), 7.55-7.28 (m, 5H), 6.09 (s, 1H), 4.20-4.09 (m, 2H), 4.09-4.00 (m, 2H), 1.28 (s, 9H).

Step 3: rac-N-{1-(3-Chlorophenyl)-1-[5-(1,3-dioxolan-2-yl)-3-thienyl]ethyl}-2-methylpropane-2-sulfinamide 1.6 M of MeLi in ether (4.12 mL, 6.60 mmol) was added dropwise to a solution of N-{(E)-(3-chlorophenyl)[5-(1,3-dioxolan-2-yl)-3-thienyl]methylene}-2-methylpropane-2-sulfinamide (2.10 g, 5.28 mmol) in THF (20 mL) at −78° C. and the resulting solution allowed to stir for 40 min. After the reaction was warmed to 0° C., the mixture was diluted with ether and quenched with water. The mixture was extracted with EtOAc (3×) and the combined organic layers were dried over MgSO₄, filtered, and concentrated in vacuo to yield 2.1 g of the title compound. ¹H NMR (400 MHz, Chloroform-d) δ 7.40-7.37 (m, 1H), 7.28-7.22 (m, 3H), 7.20 (d, J=1.6 Hz, 1H), 6.95 (d, J=1.2 Hz, 1H), 6.00 (s, 1H), 4.13-4.08 (m, 2H), 4.02-3.96 (m, 2H), 3.74 (s, 1H), 2.06 (s, 3H), 1.23 (s, 9H).

Step 4: rac-N-[1-(3-Chlorophenyl)-1-(5-formyl-3-thienyl)ethyl]-2-methylpropane-2-sulfinamide Dowex 50WX2-200 (H) (1.0 g) was added to a solution of rac-N-{1-(3-chlorophenyl)-1-[5-(1,3-dioxolan-2-yl)-3-thienyl]ethyl}-2-methylpropane-2-sulfinamide (2.10 g, 5.07 mmol) in acetone (39 mL) at rt. The reaction was allowed to stir for 1 hour. The reaction was filtered to remove solid resin and the filtrate was concentrated in vacuo. The crude material was purified on silica gel (40 g ISCO column; hex then 0-75% EtOAc/hex) to yield 1.8 g of the title compound. ¹H NMR (400 MHz, Chloroform-d) δ 9.87 (d, J=1.2 Hz, 1H), 7.72 (t, J=1.4 Hz, 1H), 7.62 (d, J=1.6 Hz, 1H), 7.37-7.35 (m, 1H), 7.34-7.29 (m, 2H), 7.28-7.23 (m, 1H), 3.81 (s, 1H), 2.10 (s, 3H), 1.28 (s, 9H).

Example 93: [4-({(1R,3R,4S)-3-({[tert-Butyl(dimethyl)silyl]oxy}methyl)-4-[(triisopropylsilyl)oxy]cyclopentyl}amino)pyrimidin-5-yl]{5-chloro-4-[(S)-(3-chlorophenyl)(hydroxy)methyl]-2-thienyl}methanone Int-159

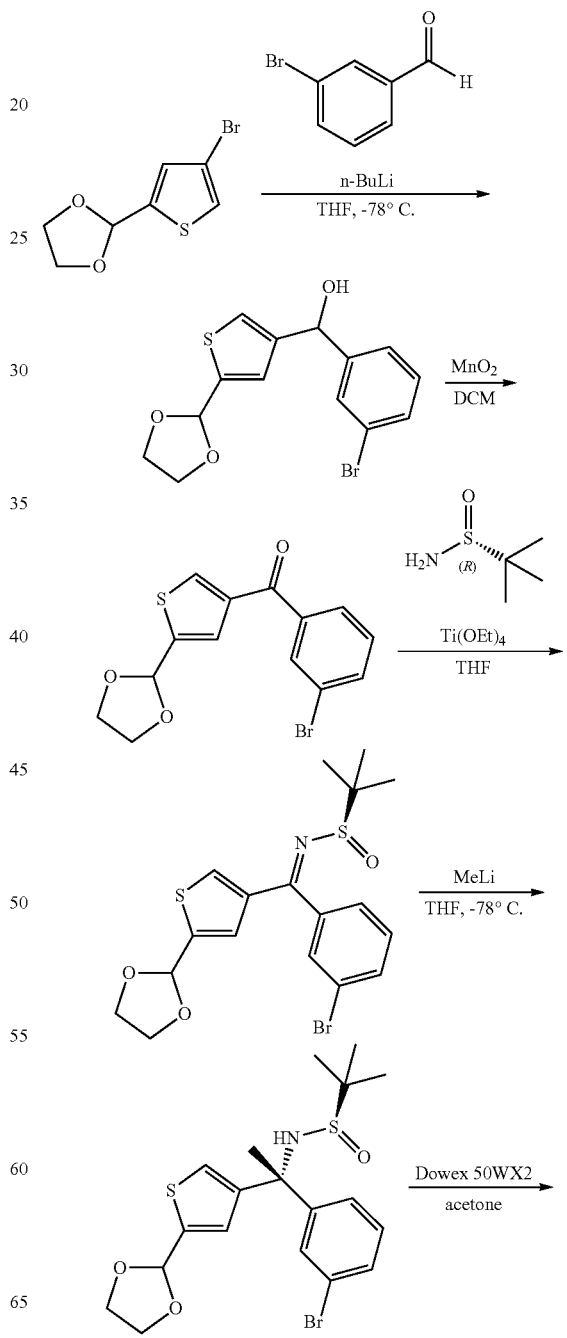

-continued

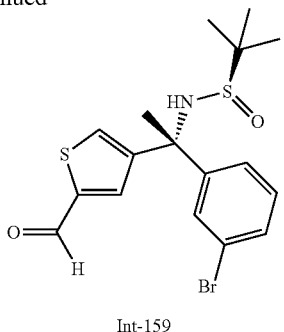

Int-159

Step 1: rac-(3-Bromophenyl)[5-(1,3-dioxolan-2-yl)-3-thienyl]methanol

An oven-dried 500 mL two-neck round bottom flask under nitrogen was charged with THF (200 mL) and cooled to −70° C. A solution of 2.50 M of n-BuLi in hexane (21.3 mL, 53.2 mmol) was added. To the cooled solution was added 2-(4-bromothiophen-2-yl)-1,3-dioxolane (10.0 g, 42.5 mmol) in THF (10 mL) in small portions keeping the internal temperature less than −70° C. The mixture was stirred for 5 min. Then a solution of 3-bromobenzaldehyde (4.96 mL, 42.5 mmol) in THF (10 mL) was added fast in a single portion. Internal temperature increased to −45° C. The resulting mixture stirred for 5 min. Then saturated NaHCO$_3$ was added slowly to quench reaction. The solution was warmed to rt and extracted three times with EtOAc. The combined organic layers were then washed with brine, dried with MgSO$_4$, filtered, concentrated to dryness. The residue was purified by ISCO column chromatography (eluting with EtOAc/hexanes gradient) to give 9.27 g (64%) of the title compound. LCMS (FA): m/z=343.2 (M+H).

Step 2: (3-Bromophenyl)[5-(1,3-dioxolan-2-yl)-3-thienyl]methanone

A 500 mL round bottom flask was charged with rac-(3-bromophenyl)[5-(1,3-dioxolan-2-yl)-3-thienyl]methanol (9.00 g, 26.4 mmol) in DCM (200 mL). MnO$_2$ (22.9 g, 264 mmol) was added and the reaction was stirred at rt for 18 h. The reaction was then filtered through Celite pad, rinsed with DCM several times and the filtrate was concentrated to dryness. The residue was purified by ISCO column chromatography (eluting with EtOAc/hexanes gradient) to give 8.89 g (99%) of the title compound. $^1$H NMR (400 MHz, Chloroform-d) δ 7.98-7.90 (m, 2H), 7.77-7.68 (m, 2H), 7.64-7.60 (m, 1H), 7.40-7.33 (m, 1H), 6.11 (s, 1H), 4.20-4.10 (m, 2H), 4.10-4.01 (m, 2H).

Step 3: N-{(E)-(3-Bromophenyl)[5-(1,3-dioxolan-2-yl)-3-thienyl]methylene}-2-methylpropane-2-sulfinamide A 500 mL round bottom flask under nitrogen was charged with THF (30 mL) and Ti(OEt)$_4$ (6.7 g, 29 mmol) was added. To this solution was added a solution of (3-bromophenyl)[5-(1,3-dioxolan-2-yl)-3-thienyl]methanone (2.50 g, 7.37 mmol) in a minimum amount of THF. Next was added (R)-(−)-2-methyl-2-propanesulfinamide (1.43 g, 11.8 mmol). The mixture was heated to reflux and stirred for 1 day. The reaction was cooled to rt and poured into 20 mL of brine with rapid stirring. The white precipitate was filtered off, and the filtrate was extracted with EtOAc (×2). The combined organic layers were then dried with MgSO$_4$, filtered, and concentrated to dryness. The residue was purified by ISCO column chromatography (eluting with 0%-60% EtOAc/hexanes) to give 2.67 g (82%) of product. $^1$H NMR (400 MHz, Chloroform-d) δ 7.80-7.27 (m, 6H), 6.09 (s, 1H), 4.19-4.09 (m, 2H), 4.09-3.99 (m, 2H), 1.28 (s, 9H).

Step 4: N-{(1R)-1-(3-Bromophenyl)-1-[5-(1,3-dioxolan-2-yl)-3-thienyl]ethyl}-2-methylpropane-2-sulfinamide A 100 mL round bottom flask under nitrogen was charged with N-{(E)-(3-bromophenyl)[5-(1,3-dioxolan-2-yl)-3-thienyl]methylene}-2-methylpropane-2-sulfinamide (2.67 g, 6.03 mmol) and THF (25.0 mL). The solution was cooled to −78° C. and a solution of 1.6 M of MeLi in Et$_2$O (5.65 mL, 9.04 mmol) was added dropwise over 20 min. The resulting solution was stirred for an additional 10 min with cooling. The reaction was quenched with saturated NH$_4$Cl and extracted with EtOAc (×3). The combined organic layers were then washed with water, brine, dried using Na$_2$SO$_4$, filtered and concentrated. The residue was purified by ISCO column chromatography (eluting with 0%-50% EtOAc/hexanes) to give 1.30 g (47%) of the title compound (80% de). $^1$H NMR (400 MHz, Chloroform-d) δ 7.56-7.53 (m, 1H), 7.42-7.37 (m, 1H), 7.33-7.28 (m, 1H), 7.21-7.16 (m, 2H), 6.95 (d, J=1.3 Hz, 1H), 6.00 (s, 1H), 4.16-4.06 (m, 2H), 4.04-3.96 (m, 2H), 3.74 (s, 1H), 2.06 (s, 3H), 1.23 (s, 9H).

Step 5: N-[(1R)-1-(3-Bromophenyl)-1-(5-formyl-3-thienyl)ethyl]-2-methylpropane-2-sulfinamide Dowex 50WX2-200 (H) (1 g) was added to a solution of N-{(1R)-1-(3-bromophenyl)-1-[5-(1,3-dioxolan-2-yl)-3-thienyl]ethyl}-2-methylpropane-2-sulfinamide (993 mg, 2.17 mmol)(80% de) in acetone (20.0 mL) at rt. The reaction was allowed to stir for 1 hour. The reaction was then filtered to remove solid resin and the resin was washed with acetone, and the filtrate was concentrated to dryness. The crude material was then azetroped with toluene. The residue was purified by ISCO column chromatography (eluting with 0%-80% EtOAc/hexanes) to give 0.865 g (96%) of the title compound (80% de). $^1$H NMR (400 MHz, Chloroform-d) δ 9.85 (d, J=1.1 Hz, 1H), 7.70-7.67 (m, 1H), 7.59 (d, J=1.5 Hz, 1H), 7.51-7.48 (m, 1H), 7.46-7.42 (m, 1H), 7.30-7.19 (m, 2H), 3.78 (s, 1H), 2.08 (s, 3H), 1.25 (s, 9H).

The compound listed in the table below was prepared in an analogous fashion to that described above starting from the listed starting material:

| Step 3 Reagent | Compound Name/No. | Characterization Data |
|---|---|---|
| 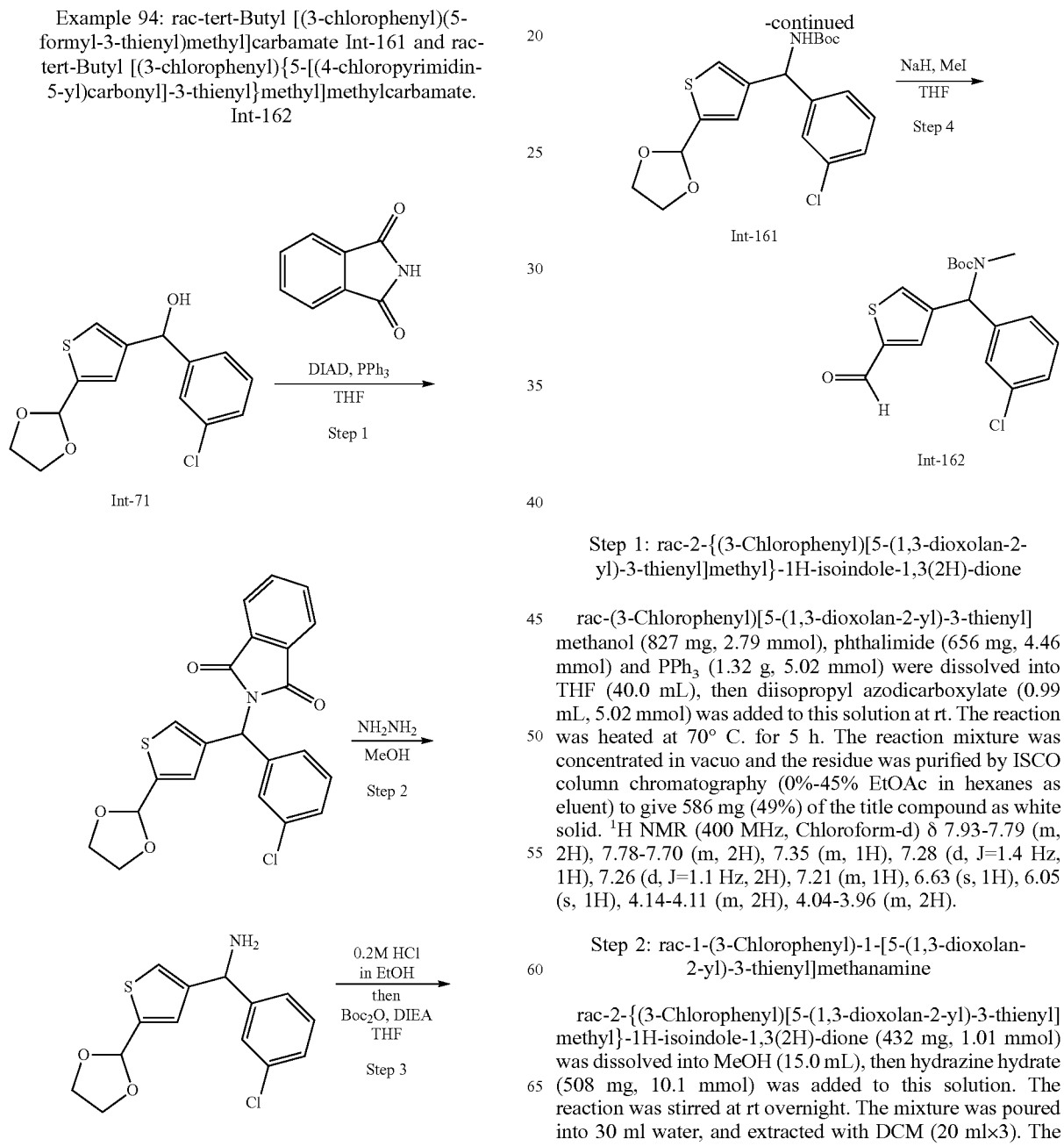 | | ¹H NMR (400 MHz, Chloroform-d) δ 9.85 (d, J = 1.2 Hz, 1H), 7.69 (t, J = 1.4 Hz, 1H), 7.59 (d, J = 1.5 Hz, 1H), 7.50 (t, J = 1.7 Hz, 1H), 7.44 (dd, J = 7.7, 1.8 Hz, 1H), 7.32-7.18 (m, 2H), 3.78 (s, 1H), 2.08 (s, 3H), 1.25 (s, 9H). LCMS (FA): m/z = 416.2 (M + H) |
| | Int-160 | |

Example 94: rac-tert-Butyl [(3-chlorophenyl)(5-formyl-3-thienyl)methyl]carbamate Int-161 and rac-tert-Butyl [(3-chlorophenyl){5-[(4-chloropyrimidin-5-yl)carbonyl]-3-thienyl}methyl]methylcarbamate. Int-162

Step 1: rac-2-{(3-Chlorophenyl)[5-(1,3-dioxolan-2-yl)-3-thienyl]methyl}-1H-isoindole-1,3(2H)-dione rac-(3-Chlorophenyl)[5-(1,3-dioxolan-2-yl)-3-thienyl]methanol (827 mg, 2.79 mmol), phthalimide (656 mg, 4.46 mmol) and PPh₃ (1.32 g, 5.02 mmol) were dissolved into THF (40.0 mL), then diisopropyl azodicarboxylate (0.99 mL, 5.02 mmol) was added to this solution at rt. The reaction was heated at 70° C. for 5 h. The reaction mixture was concentrated in vacuo and the residue was purified by ISCO column chromatography (0%-45% EtOAc in hexanes as eluent) to give 586 mg (49%) of the title compound as white solid. ¹H NMR (400 MHz, Chloroform-d) δ 7.93-7.79 (m, 2H), 7.78-7.70 (m, 2H), 7.35 (m, 1H), 7.28 (d, J=1.4 Hz, 1H), 7.26 (d, J=1.1 Hz, 2H), 7.21 (m, 1H), 6.63 (s, 1H), 6.05 (s, 1H), 4.14-4.11 (m, 2H), 4.04-3.96 (m, 2H).

Step 2: rac-1-(3-Chlorophenyl)-1-[5-(1,3-dioxolan-2-yl)-3-thienyl]methanamine rac-2-{(3-Chlorophenyl)[5-(1,3-dioxolan-2-yl)-3-thienyl]methyl}-1H-isoindole-1,3(2H)-dione (432 mg, 1.01 mmol) was dissolved into MeOH (15.0 mL), then hydrazine hydrate (508 mg, 10.1 mmol) was added to this solution. The reaction was stirred at rt overnight. The mixture was poured into 30 ml water, and extracted with DCM (20 ml×3). The combined the organic layers were concentrated and the residue was purified by ISCO column (0%-15% MeOH in EtOAc as eluent) to give 95.3 mg (32%) of the title compound. $^1$H NMR (400 MHz, Chloroform-d) δ 7.38 (s, 1H), 7.29-7.20 (m, 3H), 7.20-7.13 (d, 1H), 7.03 (d, 1H), 6.02 (s, 1H), 5.15 (s, 1H), 4.20-4.09 (m, 2H), 4.04-3.96 (m, 2H), 1.93-1.67 (broad, 2H)

Step 3: rac-tert-Butyl [(3-chlorophenyl)(5-formyl-3-thienyl)methyl]carbamate rac-1-(3-Chlorophenyl)-1-[5-(1,3-dioxolan-2-yl)-3-thienyl]methanamine (297 mg, 1.00 mmol) was dissolved into the solution of 0.2 M of HCl in EtOH (15.0 mL, 3.00 mmol) and water (0.20 mL, 11 mmol). The reaction was stirred at rt overnight and then was concentrated in vacuo. The residues were dissolved in THF (15.0 mL). To the solution was added N,N-diisopropylethylamine (0.70 mL, 4.02 mmol) followed by di-tert-butyldicarbonate (658 mg, 3.02 mmol) and the mixture was heated at 45° C. for 2 h. The reaction mixture was concentrated in vacuo and the residue was purified by ISCO column chromatography (0%-45% EtOAc in hexanes as eluent) to give 273 mg (77%) of the title compound. $^1$H NMR (400 MHz, Chloroform-d) δ 9.84 (d, J=1.3 Hz, 1H), 7.57 (d, J=1.4 Hz, 1H), 7.46 (q, J=1.3 Hz, 1H), 7.32-7.28 (m, 2H), 7.29-7.26 (m, 1H), 7.18-7.14 (m, 1H), 5.96 (s, 1H), 5.24 (d, J=8.0 Hz, 1H), 1.44 (s, 9H).

Step 4: rac-tert-Butyl [(3-chlorophenyl)(5-formyl-3-thienyl)methyl]methylcarbamate To a solution of rac-tert-butyl [(3-chlorophenyl)(5-formyl-3-thienyl)methyl]carbamate (102 mg, 0.29 mmol) in THF (10.0 mL) was added 60% NaH in mineral oil (25.0 mg, 1.04 mmol) at rt and the mixture was stirred for 30 min. To the mixture was added methyl iodide (0.13 mL, 2.08 mmol) and the reaction was heated at 60° C. for 30 min. The reaction mixture was poured into 30 ml water, and extracted with DCM (30 ml×2). The combined organic layers were concentrated in vacuo and the residue was purified by ISCO column (0%-50% EtOAc in hexanes as eluent) to give 50 mg of the title compound. $^1$H NMR (400 MHz, Chloroform-d) δ 9.92 (s, 1H), 7.61 (s, 1H), 7.54-7.45 (m, 1H), 7.35-7.32 (m, 2H), 7.25-7.22 (m, 1H), 7.16-7.11 (m, 1H), 6.61 (s, 1H), 2.73 (s, 3H).

Example 95: rac-4-[1-(3-Chlorophenyl)-1-hydroxyethyl]-5-methylthiophene-2-carbaldehyde. Int-163

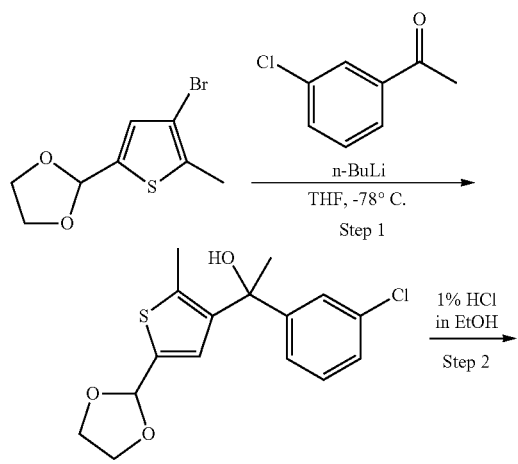

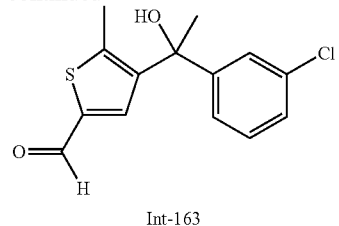

Int-163

Step 1: rac-1-(3-Chlorophenyl)-1-[5-(1,3-dioxolan-2-yl)-2-methyl-3-thienyl]ethanol A 100 mL 2-neck round bottom flask was charged with THF (30 mL) then the flask was purged with argon, and was cooled at −78° C. To the THF, 2.50 M of n-BuLi in hexane (2.61 mL, 6.52 mmol) was added dropwise via syringe and the mixture was stirred for 10 min at −78° C. 2-(4-Bromo-5-methyl-2-thienyl)-1,3-dioxolane (1.3 g, 5.2 mmol) was added dropwise at −78° C. The solution was stirred for 30 min at −78° C. 3'-chloroacetophenone (807 mg, 5.22 mmol)) was added to the solution at once at −78° C. and stirred for 15 min. The reaction was quenched by addition of saturated NH$_4$Cl (50 mL) and extracted with EtOAc (50 mL×3). The combined organic layers were dried over Na$_2$SO$_4$, filtered, and concentrated in vacuo. The residue was purified by ISCO column chromatography (0%-50% EtOAc in hexanes as eluent) to give 1.3 g (77%) of the title compound. $^1$H NMR (400 MHz, Chloroform-d) δ 7.41 (s, 1H), 7.22-7.19 (m, 3H), 7.15 (s, 1H), 5.99 (s, 1H), 4.18-4.09 (m, 2H), 4.03-3.95 (m, 2H), 2.13 (s, 3H), 1.86 (s, 3H).

Step 2: rac-4-[1-(3-Chlorophenyl)-1-hydroxyethyl]-5-methylthiophene-2-carbaldehyde rac-1-(3-Chlorophenyl)-1-[5-(1,3-dioxolan-2-yl)-2-methyl-3-thienyl]ethanol (1.1 g, 3.4 mmol) was dissolved in 1% HCl in EtOH (20 mL) and the reaction was stirred at rt for 2 h. The reaction mixture was diluted with water, extracted with DCM (20 mL×2). The combined organic layers were dried over Na$_2$SO$_4$, filtered, concentrated in vacuo. The residue was purified by ISCO column chromatography (0%-50% EtOAc in hexanes as eluent) to give 580 mg (61%) of the title compound. $^1$H NMR (400 MHz, Chloroform-d) δ 9.77 (s, 1H), 7.75 (s, 1H), 7.41-7.36 (m, 1H), 7.24-7.24 (m, 1H), 7.23 (t, J=1.1 Hz, 1H), 7.20-7.14 (m, 1H), 2.22 (s, 3H), 1.92 (s, 3H).

Example 96: 4-(3,4-Dihydro-1H-isochromen-1-yl)-5-methylthiophene-2-carbaldehyde Int-164

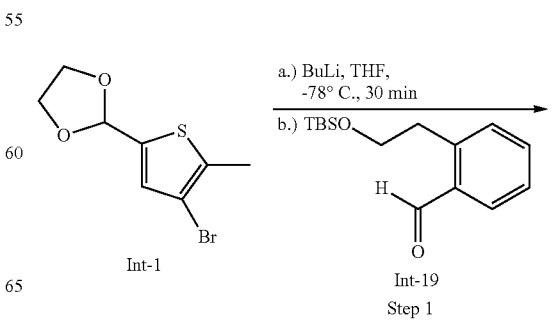

Step 1

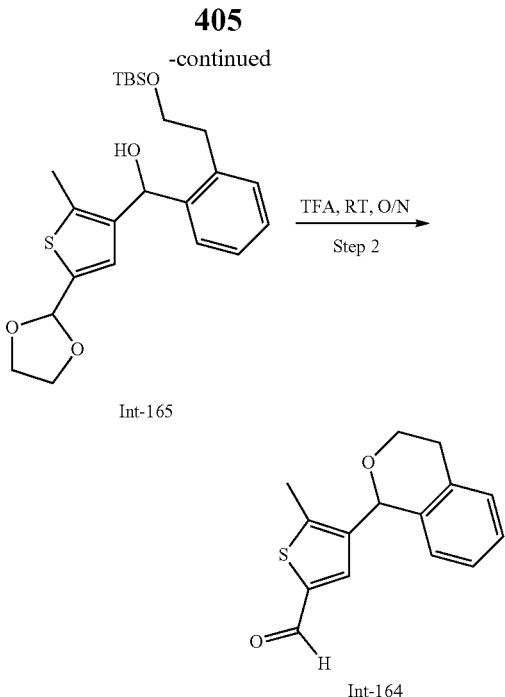

Step 1: Reaction Conditions A (as Depicted in Example 96): [2-(2-{[tert-Butyl(dimethyl)silyl]oxy}ethyl)phenyl][5-(1,3-dioxolan-2-yl)-2-methyl-3-thienyl]methanol Int-165

A solution of bromide Int-1 (1.70 g, 6.82 mmol) in THF (26.6 mL, 328 mmol) was cooled to −78° C., and then 2.50 M of n-BuLi in hexane (2.940 mL, 7.349 mmol) was added and the mixture was stirred for 10 min at −78° C. A solution of aldehyde Int-19 (1.39 g, 5.25 mmol) in THF (13.3 mL, 164 mmol) was then added, and the reaction was stirred for 10 min at −78° C. The reaction was quenched by adding brine and then warmed to rt. The aqueous mixture was extracted 2×EtOAc. The combined organic solvents were washed with brine, dried and concentrated in vacuo. The residue was purified by ISCO (80 g column, 0 to 20% EtOAc in hexanes as eluent) to afford the title compound as a pale yellow oil (yield=1.96 g) that solidified upon standing in the refrigerator over the weekend. $^1$H NMR (400 MHz, Chloroform-d) δ 7.30-7.26 (m, 2H), 7.26-7.21 (m, 2H), 7.07 (s, 1H), 6.09 (d, J=2.7 Hz, 1H), 6.03 (s, 1H), 4.19-4.13 (m, 2H), 4.06-4.00 (m, 2H), 3.96-3.89 (m, 1H), 3.87-3.77 (m, 1H), 3.52 (d, J=2.9 Hz, 1H), 3.06 (ddd, J=14.3, 8.4, 6.2 Hz, 1H), 2.87 (dt, J=13.9, 5.2 Hz, 1H), 2.37 (s, 3H), 0.86 (s, 9H), −0.00 (s, 3H), −0.01 (s, 3H).

Step 2: 4-(3,4-Dihydro-1H-isochromen-1-yl)-5-methylthiophene-2-carbaldehyde

A 100 mL round bottom flask was charged with [2-(2-{[tert-butyl(dimethyl)silyl]oxy}ethyl)phenyl][5-(1,3-dioxolan-2-yl)-2-methyl-3-thienyl]methanol (1.96 g, 4.51 mmol) and TFA (6.60 mL, 85.7 mmol) at rt. The resulting purple solution was stirred at rt overnight. The reaction mixture was carefully poured into saturated aqueous NaHCO$_3$ (~50 mL). The layers were separated, and the aqueous layer was extracted three times with EtOAc. The combined organic layers were washed with brine, then dried over sodium sulfate, filtered, and concentrated in vacuo. The residue was purified by ISCO (40 g column, 0 to 10% EtOAc in hexane as eluent) to afford the title compound as a pale brown oil (yield=1.03 g). $^1$H NMR (400 MHz, Chloroform-d) δ 9.73 (s, 1H), 7.41 (s, 1H), 7.27-7.19 (m, 2H), 7.18-7.12 (m, 1H), 6.75 (d, J=7.7 Hz, 1H), 5.86 (s, 1H), 4.21 (ddd, J=11.3, 5.5, 3.7 Hz, 1H), 3.97 (ddd, J=11.4, 9.7, 4.0 Hz, 1H), 3.16 (ddd, J=15.9, 9.4, 5.4 Hz, 1H), 2.85 (dt, J=16.6, 3.6 Hz, 1H), 2.59 (s, 3H).

Alternative Conditions for Step 1. Reaction Conditions B (e.g., Entry 1, Below): [2-(2-{[tert-Butyl(dimethyl)silyl]oxy}ethyl)phenyl][5-(1,3-dioxolan-2-yl)-3-thienyl]methanol An oven-dried 250 mL 2-neck flask under nitrogen was charged with THF (100 mL) and cooled in an ice bath to −76° C. To this was added 2.50 M n-BuLi in hexane (8.365 mL, 20.91 mmol) followed by a solution of 2-(4-bromothiophen-2-yl)-1,3-dioxolane (4.565 g, 19.42 mmol) in THF in small portions keeping the internal temperature less than −70° C. Next, a solution of aldehyde Int-19 (3.95 g, 14.9 mmol) in THF (5 mL, 60 mmol) was added in a single portion quickly, during which the temperature increased to −45° C. Reaction was immediately quenched by slowly adding saturated ammonium chloride solution, and then was warmed to rt. The layers were separated, and the aqueous layer was extracted three times with EtOAc. The combined organic portions were washed with brine; dried with anhydrous magnesium sulfate, filtered, and concentrated in vacuo. Crude residue was purified by column chromatography with a hexane/EtOAc gradient as eluent to provide the title compound as a yellow oil (yield=4.20 g). $^1$H NMR (400 MHz, Chloroform-d) δ 7.36-7.21 (m, 5H), 7.09-7.03 (m, 1H), 6.11-6.06 (m, 1H), 6.06-6.02 (m, 1H), 4.24-4.14 (m, 3H), 4.08-4.02 (m, 2H), 3.96-3.93 (m, 1H), 3.05-2.89 (m, 2H), 0.93-0.77 (m, 9H), 0.00 (s, 6H).

The compounds listed in the table below were prepared in an analogous fashion to that described in Example 96 starting from the appropriate starting materials:

| Entry | Bromide, aldehyde (starting materials) | Reaction conditions for Step 1 | Product (Int #) | Characterization data |
|---|---|---|---|---|
| 1 | 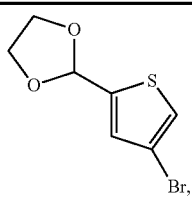 Int-19 | B | 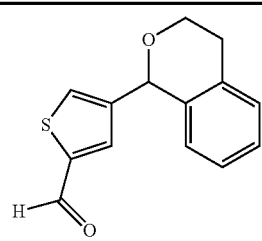 Int-166 | LCMS (FA): m/z = 245.1 (M + H) |

-continued
| Entry | Bromide, aldehyde (starting materials) | Reaction conditions for Step 1 | Product (Int #) | Characterization data |
|---|---|---|---|---|
| 2 | Int-1, Int-29 | A | 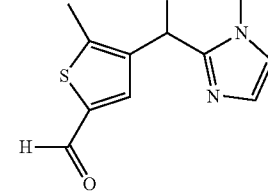<br>Int-167 | LCMS (FA): m/z = 263.1 (M + H) |
| 3 | Int-1, Int-28 | A | 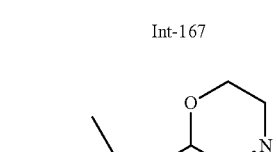<br>Int-168 | LCMS (FA): m/z = 263.1 (M + H) |
| 4 | Int-1, Int-27 | A | 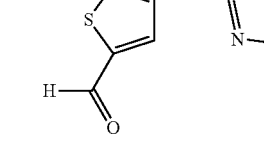<br>Int-169 | $^1$H NMR (400 MHz, Chloroform-d) δ 9.66 (s, 1H), 7.49 (s, 1H), 7.13 (d, J = 5.2 Hz, 1H), 6.49 (d, J = 5.2 Hz, 1H), 5.97-5.78 (m, 1H), 4.27-4.20 (m, 1H), 3.99 (ddd, J = 11.4, 8.6, 4.2 Hz, 1H), 3.16-3.06 (m, 1H), 2.97-2.88 (m, 1H), 2.58 (s, 3H). |
| 5 | 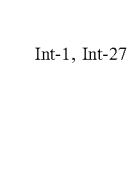<br>Int-17 | B | 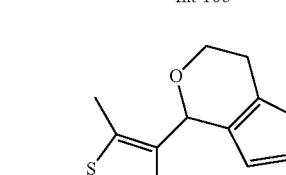<br>Int-170 | LCMS (FA): m/z = 279.1, 281.1 (M + H) |
| 6 | <br>Int-15 | B | 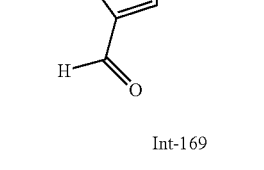<br>Int-171 | LCMS (FA): m/z = 279.3, 281.3 (M + H) |

| Entry | Bromide, aldehyde (starting materials) | Reaction conditions for Step 1 | Product (Int #) | Characterization data |
|---|---|---|---|---|
| 7 | Int-1, Int-15 | A | 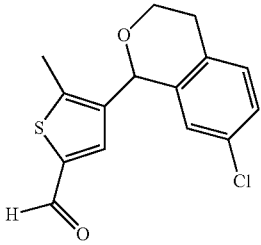<br>Int-172 | LCMS (FA): m/z = 293.4, 295.5 (M + H) |
| 8 | Int-1, Int-20 | A | 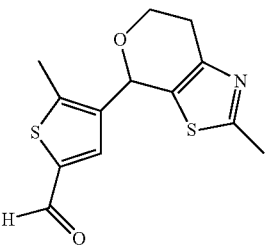<br>Int-173 | LCMS (FA): m/z = 280.2 (M + H) |
| 9 | 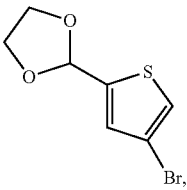<br>Int-25 | B | 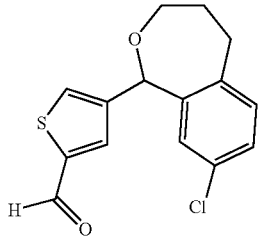<br>Int-174 | LCMS (FA): m/z = 292.8, 295.0 (M + H) |
| 10 | <br>Int-32 | B | 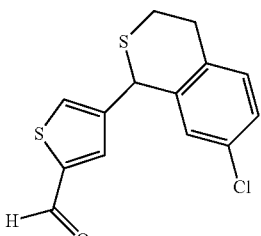<br>Int-175 | $^1$H NMR (400 MHz, Chloroform-d) δ 9.88 (s, 1H), 7.71 (s, 1H), 7.26 (s, 1H), 7.22 (dd, J = 8.2, 2.1 Hz, 1H), 7.14 (d, J = 8.2 Hz, 1H), 7.00 (d, J = 2.0 Hz, 1H), 5.11 (s, 1H), 3.09-3.01 (m, 2H), 2.93-2.75 (m, 2H). |
| 11 | Int-2, Int-15 | A | 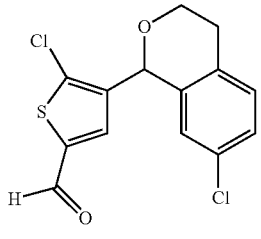<br>Int-176 | LCMS (FA): m/z = 313.0, 315.0, 317.1 (M + H) |

-continued

| Entry | Bromide, aldehyde (starting materials) | Reaction conditions for Step 1 | Product (Int #) | Characterization data |
|---|---|---|---|---|
| 12 | Int-1, Int-30 | A | Int-177 | LCMS (FA): m/z = 317.0 (M + H) |
| 13 | Int-1, Int-16 | A | Int-178 | LCMS (FA): m/z = 327.0 (M + H) |
| 14 | Int-1, Int-33 | A | Int-179 | LCMS (FA): m/z = 334.0 (M + H) |
| 15 | Int-9, Int-36 | A | Int-180 | $^1$H NMR (400 MHz, DMSO-d6) δ 9.71 (s, 1H), 7.53-7.42 (m, 2H), 7.18 (d, J = 8.3 Hz, 1H), 6.09 (s, 1H), 3.91-3.72 (m, 2H), 2.98-2.81 (m, 2H), 2.58 (s, 3H). |
| 16 | Int-38, Int-36 | A | Int-181 | LCMS (FA): m/z = 289.0 (M + H) |

| Entry | Bromide, aldehyde (starting materials) | Reaction conditions for Step 1 | Product (Int #) | Characterization data |
|---|---|---|---|---|
| 17 | Int-2, Int-19 | A | 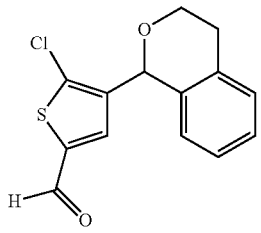<br>Int-182 | LCMS (FA): m/z = 279.0 (M + H) |
| 18 | Int-2, Int-21 | A | 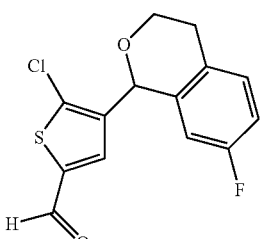<br>Int-183 | $^1$H NMR (400 MHz, Chloroform-d) δ 9.70 (s, 1H), 7.35 (s, 1H), 7.20-7.10 (m, 1H), 7.00-6.90 (m, 1H), 6.55-6.45 (m, 1H), 5.85-5.80 (m, 1H), 4.30-4.20 (m, 1H), 4.00-3.85 (m, 1H), 3.20-3.05 (m, 1H), 2.80-2.70 (m, 1H) |
| 19 | Int-2, Int-22 | A | 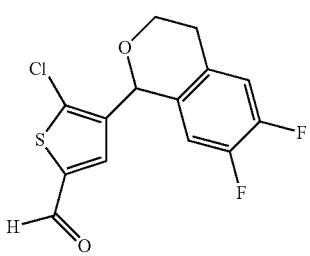<br>Int-184 | $^1$H NMR (400 MHz, Chloroform-d) δ 9.70 (s, 1H), 7.40 (s, 1H), 7.05-7.00 (m, 1H), 6.70-6.65 (m, 1H), 5.75 (s, 1H), 4.25-4.20 (m, 1H), 3.95-3.80 (m, 1H), 3.20-3.00 (m, 1H), 2.75-2.70 (m, 1H) |
| 20 | Int-49, Int-36 | Performed in analogous fashion to Example 11, step 2, Reaction Conditions B | 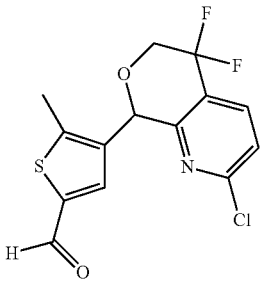<br>Int-185 | LCMS (FA): m/z = 330.0, 332.0 (M + H) |

Example 97: 5-Chloro-4-(5,8-dihydro-6H-pyrano[3,4-b]pyridin-8-yl)thiophene-2-carbaldehyde Int-186

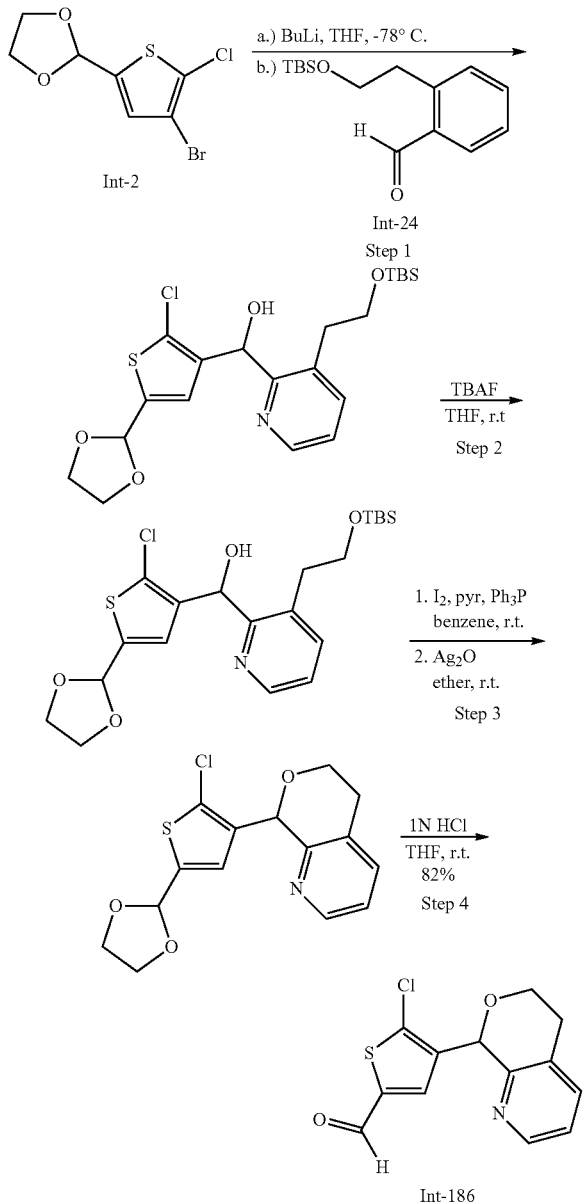

Step 1: [3-(2-{[tert-Butyl(dimethyl)silyl]oxy}ethyl)pyridin-2-yl][2-chloro-5-(1, 3-dioxolan-2-yl)-3-thienyl]methanol To a −78° C. cooled solution of 2.50 M of n-BuLi in hexane (2.727 mL, 6.818 mmol) in THF (25.0 mL, 308 mmol) was added a solution of bromide Int-2 (1.648 g, 6.112 mmol) in THF (10.0 mL, 123 mmol), dropwise, via syringe. After 20 min, a solution of aldehyde Int-24 (1.248 g, 4.702 mmol) in THF (10.0 mL, 123 mmol) was added dropwise via syringe. The reaction mixture was stirred at −78° C. for 20 min then quenched with saturated aqueous NaHCO₃. The layers were separated, and the aqueous layer was extracted 3×EtOAc. The combined organic layers were washed with brine, dried over magnesium sulfate, filtered and then concentrated to give 2.689 g of crude product. The crude material was purified by silica gel chromatography to give 1.775 g (83% yield) of the title compound as a light brown oil. ¹H NMR (400 MHz, Chloroform-d) δ 8.61 (d, J=4.8, 1.4 Hz, 1H), 7.72 (d, J=7.0 Hz, 1H), 7.37-7.34 (m, 1H), 6.70 (s, 1H), 6.11 (s, 1H), 5.96 (s, 1H), 4.20-4.09 (m, 2H), 4.09-3.99 (m, 2H), 3.84-3.77 (m, 1H), 3.62-3.54 (m, 1H), 2.93-2.83 (m, 1H), 2.72 (dt, J=14.3, 5.7 Hz, 1H), 0.93 (s, 9H), 0.01 (d, J=5.0 Hz, 6H); LCMS (FA) M+1 456.1

Step 2: 2-(2-{[2-Chloro-5-(1,3-dioxolan-2-yl)-3-thienyl](hydroxy)methyl}pyridin-3-yl)ethanol To a solution of [3-(2-{[tert-butyl(dimethyl)silyl]oxy}ethyl)pyridin-2-yl][2-chloro-5-(1,3-dioxolan-2-yl)-3-thienyl]methanol (1.035 g, 2.269 mmol) in THF (29.2 mL, 3.60E2 mmol) was added TBAF hydrate (0.9514 g, 3.404 mmol) The reaction mixture was stirred at rt overnight and then concentrated in vacuo. The crude residue was purified by silica gel chromatography to give 0.746 g (96% yield) of the title compound. ¹H NMR (400 MHz, Chloroform-d) δ 8.56-8.50 (m, 1H), 7.64 (d, J=6.3 Hz, 1H), 7.36-7.30 (m, 1H), 6.15 (s, 1H), 5.97 (s, 1H), 5.32 (s, 1H), 4.11-4.00 (m, 2H), 4.00-3.92 (m, 1H), 3.83-3.75 (m, 1H), 3.66-3.57 (m, 1H), 3.54-3.43 (m, 1H), 2.82-2.72 (m, 1H), 2.71-2.61 (m, 1H).

Step 3a: [2-Chloro-5-(1,3-dioxolan-2-yl)-3-thienyl][3-(2-iodoethyl)pyridin-2-yl]methanol To a solution of 2-(2-{[2-chloro-5-(1,3-dioxolan-2-yl)-3-thienyl](hydroxy)methyl}pyridin-3-yl)ethanol (2.004 g, 5.863 mmol) in benzene (59.3 mL, 663 mmol) was added pyridine (1.43 mL, 17.7 mmol), triphenylphosphine (2.33 g, 8.88 mmol), and iodine (1.637 g, 6.449 mmol). The reaction mixture was stirred at 38° C. for 2 h, then filtered and the filter cake was washed with ether (50 mL). The filtrate was diluted with water (30 mL), the layers were separated, and the aqueous layer was extracted with ether (1×30 mL). Combined organic layers were washed with water (20 mL) and brine (2×20 mL), dried over magnesium sulfate, filtered, and then concentrated in vacuo. The crude residue was purified by silica gel chromatography to give 1.690 g (64% yield) of the title compound as a clear oil. ¹H NMR (400 MHz, Chloroform-d) δ 8.59-8.55 (m, 1H), 7.57 (d, J=7.7, 1.5 Hz, 1H), 7.35-7.29 (m, 1H), 6.59 (s, 1H), 5.97 (s, 1H), 5.87 (s, 1H), 4.10-4.00 (m, 2H), 4.00-3.90 (m, 2H), 3.17-3.05 (m, 2H), 3.05-2.91 (m, 2H); LCMS (FA) M+1 452.0.

Step 3b: 8-[2-Chloro-5-(1,3-dioxolan-2-yl)-3-thienyl]-5,8-dihydro-6H-pyrano[3,4-b]pyridine A solution of [2-chloro-5-(1,3-dioxolan-2-yl)-3-thienyl][3-(2-iodoethyl)pyridin-2-yl]methanol (1.690 g, 3.741 mmol) and silver(I) oxide (6.07 g, 26.2 mmol) in ether (50.0 mL, 476 mmol) was stirred at rt overnight, then at 40° C. for an additional 45 min. The reaction mixture was filtered over a pad of Celite and the filter cake was washed with methanol. The filtrate was concentrated in vacuo and the residue was purified by silica gel chromatography to provide 0.331 g (66% yield) of the title compound. ¹H NMR (400 MHz, Chloroform-d) δ 8.43 (d, J=4.7, 1.6 Hz, 1H), 7.51 (d, J=7.7 Hz, 1H), 7.19-7.14 (m, 1H), 6.57 (s, 1H), 5.94 (s, 1H), 5.94 (s, 1H), 4.19-4.13 (m, 1H), 4.11-4.02 (m, 3H), 4.01-3.91 (m, 4H); LCMS (FA) M+1 324.1

Step 4: 5-Chloro-4-(5,8-dihydro-6H-pyrano[3,4-b]pyridin-8-yl)thiophene-2-carbaldehyde To a solution of 8-[2-chloro-5-(1,3-dioxolan-2-yl)-3-thienyl]-5,8-dihydro-6H-pyrano[3,4-b]pyridine (799 mg, 2.47 mmol) in THF (24.2 mL, 298 mmol) was added a 1.0 M solution of HCl in water (12.0 mL, 12.0 mmol). The reaction mixture was stirred at rt overnight. Reaction was quenched with saturated aqueous $NaHCO_3$, the layers were separated, and the aqueous layer was extracted with EtOAc. The combined organic layers were washed with brine, dried over magnesium sulfate, filtered and then concentrated in vacuo. The crude residue was purified by silica gel chromatography to give 0.567 g (82% yield) of the title compound as a white solid. $^1$H NMR (400 MHz, Chloroform-d) δ 9.69 (s, 1H), 8.45 (d, J=3.6 Hz, 1H), 7.56 (d, J=8.3 Hz, 1H), 7.25-7.17 (m, 1H), 5.98 (s, 1H), 4.25-4.16 (m, 1H), 4.07-3.97 (m, 1H), 3.22-3.11 (m, 1H), 2.96-2.84 (m, 1H); LCMS (FA) M+1 280.0

The compounds listed in the table below were prepared in an analogous fashion to that described in Example 97 starting from the appropriate starting materials:

| Entry | Bromide, aldehyde (starting materials) | Product (Int #) | LC/MS data |
|---|---|---|---|
| 1 | Int-1, Int-23 | Int-187 | LCMS (FA): 294.1 ( M + 1) |
| 2 | Int-2, Int-23 | Int-188 | LCMS (FA) M + 1 314.0 |
| 3 | Int-1, Int-26 | Int-189 | LCMS (FA): 328.0 (M + 1) |
| 4 | Int-1, Int-24 | Int-190 | $^1$H NMR (400 MHz, Chloroform-d) δ 9.66 (s, 1H), 8.43-8.37 (m, 1H), 7.55-7.48 (m, 1H), 7.24 (s, 1H), 7.16 (ddd, J = 7.7, 4.7, 0.6 Hz, 1H), 5.86 (s, 1H), 4.12 (dt, J = 11.6, 5.0 Hz, 1H), 3.92 (ddd, J = 11.6, 8.4, 4.2 Hz, 1H), 3.15-3.04 (m, 1H), 2.88 (dt, J = 16.5, 4.3 Hz, 1H), 2.61-2.55 (m, 3H). |

Example 98: 4-(3,4-Dihydro-1H-isochromen-1-yl)-5-methylthiophene-2-carbaldehyde Int-191

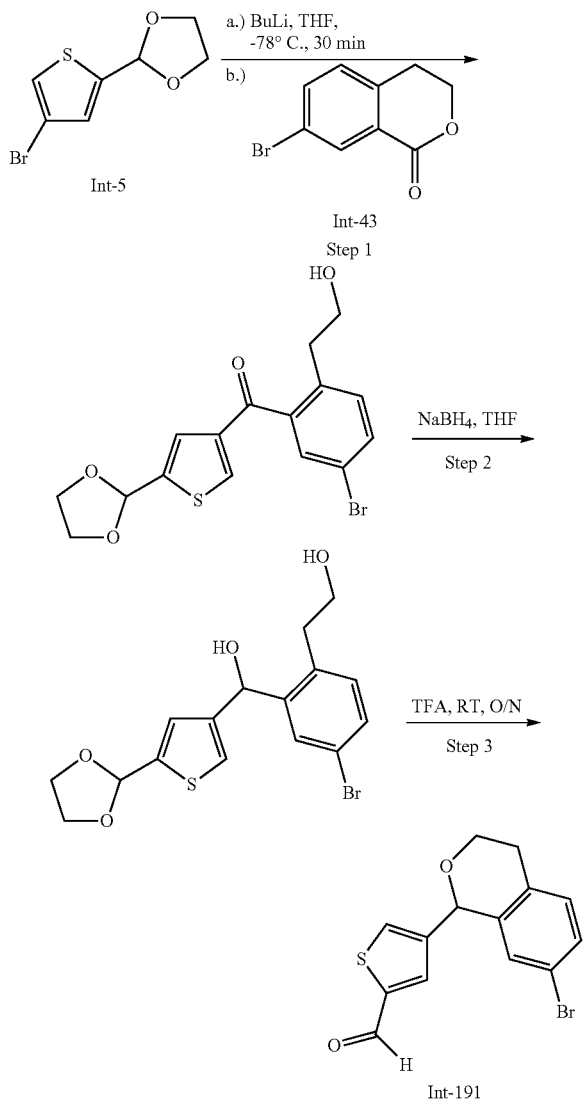 [SMILES: Brc1csc(C2OCCO2)c1 ; O=C1OCCc2ccc(Br)cc21 ; O=C(c1csc(C2OCCO2)c1)c1cc(Br)ccc1CCO ; OCCc1ccc(Br)cc1C(O)c1csc(C2OCCO2)c1 ; O=Cc1cc(C2OCCc3ccc(Br)cc32)cs1]

Step 1: [5-Bromo-2-(2-hydroxyethyl)phenyl][5-(1,3-dioxolan-2-yl)-3-thienyl]methanone To a two-neck 100 mL round-bottom flask was cooled at −78° C. was added 2.50 M of n-BuLi in hexane (1.00 mL, 2.50 mmol). The solution was stirred for 10 min under an atmosphere of argon at −78° C. A solution of Int-5 (0.473 g, 2.01 mmol) in THF (4.00 mL, 49.3 mmol) was added dropwise quickly and a light yellow precipitate formed. The mixture was stirred at −78° C. for 10 min. A solution of Int-43 (461 mg, 2.03 mmol) in THF (4.00 mL, 49.3 mmol) was added quickly and the reaction turned to a dark yellow/orange solution. The solution was allowed to stir for 10 min. The reaction was removed from the dry ice bath and quenched with saturated NH₄Cl. After warming to rt, the reaction was diluted with EtOAc and saturated NH₄Cl. The layers were separated and the organic layer was washed with brine, dried over Na₂SO₄, filtered and concentrated in vacuo. The residue was purified via column chromatography (80 g gold ISCO, 30% EtOAc in hexanes 5 min to 70% EtOAc in hexanes over 30 min). The appropriate fractions were concentrated to afford the title compound as a clear colorless oil (489 mg, 63%). LCMS: (FA) 385.0 (M+1).

Step 2: 2-(4-Bromo-2-{[5-(1,3-dioxolan-2-yl)-3-thienyl](hydroxy)methyl}phenyl)ethanol To a solution of [5-bromo-2-(2-hydroxyethyl)phenyl][5-(1,3-dioxolan-2-yl)-3-thienyl]methanone (0.489 g, 1.28 mmol) in methanol (7.85 mL, 194 mmol) was added sodium tetrahydroborate (57.9 mg, 1.53 mmol) at rt. When no further gas evolution was observed, the reaction was concentrated in vacuo to remove the methanol. The residue was diluted with EtOAc, washed with water and brine, dried over Na₂SO₄, filtered and concentrated in vacuo. Purification was accomplished via column chromatography (80 g Gold ISCO column, 50% EtOAc in hexanes to 100% EtOAc in hexanes over 30 min (50 mL/min) to give the title compound as a clear colorless oil (438 mg, 89%). LCMS: (FA) 369.0 (M−OH)

Step 3: 4-(7-Bromo-3,4-dihydro-1H-isochromen-1-yl)thiophene-2-carbaldehyde

A 100 mL round bottom flask was charged with 2-(4-bromo-2-{[5-(1,3-dioxolan-2-yl)-3-thienyl](hydroxy)methyl}phenyl)ethanol (438 mg, 1.14 mmol) and TFA (3.00 mL, 38.9 mmol), and the mixture was stirred at rt for 1 h. The reaction was carefully poured into saturated NaHCO₃, extracted 2× with EtOAc, dried over Na₂SO₄, filtered and concentrated in vacuo. The residue was purified via column chromatography (20% EtOAc in hexanes isocratic) to give the material as clear colorless oil (348 mg, 79%). LCMS: (FA) 325.0 (M+1)

Alternative Conditions for Step 3. Reaction Conditions B (e.g., Entry 1, Below): 4-(4-{[tert-Butyl(dimethyl)silyl]oxy}-3,4-dihydro-1H-isochromen-1-yl)thiophene-2-carbaldehyde This step was accomplished by first generating the requisite isochroman ring system in an analogous fashion to that described in Example 97, Step 3. The resulting acetal was then converted to the title aldehyde as follows:

To a solution of tert-butyl({1-[5-(1,3-dioxolan-2-yl)-3-thienyl]-3,4-dihydro-1H-isochromen-4-yl}oxy)dimethylsilane (1.021 g, 2.439 mmol) in acetone (15 mL, 2.0E2 mmol) was added Dowex 50WX2-200 (H) (1500 mg) at rt. The reaction was allowed to stir at rt and monitored by LCMS. TLC and LCMS show the reaction 50% conversion in 15 min. The reaction was done after 90 min at rt by LCMS monitor. The reaction solution was filtered to remove solid resin. The crude product was purified on silica gel (40 g ISCO column; hexanes then 0-30% EtOAc/hexanes) to give the title compound 712.3 mg (78%). ¹H NMR (400 MHz, Chloroform-d) δ 9.72 (s, 1H), 7.60 (d, J=1.4 Hz, 1H), 7.39 (q, J=1.3 Hz, 1H), 7.31 (d, J=7.7 Hz, 1H), 7.21-7.14 (m, 1H), 7.10-7.06 (m, 1H), 6.77 (d, J=7.5 Hz, 1H), 5.69 (s, 1H), 4.69 (dd, J=6.7, 4.6 Hz, 1H), 3.73 (dd, J=11.4, 4.5 Hz, 1H), 3.57 (dd, 1H), 0.79 (s, 9H), 0.05 (s, 3H), −0.00 (s, 3H). LCMS (AA) M+1 375.

The compounds listed in the table below were prepared in an analogous fashion to that described in Example 98 starting from the appropriate starting materials:

| Entry | Bromide, lactone (starting materials) | Reaction conditions for Step 3 | Product (Int #) | LC/MS data |
|---|---|---|---|---|
| 1 |  Int-45 | B | 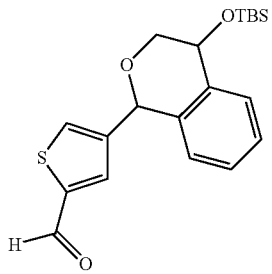 Int-192 | FA: m/z = 375.2 (M + H) |
| 2 | Int-1, Int-44 | B | 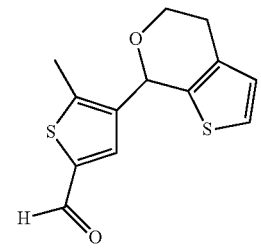 Int-193 | FA: m/z = 265.1 (M + H) |
| 3 | Int-1, Int-46 | A | 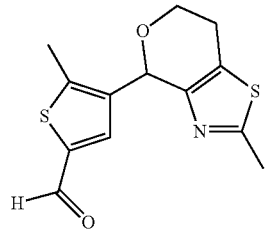 Int-194 | FA: m/z = 280.1 (M + H) |
| 4 | 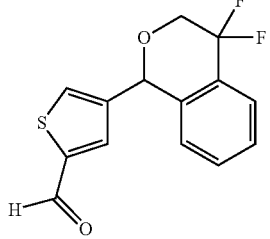 Int-39 | A | 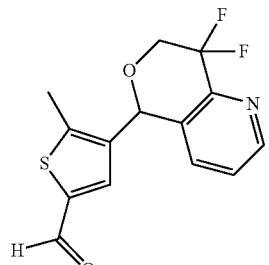 Int-195 | FA: m/z = 281.0 (M + H) |
| 5 | Int-1, Int-41 | A | Int-196 | FA: m/z = 296.2 (M + H) |

| Entry | Bromide, lactone (starting materials) | Reaction conditions for Step 3 | Product (Int #) | LC/MS data |
|---|---|---|---|---|
| 6 | Int-2 | A | Int-197 | ¹H NMR (400 MHz, Chloroform-d) δ 9.72 (s, 1H), 7.43 (s, 1H), 7.35 (dd, J = 8.1, 1.5 Hz, 1H), 7.28 (d, J = 2.9 Hz, 1H), 7.13 (s, 1H), 6.37 (s, 1H), 5.32 (dd, J = 12.4, 2.5 Hz, 1H), 5.20 (dd, J = 12.4, 1.4 Hz, 1H). |
| 7 | Int-40 | A | Int-198 | LCMS: (FA) M + 1 315.0 |
| 8 | Int-1, Int-40 | A | Int-199 | LCMS: (FA) M + 1 329.2 |
| 9 | Int-1, Int-43 | A | Int-200 | LCMS: (FA) M + 1 337.0 |

Example 99: 5-Chloro-4-(7-chloro-3,4-dihydro-1H-pyrano[4,3-c]pyridin-1-yl)thiophene-2-carbaldehyde Int-201

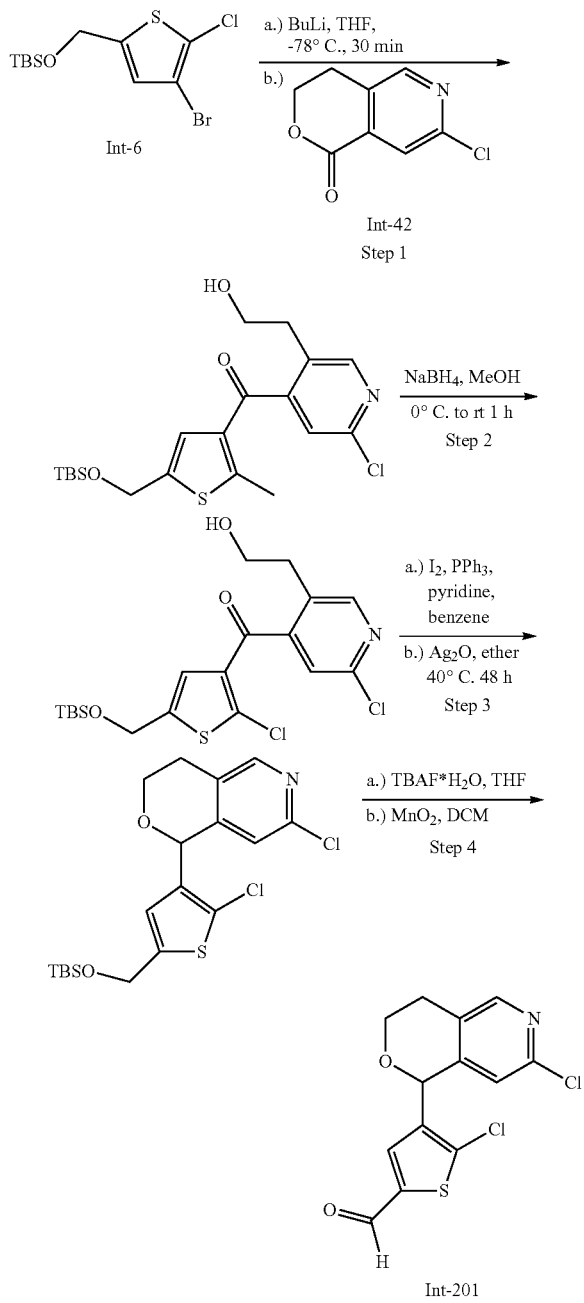

Steps 1 and 2: 2-(4-{[5-({[tert-Butyl(dimethyl)silyl]oxy}methyl)-2-chloro-3-thienyl](hydroxy)methyl}-6-chloropyridin-3-yl)ethanol Steps 1 and 2 were performed in an analogous fashion to that described in Example 98, Steps 1 and 2 starting from Int-6 and Int-42. Step 3 was performed as follows.

Step 3a: [5-({[tert-Butyl(dimethyl)silyl]oxy}methyl)-2-chloro-3-thienyl][2-chloro-5-(2-iodoethyl)pyridin-4-yl]methanol To a solution of 2-(4-{[5-({[tert-butyl(dimethyl)silyl]oxy}methyl)-2-chloro-3-thienyl](hydroxy)methyl}-6-chloropyridin-3-yl)ethanol (871.0 mg, 1.942 mmol) in benzene (22.8 mL) was added pyridine (475.6 uL, 5.881 mmol) and triphenylphosphine (771 mg, 2.94 mmol), followed by iodine (0.518 g, 2.04 mmol). The yellow mixture was stirred at rt under argon for 16 h. The reaction mixture was filtered through a pad of Celite, and the cake was washed with EtOAc. The filtrate was washed with water, and the aqueous layer was extracted with EtOAc twice. The combined organics were washed with brine, dried over $Na_2SO_4$, filtered, concentrated, and purified by silica gel column chromatography (0 to 30% EtOAc in hexane as eluent) to provide 1.003 g (92%) of the title compound as a white solid. $^1$H NMR (400 MHz, DMSO-d6) δ 8.28 (s, 1H), 7.64 (s, 1H), 6.61-6.58 (m, 1H), 6.39 (d, J=4.5 Hz, 1H), 5.86 (d, J=4.4 Hz, 1H), 4.72 (d, J=0.9 Hz, 2H), 3.28-3.19 (m, 1H), 3.11-2.89 (m, 3H), 0.84 (s, 9H), 0.02 (s, 6H); LCMS (AA): (M+1) 558.0

Step 3b: 1-[5-({[tert-Butyl(dimethyl)silyl]oxy}methyl)-2-chloro-3-thienyl]-7-chloro-3,4-dihydro-1H-pyrano[4,3-c]pyridine To a solution of [5-({[tert-butyl(dimethyl)silyl]oxy}methyl)-2-chloro-3-thienyl][2-chloro-5-(2-iodoethyl)pyridin-4-yl]methanol (1.003 g, 1.796 mmol) in ether (27.8 mL) was added silver(I) oxide (2.08 g, 8.98 mmol), and the reaction was stirred at rt under argon for 15 h. The reaction mixture was then stirred at reflux at 40° C. for 36 h. The reaction was cooled to rt, filtered through a pad of Celite, and the cake was washed with EtOAc. The filtrate was concentrated and purified by silica gel column chromatography (0 to 30% EtOAc in hexane as eluent) to give 707 mg (91%) of the title compound as a colorless oil. $^1$H NMR (400 MHz, DMSO-d6) δ 8.32 (s, 1H), 6.75 (s, 1H), 6.64-6.59 (m, 1H), 5.85-5.80 (m, 1H), 4.78-4.69 (m, 2H), 4.16-4.08 (m, 1H), 3.92-3.83 (m, 1H), 3.02-2.91 (m, 1H), 2.86-2.77 (m, 1H), 0.85 (s, 9H), 0.03 (s, 6H); LCMS (AA): (M+1) 430.1

Step 4a: [5-Chloro-4-(7-chloro-3,4-dihydro-1H-pyrano[4,3-c]pyridin-1-yl)-2-thienyl]methanol To a solution of 1-[5-({[tert-butyl(dimethyl)silyl]oxy}methyl)-2-chloro-3-thienyl]-7-chloro-3,4-dihydro-1H-pyrano[4,3-c]pyridine (705 mg, 1.64 mmol) in THF (24.2 mL) under argon was added a solution of TBAF hydrate (686.6 mg, 2.457 mmol) in THF (7.3 mL), and the yellow solution was stirred at rt for 1 hour. The reaction was quenched by addition of water (20 mL) and extracted with EtOAc (2×25 mL). The combined organic layers were washed with brine, dried over $Na_2SO_4$, filtered, and concentrated. The residue was purified by silica gel column chromatography (0 to 75% EtOAc in hexane as eluent) to afford 0.350 g (68%) of the title compound as a white solid. $^1$H NMR (400 MHz, DMSO-d6) δ 8.32 (s, 1H), 6.76 (s, 1H), 6.62-6.57 (m, 1H), 5.85-5.80 (m, 1H), 5.59 (t, J=5.8 Hz, 1H), 4.51 (dd, J=5.8, 0.8 Hz, 2H), 4.16-4.08 (m, 1H), 3.92-3.83 (m, 1H), 3.03-2.91 (m, 1H), 2.87-2.77 (m, 1H); LCMS (AA): (M+1) 316.0

Step 4b: 5-Chloro-4-(7-chloro-3,4-dihydro-1H-pyrano[4,3-c]pyridin-1-yl)thiophene-2-carbaldehyde To a solution of [5-chloro-4-(7-chloro-3,4-dihydro-1H-pyrano[4,3-c]pyridin-1-yl)-2-thienyl]methanol (348.0 mg, 1.100 mmol) in DCM (40.6 mL) was added MnO$_2$ (0.9568 g, 11.00 mmol) at rt, and the reaction was stirred for 14 h under argon. The mixture was filtered through a pad of Celite, and the cake was washed with EtOAc. The filtrate was concentrated in vacuo and dried to afford 291 mg of the title compound as a white solid. $^1$H NMR (400 MHz, DMSO-d6) δ 9.76 (s, 1H), 8.36 (s, 1H), 7.75 (s, 1H), 6.94 (s, 1H), 5.96 (s, 1H), 4.15-4.07 (m, 1H), 3.95-3.86 (m, 1H), 3.05-2.94 (m, 1H), 2.90-2.81 (m, 1H); LCMS (AA): (M+1) 314.0.

The compounds listed in the table below were prepared in an analogous fashion to that described in Example 99 starting from the appropriate starting materials:

| Entry | Bromide, lactone (starting materials) | Product (Int #) | LC/MS data |
|---|---|---|---|
| 1 | Int-4, Int-47 | Int-202 | LCMS: (FA) M + 1 249.0 |
| 2 | Int-4, Int-48 | Int-203 | $^1$H NMR (400 MHz, Chloroform-d) δ 9.81 (d, J = 1.0 Hz, 1H), 7.63 (s, 1H), 7.50 (s, 1H), 7.17 (s, 1H), 5.80 (s, 1H), 4.20-4.09 (m, 2H), 4.07-3.89 (m, 2H), 1.63 (s, 3H). |

Example 100: 4-(3,4-Dihydro-1H-isochromen-1-yl)-5-methylthiophene-2-carbaldehyde Int-204

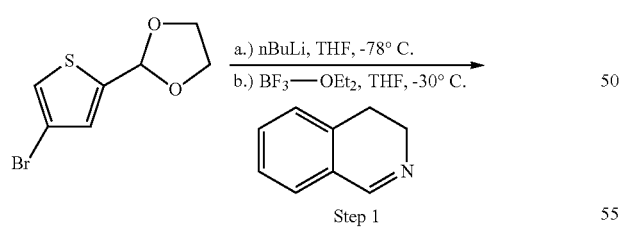

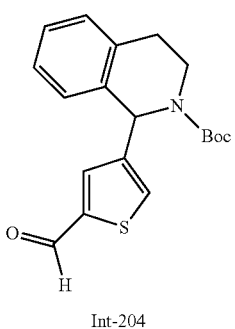

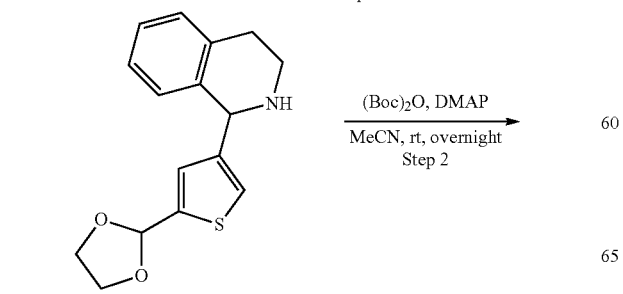

Step 1: 1-[5-(1,3-Dioxolan-2-yl)-3-thienyl]-1,2,3,4-tetrahydroisoquinoline

A solution of 3,4-dihydroisoquinoline (500 mg, 3.81 mmol) in THF (15.4 mL) was cooled at −30° C. To this solution was added dropwise boron trifluoride etherate (0.53 mL, 4.19 mmol) at −30° C., and the mixture was stirred for 20 min. Into a separate 50 mL 2-neck flask 2.50 M of n-BuLi in hexane (1.83 mL, 4.57 mmol) was added at −78° C. followed by a solution of 2-(4-bromothiophen-2-yl)-1,3- dioxolane (1.08 g, 4.57 mmol) in THF (10.0 mL). After 5 min, lithiated thiophene suspension was added to the above solution of dihydroisoquinoline BF3-OEt2 complex at −78° C. The reaction was stirred for 20 min at −78° C. and then quenched by addition of water. The layers were separated and the aqueous layer was extracted with EtOAc. The combined organic layers were dried over $Na_2SO_4$, filtered, and concentrated in vacuo. The residue was purified by silica gel column chromatography (0 to 5% MeOH in DCM). All fractions with Rf ranging from 0.1 to 0.25 in TLC (5% MeOH in DCM, ninhydrin stain) were combined to give 513 mg of a mixture of the title compound and some impurities as a red amorphous solid. This mixture was used for the next step without further purification.

Step 2: tert-Butyl 1-[5-(1,3-dioxolan-2-yl)-3-thienyl]-3,4-dihydroisoquinoline-2(1H)-carboxylate The crude mixture from step 1 was dissolved in MeCN (6.97 mL), to which was added $(Boc)_2O$ (1.25 g, 5.72 mmol) and N,N-dimethylaminopyridine (2.33 mg, 19.1 μmol) at rt. After stirring for 2 h, the reaction was quenched by adding water. The layers were separated and the aqueous layer was extracted with EtOAc 2×. The combined organics were washed with brine, dried over $Na_2SO_4$, filtered and concentrated in vacuo. The residue was purified by silica gel column chromatography (0 to 20% EtOAc in hexane) to give 393 mg (27% for 2 steps) of the title compound. $^1$H NMR (400 MHz, Chloroform-d) δ 7.26-7.03 (m, 6H), 6.82 (s, 1H), 6.01 (s, 1H), 4.17-3.93 (m, 5H), 3.20-3.04 (m, 1H), 3.04-2.86 (m, 1H), 2.79-2.68 (m, 1H), 1.57-1.46 (m, 9H); LCMS (FA): m/z=388.3 (M+H).

Step 3 (Reaction Conditions A, as in Example 100): tert-Butyl 1-(5-formyl-3-thienyl)-3,4-dihydroisoquinoline-2(1H)-carboxylate To a solution of tert-butyl 1-[5-(1,3-dioxolan-2-yl)-3-thienyl]-3,4-dihydroisoquinoline-2(1H)-carboxylate (393 mg, 1.01 mmol) in acetone (7.72 mL) was added 500 mg of Dowex 50WX-2-200 (H) (acid resin), and the mixture was shaken for 18 h at rt. The reaction was filtered through a glass frit funnel and the residual resin was rinsed with acetone several times. To the filtrate was added saturated aqueous $NaHCO_3$ (25.0 mL) and the mixture was concentrated to half volume in vacuo. The residue was diluted with EtOAc, the layers were separated, and the aqueous layer was extracted with EtOAc. The combined organic layers were dried over $Na_2SO_4$, filtered, and concentrated in vacuo. The residue was purified by silica gel column chromatography (0 to 15% EtOAc in hexane) to give 319 mg (91%) of the title compound as a colorless amorphous solid. $^1$H NMR (400 MHz, Chloroform-d) δ 9.84 (s, 1H), 7.64 (s, 1H), 7.30-7.07 (m, 5H), 6.48-6.23 (br s, 1H), 4.09-3.88 (m, 1H), 3.22-3.06 (m, 1H), 3.05-2.89 (m, 1H), 2.81-2.69 (m, 1H), 1.52 (s, 9H). Alternative Conditions for Step 3.

Reaction Conditions B (e.g., Entry 2, Below): tert-Butyl 7-chloro-1-(5-formyl-2-methyl-3-thienyl)-3,4-dihydroisoquinoline-2(1H)-carboxylate To a solution of tert-butyl 7-chloro-1-[5-(1,3-dioxolan-2-yl)-2-methyl-3-thienyl]-3,4-dihydroisoquinoline-2(1H)-carboxylate (7.30 g, 16.7 mmol) in methanol (200 mL) and water (20 mL) was added a solution of HCl (4.00 mL, 130 mmol) in methanol (200 mL) and the reaction as stirred at rt for 1 hour. Reaction was quenched via addition of 50 mL of saturated $NaHCO_3$ with stirring for 5 min. MeOH was removed in vacuo, and the resulting aqueous mixture was diluted with EtOAc, the layers were separated, and the aqueous layer was extracted three times with EtOAc. The combined organic portions were washed with brine, dried over anhydrous sodium sulfate, filtered, and concentrated in vacuo. The residue was purified via silica gel chromatography eluting with a hexane/EtOAc gradient to afford the title compound (4.55 g, 70%). $^1$H NMR (400 MHz, Chloroform-d) δ 9.67 (s, 1H), 7.27-7.15 (m, 2H), 7.12 (s, 1H), 6.98-6.94 (m, 1H), 6.34 (m, 1H), 4.15 (s, 1H), 3.18-3.06 (m, 1H), 3.05-2.93 (m, 1H), 2.82-2.73 (m, 1H), 2.69 (s, 3H), 1.50 (s, 9H). LCMS: (AA) M+Na 414.2

The compounds listed in the table below were prepared in an analogous fashion to that described in Example 100 starting from the appropriate starting materials:

| Entry | Bromide, imine (starting materials) | Reaction conditions for Step 3 | Product (Int #) | Characterization data |
|---|---|---|---|---|
| 1 | Int-1, | A | 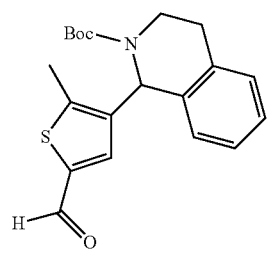<br>Int-205 | LCMS: (FA) M + 1 358.2 |

-continued

| Entry | Bromide, imine (starting materials) | Reaction conditions for Step 3 | Product (Int #) | Characterization data |
|---|---|---|---|---|
| 2 | Int-1, Int-50 | B | 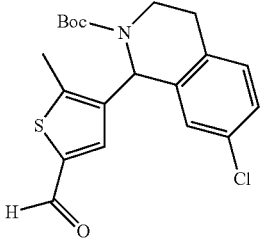<br>Int-206 | ¹H NMR (400 MHz, Chloroform-d) δ 9.67 (s, 1H), 7.27-7.15 (m, 2H), 7.12 (s, 1H), 6.98-6.94 (m, 1H), 6.34 (m, 1H), 4.15 (s, 1H), 3.18-3.06 (m, 1H), 3.05-2.93 (m, 1H), 2.82-2.73 (m, 1H), 2.69 (s, 3H), 1.50 (s, 9H). LCMS: (AA) M + Na 414.2 |
| 3 | Int-3, Int-50 | B | 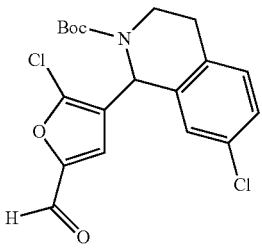<br>Int-207 | ¹H NMR (400 MHz, Chloroform-d) δ 9.48 (s, 1H), 7.20 (dd, J = 8.2, 1.8 Hz, 1H), 7.13 (d, J = 8.2 Hz, 1H), 7.06-6.97 (m, 2H), 6.18 (br s, 1H), 4.17 (br s, 1H), 3.27-3.15 (m, 1H), 3.01-2.89 (m, 1H), 2.82-2.72 (m, 1H), 1.48 (s, 9H). |
| 4 | Int-2, Int-50 | A | 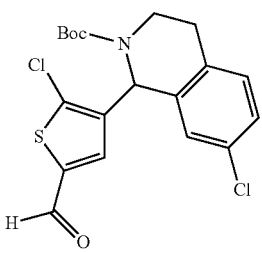<br>Int-208 | ¹H NMR (400 MHz, DMSO-d₆) δ 9.74 (s, 1H), 7.79 (s, 1H), 7.32 (d, J = 1.2 Hz, 2H), 7.14 (s, 1H), 6.24 (s, 1H), 3.97 (d, J = 13.3 Hz, 1H), 3.41 (s, 1H), 2.97-2.81 (m, 2H), 1.38 (s, 9H). |
| 5 | Int-1, Int-51 | B | 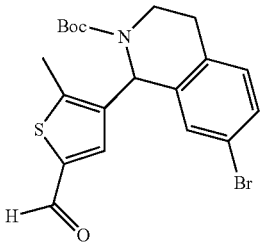<br>Int-209 | LCMS: (FA) M + 1 438.3 |
| 6 | Int-2, Int-51 | A | 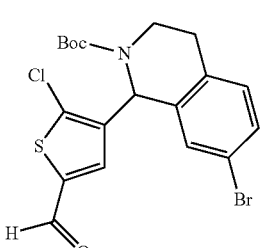<br>Int-210 | ¹H NMR (400 MHz, Chloroform-d) δ 9.60 (s, 1H), 7.28 (dd, J = 8.2, 1.9 Hz, 1H), 7.22 (s, 1H), 7.10 (d, J = 1.6 Hz, 1H), 7.02 (d, J = 8.2 Hz, 1H), 6.23 (s, 1H), 4.11 (s, 1H), 3.26-3.17 (m, 1H), 2.87 (ddd, J = 16.4, 10.8, 5.6 Hz, 1H), 2.73 (d, J = 16.4 Hz, 1H), 1.38 (s, 9H). |

| Entry | Bromide, imine (starting materials) | Reaction conditions for Step 3 | Product (Int #) | Characterization data |
|---|---|---|---|---|
| 7 | Int-2, Int-52 | A | 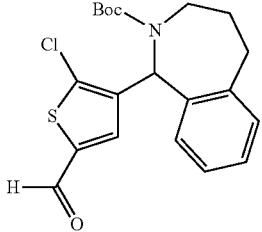<br>Int-211 | Rotameric mixture gave complex $^1$H NMR spectra |
| 8 | Int-5, Int-50 | Performed in analogous fashion to Example 99, Step 4 | 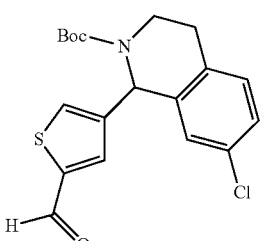<br>Int-212 | $^1$H NMR (400 MHz, Chloroform-d) δ 9.88 (s, J = 1.2 Hz, 1H), 7.65 (s, 1H), 7.38 (s, 1H), 7.25 (dd, J = 8.2, 2.1 Hz, 1H), 7.18 (d, J = 8.2 Hz, 1H), 7.13 (s, 1H), 6.37 (s, 1H), 4.15 (d, J = 7.3 Hz, 1H), 3.11 (s, 1H), 2.96 (s, 1H), 2.75 (d, J = 16.1 Hz, 1H), 1.54 (s, 9H). |
| 9 | Int-6,<br>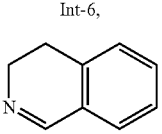 | Performed in analogous fashion to Example 99, step 4 | 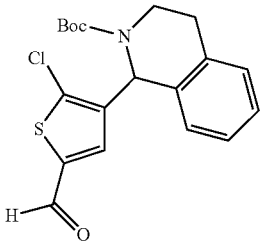<br>Int-213 | |

Example 101: 5-Chloro-4-(6-chloro-2-methyl-2,3-dihydro-1H-isoindol-1-yl)thiophene-2-carbaldehyde Int-214

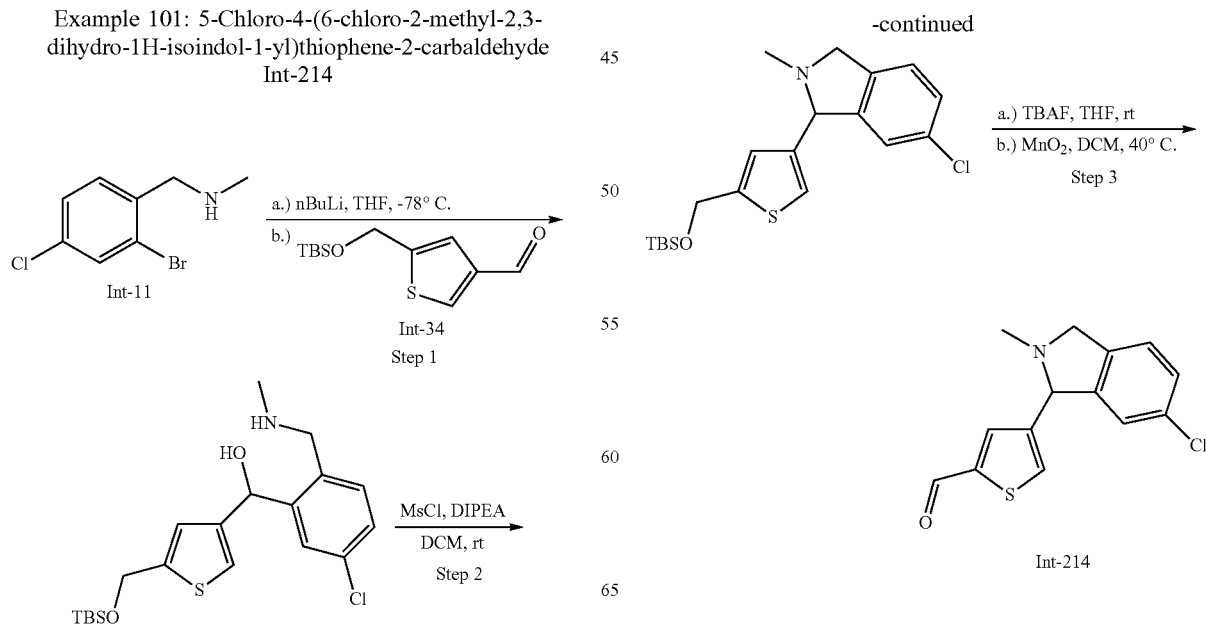

Step 1: [5-({[tert-Butyl(dimethyl)silyl]oxy}methyl)-3-thienyl]{5-chloro-2-[(methylamino)methyl]phenyl}methanol To a solution of bromide Int-11 (300.0 mg, 1.28 mmol) in THF (10 mL) was added dropwise 2.50 M of n-BuLi in hexane (1.02 mL, 2.56 mmol) at −78° C. under atmosphere of argon and the mixture was stirred for 30 min. To the mixture was added dropwise a solution of aldehyde Int-34 (298 mg, 1.16 mmol) in THF (2.0 mL) at −78° C. and the resulting mixture was stirred for 30 min. The reaction was quenched by addition of brine (50 mL) and extracted with EtOAc (70 mL×3). The combined organic layers were dried over Na$_2$SO$_4$, filtered, and concentrated in vacuo. The residue was purified by ISCO silica gel column chromatography (24 g, eluting with 5% (5% MeOH:45% MeCN:48% DCM:2% NH4OH) in DCM to 100% (5% MeOH:45% MeCN:48% DCM:2% NH4OH), 35 mL/min flow) to give 166 mg (33%) of the title compound as colorless oil. $^1$H NMR (400 MHz, Methanol-d4) δ 7.37 (d, J=1.8 Hz, 1H), 7.34-7.26 (m, 2H), 7.16 (t, J=1.3 Hz, 1H), 6.73 (s, 1H), 5.90 (s, 1H), 4.82 (d, J=0.8 Hz, 2H), 3.72 (d, J=12.9 Hz, 1H), 3.64 (d, J=12.9 Hz, 1H), 2.35 (s, 3H), 0.90 (s, 9H), 0.07 (s, 6H).

Step 2: 1-[5-({[tert-Butyl(dimethyl)silyl]oxy}methyl)-3-thienyl]-6-chloro-2-methylisoindoline To a solution of [5-({[tert-butyl(dimethyl)silyl]oxy}methyl)-3-thienyl]{5-chloro-2-[(methylamino)methyl]phenyl}methanol (560 mg, 1.29 mmol) in DCM (13.3 mL) was added N,N-diisopropylethylamine (0.34 mL, 1.94 mmol) followed by methanesulfonyl chloride (155 mg, 1.36 mmol) at 0° C. under atmosphere of argon, and the mixture was stirred for 30 min. The reaction was quenched by addition of saturated NaHCO$_3$ (60 mL) and extracted with DCM (60 mL×3). The combined organic layers were dried over Na$_2$SO$_4$, filtered, and concentrated in vacuo. The residue was purified by ISCO silica gel column chromatography (24 g, eluting with 10% EtOAc in DCM, 40 mL/min flow) to give 432 mg (85%) of product as colorless oil. $^1$H NMR (400 MHz, DMSO-d6) δ 7.41 (d, J=1.2 Hz, 1H), 7.32 (d, J=8.0 Hz, 1H), 7.27 (dd, J=8.0, 1.4 Hz, 1H), 6.83 (s, 1H), 6.75 (s, 1H), 4.81 (d, J=0.7 Hz, 2H), 4.63 (s, 1H), 4.22 (d, J=13.2 Hz, 1H), 3.63 (dd, J=13.1, 2.9 Hz, 1H), 2.38 (s, 3H), 0.86 (s, 9H), 0.05 (s, 6H).

Step 3: 5-Chloro-4-(6-chloro-2-methyl-2,3-dihydro-1H-isoindol-1-yl)thiophene-2-carbaldehyde Step 3 was performed in an analogous fashion to that described in Example 99, step 4 from the appropriate starting materials. LCMS: (FA) M+1 278.0

The compounds listed in the table below were prepared in an analogous fashion to that described in Example 101 starting from the appropriate starting materials:

| Entry | Bromide, aldehyde (starting materials) | Product (Int #) | LC/MS data |
|---|---|---|---|
| 1 | Int-13, Int-35 | Int-215 | LCMS: (FA) M + 1 278.3 |
| 2 | Int-12, Int-34 | Int-216 | LCMS: (FA) M + 1 278.3 |
| 3 | Int-14, Int-35 | Int-217 | LCMS: (FA) M + 1 398.0 |

-continued

| Entry | Bromide, aldehyde (starting materials) | Product (Int #) | LC/MS data |
|---|---|---|---|
| 4 | Int-13, Int-34 | Int-218 | |
| 5 | Int-11, Int-35 | Int-219 | LCMS: (FA) M + 1 314.1 |

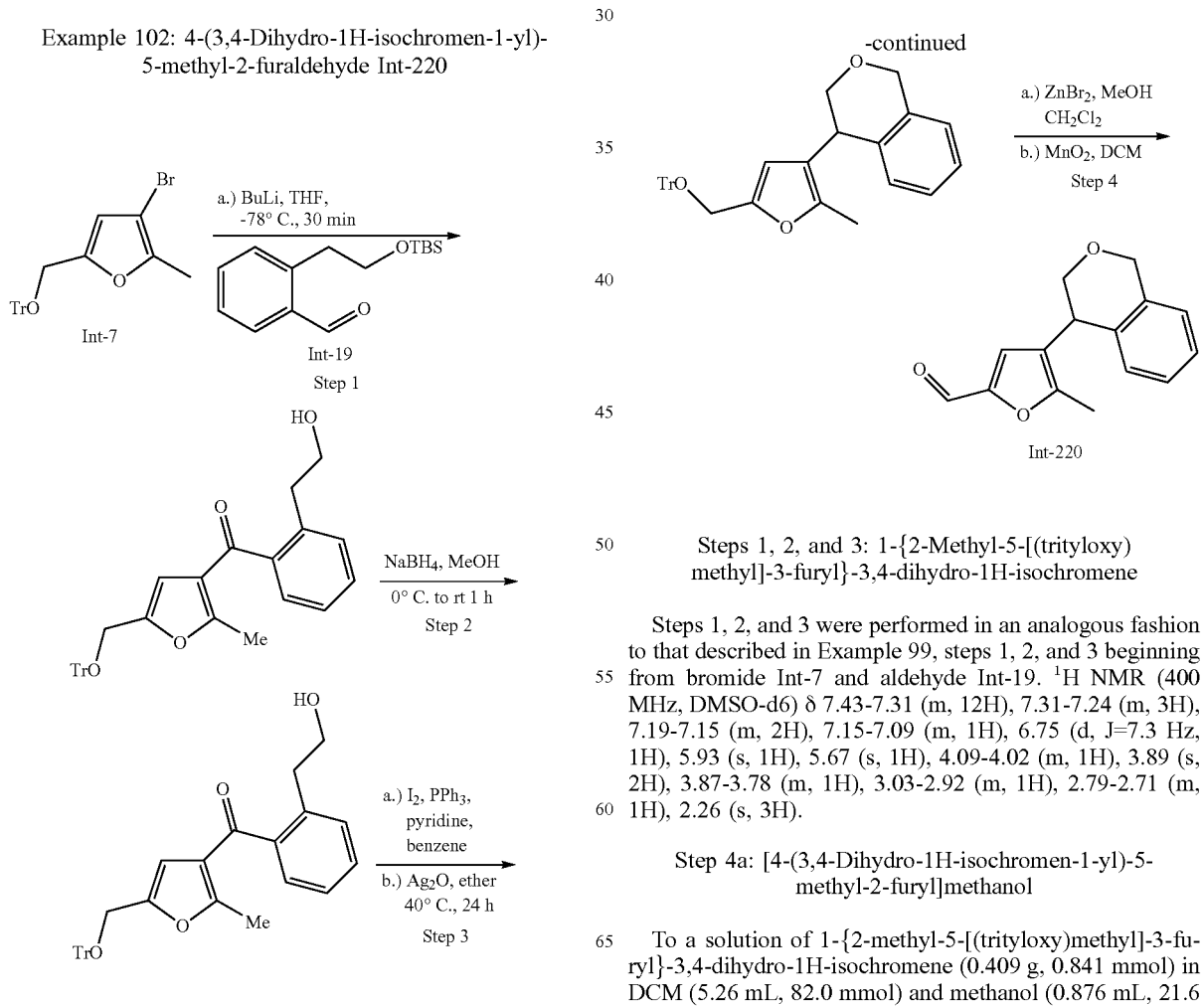

Example 102: 4-(3,4-Dihydro-1H-isochromen-1-yl)-5-methyl-2-furaldehyde Int-220

Steps 1, 2, and 3: 1-{2-Methyl-5-[(trityloxy)methyl]-3-furyl}-3,4-dihydro-1H-isochromene Steps 1, 2, and 3 were performed in an analogous fashion to that described in Example 99, steps 1, 2, and 3 beginning from bromide Int-7 and aldehyde Int-19. $^1$H NMR (400 MHz, DMSO-d6) δ 7.43-7.31 (m, 12H), 7.31-7.24 (m, 3H), 7.19-7.15 (m, 2H), 7.15-7.09 (m, 1H), 6.75 (d, J=7.3 Hz, 1H), 5.93 (s, 1H), 5.67 (s, 1H), 4.09-4.02 (m, 1H), 3.89 (s, 2H), 3.87-3.78 (m, 1H), 3.03-2.92 (m, 1H), 2.79-2.71 (m, 1H), 2.26 (s, 3H).

Step 4a: [4-(3,4-Dihydro-1H-isochromen-1-yl)-5-methyl-2-furyl]methanol

To a solution of 1-{2-methyl-5-[(trityloxy)methyl]-3-furyl}-3,4-dihydro-1H-isochromene (0.409 g, 0.841 mmol) in DCM (5.26 mL, 82.0 mmol) and methanol (0.876 mL, 21.6 mmol) was added zinc dibromide (0.946 g, 4.20 mmol) and the reaction was stirred at rt for 4 h. The reaction was quenched by pouring into saturated aqueous NaHCO₃, and then diluted with Et₂O (50 mL) and water (10 mL). Layers were separated, and the organic layer was dried over Na₂SO₄, filtered, and concentrated in vacuo. Chromatography was performed (12 g column, 0-50% EA:hex as eluent) to afford 184 mg of the title compound. ¹H NMR (400 MHz, Chloroform-d) δ 7.25-7.09 (m, 3H), 6.85 (d, J=7.6 Hz, 1H), 6.03 (s, 1H), 5.67 (s, 1H), 4.52 (d, J=6.0 Hz, 2H), 4.27-4.18 (m, 1H), 3.99-3.84 (m, 1H), 3.19-3.05 (m, 1H), 2.87-2.74 (m, 1H), 2.34 (s, 3H), 1.59 (t, J=6.1 Hz, 1H).

Step 4b: 4-(3,4-Dihydro-1H-isochromen-1-yl)-5-methyl-2-furaldehyde

Step 4b was performed in an analogous fashion to that described in Example 99, step 4b beginning from the above starting material to afford the title compound. ¹H NMR (400 MHz, Chloroform-d) δ 9.48 (s, 1H), 7.27-7.13 (m, 3H), 7.00 (s, 1H), 6.80 (d, J=7.7 Hz, 1H), 5.75 (s, 1H), 4.23-4.14 (m, 1H), 4.00-3.90 (m, 1H), 3.17-3.06 (m, 1H), 2.89-2.80 (m, 1H), 2.45 (s, 3H).

The compound listed in the table below was prepared in an analogous fashion to that described in Example 102 starting from the appropriate starting materials:

| Entry | Bromide, aldehyde (starting materials) | Product (Int #) | LC/MS data |
|---|---|---|---|
| 1 | Int-7, Int-15 | 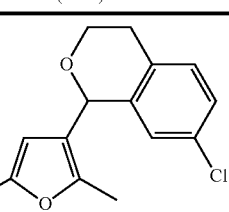 Int-221 | LCMS: (FA) M + 1 314.1 |

Example 103: 4-(4H-1,3-Benzodioxin-4-yl)-5-methylthiophene-2-carbaldehyde Int-222

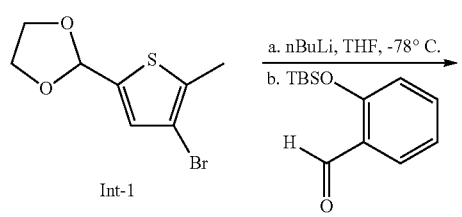

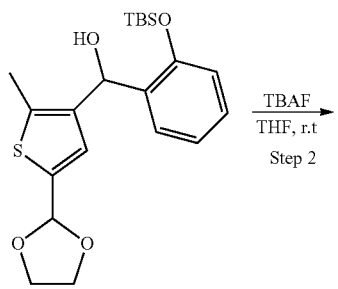

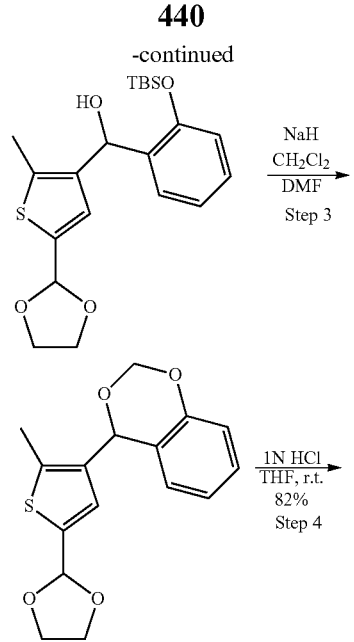

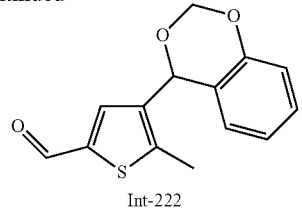

Int-222

Steps 1 and 2: 2-{[5-(1,3-Dioxolan-2-yl)-2-methyl-3-thienyl](hydroxy)methyl}phenol Steps 1 and 2 were performed in an analogous fashion to that described in Example 97, steps 1 and 2 beginning from bromide Int-1 and aldehyde Int-37. LCMS (FA): m/z=293.1 (M+H).

Step 3: 4-[5-(1,3-Dioxolan-2-yl)-2-methyl-3-thienyl]-4H-1,3-benzodioxine

In a sealable reaction vessel, to a solution of 2-{[5-(1,3-dioxolan-2-yl)-2-methyl-3-thienyl](hydroxy)methyl}phenol (1.45 g, 4.96 mmol) in DCM (30.4 mL, 475 mmol) and DMF (60.8 mL, 786 mmol) was added NaH 60% in mineral oil (0.800 g, 20.0 mmol). The vessel was sealed and the mixture was heated with stirring at bath temp 35° C. overnight After cooling to rt, the solution was carefully poured onto 150 mL of saturated aqueous NaHCO$_3$ and diluted with 100 mL DCM. Layers were separated, and the aqueous layer was extracted 1×DCM (100 mL). Combined organic layers were washed 2× brine, then dried over Na$_2$SO$_4$, filtered, and concentrated in vacuo to afford the title compound (1.94 g) which was used without further purification. LCMS (FA): m/z=305.0 (M+H).

Step 4: 4-(4H-1,3-Benzodioxin-4-yl)-5-methylthiophene-2-carbaldehyde

Step 4 was performed in an analogous fashion to that described in Example 97, step 4 beginning from the above starting material. $^1$H NMR (400 MHz, Chloroform-d) δ 9.74 (s, 1H), 7.47 (s, 1H), 7.28-7.22 (m, 1H), 7.00-6.89 (m, 2H), 6.76 (d, J=7.7 Hz, 1H), 6.08 (s, 1H), 5.33 (s, 2H), 2.64-2.58 (m, 3H).

Example 104: 3-(3,4-Dihydro-1H-isochromen-1-yl)-5-formylthiophene-2-carbonitrile Int-223

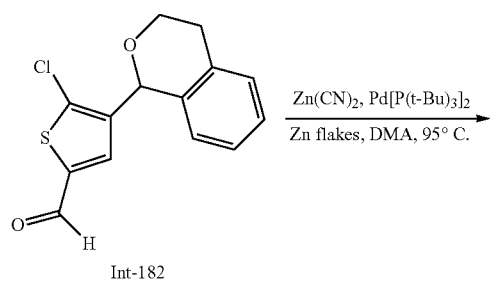

Int-182

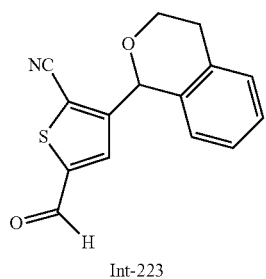

Int-223

A microwave tube was charged with aldehyde Int-182 (1.25 g, 4.48 mmol), N,N-dimethylacetamide (15 mL), zinc cyanide (0.395 g, 3.36 mmol), and zinc flakes (58.6 mg, 0.897 mmol), and then degassed by bubbling nitrogen through. To this was added bis(tri-t-butylphosphine)palladium(0) (229 mg, 0.448 mmol), the vessel was sealed, and the reaction was heated in a 90° C. oil bath for 18 h. The reaction was cooled to rt and poured into saturated NaHCO$_3$ and water. Layers were separated, and the aqueous layer was extracted three times with EtOAc. The combined organic portions were washed with brine, then dried with anhydrous sodium sulfate, filtered, and concentrated in vacuo. Crude residue was purified via column chromatography eluting with a hexanes/EtOAc gradient to afford the title compound as a yellow foam, 609 mg (40%). LCMS: (AA) M+1 270.0

Example 105: 5-Methyl-4-{7-[(trimethylsilyl)ethynyl]-3,4-dihydro-1H-isochromen-1-yl}thiophene-2-carbaldehyde Int-224

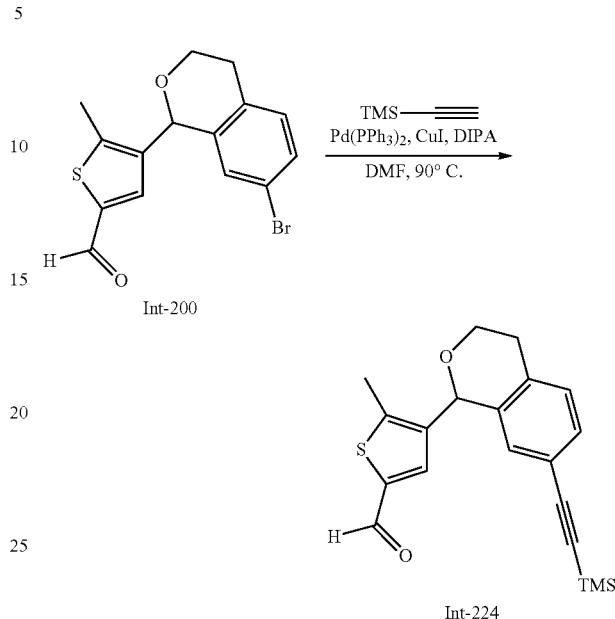

Int-224

A 100 ml. round bottomed flask was charged with bis(triphenylphosphine)palladium(II) chloride (208.1 mg, 0.2965 mmol), copper(I) iodide (56.47 mg, 0.2965 mmol), and triphenylphosphine (311.1 mg, 1.186 mmol). To the mixture was added a solution of bromide Int-200 (2.0 g, 5.9 mmol) in DMF (20.1 mL) followed by N,N-diisopropylamine (20.1 mL). To the mixture was added (trimethylsilyl)acetylene (1.257 mL, 8.896 mmol) via syringe and the reaction was heated with stirring at 90° C. for 4 h. The reaction mixture was transferred into a separatory funnel with EtOAc (60 mL). The organic layer was washed with 0.5N HCl followed by 1N LiCl solution and then dried over Na$_2$SO$_4$. The mixture was filtered, and the filtrate was concentrated in vacuo. The residue was purified by ISCO silica gel column chromatography eluting with 0-40% EtOAc in hexane to give 1.9 g (90%) of target compound as a light yellow amorphous solid. $^1$H NMR (400 MHz, Chloroform-d) δ 9.72 (s, 1H), 7.36 (s, 1H), 7.34-7.30 (m, 1H), 7.13 (d, J=7.9 Hz, 1H), 6.83 (s, 1H), 5.77 (s, 1H), 4.19-4.09 (m, 1H), 3.94-3.84 (m, 1H), 3.16-3.04 (m, 1H), 2.87-2.76 (m, 1H), 0.21 (s, 9H).

Example 106: 4-(7-Cyclopropyl-3,4-dihydro-1H-isochromen-1-yl)-5-methylthiophene-2-carbaldehyde Int-225

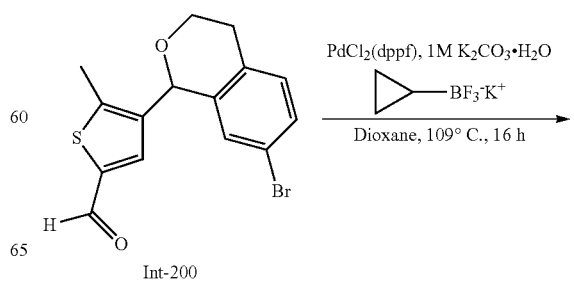

Int-200

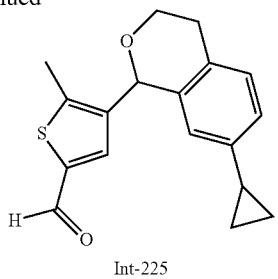

Int-225

A 500 ml round bottomed flask was charged with bromide Int-200 (1.5 g, 4.4 mmol), potassium cyclopropyltrifluoroborate (1.32 g, 8.90 mmol), 1.00 M of potassium carbonate in water (13.3 mL, 13.3 mmol) [1,1'-bis(diphenylphosphino)ferrocene]dichloropalladium(II) complex with dichloromethane (1:1) (363 mg, 0.445 mmol) and 1,4-dioxane (40.0 mL). The mixture was stirred at 100° C. for 16 h. The reaction mixture was quenched with water, the layers were separated, and the aqueous layer was extracted with EtOAc (20 mL×2). The combined organic layers were washed with brine, dried over $Na_2SO_4$, filtered, and concentrated in vacuo. The residue was purified by ISCO silica gel column chromatography eluting with 0-40% EtOAc in hexane to give 921 mg (70%) of the title compound as an oil. $^1$H NMR (400 MHz, Chloroform-d) δ 9.72 (s, 1H), 7.38 (s, 1H), 7.08 (d, J=7.9 Hz, 1H), 6.87 (dd, J=7.9, 1.8 Hz, 1H), 6.47 (s, 1H), 5.79 (s, 1H), 4.18-4.12 (m, 1H), 3.93-3.86 (m, 1H), 3.12-3.02 (m, 1H), 2.82-2.72 (m, 1H), 2.57 (s, 3H), 1.80-1.72 (m, 1H), 0.93-0.85 (m, 2H), 0.62-0.50 (m, 2H). LCMS (FA): m/z 299.5 (M+1).

Example 107: 4-{7-[(Dimethylamino)methyl]-3,4-dihydro-1H-isochromen-1-yl}-5-methylthiophene-2-carbaldehyde Int-226

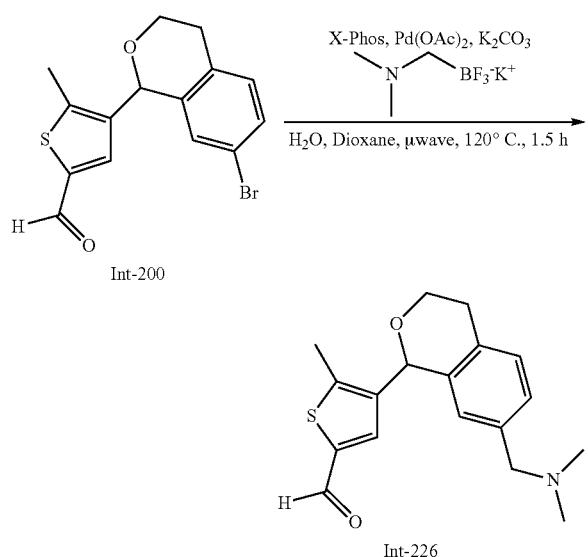

A solution of bromide Int-200 (880 mg, 2.6 mmol), palladium(II) acetate (10 mg, 0.05 mmol), 2-dicyclohexylphosphino-2',4',6'-tri-i-propyl-1,1'-biphenyl (45 mg, 0.094 mmol), potassium [(dimethylamino)methyl](trifluoro)borate(1-) (645.87 mg, 3.9142 mmol), and potassium carbonate (720 mg, 5.2 mmol) in 1,4-dioxane (10 ml) and water (10 ml) was stirred at reflux for 16 h under argon. The reaction mixture was allowed to cool at rt and the volatiles were removed in vacuo. The resulting aqueous mixture was extracted 2×EtOAc, and the combined organic layers were dried over $Na_2SO_4$, filtered, and concentrated in vacuo. The residue was purified by ISCO silica gel column chromatography eluting with using 0-20% MeOH in DCM to give 741 mg (90%) of the title compound. $^1$H NMR (400 MHz, Chloroform-d) δ 9.69 (s, 1H), 7.34 (s, 1H), 7.21-7.10 (m, 2H), 6.69 (s, 1H), 5.84 (s, 1H), 4.19-4.09 (m, 1H), 3.97-3.86 (m, 1H), 3.40 (d, J=12.8 Hz, 1H), 3.28 (d, J=12.8 Hz, 1H), 3.14-3.03 (m, 1H), 2.87-2.77 (m, 1H), 2.56 (s, 3H), 2.19 (s, 6H). LCMS (FA): m/z 316.0 (M+1).

Example 108: 1-(5-Formyl-2-methyl-3-thienyl)-3,4-dihydro-1H-isochromene-7-carbonitrile Int-227

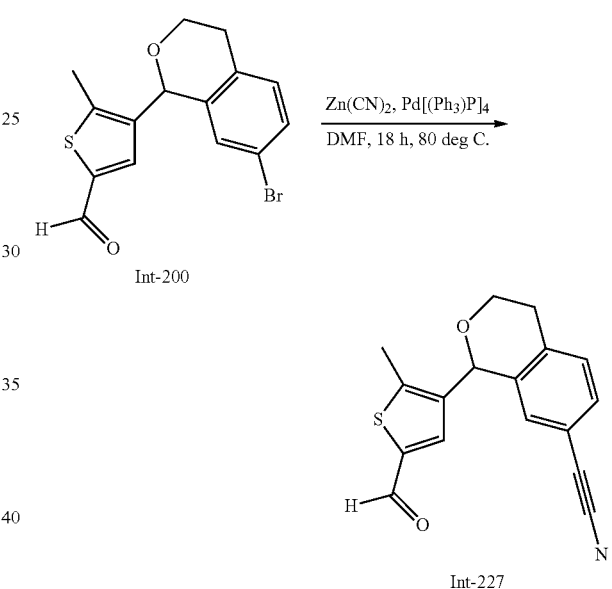

A microwave tube was charged with bromide Int-200 (2.00 g, 5.93 mmol), DMF (7 mL), and zinc cyanide (0.42 g, 3.6 mmol), and the vessel was degassed by bubbling nitrogen through. Tetrakis(triphenylphosphine) palladium (0) (0.548 g, 0.474 mmol) was then added, the vessel was sealed, and the mixture was heated in an 80° C. oil bath for 90 min. After cooling to room temp, the mixture was poured into saturated $NaHCO_3$, the layers were separated, and the aqueous layer was extracted three times with EtOAc. The combined organic portions were washed with brine, dried with anhydrous sodium sulfate, filtered, and concentrated in vacuo. The residue was subjected to ISCO chromatography eluting with a hexane/EtOAc gradient to afford the title compound as a white solid remained (1.27 g, 76%). $^1$H NMR (400 MHz, Chloroform-d) δ 9.76 (s, 1H), 7.57-7.47 (m, 1H), 7.36 (s, 1H), 7.35-7.31 (m, 1H), 7.06 (s, 1H), 5.82 (s, 1H), 4.33-4.15 (m, 1H), 4.02-3.91 (m, 1H), 3.27-3.12 (m, 1H), 3.00-2.83 (m, 1H), 2.60 (s, 3H).

The compounds listed in the table below were prepared in an analogous fashion to that described above starting from the organozinc reagent in step 2 using the solvent and temperature listed.

445

Step 2

| organozinc, solvent, temperature | Product | LC/MS data |
|---|---|---|
| Methylzinc chloride, THF, 60° C. | Int-228 | LCMS (FA): m/z 273.1 (M + 1) |
| Diethylzinc, THF, 60° C. | Int-229 | LCMS (FA): m/z 287.1 (M + 1) |

Example 109: 4-(1'H-Spiro[cyclopropane-1,4'-isochromen]-1'-yl)thiophene-2-carbaldehyde Int-230

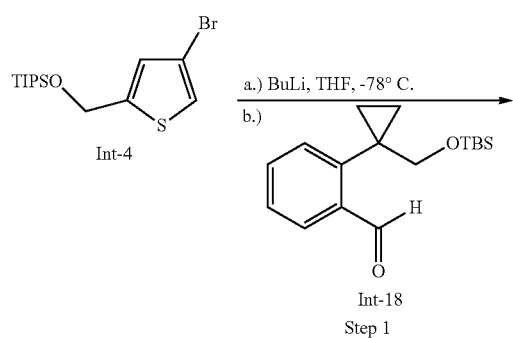

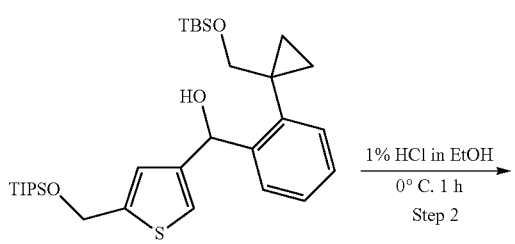

446

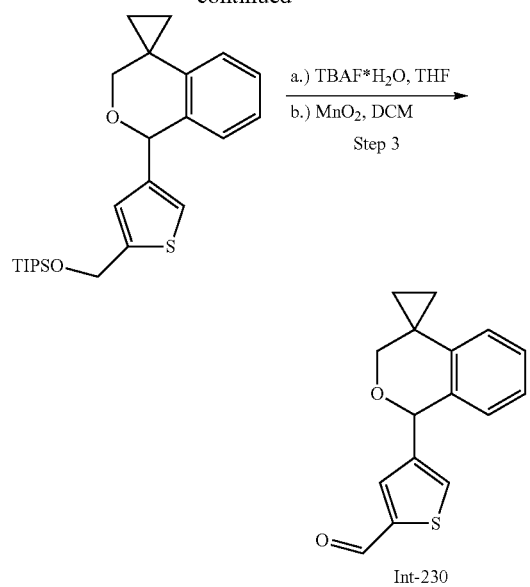

Steps 1 and 2 were performed in an analogous fashion to that described in Example 96, steps 1 and 2 beginning from bromide Int-4 and aldehyde Int-18, using 1% HCl in ethanol in place of TFA for step 2. Step 3 was performed in an analogous fashion to that described in Example 99, Step 4. ¹H NMR (400 MHz, Chloroform-d) δ 9.88 (d, J=1.2 Hz, 1H), 7.74 (d, J=1.3 Hz, 1H), 7.62-7.59 (m, 1H), 7.22 (t, J=7.6 Hz, 1H), 7.13-7.07 (m, 1H), 6.86 (d, J=7.7 Hz, 1H), 6.79 (d, J=8.0 Hz, 1H), 5.99 (s, 1H), 3.79-3.65 (m, 2H), 1.14-1.04 (m, 2H), 1.00-0.91 (m, 2H).

Example 110: 2-Chloro-8-[5-(1,3-dioxolan-2-yl)-2-methyl-3-thienyl]-5,8-dihydro-6H-pyrano[3,4-b]pyridine Int-231 and 5-Methyl-4-(2-methyl-5,8-dihydro-6H-pyrano[3,4-b]pyridin-8-yl)thiophene-2-carbaldehyde Int-232

447

-continued

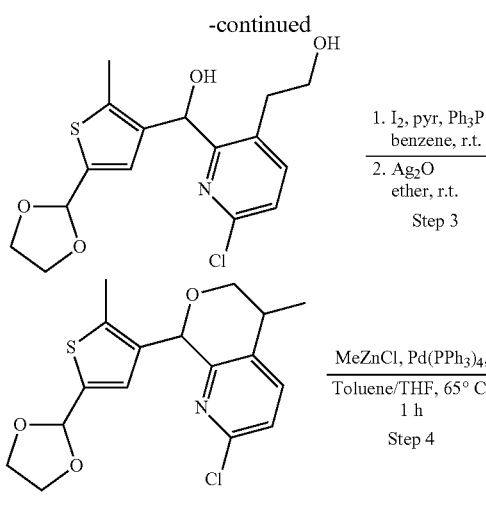

Steps 1, 2, and 3 were performed in an analogous fashion to that described in Example 97, steps 1, 2, and 3 beginning from bromide Int-1 and aldehyde Int-23 to afford 2-chloro-8-[5-(1,3-dioxolan-2-yl)-2-methyl-3-thienyl]-5,8-dihydro-6H-pyrano[3,4-b]pyridine Int-231. Step 4 was performed as follows: In a 100 mL round-bottom flask equipped with a reflux condenser, to a solution of chloropyridine Int-231 (569 mg, 1.68 mmol) in THF (12.0 mL) under atmosphere of argon was added Pd(PPh$_3$)$_4$ (195 mg, 0.17 mmol) followed by 2.0 M of MeZnCl in THF solution (1.68 mL, 3.37 mmol). The reaction was heated at 65° C. for 1 hour. Toluene (6.00 mL, 56.3 mmol) was next added to the reaction and the mixture was heated at 65° C. for 1 hour, during which a black precipitate formed. The reaction was cooled to rt and diluted with brine and EtOAc. The mixture was filtered through a pad of Celite and the layers were separated. The organic layer was concentrated in vacuo, the residue was diluted with 1M HCl and the mixture was stirred for 1 hour. The reaction was quenched with saturated NaHCO$_3$ and diluted with EtOAc. The layers were separated and the aqueous layer was extracted with EtOAc (×2). The combined organic layers were washed with brine, dried over Na$_2$SO$_4$, filtered and concentrated in vacuo. The residue was purified via column chromatography (40 g ISCO 30% EtOAc in hexanes isocratic) to give 415 mg (90%) of the title compound as an off-white solid. $^1$H NMR (400 MHz, DMSO-d6) δ 9.71 (s, 1H), 7.53 (d, J=7.8 Hz, 1H), 7.48 (s, 1H), 7.10 (d, J=7.9 Hz, 1H), 5.82 (s, 1H), 4.07-3.97 (m, 1H), 3.84 (dq, J=11.6, 4.1 Hz, 1H), 3.06-2.92 (m, 1H), 2.84-2.75 (m, 1H), 2.54 (s, 3H), 2.33 (s, 3H).

448

Example 111: 4-(2-Methoxy-5,8-dihydro-6H-pyrano[3,4-b]pyridin-8-yl)-5-methylthiophene-2-carbaldehyde Int-233

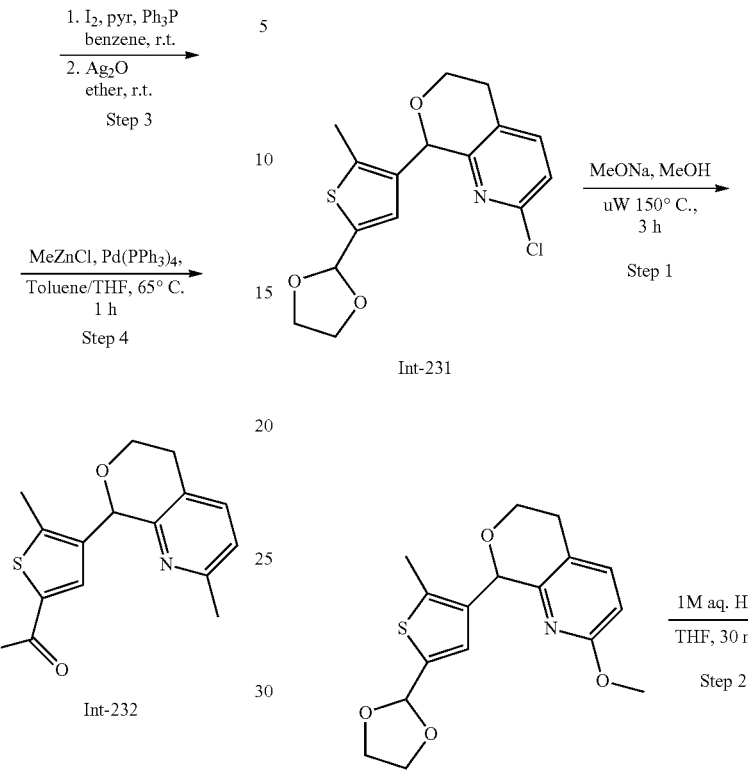

Step 1: 8-[5-(1,3-Dioxolan-2-yl)-2-methyl-3-thienyl]-2-methoxy-5,8-dihydro-6H-pyrano[3,4-b]pyridine A suspension of chloropyrimidine Int-231 (914 mg, 2.70 mmol) and sodium methoxide (731 mg, 13.5 mmol) in methanol (12.0 mL, 296 mmol) was purged with argon, capped and stirred with microwave irradiation at 150° C. for 3 h. The reaction was concentrated in vacuo, and the residue was diluted with saturated NH$_4$Cl, water, and DCM. The layers were separated and the aqueous layer was extracted 2× with DCM. The combined organics were dried over Na$_2$SO$_4$, filtered and concentrated in vacuo. The residue was purified via column chromatography (80 g column, 20% EtOAc in hexanes as eluent) to provide the title compound (0.762 g, 85%). ¹H NMR (400 MHz, Chloroform-d) δ 7.33 (d, J=8.4 Hz, 1H), 6.71 (s, 1H), 6.56 (d, J=8.3 Hz, 1H), 5.93 (s, 1H), 5.71 (s, 1H), 4.16-3.90 (m, 5H), 3.89-3.80 (m, 1H), 3.72 (s, 3H), 3.01-2.90 (m, 1H), 2.77-2.66 (m, 1H), 2.53 (s, 3H).

Step 2: 4-(2-Methoxy-5,8-dihydro-6H-pyrano[3,4-b]pyridin-8-yl)-5-methylthiophene-2-carbaldehyde Step 4 was performed in an analogous fashion to that described in Example 97, step 4 beginning from the above starting material to afford the title compound. ¹H NMR (400 MHz, Chloroform-d) δ 9.70 (s, 1H), 7.42-7.32 (m, 2H), 6.59 (d, J=8.4 Hz, 1H), 5.74 (s, 1H), 4.22-4.13 (m, 1H), 3.95-3.84 (m, 1H), 3.70 (s, 3H), 3.09-2.98 (m, 1H), 2.77-2.69 (m, 1H), 2.65 (s, 3H).

Example 112: 4-(7-Chloro-1,2,3,4-tetrahydronaphthalen-1-yl)thiophene-2-carbaldehyde Int-234

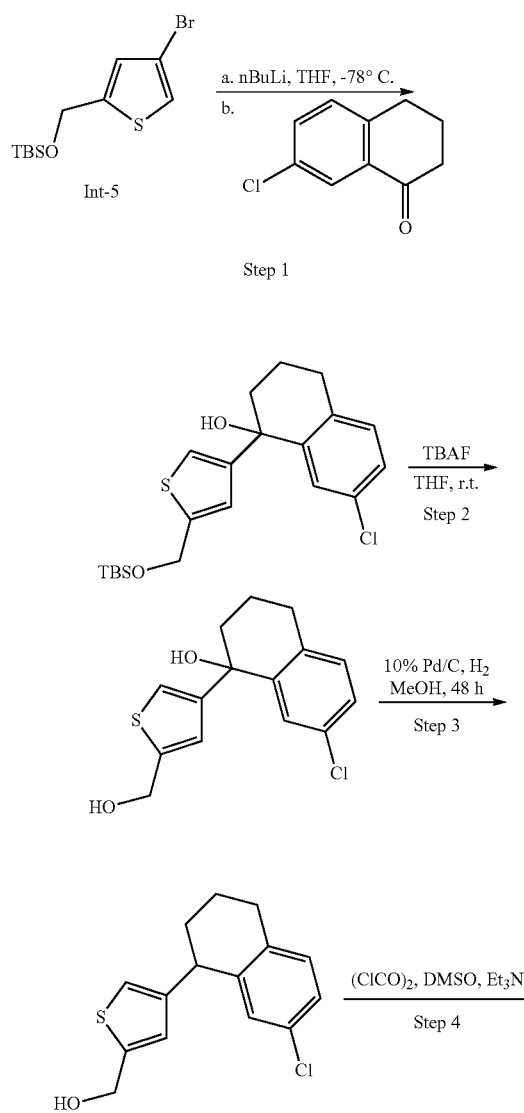

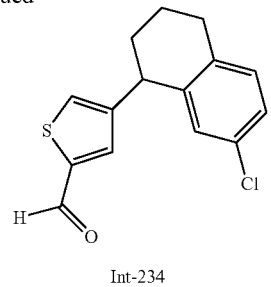

Int-234

Steps 1 and 2 were performed in an analogous fashion to that described in Example 97, steps 1 and 2 beginning from bromide Int-5 and commercially available 7-chloro-1-tetralone. Steps 3 and 4 were performed as follows:

Step 3: [4-(7-Chloro-1,2,3,4-tetrahydronaphthalen-1-yl)-2-thienyl]methanol

A Parr bottle was charged with [4-(7-chloro-3,4-dihydronaphthalen-1-yl)-2-thienyl]methanol (the product of step 2 above, 0.512 g, 1.74 mmol), and methanol (100 mL) and the contents were degassed with nitrogen. 10% palladium on carbon, (0.250 g) was added, the vessel was purged with vacuum and charged with hydrogen gas, and the mixture was stirred under hydrogen atmosphere at 53 psi for 48 h. Mixture was filtered through Celite and the filtrate was concentrated in vacuo. Crude residue was subjected to ISCO chromatography eluting with a hexane/EtOAc gradient to afford the title compound, 0.192 g (40%). ¹H NMR (400 MHz, Chloroform-d) δ 7.11-7.02 (m, 2H), 6.95-6.91 (m, 1H), 6.79-6.72 (m, 2H), 4.81-4.72 (m, 2H), 4.14-4.05 (m, 1H), 2.88-2.70 (m, 2H), 2.13-2.01 (m, 1H), 1.95-1.79 (m, 2H), 1.79-1.68 (m, 2H).

Step 4: 4-(7-Chloro-1,2,3,4-tetrahydronaphthalen-1-yl)thiophene-2-carbaldehyde

A 100 mL round bottom flask under nitrogen was charged with DCM (4.89 mL) and oxalyl chloride (0.182 mL, 2.15 mmol), and the contents were cooled to −60° C. Dimethyl sulfoxide (0.333 mL, 4.69 mmol) was added dropwise with stirring, followed by a solution of [4-(7-chloro-1,2,3,4-tetrahydronaphthalen-1-yl)-2-thienyl]methanol (0.545 g, 1.95 mmol) in DCM (2.51 mL) in a slow stream. The reaction was stirred for 10 min at −60° C. Triethylamine (1.36 mL, 9.77 mmol) was added, and the reaction was allowed to warm to rt. The mixture was poured into saturated NaHCO₃, the layers were separated, and the aqueous layer was extracted three times with DCM. The combined organic portions were washed with brine, dried with anhydrous magnesium sulfate, filtered, and concentrated in vacuo. The resulting residue was subjected to ISCO chromatography eluting with a hexanes/EtOAc gradient to afford the title compound as a yellow oil (0.489 g, 90%). ¹H NMR (400 MHz, Chloroform-d) δ 9.89-9.81 (m, 1H), 7.54-7.48 (m, 1H), 7.29-7.27 (m, 1H), 7.15-7.10 (m, 1H), 7.10-7.06 (m, 1H), 6.91-6.87 (m, 1H), 4.23-4.15 (m, 1H), 2.91-2.74 (m, 2H), 2.20-2.06 (m, 1H), 1.97-1.69 (m, 3H).

The compound listed in the table below was prepared in an analogous fashion to that described in Example 112 starting from the appropriate starting materials:

| Bromide, ketone (starting materials) | Product (Int #) | LC/MS data |
|---|---|---|
| Int-5 | Int-235 | 1H NMR (400 MHz, DMSO-d6) δ 9.87 (d, J = 1.0 Hz, 1H), 7.90 (s, 2H), 7.33 (d, J = 8.0 Hz, 1H), 7.27-7.19 (m, 1H), 7.00 (s, 1H), 4.52 (t, J = 7.9 Hz, 1H), 3.08-2.96 (m, 1H), 2.96-2.83 (m, 1H), 2.60-2.50 (m, 1H), 2.19-2.05 (m, 1H). |

Example 113: 4-(2-Chloro-6,7-dihydro-4H-furo[3,2-c]pyran-4-yl)-5-methylthiophene-2-carbaldehyde Int-236

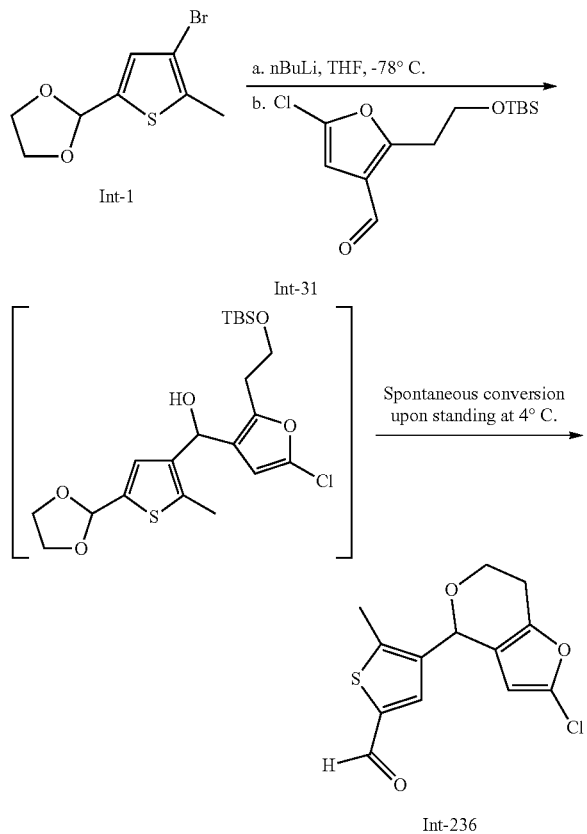

4-(2-Chloro-6,7-dihydro-4H-furo[3,2-c]pyran-4-yl)-5-methylthiophene-2-carbaldehyde To an oven-dried 100 mL 3-neck round bottom flask was added bromide Int-1 (459.7 mg, 1.845 mmol) and THF (7.19 mL). The solution was cooled to −78° C. under argon. 2.50 M of n-BuLi in hexane (0.7949 mL, 1.987 mmol) was added dropwise, keeping the temperature below −70° C., and the resulting mixture was stirred for 10 min. A solution of aldehyde Int-31 (410.0 mg, 1.419 mmol) in THF (1.80 mL) was added, and the resulting solution was stirred for 10 min at −78° C. The reaction was quenched with water and allowed to warm to rt. The biphasic mixture was extracted with EtOAc, washed with brine, dried over Na₂SO₄, filtered, and concentrated. The residue was purified by silica gel column chromatography (0 to 30% EtOAc in hexane) to obtain the intermediate [2-(2-{[tert-butyl(dimethyl)silyl]oxy}ethyl)-5-chloro-3-furyl][5-(1,3-dioxolan-2-yl)-2-methyl-3-thienyl]-methanol (352 mg, 54%) as a yellow oil. ¹H NMR (400 MHz, Chloroform-d) δ 7.07 (s, 1H), 5.99 (s, 1H), 5.86 (s, 1H), 5.69 (d, J=2.9 Hz, 1H), 4.15-4.07 (m, 2H), 4.03-3.95 (m, 2H), 3.85-3.79 (m, 2H), 3.30 (d, J=2.9 Hz, 1H), 3.02-2.85 (m, 2H), 2.38 (s, 3H), 0.87 (s, 9H), 0.04 (s, 6H); LCMS (AA): (M+H) 441/443. This intermediate was stored in the refrigerator for 63 h, during which the oil turned orange, and LC/MS analysis indicated that spontaneous desilylation, cyclization, and acetal deprotection had occurred. The orange oil was purified by silica gel column chromatography (0 to 25% EtOAc in hexane) to give 143 mg (36%) of 4-(2-chloro-6,7-dihydro-4H-furo[3,2-c]pyran-4-yl)-5-methylthiophene-2-carbaldehyde as an off-white solid. ¹H NMR (400 MHz, Chloroform-d) δ 9.75 (s, 1H), 7.47 (s, 1H), 5.83 (s, 1H), 5.61 (s, 1H), 4.21-4.12 (m, 1H), 3.96-3.85 (m, 1H), 2.97-2.85 (m, 1H), 2.73-2.64 (m, 1H), 2.58 (s, 3H); LCMS (AA): (M+H) 283.0/285.0.

Example 114: 4-(7-Chloro-1-methyl-3,4-dihydro-1H-isochromen-1-yl)thiophene-2-carbaldehyde Int-237

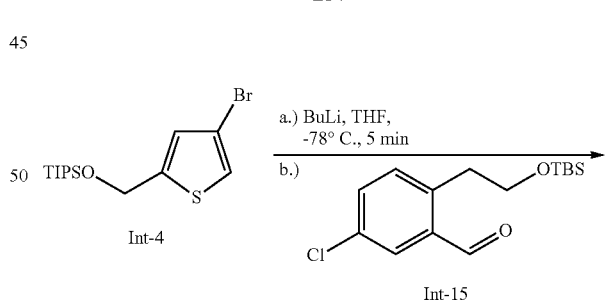

Step 1

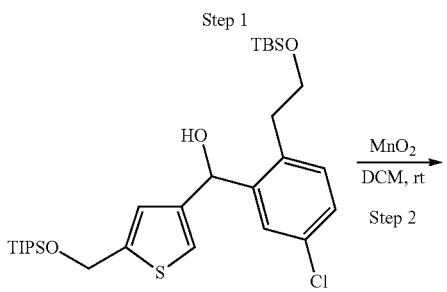

Step 2

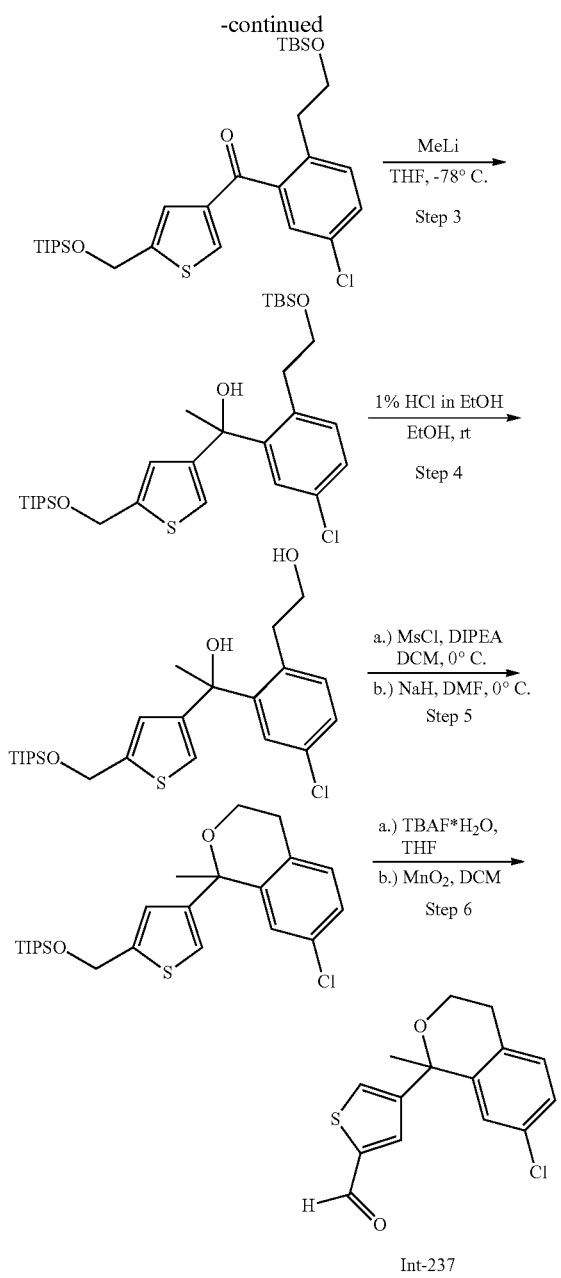

Int-237

Step 1 was performed in an analogous fashion to that described in Example 98, step 1 beginning from bromide Int-4 and aldehyde Int-15 to afford [2-(2-{[tert-butyl(dimethyl)silyl]oxy}ethyl)-5-chlorophenyl](5-{[(triisopropylsilyl)oxy]methyl}-3-thienyl)methanol. Steps 2-6 were performed as follows:

Step 2: [2-(2-{[tert-Butyl(dimethyl)silyl]oxy}ethyl)-5-chlorophenyl](5-{[(triisopropylsilyl)oxy]methyl}-3-thienyl)methanone To a solution of [2-(2-{[tert-butyl(dimethyl)silyl]oxy}ethyl)-5-chlorophenyl](5-{[(triisopropylsilyl)oxy]methyl}-3-thienyl)methanol (950 mg, 1.67 mmol) in DCM (20 mL) was added MnO2 (1.45 g, 16.7 mmol) at rt, and the mixture was stirred for 16 h. The reaction was filtered through a Celite pad and the filter cake was rinsed with DCM several times. The filtrate was concentrated in vacuo and the residue was purified by ISCO silica gel column chromatography (80 g, eluting with 0% EtOAc in hexane for 3 min then gradient to 5% EtOAc in Hexane, 50 mL/min flow) to give 722 mg (76%) of the title compound as a colorless oil. $^1$H NMR (400 MHz, DMSO-d6) δ 7.97 (d, J=1.5 Hz, 1H), 7.53 (dd, J=8.3, 2.2 Hz, 1H), 7.45-7.40 (m, 2H), 7.33 (d, J=1.2 Hz, 1H), 4.97 (d, J=1.0 Hz, 2H), 3.64 (t, J=7.0 Hz, 2H), 2.73 (t, J=7.0 Hz, 2H), 1.21-1.09 (m, 3H), 1.05 (d, J=6.7 Hz, 18H), 0.76 (s, 9H), −0.13 (s, 6H).

Step 3: 1-[2-(2-{[tert-Butyl(dimethyl)silyl]oxy}ethyl)-5-chlorophenyl]-1-(5-{[(triisopropylsilyl)oxy]methyl}-3-thienyl)ethanol To a solution of [2-(2-{[tert-butyl(dimethyl)silyl]oxy}ethyl)-5-chlorophenyl](5-{[(triisopropylsilyl)oxy]methyl}-3-thienyl)methanone (720 mg, 1.27 mmol) in THF (15 mL) was added dropwise 1.6 M of MeLi in Et2O solution (0.87 mL, 1.40 mmol) at −78° C. under atmosphere of argon and the reaction was stirred for 30 min. The reaction was quenched by addition of water (80 mL), the layers were separated, and the aqueous layer was extracted with EtOAc (80 mL×3). The combined organic layers were washed with brine, dried over Na2SO4, filtered, and concentrated in vacuo. The residue was purified by ISCO silica gel column chromatography (40 g, eluting with 5% EtOAc in hexane, 40 mL/min flow) to give 351 mg (47%) of product as a colorless oil. $^1$H NMR (400 MHz, DMSO-d6) δ 7.56 (d, J=2.2 Hz, 1H), 7.23 (dd, J=8.2, 2.2 Hz, 1H), 7.17 (d, J=8.2 Hz, 1H), 7.09 (d, J=1.4 Hz, 1H), 6.62 (s, 1H), 5.73 (s, 1H), 4.83 (s, 2H), 3.39 (t, J=7.0 Hz, 2H), 2.72 (t, J=7.0 Hz, 2H), 1.78 (s, 3H), 1.18-1.03 (m, 3H), 1.01 (d, J=6.4 Hz, 18H), 0.80 (s, 9H), −0.09 (s, 6H).

Step 4: 1-[5-Chloro-2-(2-hydroxyethyl)phenyl]-1-(5-{[(triisopropylsilyl)oxy]methyl}-3-thienyl)ethanol To a solution of 1-[2-(2-{[tert-butyl(dimethyl)silyl]oxy}ethyl)-5-chlorophenyl]-1-(5-{[(triisopropylsilyl)oxy]methyl}-3-thienyl)ethanol (340 mg, 0.58 mmol) in EtOH (5.0 mL, 85.6 mmol) was added 1% HCl in EtOH solution (5.00 mL, 0.60 mmol) at rt and the reaction was stirred for 1 hour. The reaction was quenched by addition of saturated NaHCO3 (50 mL) and concentrated in vacuo. To the residue was added water and the aqueous mixture was extracted with EtOAc (100 mL×3). The combined organic layers were dried over Na2SO4, filtered, and concentrated in vacuo. The residue was purified by ISCO silica gel column chromatography (24 g, eluting with 20% EtOAc in hexane, 40 mL/min flow) to give 218 mg (80%) of the title compound as a colorless solid. $^1$H NMR (400 MHz, DMSO-d6) δ 7.54 (d, J=2.2 Hz, 1H), 7.23 (dd, J=8.2, 2.2 Hz, 1H), 7.19 (d, J=8.2 Hz, 1H), 7.11 (d, J=1.5 Hz, 1H), 6.61 (s, 1H), 5.77 (s, 1H), 4.83 (s, 2H), 4.53 (t, J=5.1 Hz, 1H), 3.31 (s, 2H), 2.76-2.66 (m, 1H), 2.65-2.55 (m, 1H), 1.79 (s, 3H), 1.14-1.03 (m, 3H), 1.00 (d, J=6.4 Hz, 18H).

Step 5: {[4-(7-Chloro-1-methyl-3,4-dihydro-1H-isochromen-1-yl)-2-thienyl]methoxy}(triisopropyl)silane To a solution of 1-[5-chloro-2-(2-hydroxyethyl)phenyl]-1-(5-{[(triisopropylsilyl)oxy]methyl}-3-thienyl)ethanol (180 mg, 0.38 mmol) in DCM (5.0 mL) was added N,N-diisopropylethylamine (0.13 mL, 0.77 mmol) followed by methanesulfonyl chloride (32.7 uL, 0.42 mmol) at rt, and the mixture was stirred for 30 min. The reaction was quenched by addition of water (60 mL) and extracted with DCM (60 mL×3). The combined organic layers were dried over $Na_2SO_4$, filtered, and concentrated in vacuo. The crude residue was dissolved in DMF (2.0 mL) and the mixture was cooled to 0° C. NaH 60% in mineral oil (30.7 mg, 0.77 mmol) was added to the solution at 0° C. and the reaction was stirred for 1 hour. The reaction was quenched by addition of water (50 mL), the layers were separated, and the aqueous layer was extracted with EtOAc (50 mL×3). The combined organic layers were dried over $Na_2SO_4$, filtered, and concentrated in vacuo. The residue was purified by ISCO silica gel column chromatography (24 g, eluting with 0% EtOAc in hexane for 2 min then gradient to 10% EtOAc in hexane over 15 min, 40 mL/min flow) to give 68 mg (39%) of title compound. $^1$H NMR (400 MHz, Chloroform-d) δ 7.20-7.12 (m, 2H), 7.07 (d, J=8.1 Hz, 1H), 6.87 (s, 1H), 6.68 (d, J=1.5 Hz, 1H), 4.91 (d, J=0.8 Hz, 2H), 3.87 (ddd, J=11.6, 5.9, 3.0 Hz, 1H), 3.73-3.63 (m, 1H), 2.99 (ddd, J=16.2, 10.2, 6.0 Hz, 1H), 2.64 (dt, J=16.4, 3.3 Hz, 1H), 1.82 (s, 3H), 1.19-1.10 (m, 3H), 1.07 (d, J=6.1 Hz, 18H).

Step 6: 4-(7-Chloro-1-methyl-3,4-dihydro-1H-isochromen-1-yl) thiophene-2-carbaldehyde Step 6 was performed in an analogous fashion to that described in Example 35, Step 4 to provide the title compound. $^1$H NMR (400 MHz, Chloroform-d) δ 9.89 (s, 1H), 7.73 (s, 1H), 7.32 (s, 1H), 7.22 (dd, J=8.2, 2.0 Hz, 1H), 7.16-7.08 (m, 2H), 3.93 (ddd, J=11.6, 5.7, 3.4 Hz, 1H), 3.70-3.59 (m, 1H), 3.01 (ddd, J=15.9, 9.8, 5.8 Hz, 1H), 2.69 (dt, J=16.4, 3.6 Hz, 1H), 1.88 (s, 3H).

Example 115: 4-(7-Chloro-3,4-dihydro-1H-isochromen-1-yl)-5-methyl-1,3-thiazole-2-carbaldehyde Int-238

Steps 1 and 2 were performed in an analogous fashion to that described in Example 96, beginning from bromide Int-8 and aldehyde Int-15 using HCl/THF in place of TFA for step 2. Step 3 was performed in an analogous fashion to that described in Example 99, step 4b to afford the title compound. $^1$H NMR (400 MHz, DMSO-$d_6$) δ 9.78 (s, 1H), 7.26 (d, J=1.0 Hz, 2H), 6.75 (s, 1H), 6.11 (s, 1H), 4.19-4.11 (m, 1H), 3.92-3.83 (m, 1H), 3.02-2.92 (m, 1H), 2.86-2.75 (m, 1H), 2.57 (s, 3H).

Example 116: 4-(1-Methyl-1,2,3,4-tetrahydroisoquinolin-1-yl)thiophene-2-carbaldehyde Int-239

457

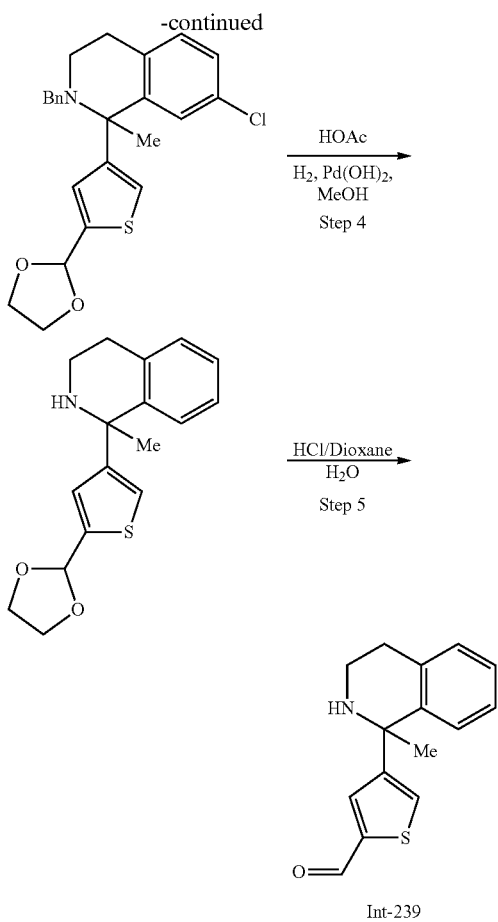

Steps 1 and 2: 7-Chloro-1-[5-(1,3-dioxolan-2-yl)-3-thienyl]-3,4-dihydroisoquinoline Step 1 was performed in an analogous fashion to that described in Example 100, step 1 beginning from 2-(4-bromothiophen-2-yl)-1,3-dioxolane and imine Int-50 as starting materials. Step 2 was performed in an analogous fashion to that described in Example 99, step 4b. LCMS (FA) M+1 320.

Step 3: 2-Benzyl-7-chloro-1-[5-(1,3-dioxolan-2-yl)-3-thienyl]-1-methyl-1,2,3,4-tetrahydroisoquinoline To a solution of 7-chloro-1-[5-(1,3-dioxolan-2-yl)-3-thienyl]-3,4-dihydroisoquinoline (0.173 g, 0.541 mmol) in CH₃CN (20.0 mL, 383 mmol) was added benzyl bromide (0.120 g, 0.703 mmol) and the solution was stirred at reflux for 2 hrs. The reaction was concentrated in vacuo and the residue was suspended in THF (30.0 mL, 3.70E2 mmol). 3.00 M of methylmagnesium bromide in ether (0.541 mL, 1.62 mmol) was added and the reaction was stirred at rt for 3 hrs. Quenched by pouring into 30 ml saturated NH₄Cl solution, then extracted with 30 ml EtOAc two times. The combined organic layers were dried over Na₂SO₄, filtered, and concentrated in vacuo. The residue was purified by flash column (40 g, eluent 20-100% EtOAc in hexane) to provide the title compound (0.143 g, 62%). LCMS (AA) M+1 426

458

Step 4: 1-[5-(1,3-Dioxolan-2-yl)-3-thienyl]-1-methyl-1,2,3,4-tetrahydroisoquinoline To a solution of 2-benzyl-7-chloro-1-[5-(1,3-dioxolan-2-yl)-3-thienyl]-1-methyl-1,2,3,4-tetrahydroisoquinoline (0.722 g, 1.69 mmol) in methanol (40.0 mL, 987 mmol) and acetic acid (1.00 mL, 17.6 mmol) was added 0.20 g 20% palladium hydroxide and the reaction mixture was stirred under atmosphere of hydrogen (balloon pressure) overnight. The reaction mixture was filtered and concentrated in vacuo. The residue was purified by flash column (40 g, eluent 20-100% EtOAc in hexane) to provide the title compound (138 mg, 24%). LCMS (AA) M+1 302.

Step 5: (1-Methyl-1,2,3,4-tetrahydroisoquinolin-1-yl)thiophene-2-carbaldehyde

To a solution of 1-[5-(1,3-dioxolan-2-yl)-3-thienyl]-1-methyl-1,2,3,4-tetrahydroisoquinoline (0.1108 g, 0.3676 mmol) in water (1.0 mL, 56 mmol) was added toluenesulfonic acid (15.0 mL, 93.2 mmol) and the reaction was stirred at rt for 1 hr. Reaction was poured into 50 ml water and extracted twice with 20 ml DCM. Combined organic layers were washed with 20 ml saturated NaHCO₃ solution, then dried over MgSO4, filtered and concentrated to afford the title compound (75 mg, 80% yield). LCMS (AA) M+1 258.

The compound listed in the table below was prepared in an analogous fashion to that described in Example 116, except that Step 4 was not performed:

| Entry | Product (Int #) | LC/MS data |
|---|---|---|
| 1 | Int-240 | LCMA (AA) M + 1 292 |

Example 117: 4-(7-Chloro-2-methyl-1,2,3,4-tetrahydroisoquinolin-1-yl)thiophene-2-carbaldehyde Int-241

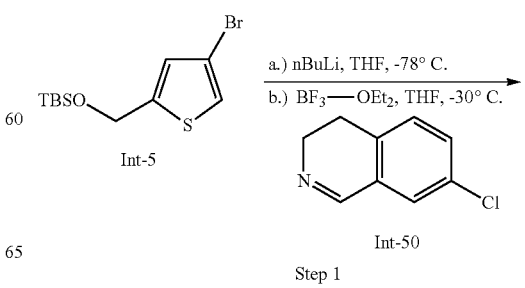

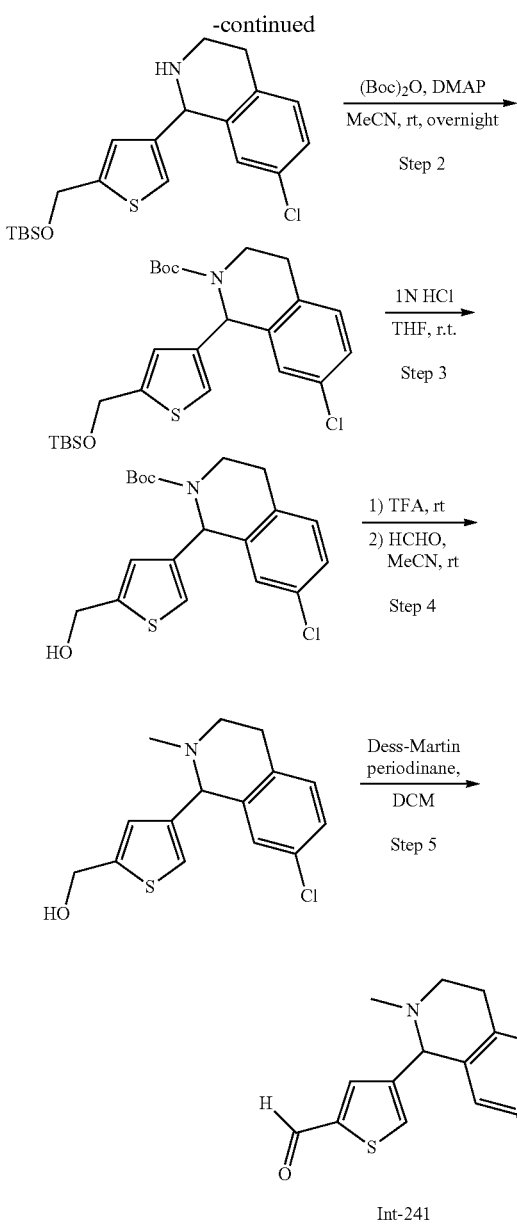

Steps 1, 2, and 3: tert-Butyl 7-chloro-1-[5-(hydroxymethyl)-3-thienyl]-3,4-dihydroisoquinoline-2(1H)-carboxylate Steps 1 and 2 were performed in an analogous fashion to that described in Example 100, steps 1 and 2 beginning from Int-5 and imine Int-50. Step 3 was performed in an analogous fashion to that described in Example 97, step 4. $^1$H NMR (400 MHz, Chloroform-d) δ 7.14-7.02 (m, 3H), 6.78-6.72 (m, 2H), 4.75 (s, 2H), 4.30 (s, 1H), 3.15-3.02 (m, 2H), 2.84-2.75 (m, 1H), 2.61 (s, 1H), 2.60-2.53 (m, 1H), 2.27 (s, 3H).

Step 4: [4-(7-Chloro-2-methyl-1,2,3,4-tetrahydroisoquinolin-1-yl)-2-thienyl]methanol A solution of tert-butyl 7-chloro-1-[5-(hydroxymethyl)-3-thienyl]-3,4-dihydroisoquinoline-2(1H)-carboxylate (220 mg, 0.58 mmol) in TFA (4.00 mL, 51.9 mmol) was stirred for 5 min at rt and then concentrated in vacuo. The residue was azeotroped with toluene twice and the residue was dried under high vacuum for 2 h. The residue was dissolved in CH$_3$CN (5.0 mL), at which point was added 10 M of formaldehyde in water solution (0.24 mL, 2.90 mmol) followed by sodium triacetoxyborohydride (246 mg, 1.16 mmol) at rt, and the mixture was stirred for 30 min. The reaction was que by addition of saturated NaHCO$_3$ (60 mL) and extracted with EtOAc (60 mL×3). The combined organic layers were dried over Na$_2$SO$_4$, filtered, and concentrated in vacuo. The residue was purified by silica gel column chromatography (24 g, eluting with 1% MeOH in DCM to 10% MeOH in DCM, 40 mL/min flow) to give 150 mg (88%) of the title compound as a colorless amorphous solid. $^1$H NMR (400 MHz, Chloroform-d) δ 7.14-7.02 (m, 3H), 6.78-6.72 (m, 2H), 4.75 (s, 2H), 4.30 (s, 1H), 3.15-3.02 (m, 2H), 2.84-2.75 (m, 1H), 2.61 (s, 1H), 2.60-2.53 (m, 1H), 2.27 (s, 3H).

Step 5: 4-(7-Chloro-2-methyl-1,2,3,4-tetrahydroisoquinolin-1-yl)thiophene-2-carbaldehyde To a solution of [4-(7-chloro-2-methyl-1,2,3,4-tetrahydroisoquinolin-1-yl)-2-thienyl]methanol (145 mg, 0.49 mmol) in DCM (3.0 mL) was added Dess-Martin periodinane (314 mg, 0.74 mmol) at rt, and the mixture was stirred for 30 min. The reaction was quenched by addition of saturated NaHCO$_3$ (50 mL) and extracted with DCM (50 mL×3). The combined organic layers were dried over Na$_2$SO$_4$, filtered, and concentrated in vacuo. The residue was purified by silica gel column chromatography (24 g, eluting with 10% EtOAc in DCM for 5 min then gradient to 30% EtOAc in DCM, 40 mL/min flow) to give 80 mg (60%) of the title compound as a colorless solid. $^1$H NMR (400 MHz, Methanol-d4) δ 9.83 (d, J=1.2 Hz, 1H), 7.85 (s, 1H), 7.68 (d, J=1.4 Hz, 1H), 7.21-7.12 (m, 2H), 6.73 (s, 1H), 4.61 (s, 1H), 3.15-3.05 (m, 2H), 2.95-2.85 (m, 1H), 2.72-2.62 (m, 1H), 2.29 (s, 3H). LCMS (FA): m/z=292.3 (M+H).

The compound listed in the table below was prepared in an analogous fashion to that described in Example 117, beginning with bromide Int-6:

| Entry | Product (Int #) | LC/MS data |
|---|---|---|
| 1 | Int-242 | LCMS (FA): m/z = 326.2 (M + H) |

Example 118: tert-Butyl 2-chloro-8-(2-chloro-5-formyl-3-thienyl)-5,8-dihydro-1,7-naphthyridine-7(6H)-carboxylate Int-243

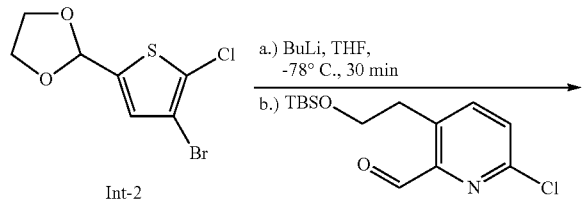

Int-2    Int-23

Step 1

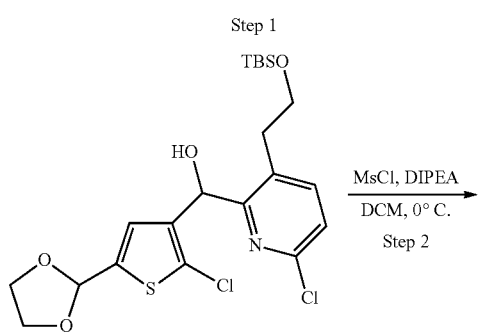

Step 2

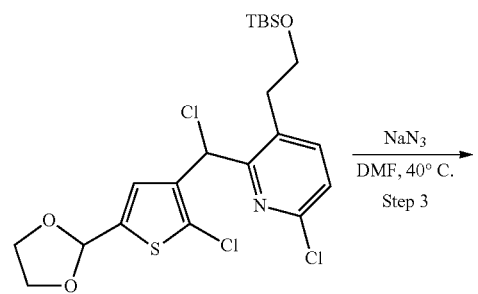

Step 3

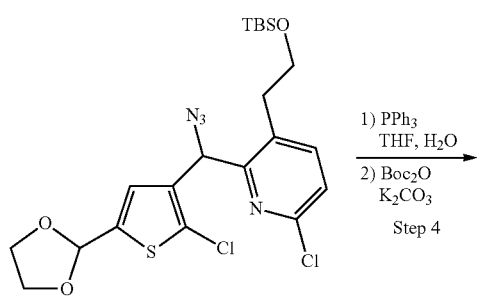

Step 4

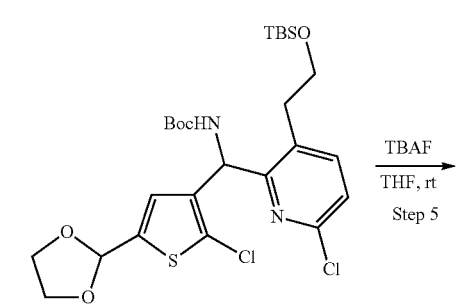

Step 5

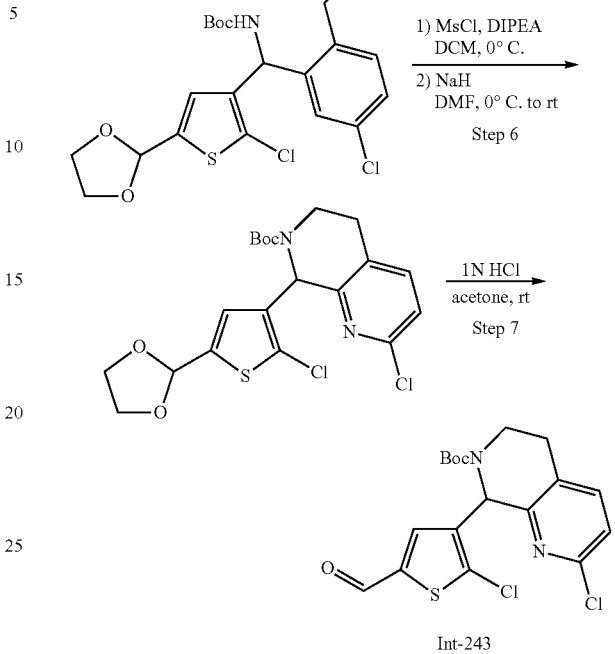

Int-243

Step 1: [3-(2-{[tert-Butyl(dimethyl)silyl]oxy}ethyl)-6-chloropyridin-2-yl][2-chloro-5-(1,3-dioxolan-2-yl)-3-thienyl]methanol Step 1 was performed in an analogous fashion to that described in Example 96, step 1 beginning from Int-2 and aldehyde Int-23. The remaining steps were performed as follows:

Step 2: 3-(2-{[tert-Butyl(dimethyl)silyl]oxy}ethyl)-6-chloro-2-{chloro[2-chloro-5-(1,3-dioxolan-2-yl)-3-thienyl]methyl}pyridine To a solution of [3-(2-{[tert-butyl(dimethyl)silyl]oxy}ethyl)-6-chloropyridin-2-yl][2-chloro-5-(1,3-dioxolan-2-yl)-3-thienyl]methanol (270 mg, 0.55 mmol) in DCM (6.0 mL) was added N,N-diisopropylethylamine (0.14 mL, 0.83 mmol) followed by methanesulfonyl chloride (44.7 uL, 0.58 mmol) at 0° C., and the reaction was stirred for 16 h. The reaction was quenched by addition of water (50 mL) and extracted with DCM (50 mL×3). The combined organic layers were washed with brine, dried over $Na_2SO_4$, filtered, and concentrated in vacuo. The residue was purified by silica gel column chromatography (24 g, eluting with 10% EtOAc in hexanes, 40 mL/min flow) to give 231 mg (82%) of the title compound as a colorless oil. $^1$H NMR (400 MHz, DMSO-d6) δ 7.77 (d, J=8.2 Hz, 1H), 7.49 (d, J=8.1 Hz, 1H), 7.41 (s, 1H), 6.58 (s, 1H), 6.02 (s, 1H), 4.05-3.96 (m, 2H), 3.96-3.89 (m, 2H), 3.86 (dt, J=11.3, 5.8 Hz, 1H), 3.77-3.69 (m, 1H), 2.94 (t, J=5.7 Hz, 2H), 0.77 (s, 9H), −0.11 (s, 3H), −0.12 (s, 3H).

Step 3: 2-{Azido[2-chloro-5-(1,3-dioxolan-2-yl)-3-thienyl]methyl}-3-(2-{[tert-butyl(dimethyl)silyl]oxy}ethyl)-6-chloropyridine To a solution of 3-(2-{[tert-butyl(dimethyl)silyl]oxy}ethyl)-6-chloro-2-{chloro[2-chloro-5-(1,3-dioxolan-2- yl)-3-thienyl]methyl}pyridine (225 mg, 0.44 mmol) in DMF (2.0 mL) was added sodium azide (43.1 mg, 0.66 mmol) at rt, and the reaction was stirred for 1 hour at 40° C. The reaction was quenched by addition of water (50 mL) and extracted with hexane:EtOAc (1:1) solution (50 mL×3). The combined organic layers were dried over $Na_2SO_4$, filtered, and concentrated in vacuo. The residue was purified by silica gel column chromatography (24 g, eluting with 5% EtOAc in hexane, 40 mL/min flow) to give 222 mg (97%) of the title compound as a colorless oil. $^1H$ NMR (400 MHz, DMSO-d6) δ 7.76 (d, J=8.2 Hz, 1H), 7.51 (d, J=8.1 Hz, 1H), 7.01 (s, 1H), 6.04 (s, 1H), 5.98 (s, 1H), 4.03-3.94 (m, 2H), 3.94-3.85 (m, 2H), 3.76 (dt, J=10.6, 5.5 Hz, 1H), 3.58 (dt, J=10.1, 6.7 Hz, 1H), 2.77 (t, J=6.2 Hz, 2H), 0.77 (s, 9H), −0.12 (s, 3H), −0.14 (s, 3H).

Step 4: tert-Butyl {[3-(2-{[tert-butyl(dimethyl)silyl]oxy}ethyl)-6-chloropyridin-2-yl][2-chloro-5-(1,3-dioxolan-2-yl)-3-thienyl]methyl}carbamate To a solution of 2-{azido[2-chloro-5-(1,3-dioxolan-2-yl)-3-thienyl]methyl}-3-(2-{[tert-butyl(dimethyl)silyl]oxy}ethyl)-6-chloropyridine (1.52 g, 2.95 mmol) in THF (20.0 mL) was added water (2.00 mL, 111 mmol) followed by $PPh_3$ (850 mg, 3.24 mmol) at rt, and the reaction was stirred for 11 h. To the mixture was added $K_2CO_3$ (611 mg, 4.42 mmol) followed by $Boc_2O$ (965 mg, 4.42 mmol) at rt and the resulting mixture was stirred for 12 h. The reaction was quenched by addition of water (100 mL) and extracted with EtOAc (100 mL×3). The combined organic layers were dried over $Na_2SO_4$, filtered, and concentrated in vacuo. The residue was purified by silica gel column chromatography (80 g, eluting with 5% EtOAc in hexane for 15 min then gradient to 30% EtOAc in hexane over 10 min, 40 mL/min flow) to give 1.62 g (93%) of the title compound as a colorless amorphous solid. $^1H$ NMR (400 MHz, DMSO-d6) δ 7.76 (d, J=8.6 Hz, 1H), 7.67 (d, J=8.1 Hz, 1H), 7.39 (d, J=8.0 Hz, 1H), 7.12 (s, 1H), 6.12 (d, J=8.2 Hz, 1H), 5.94 (s, 1H), 4.04-3.94 (m, 2H), 3.94-3.85 (m, 2H), 3.82-3.67 (m, 2H), 2.95-2.77 (m, 2H), 1.36 (s, 9H), 0.79 (s, 9H), −0.10 (s, 3H), −0.12 (s, 3H).

Step 5: tert-Butyl {[2-chloro-5-(1,3-dioxolan-2-yl)-3-thienyl][6-chloro-3-(2-hydroxyethyl)pyridin-2-yl]methyl}carbamate To a solution of tert-butyl {[3-(2-{[tert-butyl(dimethyl)silyl]oxy}ethyl)-6-chloropyridin-2-yl][2-chloro-5-(1,3-dioxolan-2-yl)-3-thienyl]methyl}carbamate (190 mg, 0.32 mmol) in THF (5.0 mL) was added TBAF hydrate (108 mg, 0.387 mmol) at rt and the reaction was stirred for 30 min. The reaction was concentrated in vacuo and the residue was purified by silica gel column chromatography (12 g, eluting with 50% EtOAc in hexane for 5 min then gradient to 80% EtOAc in hexane over 10 min, 40 mL/min flow) to give 148 mg (97%) of the title compound as a colorless amorphous solid. $^1H$ NMR (400 MHz, DMSO-d6) δ 7.74 (d, J=8.0 Hz, 1H), 7.70 (d, J=8.1 Hz, 1H), 7.38 (d, J=8.1 Hz, 1H), 7.10 (s, 1H), 6.12 (d, J=8.4 Hz, 1H), 5.94 (s, 1H), 4.77 (t, J=5.0 Hz, 1H), 4.01-3.95 (m, 2H), 3.95-3.86 (m, 2H), 3.62-3.52 (m, 2H), 2.88-2.71 (m, 2H), 1.36 (s, 9H).

Step 6: tert-Butyl 2-chloro-8-[2-chloro-5-(1,3-dioxolan-2-yl)-3-thienyl]-5,8-dihydro-1,7-naphthyridine-7(6H)-carboxylate To a solution of tert-butyl {[2-chloro-5-(1,3-dioxolan-2-yl)-3-thienyl][6-chloro-3-(2-hydroxyethyl)pyridin-2-yl]methyl}carbamate (500 mg, 1.05 mmol) in DCM (15 mL) was added N,N-diisopropylethylamine (0.37 mL, 2.10 mmol) followed by methanesulfonyl chloride (0.09 mL, 1.16 mmol) at 0° C., and the reaction was stirred for 10 min. The reaction was quenched by addition of water (100 mL) and extracted with DCM (100 mL×2). The combined organic layers were dried over $Na_2SO_4$, filtered, and concentrated in vacuo. The residue was dissolved in DMF (7.0 mL) and then NaH 60% in mineral oil (63.1 mg, 1.58 mmol) was added to the solution at 0° C. The reaction as stirred for 18 h at room temp. The reaction was quenched by addition of water (100 mL) and extracted with EtOAc (100 mL×3). The combined organic layers were dried over $Na_2SO_4$, filtered, and concentrated in vacuo. The residue was purified by silica gel column chromatography (Gold 40 g, eluting with 20% EtOAc in hexane, 35 mL/min flow) to give 445 mg (93%) of the title compound as a colorless amorphous solid. $^1H$ NMR (400 MHz, DMSO-d6) δ 7.76 (d, J=8.2 Hz, 1H), 7.39 (d, J=8.1 Hz, 1H), 6.91 (s, 1H), 6.12 (s, 1H), 5.89 (s, 1H), 4.15-4.04 (m, 1H), 4.03-3.95 (m, 2H), 3.94-3.84 (m, 2H), 3.29-3.19 (m, 1H), 2.94-2.83 (m, 2H), 1.39 (s, 9H).

Step 7: tert-Butyl 2-chloro-8-(2-chloro-5-formyl-3-thienyl)-5,8-dihydro-1,7-naphthyridine-7(6H)-carboxylate To a solution of tert-butyl 2-chloro-8-[2-chloro-5-(1,3-dioxolan-2-yl)-3-thienyl]-5,8-dihydro-1,7-naphthyridine-7(6H)-carboxylate (470 mg, 1.03 mmol) in acetone (18.8 mL) was added 1.0 M of HCl in water (5.00 mL, 5.00 mmol) at rt and the reaction was stirred for 15 h. The reaction was quenched by addition of saturated $NaHCO_3$ (50 mL) and the mixture was concentrated in vacuo. The resulting aqueous mixture was transferred to a separatory funnel and extracted with EtOAc (100 mL×3). The combined organic layers were dried over $Na_2SO_4$, filtered, and concentrated in vacuo. The residue was purified by silica gel column chromatography (40 g, eluting with 30% EtOAc in hexane for 10 min then gradient to 50% EtOAc in Hexane over 10 min, 40 mL/min flow) to give 411 mg (97%) of the title compound as a colorless amorphous solid. $^1H$ NMR (400 MHz, DMSO-d6) δ 9.72 (s, 1H), 7.84-7.75 (m, 2H), 7.41 (d, J=8.1 Hz, 1H), 6.17 (s, 1H), 4.19-4.07 (m, 1H), 3.39-3.28 (m, 1H), 2.98-2.87 (m, 2H), 1.38 (s, 9H).

Example 119: 5-Chloro-4-(7-chloro-3,4-dihydro-1H-pyrano[4,3-c]pyridin-1-yl)thiophene-2-carbaldehyde Int-244

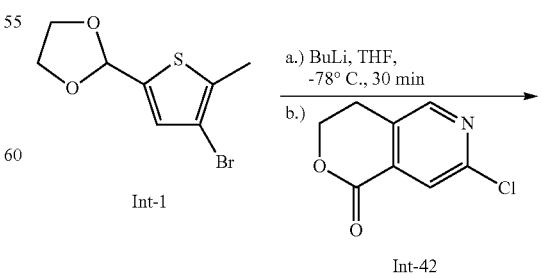

Step 1

465
-continued

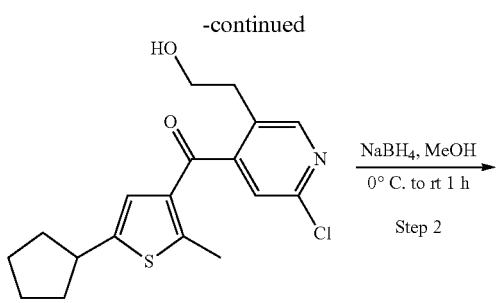

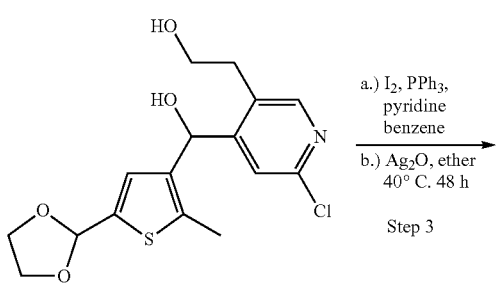

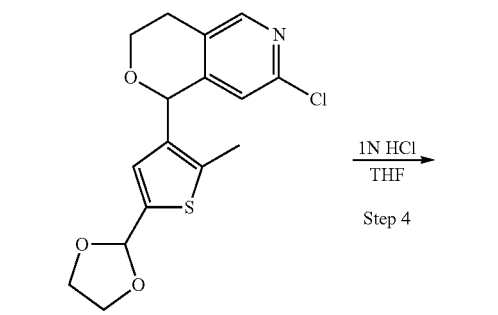

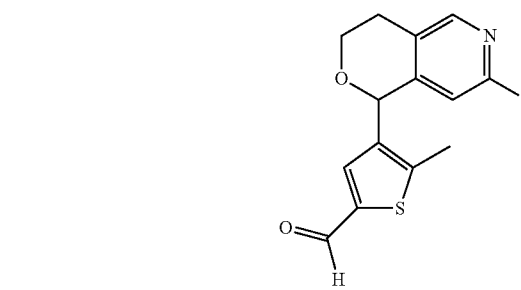

Int-244

Steps 1 and 2 were performed in an analogous fashion to that described in Example 98, Steps 1 and 2 starting from the appropriate starting materials Int-1 and Int-42. Steps 3 and 4 were performed in an analogous fashion to Example 97, steps 3 and 4 to afford the title compound. $^1$H NMR (400 MHz, DMSO-d6) δ 9.74 (s, 1H), 8.34 (s, 1H), 7.61 (s, 1H), 6.84 (s, 1H), 5.95 (s, 1H), 4.10 (ddd, J=11.5, 5.5, 3.8 Hz, 1H), 3.87 (ddd, J=11.5, 9.3, 4.1 Hz, 1H), 3.00 (ddd, J=15.2, 9.3, 5.5 Hz, 1H), 2.90-2.79 (m, 1H), 2.56 (s, 3H).

466

Example 120: 4-(3,4-Dihydro-1H-benzo[4,5]imidazo[2,1-c][1,4]oxazin-1-yl)-5-methylthiophene-2-carbaldehyde Int-245

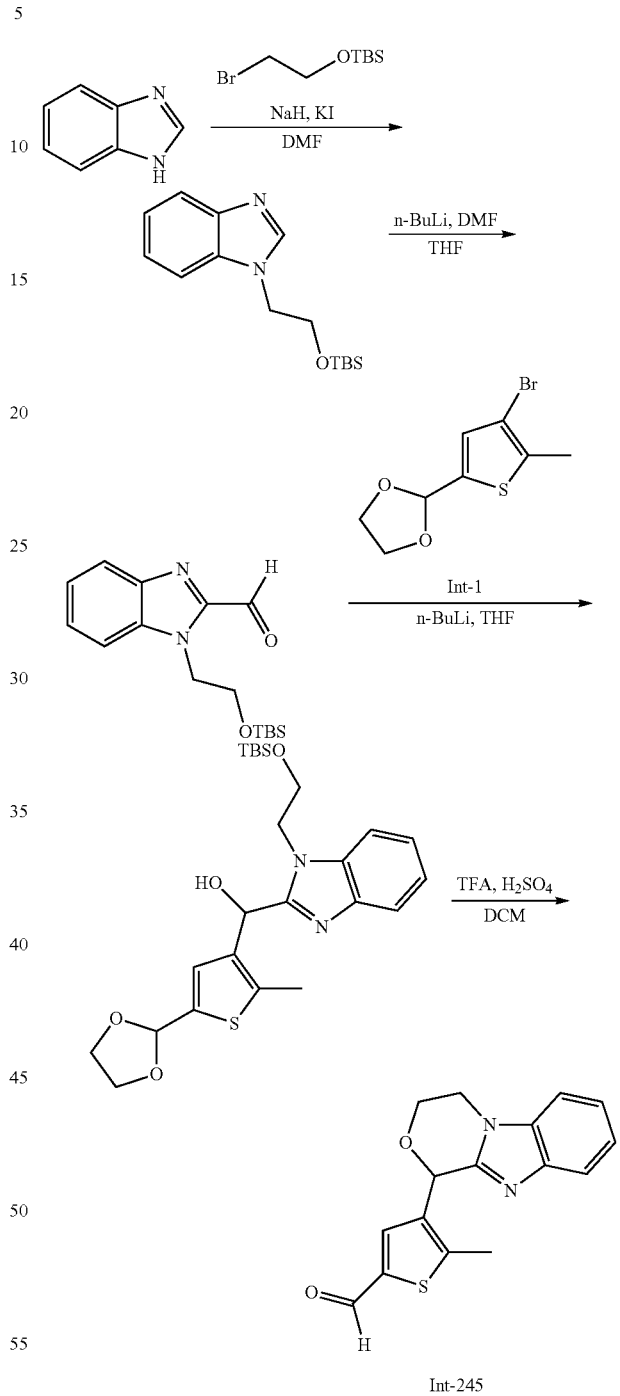

Step 1: 1-(2-{[tert-Butyl(dimethyl)silyl]oxy}ethyl)-1H-benzimidazole

Into a round bottom flask was added 1H-benzimidazole (0.802 g, 6.78 mmol) dissolved into DMF (20.0 mL) and sodium hydride (0.543 g, 13.57 mmol) was slowly added to the solution at 0° C. Potassium iodide (3.38 g, 20.35 mmol) and (2-bromoethoxy)-tert-butyldimethylsilane (Int-1, 2.91 mL, 13.57 mmol) were added to the slurry and the reaction was heated at 40° C. overnight. Methanol (3 mL) was added to quench the reaction and the solution was poured into water. This was then extracted using EtOAc (3×). The combined organic layers were washed with water, dried with MgSO$_4$, filtered and concentrated. The residue was purified by ISCO silica gel column chromatography (40 g column, 30-100% EtOAc/Hex over 15 min) to afford 1.15 g (61%) of the title compound. $^1$H NMR (400 MHz, Chloroform-d) δ 8.11 (s, 1H), 7.99-7.91 (m, 1H), 7.57-7.51 (m, 1H), 7.44-7.40 (m, 2H), 4.42 (t, J=5.2 Hz, 2H), 4.08 (t, J=5.2 Hz, 2H), 0.96 (s, 9H), 0.00 (s, 6H).

Step 2: 1-(2-{[tert-Butyl(dimethyl)silyl]oxy}ethyl)-1H-benzimidazole-2-carbaldehyde Into a flask 1-(2-{[tert-butyl(dimethyl)silyl]oxy}ethyl)-1H-benzimidazole (1.05 g, 3.80 mmol) was dissolved into THF (100.0 mL) and cooled to −78° C. A solution of 2.50 M of n-BuLi in hexane (2.28 mL, 5.70 mmol) was added via syringe at −78° C. DMF (0.833 g, 11.39 mmol) was then added to the solution at −78° C. The reaction was stirred for 30 min, and then acetic acid (0.684 g, 11.39 mmol) in 1 mL of THF was added to quench the reaction. The solvent was removed and the residue was purified by ISCO silica gel column chromatography (80 g column, 0-50% EtOAc/Hex) to afford 0.823 g (71%) of the title compound. $^1$H NMR (400 MHz, Chloroform-d) δ 10.36 (s, 1H), 8.15 (dt, J=8.2, 1.0 Hz, 1H), 7.81 (dt, J=8.4, 0.9 Hz, 1H), 7.69 (ddd, J=8.3, 7.1, 1.2 Hz, 1H), 7.61 (ddd, J=8.2, 7.0, 1.2 Hz, 1H), 4.96 (t, J=5.3 Hz, 2H), 4.22 (t, J=5.3 Hz, 2H), 0.94 (s, 9H), 0.00 (s, 6H).

Step 3: [1-(2-{[tert-Butyl(dimethyl)silyl]oxy}ethyl)-1H-benzimidazol-2-yl][5-(1,3-dioxolan-2-yl)-2-methyl-3-thienyl]methanol A solution of 2.50 M of n-BuLi in hexane (1.95 mL, 4.88 mmol) was added to a flask and dissolved in THF (60.0 mL). The mixture was cooled to −78° C., and 1-(2-{[tert-butyl(dimethyl)silyl]oxy}ethyl)-1H-benzimidazole-2-carbaldehyde (0.825 g, 2.71 mmol) dissolved in THF (10.0 mL) was added to the solution quickly. The resulting solution stirred for 5 min, then 2-(4-bromo-5-methyl-2-thienyl)-1,3-dioxolane (0.945 g, 3.79 mmol) was added to the solution at −78° C. The reaction stirred for 30 min, then quenched with a saturated aqueous NH$_4$Cl solution. The mixture was extracted with EtOAc (3×) and the combined organic layers were concentrated to dryness. The residue was purified by ISCO silica gel column chromatography (40 g column, 0-100% EtOAc/Hex over 15 min) to afford 0.732 g (57%) of the title compound. LCMS (FA): m/z=475.2 (M+H).

Step 4: 4-(3,4-Dihydro-1H-benzo[4,5]imidazo[2,1-c][1,4]oxazin-1-yl)-5-methylthiophene-2-carbaldehyde

[1-(2-{[tert-Butyl(dimethyl)silyl]oxy}ethyl)-1H-benzimidazol-2-yl][5-(1,3-dioxolan-2-yl)-2-methyl-3-thienyl]methanol (0.721 g, 1.52 mmol) was dissolved into DCM (3.0 mL). TFA (10.0 mL, 130 mmol) was added to the solution and the reaction was stirred for 30 min at RT. Then 98% H$_2$SO$_4$ (4 mL) was added to the reaction and the resulting mixture was stirred at RT for 6 h. The solution was poured into water and extracted with DCM (3×). The combined organic layers were washed with a saturated NaHCO$_3$ solution and the organic layer was concentrated to dryness. The residue was purified by ISCO silica gel column chromatography (40 g column, 50-100% EtOAc/Hex over 15 min) to afford 0.187 g (41%) of the title compound. LCMS (AA): m/z=299.0 (M+H).

Example 121: 4-(3-Methylbenzyl)-1,3-thiazole-2-carbaldehyde. Int-246

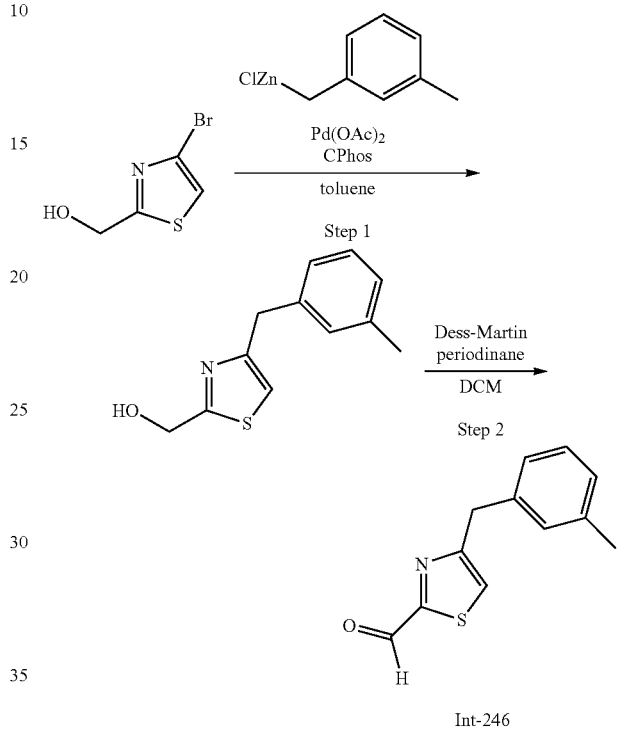

Step 1: [4-(3-Methylbenzyl)-1,3-thiazol-2-yl]methanol

A microwave reaction tube was charged with (4-bromothiazol-2-yl)-methanol (300 mg, 1.55 mmol), Pd(OAc)$_2$ (24.3 mg, 0.11 mmol) and 2-dicyclohexylphosphino-2',6'-bis(N,N-dimethylamino)biphenyl (CPhos) (74.3 mg, 0.17 mmol), and the contents were dissolved in toluene (5.0 mL). This reaction vessel was purged with argon and then sealed with cap. To this mixture was added dropwise 0.5 M of 3-methylbenzylzinc chloride in THF (7.73 mL, 3.87 mmol) at rt, and the resulting mixture was stirred for 4 h at room temp. The reaction was diluted with EtOAc and the organic layer was washed with 0.5 N HCl followed by water and brine. The organic layer was dried over Na$_2$SO$_4$, filtered, and concentrated in vacuo. The residue was purified by ISCO column chromatography (20%-50% EtOAc in hexanes as eluent) to give 94 mg (28%) of the title compound as light yellow sticky oil. $^1$H NMR (400 MHz, Chloroform-d) δ 7.20 (t, J=7.5 Hz, 1H), 7.10-7.02 (m, 3H), 6.79 (s, 1H), 4.92 (d, J=4.7 Hz, 2H), 4.07 (s, 2H), 2.59-2.50 (br s, 1H), 2.33 (s, 3H).

Step 2: 4-(3-Methylbenzyl)-1,3-thiazole-2-carbaldehyde

To a solution of [4-(3-methylbenzyl)-1,3-thiazol-2-yl] methanol (170 mg, 0.78 mmol) in DCM (10.0 mL) was added Dess-Martin periodinane (493 mg, 1.16 mmol) at rt, and the mixture was stirred for 1 hour. The reaction was quenched by addition of saturated NaHCO$_3$ and the mixture was extracted with DCM (×3). The combined organic layers were washed with brine and dried over Na$_2$SO$_4$. The suspension was filtered and concentrated in vacuo. The residue was purified by ISCO column chromatography (10% EtOAc in hexanes as eluent) to give 157 mg (93%) of the title compound as a colorless oil. $^1$H NMR (400 MHz, Chloroform-d) δ 9.98 (d, J=1.2 Hz, 1H), 7.30-7.18 (m, 2H), 7.12-7.04 (m, 3H), 4.20 (s, 2H), 2.34 (s, 3H)

Example 122: 4-(3-Bromobenzyl)-5-methyl-1,3-thiazole-2-carbaldehyde Int-247

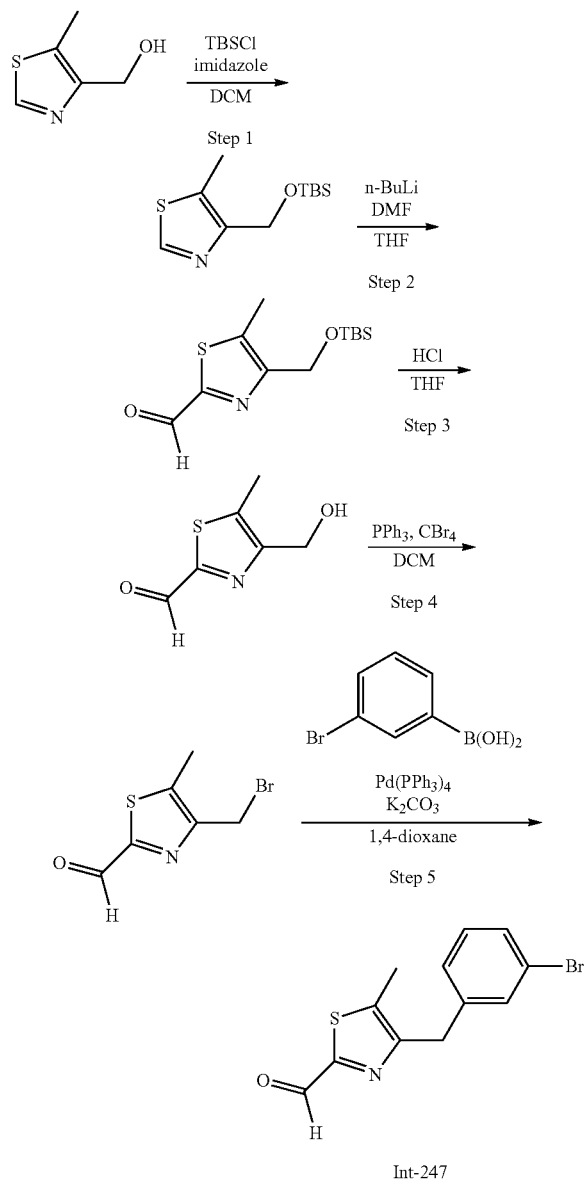

Int-247

Step 1: 4-({[tert-Butyl(dimethyl)silyl]oxy}methyl)-5-methyl-1,3-thiazole

To a solution of (5-methylthiazol-4-yl)methanol (431 mg, 3.34 mmol) in DCM (10.0 mL) was added imidazole (341 mg, 5.00 mmol) followed by TBSCl (553 mg, 3.67 mmol) at rt, and the mixture was stirred for 1 hour. The reaction was quenched by addition of 0.5 M HCl and the mixture was extracted with DCM (×2). The combined organic layers were washed with brine, dried over Na$_2$SO$_4$, filtered, and concentrated in vacuo. The residue was purified by ISCO column chromatography (10% EtOAc in hexanes as eluent) to give 507 mg of the title compound as colorless oil. $^1$H NMR (400 MHz, Chloroform-d) δ 8.52 (s, 1H), 4.82 (s, 2H), 2.50 (s, 3H), 0.91 (s, 9H), 0.09 (s, 6H).

Step 2: 4-({[tert-Butyl(dimethyl)silyl]oxy}methyl)-5-methyl-1,3-thiazole-2-carbaldehyde To a solution of 4-({[tert-butyl(dimethyl)silyl]oxy}methyl)-5-methyl-1,3-thiazole (455 mg, 1.87 mmol) in THF (15.0 mL) was added dropwise 2.50 M of n-BuLi in hexane (0.79 mL, 1.96 mmol) at −78° C. under atmosphere of argon and the mixture was stirred for 1 hour. To the mixture was added DMF (0.16 mL, 2.06 mmol) at −78° C. and the resulting mixture was stirred for 30 min. The reaction was quenched by addition of saturated NH$_4$Cl and extracted with EtOAc (×3). The combined organic layers were dried over Na$_2$SO$_4$, filtered, and concentrated in vacuo. The residue was purified by ISCO column chromatography (5% EtOAc in hexanes as eluent) to give 360 mg of the title compounds as a light yellow oil. $^1$H NMR (400 MHz, Chloroform-d) δ 9.87 (s, 1H), 4.87 (s, 2H), 2.60 (s, 3H), 0.91 (s, 9H), 0.11 (s, 6H).

Step 3: 4-(Hydroxymethyl)-5-methyl-1,3-thiazole-2-carbaldehyde

To a solution of 4-({[tert-butyl(dimethyl)silyl]oxy}methyl)-5-methyl-1,3-thiazole-2-carbaldehyde (360 mg, 1.33 mmol) in THF (2.5 mL) was added 3.0 M of HCl (0.72 mL, 2.16 mmol) and the mixture was stirred for 1 hour at rt. The reaction was quenched by addition of saturated NaHCO$_3$ and extracted with EtOAc (×3). The combined organic layers were washed with brine, dried over Na$_2$SO$_4$, filtered, and concentrated in vacuo. The residue was purified by ISCO column chromatography (60% EtOAc in hexanes as eluent) to give 112 mg of the title compound as colorless solid. $^1$H NMR (400 MHz, Chloroform-d) δ 9.88 (s, 1H), 4.79 (s, 2H), 2.57 (s, 3H), 2.46-2.07 (br s, 1H).

Step 4: 4-(Bromomethyl)-5-methyl-1,3-thiazole-2-carbaldehyde

To a solution of 4-(hydroxymethyl)-5-methyl-1,3-thiazole-2-carbaldehyde (542 mg, 3.45 mmol) in DCM (15.0 mL) was added PPh$_3$ (1.09 g, 4.14 mmol) followed by CBr$_4$ (1.37 g, 4.14 mmol) at rt, and the mixture was stirred for 1 hour. The reaction was concentrated in vacuo and the residue was purified by ISCO column chromatography (10% EtOAc in hexanes as eluent) to give 493 mg of the title compound as colorless oil. $^1$H NMR (400 MHz, DMSO-d$_6$) δ 9.84 (s, 1H), 4.85 (s, 2H), 2.58 (s, 3H).

Step 5: 4-(3-Bromobenzyl)-5-methyl-1,3-thiazole-2-carbaldehyde

A microwave reaction vial was charged with 4-(bromomethyl)-5-methyl-1,3-thiazole-2-carbaldehyde (493 mg, 2.24 mmol), 3-bromophenylboronic acid (562 mg, 2.69 mmol), K$_2$CO$_3$ (619 mg, 4.48 mmol), and Pd(PPh$_3$)$_4$ (129 mg, 0.11 mmol). To the vial was added 1,4-dioxane (16.4 mL) followed by water (3.3 mL) at rt. After the vial was sealed with cap under atmosphere of argon, the reaction was heated at 70° C. for 90 min in an oil bath. The reaction was quenched by addition of water and extracted with EtOAc. The combined organic layers were washed with brine and dried over $Na_2SO_4$. The suspension was filtered and concentrated in vacuo. The residue was purified by ISCO column chromatography (10% EtOAc in hexanes as eluent) followed by preparative HPLC to give 237 mg of the title compound a light yellow oil. LCMS (FA): m/z=298.1 (M+H).

Example 123: 4-(3-Chlorobenzyl)-5-methyl-1,3-thiazole-2-carbaldehyde Int-248

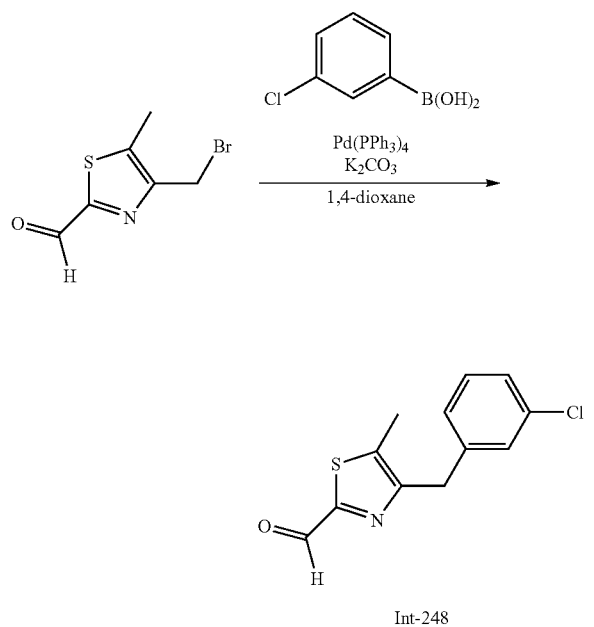

Int-248

Example 124: 5-Benzyl-1,3-thiazole-2-carbaldehyde. Int-249

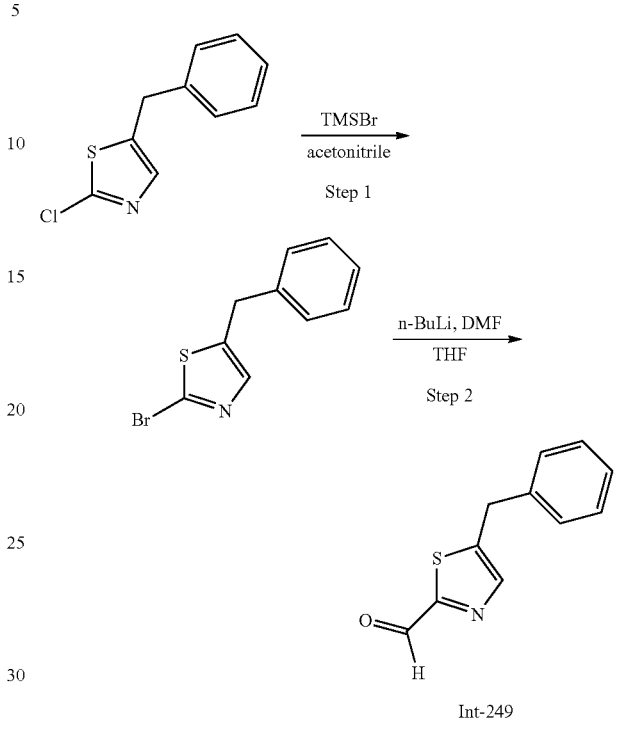

Int-249

Step 1: 5-Benzyl-2-bromo-1,3-thiazole

Bromotrimethylsilane (2.20 mL, 17 mmol) was added to a solution of 5-benzyl-2-chloro-1,3-thiazole (0.70 g, 3.30 mmol) in MeCN (10.0 mL). The solution was heated at 60° C. overnight. The solvent was then removed via rotovap. The resulting solid was washed with 1N NaOH and the solid was collected via filtration. The solid was washed with water then dried in the oven overnight to give 780 mg (92%) of the title compound. $^1$H NMR (400 MHz, Chloroform-d) δ 7.43-7.16 (m, 6H), 4.10 (s, 2H).

Step 2: 5-Benzyl-1,3-thiazole-2-carbaldehyde

To a solution of 5-benzyl-2-bromo-1,3-thiazole (250 mg, 0.98 mmol) in THF (10.0 mL) was added dropwise 2.5 M of n-BuLi in hexane (0.43 mL, 1.08 mmol) at −78° C. under an atmosphere of argon and the resulting brown solution was kept at −78° C. for 30 min. To the mixture was added dropwise a solution of DMF (0.76 mL, 9.84 mmol) in THF (1.00 mL). After 30 min, the reaction was quenched with saturated $NH_4Cl$. This mixture was allowed to warm to rt and stir. It was diluted with water and aqueous layer was then extracted with EtOAc (×3). The combined organic layers were dried over $Na_2SO_4$, filtered and concentrated in vacuo. The residue was purified by ISCO column chromatography (0%-30% EtOAc in hexanes as eluent) to give 157 mg (78%) of the title compound. $^1$H NMR (400 MHz, Chloroform-d) δ 9.90 (s, 1H), 7.83 (s, 1H), 7.42-7.18 (m, 5H), 4.24 (s, 2H).

Step 1: 4-(3-Chlorobenzyl)-5-methyl-1,3-thiazole-2-carbaldehyde

A microwave reaction vial was charged with 4-(bromomethyl)-5-methyl-1,3-thiazole-2-carbaldehyde (225 mg, 1.02 mmol), 3-chlorophenylboronic acid (192 mg, 1.23 mmol), $K_2CO_3$ (283 mg, 2.05 mmol), and $Pd(PPh_3)_4$ (59.1 mg, 0.05 mmol). To the vial was added 1,4-dioxane (7.5 mL) followed by water (1.5 mL) at rt. After the vial was sealed with cap under atmosphere of argon, the reaction was heated at 70° C. for 1 hour. The reaction was quenched by addition of water and the mixture was extracted with EtOAc (×3). The combined organic layers were washed with brine and dried over $Na_2SO_4$. The suspension was filtered and concentrated in vacuo. The residue was purified by ISCO silica gel column chromatography (5% EtOAc in hexanes as eluent) to give 151 mg (56%) of the title compound as colorless oil. $^1$H NMR (400 MHz, Chloroform-d) δ 9.87 (s, 1H), 7.24-7.17 (m, 3H), 7.10 (d, J=7.0 Hz, 1H), 4.13 (s, 2H), 2.50 (s, 3H).

Example 125: 4-[{[tert-Butyl(dimethyl)silyl]oxy}(3-chlorophenyl)methyl]-5-methyl-1,3-thiazole-2-carbaldehyde. Int-250

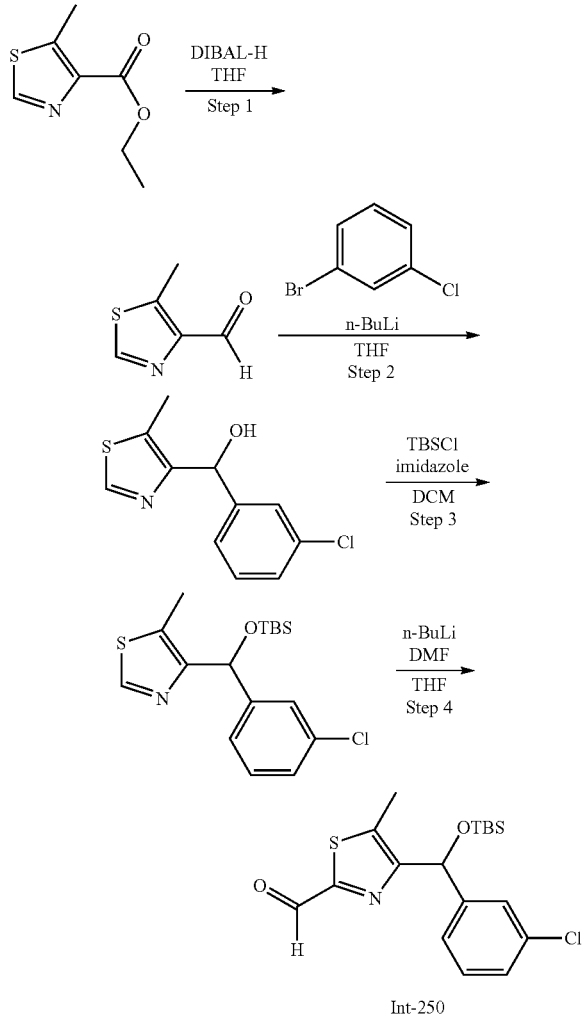

Step 1: 5-Methylthiazole-4-carbaldehyde

To a solution of ethyl 5-methylthiazole-4-carboxylate (794 mg, 5.05 mmol) in THF (21.6 mL) was added dropwise 1.0 M of DIBAL-H in toluene (5.56 mL, 5.56 mmol) under an atmosphere of argon at −78° C. and the reaction was stirred for 30 min. The reaction was quenched with water (12.4 mL) at −78° C. The reaction was warmed to rt. The reaction was poured into 300 mL of saturated Rochelle salt in water and diluted with EtOAc. The layers were stirred together for 1 hour. The layers were separated and the aqueous layer was extracted with EtOAc (×3). The combined organics were washed with brine, dried over $Na_2SO_4$, filtered and concentrated in vacuo. The residue was purified by ISCO column chromatography (10% EtOAc in DCM as eluent) to give 642 mg (54%) of the title compound as yellow oil. $^1$H NMR (400 MHz, Chloroform-d) δ 10.22 (s, 1H), 8.62 (s, 1H), 2.83 (s, 3H).

Step 2: rac-(3-Chlorophenyl)(5-methyl-1,3-thiazol-4-yl)methanol

3-Chlorobromobenzene (0.65 mL, 5.50 mmol) in THF (24 mL) was cooled at −78° C. under an atmosphere of argon. To the solution was added dropwise 2.5 M of n-BuLi in hexane (2.31 mL, 5.78 mmol) and the solution was allowed to stir at −78° C. for 30 min. To the mixture was added a solution of 5-methylthiazole-4-carbaldehyde (350 mg, 2.75 mmol) in THF (12.3 mL) and the reaction was stirred at −78° C. for 1 hour. The resulting mixture was quenched with saturated $NH_4Cl$ and diluted with EtOAc and water. The layers were separated and the organic layer was washed with brine, dried over $Na_2SO_4$, filtered and concentrated in vacuo. The residue was purified by ISCO column chromatography (10% EtOAc in DCM as eluent) to give 660 mg (56%) of the title compound as colorless oil. $^1$H NMR (400 MHz, Methanol-$d_4$) δ 8.70 (s, 1H), 7.50-7.43 (m, 1H), 7.32-7.19 (m, 3H), 6.01 (s, 1H), 2.51 (s, 3H). LCMS (FA): 241.9 (M+1).

Step 3: rac-4-[{[tert-Butyl(dimethyl)silyl]oxy}(3-chlorophenyl)methyl]-5-methyl-1,3-thiazole To a solution of rac-(3-chlorophenyl)(5-methyl-1,3-thiazol-4-yl)methanol (372 mg, 1.55 mmol) in DCM (10.0 mL) was added imidazole (279 mg, 4.10 mmol) followed by TBSCl (257 mg, 1.71 mmol) at rt and the reaction was stirred overnight. The reaction mixture was concentrated in vacuo and the residue was purified by ISCO column chromatography (5% EtOAc in hexanes as eluent) to give 549 mg (74%) of the title compound as colorless oil. $^1$H NMR (400 MHz, Chloroform-d) δ 8.51 (s, 1H), 7.40 (s, 1H), 7.30-7.25 (m, 1H), 7.23 (t, J=7.6 Hz, 1H), 7.18 (dt, J=7.8, 1.7 Hz, 1H), 6.14 (s, 1H), 2.43 (s, 3H), 0.92 (s, 9H), 0.08 (s, 3H), −0.07 (s, 3H).

Step 4: rac-4-[{[tert-Butyl(dimethyl)silyl]oxy}(3-chlorophenyl)methyl]-5-methyl-1,3-thiazole-2-carbaldehyde To a solution of rac-4-[{[tert-butyl(dimethyl)silyl]oxy}(3-chlorophenyl)methyl]-5-methyl-1,3-thiazole (405 mg, 1.14 mmol) in THF (9.0 mL) was added dropwise 2.50 M of n-BuLi in hexane (0.48 mL, 1.20 mmol) at −78° C. under atmosphere of argon and the mixture was stirred for 15 min. To the mixture was added DMF (0.10 mL, 1.29 mmol) at −78° C. and the resulting mixture was stirred for 1 hour. The reaction was quenched by addition of saturated $NH_4Cl$ and extracted with $Et_2O$ (×3). The combined organic layers were dried over $Na_2SO_4$, filtered, and concentrated in vacuo. The residue was purified by ISCO column chromatography (5% EtOAc in hexanes as eluent) to give 437 mg (87%) of the product as a clear colorless oil. $^1$H NMR (400 MHz, Chloroform-d) δ 9.88 (s, 1H), 7.41 (s, 1H), 7.30-7.19 (m, 3H), 6.19 (s, 1H), 2.48 (s, 3H), 0.93 (s, 9H), 0.10 (s, 3H), −0.05 (s, 3H).

Example 126: 5-Chloro-4-[(3-chlorophenyl)sulfanyl]thiophene-2-carbaldehyde Int-251

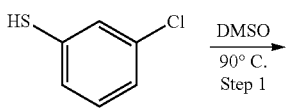

-continued

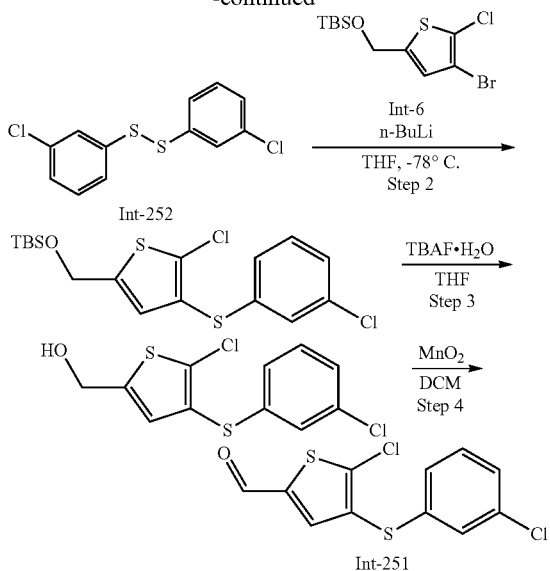

Step 1: Bis(3-chlorophenyl) disulfide Int-252

A solution of 3-chlorothiophenol (3.74 g, 25.8 mmol) in DMSO (1.83 mL, 25.8 mmol) was stirred and heated at 90° C. for 4 hrs under argon. The reaction was cooled to rt. The reaction was then diluted with EtOAc, washed with water (2×), brine, dried over Na$_2$SO$_4$, filtered, and concentrated in vacuo to give 3.66 g (98%) of the title compound as a yellow oil. $^1$H NMR (400 MHz, DMSO-d$_6$) δ 7.61-7.56 (m, 2H), 7.53-7.48 (m, 2H), 7.44 (t, J=7.8 Hz, 2H), 7.41-7.35 (m, 2H).

Step 2: tert-Butyl({5-chloro-4-[(3-chlorophenyl) sulfanyl]-2-thienyl}methoxy)dimethylsilane In a 3-neck 100 mL round bottom flask [(4-bromo-5-chloro-2-thienyl)methoxy](tert-butyl)dimethylsilane (Int-6, 0.268 g, 0.784 mmol) was dissolved in THF (6.700 mL) under an argon atmosphere, and the solution was cooled at −78° C. To the solution was added dropwise 2.50 M of n-BuLi in hexane (0.345 mL, 0.862 mmol), and the yellow solution was stirred for 30 mins at −78° C. To the mixture was added bis(3-chlorophenyl) disulfide (0.338 g, 1.18 mmol) in a minimal amount of THF, and the reaction was stirred for 15 mins. The reaction was then quenched by addition of saturated NH$_4$Cl (100 mL), and the reaction was warmed to rt. The mixture was extracted with EtOAc (2×). The combined organic layers were washed with brine, dried over Na$_2$SO$_4$, filtered, and concentrated in vacuo. The yellow oil was purified by silica gel column chromatography (0% to 5% EtOAc in hexane) to give 454 mg of impure title compound as an oil. $^1$H NMR (400 MHz, Chloroform-d) δ 7.21-7.10 (m, 3H), 7.07-7.02 (m, 1H), 6.69 (m, 1H), 4.76 (d, J=1.0 Hz, 2H), 0.92 (s, 9H), 0.10 (s, 6H).

Step 3: {5-Chloro-4-[(3-chlorophenyl)sulfanyl]-2-thienyl}methanol

To a solution of tert-butyl({5-chloro-4-[(3-chlorophenyl) sulfanyl]-2-thienyl}methoxy)dimethylsilane (496.0 mg, 1.223 mmol) in THF (18.1 mL) was added a solution of TBAF hydrate (512.8 mg, 1.835 mmol) in THF (5.43 mL) at rt, and the yellow solution was stirred for 1 h. The reaction was quenched by addition of water (20 mL) and extracted with EtOAc (25 mL×2). The combined organic layers were washed with brine, dried over Na$_2$SO$_4$, filtered, and concentrated in vacuo. The residue was purified by silica gel column chromatography (0% to 50% EtOAc in Hexane) and then repurified (0 to 25% EtOAc in hexane) to give 273 mg (73%) of the title compound as a cloudy yellow oil. $^1$H NMR (400 MHz, DMSO-d$_6$) δ 7.37 (t, J=7.9 Hz, 1H), 7.32-7.28 (m, 1H), 7.19-7.16 (m, 1H), 7.13-7.09 (m, 1H), 6.95-6.92 (m, 1H), 5.72 (t, J=5.8 Hz, 1H), 4.59 (dd, J=5.8, 0.9 Hz, 2H); LCMS (AA): m/z=272.9 (M−OH)

Step 4: 5-Chloro-4-[(3-chlorophenyl)sulfanyl]thiophene-2-carbaldehyde

To a solution of {5-chloro-4-[(3-chlorophenyl)sulfanyl]-2-thienyl}methanol (270.5 mg, 0.9288 mmol) in DCM (34.24 mL) was added MnO$_2$ (807.5 mg, 9.288 mmol), and the reaction was stirred for 3 hr at rt. The reaction was filtered through a pad of Celite and rinsed with EtOAc several times. The filtrate was concentrated, and the residue was purified by silica gel column chromatography (0 to 10% EtOAc in hexane) to give 0.229 g (85%) of the title compound as a yellow oil. $^1$H NMR (400 MHz, Chloroform-d) δ 9.75 (s, 1H), 7.54 (s, 1H), 7.25-7.22 (m, 3H), 7.16-7.11 (m, 1H).

The compounds listed in the table below were prepared in an analogous fashion to that described above starting from the listed starting thiol in Step 1:

| Starting material thiol | Product | Characterization Data |
|---|---|---|
| HS–C$_6$H$_4$–CF$_3$ (3-position) | Int-253 (aldehyde thiophene with 3-CF$_3$-phenylsulfanyl) | $^1$H NMR (400 MHz, Chloroform-d) δ 9.76 (s, 1H), 7.57 (s, 1H), 7.54-7.48 (m, 2H), 7.44 (t, J = 7.6 Hz, 1H), 7.40-7.35 (m, 1H). |

Example 127: 4-[(3-Chlorophenyl)sulfanyl]-5-methylthiophene-2-carbaldehyde Int-254

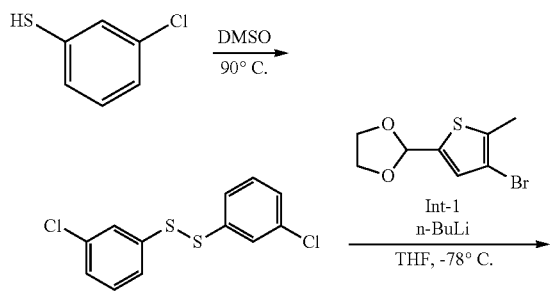

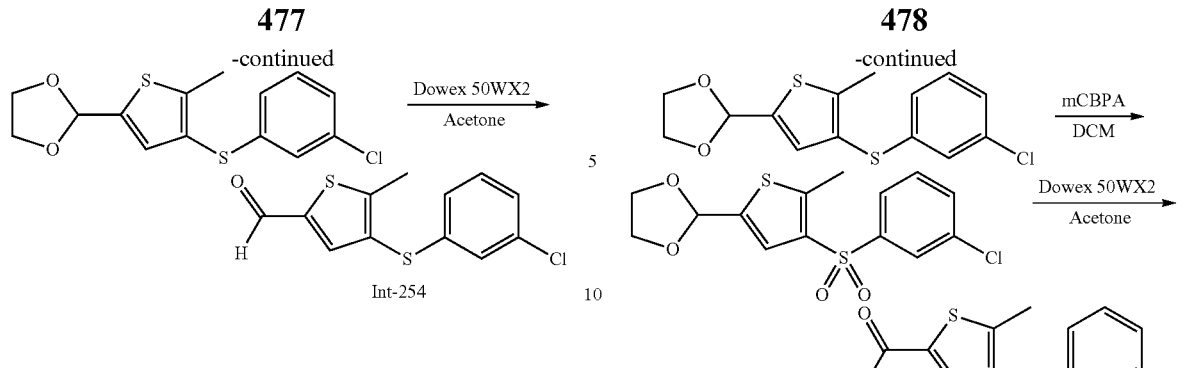

Steps 1 and 2: 2-[4-(3-Chlorophenyl)sulfanyl-5-methyl-2-thienyl]-1,3-dioxolane Steps 1 and 2 were performed in an analogous fashion to Example 126, steps 1 and 2. Step 3 was performed as follows:

Step 3: 4-[(3-Chlorophenyl)sulfanyl]-5-methylthiophene-2-carbaldehyde

Dowex 50WX2-200 (H) (2.5 g) was added to a solution of 2-{4-[(3-chlorophenyl)sulfanyl]-5-methyl-2-thienyl}-1,3-dioxolane (2.5 g, 8.0 mmol) in acetone (84.3 mL, 1150 mmol) at RT. The reaction was allowed to stir for 16 hr. The reaction was filtered to remove solid resin and the filtrate was washed with acetone, then concentrated to dryness. The residue was purified by silica gel column chromatography (0-60-100% EtOAc in hexane) to give 2.0 g (93%) of the title compound. $^1$H NMR (400 MHz, Chloroform-d) δ 9.81 (s, 1H), 7.67 (s, 1H), 7.21-7.10 (m, 2H), 7.06-7.03 (m, 1H), 6.97-6.93 (m, 1H), 2.55 (s, 3H).

The compounds listed in the table below were prepared using an analogous method to that described above starting from the listed starting thiol:

Steps 1: 2-[4-(3-Chlorophenyl)sulfanyl-5-methyl-2-thienyl]-1,3-dioxolane

Step 1 was performed in an analogous fashion to Example 127 step 2. Step 2 was performed as follows:

Step 2: 2-{4-[(3-Chlorophenyl)sulfonyl]-5-methyl-2-thienyl}-1,3-dioxolane

A 100 mL round bottom flask was charged with 2-{4-[(3-chlorophenyl)sulfanyl]-5-methyl-2-thienyl}-1,3-dioxolane (0.620 g, 1.98 mmol) in DCM (19 mL, 3.0E2 mmol) under nitrogen. To this solution m-chloroperbenzoic acid (1.02 g, 5.90 mmol) was added. The solution was stirred at rt for 30 mins. The reaction was diluted with DCM and saturated NaHCO$_3$ was added. The mixture was extracted with DCM (3×) and the combined organic portions were washed with brine, dried with anhydrous magnesium sulfate, filtered, and concentrated to dryness. The residue was purified by silica gel column chromatography (0-25% EtOAc in hexanes) to give 0.680 g (99%) of the title compound. LCMS (FA): m/z=345.1 (M+H)

Step 3: 4-[(3-Chlorophenyl)sulfonyl]-5-methylthiophene-2-carbaldehyde

Dowex 50WX2-200 (H) (0.605 g) was added to a solution of 2-{4-[(3-chlorophenyl)sulfonyl]-5-methyl-2-thienyl}-1,3-dioxolane (0.635 g, 1.84 mmol) in acetone (19.4 mL, 264 mmol) at rt. The reaction was allowed to stir for 16 hr. The

| Starting material | Product | Characterization Data |
|---|---|---|
| HS-C6H4-CF3 (3-CF3) | Int-255 | $^1$H NMR (400 MHz, Chloroform-d) δ 9.82 (s, 1H), 7.68 (s, 1H), 7.44-7.30 (m, 3H), 7.22-7.16 (m, 1H), 2.56 (s, 3H). |
| HS-C6H5 | Int-256 | $^1$H NMR (400 MHz, Chloroform-d) δ 9.79 (s, 1H), 7.65 (s, 1H), 7.29-7.23 (m, 2H), 7.21-7.15 (m, 1H), 7.15-7.09 (m, 2H), 2.55 (s, 3H). |

Example 128: 4-[(3-Chlorophenyl)sulfonyl]-5-methylthiophene-2-carbaldehyde Int-257

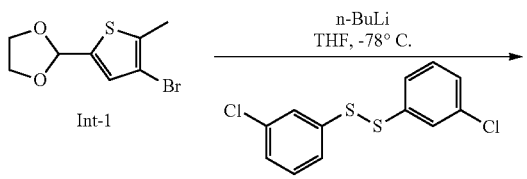

reaction was filtered to remove solid resin and the filtrate was washed with acetone, then concentrated to dryness. The residue was purified by silica gel column chromatography (0-60-100% EtOAc in hexanes) to give 0.525 g (95%) of product. $^1$H NMR (400 MHz, Chloroform-d) δ 9.82 (s, 1H), 8.02 (s, 1H), 7.93-7.89 (m, 1H), 7.85-7.80 (m, 1H), 7.63-7.58 (m, 1H), 7.54-7.48 (m, 1H), 2.75 (s, 3H).

The compounds listed in the table below were prepared in an analogous fashion to that described above starting from the thiophene intermediate shown:

| Starting thiophene | Product | Characterization Data |
|---|---|---|
| Int-2 | Int-258 | $^1$H NMR (400 MHz, Chloroform-d) δ 9.81 (s, 1H), 8.07 (s, 1H), 8.01-7.98 (m, 1H), 7.94-7.90 (m, 1H), 7.66-7.62 (m, 1H), 7.56-7.50 (m, 1H). | and cooled in an ice/water bath. tert-Butyldimethylsilylchloride (2.9 g, 19 mmol) was added as a solution in DCM (40 mL). The reaction was allowed to warm to rt and stirred for 16 h. The reaction was quenched by addition of water (150 mL) and the mixture was transferred to separatory funnel. The organic layer was collected and the residual water layer was extracted with DCM (150 mL×2). The combined organic layers were dried over Na$_2$SO$_4$, filtered, and concentrated. The residue was purified on silica gel to provide the title compound (5.21 g, 87%). $^1$H NMR (CDCl$_3$) δ 4.73 (s, 1H), 4.20-4.05 (m, 2H), 3.81 (dd, J=9.8, 4.2 Hz, 1H), 3.54 (dd, J=9.7, 7.1 Hz, 1H), 2.33-2.10 (m, 2H), 2.05-1.79 (m, 3H), 1.43 (s, 9H), 1.20-1.08 (m, 1H), 0.90 (s, 9H), 0.08 (s, 6H).

Step 2: tert-Butyl {(1R,3R,4S)-3-({[tert-butyl(dimethyl)silyl]oxy}methyl)-4-[(triisopropylsilyl)oxy]cyclopentyl}carbamate To a solution of tert-butyl [(1R,3R,4S)-3-({[tert-butyl(dimethyl)silyl]oxy}methyl)-4-hydroxycyclopentyl]carbamate (3.8 g, 11 mmol) in DMF (57 mL) under an atmosphere of argon was added imidazole (2.25 g, 33 mmol) followed by triisopropylchlorosilane (4.7 mL, 22 mmol) at RT, and the mixture was stirred for 61 h. The reaction was quenched by addition of saturated NH$_4$Cl (150 mL) and extracted with EtOAc (200 mL×5). The combined organic layers were washed with brine, dried over Na$_2$SO$_4$, filtered, and concentrated in vacuo. The residue was purified on silica gel to afford the title compound (5.13 g, 93%) as a colorless oil. $^1$H NMR (CDCl$_3$) δ 4.90 (s, 1H), 4.35-4.20 (m, 1H), 4.19-3.99 (m, 1H), 3.75-3.44 (m, 2H), 2.37-2.17 (m, 1H), 2.03 (s, 1H), 1.96-1.69 (m, 2H), 1.43 (s, 9H), 1.31-1.13 (m, 1H), 1.04 (s, 2H), 0.90 (s, 9H), 0.06 (s, 6H).

Step 3: (1R,3R,4S)-3-({[tert-Butyl(dimethyl)silyl]oxy}methyl)-4-[(triisopropylsilyl)oxy]cyclopentanamine Int-260

To solution of tert-butyl {(1R,3R,4S)-3-({[tert-butyl(dimethyl)silyl]oxy}methyl)-4-[(triisopropylsilyl)oxy]cyclopentyl}carbamate (1.5 g, 3.0 mmol) in DCM (100 mL) was added EtOH (0.38 mL, 6.6 mmol) followed by zinc bromide (5.4 g, 24 mmol) at RT, and the mixture was stirred for 37 h. The reaction was quenched by addition of 1N NaOH (100 mL) and extracted with DCM (100 mL×5). The combined organic layers were washed with brine and then dried over Na$_2$SO$_4$. After filtration, the filtrate was concentrated in vacuo. The residue was purified on silica gel to give the title compound (1.09 g, 91%) as a colorless oil. LCMS (FA): m/z=402.6 (M+H).

Step 4: {(1R,2S,4R)-4-Amino-2-[(triisopropylsilyl)oxy]cyclopentyl}methanol

A 1-neck 3 L round bottom flask was charged with (1R,3R,4S)-3-({[tert-butyl(dimethyl)silyl]oxy}methyl)-4-

Example 129. {(1R,2S,4R)-4-Amino-2-[(triisopropylsilyl)oxy]cyclopentyl}methanol Int-259

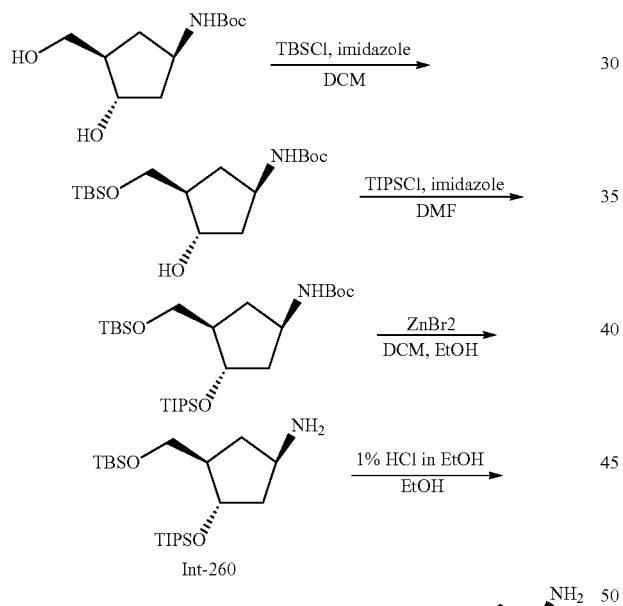

Step 1: tert-Butyl [(1R,3R,4S)-3-({[tert-butyl(dimethyl)silyl]oxy}methyl)-4-hydroxycyclopentyl]carbamate A solution of tert-butyl [(1R,3S,4R)-3-hydroxy-4-(hydroxymethyl)cyclopentyl]carbamate (4.0 g, 17 mmol) (for synthesis of starting material see: Ober, M. et. al. *J. Am. Chem. Soc.* 2005, 127, 18143-18149.) and imidazole (1.4 g, 21 mmol) in DMF (40 mL) was diluted with DCM (200 mL)

[(triisopropylsilyl)oxy]cyclopentanamine (45.0 g, 112 mmol) and a solution of 12 M of HCl in water (20.0 mL, 240 mmol) in ethanol (2000 mL) was added. The reaction was stirred at RT for 3 h. The reaction was quenched by addition of a solution of sodium carbonate (26.7 g, 252 mmol) in water (130 mL), stirred 5 min, then concentrated. The residue was azeotroped from ethanol several times to give a brown solid. DCM (1000 mL) was added and the mixture was stirred at RT overnight, filtered to remove inorganic solids and evaporated filtrate to dryness. The residue was subjected to flash column chromatography (eluting with DCM then 95 DCM/5 MeOH/0.5 NH$_4$OH) to give 26.6 g (83%) of the title compound. $^1$H NMR (400 MHz, DMSO-d$_6$) δ 4.22-4.15 (m, 1H), 3.42-3.25 (m, 4H), 2.07-1.96 (m, 1H), 1.96-1.84 (m, 1H), 1.74-1.64 (m, 1H), 1.56-1.45 (m, 1H), 1.02 (s, 21H).

Example 130: {(1R,2S,4R)-4-Amino-2-[(triisopropylsilyl)oxy]cyclopentyl}methanol.CF$_3$CO$_2$H Int-261

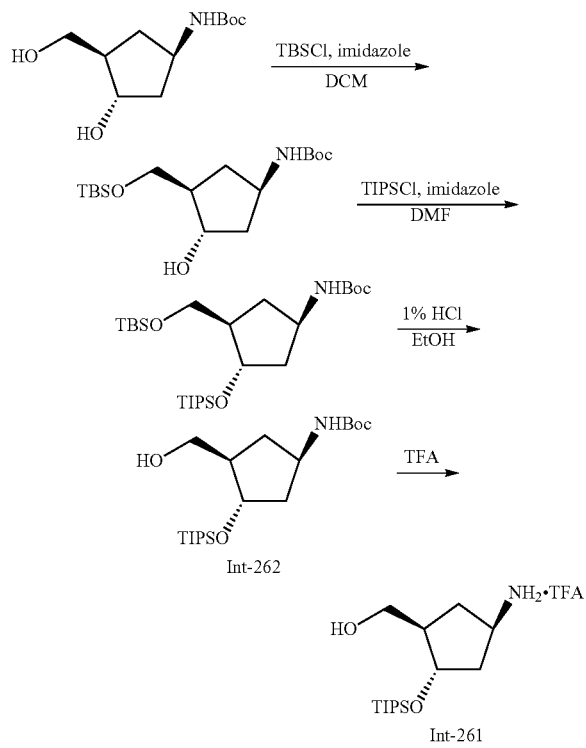

Step 1: tert-Butyl [(1R,3R,4S)-3-({[tert-butyl(dimethyl)silyl]oxy}methyl)-4-hydroxycyclopentyl]carbamate A solution of tert-butyl [(1R,3S,4R)-3-hydroxy-4-(hydroxymethyl)cyclopentyl]carbamate (4.0 g, 17 mmol) (for synthesis of starting material see: Ober, M. et. al. *J. Am. Chem. Soc.* 2005, 127, 18143-18149.) and imidazole (1.4 g, 21 mmol) in DMF (40 mL) was diluted with DCM (200 mL) and cooled in an ice/water bath. tert-Butyldimethylsilylchloride (2.9 g, 19 mmol) was added as a solution in DCM (40 mL). The reaction was allowed to warm to ambient temperature and stirred overnight. The reaction was quenched by addition of water (150 mL) and the mixture was transferred to separatory funnel. The organic layer was collected and the residual water layer was extracted with DCM (150 mL×2). The combined organic layers were dried over Na$_2$SO$_4$, filtered, and concentrated. The residue was purified on silica gel to provide the title compound (5.21 g, 87%). $^1$H NMR (CDCl$_3$) δ 4.73 (s, 1H), 4.20-4.05 (m, 2H), 3.81 (dd, J=9.8, 4.2 Hz, 1H), 3.54 (dd, J=9.7, 7.1 Hz, 1H), 2.33-2.10 (m, 2H), 2.05-1.79 (m, 3H), 1.43 (s, 9H), 1.20-1.08 (m, 1H), 0.90 (s, 9H), 0.08 (s, 6H).

Step 2: tert-Butyl {(1R,3R,4S)-3-({[tert-butyl(dimethyl)silyl]oxy}methyl)-4-[(triisopropylsilyl)oxy]cyclopentyl}carbamate To a solution of tert-butyl [(1R,3R,4S)-3-({[tert-butyl(dimethyl)silyl]oxy}methyl)-4-hydroxycyclopentyl]carbamate (3.8 g, 11 mmol) in DMF (57 mL) under an atmosphere of argon was added imidazole (2.25 g, 33 mmol) followed by triisopropylchlorosilane (4.7 mL, 22 mmol) at rt, and the mixture was stirred for 61 h. The reaction was quenched by addition of saturated NH$_4$Cl (150 mL) and extracted with EtOAc (200 mL×5). The combined organic layers were washed with brine, dried over Na$_2$SO$_4$, filtered, and concentrated in vacuo. The residue was purified on silica gel to afford the title compound (5.13 g, 93%) as a colorless oil. $^1$H NMR (CDCl$_3$) δ 4.90 (s, 1H), 4.35-4.20 (m, 1H), 4.19-3.99 (m, 1H), 3.75-3.44 (m, 2H), 2.37-2.17 (m, 1H), 2.03 (s, 1H), 1.96-1.69 (m, 2H), 1.43 (s, 9H), 1.31-1.13 (m, 1H), 1.04 (s, 2H), 0.90 (s, 9H), 0.06 (s, 6H).

Step 3: tert-Butyl {(1R,3R,4S)-3-(hydroxymethyl)-4-[(triisopropylsilyl)oxy]cyclopentyl}carbamate Int-262

To a solution of tert-butyl {(1R,3R,4S)-3-({[tert-butyl(dimethyl)silyl]oxy}methyl)-4-[(triisopropylsilyl)oxy]cyclopentyl}carbamate (535 mg, 0.91 mmol) in EtOH (9.7 mL) was added 1% HCl in EtOH (9.7 mL, 1.2 mmol) at rt, and the mixture was allowed to stand at 4° C. for 13 h. The reaction was then stirred for 4 h at rt. The reaction was quenched by addition of saturated NaHCO$_3$ (50 mL) and extracted with DCM (50 mL×3). The combined organic layers were dried over Na$_2$SO$_4$, filtered, and concentrated in vacuo. The residue was purified on silica gel to give the title compound (327 mg, 93%) as a colorless oil. $^1$H NMR (CDCl$_3$) δ 4.65 (s, 1H), 4.22 (dd, J=10.9, 5.1 Hz, 1H), 4.19-4.05 (m, 1H), 3.72-3.58 (m, 2H), 2.41-2.27 (m, 1H), 2.13-2.04 (m, 1H), 2.00 (m, 1H), 1.80-1.63 (m, 2H), 1.44 (s, 9H), 1.23-1.09 (m, 1H), 1.06 (s, 21H).

Step 4: {(1R,2S,4R)-4-Amino-2-[(triisopropylsilyl)oxy]cyclopentyl}methanol.CF$_3$CO$_2$H A 250 mL RBF was charged with tert-butyl {(1R,3R,4S)-3-(hydroxymethyl)-4-[(triisopropylsilyl)oxy]cyclopentyl}carbamate (1.0 g, 2.6 mmol). To the reaction vessel was added TFA (6.5 mL, 84 mmol) at rt, and the mixture was stirred for 5 min. To the mixture was added toluene (50 mL) and the mixture was concentrated in vacuo. This was repeated twice more to remove water and the resulting residue was dried under high vacuum to give the title compound (1.31 g, 100%) as colorless oil. LCMS (FA): m/z=288.6 (M+H).

Example 131: [(1R,2S,4R)-4-{[5-({4-[(1R)-3,4-Dihydro-1H-isochromen-1-yl]-5-methyl-2-thienyl}carbonyl)pyrimidin-4-yl]amino}-2-hydroxy-cyclopentyl]methyl sulfamate I-256b
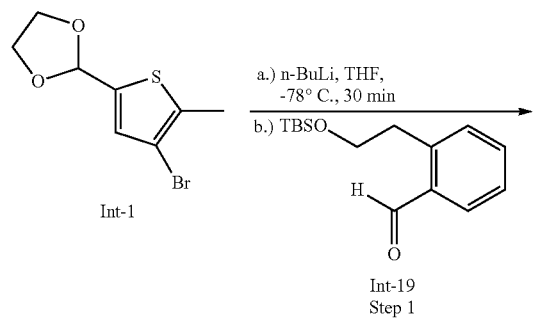
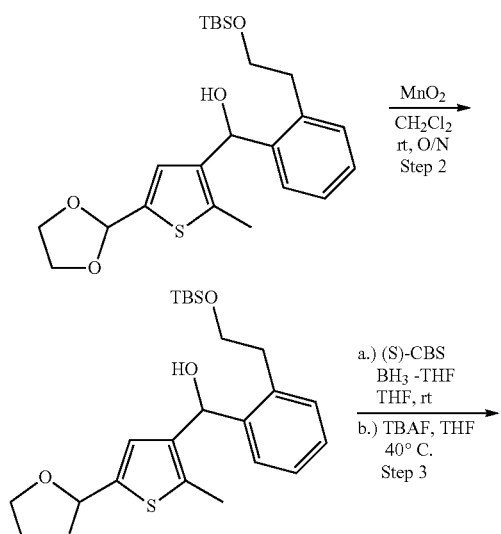
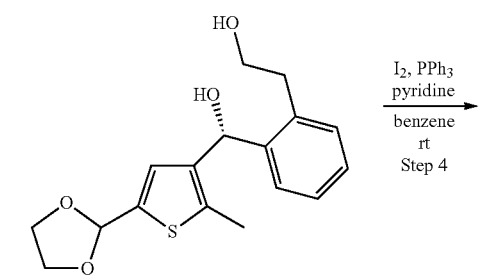
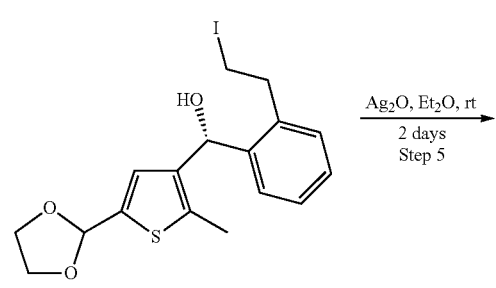
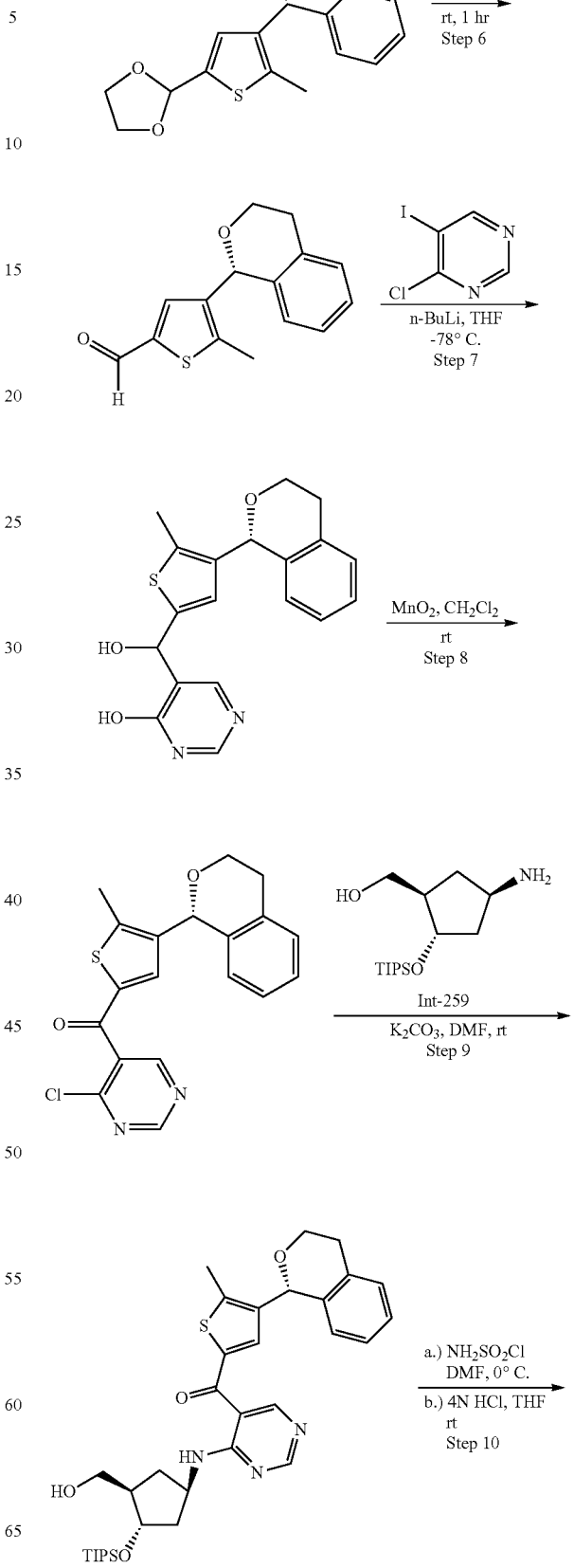

-continued

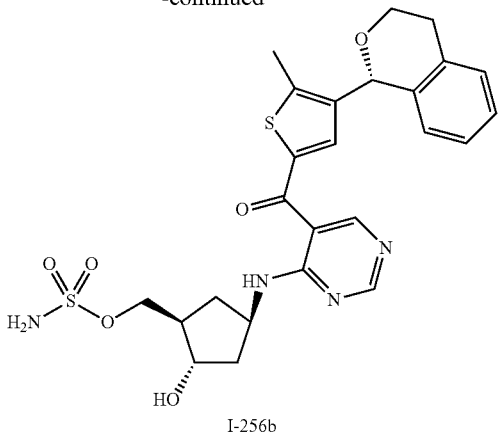

I-256b

Step 1: [2-(2-{[tert-Butyl(dimethyl)silyl]oxy}ethyl)phenyl][5-(1,3-dioxolan-2-yl)-2-methyl-3-thienyl]methanol A solution of bromide Int-1 (1.70 g, 6.82 mmol) in THF (26.6 mL) was cooled to −78° C., and then 2.50 M of n-BuLi in hexane (2.94 mL, 7.34 mmol) was added and the mixture was stirred for 10 min at −78° C. A solution of aldehyde Int-19 (1.39 g, 5.25 mmol) in THF (13.3 mL, 164 mmol) was then added, and the reaction was stirred for 10 min at −78° C. The reaction was quenched by adding brine and then warmed to rt. The aqueous mixture was extracted 2×EtOAc. The combined organic solvents were washed with brine, dried and concentrated in vacuo. The residue was purified by flash column chromatography (0 to 20% EtOAc in hexanes as eluent) to afford the title compound as a pale yellow oil (yield=1.96 g) that solidified upon standing in the refrigerator over the weekend. $^1$H NMR (400 MHz, Chloroform-d) δ 7.30-7.26 (m, 2H), 7.26-7.21 (m, 2H), 7.07 (s, 1H), 6.09 (d, J=2.7 Hz, 1H), 6.03 (s, 1H), 4.19-4.13 (m, 2H), 4.06-4.00 (m, 2H), 3.96-3.89 (m, 1H), 3.87-3.77 (m, 1H), 3.52 (d, J=2.9 Hz, 1H), 3.06 (ddd, J=14.3, 8.4, 6.2 Hz, 1H), 2.87 (dt, J=13.9, 5.2 Hz, 1H), 2.37 (s, 3H), 0.86 (s, 9H), −0.00 (s, 3H), −0.01 (s, 3H).

Step 2: [2-(2-{[tert-Butyl(dimethyl)silyl]oxy}ethyl)phenyl][5-(1,3-dioxolan-2-yl)-2-methyl-3-thienyl]methanone To a solution of [2-(2-{[tert-butyl(dimethyl)silyl]oxy}ethyl)phenyl][5-(1,3-dioxolan-2-yl)-2-methyl-3-thienyl]methanol (11.4 g, 26.2 mmol) in DCM (77.9 mL) was added MnO$_2$ (22.8 g, 262 mmol) at rt and the reaction was stirred for 24 h. The reaction was filtered through a Celite pad and the residual solid was rinsed with DCM several times. The filtrate was concentrated in vacuo and the residue was purified by silica gel column chromatography (5% EtOAc in hexane) to give 9.58 g (84%) of the title compound as a colorless solid. $^1$H NMR (400 MHz, Chloroform-d) δ 7.41-7.31 (m, 2H), 7.32-7.21 (m, 2H), 7.03 (s, 1H), 5.91 (s, 1H), 4.15-4.04 (m, 2H), 4.03-3.93 (m, 2H), 3.78 (t, J=7.0 Hz, 2H), 2.89 (t, J=7.0 Hz, 2H), 2.65 (s, 3H), 0.83 (s, 9H), −0.06 (s, 6H); LCMS (FA): m/z=433.2 (M+H).

Step 3: 2-{2-[(R)-[5-(1,3-Dioxolan-2-yl)-2-methyl-3-thienyl](hydroxy)methyl]phenyl}ethanol To a solution of [2-(2-{[tert-butyl(dimethyl)silyl]oxy}ethyl)phenyl][5-(1,3-dioxolan-2-yl)-2-methyl-3-thienyl]methanone (13.8 g, 32.0 mmol) in THF (448 mL) was added 0.5 M of (S)-(−)-o-tolyl-CBS-oxazaborolidine in toluene (32.0 mL, 16.0 mmol), followed by 1.00 M of BH$_3$-THF complex in THF (35.2 mL, 35.2 mmol) at rt. After stirring for 1 h at rt, the reaction was quenched by addition of MeOH. The mixture was stirred for 25 min, and then the volatiles were removed in vacuo. The residue was dissolved in EtOAc and water and the aqueous layer was extracted with EtOAc. The combined organic layers were dried over Na$_2$SO$_4$, filtered, and concentrated in vacuo. The residue was purified by silica gel column chromatography (10 to 30% EtOAc in hexane) to provide 14.6 g of the alcohol intermediate. The obtained alcohol was dissolved in THF (290 mL) and TBAF hydrate (10.7 g, 38.4 mmol) was added to the solution. After stirring for 10 min at 40° C., the reaction was concentrated in vacuo. To the residue was added water and the mixture was extracted with EtOAc. The combined organic layers were dried over Na$_2$SO$_4$, filtered, and concentrated in vacuo. The residue was purified by silica gel column chromatography (30 to 80% EtOAc in hexane) to give 9.86 g (94% over two steps) of the title compound as a colorless oil. The enantiomeric purity was determined to be 87% ee by HPLC (80/20/0.1 hexane/EtOH/DEA; 1.0 mL/min for 20 min; using a CHIRALPAK ID column (4.6×250 mm)): 8.65 min (minor) and 12.8 min (major). $^1$H NMR (400 MHz, DMSO-d$_6$) δ 7.50 (d, J=7.4 Hz, 1H), 7.25-7.11 (m, 3H), 6.73 (s, 1H), 5.89 (d, J=4.5 Hz, 1H), 5.84 (s, 1H), 5.59 (d, J=4.5 Hz, 1H), 4.68 (t, J=5.1 Hz, 1H), 4.00-3.92 (m, 2H), 3.90-3.81 (m, 2H), 3.54-3.36 (m, 2H), 2.74-2.58 (m, 2H), 2.39 (s, 3H); LCMS (FA) m/z=304.1 (M+H−18).

Step 4: (R)-[5-(1,3-Dioxolan-2-yl)-2-methyl-3-thienyl][2-(2-iodoethyl)phenyl]methanol To a solution of 2-{2-[(R)-[5-(1,3-dioxolan-2-yl)-2-methyl-3-thienyl](hydroxy)methyl]phenyl}ethanol (10.4 g, 32.4 mmol) in benzene (380 mL) were added pyridine (7.93 mL, 98.0 mmol) and PPh$_3$ (12.8 g, 49.0 mmol), followed by I$_2$ (8.63 g, 34.0 mmol). After stirring overnight at rt, the reaction mixture was filtered and the filter cake was rinsed with Et$_2$O. To the filtrate was added water and hexane, the layers were separated, and the aqueous layer was extracted with hexane. The combined organic layers were washed with brine, then dried over Na$_2$SO$_4$, filtered, and concentrated in vacuo. The residue was purified by silica gel column chromatography (10 to 20% EtOAc in hexane) to afford 10 g (73%) of the title compound as a pale yellow solid. $^1$H NMR (400 MHz, Chloroform-d) δ 7.62 (d, J=7.5 Hz, 1H), 7.29 (d, J=25.4 Hz, 2H), 7.15 (d, J=7.3 Hz, 1H), 6.78 (s, 1H), 6.02 (s, 1H), 5.91 (s, 1H), 4.16-4.02 (m, 2H), 4.02-3.90 (m, 2H), 3.23-3.03 (m, 3H), 3.01-2.92 (m, 1H), 2.51 (s, 3H), 1.99 (d, J=3.0 Hz, 1H).

Step 5: (1R)-1-[5-(1,3-Dioxolan-2-yl)-2-methyl-3-thienyl]-3,4-dihydro-1H-isochromene To a solution of (R)-[5-(1,3-dioxolan-2-yl)-2-methyl-3-thienyl][2-(2-iodoethyl)phenyl]methanol (10.2 g, 23.7 mmol) in Et$_2$O (366 mL) was added silver(I) oxide (27.4 g, 118 mmol) and the reaction was stirred for two days at rt. The reaction was filtered through a Celite pad and the residual solid was rinsed with Et$_2$O several times. The filtrate was concentrated in vacuo and the residue was purified by silica gel column chromatography (30% EtOAc in hexane) to give 7.01 g (98%) of the title compound as a colorless oil. $^1$H NMR (400 MHz, Chloroform-d) δ 7.22-

7.05 (m, 3H), 6.78-6.72 (m, 2H), 5.92 (s, 1H), 5.77 (s, 1H), 4.19 (ddd, J=11.3, 5.5, 3.6 Hz, 1H), 4.12-4.03 (m, 2H), 4.01-3.86 (m, 3H), 3.11 (ddd, J=15.9, 9.4, 5.7 Hz, 1H), 2.78 (dt, J=16.5, 3.6 Hz, 1H), 2.46 (s, 3H).

Step 6: 4-[(1R)-3,4-Dihydro-1H-isochromen-1-yl]-5-methylthiophene-2-carbaldehyde Int-263

To a solution of (1R)-1-[5-(1,3-dioxolan-2-yl)-2-methyl-3-thienyl]-3,4-dihydro-1H-isochromene (9.14 g, 30.2 mmol) in THF (117 mL) was added HCl (1 M aqueous solution, 117 mL, 117 mmol) at rt and the reaction was stirred for 1 h. The reaction was quenched by addition of saturated aqueous NaHCO$_3$ and extracted with EtOAc. The combined organic layers were washed with brine, dried over Na$_2$SO$_4$, filtered, and concentrated in vacuo. The residue was purified by silica gel column chromatography (20% EtOAc in hexane) to give 7.36 g (94%) of the title compound as a pale yellow oil. $^1$H NMR (400 MHz, Chloroform-d) δ 9.71 (s, 1H), 7.39 (s, 1H), 7.25-7.09 (m, 3H), 6.73 (d, J=7.7 Hz, 1H), 5.84 (s, 1H), 4.19 (ddd, J=11.4, 5.5, 3.7 Hz, 1H), 3.94 (ddd, J=11.4, 9.7, 4.0 Hz, 1H), 3.14 (ddd, J=15.8, 9.7, 5.8 Hz, 1H), 2.83 (dt, J=16.4, 3.7 Hz, 1H), 2.57 (s, 3H); LCMS (FA) m/z=259.1 (M+H).

Step 7: (R)-(4-Chloropyrimidin-5-yl)-[4-[(1R)-isochroman-1-yl]-5-methyl-2-thienyl]methanol and (S)-(4-Chloropyrimidin-5-yl)-[4-[(1R)-isochroman-1-yl]-5-methyl-2-thienyl]methanol A solution of 4-chloro-5-iodopyrimidine (8.22 g, 34.2 mmol) in THF (200 mL) was cooled at −78° C. To the solution was added 2.50 M of n-BuLi in hexane (27.4 mL, 68.4 mmol) at the same temperature. After stirring for 10 min, a solution of 4-[(1R)-3,4-dihydro-1H-isochromen-1-yl]-5-methylthiophene-2-carbaldehyde (7.36 g, 28.5 mmol) in THF (33.4 mL) was added at −78° C., and the resulting mixture was stirred for 10 min at the same temperature. The reaction was quenched by addition of water and extracted with EtOAc. The combined organic layers were washed with brine, dried over Na$_2$SO$_4$, filtered, and concentrated in vacuo. The residue was purified by silica gel column chromatography (0 to 50% EtOAc in hexane) to give 10.1 g (95%) of the title compound mixture as a pale yellow amorphous solid. $^1$H NMR (400 MHz, Chloroform-d) δ 8.96 (s, 0.5H), 8.93 (s, 0.5H), 8.92 (s, 0.5H), 8.91 (s, 0.5H), 7.22-7.04 (m, 3H), 6.72-6.62 (m, 2H), 6.16 (s, 0.5H), 6.13 (s, 0.5H), 5.73 (s, 1H), 4.24-4.15 (m, 1H), 3.97-3.85 (m, 1H), 3.21-3.06 (m, 1H), 2.81-2.70 (m, 1H), 2.67-2.48 (br s, 1H), 2.43 (s, 1.5H), 2.41 (s, 1.5H); LCMS (FA) m/z=373.1 (M+H).

Step 8: (4-Chloropyrimidin-5-yl){4-[(1R)-3,4-dihydro-1H-isochromen-1-yl)-5-methyl-2-thienyl}methanone To a solution of the product mixture from step 7 (10.1 g, 27.2 mmol) in DCM (363 mL) was added MnO$_2$ (23.6 g, 272 mmol) at rt, and the reaction was stirred for 20 h. The reaction was filtered through a Celite pad and the residual solid was rinsed with DCM several times. The filtrate was concentrated in vacuo and the residue was purified by silica gel column chromatography (0 to 40% EtOAc in hexanes) to give 9.15 g (91%) of the title compound as an off-white amorphous solid. $^1$H NMR (400 MHz, Chloroform-d) δ 9.06 (s, 1H), 8.69 (s, 1H), 7.23-7.07 (m, 4H), 6.68 (d, J=7.7 Hz, 1H), 5.79 (s, 1H), 4.19 (ddd, J=11.4, 5.8, 3.0 Hz, 1H), 3.92 (dt, J=10.9, 3.8 Hz, 1H), 3.13 (ddd, J=16.1, 10.2, 5.8 Hz, 1H), 2.82-2.72 (m, 1H), 2.56 (s, 3H); LCMS (FA) m/z=371.1 (M+H).

Step 9: (4-(((1R,3R,4S)-3-(Hydroxymethyl)-4-((triisopropylsilyl)oxy)cyclopentyl)amino)pyrimidin-5-yl)(4-((R)-isochroman-1-yl)-5-methylthiophen-2-yl)methanone To a solution of (4-chloropyrimidin-5-yl){4-[(1R)-3,4-dihydro-1H-isochromen-1-yl)-5-methyl-2-thienyl}methanone (8.59 g, 23.2 mmol) in DMF (102 mL) was added Int-259 (7.99 g, 27.8 mmol) and K$_2$CO$_3$ (9.60 g, 69.5 mmol) at rt. After stirring for 21 h at rt, the reaction was concentrated in vacuo and the residue was diluted with water and EtOAc. The layers were separated and the aqueous layer was extracted with EtOAc. The combined organic layers were dried over Na$_2$SO$_4$, filtered, and concentrated in vacuo. The residue was purified by silica gel column chromatography (0 to 50% EtOAc in hexanes) to give 13.0 g (90%) of the title compound as a light yellow amorphous solid. $^1$H NMR (400 MHz, Chloroform-d) δ 8.73-8.63 (m, 2H), 8.60 (s, 1H), 7.24 (s, 1H), 7.22-7.14 (m, 2H), 7.13-7.07 (m, 1H), 6.69 (d, J=7.7 Hz, 1H), 5.81 (s, 1H), 4.85-4.71 (m, 1H), 4.35-4.27 (m, 1H), 4.23 (ddd, J=11.4, 5.7, 2.9 Hz, 1H), 3.94 (dt, J=10.9, 3.7 Hz, 1H), 3.75-3.61 (m, 2H), 3.17 (ddd, J=16.1, 10.3, 5.8 Hz, 1H), 2.83-2.73 (m, 1H), 2.55 (s, 3H), 2.48 (dt, J=13.2, 8.0 Hz, 1H), 2.16 (ddd, J=12.5, 8.0, 3.9 Hz, 2H), 1.88-1.76 (m, 1H), 1.74-1.66 (m, 1H), 1.35-1.23 (m, 1H), 1.06 (s, 21H); LCMS (FA) m/z=622.3 (M+H).

Step 10: [(1R,2S,4R)-4-{[5-({4-[(1R)-3,4-Dihydro-1H-isochromen-1-yl]-5-methyl-2-thienyl}carbonyl)pyrimidin-4-yl]amino}-2-hydroxycyclopentyl]methyl sulfamate A solution of (4-(((1R,3R,4S)-3-(hydroxymethyl)-4-((triisopropylsilyl)oxy)cyclopentyl)amino)pyrimidin-5-yl)(4-((R)-isochroman-1-yl)-5-methylthiophen-2-yl)methanone (13.0 g, 21.0 mmol) in DMF (102 mL) was cooled at 0° C. Chlorosulfonamide (4.84 g, 41.9 mmol) was added to the solution and the mixture was stirred for 10 min at 0° C. The reaction was quenched by addition of saturated NaHCO$_3$ at 0° C. and diluted with EtOAc and water. The two layers were separated and the aqueous layer was extracted with EtOAc. The combined organic layers were washed with brine, dried over Na$_2$SO$_4$, filtered, and concentrated in vacuo. The obtained crude product was dissolved in THF (114 mL). To the solution was added HCl (4 N aqueous solution, 91.7 mL, 367 mmol) at rt. After stirring for 4 h, the reaction was cooled to 0° C. and quenched by addition of saturated aqueous NaHCO$_3$. The resulting mixture was extracted with EtOAc. The combined organic layers were dried over Na$_2$SO$_4$, filtered, and concentrated in vacuo. The residue was purified by silica gel column chromatography (0 to 6% MeOH in DCM) to afford 11.1 g (97% over two steps) of the title compound as a light yellow amorphous solid. The diastereomeric purity was determined to be 86% de by HPLC (70/30/0.1 hexane/EtOH/DEA; 1.0 mL/min for 60 min; using a CHIRALPAK ID column (4.6×250 mm)): 23.1 min (minor) and 31.7 min (major). $^1$H NMR (400 MHz, Methanol-d$_4$) δ 8.59 (s, 1H), 8.53 (s, 1H), 7.24 (s, 1H), 7.22-7.15 (m, 2H), 7.16-7.07 (m, 1H), 6.76 (d, J=7.6 Hz, 1H), 5.93 (s, 1H), 4.83-4.70 (m, 1H), 4.24-4.10 (m, 4H), 4.01-3.89 (m, 1H), 3.16-3.03 (m, 1H), 2.87-2.76 (m, 1H), 2.54 (s, 3H), 2.52-2.43 (m, 1H), 2.31-2.19 (m, 1H), 2.13

(ddd, J=12.7, 7.4, 4.2 Hz, 1H), 1.88 (dt, J=13.6, 7.2 Hz, 1H), 1.40 (dt, J=13.1, 9.1 Hz, 1H); LCMS (FA) m/z=545.2 (M+H).

Example 132: [(1R,2S,4R)-4-{[5-({4-[(1R)-7-Chloro-3,4-dihydro-1H-isochromen-1-yl]-5-methyl-2-thienyl}carbonyl)pyrimidin-4-yl]amino}-2-hydroxycyclopentyl]methyl sulfamate I-257b

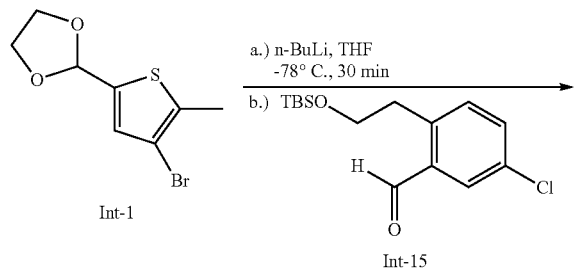
Int-1 a.) n-BuLi, THF
-78° C., 30 min
b.) 
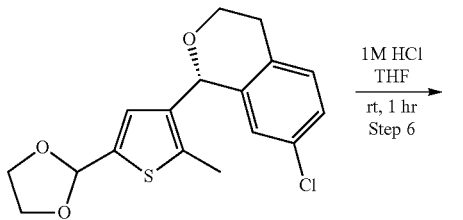
Int-15
Step 1

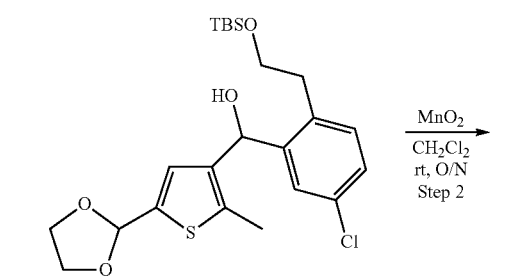

MnO₂
CH₂Cl₂
rt, O/N
Step 2

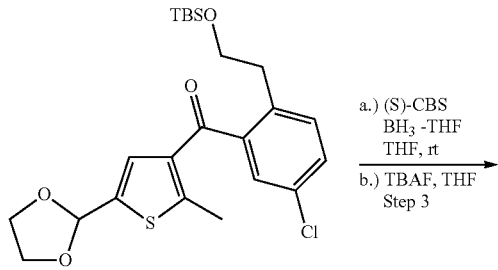

a.) (S)-CBS
BH₃-THF
THF, rt
b.) TBAF, THF
Step 3

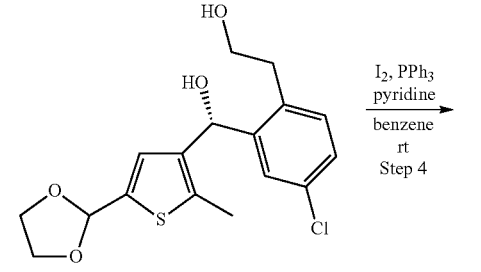

I₂, PPh₃
pyridine
benzene
rt
Step 4

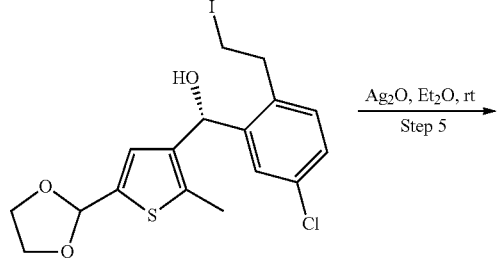

Ag₂O, Et₂O, rt
Step 5

-continued

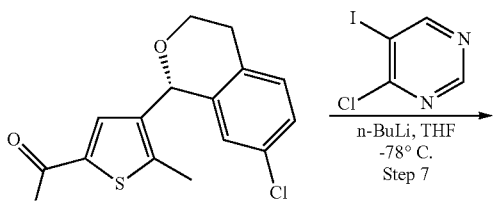

1M HCl
THF
rt, 1 hr
Step 6

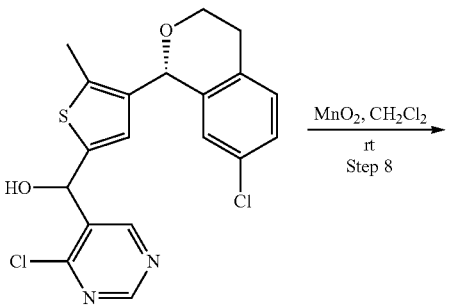

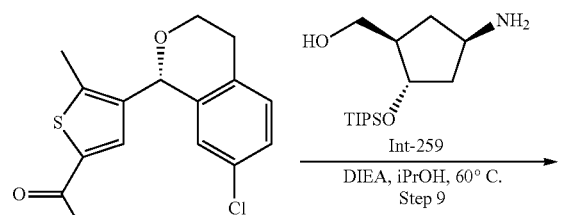

n-BuLi, THF
-78° C.
Step 7

MnO₂, CH₂Cl₂
rt
Step 8

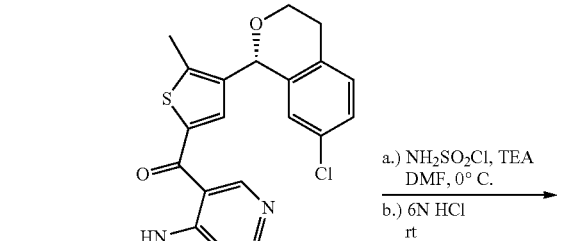

Int-259
DIEA, iPrOH, 60° C.
Step 9 a.) NH₂SO₂Cl, TEA
DMF, 0° C.
b.) 6N HCl
rt
Step 10

-continued

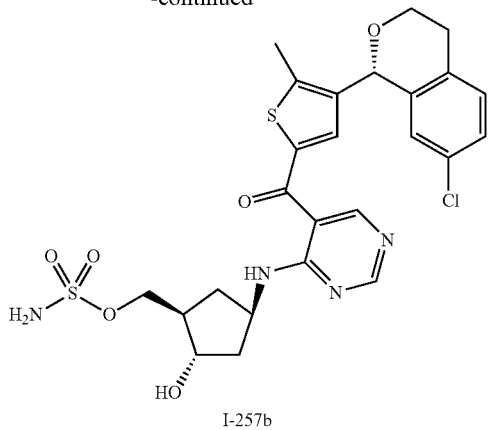

I-257b

Step 1: [2-(2-{[tert-Butyl(dimethyl)silyl]oxy}ethyl)-5-chlorophenyl][5-(1,3-dioxolan-2-yl)-2-methyl-3-thienyl]methanol A solution of bromide Int-1 (19.4 g, 77.9 mmol) in THF (200.0 mL) was cooled to −78° C. 2.50 M of n-BuLi in hexane (33.5 mL, 83.8 mmol) was added and the mixture was stirred for 10 min at −78° C. After stirring for 10 min, a solution of aldehyde Int-15 (17.9 g, 59.9 mmol) in THF (50.0 mL) was added and the reaction was stirred at −78° C. for 10 min. The reaction was quenched by adding brine (150 mL) and then warmed to rt. Layers were separated, and the organic layer was washed 3× brine, then dried over $Na_2SO_4$, filtered, and concentrated in vacuo. The crude residue was purified by flash column chromatography eluting with a hexane:EtOAc gradient to afford the title compound (22.0 g, 78%). $^1$H NMR (400 MHz, Chloroform-d) δ 7.39 (d, J=2.2 Hz, 1H), 6.99 (s, 1H), 6.06 (d, J=2.6 Hz, 1H), 6.03 (s, 1H), 4.22-4.13 (m, 3H), 4.07-4.01 (m, 2H), 3.91-3.84 (m, 1H), 3.79-3.71 (m, 1H), 3.27 (d, J=2.9 Hz, 1H), 2.96 (ddd, J=14.4, 8.3, 6.1 Hz, 1H), 2.82-2.73 (m, 1H), 2.43 (s, 3H), 0.88 (s, 10H), 0.01 (d, J=4.5 Hz, 6H).

Step 2: [2-(2-{[tert-Butyl(dimethyl)silyl]oxy}ethyl)-5-chlorophenyl][5-(1,3-dioxolan-2-yl)-2-methyl-3-thienyl]methanone To a solution of [2-(2-{[tert-butyl(dimethyl)silyl]oxy}ethyl)-5-chlorophenyl][5-(1,3-dioxolan-2-yl)-2-methyl-3-thienyl]methanol (22.0 g, 46.9 mmol) in DCM (250 mL) was added $MnO_2$ (40.8 g, 469 mmol) at rt and the reaction was stirred for 13 h. Added $MnO_2$ (40.8 g, 469 mmol), and then reaction was mechanically shaken at rt for 13 h. The reaction was filtered through a Celite pad and the residual solid was rinsed with EtOAc (1 L). The filtrate was concentrated in vacuo and the residue was purified by silica gel column chromatography (5% EtOAc in hexane) to give 22.9 g (77%) of the title compound as a colorless solid. $^1$H NMR (400 MHz, DMSO-d6) δ 7.62 (dd, J=8.3, 2.3 Hz, 1H), 7.53 (d, J=8.3 Hz, 1H), 7.47 (d, J=2.3 Hz, 1H), 7.11 (s, 1H), 6.04 (s, 1H), 4.13-4.06 (m, 2H), 4.05-3.98 (m, 2H), 3.76 (t, J=6.9 Hz, 2H), 2.83 (t, J=6.9 Hz, 2H), 2.69 (s, 3H), 0.88 (s, 9H), −0.00 (s, 6H).

Step 3: 2-[4-Chloro-2-[(R)-[5-(1,3-dioxolan-2-yl)-2-methyl-3-thienyl]-hydroxymethyl]phenyl]ethanol To a solution of [2-(2-{[tert-butyl(dimethyl)silyl]oxy}ethyl)-5-chlorophenyl][5-(1,3-dioxolan-2-yl)-2-methyl-3-thienyl]methanone (15.9 g, 34.0 mmol) in THF (477 mL) was added 0.5 M of(S)-(−)-o-tolyl-CBS-oxazaborolidine in toluene (34.0 mL, 17.0 mmol), followed by 1.00 M of $BH_3$-THF complex in THF (37.4 mL, 37.4 mmol) at rt. After stirring for 1 h at rt, the reaction was quenched by addition of MeOH. The mixture was stirred for 25 min, and then the volatiles were removed in vacuo. The residue was dissolved in EtOAc and water and the aqueous layer was extracted with EtOAc. The combined organic layer was dried over $Na_2SO_4$, filtered, and concentrated in vacuo. The residue was purified by silica gel column chromatography (10 to 30% EtOAc in hexane) to give 15.3 g (90%) of (R)-[2-(2-{[tert-butyl(dimethyl)silyl]oxy}ethyl)-5-chlorophenyl][5-(1,3-dioxolan-2-yl)-2-methyl-3-thienyl]methanol. The crude alcohol was dissolved in THF (200 mL) and TBAF hydrate (10.9 g, 39.0 mmol) was added to the solution. After stirring for 10 min at 40° C., the reaction was concentrated in vacuo. To the residue was added water and the mixture was extracted with EtOAc. The combined organic layers were dried over $Na_2SO_4$, filtered, and concentrated in vacuo. The residue was purified by silica gel column chromatography (30 to 80% EtOAc in hexane) to give 9.9 g of the title compound as a colorless oil. $^1$H NMR (400 MHz, DMSO-d6) δ 7.55 (d, J=2.2 Hz, 1H), 7.25 (dd, J=8.2, 2.3 Hz, 1H), 7.19 (d, J=8.2 Hz, 1H), 6.68 (s, 1H), 5.92-5.82 (m, 2H), 5.78 (d, J=4.6 Hz, 1H), 4.69 (t, J=5.1 Hz, 1H), 4.01-3.92 (m, 2H), 3.91-3.82 (m, 2H), 3.42 (dt, J=13.1, 7.4 Hz, 2H), 2.65-2.53 (m, 2H), 2.43 (s, 3H).

Step 4: (R)-[5-Chloro-2-(2-iodoethyl)phenyl]-[5-(1,3-dioxolan-2-yl)-2-methyl-3-thienyl]methanol To a solution of 2-[4-chloro-2-[(R)-[5-(1,3-dioxolan-2-yl)-2-methyl-3-thienyl]-hydroxymethyl]phenyl]ethanol (9.90 g, 27.9 mmol) in benzene (327 mL) were added pyridine (6.83 mL, 84.5 mmol) and $PPh_3$ (9.90 g, 27.9 mmol), followed by $I_2$ (7.43 g, 29.3 mmol). After stirring overnight at rt, the reaction mixture was filtered and the filter cake was rinsed with $Et_2O$. To the filtrate was added water and hexane, the layers were separated, and the aqueous layer was extracted with hexane. The combined organic layers were washed with brine, then dried over $Na_2SO_4$, filtered, and concentrated in vacuo. The residue was purified by silica gel column chromatography (10 to 20% EtOAc in hexane) to afford 13 g (99%) of the title compound as a pale yellow solid. LCMS (FA) m/z=465.2 (M+H)

Step 5: (1R)-7-Chloro-1-[5-(1,3-dioxolan-2-yl)-2-methyl-3-thienyl]isochromane To a solution of (R)-[5-chloro-2-(2-iodoethyl)phenyl]-[5-(1,3-dioxolan-2-yl)-2-methyl-3-thienyl]methanol (13.0 g, 28.0 mmol) in $Et_2O$ (433 mL) was added silver(I) oxide (32.4 g, 140 mmol) and the reaction was stirred for two days at rt. The reaction was filtered through a Celite pad and the residual solid was rinsed with $Et_2O$ several times. The filtrate was concentrated in vacuo and the residue was purified by silica gel column chromatography (30% EtOAc in hexane) to give 8.4 g (89%) of the title compound as a colorless oil. $^1$H NMR (400 MHz, DMSO-d6) δ 7.25 (s, 2H), 6.72 (s, 1H), 6.65 (s, 1H), 5.88 (s, 1H), 5.79 (s, 1H), 4.07 (ddd, J=11.3, 5.5, 3.4 Hz, 1H), 4.02-3.95 (m, 2H), 3.92-3.86 (m, 2H), 3.86-3.77 (m, 1H), 3.05-2.92 (m, 1H), 2.76 (d, J=16.5 Hz, 1H), 2.43 (s, 3H).

Step 6: 4-[(1R)-7-Chloroisochroman-1-yl]-5-methyl-thiophene-2-carbaldehyde

To a solution of (1R)-7-chloro-1-[5-(1,3-dioxolan-2-yl)-2-methyl-3-thienyl]isochromane (8.40 g, 24.9 mmol) in THF (96.6 mL) was added HCl (1 M aqueous solution, 96.6 mL, 96.6 mmol) at rt and the reaction was stirred for 1 h. The reaction was quenched by addition of saturated aqueous NaHCO$_3$ and extracted with EtOAc. The combined organic layers were washed with brine, dried over Na$_2$SO$_4$, filtered, and concentrated in vacuo. The residue was purified by silica gel column chromatography (20% EtOAc in hexane) to give 7.15 g (98%) of the title compound. $^1$H NMR (400 MHz, DMSO-d6) δ 9.75 (s, 1H), 7.58 (s, 1H), 7.29 (d, J=1.1 Hz, 2H), 6.74 (s, 1H), 5.92 (s, 1H), 4.12-4.02 (m, 1H), 3.90-3.79 (m, 1H), 3.07-2.94 (m, 1H), 2.85-2.75 (m, 1H), 2.55 (s, 3H).

Step 7: (R)-[4-[(1R)-7-Chloroisochroman-1-yl]-5-methyl-2-thienyl]-(4-chloropyrimidin-5-yl)methanol and (S)-[4-[(1R)-7-Chloroisochroman-1-yl]-5-methyl-2-thienyl]-(4-chloropyrimidin-5-yl)methanol A solution of 4-chloro-5-iodopyrimidine (7.05 g, 29.3 mmol) in THF (100 mL) was cooled at −78° C. To the solution was added 2.50 M of n-BuLi in hexane (23.4 mL, 58.6 mmol) at the same temperature. After stirring for 10 min, a solution of 4-[(1R)-7-chloroisochroman-1-yl]-5-methyl-thiophene-2-carbaldehyde (7.15 g, 24.4 mmol) in THF (28.6 mL) was added at −78° C., and the resulting mixture was stirred for 10 min at the same temperature. The reaction was quenched by addition of water and extracted with EtOAc. The combined organic layers were washed with brine, dried over Na$_2$SO$_4$, filtered, and concentrated in vacuo. The residue was purified by silica gel column chromatography (0 to 50% EtOAc in hexane) to give 9.34 g (94%) of the title compound mixture. $^1$H NMR (400 MHz, DMSO-d6) δ 8.99 (s, 1H), 8.94 (d, J=3.1 Hz, 1H), 7.23 (d, J=2.6 Hz, 2H), 6.67 (d, J=4.6 Hz, 1H), 6.61 (d, J=6.9 Hz, 1H), 6.53 (d, J=5.5 Hz, 1H), 6.02 (dd, J=8.1, 4.6 Hz, 1H), 5.74 (s, 1H), 4.11-4.04 (m, 1H), 3.84-3.74 (m, 1H), 3.02-2.92 (m, 1H), 2.73 (d, J=16.6 Hz, 1H), 2.37 (s, 2H), 2.36 (s, 1H).

Step 8: [4-[(1R)-7-Chloroisochroman-1-yl]-5-methyl-2-thienyl]-(4-chloropyrimidin-5-yl)methanone To a solution of the product mixture from step 7 (9.34 g, 22.9 mmol) in DCM (306 mL) was added MnO$_2$ (19.9 g, 229 mmol) at rt, and the reaction was stirred for 20 h. The reaction was filtered through a Celite pad and the residual solid was rinsed with DCM several times. The filtrate was concentrated in vacuo and the residue was purified by silica gel column chromatography (0 to 40% EtOAc in hexane) to give 9.10 g (86%) of the title compound as an off-white amorphous solid. $^1$H NMR (400 MHz, DMSO-d6) δ 9.21 (s, 1H), 9.06 (s, 1H), 7.43 (s, 1H), 7.29-7.20 (m, 2H), 6.69 (s, 1H), 5.86 (s, 1H), 4.11 (ddd, J=11.3, 5.7, 2.6 Hz, 1H), 3.87-3.75 (m, 1H), 3.07-2.94 (m, 1H), 2.74 (d, J=16.6 Hz, 1H), 2.49 (s, 3H).

Step 9: [4-[(1R)-7-Chloroisochroman-1-yl]-5-methyl-2-thienyl]-[4-[[(1R,3R,4S)-3-(hydroxymethyl)-4-triisopropylsilyloxy-cyclopentyl]amino]pyrimidin-5-yl]methanone To a solution of [4-[(1R)-7-chloroisochroman-1-yl]-5-methyl-2-thienyl]-(4-chloropyrimidin-5-yl)methanone (8.01 g, 19.8 mmol) in iPrOH (274 mL) was added Int-259 (8.94 g, 31.1 mmol) and N,N-diisopropylethylamine (6.91 mL, 39.7 mmol) and the reaction was heated with stirring at 60° C. for 2 h. The reaction was concentrated in vacuo and the residue was purified by silica gel column chromatography (0 to 50% EtOAc in hexane) to give 12.5 g (96%) of the title product. $^1$H NMR (400 MHz, DMSO-d6) δ 8.58 (d, J=5.9 Hz, 2H), 8.23 (d, J=7.6 Hz, 1H), 7.34 (s, 1H), 7.28-7.22 (m, 2H), 6.74 (s, 1H), 5.90 (s, 1H), 4.70-4.64 (m, 2H), 4.23 (d, J=5.5 Hz, 1H), 4.15-4.07 (m, 1H), 3.87-3.77 (m, 1H), 3.42-3.35 (m, 2H), 3.01 (t, J=10.2 Hz, 1H), 2.76 (d, J=16.8 Hz, 1H), 2.47 (s, 3H), 2.34-2.23 (m, 1H), 1.98-1.90 (m, 2H), 1.79-1.71 (m, 1H), 1.24 (dd, J=13.1, 7.7 Hz, 1H), 1.03 (d, J=2.0 Hz, 21H).

Step 10: [(1R,2S,4R)-4-{[5-({4-[(1R)-7-Chloro-3,4-dihydro-1H-isochromen-1-yl]-5-methyl-2-thienyl}carbonyl)pyrimidin-4-yl]amino}-2-hydroxy-cyclopentyl]methyl sulfamate To a solution of [4-[(1R)-7-chloroisochroman-1-yl]-5-methyl-2-thienyl]-[4-[[(1R,3R,4S)-3-(hydroxymethyl)-4-triisopropylsilyloxy-cyclopentyl]amino]pyrimidin-5-yl]methanone (12.4 g, 18.9 mmol) in DMF (186 mL) was added triethylamine (18.4 mL, 132 mmol) followed by chlorosulfonamide (10.9 g, 94.5 mmol) and the reaction was stirred at rt for 1 h. The reaction mixture was placed in an ice bath, and then 6.0 M of HCl in water (271 mL) was added, followed by DMF (300 mL) and the reaction was stirred at rt for 2 h. The reaction was quenched via addition of concentrated aqueous NaOH until pH 9. Reaction mixture was partitioned between water (100 mL more) and EtOAc (400 mL). Sodium chloride was added to saturate the aqueous layer and aid separation of layers. Layers were separated, and the aqueous layer was extracted 2×EtOAc (250 mL each). Combined organic layers were washed 3× brine, then dried over Na$_2$SO$_4$, filtered, and concentrated in vacuo. Crude residue was purified by silica gel column chromatography (0 to 10% MeOH in DCM) to afford 10.5 g (96% over two steps) of the title compound as an off-white amorphous solid. $^1$H NMR (400 MHz, DMSO-d6) δ 8.61 (s, 1H), 8.59 (s, 1H), 8.19 (d, J=7.5 Hz, 1H), 7.44 (s, 2H), 7.36 (s, 1H), 7.26 (d, J=1.8 Hz, 2H), 6.75 (s, 1H), 5.91 (s, 1H), 4.88 (d, J=4.6 Hz, 1H), 4.69 (q, J=8.1 Hz, 1H), 4.17-4.05 (m, 2H), 3.96 (dd, J=9.5, 7.1 Hz, 2H), 3.88-3.79 (m, 1H), 3.08-2.96 (m, 1H), 2.79 (s, 1H), 2.48 (s, 3H), 2.36-2.24 (m, 1H), 2.11 (d, J=5.8 Hz, 1H), 1.99-1.89 (m, 1H), 1.80-1.70 (m, 1H), 1.33-1.21 (m, 1H). LCMS (FA) m/z=579.1 (M+H).

Example 133: [(1R,2S,4R)-4-[[5-[4-[(1R)-7-Chloro-1,2,3,4-tetrahydroisoquinolin-1-yl]-5-methyl-thiophene-2-carbonyl]pyrimidin-4-yl]amino]-2-hydroxy-cyclopentyl]methyl sulfamate I-263a

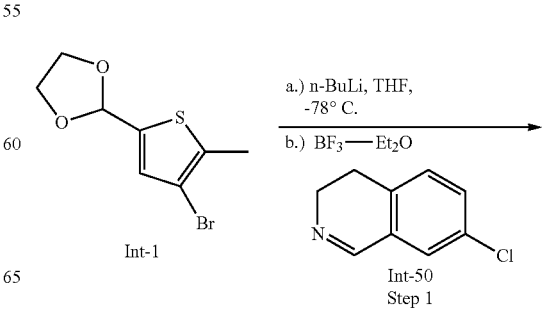

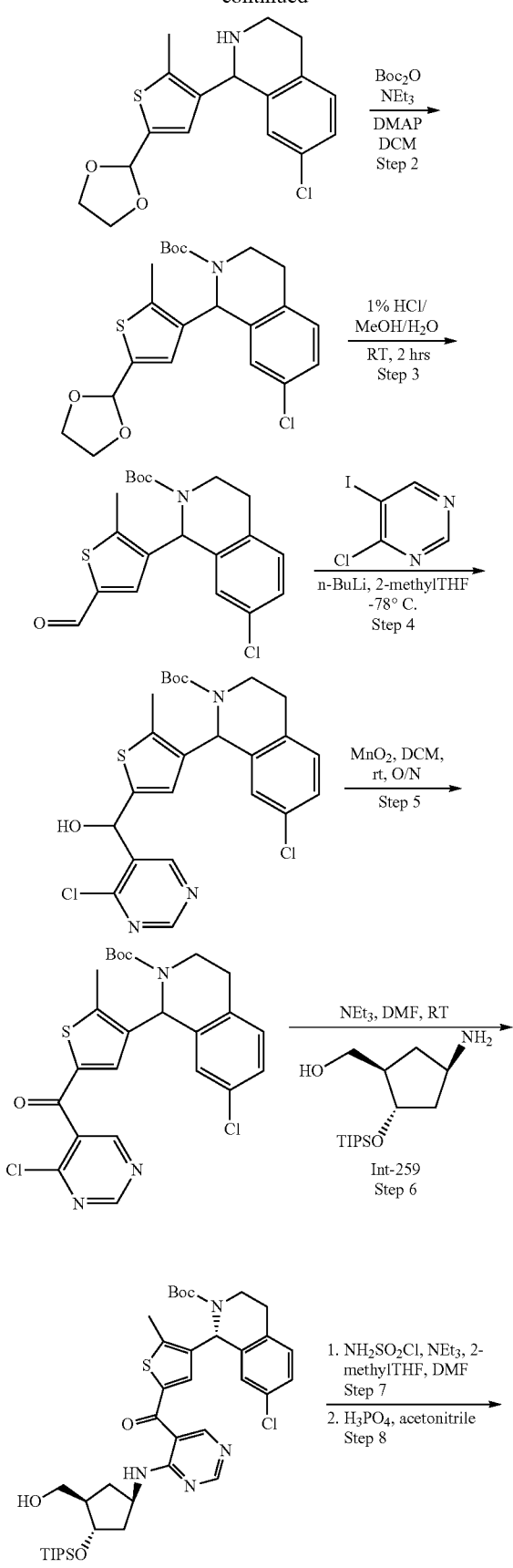

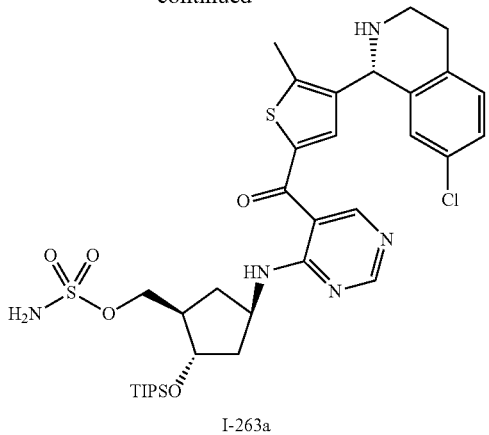

I-263a

Step 1: 7-Chloro-1-[5-(1,3-dioxolan-2-yl)-2-methyl-3-thienyl]-1,2,3,4-tetrahydroisoquinoline An oven-dried 2-neck 250 mL round bottom flask under nitrogen was charged with THF (40 mL) and cooled to −74° C. Added 2.50 M n-BuLi in hexane (6.92 mL, 17.3 mmol). Added a solution of Int-1 (4.00 g, 16.0 mmol) in THF (60 mL) slowly keeping the internal temperature less than −70° C. Stirred with cooling 5 min. A second oven-dried 250 mL round bottom flask under nitrogen was charged with THF (60 mL) and Int-50 (2.04 g, 12.4 mmol) and the resulting solution was cooled to 0° C. Added boron trifluoride diethyl ether complex (1.71 mL, 13.6 mmol) slowly and cooled to −30° C. The contents of the first flask were transferred via cannula to the second flask. Reaction was quenched with saturated aqueous $NaHCO_3$ and warmed to rt. Water was added, and the mixture was extracted three times with EtOAc. Combined organic portions were washed with brine, dried over anhydrous $Na_2SO_4$, filtered, and concentrated in vacuo. Residue was purified via flash column chromatography eluting with a hexane/EtOAc gradient (0 to 100% EtOAc) to afford the title compound as a white solid (1.88 g, 45%). $^1$H NMR (400 MHz, Chloroform-d) δ 7.17-7.01 (m, 2H), 6.83-6.61 (m, 2H), 5.92 (s, 1H), 5.09 (s, 1H), 4.17-4.04 (m, 2H), 4.03-3.92 (m, 2H), 3.37-3.25 (m, 1H), 3.13-2.91 (m, 2H), 2.82-2.69 (m, 1H), 2.46 (s, 3H). LCMS: (AA) M+1 336.1

Step 2: tert-Butyl 7-chloro-1-[5-(1,3-dioxolan-2-yl)-2-methyl-3-thienyl]-3,4-dihydroisoquinoline-2(1H)-carboxylate A 50 mL round bottom flask under nitrogen was charged with 7-chloro-1-[5-(1,3-dioxolan-2-yl)-2-methyl-3-thienyl]-1,2,3,4-tetrahydroisoquinoline (5.67 g, 16.9 mmol) and DCM (100 mL), to which was added triethylamine (4.71 mL, 33.8 mmol), di-tert-butyldicarbonate (4.61 g, 21.1 mmol), and N,N-dimethylaminopyridine (23 mg, 0.18 mmol). Reaction was stirred for 1 h at rt and then poured into saturated $NaHCO_3$ solution. Mixture was extracted three times with DCM, and the combined organic portions were washed with brine, dried over $Na_2SO_4$, filtered, and concentrated in vacuo. The residue was subjected to flash column chromatography eluting with a hexane/EtOAc gradient to afford 6.96 g (95%) of the title compound. LCMS: (AA) M+1 436.1

Step 3: tert-Butyl 7-chloro-1-(5-formyl-2-methyl-3-thienyl)-3,4-dihydroisoquinoline-2(1H)-carboxylate A 1 L round bottom flask was charged with tert-butyl 7-chloro-1-[5-(1,3-dioxolan-2-yl)-2-methyl-3-thienyl]-3,4-dihydroisoquinoline-2(1H)-carboxylate (7.30 g, 16.7 mmol), methanol (200 mL), and water (20 mL), to which was added a solution of 12M HCl (4.00 mL, 130 mmol) in methanol (200 mL), and the reaction was stirred at rt for 1 h. Reaction was quenched via addition of 50 mL of saturated NaHCO$_3$ and stirred for 5 min. Methanol was removed in vacuo, and the resulting aqueous mixture was extracted three times with EtOAc, and then the combined organic layers were washed with brine, dried over anhydrous Na$_2$SO$_4$ and concentrated in vacuo. The residue was subjected to flash column chromatography eluting with a hexane/EtOAc gradient to afford the title compound (4.55 g, 70%). $^1$H NMR (400 MHz, Chloroform-d) δ 9.67 (s, 1H), 7.27-7.15 (m, 2H), 7.12 (s, 1H), 6.98-6.94 (m, 1H), 6.34 (m, 1H), 4.15 (s, 1H), 3.18-3.06 (m, 1H), 3.05-2.93 (m, 1H), 2.82-2.73 (m, 1H), 2.69 (s, 3H), 1.50 (s, 9H). LCMS: (AA) M+Na 414.2

Step 4: tert-Butyl 7-chloro-1-{5-[(4-chloropyrimidin-5-yl)(hydroxy)methyl]-2-methyl-3-thienyl}-3,4-dihydroisoquinoline-2(1H)-carboxylate An oven-dried 500 mL 3-neck round bottom flask under nitrogen was charged with 4-chloro-5-iodopyrimidine (4.08 g, 17.0 mmol) and 2-methyltetrahydrofuran (150 mL). An addition funnel containing a solution of tert-butyl 7-chloro-1-(5-formyl-2-methyl-3-thienyl)-3,4-dihydroisoquinoline-2 (1H)-carboxylate (4.75 g, 12.1 mmol) in 2-methyltetrahydrofuran (50 mL) was attached, and the contents of the reaction flask were cooled to −75° C. 2.50 M n-BuLi in hexane (14.1 mL, 35.2 mmol) was added in small portions keeping the internal temperature less than −70° C., at which point the contents of addition funnel were added in a single portion. Upon completion of addition, the reaction was quenched by adding 20 mL of saturated NaHCO$_3$ in small portions and warmed to rt. The aqueous mixture was extracted three times with EtOAc, and then the combined organic layers were washed with brine, dried over anhydrous Na$_2$SO$_4$ and concentrated in vacuo. The residue was subjected to flash column chromatography eluting with a hexane/EtOAc gradient to afford the title compound (4.85 g, 79%). LCMS: (AA) M+Na 528.1

Step 5: tert-Butyl 7-chloro-1-{5-[(4-chloropyrimidin-5-yl)(hydroxy)methyl]-2-methyl-3-thienyl}-3,4-dihydroisoquinoline-2(1H)-carboxylate A 1 L round bottom flask was charged with tert-butyl 7-chloro-1-{5-[(4-chloropyrimidin-5-yl)(hydroxy)methyl]-2-methyl-3-thienyl}-3,4-dihydroisoquinoline-2(1H)-carboxylate (4.85 g, 9.58 mmol) and DCM (300 mL). Manganese (IV) oxide (14.2 g, 163 mmol) was added and the reaction was stirred at rt for 18 h. Mixture was filtered through Celite, and the filter cake was rinsed with hot EtOAc. Filtrate was concentrated in vacuo to afford the title compound (4.47 g, 93%). $^1$H NMR (400 MHz, Chloroform-d) δ 9.09 (s, 1H), 8.70 (s, 1H), 7.24-7.16 (m, 1H), 7.16-7.07 (m, 1H), 7.00-6.90 (m, 2H), 6.32 (s, 1H), 4.28-3.97 (m, 1H), 3.14-2.89 (m, 2H), 2.78-2.65 (m, 4H), 1.53-1.43 (m, 9H).

Step 6: tert-Butyl (1R)-7-chloro-1-[5-[4-[[(1R,3R,4S)-3-(hydroxymethyl)-4-triisopropylsilyloxy-cyclopentyl]amino]pyrimidine-5-carbonyl]-2-methyl-3-thienyl]-3,4-dihydro-1H-isoquinoline-2-carboxylate A 1 L round bottom flask under nitrogen was charged with tert-butyl 7-chloro-1-{5-[(4-chloropyrimidin-5-yl)carbonyl]-2-methyl-3-thienyl}-3,4-dihydroisoquinoline-2(1H)-carboxylate (4.47 g, 8.86 mmol), DMF (20.0 mL, 258 mmol), Int-259 (3.06 g, 10.6 mmol), and triethylamine (3.09 mL, 22.2 mmol) and the mixture was stirred at rt for 18 h. Reaction mixture was poured into water and saturated NaHCO$_3$, and then extracted three times with EtOAc, and then the combined organic layers were washed with brine, dried over anhydrous Na$_2$SO$_4$ and concentrated in vacuo. The residue was subjected to flash column chromatography eluting with a 70/30 to 60/40 hexane/EtOAc gradient to afford 0.56 g of first-eluting diastereomer 1 (not pictured), 4.31 g of a mixture of diastereomers, and 1.11 g (17%) of second-eluting diastereomer 2 (the title compound). The mixture of diastereomers thus obtained was resubjected to the described chromatography conditions two additional times to afford a total of 2.62 g of the desired diastereomer. $^1$H NMR (400 MHz, Methanol-d4) δ 8.54-8.46 (m, 2H), 7.27-7.19 (m, 2H), 7.09-6.99 (m, 2H), 6.37 (s, 1H), 4.87-4.75 (m, 1H), 4.38-4.29 (m, 1H), 4.20-4.09 (m, 1H), 3.66-3.52 (m, 2H), 3.28-3.14 (m, 2H), 3.02-2.89 (m, 1H), 2.89-2.78 (m, 1H), 2.68 (s, 3H), 2.54-2.41 (m, 1H), 2.22-2.09 (m, 2H), 1.86-1.73 (m, 1H), 1.50 (s, 8H), 1.39-1.23 (m, 2H), 1.15-1.04 (m, 20H). LCMS: (AA) M+1 755.3

Step 7: tert-Butyl (1R)-7-chloro-1-[2-methyl-5-[4-[[(1R,3R,4S)-3-(sulfamoyloxymethyl)-4-triisopropylsilyloxy-cyclopentyl]amino]pyrimidine-5-carbonyl]-3-thienyl]-3,4-dihydro-1H-isoquinoline-2-carboxylate A solution of tert-butyl (1R)-7-chloro-1-[5-[4-[[(1R,3R,4S)-3-(hydroxymethyl)-4-triisopropylsilyloxy-cyclopentyl]amino]pyrimidine-5-carbonyl]-2-methyl-3-thienyl]-3,4-dihydro-1H-isoquinoline-2-carboxylate (2.46 g, 3.26 mmol) in 2-methyltetrahydrofuran (25 mL), and DMF (25 mL) was cooled to 0° C. Triethylamine (1.82 mL, 13.0 mmol) and chlorosulfonamide (1.50 g, 13.0 mmol) were added and the reaction was stirred for 10 min. Added methanol (0.53 mL, 13.0 mmol) and stirred for 15 min. Reaction mixture was poured into saturated NaHCO$_3$, extracted three times with EtOAc, and then the combined organic layers were washed with brine, dried over anhydrous Na$_2$SO$_4$ and concentrated in vacuo. The residue was subjected to flash column chromatography eluting with a hexane/EtOAc gradient to afford the title compound (2.41 g, 89%). $^1$H NMR (400 MHz, Methanol-d4) δ 8.58-8.45 (m, 2H), 7.29-7.17 (m, 2H), 7.11-6.98 (m, 2H), 6.36 (s, 1H), 4.84-4.73 (m, 1H), 4.44-4.33 (m, 1H), 4.21-4.08 (m, 4H), 3.27-3.17 (m, 1H), 3.02-2.89 (m, 1H), 2.88-2.78 (m, 1H), 2.67 (s, 3H), 2.57-2.47 (m, 1H), 2.41-2.30 (m, 1H), 2.23-2.13 (m, 1H), 1.87-1.78 (m, 1H), 1.50 (s, 9H), 1.43-1.33 (m, 1H), 1.17-1.04 (m, 20H). LCMS: (AA) M+1 834.3

Step 8: [(1R,2S,4R)-4-[[5-[4-[(1R)-7-Chloro-1,2,3,4-tetrahydroisoquinolin-1-yl]-5-methyl-thiophene-2-carbonyl]pyrimidin-4-yl]amino]-2-hydroxy-cyclopentyl]methyl sulfamate A solution of tert-butyl (1R)-7-chloro-1-[2-methyl-5-[4-[[(1R,3R,4S)-3-(sulfamoyloxymethyl)-4-triisopropylsilyloxy-cyclopentyl]amino]pyrimidine-5-carbonyl]-3-thienyl]-3,4-dihydro-1H-isoquinoline-2-carboxylate (2.41 g, 2.89 mmol) in CH$_3$CN (10 mL) was cooled in an ice bath to +1° C. Phosphoric acid (10 mL, 200 mmol) was added dropwise and the reaction was stirred with ice bath cooling for 60 min. The mixture was warmed to rt and stirred for an additional 3 h. Reaction was poured into a stirring mixture of 50 mL water and 50 mL EtOAc, and the pH was adjusted to ~9 by slowly adding 200 mL of saturated NaHCO₃ with stirring. Resulting aqueous mixture was extracted three times with EtOAc, and then the combined organic layers were washed with brine, dried over anhydrous Na₂SO₄ and concentrated in vacuo. The residue was subjected to flash column chromatography eluting with a gradient that began with 100% DCM and increased in polarity to 80% DCM/20% methanol/2% ammonium hydroxide gradient to afford the title compound (1.50 g, 90%). ¹H NMR (400 MHz, Methanol-d4) δ 8.61 (s, 1H), 8.52 (s, 1H), 7.27 (s, 1H), 7.18-7.13 (m, 2H), 6.73-6.68 (m, 1H), 5.23 (s, 1H), 4.81-4.70 (m, 1H), 4.26-4.10 (m, 3H), 3.29-3.23 (m, 2H), 3.11-2.96 (m, 2H), 2.87-2.76 (m, 1H), 2.60 (s, 3H), 2.55-2.42 (m, 1H), 2.33-2.19 (m, 1H), 2.18-2.07 (m, 1H), 1.95-1.81 (m, 1H), 1.47-1.35 (m, 1H). LCMS: (AA) M+1 580.0

Example 134: {(1R,2R,3S,4R)-4-[(5-{[4-(3-Bromobenzyl)-2-thienyl]carbonyl}pyrimidin-4-yl)amino]-2,3-dihydroxycyclopentyl}methyl sulfamate I-26

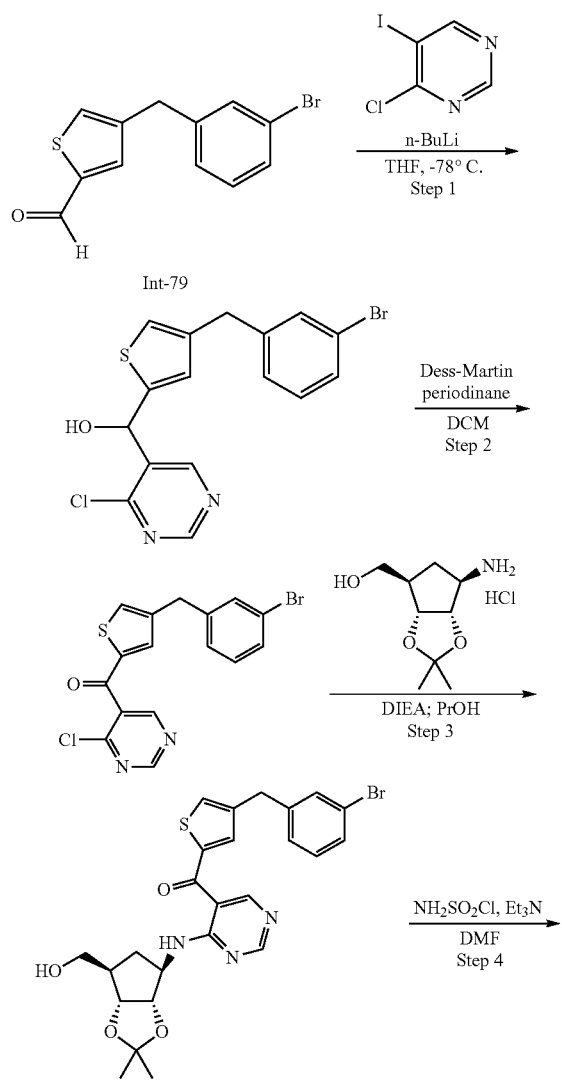

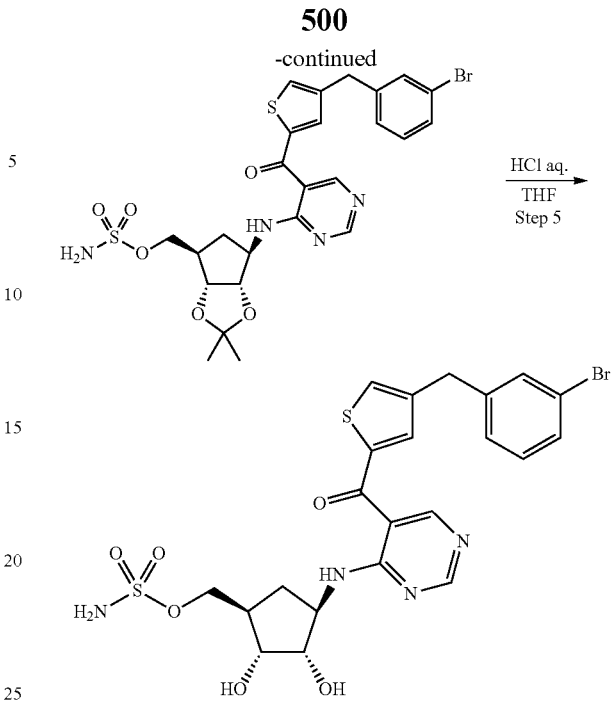

Step 1: rac-[4-(3-Bromobenzyl)-2-thienyl](4-chloropyrimidin-5-yl)methanol

A solution of 4-chloro-5-iodopyrimidine (216 mg, 0.90 mmol) in THF (5.0 mL) was cooled to −78° C. with dry-ice bath. To the solution was added dropwise 2.50 M of n-BuLi in hexane (0.36 mL, 0.90 mmol) at −78° C., and the mixture was stirred for 20 min. To the mixture was added a solution of Int-79 (210 mg, 0.75 mmol) in THF (2.0 mL) at −78° C., and the resulting mixture was stirred for 30 min. The reaction was quenched by addition of saturated NH₄Cl (50 mL) and extracted with EtOAc (50 mL×3). The combined organic layers were dried over Na₂SO₄, filtered, and concentrated in vacuo. Residue was subjected to flash column chromatography eluting with a hexanes/EtOAc gradient to afford the title compound as a colorless oil (yield=260 mg). ¹H NMR (400 MHz, Chloroform-d) δ 9.02 (s, 1H), 8.94 (s, 1H), 7.35 (d, J=7.9 Hz, 1H), 7.32 (s, 1H), 7.17 (t, J=7.7 Hz, 1H), 7.09 (d, J=7.7 Hz, 1H), 6.91 (s, 1H), 6.82 (s, 1H), 6.27 (s, 1H), 3.86 (s, 2H), 2.86-2.60 (br s, 1H).

Step 2: [4-(3-Bromobenzyl)-2-thienyl](4-chloropyrimidin-5-yl)methanone

To a solution of rac-[4-(3-bromobenzyl)-2-thienyl](4-chloropyrimidin-5-yl)methanol (255 mg, 0.64 mmol) in DCM (10.0 mL) was added Dess-Martin periodinane (410 mg, 0.97 mmol) at rt, and the mixture was stirred for 15 min. The reaction was quenched by addition of saturated NaHCO₃ (50 mL) and extracted with DCM (50 mL×3). The combined organic layers were washed with brine, dried over Na₂SO₄, filtered, and concentrated in vacuo. The residue was purified by flash column chromatography eluting with a hexanes/EtOAc gradient to afford the title compound as a colorless oil (yield=247 mg). ¹H NMR (400 MHz, Chloroform-d) δ 9.12 (s, 1H), 8.75 (s, 1H), 7.49-7.45 (m, 1H), 7.38 (d, J=8.0 Hz, 1H), 7.31 (s, 1H), 7.28 (d, J=1.4 Hz, 1H), 7.18 (t, J=7.8 Hz, 1H), 7.09 (d, J=7.7 Hz, 1H), 3.94 (s, 2H).

Step 3: [4-(3-Bromobenzyl)-2-thienyl](4-{[(3aS,4R, 6R,6aR)-6-(hydroxymethyl)-2,2-dimethyltetrahydro-3aH-cyclopenta[d][1,3]dioxol-4-yl]amino}pyrimidin-5-yl)methanone To a mixture of [4-(3-Bromobenzyl)-2-thienyl](4-chloro-pyrimidin-5-yl)methanone (105 mg, 0.27 mmol) and [(3aR, 4R,6R,6aS)-6-amino-2,2-dimethyltetrahydro-3aH-cyclopenta[d][1,3]dioxol-4-yl]methanol hydrochloride (65.6 mg, 0.29 mmol) (for synthesis of this starting material see: Claiborne, C. F. et al. PCT Application Publication WO2008/019124) in i-PrOH (2.2 mL) was added N,N-diisopropylethylamine (0.14 mL, 0.80 mmol). The resulting mixture was stirred at 50° C. for 4 h. After cooling to rt, the reaction was concentrated in vacuo. Subjected to ISCO chromatography eluting with a hexanes/EtOAc gradient to afford the title compound as a white solid (yield=127 mg). LCMS (FA): m/z=546.2 (M+H)

Step 4: {(3aR,4R,6R,6aS)-6-[(5-{[4-(3-Bromobenzyl)-2-thienyl]carbonyl}pyrimidin-4-yl)amino]-2,2-dimethyltetrahydro-3aH-cyclopenta[d][1,3]dioxol-4-yl}methyl sulfamate To a solution of [4-(3-bromobenzyl)-2-thienyl](4-{[(3 aS,4R,6R,6aR)-6-(hydroxymethyl)-2,2-dimethyltetrahydro-3aH-cyclopenta[d][1,3]dioxol-4-yl]amino}pyrimidin-5-yl)methanone (125 mg, 0.23 mmol) in DMF (3.6 mL) and triethylamine (0.08 mL, 0.56 mmol) was added chlorosulfonamide (66.3 mg, 0.57 mmol) at rt, and the mixture was stirred for 2 h. The reaction was quenched with saturated NaHCO₃ end the mixture was extracted with EtOAc (×3). The combined organic layers were then dried using MgSO₄, filtered and concentrated in vacuo to yield 140 mg of the crude title compound. LCMS (FA): m/z=625.2 (M+H)

Step 5: {(1R,2R,3S,4R)-4-[(5-{[4-(3-Bromobenzyl)-2-thienyl]carbonyl}pyrimidin-4-yl)amino]-2,3-dihydroxycyclopentyl}methyl sulfamate To a solution of {(3aR,4R,6R,6aS)-6-[(5-{[4-(3-bromobenzyl)-2-thienyl]carbonyl}pyrimidin-4-yl)amino]-2,2-dimethyltetrahydro-3aH-cyclopenta[d][1,3]dioxol-4-yl}methyl sulfamate (0.14 g, 0.22 mmol) in THF (1.6 mL) was added water (1.6 mL) and 12 M of HCl (0.28 mL, 3.37 mmol) at rt, and the mixture was stirred at rt for 45 min. The reaction was quenched by addition of saturated NaHCO₃ and water and extracted with EtOAc (50 mL×4). The combined organic layers were dried over MgSO₄, filtered, and concentrated in vacuo. The crude mixture was purified by preparative HPLC to yield 57 mg of the title compound. $^1$H NMR (400 MHz, DMSO-$d_6$) δ 8.70 (s, 1H), 8.63 (s, 1H), 8.35 (d, J=7.6 Hz, 1H), 7.82 (d, J=1.2 Hz, 1H), 7.71 (d, J=1.3 Hz, 1H), 7.51 (d, J=1.6 Hz, 1H), 7.45 (s, 2H), 7.40 (dt, J=7.4, 1.7 Hz, 1H), 7.32-7.23 (m, 2H), 4.87 (d, J=5.9 Hz, 1H), 4.72 (d, J=4.8 Hz, 1H), 4.50-4.40 (m, 1H), 4.06 (dd, J=9.7, 6.2 Hz, 1H), 4.00 (s, 2H), 3.96 (dd, J=9.7, 6.7 Hz, 1H), 3.82-3.74 (m, 1H), 3.72-3.66 (m, 1H), 2.32-2.23 (m, 1H), 2.23-2.12 (m, 1H), 1.14 (dt, J=12.7, 8.7 Hz, 1H). LCMS (FA): m/z=585.3 (M+H)

The compounds listed in the table below were prepared in an analogous fashion to that described above starting from the appropriate starting materials. The following alternative conditions were employed in the described reaction steps.
Step 2 Oxidant was A: Dess-Martin Periodinane, B: MnO₂.
Step 3 Base and solvent were A: N,N-diisopropylethylamine, iPrOH, B: triethylamine, iPrOH, C: K₂CO₃, DMF
Step 4: Reaction was run A: With triethylamine. B: Without triethylamine
Step 5: Solvent used was A: THF, B: MeOH, C: DMF, D: DMF/MeOH

| Starting material | Conditions | Compound No. |
|---|---|---|
| Int-137 | Step 2: A<br>Step 3: A<br>Step 4: A<br>Step 5: A | I-24a |
| Int-139 | Step 2: A<br>Step 3: A<br>Step 4: A<br>Step 5: A | I-10 |
| Int-108 | Step 2: A<br>Step 3: A<br>Step 4: A<br>Step 5: A | I-76 |
| Int-115 | Step 2: B<br>Step 3: A<br>Step 4: B<br>Step 5: A | I-115 |
| Int-81 | Step 2: B<br>Step 3: A<br>Step 4: B<br>Step 5: A | I-31 |
| Int-70 | Step 2: B<br>Step 3: A<br>Step 4: B<br>Step 5: A | I-1 |
| 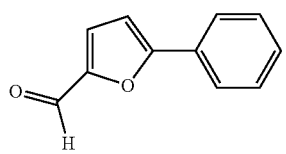 [SMILES: O=Cc1ccc(-c2ccccc2)o1] | Step 2: B<br>Step 3: A<br>Step 4: B<br>Step 5: A | I-134 |
| 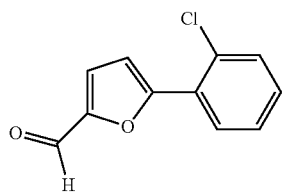 [SMILES: O=Cc1ccc(-c2ccccc2Cl)o1] | Step 2: B<br>Step 3: A<br>Step 4: B<br>Step 5: A | I-158 |
| Int-57 | Step 2: B<br>Step 3: A<br>Step 4: B<br>Step 5: A | I-87 |
| Int-164 | Step 2: B<br>Step 3: C<br>Step 4: B<br>Step 5: A | I-250 |
| Int-175 | Step 2: B<br>Step 3: A<br>Step 4: B<br>Step 5: C | I-278 |
| Int-164 | Step 2: B<br>Step 3: C<br>Step 4: A<br>Step 5: Analogous to Example 174, steps 5 and 6 | I-250 |
| Int-175 | Step 2: B<br>Step 3: C<br>Step 4: A<br>Step 5: Analogous to Example 174, steps 5 and 6 | I-278 |
| Int-204 | Step 2: B<br>Step 3: C<br>Step 4: A<br>Step 5: Analogous to Example 174, steps 5 and 6 | I-295 |

-continued

| Starting material | Conditions | Compound No. |
|---|---|---|
| Int-213 | Step 2: B<br>Step 3: C<br>Step 4: A<br>Step 5: Analogous to Example 174, steps 5 and 6 | I-302 |
| Int-208 | Step 2: B<br>Step 3: B<br>Step 4: B<br>Step 5: C | I-249a** |
| Int-208 | Step 2: B<br>Step 3: B<br>Step 4: B<br>Step 5: C | I-249b** |
| Int-209 | Step 2: B<br>Step 3: B<br>Step 4: A<br>Step 5: Analogous to Example 174, steps 5 and 6 | I-247a** |
| Int-209 | Step 2: B<br>Step 3: C<br>Step 4: B<br>Step 5: C | I-247b** |
| Int-210 | Step 2: B<br>Step 3: C<br>Step 4: B<br>Step 5: C | I-259 |
| Int-247 | Step 2: B<br>Step 3: C<br>Step 4: B<br>Step 5: C | I-354 |
| Int-249 | Step 2: B<br>Step 3: C<br>Step 4: B<br>Step 5: A | I-350 |
| Int-248 | Step 2: B<br>Step 3: A<br>Step 4: B<br>Step 5: C | I-352 |

**Diastereomers were resolved in step 3 by silica gel flash chromatography in analogous fashion to Example 133, step 6.

Example 135: [(1R,2S,4R)-2-Hydroxy-4-({5-[(2S)-2,3,4,5-tetrahydro-2,3'-bifuran-5'-ylcarbonyl]pyrimidin-4-yl}amino)cyclopentyl]methyl sulfamate and [(1R,2S,4R)-2-Hydroxy-4-({5-[(2R)-2,3,4,5-tetrahydro-2,3'-bifuran-5'-ylcarbonyl]pyrimidin-4-yl}amino)cyclopentyl]methyl sulfamate

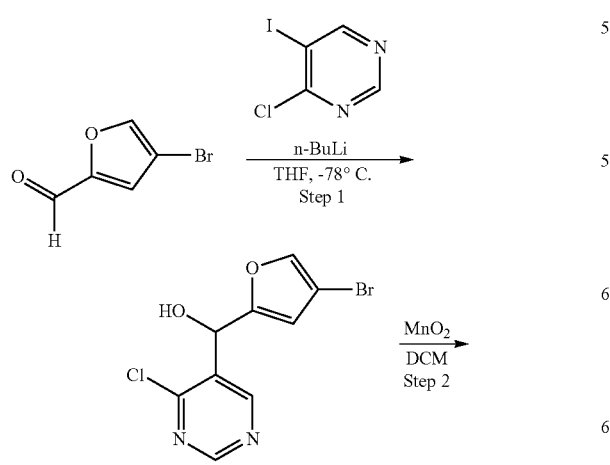

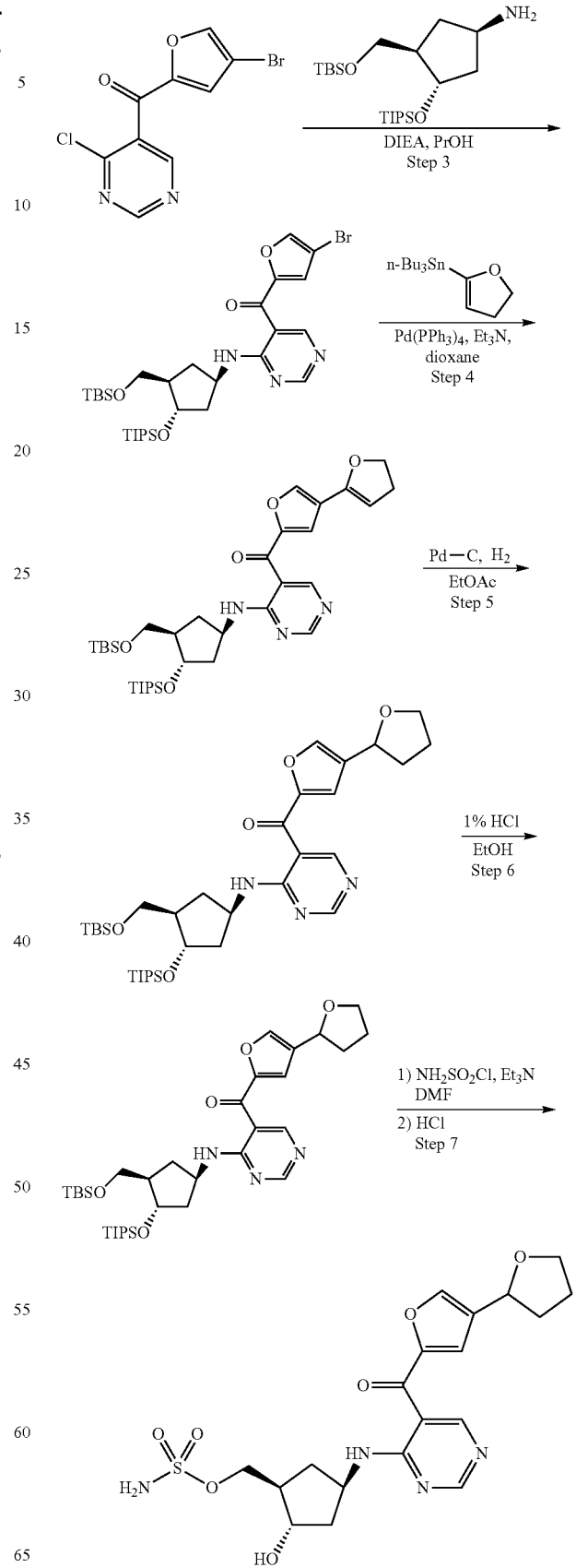

Step 1: rac-(4-Bromo-2-furyl)(4-chloropyrimidin-5-yl)methanol

Step 1 was performed in an analogous fashion to that described in Example 131, step 7. LCMS (FA): m/z=291.3 (M+H).

Step 2: (4-Bromo-2-furyl)(4-chloropyrimidin-5-yl)methanone

Step 2 was performed in an analogous fashion to that described in Example 131, step 8. LCMS (FA): m/z=288.9 (M+H).

Step 3: (4-Bromo-2-furyl)[4-({(1R,3R,4S)-3-({[tert-butyl(dimethyl)silyl]oxy}methyl)-4-[(triisopropylsilyl)oxy]cyclopentyl}amino)pyrimidin-5-yl]methanone To a solution of (4-bromo-2-furyl)(4-chloropyrimidin-5-yl)methanone (1.20 g, 4.17 mmol) and Int-260 (2.35 g, 5.84 mmol) in i-PrOH (72.1 mL) was added N,N-diisopropylethylamine (1.82 mL, 10.4 mmol) and the reaction was heated at 60° C. with stirring for 1 hour. Volatiles were removed in vacuo, and the resulting crude residue was purified via column chromatography (0%-30% EtOAc in hexanes as eluent) to afford 2.56 g of the title compound. $^1$H NMR (400 MHz, Chloroform-d) δ 9.03 (s, 1H), 8.85 (d, J=7.2 Hz, 1H), 8.62 (s, 1H), 7.64 (d, J=0.7 Hz, 1H), 7.21 (d, J=0.7 Hz, 1H), 4.84-4.71 (m, 1H), 4.29-4.23 (m, 1H), 3.59 (dd, J=10.0, 5.4 Hz, 1H), 3.52 (dd, J=10.1, 5.7 Hz, 1H), 2.45-2.34 (m, 1H), 2.19-2.05 (m, 2H), 1.73-1.63 (m, 1H), 1.29-1.19 (m, 1H), 1.03 (s, 21H), 0.84 (s, 9H), −0.00 (s, 6H). LCMS (FA): m/z=652.7 (M+H).

Step 4: [4-({(1R,3R,4S)-3-({[tert-Butyl(dimethyl)silyl]oxy}methyl)-4-[(triisopropylsilyl)oxy]cyclopentyl}amino)pyrimidin-5-yl](4,5-dihydro-2,3'-bifuran-5'-yl)methanone A solution of (4-bromo-2-furyl)[4-({[tert-butyl(dimethyl)silyl]oxy}methyl)-4-[(triisopropylsilyl)oxy]cyclopentyl}amino)pyrimidin-5-yl]methanone (286 mg, 0.44 mmol), tributyl(4,5-dihydrofuran-2-yl)stannane (0.18 mL, 0.57 mmol) and triethylamine (80.1 uL, 0.57 mmol) in 1,4-dioxane (6.10 mL) was purged with argon then Pd(PPh$_3$)$_4$ (50.6 mg, 0.04 mmol) was added. The resulting solution was heated to 110° C. and stirred overnight. The reaction mixture was filtered through Celite (rinsing with EtOAc) and then partitioned between water (30 mL) and EtOAc (80 mL). Layers were separated, and the aqueous layer was extracted 2×EtOAc (20 mL each). Combined organic layers were washed 1× brine, then dried over Na$_2$SO$_4$, filtered, and concentrated in vacuo. Crude residue was purified by ISCO column chromatography (0%-40% EtOAc in hexanes as eluent) to afford 44 mg of the title compound. LCMS (FA): m/z=642.8 (M+1).

Step 5: [4-({(1R,3R,4S)-3-({[tert-Butyl(dimethyl)silyl]oxy}methyl)-4-[(triisopropylsilyl)oxy]cyclopentyl}amino)pyrimidin-5-yl][(2S)-2,3,4,5-tetrahydro-2,3'-bifuran-5'-yl]methanone and [4-({(1R,3R,4S)-3-({[tert-Butyl(dimethyl)silyl]oxy}methyl)-4-[(triisopropylsilyl)oxy]cyclopentyl}amino)pyrimidin-5-yl][(2R)-2,3,4,5-tetrahydro-2,3'-bifuran-5'-yl]methanone In a Parr bottle, to a solution of [4-({(1R,3R,4S)-3-({[tert-butyl(dimethyl)silyl]oxy}methyl)-4-[(triisopropylsilyl)oxy]cyclopentyl}amino)pyrimidin-5-yl](4,5-dihydro-2,3'-bifuran-5'-yl)methanone (232 mg, 0.36 mmol) in EtOAc (29.0 mL) was added 10% palladium on carbon (87.0 mg, 0.08 mmol) and the mixture was purged with hydrogen gas (×3). The bottle was then charged to 60 PSI with hydrogen gas and the reaction was stirred at rt overnight. Added 10% palladium on carbon (87 mg, 0.08 mmol) then purged and recharged hydrogen to 60 PSI. Stirred at rt for 4 h. The reaction mixture was filtered through Celite pad. Crude residue was purified by column chromatography (0%-40% EtOAc in hexanes as eluent) to afford 125 mg of the title compound. $^1$H NMR (400 MHz, Chloroform-d) δ 9.06 (s, 1H), 8.83 (d, J=7.2 Hz, 1H), 8.61 (s, 1H), 7.58 (s, 1H), 7.16 (s, 1H), 4.84 (t, J=6.9 Hz, 1H), 4.80-4.69 (m, 1H), 4.26 (dd, J=6.0, 3.1 Hz, 1H), 4.01-3.93 (m, 1H), 3.88-3.79 (m, 1H), 3.61-3.46 (m, 2H), 2.45-2.35 (m, 1H), 2.30-2.19 (m, 1H), 2.20-2.05 (m, 2H), 1.99-1.93 (m, 2H), 1.85-1.74 (m, 1H), 1.73-1.61 (m, 1H), 1.03 (s, 21H), 0.85 (s, 9H), −0.00 (s, 6H). LCMS (FA): m/z=644.8 (M+1).

Step 6: [4-({(1R,3R,4S)-3-(Hydroxymethyl)-4-[(triisopropylsilyl)oxy]cyclopentyl}amino)pyrimidin-5-yl][(2S)-2,3,4,5-tetrahydro-2,3'-bifuran-5'-yl]methanone and [4-({(1R,3R,4S)-3-(Hydroxymethyl)-4-[(triisopropylsilyl)oxy]cyclopentyl}amino)pyrimidin-5-yl][(2R)-2,3,4,5-tetrahydro-2,3'-bifuran-5'-yl]methanone To a vial containing the diastereomeric mixture produced in Step 5 (105 mg, 0.16 mmol) was added a solution of 1% HCl in EtOH solution (5.35 mL, 0.65 mmol). The solution was stirred at rt for 2 h. Reaction mixture was added to a separatory funnel containing saturated aqueous NaHCO$_3$ (10 mL) and diluted with EtOAc (30 mL). Layers were separated, and the aqueous layer was extracted 2×EtOAc (20 mL each). The combined organic layers were then dried using Na$_2$SO$_4$, filtered and concentrated in vacuo. The crude residue was purified by ISCO column chromatography (0%-70% EtOAc in hexanes as eluent) to afford 87 mg of the title mixture. $^1$H NMR (400 MHz, Chloroform-d) δ 9.12 (s, 1H), 8.96 (d, J=7.1 Hz, 1H), 8.68 (s, 1H), 7.65 (s, 1H), 7.23 (s, 1H), 4.90 (t, J=6.9 Hz, 1H), 4.87-4.78 (m, 1H), 4.38-4.31 (m, 1H), 4.09-3.98 (m, 1H), 3.94-3.86 (m, 1H), 3.73 (t, J=5.5 Hz, 2H), 2.59-2.46 (m, 1H), 2.36-2.25 (m, 1H), 2.26-2.16 (m, 2H), 2.10-1.99 (m, 2H), 1.93-1.80 (m, 2H), 1.74 (t, J=5.0 Hz, 1H), 1.39-1.30 (m, 1H), 1.09 (d, J=1.9 Hz, 21H). LCMS (FA): m/z=530.7 (M+1).

Step 7: [(1R,2S,4R)-2-Hydroxy-4-({5-[(2S)-2,3,4,5-tetrahydro-2,3'-bifuran-5'-ylcarbonyl]pyrimidin-4-yl}amino)cyclopentyl]methyl sulfamate and [(1R,2S,4R)-2-Hydroxy-4-({5-[(2R)-2,3,4,5-tetrahydro-2,3'-bifuran-5'-ylcarbonyl]pyrimidin-4-yl}amino)cyclopentyl]methyl sulfamate To solution of [4-({(1R,3R,4S)-3-(hydroxymethyl)-4-[(triisopropylsilyl)oxy]cyclopentyl}amino)pyrimidin-5-yl][(2S and 2R)-2,3,4,5-tetrahydro-2,3'-bifuran-5'-yl]methanone (85 mg, 0.16 mmol) in DMF (5.0 mL) was added triethylamine (0.16 mL, 1.12 mmol) followed by chlorosulfonamide (92.7 mg, 0.80 mmol). Stirred at rt for 1.5 h. Added chlorosulfonamide (40.0 mg, 0.35 mmol), continued stirring at rt for 1 hour. Added 3.0 M of HCl in water (3.00 mL, 9.00 mmol), and the mixture was stirred at rt for 1 hour. Reaction was quenched via addition of 1N NaOH until pH 9. Reaction mixture was partitioned between water (10 mL more) and EtOAc (40 mL). Layers were separated, and the aqueous layer was extracted 3×EtOAc (20 mL each). The combined organic layers were dried over Na$_2$SO$_4$, filtered, and concentrated in vacuo. The crude residue was purified by ISCO column chromatography (0%-10% MeOH in DCM as eluent) to afford 68 mg of the title compound. $^1$H NMR (400 MHz, DMSO-d$_6$) δ 8.89 (s, 1H), 8.65 (s, 1H), 8.50 (d, J=7.4 Hz, 1H), 8.04 (s, 1H), 7.44 (s, 2H), 7.40 (s, 1H), 4.90 (d, J=4.5 Hz, 1H), 4.82 (t, J=6.9 Hz, 1H), 4.77-4.65 (m, 1H), 4.10 (dd, J=9.7, 6.0 Hz, 1H), 3.97 (dd, J=9.7, 7.0 Hz, 2H), 3.94-3.86 (m, 1H), 3.78-3.70 (m, 1H), 2.39-2.29 (m, 1H), 2.26-2.16 (m, 1H), 2.16-2.07 (m, 1H), 2.03-1.86 (m, 3H), 1.87-1.72 (m, 2H), 1.33-1.22 (m, 1H). LCMS (FA): m/z=453.5 (M+1).

Example 136: 5-{[4-({(1R,3R,4S)-3-({[tert-Butyl (dimethyl)silyl]oxy}methyl)-4-[(triisopropylsilyl) oxy]cyclopentyl}amino)pyrimidin-5-yl]carbonyl}-3-furaldehyde Int-264

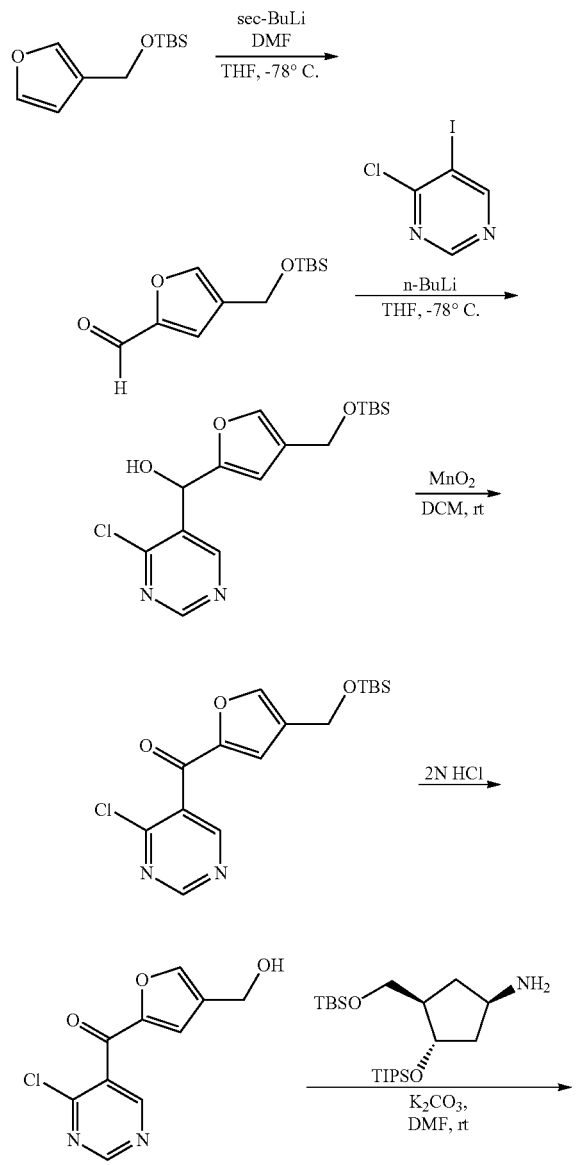

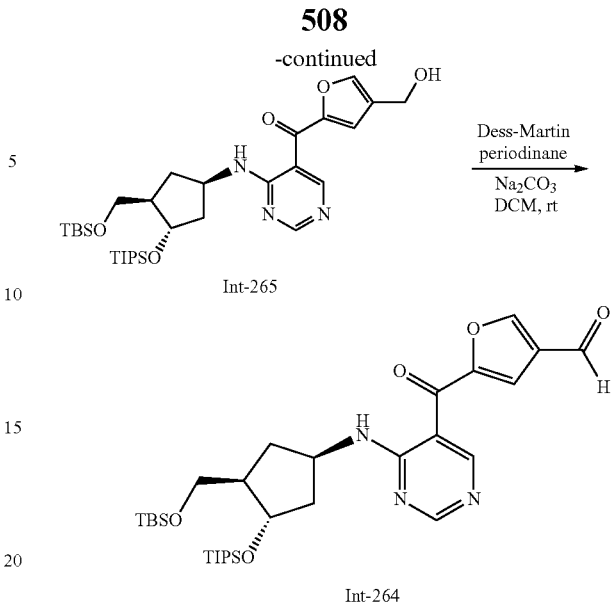

Step 1: 4-({[tert-Butyl(dimethyl)silyl]oxy}methyl)-2-furaldehyde

A solution of tert-butyl(3-furylmethoxy)dimethylsilane (3.40 g, 16.0 mmol) in THF (73.5 mL) was cooled at −78° C. 1.40 M of sec-BuLi in cyclohexane (14.9 mL, 20.8 mmol) was added to the solution at −78° C. After stirring for 30 min, DMF (3.72 mL, 48.0 mmol) was added to the solution at the same temperature and the resulting mixture was stirred for 1 hour. The reaction was quenched by adding saturated aqueous NH$_4$Cl, warmed to rt, and extracted with EtOAc. The combined organic layers were washed with brine, dried over Na$_2$SO$_4$ and concentrated in vacuo. The residue was purified by column chromatography (0%-10% EtOAc in hexanes as eluent) to afford 1.17 g (30%) of the title compound as a pale yellow oil. $^1$H NMR (400 MHz, Chloroform-d) δ 9.63 (s, 1H), 7.60 (s, 1H), 7.19 (s, 1H), 4.63 (s, 2H), 0.92 (s, 9H), 0.10 (s, 6H).

Step 2: rac-[4-({[tert-Butyl(dimethyl)silyl] oxy}methyl)-2-furyl](4-chloropyrimidin-5-yl)methanol To a solution of 4-chloro-5-iodopyrimidine (1.04 g, 4.32 mmol) in THF (30.5 mL) was added 2.50 M of n-BuLi in hexane (3.76 mL, 9.39 mmol) at −78° C. After 20 min of stirring at the same temperature, a solution of 4-({[tert-butyl (dimethyl)silyl]oxy}methyl)-2-furaldehyde (0.91 g, 3.76 mmol) in THF (10.2 mL) was added and the resulting mixture was stirred for 15 min. The reaction was quenched by adding saturated aqueous NH$_4$Cl and allowed to warm to rt. The aqueous layer was extracted with EtOAc. The combined organic layers were washed with brine, dried over Na$_2$SO$_4$, filtered and concentrated in vacuo. The residue was purified by ISCO column chromatography (0%-30% EtOAc in hexanes as eluent) to give 1.25 g (94%) of the title compound as a colorless oil. $^1$H NMR (400 MHz, Chloroform-d) δ 9.02 (s, 1H), 8.97 (s, 1H), 7.32 (s, 1H), 6.22 (s, 1H), 6.09 (s, 1H), 4.54 (s, 2H), 0.90 (s, 9H), 0.07 (s, 6H).

Step 3: [4-({[tert-Butyl(dimethyl)silyl]oxy}methyl)-2-furyl](4-chloropyrimidin-5-yl)methanone To a solution of rac-[4-({[tert-butyl(dimethyl)silyl] oxy}methyl)-2-furyl](4-chloropyrimidin-5-yl)methanol (1.25 g, 3.51 mmol) in DCM (74.1 mL) was added MnO$_2$ (3.06 g, 35.1 mmol) at rt, and the reaction was stirred overnight. The reaction was diluted with DCM and the mixture was filtered through a Celite pad. The residual solid was rinsed with DCM and EtOAc several times. The filtrate was concentrated in vacuo and the residue was purified by ISCO column chromatography (0%-30% EtOAc in hexanes as eluent) to give 1.12 g (91%) of the title compound as a pale yellow oil. $^1$H NMR (400 MHz, Chloroform-d) δ 9.12 (s, 1H), 8.78 (s, 1H), 7.63 (s, 1H), 7.22 (s, 1H), 4.64 (s, 2H), 0.92 (s, 9H), 0.10 (s, 6H).

Step 4: (4-Chloropyrimidin-5-yl)[4-(hydroxymethyl)-2-furyl]methanone

To a solution of [4-({[tert-butyl(dimethyl)silyl]oxy}methyl)-2-furyl](4-chloropyrimidin-5-yl)methanone (0.58 g, 1.65 mmol) in THF (2.99 mL) was added 2.0 M of HCl in ether (1.65 mL, 3.31 mmol) and the mixture was stirred for 1 hour at rt. The reaction was quenched by addition of saturated aqueous NaHCO$_3$ and extracted with EtOAc. The combined organic layers were washed with brine, dried over Na$_2$SO$_4$, filtered, and concentrated in vacuo. The residue was purified by column chromatography (0%-100% EtOAc in hexanes as eluent) to give 379 mg (96%) of the title compound as a yellow solid. $^1$H NMR (400 MHz, Chloroform-d) δ 9.12 (s, 1H), 8.79 (s, 1H), 7.71 (s, 1H), 7.28 (s, 1H), 4.66 (d, J=5.5 Hz, 2H), 1.68 (t, J=5.5 Hz, 1H).

Step 5: [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(hydroxymethyl)-2-furyl]methanone Int-265

Int-260 (766 mg, 1.91 mmol) was dissolved in DMF (11.5 mL) and (4-chloropyrimidin-5-yl)[4-(hydroxymethyl)-2-furyl]methanone (379 mg, 1.59 mmol) and K$_2$CO$_3$ (659 mg, 4.77 mmol) were added to the reaction vessel at rt and the resulting mixture was stirred overnight at rt. The reaction was quenched by addition of water and extracted with EtOAc. The combined organic layers were washed with water and brine, dried over Na$_2$SO$_4$, filtered, and concentrated in vacuo. The residue was purified by ISCO column chromatography (0%-100% EtOAc in hexanes as eluent) to give 855 mg (89%) of the title compound. $^1$H NMR (400 MHz, Methanol-d$_4$) δ 9.08 (s, 1H), 8.58 (s, 1H), 7.84 (d, J=0.8 Hz, 1H), 7.39 (s, 1H), 4.84-4.75 (m, 1H), 4.55 (s, 2H), 4.45-4.38 (m, 1H), 3.77-3.57 (m, 2H), 2.51-2.38 (m, 1H), 2.23-2.08 (m, 2H), 1.80 (ddd, J=12.9, 8.4, 5.5 Hz, 1H), 1.43-1.31 (m, 1H), 1.10 (s, 21H), 0.91 (s, 9H), 0.07 (s, 6H). LCMS (FA): m/z=588.7 (M+H).

Step 6: 5-{[4-({(1R,3R,4S)-3-({[tert-Butyl(dimethyl)silyl]oxy}methyl)-4-[(triisopropylsilyl)oxy]cyclopentyl}amino)pyrimidin-5-yl]carbonyl}-3-furaldehyde To a solution of Int-265 (624 mg, 1.03 mmol) in DCM (10.2 mL) were added Na$_2$CO$_3$ (347 mg, 4.13 mmol) and Dess-Martin periodinane (876 mg, 2.07 mmol) at rt, and the mixture was stirred for 1 hour. The reaction mixture was diluted with DCM and then a 1:1:1 mixture of water: saturated aqueous NaHCO$_3$:saturated aqueous sodium thiosulfate was slowly added to the reaction mixture. The resulting mixture was stirred for 1 h and then extracted with DCM 2×. The combined organic layers were dried over Na$_2$SO$_4$, filtered and concentrated in vacuo. The residue was purified by column chromatography (0%-80% EtOAc in hexanes as eluent) to afford 404 mg (65%) of the title compound as a brown oil. $^1$H NMR (400 MHz, Chloroform-d) δ 10.02 (s, 1H), 9.08 (s, 1H), 8.91 (d, J=7.3 Hz, 1H), 8.68 (s, 1H), 8.27 (d, J=0.8 Hz, 1H), 7.54 (s, 1H), 4.90-4.76 (m, 1H), 4.36-4.28 (m, 1H), 3.63 (dd, J=10.0, 5.3 Hz, 1H), 3.57 (dd, J=10.0, 5.7 Hz, 1H), 2.51-2.39 (m, 1H), 2.25-2.09 (m, 2H), 1.74 (ddd, J=12.9, 9.0, 5.9 Hz, 1H), 1.34-1.28 (m, 1H), 1.07 (s, 21H), 0.89 (s, 9H), 0.04 (s, 6H).

Example 137: [(1R,2S,4R)-2-Hydroxy-4-({5-[4-(hydroxymethyl)-2-furoyl]pyrimidin-4-yl}amino)cyclopentyl]methyl sulfamate I-216

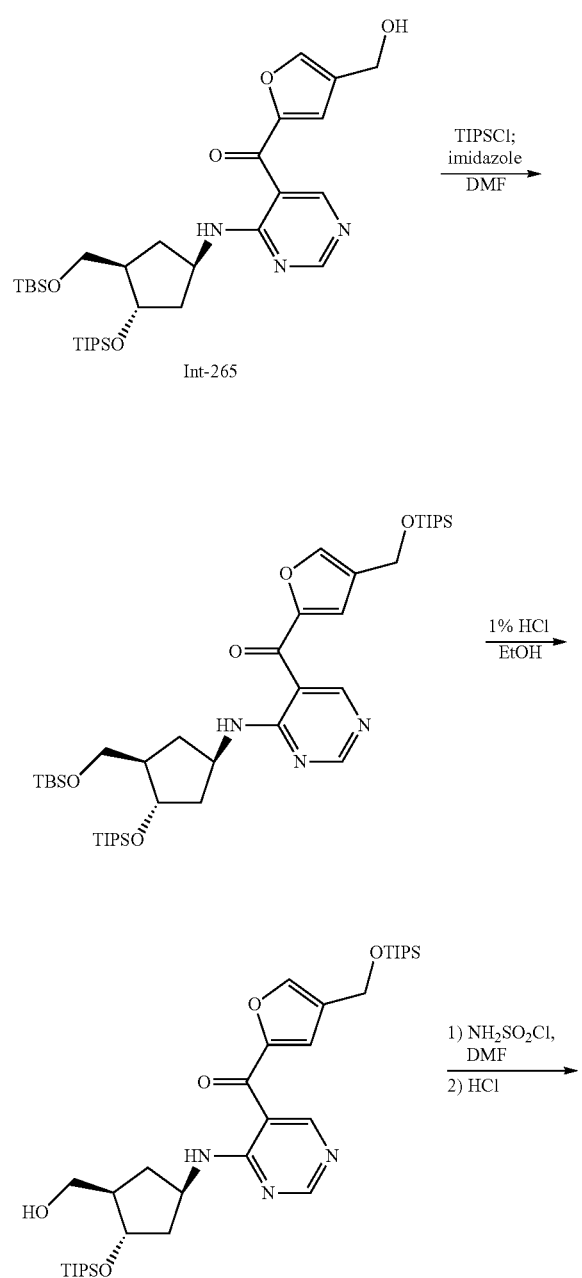

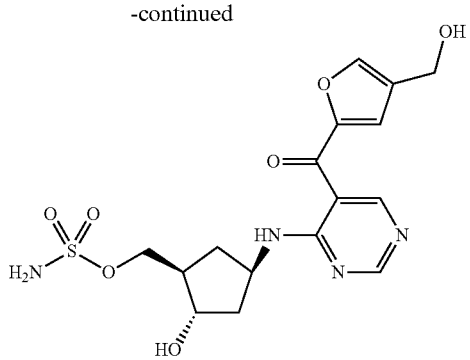

Step 1: [4-({(1R,3R,4S)-3-({[tert-Butyl(dimethyl) silyl]oxy}methyl)-4-[(triisopropylsilyl)oxy] cyclopentyl}amino)pyrimidin-5-yl](4-{[(triisopropylsilyl)oxy]methyl}-2-furyl)methanone To a solution of Int-265 (119 mg, 0.20 mmol) in DMF (2.00 mL) were added imidazole (26.9 mg, 0.39 mmol) and TIPSCl (62.7 uL, 0.30 mmol) at 0° C. The reaction mixture was allowed to warm to rt and stirred for 1.5 h. The reaction was quenched by adding water and extracted with EtOAc. The extract was washed with brine, dried over Na₂SO₄, filtered and concentrated in vacuo. The residue was purified by ISCO column chromatography (0%-20% EtOAc in hexanes as eluent) to give 138 mg (92%) of the title compound as a colorless oil. ¹H NMR (400 MHz, Chloroform-d) δ 9.12 (s, 1H), 8.91 (d, J=7.3 Hz, 1H), 8.65 (s, 1H), 7.62 (s, 1H), 7.21 (s, 1H), 4.86-4.76 (m, 1H), 4.74 (s, 2H), 4.34-4.27 (m, 1H), 3.62 (dd, J=10.1, 5.4 Hz, 1H), 3.56 (dd, J=10.0, 5.8 Hz, 1H), 2.51-2.39 (m, 1H), 2.25-2.09 (m, 2H), 1.78-1.67 (m, 1H), 1.32-0.99 (m, 43H), 0.88 (s, 9H), 0.04 (s, 6H).

Step 2: [4-({(1R,3R,4S)-3-(Hydroxymethyl)-4-[(triisopropylsilyl)oxy]cyclopentyl}amino)pyrimidin-5-yl](4-{[(triisopropylsilyl)oxy]methyl}-2-furyl) methanone To a solution of [4-({(1R,3R,4S)-3-({[tert-butyl(dimethyl)silyl]oxy}methyl)-4-[(triisopropylsilyl)oxy] cyclopentyl}amino)pyrimidin-5-yl](4-{[(triisopropylsilyl) oxy]methyl}-2-furyl)methanone (138 mg, 0.18 mmol) in EtOH (2.1 mL) was added 1% HCl in EtOH solution (2.62 mL, 0.32 mmol) at rt. The reaction mixture was placed inside the refrigerator (~4° C.) for 15 h, and then neutralized with saturated aqueous NaHCO₃. The mixture was concentrated to remove most of the ethanol, diluted with EtOAc and water and extracted with EtOAc. The combined organic layers were washed with water and brine, dried over Na₂SO₄, filtered and concentrated. The residue was purified by ISCO column chromatography (0%-60% EtOAc in hexanes as eluent) to afford 73 mg (62%) of the title compound as a pale yellow oil. ¹H NMR (400 MHz, Chloroform-d) δ 9.11 (s, 1H), 8.98 (d, J=7.1 Hz, 1H), 8.65 (s, 1H), 7.65-7.60 (m, 1H), 7.22 (s, 1H), 4.86-4.75 (m, 1H), 4.74 (s, 2H), 4.36-4.29 (m, 1H), 3.70 (t, J=5.4 Hz, 2H), 2.55-2.45 (m, 1H), 2.25-2.14 (m, 2H), 1.86 (dt, J=13.4, 6.9 Hz, 1H), 1.69 (t, J=5.1 Hz, 1H), 1.38-0.98 (m, 43H)

Step 3: [(1R,2S,4R)-2-Hydroxy-4-({5-[4-(hydroxymethyl)-2-furoyl]pyrimidin-4-yl}amino)cyclopentyl]methyl sulfamate To a solution of [4-({(1R,3R,4S)-3-(hydroxymethyl)-4-[(triisopropylsilyl)oxy]cyclopentyl}amino)pyrimidin-5-yl] (4-{[(triisopropylsilyl)oxy]methyl}-2-furyl)methanone (72.0 mg, 0.11 mmol) in DMF (1.62 mL) was added chlorosulfonamide (25.8 mg, 0.22 mmol) at 0° C. After stirring for 10 min, the reaction mixture was quenched by adding saturated aqueous NaHCO₃ and extracted with EtOAc. The extract was washed with brine, dried over Na₂SO₄, filtered, and concentrated in vacuo. The obtained crude product was dissolved in THF (0.49 mL), and HCl (4 N aqueous solution, 0.49 mL, 2.00 mmol) was added at rt. The reaction mixture was stirred overnight before neutralized by addition of saturated aqueous NaHCO₃. The two phases were separated, and the aqueous phase was extracted with EtOAc. The extract was washed with brine, dried over Na₂SO₄, filtered and concentrated in vacuo. The residue was purified by ISCO column chromatography (0%-10% MeOH in EtOAc as eluent) to give 18 mg (39%) of the title compound as an off-white solid. ¹H NMR (400 MHz, Methanol-d₄) δ 9.07 (s, 1H), 8.58 (s, 1H), 7.84 (s, 1H), 7.39 (s, 1H), 4.83-4.76 (m, 1H), 4.55 (s, 2H), 4.26-4.08 (m, 3H), 2.61-2.44 (m, 1H), 2.34-2.23 (m, 1H), 2.23-2.10 (m, 1H), 1.98-1.85 (m, 1H), 1.51-1.37 (m, 1H). LCMS (FA): m/z=413.2 (M+H).

Example 138: [(1R,2S,4R)-2-Hydroxy-4-({5-[4-(methoxymethyl)-2-furoyl]pyrimidin-4-yl}amino) cyclopentyl]methyl sulfamate I-223

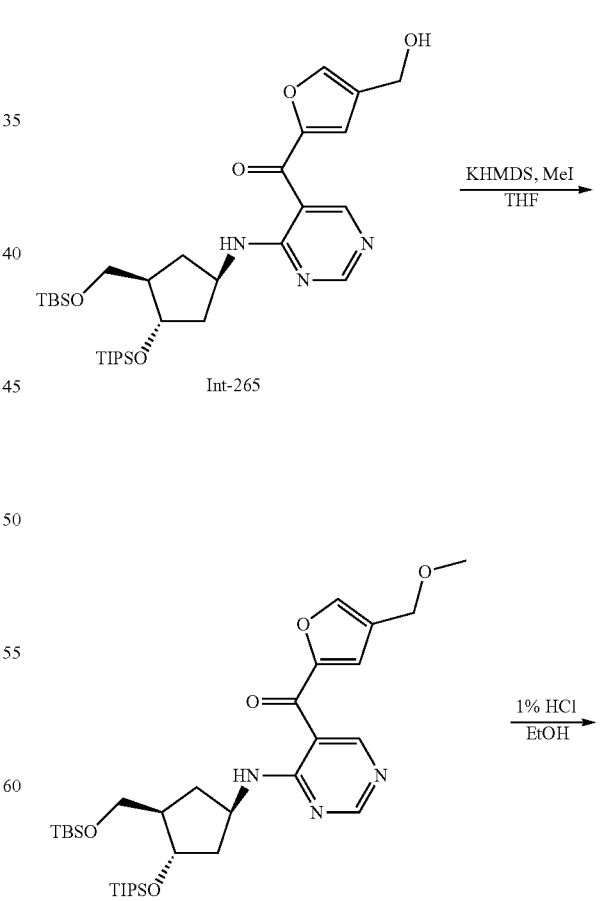

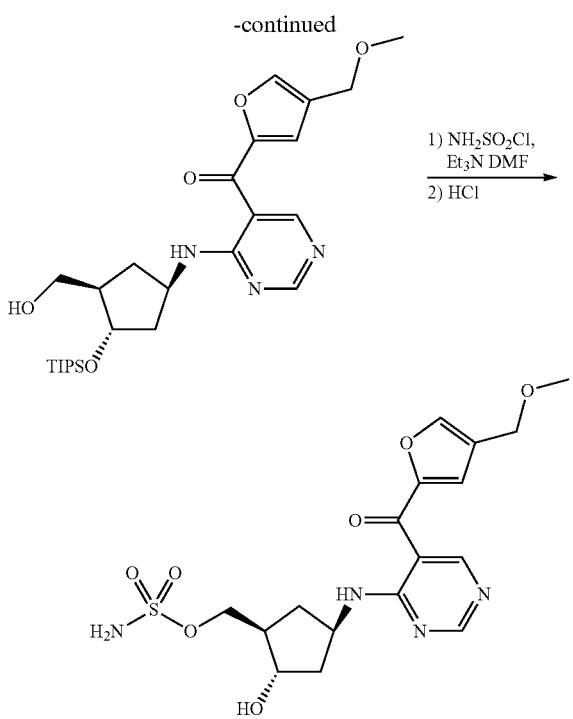

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(methoxymethyl)-2-furyl]methanone A solution of Int-265 (400 mg, 0.66 mmol) in THF (26.7 mL) was cooled to 0° C. and degassed via vacuum/backfilling with argon. At this point MeI (0.21 mL, 3.31 mmol) was added, followed by dropwise addition of 1.0 M of potassium bis(trimethylsilyl)amide in THF (0.66 mL, 0.66 mmol). After stirring for 5 min at 0° C., the reaction was quenched via addition of saturated NaHCO$_3$, and then diluted with Et$_2$O (30 ml) and enough water to dissolve all the solids. The layers were separated, and the aqueous layer was extracted with Et$_2$O (1×20 mL). The combined organic layers were washed brine, then dried over Na$_2$SO$_4$, filtered, and concentrated in vacuo. The crude residue was purified by ISCO column chromatography was performed (0%-10% MeOH in DCM as eluent) to afford 198 mg of the title compound. $^1$H NMR (400 MHz, Chloroform-d) δ 9.07 (s, 1H), 8.88 (d, J=7.4 Hz, 1H), 8.61 (s, 1H), 7.62 (s, 1H), 7.21 (s, 1H), 4.81-4.70 (m, 1H), 4.34 (s, 2H), 4.29-4.24 (m, 1H), 3.61-3.49 (m, 2H), 3.36 (s, 3H), 2.46-2.34 (m, 1H), 2.21-2.05 (m, 2H), 1.73-1.65 (m, 1H), 1.29-1.17 (m, 2H), 1.03 (s, 20H), 0.85 (s, 9H), 0.00 (s, 6H). LCMS (FA): m/z=618.7 (M+H).

Step 2: [4-({(1R,3R,4S)-3-(Hydroxymethyl)-4-[(triisopropylsilyl)oxy]cyclopentyl}amino)pyrimidin-5-yl][4-(methoxymethyl)-2-furyl]methanone The title compound was prepared in an analogous fashion to Example 137 Step 2. $^1$H NMR (400 MHz, Chloroform-d) δ 9.06 (s, 1H), 8.92 (d, J=7.2 Hz, 1H), 8.61 (s, 1H), 7.62 (s, 1H), 7.21 (s, 1H), 4.82-4.70 (m, 1H), 4.34 (s, 2H), 4.32-4.24 (m, 1H), 3.66 (t, J=5.3 Hz, 2H), 3.36 (s, 3H), 2.46 (d, J=13.3, 8.1 Hz, 1H), 2.21-2.09 (m, 2H), 1.87-1.76 (m, 1H), 1.70 (t, J=5.0 Hz, 1H), 1.33-1.23 (m, 1H), 1.03 (s, 21H). LCMS (FA): m/z=504.7 (M+H).

Step 3: [(1R,2S,4R)-2-Hydroxy-4-({5-[4-(methoxymethyl)-2-furoyl]pyrimidin-4-yl}amino)cyclopentyl]methyl sulfamate The title compound was prepared in an analogous fashion to Example 137 Step 3. $^1$H NMR (400 MHz, DMSO-d$_6$) δ 8.90 (s, 1H), 8.65 (s, 1H), 8.53 (d, J=7.5 Hz, 1H), 8.11-8.08 (m, 1H), 7.44 (s, 2H), 7.41 (s, 1H), 4.90 (d, J=4.5 Hz, 1H), 4.77-4.66 (m, 1H), 4.35 (s, 2H), 4.11 (dd, J=9.7, 6.0 Hz, 1H), 3.98 (dd, J=9.7, 7.0 Hz, 2H), 3.29 (s, 3H), 2.39-2.30 (m, 1H), 2.18-2.08 (m, 1H), 2.03-1.93 (m, 1H), 1.84-1.73 (m, 1H), 1.34-1.23 (m, 1H). LCMS (FA): m/z=427.5 (M+H).

Example 139: [(1R,2S,4R)-4-{[5-(4-Acetyl-2-furoyl)pyrimidin-4-yl]amino}-2-hydroxycyclopentyl]methyl sulfamate I-234

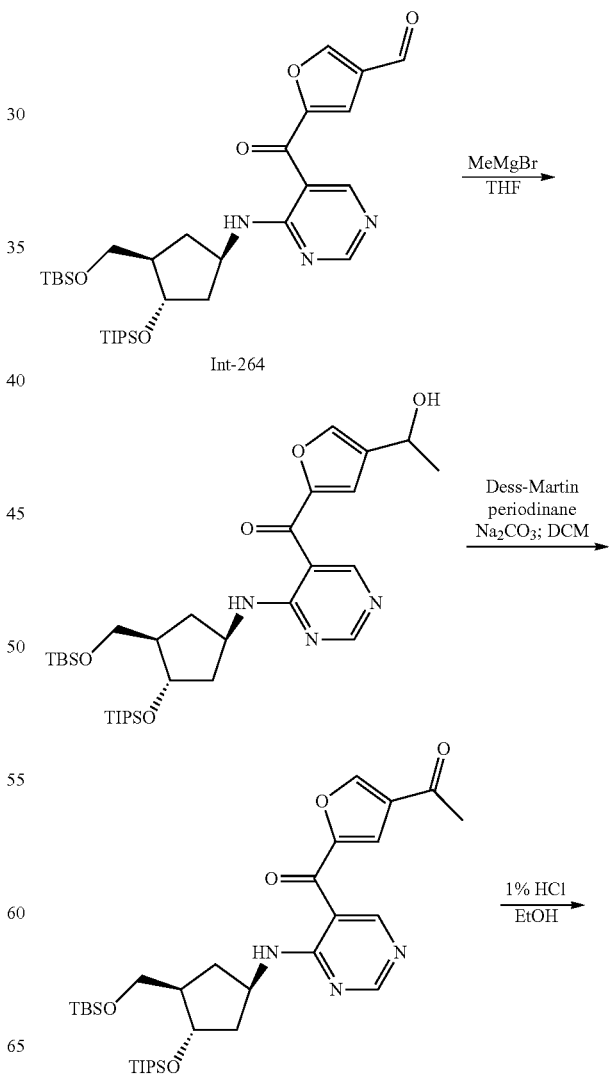

-continued

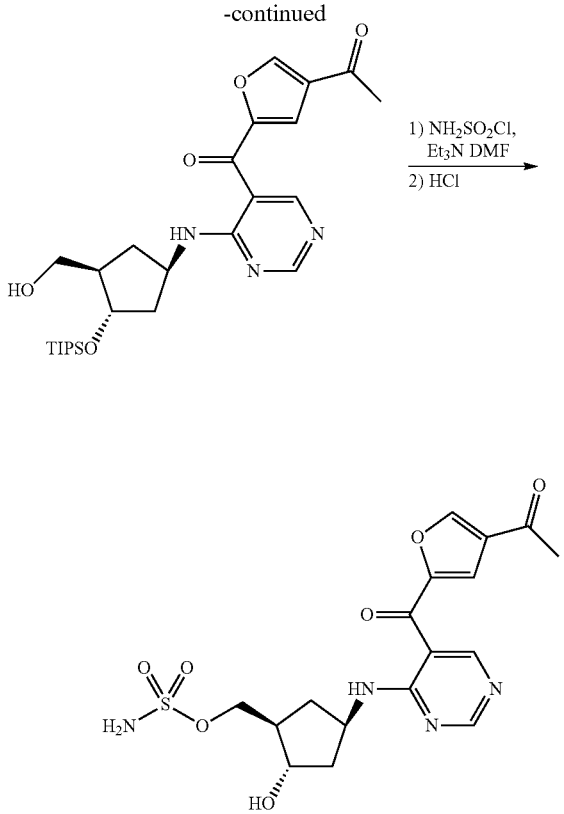

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(1S)-1-hydroxyethyl]-2-furyl}methanone and [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(1R)-1-hydroxyethyl]-2-furyl}methanone A solution of Int-264 (318 mg, 0.53 mmol) in THF (12.7 mL) was cooled to 0° C. and 3.0 M methylmagnesium bromide in Et$_2$O (352.2 uL, 1.057 mmol) was added dropwise. The mixture was then stirred at 0° C. for 1 hour. The reaction was quenched via addition of saturated NaHCO$_3$ (15 mL). Reaction mixture was then diluted with water (15 mL) and Et$_2$O (50 mL). Layers were separated, and the aqueous layer was extracted 2×Et$_2$O (40 mL each). Combined organic layers were dried over Na$_2$SO$_4$, filtered, and concentrated in vacuo. Crude residue was purified by ISCO column chromatography (0%-100% EtOAc in hexanes as eluent) to afford 199 mg of the title compound. $^1$H NMR (400 MHz, Chloroform-d) δ 9.04 (s, 1H), 8.86 (d, J=7.1 Hz, 1H), 8.60 (s, 1H), 7.61 (s, 1H), 7.22 (s, 1H), 4.93-4.85 (m, 1H), 4.82-4.68 (m, 1H), 4.29-4.23 (m, 1H), 3.62-3.48 (m, 2H), 2.46-2.35 (m, 1H), 2.20-2.06 (m, 2H), 1.73-1.64 (m, 1H), 1.49 (d, J=6.5 Hz, 3H), 1.28-1.17 (m, 2H), 1.03 (s, 21H), 0.84 (s, 9H), −0.00 (s, 6H). LCMS (FA): m z=618.9 (M+H).

Step 2: 1-(5-{[4-({(1R,3R,4S)-3-({[tert-Butyl(dimethyl)silyl]oxy}methyl)-4-[(triisopropylsilyl)oxy]cyclopentyl}amino)pyrimidin-5-yl]carbonyl}-3-furyl)ethanone To a solution of the mixture produced in Step 1 (50.0 mg, 0.08 mmol) in DCM (1.92 mL) were added NaHCO$_3$ (27.2 mg, 0.32 mmol) and then Dess-Martin periodinane (68.6 mg, 0.16 mmol) and the mixture was stirred at rt for 1 hour. The reaction was quenched by addition of a 1:1:1 mixture of water, saturated NaHCO$_3$ and saturated sodium thiosulfate (30 mL). The resulting mixture was diluted with DCM (30 mL) and the layers were separated. The aqueous layer was extracted 2×DCM (20 mL each). The combined organic layers were washed with brine, dried over Na$_2$SO$_4$, filtered, and concentrated in vacuo. Crude residue was purified by ISCO column chromatography (0%-70% EtOAc in hexanes as eluent) afforded 45 mg of the title compound. $^1$H NMR (400 MHz, Chloroform-d) δ 9.03 (s, 1H), 8.86 (d, J=7.2 Hz, 1H), 8.64 (s, 1H), 8.17 (s, 1H), 7.48 (s, 1H), 4.84-4.71 (m, 1H), 4.30-4.21 (m, 1H), 3.63-3.48 (m, 2H), 2.47 (s, 3H), 2.45-2.35 (m, 1H), 2.20-2.06 (m, 2H), 1.75-1.62 (m, 1H), 1.30-1.17 (m, 1H), 1.03 (s, 21H), 0.84 (s, 9H), −0.00 (s, 6H). LCMS (FA): m/z=616.6 (M+H).

Step 3: 1-(5-{[4-({(1R,3R,4S)-3-(Hydroxymethyl)-4-[(triisopropylsilyl)oxy]cyclopentyl}amino)pyrimidin-5-yl]carbonyl}-3-furyl)ethanone The title compound was prepared in an analogous fashion to Example 137 Step 2. $^1$H NMR (400 MHz, Chloroform-d) δ 9.09 (s, 1H), 9.01 (d, J=7.2 Hz, 1H), 8.70 (s, 1H), 8.23 (d, J=0.7 Hz, 1H), 7.55 (d, J=0.7 Hz, 1H), 4.92-4.79 (m, 1H), 4.40-4.33 (m, 1H), 3.77-3.69 (m, 2H), 2.53 (s, 4H), 2.28-2.17 (m, 2H), 1.93-1.83 (m, 1H), 1.74-1.68 (m, 1H), 1.37 (dt, J=13.3, 7.9 Hz, 1H), 1.10 (d, J=2.0 Hz, 21H). LCMS (FA): m/z=502.6 (M+H).

Step 4: [(1R,2S,4R)-4-{[5-(4-Acetyl-2-furoyl)pyrimidin-4-yl]amino}-2-hydroxycyclopentyl]methyl sulfamate The title compound was prepared in an analogous fashion to Example 137 Step 3. $^1$H NMR (400 MHz, DMSO-d$_6$) δ 8.92-8.88 (m, 2H), 8.67 (s, 1H), 8.53 (d, J=7.5 Hz, 1H), 7.62 (d, J=0.7 Hz, 1H), 7.45 (s, 2H), 4.92 (s, 1H), 4.78-4.65 (m, 1H), 4.09 (dd, J=9.7, 6.0 Hz, 1H), 4.00-3.93 (m, 2H), 2.49 (s, 3H), 2.38-2.28 (m, 1H), 2.13 (s, 1H), 1.97 (s, 1H), 1.83-1.73 (m, 1H), 1.34-1.25 (m, 1H). LCMS (FA): m/z=425.4 (M+H).

The compound listed in the table below were prepared in an analogous fashion to that described above starting from the appropriate starting materials.

| Grignard reagent | Compound No. |
|---|---|
|  | I-208 |

Example 140: {(1R,2S,4R)-2-Hydroxy-4-[(5-{4-[(1S)-1-hydroxy-2-methylprop-2-en-1-yl]-2-furoyl}pyrimidin-4-yl)amino]cyclopentyl}methyl sulfamate and {(1R,2S,4R)-2-Hydroxy-4-[(5-{4-[(1R)-1-hydroxy-2-methylprop-2-en-1-yl]-2-furoyl}pyrimidin-4-yl)amino]cyclopentyl}methyl sulfamate I-197

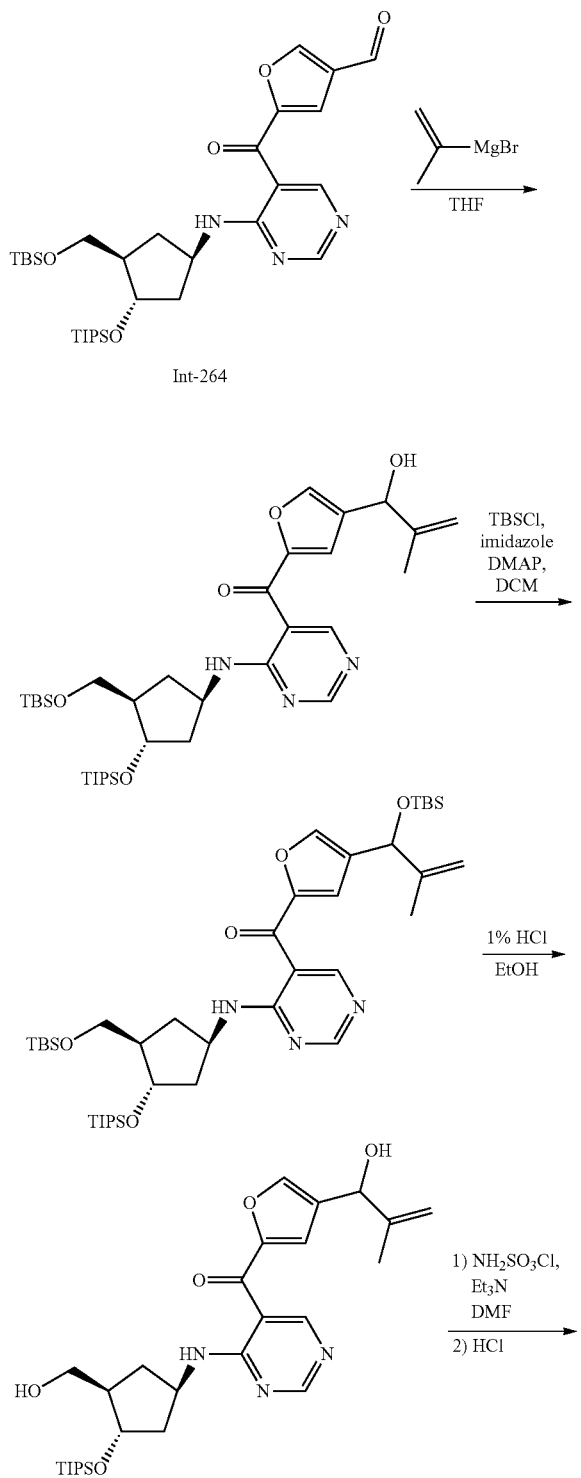

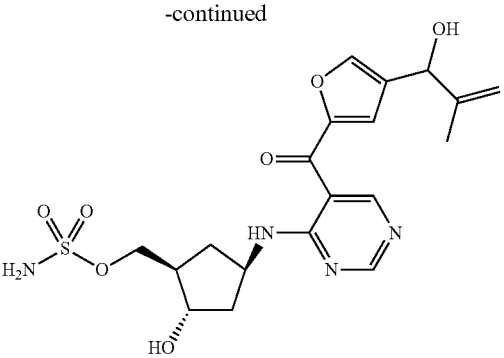

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(1S)-1-hydroxy-2-methylprop-2-en-1-yl]-2-furyl}methanone and [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(1R)-1-hydroxy-2-methylprop-2-en-1-yl]-2-furyl}methanone A solution of Int-264 (485 mg, 0.81 mmol) in THF (7.53 mL) was cooled to −30° C. at which point 0.5 M isopropenylmagnesium bromide in THF (3.22 mL, 1.61 mmol) was added dropwise over 10 min. After stirring for 10 min, the reaction was quenched via addition of saturated NaHCO$_3$ and allowed to warm to rt. Reaction mixture was then partitioned between water (10 mL additional) and EtOAc (60 mL). Layers were separated, and the aqueous layer was extracted 2×EtOAc (40 mL each). Combined organic layers were dried over Na$_2$SO$_4$, filtered, and concentrated in vacuo. The crude residue was purified by ISCO column chromatography (0%-80% EtOAc in hexanes as eluent) to afford 253 mg of the title compound. $^1$H NMR (400 MHz, Chloroform-d) δ 9.04 (s, 1H), 8.83 (d, J=7.1 Hz, 1H), 8.61 (s, 1H), 7.63 (s, 1H), 7.13 (s, 1H), 5.15 (d, J=4.9 Hz, 2H), 4.98-4.93 (m, 1H), 4.82-4.70 (m, 1H), 4.29-4.24 (m, 1H), 3.61-3.49 (m, 2H), 2.46-2.35 (m, 1H), 2.20-2.03 (m, 3H), 1.73-1.64 (m, 4H), 1.28-1.17 (m, 1H), 1.03 (s, 21H), 0.88-0.82 (m, 9H), 0.00 (s, 6H). LCMS (FA): m/z=644.5 (M+H).

Step 2: {4-[(1S)-1-{[tert-Butyl(dimethyl)silyl]oxy}-2-methylprop-2-en-1-yl]-2-furyl}[4-({(1R,3R,4S)-3-({[tert-butyl(dimethyl)silyl]oxy}methyl)-4-[(triisopropylsilyl)oxy]cyclopentyl}amino)pyrimidin-5-yl]methanone and {4-[(1R)-1-{[tert-Butyl(dimethyl)silyl]oxy}-2-methylprop-2-en-1-yl]-2-furyl}[4-({(1R,3R,4S)-3-({[tert-butyl(dimethyl)silyl]oxy}methyl)-4-[(triisopropylsilyl)oxy]cyclopentyl}amino)pyrimidin-5-yl]methanone To a solution of the mixture produced in Step 1 (245 mg, 0.38 mmol) in DMF (2.42 mL) were added 1H-imidazole (77.7 mg, 1.14 mmol), N,N-dimethylaminopyridine (4.65 mg, 0.04 mmol) and TBSCl (86.0 mg, 0.57 mmol). The reaction was stirred at rt for 6 h. Additional portions of 1H-imidazole (129 mg, 1.90 mmol) and TBSCl (172 mg, 1.14 mmol) were added, and stirring was continued at rt overnight. The reaction was poured into saturated NaHCO$_3$ (10 mL), and then diluted with water (10 mL) and EtOAc (40 mL). The layers were separated and the organic layer was washed with brine, dried over Na$_2$SO$_4$, filtered and concentrated in vacuo. The crude residue was purified by ISCO column chromatography (0%-10% EtOAc in hexanes as eluent) to afford 239 mg of the title compound. $^1$H NMR (400 MHz, Chloroform-d) δ 9.04 (s, 1H), 8.83 (d, J=7.0 Hz, 1H), 8.61 (s, 1H), 7.54 (s, 1H), 7.05 (s, 1H), 5.26 (s, 1H), 5.07 (d, J=16.0 Hz, 2H), 4.85 (s, 1H), 4.82-4.69 (m, 1H), 4.30-4.22 (m, 1H), 3.62-3.45 (m, 2H), 2.45-2.33 (m, 1H), 2.21-2.05 (m, 2H), 1.74-1.63 (m, 1H), 1.59 (s, 3H), 1.03 (s, 21H), 0.88 (s, 9H), 0.85 (s, 9H), 0.05 (s, 3H), 0.03 (s, 3H), −0.00 (s, 6H).

Step 3: {4-[(1S)-1-Hydroxy-2-methylprop-2-en-1-yl]-2-furyl}[4-({(1R,3R,4S)-3-(hydroxymethyl)-4-[(triisopropylsilyl)oxy]cyclopentyl}amino)pyrimidin-5-yl]methanone and {4-[(1R)-1-Hydroxy-2-methylprop-2-en-1-yl]-2-furyl}[4-({(1R,3R,4S)-3-(hydroxymethyl)-4-[(triisopropylsilyl)oxy]cyclopentyl}amino)pyrimidin-5-yl]methanone To an ice cooled solution of the mixture produced in Step 2 (235 mg, 0.31 mmol) in EtOH (5.00 mL, 85.6 mmol) was added 1% HCl in EtOH solution (5.00 mL, 0.60 mmol) at 0° C. The reaction flask was capped and the reaction was placed in the freezer overnight. The mixture was allowed to warm to rt with stirring for 5 h. The reaction was quenched by addition of saturated NaHCO$_3$ solution (20 mL) and diluted with water (10 mL) and EtOAc (50 mL). Layers were separated, and the aqueous layer was extracted EtOAc (40 mL). Combined organic layers were dried over Na$_2$SO$_4$, filtered, and concentrated in vacuo. The crude residue was purified by ISCO column chromatography (0%-40% EtOAc in hexanes as eluent) to afford 161 mg of the title compound. $^1$H NMR (400 MHz, Chloroform-d) δ 9.00 (s, 1H), 8.86 (d, J=7.2 Hz, 1H), 8.56 (s, 1H), 7.50 (s, 1H), 7.01 (s, 1H), 5.04 (s, 1H), 5.00 (s, 1H), 4.81 (s, 1H), 4.77-4.66 (m, 1H), 4.27-4.20 (m, 1H), 3.62 (t, J=5.5 Hz, 2H), 2.47-2.34 (m, 1H), 2.16-2.04 (m, 2H), 1.81-1.71 (m, 1H), 1.54 (s, 3H), 1.28-1.15 (m, 1H), 0.98 (d, J=1.8 Hz, 21H), 0.84 (s, 9H), −0.01 (d, J=7.4 Hz, 6H). LCMS (FA): m/z=644.5 (M+H).

Step 4: {(1R,2S,4R)-4-[(5-{4-[(1S)-1-Hydroxy-2-methylprop-2-en-1-yl]-2-furoyl}pyrimidin-4-yl)amino]-2-[(triisopropylsilyl)oxy]cyclopentyl}methyl sulfamate and {(1R,2S,4R)-4-[(5-{4-[(1R)-1-Hydroxy-2-methylprop-2-en-1-yl]-2-furoyl}pyrimidin-4-yl)amino]-2-[(triisopropylsilyl)oxy]cyclopentyl}methyl sulfamate To a solution of the mixture produced in Step 3 (155 mg, 0.24 mmol) in DMF (2.00 mL) and N,N-diisopropylethylamine (0.21 mL, 1.20 mmol) was added chlorosulfonamide (111 mg, 0.96 mmol) at 0° C., and the mixture was stirred for 10 min. The reaction was quenched by addition of saturated NaHCO$_3$ (30 mL) and extracted with EtOAc (50 mL×2). The combined organic layers were dried over Na$_2$SO$_4$, filtered, and concentrated in vacuo. The crude residue was purified by ISCO column chromatography (0%-40% EtOAc in hexanes as eluent) to afford 146 mg of the title compound. $^1$H NMR (400 MHz, Chloroform-d) δ 9.03 (s, 1H), 8.82 (d, J=7.2 Hz, 1H), 8.59 (s, 1H), 7.53 (s, 1H), 7.02 (s, 1H), 5.04 (d, J=14.8 Hz, 4H), 4.83 (s, 1H), 4.79-4.67 (m, 1H), 4.31-4.25 (m, 1H), 4.22 (d, J=4.8 Hz, 2H), 2.59-2.46 (m, 1H), 2.34-2.24 (m, 1H), 2.15-2.04 (m, 1H), 1.90-1.79 (m, 1H), 1.55 (s, 3H), 1.44-1.34 (m, 1H), 0.99 (d, J=2.6 Hz, 21H), 0.85 (s, 9H), 0.01 (d, J=6.9 Hz, 6H). LCMS (FA): m/z=732.5 (M+H).

Step 5: {(1R,2S,4R)-2-Hydroxy-4-[(5-{4-[(1S)-1-hydroxy-2-methylprop-2-en-1-yl]-2-furoyl}pyrimidin-4-yl)amino]cyclopentyl}methyl sulfamate and {(1R,2S,4R)-2-Hydroxy-4-[(5-{4-[(1R)-1-hydroxy-2-methylprop-2-en-1-yl]-2-furoyl}pyrimidin-4-yl)amino]cyclopentyl}methyl sulfamate To a solution of the mixture produced in Step 4 (142 mg, 0.20 mmol) in THF (4.78 mL) was added TBAF hydrate (110 mg, 0.39 mmol), and the mixture was stirred at rt for 1 hour. Reaction mixture was partitioned between water (10 mL) and EtOAc (30 mL). Layers were separated, and the aqueous layer was extracted EtOAc (20 mL×2). The combined organic layers were dried over Na$_2$SO$_4$, filtered, and concentrated in vacuo. The crude residue was purified by ISCO column chromatography (0%-10% MeOH in DCM as eluent) to afford 38 mg of the title compound. $^1$H NMR (400 MHz, DMSO-d$_6$) δ 8.87 (s, 1H), 8.65 (s, 1H), 8.49 (d, J=7.4 Hz, 1H), 7.97 (s, 1H), 7.44 (s, 2H), 7.21 (s, 1H), 5.58 (d, J=4.5 Hz, 1H), 5.09 (s, 1H), 5.05 (d, J=3.3 Hz, 1H), 4.90 (d, J=4.1 Hz, 1H), 4.87 (s, 1H), 4.71 (q, J=8.2 Hz, 1H), 4.11 (dd, J=9.7, 6.0 Hz, 1H), 3.97 (dd, J=9.7, 7.0 Hz, 2H), 2.40-2.24 (m, 1H), 2.19-2.04 (m, 1H), 2.03-1.89 (m, 1H), 1.84-1.70 (m, 1H), 1.63 (s, 3H), 1.33-1.23 (m, 1H). LCMS (FA): m/z=453.5 (M+H).

Example 141: 4-({[tert-Butyl(dimethyl)silyl]oxy}methyl)thiophene-2-carbaldehyde Int-266

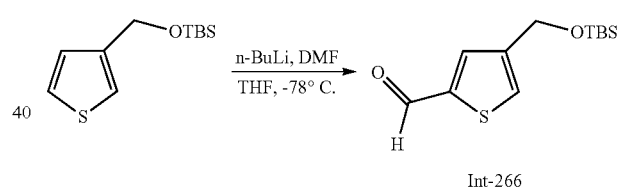

Int-266

Step 1: 4-({[tert-Butyl(dimethyl)silyl]oxy}methyl)thiophene-2-carbaldehyde

A solution of tert-butyl(dimethyl)(3-thienylmethoxy)silane (8.78 g, 38.4 mmol) in THF (140 mL) was cooled at −78° C. 1.40 M of sec-BuLi in cyclohexane (35.7 mL, 50.0 mmol) was added dropwise via syringe to the solution at −78° C. and the mixture was stirred for 30 seconds. DMF (5.95 mL, 76.9 mmol) was added at −78° C., and the reaction mixture was allowed to warm to rt over 30 min. Reaction was quenched with 5 ml acetic acid, and the solution was poured into 60 mL water and extracted with 100 ml EtOAc (×2). The combined organic layers were concentrated in vacuo and the mixture was purified by ISCO column chromatography (0%-30% EtOAc in hexanes as eluent) to give the title compound as colorless oil (yield=6.91 g). $^1$H NMR (400 MHz, Chloroform-d) δ 9.79 (d, J=1.3 Hz, 1H), 7.58 (d, J=1.4 Hz, 1H), 7.47 (p, J=1.2 Hz, 1H), 4.70-4.54 (s, 2H), 0.83 (s, 9H), −0.00 (s, 6H).

521

Example 142: 5-{[4-({(1R,3R,4S)-3-({[tert-Butyl(dimethyl)silyl]oxy}methyl)-4-[(triisopropylsilyl)oxy]cyclopentyl}amino)pyrimidin-5-yl]carbonyl}thiophene-3-carbaldehyde Int-267

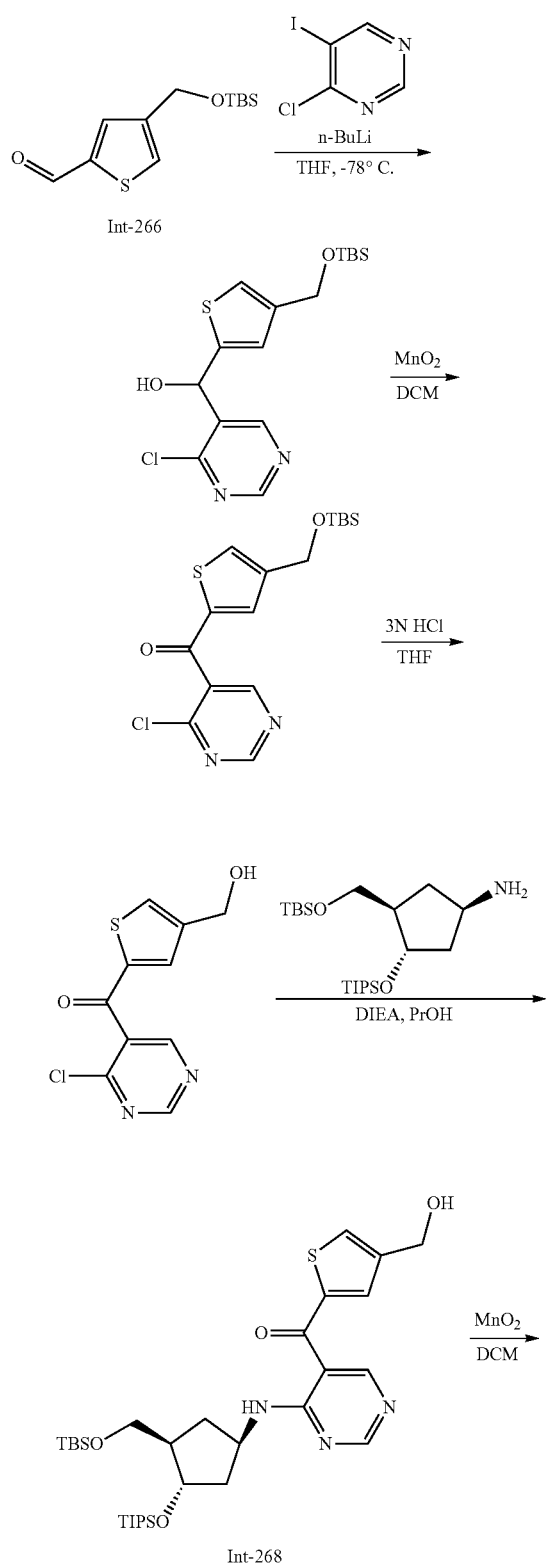

522

-continued

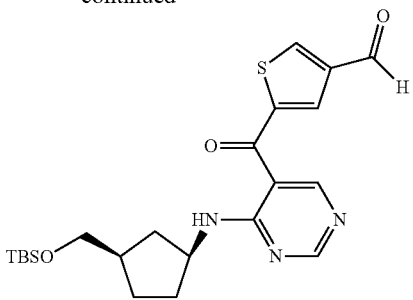

Int-267

Step 1: rac-[4-({[tert-Butyl(dimethyl)silyl]oxy}methyl)-2-thienyl](4-chloropyrimidin-5-yl)methanol The title compounds were prepared in an analogous fashion to Example 131, step 7. LCMS (AA) M+1 371.1

Step 2: [4-({[tert-Butyl(dimethyl)silyl]oxy}methyl)-2-thienyl](4-chloropyrimidin-5-yl)methanone The title compounds were prepared in an analogous fashion to Example 131, step 8. LCMS (FA) M+1 369.1

Step 3: (4-Chloropyrimidin-5-yl)[4-(hydroxymethyl)-2-thienyl]methanone

A solution of [4-({[tert-butyl(dimethyl)silyl]oxy}methyl)-2-thienyl](4-chloropyrimidin-5-yl)methanone (7.51 g, 20.4 mmol) in 40 ml 2% HCl in EtOH was stirred at rt for 2 h. The mixture was concentrated in vacuo and the residue was purified by ISCO column chromatography (30%-100% EtOAc in hexanes as eluent) to give 3.24 g (62.5%) of the title compound as colorless oil. LCMS (AA): m/z=255.0 (M+1).

Step 4: [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(hydroxymethyl)-2-thienyl]methanone Int-268

A solution of (4-chloropyrimidin-5-yl)[4-(hydroxymethyl)-2-thienyl]methanone (2.66 g, 10.4 mmol), Int-260 (4.82 g, 12.0 mmol) and N,N-diisopropylethylamine (5.45 mL, 31.3 mmol) in i-PrOH (70.0 mL) was stirred at 60° C. for 1 hour. The solution was poured into 50 ml water and the mixture was extracted with DCM (80 ml×2). The combined organics were concentrated in vacuo and the residue was purified by ISCO column chromatography (50%-100% EtOAc in hexanes as eluent) to give the title compound (yield=6.14 g). $^1$H NMR (400 MHz, Chloroform-d) δ 8.79 (s, 1H), 8.62 (s, 1H), 8.58 (d, J=7.2 Hz, 1H), 7.58 (s, 1H), 7.54 (s, 1H), 4.78 (m, 1H), 4.69 (s, 2H), 4.26 (m, 1H), 3.61-3.49 (m, 2H), 2.41 (m, 1H), 2.21-2.08 (m, 2H), 1.68 (m, 2H), 1.03 (s, 21H), 0.85 (s, 9H), 0.00 (s, 6H).

Step 5: 5-{[4-({(1R,3R,4S)-3-({[tert-Butyl(dimethyl)silyl]oxy}methyl)-4-[(triisopropylsilyl)oxy]cyclopentyl}amino)pyrimidin-5-yl]carbonyl}thiophene-3-carbaldehyde A solution of [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(hydroxymethyl)-2-thienyl]methanone (1.28 g, 2.06 mmol) in DCM (180.0 mL), then MnO$_2$ (3.59 g, 41.3 mmol) was added to this solution with stirring for 2 h. Additional MnO$_2$ (0.90 g, 10.3 mmol) was added and the mixture was stirred for 4 h at rt. The reaction was filtered through a Celite pad and the filter cake was washed with DCM several times. The filtrate was concentrated to yield 0.98 g (77%) of the title compound. $^1$H NMR (400 MHz, Chloroform-d) δ 9.90 (s, 1H), 8.81 (s, 1H), 8.38 (s, 1H), 7.93 (s, 1H), 4.78 (m, 1H), 4.30-4.19 (m, 1H), 3.56 (m, 2H), 2.42 (m, 1H), 2.24-2.02 (m, 2H), 1.69 (m, 1H), 1.31-1.22 (m, 1H), 1.03 (s, 21H), 0.84 (s, 9H), −0.00 (s, 6H).

Example 143: 4-({[tert-Butyl(dimethyl)silyl]oxy}methyl)-5-chlorothiophene-2-carbaldehyde Int-269

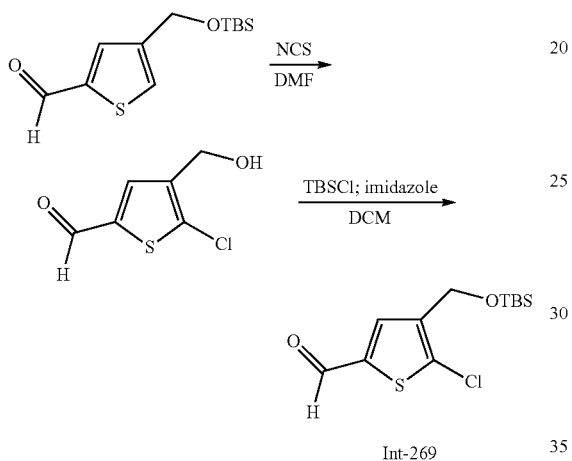

Step 1: 5-Chloro-4-(hydroxymethyl)thiophene-2-carbaldehyde

To a solution of 4-({[tert-butyl(dimethyl)silyl]oxy}methyl)thiophene-2-carbaldehyde (1.75 g, 6.82 mmol) in DMF (30 mL) was added NCS (1.88 g, 14.1 mmol) in one portion. The reaction mixture was then stirred at 50° C. for 3 h. The reaction mixture was allowed to cool to rt. The reaction was diluted with 50 mL water and extracted with EtOAc (×2). The combined EtOAc layer was washed with brine, dried under Na$_2$SO$_4$, filtered and concentrated under reduced pressure to give the title compound as colorless oil. $^1$H NMR (400 MHz, Chloroform-d) δ 9.76 (s, 1H), 7.74 (s, 1H), 4.65 (s, 2H), 3.41-3.18 (br s, 1H).

Step 2: 4-({[tert-Butyl(dimethyl)silyl]oxy}methyl)-5-chlorothiophene-2-carbaldehyde To a solution of 5-chloro-4-(hydroxymethyl)thiophene-2-carbaldehyde in DCM (30 mL), TBSCl (1.23 g, 8.19 mmol) and 1H-imidazole (0.93 g, 13.6 mmol) and the reaction was stirred at rt for 1 hour. The reaction mixture was quenched by addition of water (60 mL) and extracted with DCM (3×50 ml). The combined organic layers were washed by brine, dried by Na$_2$SO$_4$, filtered and concentrated in vacuo. Residue was subjected to ISCO chromatography eluting with a hexane/EtOAc gradient to afford the title compound as a colorless oil (yield=1.7 g). $^1$H NMR (400 MHz, Chloroform-d) δ 9.78 (s, 1H), 7.66 (s, 1H), 4.65 (d, 2H), 0.92 (s, 9H), 0.08 (s, 6H).

Example 144: 5-{[4-({(1R,3R,4S)-3-({[tert-Butyl(dimethyl)silyl]oxy}methyl)-4-[(triisopropylsilyl)oxy]cyclopentyl}amino)pyrimidin-5-yl]carbonyl}-2-chlorothiophene-3-carbaldehyde Int-270

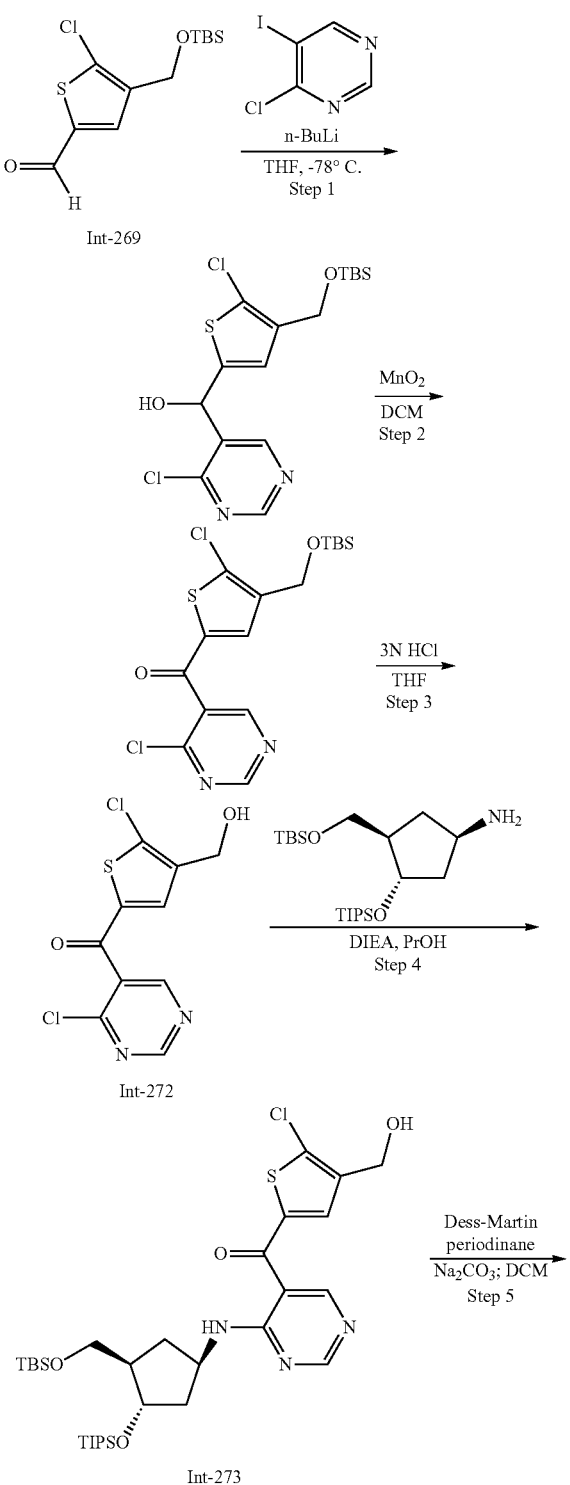

-continued

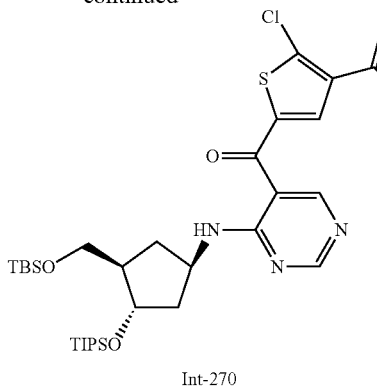

Int-270

Step 1: [4-({[tert-Butyl(dimethyl)silyl]oxy}methyl)-5-chloro-2-thienyl](4-chloropyrimidin-5-yl)methanol A solution of 4-chloro-5-iodopyrimidine (1.2 g, 5.0 mmol) in THF (37.3 mL) was cooled at −78° C. To the solution was added dropwise 2.50 M of n-BuLi in hexane (3.96 mL, 9.90 mmol) at −78° C. and the mixture was stirred for 30 min at same temp. To the mixture was added dropwise a solution of 4-({[tert-butyl(dimethyl)silyl]oxy}methyl)-5-chlorothiophene-2-carbaldehyde (1.2 g, 4.1 mmol) in THF (7.5 mL) at −78° C., and the reaction was stirred for 15 min. The reaction was quenched by addition of saturated NH$_4$Cl (150 mL) and extracted with EtOAc (50 mL×3). The combined organic layers were dried over Na$_2$SO$_4$, filtered, and concentrated in vacuo. The residue was purified by ISCO column chromatography (30% EtOAc in hexanes as eluent) to give 1.4 g of the title compound as light yellow oil. $^1$H NMR (400 MHz, Chloroform-d) δ 8.97 (s, 1H), 8.91 (s, 1H), 6.88 (s, 1H), 6.21 (s, 1H), 4.56 (s, 2H), 3.48-3.09 (br s, 1H), 0.87 (s, 9H), 0.06 (s, 6H).

Step 2: [4-({[tert-Butyl(dimethyl)silyl]oxy}methyl)-5-chloro-2-thienyl](4-chloropyrimidin-5-yl)methanone Int-271

To a solution of [4-({[tert-butyl(dimethyl)silyl]oxy}methyl)-5-chloro-2-thienyl](4-chloropyrimidin-5-yl)methanol (1.88 g, 4.64 mmol) in DCM (97.2 mL) was added MnO$_2$ (4.03 g, 46.4 mmol) at rt, and the mixture was stirred for 12 h. The reaction was filtered through a Celite pad and the residual solid was rinsed with DCM several times. The filtrate was concentrated in vacuo to give 1.59 g (85%) of the title compound as light yellow oil. $^1$H NMR (400 MHz, Chloroform-d) δ 9.13 (s, 1H), 8.75 (s, 1H), 7.32 (s, 1H), 4.65-4.58 (m, 2H), 0.86 (s, 10H), 0.07 (s, 6H).

Step 3: [5-Chloro-4-(hydroxymethyl)-2-thienyl](4-chloropyrimidin-5-yl)methanone Int-272

In a 100 mL round-bottom flask, was placed [4-({[tert-butyl(dimethyl)silyl]oxy}methyl)-5-chloro-2-thienyl](4-chloropyrimidin-5-yl)methanone (2.07 g, 5.13 mmol), THF (24.0 mL) and 2.0 M of HCl in water (4.00 mL, 8.00 mmol). The reaction was stirred at rt. The reaction was quenched with saturated NaHCO$_3$ and the aqueous layer was extracted 3× with EtOAc. The combined organics were dried over Na$_2$SO$_4$, filtered and concentrated in vacuo. Residue was subjected to ISCO chromatography eluting with a DCM/EtOAc gradient to afford the title compound as a yellow solid (yield=1.17 g). LCMS (FA): m/z=291.1 (M+1)

Step 4: [4-({(1R,3R,4S)-3-({[tert-Butyl(dimethyl)silyl]oxy}methyl)-4-[(triisopropylsilyl)oxy]cyclopentyl}amino)pyrimidin-5-yl][5-chloro-4-(hydroxymethyl)-2-thienyl]methanone Int-273

In a microwave reaction vessel, to a solution of Int-260 (764 mg, 1.90 mmol) and [5-chloro-4-(hydroxymethyl)-2-thienyl](4-chloropyrimidin-5-yl)methanone (500 mg, 1.73 mmol) in 1-propanol (14.0 mL) was added N,N-diisopropylethylamine (1.00 mL, 5.74 mmol). The reaction vessel was purged with argon and then sealed. The mixture was stirred for 2 h at 70° C., then concentrated in vacuo. To the residue was added EtOAc. The organic layer was washed with saturated NH$_4$Cl (×2), water (×1), brine (×1) and dried over Na$_2$SO$_4$, filtered, and concentrated in vacuo. Residue was subjected to ISCO chromatography eluting with a DCM/EtOAc gradient to afford the title compound as a yellow residue (yield=1.04 g). $^1$H NMR (400 MHz, Chloroform-d) δ 8.80 (s, 1H), 8.66 (s, 1H), 8.51 (d, J=7.1 Hz, 1H), 7.54 (s, 1H), 4.86-4.73 (m, 1H), 4.68 (s, 2H), 4.34-4.26 (m, 1H), 3.65-3.51 (m, 2H), 2.49-2.39 (m, 1H), 2.23-2.09 (m, 2H), 1.92 (s, 1H), 1.77-1.65 (m, 1H), 1.32-1.19 (m, 1H), 1.07 (s, 21H), 0.89 (s, 9H), 0.04 (s, 6H).

Step 5: 5-{[4-({(1R,3R,4S)-3-({[tert-Butyl(dimethyl)silyl]oxy}methyl)-4-[(triisopropylsilyl)oxy]cyclopentyl}amino)pyrimidin-5-yl]carbonyl}-2-chlorothiophene-3-carbaldehyde A 50 mL round bottom flask under nitrogen was charged with [4-({(1R,3R,4S)-3-({[tert-butyl(dimethyl) silyl]oxy}methyl)-4-[(triisopropylsilyl)oxy]cyclopentyl}amino)pyrimidin-5-yl][5-chloro-4-(hydroxymethyl)-2-thienyl]methanone (0.57 g, 0.87 mmol) and DCM (10 mL). To the mixture was added Dess-Martin periodinane (0.55 g, 1.31 mmol) in a single portion and the mixture was stirred with cooling at 0° C. for 30 min. The reaction mixture was quenched by addition of saturated NaHCO$_3$ followed by extraction with DCM. The organic portion was dried with Na$_2$SO$_4$, filtered and concentrated in vacuo. The residue was subjected to ISCO chromatography eluting with a hexane/EtOAc gradient to give the title compound as a yellow residue (yield=0.88 g). $^1$H NMR (400 MHz, Chloroform-d) δ 10.04 (s, 1H), 8.81 (s, 1H), 8.69 (s, 1H), 8.55 (d, J=7.1 Hz, 1H), 7.79 (s, 1H), 4.88-4.76 (m, 1H), 4.34-4.27 (m, 1H), 3.66-3.53 (m, 2H), 2.51-2.39 (m, 1H), 2.24-2.09 (m, 2H), 1.78-1.66 (m, 1H), 1.34-1.21 (m, 1H), 1.07 (s, 21H), 0.89 (s, 9H), 0.04 (s, 6H).

527

Example 145: {(1R,2S,4R)-4-[(5-{[5-Chloro-4-(methoxymethyl)-2-thienyl]carbonyl}pyrimidin-4-yl)amino]-2-hydroxycyclopentyl}methyl sulfamate. I-218

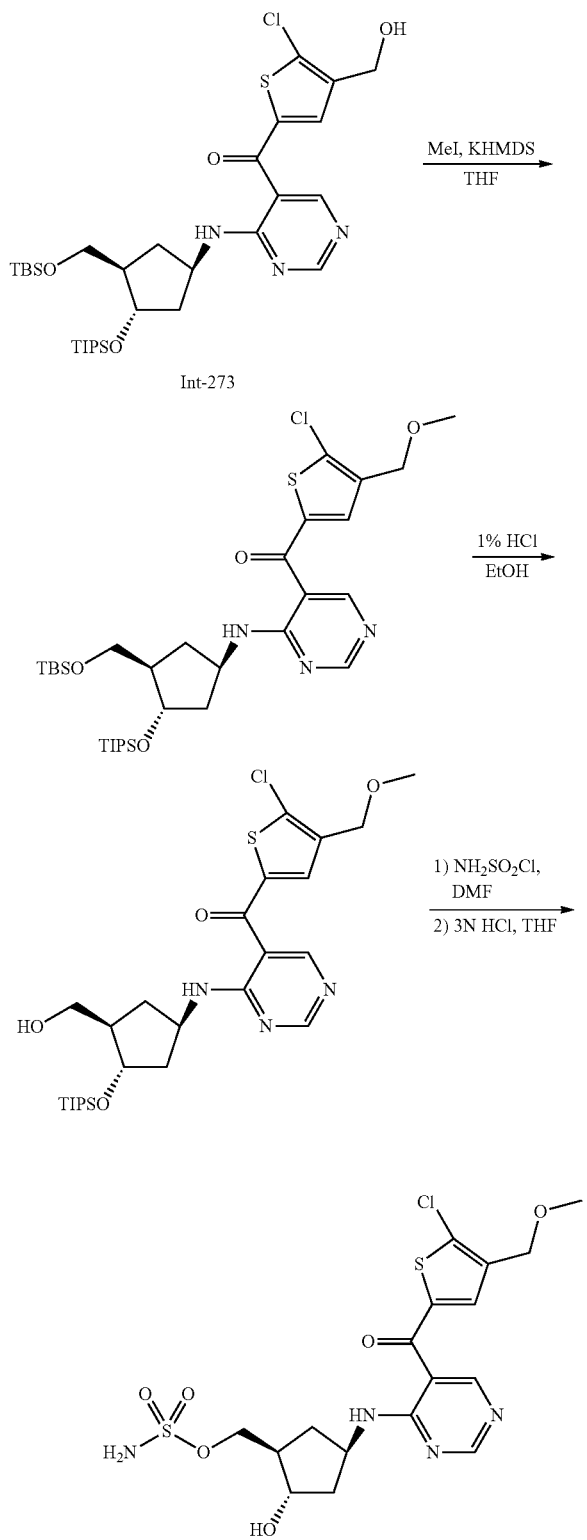

528

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl][5-chloro-4-(methoxymethyl)-2-thienyl]methanone To a solution of Int-273 (369 mg, 0.56 mmol) in THF (25.0 mL) was added MeI (0.19 mL, 2.96 mmol) followed by dropwise addition of 1.0 M of potassium bis(trimethylsilyl)amide in THF (0.59 mL, 0.59 mmol) at 10° C., and the reaction was stirred for 30 min. The reaction was quenched via addition of saturated NaHCO₃, and then diluted with Et₂O (30 ml) and enough water to dissolve all the solids. The layers were separated, and the aqueous layer was extracted with Et₂O (20 mL×2). The combined organic layers were washed brine, then dried over Na₂SO₄, filtered, and concentrated in vacuo. The crude residue was purified by ISCO column chromatography (10%-50% EtOAc in hexanes as eluent) to give 127 mg (34%) of the title compound as yellow oil. ¹H NMR (400 MHz, Chloroform-d) δ 8.80 (s, 1H), 8.66 (s, 1H), 8.49 (d, J=7.0 Hz, 1H), 7.49 (s, 1H), 4.87-4.73 (m, 1H), 4.41 (s, 2H), 4.34-4.26 (m, 1H), 3.62 (dd, J=10.1, 5.4 Hz, 1H), 3.55 (dd, J=10.0, 5.7 Hz, 1H), 3.40 (s, 3H), 2.50-2.38 (m, 1H), 2.24-2.09 (m, 2H), 1.71 (ddd, J=12.9, 9.1, 6.0 Hz, 1H), 1.30-1.22 (m, 1H), 1.07 (s, 21H), 0.88 (s, 9H), 0.04 (s, 6H).

Step 2: [5-Chloro-4-(methoxymethyl)-2-thienyl][4-({(1R,3R,4S)-3-(hydroxymethyl)-4-[(triisopropylsilyl)oxy]cyclopentyl}amino)pyrimidin-5-yl]methanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl][5-chloro-4-(methoxymethyl)-2-thienyl]methanone (127 mg, 0.19 mmol) in EtOH (3.5 mL) was added 1% HCl in EtOH solution (4.50 mL, 0.54 mmol) at rt, and the mixture was settled in a refrigerator for 19 h. The reaction was quenched with saturated NaHCO₃ and diluted with water and EtOAc. After separation of the two layers, the water layer was extracted with EtOAc (×3). The combined organic layers were washed with brine, dried over Na₂SO₄, filtered, and concentrated in vacuo. The residue was purified by ISCO column chromatography (20%-50% EtOAc in DCM as eluent) to give 87 mg (83%) of the title compound. ¹H NMR (400 MHz, Chloroform-d) δ 8.80 (s, 1H), 8.66 (s, 1H), 8.56 (d, J=7.4 Hz, 1H), 7.49 (s, 1H), 4.80 (h, J=7.6 Hz, 1H), 4.41 (s, 2H), 4.32 (q, J=4.6 Hz, 1H), 3.70 (t, J=4.6 Hz, 2H), 3.40 (s, 3H), 2.49 (dt, J=13.4, 8.1 Hz, 1H), 2.25-2.13 (m, 2H), 1.84 (dt, J=13.4, 6.5 Hz, 1H), 1.31 (dt, J=13.1, 7.9 Hz, 1H), 1.07 (s, 21H).

Step 3: {(1R,2S,4R)-4-[(5-{[5-Chloro-4-(methoxymethyl)-2-thienyl]carbonyl}pyrimidin-4-yl)amino]-2-hydroxycyclopentyl}methyl sulfamate To a solution of [5-chloro-4-(methoxymethyl)-2-thienyl][4-({(1R,3R,4S)-3-(hydroxymethyl)-4-[(triisopropylsilyl)oxy]cyclopentyl}amino)pyrimidin-5-yl]methanone (87.1 mg, 0.16 mmol) in DMF (1.87 mL, 24.2 mmol) was added triethylamine (0.15 mL, 1.10 mmol) followed by chlorosulfonamide (90.8 mg, 0.79 mmol) at 0° C. and the reaction was stirred at for 30 min. To the reaction was added 3.0 M of HCl (2.00 mL, 6.00 mmol) at 0° C., and then the reaction was warmed to rt for 3 h. The reaction was quenched by addition of saturated NaHCO₃ and the resulting mixture was extracted with EtOAc (×3). The combined organics extracts were washed with 10% aqueous LiCl solution, brine, dried over Na₂SO₄, filtered and concentrated in vacuo. The residue was purified via ISCO column chromatography (10% MeOH in DCM as eluent) to give 67 mg (90%) of the title compound as off-white solid. $^1$H NMR (400 MHz, MeOD) δ 8.76 (s, 1H), 8.60 (s, 1H), 7.61 (s, 1H), 4.86-4.75 (m, 1H), 4.46 (s, 2H), 4.24-4.12 (m, 3H), 3.40 (s, 3H), 2.55-2.46 (m, 1H), 2.32-2.10 (m, 2H), 1.96-1.85 (m, 1H), 1.48-1.38 (m, 1H). LCMS (FA): m/z=479.1 (M+H).

Example 146: {(1R,2S,4R)-4-[(5-{[5-Chloro-4-(hydroxymethyl)-2-thienyl]carbonyl}pyrimidin-4-yl)amino]-2-hydroxycyclopentyl}methyl sulfamate. I-211

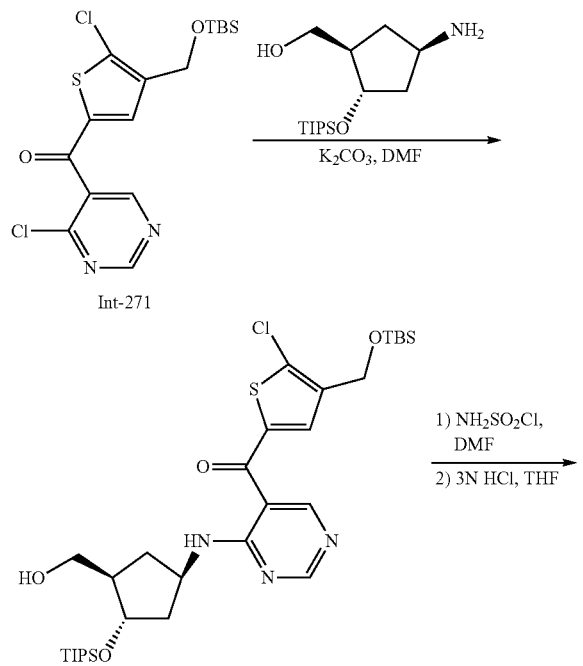

Step 1: [4-({[tert-Butyl(dimethyl)silyl]oxy}methyl)-5-chloro-2-thienyl][4-({(1R,3R,4S)-3-(hydroxymethyl)-4-[(triisopropylsilyl)oxy]cyclopentyl}amino)pyrimidin-5-yl]methanone Int-259 (84.3 mg, 0.29 mmol), Int-271 (105 mg, 0.26 mmol), N,N-diisopropylethylamine (0.14 mL, 0.78 mmol), and i-PrOH (2.1 mL) were placed in a microwave reaction vial under nitrogen and stirred at 70° C. for 1 hour. The reaction was cooled at rt. The reaction was concentrated in vacuo. The residue was diluted with EtOAc and the mixture was washed with saturated NH₄Cl (×2), brine, dried over Na₂SO₄, filtered and concentrated in vacuo. The residue was purified via ISCO column chromatography (0%-100% EtOAc in DCM as eluent) to give the title compound as yellow oil (yield=143 mg). $^1$H NMR (400 MHz, Chloroform-d) δ 8.79 (s, 1H), 8.67 (s, 1H), 8.59 (d, J=7.2 Hz, 1H), 7.50 (s, 1H), 4.81 (q, J=7.8 Hz, 1H), 4.65 (s, 2H), 4.35-4.29 (m, 1H), 3.70 (t, J=4.8 Hz, 2H), 2.55-2.43 (m, 1H), 2.25-2.14 (m, 2H), 1.90-1.79 (m, 1H), 1.67 (t, J=5.0 Hz, 1H), 1.37-1.28 (m, 1H), 1.07 (s, 21H), 0.92 (s, 9H), 0.11 (s, 6H).

Step 2: {(1R,2S,4R)-4-[(5-{[5-Chloro-4-(hydroxymethyl)-2-thienyl]carbonyl}pyrimidin-4-yl)amino]-2-hydroxycyclopentyl}methyl sulfamate To a solution of [4-({[tert-butyl(dimethyl)silyl]oxy}methyl)-5-chloro-2-thienyl][4-({(1R,3R,4S)-3-(hydroxymethyl)-4-[(triisopropylsilyl)oxy]cyclopentyl}amino)pyrimidin-5-yl]methanone (143 mg, 0.22 mmol) in DMF (4.0 mL) was added chlorosulfonamide (41.0 mg, 0.36 mmol) at rt, and the mixture was stirred for 20 min. A small amount of additional chlorosulfonamide was added and the reaction was stirred for 20 min. The reaction was quenched by addition of saturated NaHCO₃ and water was added. The reaction was extracted EtOAc (×3). The combined organics were washed with 10% LiCl in water (×2), brine, dried over MgSO₄, filtered and concentrated in vacuo. The residue was purified via ISCO column chromatography (10%-70% EtOAc in DCM as eluent) to give a yellow oil. This oil was diluted with THF (1.41 mL, 17.4 mmol), 4.0 M of HCl (0.94 mL, 3.76 mmol) was added at rt, and the mixture was stirred for overnight. The reaction was quenched by addition of saturated NaHCO₃ and the mixture was extracted with EtOAc (×3). The combined organic layers were dried over MgSO₄, filtered, and concentrated in vacuo. The residue was triturated with hexanes. The precipitate collected via vacuum filtration, washed with hexanes and dried under high vacuum to give the title compound as yellow solid (yield=45 mg). $^1$H NMR (400 MHz, Methanol-d₄) δ 8.77 (s, 1H), 8.61 (s, 1H), 7.64 (s, 1H), 4.84-4.75 (m, 1H), 4.59 (s, 2H), 4.25-4.12 (m, 3H), 2.57-2.45 (m, 1H), 2.33-2.21 (m, 1H), 2.16 (ddd, J=12.5, 7.2, 4.0 Hz, 1H), 1.91 (dt, J=13.6, 7.4 Hz, 1H), 1.43 (dt, J=13.0, 9.2 Hz, 1H).

Example 147: [(1R,2S,4R)-4-{[5-({5-Chloro-4-[(S)-(3-chlorophenyl)(hydroxy)methyl]-2-thienyl}carbonyl)pyrimidin-4-yl]amino}-2-hydroxycyclopentyl]methyl sulfamate and [(1R,2S,4R)-4-{[5-({5-Chloro-4-[(R)-(3-chlorophenyl)(hydroxy)methyl]-2-thienyl}carbonyl)pyrimidin-4-yl]amino}-2-hydroxycyclopentyl]methyl sulfamate I-9

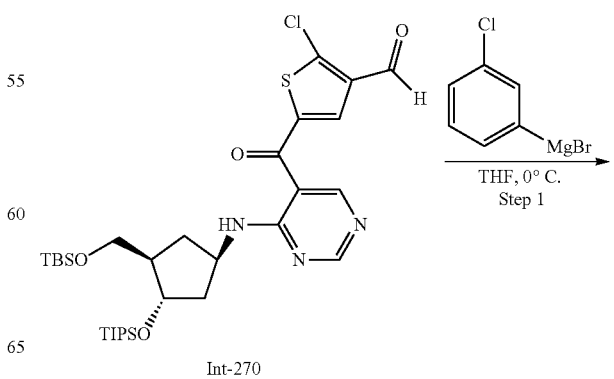

Int-270

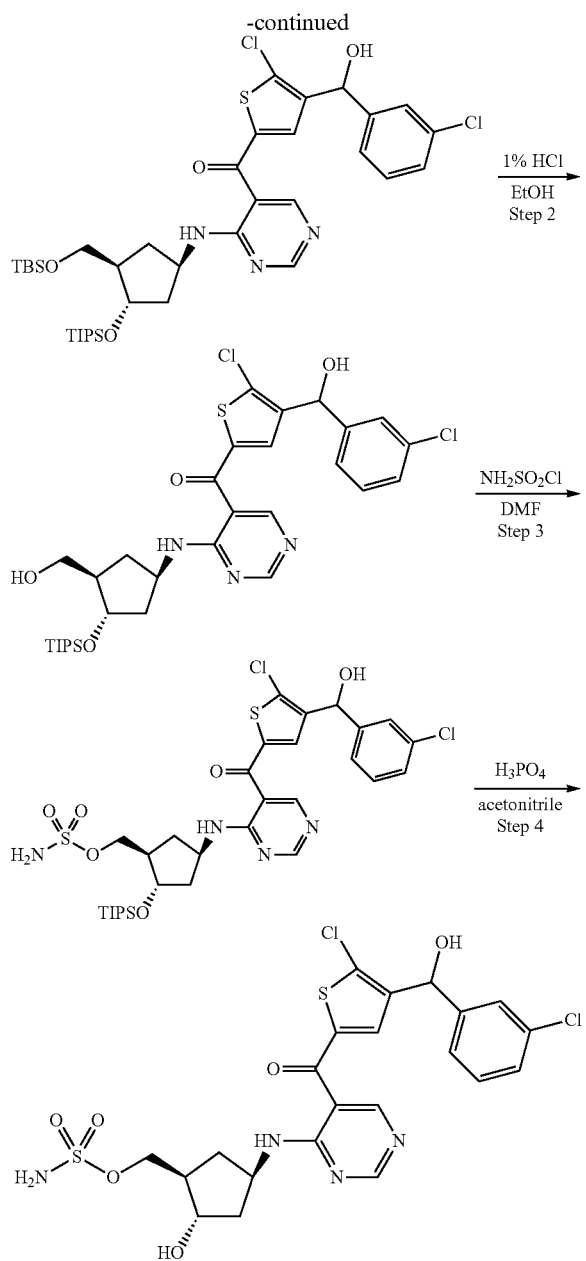

Step 1: [[4-({(1R,3R,4S)-3-({[tert-Butyl(dimethyl)silyl]oxy}methyl)-4-[(triisopropylsilyl)oxy]cyclopentyl}amino)pyrimidin-5-yl]{5-chloro-4-[(S)-(3-chlorophenyl)(hydroxy)methyl]-2-thienyl}methanone and [[4-({(1R,3R,4S)-3-({[tert-Butyl(dimethyl)silyl]oxy}methyl)-4-[(triisopropylsilyl)oxy]cyclopentyl}amino)pyrimidin-5-yl]{5-chloro-4-[(R)-(3-chlorophenyl)(hydroxy)methyl]-2-thienyl}methanone Int-274

To a solution of Int-270 (373 mg, 0.57 mmol) in THF (5.34 mL) was added 0.5 M of 3-chlorophenylmagnesium bromide in THF (2.29 mL, 1.14 mmol) at 0° C., and the mixture was then stirred at 0° C. for 1 hour. To the reaction was added more 0.5 M of 3-chlorophenylmagnesium bromide in THF (1.5 mL) and the mixture was stirred for 1 hour. The reaction was quenched by addition of saturated NH₄Cl and the mixture was extract with EtOAc (×3). The combined organic layers were then washed with water, brine, dried over Na₂SO₄, filtered and concentrated in vacuo to give 220 mg (50%) of the title compounds. LCMS (FA): m/z=766.3 (M+H).

Step 2: {5-Chloro-4-[(S)-(3-chlorophenyl)(hydroxy)methyl]-2-thienyl}[4-({(1R,3R,4S)-3-(hydroxymethyl)-4-[(triisopropylsilyl)oxy]cyclopentyl}amino)pyrimidin-5-yl]methanone and {5-Chloro-4-[(R)-(3-chlorophenyl)(hydroxy)methyl]-2-thienyl}[4-({(1R,3R,4S)-3-(hydroxymethyl)-4-[(triisopropylsilyl)oxy]cyclopentyl}amino)pyrimidin-5-yl]methanone To a solution of Int-274 (122 mg, 0.16 mmol) in EtOH (1 mL) was added 1% HCl in EtOH solution (4.62 mL, 0.56 mmol) at 0° C., and the reaction was stirred for 1 hour at 0° C. then kept in the refrigerator for overnight. The reaction was quenched by addition of saturated NaHCO₃, and the mixture was concentrated in vacuo. To the residue was added water and extracted with EtOAc (×3). The combined organic layers were dried over Na₂SO₄, filtered, and concentrated in vacuo to give 100 mg (96%) of the title compound. LCMS (FA): m/z=652.1 (M+H).

Step 3: {(1R,2S,4R)-4-{[5-({5-Chloro-4-[(S)-(3-chlorophenyl)(hydroxy)methyl]-2-thienyl}carbonyl)pyrimidin-4-yl]amino}-2-[(triisopropylsilyl)oxy]cyclopentyl}methyl sulfamate and {(1R,2S,4R)-4-{[5-({5-Chloro-4-[(R)-(3-chlorophenyl)(hydroxy)methyl]-2-thienyl}carbonyl)pyrimidin-4-yl]amino}-2-[(triisopropylsilyl)oxy]cyclopentyl}methyl sulfamate To a solution of the product from step 2 (114 mg, 0.18 mmol) in DMF (0.8 mL) was added chlorosulfonamide (40.5 mg, 0.35 mmol) at rt, and the mixture was stirred for 1 hour. The reaction was quenched by addition of saturated NaHCO₃ and the mixture was extracted with EtOAc (×2). The combined organic layers were dried over Na₂SO₄, filtered, and concentrated in vacuo to give 120 mg (94%) of the title compound. LCMS (FA): m/z=731.2 (M+H).

Step 4: [(1R,2S,4R)-4-{[5-({5-Chloro-4-[(S)-(3-chlorophenyl)(hydroxy)methyl]-2-thienyl}carbonyl)pyrimidin-4-yl]amino}-2-hydroxycyclopentyl]methyl sulfamate and [(1R,2S,4R)-4-{[5-({5-Chloro-4-[(R)-(3-chlorophenyl)(hydroxy)methyl]-2-thienyl}carbonyl)pyrimidin-4-yl]amino}-2-hydroxycyclopentyl]methyl sulfamate To a solution of the product from step 3 (125 mg, 0.17 mmol) in CH₃CN (1 mL) was added H₃PO₄ (1 mL) at 0° C. and the reaction was stirred at rt for 1 hour. The reaction was quenched by addition of 1M Na₂CO₃ and the mixture was extracted with EtOAc (×3). The combined organic layers were dried over Na₂SO₄, filtered, and concentrated in vacuo. The residue was purified by preparative HPLC to give 33 mg of the title compound. $^1$H NMR (400 MHz, MeOD) δ 8.68 (s, 1H), 8.59 (s, 1H), 7.55 (s, 1H), 7.44 (s, 1H), 7.40-7.20 (m, 3H), 5.92 (s, 1H), 4.84-4.73 (m, 1H), 4.27-4.10 (m, 3H), 2.54-2.42 (m, 1H), 2.32-2.21 (m, 1H), 2.20-2.08 (m, 1H), 1.96-1.83 (m, 1H), 1.47-1.39 (m, 1H). LCMS (FA): m/z=574.9 (M+H).

The compounds listed in the table below were prepared in an analogous fashion to that described above starting from the appropriate Grignard reagent at step 1.

| Step 1 Grignard reagent | Compound No. |
|---|---|
| 2-methoxyphenyl MgBr | I-85 |
| 2-chlorophenyl MgBr | I-86 |
| phenyl MgBr | I-56 |

Example 148: [(1R,2S,4R)-4-{[5-({4-[(S)-(3-Bromophenyl)(hydroxy)methyl]-5-chloro-2-thienyl}carbonyl)pyrimidin-4-yl]amino}-2-hydroxycyclopentyl]methyl sulfamate or [(1R,2S,4R)-4-{[5-({4-[(R)-(3-Bromophenyl)(hydroxy)methyl]-5-chloro-2-thienyl}carbonyl)pyrimidin-4-yl]amino}-2-hydroxycyclopentyl]methyl sulfamate I-16a and [(1R,2S,4R)-4-{[5-({4-[(S)-(3-Bromophenyl)(hydroxy)methyl]-5-chloro-2-thienyl}carbonyl)pyrimidin-4-yl]amino}-2-hydroxycyclopentyl]methyl sulfamate or [(1R,2S,4R)-4-{[5-({4-[(R)-(3-Bromophenyl)(hydroxy)methyl]-5-chloro-2-thienyl}carbonyl)pyrimidin-4-yl]amino}-2-hydroxycyclopentyl]methyl sulfamate. I-16b

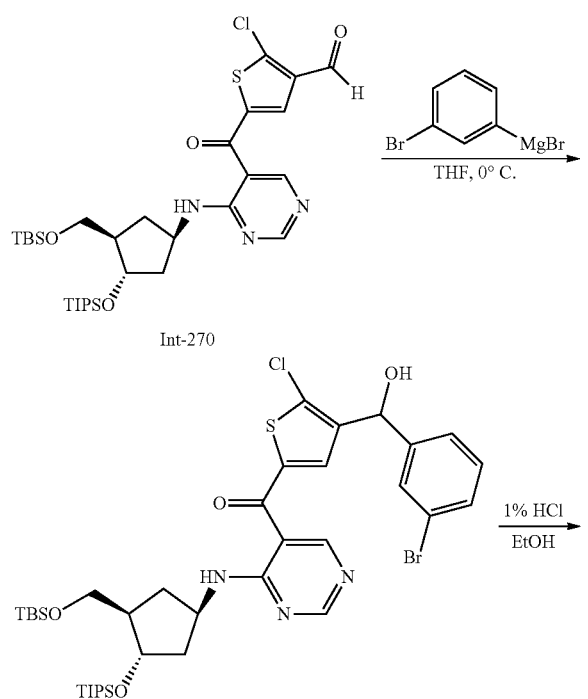

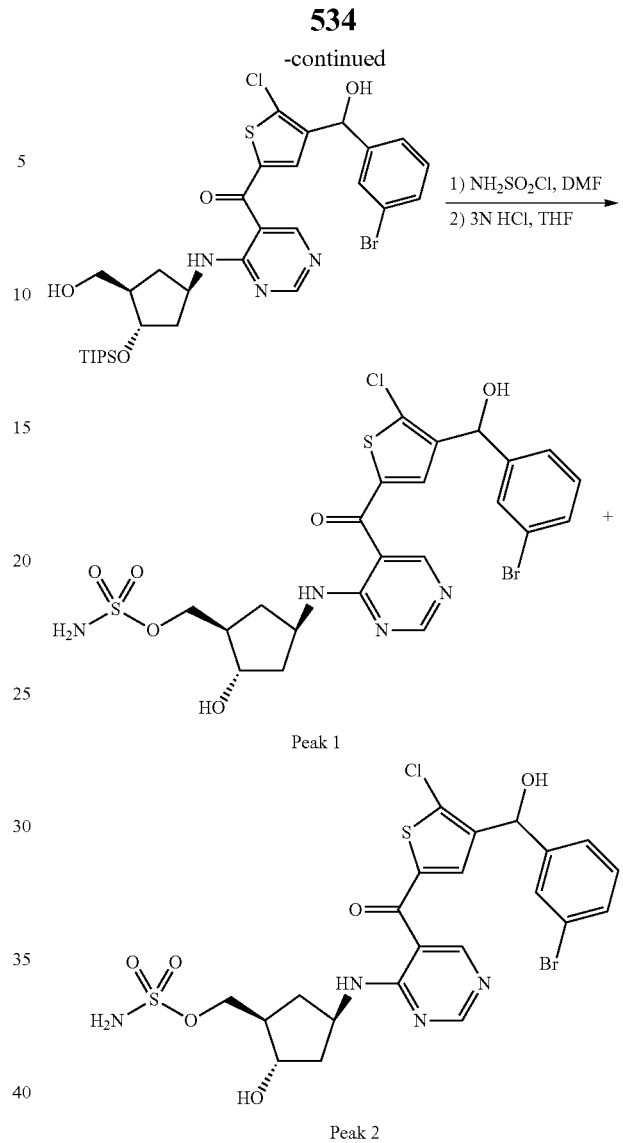

Peak 1

Peak 2

Step 1: {4-[(S)-(3-Bromophenyl)(hydroxy)methyl]-5-chloro-2-thienyl}[4-({(1R,3R,4S)-3-({[tert-butyl(dimethyl)silyl]oxy}methyl)-4-[(triisopropylsilyl)oxy]cyclopentyl}amino)pyrimidin-5-yl]methanone and {4-[(R)-(3-Bromophenyl)(hydroxy)methyl]-5-chloro-2-thienyl}[4-({(1R,3R,4S)-3-({[tert-butyl(dimethyl)silyl]oxy}methyl)-4-[(triisopropylsilyl)oxy]cyclopentyl}amino)pyrimidin-5-yl]methanone To a solution of Int-270 (236 mg, 0.36 mmol) in THF (12.0 mL) was added 0.5 M 3-bromophenylmagnesium bromide in THF (0.87 mL, 0.43 mmol) at 0° C. The reaction was allowed to stir at 0° C. for 5 min and then was warmed to rt for 3 h. The reaction mixture was quenched by addition of saturated NH$_4$Cl and extracted with EtOAc (×2). The combined organic layers were washed with brine, dried under MgSO$_4$, and concentrated in vacuo. The residue was purified by ISCO column chromatography (50% EtOAc in hexanes as eluent) to give 94 mg (32%) of the title compounds. LCMS (FA): m/z=810.2 (M+H).

Step 2: {4-[(S)-(3-Bromophenyl)(hydroxy)methyl]-5-chloro-2-thienyl}[4-({(1R,3R,4S)-3-(hydroxymethyl)-4-[(triisopropylsilyl)oxy]cyclopentyl}amino)pyrimidin-5-yl]methanone and {4-[(R)-(3-Bromophenyl)(hydroxy)methyl]-5-chloro-2-thienyl}[4-({(1R,3R,4S)-3-(hydroxymethyl)-4-[(triisopropylsilyl)oxy]cyclopentyl}amino)pyrimidin-5-yl]methanone To a solution of the products from step 1 (94 mg, 0.12 mmol) in EtOH (2.00 mL) was added 1% HCl in EtOH solution (12 mL) at rt and the reaction was put into the refrigerator overnight. The reaction mixture was quenched by addition of saturated NaHCO$_3$ and the mixture was extracted with EtOAc (×3). The combined organic layers were washed with brine, dried over MgSO$_4$, and concentrated in vacuo to give 76 mg (94%) of the crude title compounds. LCMS (FA): m/z=650.2 (M+H).

Step 3: [(1R,2S,4R)-4-{[5-({4-[(S)-(3-Bromophenyl)(hydroxy)methyl]-5-chloro-2-thienyl}carbonyl)pyrimidin-4-yl]amino}-2-hydroxycyclopentyl]methyl sulfamate and [(1R,2S,4R)-4-{[5-({4-[(R)-(3-Bromophenyl)(hydroxy)methyl]-5-chloro-2-thienyl}carbonyl)pyrimidin-4-yl]amino}-2-hydroxycyclopentyl]methyl sulfamate To a solution of the products from step 2 in DMF (15.0 mL) were added triethylamine (0.14 mL, 1.01 mmol) followed by chlorosulfonamide (0.24 g, 2.1 mmol) at rt. The reaction was stirred for 2 h. To the mixture was added 4 ml of water and 4 ml of 12 M HCl and the resulting mixture was stirred at rt overnight. The reaction mixture was quenched by addition of saturated NaHCO$_3$ and extracted with EtOAc (×3). The combined organics were washed with brine, dried over MgSO$_4$, and concentrated in vacuo. The residue was purified by preparative HPLC to give 112 mg (18%) of the first eluting compound and 152 mg (24%) of the second eluting compound, the characterization of which are described below

[(1R,2S,4R)-4-{[5-({4-[(S)-(3-Bromophenyl)(hydroxy)methyl]-5-chloro-2-thienyl}carbonyl)pyrimidin-4-yl]amino}-2-hydroxycyclopentyl]methyl sulfamate or [(1R,2S,4R)-4-{[5-({4-[(R)-(3-Bromophenyl)(hydroxy)methyl]-5-chloro-2-thienyl}carbonyl)pyrimidin-4-yl]amino}-2-hydroxycyclopentyl]methyl sulfamate Peak 1: $^1$H NMR (400 MHz, MeOD) δ 8.69 (s, 1H), 8.60 (s, 1H), 7.61 (s, 1H), 7.57 (s, 1H), 7.45 (d, J=7.3 Hz, 1H), 7.38 (d, J=7.8 Hz, 1H), 7.28 (t, J=7.8 Hz, 1H), 5.93 (s, 1H), 4.87-4.73 (m, 1H), 4.28-4.09 (m, 3H), 2.59-2.44 (m, 1H), 2.35-2.22 (m, 1H), 2.21-2.09 (m, 1H), 1.98-1.83 (m, 1H), 1.51_1.37 (m, 1H). LCMS (FA): m/z=618.9 (M+H)

[(1R,2S,4R)-4-{[5-({4-[(S)-(3-Bromophenyl)(hydroxy)methyl]-5-chloro-2-thienyl}carbonyl)pyrimidin-4-yl]amino}-2-hydroxycyclopentyl]methyl sulfamate or [(1R,2S,4R)-4-{[5-({4-[(R)-(3-Bromophenyl)(hydroxy)methyl]-5-chloro-2-thienyl}carbonyl)pyrimidin-4-yl]amino}-2-hydroxycyclopentyl]methyl sulfamate Peak 2: $^1$H NMR (400 MHz, MeOD) δ 8.69 (s, 1H), 8.61 (s, 1H), 7.61 (s, 1H), 7.57 (s, 1H), 7.49-7.41 (m, 1H), 7.37 (d, J=7.8 Hz, 1H), 7.28 (t, J=7.8 Hz, 1H), 5.93 (s, 1H), 4.87-4.73 (m, 1H), 4.31-4.07 (m, 3H), 2.59_2.41 (m, 1H), 2.35-2.22 (m, 1H), 2.21-2.09 (m, 1H), 1.99_1.83 (m, 1H), 1.52-1.34 (m, 1H). LCMS (FA): m/z=618.9 (M+H).

Example 149: [(1R,2S,4R)-4-{[5-({5-Chloro-4-[(S)-(5-chloro-2-fluorophenyl)(hydroxy)methyl]-2-thienyl}carbonyl)pyrimidin-4-yl]amino}-2-hydroxycyclopentyl]methyl sulfamate and [(1R,2S,4R)-4-{[5-({5-Chloro-4-[(R)-(5-chloro-2-fluorophenyl)(hydroxy)methyl]-2-thienyl}carbonyl)pyrimidin-4-yl]amino}-2-hydroxycyclopentyl]methyl sulfamate. I-48

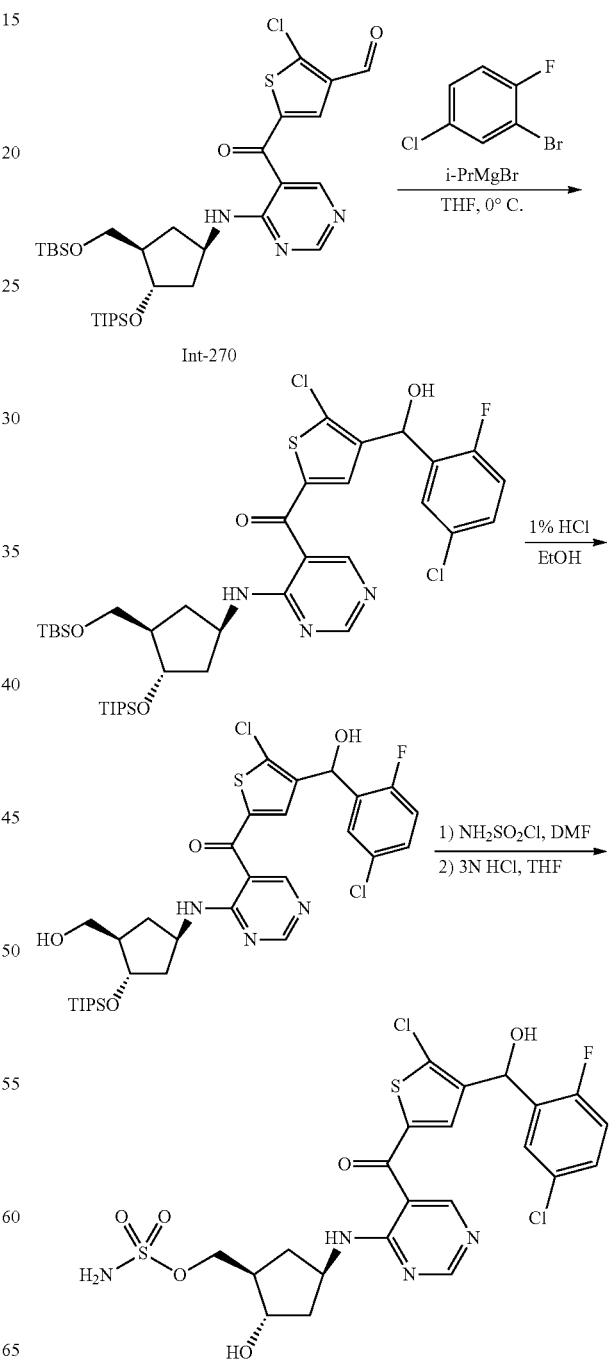

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl]{5-chloro-4-[(S)-(5-chloro-2-fluorophenyl)(hydroxy)methyl]-2-thienyl}methanone and [4-({(1R,3R,4S)-3-({[tert-Butyl(dimethyl)silyl]oxy}methyl)-4-[(triisopropylsilyl)oxy]cyclopentyl}amino)pyrimidin-5-yl]{5-chloro-4-[(R)-(5-chloro-2-fluorophenyl)(hydroxy)methyl]-2-thienyl}methanone To a solution of 3-bromo-1-chloro-4-fluorobenzene (69.0 uL, 0.57 mmol) in THF (5.00 mL) at 0° C. was added dropwise 2 M isopropylmagnesium chloride in $Et_2O$ (0.31 mL, 0.62 mmol) and the mixture was stirred at 0° C. for 1 hour, and then warmed to rt overnight. This mixture was added dropwise to a solution of Int-270 (185 mg, 0.28 mmol) in THF (8.0 mL) at −40° C. and the reaction was allowed to stir at for 30 min at same temperature. The reaction was quenched by addition of saturated $NH_4Cl$ and extracted with EtOAc (×2). The combined organic layers were washed with brine, dried over $MgSO_4$, and concentrated in vacuo. The residue was purified by ISCO column chromatography (20% EtOAc in hexanes as eluent) to give 0.14 g (63%) of the title compounds. LCMS (FA): m/z=782.2 (M+H)

Step 2: {5-Chloro-4-[(S)-(5-chloro-2-fluorophenyl)(hydroxy)methyl]-2-thienyl}[4-({(1R,3R,4S)-3-(hydroxymethyl)-4-[(triisopropylsilyl)oxy]cyclopentyl}amino)pyrimidin-5-yl]methanone and {5-Chloro-4-[(R)-(5-chloro-2-fluorophenyl)(hydroxy)methyl]-2-thienyl}[4-({(1R,3R,4S)-3-(hydroxymethyl)-4-[(triisopropylsilyl)oxy]cyclopentyl}amino)pyrimidin-5-yl]methanone To a solution of the products from step 1 (0.15 g, 0.20 mmol) in EtOH (2.0 mL) was added 15 ml of 1% HCl in EtOH solution and the reaction was left to stand at 4° C. overnight. The reaction mixture was quenched by addition of saturated $NaHCO_3$ and extracted with EtOAc (×3). The combined organics were washed with brine, dried over $MgSO_4$, and concentrated in vacuo to give 0.12 g (91%) of the crude title compounds. LCMS (FA): m/z=668.6 (M+H)

Step 3: [(1R,2S,4R)-4-{[5-({5-Chloro-4-[(S)-(5-chloro-2-fluorophenyl)(hydroxy)methyl]-2-thienyl}carbonyl)pyrimidin-4-yl]amino}-2-hydroxycyclopentyl]methyl sulfamate and [(1R,2S,4R)-4-{[5-({5-Chloro-4-[(R)-(5-chloro-2-fluorophenyl)(hydroxy)methyl]-2-thienyl}carbonyl)pyrimidin-4-yl]amino}-2-hydroxycyclopentyl]methyl sulfamate To a solution of the products from step 2 (120 mg, 0.18 mmol) in DMF (0.85 mL) was added chlorosulfonamide (25.7 mg, 0.22 mmol) at rt, and the mixture was stirred for 1 hour. To the mixture was added 6 M HCl (1.5 mL) and the reaction was stirred at rt overnight. The reaction mixture was quenched by addition of saturated $NaHCO_3$ and extracted with EtOAc (×2). The combined organic layers were washed with brine, dried over $MgSO_4$, and concentrated in vacuo. The residue was purified by preparative HPLC to give 23 mg (21%) of the title compounds. $^1$H NMR (400 MHz, MeOD) δ 8.68 (s, 1H), 8.60 (s, 1H), 7.66-7.59 (m, 1H), 7.52 (s, 1H), 7.40-7.28 (m, 1H), 7.10 (t, J=9.3 Hz, 1H), 6.12 (s, 1H), 4.85-4.75 (m, 1H), 4.27-4.09 (m, 3H), 2.60-2.44 (m, 1H), 2.36-2.23 (m, 1H), 2.21-2.09 (m, 1H), 1.97-1.83 (m, 1H), 1.52-1.33 (m, 1H). LCMS (FA): m/z=591.1 (M+H).

The compounds listed in the table below were prepared in an analogous fashion to that described above starting from the appropriate starting materials.

| Step 1 halogenated reagent | Compound No. |
|---|---|
| ![structure with Cl, I, F] | I-40 |
| ![structure with Cl, I, OMe] | I-63 |
| ![structure with Cl, Cl, I] | I-149 |

Example 150: [(1R,2S,4R)-4-{[5-({5-Chloro-4-[(1S)-1-hydroxyethyl]-2-thienyl}carbonyl)pyrimidin-4-yl]amino}-2-hydroxycyclopentyl]methyl sulfamate and [(1R,2S,4R)-4-{[5-({5-Chloro-4-[(1R)-1-hydroxyethyl]-2-thienyl}carbonyl)pyrimidin-4-yl]amino}-2-hydroxycyclopentyl]methyl sulfamate I-226

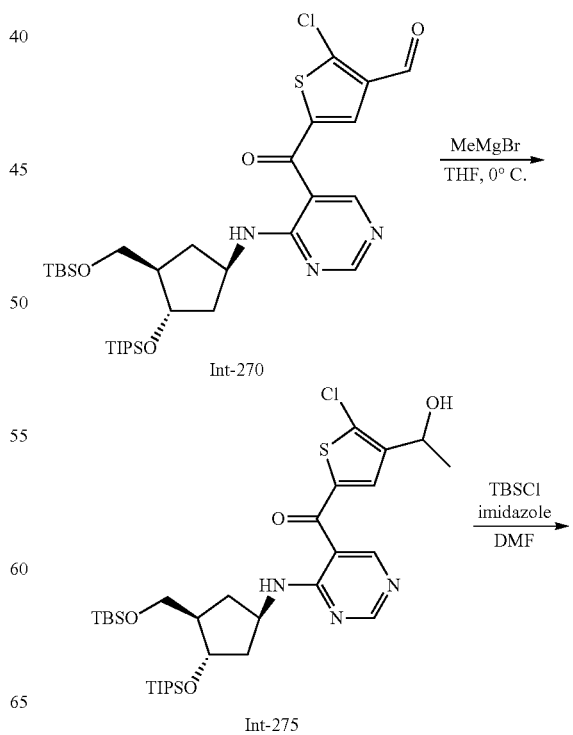

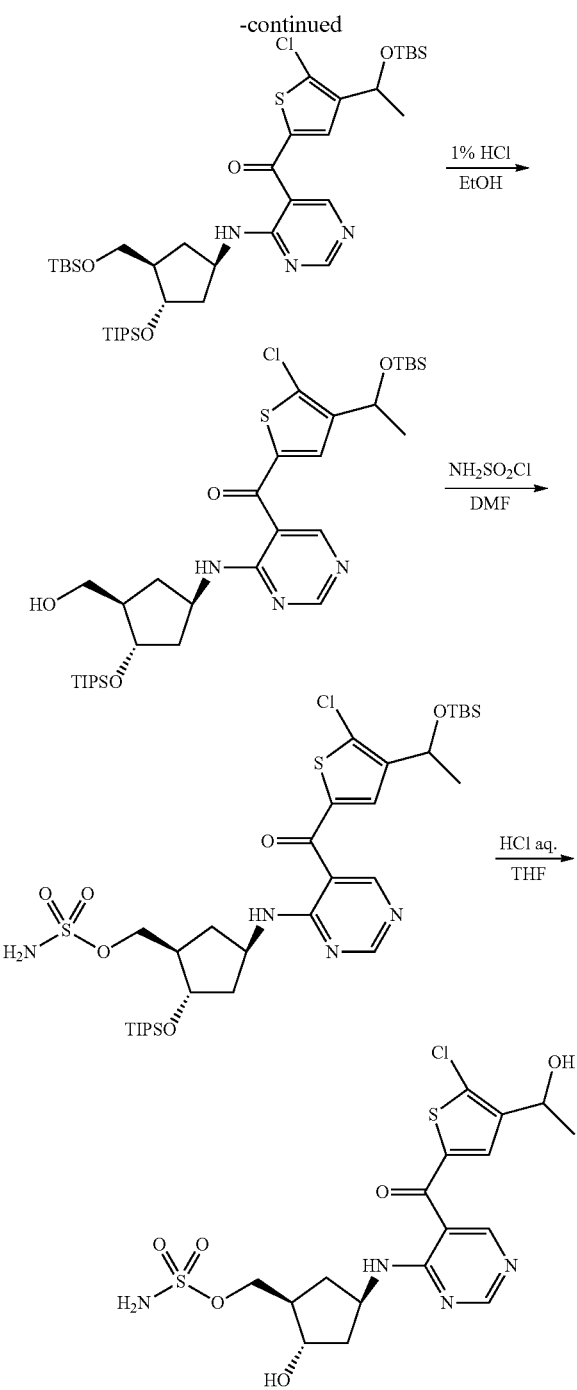

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl]{5-chloro-4-[(S)-1-hydroxyethyl]-2-thienyl}methanone and [4-({(1R,3R,4S)-3-({[tert-Butyl(dimethyl)silyl]oxy}methyl)-4-[(triisopropylsilyl)oxy]cyclopentyl}amino)pyrimidin-5-yl]{5-chloro-4-[(R)-1-hydroxyethyl]-2-thienyl}methanone Int-275

Int-270 (881 mg, 1.35 mmol) was dissolved in THF (15.0 mL). The mixture was cooled to 0° C. and 3.0M of methylmagnesium bromide was added dropwise. The mixture was then stirred at 0° C. for 30 min. The reaction was quenched by adding saturated NH$_4$Cl and the mixture was extract with EtOAc (×3). The combined organic layers were then washed with water, brine, dried using MgSO$_4$, filtered and concentrated. The residue was purified by ISCO (50% EtOAc in hexanes as eluent) to give the title compounds as yellow foam (yield=525 mg). $^1$H NMR (400 MHz, Chloroform-d) δ 8.80 (s, 1H), 8.66 (s, 1H), 8.50 (d, J=7.2 Hz, 1H), 7.56 (s, 1H), 5.12-5.03 (m, 1H), 4.88-4.74 (m, 1H), 4.34-4.26 (m, 1H), 3.65-3.52 (m, 2H), 2.49-2.37 (m, 1H), 2.24-2.09 (m, 2H), 2.01 (d, J=3.5 Hz, 1H), 1.76-1.65 (m, 1H), 1.50 (d, J=6.5 Hz, 3H), 1.32-1.19 (m, 1H), 1.07 (s, 21H), 0.89 (d, J=0.6 Hz, 9H), 0.04 (s, 6H).

Step 2: {4-[(S)-1-{[tert-Butyl(dimethyl)silyl]oxy}ethyl]-5-chloro-2-thienyl}[4-({(1R,3R,4S)-3-({[tert-butyl(dimethyl)silyl]oxy}methyl)-4-[(triisopropylsilyl)oxy]cyclopentyl}amino)pyrimidin-5-yl]methanone and {4-[(R)-1-{[tert-Butyl(dimethyl)silyl]oxy}ethyl]-5-chloro-2-thienyl}[4-({(1R,3R,4S)-3-({[tert-butyl(dimethyl)silyl]oxy}methyl)-4-[(triisopropylsilyl)oxy]cyclopentyl}amino)pyrimidin-5-yl]methanone To a solution of the products from step 1 (525 mg, 0.79 mmol) in DMF (5.0 mL) was added 1H-imidazole (160 mg, 2.36 mmol), N,N-dimethylaminopyridine (9.59 mg, 78.5 umol) and TBSCl (148 mg, 0.98 mmol) and the reaction was stirred overnight at rt. The reaction was quenched with saturated NH$_4$Cl and diluted with water and EtOAc. The layers were separated and the aqueous layer was extracted with EtOAc. The combined organics were washed with 10% aqueous LiCl (×3), brine, dried over Na$_2$SO$_4$, filtered and concentrated in vacuo. The residue was purified via ISCO column chromatography (0%-10% EtOAc in hexanes as eluent) to give the title compounds as yellow oil (yield=556 mg). $^1$H NMR (400 MHz, Chloroform-d) δ 8.78 (s, 1H), 8.67 (s, 1H), 8.55 (d, J=7.3 Hz, 1H), 7.53 (s, 1H), 4.98 (q, J=6.3 Hz, 1H), 4.80 (q, J=8.1 Hz, 1H), 4.30 (s, 1H), 3.66-3.51 (m, 2H), 2.50-2.38 (m, 1H), 2.24-2.08 (m, 2H), 1.79-1.65 (m, 1H), 1.39 (d, J=6.3 Hz, 3H), 1.34-1.20 (m, 1H), 1.07 (s, 21H), 0.88 (d, J=2.5 Hz, 18H), 0.10--0.03 (m, 12H).

Step 3: {4-[(S)-1-{[tert-Butyl(dimethyl)silyl]oxy}ethyl]-5-chloro-2-thienyl}[4-({(1R,3R,4S)-3-(hydroxymethyl)-4-[(triisopropylsilyl)oxy]cyclopentyl}amino)pyrimidin-5-yl]methanone and {4-[(R)-1-{[tert-Butyl(dimethyl)silyl]oxy}ethyl]-5-chloro-2-thienyl}[4-({(1R,3R,4S)-3-(hydroxymethyl)-4-[(triisopropylsilyl)oxy]cyclopentyl}amino)pyrimidin-5-yl]methanone To a solution of the products from step 2 (556 mg, 0.71 mmol) in EtOH (15.0 mL) was added 1% HCl in EtOH (20.0 mL, 2.42 mmol) at rt, and the mixture was allowed to stand at 4° C. for 24 h. The reaction was quenched with saturated NaHCO$_3$ and diluted with water and EtOAc. The organic layer was washed with brine, dried over Na$_2$SO$_4$, filtered, and concentrated in vacuo. The residue was purified by ISCO silica gel column chromatography (20%-50% EtOAc in hexanes as eluent) to give the title compounds as light yellow foam (yield=244 mg). LCMS (FA): m/z=668.3 (M+1)

Step 4: {(1R,2S,4R)-4-{[5-({4-[(1S)-1-{[tert-Butyl (dimethyl)silyl]oxy}ethyl]-5-chloro-2-thienyl}carbonyl)pyrimidin-4-yl]amino}-2-[(triisopropylsilyl)oxy]cyclopentyl}methyl sulfamate and {(1R,2S,4R)-4-{[5-({4-[(1R)-1-{[tert-Butyl(dimethyl)silyl]oxy}ethyl]-5-chloro-2-thienyl}carbonyl)pyrimidin-4-yl]amino}-2-[(triisopropylsilyl)oxy]cyclopentyl}methyl sulfamate A solution of the products from step 3 (244 mg, 0.37 mmol) in DMF (5.0 mL) was cooled at 0° C. under an atmosphere of argon. Chlorosulfonamide (63.2 mg, 0.55 mmol) was added and the reaction was stirred for 20 min. The reaction was quenched by addition of saturated NaHCO$_3$ and water. The reaction was extracted with EtOAc (×3). The combined organics were washed with 10% LiCl in water, brine, dried over Na$_2$SO$_4$, filtered and concentrated in vacuo. The residue was purified via ISCO column chromatography (10%-30% EtOAc in hexanes as elute) to give 210 mg (77%) of the title compound as light yellow foam. LCMS (FA): m/z=747.3 (M+1).

Step 5: [(1R,2S,4R)-4-{[5-({5-Chloro-4-[(1S)-1-hydroxyethyl]-2-thienyl}carbonyl)pyrimidin-4-yl]amino}-2-hydroxycyclopentyl]methyl sulfamate and [(1R,2S,4R)-4-{[5-({5-Chloro-4-[(1R)-1-hydroxyethyl]-2-thienyl}carbonyl)pyrimidin-4-yl]amino}-2-hydroxycyclopentyl]methyl sulfamate To a solution of the products from step 5 in THF (5.00 mL, 61.6 mmol) was added 4.0 M of HCl (4.00 mL, 16.0 mmol) at rt, and the mixture was stirred overnight. The reaction was quenched by addition of saturated NaHCO$_3$ and extracted with EtOAc (×3). The combined organic layers were dried over MgSO$_4$, filtered, and concentrated in vacuo. The residue was triturated with hexanes. The precipitate was collected via vacuum filtration, washed with hexanes and dried under high vacuum to give 134 mg (99%) of the title compounds as yellow solid. $^1$H NMR (400 MHz, MeOD) δ 8.76 (s, 1H), 8.61 (s, 1H), 7.64 (s, 1H), 4.99 (q, J=6.6 Hz, 2H), 4.86-4.76 (m, 1H), 4.24-4.12 (m, 3H), 2.56-2.46 (m, 1H), 2.32-2.11 (m, 2H), 1.95-1.86 (m, 1H), 1.48-1.38 (m, 4H). LCMS (FA): m/z=477.1 (M+1).

The compound listed in the table below was prepared in an analogous fashion to that described above starting from the listed starting materials used in step 1:

| Step 1 Grignard reagent | Compound No. |
|---|---|
| ![structure with MgBr] | I-141 |

Example 151: [(1R,2S,4R)-4-{[5-({5-Chloro-4-[(1S)-3-cyclopropyl-1-hydroxyprop-2-yn-1-yl]-2-thienyl}carbonyl)pyrimidin-4-yl]amino}-2-hydroxycyclopentyl]methyl sulfamate and [(1R,2S,4R)-4-{[5-({5-Chloro-4-[(1R)-3-cyclopropyl-1-hydroxyprop-2-yn-1-yl]-2-thienyl}carbonyl)pyrimidin-4-yl]amino}-2-hydroxycyclopentyl]methyl sulfamate.
I-150

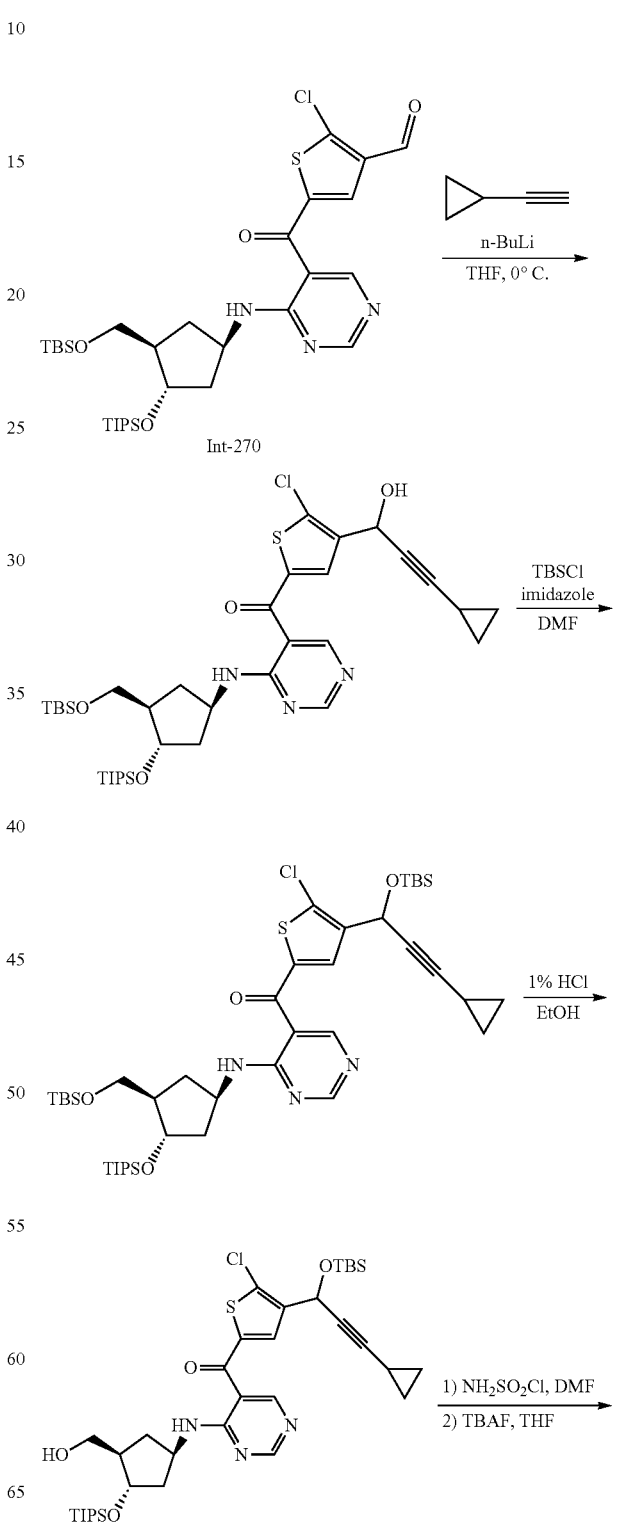

-continued

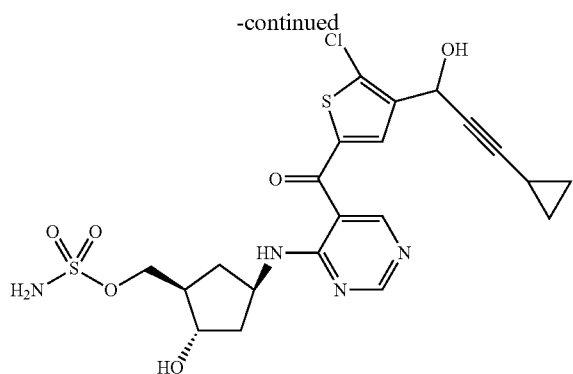

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl]{5-chloro-4-[(1S)-3-cyclopropyl-1-hydroxyprop-2-yn-1-yl]-2-thienyl}methanone and [4-({(1R,3R,4S)-3-({[tert-Butyl(dimethyl)silyl]oxy}methyl)-4-[(triisopropylsilyl)oxy]cyclopentyl}amino)pyrimidin-5-yl]{5-chloro-4-[(1R)-3-cyclopropyl-1-hydroxyprop-2-yn-1-yl]-2-thienyl}methanone A solution of cyclopropyl acetylene (0.20 mL, 2.41 mmol) in THF (5.00 mL) was cooled at −78° C. under an atmosphere of argon. To the solution was added dropwise 2.5 M of n-BuLi in hexane (1.00 mL, 2.50 mmol) and the solution was stirred for 30 min. This mixture was added to a solution of Int-270 (511 mg, 0.78 mmol) in THF (9.0 mL) at −78° C. under an atmosphere of argon and the reaction was stirred for 5 min. The reaction was quenched with 10 mL of saturated NH$_4$Cl and allowed to warm to rt. The reaction was extracted with Et$_2$O (×2). The combined organic extracts were washed with brine, dried over Na$_2$SO$_4$, filtered and concentrated in vacuo. The residue was purified via ISCO column chromatography (20% EtOAc in hexanes as eluent) to give the title compounds as a yellow foam (yield=373 mg). LCMS (FA): m/z=718.4 (M+1).

Step 2: {4-[(1S)-1-{[tert-Butyl(dimethyl)silyl]oxy}-3-cyclopropylprop-2-yn-1-yl]-5-chloro-2-thienyl}[4-({(1R,3R,4S)-3-({[tert-butyl(dimethyl)silyl]oxy}methyl)-4-[(triisopropylsilyl)oxy]cyclopentyl}amino)pyrimidin-5-yl]methanone and {4-[(1R)-1-{[tert-Butyl(dimethyl)silyl]oxy}-3-cyclopropylprop-2-yn-1-yl]-5-chloro-2-thienyl}[4-({(1R,3R,4S)-3-({[tert-butyl(dimethyl)silyl]oxy}methyl)-4-[(triisopropylsilyl)oxy]cyclopentyl}amino)pyrimidin-5-yl]methanone To a solution of the products of step 1 (377 mg, 0.53 mmol) in DMF (3.34 mL) were added 1H-Imidazole (107 mg, 1.57 mmol), N,N-dimethylaminopyridine (6.41 mg, 52.5 umol) and TBSCl (98.8 mg, 0.66 mmol). The reaction was stirred overnight at rt, and then quenched with saturated NH$_4$Cl and diluted with water and EtOAc. The layers were separated and the aqueous layer was extracted with EtOAc. The combined organics were washed with 10% aqueous LiCl (×3), brine, dried over Na$_2$SO$_4$, filtered and concentrated in vacuo. The residue was purified via ISCO column chromatography (10% EtOAc in hexanes as eluent) to give the title compounds as yellow oil (yield=311 mg). $^1$H NMR (400 MHz, Chloroform-d) δ 8.81 (s, 1H), 8.67 (s, 1H), 8.53 (d, J=7.1 Hz, 1H), 7.62 (s, 1H), 5.47 (d, J=1.6 Hz, 1H), 4.80 (q, J=8.4, 8.0 Hz, 1H), 4.30 (s, 1H), 3.65-3.51 (m, 2H), 2.49-2.38 (m, 1H), 2.24-2.09 (m, 2H), 1.76-1.66 (m, 1H), 1.32-1.20 (m, 2H), 1.07 (s, 21H), 0.89 (d, J=2.7 Hz, 18H), 0.81-0.65 (m, 4H), 0.14 (d, J=16.8 Hz, 6H), 0.04 (s, 6H).

Step 3: {4-[(1S)-1-{[tert-Butyl(dimethyl)silyl]oxy}-3-cyclopropylprop-2-yn-1-yl]-5-chloro-2-thienyl}[4-({(1R,3R,4S)-3-(hydroxymethyl)-4-[(triisopropylsilyl)oxy]cyclopentyl}amino)pyrimidin-5-yl]methanone and {4-[(1R)-1-{[tert-Butyl(dimethyl)silyl]oxy}-3-cyclopropylprop-2-yn-1-yl]-5-chloro-2-thienyl}[4-({(1R,3R,4S)-3-(hydroxymethyl)-4-[(triisopropylsilyl)oxy]cyclopentyl}amino)pyrimidin-5-yl]methanone To a solution of the products from step 2 (311 mg, 0.37 mmol) in EtOH (8.0 mL) was added 1% HCl in EtOH (10.5 mL, 1.27 mmol) at rt, and the mixture was allowed to stand at 4° C. for 24 h. The reaction was quenched with saturated NaHCO$_3$ and diluted with water and EtOAc. The organic layer was washed with brine, dried over Na$_2$SO$_4$, filtered, and concentrated in vacuo. The residue was purified by ISCO column chromatography (25% EtOAc in hexanes as eluent) to give the title compounds as light yellow foam (yield=179 mg). $^1$H NMR (400 MHz, Methanol-d$_4$) δ 8.70 (s, 1H), 8.60 (s, 1H), 7.62 (s, 1H), 5.55 (d, J=1.7 Hz, 1H), 4.39-4.31 (m, 1H), 3.64-3.51 (m, 2H), 2.55-2.41 (m, 1H), 2.25-2.11 (m, 2H), 1.88-1.75 (m, 1H), 1.40-1.26 (m, 2H), 1.11 (s, 21H), 0.91 (s, 9H), 0.84-0.75 (m, 2H), 0.68-0.56 (m, 2H), 0.16 (d, J=18.5 Hz, 6H).

Step 4: [(1R,2S,4R)-4-{[5-({5-Chloro-4-[(1S)-3-cyclopropyl-1-hydroxyprop-2-yn-1-yl]-2-thienyl}carbonyl)pyrimidin-4-yl]amino}-2-hydroxycyclopentyl]methyl sulfamate and [(1R,2S,4R)-4-{[5-({5-Chloro-4-[(1R)-3-cyclopropyl-1-hydroxyprop-2-yn-1-yl]-2-thienyl}carbonyl)pyrimidin-4-yl]amino}-2-hydroxycyclopentyl]methyl sulfamate A solution of the products of step 3 (179 mg, 0.25 mmol) in DMF (3.0 mL) was cooled to 0° C., to which was added triethylamine (0.25 mL, 1.79 mmol) followed by chlorosulfonamide (0.16 g, 1.39 mmol). The reaction was stirred at 0° C. for 30 min and then the mixture was warmed to rt. After 3 h, the reaction was quenched with saturated NaHCO$_3$ and the mixture was extracted with EtOAc (×3). The combined organics extracts were washed with 10% aqueous LiCl solution (×3), brine, dried over Na$_2$SO$_4$, filtered and concentrated in vacuo. The residue was purified via ISCO column chromatography (30% EtOAc in hexanes as eluent) to give the product as off-white solid. The residue was diluted with THF (2.0 mL) and then added to a solution of TBAF hydrate (93.7 mg, 0.34 mmol) in THF (0.75 mL) at rt, and the mixture was stirred for 4 h. The reaction was quenched by addition of water (50 mL) and extracted with EtOAc (50 mL×3). The combined organic layers were dried over Na$_2$SO$_4$, filtered, and concentrated in vacuo. The residue was purified by ISCO column chromatography (5% MeOH in DCM as eluent) to give the title compounds as light orange amorphous solid (yield=57 mg). $^1$H NMR (400 MHz, MeOD) δ 8.75 (s, 1H), 8.62 (s, 1H), 7.67 (s, 1H), 5.44 (d, J=1.7 Hz, 1H), 4.86-4.76 (m, 1H), 4.24-4.11 (m, 3H), 2.56-2.45 (m, 1H), 2.33-2.10 (m, 2H), 1.97-1.86 (m, 1H), 1.48-1.38 (m, 1H), 1.34-1.26 (m, 1H), 0.82-0.76 (m, 2H), 0.67-0.60 (m, 2H). LCMS: (FA) M+1 527.1

Example 152: {(1R,2S,4R)-4-[(5-{[5-Chloro-4-(3-chlorobenzoyl)-2-thienyl]carbonyl}pyrimidin-4-yl)amino]-2-hydroxycyclopentyl}methyl sulfamate I-207

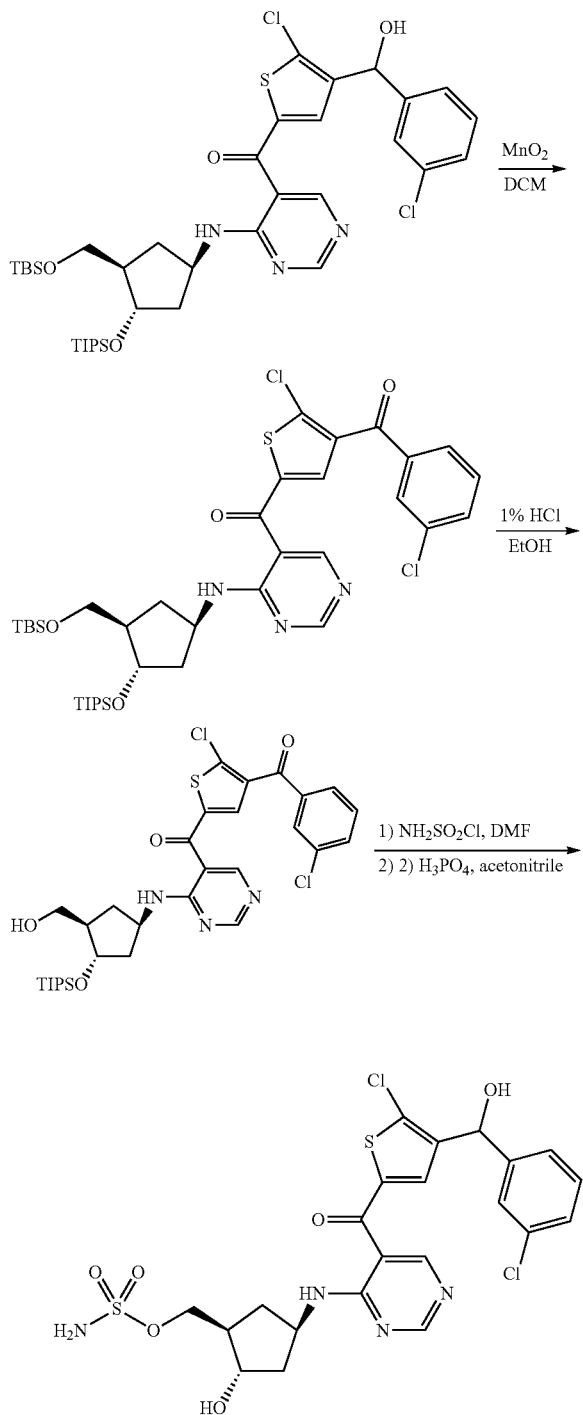

Step 1: 4-({(1R,3R,4S)-3-({[tert-Butyl(dimethyl)silyl]oxy}methyl)-4-[(triisopropylsilyl)oxy]cyclopentyl}amino)pyrimidin-5-yl][5-chloro-4-(3-chlorobenzoyl)-2-thienyl]methanone To a solution of Int-274 (251 mg, 0.33 mmol) in DCM (5 mL) was added $MnO_2$ (280 mg, 3.3 mmol) at rt and the mixture was stirred for 16 h. The reaction mixture was filtered through a Celite pad, washed with DCM followed by EtOAc provided 235 mg (94%) of the title compound. LCMS (FA): m/z=762.7 (M+1).

Step 2: [5-Chloro-4-(3-chlorobenzoyl)-2-thienyl][4-({(1R,3R,4S)-3-(hydroxymethyl)-4-[(triisopropylsilyl)oxy]cyclopentyl}amino)pyrimidin-5-yl]methanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl][5-chloro-4-(3-chlorobenzoyl)-2-thienyl]methanone (230 mg, 0.30 mmol) in EtOH (2 mL) was added 1% HCl in EtOH (8.74 mL, 1.05 mmol) at 0° C., and the mixture was stirred for 1 hour at 0° C. then kept in the refrigerator for overnight. The reaction mixture was quenched by addition of saturated $NaHCO_3$ (5 mL) and concentrated in vacuo. Residue was diluted with water and extracted with EtOAc (5 mL×3). The combined organic layers were dried over $Na_2SO_4$, filtered, and concentrated in vacuo. The residue was purified by ISCO column chromatography (0%-45% EtOAc in hexanes as eluent) to give 160 mg (82%) of the title compound. $^1$H NMR (400 MHz, Chloroform-d) δ 8.79 (s, 1H), 8.66 (s, 1H), 7.81-7.78 (m, 1H), 7.68 (d, J=7.7 Hz, 1H), 7.62-7.56 (m, 2H), 7.49-7.43 (m, 1H), 4.88-4.78 (m, 1H), 4.37-4.31 (m, 1H), 3.74-3.68 (m, 2H), 2.55-2.47 (m, 1H), 2.25-2.16 (m, 2H), 1.90-1.80 (m, 1H), 1.38-1.30 (m, 1H), 1.07 (s, 21H).

Step 3: {(1R,2S,4R)-4-[(5-{[5-Chloro-4-(3-chlorobenzoyl)-2-thienyl]carbonyl}pyrimidin-4-yl)amino]-2-[(triisopropylsilyl)oxy]cyclopentyl}methyl sulfamate To a solution of 5-chloro-4-(3-chlorobenzoyl)-2-thienyl][4-({(1R,3R,4S)-3-(hydroxymethyl)-4-[(triisopropylsilyl)oxy]cyclopentyl}amino)pyrimidin-5-yl]methanone (150 mg, 0.23 mmol) in DMF (3 mL) was added chlorosulfonamide (53.4 mg, 0.46 mmol) at 0° C. and the reaction was stirred for 10 min. The reaction mixture was quenched by addition of saturated $NaHCO_3$ (7 mL), extracted with EtOAc (5 mL×3). The combined organic layers were dried over $Na_2SO_4$, filtered, and concentrated in vacuo. This residue was used in next step without purification. LCMS (FA): m/z=727.1 (M+1).

Step 4: {(1R,2S,4R)-4-[(5-{[5-Chloro-4-(3-chlorobenzoyl)-2-thienyl]carbonyl}pyrimidin-4-yl)amino]-2-hydroxycyclopentyl}methyl sulfamate A 50 mL round bottom flask was charged with {(1R,2S,4R)-4-[(5-{[5-chloro-4-(3-chlorobenzoyl)-2-thienyl]carbonyl}pyrimidin-4-yl)amino]-2-[(triisopropylsilyl)oxy]cyclopentyl}methyl sulfamate (170 mg, 0.23 mmol) and $CH_3CN$ (1 mL). Phosphoric acid (1 mL) was added at 0° C. and stirred at rt for 1 hour. The reaction mixture was quenched by addition of 1M $Na_2CO_3$ (5 mL), extracted with EtOAc (5 mL×3). The combined organic layers were dried over $Na_2SO_4$, filtered, and concentrated in vacuo. The crude product was purified by preparative HPLC to give (51 mg, 38%) of the title compound. $^1$H NMR (400 MHz, Methanol-d4) δ 8.82 (s, 1H), 8.60 (s, 1H), 7.85 (s, 1H), 7.79-7.74 (m, 2H), 7.71-7.66 (m, 1H), 7.58-7.51 (m, 1H), 4.84-4.74 (m, 1H), 4.25-4.12 (m, 3H), 2.56-2.45 (m, 1H), 2.33-2.21 (m, 1H), 2.21-2.10 (m, 1H), 1.98-1.86 (m, 1H), 1.50-1.39 (m, 1H)

Example 153: [(1R,2S,4R)-4-({5-[(4-Acetyl-5-chloro-2-thienyl)carbonyl]pyrimidin-4-yl}amino)-2-hydroxycyclopentyl]methyl sulfamate I-242

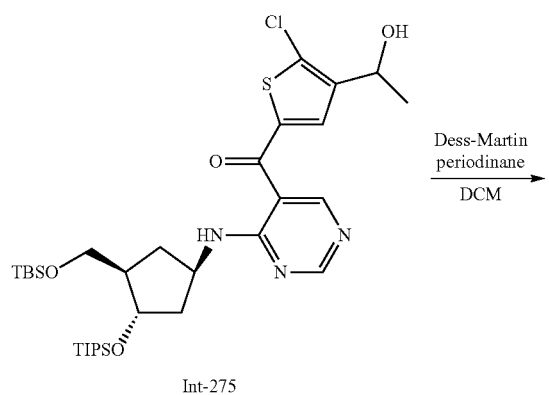

Step 1: 1-(5-{[4-({(1R,3R,4S)-3-({[tert-Butyl(dimethyl)silyl]oxy}methyl)-4-[(triisopropylsilyl)oxy]cyclopentyl}amino)pyrimidin-5-yl]carbonyl}-2-chloro-3-thienyl)ethanone Int-276

A 100 mL round bottom flask under nitrogen was charged with Int-275 (0.11 g, 0.16 mmol) and DCM (2.0 mL). To the solution was added Dess-Martin periodinane (0.11 g, 0.25 mmol) in a single portion and the reaction was stirred for 5 min. The reaction was poured into saturated NaHCO$_3$ and extracted with DCM (×3). The combined organics were dried with anhydrous Na$_2$SO$_4$, filtered, and concentrated in vacuo. The residue was subjected to ISCO chromatography (15% EtOAc in hexanes as eluent) to give the title compound as yellow amorphous solid (yield=101 mg). $^1$H NMR (400 MHz, Chloroform-d) δ 8.82 (s, 1H), 8.68 (s, 1H), 8.55 (d, J=7.5 Hz, 1H), 7.83 (s, 1H), 4.88-4.74 (m, 1H), 4.33-4.27 (m, 1H), 3.66-3.52 (m, 2H), 2.64 (s, 3H), 2.51-2.38 (m, 1H), 2.24-2.09 (m, 2H), 1.77-1.66 (m, 1H), 1.33-1.20 (m, 1H), 1.07 (s, 21H), 0.89 (s, 9H), 0.04 (s, 6H).

Step 2: 1-(2-Chloro-5-{[4-({(1R,3R,4S)-3-(hydroxymethyl)-4-[(triisopropylsilyl)oxy]cyclopentyl}amino)pyrimidin-5-yl]carbonyl}-3-thienyl)ethanone To a solution of 1-(5-{[4-({(1R,3R,4S)-3-({[tert-butyl(dimethyl)silyl]oxy}methyl)-4-[(triisopropylsilyl)oxy]cyclopentyl}amino)pyrimidin-5-yl]carbonyl}-2-chloro-3-thienyl)ethanone (101 mg, 0.15 mmol) in Ethanol (3.0 mL) was added 1% HCl in EtOH (3.59 mL, 0.43 mmol) at rt, and the mixture left to stand at 4° C. overnight. The reaction was quenched with saturated NaHCO$_3$ and diluted with water and EtOAc. The organic layer was washed with brine, dried over Na$_2$SO$_4$, filtered, and concentrated in vacuo. The residue was purified by ISCO column chromatography (40%-70% EtOAc in DCM as eluent) to give the title compound as a dark yellow residue (yield=70 mg). LCMS (FA): m/z=552.2 (M+1)

Step 3: [(1R,2S,4R)-4-({5-[(4-Acetyl-5-chloro-2-thienyl)carbonyl]pyrimidin-4-yl}amino)-2-hydroxycyclopentyl]methyl sulfamate To a solution of 1-(2-chloro-5-{[4-({(1R,3R,4S)-3-(hydroxymethyl)-4-[(triisopropylsilyl)oxy]cyclopentyl}amino)pyrimidin-5-yl]carbonyl}-3-thienyl)ethanone (70 mg, 0.13 mmol) in DMF (3.0 mL) cooled at 0° C. under an atmosphere of argon was added chlorosulfonamide (21.9 mg, 0.19 mmol). The reaction was stirred for 20 min. The reaction was quenched by addition of saturated NaHCO₃ and water was added. The mixture was extracted with EtOAc (×3). The combined organics were washed with 10% LiCl in water (×3), brine, dried over Na₂SO₄, filtered and concentrated in vacuo. The residue was purified via ISCO column chromatography (50% EtOAc in DCM as eluent) to give the sulfamate product as yellow foam. The compound was diluted with THF (2.0 mL), 4.0 M of HCl in water (1.50 mL, 6.00 mmol) was added at rt, and the reaction was stirred overnight. The reaction was quenched by addition of saturated NaHCO₃ and extracted with EtOAc (×3). The combined organic layers were washed with brine, dried over Na₂SO₄, filtered, and concentrated in vacuo. The residue was purified via ISCO column chromatography (5% MeOH in DCM as eluent) to give the title compound as light yellow foam (yield=54 mg). $^1$H NMR (400 MHz, MeOD) δ 8.82 (s, 1H), 8.62 (s, 1H), 7.95 (s, 1H), 4.87-4.77 (m, 1H), 4.25-4.12 (m, 3H), 2.62 (s, 3H), 2.56-2.45 (m, 1H), 2.32-2.11 (m, 2H), 1.96-1.86 (m, 1H), 1.50-1.39 (m, 1H); LCMS: (FA) M+1 475.1

Example 154: [(1R,2S,4R)-4-{[5-({5-Chloro-4-[(1S)-1-(3-chlorophenyl)-1-hydroxyethyl]-2-thienyl}carbonyl)pyrimidin-4-yl]amino}-2-hydroxycyclopentyl]methyl sulfamate and [(1R,2S,4R)-4-{[5-({5-Chloro-4-[(1R)-1-(3-chlorophenyl)-1-hydroxyethyl]-2-thienyl}carbonyl)pyrimidin-4-yl]amino}-2-hydroxycyclopentyl]methyl sulfamate. I-102

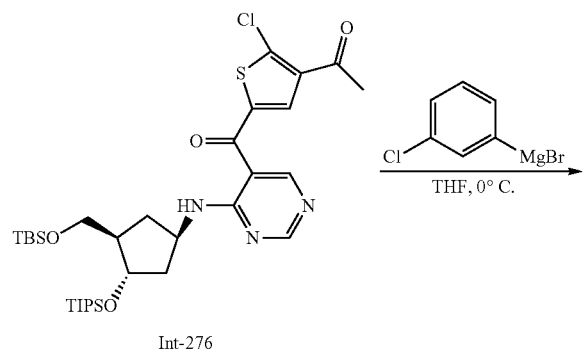

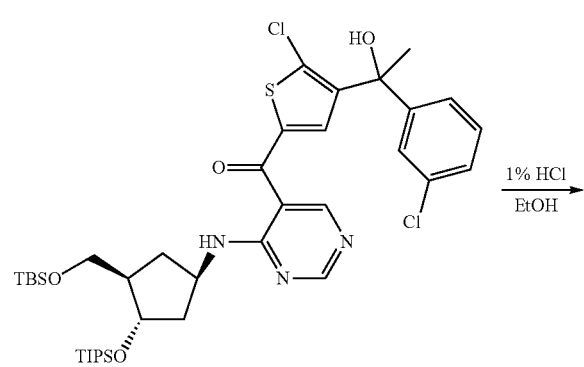

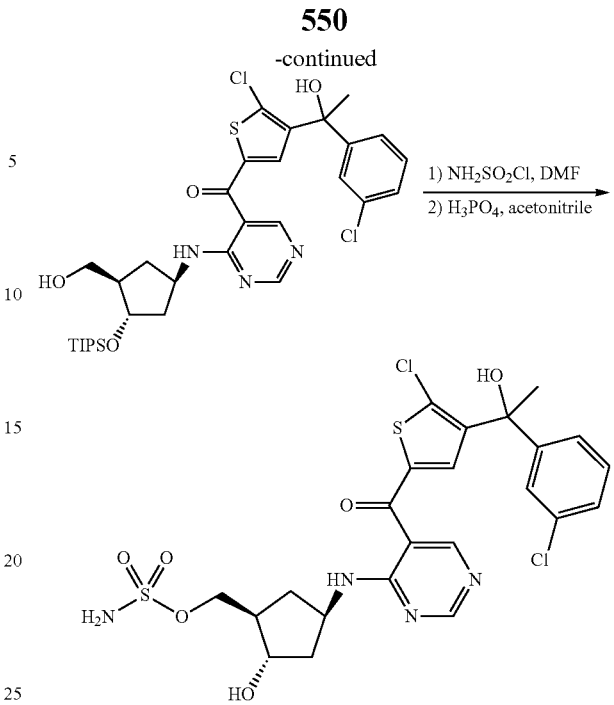

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl]{5-chloro-4-[(1S)-1-(3-chlorophenyl)-1-hydroxyethyl]-2-thienyl}methanone and [4-({(1R,3R,4S)-3-({[tert-Butyl(dimethyl)silyl]oxy}methyl)-4-[(triisopropylsilyl)oxy]cyclopentyl}amino)pyrimidin-5-yl]{5-chloro-4-[(1R)-1-(3-chlorophenyl)-1-hydroxyethyl]-2-thienyl}methanone A round bottom flask with condenser was charged with Int-276 (150 mg, 0.22 mmol) and purged with argon. To the reaction vessel was added THF (2.10 mL) and the solution was cooled to 0° C. To the solution was added dropwise 0.5 M of 3-chlorophenylmagnesium bromide in THF (2.93 mL, 1.46 mmol) over 10 min and the mixture was stirred at 0° C. for 1 hour. The reaction was quenched by addition of saturated aqueous NH₄Cl and extracted with EtOAc. The combined organic layers were dried over Na₂SO₄, filtered, and concentrated in vacuo. The residue was purified by ISCO column chromatography (0%-50% EtOAc in hexanes as eluent) to give 113 mg (64%) of the title products. $^1$H NMR (400 MHz, Chloroform-d) δ 8.77 (s, 1H), 8.58 (s, 1H), 7.70 (s, 1H), 7.43-7.38 (m, 1H), 7.25-7.22 (m, 3H), 4.84-4.73 (m, 1H), 4.33-4.26 (m, 1H), 3.64-3.59 (m, 1H), 3.58-3.52 (m, 1H), 2.48-2.39 (m, 1H), 2.21-2.10 (m, 3H), 2.03 (s, 3H), 1.75-1.66 (m, 1H), 1.06 (s, 21H), 0.88 (s, 9H), 0.03 (s, 6H).

Step 2: {5-Chloro-4-[(1S)-1-(3-chlorophenyl)-1-hydroxyethyl]-2-thienyl}[4-({(1R,3R,4S)-3-(hydroxymethyl)-4-[(triisopropylsilyl)oxy]cyclopentyl}amino)pyrimidin-5-yl]methanone and {5-Chloro-4-[(1R)-1-(3-chlorophenyl)-1-hydroxyethyl]-2-thienyl}[4-({(1R,3R,4S)-3-(hydroxymethyl)-4-[(triisopropylsilyl)oxy]cyclopentyl}amino)pyrimidin-5-yl]methanone To a solution of the product mixture from step 1 (113 mg, 0.15 mmol) in EtOH (0.9 mL) was added 1% HCl in EtOH (4.20 mL, 0.51 mmol) at 0° C. and the reaction was allowed to stir for 1 hour at 0° C. then kept in the refrigerator overnight. The reaction mixture was quenched by addition of saturated NaHCO₃ (6 mL) solution, concentrated in vacuo, added water and extracted with EtOAc (5 mL×3). The combined organic layers were dried over Na₂SO₄, filtered, and concentrated in vacuo. The residue was used in next step without purification. LCMS (FA): m/z=664.2 (M+1).

Step 3: {(1R,2S,4R)-4-{[5-({5-Chloro-4-[(1S)-1-(3-chlorophenyl)-1-hydroxyethyl]-2-thienyl}carbonyl)pyrimidin-4-yl]amino}-2-[(triisopropylsilyl)oxy]cyclopentyl}methyl sulfamate and {(1R,2S,4R)-4-{[5-({5-Chloro-4-[(1R)-1-(3-chlorophenyl)-1-hydroxyethyl]-2-thienyl}carbonyl)pyrimidin-4-yl]amino}-2-[(triisopropylsilyl)oxy]cyclopentyl}methyl sulfamate To a solution of the product mixture from step 2 (91 mg, 0.14 mmol)) in DMF (1 mL) at 0° C. was added chlorosulfonamide (31.6 mg, 0.27 mmol) and the reaction was allowed to stir for 10 min. The reaction mixture was quenched by addition of saturated NaHCO₃ (5 mL), extracted with EtOAc (5 mL×3). The combined organic layers were dried over Na₂SO₄, filtered, and concentrated in vacuo. The residue was used in next step without purification. LCMS (FA): m/z=743.4 (M+1).

Step 4: [(1R,2S,4R)-4-{[5-({5-Chloro-4-[(1S)-1-(3-chlorophenyl)-1-hydroxyethyl]-2-thienyl}carbonyl)pyrimidin-4-yl]amino}-2-hydroxycyclopentyl]methyl sulfamate and [(1R,2S,4R)-4-{[5-({5-Chloro-4-[(1R)-1-(3-chlorophenyl)-1-hydroxyethyl]-2-thienyl}carbonyl)pyrimidin-4-yl]amino}-2-hydroxycyclopentyl]methyl sulfamate A 50 mL round bottom flask was charged with the product mixture from step 3 (100 mg, 0.1 mmol) and CH₃CN (1 mL). To the solution was added phosphoric acid (1 mL) at 0° C. and the reaction was allowed to stir at for 1 hour. The reaction mixture was quenched by addition of 1M Na₂CO₃ (5 mL), extracted with EtOAc (5 mL×3). The combined organic layers were dried over Na₂SO₄, filtered, and concentrated in vacuo. The crude product was purified by preparative HPLC to give (7 mg, 9%) of the title compounds. ¹H NMR (400 MHz, Methanol-d4) δ 8.78 (s, 1H), 8.61 (s, 1H), 7.77 (s, 1H), 7.46 (s, 1H), 7.40-7.18 (m, 3H), 4.83-4.73 (m, 1H), 4.30-4.06 (m, 3H), 2.58-2.43 (m, 1H), 2.27 (s, 1H), 2.20-2.11 (m, 1H), 1.95 (s, 3H), 1.96-1.85 (m, 1H), 1.56-1.46 (m, 1H).

Example 155: [(1R,2S,4R)-4-({5-[(4-Benzoyl-5-chloro-2-thienyl)carbonyl]pyrimidin-4-yl}amino)-2-hydroxycyclopentyl]methyl sulfamate I-215

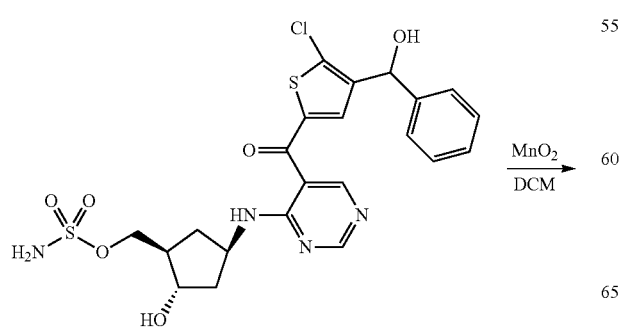

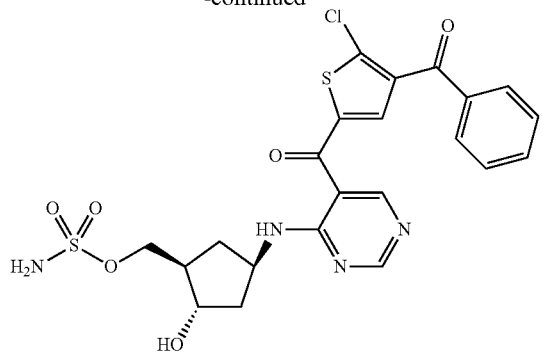

Step 1: [(1R,2S,4R)-4-({5-[(4-Benzoyl-5-chloro-2-thienyl)carbonyl]pyrimidin-4-yl}amino)-2-hydroxy-cyclopentyl]methyl sulfamate 9To a solution of I-56 (12.0 mg, 22.3 umol) in THF (1.0 mL) was added MnO₂ (19.4 mg, 0.22 mmol) at rt and the reaction was monitored by TLC. The reaction was filtered through a pad of Celite. The filtrate was concentrated in vacuo and the residue was purified via ISCO column chromatography (5% MeOH in DCM as eluent) to give the title compound (yield=2 mg). ¹H NMR (400 MHz, MeOD) δ 8.81 (s, 1H), 8.59 (s, 1H), 7.91-7.84 (m, 2H), 7.74-7.65 (m, 2H), 7.60-7.52 (m, 2H), 4.87-4.76 (m, 1H), 4.24-4.12 (m, 3H), 2.56-2.45 (m, 1H), 2.33-2.10 (m, 2H), 1.98-1.86 (m, 1H), 1.52-1.39 (m, 1H). LCMS: (FA) M+1 537.4

Example 156: {(1R,2S,4R)-2-Hydroxy-4-[(5-{[4-(methoxymethyl)-2-thienyl]carbonyl}pyrimidin-4-yl)amino]cyclopentyl}methyl sulfamate I-217

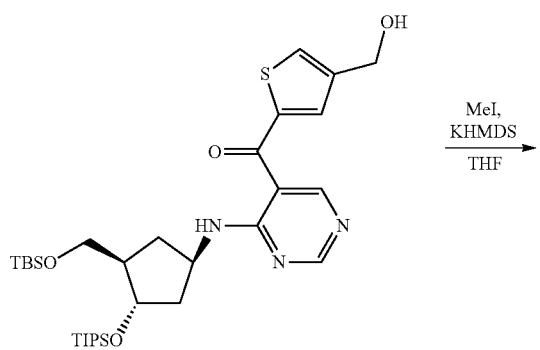

Int-268

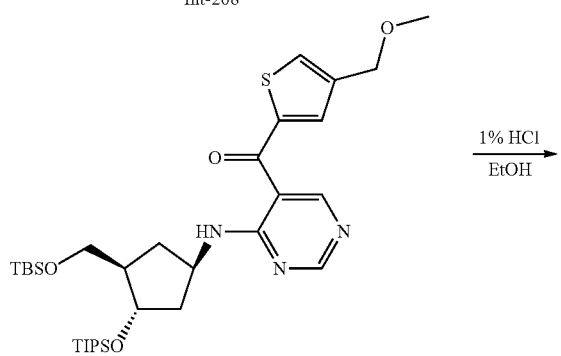

553

-continued

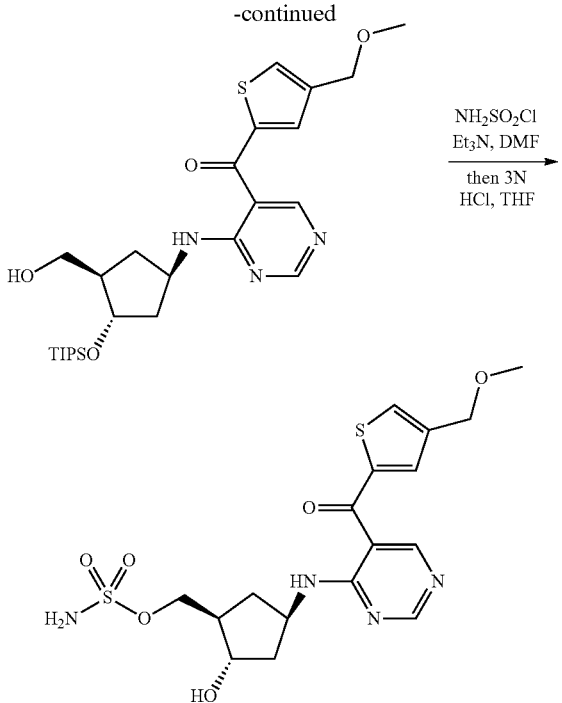

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(meth oxymethyl)-2-thienyl]methanone A solution of Int-268 (0.50 g, 0.81 mmol) in THF (33 mL) was cooled to 0° C. To the solution was added MeI (0.25 mL, 4.03 mmol) followed by dropwise addition of 1.0 M of potassium bis(trimethylsilyl)amide in THF (0.81 mL, 0.81 mmol). The reaction mixture was allowed to stir at 0° C. for 1 hour. The reaction was quenched via addition of water and the mixture was extracted with ether (3x). The combined organic layers were dried over MgSO$_4$, filtered, and concentrated in vacuo. The crude product was purified on ISCO chromatography eluting with a hexane/EtOAc gradient to afford the title compound as (yield=0.23 g). LCMS (FA): m/z=635.1 (M+H)

Step 2: [4-({(1R,3R,4S)-3-(Hydroxymethyl)-4-[(triisopropylsilyl)oxy]cyclopentyl}amino)pyrimidin-5-yl][4-(methoxymethyl)-2-thienyl]methanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl][4-(methoxymethyl)-2-thienyl]methanone (0.22 g, 0.35 mmol) in EtOH (8.7 mL) was added 1% HCl in EtOH (8.8 mL, 1.0 mmol) at rt. The solution was sealed and placed in a refrigerator for 19 h. The reaction was quenched by addition of saturated NaHCO$_3$. To the residue was added water and extracted with EtOAc (3x). The combined organic layers were dried over MgSO$_4$, filtered, and concentrated in vacuo. The residue was purified on ISCO chromatography eluting with a DCM/MeOH gradient to afford the title compound as (yield=0.16 g). LCMS (FA): m/z=520.3 (M+H)

554

Step 3: {(1R,2S,4R)-2-Hydroxy-4-[(5-{[4-(methoxymethyl)-2-thienyl]carbonyl}pyrimidin-4-yl)amino]cyclopentyl}methyl sulfamate To a solution of [4-({(1R,3R,4S)-3-(hydroxymethyl)-4-[(triisopropylsilyl)oxy]cyclopentyl}amino)pyrimidin-5-yl][4-(methoxymethyl)-2-thienyl]methanone (0.16 g, 0.31 mmol) in DMF (4.2 mL) was added triethylamine (0.13 mL, 0.92 mmol) and chlorosulfonamide (88.9 mg, 0.77 mmol) and the reaction was stirred for 45 min at rt. To the reaction mixture was added EtOH (1 mL) and THF (1 mL) followed by addition of 3.0 M of HCl in water (2.57 mL, 7.70 mmol). The mixture was stirred at rt for 18 h. The reaction was quenched via addition of 3N NaOH until pH 10 and the mixture was partitioned between water and EtOAc. The organic layer was separated, and the aqueous layer was extracted w/EtOAc (2x). The combined organic layers were dried over MgSO$_4$, filtered, and concentrated in vacuo. Residue was subjected to ISCO chromatography eluting with a DCM/MeOH gradient to afford the title compound (yield=87 mg). $^1$H NMR (400 MHz, Methanol-d$_4$) δ 8.78 (s, 1H), 8.61 (s, 1H), 7.84 (s, 1H), 7.67 (s, 1H), 4.86-4.76 (m, 1H), 4.50 (s, 2H), 4.28-4.14 (m, 3H), 3.42 (s, 3H), 2.53 (dt, J=13.8, 7.7 Hz, 1H), 2.29 (tq, J=11.4, 5.7 Hz, 1H), 2.19 (ddd, J=12.5, 7.5, 4.4 Hz, 1H), 2.00-1.89 (m, 1H), 1.45 (dt, J=13.0, 9.1 Hz, 1H). LCMS (FA): m/z=443.5 (M+H)

Example 157: [(1R,2S,4R)-4-({5-[(4-Acetyl-2-thienyl)carbonyl]pyrimidin-4-yl}amino)-2-hydroxycyclopentyl]methyl sulfamate I-229

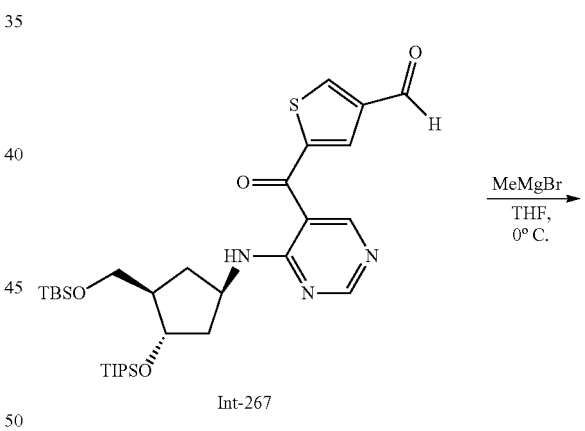

Int-267

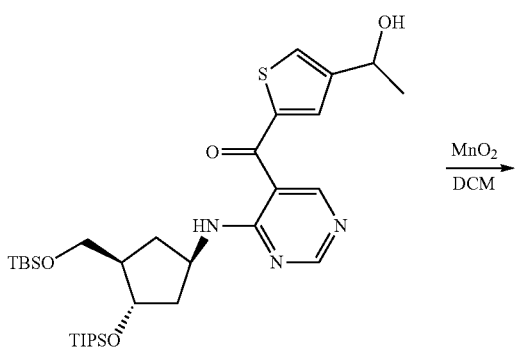

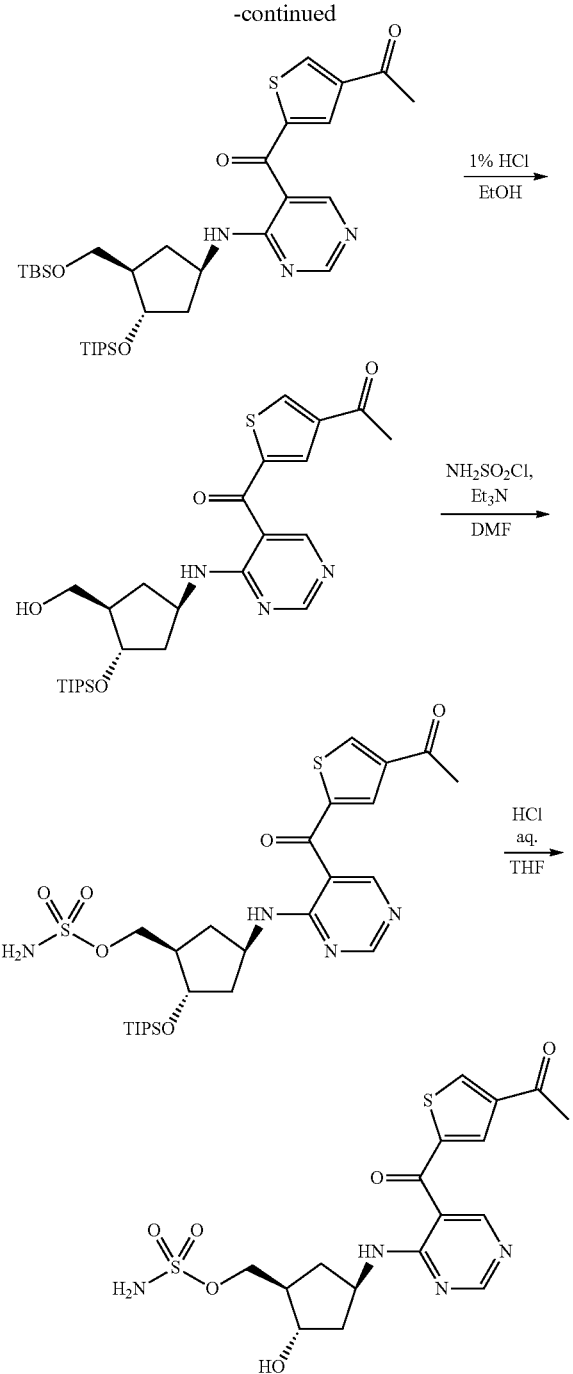

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(1S)-1-hydroxyethyl]-2-thienyl}methanone and [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(1R)-1-hydroxyethyl]-2-thienyl}methanone A solution of Int-267 (167 mg, 0.27 mmol) in THF (8.0 mL) was cooled to −40° C., and 3.0 M of methylmagnesium bromide in Et$_2$O (0.18 mL, 0.54 mmol) was added dropwise via syringe. The reaction was stirred for 10 min at −40° C.

The reaction was quenched by addition of saturated NH$_4$Cl and extracted with EtOAc (×3). The combined organic layers were washed with water followed by brine, dried over MgSO$_4$, filtered and concentrated in vacuo. The residue was purified by ISCO column chromatography (60% EtOAc in hexanes as eluent) to give 91 mg (53%) of the title compound. LCMS (FA): m/z=634.4 (M+H).

Step 2: 1-(5-{[4-({(1R,3R,4S)-3-({[tert-Butyl(dimethyl)silyl]oxy}methyl)-4-[(triisopropylsilyl)oxy]cyclopentyl}amino)pyrimidin-5-yl]carbonyl}-3-thienyl)ethanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl]{4-[(1S and 1R)-1-hydroxyethyl]-2-thienyl}methanone (91 mg, 0.14 mmol) in DCM (20.0 mL) was added MnO$_2$ (187 mg, 2.15 mmol) and the reaction was stirred at rt overnight. The mixture was filtered through Celite pad and the filtrate was concentrated in vacuo to give 87 mg (96%) of the crude product. LCMS (FA): m/z=632.4 (M+H).

Step 3: 1-(5-{[4-({(1R,3R,4S)-3-(Hydroxymethyl)-4-[(triisopropylsilyl)oxy]cyclopentyl}amino)pyrimidin-5-yl]carbonyl}-3-thienyl)ethanone To a solution of 1-(5-{[4-({(1R,3R,4S)-3-({[tert-butyl(dimethyl)silyl]oxy}methyl)-4-[(triisopropylsilyl)oxy]cyclopentyl}amino)pyrimidin-5-yl]carbonyl}-3-thienyl)ethanone (87 mg, 0.14 mmol) in EtOH (2.0 mL) was added 1% HCl in EtOH solution (10 mL) and the reaction was put into the refrigerator overnight. The reaction was quenched by addition of saturated NaHCO$_3$ and extracted with EtOAc (×3). The combined organic layers were washed with brine, dried over MgSO$_4$, and concentrated in vacuo to give 68 mg (95%) of the crude product. LCMS (FA): m/z=519.2 (M+H).

Step 4: [(1R,2S,4R)-4-({5-[(4-Acetyl-2-thienyl)carbonyl]pyrimidin-4-yl}amino)-2-hydroxycyclopentyl]methyl sulfamate To a solution of 1-(5-{[4-({(1R,3R,4S)-3-(hydroxymethyl)-4-[(triisopropylsilyl)oxy]cyclopentyl}amino)pyrimidin-5-yl]carbonyl}-3-thienyl)ethanone (22 mg, 0.04 mmol) in DMF (0.19 mL) was added chlorosulfonamide (5.79 mg, 0.05 mmol) at rt, and the reaction was stirred for 1 hour. To the mixture was added 6 M HCl (3 mL) and the reaction stirred at rt overnight. The resulting mixture was quenched by addition of saturated NaHCO$_3$ extracted with EtOAc (×2). The combined organic layers were washed with brine, dried over MgSO$_4$, and concentrated in vacuo. The residue was purified by preparative HPLC to give 18 mg (87%) of the title compound. $^1$H NMR (400 MHz, MeOD) δ 8.80 (s, 1H), 8.73 (d, J=1.3 Hz, 1H), 8.62 (d, J=8.3 Hz, 1H), 8.02 (d, J=1.3 Hz, 1H), 4.88-4.77 (m, 1H), 4.27-4.13 (m, 3H), 2.58 (s, 3H), 2.56-2.47 (m, 1H), 2.36-2.24 (m, 1H), 2.23-2.12 (m, 1H), 1.99-1.88 (m, 1H), 1.53-1.39 (m, 1H). LCMS (FA): m/z=441.0 (M+H).

Example 158: [(1R,2S,4R)-4-{[5-({4-[(S)-(6-Chloropyridin-2-yl)(hydroxy)methyl]-2-thienyl}carbonyl)pyrimidin-4-yl]amino}-2-hydroxycyclopentyl]methyl sulfamate and [(1R,2S,4R)-4-{[5-({4-[(R)-(6-Chloropyridin-2-yl)(hydroxy)methyl]-2-thienyl}carbonyl)pyrimidin-4-yl]amino}-2-hydroxycyclopentyl]methyl sulfamate I-29

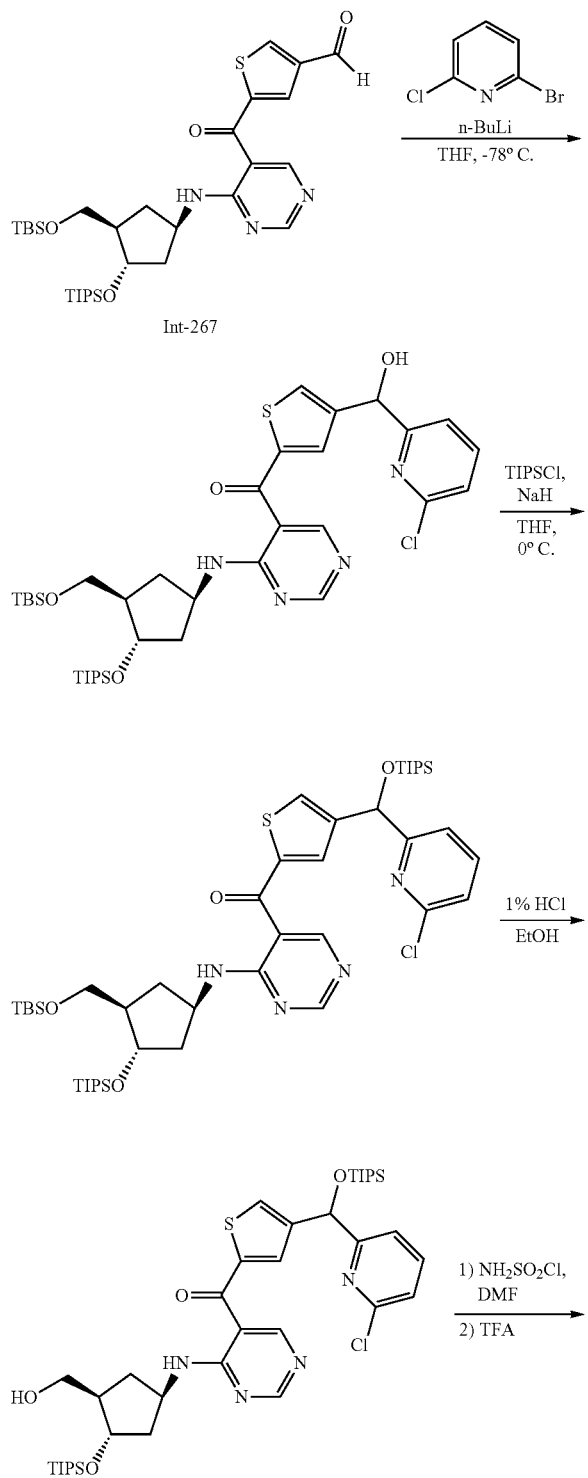

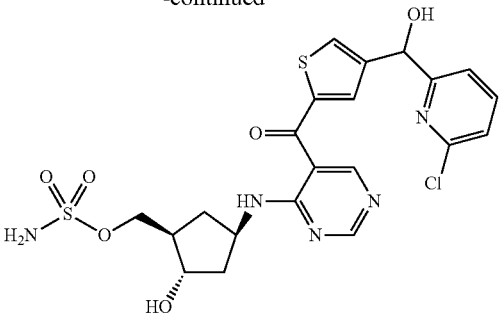

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(S)-(6-chloropyridin-2-yl)(hydroxy)methyl]-2-thienyl}methanone and [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(R)-(6-chloropyridin-2-yl)(hydroxy)methyl]-2-thienyl}methanone A solution of 2-bromo-6-chloropyridine (339 mg, 1.76 mmol) in THF (40.0 mL) was cooled to −78° C. 2.50 M of n-BuLi in hexane (0.81 mL, 2.03 mmol) was added dropwise via syringe to this solution at −78° C. and stirred for 3 min. The solution was cooled to −100° C. in a liquid nitrogen and hexane bath. To the mixture was added a solution of Int-267 (838 mg, 1.36 mmol) in THF (3 mL), and the reaction was warmed to −78° C. and stirred for 30 min. The reaction mixture was poured into 40 ml water and the mixture was extracted with DCM (50 ml×2). The combined organic layers were concentrated in vacuo and the residue was purified by ISCO column chromatography (0%-50% EtOAc in hexanes as eluent) to give 308 mg (31%) of the title compounds. $^1$H NMR (400 MHz, Chloroform-d) δ 8.75 (s, 1H), 8.66-8.56 (m, 2H), 7.71-7.61 (m, 2H), 7.55 (d, J=1.2 Hz, 1H), 7.30-7.21 (m, 2H), 5.85 (s, 1H), 4.85-4.72 (m, 1H), 4.66 (s, 1H), 4.33-4.25 (m, 1H), 3.60 (dd, J=10.1, 5.4 Hz, 1H), 3.54 (dd, J=10.1, 5.8 Hz, 1H), 2.42 (dt, J=14.2, 7.9 Hz, 1H), 2.23-2.08 (m, 2H), 1.69 (tdd, J=12.9, 5.9, 2.0 Hz, 1H), 1.26-1.19 (m, 1H), 1.06 (s, 21H), 0.87 (d, J=0.8 Hz, 9H), 0.02 and 0.02 (each s, each 3H).

Step 2: [4-({(1R,3R,4S)-3-({[tert-Butyl(dimethyl)silyl]oxy}methyl)-4-[(triisopropylsilyl)oxy]cyclopentyl}amino)pyrimidin-5-yl](4-{(S)-(6-chloropyridin-2-yl)[(triisopropylsilyl)oxy]methyl}-2-thienyl)methanone and [4-({(1R,3R,4S)-3-({[tert-Butyl(dimethyl)silyl]oxy}methyl)-4-[(triisopropylsilyl)oxy]cyclopentyl}amino)pyrimidin-5-yl](4-{(R)-(6-chloropyridin-2-yl)[(triisopropylsilyl)oxy]methyl}-2-thienyl)methanone To a solution of the product mixture from step 1 (302 mg, 0.41 mmol) in THF (20.0 mL, 246 mmol) was added 60% sodium hydride in mineral oil (39.6 mg, 1.65 mmol). The reaction was stirred at 60° C. for 30 min. To the mixture was added TIPSCl (239 mg, 1.24 mmol) and the mixture was stirred at 60° C. for 2 h. The solution was poured into 30 ml saturated NH$_4$Cl solution and then extracted with EtOAc (30 mL×2). The combined organic layers were concentrated in vacuo and the residue was purified via ISCO column chromatography (0%-25% EtOAc in hexanes as eluent) to give 301 mg (82%) of the title compounds. ¹H NMR (400 MHz, Chloroform-d) δ 8.71 (s, 1H), 8.63 (s, 1H), 8.61 (d, J=7.2 Hz, 1H), 7.71 (s, 1H), 7.63 (t, J=7.7 Hz, 1H), 7.60 (d, J=1.2 Hz, 1H), 7.54 (d, J=7.5 Hz, 1H), 7.19-7.11 (m, 1H), 5.96 (s, 1H), 4.76 (h, J=8.0 Hz, 1H), 4.28-4.20 (m, 1H), 3.60-3.46 (m, 2H), 2.47-2.32 (m, 1H), 2.14 (m, 2H), 1.71-1.62 (m, 1H), 1.41 (s, 1H), 1.03 (m, 42H), 0.85 (d, J=4.3 Hz, 9H), 0.00 (s, 6H).

Step 3: (4-{(S)-(6-Chloropyridin-2-yl)[(triisopropylsilyl)oxy]methyl}-2-thienyl)[4-({(1R,3R,4S)-3-(hydroxymethyl)-4-[(triisopropylsilyl)oxy]cyclopentyl}amino)pyrimidin-5-yl]methanone and (4-{(R)-(6-Chloropyridin-2-yl)[(triisopropylsilyl)oxy]methyl}-2-thienyl)[4-({(1R,3R,4S)-3-(hydroxymethyl)-4-[(triisopropylsilyl)oxy]cyclopentyl}amino)pyrimidin-5-yl]methanone A solution of the product mixture from step 2 (302 mg, 0.34 mmol) in 20 ml of 1% HCl in EtOH solution was stirred for 1 hour at rt. The mixture was poured into 40 ml saturated NaHCO₃ solution, and then extracted with DCM (30 ml×2). The combined organic layers were concentrated in vacuo and the residue was purified by ISCO column chromatography (0%-50% EtOAc in hexanes as eluent) to give 162 mg (62%) of the title compounds.

Step 4: [(1R,2S,4R)-4-{[5-({4-[(S)-(6-Chloropyridin-2-yl)(hydroxy)methyl]-2-thienyl}carbonyl)pyrimidin-4-yl]amino}-2-hydroxycyclopentyl]methyl sulfamate and [(1R,2S,4R)-4-{[5-({4-[(R)-(6-Chloropyridin-2-yl)(hydroxy)methyl]-2-thienyl}carbonyl)pyrimidin-4-yl]amino}-2-hydroxycyclopentyl]methyl sulfamate To a solution of the product mixture from step 3 (220 mg, 0.28 mmol) in DMF (6.0 mL) was added chlorosulfonamide (98.4 mg, 0.85 mmol) at rt with stirring for 30 min. The reaction mixture was poured into a solution of 25 ml water and 25 ml saturated NaHCO₃. The resulting mixture was extracted with EtOAc (40 ml×2). The combined organic layers were concentrated in vacuo. The residues were dissolved into a solution of TFA (16.0 mL, 208 mmol) and water (4.0 mL, 222 mmol) and the mixture was stirred at 80° C. for 1 hour. The reaction mixture was concentrated in vacuo and the residues were dissolved into 15 ml MeOH. 1 ml N,N-diisopropylethylamine was added to neutralize the solution. The resulting mixture was poured into 40 ml water, and then extracted with EtOAc (40 mL×2). The combined organic layers were concentrated in vacuo and the residue was purified by ISCO column chromatography (0%-25% MeOH in EtOAc as eluent) to give 79.5 mg (52%) of the title compounds. ¹H NMR (400 MHz, Methanol-d₄) δ 8.73 (s, 1H), 8.60 (s, 1H), 7.89-7.80 (m, 2H), 7.71 (d, J=1.3 Hz, 1H), 7.62 (d, J=7.6 Hz, 1H), 7.35 (d, J=7.9 Hz, 1H), 5.86 (s, 1H), 4.86-4.75 (m, 1H), 4.25-4.14 (m, 3H), 2.52 (m, 1H), 2.28 (m, 1H), 2.22-2.12 (m, 1H), 1.98-1.88 (m, 1H), 1.43 (m, 1H).

Example 159: [(1R,2S,4R)-4-({5-[(4-{[(3-Chlorophenyl)(methyl)amino]methyl}-2-thienyl)carbonyl]pyrimidin-4-yl}amino)-2-hydroxycyclopentyl] methyl sulfamate I-138

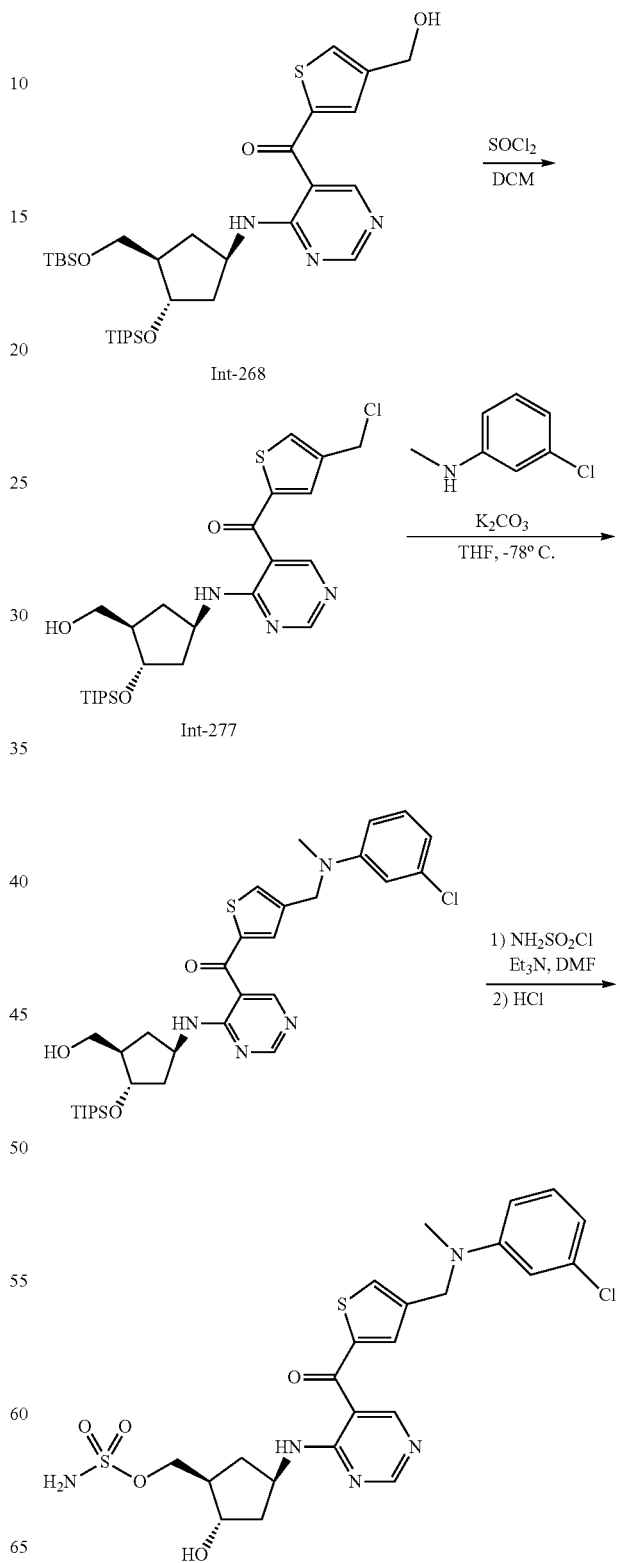

Step 1: [4-(Chloromethyl)-2-thienyl][4-({(1R,3R,4S)-3-(hydroxymethyl)-4-[(triisopropylsilyl)oxy]cyclopentyl}amino)pyrimidin-5-yl]methanone Int-277

To a solution of Int-268 (3.00 g, 4.84 mmol) in DCM (136 mL) at 0° C. was added thionyl chloride (0.35 mL, 4.84 mmol) and the reaction was allowed to stir at 0° C. for 1 hour, and then put into refrigerator overnight. After the mixture was concentrated in vacuo, the residue was purified by ISCO column chromatography (10% MeOH in DCM as eluent) to give 1.60 g (63%) of the title compound. LCMS (FA): m/z=526.1 (M+H).

Step 2: (4-{[(3-Chlorophenyl)(methyl)amino]methyl}-2-thienyl)[4-({(1R,3R,4S)-3-(hydroxymethyl)-4-[(triisopropylsilyl)oxy]cyclopentyl}amino)pyrimidin-5-yl]methanone A microwave reaction tube was charged with [4-(chloromethyl)-2-thienyl][4-({(1R,3R,4S)-3-(hydroxymethyl)-4-[(triisopropylsilyl)oxy]cyclopentyl}amino)pyrimidin-5-yl]methanone (0.18 g, 0.34 mmol), N-methyl-m-chloroaniline (194 mg, 1.37 mmol), K$_2$CO$_3$ (474 mg, 3.43 mmol), and DMF (6.00 mL). The resulting mixture was stirred at 100° C. for 5 h. After cooling to rt, the mixture was concentrated in vacuo and the residue was diluted with EtOAc. The mixture was filtered through Celite pad and the filtrate was concentrated in vacuo. The residue was purified by ISCO column chromatography (50% EtOAc in hexanes as eluent) to give 0.10 g (46%) of the title compound. LCMS (FA): m/z=629.6 (M+H).

Step 3: [(1R,2S,4R)-4-({5-[(4-{[(3-Chlorophenyl)(methyl)amino]methyl}-2-thienyl)carbonyl]pyrimidin-4-yl}amino)-2-hydroxycyclopentyl]methyl sulfamate To a solution of (4-{[(3-chlorophenyl)(methyl)amino]methyl}-2-thienyl)[4-({(1R,3R,4S)-3-(hydroxymethyl)-4-[(triisopropylsilyl)oxy]cyclopentyl}amino)pyrimidin-5-yl]methanone (0.10 g, 0.16 mmol) in DMF (1.9 mL) was added triethylamine (26.6 uL, 0.19 mmol) followed by chlorosulfonamide (36.7 mg, 0.32 mmol) at rt, and the mixture was stirred for 15 min. To the mixture was added 6 M HCl (2 mL) and the resulting mixture was stirred at rt overnight. The reaction was quenched by addition of water and the mixture was extracted with EtOAc (×3). The combined organic layers were washed with brine, dried over MgSO$_4$, and concentrated in vacuo. The residue was purified by preparative HPLC to give 60 mg (68%) of the title compound. $^1$H NMR (400 MHz, MeOD) δ 8.70 (s, 1H), 8.58 (s, 1H), 7.62 (d, J=1.2 Hz, 1H), 7.54 (d, J=1.3 Hz, 1H), 7.13 (t, J=8.1 Hz, 1H), 6.80-6.68 (m, 2H), 6.65 (dd, J=7.9, 1.1 Hz, 1H), 4.84-4.73 (m, 1H), 4.58 (s, 2H), 4.29-4.11 (m, 3H), 3.03 (s, 3H), 2.58-2.43 (m, 1H), 2.37-2.22 (m, 1H), 2.20-2.10 (m, 1H), 1.97-1.82 (m, 1H), 1.48-1.32 (m, 1H). LCMS (FA): m/z=552.1 (M+H).

Example 160: [(1R,2S,4R)-4-{[5-({4-[(3,3-Difluoropyrrolidin-1-yl)methyl]-2-thienyl}carbonyl)pyrimidin-4-yl]amino}-2-hydroxycyclopentyl]methyl sulfamate I-228

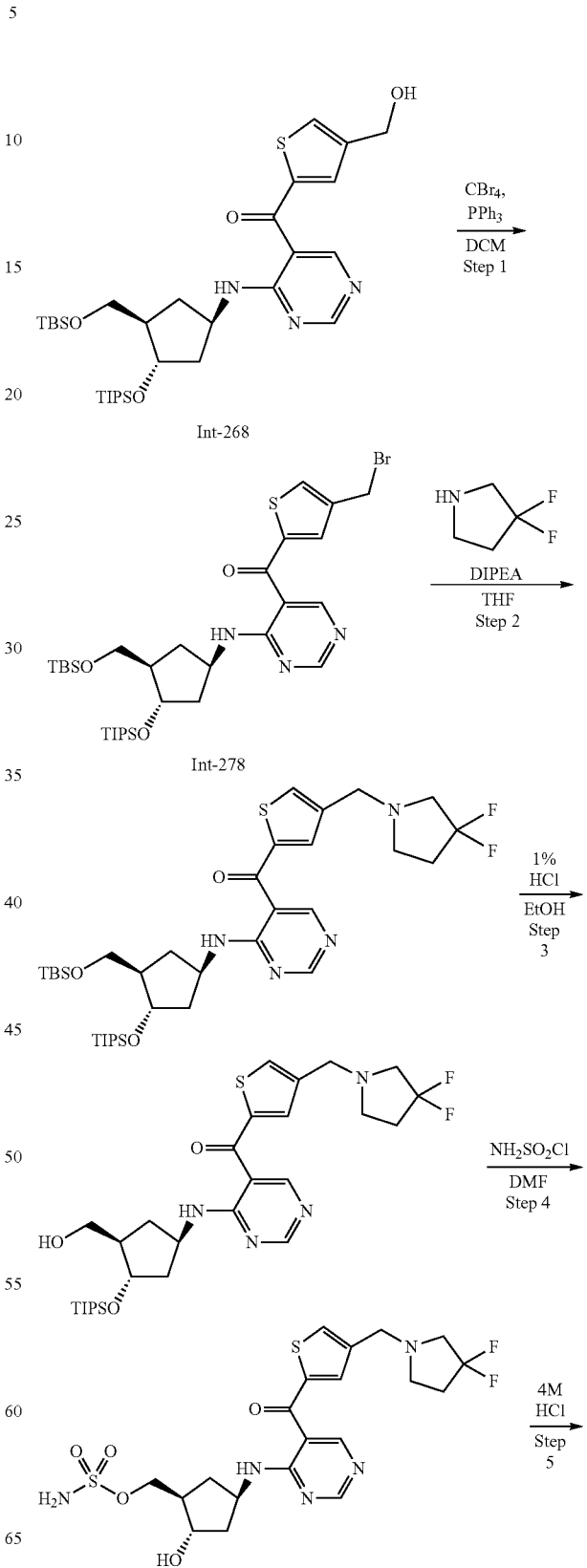

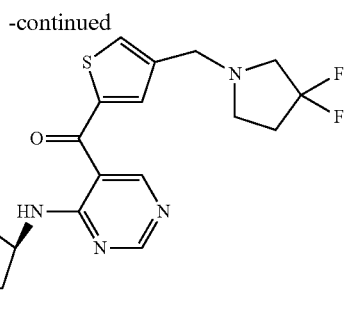

Step 1: [4-(Bromomethyl)-2-thienyl][4-({(1R,3R,4S)-3-({[tert-butyl(dimethyl)silyl]oxy}methyl)-4-[(triisopropylsilyl)oxy]cyclopentyl}amino)pyrimidin-5-yl]methanone Int-278

Int-268 (5.14 g, 8.29 mmol) and CBr$_4$ (3.02 g, 9.12 mmol) were dissolved into DCM (50.0 mL), and then PPh$_3$ (2.61 g, 9.95 mmol) was added to this solution at 0° C. The reaction was stirred for 1 hour at rt. The mixture was concentrated in vacuo and the residue purified by ISCO column chromatography in (0%-50% EtOAc/hexanes as eluent) to give the title compound (yield=4.92 g). $^1$H NMR (400 MHz, Chloroform-d) δ 8.83 (s, 1H), 8.67 (s, 1H), 8.63 (d, J=7.3 Hz, 1H), 7.67-7.64 (m, 1H), 7.59 (d, J=1.4 Hz, 1H), 4.89-4.74 (m, 1H), 4.48 (s, 2H), 4.30 (dt, J=6.3, 3.3 Hz, 1H), 3.62 (dd, J=10.1, 5.4 Hz, 1H), 3.55 (dd, J=10.1, 5.8 Hz, 1H), 2.44 (dt, J=13.5, 8.1 Hz, 1H), 2.24-2.09 (m, 2H), 1.71 (ddd, J=12.9, 9.1, 5.9 Hz, 1H), 1.31-1.20 (m, 1H), 1.06 (d, J=1.4 Hz, 21H), 0.88 (s, 9H), 0.03 (s, 6H).

Step 2: [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(3,3-difluoropyrrolidin-1-yl)methyl]-2-thienyl}methanone To a solution of [4-(bromomethyl)-2-thienyl][4-({(1R,3R,4S)-3-({[tert-butyl(dimethyl) silyl]oxy}methyl)-4-[(triisopropylsilyl)oxy]cyclopentyl}amino)pyrimidin-5-yl]methanone (170 mg, 0.25 mmol) in THF (10.0 mL) was added N,N-diisopropylethylamine (1.00 mL, 5.74 mmol) and 3,3-difluoropyrrolidine hydrochloride (357 mg, 2.49 mmol). The reaction was stirred at 50° C. for 40 h. The material was cooled to rt and concentrated in vacuo. The residue was purified by ISCO column chromatography (30%-100% EtOAc in hexanes as eluent) to give the title compound as orange oil (yield=72 mg). LCMS (FA): m/z=710 (M+1)

Step 3: {4-[(3,3-Difluoropyrrolidin-1-yl)methyl]-2-thienyl}[4-({(1R,3R,4S)-3-(hydroxymethyl)-4-[(triisopropylsilyl)oxy]cyclopentyl}amino)pyrimidin-5-yl]methanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl]{4-[(3,3-difluoropyrrolidin-1-yl)methyl]-2-thienyl}methanone (71.6 mg, 0.10 mmol) in ethanol (2.0 mL) was added 1% HCl in EtOH (2.50 mL, 0.30 mmol) at rt, and the mixture was allowed to stand at 4° C. for 24 h. The reaction was quenched with saturated NaHCO$_3$ and diluted with water and EtOAc. The organic layer was washed with brine, dried over Na$_2$SO$_4$, filtered, and concentrated in vacuo. The residue was purified by ISCO column chromatography (50%-100% EtOAc in hexanes as eluent) to give the title compound as light yellow oil (yield=41 mg). LCMS (FA): m/z=596.3 (M+1)

Step 4: {(1R,2S,4R)-4-{[5-({4-[(3,3-Difluoropyrrolidin-1-yl)methyl]-2-thienyl}carbonyl)pyrimidin-4-yl]amino}-2-[(triisopropylsilyl)oxy]cyclopentyl}methyl sulfamate {4-[(3,3-Difluoropyrrolidin-1-yl)methyl]-2-thienyl}[4-({(1R,3R,4S)-3-(hydroxymethyl)-4-[(triisopropylsilyl)oxy]cyclopentyl}amino)pyrimidin-5-yl]methanone (41 mg, 69.0 umol), DMF (2.0 mL) and chlorosulfonamide (11.9 mg, 0.10 mmol) were combined in a 50 mL round-bottom flask and stirred at rt for 20 min. The reaction was quenched with saturated NaHCO$_3$. The reaction was transferred to a separatory funnel and diluted with EtOAc and 10% aqueous solution of LiCl. The layers were separated and the organic layer was washed with 10% LiCl solution (×2), brine, dried over Na$_2$SO$_4$, filtered and concentrated in vacuo to give the title compound (yield=42 mg). LCMS (FA): m/z=674.2 (M+1)

Step 5: [(1R,2S,4R)-4-{[5-({4-[(3,3-Difluoropyrrolidin-1-yl)methyl]-2-thienyl}carbonyl)pyrimidin-4-yl]amino}-2-hydroxycyclopentyl]methyl sulfamate To a solution of {(1R,2S,4R)-4-{[5-({4-[(3,3-difluoropyrrolidin-1-yl)methyl]-2-thienyl}carbonyl)pyrimidin-4-yl]amino}-2-[(triisopropylsilyl)oxy]cyclopentyl}methyl sulfamate (41.8 mg, 0.06 mmol) in THF (1.50 mL) was added 4.0 M of HCl in water (1.00 mL, 4.00 mmol) at rt, and the mixture was stirred for overnight. The reaction was quenched by addition of saturated NaHCO$_3$ and the mixture was extracted with EtOAc (×3). The combined organic layers were dried over Na$_2$SO$_4$, filtered, and concentrated in vacuo. The residue was purified via ISCO column chromatography (0%-10% MeOH/DCM as eluent) to give the title compound as white foam (yield=27 mg). $^1$H NMR (400 MHz, MeOD) δ 8.78 (s, 1H), 8.60 (s, 1H), 7.81 (s, 1H), 7.69 (s, 1H), 4.86-4.76 (m, 1H), 4.24-4.12 (m, 3H), 3.71 (s, 2H), 2.93 (t, J=13.1 Hz, 2H), 2.79 (t, J=7.0 Hz, 2H), 2.58-2.47 (m, 1H), 2.36-2.11 (m, 4H), 1.96-1.87 (m, 1H), 1.49-1.39 (m, 1H). LCMS (FA): m/z=518.1 (M+1).

The compounds listed in the table below were prepared in an analogous fashion to that described above starting from the appropriate amine, base, and solvent in step 2. The following alternative conditions were employed in the described reaction steps. The desilylating agent employed in step 5 is also listed.

| Step 2 amine, base, and solvent | Step 5 desilylating agent | Compound No. |
|---|---|---|
| ![piperidine with gem-difluoro]<br>N,N-diisopropylethylamine<br>THF | TBAF | I-224 |
| ![indole] | TBAF | I-114 |

565

-continued

| Step 2 amine, base, and solvent | Step 5 desilylating agent | Compound No. |
|---|---|---|
| KOH, DMF<br>6-chloroindole | aq. HCl | I-83 |
| K₂CO₃, DMF<br>imidazoline | aq. HCl | I-231 |
| Cs₂CO₃, THF | | |

Example 161: [(1R,2S,4R)-2-Hydroxy-4-{[5-({4-[(5-methyl-2-furyl)methyl]-2-thienyl}carbonyl)pyrimidin-4-yl]amino}cyclopentyl]methyl sulfamate I-237

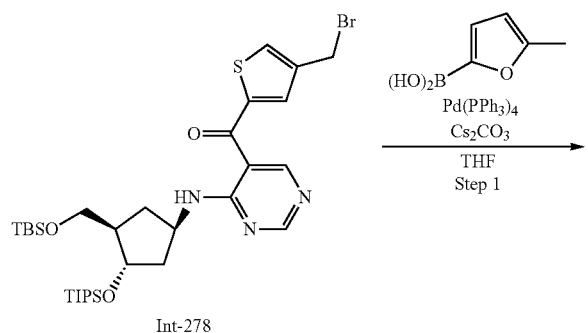

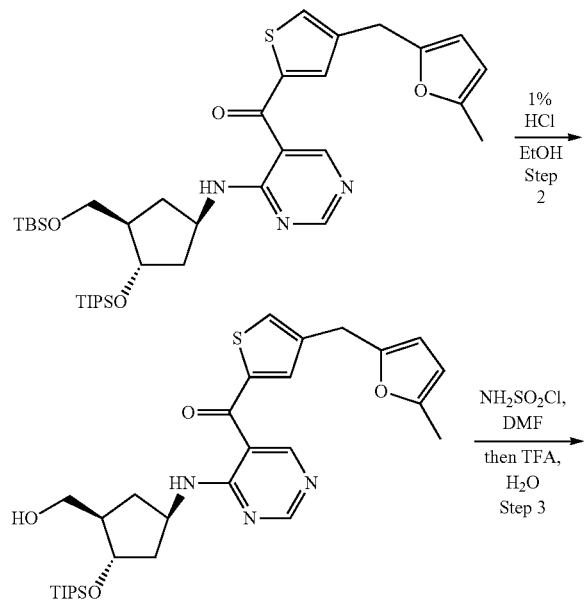

566

-continued

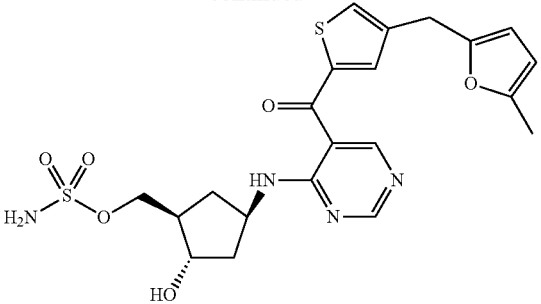

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(5-methyl-2-furyl)methyl]-2-thienyl}methanone Int-278 (213 mg, 0.31 mmol) and 5-methylfuran-2-boronic acid (59.0 mg, 0.47 mmol) were dissolved into THF (10.0 mL) in a round bottom flask, then Cs₂CO₃ (305 mg, 0.94 mmol) and water (2.00 mL, 111 mmol) were added to the solution. To the mixture was added Pd(PPh₃)₄ (36.1 mg, 0.03 mmol) and the reaction was allowed to stir at 40° C. for 10 h. To the reaction was added 20 ml water and then extracted with EtOAc (×2). The combined the organic layers were dried over MgSO₄, filtered, and concentrated in vacuo. The residue was purified by ISCO column chromatography (0%-30% EtOAc in hexanes as eluent) to give 62.2 mg (29%) of the title compound. ¹H NMR (400 MHz, Chloroform-d) δ 8.77 (s, 1H), 8.62 (s, 1H), 8.58 (d, J=7.0 Hz, 1H), 7.43 (s, 1H), 7.40 (s, 1H), 5.88 (d, J=2.9 Hz, 1H), 5.83 (s, 1H), 4.76 (q, J=7.7 Hz, 1H), 4.28-4.21 (m, 1H), 3.90 (s, 2H), 3.61-3.45 (m, 2H), 2.40 (d, J=13.0 Hz, 1H), 2.22 (s, 3H), 2.12 (s, 2H), 1.74-1.60 (m, 1H), 1.03 (s, 21H), 0.84 (s, 9H), −0.00 (s, 6H).

Step 2: [4-({(1R,3R,4S)-3-(Hydroxymethyl)-4-[(triisopropylsilyl)oxy]cyclopentyl}amino)pyrimidin-5-yl]{4-[(5-methyl-2-furyl)methyl]-2-thienyl}methanone A solution of [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(5-methyl-2-furyl)methyl]-2-thienyl}methanone (62.1 mg, 0.09 mmol) in 1% HCl in EtOH solution (10 mL) was stirred at rt for 1 hour and then poured into 25 ml saturated NaHCO₃. The mixture was extracted with EtOAc (×3). The combined the organic layers were dried over MgSO₄, filtered, and concentrated in vacuo. The residue was purified by ISCO column chromatography (0%-55% EtOAc in hexanes as eluent) to give 40.5 mg (78%) of the title compound. LCMS (FA): m/z=571.3 (M+H).

Step 3: [(1R,2S,4R)-2-Hydroxy-4-{[5-({4-[(5-methyl-2-furyl)methyl]-2-thienyl}carbonyl)pyrimidin-4-yl]amino}cyclopentyl]methyl sulfamate To a solution of [4-({(1R,3R,4S)-3-(hydroxymethyl)-4-[(triisopropylsilyl)oxy]cyclopentyl}amino)pyrimidin-5-yl]{4-[(5-methyl-2-furyl)methyl]-2-thienyl}methanone (40.5 mg, 0.07 mmol) in DMF (3.0 mL) was added chlorosulfonamide (37.8 mg, 0.33 mmol) at rt and the reaction was stirred for 30 min. The reaction was poured into saturated NaHCO₃ (50 mL) and then extracted with EtOAc (×2). The combined organic layers were concentrated in vacuo. The residues were dissolved into the solution of TFA (14.0 mL) and water (6.0 mL) and the mixture was stirred at 40° C. for 30 min. The reaction was concentrated in vacuo, and MeOH (5 mL), water (25 mL), and saturated NaHCO₃ (25 mL) were added to the residue. The mixture was extracted with EtOAc (×3). The combined organics were dried over MgSO4, filtered, and concentrated in vacuo. The residue was purified by ISCO column chromatography (0%-15% MeOH in EtOAc as eluent) to give 3.2 mg (9%) of the title compound. ¹H NMR (400 MHz, Methanol-d4) δ 8.82 (s, 1H), 8.63 (s, 1H), 8.55 (s, 1H), 7.99 (d, J=1.2 Hz, 1H), 7.80 (d, J=1.3 Hz, 1H), 4.82 (p, J=7.9 Hz, 1H), 4.26-4.13 (m, 3H), 2.85 (s, 3H), 2.57-2.48 (m, 1H), 2.29 (m, 1H), 2.18 (m, 1H), 1.90-1.84 (m, 1H), 1.45 (m, 1H). LCMS (AA): m/z=493.2 (M+H).

The compounds listed in the table below were prepared in an analogous fashion to that described above starting from the appropriate Grignard reagent at step 1.

| Step 1 boronic acid | Compound No. |
|---|---|
| (HO)₂B—furan—Cl | I-66 |
| (HO)₂B—dihydropyran | I-196 |

Example 162: {(1R,2S,4R)-4-[(5-{[4-(Cyclohex-1-en-1-ylmethyl)-2-thienyl]carbonyl}pyrimidin-4-yl)amino]-2-hydroxycyclopentyl}methyl sulfamate I-140

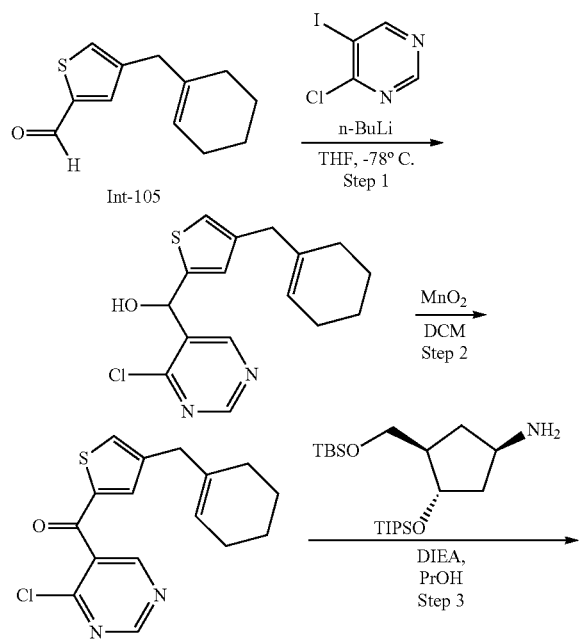

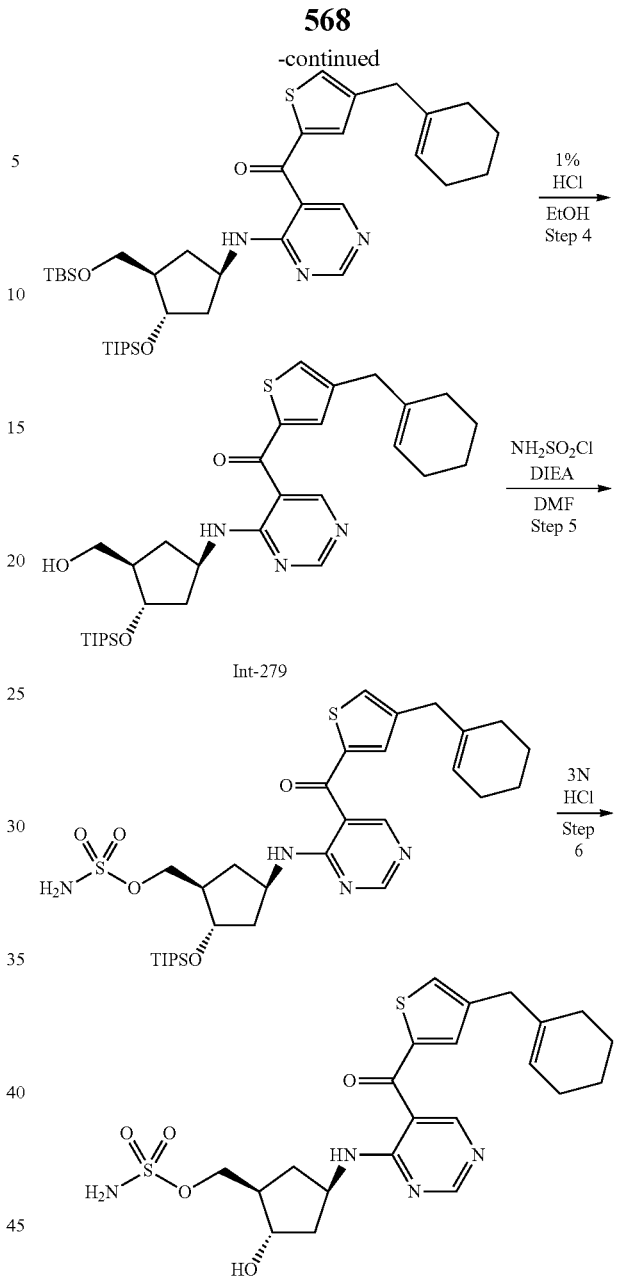

Step 1: rac-(4-Chloropyrimidin-5-yl)[4-(cyclohex-1-en-1-ylmethyl)-2-thienyl]methanol The title compound was prepared in an analogous fashion to Example 131, step 7 using aldehyde Int-105. LCMS (FA): m/z=323.1 (M+H).

Step 2: (4-Chloropyrimidin-5-yl)[4-(cyclohex-1-en-1-ylmethyl)-2-thienyl]methanone The title compound was prepared in an analogous fashion to Example 131, step 8. LCMS (FA): m/z=320.1 (M+H).

Step 3: [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(cyclohex-1-en-1-ylmethyl)-2-thienyl]methanone (4-Chloropyrimidin-5-yl)[4-(cyclohex-1-en-1-ylmethyl)-2-thienyl]methanone (0.15 g, 0.47 mmol) and Int-260 (0.21 g, 0.52 mmol) were weighed into a 250 mL round bottom flask fitted with a reflux condenser. To this mixture was added i-PrOH (3.8 mL) and N,N-diisopropylethylamine (0.16 mL, 0.94 mmol). The resulting mixture was stirred at 50° C. for 16 h. After cooling to rt, the reaction was concentrated in vacuo. The residue was purified by ISCO chromatography eluting with a hexanes/EtOAc gradient to afford the title compound (yield=287 mg). $^1$H NMR (400 MHz, Chloroform-d) δ 8.81 (s, 1H), 8.66 (s, 1H), 8.62 (d, J=7.6 Hz, 1H), 7.39 (d, J=1.3 Hz, 1H), 7.35 (d, J=1.3 Hz, 1H), 5.49-5.43 (m, 1H), 4.85-4.74 (m, 1H), 4.33-4.27 (m, 1H), 3.61 (dd, J=10.0, 5.5 Hz, 2H), 3.55 (dd, J=10.1, 5.8 Hz, 2H), 3.25 (s, 2H), 2.50-2.39 (m, 1H), 2.24-2.10 (m, 2H), 2.04-1.96 (m, 2H), 1.91-1.84 (m, 2H), 1.76-1.69 (m, 1H), 1.65-1.49 (m, 4H), 1.32-1.21 (m, 1H), 1.10-1.02 (m, 21H), 0.88 (s, 9H), 0.04 (s, 6H).

Step 4: [4-(Cyclohex-1-en-1-ylmethyl)-2-thienyl][4-({(1R,3R,4S)-3-(hydroxymethyl)-4-[(triisopropylsilyl)oxy]cyclopentyl}amino)pyrimidin-5-yl]methanone Int-279

To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl][4-(cyclohex-1-en-1-ylmethyl)-2-thienyl]methanone (0.27 g, 0.39 mmol) in EtOH (9.8 mL) was added 1% HCl in EtOH solution (9.80 mL, 1.18 mmol) at rt. The solution was sealed and placed in a refrigerator overnight. After 19 h, the reaction was quenched by addition of saturated NaHCO$_3$. To the residue was added water and extracted with EtOAc. The combined organic layers were dried over MgSO$_4$, filtered, and concentrated in vacuo. Residue was subjected to ISCO chromatography eluting with a hexanes/EtOAc gradient to afford the title compound (yield=208 mg).

Step 5: {(1R,2S,4R)-4-[(5-{[4-(Cyclohex-1-en-1-ylmethyl)-2-thienyl]carbonyl}pyrimidin-4-yl)amino]-2-[(triisopropylsilyl)oxy]cyclopentyl}methyl sulfamate To a solution of [4-(cyclohex-1-en-1-ylmethyl)-2-thienyl][4-({(1R,3R,4S)-3-(hydroxymethyl)-4-[(triisopropylsilyl)oxy]cyclopentyl}amino)pyrimidin-5-yl]methanone (0.12 g, 0.21 mmol) in DMF (3.3 mL) and N,N-diisopropylethylamine (0.09 mL, 0.51 mmol) was added chlorosulfonamide (91.2 mg, 0.80 mmol) at rt, and the mixture was stirred for 4 h. The reaction was quenched with saturated NaHCO$_3$ and the mixture was extracted with EtOAc (3×). The combined organic layers were then dried using MgSO$_4$, filtered and concentrated in vacuo to yield 140 mg of crude title compound.

Step 6: {(1R,2S,4R)-4-[(5-{[4-(Cyclohex-1-en-1-ylmethyl)-2-thienyl]carbonyl}pyrimidin-4-yl)amino]-2-hydroxycyclopentyl}methyl sulfamate To a solution of crude {(1R,2S,4R)-4-[(5-{[4-(cyclohex-1-en-1-ylmethyl)-2-thienyl]carbonyl}pyrimidin-4-yl)amino]-2-[(triisopropylsilyl)oxy]cyclopentyl}methyl sulfamate (0.14 g, 0.22 mmol) in THF (6.8 mL) was added 3.0 M of HCl (1.2 mL, 3.6 mmol). The reaction was stirred at rt overnight and then the reaction was heated to 45° C. for 7 h and then to 50° C. for 1 hour. The reaction was quenched by addition of saturated NaHCO$_3$ and extracted with EtOAc. The combined organic extracts were dried, filtered, and concentrated in vacuo. The residue was purified by preparative HPLC to yield 36 mg of the title compound. $^1$H NMR (400 MHz, DMSO-d$_6$) δ 8.67 (s, 1H), 8.64 (s, 1H), 8.27 (d, J=7.5 Hz, 1H), 7.73 (s, 1H), 7.54 (s, 1H), 7.44 (s, 2H), 5.48-5.42 (m, 1H), 4.97-4.84 (m, 1H), 4.77-4.64 (m, 1H), 4.09 (dd, J=9.7, 6.0 Hz, 1H), 4.00-3.91 (m, 2H), 3.26 (s, 2H), 2.37-2.26 (m, 1H), 2.17-2.06 (m, 1H), 2.01-1.90 (m, 3H), 1.90-1.82 (m, 2H), 1.82-1.72 (m, 1H), 1.59-1.43 (m, 4H), 1.28 (dt, J=12.6, 9.3 Hz, 1H). LCMS (FA): m/z=493.4 (M+H).

Example 163: {(1R,2S,4R)-4-[(5-{[4-(Cyclohexylmethyl)-2-thienyl]carbonyl}pyrimidin-4-yl)amino]-2-hydroxycyclopentyl}methyl sulfamate I-199

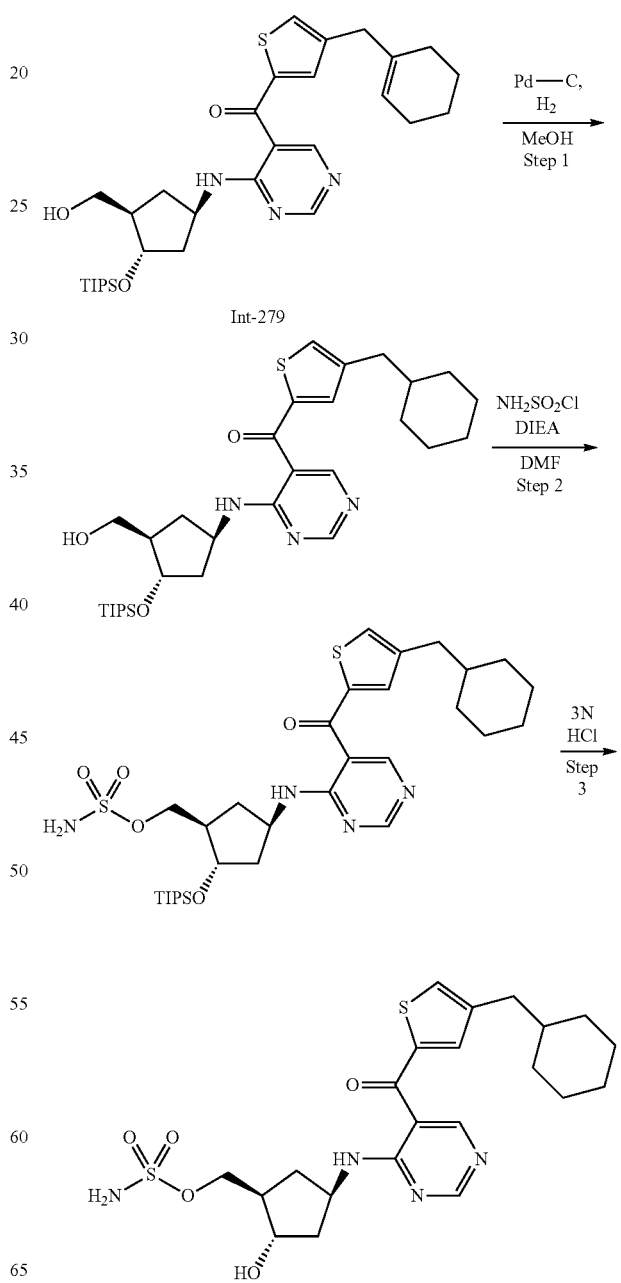

Step 1: [4-(Cyclohexylmethyl)-2-thienyl][4-({(1R,3R,4S)-3-(hydroxymethyl)-4-[(triisopropylsilyl)oxy]cyclopentyl}amino)pyrimidin-5-yl]methanone To a solution of Int-279 (80.0 mg, 0.14 mmol) in MeOH (4 mL) was added 20% Pd(OH)$_2$/carbon, 50% water (30.0 mg, 0.02 mmol) and the reaction was allowed to stir for 4 days under an atmosphere of hydrogen (balloon). The reaction was filtered through a pad of Celite and the filtrate was concentrated in vacuo to yield 60 mg of the title compound. LCMS (FA): m/z=572.6 (M+H).

Step 1: {(1R,2S,4R)-4-[(5-{[4-(Cyclohexylmethyl)-2-thienyl]carbonyl}pyrimidin-4-yl)amino]-2-[(triisopropylsilyl)oxy]cyclopentyl}methyl sulfamate The title compound was prepared in an analogous fashion to Example 162, step 5. LCMS (FA): m/z=651.7 (M+H).

Step 3: {(1R,2S,4R)-4-[(5-{[4-(Cyclohexylmethyl)-2-thienyl]carbonyl}pyrimidin-4-yl)amino]-2-hydroxycyclopentyl}methyl sulfamate The title compound was prepared in an analogous fashion to Example 162, step 6. $^1$H NMR (400 MHz, DMSO) δ 8.70 (s, 1H), 8.66 (s, 1H), 8.28 (d, J=7.4 Hz, 1H), 7.73 (s, 1H), 7.63 (s, 1H), 7.46 (s, 2H), 4.78-4.61 (m, 1H), 4.10 (dd, J=9.7, 6.0 Hz, 1H), 3.97 (m, 2H), 2.38-2.26 (m, 1H), 2.18-2.04 (m, 1H), 2.03-1.91 (m, 1H), 1.84-1.72 (m, 1H), 1.71-1.47 (m, 6H), 1.35-1.06 (m, 5H), 0.99-0.82 (m, 2H). LCMS (FA): m/z=495.4 (M+H).

Example 164: [(1R,2S,4R)-4-{[5-({4-[1-(3-Chlorophenyl)vinyl]-5-methyl-2-thienyl}carbonyl)pyrimidin-4-yl]amino}-2-hydroxycyclopentyl]methyl sulfamate I-100

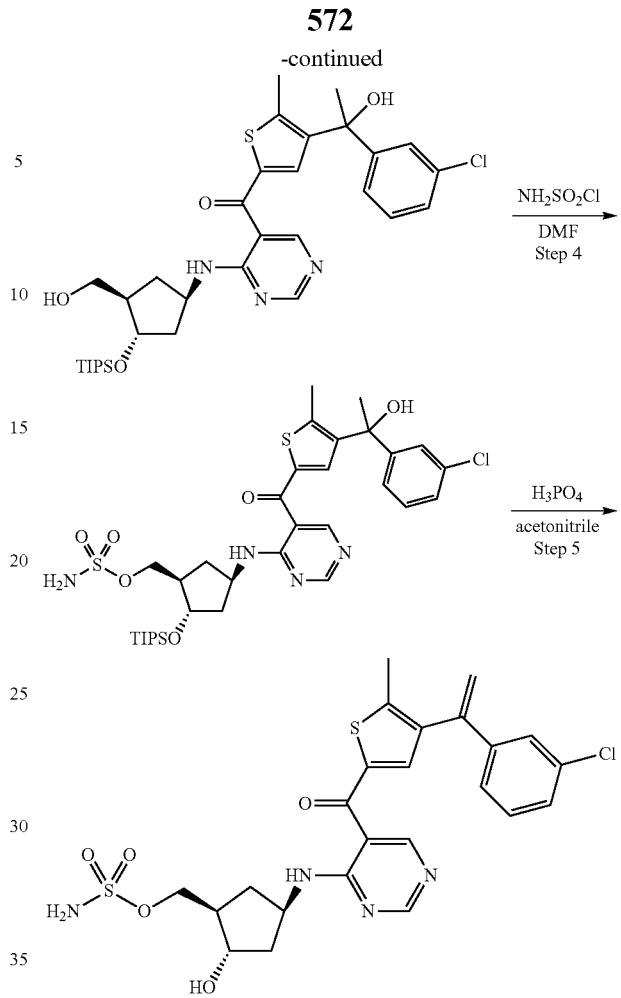

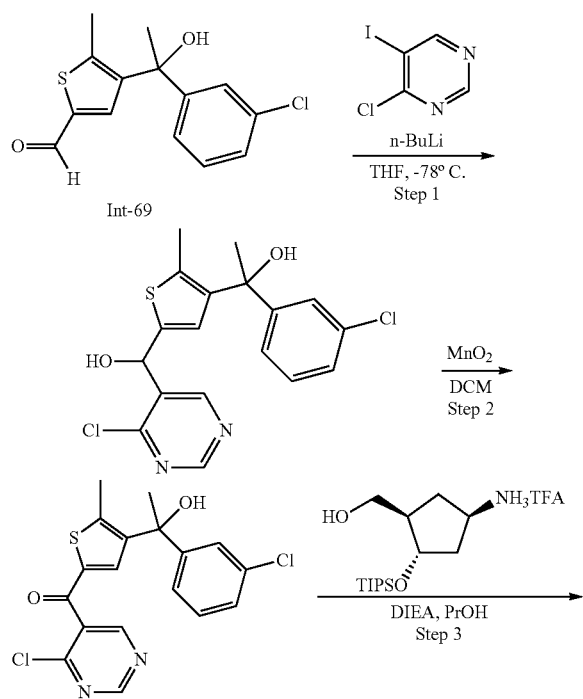

Step 1: (1S)-1-(3-Chlorophenyl)-1-{5-[(S)-(4-chloropyrimidin-5-yl)(hydroxy)methyl]-2-methyl-3-thienyl}ethanol, (1S)-1-(3-Chlorophenyl)-1-{5-[(R)-(4-chloropyrimidin-5-yl)(hydroxy)methyl]-2-methyl-3-thienyl}ethanol, (1R)-1-(3-Chlorophenyl)-1-{5-[(S)-(4-chloropyrimidin-5-yl)(hydroxy)methyl]-2-methyl-3-thienyl}ethanol, and (1R)-1-(3-Chlorophenyl)-1-{5-[(R)-(4-chloropyrimidin-5-yl)(hydroxy)methyl]-2-methyl-3-thienyl}ethanol The title compound was prepared in an analogous fashion to Example 131, step 7 using aldehyde Int-69. LCMS (FA): m/z=395.0 (M+H).

Step 2: rac-{4-[1-(3-Chlorophenyl)-1-hydroxyethyl]-5-methyl-2-thienyl}(4-chloropyrimidin-5-yl)methanone The title compound mixture was prepared in an analogous fashion to Example 131, step 8. $^1$H NMR (400 MHz, Chloroform-d) δ 9.12 (s, 1H), 8.79 (s, 1H), 7.52 (s, 1H), 7.41-7.37 (m, 1H), 7.28-7.23 (m, 2H), 7.19-7.16 (m, 1H), 2.24 (s, 3H), 1.88 (s, 3H). LCMS (FA): m/z=392.9 (M+H).

573

Step 3: {4-[(1S)-1-(3-Chlorophenyl)-1-hydroxy-ethyl]-5-methyl-2-thienyl}[4-({(1R,3R,4S)-3-(hydroxymethyl)-4-[(triisopropylsilyl)oxy]cyclopentyl}amino)pyrimidin-5-yl]methanone and {4-[(1R)-1-(3-Chlorophenyl)-1-hydroxyethyl]-5-methyl-2-thienyl}[4-({(1R,3R,4S)-3-(hydroxymethyl)-4-[(triisopropylsilyl)oxy]cyclopentyl}amino)pyrimidin-5-yl]methanone Int-262 (259 mg, 0.67 mmol) was weighed in a round bottom flask. To the reaction vessel was added TFA (3.74 mL, 48.6 mmol), and the mixture was stirred for 5 min. The mixture was diluted with toluene and concentrated in vacuo. The residue was azeotroped with toluene three times and the residue was then dissolved in i-PrOH (5.8 mL). To the solution was added a solution of {4-[1-(3-chlorophenyl)-1-hydroxyethyl]-5-methyl-2-thienyl}(4-chloropyrimidin-5-yl)methanone (175 mg, 0.45 mmol) in i-PrOH (3 mL) and the reaction was stirred at 70° C. for 2 h. The reaction was concentrated in vacuo. To the residue was added water and extracted with EtOAc (×4). The combined organic layers were dried over $Na_2SO_4$, filtered, and concentrated in vacuo. The residue was purified by ISCO column chromatography (0%-70% EtOAc in hexanes as eluent) to give 194 mg (68%) of the title compounds. LCMS (FA): m/z=644.6 (M+H).

Step 4: {(1R,2S,4R)-4-{[5-({4-[(1S)-1-(3-Chlorophenyl)-1-hydroxyethyl]-5-methyl-2-thienyl}carbonyl)pyrimidin-4-yl]amino}-2-[(triisopropylsilyl)oxy]cyclopentyl}methyl sulfamate and {(1R,2S,4R)-4-{[5-({4-[(1R)-1-(3-Chlorophenyl)-1-hydroxyethyl]-5-methyl-2-thienyl}carbonyl)pyrimidin-4-yl]amino}-2-[(triisopropylsilyl)oxy]cyclopentyl}methyl sulfamate To a solution of the products from step 1 (185 mg, 0.29 mmol) in DMF (1.32 mL) was added chlorosulfonamide (60 mg, 0.5 mmol) at rt, and the mixture was stirred for 1 hour. The reaction was quenched by addition of saturated $NaHCO_3$ and extracted with EtOAc (×2). The combined organic layers were dried over $Na_2SO_4$, filtered, and concentrated in vacuo to give 200 mg (99%) of the crude title compounds as a mixture. LCMS (FA): m/z=723.6 (M+H).

Step 5: [(1R,2S,4R)-4-{[5-({4-[1-(3-Chlorophenyl)vinyl]-5-methyl-2-thienyl}carbonyl)pyrimidin-4-yl]amino}-2-hydroxycyclopentyl]methyl sulfamate To a solution of products from step 2 (200 mg, 0.3 mmol) in $CH_3CN$ (2 mL) was added $H_3PO_4$ (2 mL, 30 mmol) and the reaction was stirred at rt for 1 hour. The reaction was quenched by addition of 1 M $Na_2CO_3$ and the mixture was extracted with EtOAc (×3). The combined organics were dried over $Na_2SO_4$, filtered, and concentrated in vacuo. The crude residue was purified by preparative HPLC to give 90 mg (60%) of the title compound as white amorphous solid. $^1$H NMR (400 MHz, MeOD) δ 8.70 (s, 1H), 8.53 (s, 1H), 7.37 (s, 1H), 7.35-7.27 (m, 3H), 7.22 (dd, J=5.9, 2.2 Hz, 1H), 5.82 (s, 1H), 5.38 (s, 1H), 4.81-4.69 (m, 1H), 4.25-4.13 (m, 3H), 2.52-2.45 (m, 1H), 2.34 (s, 3H), 2.30-2.21 (m, 1H), 2.19-2.09 (m, 1H), 1.94-1.85 (m, 1H), 1.45-1.37 (m, 1H). LCMS (FA): m/z=549.1 (M+H).

574

Example 165: [(1R,2S,4R)-4-{[5-({4-[(R)-(3-Chlorophenyl)(dimethylamino)methyl]-2-thienyl}carbonyl)pyrimidin-4-yl]amino}-2-hydroxycyclopentyl]methyl sulfamate and [(1R,2S,4R)-4-{[5-({4-[(S)-(3-chlorophenyl)(dimethylamino)methyl]-2-thienyl}carbonyl)pyrimidin-4-yl]amino}-2-hydroxycyclopentyl]methyl sulfamate I-153

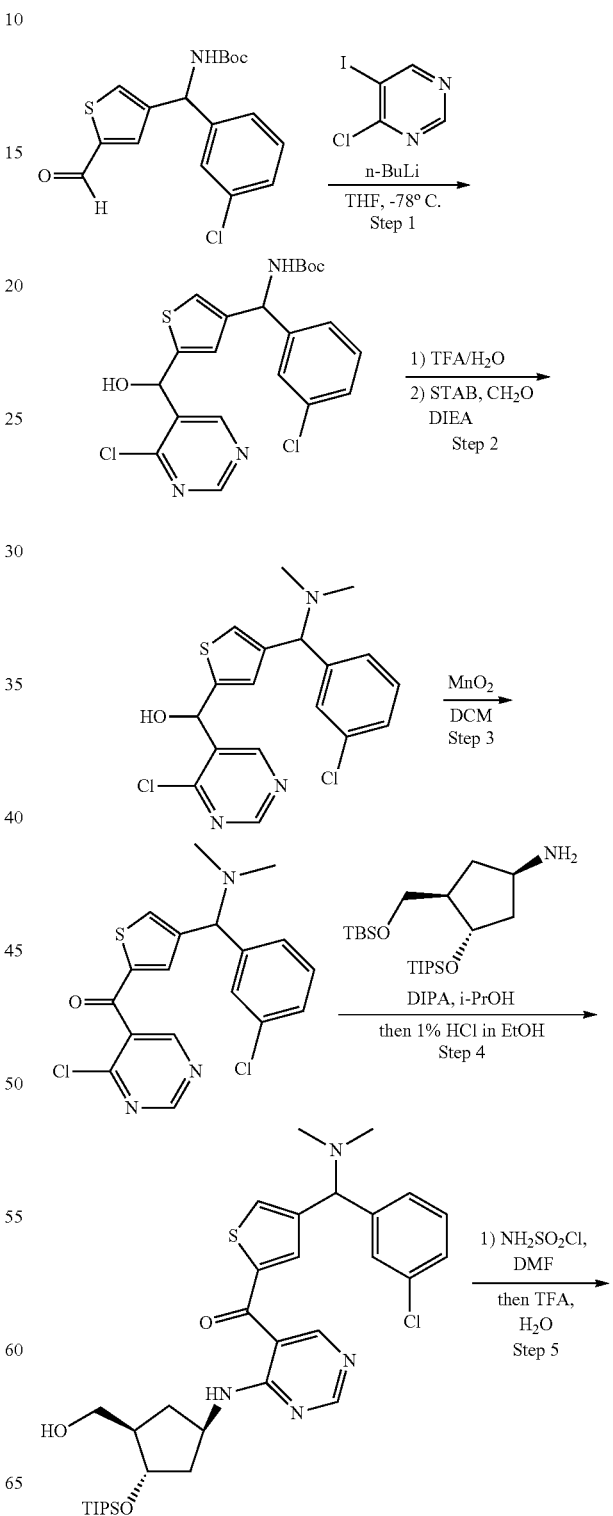

-continued

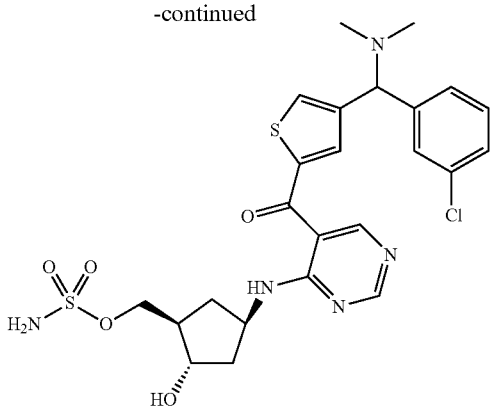

Step 1: tert-Butyl [(S)-(3-chlorophenyl){5-[(S)-(4-chloropyrimidin-5-yl)(hydroxy)methyl]-3-thienyl}methyl]carbamate, tert-Butyl [(S)-(3-chlorophenyl){5-[(R)-(4-chloropyrimidin-5-yl)(hydroxy)methyl]-3-thienyl}methyl]carbamate, tert-Butyl [(R)-(3-chlorophenyl){5-[(S)-(4-chloropyrimidin-5-yl)(hydroxy)methyl]-3-thienyl}methyl]carbamate, and tert-Butyl [(R)-(3-chlorophenyl){5-[(R)-(4-chloropyrimidin-5-yl)(hydroxy)methyl]-3-thienyl}methyl]carbamate A solution of 4-chloro-5-iodopyrimidine (293 mg, 1.22 mmol) in THF (10.0 mL) was cooled at −78° C. To the solution was added dropwise 2.50 M of n-BuLi in hexane (1.14 mL, 2.85 mmol) and the mixture was stirred for 10 min. To the mixture was added dropwise a solution of tert-butyl [(3-chlorophenyl)(5-formyl-3-thienyl)methyl]carbamate (143 mg, 0.41 mmol) in THF (3.0 mL) at −78° C., and the resulting mixture was stirred for 30 min at −78° C. The reaction was quenched by addition of a solution of acetic acid (0.23 mL, 4.06 mmol) in THF (1.0 mL) at −78° C. and the mixture was warmed to rt. To the mixture was added 30 ml water and extracted with EtOAc (30 mL×3). The combined organic layers were washed with brine, dried over Na$_2$SO$_4$, filtered, and concentrated in vacuo. The residue was purified by ISCO column chromatography (0%-60% EtOAc in hexanes as eluent) to give 136 mg (72%) of the title compounds. $^1$H NMR (400 MHz, Chloroform-d) δ 8.95 (d, J=4.9 Hz, 1H), 8.91 (s, 1H), 7.30-7.24 (m, 2H), 7.22 (s, 1H), 7.14-7.10 (m, 1H), 6.94 (s, 1H), 6.85 (s, 1H), 6.25 (s, 1H), 5.96-5.38 (m, 2H), 5.28-5.14 (br s, 1H), 1.41 (s, 9H).

Step 2: (S)-(4-Chloropyrimidin-5-yl){4-[(S)-(dimethylamino)(phenyl)methyl]-2-thienyl}methanol, (S)-(4-Chloropyrimidin-5-yl){4-[(R)-(dimethylamino)(phenyl)methyl]-2-thienyl}methanol, (R)-(4-Chloropyrimidin-5-yl){4-[(S)-(dimethylamino)(phenyl)methyl]-2-thienyl}methanol, and (R)-(4-Chloropyrimidin-5-yl){4-[(R)-(dimethylamino)(phenyl)methyl]-2-thienyl}methanol The product mixture prepared in step 1 (723 mg, 1.55 mmol) was dissolved in a solution of TFA (24.0 mL, 311 mmol) and water (6.00 mL, 333 mmol). The mixture was heated at 50° C. for 30 min. The reaction mixture was concentrated in vacuo and the residue was diluted with 30 mL MeOH, and 1 ml N,N-diisopropylethylamine was added to neutralize the solution. To the solution was added formaldehyde (1.73 mL, 23.3 mmol) followed by sodium triacetoxyborohydride (2.96 g, 14.0 mmol) at rt and the resulting mixture was stirred overnight. The reaction mixture was poured into 50 ml water, and then extracted with DCM (50 ml×2). The combined organic layers were concentrated in vacuo and the residue was purified by flash column (20%-100% EtOAc in hexanes as eluent) to give 163 mg (27%) of the title compound mixture. $^1$H NMR (400 MHz, Chloroform-d) δ 9.01 (s, 1H), 8.89 (s, 1H), 7.37 (d, J=1.8 Hz, 1H), 7.29-7.25 (m, 1H), 7.25-7.18 (m, 2H), 7.15 (d, J=1.3 Hz, 1H), 7.08 (s, 1H), 6.24 (s, 1H), 6.11-5.65 (br s, 1H), 4.19 (s, 1H), 2.14 (s, 6H).

Step 3: rac-{4-[(3-Chlorophenyl)(dimethylamino)methyl]-2-thienyl}(4-chloropyrimidin-5-yl)methanone To a solution of the products from step 2 (163 mg, 0.41 mmol) in DCM (18.0 mL) was added MnO$_2$ (539 mg, 6.20 mmol), and the reaction was stirred at rt overnight. To the mixture was added MnO$_2$ (180 mg, 2.07 mmol), and the reaction was stirred at 40° C. for 2 h. The reaction mixture was filtered through a Celite pad and the filter cake was washed with DCM. The filtrate was concentrated in vacuo to give 152 mg (94%) of the title compound as a white solid. $^1$H NMR (400 MHz, Chloroform-d) δ 9.13 (s, 1H), 8.75 (s, 1H), 7.68 (s, 1H), 7.45 (s, 1H), 7.32 (s, 1H), 7.28-7.17 (m, 3H), 4.25 (s, 1H), 2.16 (s, 6H).

Step 4: {4-[(S)-(3-Chlorophenyl)(dimethylamino)methyl]-2-thienyl}[4-({(1R,3R,4S)-3-(hydroxymethyl)-4-[(triisopropylsilyl)oxy]cyclopentyl}amino)pyrimidin-5-yl]methanone and {4-[(R)-(3-Chlorophenyl)(dimethylamino)methyl]-2-thienyl}[4-({(1R,3R,4S)-3-(hydroxymethyl)-4-[(triisopropylsilyl)oxy]cyclopentyl}amino)pyrimidin-5-yl]methanone To a solution of the product from step 3 (203.5 mg, 0.52 mmol), Int-260 (416.8 mg, 1.04 mmol) and N,N-diisopropylethylamine (0.36 mL, 2.08 mmol) in i-PrOH (20.0 mL). The reaction was stirred at 60° C. for 1 hour. The reaction was concentrated in vacuo, and then 1% HCl in EtOH solution (40 mL) was added to the residues. The reaction was stirred at rt for 30 min. The solution was poured into 1N NaOH solution (40 mL) and the mixture was extracted with DCM (×2). The combined organic layers were concentrated in vacuo and purified by ISCO column chromatography (0%-100% EtOAc in hexanes as eluent) to give 289 mg (87%) of the title compounds. $^1$H NMR (400 MHz, DMSO-d$_6$) δ 9.25 (s, 1H), 9.10 (s, 1H), 8.39 (d, J=1.4 Hz, 1H), 7.94 (d, J=1.4 Hz, 1H).

Step 5: [(1R,2S,4R)-4-{[5-({4-[(S)-(3-Chlorophenyl)(dimethylamino)methyl]-2-thienyl}carbonyl)pyrimidin-4-yl]amino}-2-hydroxycyclopentyl]methyl sulfamate and [(1R,2S,4R)-4-{[5-({4-[(R)-(3-Chlorophenyl)(dimethylamino)methyl]-2-thienyl}carbonyl)pyrimidin-4-yl]amino}-2-hydroxycyclopentyl]methyl sulfamate To a solution of the products from step 4 (275 mg, 0.43 mmol) in DMF (6.0 mL) was added chlorosulfonamide (147.9 mg, 1.28 mmol) at rt and the reaction was stirred for 30 min. The reaction was poured into the solution of saturated NaHCO$_3$ and the mixture was extracted with EtOAc (×3). The combined organic layers were concentrated in vacuo. The residues were dissolved into a solution of TFA (16.0 mL, 208 mmol) and water (4.0 mL). The mixture was stirred at 50° C. for 30 min. The reaction mixture was concentrated in vacuo and MeOH (5 mL) was added to the residue and the 1N NaOH solution was added to the mixture to basify it to pH 12. After concentration, the residue was purified by ISCO column chromatography (0%-15% MeOH in EtOAc as eluent) to give 168 mg (70%) of the title compounds. $^1$H NMR (400 MHz, MeOD) δ 8.61 (s, 1H), 8.52 (s, 1H), 7.76 (s, 1H), 7.64 (s, 1H), 7.41 (s, 1H), 7.33 (d, J=7.7 Hz, 1H), 7.26 (t, J=7.8 Hz, 1H), 7.18 (d, 1H), 4.78-4.66 (m, 1H), 4.17-4.06 (m, 3H), 2.48-2.33 (m, 1H), 2.24-2.18 (m, 1H), 2.16 (s, 6H), 2.12-2.02 (m, 1H), 1.81 (dd, J=8.4, 4.8 Hz, 1H), 1.38-1.27 (m, 1H). LCMS (FA): m/z=566.1 (M+H).

Example 166: [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(4,4,5,5-tetramethyl-1,3,2-dioxaborolan-2-yl)-2-thienyl]methanone. Int-280

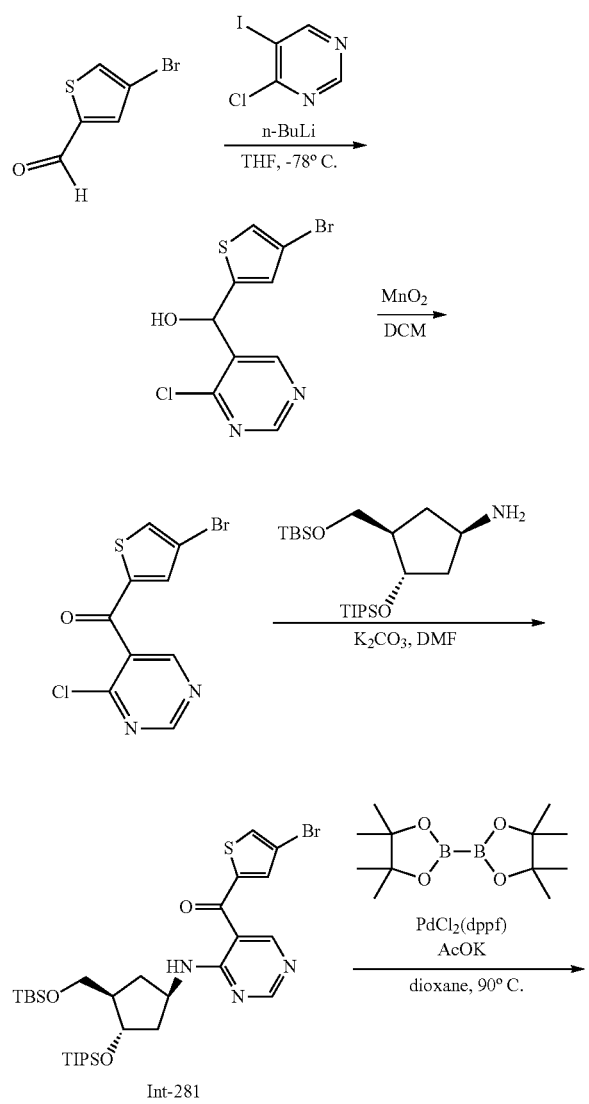

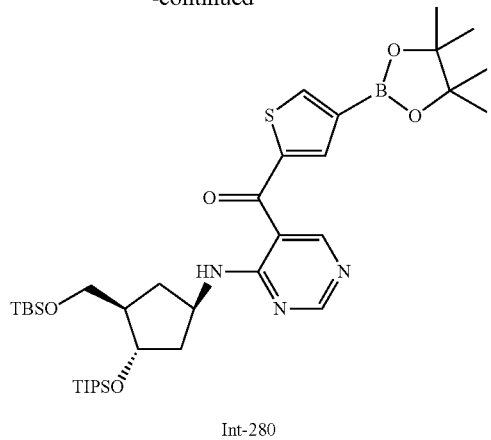

Int-280

Step 1: rac-(4-Bromo-2-thienyl)(4-chloropyrimidin-5-yl)methanol

The title compound was prepared in analogous fashion to Example 131, step 7. $^1$H NMR (400 MHz, Chloroform-d) δ 8.99 (s, 1H), 8.94 (s, 1H), 7.23 (d, J=1.2 Hz, 1H), 6.93 (s, 1H), 6.31 (s, 1H), 3.37-2.51 (br s, 1H).

Step 2: (4-Bromo-2-thienyl)(4-chloropyrimidin-5-yl)methanone

The title compound was prepared in analogous fashion to Example 131, step 8. $^1$H NMR (400 MHz, DMSO-$d_6$) δ 9.25 (s, 1H), 9.10 (s, 1H), 8.39 (d, J=1.4 Hz, 1H), 7.94 (d, J=1.4 Hz, 1H).

Step 3: (4-Bromo-2-thienyl)[4-({(1R,3R,4S)-3-({[tert-butyl(dimethyl)silyl]oxy}methyl)-4-[(triisopropylsilyl)oxy]cyclopentyl}amino)pyrimidin-5-yl]methanone Int-281

To a solution of Int-260 (4.66 g, 11.6 mmol) in DMF (50 mL) was added (4-bromo-2-thienyl)(4-chloropyrimidin-5-yl)methanone (3.20 g, 10.5 mmol). The reaction mixture was stirred at rt for 24 h and then quenched with water and extracted with EtOAc. The combined organic layers were washed with brine, dried over magnesium sulfate, filtered and concentrated in vacuo. The crude material was purified by ISCO column chromatography (0%-15% EtOAc in hexanes as eluent) to give 6.58 g (93%) of the title compound as a yellow oil. $^1$H NMR (400 MHz, DMSO-d6) δ 8.72 (s, 1H), 8.63 (s, 1H), 8.32 (d, J=7.6 Hz, 1H), 8.20 (d, J=1.4 Hz, 1H), 7.80 (d, J=1.4 Hz, 1H), 4.77-4.69 (m, 1H), 4.28-4.23 (m, 1H), 3.56-3.49 (m, 2H), 2.31-2.25 (m, 1H), 2.05-1.99 (m, 1H), 1.96-1.90 (m, 1H), 1.83-1.76 (m, 1H), 1.24-1.18 (m, 1H), 1.04-0.97 (m, 21H), 0.83 (s, 9H), 0.00 (s, 6H).

Step 4: [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(4,4,5,5-tetramethyl-1,3,2-dioxaborolan-2-yl)-2-thienyl]methanone (4-Bromo-2-thienyl)[4-({(1R,3R,4S)-3-({[tert-butyl(dimethyl)silyl]oxy}methyl)-4-[(triisopropylsilyl)oxy]cyclopentyl}amino)pyrimidin-5-yl]methanone (1.00 g, 1.50 mmol), bis(pinacolato)diboron (494 mg, 1.94 mmol), and potassium acetate (440 mg, 4.49 mmol) were weighed into a microwave vial and 1,4-dioxane (26.0 mL) was added to the vial. [1,1'-bis(diphenylphosphino)ferrocene]palladium (II)dichloride (61.5 mg, 0.07 mmol) was added to the mixture and the reaction vessel was purged with argon. The reaction was heated at 100° C. for 5 h. To the mixture was added [1,1'-Bis(diphenylphosphino)ferrocene]palladium(II) dichloride (110 mg), bis(pinacolato)diboron (650 mg), and potassium acetate (530 mg) and the resulting mixture was heated at 100° C. for 7 h. After cooling to rt, the mixture was diluted with 40 ml of water and extracted with EtOAc (×3). The combined organic layers were concentrated in vacuo and the residue was purified by ISCO column chromatography (30% EtOAc in DCM as eluent) to give 400 mg (37%) of the title compound. LCMS (FA): m/z=716.5 (M+H).

Example 167: {(1R,2S,4R)-2-Hydroxy-4-[(5-{[4-(2-phenylethyl)-2-thienyl]carbonyl}pyrimidin-4-yl)amino]cyclopentyl}methyl sulfamate I-108

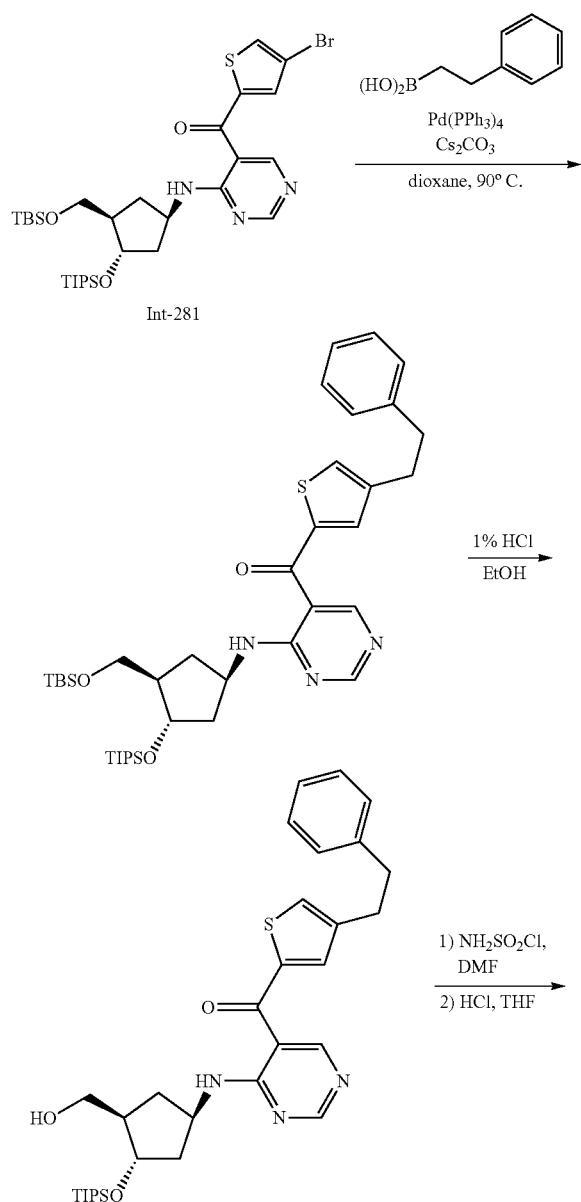

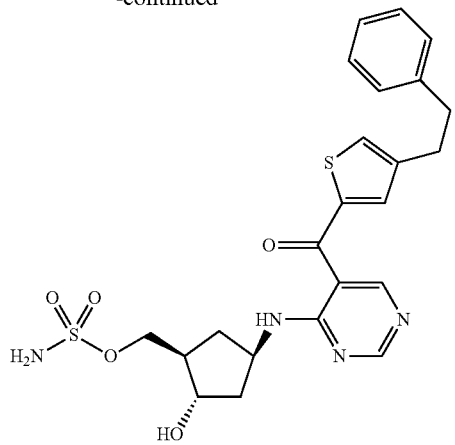

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(2-phenylethyl)-2-thienyl]methanone Phenethylboronic acid (118 mg, 0.79 mmol) and Int-281 (0.35 g, 0.52 mmol) were weighed into a microwave vial with stir bar. 1,4-Dioxane (12.0 mL), water (0.80 mL, 44 mmol), and $Cs_2CO_3$ (597 mg, 1.83 mmol) were added to the mixture and the reaction vessel was purged with argon. $Pd(PPh_3)_4$ (90.7 mg, 0.08 mmol) was added to the mixture and the reaction was heated at 140° C. in microwave for 30 min. The mixture was filtered through Celite pad and the filtrate was concentrated in vacuo. The residue was purified by ISCO column chromatography (15% EtOAc in hexanes as eluent) to give 60 mg (16%) of the title compound. LCMS (FA): m/z=695.4 (M+H).

Step 2: [4-({(1R,3R,4S)-3-(Hydroxymethyl)-4-[(triisopropylsilyl)oxy]cyclopentyl}amino)pyrimidin-5-yl][4-(2-phenylethyl)-2-thienyl]methanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl][4-(2-phenylethyl)-2-thienyl]methanone (60.0 mg, 0.09 mmol) in EtOH (2.0 mL) was added 1% HCl in EtOH solution (12.0 mL, 1.45 mmol) and the reaction was put in a refrigerator for 14 h. The reaction was quenched by addition of saturated $NaHCO_3$ and extracted with EtOAc (×3). The combined organic layers were washed with brine, dried over $Na_2SO_4$, filtered, and concentrated in vacuo to give 50 mg (100%) of the crude title compound. LCMS (FA): m/z=581.3 (M+H)

Step 3: {(1R,2S,4R)-2-Hydroxy-4-[(5-{[4-(2-phenylethyl)-2-thienyl]carbonyl}pyrimidin-4-yl)amino]cyclopentyl}methyl sulfamate To a solution of [4-({(1R,3R,4S)-3-(hydroxymethyl)-4-[(triisopropylsilyl)oxy]cyclopentyl}amino)pyrimidin-5-yl][4-(2-phenylethyl)-2-thienyl]methanone (50 mg, 0.09 mmol) in DMF (1.0 mL) was added triethylamine (14.4 uL, 0.10 mmol) and chlorosulfonamide (19.9 mg, 0.17 mmol) at rt, and the mixture was stirred for 15 min. To the mixture was added 6 M HCl (5 mL) and the resulting mixture was stirred at rt overnight. The reaction was quenched by addition of water extracted with EtOAc (×3). The combined organics were washed with brine, dried over MgSO₄, and concentrated in vacuo. The residue was purified by preparative HPLC to give 23 mg (53%) of the title compound. ¹H NMR (400 MHz, MeOD) δ 8.72_8.42 (m, 2H), 7.59 (dd, J=42.0, 1.2 Hz, 1H), 7.44 (dd, J=18.2, 1.3 Hz, 1H), 7.35-7.24 (m, 3H), 7.23-7.14 (m, 2H), 4.85-4.73 (m, 1H), 4.29-4.10 (m, 3H), 3.37-3.27 (m, 2H), 3.06-2.88 (m, 2H), 2.58-2.44 (m, 1H), 2.35-2.23 (m, 1H), 2.21-2.10 (m, 1H), 1.96-1.83 (m, 1H), 1.49-1.34 (m, 1H). LCMS (FA): m/z=503.2 (M+H).

The compounds listed in the table below were prepared in an analogous fashion to that described above starting from the appropriate starting materials.

| Step 1 reagent | Compound No. |
|---|---|
| 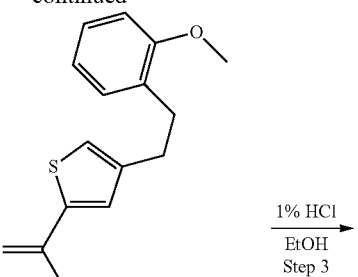 | I-146 |
| | I-178 |

Example 168: [(1R,2S,4R)-2-Hydroxy-4-{[5-({4-[2-(2-methoxyphenyl)ethyl]-2-thienyl}carbonyl)pyrimidin-4-yl]amino}cyclopentyl]methyl sulfamate I-183

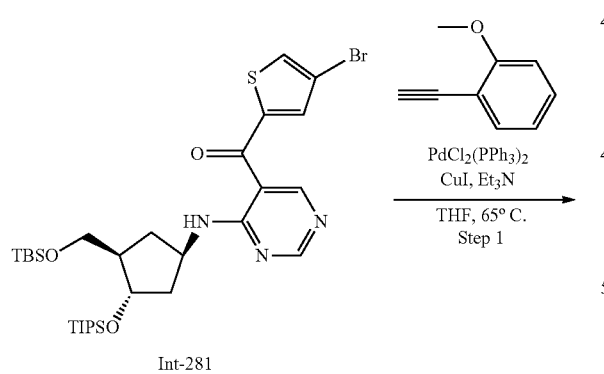

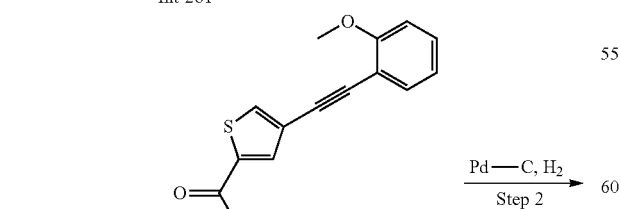

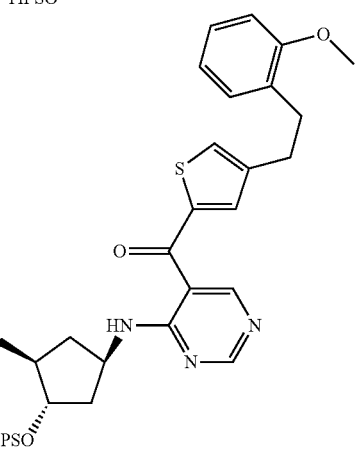

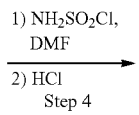

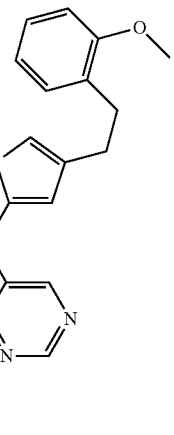

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[(2-methoxyphenyl)ethynyl]-2-thienyl}methanone To a round bottom flask was added Int-281 (0.93 g, 1.4 mmol), 1-ethynyl-2-methoxy-benzene (202 mg, 1.53 mmol), CuI (26.5 mg, 0.139 mmol), Pd(PPh₃)₂Cl₂ (97.6 mg, 0.14 mmol), triethylamine (5.00 mL, 35.9 mmol), and THF (5 mL). The reaction was stirred at 65° C. overnight. The mixture was filtered through Celite pad and the filtrate was concentrated in vacuo. The residue was purified by ISCO column chromatography (20% EtOAc in hexanes as eluent) to give 0.20 g (20%) of the title compound. LCMS (FA): m/z=721.3 (M+H).

Step 2: [4-({(1R,3R,4S)-3-({[tert-Butyl(dimethyl)silyl]oxy}methyl)-4-[(triisopropylsilyl)oxy]cyclopentyl}amino)pyrimidin-5-yl]{4-[2-(2-methoxyphenyl)ethyl]-2-thienyl}methanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl]{4-[(2-methoxyphenyl)ethynyl]-2-thienyl}methanone (0.20 g, 0.28 mmol;) in EtOAc (20 mL) was added 10% Palladium on carbon (100 mg). The mixture was stirred under atmosphere of hydrogen at rt overnight. The mixture was filtered through Celite pad and the filtrate was concentrated in vacuo to give 0.18 g (90%) of the crude title compound. LCMS (FA): m/z=725.3 (M+H).

Step 3: [4-({(1R,3R,4S)-3-(Hydroxymethyl)-4-[(triisopropylsilyl)oxy]cyclopentyl}amino)pyrimidin-5-yl]{4-[2-(2-methoxyphenyl)ethyl]-2-thienyl}methanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl]{4-[2-(2-methoxyphenyl)ethyl]-2-thienyl}methanone (0.18 g, 0.25 mmol) in EtOH (5.8 mL) was added 1% HCl in EtOH solution (29.6 mL, 3.57 mmol) and the reaction was allowed to stand in a refrigerator for 14 h. The reaction was quenched by addition of saturated NaHCO₃ and extracted with EtOAc (×3). The combined organic layers were washed with brine, dried over Na₂SO₄, filtered, and concentrated in vacuo to give 0.15 g (99%) of the crude title compound. LCMS (FA): m/z=611.2 (M+H).

Step 4: [(1R,2S,4R)-2-Hydroxy-4-{[5-({4-[2-(2-methoxyphenyl)ethyl]-2-thienyl}carbonyl)pyrimidin-4-yl]amino}cyclopentyl]methyl sulfamate To a solution of [4-({(1R,3R,4S)-3-(hydroxymethyl)-4-[(triisopropylsilyl)oxy]cyclopentyl}amino)pyrimidin-5-yl]{4-[2-(2-methoxyphenyl)ethyl]-2-thienyl}methanone (0.15 g, 0.24 mmol) in DMF (3.0 mL) was added triethylamine (41.1 uL, 0.30 mmol) and chlorosulfonamide (56.8 mg, 0.49 mmol) at rt, and the mixture was stirred for 15 min. To the mixture was added 6 M HCl (5 mL) and the reaction was stirred at rt overnight. The reaction was quenched by addition of water and extracted with EtOAc (×3). The combined organic layers were washed with brine, dried over MgSO₄, and concentrated in vacuo. The residue was purified by preparative HPLC to give 64 mg (49%) of the title compound. ¹H NMR (400 MHz, MeOD) δ 8.59 (s, 2H), 7.50 (d, J=1.2 Hz, 1H), 7.37 (d, J=1.3 Hz, 1H), 7.19 (td, J=8.2, 1.7 Hz, 1H), 7.03 (dd, J=7.4, 1.6 Hz, 1H), 6.93 (d, J=8.2 Hz, 1H), 6.83 (td, J=7.4, 1.0 Hz, 1H), 4.86-4.73 (m, 1H), 4.30-4.13 (m, 3H), 3.82 (s, 3H), 2.94 (s, 4H), 2.60-2.45 (m, 1H), 2.38-2.23 (m, 1H), 2.22-2.11 (m, 1H), 1.98-1.81 (m, 1H), 1.52-1.34 (m, 1H). LCMS (FA): m/z=533.2 (M+H).

Example 169: [(1R,2S,4R)-2-Hydroxy-4-({5-[(4-{[5-(trifluoromethyl)-2-furyl]methyl}-2-thienyl)carbonyl]pyrimidin-4-yl}amino)cyclopentyl]methyl sulfamate I-119

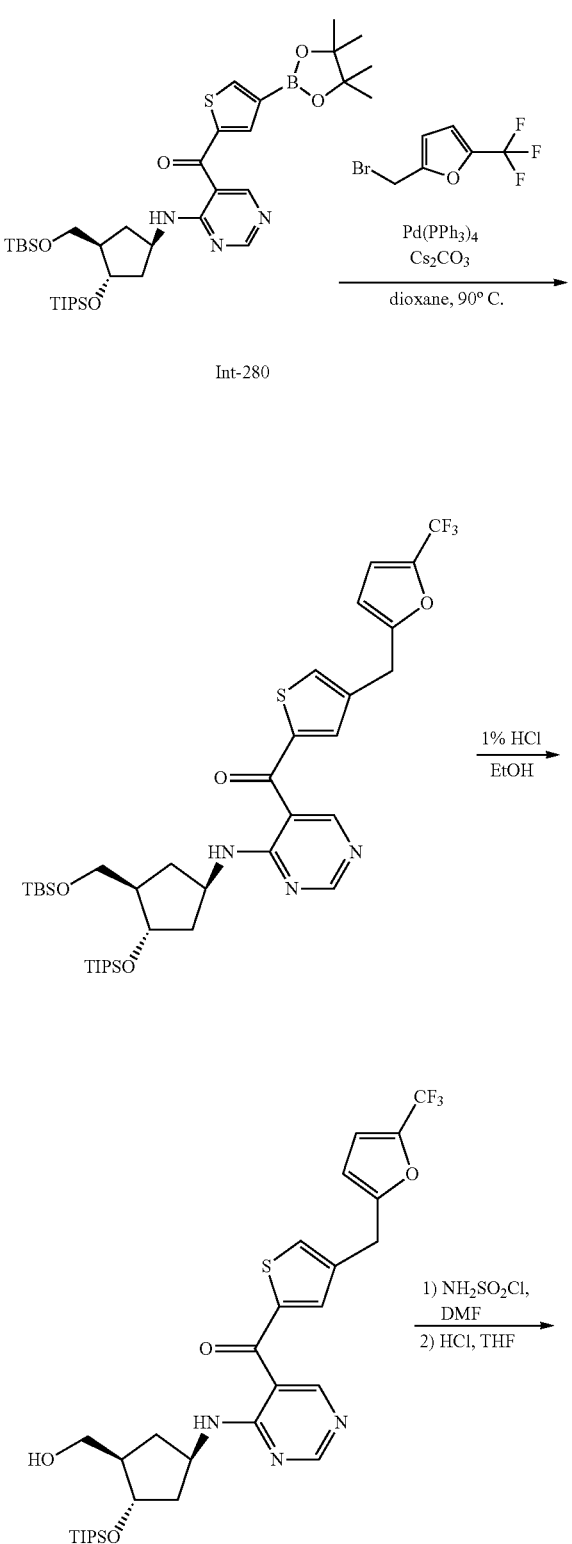

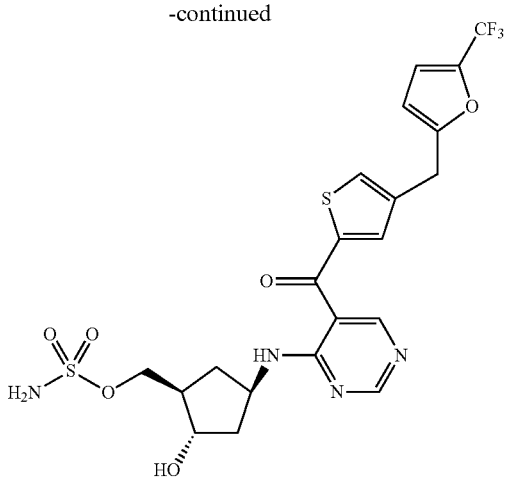

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl](4-{[5-(trifluoromethyl)-2-furyl]methyl}-2-thienyl)methanone 2-(Bromomethyl)-5-(trifluoromethyl)furan (54.1 mg, 0.24 mmol) and Int-280 (141 mg, 0.20 mmol) were weighed into a microwave vial with stir bar. 1,4-Dioxane (4.5 mL), water (0.30 mL, 17 mmol) and $Cs_2CO_3$ (224 mg, 0.69 mmol) were added and the reaction vessel was purged with argon. To the mixture was added $Pd(PPh_3)_4$ (34.1 mg, 0.03 mmol) and the reaction mixture was then heated at 125° C. in microwave for 30 min. The mixture was filtered through Celite pad and the filtrate was concentrated in vacuo. The residue was purified by ISCO column chromatography (30% EtOAc in hexanes as eluent) to give 80 mg (55%) of the title compound. LCMS (FA): m/z=739.4 (M+H).

Step 2: [4-({(1R,3R,4S)-3-(Hydroxymethyl)-4-[(triisopropylsilyl)oxy]cyclopentyl}amino)pyrimidin-5-yl](4-{[5-(trifluoromethyl)-2-furyl]methyl}-2-thienyl)methanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl](4-{[5-(trifluoromethyl)-2-furyl]methyl}-2-thienyl)methanone (80 mg, 0.11 mmol) in EtOH (2.0 mL) was added 1% HCl in EtOH solution (15.0 mL, 1.81 mmol), and the reaction was put in a refrigerator for 14 h. The reaction was quenched by addition of saturated $NaHCO_3$ and extracted with EtOAc (×3). The combined organic layers were washed with brine, dried over $Na_2SO_4$, filtered, and concentrated in vacuo to give 64 mg (95%) of the crude title compound. LCMS (FA): m/z=624.3 (M+H).

Step 3: [(1R,2S,4R)-2-Hydroxy-4-({5-[(4-{[5-(trifluoromethyl)-2-furyl]methyl}-2-thienyl)carbonyl]pyrimidin-4-yl}amino)cyclopentyl]methyl sulfamate To a solution of [4-({(1R,3R,4S)-3-(hydroxymethyl)-4-[(triisopropylsilyl)oxy]cyclopentyl}amino)pyrimidin-5-yl](4-{[5-(trifluoromethyl)-2-furyl]methyl}-2-thienyl)methanone (64 mg, 0.10 mmol) in DMF (1.24 mL) was added triethylamine (17.2 uL, 0.12 mmol) and chlorosulfonamide (23.7 mg, 0.21 mmol) at rt, and the mixture was stirred for 15 min. To the mixture was added 6 M HCl (5 mL) and the resulting mixture was stirred at rt overnight. The reaction was quenched by addition of water and extracted with EtOAc (×3). The combined organics were washed with brine, dried over $MgSO_4$, and concentrated in vacuo. The residue was purified via preparative HPLC to give 16 mg (28%) of the title compound. $^1$H NMR (400 MHz, MeOD) δ 8.75 (s, 1H), 8.60 (s, 1H), 7.79-7.70 (m, 1H), 7.63 (d, J=1.4 Hz, 1H), 6.89 (dd, J=3.4, 1.3 Hz, 1H), 6.31 (dd, J=3.4, 0.7 Hz, 1H), 4.88-4.74 (m, 1H), 4.26-4.16 (m, 3H), 4.14 (s, 2H), 2.62-2.43 (m, 1H), 2.35-2.24 (m, 1H), 2.23-2.11 (m, 1H), 1.95-1.88 (m, 1H), 1.53-1.38 (m, 1H). LCMS (FA): m/z=547.1 (M+H).

Example 170: [(1R,2R,3S,4R)-4-{[5-({4-[(1S)-1-Amino-1-(3-chlorophenyl)ethyl]-2-thienyl}carbonyl)pyrimidin-4-yl]amino}-2,3-dihydroxycyclopentyl]methyl sulfamate and [(1R,2R,3S,4R)-4-{[5-({4-[(1R)-1-Amino-1-(3-chlorophenyl)ethyl]-2-thienyl}carbonyl)pyrimidin-4-yl]amino}-2,3-dihydroxycyclopentyl]methyl sulfamate I-8

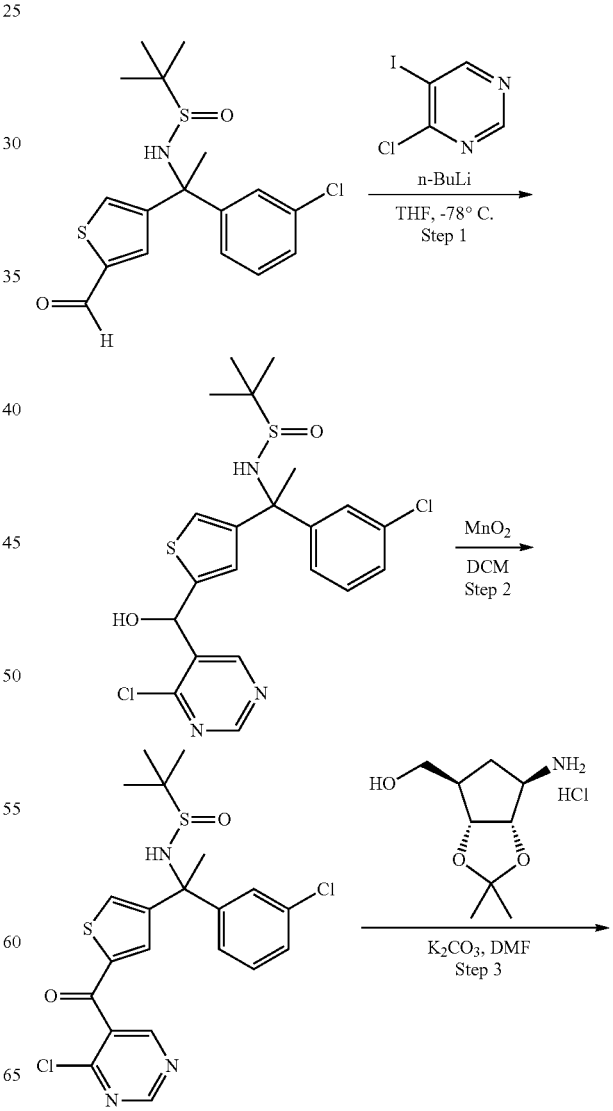

-continued

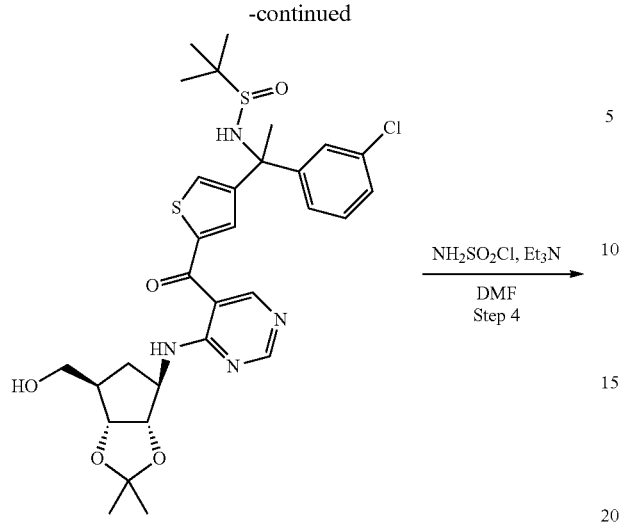

NH₂SO₂Cl, Et₃N
DMF
Step 4

[ 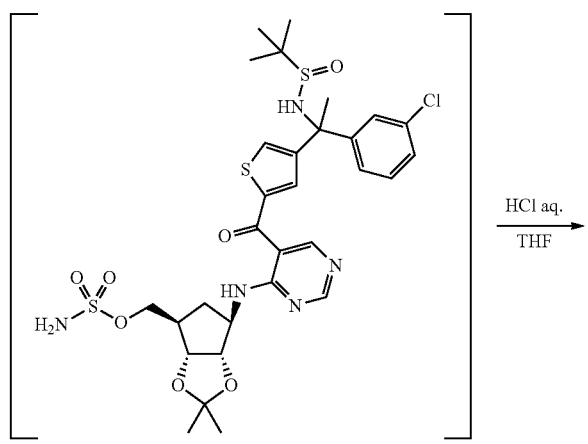 ]

HCl aq.
THF

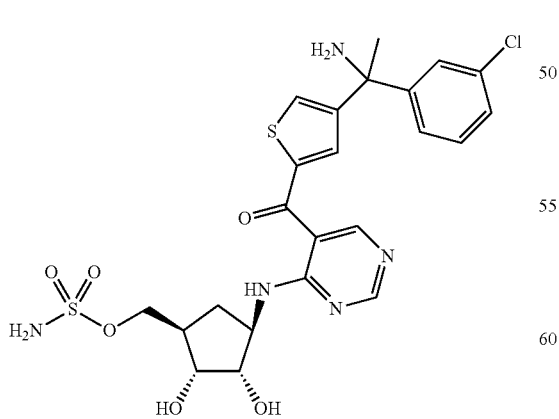

Step 1: N-[(1S)-1-(3-Chlorophenyl)-1-{5-[(S)-(4-chloropyrimidin-5-yl)(hydroxy)methyl]-3-thienyl}ethyl]-2-methylpropane-2-sulfinamide, N-[(1S)-1-(3-Chlorophenyl)-1-{5-[(R)-(4-chloropyrimidin-5-yl)(hydroxy)methyl]-3-thienyl}ethyl]-2-methylpropane-2-sulfinamide, N-[(1R)-1-(3-Chlorophenyl)-1-{5-[(S)-(4-chloropyrimidin-5-yl)(hydroxy)methyl]-3-thienyl}ethyl]-2-methylpropane-2-sulfinamide, and N-[(1R)-1-(3-Chlorophenyl)-1-{5-[(R)-(4-chloropyrimidin-5-yl)(hydroxy)methyl]-3-thienyl}ethyl]-2-methylpropane-2-sulfinamide The title compound was prepared in analogous fashion to Example 131, step 7. LCMS (FA): m/z=482.5 (M−H)

Step 2: rac-N-[1-(3-Chlorophenyl)-1-{5-[(4-chloropyrimidin-5-yl)carbonyl]-3-thienyl}ethyl]-2-methylpropane-2-sulfinamide The title compound was prepared in analogous fashion to Example 131, step 8. LCMS (FA): m/z=482.3 (M+H)

Step 3: N-[(1S)-1-(3-Chlorophenyl)-1-{5-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-3-thienyl}ethyl]-2-methylpropane-2-sulfinamide and N-[(1R)-1-(3-Chlorophenyl)-1-{5-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-3-thienyl}ethyl]-2-methylpropane-2-sulfinamide To a solution of the products from step 2 (0.30 g, 0.62 mmol) and [(3aR,4R,6R,6aS)-6-amino-2,2-dimethyltetrahydro-3aH-cyclopenta[d][1,3]dioxol-4-yl]methanol hydrochloride (167 mg, 0.75 mmol) (for synthesis of this starting material see: Claiborne, C. F. et al. PCT Application Publication WO2008/019124) in DMF (9.4 mL) was added potassium carbonate (258 mg, 1.87 mmol) and the mixture was stirred at rt for 20 h. The reaction was quenched by addition of water. A solid precipitated and was collected by filtration and washed with water. The residual solid was dried under high vacuum and 315 mg of the title compounds was obtained. LCMS (FA): m/z=633.7 (M+H)

Step 4: [(1R,2R,3S,4R)-4-{[5-({4-[(1S)-1-Amino-1-(3-chlorophenyl)ethyl]-2-thienyl}carbonyl)pyrimidin-4-yl]amino}-2,3-dihydroxycyclopentyl]methyl sulfamate and [(1R,2R,3S,4R)-4-{[5-({4-[(1R)-1-Amino-1-(3-chlorophenyl)ethyl]-2-thienyl}carbonyl)pyrimidin-4-yl]amino}-2,3-dihydroxycyclopentyl]methyl sulfamate A solution of the product mixture from step 3 (0.30 g, 0.47 mmol) in DMF (4.0 mL) and THF (4.0 mL) was cooled to −78° C., to which was added triethylamine (1.65 mL, 11.9 mmol) followed by chlorosulfonamide (1.26 g, 10.9 mmol) and the reaction was stirred at −78° C. for 80 min. The reaction was quenched by addition of EtOH (15 mL) and the mixture was allowed to warm to rt. To the mixture was added 3.0 M of HCl in water (7.85 mL, 23.6 mmol) was added and the reaction was stirred at rt for 5 h. The reaction was quenched via addition of 3M NaOH until pH 10. The resulting mixture was extracted with EtOAc (3×). The combined organic layers were dried over MgSO₄, filtered, and concentrated in vacuo. The crude product was purified on ISCO chromatography eluting with a DCM/MeOH gradient to afford the title compounds as a white solid (yield=220 mg). $^1$H NMR (400 MHz, Chloroform-d) δ 8.67 (d, J=2.3 Hz, 1H), 8.63 (s, 1H), 8.39 (d, J=7.1 Hz, 1H), 7.97 (s, 1H), 7.77 (d, J=1.2 Hz, 1H), 7.56 (s, 1H), 7.44 (s, 2H), 7.41-7.30 (m, 3H), 4.86 (d, J=5.2 Hz, 1H), 4.72 (t, J=4.3 Hz, 1H), 4.51-4.39 (m, 1H), 4.13-4.02 (m, 2H), 4.00-3.93 (m, 1H), 3.78 (q, J=5.8 Hz, 1H), 3.73-3.67 (m, 1H), 3.09-2.98 (m, 2H), 2.31-2.23 (m, 1H), 2.23-2.13 (m, 1H), 1.17-1.11 (m, 1H). LCMS (FA): m/z=568.2 (M+H).

The compounds listed in the table below were prepared in an analogous fashion to that described above starting from the appropriate starting materials.

| Starting material | Compound No. |
| --- | --- |
| Int-158 | I-27b |
| Int-160 | I-27a |
| Int-92 | I-202 |

Example 171: {(1R,2S,4R)-4-[(5-{[4-(3-Bromobenzyl)-2-thienyl]carbonyl}pyrimidin-4-yl)amino]-2-hydroxycyclopentyl}methyl sulfamate I-59

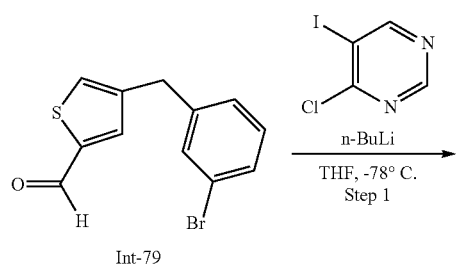

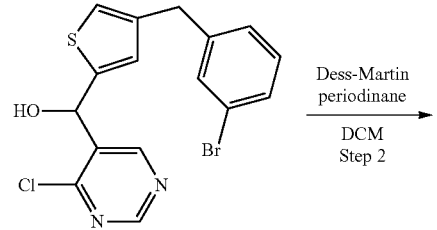

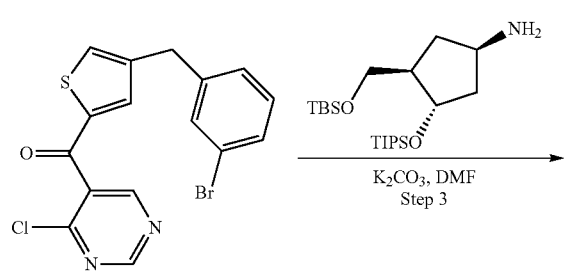

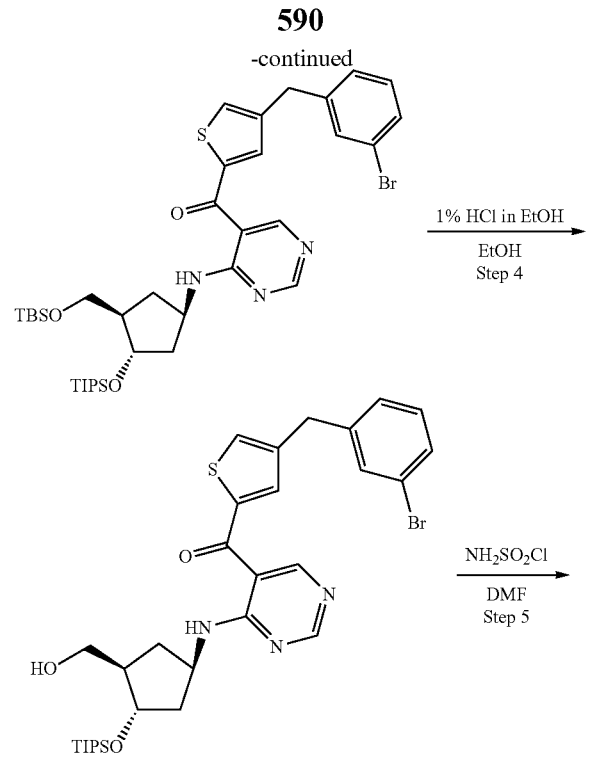

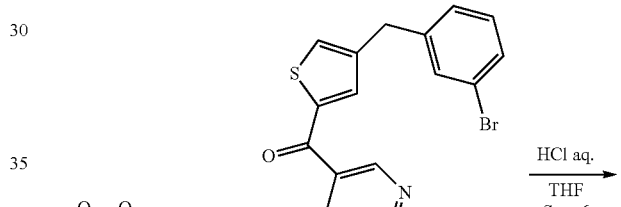

Int-282

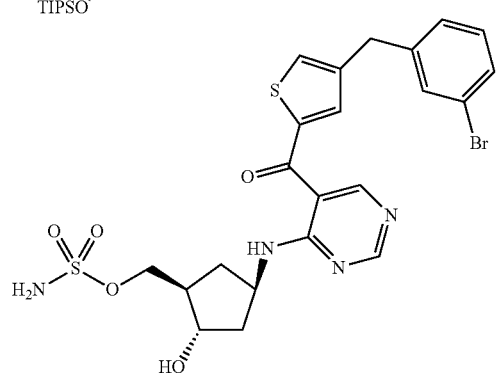

Step 1: rac-[4-(3-Bromobenzyl)-2-thienyl](4-chloropyrimidin-5-yl)methanol

The title compounds were prepared in an analogous fashion to Example 134, step 1 beginning with Int-79. LCMS (FA): m/z=396.9 (M+1).

Step 2: [4-(3-Bromobenzyl)-2-thienyl](4-chloropyrimidin-5-yl)methanone

The title compounds were prepared in an analogous fashion to Example 134, step 2. LCMS (FA): m/z=394.9 (M+1).

Step 3: [4-(3-Bromobenzyl)-2-thienyl][4-({(1R,3R,4S)-3-({[tert-butyl(dimethyl)silyl]oxy}methyl)-4-[(triisopropylsilyl)oxy]cyclopentyl}amino)pyrimidin-5-yl]methanone To a solution of [4-(3-bromobenzyl)-2-thienyl](4-chloropyrimidin-5-yl)methanone (245 mg, 0.62 mmol) in DMF (10 mL) was added Int-260 (375 mg, 0.93 mmol) followed by K$_2$CO$_3$ (215 mg, 1.56 mmol), and the reaction was stirred for 13 h at rt. The reaction was concentrated in vacuo. To the residue was added water (50 mL) and the mixture was extracted with EtOAc (50 mL×3). The combined organic layers were dried over Na$_2$SO$_4$, filtered, and concentrated in vacuo. The residue was purified by ISCO column chromatography (15% EtOAc in hexanes as eluent) to give 445 mg (94%) of the title compound as a light yellow oil. $^1$H NMR (400 MHz, Chloroform-d) δ 8.78 (s, 1H), 8.69-8.56 (m, 2H), 7.42-7.30 (m, 4H), 7.18 (t, J=7.7 Hz, 1H), 7.12 (d, J=7.7 Hz, 1H), 4.86-4.72 (m, 1H), 4.33-4.25 (m, 1H), 3.96 (s, 2H), 3.61 (dd, J=10.1, 5.4 Hz, 1H), 3.55 (dd, J=10.0, 5.8 Hz, 1H), 2.49-2.36 (m, 1H), 2.24-2.08 (m, 2H), 1.77-1.66 (m, 1H), 1.34-1.17 (m, 1H), 1.06 (s, 21H), 0.88 (s, 9H), 0.03 (s, 6H).

Step 4: [4-(3-Bromobenzyl)-2-thienyl][4-({(1R,3R,4S)-3-(hydroxymethyl)-4-[(triisopropylsilyl)oxy]cyclopentyl}amino)pyrimidin-5-yl]methanone Int-282

To a solution of [4-(3-bromobenzyl)-2-thienyl][4-({(1R,3R,4S)-3-({[tert-butyl(dimethyl)silyl]oxy}methyl)-4-[(triisopropylsilyl)oxy]cyclopentyl}amino)pyrimidin-5-yl]methanone (150 mg, 0.20 mmol) in EtOH (8.0 mL) was added 1% HCl in EtOH solution (2.0 mL, 0.24 mmol), and the mixture was stirred for 8 h at rt. The reaction was quenched by addition of saturated NaHCO$_3$ (50 mL) and extracted with EtOAc (60 mL×3). The combined organic layers were washed with brine, dried over Na$_2$SO$_4$, filtered, and concentrated in vacuo. The residue was purified by ISCO column chromatography (20%-40% EtOAc in DCM as eluent) to give 113 mg (89%) of the title compound as a light yellow oil. $^1$H NMR (400 MHz, Chloroform-d) δ 8.78 (s, 1H), 8.69 (d, J=7.3 Hz, 1H), 8.64 (s, 1H), 7.43-7.29 (m, 4H), 7.18 (t, J=7.7 Hz, 1H), 7.12 (d, J=7.6 Hz, 1H), 4.86-4.74 (m, 1H), 4.31 (q, J=4.5 Hz, 1H), 3.96 (s, 2H), 3.74-3.63 (m, 2H), 2.49 (dt, J=13.3, 8.2 Hz, 1H), 2.25-2.12 (m, 2H), 1.84 (dt, J=13.4, 6.7 Hz, 1H), 1.74 (t, J=4.8 Hz, 1H), 1.36-1.23 (m, 2H), 1.06 (s, 21H). LCMS (FA): m/z=646.1 (M+H).

Step 5: {(1R,2S,4R)-4-[(5-{[4-(3-Bromobenzyl)-2-thienyl]carbonyl}pyrimidin-4-yl)amino]-2-[(triisopropylsilyl)oxy]cyclopentyl}methyl sulfamate To a solution of [4-(3-bromobenzyl)-2-thienyl][4-({(1R,3R,4S)-3-(hydroxymethyl)-4-[(triisopropylsilyl)oxy]cyclopentyl}amino)pyrimidin-5-yl]methanone (110 mg, 0.17 mmol) in DMF (2.0 mL) was added chlorosulfonamide (39.4 mg, 0.34 mmol) at rt, and the mixture was stirred for 15 min. The reaction was cooled to at 0° C. and quenched by addition of saturated NaHCO$_3$ (50 mL). The mixture was extracted with EtOAc (50 mL×3). The combined organic layers were dried over Na$_2$SO$_4$, filtered, and concentrated in vacuo. The residue was purified by ISCO column chromatography (1%-5% MeOH in DCM as eluent) to give 101 mg (78%) of the title compound as a light yellow sticky oil. $^1$H NMR (400 MHz, Chloroform-d) δ 8.79 (s, 1H), 8.72-8.59 (m, 2H), 7.45-7.30 (m, 4H), 7.19 (t, J=7.7 Hz, 1H), 7.12 (d, J=7.5 Hz, 1H), 5.15 (s, 2H), 4.88-4.75 (m, 1H), 4.34 (q, J=5.2 Hz, 1H), 4.27 (d, J=4.7 Hz, 2H), 3.96 (s, 2H), 2.67-2.53 (m, 1H), 2.43-2.30 (m, 1H), 2.22-2.11 (m, 1H), 1.90 (dt, J=13.1, 6.4 Hz, 1H), 1.46 (dt, J=13.2, 6.6 Hz, 1H), 1.05 (s, 21H). LCMS (FA): m/z=725.1 (M+H)

Step 6 {(1R,2S,4R)-4-[(5-{[4-(3-Bromobenzyl)-2-thienyl]carbonyl}pyrimidin-4-yl)amino]-2-hydroxycyclopentyl}methyl sulfamate To a solution of {(1R,2S,4R)-4-[(5-{[4-(3-bromobenzyl)-2-thienyl]carbonyl}pyrimidin-4-yl)amino]-2-[(triisopropylsilyl)oxy]cyclopentyl}methyl sulfamate (95.0 mg, 0.13 mmol) in THF (2.0 mL) was added 4.0 M of HCl (2.00 mL, 8.00 mmol) at rt, and the mixture was stirred for 4 hour. The reaction was quenched by addition of saturated NaHCO$_3$ (60 mL) and extracted with EtOAc (60 mL×3). The combined organic layers were washed with brine, dried over Na$_2$SO$_4$, filtered, and concentrated in vacuo. The residue was purified by ISCO column chromatography (5% MeOH in DCM as eluent) to give 66 mg (87%) of the title compound as an off-white solid. $^1$H NMR (400 MHz, DMSO-d$_6$) δ 8.68 (s, 1H), 8.64 (s, 1H), 8.26 (d, J=7.4 Hz, 1H), 7.82 (s, 1H), 7.70 (s, 1H), 7.51 (s, 1H), 7.48-7.35 (m, 3H), 7.35-7.20 (m, 2H), 4.88 (d, J=4.5 Hz, 1H), 4.77-4.62 (m, 1H), 4.09 (dd, J=9.6, 6.1 Hz, 1H), 4.04-3.87 (m, 4H), 2.31 (dt, J=13.6, 7.5 Hz, 1H), 2.17-2.05 (m, 1H), 2.01-1.90 (m, 1H), 1.82-1.70 (m, 1H), 1.33-1.20 (m, 1H). LCMS (FA): m/z=569.1 (M+H).

The compounds listed in the table below were prepared in an analogous fashion to that described above starting from the appropriate starting materials. The following alternative conditions were employed in the described reaction steps.

Step 2: Oxidant was A: MnO$_2$, B: Dess-Martin periodinane
Step 3: Base/solvent were A: K$_2$CO$_3$/DMF, B: N,N-diisopropylethylamine/i-PrOH
Step 5: Reaction was run A: Without triethylamine, B: With triethylamine
Step 6: Desilylating agent/solvent were A: HCl/THF, B: TBAF/THF, C: TFA/water, D: H$_3$PO$_4$/CH$_3$CN

| Starting material | Reaction condition | Compound No. |
|---|---|---|
| Int-90 | Step 2: A<br>Step 3: A<br>Step 5: B<br>Step 6: A | I-19 |
| 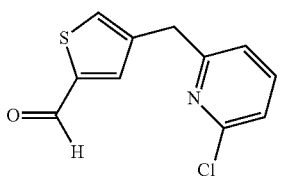 [SMILES: O=Cc1cc(Cc2cccc(Cl)n2)cs1] | Step 2: A<br>Step 3: A<br>Step 5: B<br>Step 6: A | I-71 |
| Int-104 | Step 2: A<br>Step 3: A<br>Step 5: B<br>Step 6: A | I-53 |

593 -continued

| Starting material | Reaction condition | Compound No. |
|---|---|---|
| Int-109 | Step 2: A<br>Step 3: A<br>Step 5: B<br>Step 6: A | I-46 |
| Int-78 | Step 2: B<br>Step 3: A<br>Step 5: B<br>Step 6: A | I-43 |
| Int-114 | Step 2: B<br>Step 3: A<br>Step 5: B<br>Step 6: D | I-62 |
| Int-234 | Step 2: B<br>Step 3: A<br>Step 5: A<br>Step 6: D | I-335 |
| Int-59 | Step 2: B<br>Step 3: A<br>Step 5: B<br>Step 6: A | I-82 |
| Int-98 | Step 2: A<br>Step 3: B<br>Step 5: B<br>Step 6: A | I-88 |
| Int-99 | Step 2: A<br>Step 3: B<br>Step 5: B<br>Step 6: A | I-97 |
| Int-100 | Step 2: A<br>Step 3: B<br>Step 5: B<br>Step 6: A | I-165 |
| Int-101 | Step 2: A<br>Step 3: B<br>Step 5: B<br>Step 6: A | I-157 |
| Int-105 | Step 2: A<br>Step 3: B<br>Step 5: B<br>Step 6: A | I-140 |
| Int-106 | Step 2: A<br>Step 3: B<br>Step 5: B<br>Step 6: A | I-118 |
| Int-107 | Step 2: A<br>Step 3: B<br>Step 5: B<br>Step 6: A | I-107 |
| Int-108 | Step 2: A<br>Step 3: B<br>Step 5: B<br>Step 6: A | I-112 |
| Int-113 | Step 2: A<br>Step 3: B<br>Step 5: B<br>Step 6: A | I-179 |
| Int-117 | Step 2: A<br>Step 3: B<br>Step 5: B<br>Step 6: A | I-135 |
| Int-67 | Step 2: A<br>Step 3: B<br>Step 5: B<br>Step 6: A | I-96 |
| Int-97 | Step 2: A<br>Step 3: B<br>Step 5: B<br>Step 6: A | I-77 |
| Int-81 | Step 2: A<br>Step 3: B<br>Step 5: A<br>Step 6: A | I-106 |
| Int-82 | Step 2: A<br>Step 3: B<br>Step 5: A<br>Step 6: B | I-117 |

594 -continued

| Starting material | Reaction condition | Compound No. |
|---|---|---|
| Int-69 | Step 2: A<br>Step 3: B<br>Step 5: A<br>Step 6: B | I-5 |
| Int-84 | Step 2: A<br>Step 3: B<br>Step 5: A<br>Step 6: C | I-51 |
| Int-88 | Step 2: A<br>Step 3: B<br>Step 5: A<br>Step 6: C | I-17 |
| Int-91 | Step 2: A<br>Step 3: B<br>Step 5: A<br>Step 6: C | I-4 |
| 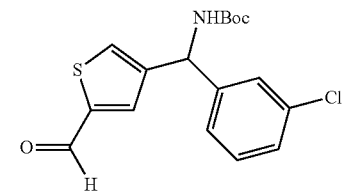 [SMILES: CC(C)(C)OC(=O)NC(c1cccc(Cl)c1)c1csc(C=O)c1] | Step 2: A<br>Step 3: B<br>Step 5: A<br>Step 6: C | I-36 |
| Int-161 | Step 2: A<br>Step 3: B<br>Step 5: A<br>Step 6: C | I-47 |
| Int-60 | Step 2: A<br>Step 3: B<br>Step 5: A<br>Step 6: A | I-72 |
| Int-61 | Step 2: A<br>Step 3: B<br>Step 5: A<br>Step 6: A | I-33 |
| Int-64 | Step 2: A<br>Step 3: B<br>Step 5: B<br>Step 6: A | I-57 |

Example 172: {(1R,2S,4R)-4-[(5-{[4-(3-Ethynyl-benzyl)-2-thienyl]carbonyl}pyrimidin-4-yl)amino]-2-hydroxycyclopentyl}methyl sulfamate. I-70

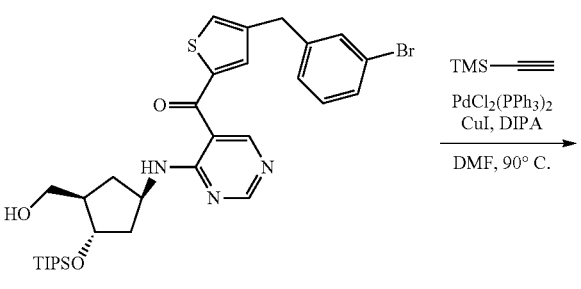

Int-282

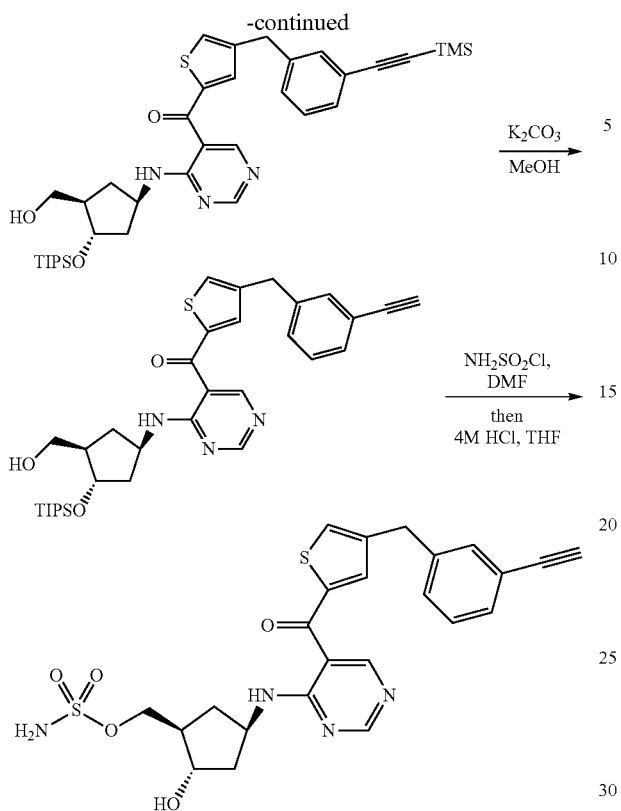

Step 1: [4-({(1R,3R,4S)-3-(Hydroxymethyl)-4-[(triisopropylsilyl)oxy]cyclopentyl}amino)pyrimidin-5-yl](4-{3-[(trimethylsilyl)ethynyl]benzyl}-2-thienyl)methanone A microwave reaction tube was charged with Pd(PPh₃)₂Cl₂ (10.3 mg, 0.015 mmol), CuI (2.81 mg, 0.015 mmol), and PPh₃ (15.5 mg, 0.06 mmol). To the mixture was added a solution of Int-282 (190 mg, 0.29 mmol) in DMF (1.0 mL) followed by N,N-diisopropylamine (1.00 mL, 7.14 mmol), and the reaction vessel was sealed with cap under argon. To the mixture was added (trimethylsilyl)acetylene (62.5 uL, 0.44 mmol) via syringe and the reaction was heated at 90° C. for 1 hour. The reaction was transferred into a separatory funnel with EtOAc (60 mL). The solution was washed with 0.5N HCl followed by brine and then dried over Na₂SO₄. The mixture was filtered, and the filtrate was concentrated in vacuo. The residue was purified by ISCO column chromatography (20% EtOAc in DCM as eluent) to give 162 mg (79%) of the title compound as a light yellow amorphous solid. LCMS (FA): m/z=662.4 (M+H).

Step 2: [4-(3-Ethynylbenzyl)-2-thienyl][4-({(1R,3R,4S)-3-(hydroxymethyl)-4-[(triisopropylsilyl)oxy]cyclopentyl}amino)pyrimidin-5-yl]methanone To a solution of [4-({(1R,3R,4S)-3-(hydroxymethyl)-4-[(triisopropylsilyl)oxy]cyclopentyl}amino)pyrimidin-5-yl](4-{3-[(trimethylsilyl)ethynyl]benzyl}-2-thienyl)methanone (155 mg, 0.23 mmol) in MeOH (2.0 mL) was added K₂CO₃ (64.7 mg, 0.47 mmol), and the mixture was stirred for 2 h at rt. The reaction was concentrated in vacuo and the residue was diluted with water (50 mL). The mixture was extracted with DCM (50 mL×3). The combined organic layers were washed with brine, dried over Na₂SO₄, filtered, and concentrated in vacuo. The residue was purified by ISCO column chromatography (30% EtOAc in DCM as eluent) to give 91 mg (80%) of the title compound as a light yellow oil. ¹H NMR (400 MHz, Chloroform-d) δ 8.78 (s, 1H), 8.71-8.59 (m, 2H), 7.43-7.27 (m, 5H), 7.18 (d, J=7.6 Hz, 1H), 4.86-4.73 (m, 1H), 4.36-4.27 (m, 1H), 3.97 (s, 2H), 3.76-3.63 (m, 2H), 3.06 (s, 1H), 2.55-2.42 (m, 1H), 2.25-2.12 (m, 2H), 1.84 (dt, J=13.5, 6.8 Hz, 1H), 1.69 (t, J=5.0 Hz, 1H), 1.36-1.23 (m, 1H), 1.07 (s, 21H). LCMS (FA): m/z=590.3 (M+H)

Step 3: {(1R,2S,4R)-4-[(5-{[4-(3-Ethynylbenzyl)-2-thienyl]carbonyl}pyrimidin-4-yl)amino]-2-hydroxycyclopentyl}methyl sulfamate To a solution of [4-(3-ethynylbenzyl)-2-thienyl][4-({(1R,3R,4S)-3-(hydroxymethyl)-4-[(triisopropylsilyl)oxy]cyclopentyl}amino)pyrimidin-5-yl]methanone (90.0 mg, 0.15 mmol) in DMF (2.0 mL) was added chlorosulfonamide (35.2 mg, 0.31 mmol) at rt, and the mixture was stirred for 15 min. The reaction was quenched by addition of saturated NaHCO₃ (50 mL) and extracted with EtOAc (50 mL×3). The combined organic layers were dried over Na₂SO₄, filtered, and concentrated in vacuo. The residue was dried under high vac for a while. The residue was diluted with THF (2.0 mL) and 4.0 M of HCl in water (2.00 mL, 8.00 mmol) was added to the solution at rt. The reaction was stirred for 2 h at 40° C. The reaction was quenched by addition of saturated NaHCO₃ (50 mL) and extracted with EtOAc (50 mL×3). The combined organic layers were dried over Na₂SO₄, filtered, and concentrated in vacuo. The residue was purified by ISCO column chromatography (5% MeOH in DCM as eluent) to give 68 mg (87%) of the title compound as an off-white amorphous solid. ¹H NMR (400 MHz, DMSO-d₆) δ 8.67 (s, 1H), 8.64 (s, 1H), 8.26 (d, J=7.5 Hz, 1H), 7.81 (s, 1H), 7.69 (s, 1H), 7.41 (d, J=11.9 Hz, 3H), 7.32 (s, 3H), 4.88 (d, J=4.5 Hz, 1H), 4.77-4.63 (m, 1H), 4.16 (s, 1H), 4.08 (dd, J=9.7, 6.1 Hz, 1H), 4.03-3.89 (m, 3H), 3.29 (s, 1H), 2.37-2.25 (m, 1H), 2.17-2.05 (m, 1H), 2.00-1.89 (m, 1H), 1.82-1.71 (m, 1H), 1.32-1.20 (m, 1H). LCMS (FA): m/z=513.2 (M+H).

Example 173: {(1R,2S,4R)-4-[(5-{[5-(3-Chlorobenzyl)-3-methyl-2thienyl]carbonyl}pyrimidin-4-yl)amino]-2-hydroxycyclopentyl}methyl sulfamate I-233

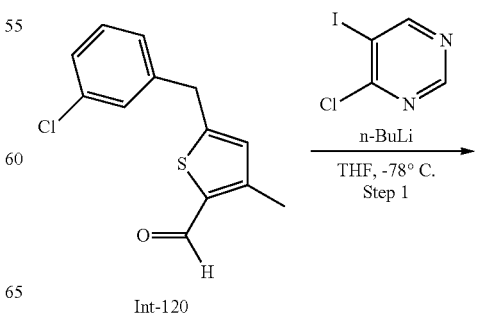

-continued

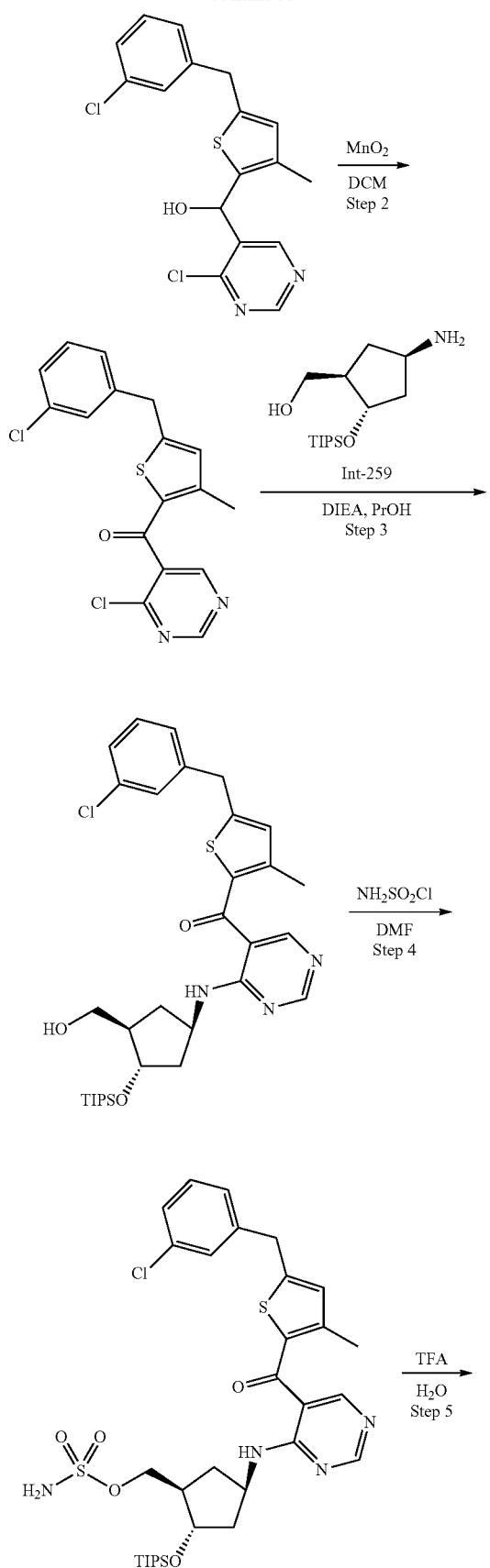

-continued

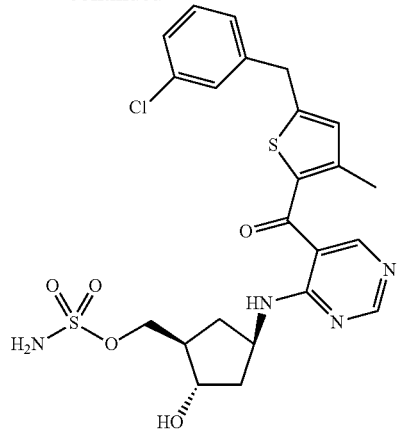

Step 1: rac-[5-(3-Chlorobenzyl)-3-methyl-2-thienyl](4-chloropyrimidin-5-yl)methanol To a solution of 4-chloro-5-iodopyrimidine (1.06 g, 4.39 mmol) in THF (60.0 mL) was added 2.50 M of n-BuLi in hexane (3.92 mL, 9.81 mmol) at −78° C. under atmosphere of argon and the mixture was stirred for 15 min. To the mixture was added Int-120 (1.00 g, 3.99 mmol) as a solution in THF (10.0 mL, 123 mmol) at −78° C. and the reaction was allowed to stir at −78° C. for 30 min. The reaction mixture was quenched by addition of a solution of AcOH (0.60 g, 9.97 mmol) in THF (15 mL) and the solution was warmed to rt. Water was added and the mixture extracted with EtOAc (×3). The combined the organic layers were dried over MgSO4, filtered, and concentrated in vacuo. The residue was purified by ISCO column chromatography (0%-50% EtOAc in hexanes as eluent) to give 1.14 g (78%) of the title compound. LCMS (FA): m/z=366.9 (M+H).

Step 2: [5-(3-Chlorobenzyl)-3-methyl-2-thienyl](4-chloropyrimidin-5-yl)methanone To a solution of [5-(3-chlorobenzyl)-3-methyl-2-thienyl](4-chloropyrimidin-5-yl)methanol (243 mg, 0.67 mmol) in DCM (30 mL) was added MnO₂ (578 mg, 6.65 mmol) and the mixture was stirred for 19 h at rt. The mixture was filtered through a Celite pad and the residual solid was washed with DCM several times. The filtrate was concentrated in vacuo. The residue was purified by ISCO column chromatography (0-50% EtOAc in hexanes as eluent) to give 182 mg (75%) of the title compound as white solid. ¹H NMR (400 MHz, Chloroform-d) δ 9.13 (s, 1H), 8.75 (s, 1H), 7.37-7.28 (m, 2H), 7.19-7.13 (m, 1H), 6.84 (s, 1H), 4.14 (s, 2H), 2.51 (s, 3H).

Step 3: [5-(3-Chlorobenzyl)-3-methyl-2-thienyl][4-({(1R,3R,4S)-3-(hydroxymethyl)-4-[(triisopropylsilyl)oxy]cyclopentyl}amino)pyrimidin-5-yl]methanone To a solution of {(1R,2S,4R)-4-amino-2-[(triisopropylsilyl)oxy]cyclopentyl}methanol (Int-259, 46 mg, 0.16 mmol) in i-PrOH (8.0 mL) was added N,N-diisopropylethylamine (0.17 mL, 0.95 mmol) followed by [5-(3-chlorobenzyl)-3-methyl-2-thienyl](4-chloropyrimidin-5-yl)methanone (71.5 mg, 0.20 mmol), and the reaction was stirred at 50° C. for 1 hour. The reaction was concentrated in vacuo and the residue was purified by ISCO column chromatography (0%-60% EtOAc in hexanes as eluent) to give 36.1 mg (37%) of the title compound. LCMS (FA): m/z=614.3 (M+H).

Step 4: {(1R,2S,4R)-4-[(5-{[5-(3-Chlorobenzyl)-3-methyl-2-thienyl]carbonyl}pyrimidin-4-yl)amino]-2-[(triisopropylsilyl)oxy]cyclopentyl}methyl sulfamate To a solution of [5-(3-chlorobenzyl)-3-methyl-2-thienyl][4-({(1R,3R,4S)-3-(hydroxymethyl)-4-[(triisopropylsilyl)oxy]cyclopentyl}amino)pyrimidin-5-yl]methanone (51.1 mg, 0.08 mmol) in THF (8.0 mL) was added N,N-diisopropylethylamine (58 uL, 0.33 mmol) followed by chlorosulfonamide (19.2 mg, 0.17 mmol) at 0° C. and the reaction was stirred for 30 min. The reaction was concentrated in vacuo and the residue was purified by ISCO column chromatography (10%-60% EtOAc in hexanes as eluent) to give 38.7 mg (67%) of the title compound. LCMS (FA): m/z=693.3 (M+H).

Step 5: {(1R,2S,4R)-4-[(5-{[5-(3-Chlorobenzyl)-3-methyl-2-thienyl]carbonyl}pyrimidin-4-yl)amino]-2-hydroxycyclopentyl}methyl sulfamate {(1R,2S,4R)-4-[(5-{[5-(3-chlorobenzyl)-3-methyl-2-thienyl]carbonyl}pyrimidin-4-yl)amino]-2-[(triisopropylsilyl)oxy]cyclopentyl}methyl sulfamate (48.1 mg, 0.07 mmol) was dissolved into the solution of TFA (7.20 mL, 93.4 mmol) and water (0.80 mL, 44 mmol). The reaction was stirred at rt for 30 min. The reaction mixture was concentrated in vacuo, and the residue was diluted with MeOH (5 mL) and triethylamine (0.5 mL). After concentration of the mixture in vacuo, the residue was diluted with EtOAc (20 mL) and the mixture was washed with water (×2). The organic layer was dried over $Na_2SO_4$, filtered, and concentrated in vacuo. the residue was purified by ISCO column chromatography (0%-10% MeOH in DCM as eluent) to give 28.3 mg (76%) of the title compound. $^1$H NMR (400 MHz, Chloroform-d) δ 8.67 (s, 1H), 8.61 (s, 1H), 8.57 (d, J=7.3 Hz, 1H), 7.29-7.20 (m, 3H), 7.12 (d, J=6.6 Hz, 1H), 6.71 (s, 1H), 5.75-5.58 (br s, 2H), 4.81-4.69 (m, 1H), 4.38-4.28 (m, 2H), 4.23 (dd, J=9.9, 5.8 Hz, 1H), 4.08 (s, 2H), 2.73-2.24 (m, 6H), 2.20-2.09 (m, 1H), 2.03-1.93 (m, 1H), 1.48-1.37 (m, 1H). LCMS (FA): m/z=537.1 (M+H).

The compounds listed in the table below were prepared in an analogous fashion to that described above starting from the appropriate starting materials. The following alternative conditions were employed in the described reaction steps.
Step 3: Base/solvent were A: N,N-diisopropylethylamine/i-PrOH, B: $K_2CO_3$/DMF, C: triethylamine/DMF
Step 4: Reaction was run A: Without triethylamine, B: With triethylamine
Step 5: Desilylating agent/solvent were A: HCl/THF, B: TBAF/THF, C: TFA/water, D: $H_3PO_4$/$CH_3CN$, E: TAS-F/DMF

| Starting material | Reaction Condition | Compound No. |
|---|---|---|
| Int-95 | Step 3: A<br>Step 4: B<br>Step 5: A | I-44 |
| Int-96 | Step 3: A<br>Step 4: B<br>Step 5: A | I-35 |
| Int-95 | Step 3: A<br>Step 4: B<br>Step 5: A | I-7 |
| Int-74 | Step 3: A<br>Step 4: B<br>Step 5: A | I-13 |
| Int-137 | Step 3: A<br>Step 4: B<br>Step 5: A | I-22 |
| Int-138 | Step 3: A<br>Step 4: B<br>Step 5: A | I-25 |
| Int-139 | Step 3: A<br>Step 4: B<br>Step 5: A | I-18 |
| Int-157 | Step 3: A<br>Step 4: B<br>Step 5: A | I-6 |
| Int-140 | Step 3: A<br>Step 4: A<br>Step 5: A | I-151 |
| Int-118 | Step 3: A<br>Step 4: A<br>Step 5: B | I-11 |
| Int-70 | Step 3: A<br>Step 4: A<br>Step 5: B | I-54 |
| Int-75 | Step 3: A<br>Step 4: A<br>Step 5: B | I-21 |
| Int-129 | Step 3: A<br>Step 4: A<br>Step 5: B | I-174 |
| Int-126 | Step 3: A<br>Step 4: A<br>Step 5: B | I-195 |
| Int-131 | Step 3: A<br>Step 4: A<br>Step 5: C | I-2 |
| Int-133 | Step 3: A<br>Step 4: A<br>Step 5: D | I-103 |
| Int-111 | Step 3: A<br>Step 4: A<br>Step 5: D | I-110 |
| Int-112 | Step 3: A<br>Step 4: A<br>Step 5: D | I-41 |
| Int-145 | Step 3: A<br>Step 4: A<br>Step 5: D | I-154 |
| Int-134 | Step 3: A<br>Step 4: A<br>Step 5: D | I-90 |
| Int-57 | Step 3: A<br>Step 4: A<br>Step 5: A | I-127 |
| Int-58 | Step 3: A<br>Step 4: A<br>Step 5: A | I-93 |
| Int-66 | Step 3: A<br>Step 4: B<br>Step 5: A | I-139 |
| Int-266 | Step 3: B<br>Step 4: A<br>Step 5: A | I-230 |
| Int-136 | Step 3: B<br>Step 4: B<br>Step 5: A | I-15 |
| Int-158 | Step 3: B<br>Step 4: B<br>Step 5: A | I-12 |
| Int-86 | Step 3: B<br>Step 4: A<br>Step 5: A | I-52 |

| Starting material | Reaction Condition | Compound No. |
|---|---|---|
| Int-87 | Step 3: B<br>Step 4: A<br>Step 5: A | I-111 |
| Int-124 | Step 3: B<br>Step 4: A<br>Step 5: A | I-45 |
| Int-80 | Step 3: B<br>Step 4: A<br>Step 5: A | I-60 |
| Int-83 | Step 3: B<br>Step 4: A<br>Step 5: A | I-89 |
| Int-102 | Step 3: B<br>Step 4: A<br>Step 5: A | I-123 |
| Int-121 | Step 3: B<br>Step 4: A<br>Step 5: A | I-38 |
| Int-123 | Step 3: B<br>Step 4: A<br>Step 5: A | I-227 |
| Int-128 | Step 3: B<br>Step 4: A<br>Step 5: A | I-172 |
| Int-144 | Step 3: B<br>Step 4: A<br>Step 5: A | I-209 |
| Int-154 | Step 3: B<br>Step 4: A<br>Step 5: A | I-238 |
| Int-155 | Step 3: B<br>Step 4: A<br>Step 5: A | I-166 |
| Int-235 | Step 3: B<br>Step 4: A<br>Step 5: A | I-349 |
| Int-147 | Step 3: B<br>Step 4: B<br>Step 5: B | I-32 |
| Int-146 | Step 3: B<br>Step 4: B<br>Step 5: B | I-121 |
| Int-125 | Step 3: B<br>Step 4: A<br>Step 5: B | I-67 |
| Int-156 | Step 3: B<br>Step 4: A<br>Step 5: B | I-116 |
| Int-150 | Step 3: B<br>Step 4: A<br>Step 5: B | I-20a |
| Int-152 | Step 3: B<br>Step 4: A<br>Step 5: B | I-20b |
| Int-92 | Step 3: B<br>Step 4: B<br>Step 5: E | I-235 |
| Int-93 | Step 3: B<br>Step 4: B<br>Step 5: E | I-152 |
| Int-119 | Step 3: B<br>Step 4: B<br>Step 5: E | I-50 |
| Int-54 | Step 3: B<br>Step 4: A<br>Step 5: B | I-220 |
| Int-169 | Step 3: B<br>Step 4: A<br>Step 5: B | I-34 |
| Int-56 | Step 3: B<br>Step 4: A<br>Step 5: B | I-30 |
| Int-55 | Step 3: B<br>Step 4: A<br>Step 5: B | I-42 |
| Int-53 | Step 3: B<br>Step 4: A<br>Step 5: B | I-58 |
| Int-62 | Step 3: B<br>Step 4: A<br>Step 5: A | I-79 |
| 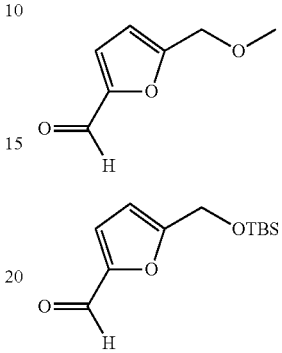 | Step 3: B<br>Step 4: A<br>Step 5: A | I-212 |
| 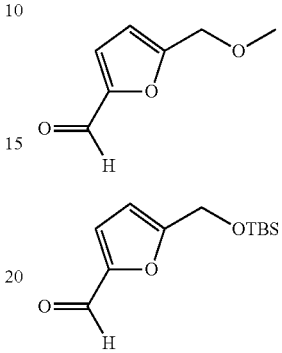 | Step 3: B<br>Step 4: B<br>Step 5: A | I-206 |
| Int-220 | Step 3: A<br>Step 4: B<br>Step 5: B | I-283 |
| Int-166 | Step 3: B<br>Step 4: B<br>Step 5: | I-254 |
| Int-203 | Step 3: B<br>Step 4: A<br>Step 5: A | I-333 |
| Int-202 | Step 3: B<br>Step 4: A<br>Step 5: A | I-332 |
| Int-164 | Step 3: A<br>Step 4: B<br>Step 5: A | I-256 |
| Int-190 | Step 3: B<br>Step 4: A<br>Step 5: B | I-285 |
| Int-222 | Step 3: A<br>Step 4: B<br>Step 5: B | I-280 |
| Int-167 | Step 3: B<br>Step 4: A<br>Step 5: A | I-296 |
| Int-168 | Step 3: B<br>Step 4: A<br>Step 5: A | I-309 |
| Int-169 | Step 3: B<br>Step 4: A<br>Step 5: A | I-275 |
| Int-193 | Step 3: B<br>Step 4: A<br>Step 5: A | I-269 |
| Int-230 | Step 3: B<br>Step 4: A<br>Step 5: B | I-281 |
| Int-232 | Step 3: B<br>Step 4: A<br>Step 5: B | I-291 |
| Int-221 | Step 3: A<br>Step 4: B<br>Step 5: B | I-270 |
| Int-234 | Step 3: B<br>Step 4: A<br>Step 5: D | I-335 |
| Int-170 | Step 3: B<br>Step 4: A<br>Step 5: A | I-301 |
| Int-171 | Step 3: C<br>Step 4: A<br>Step 5: A | I-261 |
| Int-194 | Step 3: B<br>Step 4: A<br>Step 5: A | I-287 |

| Starting material | Reaction Condition | Compound No. |
|---|---|---|
| Int-173 | Step 3: B / Step 4: A / Step 5: A | I-305 |
| Int-186 | Step 3: A / Step 4: B / Step 5: B | I-266 |
| Int-195 | Step 3: A / Step 4: B / Step 5: A | I-293 |
| Int-236 | Step 3: B / Step 4: B / Step 5: E | I-298 |
| Int-178 | Step 3: B / Step 4: A / Step 5: A | I-341 |
| Int-233 | Step 3: B / Step 4: A / Step 5: B | I-339 |
| Int-172 | Step 3: C / Step 4: A / Step 5: A | I-257 |
| Int-237 | Step 3: B / Step 4: A / Step 5: B | I-317 |
| Int-174 | Step 3: B / Step 4: B / Step 5: A | I-314 |
| Int-187 | Step 3: B / Step 4: A / Step 5: B | I-286 |
| Int-244 | Step 3: B / Step 4: A / Step 5: B | I-316 |
| Int-175 | Step 3: A / Step 4: A / Step 5: A | I-320 |
| Int-196 | Step 3: B / Step 4: A / Step 5: B | I-331 |
| Int-183 | Step 3: A / Step 4: B / Step 5: A | I-294 |
| Int-225 | Step 3: B / Step 4: A / Step 5: D | I-277 |
| Int-197 | Step 3: A / Step 4: A / Step 5: A | I-310 |
| Int-180 | Step 3: B / Step 4: A / Step 5: A | I-303 |
| Int-176 | Step 3: A / Step 4: A / Step 5: D | I-282 |
| Int-201 | Step 3: B / Step 4: A / Step 5: B | I-323 |
| Int-188 | Step 3: A / Step 4: B / Step 5: B | I-276 |
| Int-198 | Step 3: B / Step 4: A / Step 5: A | I-289 |
| Int-226 | Step 3: B / Step 4: A / Step 5: D | I-329 |
| Int-177 | Step 3: B / Step 4: A / Step 5: A | I-337 |
| Int-191 | Step 3: B / Step 4: A / Step 5: A | I-268 |
| Int-178 | Step 3: A / Step 4: B / Step 5: A | I-258 |
| Int-189 | Step 3: B / Step 4: A / Step 5: B | I-297 |
| Int-199 | Step 3: B / Step 4: A / Step 5: B | I-288 |
| Int-185 | Step 3: B / Step 4: B / Step 5: A | I-260 |
| Int-179 | Step 3: B / Step 4: A / Step 5: A | I-315 |
| Int-228 | Step 3: B / Step 4: B / Step 5: A | I-347 |
| Int-229 | Step 3: B / Step 4: B / Step 5: A | I-346 |
| Int-245 | Step 3: B / Step 4: A / Step 5: A | I-344 |
| Int-215 | Step 3: B / Step 4: B / Step 5: E | I-304 |
| Int-251 | Step 3: B / Step 4: A / Step 5: A | I-175 |
| Int-253 | Step 3: B / Step 4: A / Step 5: A | I-189 |
| Int-254 | Step 3: B / Step 4: A / Step 5: D | I-143 |
| Int-255 | Step 3: B / Step 4: A / Step 5: D | I-145 |
| Int-256 | Step 3: B / Step 4: A / Step 5: D | I-137 |
| Int-257 | Step 3: B / Step 4: A / Step 5: D | I-181 |
| Int-258 | Step 3: B / Step 4: A / Step 5: D | I-203 |
| Int-192 | Step 3: B / Step 4: A / Step 5: C | I-342 |
| Int-223 | Step 3: B / Step 4: A / Step 5: B | I-324 |
| Int-227 | Step 3: B / Step 4: A / Step 5: B | I-313 |
| Int-239 | Step 3: A / Step 4: A / Step 5: B | I-318 |
| Int-240 | Step 3: A / Step 4: A / Step 5: B | I-321 |
| Int-250 | Step 3: B / Step 4: A / Step 5: A: | I-355 |
| Int-246 | Step 3: B / Step 4: A / Step 5: A | I-351 |
| Int-248 | Step 3: B / Step 4: A / Step 5: A | I-353 |
| Int-184 | Step 3: A / Step 4: B / Step 5: A | I-290a** |
| Int-184 | Step 3: A / Step 4: B / Step 5: A | I-290b** |

605
-continued

| Starting material | Reaction Condition | Compound No. |
|---|---|---|
| Int-238 | Step 3: B<br>Step 4: A<br>Step 5: A | I-300a |
| Int-238 | Step 3: B<br>Step 4: A<br>Step 5: A | I-300b |

**Diastereomers were resolved in step 3 by silica gel flash chromatography in analogous fashion to Example 133, step 6.

Example 174: [(1R,2S,4R)-2-Hydroxy-4-{[5-({4-[(1R)-1,2,3,4-tetrahydroisoquinolin-1-yl]-2-thienyl}carbonyl)pyrimidin-4-yl]amino}cyclopentyl] methyl sulfamate and [(1R,2S,4R)-2-Hydroxy-4-{[5-({4-[(1S)-1,2,3,4-tetrahydroisoquinolin-1-yl]-2-thienyl}carbonyl)pyrimidin-4-yl]amino}cyclopentyl] methyl sulfamate I-283

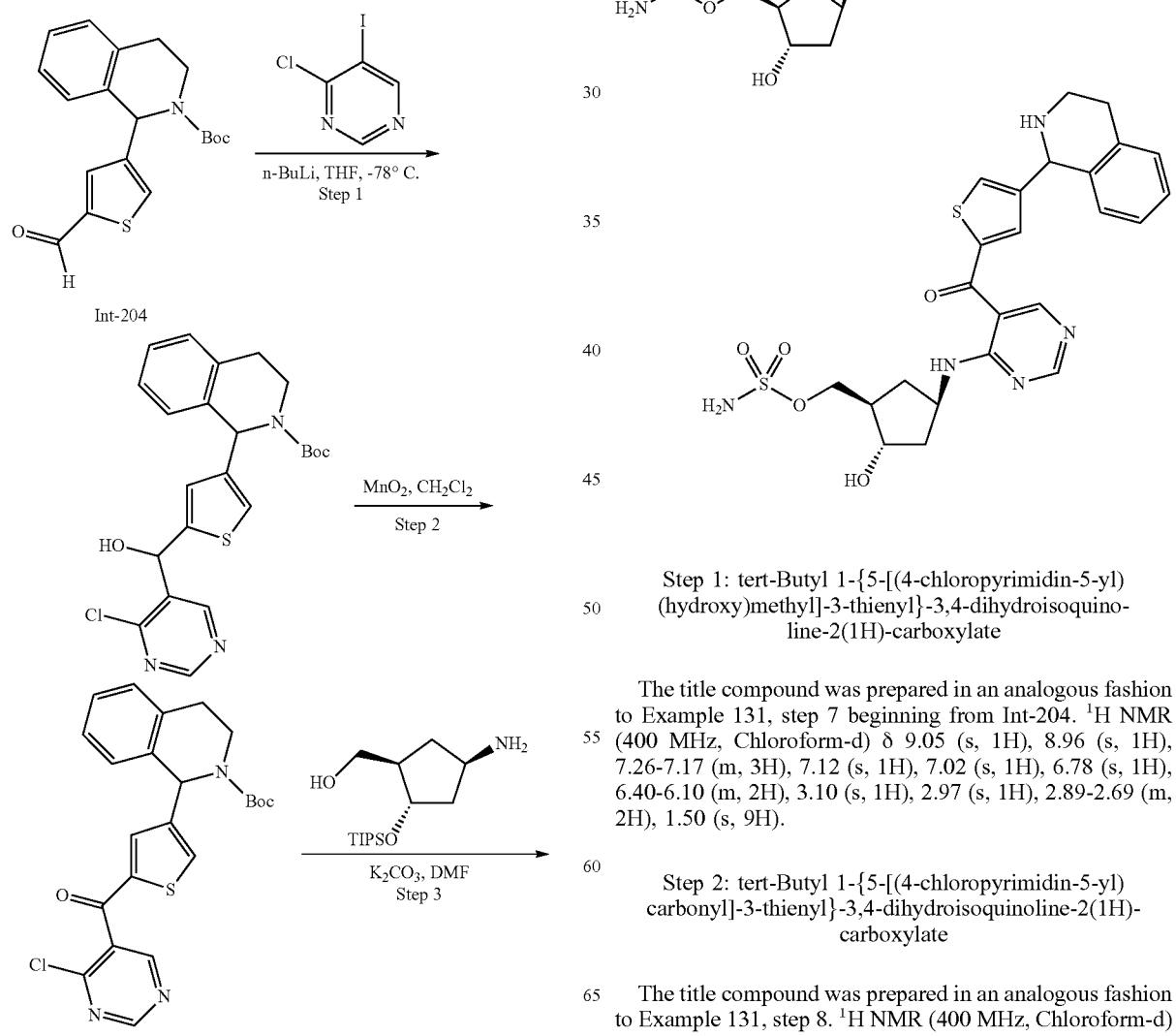

Step 1: tert-Butyl 1-{5-[(4-chloropyrimidin-5-yl)(hydroxy)methyl]-3-thienyl}-3,4-dihydroisoquinoline-2(1H)-carboxylate The title compound was prepared in an analogous fashion to Example 131, step 7 beginning from Int-204. $^1$H NMR (400 MHz, Chloroform-d) δ 9.05 (s, 1H), 8.96 (s, 1H), 7.26-7.17 (m, 3H), 7.12 (s, 1H), 7.02 (s, 1H), 6.78 (s, 1H), 6.40-6.10 (m, 2H), 3.10 (s, 1H), 2.97 (s, 1H), 2.89-2.69 (m, 2H), 1.50 (s, 9H).

Step 2: tert-Butyl 1-{5-[(4-chloropyrimidin-5-yl)carbonyl]-3-thienyl}-3,4-dihydroisoquinoline-2(1H)-carboxylate The title compound was prepared in an analogous fashion to Example 131, step 8. $^1$H NMR (400 MHz, Chloroform-d) δ 9.13 (s, 1H), 8.76 (s, 1H), 7.46 (s, 1H), 7.39 (s, 1H), 7.28-7.21 (m, 3H), 7.11 (d, J=7.6 Hz, 1H), 6.36 (s, 1H), 3.12 (s, 1H), 3.06-2.91 (m, 1H), 2.76 (d, J=16.0 Hz, 1H), 1.47 (s, 9H).

Step 3: tert-Butyl (1S)-1-[5-[4-[[(1R,3R,4S)-3-(hydroxymethyl)-4-triisopropylsilyloxy-cyclopentyl]amino]pyrimidine-5-carbonyl]-3-thienyl]-3,4-dihydro-1H-isoquinoline-2-carboxylate and tert-Butyl (1R)-1-[5-[4-[[(1R,3R,4S)-3-(hydroxymethyl)-4-triisopropylsilyloxy-cyclopentyl]amino]pyrimidine-5-carbonyl]-3-thienyl]-3,4-dihydro-1H-isoquinoline-2-carboxylate The title compound was prepared in an analogous fashion to Example 131, step 9. LCMS (FA): m/z=708.1 (M+H)

Step 4: tert-Butyl (1S)-1-[5-[4-[[(1R,3R,4S)-3-(sulfamoyloxymethyl)-4-triisopropylsilyloxy-cyclopentyl]amino]pyrimidine-5-carbonyl]-3-thienyl]-3,4-dihydro-1H-isoquinoline-2-carboxylate and tert-Butyl (1R)-1-[5-[4-[[(1R,3R,4S)-3-(sulfamoyloxymethyl)-4-triisopropylsilyloxy-cyclopentyl]amino]pyrimidine-5-carbonyl]-3-thienyl]-3,4-dihydro-1H-isoquinoline-2-carboxylate The title compounds were prepared in an analogous fashion to Example 134, step 4. LCMS (FA): m/z=787.1 (M+H)

Step 5: tert-Butyl (1S)-1-[5-[4-[[(1R,3S,4R)-3-hydroxy-4-(sulfamoyloxymethyl)cyclopentyl]amino]pyrimidine-5-carbonyl]-3-thienyl]-3,4-dihydro-1H-isoquinoline-2-carboxylate and tert-Butyl (1R)-1-[5-[4-[[(1R,3S,4R)-3-hydroxy-4-(sulfamoyloxymethyl)cyclopentyl]amino]pyrimidine-5-carbonyl]-3-thienyl]-3,4-dihydro-1H-isoquinoline-2-carboxylate To a solution of the product mixture from Step 4 (391.57 mg, 0.49812 mmol) in THF (7.73 mL) was added a solution of TBAF hydrate (278.4 mg, 0.9962 mmol) in THF (7.73 mL, 95.3 mmol) at rt, and the mixture was stirred for 3 h. The reaction was quenched by addition of water and extracted with EtOAc (×3). The combined organic layers were dried over Na$_2$SO$_4$, filtered, and concentrated in vacuo. The residue was purified by ISCO silica gel column chromatography (eluting with 0 to 90% EtOAc in Hexane) to give 245 mg of the title compound mixture as a light yellow amorphous solid LCMS (FA): m/z=630.9 (M+H)

Step 6: [(1R,2S,4R)-2-Hydroxy-4-{[5-({4-[(1R)-1,2,3,4-tetrahydroisoquinolin-1-yl]-2-thienyl}carbonyl)pyrimidin-4-yl]amino}cyclopentyl]methyl sulfamate and [(1R,2S,4R)-2-Hydroxy-4-{[5-({4-[(1S)-1,2,3,4-tetrahydroisoquinolin-1-yl]-2-thienyl}carbonyl)pyrimidin-4-yl]amino}cyclopentyl]methyl sulfamate To a flask containing the product mixture from step 5 (245.0 mg, 0.3890 mmol) was added TFA (3.08 mL, 39.9 mmol) and the mixture was stirred at rt for 15 min. The mixture was concentrated in vacuo and small amount of saturated NaHCO$_3$ was added to the residue. The resulting mixture was concentrated in vacuo and the residue was purified by ISCO silica gel column chromatography [eluting with 50% DCM in mixed solution of (2% NH4OH: 5% MeOH: 43% CH$_3$CN in 50% DCM) for 3 min then gradient to 100% of mixed solution (2% NH4OH: 5% MeOH: 43% CH$_3$CN in 50% DCM)] to provide 196 mg of the title compound mixture as light yellow amorphous solid. $^1$H NMR (400 MHz, Methanol-d4) δ 8.73 (s, 1H), 8.57 (s, 1H), 7.67 (s, 1H), 7.58 (s, 1H), 7.19 (d, J=3.9 Hz, 2H), 7.17-7.07 (m, 1H), 6.89 (d, J=7.6 Hz, 1H), 5.32 (s, 1H), 4.83-4.73 (m, 1H), 4.26-4.11 (m, 3H), 3.26-3.16 (m, 1H), 3.15-2.90 (m, 3H), 2.56-2.45 (m, 1H), 2.33-2.21 (m, 1H), 2.22-2.09 (m, 1H), 1.95-1.85 (m, 1H), 1.49-1.36 (m, 1H); LCMS: (FA) M+1 530.4

The compounds listed in the table below were prepared in an analogous fashion to that described above starting from the appropriate starting materials. The following alternative conditions were employed in the described reaction steps.
Step 3: Base/solvent were A: N,N-diisopropylethylamine/i-PrOH, B: K$_2$CO$_3$/DMF, C: triethylamine,/DMF
Step 4: Reaction was run A: Without triethylamine, B: With triethylamine
Final deprotection conditions were A: analogous to steps 5 and 6 above, B: Analogous to step 5, C: Analogous to step 5, using TFA/water as the deprotecting agent and solvent, D: Analogous to step 5, using H$_3$PO$_4$/CH$_3$CN as the deprotecting agent and solvent E: Analogous to step 5, using HCl/MeOH as the deprotecting agent and solvent. When conditions B, C, D, or E were employed, step 6 was not performed.

| Starting material | Reaction Conditions for Step 3, 4, and final deprotection (Deprot.) | Compound No. |
|---|---|---|
| Int-205 | Step 3: C<br>Step 4: A<br>Deprot: E | Int-284 |
| Int-235 | Step 3: B<br>Step 4: A<br>Deprot: E | I-349 |
| Int-212 | Step 3: B<br>Step 4: A<br>Deprot: A | I-274 |
| Int-213 | Step 3: B<br>Step 4: B<br>Deprot: A | I-279 |
| Int-216 | Step 3: B<br>Step 4: A<br>Deprot: E | I-322 |
| Int-206 | Step 3: C<br>Step 4: A<br>Deprot: E | I-263a** |
| Int-206 | Step 3: C<br>Step 4: A<br>Deprot: E | I-263b** |
| Int-241 | Step 3: B<br>Step 4: A<br>Deprot: E | I-307 |
| Int-211 | Step 3: B<br>Step 4: B<br>Deprot: A | I-319 |
| Int-207 | Step 3: B<br>Step 4: B<br>Deprot: A | I-299 |
| Int-217 | Step 3: B<br>Step 4: A<br>Deprot: A | I-262 |
| Int-208 | Step 3: B<br>Step 4: A<br>Deprot: A | I-255a** |
| Int-208 | Step 3: B<br>Step 4: A<br>Deprot: A | I-255b** |
| Int-219 | Step 3: B<br>Step 4: A<br>Deprot: B | I-284a** |

609
-continued

| Starting material | Reaction Conditions for Step 3, 4, and final deprotection (Deprot.) | Compound No. |
|---|---|---|
| Int-219 | Step 3: B<br>Step 4: A<br>Deprot: B | I-284b** |
| Int-243 | Step 3: B<br>Step 4: A<br>Deprot: A | I-253 |
| Int-242 | Step 3: B<br>Step 4: A<br>Deprot: E | I-311a** |
| Int-242 | Step 3: B<br>Step 4: A<br>Deprot: E | I-311b** |
| Int-209 | Step 3: C<br>Step 4: A<br>Deprot: E | Int-285 |

610
-continued

| Starting material | Reaction Conditions for Step 3, 4, and final deprotection (Deprot.) | Compound No. |
|---|---|---|
| Int-210 | Step 3: A<br>Step 4: B<br>Deprot: A | I-251 |
| Int-212 | Step 3: B<br>Step 4: A<br>Deprot: B | I-334 |
| Int-208 | Step 3: C<br>Step 4: A<br>Deprot: B | I-336 |
| Int-214 | Step 3: B<br>Step 4: A<br>Deprot: B | I-265 |

**Diastereomers were resolved in step 3 by silica gel flash chromatography in analogous fashion to Example 133, step 6.

Example 175: {(1R,2S,4R)-2-Hydroxy-4-[(5-{[4-(2-hydroxypropan-2-yl)-2-thienyl]carbonyl}pyrimidin-4-yl)amino]cyclopentyl}methyl sulfamate I-240

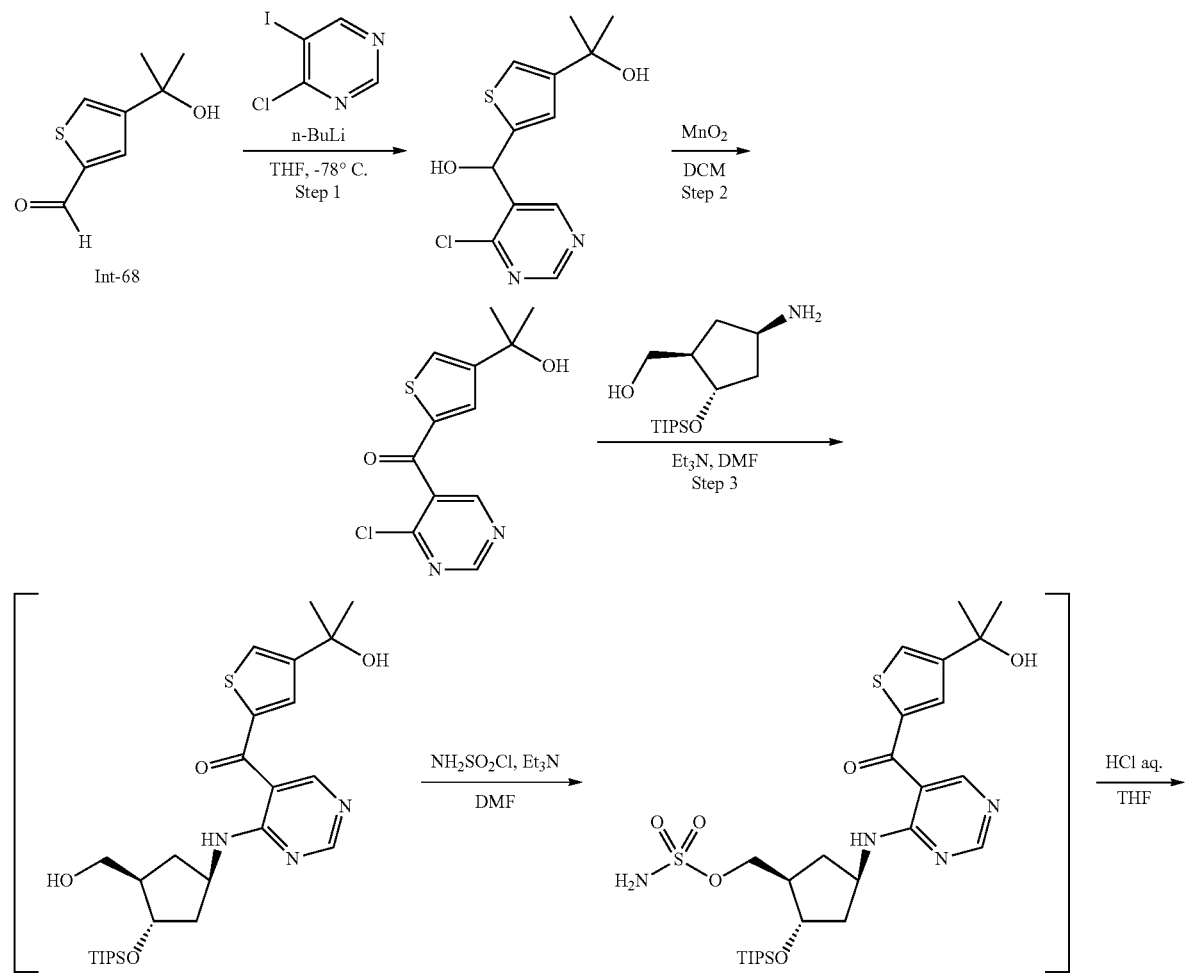

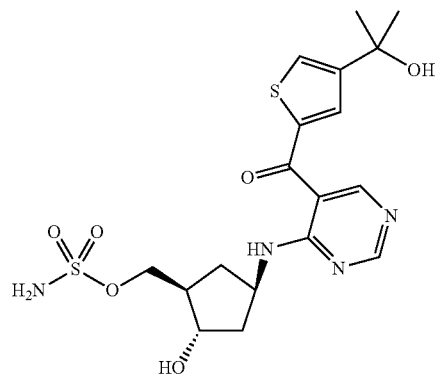

Step 1: rac-2-{5-[(4-Chloropyrimidin-5-yl)(hydroxy)methyl]-3-thienyl}propan-2-ol The title compound was prepared in an analogous fashion to Example 131, step 7 beginning from Int-68. LCMS (FA): m/z=285.3 (M+H).

Step 2: (4-Chloropyrimidin-5-yl)[4-(2-hydroxypropan-2-yl)-2-thienyl]methanone

The title compound was prepared in an analogous fashion to Example 131, step 8. LCMS (FA): m/z=283.3 (M+H).

Step 3: {(1R,2S,4R)-2-Hydroxy-4-[(5-{[4-(2-hydroxypropan-2-yl)-2-thienyl]carbonyl}pyrimidin-4-yl)amino]cyclopentyl}methyl sulfamate To a round bottom flask was added Int-259 (115 mg, 0.40 mmol), (4-chloropyrimidin-5-yl)[4-(2-hydroxypropan-2-yl)-2-thienyl]methanone (94 mg, 0.33 mmol), DMF (5.0 mL), and triethylamine (92.7 uL, 0.67 mmol). The reaction was stirred at rt for 5 h. To the mixture was added chlorosulfonamide (57.6 mg, 0.50 mmol) and the reaction was stirred 2 h at rt. To the mixture was then added 3 M HCl (2 mL) and the resulting mixture was stirred at rt overnight. The reaction mixture was quenched by addition of saturated NaHCO$_3$ and extracted with EtOAc (x3). The combined organic layers were washed with brine, dried over MgSO$_4$, and concentrated in vacuo. The residue was purified by preparative HPLC to give 89 mg (59%) of the title compound. $^1$H NMR (400 MHz, MeOD) δ 8.77 (s, 1H), 8.61 (s, 1H), 7.77 (s, 1H), 7.73 (s, 1H), 4.86-4.74 (m, 1H), 4.31-4.08 (m, 3H), 2.61-2.45 (m, 1H), 2.38-2.23 (m, 1H), 2.22-2.11 (m, 1H), 2.00-1.84 (m, 1H), 1.57 (s, 6H), 1.47-1.35 (m, 1H). LCMS (FA): m/z=457.3 (M+H).

The compounds listed in the table below were prepared in an analogous fashion to that described above starting from the appropriate starting materials.

| Starting material | Compound No. |
| --- | --- |
| Int-132 | I-136 |
| Int-126 | I-142 |

Example 176: {(1R,2R,3R,4R)-4-[(5-{[5-(3-Chlorobenzyl)-2-thienyl]carbonyl}pyrimidin-4-yl)amino]-3-fluoro-2-hydroxycyclopentyl}methyl sulfamate I-205

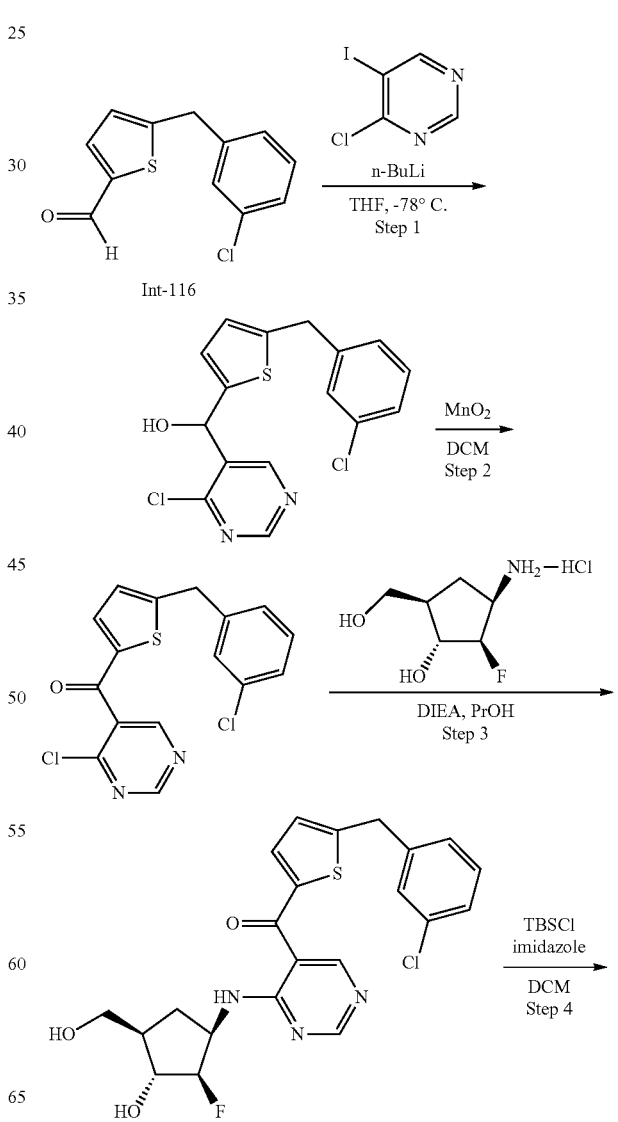

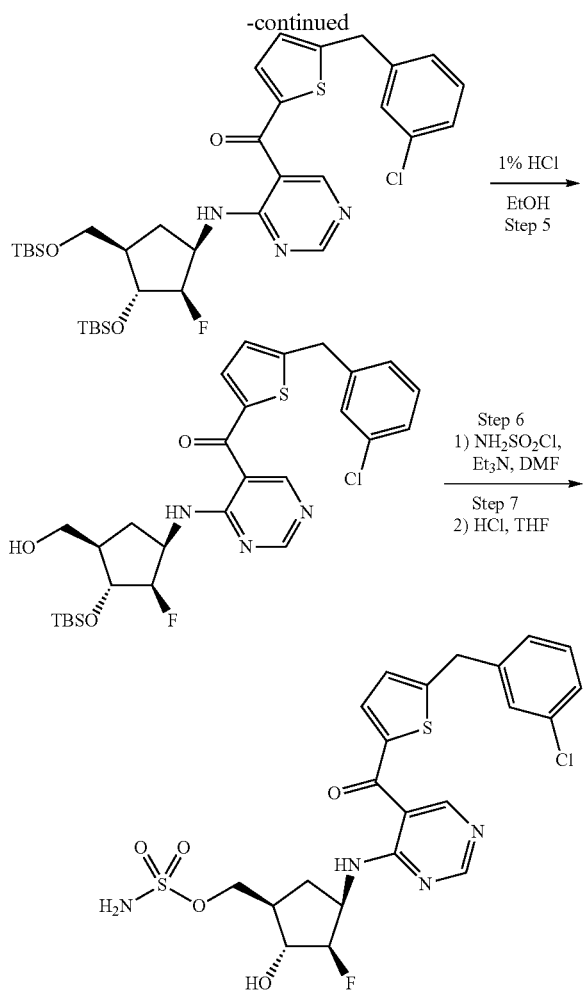

Step 1: rac-[5-(3-Chlorobenzyl)-2-thienyl](4-chloro-pyrimidin-5-yl)methanol

The title compound was prepared in an analogous fashion to Example 131, step 7 beginning with aldehyde Int-116. $^1$H NMR (400 MHz, DMSO-d$_6$) δ 8.99 (s, 1H), 8.96 (s, 1H), 7.38-7.25 (m, 3H), 7.22 (d, J=7.4 Hz, 1H), 6.76 (q, J=3.6 Hz, 2H), 6.64 (d, J=4.2 Hz, 1H), 6.06 (d, J=4.0 Hz, 1H), 4.10 (s, 2H).

Step 2: [5-(3-Chlorobenzyl)-2-thienyl](4-chloropyrimidin-5-yl)methanone

The title compound was prepared in an analogous fashion to Example 131, step 8. LCMS (FA): m/z=349.2 (M+H).

Step 3: [5-(3-Chlorobenzyl)-2-thienyl](4-{[(1R,2R,3R,4R)-2-fluoro-3-hydroxy-4-(hydroxymethyl)cyclopentyl]amino}pyrimidin-5-yl)methanone To a solution of (1R,2R,3R,5R)-3-amino-2-fluoro-5-(hydroxymethyl)cyclopentanol hydrochloride (146 mg, 0.79 mmol) (for synthesis see: Biggadike, K. et al. *J. Chem. Soc. Perkin Trans.* 1988, 3, 549-554; Borthwick, A. D. et al. *J. Med. Chem.* 1990, 33, 179-186.) in i-PrOH (7.9 mL) was added [5-(3-chlorobenzyl)-2-thienyl](4-chloropyrimidin-5-yl)methanone (183 mg, 0.52 mmol) and N,N-diisopropylethylamine (203 mg, 1.57 mmol). The reaction mixture was stirred at rt for 19 h then concentrated in vacuo. The crude material was purified by ISCO column chromatography (0%-5% MeOH in DCM as eluent) to give 195 mg (81%) of the title compound as a light yellow oil. LCMS (FA): m/z=462.1 (M+H).

Step 4: (4-{[(1R,2R,3R,4R)-3-{[tert-Butyl(dimethyl)silyl]oxy}-4-({[tert-butyl(dimethyl)silyl]oxy}methyl)-2-fluorocyclopentyl]amino}pyrimidin-5-yl)[5-(3-chlorobenzyl)-2-thienyl]methanone To a solution of [5-(3-chlorobenzyl)-2-thienyl](4-{[(1R,2R,3R,4R)-2-fluoro-3-hydroxy-4-(hydroxymethyl)cyclopentyl]amino}pyrimidin-5-yl)methanone (195 mg, 0.42 mmol) in DMF (5.0 mL) was added TBSCl (191 mg, 1.27 mmol) and 1H-imidazole (114 mg, 1.67 mmol). The reaction mixture was stirred at rt for 3 h then quenched with water and extracted with EtOAc. The combined organic layers were washed with 10% aqueous LiCl, dried over magnesium sulfate, filtered and concentrated in vacuo. The crude material was purified by ISCO column chromatography (0%-30% EtOAc in hexanes as eluent) to give 190 mg (65%) of the title compound as a clear oil. $^1$H NMR (400 MHz, DMSO-d6) δ 8.69 (s, 1H), 8.59 (s, 1H), 8.39-8.34 (m, 1H), 7.57 (d, J=3.9 Hz, 1H), 7.35-7.32 (m, 1H), 7.32-7.20 (m, 3H), 7.02 (d, J=3.9 Hz, 1H), 4.82-4.79 (m, 1H), 4.68-4.63 (m, 1H), 4.19 (s, 2H), 4.10-4.01 (m, 1H), 3.53-3.48 (m, 2H), 2.17-2.08 (m, 1H), 1.40-1.29 (m, 1H), 0.79 (s, 9H), 0.76 (s, 9H), −0.00 (s, 6H), −0.06 (d, J=2.8 Hz, 6H). LCMS (FA): m/z=690.5 (M+H).

Step 5: (4-{[(1R,2R,3R,4R)-3-{[tert-Butyl(dimethyl)silyl]oxy}-2-fluoro-4-(hydroxymethyl)cyclopentyl]amino}pyrimidin-5-yl)[5-(3-chlorobenzyl)-2-thienyl]methanone To a 0° C. cooled solution of (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)[5-(3-chlorobenzyl)-2-thienyl]methanone (0.19 g, 0.28 mmol) in EtOH (13.0 mL) was added 1% HCl in EtOH (11.4 mL, 1.38 mmol). The reaction mixture was placed in a refrigerator for 24 h then quenched with saturated aqueous NaHCO$_3$ and extracted with EtOAc. The combined organic layers were washed with brine, dried over magnesium sulfate, filtered and concentrated in vacuo. The crude material was purified by ISCO column chromatography (0%-5% MeOH in DCM as eluent) to give 78 mg (49%) of the title compound as a clear oil. LCMS (FA): m/z=576.2 (M+H).

Step 4: {(1R,2R,3R,4R)-4-[(5-{[5-(3-Chlorobenzyl)-2-thienyl]carbonyl}pyrimidin-4-yl)amino]-3-fluoro-2-hydroxycyclopentyl}methyl sulfamate To a solution of (4-{[(1R,2R,3R,4R)-3-{[tert-butyl(dimethyl)silyl]oxy}-2-fluoro-4-(hydroxymethyl)cyclopentyl]amino}pyrimidin-5-yl)[5-(3-chlorobenzyl)-2-thienyl]methanone (78 mg, 0.14 mmol) in DMF (2.1 mL) was added chlorosulfonamide (47 mg, 0.41 mmol) and triethylamine (94.5 uL, 0.68 mmol). The reaction mixture was stirred at rt for 10 min, followed by the addition of a 3.0 M solution of HCl (1.71 mL, 5.14 mmol). The resulting mixture was stirred at rt for 1 hour then quenched with saturated aqueous NaHCO$_3$ and extracted with EtOAc. The combined organic layers were washed with brine, dried over magnesium sulfate, filtered and concentrated in vacuo. The crude material was purified by ISCO column chromatography (0%-5% MeOH in DCM as eluent) to give 20 mg (27%) of the title compound. ¹H NMR (400 MHz, DMSO-d6) δ 8.78 (s, 1H), 8.70 (s, 1H), 8.45 (d, J=7.0 Hz, 1H), 7.67 (d, J=3.8 Hz, 1H), 7.48 (s, 2H), 7.45-7.42 (m, 1H), 7.41-7.30 (m, 3H), 7.12 (d, J=3.8 Hz, 1H), 5.60-5.48 (m, 1H), 4.79-4.67 (m, 1H), 4.29 (s, 2H), 4.15-3.98 (m, 2H), 3.97-3.87 (m, 1H), 2.47-2.42 (m, 1H), 2.37-2.24 (m, 2H), 2.22-2.08 (m, 1H), 1.55-1.42 (m, 1H). LCMS (FA): m/z=541.2 (M+H).

The compounds listed in the table below were prepared in an analogous fashion to that described above starting from the appropriate starting materials. The following alternative conditions were employed in the described reaction steps.
Step 6: Reaction was run A: With triethylamine, B: Without triethylamine
Step 7: Desilylating agent/solvent were A: $H_3PO_4/CH_3CN$ B: TBAF/THF, C: HCl/THF

| Starting material | Reaction Condition | Compound No. |
|---|---|---|
| Int-114 | Step 6: A<br>Step 7: A | I-99 |
| Int-61 | Step 6: B<br>Step 7: B | I-75 |
| Int-63 | Step 6: B<br>Step 7: B | I-64 |
| Int-176 | Step 6: B<br>Step 7: C | I-264 |
| Int-164 | Step 6: B<br>Step 7: C | I-271a |
| Int-172 | Step 6: B<br>Step 7: C | I-264a** |
| Int-172 | Step 6: B<br>Step 7: C | I-264b** |

**Diastereomers were resolved in step 3 by silica gel flash chromatography in analogous fashion to Example 133, step 6.

Example 177: [(1R,2R,3R,4R)-4-({5-[(4-Benzyl-5-chloro-2-thienyl)carbonyl]pyrimidin-4-yl}amino)-3-fluoro-2-hydroxycyclopentyl]methyl sulfamate I-162

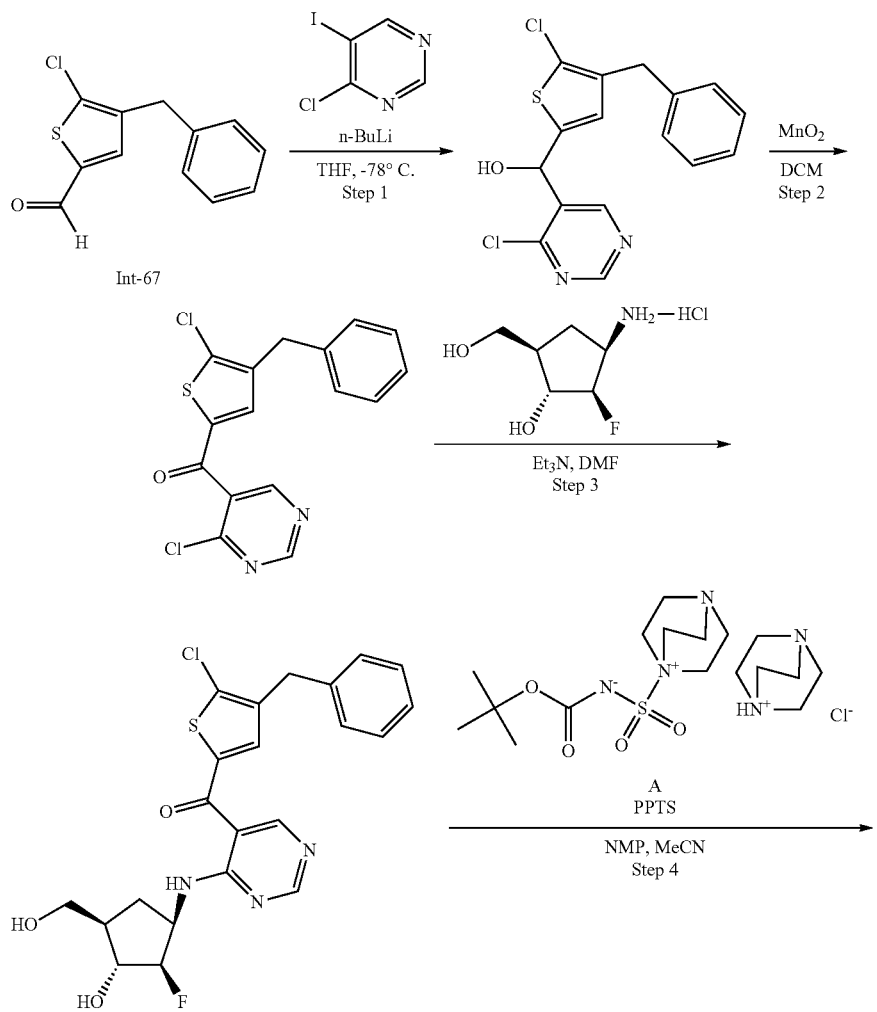

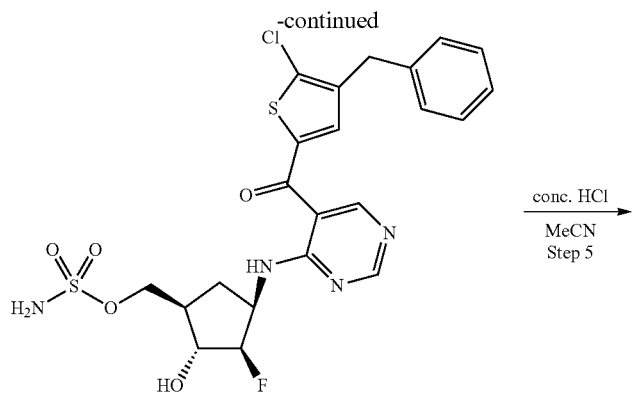

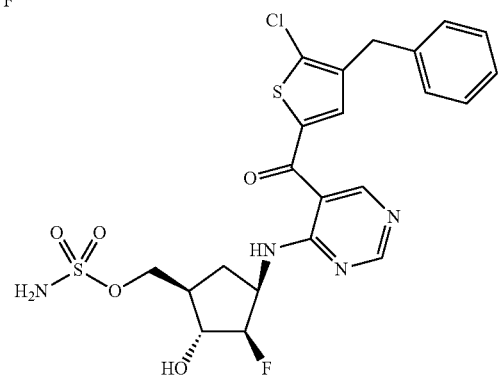

Step 1: rac-(4-Benzyl-5-chloro-2-thienyl)(4-chloropyrimidin-5-yl)methanol

The title compound was prepared in an analogous fashion to Example 131, step 7 beginning with aldehyde Int-67. LCMS (FA): m/z=352.9 (M+H)

Step 2: (4-Benzyl-5-chloro-2-thienyl)(4-chloropyrimidin-5-yl)methanone

The title compound was prepared in an analogous fashion to Example 131, step 8. LCMS (FA): m/z=350.8 (M+H)

Step 3: (4-Benzyl-5-chloro-2-thienyl)(4-{[(1R,2R,3R,4R)-2-fluoro-3-hydroxy-4-(hydroxymethyl)cyclopentyl]amino}pyrimidin-5-yl)methanone (4-Benzyl-5-chloro-2-thienyl)(4-chloropyrimidin-5-yl)methanone (0.11 g, 0.31 mmol) and (1R,2R,3R,5R)-3-amino-2-fluoro-5-(hydroxymethyl)cyclopentanol hydrochloride (70.2 mg, 0.38 mmol) (for synthesis see: Biggadike, K. et al. J. Chem. Soc. Perkin Trans. 1988, 3, 549-554; Borthwick, A. D. et al. J. Med. Chem. 1990, 33, 179-186.) were weighed into a reaction vessel. To this mixture was added i-PrOH (3.8 mL) and N,N-diisopropylethylamine (0.17 mL, 0.95 mmol) and the resulting mixture was stirred at 50° C. for 16 h. The reaction was cooled to rt and the reaction was concentrated in vacuo. The crude product was purified on ISCO column chromatography (0%-10% MeOH/DCM as eluent) to give the title compound (yield=147 mg). LCMS (FA): m/z=541.0 (M+H)

Step 4: tert-Butyl ({[(1R,2R,3R,4R)-4-({5-[(4-benzyl-5-chloro-2-thienyl)carbonyl]pyrimidin-4-yl}amino)-3-fluoro-2-hydroxycyclopentyl]methoxy}sulfonyl)carbamate To a solution of (4-benzyl-5-chloro-2-thienyl)(4-{[(1R,2R,3R,4R)-2-fluoro-3-hydroxy-4-(hydroxymethyl)cyclopentyl]amino}pyrimidin-5-yl)methanone (0.13 g, 0.28 mmol) in NMP (1.4 mL) and CH₃CN (0.69 mL, 13 mmol) was added PPTS (70.7 mg, 0.28 mmol). To the mixture was added (4-aza-1-azoniabicyclo[2.2.2]oct-1-ylsulfonyl)(tert-butoxycarbonyl)azanide-1,4-diazabicyclo[2.2.2]octane hydrochloride (0.37 g, 0.84 mmol), followed by additional aliquots of (4-aza-1-azoniabicyclo[2.2.2]oct-1-ylsulfonyl)(tert-butoxycarbonyl)azanide-1,4-diazabicyclo[2.2.2]octane hydrochloride until the reaction completed (total 525 mg, 1.19 mmol). The reaction was quenched by the addition of water and the mixture was extracted with EtOAc (3×). The combined organic layers were washed with water, dried over MgSO₄, filtered and concentrated in vacuo. The crude product was purified on ISCO column chromatography (0%-10% MeOH/DCM as eluent) to give the title compound (yield=180 mg). LCMS (FA): m/z=641.0 (M+H)

Step 5: [(1R,2R,3R,4R)-4-({5-[(4-Benzyl-5-chloro-2-thienyl)carbonyl]pyrimidin-4-yl}amino)-3-fluoro-2-hydroxycyclopentyl]methyl sulfamate A solution of tert-butyl ({[(1R,2R,3R,4R)-4-({5-[(4-benzyl-5-chloro-2-thienyl)carbonyl]pyrimidin-4-yl}amino)-3-fluoro-2-hydroxycyclopentyl]methoxy}sulfonyl)carbamate (0.18 g, 0.28 mmol) in CH₃CN (2.8 mL) and cooled to 0° C. To this mixture was added 12.0 M of (1.87 mL, 22.2 mmol). The mixture was then allowed to stir at rt for 30 h. The reaction was quenched by addition of saturated NaHCO₃. The mixture was diluted with a little water and extracted with EtOAc (×3). The combined organic layers were dried over MgSO₄, filtered, and concentrated in vacuo. The crude mixture was purified by preparative HPLC to give the title compound (yield=65 mg) (43%). ¹H NMR (400 MHz, DMSO-d₆) δ 8.78 (s, 1H), 8.71 (s, 1H), 8.42 (d, J=7.9 Hz, 1H), 7.76 (s, 1H), 7.50 (s, 2H), 7.34-7.24 (m, 4H), 7.24-7.17 (m, 1H), 5.76-5.39 (m, 1H), 4.93-4.61 (m, 2H), 4.10 (dd, J=9.8, 5.9 Hz, 1H), 4.05-3.96 (m, 3H), 3.91 (dd, J=22.3, 4.2 Hz, 1H), 2.34-2.24 (m, 1H), 2.20-2.12 (m, 1H), 1.55-1.42 (m, 1H). LCMS (FA): m/z=541.0 (M+H)

The compounds listed in the table below were prepared in an analogous fashion to that described above starting from the appropriate starting materials. The desilylating agent and solvent described were used in step 5.

| Starting material | Step 5 condition | Compound No. |
|---|---|---|
| Int-79 | H3PO4/ CH3CN | I-101 |
| Int-65 | HCl/ CH3CN | I-65 |

Example 178: [(1R,2S,4R)-4-{[5-({5-Chloro-4-[(1S)-1-(3-chlorophenyl)-1,3-dihydroxypropyl]-2-thienyl}carbonyl)pyrimidin-4-yl]amino}-2-hydroxycyclopentyl]methyl sulfamate and [(1R,2S,4R)-4-{[5-({5-Chloro-4-[(1R)-1-(3-chlorophenyl)-1,3-dihydroxypropyl]-2-thienyl}carbonyl)pyrimidin-4-yl]amino}-2-hydroxycyclopentyl]methyl sulfamate. I-49

Step 1: [(1R,2S,4R)-4-{[5-({5-Chloro-4-[(1S)-1-(3-chlorophenyl)-1,3-dihydroxypropyl]-2-thienyl}carbonyl)pyrimidin-4-yl]amino}-2-hydroxycyclopentyl]methyl sulfamate and [(1R,2S,4R)-4-{[5-({5-Chloro-4-[(1R)-1-(3-chlorophenyl)-1,3-dihydroxypropyl]-2-thienyl}carbonyl)pyrimidin-4-yl]amino}-2-hydroxycyclopentyl]methyl sulfamate To a solution of I-67 (40.0 mg, 66.7 umol) in THF (3.0 mL) was added 1.0 M of HCl (3.00 mL, 3.00 mmol) and the mixture was stirred for 10 min at 40° C. The reaction was concentrated in vacuo and the residue was purified by preparative HPLC to yield 22 mg (53%) of the title compound. $^1$H NMR (400 MHz, Methanol-$d_4$) δ 8.79 (s, 1H), 8.63 (s, 1H), 7.81 (s, 1H), 7.53-7.46 (m, 1H), 7.41-7.36 (m, 1H), 7.34 (t, J=7.7 Hz, 1H), 7.31-7.27 (m, 1H), 4.86-4.78 (m, 1H), 4.27-4.14 (m, 3H), 3.65 (t, J=7.0 Hz, 2H), 2.85-2.75 (m, 1H), 2.61-2.48 (m, 2H), 2.35-2.24 (m, 1H), 2.23-2.13 (m, 1H), 1.99-1.89 (m, 1H), 1.58-1.48 (m, 1H). LCMS (AA): m/z=619.2 (M+H)

Example 179: [(1R,2S,4R)-4-{[5-({4-[(1S)-1-(3-Bromophenyl)-1-hydroxyethyl]-2-thienyl}carbonyl)pyrimidin-4-yl]amino}-2-hydroxycyclopentyl]methyl sulfamate and [(1R,2S,4R)-4-{[5-({4-[(1R)-1-(3-Bromophenyl)-1-hydroxyethyl]-2-thienyl}carbonyl)pyrimidin-4-yl]amino}-2-hydroxycyclopentyl]methyl sulfamate I-3, and [(1R,2S,4R)-4-{[5-({4-[1-(3-Bromophenyl)vinyl]-2-thienyl}carbonyl)pyrimidin-4-yl]amino}-2-hydroxycyclopentyl]methyl sulfamate I-164

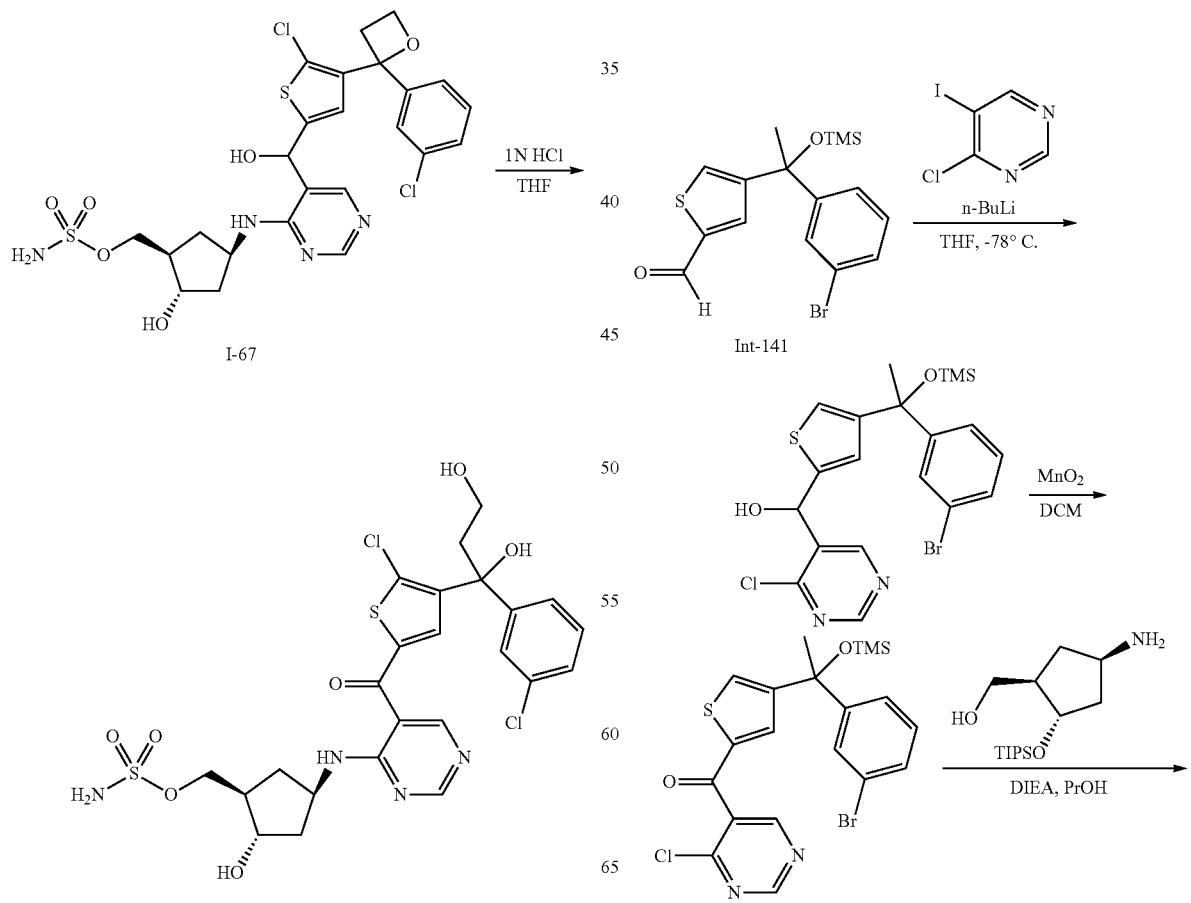

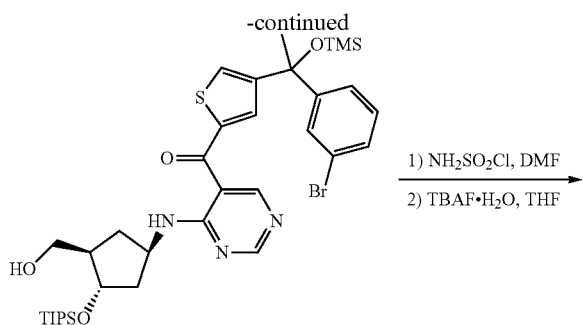

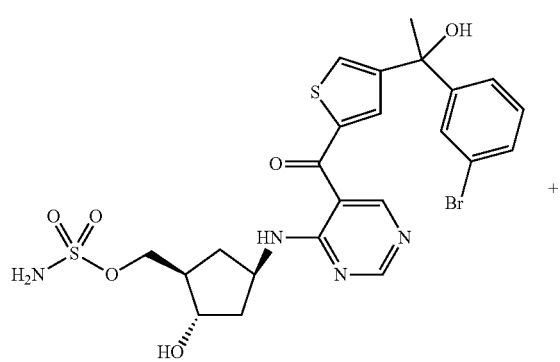

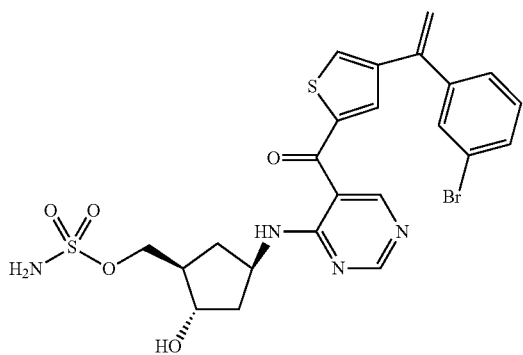 [SMILES: C=C(c1cccc(Br)c1)c1csc(C(=O)c2cncnc2N[C@@H]2C[C@H](COS(N)(=O)=O)[C@@H](O)C2)c1]

Step 1: (4-{1-(3-Bromophenyl)-1-[(trimethylsilyl)oxy]ethyl}-2-thienyl)(4-chloropyrimidin-5-yl)methanol The title compound was prepared in analogous fashion to Example 131, step 7 beginning from Int-141. 304 mg (71%) LCMS (AA): m/z=499.2 (M+1).

Step 2: rac-(4-{1-(3-Bromophenyl)-1-[(trimethylsilyl)oxy]ethyl}-2-thienyl)(4-chloropyrimidin-5-yl)methanone The title compound was prepared in analogous fashion to Example 131, step 8. 246 mg (81%) $^1$H NMR (400 MHz, Chloroform-d) δ 9.10 (s, 1H), 8.72-8.69 (m, 1H), 7.70 (d, J=1.5 Hz, 1H), 7.48 (t, J=1.8 Hz, 1H), 7.35 (ddd, J=7.7, 1.9, 1.2 Hz, 1H), 7.24-7.19 (m, 2H), 7.15 (t, J=7.8 Hz, 1H), 1.91 (s, 3H), 0.01 (s, 9H).

Step 3: (4-{(1S)-1-(3-Bromophenyl)-1-[(trimethylsilyl)oxy]ethyl}-2-thienyl)[4-({(1R,3R,4S)-3-(hydroxymethyl)-4-[(triisopropylsilyl)oxy]cyclopentyl}amino)pyrimidin-5-yl]methanone and (4-{(1R)-1-(3-Bromophenyl)-1-[(trimethylsilyl)oxy]ethyl}-2-thienyl)[4-({(1R,3R,4S)-3-(hydroxymethyl)-4-[(triisopropylsilyl)oxy]cyclopentyl}amino)pyrimidin-5-yl]methanone Int-262 (287 mg, 0.74 mmol) was dissolved into 10 ml TFA at rt, and then stirred for 1 hour at rt. The mixture was concentrated in vacuo and the residue was dissolved with i-PrOH (20.0 mL). To the solution was added N,N-diisopropylethylamine (0.86 mL, 4.94 mmol) followed by Int-141 (245 mg, 0.49 mmol) at rt and the reaction was stirred for 4 h at 70° C. After cooling to rt, the reaction mixture was concentrated in vacuo and the residue was purified by ISCO column chromatography (0%-50% EtOAc in hexanes as eluent) to give 289 mg (78%) of the title compound. LCMS (AA): m/z=746.5 (M+H)

Step 4: [(1R,2S,4R)-4-{[5-({4-[(1S)-1-(3-Bromophenyl)-1-hydroxyethyl]-2-thienyl}carbonyl)pyrimidin-4-yl]amino}-2-hydroxycyclopentyl]methyl sulfamate and (1R,2S,4R)-4-{[5-({4-[(1R)-1-(3-Bromophenyl)-1-hydroxyethyl]-2-thienyl}carbonyl)pyrimidin-4-yl]amino}-2-hydroxycyclopentyl]methyl sulfamate and [(1R,2S,4R)-4-{[5-({4-[1-(3-Bromophenyl)vinyl]-2-thienyl}carbonyl)pyrimidin-4-yl]amino}-2-hydroxycyclopentyl]methyl sulfamate To a solution of the product mixture from step 3 (289 mg, 0.39 mmol) in DMF (6.0 mL) was added chlorosulfonamide (134 mg, 1.16 mmol), and the reaction was stirred at rt for 30 min. The reaction mixture was poured into the solution of 25 ml water and 25 ml saturated NaHCO$_3$. The mixture was extracted with EtOAc (40 mL×2). The combined organic layers were concentrated in vacuo. The residues were dissolved into THF (10.0 mL), and then TBAF hydrate (541 mg, 1.94 mmol) was added to this solution. The reaction was stirred at rt overnight. The mixture was poured into 30 ml saturated NaHCO$_3$ solution and then extracted with EtOAc (30 ml×3). The combined organic layers were concentrated to dry and purified by preparative HPLC to provide the title compounds as follows:

[(1R,2S,4R)-4-{[5-({4-[(1S)-1-(3-Bromophenyl)-1-hydroxyethyl]-2-thienyl}carbonyl)pyrimidin-4-yl]amino}-2-hydroxycyclopentyl]methyl sulfamate and [(1R,2S,4R)-4-{[5-({4-[(1R)-1-(3-Bromophenyl)-1-hydroxyethyl]-2-thienyl}carbonyl)pyrimidin-4-yl]amino}-2-hydroxycyclopentyl]methyl sulfamate I-3

97.3 mg (42%). $^1$H NMR (400 MHz, Methanol-d$_4$) δ 8.67 (s, 1H), 8.58 (s, 1H), 7.82 (d, J=1.4 Hz, 1H), 7.68 (t, J=1.9 Hz, 1H), 7.57 (d, J=1.4 Hz, 1H), 7.45-7.38 (m, 2H), 7.30-7.19 (m, 1H), 4.80 (p, J=8.1 Hz, 1H), 4.26-4.15 (m, 3H), 2.50 (m, 1H), 2.33-2.23 (m, 1H), 2.16 (m, 1H), 1.92 (s, 3H), 1.91-1.86 (m, 1H), 1.42 (m, 1H). LCMS (AA): m/z=599.0 (M+1).

[(1R,2S,4R)-4-{[5-({4-[1-(3-Bromophenyl)vinyl]-2-thienyl}carbonyl)pyrimidin-4-yl]amino}-2-hydroxycyclopentyl]methyl sulfamate I-164

24.3 mg (11%). $^1$H NMR (400 MHz, MeOD) δ 8.78 (s, 1H), 8.59 (s, 1H), 7.76 (s, 1H), 7.71 (s, 1H), 7.60-7.48 (m,

2H), 7.40-7.27 (m, 2H), 5.71 (s, 1H), 5.48 (s, 1H), 4.82 (dd, J=16.2, 8.0 Hz, 1H), 4.20 (qd, J=9.9, 5.9 Hz, 3H), 2.59-2.47 (m, 1H), 2.33-2.24 (m, 1H), 2.18 (ddd, J=12.8, 7.9, 4.6 Hz, 1H), 1.92 (dd, J=10.3, 5.0 Hz, 1H), 1.46 (dt, J=13.0, 9.1 Hz, 1H). LCMS (AA): m/z=581.0 (M+1).

Example 180: [(1R,2S,4R)-4-({5-[(4,5-Dibenzyl-2-thienyl)carbonyl]pyrimidin-4-yl}amino)-2-hydroxy-cyclopentyl]methyl sulfamate I-144

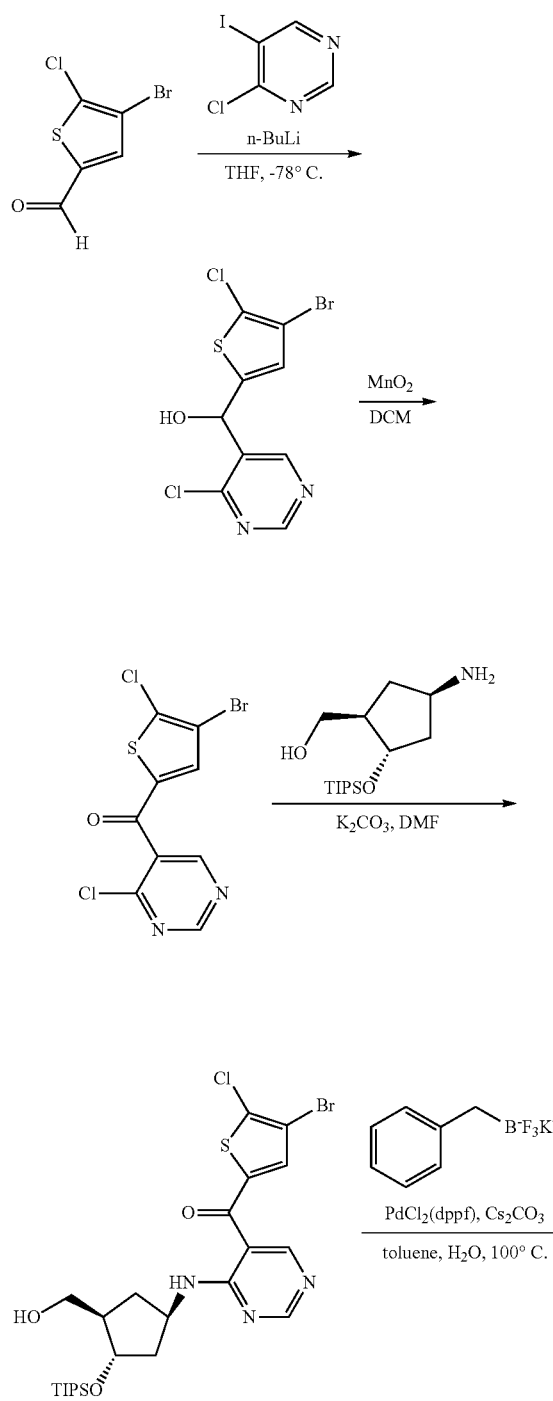

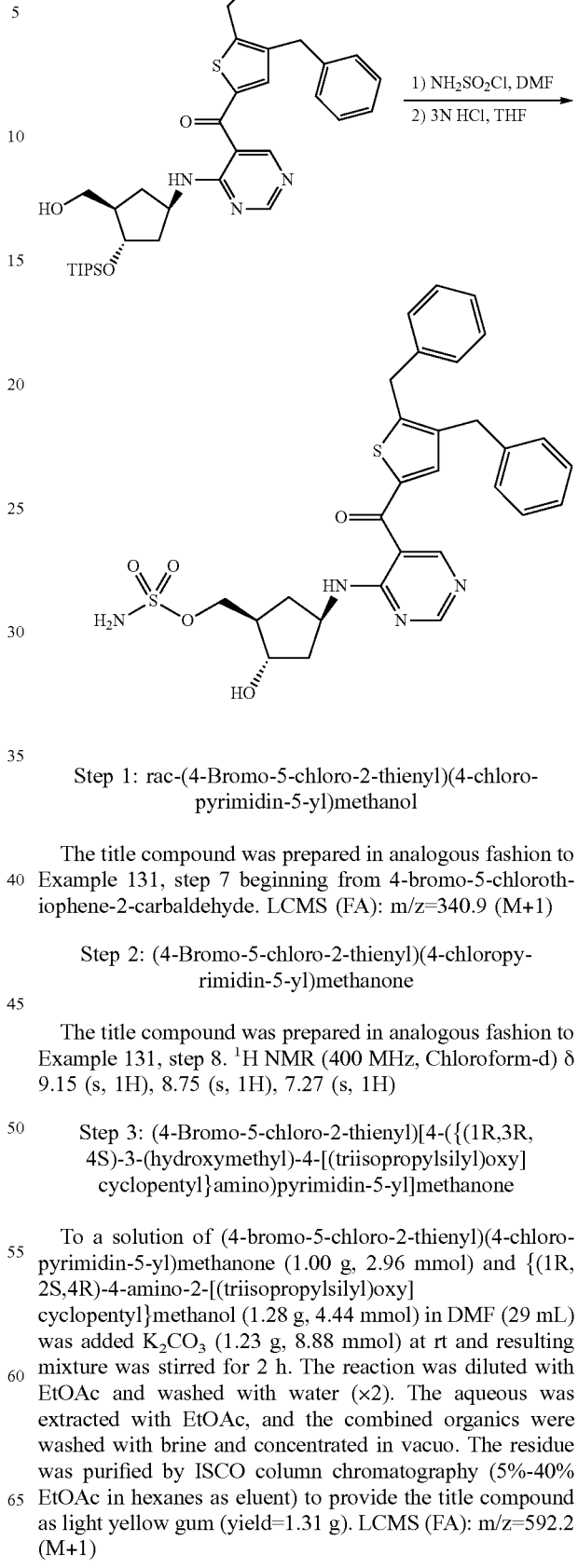

Step 1: rac-(4-Bromo-5-chloro-2-thienyl)(4-chloro-pyrimidin-5-yl)methanol

The title compound was prepared in analogous fashion to Example 131, step 7 beginning from 4-bromo-5-chlorothiophene-2-carbaldehyde. LCMS (FA): m/z=340.9 (M+1)

Step 2: (4-Bromo-5-chloro-2-thienyl)(4-chloropyrimidin-5-yl)methanone

The title compound was prepared in analogous fashion to Example 131, step 8. $^1$H NMR (400 MHz, Chloroform-d) δ 9.15 (s, 1H), 8.75 (s, 1H), 7.27 (s, 1H)

Step 3: (4-Bromo-5-chloro-2-thienyl)[4-({(1R,3R,4S)-3-(hydroxymethyl)-4-[(triisopropylsilyl)oxy]cyclopentyl}amino)pyrimidin-5-yl]methanone To a solution of (4-bromo-5-chloro-2-thienyl)(4-chloro-pyrimidin-5-yl)methanone (1.00 g, 2.96 mmol) and {(1R,2S,4R)-4-amino-2-[(triisopropylsilyl)oxy]cyclopentyl}methanol (1.28 g, 4.44 mmol) in DMF (29 mL) was added K$_2$CO$_3$ (1.23 g, 8.88 mmol) at rt and resulting mixture was stirred for 2 h. The reaction was diluted with EtOAc and washed with water (×2). The aqueous was extracted with EtOAc, and the combined organics were washed with brine and concentrated in vacuo. The residue was purified by ISCO column chromatography (5%-40% EtOAc in hexanes as eluent) to provide the title compound as light yellow gum (yield=1.31 g). LCMS (FA): m/z=592.2 (M+1)

Step 4: (4,5-Dibenzyl-2-thienyl)[4-({(1R,3R,4S)-3-(hydroxymethyl)-4-[(triisopropylsilyl)oxy]cyclopentyl}amino)pyrimidin-5-yl]methanone To a solution of (4-Bromo-5-chloro-2-thienyl)[4-({(1R,3R,4S)-3-(hydroxymethyl)-4-[(triisopropylsilyl)oxy]cyclopentyl}amino)pyrimidin-5-yl]methanone (103 mg, 0.18 mmol) in toluene (2.0 mL) and water (0.20 mL, 11.1 mmol) was added Cs$_2$CO$_3$ (285 mg, 0.87 mmol) and argon was bubbled through for 5 min. Benzyltrifluoroborate potassium salt (173 mg, 0.87 mmol) and [1,1'-bis(diphenylphosphino)ferrocene]palladium(II)dichloride (7.19 mg, 8.74 umol) were added and the vial was flushed with argon and sealed. The reaction was heated at 100° C. for 5 h. The reaction was diluted with EtOAc and filtered through a pad of Celite. The filtrate was washed with water (×2), brine, dried over Na$_2$SO$_4$, filtered and concentrated in vacuo. The residue was purified via ISCO column chromatography (30% EtOAc in hexanes as eluent) to give the title compound as yellow oil (yield=34 mg). LCMS (FA): m/z=656.4 (M+1).

Step 5: [(1R,2S,4R)-4-({5-[(4,5-Dibenzyl-2-thienyl)carbonyl]pyrimidin-4-yl}amino)-2-hydroxycyclopentyl]methyl sulfamate A solution of (4,5-dibenzyl-2-thienyl)[4-({(1R,3R,4S)-3-(hydroxymethyl)-4-[(triisopropylsilyl)oxy]cyclopentyl}amino)pyrimidin-5-yl]methanone (33 mg, 0.050 mmol) in DMF (1.0 mL) was cooled to 0° C., to which was added triethylamine (0.10 mL, 0.72 mmol) followed by chlorosulfonamide (32.5 mg, 0.28 mmol) and the reaction was stirred at 0° C. for 30 min. To the reaction was added 3.0M HCl in water at 0° C. and the mixture was warmed to rt. After stirring overnight, the reaction was quenched with saturated NaHCO$_3$ and the mixture was extracted with EtOAc (×3). The combined organic extracts were washed with 10% aqueous LiCl solution (×3), brine, dried over Na$_2$SO$_4$, filtered and concentrated in vacuo. The residue was purified via ISCO column chromatography (7% MeOH in DCM as eluent) to give the title compound as an off-white solid (yield=24 mg). $^1$H NMR (400 MHz, MeOD) δ 8.62 (s, 1H), 8.53 (s, 1H), 7.38 (s, 1H), 7.33-7.11 (m, 10H), 4.81-4.70 (m, 1H), 4.22-4.10 (m, 5H), 3.99 (s, 2H), 2.54-2.42 (m, 1H), 2.30-2.08 (m, 2H), 1.93-1.81 (m, 1H), 1.46-1.34 (m, 1H). LCMS (FA): m/z=579.4 (M+1).

Example 181: [(1R,2S,4R)-4-{[5-({4-[(S)-(3-Bromophenyl)(methoxy)methyl]-2-thienyl}carbonyl)pyrimidin-4-yl]amino}-2-hydroxycyclopentyl]methyl sulfamate or [(1R,2S,4R)-4-{[5-({4-[(R)-(3-Bromophenyl)(methoxy)methyl]-2-thienyl}carbonyl)pyrimidin-4-yl]amino}-2-hydroxycyclopentyl]methyl sulfamate (peak1) I-73a and [(1R,2S,4R)-4-{[5-({4-[(S)-(3-Bromophenyl)(methoxy)methyl]-2-thienyl}carbonyl)pyrimidin-4-yl]amino}-2-hydroxycyclopentyl]methyl sulfamate or [(1R,2S,4R)-4-{[5-({4-[(R)-(3-Bromophenyl)(methoxy)methyl]-2-thienyl}carbonyl)pyrimidin-4-yl]amino}-2-hydroxycyclopentyl]methyl sulfamate (peak2) I-73b

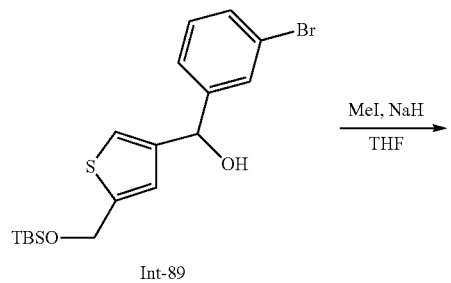

Int-89

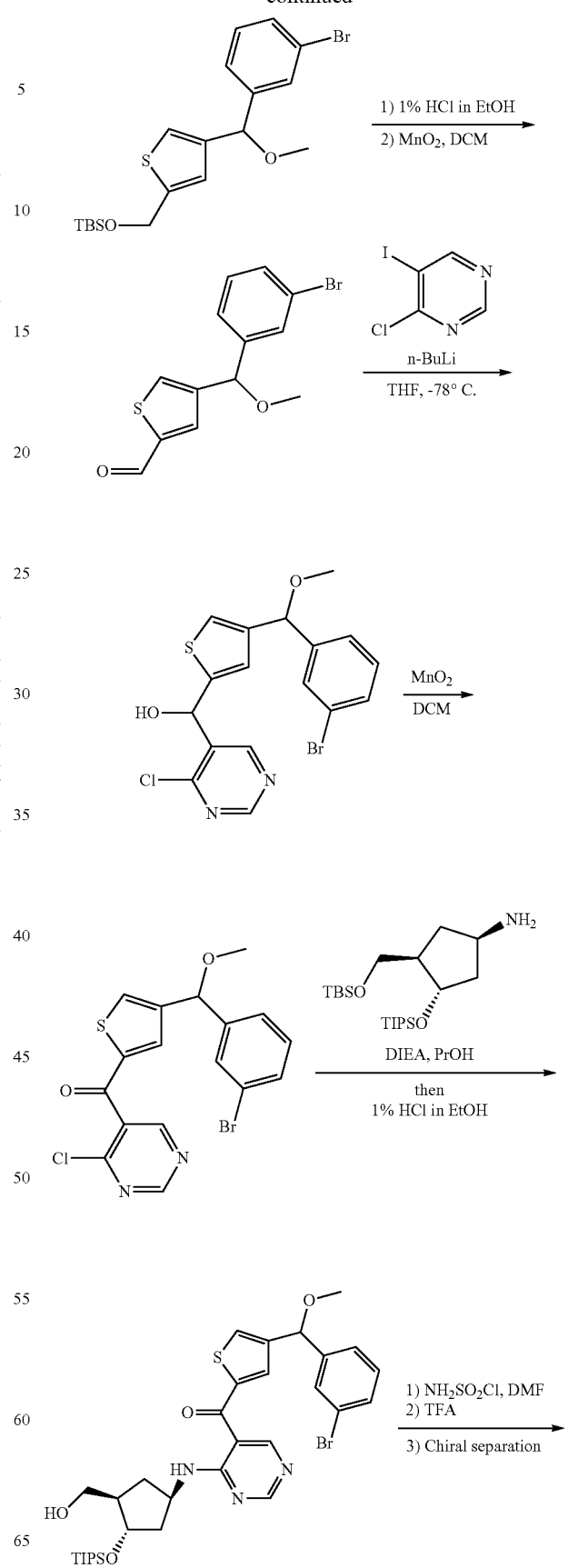

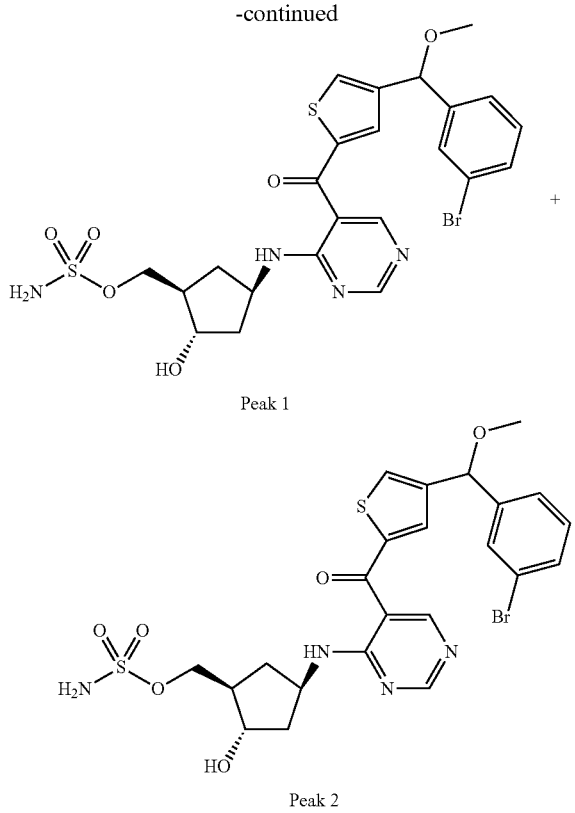

Peak 1

Peak 2

Step 1: rac-({4-[(3-Bromophenyl)(methoxy)methyl]-2-thienyl}methoxy)(tert-butyl)dimethylsilane To a solution of Int-89 (0.841 g, 2.03 mmol) in THF (20.0 mL) was added 60% NaH in mineral oil (293 mg, 6.10 mmol) followed by MeI (0.38 mL, 6.10 mmol) and the reaction was heated at 50° C. for 1 hour. The solution was poured into 30 ml saturated NH$_4$Cl solution and the mixture was extracted with DCM (30 mL×2). The combined organic layers were concentrated in vacuo and the residue was purified by ISCO column chromatography (0%-35% EtOAc in hexanes as eluent) to give 721 mg (83%) of the title compound. $^1$H NMR (400 MHz, Chloroform-d) δ 7.44 (t, J=1.8 Hz, 1H), 7.36-7.29 (m, 1H), 7.20-7.17 (m, 1H), 7.13 (t, J=7.7 Hz, 1H), 6.97 (m, 1H), 6.67 (d, J=1.1 Hz, 1H), 5.10 (s, 1H), 4.72 (s, 2H), 3.28 (s, 3H), 0.85-0.82 (s, 9H), 0.00 (s, 6H).

Step 2: rac-4-[(3-Bromophenyl)(methoxy)methyl]thiophene-2-carbaldehyde

A solution of ({4-[(3-bromophenyl)(methoxy)methyl]-2-thienyl}methoxy)(tert-butyl)dimethylsilane (352 mg, 0.82 mmol) in 1% HCl in EtOH (20 mL) was stirred at rt for 30 min. The reaction mixture was poured into 30 ml saturated NH$_4$Cl solution, and then extracted with DCM (30 mL×2). The organic layers were concentrated in vacuo and the residue was dissolved into DCM (30 mL). To the solution was added MnO$_2$ (1.07 g, 12.4 mmol) and the mixture was stirred at 40° C. for 3 h. The reaction mixture was filtered through a Celite pad and the filter cake was washed with DCM. The filtrate was concentrated in vacuo and the residue was purified by ISCO column chromatography (0%-35% EtOAc in hexanes as eluent) to give 182 mg (71%) of the title compound. $^1$H NMR (400 MHz, Chloroform-d) δ 9.86 (d, J=1.3 Hz, 1H), 7.63 (d, J=1.3 Hz, 1H), 7.59 (q, J=1.3 Hz, 1H), 7.55-7.52 (m, 1H), 7.47 (m, 1H), 7.32-7.22 (m, 2H), 5.26 (s, 1H), 3.40 (s, 3H).

Step 3: {4-[(3-Bromophenyl)(methoxy)methyl]-2-thienyl}(4-chloropyrimidin-5-yl)methanol The title compound was prepared in an analogous fashion to Example 131 Step 7. 185 mg (74%) LCMS (AA): m/z=426.9 (M+H).

Step 4: rac-{4-[(3-Bromophenyl)(methoxy)methyl]-2-thienyl}(4-chloropyrimidin-5-yl)methanone The title compound was prepared in an analogous fashion to Example 131 Step 8. 168 mg (91%). $^1$H NMR (400 MHz, Chloroform-d) δ 9.12 (s, 1H), 8.74 (s, 1H), 7.60 (s, 1H), 7.49-7.40 (m, 2H), 7.34 (d, J=1.2 Hz, 1H), 7.27-7.20 (m, 2H), 5.20 (s, 1H), 3.34 (s, 3H).

Step 5: {4-[(S)-(3-Bromophenyl)(methoxy)methyl]-2-thienyl}[4-({(1R,3R,4S)-3-(hydroxymethyl)-4-[(triisopropylsilyl)oxy]cyclopentyl}amino)pyrimidin-5-yl]methanone and {4-[(R)-(3-Bromophenyl)(methoxy)methyl]-2-thienyl}[4-({(1R,3R,4S)-3-(hydroxymethyl)-4-[(triisopropylsilyl)oxy]cyclopentyl}amino)pyrimidin-5-yl]methanone rac-{4-[(3-Bromophenyl)(methoxy)methyl]-2-thienyl}(4-chloropyrimidin-5-yl)methanone (168 mg, 0.40 mmol), amine Int-260 (175 mg, 0.44 mmol) and N,N-diisopropylethylamine (0.14 mL, 0.79 mmol) were dissolved into i-PrOH (20.0 mL). The reaction was stirred at 60° C. for 1 hour. The reaction was concentrated in vacuo and the residue was dissolved in 25 mL of 1% HCl in EtOH solution. The mixture was stirred at rt for 15 min. The solution was poured into 30 ml saturated NaHCO$_3$ solution and then extracted with DCM (30 mL×2). The combined organic layers were concentrated in vacuo and the residue was purified by ISCO column chromatography (0%-70% EtOAc in hexanes as eluent) to give 201 mg (75%) of the title compound. LCMS (AA): m/z=676.1 (M+H)

Step 6: [(1R,2S,4R)-4-{[5-({4-[(S)-(3-Bromophenyl)(methoxy)methyl]-2-thienyl}carbonyl)pyrimidin-4-yl]amino}-2-hydroxycyclopentyl]methyl sulfamate or [(1R,2S,4R)-4-{[5-({4-[(R)-(3-Bromophenyl)(methoxy)methyl]-2-thienyl}carbonyl)pyrimidin-4-yl]amino}-2-hydroxycyclopentyl]methyl sulfamate and [(1R,2S,4R)-4-{[5-({4-[(S)-(3-Bromophenyl)(methoxy)methyl]-2-thienyl}carbonyl)pyrimidin-4-yl]amino}-2-hydroxycyclopentyl]methyl sulfamate or [(1R,2S,4R)-4-{[5-({4-[(R)-(3-Bromophenyl)(methoxy)methyl]-2-thienyl}carbonyl)pyrimidin-4-yl]amino}-2-hydroxycyclopentyl]methyl sulfamate To a solution of {4-[(S and R)-(3-Bromophenyl)(methoxy)methyl]-2-thienyl}[4-({(1R,3R,4S)-3-(hydroxymethyl)-4-[(triisopropylsilyl)oxy]cyclopentyl}amino)pyrimidin-5-yl]methanone (63.2 mg, 0.09 mmol) in DMF (3.0 mL) was added chlorosulfonamide (32.5 g, 0.28 mmol) and the reaction was stirred at rt for 30 min. The reaction mixture was poured into the solution of 25 ml water and 25 ml saturated NaHCO$_3$. The mixture was extracted with EtOAc (40 mL×2). The combined organic layers were concentrated in vacuo. The residue was dissolved into the solution of TFA (14.0 mL) and water (6.0 mL). The mixture was stirred at 40° C. for 30 min. The mixture was concentrated in vacuo and added 5 ml MeOH, 25 ml water, and 25 ml saturated NaHCO$_3$ solution. The resulting mixture was extracted with EtOAc (40 ml×3) and the combined organic layers were concentrated in vacuo. The residue was purified by ISCO column chromatography (0%-15% MeOH in EtOAc as eluent) to give a diastereoisoform mixtures. The products were separated by chiral SFC (CHIRALPAK IA 4.6×100 mm with 35/65 0.3% DEA in EtOH/CO2, 3 mL/min, 10 MPa).

Peak 1: [(1R,2S,4R)-4-{[5-({4-[(S)-(3-Bromophenyl)(methoxy)methyl]-2-thienyl}carbonyl)pyrimidin-4-yl]amino}-2-hydroxycyclopentyl]methyl sulfamate or [(1R,2S,4R)-4-{[5-({4-[(R)-(3-Bromophenyl)(methoxy)methyl]-2-thienyl}carbonyl) pyrimidin-4-yl]amino}-2-hydroxycyclopentyl] methyl sulfamate 7.4 mg (13%) $^1$H NMR (400 MHz, Methanol-d$_4$) δ 8.67 (s, 1H), 8.58 (s, 1H), 7.76 (s, 1H), 7.58 (s, 1H), 7.54 (s, 1H), 7.47-7.43 (m, 1H), 7.37 (s, 1H), 7.31 (d, J=7.8 Hz, 1H), 5.41 (s, 1H), 4.79 (q, J=8.0 Hz, 1H), 4.23-4.14 (m, 3H), 3.39 (s, 3H), 2.57-2.44 (m, 1H), 2.27 (m, 1H), 2.20-2.13 (m, 1H), 1.96-1.86 (m, 1H), 1.42 (m, 1H). LCMS (AA): m/z=599.1 (M+H).

Peak 2: [(1R,2S,4R)-4-{[5-({4-[(S)-(3-Bromophenyl)(methoxy)methyl]-2-thienyl}carbonyl)pyrimidin-4-yl]amino}-2-hydroxycyclopentyl]methyl sulfamate or [(1R,2S,4R)-4-{[5-({4-[(R)-(3-Bromophenyl)(methoxy)methyl]-2-thienyl}carbonyl) pyrimidin-4-yl]amino}-2-hydroxycyclopentyl] methyl sulfamate 5.1 mg (9%)$^1$H NMR (400 MHz, Methanol-d$_4$) δ 8.68 (s, 1H), 8.59 (s, 1H), 7.78 (s, 1H), 7.58 (s, 1H), 7.55 (d, J=1.2 Hz, 1H), 7.47 (d, J=7.9 Hz, 1H), 7.39 (s, 1H), 7.31 (d, J=7.8 Hz, 1H), 5.42 (s, 1H), 4.87-4.77 (m, 1H), 4.24-4.13 (m, 3H), 3.39 (s, 3H), 2.51 (m, 1H), 2.28 (m, 1H), 2.16 (m, 1H), 1.94 (m, 1H), 1.43 (m, 1H). LCMS (AA): m/z=599.1 (M+H).

Example 182: [(1R,2R,3S,4R)-4-{[5-({4-[(S)-Amino(3-chlorophenyl)methyl]-5-chloro-2-thienyl}carbonyl)pyrimidin-4-yl]amino}-2,3-dihydroxycyclopentyl]methyl sulfamate or [(1R,2R,3S, 4R)-4-{[5-({4-[(R)-Amino(3-chlorophenyl)methyl]-5-chloro-2-thienyl}carbonyl)pyrimidin-4-yl]amino}-2,3-dihydroxycyclopentyl]methyl sulfamate (Peak1) I-14a and [(1R,2R,3S,4R)-4-{[5-({4-[(S)-Amino(3-chlorophenyl)methyl]-5-chloro-2-thienyl}carbonyl) pyrimidin-4-yl]amino}-2,3-dihydroxycyclopentyl] methyl sulfamate or [(1R,2R,3S,4R)-4-{[5-({4-[(R)-Amino(3-chlorophenyl)methyl]-5-chloro-2-thienyl}carbonyl)pyrimidin-4-yl]amino}-2,3-dihydroxycyclopentyl]methyl sulfamate (Peak2) I-14b

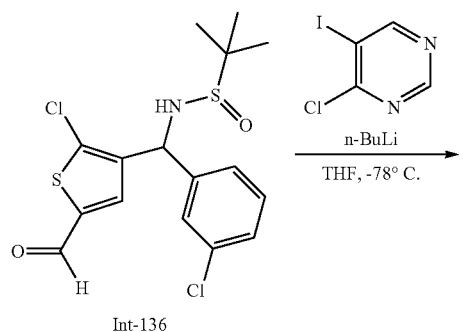

Int-136

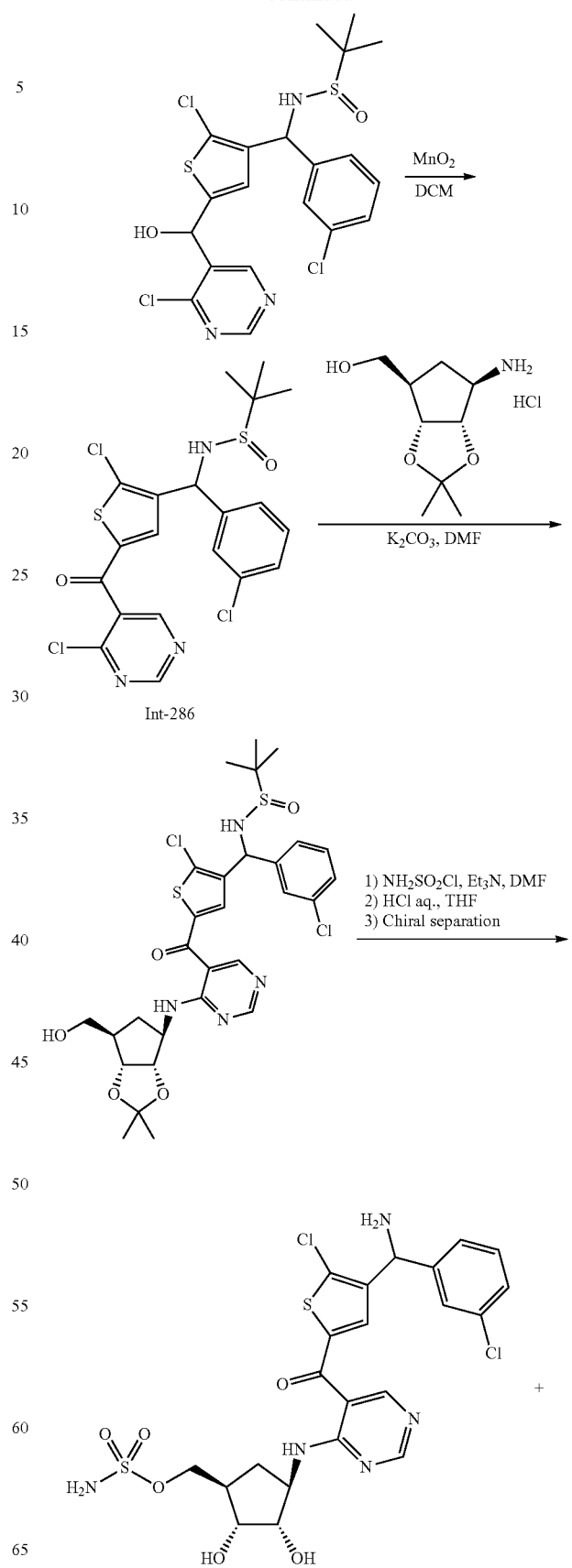

Int-286

-continued

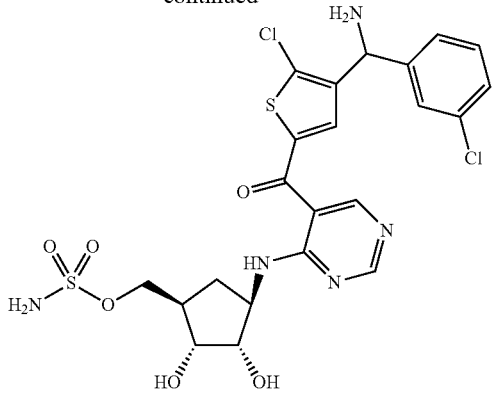

Step 1: N—[(S)-{2-Chloro-5-[(S)-(4-chloropyrimidin-5-yl)(hydroxy)methyl]-3-thienyl}(3-chlorophenyl)methyl]-2-methylpropane-2-sulfinamide, N—[(R)-{2-Chloro-5-[(R)-(4-chloropyrimidin-5-yl)(hydroxy)methyl]-3-thienyl}(3-chlorophenyl)methyl]-2-methylpropane-2-sulfinamide, N—[(S)-{2-Chloro-5-[(R)-(4-chloropyrimidin-5-yl)(hydroxy)methyl]-3-thienyl}(3-chlorophenyl)methyl]-2-methylpropane-2-sulfinamide, and N—[(R)-{2-Chloro-5-[(S)-(4-chloropyrimidin-5-yl)(hydroxy)methyl]-3-thienyl}(3-chlorophenyl)methyl]-2-methylpropane-2-sulfinamide The title compound was prepared in analogous fashion to Example 131 Step 7, beginning from Int-136. LCMS (FA): m/z=506.0 (M+H).

Step 2: rac-N-[{2-Chloro-5-[(4-chloropyrimidin-5-yl)carbonyl]-3-thienyl}(3-chlorophenyl)methyl]-2-methylpropane-2-sulfinamide Int-286

The title compound was prepared in analogous fashion to Example 131 Step 8. LCMS (FA): m/z=504.0 (M+H).

Step 3: N—[(S)-{2-Chloro-5-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-3-thienyl}(3-chlorophenyl)methyl]-2-methylpropane-2-sulfinamide and N—[(R)-{2-Chloro-5-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-3-thienyl}(3-chlorophenyl)methyl]-2-methylpropane-2-sulfinamide

[(3aR,4R,6R,6aS)-6-Amino-2,2-dimethyltetrahydro-3aH-cyclopenta[d][1,3]dioxol-4-yl]methanol hydrochloride (160 mg, 0.72 mmol) (for synthesis of this starting material see: Claiborne, C. F. et al. PCT Application Publication WO2008/019124), N-[{2-chloro-5-[(4-chloropyrimidin-5-yl)carbonyl]-3-thienyl}(3-chlorophenyl)methyl]-2-methylpropane-2-sulfinamide (0.30 g, 0.60 mmol), and $K_2CO_3$ (247 mg, 1.79 mmol) in DMF (9.0 mL) was stirred at rt for 8 h. The reaction was quenched by addition of water. A solid precipitated and it was collected by filtration and washed with water. The solid was dried on high vacuum overnight to yield 290 mg of the title compound. LCMS (FA): m/z=655.0 (M+H)

Step 4: [(1R,2R,3S,4R)-4-{[5-({4-[(S)-Amino(3-chlorophenyl)methyl]-5-chloro-2-thienyl}carbonyl)pyrimidin-4-yl]amino}-2,3-dihydroxycyclopentyl]methyl sulfamate and [(1R,2R,3S,4R)-4-{[5-({4-[(R)-Amino(3-chlorophenyl)methyl]-5-chloro-2-thienyl}carbonyl)pyrimidin-4-yl]amino}-2,3-dihydroxycyclopentyl]methyl sulfamate A solution of the product mixture from step 3 (0.28 g, 0.43 mmol) in DMF (2.7 mL) and THF (2.7 mL) was cooled to −78° C., to which was added triethylamine (1.19 mL, 8.57 mmol) followed by chlorosulfonamide (0.89 g, 7.71 mmol) and the mixture was stirred at −78° C. for 1 hour. Additional DMF (1 mL), THF (1 mL), triethylamine (0.30 mL, 2.14 mmol), and chlorosulfonamide (0.25 g, 2.14 mmol) were added to the reaction mixture and stirring was continued at −78° C. for 2 h. 1.250 M of HCl in EtOH (16.8 mL, 21.0 mmol) was added to the mixture and the reaction was allowed to warm to rt. After stirring 45 min at rt, 3.0 M of HCl in water (7.10 mL, 21.3 mmol) was added and the mixture was stirred for 18 h. The reaction was quenched via addition of saturated $NaHCO_3$ until pH 9. The resulting mixture was partitioned between water and EtOAc. Layers were separated, and the aqueous layer was extracted w/EtOAc (3×). The combined organic layers were dried over $MgSO_4$, filtered, and concentrated in vacuo. The crude product was purified on ISCO column chromatography (0%-15% MeOH/DCM as eluent) to give the mixture of the title compounds (yield=118 mg). LCMS (FA): m/z=590.0 (M+H).

Step 5: [(1R,2R,3S,4R)-4-{[5-({4-[(S)-Amino(3-chlorophenyl)methyl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(R)-Amino(3-chlorophenyl)methyl]-5-chloro-2-thienyl}carbonyl)pyrimidin-4-yl]amino}-2,3-dihydroxycyclopentyl]methyl sulfamate and [(1R,2R,3S,4R)-4-{[5-({4-[(S)-Amino(3-chlorophenyl)methyl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(R)-Amino(3-chlorophenyl)methyl]-5-chloro-2-thienyl}carbonyl)pyrimidin-4-yl]amino}-2,3-dihydroxycyclopentyl]methyl sulfamate A mixture of the two product diastereomers from step 4 (115 mg, 0.20 mmol) was separated to provide the individual diastereomers by chiral HPLC to afford I-14a (27 mg, first eluting compound) and I-14b (42 mg, second eluting compound).

Peak 1: [(1R,2R,3S,4R)-4-{[5-({4-[(S)-Amino(3-chlorophenyl)methyl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(R)-Amino(3-chlorophenyl)methyl]-5-chloro-2-thienyl}carbonyl)pyrimidin-4-yl]amino}-2,3-dihydroxycyclopentyl]methyl sulfamate I-14a $^1$H NMR (400 MHz, DMSO-$d_6$) δ 8.73 (s, 1H), 8.66 (s, 1H), 8.31 (d, J=7.7 Hz, 1H), 7.94 (s, 1H), 7.51 (s, 1H), 7.49-7.30 (br s, 2H), 7.37-7.25 (m, 3H), 5.13 (s, 1H), 4.85 (d, J=5.9 Hz, 1H), 4.70 (d, J=4.7 Hz, 1H), 4.47 (p, J=7.8 Hz, 1H), 4.06 (dd, J=9.8, 6.1 Hz, 1H), 3.96 (dd, J=9.7, 6.7 Hz, 1H), 3.83-3.74 (m, 1H), 3.70 (q, J=4.6 Hz, 1H), 2.77-2.54

(br s, 2H), 2.28 (dt, J=12.7, 8.3 Hz, 1H), 2.23-2.12 (m, 1H), 1.16 (dt, J=12.7, 8.8 Hz, 1H).

Peak 2: [(1R,2R,3S,4R)-4-{[5-({4-[(S)-Amino(3-chlorophenyl)methyl]-5-chloro-2-thienyl}carbonyl)pyrimidin-4-yl]amino}-2,3-dihydroxycyclopentyl]methyl sulfamate or [(1R,2R,3S,4R)-4-{[5-({4-[(R)-Amino(3-chlorophenyl)methyl]-5-chloro-2-thienyl}carbonyl)pyrimidin-4-yl]amino}-2,3-dihydroxycyclopentyl]methyl sulfamate I-14b $^1$H NMR (400 MHz, DMSO-d$_6$) δ 8.75 (s, 1H), 8.67 (s, 1H), 8.59-8.36 (br s, 2H), 8.32 (d, J=7.6 Hz, 1H), 7.98 (s, 1H), 7.54 (s, 1H), 7.50-7.41 (br s, 2H), 7.41-7.30 (m, 3H), 5.29 (s, 1H), 4.95-4.81 (br s, 1H), 4.74 (d, J=4.7 Hz, 1H), 4.54-4.41 (m, 1H), 4.07 (dd, J=9.7, 6.1 Hz, 1H), 3.97 (dd, J=11.4, 6.7 Hz, 2H), 3.84-3.76 (m, 1H), 3.74-3.67 (m, 1H), 2.28 (dt, J=12.6, 8.4 Hz, 1H), 2.23-2.14 (m, 1H), 1.19-1.14 (m, 1H).

Example 183: [(1R,2S,4R)-4-{[5-({5-Chloro-4-[(S)-(3-chlorophenyl)(methylamino)methyl]-2-thienyl}carbonyl)pyrimidin-4-yl]amino}-2-hydroxycyclopentyl]methyl sulfamate and [(1R,2S,4R)-4-{[5-({5-Chloro-4-[(R)-(3-chlorophenyl)(methylamino)methyl]-2-thienyl}carbonyl)pyrimidin-4-yl]amino}-2-hydroxycyclopentyl]methyl sulfamate I-95

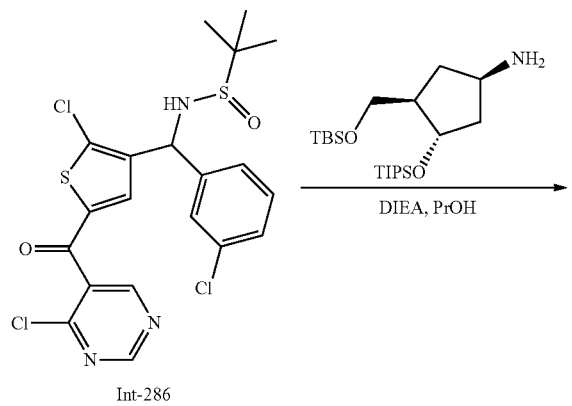

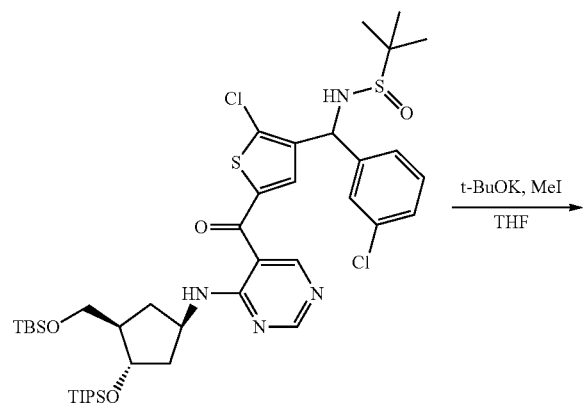

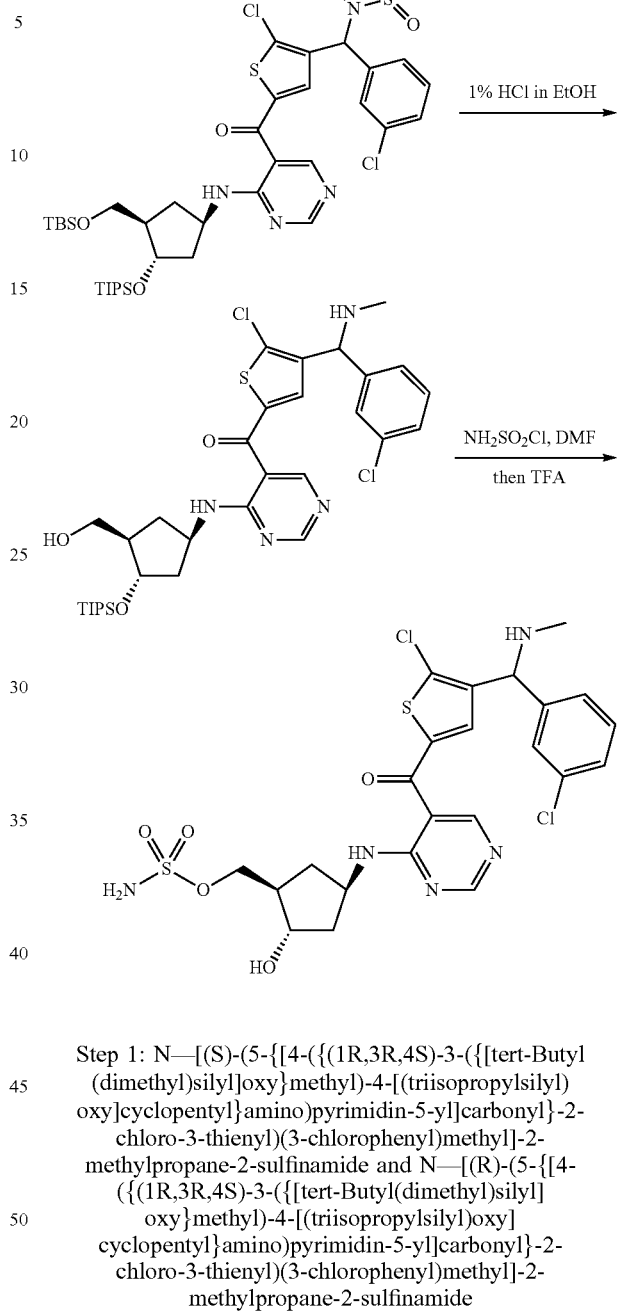

Step 1: N—[(S)-(5-{[4-({(1R,3R,4S)-3-({[tert-Butyl(dimethyl)silyl]oxy}methyl)-4-[(triisopropylsilyl)oxy]cyclopentyl}amino)pyrimidin-5-yl]carbonyl}-2-chloro-3-thienyl)(3-chlorophenyl)methyl]-2-methylpropane-2-sulfinamide and N—[(R)-(5-{[4-({(1R,3R,4S)-3-({[tert-Butyl(dimethyl)silyl]oxy}methyl)-4-[(triisopropylsilyl)oxy]cyclopentyl}amino)pyrimidin-5-yl]carbonyl}-2-chloro-3-thienyl)(3-chlorophenyl)methyl]-2-methylpropane-2-sulfinamide To a solution of Int-260 (192 mg, 0.48 mmol) in i-PrOH (20.0 mL) was added N,N-diisopropylethylamine (0.45 mL, 2.60 mmol) followed by Int-286 (120 mg, 0.24 mmol) at rt and the reaction was stirred for at 70° C. for 4 h. The reaction was concentrated in vacuo and the residue was purified by ISCO column chromatography (0%-80% EtOAc in hexanes as eluent) to give 186 mg (90%) of the title compound mixture. $^1$H NMR (400 MHz, Chloroform-d) δ 8.74 and 8.71 (each s, total 1H), 8.65 and 8.63 (each s, total 1H), 8.53 (d, J=7.3 Hz, 1H), 7.47 and 7.42 (each s, total 1H), 7.38-7.21 (m, 4H), 5.81-5.72 (m, 1H), 4.86-4.73 (m, 1H), 4.33-4.27 (m, 1H), 3.84-3.76 (m, 1H), 3.66-3.58 (m, 1H), 3.58-3.51 (m, 1H), 2.50-2.37 (m, 1H), 2.24-2.08 (m, 2H), 1.77-1.64

(m, 1H), 1.34-1.18 (m, 10H), 1.09-1.01 (m, 21H), 0.90-0.84 (m, 9H), 0.06--0.00 (m, 6H).

Step 2: N—[(S)-(5-{[4-({(1R,3R,4S)-3-({[tert-Butyl (dimethyl)silyl]oxy}methyl)-4-[(triisopropylsilyl) oxy]cyclopentyl}amino)pyrimidin-5-yl]carbonyl}-2-chloro-3-thienyl)(3-chlorophenyl)methyl]-N,2-dimethylpropane-2-sulfinamide and N—[(R)-(5-{[4-({(1R,3R,4S)-3-({[tert-Butyl(dimethyl)silyl] oxy}methyl)-4-[(triisopropylsilyl)oxy] cyclopentyl}amino)pyrimidin-5-yl]carbonyl}-2-chloro-3-thienyl)(3-chlorophenyl)methyl]-N,2-dimethylpropane-2-sulfinamide To a solution of the product mixture from step 1 (117 mg, 0.14 mmol) in THF (10.0 mL), was added dropwise 1.0 M of t-BuOK in THF (0.40 mL, 0.40 mmol) at rt, and the reaction was stirred at rt for 30 min. The solution was cooled down at 0° C., and MeI (0.04 mL, 0.67 mmol) was added to the solution. The reaction was stirred at 0° C. for 30 min. The reaction mixture was poured into saturated NH$_4$Cl solution, and then extracted with EtOAc (×2). The combined organic layers were dried over Na$_2$SO$_4$, filtered, and concentrated in vacuo. The residue was purified by ISCO column chromatography (0%-55% EtOAc in hexanes as eluent) to give 47.6 mg (40%) of the title compounds. $^1$H NMR (400 MHz, Chloroform-d) δ 8.68 (s, 1H), 8.60 (s, 1H), 8.58-8.48 (m, 1H), 7.41 (d, J=1.5 Hz, 1H), 5.75 (d, J=17.1 Hz, 1H), 4.76 (h, J=7.4 Hz, 1H), 4.26 (m, 1H), 3.62-3.46 (m, 2H), 2.57 (d, J=2.0 Hz, 3H), 2.44-2.35 (m, 1H), 2.18-2.06 (m, 2H), 1.67 (tdd, J=12.9, 8.1, 3.9 Hz, 1H), 1.02 (s, 21H), 0.88 (m, 1H), 0.86-0.80 (s, 9H), −0.00 (s, 6H).

Step 3: {5-Chloro-4-[(S)-(3-chlorophenyl)(methyl-amino)methyl]-2-thienyl}[4-({(1R,3R,4S)-3-(hydroxymethyl)-4-[(triisopropylsilyl)oxy] cyclopentyl}amino)pyrimidin-5-yl]methanone and {5-Chloro-4-[(R)-(3-chlorophenyl)(methylamino) methyl]-2-thienyl}[4-({(1R,3R,4S)-3-(hydroxymethyl)-4-[(triisopropylsilyl)oxy]cyclopentyl}amino) pyrimidin-5-yl]methanone A solution of the product mixture from step 2 (182 mg, 0.21 mmol) in 1% HCl in EtOH (20 mL) was stirred at rt for 1 hour. The reaction was poured into saturated NaHCO$_3$ solution and the mixture was extracted with DCM (×3). The combined organic layers were concentrated to dry to yield 142 mg (93%) of the crude title compounds. LCMS (FA): m/z=663.7 (M+H).

Step 4: [(1R,2S,4R)-4-{[5-({5-Chloro-4-[(S)-(3-chlorophenyl)(methylamino)methyl]-2-thienyl}carbonyl)pyrimidin-4-yl]amino}-2-hydroxy-cyclopentyl]methyl sulfamate and [(1R,2S,4R)-4-{[5-({5-Chloro-4-[(R)-(3-chlorophenyl)(methyl-amino)methyl]-2-thienyl}carbonyl)pyrimidin-4-yl] amino}-2-hydroxycyclopentyl]methyl sulfamate To a solution of the product mixture from step 3 (157 mg, 0.21 mmol) in DMF (5.0 mL) was added chlorosulfonamide (73.7 mg, 0.64 mmol) at 0° C. and the reaction was stirred for 1 hour. The reaction mixture was poured into saturated NaHCO$_3$ solution and the resulting mixture was extracted with DCM (×3). The combined organic layers were concentrated in vacuo. The residues were dissolved into the solution of TFA (8.00 mL, 104 mmol) and water (2.00 mL, 111 mmol) and the mixture was heated at 50° C. for 1 hour. The reaction mixture was concentrated in vacuo and the residues were dissolved into MeOH (15 mL) followed by addition of N,N-diisopropylethylamine (1 mL). After the mixture was concentrated in vacuo, the residue was purified by preparative HPLC to yield 29.7 mg (24%) of the title compounds. $^1$H NMR (400 MHz, Methanol-d$_4$) δ 8.72 (d, J=8.9 Hz, 1H), 8.63 (s, 1H), 7.74 (s, 1H), 7.49 (d, J=11.5 Hz, 1H), 7.42-7.31 (m, 3H), 5.11 (s, 1H), 4.81 (d, J=7.7 Hz, 1H), 4.27-4.02 (m, 3H), 2.45 (s, 3H), 2.35-2.04 (m, 2H), 1.97-1.84 (m, 1H), 1.44 (m, 1H), 0.95 (m, 1H). LCMS (FA): m/z=586.1 (M+H).

Example 184: [(1R,2S,4R)-4-{[5-({4-[(1R)-7-Fluoro-3,4-dihydro-1H-isochromen-1-yl]-2-thienyl}carbonyl)pyrimidin-4-yl]amino}-2-hydroxy-cyclopentyl]methyl sulfamate or [(1R,2S,4R)-4-{[5-({4-[(1S)-7-Fluoro-3,4-dihydro-1H-isochromen-1-yl]-2-thienyl}carbonyl)pyrimidin-4-yl]amino}-2-hydroxycyclopentyl]methyl sulfamate I-267

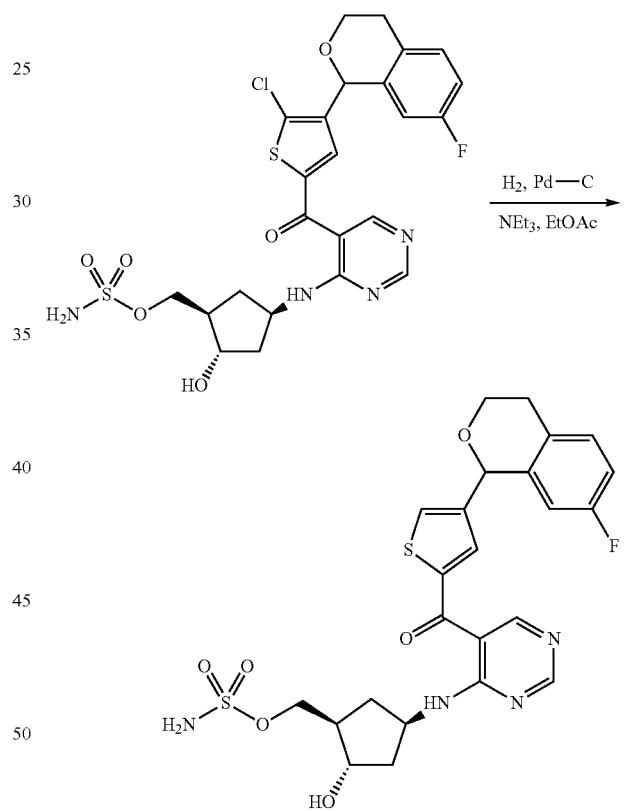

Into a 1-neck round-bottom flask was added [(1R,2S,4R)-4-[[5-[5-chloro-4-[(1R)-7-fluoroisochroman-1-yl]thiophene-2-carbonyl]pyrimidin-4-yl]amino]-2-hydroxy-cyclopentyl]methyl sulfamate or [(1R,2S,4R)-4-[[5-[5-chloro-4-[(1S)-7-fluoroisochroman-1-yl]thiophene-2-carbonyl] pyrimidin-4-yl]amino]-2-hydroxy-cyclopentyl]methyl sulfamate (I-294, 0.499 g, 0.856 mmol) dissolved in EtOAc (15.0 mL, 154 mmol) and triethylamine (0.358 mL, 2.57 mmol). The mixture was degassed with nitrogen. Pd/C (10 wt. %, 0.500 g, 37.5 mmol) was then added and the mixture was purged with a H2 (g) balloon (3×). The resulting mixture stirred at RT for 1 day under a balloon of H2 (g). The balloon was removed and the solution was purged with argon. The mixture was then filtered through Celite and rinsed with EtOAc (3×). The filtrate was concentrated to dryness and the residue was purified by ISCO silica gel chromatography (40 g column, eluting with 0-10% MeOH/DCM over 20 mins) to give 0.359 g (77%) of product. $^1$H NMR (400 MHz, DMSO-d6) δ 8.65 (s, 1H), 8.63 (s, 1H), 8.25 (d, J=7.5 Hz, 1H), 7.93 (s, 1H), 7.63 (s, 1H), 7.42 (s, 2H), 7.28-7.22 (m, 1H), 7.09-7.01 (m, 1H), 6.72-6.65 (m, 1H), 5.90 (s, 1H), 4.93-4.82 (m, 1H), 4.76-4.64 (m, 1H), 4.12-3.99 (m, 2H), 3.98-3.91 (m, 2H), 3.86-3.78 (m, 1H), 2.99-2.87 (m, 1H), 2.82-2.73 (m, 1H), 2.37-2.25 (m, 1H), 2.16-2.06 (m, 1H), 2.00-1.91 (m, 1H), 1.82-1.71 (m, 1H), 1.33-1.22 (m, 1H); LCMS: (FA) M+1 549.1

Example 185: [(1R,2S,4R)-4-{[5-({4-[(1R)-7-Ethynyl-3,4-dihydro-1H-isochromen-1-yl]-5-methyl-2-thienyl}carbonyl)pyrimidin-4-yl]amino}-2-hydroxycyclopentyl]methyl sulfamate and [(1R,2S,4R)-4-{[5-({4-[(1S)-7-Ethynyl-3,4-dihydro-1H-isochromen-1-yl]-5-methyl-2-thienyl}carbonyl)pyrimidin-4-yl]amino}-2-hydroxycyclopentyl]methyl sulfamate I-252

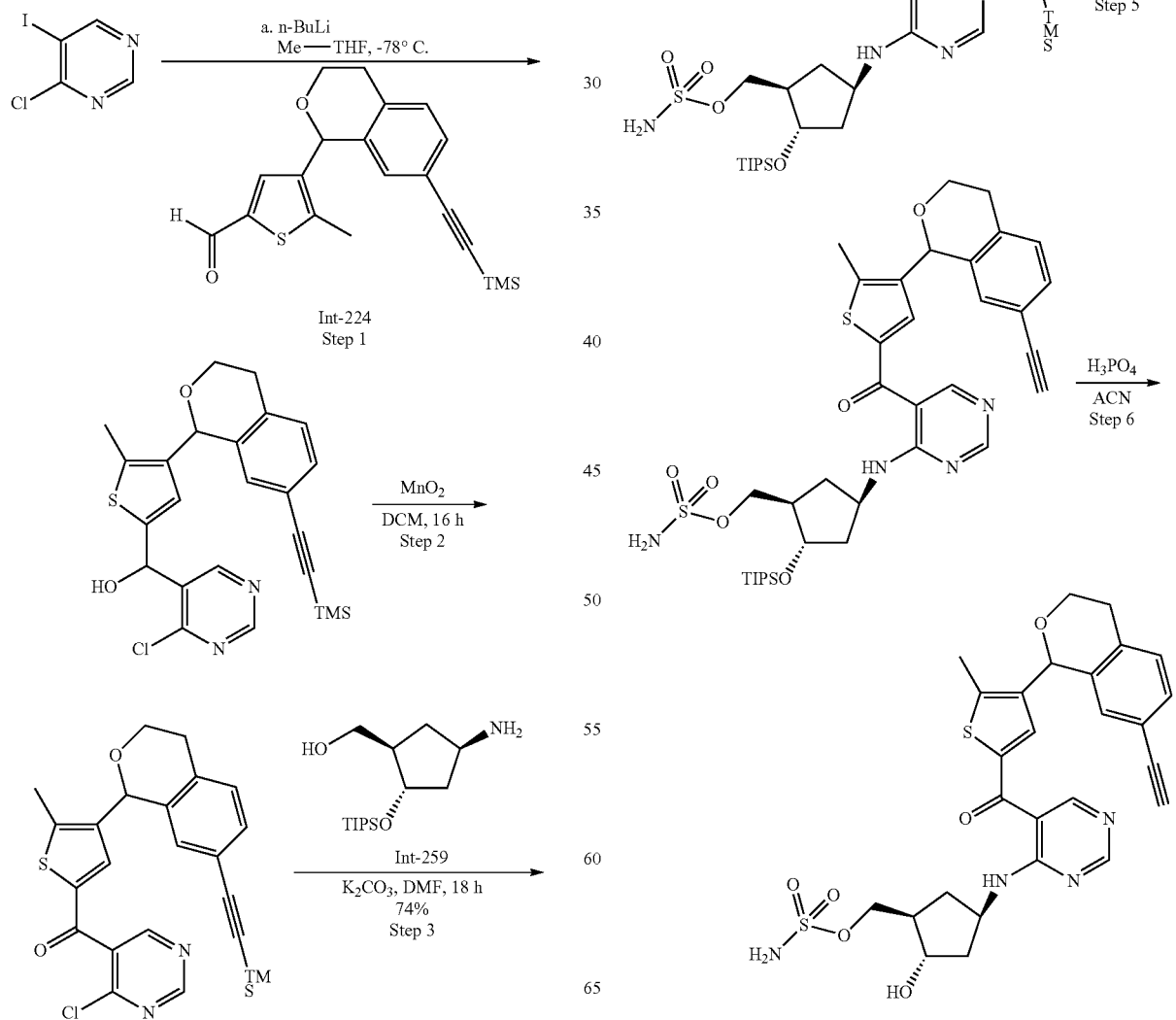

Steps 1-4: [(1R,2S,4R)-4-[[5-[5-Methyl-4-[(1R)-7-(2-trimethylsilylethynyl)isochroman-1-yl]thiophene-2-carbonyl]pyrimidin-4-yl]amino]-2-triisopropylsilyloxy-cyclopentyl]methyl sulfamate and [(1R,2S,4R)-4-[[5-[5-Methyl-4-[(1S)-7-(2-trimethylsilylethynyl)isochroman-1-yl]thiophene-2-carbonyl]pyrimidin-4-yl]amino]-2-triisopropylsilyloxy-cyclopentyl]methyl sulfamate Steps 1-4 were performed in an analogous fashion to Example 173, steps 1-4 beginning with aldehyde Int-224. Step 5 was performed as follows:

Step 5: [(1R,2S,4R)-4-[[5-[4-[(1R)-7-Ethynylisochroman-1-yl]-5-methyl-thiophene-2-carbonyl]pyrimidin-4-yl]amino]-2-triisopropylsilyloxy-cyclopentyl]methyl sulfamate and [(1R,2S,4R)-4-[[5-[4-[(1S)-7-Ethynylisochroman-1-yl]-5-methyl-thiophene-2-carbonyl]pyrimidin-4-yl]amino]-2-triisopropylsilyloxy-cyclopentyl]methyl sulfamate To a solution of [(1R,2S,4R)-4-[[5-[5-methyl-4-[(1R)-7-(2-trimethylsilylethynyl)isochroman-1-yl]thiophene-2-carbonyl]pyrimidin-4-yl]amino]-2-triisopropylsilyloxy-cyclopentyl]methyl sulfamate and [(1R,2S,4R)-4-[[5-[5-methyl-4-[(1S)-7-(2-trimethylsilylethynyl)isochroman-1-yl]thiophene-2-carbonyl]pyrimidin-4-yl]amino]-2-triisopropylsilyloxy-cyclopentyl]methyl sulfamate (1.0 g) in methanol (10.7 mL) was added Potassium carbonate (346.7 mg, 2.509 mmol), and the mixture was stirred for 2 h at rt. The reaction was concentrated in vacuo. To the residue was added water (20 mL) and the mixture was extracted with DCM (20×3). The milky white fine water layer was evaporated to dryness to provide 0.9 g (100%) of the title compounds as a white solid. $^1$H NMR (400 MHz, Methanol-d4) δ 8.61 (s, 1H), 8.52 (s, 1H), 7.27 (d, J=11.5 Hz, 2H), 7.17 (d, J=7.9 Hz, 1H), 6.81 (s, 1H), 5.87 (s, 1H), 4.42-4.34 (m, 1H), 4.23-4.15 (m, 1H), 4.15-4.10 (m, 2H), 3.99-3.87 (m, 1H), 3.36 (s, 1H), 3.18-3.04 (m, 1H), 2.87-2.76 (m, 1H), 2.51 (s, 3H), 2.50-2.45 (m, 1H), 2.38-2.29 (m, 1H), 2.21-2.13 (m, 1H), 2.01 (s, 1H), 1.87-1.77 (m, 1H), 1.40-1.29 (m, 1H), 1.12-1.04 (m, 21H). LCMS: m/z 725.0 (M+1).

Step 6: [(1R,2S,4R)-4-{[5-({4-[(1R)-7-Ethynyl-3,4-dihydro-1H-isochromen-1-yl]-5-methyl-2-thienyl}carbonyl)pyrimidin-4-yl]amino}-2-hydroxycyclopentyl]methyl sulfamate and [(1R,2S,4R)-4-{[5-({4-[(1S)-7-Ethynyl-3,4-dihydro-1H-isochromen-1-yl]-5-methyl-2-thienyl}carbonyl)pyrimidin-4-yl]amino}-2-hydroxycyclopentyl]methyl sulfamate Step 6 was performed in an analogous fashion to Example 133, step 8 to afford the title compounds. $^1$H NMR (400 MHz, Methanol-d4) δ 8.62 (s, 1H), 8.52 (s, 1H), 7.33-7.24 (m, 2H), 7.17 (d, J=7.9 Hz, 1H), 6.82 (s, 1H), 5.87 (s, 1H), 4.81-4.71 (m, 1H), 4.24-4.11 (m, 4H), 3.97-3.88 (m, 1H), 3.37 (s, 1H), 3.18-3.05 (m, 1H), 2.86-2.77 (m, 1H), 2.52 (s, 3H), 2.51-2.41 (m, 1H), 2.31-2.20 (m, 1H), 2.17-2.08 (m, 1H), 1.94-1.84 (m, 1H), 1.56-1.48 (m, 1H). m/z 569.4 (M+1).

Example 186: [(1R,2S,4R)-4-{[5-({4-[(1R)-6,7-Difluoro-3,4-dihydro-1H-isochromen-1-yl]-2-thienyl}carbonyl)pyrimidin-4-yl]amino}-2-hydroxycyclopentyl]methyl sulfamate or [(1R,2S,4R)-4-{[5-({4-[(1S)-6,7-Difluoro-3,4-dihydro-1H-isochromen-1-yl]-2-thienyl}carbonyl)pyrimidin-4-yl]amino}-2-hydroxycyclopentyl]methyl sulfamate I-273

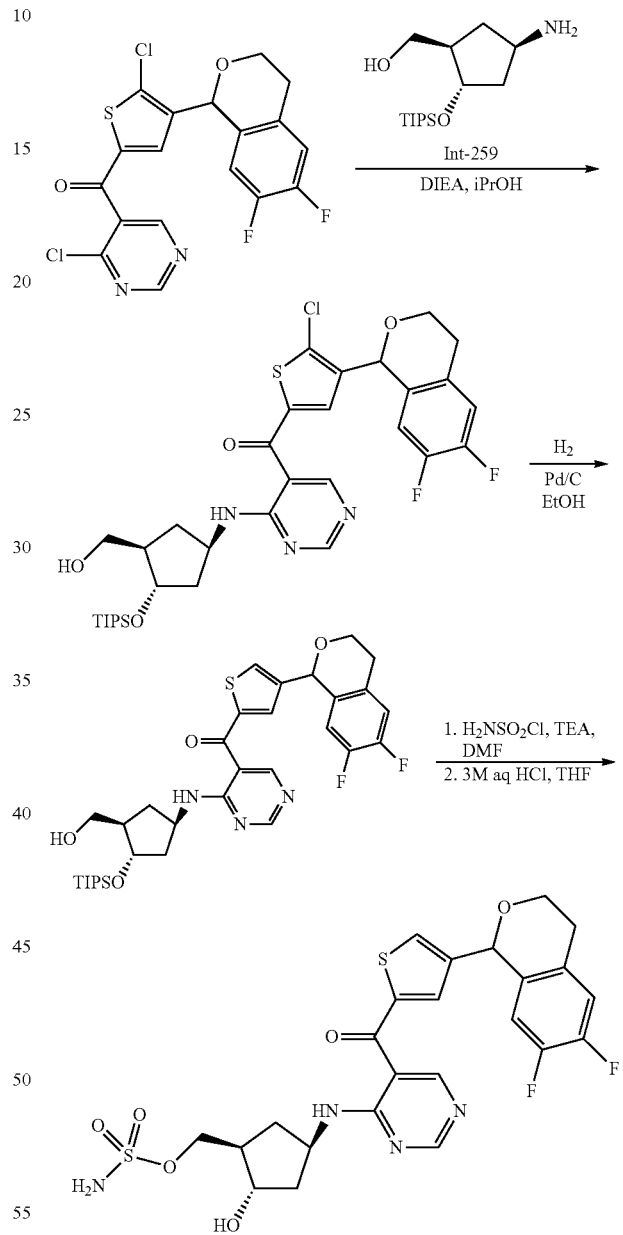

Step 1: [4-[(1R)-6,7-Difluoroisochroman-1-yl]-2-thienyl]-[4-[[(1R,3R,4S)-3-(hydroxymethyl)-4-triisopropylsilyloxy-cyclopentyl]amino]pyrimidin-5-yl]methanone or [4-[(1S)-6,7-difluoroisochroman-1-yl]-2-thienyl]-[4-[[(1R,3R,4S)-3-(hydroxymethyl)-4-triisopropylsilyloxy-cyclopentyl]amino]pyrimidin-5-yl]methanone To a solution of the product of step 2 in the production of I-290b (0.677 g, 1.58 mmol) and N,N-diisopropylethylamine (0.6900 mL, 3.961 mmol) in isopropyl alcohol (25 mL, 330 mmol) was added {(1R,2S,4R)-4-amino-2-[(triisopropylsilyl)oxy]cyclopentyl}methanol (Int-259, 0.6376 g, 2.218 mmol). The reaction mixture was stirred at rt for 2 h, and then concentrated to give 1.962 g of crude product as a mixture of two diastereomers. The crude material was purified and the diastereomers were separated by ISCO silica gel chromatography eluting with 0-25% EtOAc in hexanes to give 0.344 g of diastereomer one and 0.354 g of diastereomer 2 (65% yield). Diastereomer one: $^1$H NMR (400 MHz, Methanol-d4) δ 8.61 (s, 1H), 8.55 (s, 1H), 7.31 (s, 1H), 7.18-7.11 (m, 1H), 6.74-6.64 (m, 1H), 5.93 (s, 1H), 4.87-4.79 (m, 1H), 4.38-4.32 (m, 1H), 4.25-4.16 (m, 1H), 3.99-3.90 (m, 1H), 3.63-3.52 (m, 2H), 3.15-3.05 (m, 1H), 2.84-2.74 (m, 1H), 2.51-2.42 (m, 1H), 2.21-2.11 (m, 2H), 1.87-1.76 (m, 1H), 1.11 (s, 21H); LCMS (FA) M+1 678.6. Diastereomer two: $^1$H NMR (400 MHz, Methanol-d4) δ 8.61 (s, 1H), 8.55 (s, 1H), 7.31 (s, 1H), 7.18-7.09 (m, 1H), 6.73-6.60 (m, 1H), 5.93 (s, 1H), 4.87-4.78 (m, 1H), 4.39-4.30 (m, 1H), 4.25-4.16 (m, 1H), 3.99-3.90 (m, 1H), 3.66-3.52 (m, 2H), 3.15-3.07 (m, 1H), 2.84-2.73 (m, 1H), 2.52-2.43 (m, 1H), 2.19-2.08 (m, 2H), 1.84-1.75 (m, 1H), 1.11 (s, 21H); LCMS (FA) M+1 678.6

Step 2: [5-Chloro-4-[(1R)-6,7-difluoroisochroman-1-yl]-2-thienyl]-[4-[[(1R,3R,4S)-3-(hydroxymethyl)-4-triisopropylsilyloxy-cyclopentyl]amino]pyrimidin-5-yl]methanone To a solution of diastereomer two from step 1 (0.216 g, 0.318 mmol) and triethylamine (0.133 mL, 0.955 mmol) in EtOAc (5.00 mL, 51.2 mmol) was added Pd/C (10 wt. %, 0.216 g, 16.2 mmol). The reaction vessel was purged with hydrogen gas and then stirred, overnight, at rt under a balloon of hydrogen gas. The resulting mixture was filtered and concentrated to give 0.323 g of crude product. The crude material was purified by ISCO silica gel chromatography eluting with 0-50% EtOAc in hexanes to give 0.178 g (97% yield) of pure product as a light yellow residue. $^1$H NMR (400 MHz, DMSO-d6) δ 8.66 (s, 1H), 8.63 (s, 1H), 8.32 (d, J=7.5 Hz, 1H), 7.93 (s, 1H), 7.62 (s, 1H), 7.37-7.25 (m, 1H), 6.97-6.87 (m, 1H), 5.87 (s, 1H), 4.80-4.64 (m, 2H), 4.27-4.22 (m, 1H), 4.02-3.97 (m, 1H), 3.86-3.77 (m, 1H), 3.45-3.35 (m, 2H), 2.97-2.87 (m, 1H), 2.84-2.74 (m, 1H), 2.36-2.25 (m, 1H), 1.99-1.92 (m, 1H) 1.82-1.73 (m, 1H), 1.31-1.23 (m, 2H), 1.04 (s, 21H); LCMS (FA) M+1 644.3.

Step 3: [(1R,2S,4R)-4-{[5-({4-[(1R)-6,7-Difluoro-3,4-dihydro-1H-isochromen-1-yl]-2-thienyl}carbonyl)pyrimidin-4-yl]amino}-2-hydroxycyclopentyl]methyl sulfamate or [(1R,2S,4R)-4-{[5-({4-[(1S)-6,7-Difluoro-3,4-dihydro-1H-isochromen-1-yl]-2-thienyl}carbonyl)pyrimidin-4-yl]amino}-2-hydroxycyclopentyl]methyl sulfamate Step 3 was performed in an analogous fashion to Example 171, step 6. $^1$H NMR (400 MHz, DMSO-d$_6$) δ 8.67 (s, 1H), 8.65 (s, 1H), 8.27 (d, J=7.4 Hz, 1H), 7.93 (s, 1H), 7.65 (d, J=1.2 Hz, 1H), 7.44 (s, 2H), 7.37-7.28 (m, 1H), 6.98-6.90 (m, 1H), 5.88 (s, 1H), 4.89 (d, J=4.5 Hz, 1H), 4.76-4.66 (m, 1H), 4.13-4.07 (m, 1H), 4.05-3.93 (m, 3H), 3.88-3.77 (m, 1H), 2.98-2.87 (m, 1H), 2.84-2.73 (m, 1H), 2.38-2.27 (m, 1H), 2.16-2.07 (m, 1H), 2.00-1.90 (m, 1H), 1.81-1.72 (m, 1H), 1.34-1.22 (m, 1H).

The compounds listed in the table below were prepared in an analogous fashion to that described above starting from the appropriate starting materials. The desilylating agent and solvent for the final step were TAS-F and DMF.

| Starting material | Compound No. |
|---|---|
| The product of Step 2 in the preparation of I-304 | I-308 |

Example 187: [(1R,2S,4R)-4-[[5-[4-[(1R)-7-Chloro-2-methyl-3,4-dihydro-1H-isoquinolin-1-yl]-5-methyl-thiophene-2-carbonyl]pyrimidin-4-yl]amino]-2-hydroxy-cyclopentyl]methyl sulfamate and [(1R,2S,4R)-4-[[5-[4-[(1S)-7-Chloro-2-methyl-3,4-dihydro-1H-isoquinolin-1-yl]-5-methyl-thiophene-2-carbonyl]pyrimidin-4-yl]amino]-2-hydroxy-cyclopentyl]methyl sulfamate I-306

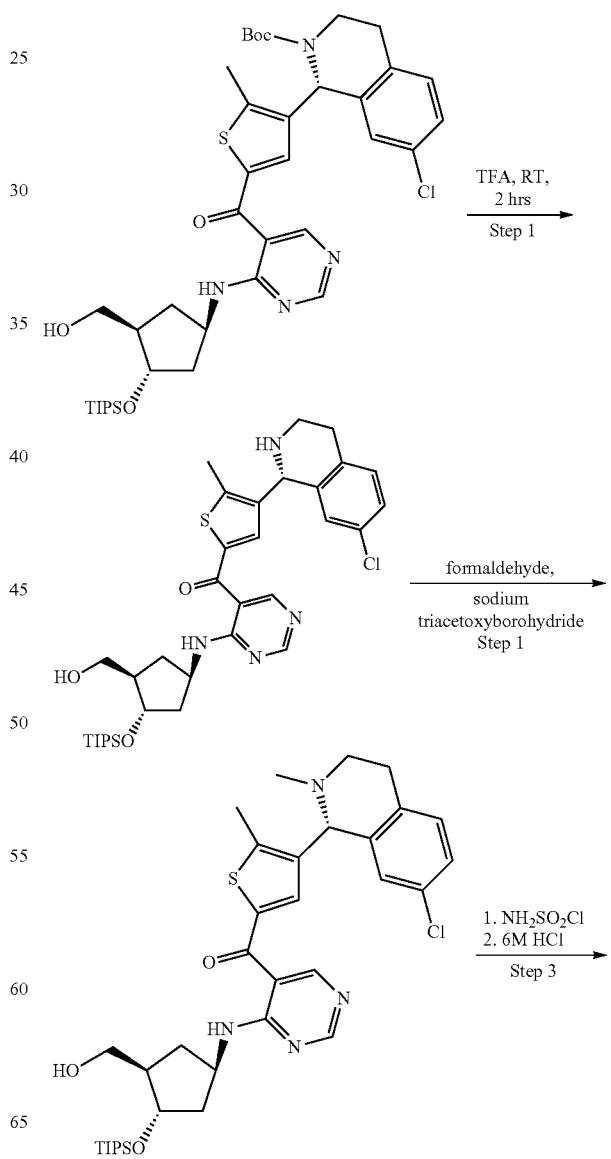

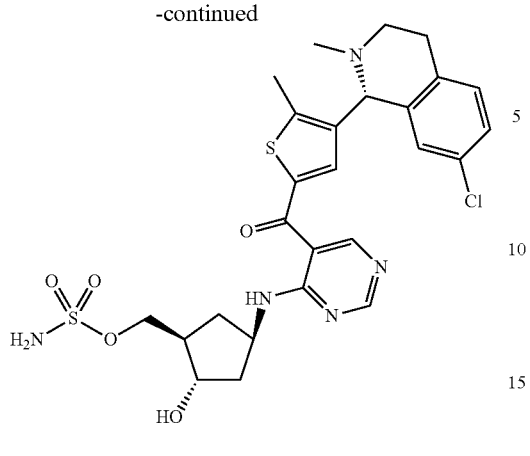
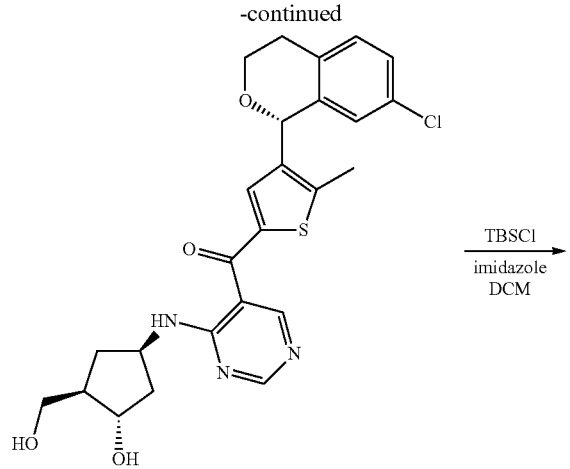

Steps 1-3: [(1R,2S,4R)-4-[[5-[4-[(1R)-7-Chloro-2-methyl-3,4-dihydro-1H-isoquinolin-1-yl]-5-methyl-thiophene-2-carbonyl]pyrimidin-4-yl]amino]-2-hydroxy-cyclopentyl]methyl sulfamate and [(1R,2S,4R)-4-[[5-[4-[(1S)-7-Chloro-2-methyl-3,4-dihydro-1H-isoquinolin-1-yl]-5-methyl-thiophene-2-carbonyl]pyrimidin-4-yl]amino]-2-hydroxy-cyclopentyl]methyl sulfamate Steps 1 and 2 were performed in an analogous fashion to Example 117, step 4, beginning from tert-butyl (1R)-7-chloro-1-[5-[4-[[(1R,3R,4S)-3-(hydroxymethyl)-4-triisopropylsilyloxy-cyclopentyl]amino]pyrimidine-5-carbonyl]-2-methyl-3-thienyl]-3,4-dihydro-1H-isoquinoline-2-carboxylate (the product of Example 133, step 6). Step 3 was performed in an analogous fashion to Example 162, steps 5 and 6. $^1$H NMR (400 MHz, MeOD) δ 8.63 (s, 1H), 8.54 (s, 1H), 7.29 (s, 1H), 7.19 (d, J=8.2 Hz, 2H), 6.64 (s, 1H), 4.79 (dd, J=16.0, 7.9 Hz, 1H), 4.66 (s, 1H), 4.29-4.09 (m, 3H), 3.28-3.10 (m, 2H), 2.95-2.85 (m, 1H), 2.83-2.71 (m, 1H), 2.60 (s, 3H), 2.55-2.41 (m, 1H), 2.36 (s, 3H), 2.31-2.21 (m, 1H), 2.19-2.07 (m, 1H), 1.95-1.82 (m, 1H), 1.50-1.32 (m, 1H).

Example 188: (1S,2R,4R)-4-{[5-({4-[(1R)-7-Chloro-3,4-dihydro-1H-isochromen-1-yl]-5-methyl-2-thienyl}carbonyl)pyrimidin-4-yl]amino}-2-[(sulfamoyloxy)methyl]cyclopentyl (2S)-2-amino-3-methylbutanoate I-338

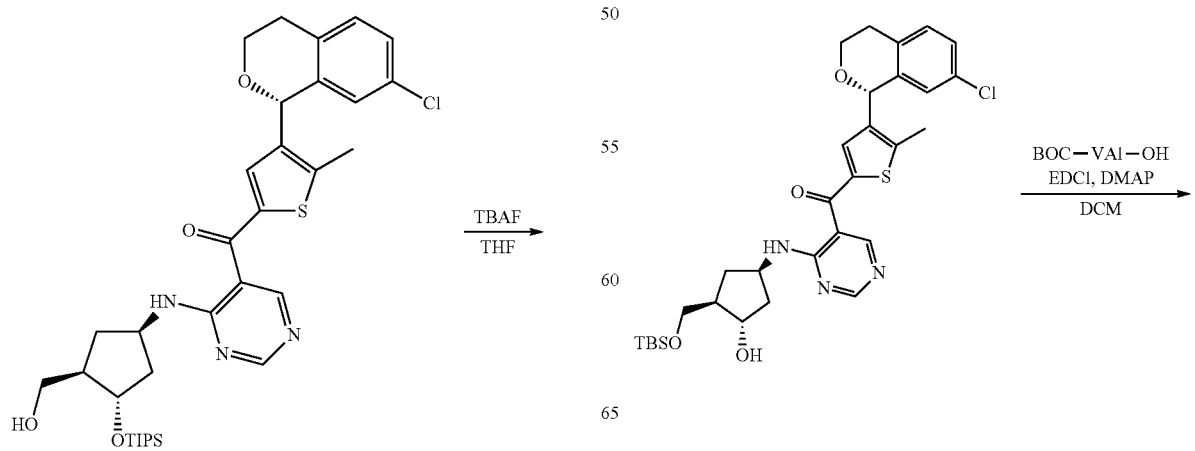

645

-continued

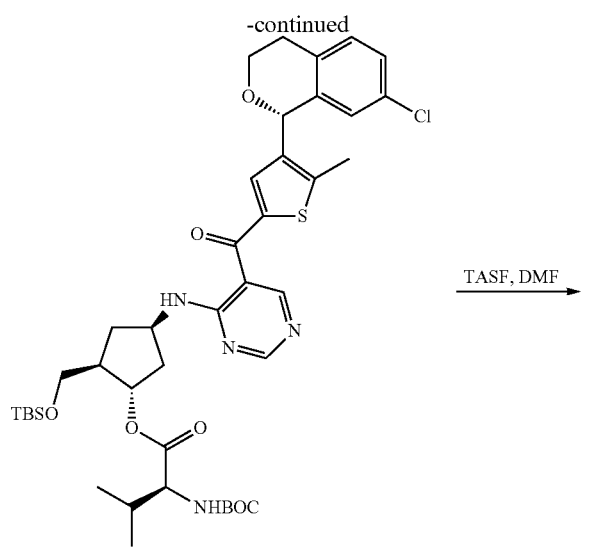

TASF, DMF →

646

-continued

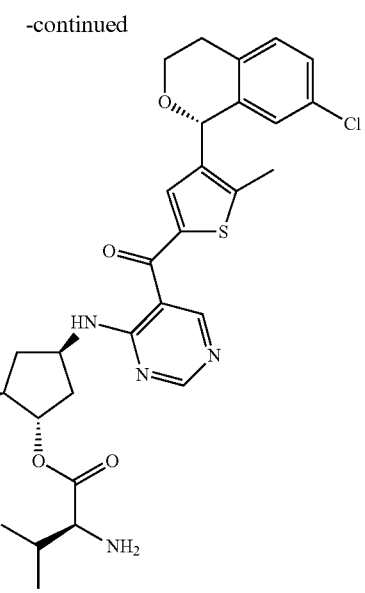

ClSO₂NH₂,
DIPEA
DMF →

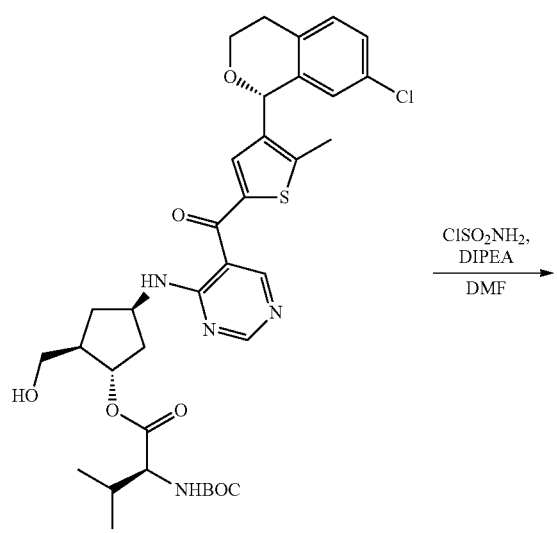

dioxane,
conc. HCl →

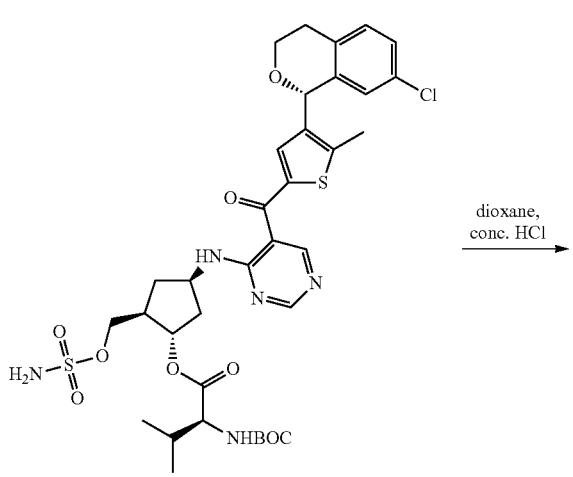

Step 1: {4-[(1R)-7-Chloro-3,4-dihydro-1H-isochromen-1-yl]-5-methyl-2-thienyl}(4-{[(1R,3S,4R)-3-hydroxy-4-(hydroxymethyl)cyclopentyl]amino}pyrimidin-5-yl)methanone To a solution of {4-[(1R)-7-chloro-3,4-dihydro-1H-isochromen-1-yl]-5-methyl-2-thienyl}[4-({(1R,3R,4S)-3-(hydroxymethyl)-4-[(triisopropylsilyl)oxy]cyclopentyl}amino)pyrimidin-5-yl]methanone (the product of Example 132, step 9, 1.60 g, 2.44 mmol) in THF (20.0 mL, 246 mmol) was added 1.00 M of TBAF in THF (2.68 mL, 2.68 mmol) dropwise. The reaction was stirred for 2 h at rt.

The reaction was diluted with EtOAc (100 ml) and washed with water (50 ml). The aqueous layer was extracted with EtOAc (50 ml) and the combined organics washed with brine, dried (Na₂SO₄) and concentrated. Purification by ISCO chromatography (80 g column eluting with neat EtOAc) gave the title compound as a yellow solid. Yield 0.97 g, 80%. Rf 0.05 in EtOAc. LCMS FA rt 3.18 ES+ 500, 502

Step 2: (4-{[(1R,3R,4S)-3-({[tert-Butyl(dimethyl)silyl]oxy}methyl)-4-hydroxycyclopentyl]amino}pyrimidin-5-yl){4-[(1R)-7-chloro-3,4-dihydro-1H-isochromen-1-yl]-5-methyl-2-thienyl}methanone To a solution of 4-[(1R)-7-chloro-3,4-dihydro-1H-isochromen-1-yl]-5-methyl-2-thienyl}(4-{[(1R,3S,4R)-3-hydroxy-4-(hydroxymethyl)cyclopentyl]amino}pyrimidin-5-yl)methanone (1.70 g, 3.40 mmol), 1H-Imidazole (0.4861 g, 7.140 mmol) in DCM (100 mL, 2000 mmol) cooled in an ice bath under argon was added a solution of tert-Butyldimethylsilyl chloride (0.5381 g, 3.570 mmol) in DCM (26 mL, 4.0E2 mmol) dropwise over 10 min. The reaction was allowed to gradually warm to ambient temperature and stirred overnight. The reaction mixture was partitioned between DCM and water, the aqueous layer extracted with DCM and the combined organics washed with brine and dried over MgSO₄ and concentrated. Purification by ISCO chromatography (80 g eluting 75% EtOAc in hexanes to neat EtOAc over 10 min) gave the title compound. Yield 1.71 g 81%. Rf 0.15 in 75% EtOAc/hexane. $^1$H NMR (400 MHz, Chloroform-d) δ 8.74 (s, 1H), 8.61 (s, 1H), 8.54 (d, J=7.1 Hz, 1H), 7.24 (s, 1H), 7.15 (dd, J=8.2, 1.8 Hz, 1H), 7.09 (d, J=8.2 Hz, 1H), 6.65 (s, 1H), 5.74 (s, 1H), 4.80-4.67 (m, 1H), 4.27-4.16 (m, 2H), 3.90 (td, J=11.0, 3.7 Hz, 1H), 3.81 (dd, J=9.8, 5.0 Hz, 1H), 3.60-3.51 (m, 1H), 3.12 (ddd, J=16.3, 10.3, 5.8 Hz, 1H), 2.74 (d, J=16.6 Hz, 1H), 2.55 (s, 3H), 2.42 (d, J=2.1 Hz, 1H), 2.36 (dt, J=14.0, 7.5 Hz, 1H), 2.20-2.01 (m, 2H), 1.91 (dt, J=13.9, 7.1 Hz, 1H), 1.23-1.12 (m, 1H), 0.90 (s, 9H), 0.07 and 0.07 (each s, each 3H).

Step 3: (1S,2R,4R)-2-({[tert-Butyl(dimethyl)silyl]oxy}methyl)-4-{[5-({4-[(1R)-7-chloro-3,4-dihydro-1H-isochromen-1-yl]-5-methyl-2-thienyl}carbonyl)pyrimidin-4-yl]amino}cyclopentyl (2S)-2-[(tert-butoxycarbonyl)amino]-3-methylbutanoate To a solution of (4-{[(1R,3R,4S)-3-({[tert-butyl(dimethyl)silyl]oxy}methyl)-4-hydroxycyclopentyl]amino}pyrimidin-5-yl){4-[(1R)-7-chloro-3,4-dihydro-1H-isochromen-1-yl]-5-methyl-2-thienyl}methanone (384.0 mg, 0.6251 mmol), in DCM (32.0 mL) was added N-(tert-butoxycarbonyl)-L-valine (277.1 mg, 1.275 mmol), N-(3-dimethylaminopropyl)-N'-ethylcarbodiimide hydrochloride (239.7 mg, 1.250 mmol), and N,N-dimethylaminopyridine (160.4 mg, 1.313 mmol), and the reaction stirred at rt for 20 h. The reaction was concentrated and partitioned between water and EtOAc. The aqueous layer was extracted with EtOAc, and the combined extracts was washed with brine, dried over Na$_2$SO$_4$, filtered, and concentrated. The crude material was purified by silica gel column chromatography (0 to 100% EtOAc in hexane) to give 514 mg (quantitative) of the title compound as a yellow foam. $^1$H NMR (400 MHz, DMSO-d$_6$) δ 8.62-8.55 (m, 2H), 8.17 (d, J=7.5 Hz, 1H), 7.35 (s, 1H), 7.27-7.22 (m, 2H), 7.18 (d, J=8.0 Hz, 1H), 6.73 (s, 1H), 5.90 (s, 1H), 5.02-4.93 (m, 1H), 4.70-4.57 (m, 1H), 4.15-4.07 (m, 1H), 3.86-3.74 (m, 2H), 3.59 (d, J=5.7 Hz, 2H), 3.01 (s, 1H), 2.81-2.71 (m, 1H), 2.47 (s, 3H), 2.31-2.19 (m, 1H), 2.19-2.08 (m, 1H), 2.04-1.84 (m, 3H), 1.41-1.32 (m, 9H), 0.91-0.86 (m, 6H), 0.84 (s, 9H), 0.04--0.04 (m, 6H); LCMS: (AA) M+1 813.4

Step 4: (1S,2R,4R)-4-{[5-({4-[(1R)-7-Chloro-3,4-dihydro-1H-isochromen-1-yl]-5-methyl-2-thienyl}carbonyl)pyrimidin-4-yl]amino}-2-(hydroxymethyl)cyclopentyl (2S)-2-[(tert-butoxycarbonyl)amino]-3-methylbutanoate To a solution of (1S,2R,4R)-2-({[tert-butyl(dimethyl)silyl]oxy}methyl)-4-{[5-({4-[(1R)-7-chloro-3,4-dihydro-1H-isochromen-1-yl]-5-methyl-2-thienyl}carbonyl)pyrimidin-4-yl]amino}cyclopentyl (2S)-2-[(tert-butoxycarbonyl)amino]-3-methylbutanoate (0.412 g, 0.506 mmol) in DMF (3.4 mL) at 0° C. under argon was added a solution of tris(dimethylamino)sulfonium difluorotrimethylsilicate (195 mg, 0.709 mmol) in DMF (2.84 mL). The resulting red solution was stirred at 0° C. for 2 h. The reaction was then diluted with minimal DCM and purified directly by silica gel column chromatography (0 to 75% EtOAc in hexane). All fractions containing product were combined and concentrated. The resulting oil was diluted with EtOAc, washed with water, brine, dried over Na$_2$SO$_4$, filtered, and concentrated to afford 337 mg (95%) of the title compound as a yellow foam. $^1$H NMR (400 MHz, DMSO-d$_6$) δ 8.62-8.55 (m, 2H), 8.23 (d, J=7.2 Hz, 1H), 7.34 (s, 1H), 7.28-7.21 (m, 2H), 7.15 (d, J=7.8 Hz, 1H), 6.74 (s, 1H), 5.90 (s, 1H), 5.02-4.94 (m, 1H), 4.79-4.71 (m, 1H), 4.71-4.60 (m, 1H), 4.15-4.07 (m, 1H), 3.87-3.74 (m, 2H), 3.43 (t, J=5.3 Hz, 2H), 3.07-2.94 (m, 1H), 2.80-2.71 (m, 1H), 2.47 (s, 3H), 2.31-2.19 (m, 1H), 2.16-2.05 (m, 1H), 2.05-1.83 (m, 3H), 1.43-1.30 (m, 9H), 0.95-0.79 (m, 6H); LCMS: (AA) M+1 699.3

Step 5: (1S,2R,4R)-4-{[5-({4-[(1R)-7-Chloro-3,4-dihydro-1H-isochromen-1-yl]-5-methyl-2-thienyl}carbonyl)pyrimidin-4-yl]amino}-2-[(sulfamoyloxy)methyl]cyclopentyl (2S)-2-[(tert-butoxycarbonyl)amino]-3-methylbutanoate To a solution of (1S,2R,4R)-4-{[5-({4-[(1R)-7-chloro-3,4-dihydro-1H-isochromen-1-yl]-5-methyl-2-thienyl}carbonyl)pyrimidin-4-yl]amino}-2-(hydroxymethyl)cyclopentyl (2S)-2-[(tert-butoxycarbonyl)amino]-3-methylbutanoate (413.0 mg, 0.5906 mmol, previously azeotroped with toluene) in DMF (9.2 mL) and N,N-diisopropylethylamine (308.6 uL, 1.772 mmol) was added chlorosulfonamide (204.7 mg, 1.772 mmol) at rt, and the yellow solution was stirred 60 min. The reaction was cooled to 0° C. and quenched with water and brine. The reaction was extracted with EtOAc (3×). The combined organic layers were then dried using Na$_2$SO$_4$, filtered and concentrated. The crude product was purified by silica gel column chromatography (0 to 7% MeOH in DCM). The isolated product still contained unreacted starting material. The mixture was azeotroped with toluene, dried on high vacuum, and dissolved in DMF (9.2 mL) under argon. N,N-diisopropylethylamine (0.1029 mL, 0.5906 mmol) was added, followed by chlorosulfonamide (68.24 mg, 0.5906 mmol). The reaction was stirred at rt for $^1$H and monitored by TLC. Chlorosulfonamide (34.12 mg, 0.2953 mmol) was then added and the reaction was stirred for 30 min. Then the reaction was cooled at 0° C., quenched with saturated NaHCO$_3$, and diluted w/water. The reaction was extracted with EtOAc (3×). The combined extracts was washed with brine, dried over Na$_2$SO$_4$, filtered, and concentrated. The crude product was purified by silica gel column chromatography (0 to 100% EA) to give 352 mg yellow foam. The product was dissolved in EtOAc, washed w/1N LiCl soln (3×) to remove DMF, dried over Na$_2$SO$_4$, filtered, and concentrated to give 317 mg (69%) of the title compound as a yellow residue. $^1$H NMR (400 MHz, DMSO-d$_6$) δ 8.63-8.54 (m, 2H), 8.18 (d, J=7.4 Hz, 1H), 7.47 (s, 2H), 7.35 (s, 1H), 7.28-7.22 (m, 2H), 7.20 (d, J=7.6 Hz, 1H), 6.74 (s, 1H), 5.90 (s, 1H), 5.02-4.90 (m, 1H), 4.76-4.60 (m, 1H), 4.15-3.99 (m, 3H), 3.88-3.74 (m, 2H), 3.07-2.94 (m, 1H), 2.81-2.70 (m, 1H), 2.47 (s, 3H), 2.40-2.26 (m, 2H), 2.09-1.86 (m, 3H), 1.48-1.30 (m, 9H), 0.89 (d, J=5.5 Hz, 6H); LCMS: (AA) M+1 778.2

Step 6: (1S,2R,4R)-4-{[5-({4-[(1R)-7-Chloro-3,4-dihydro-1H-isochromen-1-yl]-5-methyl-2-thienyl}carbonyl)pyrimidin-4-yl]amino}-2-[(sulfamoyloxy)methyl]cyclopentyl (2S)-2-amino-3-methylbutanoate.HCl (1S,2R,4R)-4-{[5-({4-[(1R)-7-chloro-3,4-dihydro-1H-isochromen-1-yl]-5-methyl-2-thienyl}carbonyl)pyrimidin-4-yl]amino}-2-[(sulfamoyloxy)methyl]cyclopentyl (2S)-2-[(tert-butoxycarbonyl)amino]-3-methylbutanoate (280 mg, 0.36 mmol) was dissolved in 1,4-dioxane (3.8 mL) and concentrated HCl (0.60 mL, 7.19 mmol) was added. The solution was stirred at rt for 2.5 h. The reaction was concentrated, azeotroped with EtOH, added water and lyophilized to give 267 mg (quantitative) of the title compound as a beige solid. $^1$H NMR (400 MHz, DMSO-d$_6$) δ

8.81-8.66 (m, 2H), 8.62 (s, 1H), 8.43 (d, J=4.5 Hz, 3H), 7.59-7.47 (m, 3H), 7.29-7.22 (m, 2H), 6.70 (s, 1H), 5.13-5.07 (m, 1H), 4.84-4.71 (m, 1H), 4.18-4.04 (m, 3H), 3.94-3.88 (m, 1H), 3.88-3.79 (m, 1H), 3.08-2.96 (m, 1H), 2.82-2.72 (m, 1H), 2.38-2.27 (m, 1H), 2.23-2.03 (m, 3H), 1.57-1.45 (m, 1H), 1.04-0.93 (m, 6H); LCMS: (AA) M+1 678.2.

Example 189: [4-(Bromomethyl)-2-thienyl][4-({(1R,3R,4S)-3-(hydroxymethyl)-4-[(triisopropylsilyl)oxy]cyclopentyl}amino)pyrimidin-5-yl]methanone Int-287

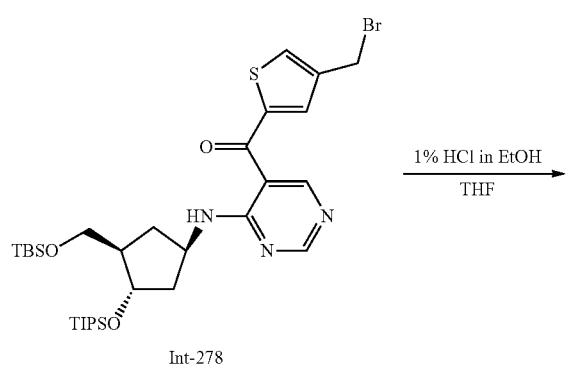

Example 190: [4-(Chloromethyl)-5-methyl-2-thienyl][4-({(1R,3R,4S)-3-(hydroxymethyl)-4-[(triisopropylsilyl)oxy]cyclopentyl}amino)pyrimidin-5-yl]methanone Int-288

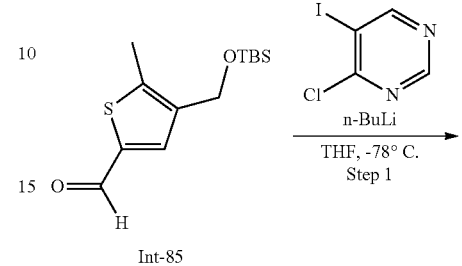

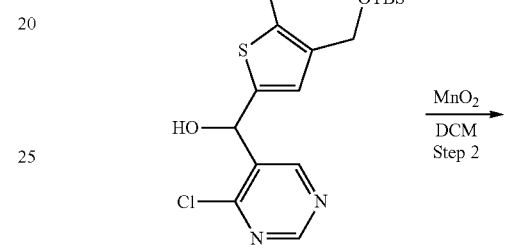

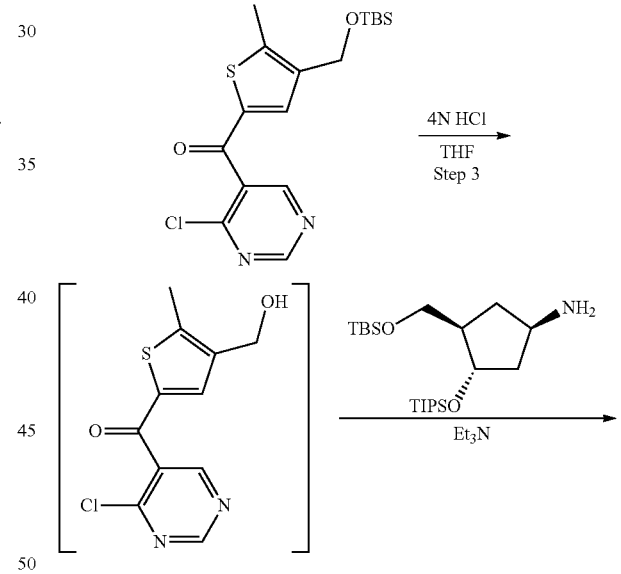

Step 1: [4-(Bromomethyl)-2-thienyl][4-({(1R,3R,4S)-3-(hydroxymethyl)-4-[(triisopropylsilyl)oxy]cyclopentyl}amino)pyrimidin-5-yl]methanone To a 25-mL round bottom flask was added Int-278 (656 mg, 0.96 mmol), THF (20.8 mL). The solution was cooled to 0° C. then 1% HCl in EtOH solution (15.9 mL, 1.92 mmol) was added. The mixture was stirred at 0° C. for 3 h. To the reaction was added saturated NaHCO₃ solution (2 mL) to quench excess acid. The solution was then extracted with EtOAc (10 mL). After separation, the aqueous layer was extracted with EtOAc (6 mL). The combined organic solutions were concentrated in vacuo to give 550 mg of the crude title compound as slightly yellow oil.

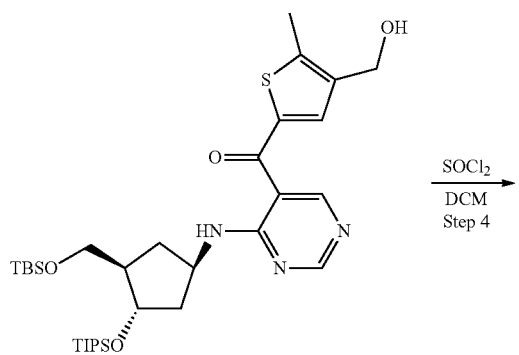

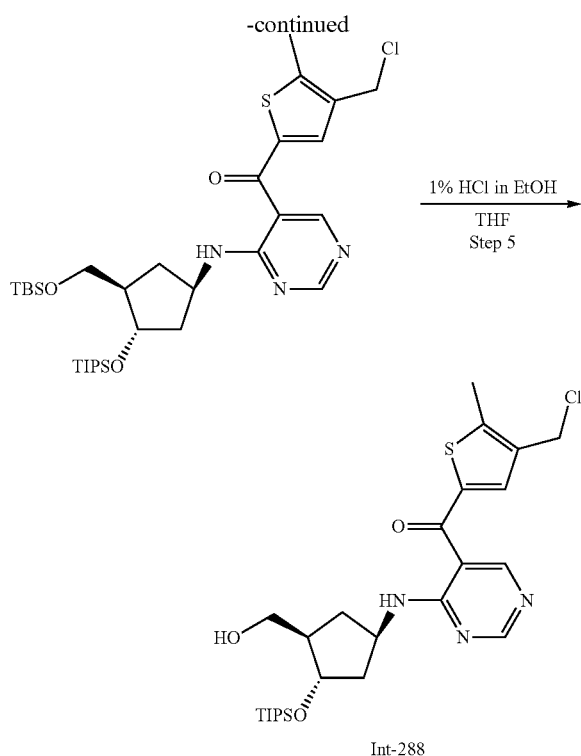

Int-288

Step 1: rac-[4-({[tert-Butyl(dimethyl)silyl]oxy}methyl)-5-methyl-2-thienyl](4-chloropyrimidin-5-yl)methanol The title compound was prepared in an analogous fashion to Example 131, step 7, beginning from Int-85. 2.53 g (94%) LCMS (FA): m/z=385.3 (M+H).

Step 2: [4-({[tert-Butyl(dimethyl)silyl]oxy}methyl)-5-methyl-2-thienyl](4-chloropyrimidin-5-yl)methanone The title compound was prepared in an analogous fashion to Example 131, step 8. 2.33 g (93%) LCMS (FA): m/z=383.3 (M+H).

Step 3: [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(hydroxymethyl)-5-methyl-2-thienyl]methanone To a solution of [4-({[tert-butyl(dimethyl)silyl]oxy}methyl)-5-methyl-2-thienyl](4-chloropyrimidin-5-yl)methanone (2.30 g, 6.00 mmol) in THF (40.0 mL) was added 4 M HCl in 1,4-dioxane (20 mL) and the reaction was stirred at rt for 2 h. After concentration in vacuo, the residue was dissolved in DCM (60.0 mL). To the solution was added triethylamine (2.93 mL, 21.0 mmol), and Int-260 (3.14 g, 7.81 mmol) and the resulting mixture was stirred at rt for 3 h. The reaction was quenched by addition of saturated NaHCO$_3$ and extracted with DCM (×2). The organic layers were concentrated in vacuo and the residue was purified by ISCO column chromatography (5% MeOH in DCM as eluent) to give 1.96 g (52%) of the title compound. LCMS (FA): m/z=635.0 (M+H).

Step 4: [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(chloromethyl)-5-methyl-2-thienyl]methanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl][4-(hydroxymethyl)-5-methyl-2-thienyl]methanone (1.90 g, 3.00 mmol) in DCM (50.0 mL) at 0° C. was added thionyl chloride (0.28 mL, 3.90 mmol) and the reaction was stirred at 0° C. for 1 hour. The reaction was quenched by addition of saturated NaHCO$_3$ and extracted with DCM (×2). The combined organic layers were washed with brine, dried over MgSO$_4$, filtered, and concentrated in vacuo. The residue was purified by ISCO column chromatography (20% EtOAc in hexanes as eluent) to give 1.32 g (68%) of the title compound. LCMS (FA): m/z=653.3 (M+H).

Step 5: [4-(Chloromethyl)-5-methyl-2-thienyl][4-({(1R,3R,4S)-3-(hydroxymethyl)-4-[(triisopropylsilyl)oxy]cyclopentyl}amino)pyrimidin-5-yl]methanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl][4-(chloromethyl)-5-methyl-2-thienyl]methanone (800 mg, 1.23 mmol) in THF (20.3 mL) was added 1% HCl in EtOH solution (20.3 mL, 2.45 mmol) and the mixture was stirred for 1.5 h at same temperature. To the reaction was added saturated NaHCO$_3$ (2 mL) to quench excess acid. The solution was then extracted with EtOAc (10 mL). After separation, the aqueous layer was extracted with EtOAc (6 mL). The combined organic solutions were concentrated in vacuo to give the title compound as slightly yellow oil. LCMS (FA): 538.2 (M+1).

Example 191: {(1R,2S,4R)-2-Hydroxy-4-[(5-{[4-(phenoxymethyl)-2-thienyl]carbonyl}pyrimidin-4-yl)amino]cyclopentyl}methyl sulfamate I-91

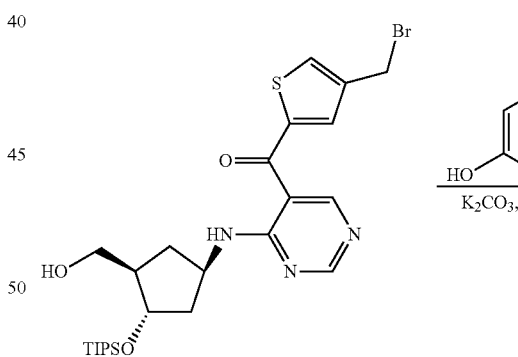

Int-287

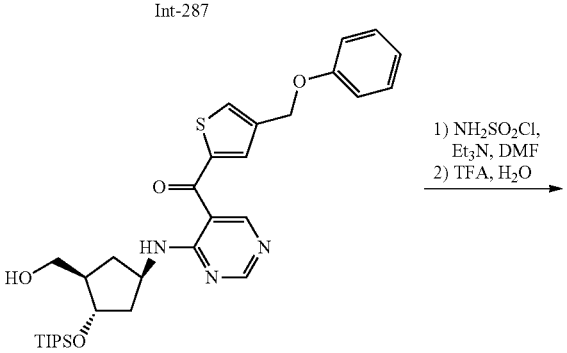

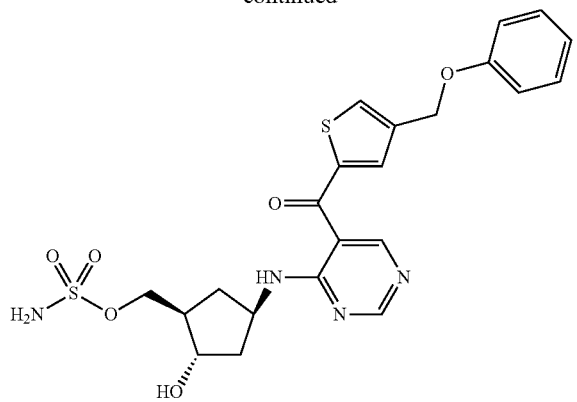

To a solution of Int-287 (25.0 mg, 0.04 mmol) in THF (0.88 mL) was added phenol (8.28 mg, 0.088 mmol). The mixture was stirred at rt for 1 hour. To the reaction was added DMF (0.50 mL). This reaction was then allowed to stir at rt overnight. To the solution was added chlorosulfonamide (20.3 mg, 0.18 mmol) and the solution was stirred for 30 min. Reaction was quenched with saturated $NaHCO_3$, then extracted with EtOAc (×2). The combined organic layers were concentrated to dryness. To the resulting residue was added TFA (1.80 mL) and water (0.20 mL). After stirring at rt for 1 hour, reaction was concentrated in vacuo. The residue was dissolved in MeOH (4.0 mL) and PL-$CO_3$ MP-Resin(2.04 mmol/g loading; 431 mg, 0.88 mmol) was added. Mixture was stirred for 30 min, and the resin was filtered and rinsed with MeOH (5 mL). The combined methanol solutions were concentrated to afford a solid residue. The residue was dissolved in DMSO (1.2 mL) and filtered. The filtrate was purified by preparative HPLC to give the title compound (4.1 mg, 18%). LC/MS (FA): 504.8 (M+H). $^1$H NMR (400 MHz, Methanol-$d_4$) δ 8.78 (s, 1H), 8.62 (s, 1H), 7.95 (s, 1H), 7.76 (s, 1H), 7.30 (dd, J=8.8, 7.4 Hz, 2H), 7.01 (d, J=7.9 Hz, 2H), 6.96 (t, J=7.4 Hz, 1H), 5.15 (s, 2H), 4.87-4.77 (m, 1H), 4.27-4.09 (m, 3H), 2.60-2.45 (m, 1H), 2.34-2.23 (m, 1H), 2.23-2.11 (m, 1H), 1.97-1.86 (m, 1H), 1.51-1.37 (m, 1H).

The compounds listed in the table below were prepared in a similar fashion to that described above starting from the listed starting materials:

| Starting material | Compound No. | LCMS Data |
|---|---|---|
| 2-methoxyphenol (HO, OMe) | I-80 | LCMS (FA): m/z = 535.3 (M + H) |
| 2-chlorobenzenethiol (HS, Cl) | I-147 | LCMS (FA): m/z = 555.2 (M + H) |
| thiophenol (HS) | I-177 | LCMS (FA): m/z = 521.2 (M + H) |
| 2-bromophenol (HO, Br) | I-98 | LCMS (FA): m/z = 583.2 (M + H) |
| 4-chlorophenol (HO, Cl) | I-163 | LCMS (FA): m/z = 539.2 (M + H) |
| 3-chlorophenol (HO, Cl) | I-120 | LCMS (FA): m/z = 539.2 (M + H) |
| 2,3-dichlorophenol (HO, Cl, Cl) | I-180 | LCMS (FA): m/z = 573.2 (M + H) |
| 2-chlorophenol (HO, Cl) | I-129 | LCMS (FA): m/z = 539.2 (M + H) |

Example 192: [(1R,2S,4R)-2-Hydroxy-4-{[5-({4-[(2-iodophenoxy)methyl]-2-thienyl}carbonyl)pyrimidin-4-yl]amino}cyclopentyl]methyl sulfamate I-161

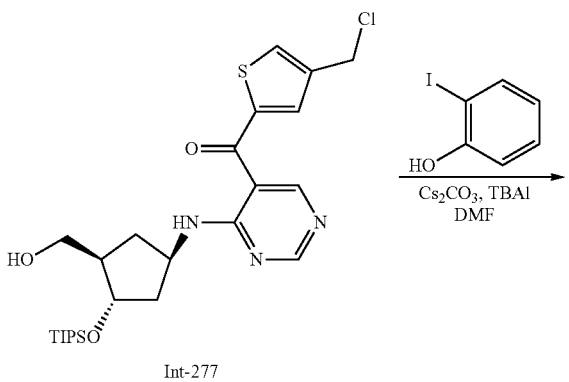

Int-277

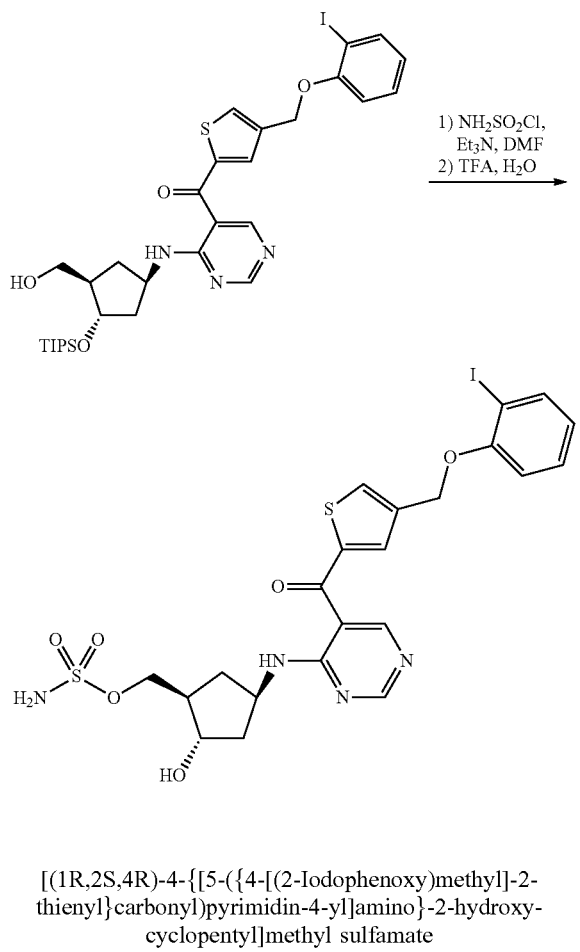

[(1R,2S,4R)-4-{[5-({4-[(2-Iodophenoxy)methyl]-2-thienyl}carbonyl)pyrimidin-4-yl]amino}-2-hydroxycyclopentyl]methyl sulfamate To a 2-dram vial containing 2-iodophenol (2.04 mg, 9.28 umol) was added a solution of Int-277 (31.4 mg, 0.06 mmol) in DMF (1.00 mL) followed by $Ce_2CO_3$ (117 mg, 0.36 mmol), and tetra-n-butylammonium iodide (3.32 mg, 0.01 mmol) in DMF (0.10 mL). The mixture was stirred at rt for 2 h. Solids were filtered and rinsed with DMF (0.5 mL). To the combined DMF solutions were added triethylamine (50.2 uL, 0.36 mmol), chlorosulfonamide (27.7 mg, 0.24 mmol). The mixture was shaken at rt for 30 min, and then saturated $NaHCO_3$ (1.5 mL) and EtOAc (8 mL) were added. After separation, the aqueous phase was extracted with EtOAc (8 mL). The combined organic solutions were concentrated in vacuo. To the residue was added TFA (1.80 mL), water (0.20 mL). After shaking for 30 min, reaction was concentrated in vacuo. To the residue was added PL-CO3 MP-Resin(2.04 mmol/g loading; 588 mg, 1.20 mmol), MeOH (3.00 mL). After shaking for 1 hour, resin was filtered and rinsed with MeOH (10 mL). The combined methanol solutions were concentrated to dryness. The residue was dissolved in DMSO (1.2 mL). After filtration, the residue was purified by preparative HPLC to give title compound. LCMS (FA): 631.2 (M+H).

The compounds listed in the table below were prepared in a similar fashion to that described above starting from the listed starting materials:

| Starting material | Compound No. | LCMS Data |
|---|---|---|
| 2-(trifluoromethyl)phenol | I-188 | LCMS (FA): m/z = 573.2 (M + H) |
| 2-(trifluoromethoxy)phenol | I-176 | LCMS (FA): m/z = 589.7 (M + H) |
| 2-hydroxybenzonitrile | I-124 | LCMS (FA): m/z = 530.7 (M + H) |
| 2-ethylphenol | I-182 | LCMS (FA): m/z = 533.3 (M + H) |
| 2-isopropoxyphenol | I-201 | LCMS (FA): m/z = 563.3 (M + H) |
| 2-ethoxyphenol | I-156 | LCMS (FA): m/z = 549.8 (M + H) |
| 2-isopropylphenol | I-191 | LCMS (FA): m/z = 547.3 (M + H) |
| 2-methylphenol | I-131 | LCMS (FA): m/z = 519.7 (M + H) |

Example 193 [(1R,2S,4R)-4-{[5-({4-[(Benzy-lamino)methyl]-2-thienyl}carbonyl)pyrimidin-4-yl]amino}-2-hydroxycyclopentyl]methyl sulfamate I-222

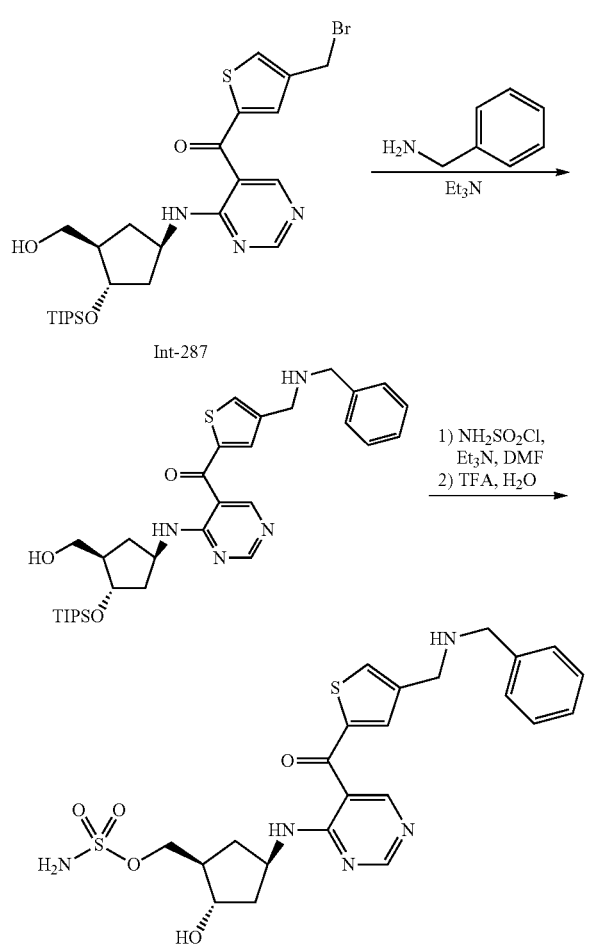

To a 3-dram vial containing benzylamine (12.8 mg, 0.12 mmol) was added triethylamine (66.9 uL, 0.48 mmol) and Int-287 (34.1 mg, 0.06 mmol) in DMF (1.0 mL). The mixture was shaken vigorously at rt for 2 h. To the mixture was added chlorosulfonamide (27.7 mg, 0.24 mmol). After shaking for 30 min, saturated NaHCO$_3$ solution (1.25 mL) and EtOAc (6 mL) were added. After separation, the aqueous phase was extracted with EtOAc (8 mL). The combined organic phases were concentrated in a 20-mL vial. To the residue was added TFA (1.80 mL), water (0.20 mL). After shaking for 1 hour, reaction was concentrated in vacuo. To the residue was added MeOH (3.00 mL), PL-CO3 MP-Resin (2.04 mmol/g loading; 588 mg, 1.20 mmol). After shaking for 30 min, resin was filtered and rinsed with MeOH (10 mL). The combined methanol solutions were concentrated to afford a solid residue. To the residue was added DMSO (1.2 mL). After filtration, the solution was purified by preparative HPLC to give the title compound. LCMS (FA): 518.3 (M+H).

The compounds listed in the table below were prepared in a similar fashion to that described above starting from the listed starting materials:

| Starting material | Compound No. | LCMS Data |
|---|---|---|
| benzimidazole | I-192 | LCMS (FA): m/z = 529.3 (M + H) |
| 1-phenylpiperazine | I-241 | LCMS (FA): m/z = 573.3 (M + H) |
| 4,5,6,7-tetrahydrothieno[3,2-c]pyridine | I-168 | LCMS (FA): m/z = 550.1 (M + H) |
| 2,5-dihydro-1H-pyrrole | I-219 | LCMS (FA): m/z = 480.3 (M + H) |
| isoindoline | I-187 | LCMS (FA): m/z = 530.1 (M + H) |
| 3-methylpiperidine | I-225 | LCMS (FA): m/z = 510.3 (M + H) |
| 1,2,3,4-tetrahydroisoquinoline | I-167 | LCMS (FA): m/z = 544.3 (M + H) |
| 1,2,3,6-tetrahydropyridine | I-204 | LCMS (FA): m/z = 493.9 (M + H) |

Example 194: [(1R,2S,4R)-2-Hydroxy-4-{[5-({4-[(3-methyl-1H-indol-1-yl)methyl]-2-thienyl}carbonyl)pyrimidin-4-yl]amino}cyclopentyl]methyl sulfamate I-105

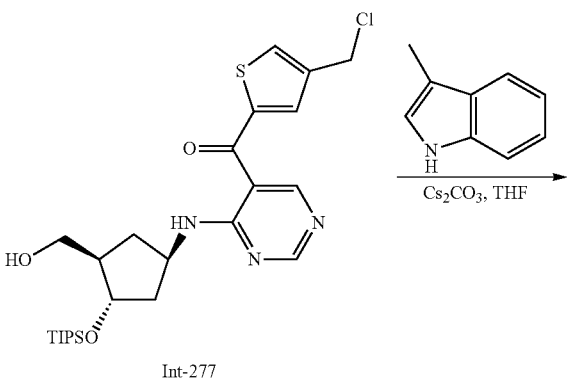

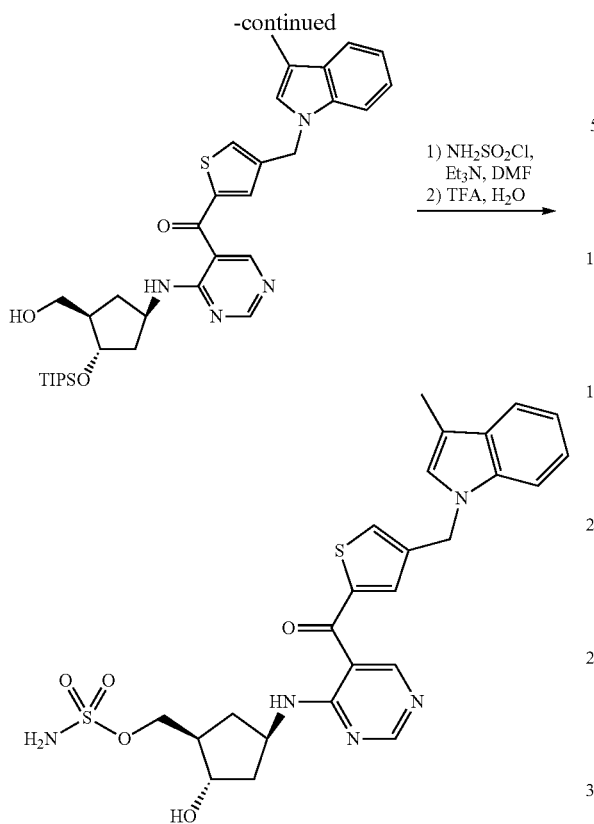

To a 2-dram vial containing 3-methylindole (12.5 mg, 0.10 mmol) were added Int-277 (25.0 mg, 0.05 mmol), DMF (1.00 mL), tetra-N-butylammonium bromide (1.54 mg, 4.77 umol) and $Cs_2CO_3$ (93.2 mg, 0.29 mmol). The mixture was heated at 42° C. for 3 h. Solids were filtered and rinsed with DMF (0.5 mL). To the combined DMF solutions were added triethylamine (0.04 mL, 0.29 mmol) and chlorosulfonamide (22.0 mg, 0.19 mmol). The mixture was shaken for 30 min, then quenched with saturated $NaHCO_3$ (1.5 mL) solution. The mixture was extracted with EtOAc (6 mL) twice. The combined organic solutions were concentrated to dryness in a 20-mL vial. To the vial was added TFA (1.80 mL, 23.4 mmol) and water (0.20 mL). After shaking for 30 min, reaction was concentrated in vacuo. To the residue was added MeOH (3.0 mL) and PL-CO3 MP-Resin (2.04 mmol/g loading; 468 mg, 0.95 mmol). After shaking for 30 min, resin was filtered and rinsed with MeOH (8 mL). The combined methanol solutions were concentrated. To the residue was added DMSO (1.2 mL). After filtration, the solution was purified by preparative HPLC to give the title compound. LCMS (FA): 542.3 (M+H).

The compounds listed in the table below were prepared in a similar fashion to that described above starting from the listed starting materials:

| Starting material | Compound No. | LCMS Data |
|---|---|---|
| ![indole-carbonitrile] | I-169 | LCMS (FA): m/z = 529.3 (M + H) |
| ![dimethylaminomethyl-indole] | I-221 | LCMS (FA): m/z = 585.2 (M + H) |
| ![trifluoromethyl-pyrazole] | I-130 | LCMS (FA): m/z = 547.2 (M + H) |
| ![7-azaindole] | I-92 | LCMS (FA): m/z = 529.2 (M + H) |
| ![methylpyrazole] | I-74 | LCMS (FA): m/z = 493.3 (M + H) |
| ![methyl-pyrazolopyridine] | I-160 | LCMS (FA): m/z = 544.2 (M + H) |

Example 195: [(1R,2S,4R)-2-Hydroxy-4-{[5-({4-[(3-methyl-1H-pyrrol-1-yl)methyl]-2-thienyl}carbonyl)pyrimidin-4-yl]amino}cyclopentyl] methyl sulfamate I-170

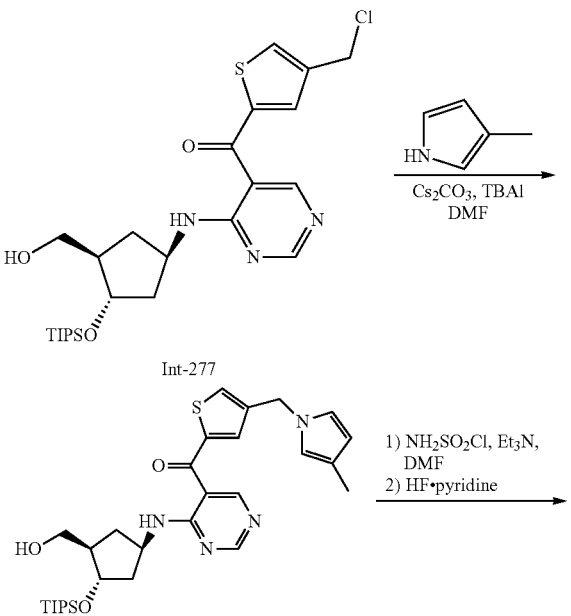

-continued

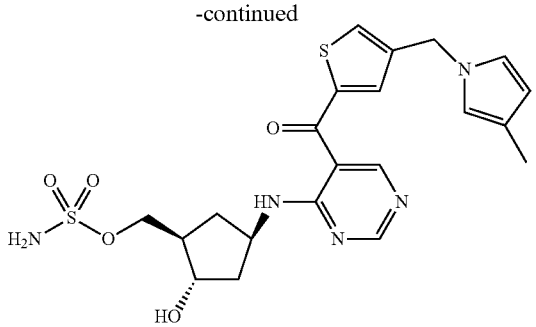

To a 2-dram vial containing 3-methylpyrrole (13.0 mg, 0.16 mmol) were added Int-277 (41.9 mg, 0.08 mmol) DMF (1.00 mL), $Cs_2CO_3$ (156 mg, 0.48 mmol), and tetra-N-butylammonium iodide (4.43 mg, 0.01 mmol) in DMF (0.1 mL). The mixture was shaken at rt for 1 hour then heated at 42° C. for 2 h. Solids were filtered and rinsed with DMF (0.5 mL). To the combined DMF solutions were added triethylamine (66.9 uL, 0.48 mmol), chlorosulfonamide (37.0 mg, 0.32 mmol). After shaking for 30 min, saturated $NaHCO_3$ (1.5 mL) and EtOAc (8 mL) were added. After separation, the aqueous phase was extracted with EtOAc (8 mL). The combined organic solutions were concentrated to dryness in a plastic centrifuge tube. To the residue in the tube was added THF (2.67 mL), pyridine hydrofluoride (0.14 mL, 1.60 mmol). After shaking for 1 hour, saturated $NaHCO_3$ solution (2.0 mL) was added to quench excess hydrogen fluoride. The mixture was extracted with EtOAc (8 mL) twice. The combined organic phases were concentrated in a 20-mL vial. The residue was dissolved in DMSO (1.2 mL). After filtration, the residue was purified by preparative HPLC to give the title compound. LCMS (FA): 492.2 (M+H).

The compounds listed in the table below were prepared in a similar fashion to that described above starting from the listed starting materials:

| Starting material | Compound No. | LCMS Data |
|---|---|---|
| imidazopyrazine | I-190 | LCMS (FA): m/z = 534.3 (M + H) |
| 4-bromoimidazole | I-243 | LCMS (FA): m/z = 557.1 (M + H) |
| 7-azaindole | I-186 | LCMS (FA): m/z = 529.2 (M + H) |
| 6-methylindole | I-132 | LCMS (FA): m/z = 542.2 (M + H) |
| 6-trifluoromethylindole | I-184 | LCMS (FA): m/z = 596.1 (M + H) |
| 6-chloroindole | I-125 | LCMS (FA): m/z = 562.1 (M + H) |

Example 196: {(1R,2S,4R)-2-Hydroxy-4-[(5-{[5-methyl-4-(1H-pyrazol-1-ylmethyl)-2-thienyl]carbonyl}pyrimidin-4-yl)amino]cyclopentyl}methyl sulfamate I-109

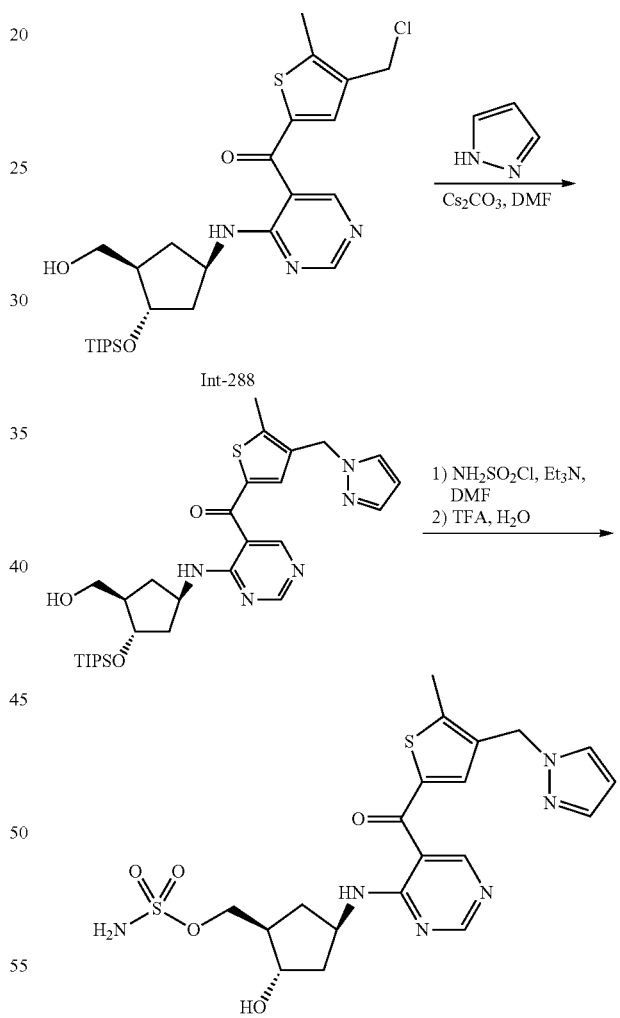

To a containing with 1H-pyrazole (8.17 mg, 0.12 mmol) was added $Cs_2CO_3$ (156 mg, 0.48 mmol), Int-288 (43.0 mg, 0.08 mmol), DMF (1.00 mL) and a solution of tetra-N-butylammonium bromide (3.87 mg, 0.01 mmol) in DMF (0.20 mL). The mixture was shaken vigorously at rt for 2 h. Solids were filtered and rinsed with DMF (1.0 mL). To the combined DMF solutions were added triethylamine (44.6 uL, 0.32 mmol), chlorosulfonamide (37.0 mg, 0.32 mmol) at 0° C. The mixture was shaken at rt for 30 min then quenched with saturated NaHCO₃ solution and EtOAc (5 mL). After layers were separated, the aqueous layer was extracted with EtOAc (6 mL). The combined organic phases were concentrated. To the solid in a 20-mL vial was added TFA (1.80 mL) and water (0.20 mL). After shaking for 30 min, the reaction mixture was concentrated in vacuo. To the residue was added MeOH (3.0 mL), PL-CO3 MP-Resin (2.04 mmol/g loading; 0.78 g, 1.60 mmol). After shaking at rt for 30 min, resin was filtered and rinsed with MeOH (8 mL). The combined methanol solutions were concentrated. The resulting solid was dissolved in DMSO (1.2 mL). After filtration, the residue was purified by preparative HPLC to give the title compound. LCMS (FA): 493.3 (M+H).

The compounds listed in the table below were prepared in a similar fashion to that described above starting from the listed starting materials:

| Starting material | Compound No. | LCMS Data |
|---|---|---|
| Br-pyrrole-CN | I-148 | LCMS (FA): m/z = 595.2 (M + H) |
| pyrrole-CN | I-194 | LCMS (FA): m/z = 517.2 (M + H) |
| methoxyindoline | I-126 | LCMS (FA): m/z = 574.3 (M + H) |
| chloroindoline | I-159 | LCMS (FA): m/z = 578.3 (M + H) |
| iodopyrazole | I-37 | LCMS (FA): m/z = 619.0 (M + H) |
| dihydropyrrolopyridine | I-171 | LCMS (FA): m/z = 545.3 (M + H) |
| bromopyrazole | I-39 | LCMS (FA): m/z = 571.1 (M + H) |
| cyanoindoline | I-128 | LCMS (FA): m/z = 569.3 (M + H) |
| chloropyrazole | I-55 | LCMS (FA): m/z = 527.1 (M + H) |
| methylpyrazole | I-78 | LCMS (FA): m/z = 507.3 (M + H) |

Example 197: {(1R,2S,4R)-4-[(5-{[4-(3,4-Dichlorobenzyl)-2-thienyl]carbonyl}pyrimidin-4-yl)amino]-2-hydroxycyclopentyl}methyl sulfamate I-104

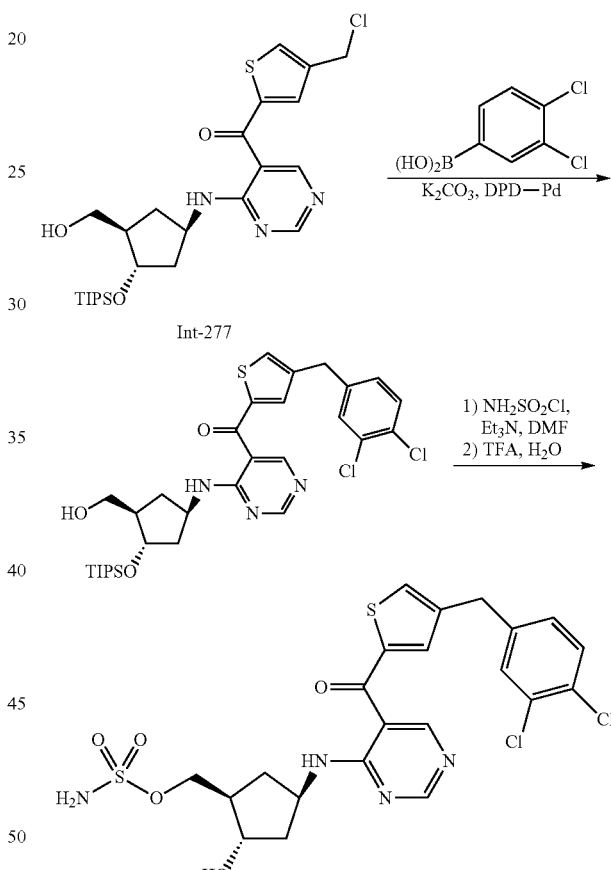

{(1R,2S,4R)-4-[(5-{[4-(3,4-Dichlorobenzyl)-2-thienyl]carbonyl}pyrimidin-4-yl)amino]-2-hydroxycyclopentyl}methyl sulfamate To a microwave vial was added Int-277 (25.0 mg, 0.04 mmol), 3,4-dichlorophenylboronic acid (16.8 mg, 0.09 mmol), SiliaCat DPP-Pd(0.26 mmol/g loading; 33.8 mg, 8.79 umol), K₂CO₃ (1.0 M in water, 0.13 mL, 0.13 mmol) and 1,4-dioxane (0.52 mL). The reaction was briefly degassed with N₂ then capped and heated at 75-80° C. with shaking for 1 hour. To the mixture was added saturated NaHCO₃ solution (1.5 mL) and EtOAc (5 mL). After separation, the aqueous layer was extracted with EtOAc (5 mL).

The combined organic phases were concentrated to dryness. To the solid residue was added DMF (1.0 mL), triethylamine (17.8 mg, 0.18 mmol) and chlorosulfonamide (20.3 mg, 0.18 mmol). After shaking at rt for 30 min, saturated NaHCO$_3$ solution (1.5 mL) was added slowly, the mixture was extracted with EtOAc twice (5 mL). The combined organic phases were concentrated in a 20-mL vial. To the residue was added TFA (1.80 mL), water (0.20 mL). After stirring for 30 min, reaction mixture was concentrated in vacuo. To the dry solid was added MeOH (3.0 mL) PL-CO3 MP-Resin (2.04 mmol/g loading; 216 mg, 0.44 mmol). After stirred for 30 min, the resin was filtered and rinsed with MeOH (5 mL). The combined methanol solutions were concentrated. The residue was dissolved in DMSO (1.2 mL). After filtration, the residue was purified by preparative HPLC to give the title compound (5.1 mg, 21%). LCMS (FA): 557.2 (M+1). $^1$H NMR (400 MHz, Methanol-d$_4$) δ 8.69 (s, 1H), 8.57 (s, 1H), 7.63 (d, J=1.3 Hz, 1H), 7.54 (d, J=1.3 Hz, 1H), 7.46-7.41 (m, 2H), 7.19 (dd, J=8.3, 2.1 Hz, 1H), 4.84-4.74 (m, 1H), 4.24-4.10 (m, 3H), 4.02 (s, 2H), 2.56-2.44 (m, 1H), 2.32-2.22 (m, 1H), 2.15 (ddd, J=12.6, 7.5, 4.5 Hz, 1H), 1.95-1.85 (m, 1H), 1.48-1.35 (m, 1H).

The compounds listed in the table below were prepared in a similar fashion to that described above starting from the listed starting materials:

| Starting material | Compound No. | LCMS Data |
|---|---|---|
| 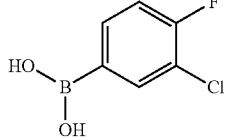 | I-61 | LCMS (FA): m/z = 540.8 (M + H) |
| 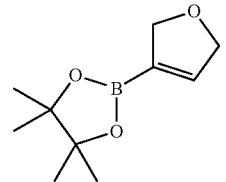 | I-193 | LCMS (FA): m/z = 480.9 (M + H) |
| 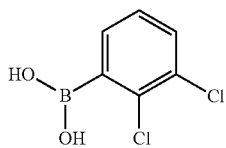 [SMILES: OB(O)c1cccc(Cl)c1Cl] | I-155 | LCMS (FA): m/z = 556.7 (M + H) |
| 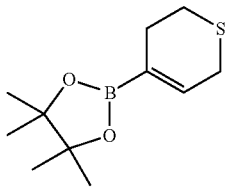 | I-173 | LCMS (FA): m/z = 510.9 (M + H) |
| 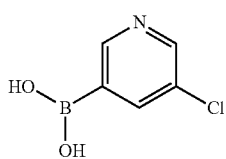 | I-210 | LCMS (FA): m/z = 523.8 (M + H) |

-continued

| Starting material | Compound No. | LCMS Data |
|---|---|---|
| 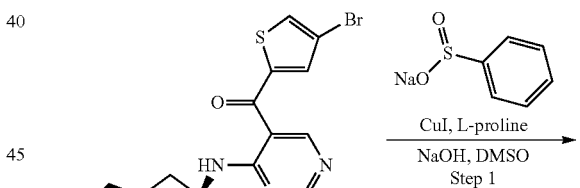 | I-185 | LCMS (FA): m/z = 513.9 (M + H) |
| | I-113 | LCMS (FA): m/z = 554.8 (M + H) |
| | I-84 | LCMS (FA): m/z = 540.8 (M + H) |
| 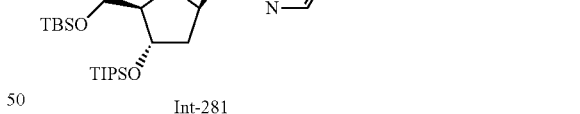 | I-81 | LCMS (FA): m/z = 534.8 (M + H) |

Example 198: {(1R,2S,4R)-2-Hydroxy-4-[(5-{[4-(phenylsulfonyl)-2-thienyl]carbonyl}pyrimidin-4-yl)amino]cyclopentyl}methyl sulfamate I-200

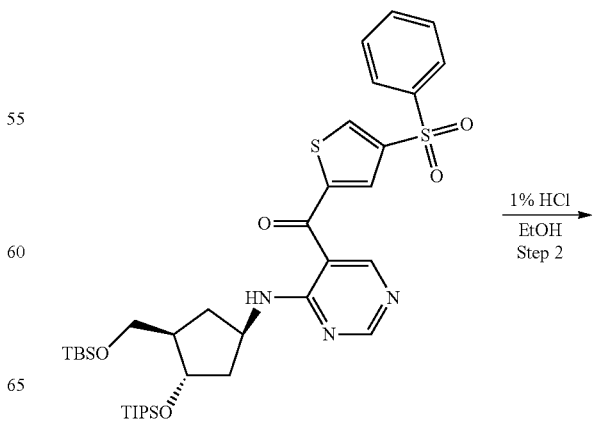

3.98-3.91 (m, 2H), 2.35-2.25 (m, 1H), 2.16-2.06 (m, 1H), 1.99-1.90 (m, 1H), 1.80-1.70 (m, 1H), 1.26 (dt, J=12.7, 9.2 Hz, 1H); LCMS: (FA) M+1 539.2

Example 199: [(1R,2S,4R)-2-Hydroxy-4-({5-[5-(phenylsulfonyl)-2-furoyl]pyrimidin-4-yl}amino)cyclopentyl]methyl sulfamate. I-239

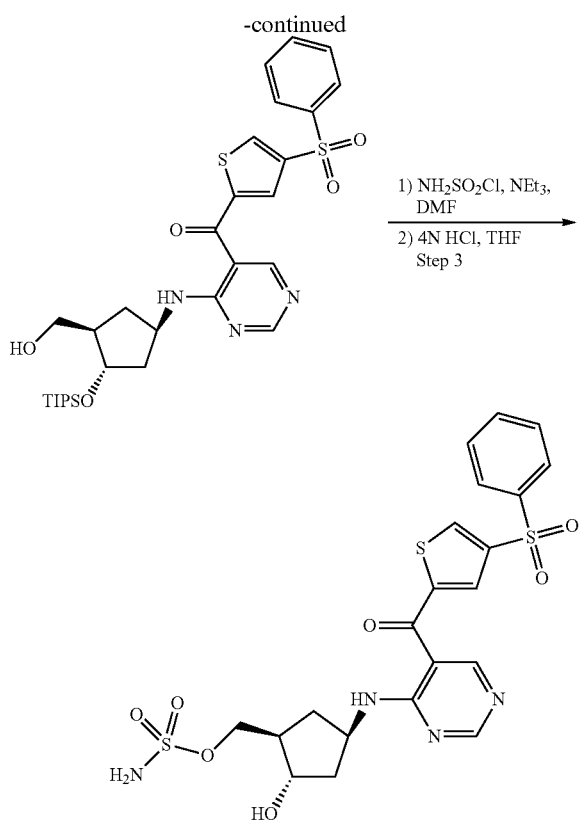

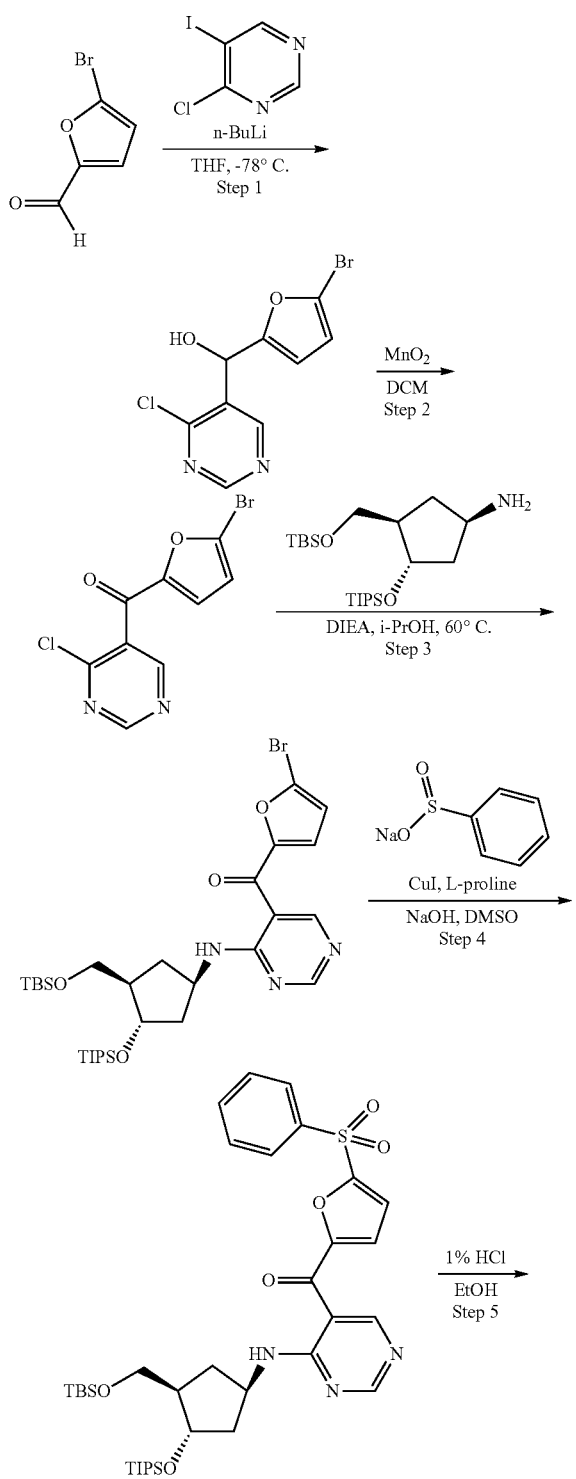

Step 1: [4-({(1R,3R,4S)-3-({[tert-Butyl(dimethyl)silyl]oxy}methyl)-4-[(triisopropylsilyl)oxy]cyclopentyl}amino)pyrimidin-5-yl][4-(phenylsulfonyl)-2-thienyl]methanone Into a microwave vial was added (4-bromo-2-thienyl)[4-({(1R,3R,4S)-3-({[tert-butyl(dimethyl)silyl]oxy}methyl)-4-[(triisopropylsilyl)oxy]cyclopentyl}amino)pyrimidin-5-yl]methanone (Int-281, 0.400 g, 0.598 mmol), sodium benzenesulfinate (0.196 g, 1.20 mmol), copper(I) iodide (17.1 mg, 0.0897 mmol), L-proline (20.6 mg, 0.179 mmol), and sodium hydroxide (7.18 mg, 0.179 mmol). The mixed solids were then dissolved in DMSO (3.0 mL, 42 mmol) purged with argon and heated to 95° C. in the microwave for 1 hr. The reaction was quenched with saturated NH₄Cl and extracted with EtOAc (3×). The combined organic layers were then washed with water, brine, dried using Na₂SO₄, filtered and concentrated. The residue was purified by ISCO silica gel chromatography (24 g column, eluting with 0-30-50-100% EtOAc/Hex. over 25 mins) to give crude product containing the de-protected mono alcohol. LCMS (FA): m/z=730.2 (M+H)

Steps 2 and 3: {(1R,2S,4R)-2-Hydroxy-4-[(5-{[4-(phenylsulfonyl)-2-thienyl]carbonyl}pyrimidin-4-yl)amino]cyclopentyl}methyl sulfamate Steps 2 and 3 were performed in an analogous fashion to Example 135, steps 6 and 7 to afford the title compound. ¹H NMR (400 MHz, DMSO-d₆) δ 8.89 (d, J=1.4 Hz, 1H), 8.68 (s, 2H), 8.27 (d, J=7.5 Hz, 1H), 8.09-8.02 (m, 3H), 7.75-7.69 (m, 1H), 7.67-7.61 (m, 2H), 7.42 (s, 2H), 4.89 (d, J=4.6 Hz, 1H), 4.77-4.65 (m, 1H), 4.08 (dd, J=9.7, 5.9 Hz, 1H),

669

-continued

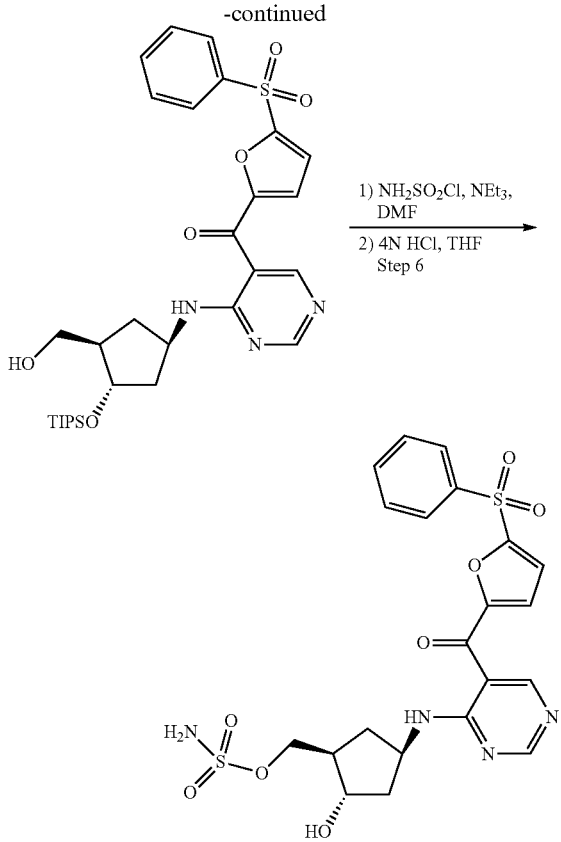

Step 1: (5-Bromo-2-furyl)(4-chloropyrimidin-5-yl)methanol

A solution of 4-chloro-5-iodopyrimidine (3.60 g, 14.80 mmol) in THF (40.0 mLl) was cooled to −78° C., at which point 2.50 M of n-BuLi in hexane (7.0 mL, 17.50 mmol) was added dropwise via syringe. At the conclusion of the addition, a solution of 5-bromo-2-furaldehyde (2.0 g, 11.40 mmol) in THF (10.0 mL) was next added dropwise, via syringe and the reaction was stirred at −78° C. for 10 min. The reaction was quenched via addition of a saturated NaHCO$_3$ solution (20 mL), and then allowed to warm to RT and extracted with EtOAc (3×). Layers were separated and the combined organic layers were washed with brine, dried over Na$_2$SO$_4$, filtered, and concentrated in vacuo. The residue was purified by silica gel chromatography (eluting with 0-50% EtOAc/Hex. over 25 mins) to give 2.5 g (75%) of product. $^1$H NMR (400 MHz, Chloroform-d) δ 9.04 (s, 1H), 8.95 (s, 1H), 6.28 (d, J=3.2 Hz, 1H), 6.19 (d, J=3.2 Hz, 1H), 6.08 (s, 1H), 3.38 (s, 1H).

Step 2: (5-Bromo-2-furyl)(4-chloropyrimidin-5-yl)methanone

To a solution of (5-bromo-2-furyl)(4-chloropyrimidin-5-yl)methanol (2.50 g, 8.64 mmol) in DCM (30.0 mL) was added MnO$_2$ (7.52 g, 86.4 mmol). The mixture was then stirred at RT overnight. The reaction was then filtered through a Celite pad and the filter cake was rinsed thoroughly with EtOAc. The filtrate was concentrated in vacuo to afford 2.3 g (93%) of product.

670

Step 3: (5-Bromofuran-2-yl)(4-(((1R,3R,4S)-3-(((tert-butyldimethylsilyl)oxy)methyl)-4-((triisopropylsilyl)oxy)cyclopentyl)amino)pyrimidin-5-yl)methanone To a solution of (5-bromo-2-furyl)(4-chloropyrimidin-5-yl)methanone (2.3 g, 8.0 mmol) and (1R,3R,4S)-3-({[tert-butyl(dimethyl)silyl]oxy}methyl)-4-[(triisopropylsilyl)oxy]cyclopentanamine (4.5 g, 11.2 mmol) in isopropyl alcohol (30 mL) was added N,N-diisopropylethylamine (3.48 mL, 20.0 mmol) and the reaction was heated at 60° C. for 1 hour. The reaction was cooled to RT and concentrated to dryness. The residue was purified by silica gel chromatography (eluting with 0-30% EtOAc/Hex. over 25 mins) to give 3.2 g (61%) of product. $^1$H NMR (400 MHz, Chloroform-d) δ 9.08 (s, 1H), 8.87 (d, J=6.8 Hz, 1H), 8.66 (s, 1H), 7.20 (d, J=3.6 Hz, 1H), 6.57 (d, J=3.6 Hz, 1H), 4.83-4.79 (m, 1H), 4.32-4.29 (m, 1H), 3.64-3.54 (m, 2H), 2.46-2.43 (m, 1H), 2.20-2.15 (m, 2H), 1.74-1.72 (m, 1H), 1.28-1.23 (m, 1H), 1.07 (s, 21H), 0.89 (s, 9H), 0.05 (s, 6H).

Steps 4, 5, and 6: [(1R,2S,4R)-2-Hydroxy-4-({5-[5-(phenylsulfonyl)-2-furoyl]pyrimidin-4-yl}amino)cyclopentyl]methyl sulfamate Steps 4, 5, and 6 were performed in an analogous fashion to Example 198, steps 1, 2, and 3 to afford the title compound. $^1$H NMR (400 MHz, DMSO-d$_6$) δ 8.75 (s, 1H), 8.65 (s, 1H), 8.45 (d, J=7.5 Hz, 1H), 8.05-8.00 (m, 2H), 7.85-7.79 (m, 1H), 7.76-7.70 (m, 2H), 7.66 (d, J=3.8 Hz, 1H), 7.55 (d, J=3.8 Hz, 1H), 7.43 (s, 2H), 4.89 (d, J=4.6 Hz, 1H), 4.76-4.64 (m, 1H), 4.08 (dd, J=9.7, 5.9 Hz, 1H), 3.98-3.91 (m, 2H), 2.36-2.26 (m, 1H), 2.16-2.06 (m, 1H), 1.99-1.91 (m, 1H), 1.80-1.71 (m, 1H), 1.26 (dt, J=12.8, 9.1 Hz, 1H); LCMS: (FA) M+1 523.2

Example 200: [(1R,2S,4R)-4-{[5-({5-Chloro-4-[(R)-(3-chlorophenyl)sulfinyl]-2-thienyl}carbonyl)pyrimidin-4-yl]amino}-2-hydroxycyclopentyl]methyl sulfamate and [(1R,2S,4R)-4-{[5-({5-chloro-4-[(S)-(3-chlorophenyl)sulfinyl]-2-thienyl}carbonyl)pyrimidin-4-yl]amino}-2-hydroxycyclopentyl]methyl sulfamate I-94

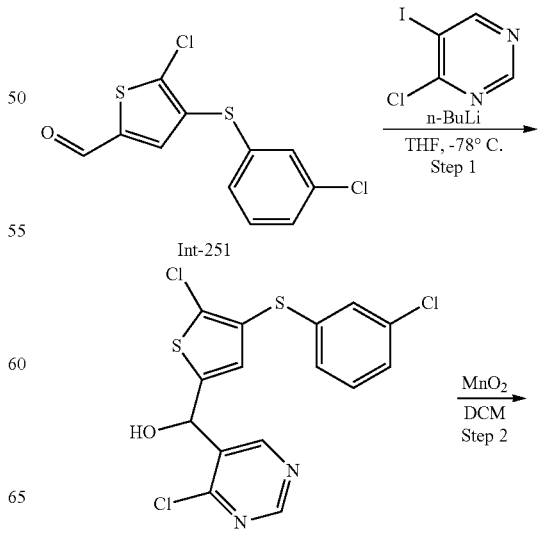

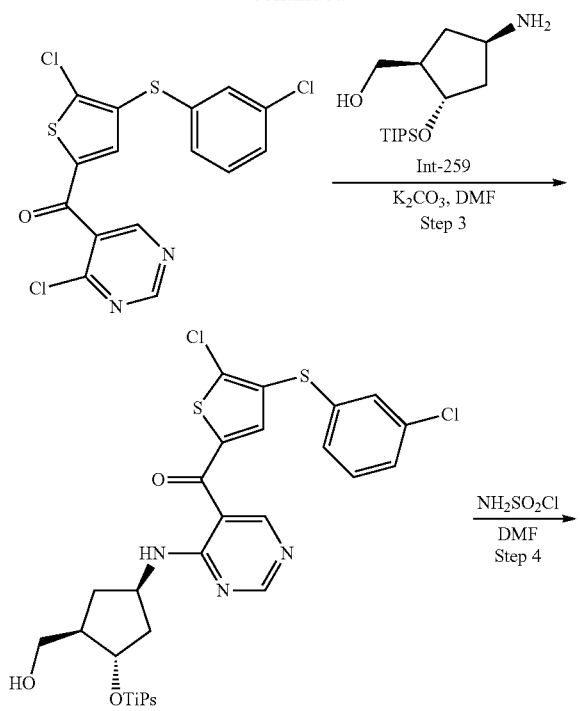
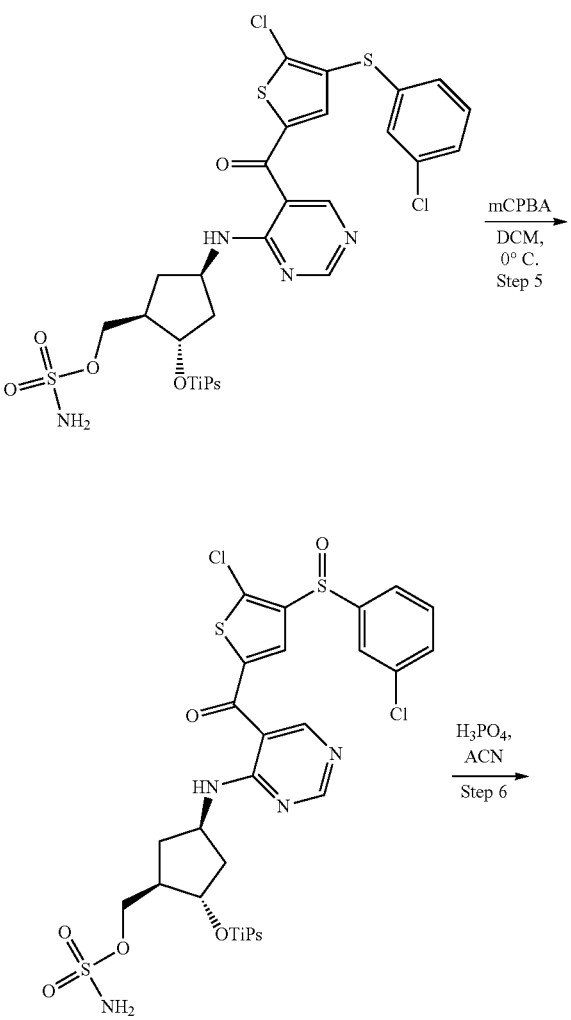
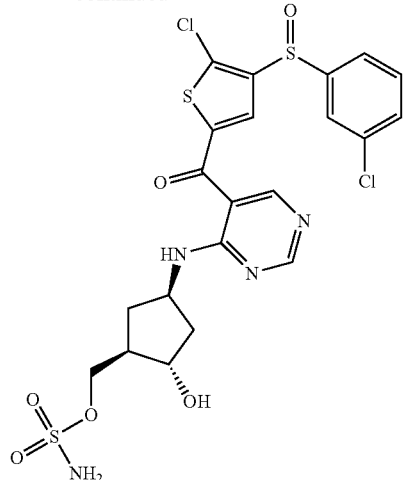

Steps 1-4: [(1R,2S,4R)-4-[[5-[5-Chloro-4-(3-chlorophenyl)sulfinyl-thiophene-2-carbonyl]pyrimidin-4-yl]amino]-2-hydroxy-cyclopentyl]methyl sulfamate Steps 1, 2, 3, and 4 were performed in an analogous fashion to Example 198, steps 1, 2, 3 and 4 beginning from Int-251 to afford the title compound. Step 5 was performed as described below.

Step 5: [(1R,2S,4R)-4-[[5-[5-Chloro-4-(3-chlorophenyl)sulfinyl-thiophene-2-carbonyl]pyrimidin-4-yl]amino]-2-triisopropylsilyloxy-cyclopentyl]methyl sulfamate A solution of [(1R,2S,4R)-4-[[5-[4-(3-chlorophenyl)sulfanyl-5-methyl-thiophene-2-carbonyl]pyrimidin-4-yl]amino]-2-triisopropylsilyloxy-cyclopentyl]methyl sulfamate (268.0 mg, 0.3662 mmol) in DCM (46.946 mL, 732.39 mmol) under argon was cooled at 0° C. by ice-water bath. Overall m-chloroperbenzoic acid (157.2 mg, 0.701 mmol) was added in 15-20 mg (~0.2 equiv.) portions over 3 h until the reaction was nearly complete by LCMS and TLC. The reaction was diluted with DCM and saturated NaHCO$_3$ was added. The reaction was extracted 3 times with DCM. The combined organic portions was washed with brine, dried over Na$_2$SO$_4$, filtered, and concentrated in vacuo. The residue was purified by silica gel column chromatography (0 to 100% EtOAc in hexane) to give 136 mg (50%) of the title compound as an orange oil. $^1$H NMR (400 MHz, DMSO-d6) δ 8.69-8.64 (m, 2H), 8.24 (d, J=7.5 Hz, 1H), 7.88-7.85 (m, 1H), 7.81 (d, J=0.9 Hz, 1H), 7.77-7.72 (m, 1H), 7.69-7.59 (m, 2H), 7.44 (s, 2H), 4.81-4.72 (m, 1H), 4.28-4.20 (m, 1H), 4.08-3.94 (m, 2H), 2.38-2.29 (m, 1H), 2.27-2.15 (m, 1H), 2.05-1.93 (m, 1H), 1.90-1.80 (m, 1H), 1.34-1.22 (m, 1H), 1.09-0.96 (m, 18H); LCMS (AA): m/z=747.2/749.2 (M+H).

Step 6: [(1R,2S,4R)-4-{[5-({5-Chloro-4-[(R)-(3-chlorophenyl)sulfinyl]-2-thienyl}carbonyl)pyrimidin-4-yl]amino}-2-hydroxycyclopentyl]methyl sulfamate and [(1R,2S,4R)-4-{[5-({5-Chloro-4-[(S)-(3-chlorophenyl)sulfinyl]-2-thienyl}carbonyl)pyrimidin-4-yl]amino}-2-hydroxycyclopentyl]methyl sulfamate Step 6 was performed in an analogous fashion to Example 133, step 8 to afford the title compound. $^1$H NMR (400 MHz, DMSO-d$_6$) δ 8.67 (s, 2H), 8.23 (d, J=7.3 Hz, 1H), 7.88-7.85 (m, 1H), 7.82 (s, 1H), 7.77-7.72 (m, 1H), 7.68-7.59 (m, 2H), 7.41 (s, 2H), 4.92-4.84 (m, 1H), 4.77-4.65 (m, 1H), 4.11-4.05 (m, 1H), 3.98-3.90 (m, 2H), 2.35-2.24 (m, 1H), 2.16-2.06 (m, 1H), 2.00-1.89 (m, 1H), 1.82-1.70 (m, 1H), 1.33-1.21 (m, 1H)); LCMS: (AA) M+1 591.1/593.1

The compounds listed in the table below were prepared in a similar fashion to that described above starting from the listed starting materials:

| Starting material | Compound No. |
|---|---|
| Int-253 | I-122 |
| Int-254 | I-28 |
| Int-255 | I-69 |
| Int-256 | I-68 |

Example 201: [(1R,2S,4R)-4-[[5-[4-[(1R)-7-Chloro-1,2,3,4-tetrahydroisoquinolin-1-yl]-5-methyl-thiophene-2-carbonyl]pyrimidin-4-yl]amino]-2-hydroxy-cyclopentyl]methyl sulfamate I-263a Form 1

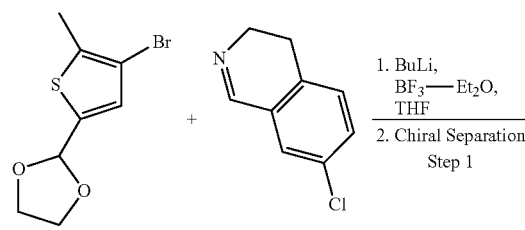

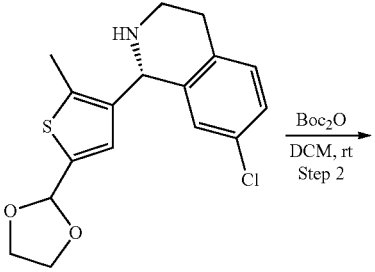

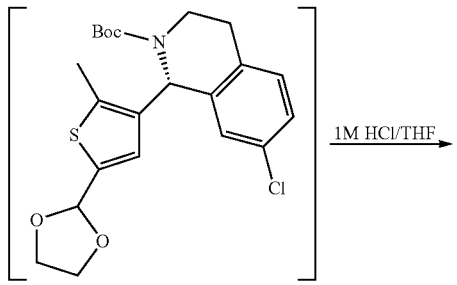

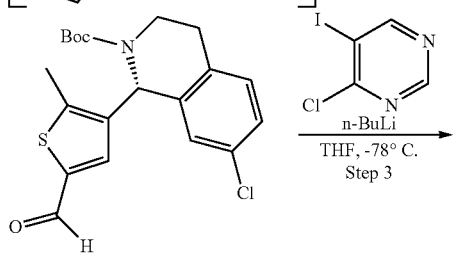

-continued

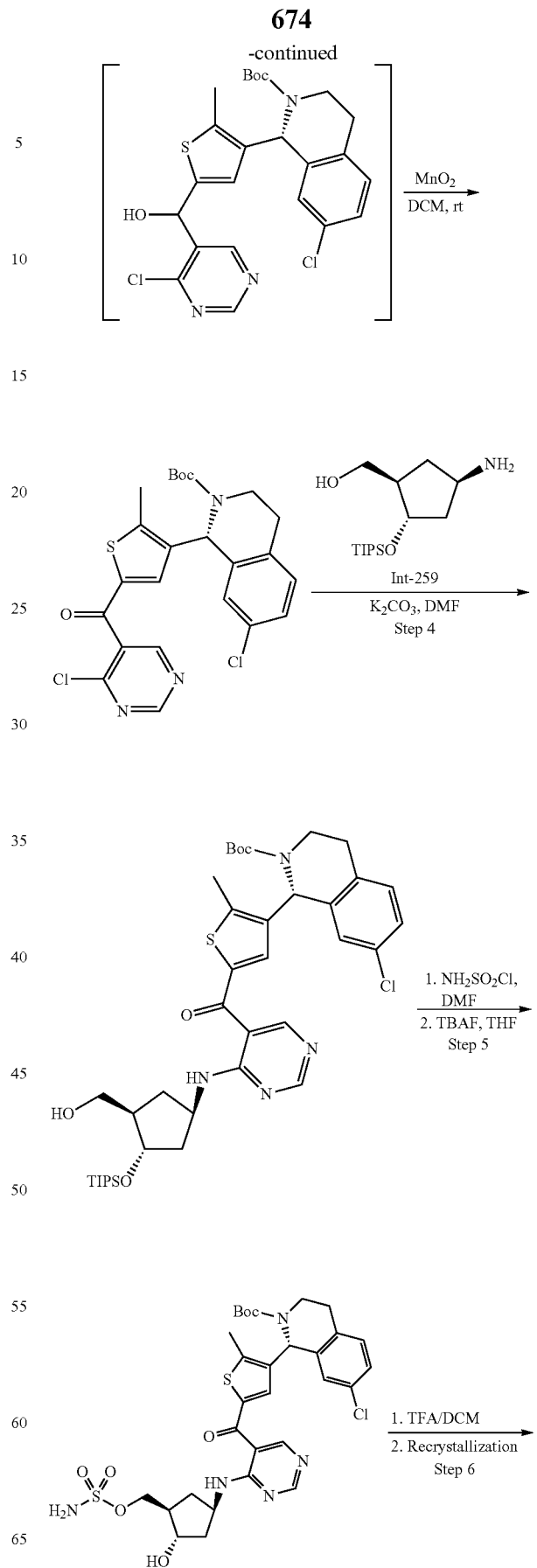

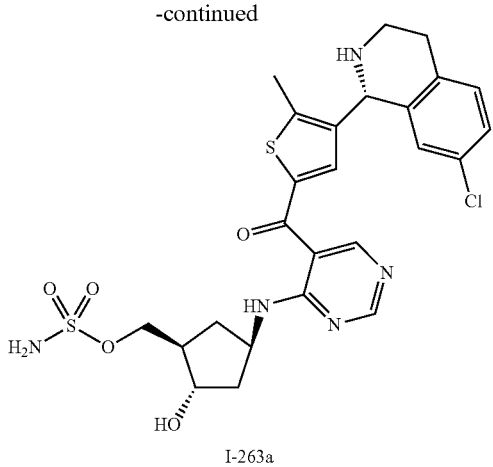

I-263a

Step 1: (1S)-7-Chloro-1-[5-(1,3-dioxolan-2-yl)-2-methyl-3-thienyl]-1,2,3,4-tetrahydroisoquinoline and (1R)-7-chloro-1-[5-(1,3-dioxolan-2-yl)-2-methyl-3-thienyl]-1,2,3,4-tetrahydroisoquinoline To a solution of 2-(4-bromo-5-methyl-2-thienyl)-1,3-dioxolane (90.3 g, 362 mmol) in THF (500 mL) was added dropwise 2.50 M of n-BuLi (193 mL, 483 mmol) at −78° C. under an atmosphere of $N_2$, and the mixture was allowed to stir at −78° C. for 20 min. Another reaction vessel was charged with 7-chloro-3,4-dihydroisoquinoline (40 g, 242 mmol) and the contents were dissolved in THF (1.3 L). To this solution was added dropwise $BF_3$-$Et_2O$ (32.8 mL, 265.7 mmol) at −30° C., and the solution was allowed to stir for 10 min. To this mixture was added dropwise the previous lithiated mixture via cannula and the resulting mixture was allowed to stir at −30° C. for 30 min. Then the reaction mixture was allowed to warm to 0° C. and stirred for 1 h. The reaction was quenched by addition of saturated aqueous $NaHCO_3$, and the mixture was extracted with EtOAc (500 mL×3). The combined organic layers were washed with brine, dried over $Na_2SO_4$, filtered, and concentrated in vacuo. The above procedure was performed on the same scale two additional times. The residues from all three procedures were then combined and purified by silica gel chromography, eluting with a 85/15 to 0/100 pentane/EtOAc gradient to provide a yellow solid. The resulting solid was washed with pentane of to provide the racemic mixture (110 g, 45%) as a yellow solid. The racemic mixture was separated into the individual component enantiomers by chiral chromatography (SFC: CHIRALPAK AD 50×300 mm with 35/65 0.1% $NH_4OH$ in $MeOH/CO_2$, 200 mL/min, 10 MPa) to obtain 51.5 g (99.7% ee) of (1R)-7-chloro-1-[5-(1,3-dioxolan-2-yl)-2-methyl-3-thienyl]-1,2,3,4-tetrahydroisoquinoline as first elute (retention time 3.7 min, LCMS: (AA) M+1 336.0) and 50.0 g (99.7% ee) of (1S)-7-chloro-1-[5-(1,3-dioxolan-2-yl)-2-methyl-3-thienyl]-1,2,3,4-tetrahydroisoquinoline as second elute (retention time 4.8 min, LCMS: (AA) M+1 336.0).

Step 2: tert-Butyl (1R)-7-chloro-1-(5-formyl-2-methyl-3-thienyl)-3,4-dihydro-1H-isoquinoline-2-carboxylate To a solution of (1R)-7-chloro-1-[5-(1,3-dioxolan-2-yl)-2-methyl-3-thienyl]-1,2,3,4-tetrahydroisoquinoline (48 g, 142 mmol) in DCM (700 mL) was added $Boc_2O$ (34 g, 156 mmol). The reaction was allowed to stir for 3 h at rt. The reaction mixture was filtered and concentrated in vacuo. Optionally, tert-butyl (R)-1-(5-(1,3-dioxolan-2-yl)-2-methylthiophen-3-yl)-7-chloro-3,4-dihydroisoquinoline-2(1H)-carboxylate may be isolated at this stage. The residue was dissolved in THF (720 mL) and 1.0 M of HCl in $H_2O$ (360 mL, 360 mmol) was added to the solution. The reaction was allowed to stir for 1 h at rt. The reaction mixture was quenched by addition of saturated aqueous $NaHCO_3$ (600 mL) and concentrated in vacuo to remove THF. The resulting mixture was extracted with EtOAc (600 mL×3). The combined organic layers were washed with brine, dried over $Na_2SO_4$, filtered, and concentrated in vacuo. The crude solid was purified by silica gel chromatography (330 g column, eluting with 95/5 to 85/15 pentane/EtOAc gradient) to provide 54 g (81%) of the title compound as a light yellow oil. $^1$H NMR (400 MHz, CHLOROFORM-d) δ 9.64 (s, 1H) 7.06-7.24 (m, 3H) 6.94 (s, 1H) 6.30 (s, 1H) 4.05-4.20 (m, 1H) 3.07-3.13 (m, 1H) 2.90-3.04 (m, 1H) 2.70-2.78 (m, 1H) 2.66 (s, 3H) 1.50 (s, 9H). The solvent may alternatively comprise any one or more of dichloromethane, THF, MeTHF, and tert-butyl methylether. The solvent or solvent system for the reaction with $Boc_2O$ may be the same as or different from the solvent or solvent system for the reaction with HCl.

Step 3: tert-Butyl (1R)-7-chloro-1-(5-formyl-2-methyl-3-thienyl)-3,4-dihydro-1H-isoquinoline-2-carboxylate A solution of 4-chloro-5-iodopyrimidine (27.85 g, 116 mmol) in THF (280 mL) was cooled to −78° C. with a dry-ice/MeOH bath. To the solution was added dropwise 2.50 M of n-BuLi in hexane (93 mL, 233 mmol) and the mixture was allowed to stir for 15 min at −78° C. To the mixture was added dropwise a solution of tert-butyl (1R)-7-chloro-1-(5-formyl-2-methyl-3-thienyl)-3,4-dihydro-1H-isoquinoline-2-carboxylate (27 g, 68.5 mmol) in THF (90 mL) at −75° C., and the resulting mixture was allowed to stir for 10 min at −40° C. followed by stirring for 30 min at 26° C. The reaction was quenched by addition of saturated aqueous $NH_4Cl$ (560 mL) and extracted with EtOAc (600 mL×3). The combined organic layers were washed with brine, dried over $Na_2SO_4$, filtered, and concentrated in vacuo to provide 90 g of a maroon oil which was used without further purification. This step can also be done using a magnesium-halogen exchange (such as isopropylmagnesium chloride lithium chloride complex). Solvent for this transformation can alternatively comprise MeTHF. This reaction also can be run at 0° C. to room temperature. The crude mixture was divided into three portions (30 g, 59 mmol each) and each portion was dissolved in DCM (500 mL). Manganese (IV) oxide (86.7 g, 1 mol) was added to each solution and the reactions were allowed to stir at 30° C. for 4 h, at which point they were combined and filtered through a Celite pad. The filter cake was rinsed with DCM/MeOH (100/1, 500 mL×3). The filtrate was concentrated in vacuo and the residue was purified by column chromatography eluting with 90/10 to 85/15 pentane/EtOAc gradient to provide 40 g (58% in 2 steps) of the title compound as a light yellow solid. The oxidation of tert-butyl (1R)-7-chloro-1-(5-((4-chloropyrimidin-5-yl)(hydroxy)methyl)-2-methylthiophen-3-yl)-3,4-dihydroisoquinoline-2

(1H)-carboxylate can also be done using TEMPO/NaClO reaction conditions. LCMS: (AA) M+Na 522.6.

Step 4: tert-Butyl (1R)-7-chloro-1-[5-[4-[[(1R,3R, 4S)-3-(hydroxymethyl)-4-triisopropylsilyloxy-cyclopentyl]amino]pyrimidine-5-carbonyl]-2-methyl-3-thienyl]-3,4-dihydro-1H-isoquinoline-2-carboxylate To a solution of tert-butyl (1R)-7-chloro-1-[5-(4-chloropyrimidine-5-carbonyl)-2-methyl-3-thienyl]-3,4-dihydro-1H-isoquinoline-2-carboxylate (25.0 g, 49.6 mmol) in DMF (50.0 mL, 646 mmol) was added [(1R,2S,4R)-4-amino-2-triisopropylsilyloxy-cyclopentyl]methanol (Int-259, 18.5 g, 64.3 mmol) followed by $K_2CO_3$ (17.2 g, 124 mmol) at rt and the reaction was allowed to stir for 5 h. The reaction mixture was concentrated in vacuo to remove DMF. To the residue was added 400 mL of water and the mixture was extracted with EtOAc (400 mL×4). The combined organic layers were washed with brine, dried over $Na_2SO_4$, filtered, and concentrated in vacuo. The residue was subjected to silica gel column chromatography eluting with 80/20 to 50/50 hexane/EtOAc gradient. The byproduct containing fractions were purified by silica gel column chromatography several times. The pure product fractions were combined and concentrated in vacuo to provide 32.6 g (84%) of the title compound as light yellow amorphous solid. This reaction also can be run with bases such as one or more of TEA, DIEA, NMM, and Pyridine. Other solvents can also be used for this transformation such as DMF, THF, DCM, toluene, ethyl acetate, ACN, DME, NMP, dioxane, and DMSO. $^1$H NMR (400 MHz, DMSO-d6) δ ppm 8.55 (s, 1H) 8.44 (s, 1H) 8.21 (d, J=7.53 Hz, 1H) 7.23-7.30 (m, 2H) 7.13 (s, 1H) 7.06 (br s, 1H) 6.33 (s, 1H) 4.61-4.74 (m, 2H) 4.18-4.24 (m, 1H) 3.95-4.03 (m, 1H) 3.33-3.43 (m, 2H) 3.09-3.20 (m, 1H) 2.78-2.86 (m, 2H) 2.59 (s, 3H) 2.27 (dt, J=12.92, 8.09 Hz, 1H) 1.88-1.98 (m, 2H) 1.68-1.79 (m, 1H) 1.41 (s, 9H) 1.19-1.26 (m, 1H) 0.99-1.05 (m, 21H). LCMS: (AA) M+1 755.3.

Step 5: tert-Butyl (1R)-7-chloro-1-[5-[4-[[(1R,3S, 4R)-3-hydroxy-4-(sulfamoyloxymethyl)cyclopentyl]amino]pyrimidine-5-carbonyl]-2-methyl-3-thienyl]-3,4-dihydro-1H-isoquinoline-2-carboxylate To a solution of tert-butyl (1R)-7-chloro-1-[5-[4-[[(1R, 3R,4S)-3-(hydroxymethyl)-4-triisopropylsilyloxy-cyclopentyl]amino]pyrimidine-5-carbonyl]-2-methyl-3-thienyl]-3,4-dihydro-1H-isoquinoline-2-carboxylate (32.5 g, 41.7 mmol) in DMF (100 mL, 1.29 mol) was added sulfamoyl chloride (10.1 g, 84.5 mmol) at 0° C. with ice/water bath, and the reaction was allowed to stir for 5 min at rt. The reaction was cooled to 0° C. with ice/water bath and quenched by addition of saturated aqueous $NaHCO_3$. The resulting mixture was extracted with EtOAc (×4). The combined organic layers were washed with brine, dried over $Na_2SO_4$, filtered, and concentrated in vacuo. The residue was dissolved in THF (200 mL) and TBAF-hydrate (17.0 g, 63.7 mmol) was added to the solution at rt. The reaction was then heated to 40° C. and allowed to stir for 2 h. The reaction was quenched by addition of water (500 mL) and extracted with EtOAc (×4). The combined organic layers were washed with brine, dried over $Na_2SO_4$, filtered, and concentrated in vacuo. The residue was partially purified by silica gel column chromatography eluting with a 100/0 to 95/5 EtOAc/MeOH gradient. The mixed fractions were purified by silica gel column chromatography eluting with a 99/1 EtOAc/MeOH. The pure fractions were combined and concentrated in vacuo to provide 30.0 g (88%) of the desired compound as light yellow amorphous solid. $^1$H NMR (400 MHz, DMSO-d6) δ ppm 8.57 (s, 1H) 8.45 (s, 1H) 8.17 (d, J=7.53 Hz, 1H) 7.43 (s, 2H) 7.23-7.31 (m, 2H) 7.13 (s, 1H) 7.07 (br s, 1H) 6.33 (s, 1H) 4.87 (br d, J=4.52 Hz, 1H) 4.60-4.72 (m, 1H) 3.88-4.11 (m, 4H) 3.09-3.21 (m, 1H) 2.77-2.86 (m, 2H) 2.59 (s, 3H) 2.22-2.32 (m, 1H) 2.03-2.14 (m, 1H) 1.87-1.96 (m, 1H) 1.68-1.77 (m, 1H) 1.41 (s, 9H) 1.22-1.30 (m, 1H). LCMS: (AA) M+1 678.2.

Step 6: [(1R,2S,4R)-4-[[5-[4-[(1R)-7-Chloro-1,2,3, 4-tetrahydroisoquinolin-1-yl]-5-methyl-thiophene-2-carbonyl]pyrimidin-4-yl]amino]-2-hydroxy-cyclopentyl]methyl sulfamate I-263a Form 1

A 2 L round bottom flask was charged with tert-butyl (1R)-7-chloro-1-[5-[4-[[(1R,3S,4R)-3-hydroxy-4-(sulfamoyloxymethyl)cyclopentyl]amino]pyrimidine-5-carbonyl]-2-methyl-3-thienyl]-3,4-dihydro-1H-isoquinoline-2-carboxylate (47.4 g, 58.0 mmol) and the content was dissolved in DCM (50.0 mL). The mixture was cooled at 0° C. with ice/water bath and then TFA (50.0 mL, 661 mmol) was added to the reaction vessel. The reaction was allowed to stir for 1 h at rt. The reaction was diluted with DCM and the mixture was concentrated in vacuo. The residue was azeotroped twice with DCM. The resulting residue was basified by addition of saturated aqueous $NaHCO_3$ and extracted with EtOAc (×4). The combined organic layers were dried over $Na_2SO_4$, filtered, and concentrated in vacuo. The crude residue was partially purified by silica gel column chromatography eluting with 3% $NH_4OH$: 5% MeOH: 42% DCM: 50% MeCN. The fractions containing the desired product were combined and concentrated in vacuo. The residue was dissolved in a small amount of column eluent and then the solution was divided into four portions. Each portion was purified by silica gel column chromatography eluting with 3% $NH_4OH$: 5% MeOH: 42% DCM: 50% MeCN. Fractions containing desired product were combined and concentrated in vacuo. To the gummy residue was added 200 mL of MeOH followed by slow addition of 1.4 L of $CH_3CN$ and the resulting solution was allowed to stir slowly at rt for 3 days. The resulting suspension was filtered through a glass fritted funnel and the filter cake was rinsed with $CH_3CN$ and then dried in vacuo at 40° C. for 5 days to provide 26.5 g of the title compound. The mother liquor was concentrated in vacuo and the residue was re-purified by silica gel column chromatography eluting with 3% $NH_4OH$: 5% MeOH: 42% DCM: 50% MeCN mixed solution. The pure fractions were combined and concentrated in vacuo. To the residue was added 20 mL of MeOH followed by addition of 500 mL of $CH_3CN$, and the resulting mixture was settled overnight at rt with slow stirring. After filtration of the resulting suspension, the filter cake was dried in a drying oven at 40° C. for 5 days to provide an additional 6.3 g of the title compound (total 32.8 g) as I-263a Form 1. 1H NMR (400 MHz, Methanol-d4) δ ppm 8.61 (s, 1H) 8.52 (s, 1H) 7.27 (s, 1H) 7.16 (d, J=1.00 Hz, 2H) 6.69-6.71 (m, 1H) 5.22 (s, 1H) 4.70-4.82 (m, 1H) 4.11-4.23 (m, 3H) 3.24-3.30 (m, 1H) 2.96-3.12 (m, 2H) 2.76-2.86 (m, 1H) 2.60 (s, 3H) 2.43-2.53 (m, 1H) 2.20-2.29 (m, 1H) 2.08-2.16 (m, 1H) 1.87 (dt, J=14.87, 6.87 Hz, 1H) 1.40 (dt, J=13.05, 9.16 Hz, 1H). 13C NMR (101 MHz, DMSO-d6) δ 185.40, 160.24, 159.23, 157.75, 146.62, 142.44, 140.41, 138.04, 136.53, 134.47, 131.00, 129.92, 126.11, 126.08, 111.79, 71.29, 70.46, 54.59, 48.74, 45.88, 42.10, 40.58, 33.95, 28.42, 13.82. LCMS:

(AA) M-1 576.4. Elemental Anal. Calcd for C25H28ClN5O5S2: C, 51.94; H, 4.88; N, 12.11. Found: C, 51.91; H, 4.81; N, 12.15.

XRPD data is shown in FIG. 2. XRPD patterns were collected using a Bruker AXS D8 Advance X-ray Diffractometer equipped with LynxEye detector and copper K-alpha (Cu Kα) radiation at 40 kV and 40 mA. A powder sample was gently flattened at the center of a sample holder making smooth surface for diffraction measurement. A 50 mm diameter polymethylmethacrylate sample holder was used. The sample was run as a continuous scan from 2.9° to 29.6° 2θ using 2θ/θ locked coupled angles with step size of 0.025° 2θ and data collection time of 0.4 seconds per step. All data analysis was performed using DIFFRAC.EVA (version 2.1) software (Bruker AXS).

The instruments used for DSC and TGA sample runs were TA Instruments, DSC model Q200 or Q2000, and TGA model Q500 or Q5000.

For DSC, the sample (1 to 2 mg) was sealed in an aluminum pan with pinhole lid. The sample was heated from 25° C. to 350° C. at a ramp rate of 10° C./min, while the nitrogen sample purge was kept constant at 50 mL/min. Data was collected using Thermal Advantage software for Q Series (version 5.3.5) and data analysis was performed using Universal Analysis 2000 (TA Instruments).

For TGA, the sample (5 to 10 mg) in an open platinum pan was heated from 25° C. to 350° C. at a ramp rate of 10° C./min with a nitrogen sample purge of 60 mL/min. Data was collected using Thermal Advantage software for Q Series (version 5.3.5) and data analysis was performed using Universal Analysis 2000 (TA Instruments).

Raman spectra were determined using a DXR Raman microscope (Thermo Scientific) equipped with a 780 nm laser. A small amount of sample dispersed on aluminum pan sample holder was observed under Olympus microscope at 10× objective magnifications. Spectra were collected using a 50 μm pinhole aperture in the wave number range of 3500 to 50 cm$^{-1}$. Spectra analysis was performed using OMINIC 8 software, version 8.3.103 (Thermo Scientific).

DSC data is shown in FIG. 4; TGA is shown in FIG. 5; and Raman data is shown in FIGS. 6-7.

The following is an alternative to steps 5 and 6.

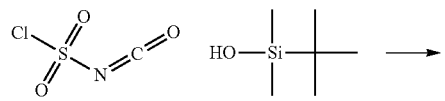

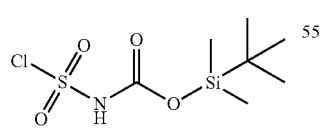

To a solution of chlorosulfonyl isocyanate (6.67 g, 47.1 mmol) in acetonitrile (47.1 mL, 901.8 mmol) at 0° C. add TBS-silanol (6.50 g, 49 mmol) while maintaining a temperature below 10° C. Stir the mixture at 0-10° C. for 30 min; reagent is ready for use as a 1M solution in acetonitrile. The reagent (TBS-chlorosulfonamide) is stable in solution for 24 hours.

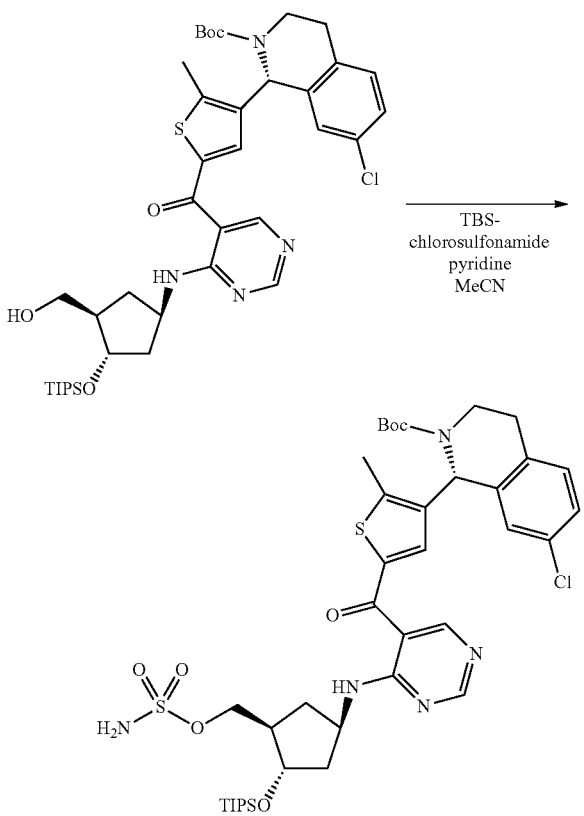

Dry solvents and reagents were used and the reaction was carried out under a nitrogen atmosphere. Add pyridine (3.85 g, 48.7 mmol) to a solution of tert-butyl (R)-7-chloro-1-(5-(4-(((1R,3R,4S)-3-(hydroxymethyl)-4-((triisopropylsilyl)oxy)cyclopentyl)amino)pyrimidine-5-carbonyl)-2-methyl-thiophen-3-yl)-3,4-dihydroisoquinoline-2(1H)-carboxylate (11.2 g, 15.7 mmol) in NMP (22.4 mL, 233 mmol) at 10° C. Add TBS-chlorosulfonamide (47.1 mL, 47.1 mmol) while maintaining a temp. below 15° C. Monitor reaction for completion via HPLC; reaction reaches completion within 15 min. Quench with sat. aq. sodium bicarbonate (20 mL) and water (50 mL), extract with ethyl acetate (50 mL). Separate organic layer, wash with brine (50 mL), and solvent swap to acetonitrile (30 mL) via distillation. Proceed to deprotection.

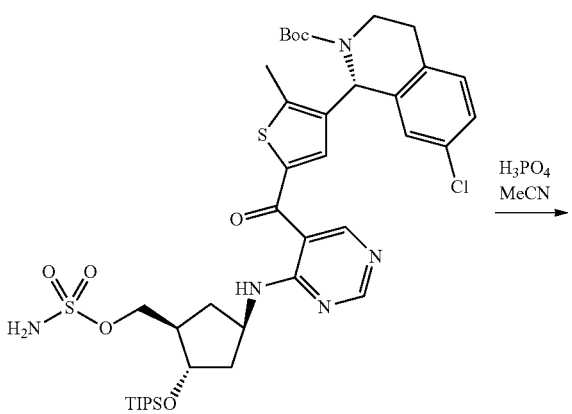

681

-continued

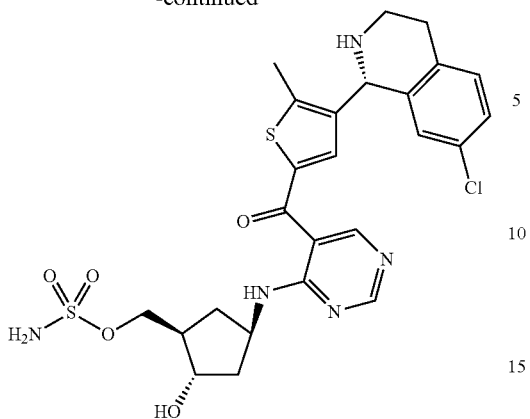

Cool the crude tert-butyl (R)-7-chloro-1-(2-methyl-5-(4-(((1R,3R,4S)-3-((sulfamoyloxy)methyl)-4-((triisopropylsilyl)oxy)cyclopentyl)amino)pyrimidine-5-carbonyl)thiophen-3-yl)-3,4-dihydroisoquinoline-2(1H)-carboxylate (13.1 g, 15.7 mmol) mixture to 10° C. Add phosphoric acid (33.6 mL, 610 mmol) to the reaction mixture while maintaining a temperature below 15° C. The mixture is warmed to ambient temperature. Monitor reaction for completion by HPLC. Reaction reaches full conversion in ~6 h. Add water (50 mL) and THF (200 mL) to the reaction mixture. Add 15% aqueous sodium carbonate (150 mL) to adjust the pH to 6-7. Vigorous off-gassing occurs during addition—add at an appropriate rate to control off-gassing and foaming. Separate the organic and aqueous phases. Wash the organic phase with brine (50 mL).). The combined organic layers were dried over $Na_2SO_4$, filtered, and concentrated in vacuo. The residue was partially purified by silica gel column chromatography eluting with a 35% 3% $NH_4OH$, 5% MeOH, 42% DCM, 50% MeCN:50% MeCN, 50% DCM to 50% 3% $NH_4OH$, 5% MeOH, 42% DCM, 50% MeCN:50% MeCN, 50% DCM over a gradient. The pure fractions were combined and concentrated in vacuo. The crude ((1R,2S,4R)-4-((5-(4-((R)-7-chloro-1,2,3,4-tetrahydroisoquinolin-1-yl)-5-methylthiophene-2-carbonyl)pyrimidin-4-yl)amino)-2-hydroxycyclopentyl)methyl sulfamate is dissolved in premixed 7:1 acetonitrile:methanol solution (90 mL). The mixture is seeded with ((1R,2S,4R)-4-((5-(4-((R)-7-chloro-1,2,3,4-tetrahydroisoquinolin-1-yl)-5-methylthiophene-2-carbonyl)pyrimidin-4-yl)amino)-2-hydroxycyclopentyl) methyl sulfamate Form 1 (45 mg, 0.078 mmol). The mixture is stirred for 16 h as a slurry develops. Filter the suspension and wash the wet cake twice with MeCN (20 mL, 2×). Dry to constant weight under vacuum at 35° C. to provide 4.9 g (54%) of the desired compound as light yellow crystalline solid. 1H NMR (400 MHz, Methanol-d4) δ ppm 8.61 (s, 1H) 8.52 (s, 1H) 7.27 (s, 1H) 7.16 (d, J=1.00 Hz, 2H) 6.69-6.71 (m, 1H) 5.22 (s, 1H) 4.70-4.82 (m, 1H) 4.11-4.23 (m, 3H) 3.24-3.30 (m, 1H) 2.96-3.12 (m, 2H) 2.76-2.86 (m, 1H) 2.60 (s, 3H) 2.43-2.53 (m, 1H) 2.20-2.29 (m, 1H) 2.08-2.16 (m, 1H) 1.87 (dt, J=14.87, 6.87 Hz, 1H) 1.40 (dt, J=13.05, 9.16 Hz, 1H). 13C NMR (101 MHz, DMSO-d6) δ 185.40, 160.24, 159.23, 157.75, 146.62, 142.44, 140.41, 138.04, 136.53, 134.47, 131.00, 129.92, 126.11, 126.08, 111.79, 71.29, 70.46, 54.59, 48.74, 45.88, 42.10, 40.58, 33.95, 28.42, 13.82.

682

Example 201B: [(1R,2S,4R)-4-[[5-[4-[(1R)-7-Chloro-1,2,3,4-tetrahydroisoquinolin-1-yl]-5-methyl-thiophene-2-carbonyl]pyrimidin-4-yl]amino]-2-hydroxy-cyclopentyl]methyl sulfamate I-263a Form 3

To a 50 mm solution of citrate buffer (15 mL, pH=4.5) was added ((1R,2S,4R)-4-((5-(4-((R)-7-chloro-1,2,3,4-tetrahydroisoquinolin-1-yl)-5-methylthiophene-2-carbonyl)pyrimidin-4-yl)amino)-2-hydroxycyclopentyl)methyl sulfamate anhydrous (150 mg, 0.259 mmol) at room temperature. The slurry is mixed for 5 day (shaking or stir bar). Filter the suspension and wash the wet cake twice with water (0.3 mL, 2×). Dry to constant weight under vacuum at 30° C. to provide 51 mg (34%) of the desired compound as light yellow crystal ((1R,2S,4R)-4-((5-(4-((R)-7-chloro-1,2,3,4-tetrahydroisoquinolin-1-yl)-5-methylthiophene-2-carbonyl)pyrimidin-4-yl)amino)-2-hydroxycyclopentyl)methyl sulfamate hydrate Form 3.

Example 202: [(1R,2S,4R)-4-{[5-({4-[(1R)-7-Chloro-3,4-dihydro-1H-isochromen-1-yl]-5-methyl-2-thienyl}carbonyl)pyrimidin-4-yl]amino}-2-hydroxycyclopentyl]methyl sulfamate I-257b Form 1

{(1R,2S,4R)-4-[(5-{[4-(7-chloro-3,4-dihydro-1H-isochromen-1-yl)-5-methyl-2-thienyl]carbonyl}pyrimidin-4-yl)amino]-2-hydroxycyclopentyl}methyl sulfamate (from Example 132, 2.5 g, 4.30 mmol) was dissolved in mixed solution of MeOH (90 mL) and DCM (10 mL). The solution was filtered through a syringe filter and the mixture was settled for 4 days. The mother liquor was then removed by pipet the resulting solid was rinsed with a small amount of MeOH and then dried in vacuo. The solid was transferred to a small vial and further dried in vacuo at 45° C. for 10 days to give 1.56 g of the title compound as a crystalline solid (needles) (I-257b Form 1). XRPD data is shown in FIG. 1. DSC data for I-257b Form 1 is shown in FIG. 8; TGA is shown in FIG. 9; and Raman data is shown in FIGS. 10-11. Procedures for XRPD pattern collection, DSC, TGA, and Raman spectroscopy were as described above in Example 201. 1H NMR (400 MHz, DMSO-d6) δ ppm 8.61 (s, 1H) 8.59 (s, 1H) 8.19 (d, J=7.53 Hz, 1H) 7.44 (s, 2H) 7.36 (s, 1H) 7.22-7.30 (m, 2H) 6.75 (s, 1H) 5.91 (s, 1H) 4.88 (d, J=4.52 Hz, 1H) 4.69 (sxt, J=8.08 Hz, 1H) 4.05-4.17 (m, 2H) 3.91-4.01 (m, 2H) 3.78-3.88 (m, 1H) 2.95-3.09 (m, 1H) 2.77 (brd, J=16.69 Hz, 1H) 2.48 (s, 3H) 2.26-2.37 (m, 1H) 2.06-2.17 (m, 1H) 1.90-1.99 (m, 1H) 1.70-1.80 (m, 1H) 1.27 (dt, J=12.67, 9.29 Hz, 1H). LCMS: (FA) M+1 579.1.

Example 203: [(1R,2S,4R)-4-{[5-({4-[(1R)-3,4-Dihydro-1H-isochromen-1-yl]-5-methyl-2-thienyl}carbonyl)pyrimidin-4-yl]amino}-2-hydroxycyclopentyl]methyl sulfamate I-256b Form 1

To a solution of [(1R,2S,4R)-4-{[5-({4-[(1R)-3,4-Dihydro-1H-isochromen-1-yl]-5-methyl-2-thienyl}carbonyl)pyrimidin-4-yl]amino}-2-hydroxycyclopentyl]methyl sulfamate (86% de, 987 mg, from Example 131) in $CH_2Cl_2$ (40.0 mL) was slowly added hexanes (25.0 mL) to give a white suspension. To the suspension was added $CH_2Cl_2$ dropwise until the suspension once again became a clear solution (10.0 mL). After stirring for 19 hours at room temperature, the precipitated solid was collected by filtration, washed with small amount of $CH_2Cl_2$ and $Et_2O$ and dried in vacuo at 45° C. to afford 799 mg of a light yellow solid as I-256b Form 1. XRPD data is shown in FIG. 3. DSC data is shown in FIG. 12 and TGA is shown in FIG. 13. Procedures for XRPD pattern collection, DSC, and TGA were as described above in Example 201. The diastereomeric purity of I-256b was determined to be 92.7% de by HPLC (70/30/0.1 hexane/EtOH/DEA; 1.0 mL/min for 60 min; using a CHIRALPAK IC column (4.6×250 mm)): 23.3 min (minor diastereomer) and 32.1 min (major diastereomer, I-256b).

Example 204: ((1R,2S,4R)-4-((5-(4-((R)-2,3-dimethyl-6,8-dihydro-5H-imidazo[2,1-c][1,4]oxazin-8-yl)-5-methylthiophene-2-carbonyl)pyrimidin-4-yl)amino)-2-hydroxycyclopentyl)methyl sulfamate and ((1R,2S,4R)-4-((5-(4-((S)-2,3-dimethyl-6,8-dihydro-5H-imidazo[2,1-c][1,4]oxazin-8-yl)-5-methylthiophene-2-carbonyl)pyrimidin-4-yl)amino)-2-hydroxycyclopentyl)methyl sulfamate I-356

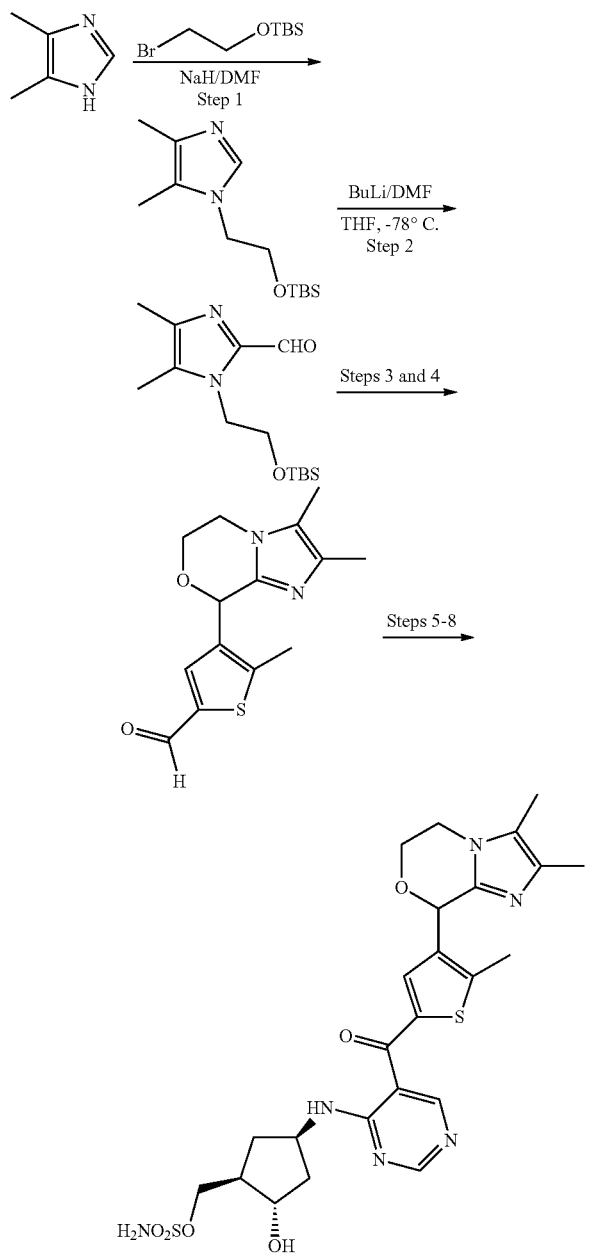

Step 1: 1-(2-((tert-butyldimethylsilyl)oxy)ethyl)-4,5-dimethyl-1H-imidazole

A solution of 4,5-dimethyl-1H-imidazole hydrochloride (2.94 g, 22.2 mmol) was in N,N-dimethylformamide (30.0 mL, 387 mmol) was cooled to 0° C. Sodium hydride (3.55 g, 88.7 mmol) was slowly added and the solution was stirred for 30 mins at 0° C. Potassium iodide (4.417 g, 26.61 mmol) and (2-bromoethoxy)-tert-butyldimethylsilane (6.365 g, 26.61 mmol) were added and the mixture was allowed to warm to room temperature with stirring over 30 minutes. The reaction as quenched with methanol (3 mL) and diluted with water (150 ml). The resulting aqueous mixture was extracted with ethyl acetate (3×70 mL). The combined organic portions was washed with brine, dried over Na₂SO₄, filtered, and concentrated in vacuo. The residue was purified by silica gel column chromatography (0 to 15% MeOH in EtOAc) to provide 4.34 g (77%) of the title compound. ¹H NMR (400 MHz, Chloroform-d) δ 7.33-7.39 (m, 1H) 3.87-3.93 (t, 2H) 3.73-3.84 (t, 2H) 2.13-2.18 (s, 3H) 2.12 (s, 3H) 0.85 (s, 9H) −0.04 (s, 6H).

Step 2: 1-(2-((tert-butyldimethylsilyl)oxy)ethyl)-4,5-dimethyl-1H-imidazole-2-carbaldehyde A solution of 1-(2-{[tert-butyl(dimethyl)silyl]oxy}ethyl)-4,5-dimethyl-1H-imidazole (2.36 g, 9.28 mmol) in tetrahydrofuran (100.0 mL) was cooled to −78° C. 2.50 M n-butyllithium in hexane (5.56 mL, 13.9 mmol) was added dropwise, followed by dropwise addition of N,N-dimethylformamide (2.03 g, 27.8 mmol) and the reaction mixture was allowed to warm to room temperature with stirring over 30 minutes. The reaction was quenched with acetic acid (1.11 g, 18.5 mmol) as a solution in THF (1 ml). The reaction mixture was concentrated in vacuo and the resulting residue was purified by silica gel column chromatography (0 to 60% EtOAc/hexanes) to provide 2.43 g (93%) of the title compound as a white solid. ¹H NMR (400 MHz, Chloroform-d) δ 9.56-9.70 (m, 1H) 4.37 (t, J=5.27 Hz, 2H) 3.88 (t, J=5.27 Hz, 2H) 2.25 (s, 4H) 2.24 (s, 3H) 0.79 (s, 10H) −0.13 (s, 6H).

Steps 3 and 4: 4-(2,3-dimethyl-6,8-dihydro-5H-imidazo[2,1-c][1,4]oxazin-8-yl)-5-methylthiophene-2-carbaldehyde Steps 3 and 4 were performed in an analogous fashion to Example 96, steps 1 and 2.

Steps 5-8: ((1R,2S,4R)-4-((5-(4-((R)-2,3-dimethyl-6,8-dihydro-5H-imidazo[2,1-c][1,4]oxazin-8-yl)-5-methylthiophene-2-carbonyl)pyrimidin-4-yl)amino)-2-hydroxycyclopentyl)methyl sulfamate and ((1R,2S,4R)-4-((5-(4-((S)-2,3-dimethyl-6,8-dihydro-5H-imidazo[2,1-c][1,4]oxazin-8-yl)-5-methylthiophene-2-carbonyl)pyrimidin-4-yl)amino)-2-hydroxycyclopentyl)methyl sulfamate Steps 5, 6, 7, and 8 were performed in an analogous fashion to Example 132, steps 7, 8, 9, and 10. ¹H NMR (400 MHz, Methanol-d4) δ ppm 8.71 (s, 1H) 8.58 (s, 1H) 8.30 (s, 1H) 7.42 (d, J=1.00 Hz, 1H) 5.94 (s, 1H) 4.73-4.85 (m, 1H) 4.31-4.39 (m, 1H) 3.95-4.23 (m, 6H) 2.45-2.57 (m, 4H) 2.24-2.32 (m, 1H) 2.20 (s, 3H) 2.13 (s, 3H) 1.86-1.97 (m, 1H) 1.43 (m, 1H). LCMS (AA) M+1 563

Example 205: [(1S,2R,4R)-4-[[5-[4-[(1R)-7-chloroisochroman-1-yl]-5-methyl-thiophene-2-carbonyl]pyrimidin-4-yl]amino]-2-(sulfamoyloxymethyl)cyclopentyl](2S)-2-aminopropanoate; hydrochloride I-362

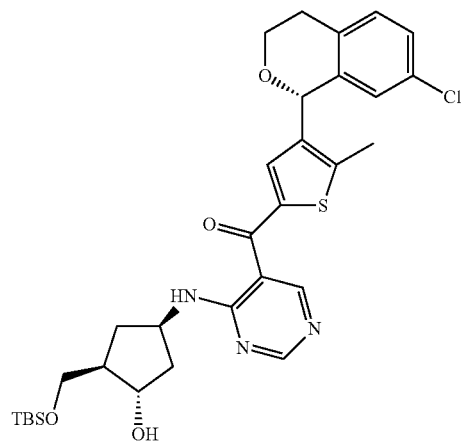

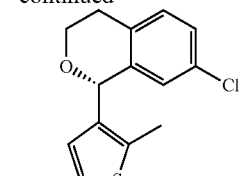

This compound was prepared in an analogous fashion to Example 188, steps 3 through 6, using Boc-Ala-OH in place of Boc-Val-OH in step 3. $^1$H NMR (400 MHz, DMSO-d6) δ 8.72 (s, 1H), 8.63-8.55 (m, 2H), 8.39-8.28 (m, 3H), 7.2 (br s, 2H), 7.46 (s, 1H), 7.29-7.22 (m, 2H), 6.71 (s, 1H), 5.90 (s, 1H), 5.11-5.05 (m, 1H), 4.81-4.71 (m, 1H), 4.20-3.74 (m, 11H, protons overlap with broad acid H$_2$O peak), 3.88-3.79 (m, 2H), 3.08-2.95 (m, 1H), 2.78 (br s, 1H), 2.81-2.71 (m, 1H), 2.48 (m, 5H), 2.38-2.29 (m, 1H), 2.15-2.02 (m, 2H), 1.53-1.43 (m, 1H), 1.41 (d, J=7.3 Hz, 3H); LCMS: (AA) M+1 579.1

Example 206: [(1S,2R,4R)-4-[[5-[4-[(1R)-7-chloroisochroman-1-yl]-5-methyl-thiophene-2-carbonyl]pyrimidin-4-yl]amino]-2-(sulfamoyloxymethyl)cyclopentyl] (2S)-2-aminopropanoate; hydrochloride
I-364
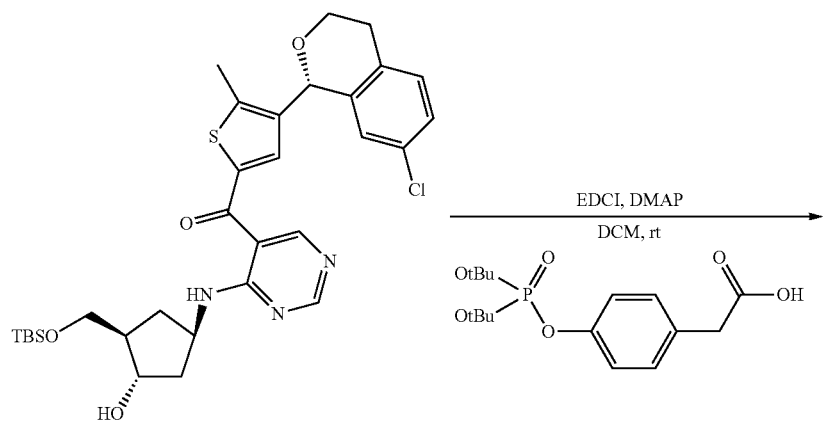
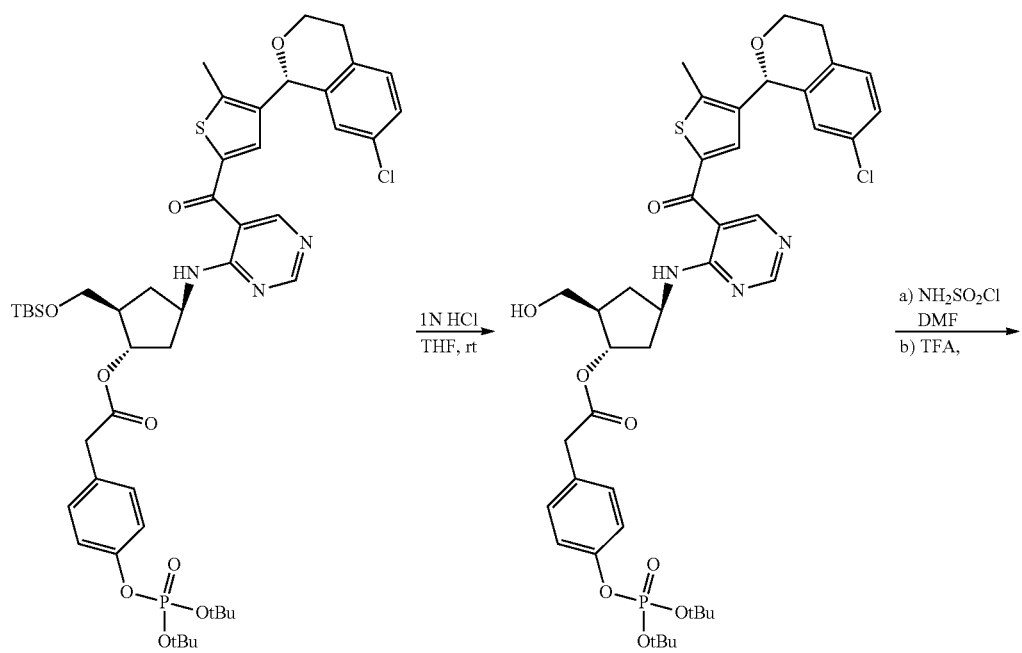

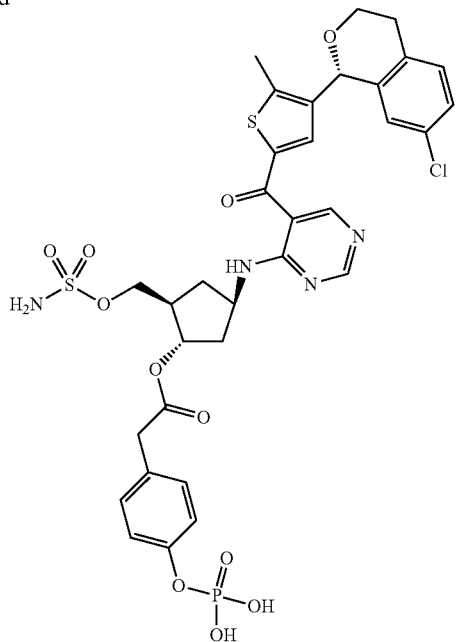

Step 1: [(1S,2R,4R)-2-[[tert-butyl(dimethyl)silyl]oxymethyl]-4-[[5-[4-[(1R)-7-chloroisochroman-1-yl]-5-methyl-thiophene-2-carbonyl]pyrimidin-4-yl]amino]cyclopentyl]2-(4-ditert-butoxyphosphoryloxyphenyl)acetate To a solution of (4-{[(1R,3R,4S)-3-({[tert-butyl(dimethyl)silyl]oxy}methyl)-4-hydroxycyclopentyl]amino}pyrimidin-5-yl){4-[(1R)-7-chloro-3,4-dihydro-1H-isochromen-1-yl]-5-methyl-2-thienyl}methanone (from Example 188, 300.0 mg, 0.49 mmol) in DCM (15.0 mL, 234 mmol) were added 2-(4-ditert-butoxyphosphoryloxyphenyl)acetic acid (202 mg, 0.59 mmol), DMAP (59.7 mg, 0.49 mmol), and N-(3-dimethylaminopropyl)-N'-ethylcarbodiimide hydrochloride (131 mg, 0.68 mmol) at room temperature. The reaction was allowed to stir for 4 h. The volatiles were removed in vacuo and the residue was dissolved in EtOAc (120 mL). The resulting solution was washed with 0.3N HCl (70 mL) twice followed by saturated NaHCO$_3$ and brine. The organic layer was dried over Na$_2$SO$_4$, filtered, and concentrated in vacuo. The residue was purified by ISCO silica gel column chromatography eluting with 90/10 to 60/40 DCM/EtOAc gradient to give 181 mg of the title compound as an off-white amorphous solid. $^1$H NMR (400 MHz, DMSO-d$_6$) δ ppm 8.61 (s, 1H) 8.58 (s, 1H) 8.17 (d, J=7.28 Hz, 1H) 7.34 (s, 1H) 7.20-7.30 (m, 4H) 7.11 (d, J=8.16 Hz, 2H) 6.73 (s, 1H) 5.90 (s, 1H) 4.93-5.00 (m, 1H) 4.56-4.67 (m, 1H) 4.07-4.16 (m, 1H) 3.77-3.87 (m, 1H) 3.48-3.68 (m, 4H) 2.95-3.07 (m, 1H) 2.75 (br d, J=17.19 Hz, 1H) 2.46 (s, 3H) 2.19-2.29 (m, 1H) 2.13 (br d, J=3.76 Hz, 1H) 1.94-2.03 (m, 1H) 1.82-1.92 (m, 1H) 1.42 (s, 18H) 1.29-1.39 (m, 1H) 0.83 (s, 9H) 0.00 (d, J=1.88 Hz, 6H).

Step 2: [(1S,2R,4R)-4-[[5-[4-[(1R)-7-chloroisochroman-1-yl]-5-methyl-thiophene-2-carbonyl]pyrimidin-4-yl]amino]-2-(hydroxymethyl)cyclopentyl]2-(4-ditert-butoxyphosphoryloxyphenyl)acetate To a solution of [(1S,2R,4R)-2-[[tert-butyl(dimethyl)silyl]oxymethyl]-4-[[5-[4-[(1R)-7-chloroisochroman-1-yl]-5-methyl-thiophene-2-carbonyl]pyrimidin-4-yl]amino]cyclopentyl]2-(4-ditert-butoxyphosphoryloxyphenyl)acetate (180 mg, 0.19 mmol) in THF (3.0 mL) was added 1N HCl (3.0 mL, 3.0 mmol) at room temperature and the reaction was allowed to stir for 2 h. The reaction was quenched by addition of saturated NaHCO$_3$ (60 mL). The aqueous layer was then saturated via addition of solid NaCl and the aqueous mixture was extracted with EtOAc (60 mL×3). The combined organic layers were washed with brine, dried over Na$_2$SO$_4$, filtered, and concentrated in vacuo. The residue was purified by ISCO silica gel column chromatography eluting with 50/50 to 90/10 EtOAc/DCM gradient to give 112 mg of product as colorless amorphous solid. LCMS: (AA) M+1 826.3.

Step 3: [(1S,2R,4R)-4-[[5-[4-[(1R)-7-chloroisochroman-1-yl]-5-methyl-thiophene-2-carbonyl]pyrimidin-4-yl]amino]-2-(sulfamoyloxymethyl)cyclopentyl]2-(4-phosphonooxyphenyl)acetate To a solution of [(1S,2R,4R)-4-[[5-[4-[(1R)-7-chloroisochroman-1-yl]-5-methyl-thiophene-2-carbonyl]pyrimidin-4-yl]amino]-2-(hydroxymethyl)cyclopentyl]2-(4-ditert-butoxyphosphoryloxyphenyl)acetate (120 mg, 0.15 mmol) in DMF (2.0 mL, 26 mmol) was added sulfamoyl chloride (36.0 mg, 0.30 mmol) at room temperature and the reaction was allowed to stir for 5 min. The reaction was quenched by addition of saturated NaHCO$_3$ and the mixture was extracted with EtOAc (×3). The combined organic layers were dried over Na$_2$SO$_4$, filtered, and concentrated in vacuo. The residue was dissolved in DCM (10 mL). To the solution was added TFA (2 mL, 26.5 mmol) at room temperature and the reaction was stirred for 1 h. The reaction was concentrated in vacuo and the residue was dried in vacuo. The resulting residue was purified by preparative HPLC to yield 43 mg of the title compound as off-white amorphous solid. $^1$H NMR (400 MHz, Methanol-d$_4$) δ ppm 8.62 (s, 1H) 8.57 (s, 1H) 7.29 (s, 1H) 7.14-7.23 (m, 6H) 6.74 (s, 1H) 5.89 (s, 1H) 5.05-5.12 (m, 1H) 4.68-4.79 (m, 1H) 4.12-4.25 (m, 3H) 3.92

(td, J=10.79, 3.76 Hz, 1H) 3.60 (s, 2H) 3.01-3.12 (m, 1H) 2.74-2.84 (m, 1H) 2.52 (s, 3H) 2.37-2.49 (m, 2H) 2.16-2.26 (m, 1H) 1.89-2.00 (m, 4H) 1.43-1.56 (m, 1H). LCMS: (FA) M+1 793.1.

Example 207: ((1R,2S,4R)-4-((5-(4-(7-chloro-3,4-dihydroisoquinolin-1-yl)-5-methylthiophene-2-carbonyl)pyrimidin-4-yl)amino)-2-hydroxycyclopentyl)methyl sulfamate I-360

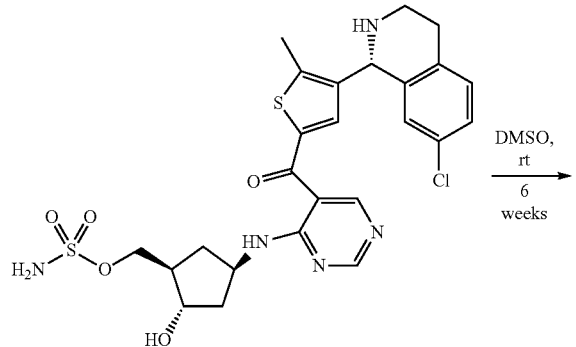

A solution of [(1R,2S,4R)-4-[[5-[4-[(1R)-7-chloro-1,2,3,4-tetrahydroisoquinolin-1-yl]-5-methyl-thiophene-2-carbonyl]pyrimidin-4-yl]amino]-2-hydroxy-cyclopentyl]methyl sulfamate (I-263a from Example 133, 250 mg, 0.43 mmol) in dimethylsulfoxide (5.0 mL) was stirred at room temperature for six weeks. The resulting mixture was directly purified by preparative HPLC (Phenomenex AXIA C$_{18}$, 250×21.2 mm, 5 micron, ammonium acetate modifier) to provide the title compound as a pale white powder (86 mg, 35%) $^1$H NMR (400 MHz, Methanol-d$_4$) δ ppm 8.82 (s, 1H) 8.57 (s, 1H) 7.61 (s, 1H) 7.46-7.51 (m, 1H) 7.34-7.40 (m, 1H) 7.11-7.15 (m, 1H) 4.76-4.85 (m, 1H) 4.13-4.26 (m, 3H) 3.81-3.92 (m, 2H) 2.81-2.93 (m, 2H) 2.42-2.56 (m, 4H) 2.12-2.33 (m, 2H) 2.00 (s, 1H) 1.89-1.98 (m, 1H) 1.35-1.53 (m, 1H) LCMS (AA): m/z=576.1 (M+H).

Example 208: [(1R,2S,4R)-4-[[5-[4-[(1R)-6-chloroisochroman-1-yl]thiophene-2-carbonyl]pyrimidin-4-yl]amino]-2-hydroxy-cyclopentyl]methyl sulfamate and [(1R,2S,4R)-4-[[5-[4-[(1S)-6-chloroisochroman-1-yl]thiophene-2-carbonyl]pyrimidin-4-yl]amino]-2-hydroxy-cyclopentyl]methyl sulfamate I-357

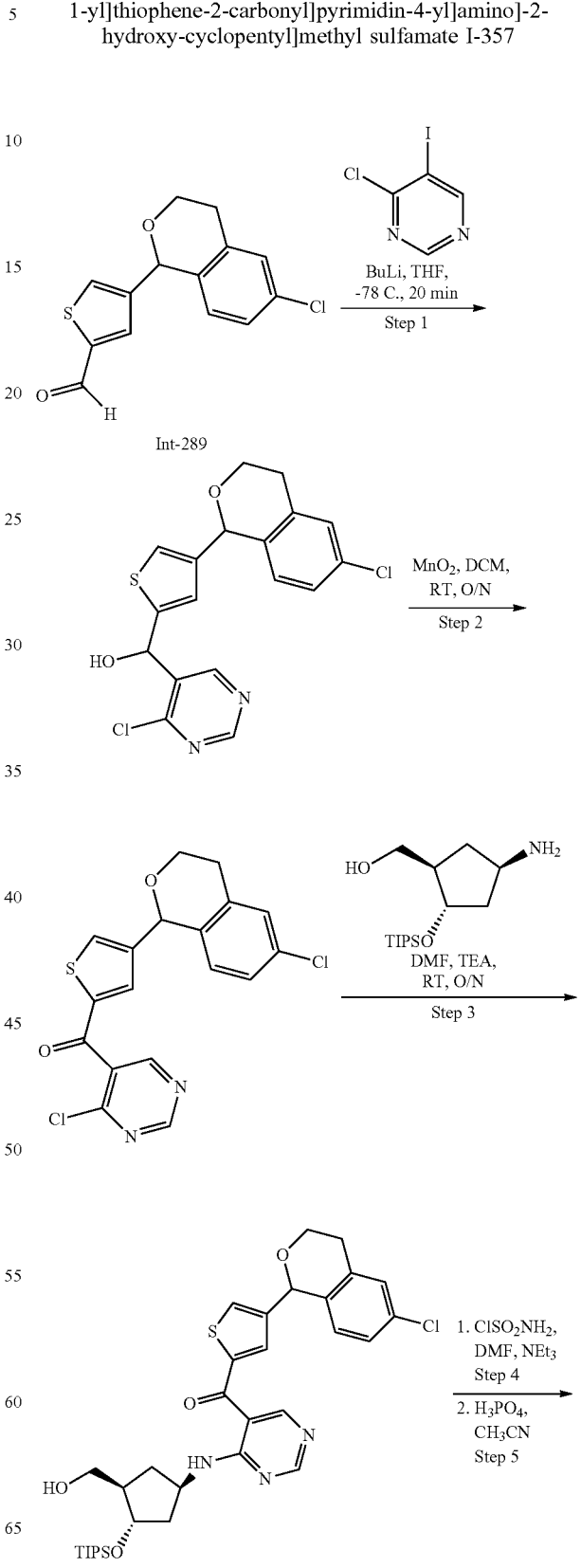

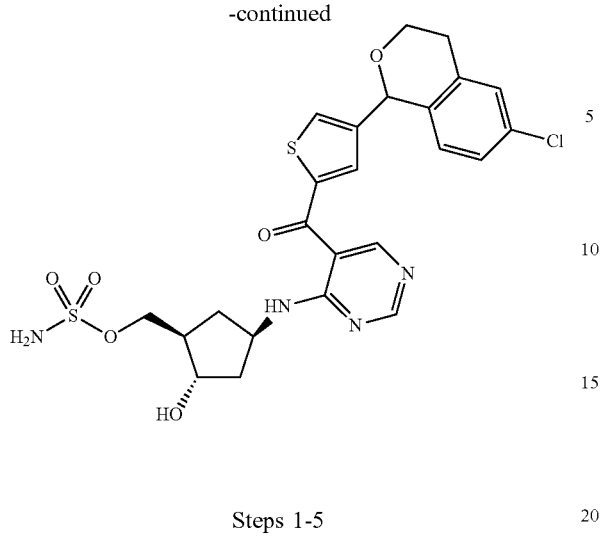

Steps 1-5

Int-289 was prepared from 2-bromo-5-chlorophenylacetic acid in analogous fashion to that employed to produce Int-171. The title compounds were then prepared in analogous fashion to Example 173, employing conditions C in Step 3, conditions B in step 4, and conditions D in step 5. $^1$H NMR (400 MHz, Methanol-d4) δ ppm 8.70 (s, 1H) 8.59 (s, 1H) 7.79 (s, 1H) 7.56 (s, 1H) 7.25 (s, 1H) 7.13-7.18 (m, 1H) 6.88-6.93 (m, 1H) 5.89 (s, 1H) 4.77-4.84 (m, 1H) 4.07-4.25 (m, 4H) 3.88-3.97 (m, 1H) 2.98-3.07 (m, 1H) 2.81-2.91 (m, 1H) 2.47-2.57 (m, 1H) 2.23-2.33 (m, 1H) 2.12-2.23 (m, 1H) 1.88-2.04 (m, 1H) 1.39-1.49 (m, 1H). LCMS: (AA) M+1 565.1

Example 209: [(1RS,2SR,4RS)-4-[[5-[4-[(1R)-6-chloro-1,3-dihydro-2-benzothiophen-1-yl]-5-methyl-thiophene-2-carbonyl]pyrimidin-4-yl]amino]-2-hydroxy-cyclopentyl]methyl sulfamate I-359a and [(1RS,2SR,4RS)-4-[[5-[4-[(1S)-6-chloro-1,3-dihydro-2-benzothiophen-1-yl]-5-methyl-thiophene-2-carbonyl]pyrimidin-4-yl]amino]-2-hydroxy-cyclopentyl]methyl sulfamate I-359b

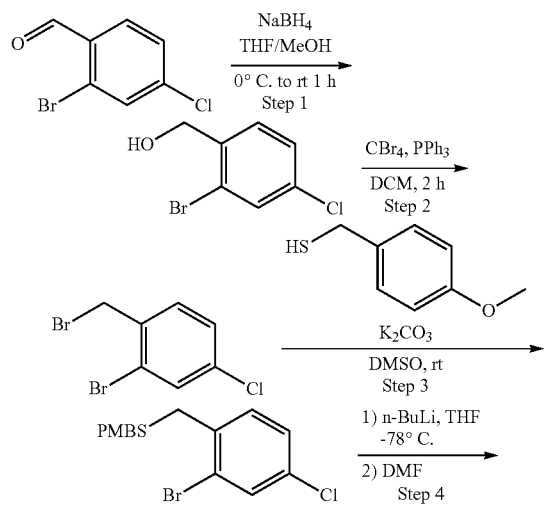

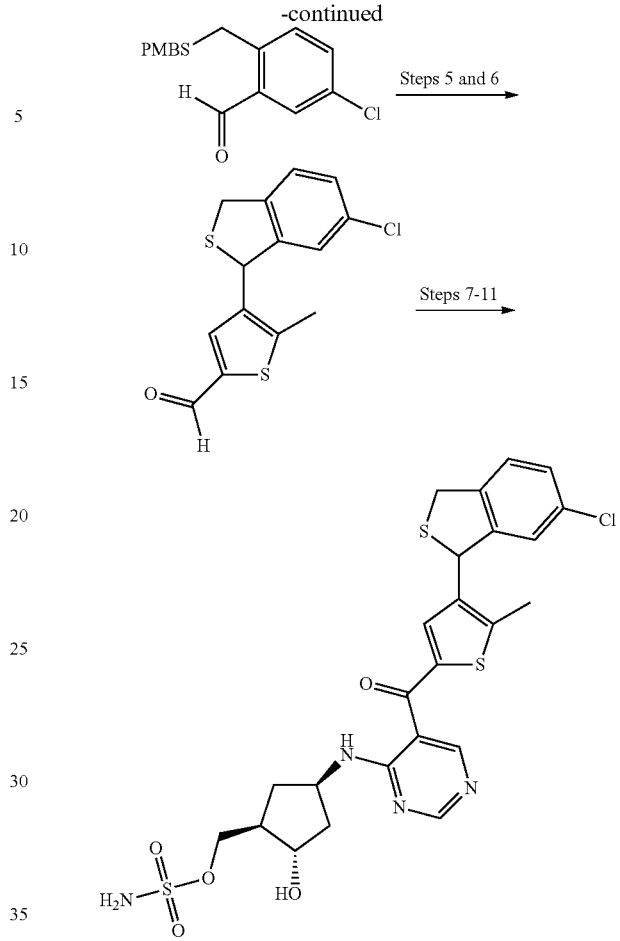

Step 1: (2-bromo-4-chloro-phenyl)methanol

To a solution of 2-bromo-4-chloro-benzaldehyde (10.1 g, 46.1 mmol) in tetrahydrofuran (101 mL) and methanol (50.6 mL) at 0° C. under argon was added sodium tetrahydroborate (2.31 g, 60.9 mmol). The reaction was allowed to warm to room temperature and stirred for 1 h. The mixture was evaporated to dryness, and partitioned between water and EtOAc. The aqueous layer was extracted with EtOAc, and the combined organic layer was washed with brine, dried over Na$_2$SO$_4$, filtered, and concentrated in vacuo to provide 10.0 g (98%) of the title compound as an off-white solid. $^1$H NMR (400 MHz, CDCl3) δ 7.57 (d, J=2.0 Hz, 1H), 7.45 (d, J=8.3 Hz, 1H), 7.33 (dd, J=2.0, 8.3 Hz, 1H), 4.73 (d, J=6.0 Hz, 2H), 1.95 (t, J=6.1 Hz, 1H).

Step 2: 2-bromo-1-(bromomethyl)-4-chloro-benzene (2-bromo-4-chloro-phenyl)methanol (10.0 g, 45.2 mmol) and carbon tetrabromide (19.5 g, 58.7 mmol) were dissolved in methylene chloride (207 mL), then triphenylphosphine (16.6 g, 63.2 mmol) was added. The reaction was stirred at room temperature under argon for 3 hours. To the stirring solution was added 250 mL hexane, resulting in a white precipitate. The mixture was filtered, and the filtrate was concentrate in vacuo. The resulting oil was purified by silica gel column chromatography (0 to 1% EtOAc in hexane) to provide 15.57 g of the title compound as a colorless oil. $^1$H NMR (400 MHz, DMSO-d6) δ 7.82 (d, J=2.0 Hz, 1H), 7.70-7.63 (m, 1H), 7.50 (dd, J=2.3, 8.3 Hz, 1H), 4.73 (s, 2H).

Step 3: 2-bromo-4-chloro-1-[(4-methoxyphenyl)methylsulfanylmethyl]benzene

To a solution of 2-bromo-1-(bromomethyl)-4-chlorobenzene (12.8 g, 43.2 mmol) in dimethyl sulfoxide (31.3 mL) was added p-methoxy-α-toluenethiol (7.66 g, 6.92 mL, 49.7 mmol) and potassium carbonate (11.900 g, 86.4 mmol). The reaction mixture was stirred at room temperature for 1 hour. The reaction was poured into water (200 mL), and extracted with DCM (2×75 mL). The combined organic layer was washed with brine, dried over Na₂SO₄, filtered, and concentrated. Purification by silica gel column chromatography (0 to 15% EtOAc in hexane) afforded the title compound (11.0 g, 71%) as a yellow oil. $^1$H NMR (400 MHz, DMSO-d6) δ 7.74 (d, J=2.0 Hz, 1H), 7.45-7.38 (m, 2H), 7.24-7.19 (m, 2H), 6.89-6.85 (m, 2H), 3.75-3.70 (m, 5H), 3.68 (s, 2H).

Step 4: 5-chloro-2-[(4-methoxyphenyl)methylsulfanylmethyl]benzaldehyde 2-bromo-4-chloro-1-[(4-methoxyphenyl)methylsulfanylmethyl]benzene (11.0 g, 30.7 mmol) was dissolved in tetrahydrofuran (108 mL) and cooled to −78° C. under argon. A solution of 2.50 M of n-butyllithium in hexane (13.5 mL, 33.8 mmol) was added dropwise, maintaining the temperature below −70° C., and the resulting dark red mixture was stirred for 10 minutes. N,N-dimethylformamide (4.76 mL, 61.5 mmol) was added, and the reaction was stirred for 1.25 hours in the cold bath. The orange reaction mixture was quenched with water and allowed to warm to room temperature. The mixture was extracted with EtOAc, washed with brine, dried over Na2SO4, filtered, and evaporated. Purification by silica gel column chromatography (0 to 20% EtOAc in hexane) afforded 4.97 g (53%) of the title compound as a yellow oil. 1H NMR (400 MHz, DMSO-d6) δ 10.20 (s, 1H), 7.83 (d, J=2.5 Hz, 1H), 7.66 (dd, J=2.4, 8.2 Hz, 1H), 7.42 (d, J=8.3 Hz, 1H), 7.22-7.17 (m, 2H), 6.88-6.84 (m, 2H), 4.08 (s, 2H), 3.73 (s, 3H), 3.67 (s, 2H); LCMS: (AA) M+1 329.1

Steps 5 and 6: 4-(6-chloro-1,3-dihydro-2-benzothiophen-1-yl)-5-methyl-thiophene-2-carbaldehyde Steps 5 and 6 were performed in analogous fashion to Example 96, steps 1 and 2.

Steps 7-11: [(1RS,2SR,4RS)-4-[[5-[4-[(1R)-6-chloro-1,3-dihydro-2-benzothiophen-1-yl]-5-methyl-thiophene-2-carbonyl]pyrimidin-4-yl]amino]-2-hydroxy-cyclopentyl]methyl sulfamate and [(1RS, 2SR,4RS)-4-[[5-[4-[(1S)-6-chloro-1,3-dihydro-2-benzothiophen-1-yl]-5-methyl-thiophene-2-carbonyl]pyrimidin-4-yl]amino]-2-hydroxy-cyclopentyl]methyl sulfamate Steps 7-11 were performed in analogous fashion to Example 173, steps 1-5. The base/solvent used in step 9 was K₂CO₃/DMF. Step 10 was run in the absence of triethylamine, and step 11 employed TAS-F in THF for the final deprotection.

I-359a: $^1$H NMR (400 MHz, DMSO-d6) δ 8.59 (s, 1H), 8.54 (s, 1H), 8.17 (d, J=7.3 Hz, 1H), 7.44 (s, 2H), 7.39 (d, J=8.8 Hz, 1H), 7.36-7.32 (m, 2H), 7.04 (d, J=1.0 Hz, 1H), 6.06 (s, 1H), 4.90-4.86 (m, 1H), 4.73-4.61 (m, 1H), 4.43 (dd, J=2.4, 14.7 Hz, 1H), 4.30 (d, J=14.3 Hz, 1H), 4.10-4.05 (m, 1H), 3.97-3.90 (m, 2H), 2.49 (s, 3H), 2.32-2.23 (m, 1H), 2.13-2.05 (m, 2H), 1.98-1.88 (m, 1H), 1.79-1.69 (m, 1H), 1.29-1.20 (m, 1H); LCMS: (AA) M+1 581.1.

I-359b: $^1$H NMR (400 MHz, DMSO-d6) δ 8.59 (s, 1H), 8.54 (s, 1H), 8.17 (d, J=7.5 Hz, 1H), 7.47-7.37 (m, 3H), 7.36-7.32 (m, 2H), 7.05-7.02 (m, 1H), 6.06 (s, 1H), 4.88 (d, J=4.5 Hz, 1H), 4.73-4.61 (m, 1H), 4.43 (dd, J=2.4, 14.7 Hz, 1H), 4.30 (d, J=14.3 Hz, 1H), 4.10-4.05 (m, 1H), 3.97-3.90 (m, 2H), 2.49 (s, 3H), 2.32-2.25 (m, 1H), 2.15-2.04 (m, 1H), 1.97-1.88 (m, 1H), 1.78-1.69 (m, 1H), 1.30-1.20 (m, 1H); LCMS: (AA) M+1 581.1

Example 210: [(1S,2R,4R)-4-[[5-[4-[(1R)-7-chloroisochroman-1-yl]-5-methyl-thiophene-2-carbonyl]pyrimidin-4-yl]amino]-2-(sulfamoyloxymethyl)cyclopentyl](2S,3S)-2-amino-3-methyl-pentanoate hydrochloride I-363

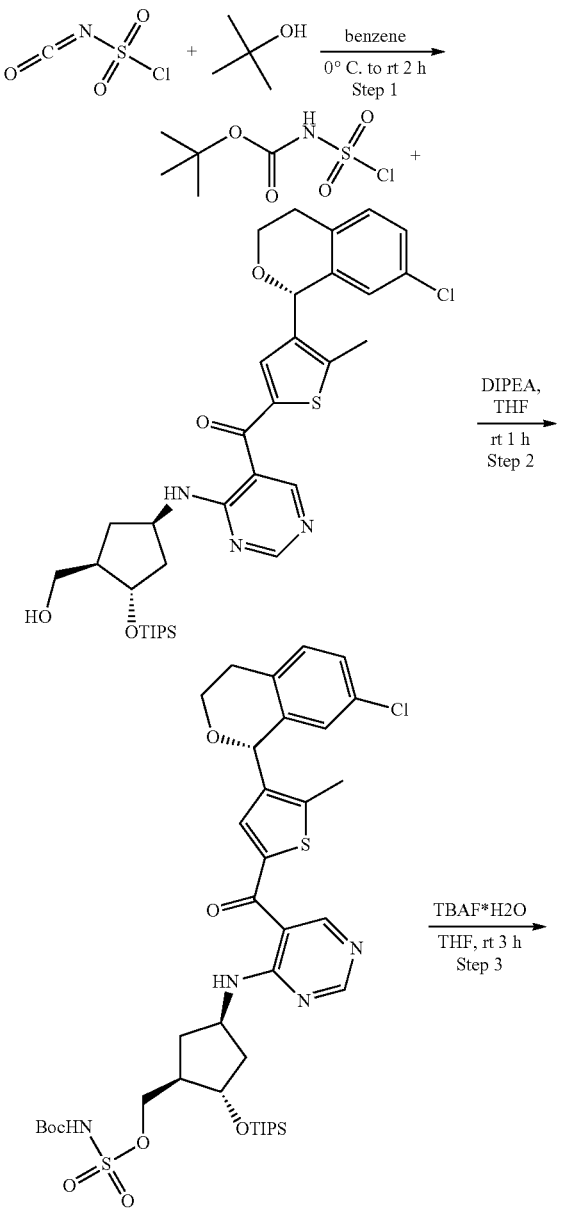

-continued

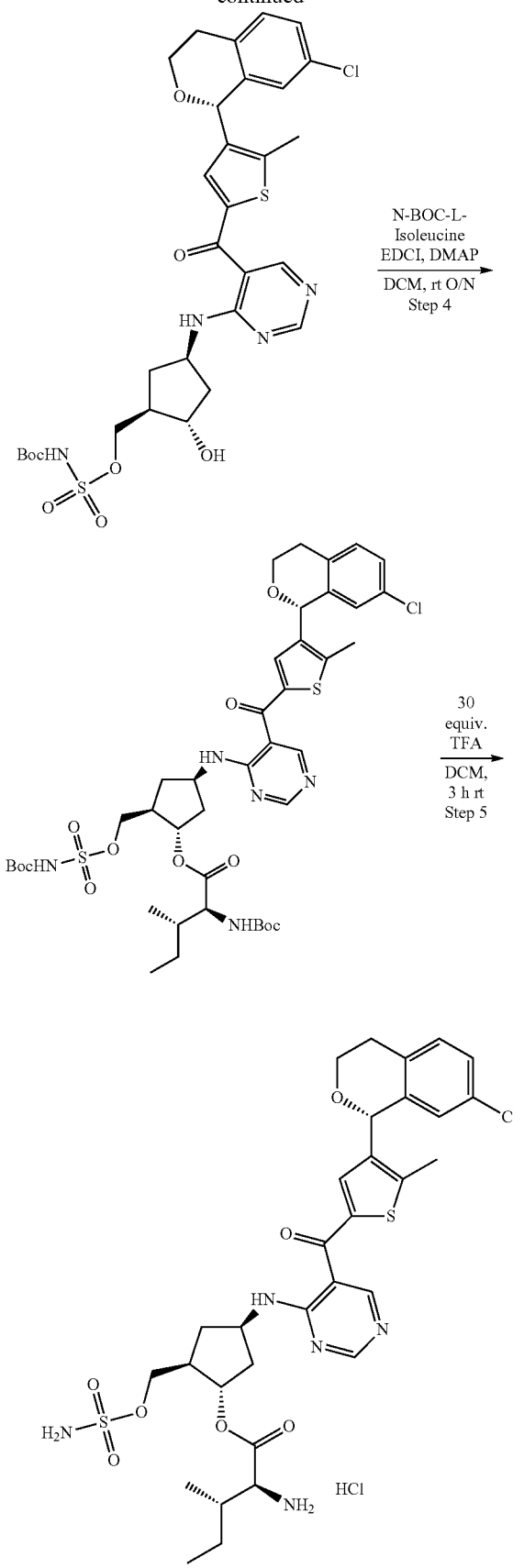

Step 1: tert-butyl (chlorosulfonyl)carbamate

To a solution of chlorosulfonyl isocyanate (3.20 mL, 0.0360 mol) in benzene (15.0 mL) at 0° C. under nitrogen was added dropwise tert-butyl alcohol (3.50 mL, 0.0362 mol). The ice-bath was removed, and the resulting gel-like mixture was stirred at room temperature for 2 hours. The reaction was diluted with hexanes (30 mL), and the resulting white precipitate was filtered and washed with hexanes (3×20 mL) to obtain 6.72 g (86%) white solid. $^1$H NMR (400 MHz, CHLOROFORM-d) δ 7.98 (br s, 1H), 1.58 (s, 9H).

Step 2: tert-butyl [({(1R,2S,4R)-4-{[5-({4-[(1R)-7-chloro-3,4-dihydro-1H-isochromen-1-yl]-5-methyl-2-thienyl}carbonyl)pyrimidin-4-yl]amino}-2-[(tri-isopropylsilyl)oxy]cyclopentyl}methoxy)sulfonyl] carbamate {4-[(1R)-7-chloro-3,4-dihydro-1H-isochromen-1-yl]-5-methyl-2-thienyl}[4-({(1R,3R,4S)-3-(hydroxymethyl)-4-[(triisopropylsilyl)oxy]cyclopentyl}amino)pyrimidin-5-yl] methanone (the product of Step 9 from Example 132, 3.907 g, 5.95 mmol) was dissolved in tetrahydrofuran (186 mL), then N,N-diisopropylethylamine (4.15 mL, 23.8 mmol) and tert-butyl (chlorosulfonyl)carbamate (2.57 g, 11.9 mmol) was added. The solution was stirred at room temperature for 2.5 hours under argon. The reaction was concentrated in vacuo. The residue was dissolved in EtOAc (200 mL), washed with saturated bicarbonate (2×250 mL), brine (250 mL), dried over Na$_2$SO$_4$, filtered, and concentrated. Purification by silica gel column chromatography (0 to 5% MeOH in DCM) gave 4.84 g yellow foam. $^1$H NMR (400 MHz, DMSO-d6) δ 11.77 (br s, 1H), 8.58 (s, 1H), 8.55 (s, 1H), 8.17 (d, J=7.5 Hz, 1H), 7.34 (s, 1H), 7.28-7.22 (m, 2H), 6.74-6.72 (m, 1H), 5.90 (s, 1H), 4.78-4.68 (m, 1H), 4.28-4.22 (m, 1H), 4.22-4.06 (m, 3H), 3.86-3.79 (m, 1H), 3.05-2.96 (m, 1H), 2.80-2.72 (m, 1H), 2.46 (s, 3H), 2.39-2.29 (m, 1H), 2.26-2.16 (m, 1H), 2.00-1.91 (m, 1H), 1.91-1.81 (m, 1H), 1.39-1.34 (m, 9H), 1.31-1.22 (m, 1H), 1.09-0.96 (m, 24H); LCMS: (AA) M+1 835.5

Step 3: tert-butyl ({[(1R,2S,4R)-4-{[5-({4-[(1R)-7-chloro-3,4-dihydro-1H-isochromen-1-yl]-5-methyl-2-thienyl}carbonyl)pyrimidin-4-yl]amino}-2-hydroxycyclopentyl]methoxy}sulfonyl)carbamate tert-Butyl [({(1R,2S,4R)-4-{[5-({4-[(1R)-7-chloro-3,4-dihydro-1H-isochromen-1-yl]-5-methyl-2-thienyl}carbonyl)pyrimidin-4-yl]amino}-2-[(triisopropylsilyl)oxy]cyclopentyl}methoxy)sulfonyl]carbamate (5.37 g, 5.95 mmol) was dissolved in tetrahydrofuran (65.0 mL). To the yellow solution was added a solution of tetrabutylammonium fluoride hydrate (4.04 g, 14.5 mmol) in tetrahydrofuran (65.0 mL) at room temperature, and the resulting red solution was stirred for 3 hours at room temperature under argon. The reaction was quenched by addition of water (125 mL) and extracted with EtOAc (3×125 mL). The combined organic layer was washed with brine (250 mL), dried over Na$_2$SO$_4$, filtered, and concentrated in vacuo. Purification by silica gel column chromatography (0 to 8% MeOH in DCM) obtained 2.77 g (68%) yellow solid. $^1$H NMR (400 MHz, DMSO-d6) δ 11.75 (br s, 1H), 8.59 (s, 1H), 8.57 (s, 1H), 8.18 (d, J=7.3 Hz, 1H), 7.35 (s, 1H), 7.28-7.22 (m, 2H), 6.73 (s, 1H), 5.90 (s, 1H), 4.96-4.88 (m, 1H), 4.70-4.62 (m, 1H), 4.26-4.19 (m, 1H), 4.15-4.06 (m, 2H), 3.97-3.90 (m, 1H), 3.86-3.78 (m, 1H), 3.06-2.95 (m, 1H), 2.79-2.72 (m, 1H), 2.46 (s, 3H), 2.32-2.25 (m, 1H), 2.17-2.05 (m, 1H), 1.96-

1.87 (m, 1H), 1.81-1.72 (m, 1H), 1.38 (s, 9H), 1.30-1.21 (m, 1H); LCMS: (AA) M+1 679.4

Step 4: [(1S,2R,4R)-2-(tert-butoxycarbonylsulfamoyloxymethyl)-4-[[5-[4-[(1R)-7-chloroisochroman-1-yl]-5-methyl-thiophene-2-carbonyl]pyrimidin-4-yl]amino]cyclopentyl](2S,3S)-2-(tert-butoxycarbonylamino)-3-methyl-pentanoate To a solution of tert-butyl N-[[(1R,2S,4R)-4-[[5-[4-[(1R)-7-chloroisochroman-1-yl]-5-methyl-thiophene-2-carbonyl]pyrimidin-4-yl]amino]-2-hydroxy-cyclopentyl]methoxysulfonyl]carbamate (4.07 mmol) in dichloromethane (41 mL) was added N-tert-butoxycarbonyl-L-isoleucine (2.39 g, 10.3 mmol),1-(3-dimethylaminopropyl)-3-ethylcarbodiimide hydrochloride (1.95 g, 10.2 mmol), and 4-dimethylaminopyridine (1.29 g, 10.6 mmol), and the reaction was stirred at room temperature for 18 hours under argon. The reaction was concentrated and partitioned between water (150 mL) and EtOAc (250 mL). The aqueous layer was extracted with EtOAc (100 mL), and the combined organic layer was washed with brine (150 mL), dried over $Na_2SO_4$, filtered, and concentrated. Purification by silica gel column chromatography (10 to 100% EtOAc, flushed with 10% MeOH in DCM; second purification (eluent: 2 to 10% MeOH in DCM) afforded 2.11 g (85% pure, 49% overall yield) of the title compound as a yellow foam. $^1$H NMR (400 MHz, DMSO-$d_6$) δ 11.80 (br s, 1H), 8.60-8.54 (m, 2H), 8.21-8.14 (m, 1H), 7.34 (s, 1H), 7.27-7.20 (m, 2H, overlaps with impurity), 6.74 (s, 1H), 5.90 (s, 1H), 4.99-4.93 (m, 1H), 4.72-4.62 (m, 1H), 4.30-4.15 (m, 2H), 4.15-4.07 (m, 1H), 3.87-3.78 (m, 2H), 3.06-2.95 (m, 1H), 2.79-2.72 (m, 1H), 2.47 (s, 4H, overlaps with DMSO peak), 2.39-2.29 (m, 2H), 2.09-1.88 (m, 2H), 1.87-1.64 (m, 1H), 1.44-1.32 (m, 19H), 1.28-1.15 (m, 1H), 0.90-0.73 (m, 7H); LCMS: (AA) M+1 892.6

Step 5: [(1S,2R,4R)-4-[[5-[4-[(1R)-7-chloroisochroman-1-yl]-5-methyl-thiophene-2-carbonyl]pyrimidin-4-yl]amino]-2-(sulfamoyloxymethyl)cyclopentyl](2S,3S)-2-amino-3-methyl-pentanoate To a stirring solution of [(1S,2R,4R)-2-(tert-butoxycarbonylsulfamoyloxymethyl)-4-[[5-[4-[(1R)-7-chloroisochroman-1-yl]-5-methyl-thiophene-2-carbonyl]pyrimidin-4-yl]amino]cyclopentyl](2S,3S)-2-(tert-butoxycarbonylamino)-3-methyl-pentanoate (2.11 g, 2.36 mmol) in dichloromethane (49 mL) was added trifluoroacetic acid (5.35 mL, 70.8 mmol). The solution was stirred at room temperature for 4 hours, then allowed to stand at 4° C. for 15 hours. The reaction was concentrated, dissolved in EtOAc (100 mL), washed with saturated $NaHCO_3$ (3×100 mL), brine (100 mL), dried over $Na_2SO_4$, filtered, and concentrated. Purification by silica gel column chromatography (eluent: 100% EtOAc to remove byproduct, then switched to 0 to 8% MeOH in DCM; repeated purification 100% EtOAc, then 0 to 4% MeOH in DCM) afforded 907 mg (56%) of the title compound as a yellow solid. $^1$H NMR (400 MHz, DMSO-d6) δ 8.64-8.55 (m, 2H), 8.19 (d, J=7.5 Hz, 1H), 7.71-7.38 (m, 2H), 7.35 (s, 1H), 7.29-7.21 (m, 2H), 6.77-6.72 (m, 1H), 5.90 (s, 1H), 4.99-4.93 (m, 1H), 4.73-4.61 (m, 1H), 4.15-4.01 (m, 3H), 3.86-3.78 (m, 1H), 3.16-3.13 (m, 1H), 3.06-2.96 (m, 1H), 2.80-2.72 (m, 1H), 2.47 (s, 3H), 2.42-2.27 (m, 2H), 2.10-1.53 (m, 5H), 1.49-1.36 (m, 2H), 1.15-1.08 (m, 1H), 0.91-0.74 (m, 7H); LCMS: (AA) M+1 692.2

Example 211: [(1R,2S,4R)-4-[[5-[4-(7-chloro-1-isoquinolyl)-5-methyl-thiophene-2-carbonyl]pyrimidin-4-yl]amino]-2-hydroxy-cyclopentyl]methyl sulfamate I-358

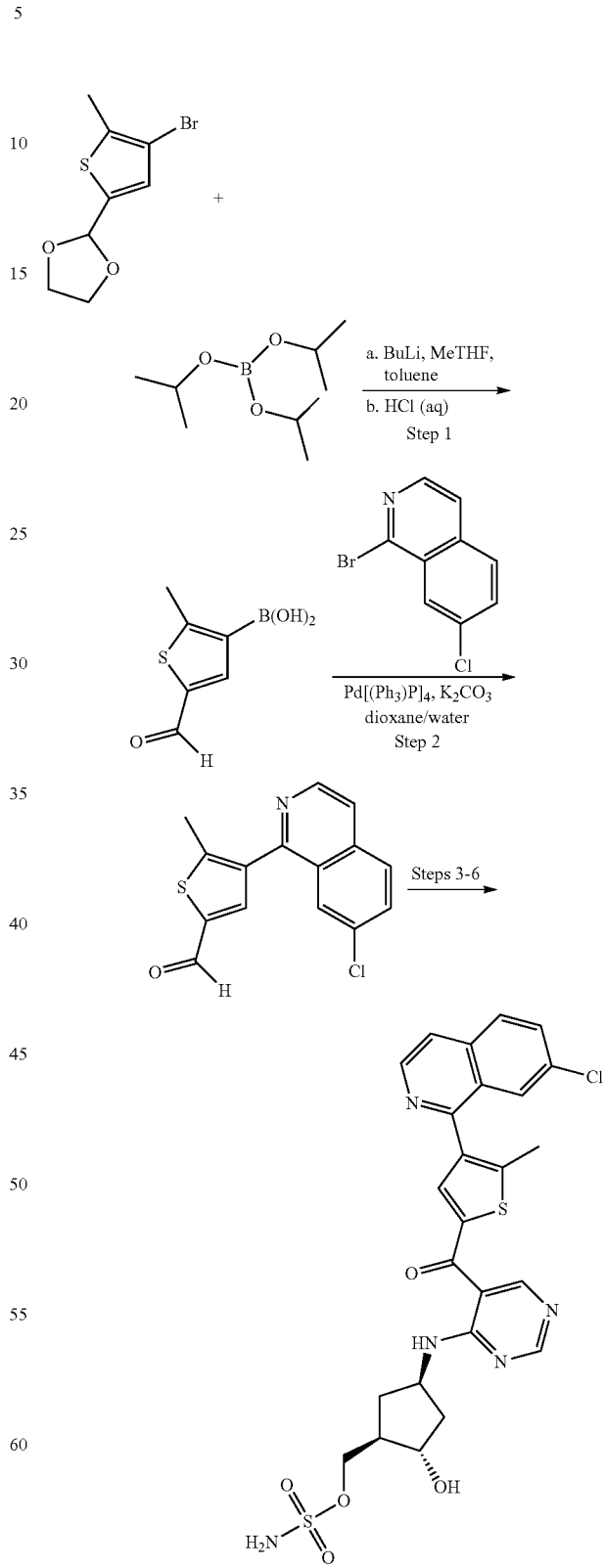

Step 1: (5-formyl-2-methylthiophen-3-yl)boronic acid

An oven-dried 500 mL 2-neck round bottom flask under nitrogen was charged with 2-(4-bromo-5-methyl-2-thienyl)-1,3-dioxolane (Int-1, 5.00 g, 20.1 mmol), toluene (32 mL), and 2-methyltetrahydrofuran (8 mL) and the mixture was cooled in an acetone/dry ice bath to −75° C. A 2.5 M solution of n-butyllithium in hexanes (24.1 mmol, 9.6 mL) was added slowly over 45 min keeping the internal temperature less than −70° C. Triisopropyl borate (24.1 mmol, 5.54 mL) was then added, keeping the internal temperature less than −70° C. The mixture was warmed to −20° C. and quenched via addition of 15 mL of 2M HCl (aq). The biphasic mixture was poured into water, the layers were separated, and the aqueous layer was extracted three times with ethyl acetate. The combined organic layers were washed with brine, dried over anhydrous magnesium sulfate, filtered, and concentrated in vacuo to afford an amber oil. To this oil was added hexane, and the mixture sonicated until complete dissolution. Diethyl ether was next added, and the resulting solid was isolated by vacuum filtration to afford the title compound (83 g, 53%). LCMS (AA): m/z=171.0 (M+H).

Step 2: 4-(7-chloroisoquinolin-1-yl)-5-methylthiophene-2-carbaldehyde

A 20 mL microwave tube was charged with (5-formyl-2-methyl-3-thienyl)boronic acid (300 mg, 1.76 mmol), 1-bromo-7-chloroisoquinoline (332 mg, 1.37 mmol), 1,4-dioxane (8.1 mL), water (2.0 mL), and potassium carbonate (632 mg, 4.58 mmol), and the mixture was degassed with nitrogen for 10 minutes. Tetrakis(triphenylphosphine)palladium(0) (310 mg, 0.27 mmol) was then added, the reaction vessel was sealed, and the mixture was heated in the microwave for 30 minutes at 100° C. The contents of the reaction vessel were poured into saturated sodium bicarbonate. The mixture was extracted three times with ethyl acetate and the combined organic portions were washed with brine, dried over anhydrous magnesium sulfate and filtered, and concentrated in vacuo. The residue was subjected to ISCO chromatography eluting with a hexane/ethyl acetate gradient. Fractions containing the desired product were evaporate to give the title compound as a white solid, 274 mg (69%). $^1$H NMR (400 MHz, Chloroform-d) δ ppm 9.93 (s, 1H) 8.63-8.68 (m, 1H) 7.87-7.92 (m, 1H) 7.83 (s, 1H) 7.82 (s, 1H) 7.67-7.74 (m, 2H) 2.49 (s, 3H). LCMS (AA): m/z=288.0 (M+H).

Steps 3-6: [(1R,2S,4R)-4-[[5-[4-(7-chloro-1-isoquinolyl)-5-methyl-thiophene-2-carbonyl]pyrimidin-4-yl]amino]-2-hydroxy-cyclopentyl]methyl sulfamate Steps 3-6 were performed in analogous fashion to Example 131, steps 7-10 to afford the title compound. $^1$H NMR (400 MHz, Methanol-d4) δ ppm 8.88 (s, 1H) 8.57-8.60 (m, 1H) 8.57 (s, 1H) 8.03-8.10 (m, 1H) 7.89-7.95 (m, 1H) 7.75-7.84 (m, 3H) 4.77-4.84 (m, 1H) 4.15-4.26 (m, 3H) 2.48-2.58 (m, 1H) 2.42 (s, 3H) 2.14-2.37 (m, 2H) 1.89-2.03 (m, 1H) 1.40-1.51 (m, 1H). LCMS (AA): m/z=574.1 (M+H).

Example 212: [(1R,2S,4R)-4-[[5-[4-[(1R)-7-chloroisochroman-1-yl]-5-(hydroxymethyl)thiophene-2-carbonyl]pyrimidin-4-yl]amino]-2-hydroxy-cyclopentyl]methyl sulfamate and [(1R,2S,4R)-4-[[5-[4-[(1S)-7-chloroisochroman-1-yl]-5-(hydroxymethyl)thiophene-2-carbonyl]pyrimidin-4-yl]amino]-2-hydroxy-cyclopentyl]methyl sulfamate I-366

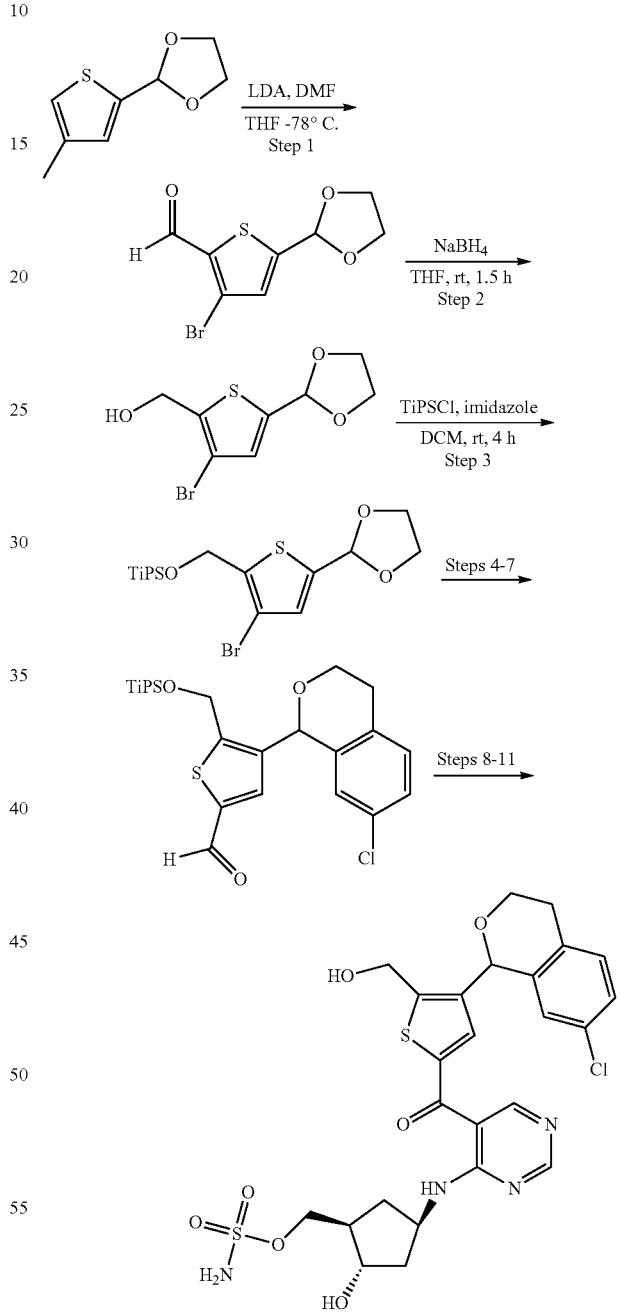

Step 1: 3-bromo-5-(1,3-dioxolan-2-yl)thiophene-2-carbaldehyde

A solution of 2-(4-bromothiophen-2-yl)-1,3-dioxolane (6.1 g, 26 mmol) in tetrahydrofuran (158 mL, 1940 mmol) was cooled to −78° C. To the solution was added 0.8 M of lithium diisopropylamide in tetrahydrofuran (36.0 mL, 28.8 mmol) dropwise via cannula. After stirring for 5 min, N,N-dimethylformamide (2.41 mL, 31.1 mmol) was added, and the reaction mixture was stirred at −78° C. for 30 min. The reaction mixture was quenched with saturated aq. NH$_4$Cl (100 mL) and then warmed to rt. The reaction mixture was further diluted with water (60 mL, enough for complete dissolution of white solid) and extracted with EtOAc (300 mL). The layers were separated, and the aqueous layer was extracted with EtOAc (70 mL×2). The combined organic layers were washed with 10% LiCl (70 mL), and brine (70 mL), dried over Na$_2$SO$_4$, filtered, and concentrated in vacuo. The residue was purified by flash column chromatography eluting with a hexanes/EtOAc gradient to afford the title compound as white powder (yield=5.31 g). $^1$H NMR (400 MHz, CHLOROFORM-d) δ ppm 9.96 (s, 1H) 7.12 (s, 1H) 6.11 (s, 1H) 3.94-4.17 (m, 4H) LCMS (FA): m/z=262.93 (M+1).

Step 2: [3-bromo-5-(1,3-dioxolan-2-yl)-2-thienyl]methanol

To a solution of 3-bromo-5-(1,3-dioxolan-2-yl)thiophene-2-carbaldehyde (0.640 g, 2.43 mmol) in THF (15 mL) was added NaBH$_4$ (0.101 g, 2.68 mmol) at rt. The reaction mixture was stirred at rt for 1.5 h. The reaction mixture was diluted with water and extracted with EtOAc (20 mL×2). The combined organic layers were dried over Na$_2$SO$_4$, filtered and concentrated in vacuo. The crude material was purified by flash column chromatography eluting with hexanes/EtOAc gradient to provide the title compound (0.640 g) as an oil. $^1$H NMR (400 MHz, CHLOROFORM-d) δ ppm 6.94 (s, 1H) 5.97 (s, 1H) 4.76 (s, 2H) 3.61-4.28 (m, 4H) LCMS (FA): m/z=264.95 (M+1).

Step 3: [3-bromo-5-(1,3-dioxolan-2-yl)-2-thienyl]methoxy-triisopropyl-silane

To a solution of [3-bromo-5-(1,3-dioxolan-2-yl)-2-thienyl]methanol (4.7 g, 18 mmol) in DCM (100 mL) was added 1H-imidazole (1.81 g, 26.6 mmol) followed by triisopropylsilyl chloride (4.13 mL, 19.5 mmol) at rt, and the reaction was stirred for 4 h. The reaction mixture was quenched by addition of water (150 mL) and extracted with DCM (50 mL×2). The combined organic layers were dried over Na$_2$SO$_4$, filtered, and concentrated in vacuo. The residue was purified by flash column chromatography eluting with a hexanes/EtOAc gradient to afford the title compound as colorless oil (yield=5.5 g). $^1$H NMR (400 MHz, CHLOROFORM-d) δ ppm 6.99 (s, 1H) 6.04 (s, 1H) 4.87 (s, 2H) 4.00-4.16 (m, 4H) 1.04-1.21 (m, 21H) LCMS (FA): m/z=421.08 (M+1).

Steps 4-7: 4-(7-chloroisochroman-1-yl)-5-(triisopropylsilyloxymethyl)thiophene-2-carbaldehyde Steps 4-7 were performed in analogous fashion to Example 119, steps 1-4 to afford the title compound.

Steps 8-11: [(1R,2S,4R)-4-[[5-[4-[(1R)-7-chloroisochroman-1-yl]-5-(hydroxymethyl)thiophene-2-carbonyl]pyrimidin-4-yl]amino]-2-hydroxy-cyclopentyl]methyl sulfamate and [(1R,2S,4R)-4-[[5-[4-[(1S)-7-chloroisochroman-1-yl]-5-(hydroxymethyl)thiophene-2-carbonyl]pyrimidin-4-yl]amino]-2-hydroxy-cyclopentyl]methyl sulfamate Steps 8-11 were performed in analogous fashion to Example 131, steps 7-10 to afford the title compounds. $^1$H NMR (400 MHz, Methanol-d4) δ 8.66 (s, 1H) 8.55 (s, 1H) 7.37 (d, J=1.25 Hz, 1H) 7.19 (s, 2H) 6.82 (s, 1H) 5.91 (s, 1H) 4.90-4.98 (m, 2H) 4.74-4.85 (m, 1H) 4.65 (d, J=15.06 Hz, 1H) 4.13-4.22 (m, 4H) 3.87-3.94 (m, 1H) 3.03-3.14 (m, 1H) 2.75-2.83 (m, 1H) 2.45-2.54 (m, 1H) 2.10-2.30 (m, 2H) 1.86-1.94 (m, 1H) 1.41 (m, J=13.30, 9.00, 9.00, 4.40 Hz, 1H). FA: m/z=596 (M+H)

Example 213: [(1R,2S,4R)-4-[[5-[4-[(1R)-7-chloroisochroman-1-yl]-5-(difluoromethyl)thiophene-2-carbonyl]pyrimidin-4-yl]amino]-2-hydroxy-cyclopentyl]methyl sulfamate and [(1R,2S,4R)-4-[[5-[4-[(1S)-7-chloroisochroman-1-yl]-5-(difluoromethyl)thiophene-2-carbonyl]pyrimidin-4-yl]amino]-2-hydroxy-cyclopentyl]methyl sulfamate I-361

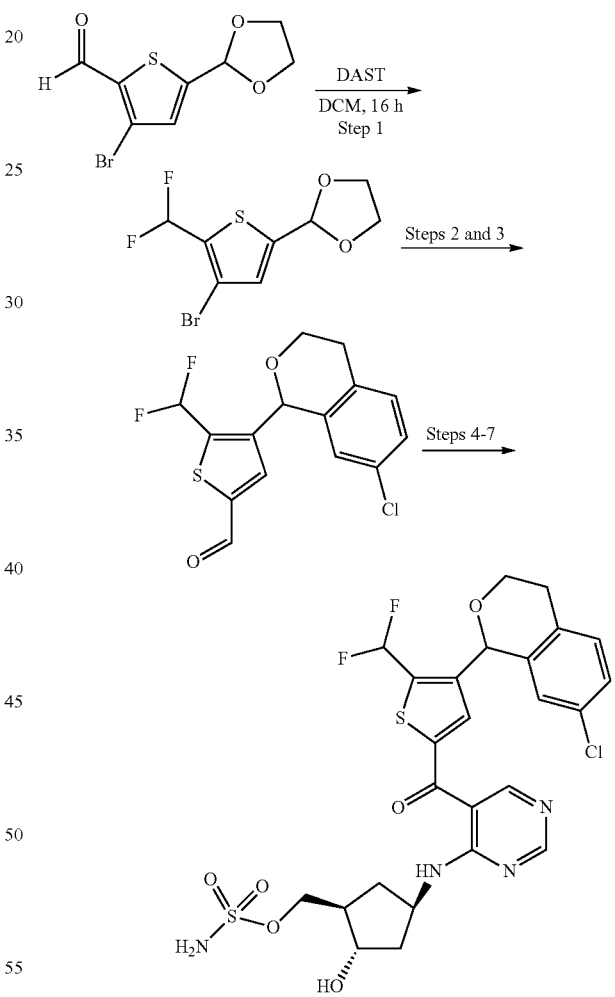

Step 1: 2-[4-bromo-5-(difluoromethyl)-2-thienyl]-1,3-dioxolane

To a solution of 3-bromo-5-(1,3-dioxolan-2-yl)thiophene-2-carbaldehyde (3 g, 10 mmol) in DCM (73.0 mL) was added diethylaminosulfur trifluoride (4.37 mL, 33.1 mmol) at 0° C., and the mixture was stirred at rt for 16 h. The reaction mixture was quenched by addition of saturated NaHCO$_3$ (30 mL) and extracted with DCM (50 mL×3). The combined organic layers were washed with brine, dried over Na₂SO₄, filtered, and concentrated in vacuo. The residue was purified by flash column chromatography eluting with a hexanes/EtOAc gradient to afford the title compound as an oil (yield=2.7 g). ¹H NMR (400 MHz, CHLOROFORM-d) δ ppm 7.07 (s, 1H) 6.72-7.01 (m, 1H) 6.1 (s, 1H) 4.03-4.16 (m, 4H) LCMS (FA): m/z=287 (M+1).

Steps 2 and 3: 4-(7-chloroisochroman-1-yl)-5-(difluoromethyl)thiophene-2-carbaldehyde Steps 2 and 3 were performed in analogous fashion to Example 96, steps 1 and 2 to afford the title compound.

Steps 4-7: [(1R,2S,4R)-4-[[5-[4-[(1R)-7-chloroisochroman-1-yl]-5-(difluoromethyl)thiophene-2-carbonyl]pyrimidin-4-yl]amino]-2-hydroxy-cyclopentyl]methyl sulfamate and [(1R,2S,4R)-4-[[5-[4-[(1S)-7-chloroisochroman-1-yl]-5-(difluoromethyl)thiophene-2-carbonyl]pyrimidin-4-yl]amino]-2-hydroxy-cyclopentyl]methyl sulfamate Steps 4-7 were performed in analogous fashion to Example 131, steps 7-10 to afford the title compounds as a 1:1 mixture of diastereomers. 8.64 (br s, 1H) 8.56 (s, 1H) 7.39 (s, 1H) 7.22 (s, 1H) 7.27 (brt, J=54.59 Hz, 1H) 7.06-7.19 (m, 1H) 6.78 (d, J=8.53 Hz, 1H) 6.01 (s, 1H) 4.73-4.83 (m, 1H) 4.09-4.25 (m, 4H) 3.87-3.99 (m, 1H) 3.05-3.27 (m, 1H) 2.79 (br d, J=16.81 Hz, 1H) 2.66 (s, 1H) 2.39-2.56 (m, 1H) 2.08-2.31 (m, 2H) 1.84-1.97 (m, 1H) 1.34-1.55 (m, 1H). LCMS (FA): m/z=625 (M+1).

Example 214: [(1R,2S,4R)-4-[[5-[4-[(1S)-8-chloroisochroman-1-yl]thiophene-2-carbonyl]pyrimidin-4-yl]amino]-2-hydroxy-cyclopentyl]methyl sulfamate and [(1R,2S,4R)-4-[[5-[4-[(1R)-8-chloroisochroman-1-yl]thiophene-2-carbonyl]pyrimidin-4-yl]amino]-2-hydroxy-cyclopentyl]methyl sulfamate I-365

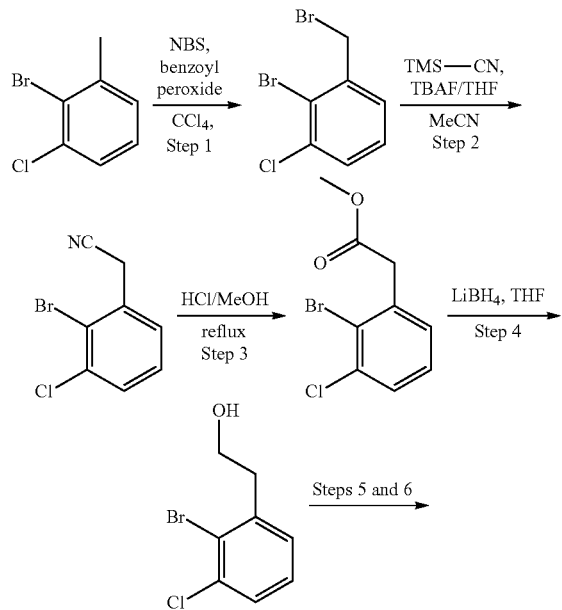

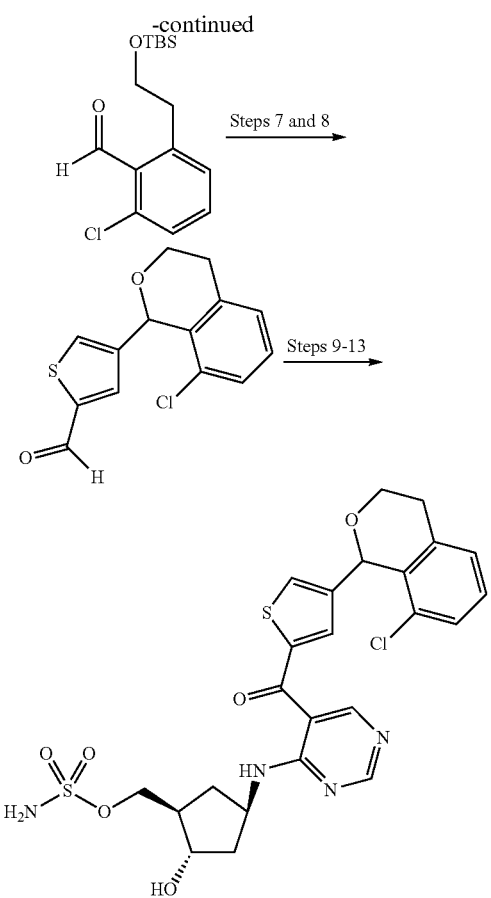

Step 1: 2-Bromo-3-chlorobenzyl bromide

To a stirred solution of 2-bromo-3-chlorotoluene (10.0 g, 48.67 mmol) in CCl₄ (150 mL) was added NBS (9.53 g, 53.53 mmol) and benzoyl peroxide (1.18 g, 4.87 mmol). The mixture was then degassed and purged with N₂, heated to 80° C., and stirred for 0.5 h. The mixture was evaporated to dryness, water (150 mL) was added, and the mixture was extracted with DCM (100 mL×2). The combined organic layers were dried over Na₂SO₄, filtered and concentrated in vacuo. The resulting residue was purified by column chromatography (pure petroleum ether as eluent) to obtain the title compound (8.0 g, 58%) as a colorless liquid. ¹H NMR (400 MHz, CDCl₃) δ 7.42 (d, J=6.8 Hz, 1H) 7.36 (d, J=7.6 Hz, 1H) 7.26-7.22 (m, 1H) 4.63 (s, 2H).

Step 2: 2-(2-bromo-3-chlorophenyl)acetonitrile

A solution of 2-bromo-3-chlorobenzyl bromide (20.0 g, 70.33 mmol) in MeCN (300 mL) was added with TMS-CN (11.86 g, 119.56 mmol) at r.t, then TBAF (1M in THF solution, 120 mL, 120 mmol) was added to the mixture dropwise at 0° C., and then the mixture was stirred at r.t overnight. The mixture was concentrated in vacuo, and the resulting residue was purified by silica gel column (pure PE to PE/EtOAc=10:1) to provide the title compound (14.3 g, 88%) as a white solid. ¹H NMR (400 MHz, CDCl₃) δ 7.48-7.44 (m, 2H) 7.33-7.26 (m, 1H) 3.89 (s, 1H).

Step 3: 2-bromo-3-chlorophenylacetic acid methyl ester

A suspension of 2-(2-bromo-3-chlorophenyl)acetonitrile (14.3 g, 62.04 mmol) in MeOH (400 mL) was added with HCl/MeOH (4 M, 200 mL). The mixture was heated at reflux for 1 h after which the mixture was concentrated in vacuo. To the resulting residue was added HCl/MeOH (4 M, 200 mL) and the mixture was heated at reflux for an additional ~3 h. The mixture was concentrated in vacuo and the resulting residue was partitioned between water (200 mL) and DCM (100 mL). The aqueous layer was extracted with DCM (200 mL×2), and the combined organic layers were washed with sat. NaHCO$_3$ and brine, and then dried over Na$_2$SO$_4$, filtered and concentrated in vacuo to provide the title compound (15 g) as a light yellow liquid that was used without further purification. $^1$H NMR (400 MHz, CDCl$_3$) δ 7.38 (dd, J=7.6, 1.2 Hz, 1H) 7.23-7.17 (m, 2H) 3.84 (s, 2H) 3.71 (s, 3H).

Step 4: 2-(2-bromo-3-chloro-phenyl)ethanol

A solution of 2-bromo-3-chlorophenylacetic acid methyl ester (15 g, 56.92 mmol) in THF (500 mL) was cooled to 0° C., and LiBH$_4$ (2M in THF, 80 mL, 160 mmol) was added. The mixture was stirred at rt for 0.5 h, followed by heating at reflux for ~2 h. A second portion of LiBH$_4$ (2M in THF, 20 mL, 40 mmol) was then added and the reaction was heated at reflux for a further ~1 h. The reaction was then cooled in an ice bath, sat. NaHCO$_3$ (500 mL) was added, and the mixture was poured into water (1000 mL). The biphasic mixture was separated, and the aqueous layer was extracted with EtOAc (200 mL×3). The combined organic layers were washed with brine, dried over Na$_2$SO$_4$, and concentrated in vacuo. The resulting residue was purified by silica gel chromatography (PE/EtOAc=10:1 to 3:1) to provide the title compound (18 g, 67%) as a light yellow liquid. $^1$H NMR (400 MHz, CDCl$_3$) δ 7.36-7.33 (m, 1H) 7.18-7.17 (m, 2H) 3.89-3.86 (m, 2H) 3.09-3.06 (m, 2H).

Steps 5 and 6: 2-[2-[tert-butyl(dimethyl)silyl]oxyethyl]-6-chloro-benzaldehyde

Steps 5 and 6 were performed in analogous fashion to Example 13 steps 4 and 5.

Steps 7 and 8: 4-(8-chloroisochroman-1-yl)thiophene-2-carbaldehyde

Steps 7 and 8 were performed in analogous fashion to Example 96, steps 1 and 2, employing 2-(4-bromothiophen-2-yl)-1,3-dioxolane as the bromide reactant in step 1.

Steps 9-13: [(1R,2S,4R)-4-[[5-[4-[(1S)-8-chloroisochroman-1-yl]thiophene-2-carbonyl]pyrimidin-4-yl]amino]-2-hydroxy-cyclopentyl]methyl sulfamate and [(1R,2S,4R)-4-[[5-[4-[(1R)-8-chloroisochroman-1-yl]thiophene-2-carbonyl]pyrimidin-4-yl]amino]-2-hydroxy-cyclopentyl]methyl sulfamate Steps 9-13 were performed in analogous fashion to Example 173, steps 1-5 employing conditions C in Step 3, conditions B in step 4, and conditions D in step 5. $^1$H NMR (400 MHz, Methanol-d4) δ ppm 8.73 (s, 1H) 8.60 (s, 1H) 7.57 (s, 1H) 7.45 (s, 1H) 7.21-7.33 (m, 3H) 6.06 (s, 1H) 4.78-4.85 (m, 1H) 4.11-4.26 (m, 3H) 3.75-3.91 (m, 2H) 3.02-3.16 (m, 1H) 2.75-2.83 (m, 1H) 2.48-2.57 (m, 1H) 2.24-2.33 (m, 1H) 2.13-2.22 (m, 1H) 1.88-1.98 (m, 1H) 1.40-1.50 (m, 1H). LCMS (AA): m/z=565.1 (M+1).

In certain instances described in the preceding examples and tables, mixtures of diastereomers were generated and subsequently separated into the individual component diastereomers. Where applicable, the preparative scale chiral chromatography conditions (HPLC or SFC) employed for the separation of the diastereomers are listed in the table below. The table below also details the chiral chromatography conditions (HPLC or SFC) that were used to analyze the diastereomeric purity of the resulting compounds as well as the retention times for each of the compounds listed.

| Compound No. of diastereomeric mixture | Preparative scale chiral chromatography conditions | Analytical chiral chromatography conditions | Retention time (min): Compound No. |
|---|---|---|---|
| I-106 | HPLC: 75/25/0.1 Hexane/EtOH/DEA on IA (20 × 250 mm; 5 micron) at 20 mL/min FR | SFC: CHIRALPAK IA 4.6 × 100 mm with 20/80 0.3% DEA in EtOH/CO2, 4 mL/min, 10 MPa | 7.6: I-106a 9.4: I-106b |
| I-117 | SFC: 30% [0.3% FA in MEOH]/70% CO2 on IC (10 × 250 mm; 5 micron) at 10 mL/min FR; BPR = 15 MPa | SFC: CHIRALPAK IC 4.6 × 100 mm with 25/75 0.3% FA in MeOH/CO2, 3 mL/min, 10 MPa | 11.1: I-117a 12.5: I-117b |
| I-4 | SFC: 45% [0.3% FA in MEOH]/55% CO2 on IA (10 × 250 mm; 5 micron) at 10 mL/min FR; BPR = 15 MPa | SFC: CHIRALPAK IA 4.6 × 100 mm with 45/55 0.3% FA in MeOH/CO2, 3 mL/min, 10 MPa | 2.9: I-4a 4.0: I-4b |
| I-36 | HPLC: 40/60/0.1 Hexane/EtOH/DEA on IC (20 × 250 mm; 5 micron) at 15 mL/min FR | HPLC: CHIRALPAK IC 4.6 × 50 mm with 40/60/0.1% hexane/EtOH/DEA, 1 mL/min | 2.4: I-36a 4.1: I-36b |
| I-47 | HPLC: 75/10/15/0.1 Hexane/IPA/EtOH/DEA on IC (20 × 250 mm; 5 micron) at 20 mL/min FR | HPLC: CHIRALPAK IC 4.6 × 50 mm with 75/10/15/0.1% hexane/IPA/EtOH/DEA, 1 mL/min | 5.3: I-47a 6.4: I-47b |

-continued

| Compound No. of diastereomeric mixture | Preparative scale chiral chromatography conditions | Analytical chiral chromatography conditions | Retention time (min): Compound No. |
|---|---|---|---|
| I-3 | HPLC: 60/40/0.1 Hexane/EtOH/DEA on IA (20 × 250 mm; 5 micron) at 18 mL/min FR | HPLC: CHIRALPAK IC 4.6 × 50 mm with 60/40/0.1% hexane/EtOH/DEA, 1 mL/min | 2.5: I-3a<br>5.2: I-3b |
| I-153 | HPLC: 80/10/10/0.1 Hexane/IPA/EtOH/DEA on IC (20 × 250 mm; 5 micron) at 20 mL/min FR | HPLC: CHIRALPAK IC 4.6 × 50 mm with 80/10/10/0.1% hexane/IPA/EtOH/DEA, 1 mL/min | 6.4: I-153a<br>7.9: I-153b |
| I-15 | HPLC: 10/90/0.1 Hexane/EtOH/DEA on IA (20 × 250 mm; 5 micron) at 10 mL/min FR | HPLC: CHIRALPAK IA 4.6 × 50 mm with 10/90/0.1% hexane/EtOH/DEA, 1 mL/min | 1.2: I-15a<br>3.2: I-15b |
| I-5 | HPLC: 60/40/0.1 Hexane/EtOH/DEA on IA (20 × 250 mm; 5 micron) at 18 mL/min FR | HPLC: CHIRALPAK IA 4.6 × 50 mm with 60/40/0.1% hexane/EtOH/DEA, 1 mL/min | 2.4: I-5a<br>5.1: I-5b |
| I-9 | HPLC: 70/30/0.1 Hexane/EtOH/DEA on IA (20 × 250 mm; 5 micron) at 20 mL/min FR | HPLC: CHIRALPAK IA 4.6 × 50 mm with 70/30/0.1% hexane/EtOH/DEA, 1 mL/min | 3.8: I-9a<br>7.0: I-9b |
| I-349 | HPLC: 60/40/0.1 Hexane/EtOH/DEA on IA (20 × 250 mm; 5 micron) at 15 mL/min FR | HPLC: CHIRALPAK IA 4.6 × 250 mm with 60/40/0.1% hexane/EtOH/DEA, 1 mL/min | 12.7: I-349a<br>22.6: I-349b |
| I-29 | SFC: 35% [0.3% DEA in MEOH]/65% CO2 on IA (10 × 250 mm; 5 micron) at 10 mL/min FR; BPR = 15 MPa | SFC: CHIRALPAK IA 4.6 × 100 mm with 35/65 0.3% DEA in EtOH/CO2, 3 mL/min, 10 MPa | 4.4: I-29a<br>5.7: I-29b |
| I-135 | HPLC: 80/20/0.1 Hexane/EtOH/DEA on IA (20 × 250 mm; 5 micron) at 20 mL/min FR | HPLC: CHIRALPAK IA 4.6 × 250 mm with 80/20/0.1% hexane/EtOH/DEA, 1 mL/min | 22.0: I-135a<br>27.8: I-135b |
| I-102 | HPLC: 70/30/0.1 Hexane/EtOH/DEA on IA (20 × 250 mm; 5 micron) at 20 mL/min FR | HPLC: CHIRALPAK IA 4.6 × 250 mm with 70/30/0.1% hexane/EtOH/DEA, 1 mL/min | 16.6: I-102a<br>23.4: I-102b |
| I-2 | SFC: 35% [0.3% DEA in EtOH]/65% CO2 on IA (10 × 250 mm; 5 micron) at 10 mL/min FR; BPR = 15 MPa | SFC: CHIRALPAK IA 4.6 × 100 mm with 35/65 0.3% DEA in EtOH/CO2, 4 mL/min, 10 MPa | 2.6: I-2a<br>4.3: I-2b |
| I-1 | SFC: 30% [0.3% DEA in EtOH]/70% CO2 on ID (10 × 250 mm; 5 micron) at 10 mL/min FR; BPR = 15 MPa | SFC: CHIRALPAK ID 4.6 × 100 mm with 30/70 0.3% DEA in EtOH/CO2, 3 mL/min, 10 MPa | 6.7: I-1a<br>8.9: I-1b |
| I-18 | HPLC: 30/70/0.1 Hexane/EtOH/DEA on IA (20 × 250 mm; 5 micron) at 12 mL/min FR | HPLC: CHIRALPAK IA 4.6 × 50 mm with 40/60/0.1% hexane/EtOH/DEA, 1 mL/min | 2.6: I-18a<br>5.2: I-18b |
| I-10 | SFC: 45% [0.3% DEA in EtOH]/55% CO2 on ID (10 × 250 mm; 5 micron) at 10 mL/min FR; BPR = 15 MPa | SFC: CHIRALPAK ID 4.6 × 100 mm with 40/60 0.3% DEA in EtOH/CO2, 3 mL/min, 10 MPa | 5.0: I-10a<br>6.7: I-10b |
| I-25 | SFC: 40% [0.3% DEA in EtOH]/60% CO2 on IA (10 × 250 mm; 5 micron) at 10 mL/min FR; BPR = 15 MPa | SFC: CHIRALPAK IA 4.6 × 100 mm with 40/60 0.3% DEA in EtOH/CO2, 3 mL/min, 10 MPa | 4.1: I-25a<br>5.7: I-25b |

-continued

| Compound No. of diastereomeric mixture | Preparative scale chiral chromatography conditions | Analytical chiral chromatography conditions | Retention time (min): Compound No. |
|---|---|---|---|
| I-22 | HPLC: 10/90/0.1 Hexane/EtOH/DEA on IA (20 × 250 mm; 5 micron) at 10 mL/min FR | HPLC: CHIRALPAK IA 4.6 × 50 mm with 10/90/0.1% hexane/EtOH/DEA, 1 mL/min | 1.2: I-22a 2.9: I-22b |
| I-11 | SFC: 25% [0.3% DEA in EtOH]/75% $CO_2$ on IC (10 × 250 mm; 5 micron) at 10 mL/min FR; BPR = 15 MPa | SFC: CHIRALPAK IC 4.6 × 100 mm with 20/80 0.3% DEA in EtOH/$CO_2$, 4 mL/min, 10 MPa | 10.4: I-11a 12.9: I-11b |
| I-19 | HPLC: 60/40/0.1 Hexane/EtOH/DEA on IA (20 × 250 mm; 5 micron) at 15 mL/min FR | HPLC: CHIRALPAK IA 4.6 × 250 mm with 60/40/0.1% hexane/EtOH/DEA, 1 mL/min | 11.6: I-19a 18.8: I-19b |
| I-90 | SFC: 20% [0.3% DEA in EtOH]/80% $CO_2$ on IA (10 × 250 mm; 5 micron) at 10 mL/min FR; BPR = 15 MPa | SFC: CHIRALPAK IA 4.6 × 100 mm with 20/80 0.3% DEA in EtOH/$CO_2$, 3 mL/min, 10 MPa | 8.9: I-90a 10.3: I-90b |
| I-12 | HPLC: 40/60/0.1 Hexane/EtOH/DEA on IC (20 × 250 mm; 5 micron) at 15 mL/min FR | HPLC: CHIRALPAK IC 4.6 × 50 mm with 40/60/0.1% hexane/EtOH/DEA, 1 mL/min | 1.8: I-12a 4.4: I-12b |
| I-151 | HPLC: 75/25/0.1 Hexane/EtOH/DEA on IC (20 × 250 mm; 5 micron) at 15 mL/min FR | HPLC: CHIRALPAK IC 4.6 × 50 mm with 75/25/0.1% hexane/EtOH/DEA, 1 mL/min | 4.1: I-151a 6.6: I-151b |
| I-8 | HPLC: 40/60/0.1 Hexane/EtOH/DEA on IC (20 × 250 mm; 5 micron) at 15 mL/min FR | HPLC: CHIRALPAK IC 4.6 × 50 mm with 40/60/0.1% hexane/EtOH/DEA, 1 mL/min | 1.9: I-8a 4.1: I-8b |
| I-6 | SFC: 45% [0.3% DEA in EtOH]/55% $CO_2$ on ID (10 × 250 mm; 5 micron) at 10 mL/min FR; BPR = 15 MPa | SFC: CHIRALPAK ID 4.6 × 100 mm with 30/70 0.3% DEA in EtOH/$CO_2$, 4 mL/min, 10 MPa | 3.7: I-6a 5.7: I-6b |
| I-7 | HPLC: 80/20/0.1 Hexane/EtOH/DEA on IC (20 × 250 mm; 5 micron) at 20 mL/min FR | HPLC: CHIRALPAK IC 4.6 × 250 mm with 80/20/0.1% hexane/EtOH/DEA, 1 mL/min | 29.5: I-7a 40.0: I-7b |
| I-41 | HPLC: 82/18/0.1 Hexane/EtOH/DEA on IB (20 × 250 mm; 5 micron) at 20 mL/min FR | HPLC: CHIRALPAK IC 4.6 × 250 mm with 82/18/0.1% hexane/EtOH/DEA, 1 mL/min | 24.3: I-41a 28.5: I-41b |
| I-38 | HPLC: 70/10/20/0.1 Hexane/IPA/EtOH/DEA on IC (20 × 250 mm; 5 micron) at 20 mL/min FR | HPLC: CHIRALPAK IC 4.6 × 250 mm with 60/40/0.1% hexane/EtOH/DEA, 1 mL/min | 10.2: I-38a 14.4: I-38b |
| I-32 | HPLC: 70/30/0.1 Hexane/IPA/DEA on IC (20 × 250 mm; 5 micron) at 20 mL/min FR | HPLC: CHIRALPAK IC 4.6 × 250 mm with 65/30/5/0.1% hexane/IPA/EtOH/DEA, 1 mL/min | 25.5: I-32a 30.1: I-32b |
| I-335 | SFC: 35% [0.3% DEA in EtOH]/65% $CO_2$ on IA (10 × 250 mm; 5 micron) at 10 mL/min FR; BPR = 15 MPa | SFC: 35% [0.3% DEA in EtOH]/65% $CO_2$ on IA (4.6 × 100 mm; 5 micron) at 3 mL/min FR; 10 min; BPR = 10 MPa | 3.26: I-335a 5.05: I-335b |
| I-289 | SFC: 40% [0.3% DEA in EtOH]/60% $CO_2$ on IF (10 × 250 mm; 5 micron) at 10 mL/min FR; BPR = 15 MPa | SFC: 40% [0.3% DEA in EtOH]/60% $CO_2$ on IF (4.6 × 100 mm; 5 micron) at 4 mL/min FR; 10 min; BPR = 10 MPa | 2.0: I-289a 3.7: I-289b |

-continued

| Compound No. of diastereomeric mixture | Preparative scale chiral chromatography conditions | Analytical chiral chromatography conditions | Retention time (min): Compound No. |
|---|---|---|---|
| I-301 | HPLC: 60/5/35/0.1 Hexane/IPA/EtOH/DEA on IC (20 × 250 mm; 5 micron) at 20 mL/min FR | HPLC: 40/60/0.1 Hexane/EtOH/DEA on IC (4.6 × 250 mm; 5 micron) at 1 mL/min FR; 20 min | 8.7: I-301a 15.7: I-301b |
| I-266 | HPLC: 70/30/0.1 Hexane/EtOH/DEA on IC (30 × 250 mm; 5 micron) at 40 mL/min FR | HPLC: 70/30/0.1 Hexane/EtOH/DEA on IC (4.6 × 250 mm; 5 micron) at 1 mL/min FR; 60 min | 30.5: I-266a 51.3: I-266b |
| I-293 | SFC: 40% [0.3% DEA in EtOH]/60% CO2 on IF (10 × 250 mm; 5 micron) at 10 mL/min FR; BPR = 15 MPa | SFC: 35% [0.3% DEA in EtOH]/65% CO2 on IF (4.6 × 100 mm; 5 micron) at 4 mL/min FR; 10 min; BPR = 10 MPa | 2.3: I-293a 5.0: I-293b |
| I-276 | HPLC: 60/40/0.1 Hexane/EtOH/DEA on IA (20 × 250 mm; 5 micron) at 20 mL/min FR | HPLC: 40/60/0.1 Hexane/EtOH/DEA on IA (4.6 × 250 mm; 5 micron) at 1 mL/min FR; 30 min | 7.6: I-276a 9.8: I-276b |
| I-258 | SFC: 25% [0.3% DEA in IPA]/75% CO2 on ID (10 × 250 mm; 5 micron) at 10 mL/min FR; BPR = 15 MPa | SFC: 25% [0.3% DEA in IPA]/75% CO2 on ID (4.6 × 100 mm; 5 micron) at 4 mL/min FR; 10 min; BPR = 10 MPa | 4.0: I-258a 4.8: I-258b |
| I-267 | SFC: 25% [0.3% DEA in EtOH]/75% CO2 on IA (10 × 250 mm; 5 micron) at 10 mL/min FR; BPR = 15 MPa | SFC: 50% [0.3% DEA in EtOH]/50% CO2 on IF (4.6 × 100 mm; 5 micron) at 4 mL/min FR; 5 min; BPR = 10 MPa | 2.0: I-267a 2.9: I-267b |
| I-294 | SFC: 30% [0.3% DEA in EtOH]/70% CO2 on IF (10 × 250 mm; 5 micron) at 10 mL/min FR; BPR = 15 MPa | SFC: 30% [0.3% DEA in EtOH]/70% CO2 on IF (4.6 × 100 mm; 5 micron) at 3 mL/min FR; 10 min; BPR = 10 MPa | 4.0: I-294a 4.8: I-294b |
| I-279 | SFC: 30% [0.3% DEA in EtOH]/70% CO2 on IF (10 × 250 mm; 5 micron) at 10 mL/min FR; BPR = 15 MPa | SFC: 30% [0.3% DEA in EtOH]/70% CO2 on IF (4.6 × 100 mm; 5 micron) at 4 mL/min FR; 10 min; BPR = 10 MPa | 4.2: I-279a 5.1: I-279b |
| I-260 | HPLC: 65/5/30/0.1 Hexane/IPA/EtOH/DEA on IA (20 × 250 mm; 5 micron) at 20 mL/min FR | HPLC: 65/5/30/0.1 Hexane/IPA/EtOH/DEA on IA (4.6 × 250 mm; 5 micron) at 1 mL/min FR; 60 min | 20.3: I-260a 29.3: I-260b |
| I-314 | SFC: 35% [0.3% DEA in EtOH]/65% CO2 on ID (10 × 250 mm; 5 micron) at 10 mL/min FR; BPR = 15 MPa | SFC: 35% [0.3% DEA in EtOH]/65% CO2 on ID (4.6 × 100 mm; 5 micron) at 4 mL/min FR; 10 min; BPR = 10 MPa | 2.5: I-314a 4.1: I-314b |
| I-314 | SFC: 60% [0.3% DEA in EtOH]/40% CO2 on IC (10 × 250 mm; 5 micron) at 10 mL/min FR; BPR = 15 MPa | SFC: 50% [0.3% DEA in EtOH]/50% CO2 on IC (4.6 × 100 mm; 5 micron) at 4 mL/min FR; 10 min; BPR = 10 MPa | 2.4: I-343a 8.2: I-343b |
| I-281 | HPLC: 60/40/0.1 Hexane/EtOH/DEA on IC (20 × 250 mm; 5 micron) at 20 mL/min FR | HPLC: 40/60/0.1 Hexane/EtOH/DEA on IC (4.6 × 250 mm; 5 micron) at 1 mL/min FR; 30 min | 11.6: I-281a 19.8: I-281b |
| I-298 | HPLC: 50/50/0.1 Hexane/EtOH/DEA on IA (20 × 250 mm; 5 micron) at 20 mL/min FR | HPLC: 40/60/0.1 Hexane/EtOH/DEA on IA (4.6 × 250 mm; 5 micron) at 1 mL/min FR; 30 min | 7.5: I-298a 10.9: I-298b |
| I-349 | HPLC: 60/40/0.1 Hexane/EtOH/DEA on IA (20 × 250 mm; 5 micron) at 15 mL/min FR | HPLC: 60/40/0.1 Hexane/EtOH/DEA on IA (4.6 × 250 mm; 5 micron) at 1 mL/min FR; 60 min | 12.7: I-349a 22.6: I-349b |

-continued

| Compound No. of diastereomeric mixture | Preparative scale chiral chromatography conditions | Analytical chiral chromatography conditions | Retention time (min): Compound No. |
|---|---|---|---|
| I-268 | SFC: 45% [0.3% DEA in IPA]/45% CO2 on IA (10 × 250 mm; 5 micron) at 10 mL/min FR; BPR = 15 MPa | SFC: 40% [0.3% DEA in EtOH]/60% CO2 on IA (4.6 × 100 mm; 5 micron) at 3 mL/min FR; 10 min; BPR = 10 MPa | 4.9: I-268a 6.2: I-268b |
| I-286 | SFC: 30% [0.3% DEA in MEOH]/70% CO2 on IA (10 × 250 mm; 5 micron) at 10 mL/min FR; BPR = 15 MPa | SFC: 30% [0.3% DEA in MEOH]/70% CO2 on IA (4.6 × 100 mm; 5 micron) at 4 mL/min FR; 10 min; BPR = 10 MPa | 3.6: I-286a 5.5: I-286b |
| I-297 | SFC: 25% [0.3% DEA in MEOH]/75% CO2 on IF (10 × 250 mm; 5 micron) at 10 mL/min FR; BPR = 15 MPa | SFC: 20% [0.3% DEA in MEOH]/80% CO2 on IF (4.6 × 100 mm; 5 micron) at 3 mL/min FR; 20 min; BPR = 10 MPa | 10.1: I-297a 12.7: I-297b |
| I-339 | SFC: 20% [0.3% DEA in EtOH]/80% CO2 on IB (10 × 250 mm; 5 micron) at 10 mL/min FR; BPR = 15 MPa | SFC: 20% [0.3% DEA in EtOH]/80% CO2 on IB (4.6 × 100 mm; 5 micron) at 4 mL/min FR; 10 min; BPR = 10 MPa | 5.2: I-339a 5.9: I-339b |
| I-287 | HPLC: 60/40/0.1 Hexane/EtOH/DEA on IC (20 × 250 mm; 5 micron) at 20 mL/min FR | HPLC: 40/60/0.1 Hexane/EtOH/DEA on IC (4.6 × 250 mm; 5 micron) at 1 mL/min FR; 30 min | 9.1: I-287a 14.2: I-287b |
| I-285 | HPLC: 20/80/0.1 Hexane/EtOH/DEA on IC (20 × 250 mm; 5 micron) at 10 mL/min FR | HPLC: 40/60/0.1 Hexane/EtOH/DEA on IC (4.6 × 250 mm; 5 micron) at 1 mL/min FR; 30 min | 9.8: I-285b 20.3: I-285a |
| I-320 | HPLC: 80/10/10/0.1 Hexane/IPA/EtOH/DEA on IB (20 × 250 mm; 5 micron) at 20 mL/min FR | HPLC: 75/25/0.1 Hexane/EtOH/DEA on IB (4.6 × 250 mm; 5 micron) at 1 mL/min FR; 30 min | 14.2: I-320a 16.0: I-320b |
| I-278 | HPLC 80/20/0.1 Hexane/EtOH/DEA on IA (20 × 250 mm; 5 micron) at 10 mL/min FR | HPLC: 10/90/0.1 Hexane/EtOH/DEA on IA (4.6 × 250 mm; 5 micron) at 0.75 mL/min FR; 45 min | 11.1: I-278a 15.6: I-278b |
| I-310 | SFC: 40% [0.3% DEA in EtOH]/60% CO2 on IA (10 × 250 mm; 5 micron) at 10 mL/min FR; BPR = 15 MPa | SFC: 40% [0.3% DEA in EtOH]/60% CO2 on IA (4.6 × 100 mm; 5 micron) at 4 mL/min FR; 5 min; BPR = 10 MPa | 2.2: I-310a 2.8: I-310b |
| I-305 | SFC: 35% [0.3% DEA in EtOH]/65% CO2 on IA (10 × 250 mm; 5 micron) at 10 mL/min FR; BPR = 15 MPa | SFC: 30% [0.3% DEA in EtOH]/70% CO2 on IA (4.6 × 100 mm; 5 micron) at 4 mL/min FR; 10 min; BPR = 10 MPa | 3.2: I-305a 4.2: I-305b |
| I-269 | SFC: 35% [0.3% DEA in MEOH]/65% CO2 on IA (10 × 250 mm; 5 micron) at 10 mL/min FR; BPR = 15 MPa | SFC: 30% [0.3% DEA in MEOH]/70% CO2 on IA (4.6 × 100 mm; 5 micron) at 4 mL/min FR; 10 min; BPR = 10 MPa | 4.1: I-269a 6.1: I-269b |
|  | SFC: 40% [0.3% DEA in EtOH]/60% CO2 on IA (10 × 250 mm; 5 micron) at 10 mL/min FR; BPR = 15 MPa | SFC: 40% [0.3% DEA in EtOH]/60% CO2 on IA (4.6 × 100 mm; 5 micron) at 4 mL/min FR; 10 min; BPR = 10 MPa | 2.8: I-247a 4.2: I-247b |
| Int-285 | SFC: 25% [0.3% DEA in EtOH]/75% CO2 on IA (10 × 250 mm; 5 micron) at 10 mL/min FR; BPR = 15 MPa | SFC: 30% [0.3% DEA in EtOH]/70% CO2 on IA (4.6 × 100 mm; 5 micron) at 4 mL/min FR; 10 min; BPR = 10 MPa | 4.8: I-248a 8.2: I-248b |
| Int-284 | SFC: 35% [0.3% DEA in EtOH]/65% CO2 on IA (10 × 250 mm; 5 micron) at 10 mL/min FR; BPR = 15 MPa | SFC: 30% [0.3% DEA in EtOH]/70% CO2 on IA (4.6 × 100 mm; 5 micron) at 4 mL/min FR; 10 min; BPR = 10 MPa | 4.2: I-292a 6.0: I-292b |

-continued

| Compound No. of diastereomeric mixture | Preparative scale chiral chromatography conditions | Analytical chiral chromatography conditions | Retention time (min): Compound No. |
|---|---|---|---|
| I-257 | SFC: 35% [0.3% DEA in MEOH]/65% CO2 on IA (10 × 250 mm; 5 micron) at 10 mL/min FR; BPR = 15 MPa | SFC: 40% [0.3% DEA in MEOH]/60% CO2 on IA (4.6 × 100 mm; 5 micron) at 4 mL/min FR; 5 min; BPR = 10 MPa | 1.4: I-257a<br>2.0: I-257b |
| I-274 | SFC: 60% [0.3% DEA in MEOH]/40% CO2 on IA (10 × 250 mm; 5 micron) at 10 mL/min FR; BPR = 15 MPa | SFC: 60% [0.3% DEA in MEOH]/40% CO2 on IA (4.6 × 100 mm; 5 micron) at 4 mL/min FR; 5 min; BPR = 10 MPa | 1.3: I-274a<br>2.0: I-274b |
| I-307 | SFC: 35% [0.3% DEA in MEOH]/65% CO2 on IA (10 × 250 mm; 5 micron) at 10 mL/min FR; BPR = 15 MPa | SFC: 25% [0.3% DEA in MEOH]/75% CO2 on IA (4.6 × 100 mm; 5 micron) at 4 mL/min FR; 5 min; BPR = 10 MPa | 2.3: I-307a<br>3.1: I-307b |
| I-291 | HPLC: 60/40/0.1 Hexane/EtOH/DEA on IC (20 × 250 mm; 5 micron) at 20 mL/min FR | HPLC: 60/40/0.1 Hexane/EtOH/DEA on IC (4.6 × 50 mm; 5 micron) at 1 mL/min FR; 10 min | 2.3: I-291a<br>4.4: I-291b |
| I-262 | HPLC: 70/5/25/0.1 Hexane/IPA/EtOH/DEA on IA (20 × 250 mm; 5 micron) at 20 mL/min FR | HPLC: 60/10/30/0.1 Hexane/IPA/EtOH/DEA on IA (4.6 × 250 mm; 5 micron) at 1 mL/min FR; 40 min | 13.7: I-262a<br>15.5: I-262b |
| I-253 | HPLC: 60/40/0.1 Hexane/IPA/DEA on IC (30 × 250 mm; 5 micron) at 40 mL/min FR | HPLC: 60/35/5/0.1 Hexane/IPA/EtOH/DEA on IC (4.6 × 250 mm; 5 micron) at 1 mL/min FR; 60 min | 31.5: I-253a<br>39.1: I-253b |
| I-283 | HPLC: 40/60/0.1 Hexane/EtOH/DEA on IA (20 × 250 mm; 5 micron) at 15 mL/min FR | HPLC: 40/60/0.1 Hexane/EtOH/DEA on IA (4.6 × 50 mm; 5 micron) at 1 mL/min FR; 10 min | 3.2: I-283a<br>5.6: I-283b |
| I-256 | SFC: 40% [0.3% FA in MEOH]/60% CO2 on IF (10 × 250 mm; 5 micron) at 10 mL/min FR; BPR = 15 MPa | SFC: 40% [0.3% FA in MEOH]/60% CO2 on IF (4.6 × 100 mm; 5 micron) at 4 mL/min FR; 5 min; BPR = 10 MPa | 2.6: I-256a<br>3.5: I-256b |
| I-250 | SFC: 35% [0.3% DEA in EtOH]/65% CO2 on IF (10 × 250 mm; 5 micron) at 10 mL/min FR; BPR = 15 MPa | SFC: 25% [0.3% DEA in EtOH]/75% CO2 on IF (4.6 × 100 mm; 5 micron) at 4 mL/min FR; 10 min; BPR = 10 MPa | 4.4: I-250a<br>5.2: I-250b |
| I-299 | HPLC: 80/20/0.1 Hexane/EtOH/DEA on IB (20 × 250 mm; 5 micron) at 20 mL/min FR | HPLC: 70/30/0.1 Hexane/EtOH/DEA on IB (4.6 × 250 mm; 5 micron) at 1 mL/min FR; 50 min | 9.4: I-299a<br>11.9: I-299b |
| I-28 | HPLC: 50/50/0.1 Hexane/EtOH/DEA on IC (20 × 250 mm; 5 micron) at 15 mL/min FR | HPLC: 40/60/0.1 Hexane/EtOH/DEA on IC (4.6 × 250 mm; 5 micron) at 1.0 mL/min FR; 30 min | 16.1: I-28a<br>23.0: I-28b |
| I-252 | SFC: 30% [0.3% DEA in MEOH]/70% CO2 on IF (10 × 250 mm; 5 micron) at 10 mL/min FR; BPR = 15 MPa | 40% [0.3% DEA in MEOH]/60% CO2 on IF (4.6 × 100 mm; 5 micron) at 4 mL/min FR; 10 min; BPR = 10 MPa | 2.3: I-252a<br>3.9: I-252b |
| I-277 | HPLC: 50/50/0.1 Hexane/IPA/DEA on ID (30 × 250 mm; 5 micron) at 40 mL/min FR | SFC: 25% [0.3% DEA in EtOH]/75% CO2 on ID (4.6 × 100 mm; 5 micron) at 4 mL/min FR; 10 min; BPR = 10 MPa | 7.0: I-277a<br>9.1: I-277b |
| I-264 | SFC: 50% [0.3% DEA in MEOH]/50% CO2 on IA (10 × 250 mm; 5 micron) at 10 mL/min FR; BPR = 15 MPa | SFC: 50% [0.3% DEA in MEOH]/50% CO2 on IA (4.6 × 100 mm; 5 micron) at 3 mL/min FR; 10 min; BPR = 10 MPa | 3.7: I-264a<br>5.4: I-264b |

-continued

| Compound No. of diastereomeric mixture | Preparative scale chiral chromatography conditions | Analytical chiral chromatography conditions | Retention time (min): Compound No. |
|---|---|---|---|
| I-282 | SFC: 35% [0.3% DEA in EtOH]/65% CO2 on IF (10 × 250 mm; 5 micron) at 10 mL/min FR; BPR = 15 MPa | SFC: 25% [0.3% DEA in EtOH]/75% CO2 on IA (4.6 × 100 mm; 5 micron) at 4 mL/min FR; 10 min; BPR = 10 MPa | 5.3: I-282a<br>6.5: I-282b |
| I-254 | SFC: 45% [0.3% DEA in IPA]/55% CO2 on IC (10 × 250 mm; 5 micron) at 10 mL/min FR; BPR = 15 MPa | SFC: 40% [0.3% DEA in IPA]/60% CO2 on IC (4.6 × 100 mm; 5 micron) at 4 mL/min FR; 10 min; BPR = 10 MPa | 4.8: I-254a<br>5.9: I-254b |
| | | HPLC: 75/25/0.1 Hexane/EtOH/DEA on IF (4.6 × 100 mm; 5 micron) at 1 mL/min FR; 15 min | 7.5: I-284a<br>9.0: I-284b |
| | | SFC: 30% [0.3% DEA in EtOH]/70% CO2 on IA (4.6 × 100 mm; 5 micron) at 4 mL/min FR; 10 min; BPR = 10 MPa | 4.4: I-263a<br>7.1: I-263b |
| | HPLC: 70/30/0.1 Hexane/EtOH/DEA on IC (30 × 250 mm; 5 micron) at 40 mL/min FR | HPLC: 70/30/0.1 Hexane/EtOH/DEA on IC (4.6 × 250 mm; 5 micron) at 1 mL/min FR; 60 min | 39.5: I-271a |
| I-261 | SFC: 40% [0.3% DEA in EtOH]/60% CO2 on IA (10 × 250 mm; 5 micron) at 10 mL/min FR; BPR = 15 MPa | SFC: 35% [0.3% DEA in EtOH]/65% CO2 on IA (4.6 × 100 mm; 5 micron) at 4 mL/min FR; 10 min; BPR = 10 MPa | 4.6: I-261a<br>6.1: I-261b |
| I-30 | HPLC: 100/0.1 EtOH/DEA on IA (20 × 250 mm; 5 micron) at 10 mL/min FR | HPLC: 100/0.1 EtOH/DEA on IA (4.6 × 50 mm; 5 micron) at 1.0 mL/min FR; 15 min | 1.4: I-30a<br>4.4: I-30b |
| I-42 | HPLC: 50/50/0.1 Hexane/EtOH/FA on IC (20 × 250 mm; 5 micron) at 15 mL/min FR | HPLC: 50/50/0.1 Hexane/EtOH/FA on IC (4.6 × 50 mm; 5 micron) at 1.0 mL/min FR; 10 min | 1.5: I-42a<br>3.2: I-42b |
| Int-283 | HPLC: 20/80/0.1 Hexane/EtOH/DEA on IC (20 × 250 mm; 5 micron) at 10 mL/min FR | HPLC: 20/80/0.1 Hexane/EtOH/DEA on IC (4.6 × 250 mm; 5 micron) at 0.5 mL/min FR; 30 min | 12.2: I-272a<br>21.7: I-272b |
| I-270 | HPLC: 20/80/0.1 Hexane/EtOH/DEA on IC (20 × 250 mm; 5 micron) at 10 mL/min FR | HPLC: 40/60/0.1 Hexane/EtOH/DEA on IC (4.6 × 250 mm; 5 micron) at 1.0 mL/min FR; 10 min | 1.3: I-270a<br>2.4: I-270b |
| I-280 | SFC: 40% [0.3% DEA in MEOH]/60% CO2 on IF (10 × 250 mm; 5 micron) at 10 mL/min FR; BPR = 15 MPa | SFC: 30% [0.3% DEA in MEOH]/70% CO2 on IF (4.6 × 100 mm; 5 micron) at 4 mL/min FR; 10 min; BPR = 10 MPa | 3.1: I-280a<br>4.6: I-280b |
| I-265 | HPLC: 82/18/0.1 Hexane/EtOH/DEA on IC (20 × 250 mm; 5 micron) at 20 mL/min FR | HPLC: CHIRALPAK IC 4.6 × 250 mm with 70/30/0.1% hexane/EtOH/DEA, 1 mL/min | 16.2: I-265a<br>19.7: I-265b |
| I-355 | SFC: 30% [0.3% DEA in EtOH]/70% CO2 on ID (10 × 250 mm; 5 micron) at 10 mL/min FR; BPR = 15 MPa | SFC: 30% [0.3% DEA in EtOH]/70% CO2 on ID (4.6 × 100 mm; 5 micron) at 3 mL/min FR; 10 min; BPR = 10 MPa | 3.1: I-355a<br>4.2: I-355b |
| I-356 | HPLC: 70/30/0.1 Hexane/ETOH/DEA on IC (20 × 250 mm; 5 micron) At 15 mL/min FR | HPLC: CHIRALPAK IC 4.6 × 250 mm: 5 micron with 60/40/0.1 Hexane/ETOH/DEA, 1 mL/min. | 24.0: I-356a<br>28.8: I-356b |

The table below describes the $^1$H NMR and LC/MS data for the compounds prepared herein.

| Compound No. | $^1$H NMR | LC/MS |
|---|---|---|
| I-27b | $^1$H NMR (400 MHz, DMSO) δ 8.64 (s, 1H), 8.62 (s, 1H), 8.36 (d, J = 7.5 Hz, 1H), 7.87 (d, J = 1.3 Hz, 1H), 7.73 (d, J = 1.3 Hz, 1H), 7.70 (t, J = 1.8 Hz, 1H), 7.43 (s, 2H), 7.40-7.34 (m, 2H), 7.28-7.20 (m, 1H), 4.86 (d, J = 5.8 Hz, 1H), 4.69 (s, 1H), 4.51-4.38 (m, 1H), 4.12-4.01 (m, 1H), 4.00-3.92 (m, 1H), 3.82-3.73 (m, 1H), 3.73-3.66 (m, 1H), 2.63 (s, 2H), 2.33-2.23 (m, 1H), 2.23-2.13 (m, 1H), 1.73 (s, 3H), 1.21-1.08 (m, 1H) | FA: m/z = 612.4 (M + H) |
| I-19a | $^1$H NMR (400 MHz, DMSO) δ 8.65 (s, 1H), 8.64 (s, 1H), 8.26 (d, J = 7.5 Hz, 1H), 7.86 (s, 1H), 7.69 (dd, J = 6.5, 2.6 Hz, 1H), 7.64 (d, J = 1.1 Hz, 1H), 7.51 (ddd, J = 8.6, 4.5, 2.7 Hz, 1H), 7.42 (s, 2H), 7.17 (dd, J = 10.0, 8.8 Hz, 1H), 6.32 (d, J = 4.9 Hz, 1H), 6.00 (d, J = 4.9 Hz, 1H), 4.88 (d, J = 4.6 Hz, 1H), 4.70 (dq, J = 16.2, 8.0 Hz, 1H), 4.08 (dd, J = 9.7, 6.0 Hz, 1H), 4.01-3.89 (m, 2H), 2.38-2.24 (m, 1H), 2.17-2.07 (m, 1H), 2.01-1.90 (m, 1H), 1.83-1.70 (m, 1H), 1.26 (dt, J = 12.7, 9.2 Hz, 1H) | FA: m/z = 601.5 (M + H) |
| I-19b | $^1$H NMR (400 MHz, DMSO) δ 8.65 (s, 1H), 8.64 (s, 1H), 8.26 (d, J = 7.5 Hz, 1H), 7.86 (s, 1H), 7.70 (dd, J = 6.5, 2.6 Hz, 1H), 7.64 (d, J = 1.2 Hz, 1H), 7.51 (ddd, J = 8.7, 4.5, 2.6 Hz, 1H), 7.38 (s, 2H), 7.17 (dd, J = 10.0, 8.8 Hz, 1H), 6.33 (s, 1H), 6.00 (s, 1H), 4.88 (s, 1H), 4.70 (dq, J = 16.3, 8.1 Hz, 1H), 4.08 (dd, J = 9.7, 6.0 Hz, 1H), 3.99-3.90 (m, 2H), 2.37-2.25 (m, 1H), 2.18-2.06 (m, 1H), 2.01-1.90 (m, 1H), 1.82-1.70 (m, 1H), 1.26 (dt, J = 12.7, 9.2 Hz, 1H) | FA: m/z = 601.5 (M + H) |
| I-202 | $^1$H NMR (400 MHz, DMSO) δ 8.69 (s, 1H), 8.62 (s, 1H), 8.32 (d, J = 7.5 Hz, 1H), 7.61 (d, J = 3.9 Hz, 1H), 7.42 (s, 2H), 7.09 (d, J = 4.0 Hz, 1H), 5.78 (s, 1H), 4.85 (d, J = 5.9 Hz, 1H), 4.71 (d, J = 4.1 Hz, 1H), 4.50-4.39 (m, 1H), 4.07 (dd, J = 9.8, 6.1 Hz, 1H), 4.01-3.92 (m, 1H), 3.84-3.75 (m, 1H), 3.74-3.66 (m, 1H), 2.36-2.24 (m, 1H), 2.18 (d, J = 4.3 Hz, 1H), 1.53 (s, 6H), 1.15 (dt, J = 12.7, 8.8 Hz, 1H) | FA: m/z = 473.1 (M + H) |
| I-235 | $^1$H NMR (400 MHz, DMSO) δ 8.67 (s, 1H), 8.63 (s, 1H), 8.24 (d, J = 7.6 Hz, 1H), 7.60 (d, J = 3.9 Hz, 1H), 7.42 (s, 2H), 7.08 (d, J = 4.0 Hz, 1H), 5.78 (s, 1H), 4.88 (s, 1H), 4.77-4.64 (m, 1H), 4.09 (dd, J = 9.7, 6.0 Hz, 1H), 4.01-3.91 (m, 2H), 2.37-2.27 (m, 1H), 2.18-2.05 (m, 1H), 2.00-1.91 (m, 1H), 1.84-1.72 (m, 1H), 1.53 (s, 6H), 1.28 (dt, J = 12.8, 9.3 Hz, 1H) | FA: m/z = 457.5 (M + H) |
| I-152 | $^1$H NMR (400 MHz, DMSO) δ 8.65 (s, 1H), 8.62 (s, 1H), 8.20 (d, J = 7.5 Hz, 1H), 7.63-7.56 (m, 2H), 7.53-7.47 (m, 1H), 7.41 (s, 2H), 7.37 (t, J = 7.9 Hz, 1H), 7.34-7.28 (m, 1H), 7.16 (d, J = 4.0 Hz, 1H), 6.63 (s, 1H), 4.87 (s, 1H), 4.76-4.62 (m, 1H), 4.08 (dd, J = 9.8, 5.8 Hz, 1H), 4.00-3.90 (m, 2H), 2.36-2.25 (m, 1H), 2.16-2.06 (m, 1H), 2.00-1.90 (m, 1H), 1.94 (s, 3H), 1.82-1.70 (m, 1H), 1.32-1.20 (m, 1H) | FA: m/z = 553.4 (M + H) |
| I-19 | $^1$H NMR (400 MHz, DMSO) δ 8.65 (s, 1H), 8.64 (s, 1H), 8.26 (d, J = 7.6 Hz, 1H), 7.86 (s, 1H), 7.70 (dd, J = 6.4, 2.6 Hz, 1H), 7.64 (d, J = 1.0 Hz, 1H), 7.51 (ddd, J = 8.7, 4.5, 2.7 Hz, 1H), 7.42 (s, 2H), 7.17 (dd, J = 10.0, 8.8 Hz, 1H), 6.32 (d, J = 4.9 Hz, 1H), 6.00 (d, J = 4.9 Hz, 1H), 4.88 (d, J = 4.6 Hz, 1H), 4.77-4.62 (m, 1H), 4.09 (dd, J = 9.7, 6.0 Hz, 1H), 3.99-3.90 (m, 2H), 2.37-2.25 (m, 1H), 2.18-2.06 (m, 1H), 2.02-1.88 (m, 1H), 1.81-1.71 (m, 1H), 1.34-1.21 (m, 1H) | FA: m/z = 601.2 (M + H) |
| I-46 | $^1$H NMR (400 MHz, DMSO) δ 8.71 (s, 1H), 8.65 (s, 1H), 8.22 (d, J = 6.9 Hz, 1H), 7.79-7.65 (m, 2H), 7.51 (d, J = 7.9 Hz, 1H), 7.44 (s, 2H), 7.33 (d, J = 7.3 Hz, 1H), 5.76 (s, 2H), 4.89 (d, J = 3.4 Hz, 1H), 4.78-4.62 (m, 1H), 4.13-4.04 (m, 1H), 4.01-3.87 (m, 2H), 2.37-2.23 (m, 1H), 2.17-2.04 (m, 1H), 2.01-1.87 (m, 1H), 1.84-1.69 (m, 1H), 1.35-1.18 (m, 1H) | FA: m/z = 604.9 (M + H) |
| I-53 | $^1$H NMR (400 MHz, DMSO) δ 8.70 (s, 1H), 8.65 (s, 1H), 8.28 (d, J = 7.6 Hz, 1H), 7.84 (s, 1H), 7.72 (s, 1H), 7.69 (t, J = 7.7 Hz, 1H), 7.50 (d, J = 7.9 Hz, 1H), 7.44 (s, 2H), 7.37 (d, J = 7.5 Hz, 1H), 4.89 (d, J = 4.2 Hz, 1H), 4.77-4.64 (m, 1H), 4.14 (s, 2H), 4.09 (dd, J = 9.7, 6.0 Hz, 1H), 4.00-3.90 (m, 2H), 2.37-2.26 (m, 1H), 2.11 (s, 1H), 2.00-1.90 (m, 1H), 1.82-1.72 (m, 1H), 1.33-1.21 (m, 1H) | FA: m/z = 568.3 (M + H) |

-continued

| Compound No. | ¹H NMR | LC/MS |
|---|---|---|
| I-71 | ¹H NMR (400 MHz, DMSO) δ 8.69 (s, 1H), 8.64 (s, 1H), 8.28 (d, J = 7.4 Hz, 1H), 7.85 (s, 1H), 7.80 (t, J = 7.8 Hz, 1H), 7.72 (s, 1H), 7.44 (s, 2H), 7.39-7.32 (m, 2H), 4.89 (d, J = 4.3 Hz, 1H), 4.76-4.64 (m, 1H), 4.14 (s, 2H), 4.08 (dd, J = 9.7, 6.0 Hz, 1H), 4.00-3.91 (m, 2H), 2.37-2.25 (m, 1H), 2.16-2.06 (m, 1H), 2.01-1.90 (m, 1H), 1.82-1.71 (m, 1H), 1.33-1.21 (m, 1H) | FA: m/z = 523.9 (M + H) |
| I-121 | ¹H NMR (400 MHz, DMSO-d₆) δ 8.70 (s, 1H), 8.65 (s, 1H), 8.21 (d, J = 7.4 Hz, 1H), 7.74 (s, 1H), 7.43 (s, 2H), 7.42-7.36 (m, 2H), 7.34-7.27 (m, 2H), 7.25-7.18 (m, 1H), 4.88 (d, J = 4.5 Hz, 1H), 4.77-4.65 (m, 1H), 4.09 (dd, J = 9.7, 6.0 Hz, 1H), 4.03-3.92 (m, 3H), 3.92-3.84 (m, 1H), 2.68-2.56 (m, 1H), 2.48-2.39 (m, 1H), 2.36-2.27 (m, 1H), 2.34 (s, 3H), 2.17-2.07 (m, 1H), 2.00-1.89 (m, 2H), 1.88-1.72 (m, 1H), 1.33-1.21 (m, 1H) | FA: m/z = 559.0 (M + H) |
| I-32 | ¹H NMR (400 MHz, DMSO-d₆) δ 8.63 (s, 1H), 8.58 (s, 1H), 8.21 (d, J = 7.5 Hz, 1H), 7.93 (d, J = 1.4 Hz, 1H), 7.61 (d, J = 1.4 Hz, 1H), 7.50-7.44 (m, 2H), 7.42 (s, 2H), 7.36-7.28 (m, 2H), 7.26-7.19 (m, 1H), 4.87 (d, J = 4.4 Hz, 1H), 4.75-4.62 (m, 1H), 4.08 (dd, J = 9.7, 6.0 Hz, 1H), 4.00-3.89 (m, 4H), 2.71-2.61 (m, 1H), 2.44-2.34 (m, 1H), 2.35-2.24 (m, 1H), 2.16-2.06 (m, 1H), 1.98-1.83 (m, 3H), 1.80-1.70 (m, 1H), 1.30-1.20 (m, 1H) | FA: m/z = 545.5 (M + H) |
| I-57 | ¹H NMR (400 MHz, DMSO) δ 8.86 (s, 1H), 8.63 (s, 1H), 8.48 (d, J = 7.4 Hz, 1H), 7.95 (s, 1H), 7.44 (s, 2H), 7.31 (s, 1H), 7.18 (t, J = 7.5 Hz, 1H), 7.10-6.99 (m, 3H), 4.90 (d, J = 4.5 Hz, 1H), 4.75-4.62 (m, 1H), 4.09 (dd, J = 9.6, 6.0 Hz, 1H), 3.99-3.91 (m, 2H), 3.77 (s, 2H), 2.38-2.28 (m, 1H), 2.27 (s, 3H), 2.16-2.08 (m, 1H), 2.00-1.92 (m, 1H), 1.80-1.70 (m, 1H), 1.26 (dt, J = 12.5, 9.2 Hz, 1H) | FA: m/z = 487.4 (M + H) |
| I-82 | ¹H NMR (400 MHz, DMSO) δ 8.80 (s, 1H), 8.62 (s, 1H), 8.43 (d, J = 7.4 Hz, 1H), 7.54 (s, 1H), 7.51-7.45 (m, 1H), 7.44 (s, 2H), 7.37 (d, J = 3.6 Hz, 1H), 7.34-7.29 (m, 2H), 6.52 (d, J = 3.5 Hz, 1H), 4.90 (d, J = 4.5 Hz, 1H), 4.74-4.62 (m, 1H), 4.17 (s, 2H), 4.08 (dd, J = 9.7, 6.0 Hz, 1H), 3.99-3.90 (m, 2H), 2.37-2.26 (m, 1H), 2.16-2.07 (m, 1H), 2.00-1.91 (m, 1H), 1.80-1.69 (m, 1H), 1.25 (dt, J = 12.5, 9.1 Hz, 1H) | FA: m/z = 552.9 (M + H) |
| I-239 | ¹H NMR (400 MHz, DMSO-d₆) δ 8.75 (s, 1H), 8.65 (s, 1H), 8.45 (d, J = 7.5 Hz, 1H), 8.05-8.00 (m, 2H), 7.85-7.79 (m, 1H), 7.76-7.70 (m, 2H), 7.66 (d, J = 3.8 Hz, 1H), 7.55 (d, J = 3.8 Hz, 1H), 7.43 (s, 2H), 4.89 (d, J = 4.6 Hz, 1H), 4.76-4.64 (m, 1H), 4.08 (dd, J = 9.7, 5.9 Hz, 1H), 3.98-3.91 (m, 2H), 2.36-2.26 (m, 1H), 2.16-2.06 (m, 1H), 1.99-1.91 (m, 1H), 1.80-1.71 (m, 1H), 1.26 (dt, J = 12.8, 9.1 Hz, 1H) | FA: m/z = 523.2 (M + H) |
| I-200 | ¹H NMR (400 MHz, DMSO-d₆) δ 8.89 (d, J = 1.4 Hz, 1H), 8.68 (s, 2H), 8.27 (d, J = 7.5 Hz, 1H), 8.09-8.02 (m, 3H), 7.75-7.69 (m, 1H), 7.67-7.61 (m, 2H), 7.42 (s, 2H), 4.89 (d, J = 4.6 Hz, 1H), 4.77-4.65 (m, 1H), 4.08 (dd, J = 9.7, 5.9 Hz, 1H), 3.98-3.91 (m, 2H), 2.35-2.25 (m, 1H), 2.16-2.06 (m, 1H), 1.99-1.90 (m, 1H), 1.80-1.70 (m, 1H), 1.26 (dt, J = 12.7, 9.2 Hz, 1H) | FA: m/z = 539.2 (M + H) |
| I-302 | ¹H NMR (400 MHz, DMSO-d₆) δ 8.59 (s, 0.5H), 8.58 (s, 0.5H), 8.55 (s, 0.5H), 8.53 (s, 0.5H), 8.26-8.19 (m, 1H), 7.36 (s, 1H), 7.15-7.10 (m, 2H), 7.10-7.03 (m, 1H), 6.70-6.64 (m, 1H), 5.17 (s, 1H), 4.48-4.38 (m, 1H), 4.09-4.01 (m, 1H), 3.99-3.91 (m, 1H), 3.79-3.73 (m, 1H), 3.70-3.65 (m, 1H), 3.22-3.12 (m, 1H), 2.99-2.88 (m, 2H), 2.75-2.65 (m, 1H), 2.31-2.11 (m, 2H), 1.18-1.05 (m, 1H) | FA: m/z = 580.4 (M + H) |
| I-279 | ¹H NMR (400 MHz, DMSO-d₆) δ 8.60 (s, 1H), 8.52 (s, 1H), 8.14 (d, J = 5.6 Hz, 1H), 7.35 (s, 1H), 7.15-7.10 (m, 2H), 7.10-7.02 (m, 1H), 6.67 (d, J = 7.6 Hz, 1H), 5.17 (s, 1H), 4.91-4.81 (m, 1H), 4.72-4.60 (m, 1H), 4.10-4.03 (m, 1H), 3.97-3.88 (m, 2H), 3.21-3.11 (m, 2H), 3.00-2.87 (m, 2H), 2.75-2.65 (m, 1H), 2.35-2.20 (m, 1H), 2.15-2.03 (m, 1H), 1.98-1.85 (m, 1H), 1.80-1.66 (m, 1H), 1.31-1.18 (m, 1H) | FA: m/z = 564.5 (M + H) |
| I-294 | ¹H NMR (400 MHz, DMSO-d₆) δ 8.61 (s, 1H), 8.58 (s, 1H), 8.15 (d, J = 7.7 Hz, 1H), 7.45-7.34 (m, 3H), 7.29-7.23 (m, 1H), 7.10-7.03 (m, 1H), 6.63-6.56 (m, 1H), 5.92 (s, 1H), 4.93-4.80 (m, 1H), 4.74-4.62 (m, 1H), 4.16-4.04 (m, 2H), 3.98-3.90 (m, 2H), 3.91- | FA: m/z = 583.4 (M + H) |

-continued

| Compound No. | ¹H NMR | LC/MS |
|---|---|---|
| | 3.81 (m, 1H), 3.06-2.95 (m, 1H), 2.79-2.70 (m, 1H), 2.35-2.22 (m, 1H), 2.16-2.04 (m, 1H), 1.98-1.87 (m, 1H), 1.80-1.68 (m, 1H), 1.31-1.20 (m, 1H) | |
| I-267 | ¹H NMR (400 MHz, DMSO-d₆) δ 8.65 (s, 1H), 8.63 (s, 1H), 8.25 (d, J = 7.5 Hz, 1H), 7.93 (s, 1H), 7.63 (s, 1H), 7.42 (s, 2H), 7.28-7.22 (m, 1H), 7.09-7.01 (m, 1H), 6.72-6.65 (m, 1H), 5.90 (s, 1H), 4.93-4.82 (m, 1H), 4.76-4.64 (m, 1H), 4.12-3.99 (m, 2H), 3.98-3.91 (m, 2H), 3.86-3.78 (m, 1H), 2.99-2.87 (m, 1H), 2.82-2.73 (m, 1H), 2.37-2.25 (m, 1H), 2.16-2.06 (m, 1H), 2.00-1.91 (m, 1H), 1.82-1.71 (m, 1H), 1.33-1.22 (m, 1H) | FA: m/z = 549.1 (M + H) |
| I-295 | ¹H NMR (400 MHz, DMSO-d₆) δ 8.69 (d, J = 4.0 Hz, 1H), 8.62 (s, 1H), 8.34 (d, J = 7.0 Hz, 1H), 7.72 (d, J = 5.2 Hz, 1H), 7.66 (s, 1H), 7.44 (s, 2H), 7.18-7.12 (m, 2H), 7.11-7.06 (m, 1H), 6.88-6.83 (m, 1H), 5.21 (s, 1H), 4.96-4.80 (m, 1H), 4.73-4.67 (m, 1H), 4.51-4.40 (m, 1H), 4.09-4.02 (m, 1H), 3.99-3.93 (m, 1H), 3.81-3.75 (m, 1H), 3.72-3.66 (m, 1H), 3.10-3.01 (m, 1H), 2.99-2.70 (m, 3H), 2.32-2.23 (m, 1H), 2.22-2.13 (m, 1H), 1.20-1.09 (m, 1H) | FA: m/z = 546.3 (M + H) |
| I-267a | ¹H NMR (400 MHz, DMSO-d₆) δ 8.65 (s, 1H), 8.63 (s, 1H), 8.25 (d, J = 7.5 Hz, 1H), 7.93 (s, 1H), 7.63 (d, J = 1.2 Hz, 1H), 7.42 (s, 2H), 7.28-7.22 (m, 1H), 7.09-7.02 (m, 1H), 6.72-6.66 (m, 1H), 5.90 (s, 1H), 4.88 (d, J = 4.5 Hz, 1H), 4.77-4.64 (m, 1H), 4.12-3.99 (m, 2H), 3.99-3.92 (m, 2H), 3.86-3.78 (m, 1H), 2.98-2.88 (m, 1H), 2.82-2.72 (m, 1H), 2.35-2.25 (m, 1H), 2.15-2.07 (m, 1H), 2.00-1.92 (m, 1H), 1.82-1.72 (m, 1H), 1.26 (dt, J = 12.7, 9.2 Hz, 1H) | FA: m/z = 549.5 (M + H) |
| I-267b | ¹H NMR (400 MHz, DMSO-d₆) δ 8.65 (s, 1H), 8.63 (s, 1H), 8.25 (d, J = 7.5 Hz, 1H), 7.93 (s, 1H), 7.62 (d, J = 1.2 Hz, 1H), 7.42 (s, 2H), 7.28-7.22 (m, 1H), 7.09-7.02 (m, 1H), 6.72-6.66 (m, 1H), 5.90 (s, 1H), 4.88 (d, J = 4.5 Hz, 1H), 4.76-4.64 (m, 1H), 4.12-3.99 (m, 2H), 3.99-3.91 (m, 2H), 3.86-3.78 (m, 1H), 2.98-2.87 (m, 1H), 2.82-2.73 (m, 1H), 2.37-2.27 (m, 1H), 2.16-2.07 (m, 1H), 1.99-1.90 (m, 1H), 1.80-1.71 (m, 1H), 1.28 (dt, J = 12.9, 9.2 Hz, 1H) | FA: m/z = 549.5 (M + H) |
| I-294a | ¹H NMR (400 MHz, DMSO-d₆) δ 8.61 (s, 1H), 8.58 (s, 1H), 8.15 (d, J = 7.6 Hz, 1H), 7.46-7.37 (m, 3H), 7.29-7.22 (m, 1H), 7.11-7.03 (m, 1H), 6.63-6.56 (m, 1H), 5.92 (s, 1H), 4.87 (d, J = 4.6 Hz, 1H), 4.74-4.62 (m, 1H), 4.16-4.04 (m, 2H), 3.98-3.91 (m, 2H), 3.90-3.81 (m, 1H), 3.07-2.94 (m, 1H), 2.80-2.70 (m, 1H), 2.35-2.23 (m, 1H), 2.15-2.05 (m, 1H), 1.99-1.88 (m, 1H), 1.81-1.70 (m, 1H), 1.25 (dt, J = 12.6, 9.3 Hz, 1H) | FA: m/z = 583.4 (M + H) |
| I-294b | ¹H NMR (400 MHz, DMSO-d₆) δ 8.61 (s, 1H), 8.58 (s, 1H), 8.15 (d, J = 7.5 Hz, 1H), 7.46-7.38 (m, 3H), 7.29-7.23 (m, 1H), 7.10-7.03 (m, 1H), 6.62-6.57 (m, 1H), 5.92 (s, 1H), 4.87 (d, J = 4.6 Hz, 1H), 4.75-4.62 (m, 1H), 4.17-4.04 (m, 2H), 3.98-3.90 (m, 2H), 3.90-3.82 (m, 1H), 3.06-2.95 (m, 1H), 2.80-2.70 (m, 1H), 2.35-2.24 (m, 1H), 2.16-2.05 (m, 1H), 1.96-1.87 (m, 1H), 1.78-1.68 (m, 1H), 1.26 (dt, J = 12.7, 9.2 Hz, 1H) | FA: m/z = 583.4 (M + H) |
| I-279a | ¹H NMR (400 MHz, DMSO-d₆) δ 8.60 (s, 1H), 8.52 (s, 1H), 8.14 (d, J = 7.5 Hz, 1H), 7.35 (s, 1H), 7.16-7.11 (m, 2H), 7.09-7.03 (m, 1H), 6.67 (d, J = 7.5 Hz, 1H), 5.17 (s, 1H), 5.04-4.75 (m, 1H), 4.73-4.60 (m, 1H), 4.08 (dd, J = 9.7, 6.0 Hz, 1H), 3.98-3.88 (m, 2H), 3.22-3.13 (m, 1H), 3.00-2.87 (m, 2H), 2.75-2.65 (m, 1H), 2.34-2.23 (m, 1H), 2.14-2.04 (m, 1H), 1.95-1.85 (m, 1H), 1.76-1.66 (m, 1H), 1.25 (dt, J = 12.7, 9.2 Hz, 1H) | FA: m/z = 564.4 (M + H) |
| I-279b | ¹H NMR (400 MHz, DMSO-d₆) δ 8.60 (s, 1H), 8.52 (s, 1H), 8.15 (d, J = 7.5 Hz, 1H), 7.42 (s, 2H), 7.36 (s, 1H), 7.17-7.11 (m, 2H), 7.10-7.02 (m, 1H), 6.67 (d, J = 7.6 Hz, 1H), 5.19 (s, 1H), 4.87 (d, J = 4.6 Hz, 1H), 4.73-4.61 (m, 1H), 4.07 (dd, J = 9.7, 6.0 Hz, 1H), 3.98-3.89 (m, 2H), 3.22-3.13 (m, 1H), 3.02-2.88 (m, 2H), 2.77-2.65 (m, 1H), 2.30-2.20 (m, 1H), 2.14-2.04 (m, 1H), 1.98-1.89 (m, 1H), 1.80-1.70 (m, 1H), 1.23 (dt, J = 12.7, 9.2 Hz, 1H) | FA: m/z = 564.4 (M + H) |

| Compound No. | ¹H NMR | LC/MS |
|---|---|---|
| I-260 | ¹H NMR (400 MHz, DMSO-d$_6$) δ 8.60 (s, 1H), 8.55 (s, 1H), 8.28 (d, J = 8.3 Hz, 1H), 8.19 (d, J = 7.5 Hz, 1H), 7.66 (d, J = 8.3 Hz, 1H), 7.42 (s, 2H), 7.35 (s, 1H), 6.13 (s, 1H), 4.87 (d, J = 4.4 Hz, 1H), 4.74-4.62 (m, 1H), 4.51-4.40 (m, 1H), 4.36-4.23 (m, 1H), 4.08 (dd, J = 9.6, 6.1 Hz, 1H), 3.98-3.90 (m, 2H), 2.35-2.24 (m, 1H), 2.15-2.04 (m, 1H), 2.00-1.87 (m, 1H), 1.81-1.69 (m, 1H), 1.32-1.20 (m, 1H) | FA: m/z = 616.0 (M + H) |
| I-260a | ¹H NMR (400 MHz, DMSO-d$_6$) δ 8.60 (s, 1H), 8.55 (s, 1H), 8.28 (d, J = 8.3 Hz, 1H), 8.19 (d, J = 7.5 Hz, 1H), 7.66 (d, J = 8.3 Hz, 1H), 7.42 (s, 2H), 7.35 (s, 1H), 6.13 (s, 1H), 4.87 (d, J = 4.5 Hz, 1H), 4.74-4.62 (m, 1H), 4.50-4.41 (m, 1H), 4.36-4.23 (m, 1H), 4.08 (dd, J = 9.7, 6.0 Hz, 1H), 3.98-3.90 (m, 2H), 2.35-2.25 (m, 1H), 2.16-2.05 (m, 1H), 1.97-1.88 (m, 1H), 1.79-1.69 (m, 1H), 1.26 (dt, J = 12.7, 9.2 Hz, 1H) | FA: m/z = 616.1 (M + H) |
| I-260b | ¹H NMR (400 MHz, DMSO-d$_6$) δ 8.60 (s, 1H), 8.55 (s, 1H), 8.28 (d, J = 8.1 Hz, 1H), 8.19 (d, J = 7.7 Hz, 1H), 7.66 (d, J = 8.4 Hz, 1H), 7.41 (s, 2H), 7.36 (s, 1H), 6.13 (s, 1H), 4.91-4.83 (m, 1H), 4.73-4.62 (m, 1H), 4.50-4.40 (m, 1H), 4.36-4.23 (m, 1H), 4.08 (dd, J = 9.6, 6.0 Hz, 1H), 3.98-3.90 (m, 2H), 2.34-2.23 (m, 1H), 2.15-2.05 (m, 1H), 1.99-1.89 (m, 1H), 1.81-1.70 (m, 1H), 1.31-1.19 (m, 1H) | FA: m/z = 616.1 (M + H) |
| I-314a | ¹H NMR (400 MHz, DMSO-d$_6$) δ 8.68 (s, 1H), 8.63 (s, 1H), 8.32 (d, J = 7.5 Hz, 1H), 7.93 (s, 1H), 7.66 (d, J = 1.2 Hz, 1H), 7.43 (s, 2H), 7.32-7.22 (m, 2H), 6.61 (d, J = 2.0 Hz, 1H), 6.02 (s, 1H), 4.88 (d, J = 4.5 Hz, 1H), 4.77-4.66 (m, 1H), 4.21-4.13 (m, 1H), 4.13-4.06 (m, 1H), 4.00-3.90 (m, 3H), 3.21-3.12 (m, 1H), 3.02-2.93 (m, 1H), 2.37-2.28 (m, 1H), 2.17-2.06 (m, 1H), 2.00-1.91 (m, 1H), 1.85-1.69 (m, 3H), 1.29 (dt, J = 13.1, 9.6 Hz, 1H) | FA: m/z = 579.2 (M + H) |
| I-314b | ¹H NMR (400 MHz, DMSO-d$_6$) δ 8.68 (s, 1H), 8.63 (s, 1H), 8.32 (d, J = 7.4 Hz, 1H), 7.93 (s, 1H), 7.66 (d, J = 1.1 Hz, 1H), 7.43 (s, 2H), 7.32-7.22 (m, 2H), 6.61 (d, J = 2.0 Hz, 1H), 6.02 (s, 1H), 4.89 (d, J = 4.4 Hz, 1H), 4.77-4.66 (m, 1H), 4.21-4.13 (m, 1H), 4.14-4.06 (m, 1H), 4.00-3.89 (m, 3H), 3.21-3.11 (m, 1H), 3.02-2.92 (m, 1H), 2.37-2.27 (m, 1H), 2.17-2.07 (m, 1H), 2.01-1.92 (m, 1H), 1.86-1.69 (m, 3H), 1.29 (dt, J = 13.2, 9.4 Hz, 1H) | FA: m/z = 579.2 (M + H) |
| I-343a | ¹H NMR (400 MHz, DMSO-d$_6$) δ 8.73 (s, 1H), 8.65 (s, 1H), 8.27 (d, J = 7.5 Hz, 1H), 7.73 (d, J = 3.9 Hz, 1H), 7.42 (s, 2H), 7.34-7.26 (m, 2H), 7.12 (d, J = 3.9 Hz, 1H), 6.81 (d, J = 1.6 Hz, 1H), 6.29 (s, 1H), 4.89 (d, J = 4.1 Hz, 1H), 4.79-4.65 (m, 1H), 4.23-4.15 (m, 1H), 4.13-4.06 (m, 1H), 4.02-3.92 (m, 3H), 3.21-3.11 (m, 1H), 3.05-2.94 (m, 1H), 2.39-2.27 (m, 1H), 2.17-2.07 (m, 1H), 2.01-1.91 (m, 1H), 1.84-1.73 (m, 3H), 1.29 (dt, J = 12.6, 9.2 Hz, 1H) | FA: m/z = 579.2 (M + H) |
| I-343b | ¹H NMR (400 MHz, DMSO-d$_6$) δ 8.74 (s, 1H), 8.65 (s, 1H), 8.28 (d, J = 7.4 Hz, 1H), 7.73 (d, J = 3.9 Hz, 1H), 7.42 (s, 2H), 7.34-7.27 (m, 2H), 7.12 (d, J = 3.9 Hz, 1H), 6.81 (d, J = 1.5 Hz, 1H), 6.29 (s, 1H), 4.89 (d, J = 4.5 Hz, 1H), 4.78-4.66 (m, 1H), 4.23-4.15 (m, 1H), 4.13-4.06 (m, 1H), 4.02-3.92 (m, 3H), 3.20-3.10 (m, 1H), 3.05-2.95 (m, 1H), 2.38-2.28 (m, 1H), 2.17-2.07 (m, 1H), 2.01-1.92 (m, 1H), 1.84-1.73 (m, 3H), 1.29 (dt, J = 12.8, 9.2 Hz, 1H) | FA: m/z = 579.2 (M + H) |
| I-348 | ¹H NMR (400 MHz, DMSO-d$_6$) δ 8.59 (s, 1H), 8.50 (s, 1H), 8.12 (d, J = 7.4 Hz, 1H), 7.42 (s, 2H), 7.32-7.24 (m, 2H), 6.29 (d, J = 8.5 Hz, 1H), 5.69 (s, 1H), 4.89-4.82 (m, 1H), 4.74-4.60 (m, 1H), 4.14-4.01 (m, 2H), 3.99-3.88 (m, 2H), 3.85-3.72 (m, 1H), 3.28-3.14 (m, 4H), 2.95-2.82 (m, 1H), 2.61 (s, 3H), 2.59-2.54 (m, 1H), 2.35-2.24 (m, 1H), 2.15-2.05 (m, 1H), 1.99-1.82 (m, 5H), 1.80-1.67 (m, 1H), 1.31-1.17 (m, 1H) | FA: m/z = 615.2 (M + H) |
| I-33 | ¹H NMR (400 MHz, Chloroform-d) δ 8.97 (s, 1H), 8.77 (d, J = 7.3 Hz, 1H), 8.56 (s, 1H), 7.22-7.12 (m, 2H), 7.11-7.07 (m, 1H), 7.04-6.97 (m, 2H), 6.41-6.01 (br s, 2H), 4.72-4.59 (m, 1H), 4.34-4.15 (m, 3H), 3.68 (s, 2H), 2.53-2.39 (m, 1H), 2.39-2.24 (m, 4H), 2.19-2.07 (m, 1H), 1.95-1.84 (m, 1H), 1.33 (m, 1H) | FA: m/z = 521.4 (M + H) |

-continued

| Compound No. | ¹H NMR | LC/MS |
|---|---|---|
| I-72 | ¹H NMR (400 MHz, CDCl₃) δ 8.95 (s, 1H), 8.76 (d, J = 6.9 Hz, 1H), 8.57 (s, 1H), 7.24-7.15 (m, 2H), 7.15-7.11 (m, 1H), 7.08-7.02 (m, 2H), 6.30-5.96 (br s, 2H), 4.75-4.61 (m, 1H), 4.36-4.13 (m, 3H), 3.71 (s, 2H), 2.52-2.38 (m, 1H), 2.37-2.24 (m, 1H), 2.18-2.08 (m, 1H), 1.97-1.85 (m, 1H), 1.39-1.27 (m, 2H) | FA: m/z = 541.1 (M + H) |
| I-30 | ¹H NMR (400 MHz, MeOD) δ 9.01 (s, 1H), 8.54 (s, 1H), 7.79 (d, J = 0.8 Hz, 1H), 7.54 (t, J = 1.8 Hz, 1H), 7.41-7.36 (m, 1H), 7.30 (t, J = 7.8 Hz, 1H), 7.28-7.21 (m, 2H), 4.81-4.71 (m, 1H), 4.25-4.11 (m, 3H), 2.54-2.44 (m, 1H), 2.31-2.20 (m, 1H), 2.19-2.09 (m, 1H), 1.94-1.83 (m, 4H), 1.40 (dt, J = 12.9, 9.1 Hz, 1H) | FA: m/z = 537.4 (M + H) |
| I-30a | ¹H NMR (400 MHz, MeOD) δ 9.03 (s, 1H), 8.56 (s, 1H), 7.81 (d, J = 0.9 Hz, 1H), 7.54 (t, J = 1.8 Hz, 1H), 7.42-7.37 (m, 1H), 7.32 (t, J = 7.8 Hz, 1H), 7.29-7.23 (m, 2H), 4.84-4.74 (m, 1H), 4.23-4.12 (m, 3H), 2.56-2.45 (m, 1H) 2.31-2.21 (m, 1H), 2.19-2.10 (m, 1H), 1.94-1.83 (m, 4H), 1.42 (dt, J = 13.0, 9.1 Hz, 1H) | |
| I-30b | ¹H NMR (400 MHz, MeOD) δ 9.04 (s, 1H), 8.57 (s, 1H), 7.82 (d, J = 0.6 Hz, 1H), 7.54 (t, J = 1.8 Hz, 1H), 7.42-7.38 (m, 1H), 7.32 (t, J = 7.8 Hz, 1H), 7.29-7.23 (m, 2H), 4.84-4.75 (m, 1H), 4.24-4.11 (m, 3H), 2.55-2.45 (m, 1H), 2.31-2.21 (m, 1H), 2.20-2.11 (m, 1H), 1.95-1.83 (m, 4H), 1.42 (dt, J = 13.0, 9.1 Hz, 1H) | |
| I-42 | ¹H NMR (400 MHz, MeOD) δ 9.00 (s, 1H), 8.53 (s, 1H), 7.73 (t, J = 0.8 Hz, 1H), 7.48-7.44 (m, 1H), 7.37-7.31 (m, 2H), 7.30-7.25 (m, 1H), 7.23 (d, J = 0.5 Hz, 1H), 5.77 (s, 1H), 4.80-4.71 (m, 1H), 4.25-4.11 (m, 3H), 2.53-2.43 (m, 1H), 2.30-2.20 (m, 1H), 2.18-2.09 (m, 1H), 1.93-1.83 (m, 1H), 1.39 (dt, J = 13.0, 9.1 Hz, 1H) | FA: m/z = 523.1 (M + H) |
| I-42a | ¹H NMR (400 MHz, MeOD) δ 9.04 (s, 1H), 8.57 (s, 1H), 7.77 (t, J = 0.8 Hz, 1H), 7.49-7.45 (m, 1H), 7.38-7.32 (m, 2H), 7.32-7.28 (m, 1H), 7.28-7.24 (m, 1H), 5.79 (s, 1H), 4.84-4.74 (m, 1H), 4.24-4.11 (m, 3H), 2.55-2.45 (m, 1H), 2.31-2.21 (m, 1H), 2.19-2.11 (m, 1H), 1.90 (ddd, J = 13.5, 8.0, 7.1 Hz, 1H), 1.42 (dt, J = 13.0, 9.1 Hz, 1H) | |
| I-42b | ¹H NMR (400 MHz, MeOD) δ 9.04 (s, 1H), 8.57 (s, 1H), 7.76 (t, J = 0.8 Hz, 1H), 7.49-7.46 (m, 1H), 7.38-7.32 (m, 2H), 7.32-7.27 (m, 1H), 7.26 (d, J = 0.4 Hz, 1H), 5.79 (s, 1H), 4.84-4.74 (m, 1H), 4.24-4.12 (m, 3H), 2.55-2.45 (m, 1H), 2.31-2.20 (m, 1H), 2.19-2.10 (m, 1H), 1.90 (ddd, J = 13.5, 8.0, 7.1 Hz, 1H), 1.42 (dt, J = 13.0, 9.1 Hz, 1H) | |
| I-34 | ¹H NMR (400 MHz, CDCl₃) δ 9.04 (s, 1H), 8.91 (d, J = 7.1 Hz, 1H), 8.63 (s, 1H), 7.37-7.31 (m, 1H), 7.29-7.26 (m, 1H), 7.16 (t, J = 7.8 Hz, 1H), 7.08 (d, J = 7.8 Hz, 1H), 7.04 (s, 1H), 5.99-5.44 (br s, 2H), 4.78-4.66 (m, 1H), 4.38-4.27 (m, 2H), 4.23 (dd, J = 10.0, 5.7 Hz, 1H), 3.71 (s, 2H), 3.26-2.63 (br s, 1H), 2.56-2.44 (m, 1H), 2.41-2.25 (m, 4H), 2.18-2.07 (m, 1H), 1.97 (m, 1H), 1.47-1.36 (m, 1H) | FA: m/z = 565.1 (M + H) |
| I-75 | ¹H NMR (400 MHz, Methanol-d₄) δ 9.05 (s, 1H), 8.59 (s, 1H), 7.31-7.18 (m, 4H), 7.18-7.13 (m, 1H), 4.96-4.74 (m, 2H), 4.22 (dd, J = 9.8, 6.2 Hz, 1H), 4.16 (dd, J = 9.8, 6.6 Hz, 1H), 4.13-4.03 (m, 1H), 3.81 (s, 2H), 2.51-2.42 (m, 1H), 2.41 (s, 3H), 2.33-2.22 (m, 1H), 1.58 (m, 1H) | FA: m/z = 539.3 (M + H) |
| I-64 | ¹H NMR (400 MHz, Methanol-d₄) δ 8.95 (s, 1H), 8.49 (s, 1H), 7.31-7.28 (m, 1H), 7.28-7.23 (m, 1H), 7.14-7.07 (m, 3H), 4.86-4.64 (m, 2H), 4.12 (dd, J = 9.8, 6.2 Hz, 1H), 4.06 (dd, J = 9.8, 6.6 Hz, 1H), 4.03-3.93 (m, 1H), 3.70 (s, 2H), 2.35 (dt, J = 12.8, 7.6 Hz, 1H), 2.30 (s, 3H), 2.24-2.11 (m, 1H), 1.54-1.42 (m, 1H) | FA: m/z = 583.2 (M + H) |
| I-266b | ¹H NMR (400 MHz, DMSO-d₆) δ 8.61 (s, 1H), 8.50 (s, 1H), 8.33 (d, J = 4.0 Hz, 1H), 8.15 (d, J = 7.5 Hz, 1H), 7.65 (d, J = 7.6 Hz, 1H), 7.55-7.30 (m, 3H), 7.26 (d, J = 7.6, 4.8 Hz, 1H), 5.89 (s, 1H), 4.89 (s, 1H), 4.75-4.63 (m, 1H), 4.20-4.12 (m, 1H), 4.12-4.03 (m, 1H), 4.00-3.88 (m, 3H), 3.19-3.07 (m, 1H), 2.82 (d, J = 16.6 Hz, 1H), 2.34-2.21 (m, 1H), 2.16-2.02 (m, 1H), 1.98-1.85 (m, 1H), 1.79-1.66 (m, 1H), 1.33-1.21 (m, 1H) | FA: m/z = 566.1 (M + H) |

| Compound No. | ¹H NMR | LC/MS |
| --- | --- | --- |
| I-266a | ¹H NMR (400 MHz, DMSO-d₆) δ 8.61 (s, 1H), 8.49 (s, 1H), 8.33 (d, J = 3.7 Hz, 1H), 8.15 (d, J = 7.5 Hz, 1H), 7.65 (d, J = 7.3 Hz, 1H), 7.43 (s, 2H), 7.36 (s, 1H), 7.31-7.19 (m, 1H), 5.89 (s, 1H), 4.90 (s, 1H), 4.74-4.63 (m, 1H), 4.21-4.12 (m, 1H), 4.13-4.04 (m, 1H), 3.99-3.88 (m, 3H), 3.19-3.05 (m, 1H), 2.88-2.78 (m, 1H), 2.31-2.19 (m, 1H), 2.15-2.05 (m, 1H), 1.98-1.87 (m, 1H), 1.81-1.68 (m, 1H), 1.31-1.19 (m, 1H) | FA: m/z = 566.2 (M + H) |
| I-266 | ¹H NMR (400 MHz, DMSO-d₆) δ 8.61 (s, 1H), 8.50 (s, 1H), 8.33 (d, J = 3.5 Hz, 1H), 8.14 (d, J = 7.2 Hz, 1H), 7.65 (d, J = 7.0 Hz, 1H), 7.45 (s, 2H), 7.36 (s, 1H), 7.30-7.22 (m, 1H), 5.89 (s, 1H), 4.89 (s, 1H), 4.73-4.63 (m, 1H), 4.21-4.12 (m, 1H), 4.12-4.04 (m, 1H), 3.99-3.88 (m, 3H), 3.18-3.07 (m, 1H), 2.88-2.78 (m, 1H), 2.36-2.24 (m, 2H), 2.16-2.03 (m, 2H), 1.98-1.86 (m, 2H), 1.82-1.68 (m, 2H), 1.32-1.21 (m, 1H) | FA: m/z = 566.2 (M + H) |
| I-276b | ¹H NMR (400 MHz, DMSO-d₆) δ 8.61 (s, 1H), 8.54 (s, 1H), 8.17 (d, J = 7.6 Hz, 1H), 7.74 (d, J = 8.1 Hz, 1H), 7.45 (s, 1H), 7.45-7.29 (m, 3H), 5.88 (s, 1H), 4.88 (s, 1H), 4.75-4.62 (m, 1H), 4.18-4.04 (m, 2H), 3.99-3.86 (m, 3H), 3.12-2.99 (m, 1H), 2.88-2.79 (m, 1H), 2.35-2.25 (m, 1H), 2.15-2.07 (m, 1H), 1.95-1.87 (m, 1H), 1.81-1.67 (m, 1H), 1.35-1.18 (m, 1H) | FA: m/z = 600.1 (M + H) |
| I-276a | ¹H NMR (400 MHz, DMSO-d₆) δ 8.61 (s, 1H), 8.54 (s, 1H), 8.17 (d, J = 7.6 Hz, 1H), 7.74 (d, J = 8.1 Hz, 1H), 7.46 (s, 1H), 7.42 (s, 2H), 7.38 (d, J = 8.1 Hz, 1H), 5.88 (s, 1H), 4.91-4.85 (m, 1H), 4.74-4.61 (m, 1H), 4.19-4.04 (m, 2H), 3.99-3.86 (m, 3H), 3.14-3.00 (m, 1H), 2.88-2.76 (m, 1H), 2.34-2.25 (m, 1H), 2.15-2.06 (m, 1H), 1.99-1.89 (m, 1H), 1.81-1.67 (m, 1H), 1.33-1.19 (m, 1H) | FA: m/z = 600.1 (M + H) |
| I-276 | ¹H NMR (400 MHz, DMSO-d₆) δ 8.62 (s, 1H), 8.54 (s, 1H), 8.18 (d, J = 7.2 Hz, 1H), 7.74 (d, J = 8.1 Hz, 1H), 7.46 (d, J = 1.5 Hz, 1H), 7.43 (s, 2H), 7.39 (d, J = 8.1 Hz, 1H), 5.89 (s, 1H), 4.88 (s, 1H), 4.74-4.64 (m, 1H), 4.19-4.06 (m, 2H), 4.00-3.86 (m, 3H), 3.13-3.02 (m, 1H), 2.83 (d, J = 16.5 Hz, 1H), 2.36-2.24 (m, 2H), 2.15-2.07 (m, 1H), 1.99-1.88 (m, 1H), 1.81-1.73 (m, 1H), 1.33-1.22 (m, 1H) | FA: m/z = 600.1 (M + H) |
| I-258b | ¹H NMR (400 MHz, DMSO-d₆) δ 8.60 (s, 1H), 8.54 (s, 1H), 8.22 (d, J = 7.5 Hz, 1H), 7.57 (d, J = 8.3 Hz, 1H), 7.49-7.37 (m, 3H), 7.33 (s, 1H), 7.05 (s, 1H), 6.01 (s, 1H), 4.88 (d, J = 4.6 Hz, 1H), 4.74-4.64 (m, 1H), 4.16-4.05 (m, 2H), 4.00-3.93 (m, 2H), 3.92-3.82 (m, 1H), 3.17-3.04 (m, 1H), 2.94-2.83 (m, 1H), 2.48 (s, 3H), 2.36-2.25 (m, 2H), 2.16-2.07 (m, 1H), 2.02-1.90 (m, 1H), 1.82-1.70 (m, 1H), 1.32-1.21 (m, 1H) | FA: m/z = 613.2 (M + H) |
| I-258a | ¹H NMR (400 MHz, DMSO-d₆) δ 8.60 (s, 1H), 8.54 (s, 1H), 8.21 (d, J = 7.5 Hz, 1H), 7.57 (d, J = 7.9 Hz, 1H), 7.50-7.36 (m, 3H), 7.33 (s, 1H), 7.05 (s, 1H), 6.01 (s, 1H), 4.88 (d, J = 4.2 Hz, 1H), 4.75-4.62 (m, 1H), 4.16-4.06 (m, 2H), 4.01-3.84 (m, 3H), 3.18-3.05 (m, 1H), 2.94-2.84 (m, 1H), 2.48 (s, 3H), 2.36-2.24 (m, 1H), 2.16-2.05 (m, 1H), 1.98-1.88 (m, 1H), 1.82-1.69 (m, 1H), 1.32-1.20 (m, 1H) | FA: m/z = 613.2 (M + H) |
| I-293b | ¹H NMR (400 MHz, DMSO-d₆) δ 8.66 (s, 1H), 8.64 (s, 1H), 8.27 (d, J = 7.5 Hz, 1H), 7.98 (s, 1H), 7.78-7.72 (m, 1H), 7.62 (s, 1H), 7.55-7.48 (m, 2H), 7.44 (s, 2H), 7.06-6.99 (m, 1H), 6.11 (s, 1H), 4.89 (d, J = 4.6 Hz, 1H), 4.76-4.66 (m, 1H), 4.36-4.26 (m, 1H), 4.13-4.06 (m, 1H), 4.00-3.92 (m, 2H), 2.38-2.28 (m, 1H), 2.16-2.08 (m, 1H), 2.00-1.90 (m, 2H), 1.82-1.72 (m, 1H), 1.35-1.24 (m, 2H) | FA: m/z = 567.2 (M + H) |
| I-293a | ¹H NMR (400 MHz, DMSO-d₆) δ 8.66 (s, 1H), 8.64 (s, 1H), 8.27 (d, J = 7.5 Hz, 1H), 8.01-7.96 (m, 1H), 7.78-7.72 (m, 1H), 7.62 (d, J = 1.2 Hz, 1H), 7.55-7.48 (m, 2H), 7.44 (s, 2H), 7.08-6.97 (m, 1H), 6.11 (s, 1H), 4.89 (d, J = 4.6 Hz, 1H), 4.77-4.65 (m, 1H), 4.37-4.26 (m, 1H), 4.14-4.06 (m, 1H), 4.01-3.92 (m, 2H), 2.37-2.24 (m, 1H), 2.19-2.07 (m, 1H), 2.01-1.91 (m, 1H), 1.84-1.73 (m, 1H), 1.33-1.22 (m, 1H) | FA: m/z = 567.2 (M + H) |

| Compound No. | ¹H NMR | LC/MS |
|---|---|---|
| I-258 | ¹H NMR (400 MHz, DMSO-d₆) δ 8.60 (s, 1H), 8.54 (s, 1H), 8.22 (d, J = 7.6 Hz, 1H), 7.57 (d, J = 7.9 Hz, 1H), 7.50-7.39 (m, 3H), 7.33 (s, 1H), 7.05 (s, 1H), 6.01 (s, 1H), 4.88 (d, J = 4.5 Hz, 1H), 4.74-4.64 (m, 1H), 4.16-4.03 (m, 2H), 4.00-3.83 (m, 3H), 3.11 (s, 1H), 2.93-2.81 (m, 1H), 2.36-2.25 (m, 1H), 2.17-2.08 (m, 1H), 2.02-1.86 (m, 1H), 1.80-1.71 (m, 1H), 1.34-1.20 (m, 1H) | FA: m/z = 613.2 (M + H) |
| I-273 | ¹H NMR (400 MHz, DMSO-d₆) δ 8.67 (s, 1H), 8.65 (s, 1H), 8.27 (d, J = 7.4 Hz, 1H), 7.93 (s, 1H), 7.65 (d, J = 1.2 Hz, 1H), 7.44 (s, 2H), 7.37-7.28 (m, 2H), 6.98-6.90 (m, 1H), 5.88 (s, 1H), 4.89 (d, J = 4.5 Hz, 1H), 4.76-4.66 (m, 1H), 4.13-4.07 (m, 1H), 4.05-3.93 (m, 3H), 3.88-3.77 (m, 1H), 2.98-2.87 (m, 1H), 2.84-2.73 (m, 1H), 2.38-2.27 (m, 1H), 2.16-2.07 (m, 1H), 2.00-1.90 (m, 1H), 1.81-1.72 (m, 1H), 1.34-1.22 (m, 1H) | FA: m/z = 567.1 (M + H) |
| I-293 | ¹H NMR (400 MHz, DMSO-d₆) δ 8.66 (s, 1H), 8.64 (s, 1H), 8.27 (d, J = 7.7 Hz, 1H), 7.98 (s, 1H), 7.79-7.72 (m, 1H), 7.62 (s, 1H), 7.57-7.48 (m, 2H), 7.44 (s, 2H), 7.06-7.00 (m, 1H), 6.11 (s, 1H), 4.89 (d, J = 3.4 Hz, 1H), 4.75-4.64 (m, 1H), 4.34-4.16 (m, 2H), 4.13-4.07 (m, 1H), 4.00-3.93 (m, 2H), 2.36-2.28 (m, 1H), 2.17-2.07 (m, 1H), 2.02-1.93 (m, 1H), 1.83-1.73 (m, 1H), 1.34-1.22 (m, 1H) | FA: m/z = 567.1 (M + H) |
| I-290b | ¹H NMR (400 MHz, DMSO-d₆) δ 8.67 (s, 1H), 8.62 (s, 1H), 8.35-8.28 (m, 1H), 7.48 (s, 1H), 7.44 (s, 2H), 7.38-7.31 (m, 1H), 6.89-6.81 (m, 1H), 5.89 (s, 1H), 4.76-4.67 (m, 1H), 4.16-4.01 (m, 3H), 4.00-3.91 (m, 2H), 3.91-3.83 (m, 1H), 3.04-2.95 (m, 1H), 2.81-2.72 (m, 1H), 2.35-2.26 (m, 1H), 2.15-2.07 (m, 1H), 1.96-1.88 (m, 1H), 1.81-1.72 (m, 1H), 1.34-1.25 (m, 1H) | FA: m/z = 601.1 (M + H) |
| I-290a | ¹H NMR (400 MHz, DMSO-d₆) δ 8.62 (d, J = 2.9 Hz, 2H), 8.19 (d, J = 7.4 Hz, 1H), 7.44 (d, J = 4.4 Hz, 3H), 7.39-7.29 (m, 1H), 6.91-6.82 (m, 1H), 5.89 (s, 1H), 4.89 (d, J = 4.5 Hz, 1H), 4.76-4.63 (m, 1H), 4.15-4.06 (m, 2H), 4.00-3.91 (m, 2H), 3.91-3.81 (m, 1H), 3.06-2.94 (m, 1H), 2.76 (d, J = 16.7 Hz, 1H), 2.35-2.25 (m, 1H), 2.17-2.06 (m, 1H), 1.98-1.89 (m, 1H), 1.84-1.72 (m, 1H), 1.33-1.21 (m, 1H) | FA: m/z = 601.1 (M + H) |
| I-24a | ¹H NMR (400 MHz, DMSO) δ 8.74 (s, 1H), 8.67 (s, 1H), 8.32 (d, J = 7.6 Hz, 1H), 7.95 (s, 1H), 7.65 (s, 1H), 7.43 (d, J = 7.8 Hz, 1H), 7.36 (d, J = 7.8 Hz, 1H), 7.28 (t, J = 7.8 Hz, 1H), 5.13 (s, 1H), 4.54-4.41 (m, 1H), 4.13-3.99 (m, 2H), 4.04-3.92 (m, 2H), 3.83-3.75 (m, 2H), 3.74-3.67 (m, 2H), 2.35-2.22 (m, 1H), 2.24-2.12 (m, 1H), 1.89 (s, 3H), 1.22-1.10 (m, 1H) | FA: m/z = 634.3 (M + H) |
| I-24b | ¹H NMR (400 MHz, DMSO) δ 8.73 (s, 1H), 8.67 (s, 1H), 8.31 (d, J = 7.6 Hz, 1H), 7.94 (s, 1H), 7.65 (s, 1H), 7.43 (d, J = 7.8 Hz, 1H), 7.36 (d, J = 7.8 Hz, 1H), 7.28 (t, J = 7.8 Hz, 1H), 5.13 (s, 1H), 4.51-4.40 (m, 1H), 4.10-4.01 (m, 2H), 4.02-3.91 (m, 2H), 3.83-3.74 (m, 2H), 3.73-3.66 (m, 2H), 2.35-2.23 (m, 1H), 2.23-2.12 (m, 1H), 1.89 (s, 4H), 1.21-1.08 (m, 1H) | FA: m/z = 634.3 (M + H) |
| I-7a | ¹H NMR (400 MHz, DMSO) δ 8.64 (d, J = 3.7 Hz, 2H), 8.25 (d, J = 7.7 Hz, 1H), 7.60 (s, 1H), 7.49-7.25 (m, 6H), 6.21 (s, 1H), 5.87 (s, 1H), 4.90 (s, 1H), 4.75-4.64 (m, 3H), 4.13-4.04 (m, 1H), 4.02-3.88 (m, 2H), 2.37-2.23 (m, 1H), 2.18-2.06 (m, 1H), 2.03-1.89 (m, 1H), 1.84-1.70 (m, 1H), 1.33-1.18 (m, 1H) | FA: m/z = 583.4 (M + H) |
| I-7b | ¹H NMR (400 MHz, DMSO) δ 8.64 (d, J = 3.4 Hz, 2H), 8.25 (d, J = 7.5 Hz, 1H), 7.60 (s, 1H), 7.47-7.42 (m, 2H), 7.40-7.25 (m, 4H), 6.22 (d, J = 4.6 Hz, 1H), 5.87 (d, J = 3.8 Hz, 1H), 4.89 (s, 1H), 4.72 (s, 3H), 4.13-4.02 (m, 1H), 4.01-3.87 (m, 2H), 2.35-2.26 (m, 1H), 2.19-2.06 (m, 1H), 2.00-1.87 (m, 1H), 1.81-1.72 (m, 1H), 1.34-1.20 (m, 1H) | FA: m/z = 583.4 (M + H) |
| I-7 | ¹H NMR (400 MHz, DMSO) δ 8.64 (d, J = 2.1 Hz, 2H), 8.26 (d, J = 7.5 Hz, 1H), 7.60 (s, 1H), 7.46-7.43 (m, 2H), 7.41-7.37 (m, 1H), 7.34-7.31 (m, 1H), 7.30-7.26 (m, 1H), 6.20 (d, J = 4.8 Hz, 1H), 5.87 (d, J = 4.6 Hz, 1H), 4.93-4.82 (m, 1H), 4.76-4.64 (m, 2H), 4.61 (s, 1H), 4.15-4.02 (m, 1H), 4.02-3.88 (m, 2H), 3.35 (s, 3H), 2.39-2.29 (m, 1H), 2.17-2.05 (m, 1H), 2.03-1.87 (m, 1H), 1.85-1.70 (m, 1H), 1.36-1.21 (m, 1H) | FA: m/z = 583.4 (M + H) |

-continued

| Compound No. | ¹H NMR | LC/MS |
|---|---|---|
| I-13 | ¹H NMR (400 MHz, DMSO) δ 8.64 (d, J = 2.0 Hz, 2H), 8.25 (d, J = 7.3 Hz, 1H), 7.59 (s, 1H), 7.44 (s, 2H), 7.38-7.27 (m, 4H), 6.14 (d, J = 4.7 Hz, 1H), 5.92-5.86 (m, 1H), 5.86-5.81 (m, 1H), 4.89 (d, J = 4.4 Hz, 1H), 4.71 (dd, J = 13.7, 7.4 Hz, 3H), 4.14-4.04 (m, 1H), 4.02-3.89 (m, 3H), 2.36-2.25 (m, 1H), 2.17-2.06 (m, 1H), 2.03-1.91 (m, 1H), 1.83-1.71 (m, 1H), 1.33-1.18 (m, 1H) | FA: m/z = 569.2 (M + H) |
| I-44 | ¹H NMR (400 MHz, DMSO) δ 8.67 (s, 1H), 8.64 (s, 1H), 8.26 (d, J = 7.5 Hz, 1H), 7.62 (s, 1H), 7.43 (s, 2H), 7.36-7.29 (m, 2H), 7.26 (d, 1H), 7.21 (d, J = 7.5 Hz, 1H), 4.88 (s, 1H), 4.75-4.62 (m, 3H), 4.09 (dd, J = 9.7, 6.0 Hz, 1H), 4.03-3.90 (m, 4H), 3.35 (s, 3H), 2.36-2.25 (m, 1H), 2.15-2.07 (m, 1H), 2.00-1.88 (m, 1H), 1.81-1.71 (m, 1H), 1.32-1.22 (m, 1H) | FA: m/z = 567.3 (M + H) |
| I-35 | ¹H NMR (400 MHz, DMSO) δ 8.66 (s, 1H), 8.64 (s, 1H), 8.26 (d, J = 7.5 Hz, 1H), 7.59 (s, 1H), 7.42 (s, 2H), 7.33 (t, J = 7.7 Hz, 2H), 7.29-7.24 (m, 1H), 7.21 (d, J = 7.4 Hz, 1H), 4.89 (s, 1H), 4.79-4.64 (m, 3H), 4.10 (dd, J = 9.8, 6.0 Hz, 1H), 4.01-3.89 (m, 4H), 2.35-2.28 (m, 1H), 2.17-2.05 (m, 2H), 2.02-1.88 (m, 1H), 1.82-1.70 (m, 1H), 1.32-1.20 (m, 1H) | FA: m/z = 553.3 (M + H) |
| I-22a | ¹H NMR (400 MHz, DMSO) δ 8.72 (s, 1H), 8.68 (s, 1H), 8.23 (d, J = 7.5 Hz, 1H), 7.94 (s, 1H), 7.66 (s, 1H), 7.46-7.41 (m, 3H), 7.37 (d, J = 7.9 Hz, 1H), 7.29 (t, J = 7.8 Hz, 1H), 5.18 (s, 1H), 4.89 (dd, J = 4.5, 2.4 Hz, 1H), 4.78-4.66 (m, 1H), 4.13-4.04 (m, 1H), 4.01-3.92 (m, 2H), 3.08-3.02 (m, 2H), 2.35-2.29 (m, 1H), 2.16-2.03 (m, 1H), 2.00-1.91 (m, 1H), 1.84-1.72 (m, 1H), 1.32-1.21 (m, 1H) | FA: m/z = 618.0 (M + H) |
| I-22b | ¹H NMR (400 MHz, DMSO) δ 8.72 (s, 1H), 8.68 (s, 1H), 8.23 (d, J = 7.5 Hz, 1H), 7.94 (s, 1H), 7.66 (s, 1H), 7.46-7.41 (m, 3H), 7.37 (d, J = 7.9 Hz, 1H), 7.29 (t, J = 7.8 Hz, 1H), 5.18 (s, 1H), 4.89 (dd, J = 4.5, 2.4 Hz, 1H), 4.78-4.66 (m, 1H), 4.13-4.04 (m, 1H), 4.01-3.92 (m, 2H), 3.08-3.02 (m, 2H), 2.35-2.29 (m, 1H), 2.16-2.03 (m, 1H), 2.00-1.91 (m, 1H), 1.84-1.72 (m, 1H), 1.32-1.21 (m, 1H) | FA: m/z = 618.0 (M + H) |
| I-25a | ¹H NMR (400 MHz, DMSO) δ 8.69 (s, 1H), 8.66 (s, 1H), 8.22 (d, J = 7.7 Hz, 1H), 7.89-7.79 (m, 2H), 7.57 (d, J = 7.6 Hz, 1H), 7.46-7.34 (m, 3H), 5.16 (s, 1H), 4.89 (d, J = 4.5 Hz, 1H), 4.76-4.68 (m, 1H), 4.13-4.05 (m, 1H), 3.99-3.91 (m, 2H), 2.91-2.59 (m, 2H), 2.35-2.23 (m, 1H), 2.15-2.05 (m, 1H), 2.01-1.92 (m, 1H), 1.83-1.72 (m, 1H), 1.32-1.20 (m, 1H) | FA: m/z = 573.2 (M + H) |
| I-25b | ¹H NMR (400 MHz, DMSO) δ 8.69 (s, 1H), 8.66 (s, 1H), 8.22 (d, J = 7.7 Hz, 1H), 7.89-7.79 (m, 2H), 7.57 (d, J = 7.6 Hz, 1H), 7.46-7.34 (m, 3H), 5.16 (s, 1H), 4.89 (d, J = 4.5 Hz, 1H), 4.76-4.68 (m, 1H), 4.13-4.05 (m, 1H), 3.99-3.91 (m, 2H), 2.91-2.59 (m, 2H), 2.35-2.23 (m, 1H), 2.15-2.05 (m, 1H), 2.01-1.92 (m, 1H), 1.83-1.72 (m, 1H), 1.32-1.20 (m, 1H) | FA: m/z = 573.2 (M + H) |
| I-22 | ¹H NMR (400 MHz, DMSO) δ 8.72 (s, 1H), 8.68 (s, 1H), 8.23 (d, J = 7.5 Hz, 1H), 7.94 (s, 1H), 7.66 (s, 1H), 7.46-7.41 (m, 3H), 7.37 (d, J = 7.9 Hz, 1H), 7.29 (t, J = 7.8 Hz, 1H), 5.18 (s, 1H), 4.89 (dd, J = 4.5, 2.4 Hz, 1H), 4.78-4.66 (m, 1H), 4.13-4.04 (m, 1H), 4.01-3.92 (m, 2H), 3.08-3.02 (m, 2H), 2.35-2.29 (m, 1H), 2.16-2.03 (m, 1H), 2.00-1.91 (m, 1H), 1.84-1.72 (m, 1H), 1.32-1.21 (m, 1H) | FA: m/z = 618.0 (M + H) |
| I-25 | ¹H NMR (400 MHz, DMSO) δ 8.69 (s, 1H), 8.67 (s, 1H), 8.23 (d, J = 7.7 Hz, 1H), 7.90-7.82 (m, 2H), 7.58 (d, J = 7.6 Hz, 1H), 7.44 (s, 2H), 7.39 (d, J = 7.9 Hz, 1H), 6.39 (s, 1H), 5.18 (s, 1H), 4.89 (dd, J = 4.5, 2.3 Hz, 1H), 4.76-4.68 (m, 1H), 4.13-4.05 (m, 1H), 3.99-3.93 (m, 2H), 2.36-2.26 (m, 2H), 2.17-2.06 (m, 1H), 2.02-1.91 (m, 1H), 1.83-1.74 (m, 1H), 1.33-1.22 (m, 1H) | FA: m/z = 573.1 (M + H) |
| I-77 | ¹H NMR (400 MHz, CDCl₃) δ 8.81 (s, 1H), 8.67 (s, 1H), 8.63-8.55 (m, 1H), 7.35-7.28 (m, 3H), 7.26-7.19 (m, 2H), 7.12 (s, 1H), 7.06-6.99 (m, 1H), 4.88-4.75 (m, 1H), 4.46-4.32 (m, 2H), 4.33-4.23 (m, 1H), 4.03-3.91 (m, 2H), 3.62 (s, 1H), 2.65-2.48 (m, 1H), 2.35 (s, 6H), 2.19-2.10 (m, 1H), 2.10-1.99 (m, 1H), 1.86-1.72 (m, 2H), 1.58-1.45 (m, 1H) | FA: m/z = 580.3 (M + H) |

| Compound No. | ¹H NMR | LC/MS |
| --- | --- | --- |
| I-179 | ¹H NMR (400 MHz, DMSO) δ 8.74 (s, 1H), 8.69 (s, 1H), 8.37 (d, J = 7.5 Hz, 1H), 7.91 (s, 1H), 7.46-7.39 (m, 2H), 7.39-7.34 (m, 1H), 7.33-7.29 (m, 1H), 7.28-7.23 (m, 1H), 4.73 (dd, J = 15.9, 8.0 Hz, 1H), 4.19 (s, 2H), 4.12-4.05 (m, 1H), 4.00-3.93 (m, 2H), 2.55 (s, 2H), 2.35-2.26 (m, 1H), 2.16-2.09 (m, 1H), 2.01-1.91 (m, 1H), 1.81-1.73 (m, 1H), 1.33-1.23 (m, 1H) | FA: m/z = 548.2 (M + H) |
| I-118 | ¹H NMR (400 MHz, DMSO) δ 8.69 (s, 1H), 8.65 (s, 1H), 8.22 (d, J = 7.5 Hz, 1H), 7.74 (s, 1H), 7.45 (s, 2H), 7.36-7.31 (m, 2H), 7.31-7.26 (m, 1H), 7.23 (d, J = 7.5 Hz, 1H), 4.91 (s, 1H), 4.76-4.63 (m, 1H), 4.13-4.05 (m, 1H), 4.01-3.89 (m, 4H), 2.34-2.27 (m, 1H), 2.14-2.09 (m, 1H), 1.98-1.92 (m, 1H), 1.80-1.70 (m, 1H), 1.31-1.22 (m, 1H) | FA: m/z = 603.0 (M + H) |
| I-107 | ¹H NMR (400 MHz, DMSO) δ 8.70 (s, 1H), 8.66 (s, 1H), 8.20 (d, J = 7.5 Hz, 1H), 7.80 (s, 1H), 7.44 (s, 2H), 7.36 (d, J = 1.6 Hz, 1H), 7.33 (d, J = 7.5 Hz, 1H), 7.30-7.26 (m, 1H), 7.25-7.21 (m, 1H), 4.90 (d, J = 4.4 Hz, 1H), 4.75-4.64 (m, 1H), 4.11-4.03 (m, 1H), 3.99 (d, J = 10.4 Hz, 2H), 3.98-3.90 (m, 2H), 2.34-2.25 (m, 1H), 2.14-2.08 (m, 1H), 1.98-1.92 (m, 1H), 1.82-1.73 (m, 1H), 1.30-1.21 (m, 1H) | FA: m/z = 557.2 (M + H) |
| I-157 | ¹H NMR (400 MHz, DMSO) δ 8.67 (s, 1H), 8.64 (s, 1H), 8.27 (d, J = 7.5 Hz, 1H), 7.79 (s, 1H), 7.67 (s, 1H), 7.44 (s, 2H), 7.39-7.33 (m, 2H), 7.33-7.25 (m, 2H), 4.89 (d, J = 4.5 Hz, 1H), 4.74-4.63 (m, 1H), 4.13-4.05 (m, 1H), 4.01-3.90 (m, 4H), 2.35-2.28 (m, 1H), 2.15-2.09 (m, 1H), 2.00-1.93 (m, 1H), 1.81-1.74 (m, 1H), 1.30-1.23 (m, 1H) | FA: m/z = 523.3 (M + H) |
| I-165 | ¹H NMR (400 MHz, DMSO) δ 8.67 (s, 1H), 8.64 (s, 1H), 8.27 (d, J = 7.5 Hz, 1H), 7.73 (s, 1H), 7.66 (s, 1H), 7.47-7.42 (m, 3H), 7.43-7.38 (m, 1H), 7.35-7.25 (m, 2H), 4.90 (d, J = 5.8 Hz, 1H), 4.76-4.65 (m, 1H), 4.14-4.05 (m, 3H), 3.99-3.89 (m, 2H), 2.35-2.25 (m, 1H), 2.15-2.08 (m, 1H), 1.99-1.93 (m, 1H), 1.81-1.71 (m, 1H), 1.31-1.22 (m, 1H) | FA: m/z = 523.3 (M + H) |
| I-97 | ¹H NMR (400 MHz, DMSO) δ 8.68 (s, 1H), 8.65 (s, 1H), 8.27 (d, J = 7.3 Hz, 1H), 7.82 (s, 1H), 7.70 (s, 1H), 7.44 (s, 2H), 7.32 (dd, J = 15.1, 7.0 Hz, 1H), 7.16-7.10 (m, 2H), 7.05-6.98 (m, 1H), 4.93-4.86 (m, 1H), 4.75-4.65 (m, 1H), 4.12-4.06 (m, 1H), 4.02 (s, 2H), 3.99-3.92 (m, 2H), 2.36-2.28 (m, 1H), 2.16-2.11 (m, 1H), 1.98-1.92 (m, 1H), 1.80-1.71 (m, 1H), 1.32-1.21 (m, 1H) | FA: m/z = 507.7 (M + H) |
| I-88 | ¹H NMR (400 MHz, DMSO) δ 8.67 (s, 1H), 8.64 (s, 1H), 8.26 (d, J = 7.4 Hz, 1H), 7.78 (s, 1H), 7.65 (d, J = 1.3 Hz, 1H), 7.44 (s, 2H), 7.34-7.24 (m, 4H), 7.23-7.17 (m, 1H), 4.90 (d, J = 4.5 Hz, 1H), 4.74-4.66 (m, 1H), 4.12-4.06 (m, 1H), 4.01-3.91 (m, 4H), 2.34-2.28 (m, 1H), 2.14-2.08 (m, 1H), 1.98-1.92 (m, 1H), 1.81-1.74 (m, 1H), 1.31-1.24 (m, 1H) | FA: m/z = 489.4 (M + H) |
| I-205 | ¹H NMR (400 MHz, DMSO) δ 8.78 (s, 1H), 8.70 (s, 1H), 8.44 (t, J = 6.9 Hz, 1H), 7.67 (d, J = 3.8 Hz, 1H), 7.51-7.45 (m, 2H), 7.43 (s, 1H), 7.41-7.35 (m, 1H), 7.32 (t, J = 8.0 Hz, 2H), 7.13-7.09 (m, 1H), 5.58-5.49 (m, 1H), 4.85-4.68 (m, 2H), 4.29 (s, 2H), 4.15-4.06 (m, 1H), 4.05-3.99 (m, 1H), 3.97-3.85 (m, 1H), 2.34-2.29 (m, 1H), 2.21-2.12 (m, 1H), 1.54-1.44 (m, 1H) | FA: m/z = 541.2 (M + H) |
| I-93 | ¹H NMR (400 MHz, DMSO) δ 8.82 (s, 1H), 8.64 (s, 1H), 8.45 (d, J = 7.5 Hz, 1H), 7.45 (s, 2H), 7.43-7.33 (m, 4H), 7.29 (d, J = 7.3 Hz, 1H), 6.54 (d, J = 3.5 Hz, 1H), 4.91 (d, J = 4.4 Hz, 1H), 4.75-4.67 (m, 1H), 4.19 (s, 2H), 4.13-4.06 (m, 1H), 3.99-3.93 (m, 2H), 2.36-2.26 (m, 1H), 2.14-2.10 (m, 1H), 2.00-1.93 (m, 1H), 1.80-1.73 (m, 1H), 1.30-1.24 (m, 1H) | FA: m/z = 507.3 (M + H) |
| I-127 | ¹H NMR (400 MHz, CDCl₃) δ 9.07 (s, 1H), 8.92 (d, J = 6.3 Hz, 1H), 8.67 (s, 1H), 7.41-7.34 (m, 2H), 7.33-7.28 (m, 3H), 7.21 (d, J = 3.6 Hz, 1H), 6.26 (d, J = 3.5 Hz, 1H), 4.85-4.73 (m, 1H), 4.45-4.32 (m, 2H), 4.32-4.24 (m, 1H), 4.11 (s, 2H), 2.63-2.50 (m, 1H), 2.40-2.34 (m, 1H), 2.17-2.04 (m, 2H) | FA: m/z = 473.5 (M + H) |
| I-323 | ¹H NMR (400 MHz, DMSO-d6) δ 8.65 (s, 1H), 8.63 (s, 1H), 8.31 (s, 1H), 8.22-8.16 (m, 1H), 7.60-7.55 (m, 1H), 7.44 (s, 2H), 6.93 (s, 1H), 5.95 (s, 1H), 4.91-4.87 (m, 1H), 4.75-4.63 (m, 1H), 4.22-4.14 (m, 1H), 4.11- | AA: m/z = 600.1 (M + H) |

-continued

| Compound No. | ¹H NMR | LC/MS |
|---|---|---|
| | 4.05 (m, 1H), 3.98-3.83 (m, 3H), 3.07-2.96 (m, 1H), 2.86-2.76 (m, 1H), 2.36-2.23 (m, 1H), 2.16-2.04 (m, 1H), 1.99-1.87 (m, 1H), 1.81-1.70 (m, 1H), 1.33-1.20 (m, 1H) | |
| I-316 | ¹H NMR (400 MHz, DMSO-$d_6$) δ 8.61 (s, 2H), 8.29 (s, 1H), 8.20 (d, J = 7.6 Hz, 1H), 7.48-7.39 (m, 3H), 6.84 (s, 1H), 5.92 (s, 1H), 4.89 (dd, J = 4.5, 1.8 Hz, 1H), 4.73-4.63 (m, 1H), 4.16 (s, 1H), 4.12-4.04 (m, 1H), 3.99-3.91 (m, 2H), 3.89-3.80 (m, 1H), 3.08-2.95 (m, 1H), 2.86-2.76 (m, 1H), 2.47 (s, 3H), 2.33-2.24 (m, 1H), 2.15-2.06 (m, 1H), 1.97-1.88 (m, 1H), 1.81-1.69 (m, 1H), 1.32-1.20 (m, 1H) | AA: m/z = 580.1 (M + H) |
| I-298 | ¹H NMR (400 MHz, DMSO-$d_6$) δ 8.62 (s, 1H), 8.59 (s, 1H), 8.19 (d, J = 7.5 Hz, 1H), 7.41 (s, 2H), 7.34 (s, 1H), 6.23 (d, J = 1.0 Hz, 1H), 5.72 (s, 1H), 4.87 (s, 1H), 4.75-4.63 (m, 1H), 4.15-4.04 (m, 2H), 3.99-3.90 (m, 2H), 3.89-3.78 (m, 1H), 2.90-2.78 (m, 1H), 2.70-2.60 (m, 1H), 2.53 (s, 3H), 2.35-2.25 (m, 1H), 2.16-2.05 (m, 1H), 1.99-1.89 (m, 1H), 1.81-1.70 (m, 1H), 1.32-1.21 (m, 1H) | AA: m/z = 569.2 (M + H) |
| I-298a | ¹H NMR (400 MHz, DMSO-$d_6$) δ 8.62 (s, 1H), 8.59 (s, 1H), 8.19 (d, J = 7.5 Hz, 1H), 7.40 (s, 2H), 7.34 (s, 1H), 6.23 (s, 1H), 5.74-5.70 (m, 1H), 4.88 (s, 1H), 4.76-4.63 (m, 1H), 4.14-4.05 (m, 2H), 3.99-3.91 (m, 2H), 3.88-3.79 (m, 1H), 2.90-2.79 (m, 1H), 2.70-2.60 (m, 1H), 2.53 (s, 3H), 2.35-2.24 (m, 1H), 2.15-2.05 (m, 1H), 1.99-1.90 (m, 1H), 1.81-1.70 (m, 1H), 1.32-1.21 (m, 1H) | AA: m/z = 569.1 (M + H) |
| I-298b | ¹H NMR (400 MHz, DMSO-$d_6$) δ 8.61 (s, 1H), 8.59 (s, 1H), 8.19 (d, J = 7.4 Hz, 1H), 7.42-7.25 (m, 3H), 6.23 (s, 1H), 5.74-5.70 (m, 1H), 4.89 (br s, 1H), 4.76-4.63 (m, 1H), 4.14-4.04 (m, 2H), 3.97-3.91 (m, 2H), 3.88-3.79 (m, 1H), 2.90-2.79 (m, 1H), 2.69-2.60 (m, 1H), 2.53 (s, 3H), 2.35-2.25 (m, 1H), 2.15-2.05 (m, 1H), 1.98-1.89 (m, 1H), 1.80-1.70 (m, 1H), 1.31-1.20 (m, 1H) | AA: m/z = 569.1 (M + H) |
| I-281 | ¹H NMR (400 MHz, DMSO-$d_6$) δ 8.65-8.62 (m, 2H), 8.25 (d, J = 7.4 Hz, 1H), 7.90-7.84 (m, 1H), 7.59 (d, J = 1.2 Hz, 1H), 7.43 (s, 2H), 7.22-7.16 (m, 1H), 7.12-7.05 (m, 1H), 6.88-6.82 (m, 2H), 6.03 (s, 1H), 4.90 (s, 1H), 4.76-4.64 (m, 1H), 4.08 (dd, J = 9.7, 6.1 Hz, 1H), 3.99-3.90 (m, 2H), 3.72 (d, J = 11.7 Hz, 1H), 3.63 (d, J = 11.7 Hz, 1H), 2.36-2.24 (m, 1H), 2.16-2.04 (m, 1H), 2.00-1.89 (m, 1H), 1.82-1.70 (m, 1H), 1.33-1.21 (m, 1H), 1.09-0.87 (m, 4H) | AA: m/z = 557.2 (M + H) |
| I-281a | ¹H NMR (400 MHz, DMSO-$d_6$) δ 8.67-8.60 (m, 2H), 8.25 (d, J = 7.6 Hz, 1H), 7.90-7.84 (m, 1H), 7.59 (d, J = 1.2 Hz, 1H), 7.42 (s, 2H), 7.23-7.15 (m, 1H), 7.13-7.05 (m, 1H), 6.89-6.81 (m, 2H), 6.03 (s, 1H), 4.91-4.84 (m, 1H), 4.75-4.64 (m, 1H), 4.09 (dd, J = 9.7, 6.0 Hz, 1H), 3.99-3.91 (m, 2H), 3.72 (d, J = 11.7 Hz, 1H), 3.64 (d, J = 11.6 Hz, 1H), 2.35-2.25 (m, 1H), 2.16-2.05 (m, 1H), 2.01-1.91 (m, 1H), 1.82-1.72 (m, 1H), 1.32-1.21 (m, 1H), 1.09-0.87 (m, 4H) | AA: m/z = 557.2 (M + H) |
| I-281b | ¹H NMR (400 MHz, DMSO-$d_6$) δ 8.66-8.60 (m, 2H), 8.24 (d, J = 7.5 Hz, 1H), 7.89-7.84 (m, 1H), 7.59 (d, J = 1.3 Hz, 1H), 7.42 (s, 2H), 7.23-7.15 (m, 1H), 7.12-7.05 (m, 1H), 6.89-6.81 (m, 2H), 6.03 (s, 1H), 4.88 (d, J = 4.2 Hz, 1H), 4.76-4.64 (m, 1H), 4.09 (dd, J = 9.7, 6.0 Hz, 1H), 3.99-3.91 (m, 2H), 3.72 (d, J = 11.7 Hz, 1H), 3.64 (d, J = 11.7 Hz, 1H), 2.36-2.26 (m, 1H), 2.16-2.06 (m, 1H), 1.99-1.90 (m, 1H), 1.81-1.70 (m, 1H), 1.33-1.22 (m, 2H), 1.08-0.88 (m, 4H) | AA: m/z = 557.2 (M + H) |
| I-249a | ¹H NMR (400 MHz, DMSO-$d_6$) δ 8.60 (s, 2H), 8.25 (d, J = 7.8 Hz, 1H), 7.49-7.41 (m, 3H), 7.18 (d, J = 8.5 Hz, 2H), 6.68 (s, 1H), 5.17 (s, 1H), 4.85 (d, J = 5.8 Hz, 1H), 4.69 (d, J = 4.3 Hz, 1H), 4.49-4.39 (m, 1H), 4.09-4.02 (m, 1H), 3.99-3.92 (m, 1H), 3.80-3.73 (m, 1H), 3.71-3.64 (m, 1H), 3.21-3.02 (m, 2H), 2.98-2.83 (m, 2H), 2.73-2.64 (m, 1H), 2.31-2.11 (m, 2H), 1.20-1.09 (m, 1H) | FA: m/z = 614.1 (M + H) |
| I-249b | ¹H NMR (400 MHz, DMSO-$d_6$) δ 8.63-8.57 (m, 2H), 8.25 (d, J = 7.5 Hz, 1H), 7.48-7.39 (m, 3H), 7.26-7.16 (m, 2H), 6.69 (s, 1H), 5.21 (s, 1H), 4.87 (d, J = 6.1 Hz, 1H), 4.70 (d, J = 4.8 Hz, 1H), 4.48-4.38 (m, 1H), 4.04 (dd, J = 9.8, 6.1 Hz, 1H), 3.95 (dd, J = 9.7, 6.5 Hz, | FA: m/z = 614.1 (M + H) |

| Compound No. | ¹H NMR | LC/MS |
|---|---|---|
| | 1H), 3.81-3.73 (m, 1H), 3.72-3.65 (m, 1H), 3.24-3.14 (m, 1H), 3.03-2.84 (m, 2H), 2.77-2.67 (m, 1H), 2.29-2.11 (m, 2H), 1.17-1.06 (m, 1H) | |
| I-338 | ¹H NMR (400 MHz, DMSO-d6) δ 8.80-8.68 (m, 2H), 8.62 (m, 1H), 8.43 (d, J = 4.5 Hz, 3H), 7.58-7.48 (m, 3H), 7.29-7.22 (m, 2H), 6.70 (s, 1H), 5.90 (s, 1H), 5.14-5.06 (m, 1H), 4.84-4.71 (m, 1H), 4.17-4.05 (m, 3H), 3.94-3.88 (m, 1H), 3.88-3.79 (m, 1H), 3.08-2.96 (m, 1H), 2.81-2.72 (m, 1H), 2.38-2.28 (m, 1H), 2.23-2.13 (m, 1H), 2.13-2.03 (m, 2H), 1.56-1.45 (m, 1H), 1.04-0.92 (m, 6H) | AA: m/z = 678.2 (M + H) |
| I-330 | ¹H NMR (400 MHz, DMSO-d6) δ 8.68 (s, 1H), 8.59 (s, 1H), 8.45 (br s, 1H), 7.90 (br s, 3H), 7.43 (s, 1H), 7.30-7.20 (m, 2H), 6.72 (s, 1H), 5.90 (s, 1H), 4.79-4.65 (m, 1H), 4.19-4.05 (m, 2H), 4.06-3.88 (m, 2H), 3.88-3.79 (m, 1H), 3.10-2.95 (m, 1H), 2.81-2.71 (m, 1H), 2.30-2.20 (m, 1H), 2.13-2.01 (m, 1H), 1.94-1.83 (m, 1H), 1.82-1.68 (m, 1H), 1.34-1.22 (m, 1H) | AA: m/z = 636.2 (M + H) |
| I-209 | ¹H NMR (400 MHz, DMSO-d6) δ 8.62 (s, 1H), 8.56 (s, 1H), 8.24 (d, J = 7.4 Hz, 1H), 7.97-7.92 (m, 1H), 7.58 (d, J = 1.2 Hz, 1H), 7.52 (t, J = 1.8 Hz, 1H), 7.47-7.28 (m, 5H), 4.88 (s, 1H), 4.75-4.63 (m, 1H), 4.08 (dd, J = 9.7, 6.0 Hz, 1H), 3.98-3.90 (m, 2H), 3.09 (t, J = 6.8 Hz, 2H), 2.82-2.74 (m, 1H), 2.62-2.53 (m, 1H), 2.33-2.25 (m, 1H), 2.15-1.90 (m, 4H), 1.80-1.70 (m, 1H), 1.31-1.20 (m, 1H) | FA: m/z = 595.1 (M + H) |
| I-175 | ¹H NMR (400 MHz, DMSO-d₆) δ 8.74 (s, 1H), 8.65 (s, 1H), 8.27 (d, J = 7.5 Hz, 1H), 7.86 (s, 1H), 7.46-7.23 (m, 5H), 7.23-7.17 (m, 1H), 4.88 (s, 1H), 4.77-4.65 (m, 1H), 4.11-4.05 (m, 1H), 3.99-3.92 (m, 2H), 2.35-2.26 (m, 1H), 2.16-2.06 (m, 1H), 2.00-1.90 (m, 1H), 1.82-1.73 (m, 1H), 1.34-1.22 (m, 1H) | AA: m/z = 575.0 (M + H) |
| I-94 | ¹H NMR (400 MHz, DMSO-d₆) δ 8.67 (s, 2H), 8.23 (d, J = 7.3 Hz, 1H), 7.88-7.85 (m, 1H), 7.82 (s, 1H), 7.77-7.72 (m, 1H), 7.68-7.59 (m, 2H), 7.41 (s, 2H), 4.92-4.84 (m, 1H), 4.77-4.65 (m, 1H), 4.11-4.05 (m, 1H), 3.98-3.90 (m, 2H), 2.35-2.24 (m, 1H), 2.16-2.06 (m, 1H), 2.00-1.89 (m, 1H), 1.82-1.70 (m, 1H), 1.33-1.21 (m, 1H)); LCMS: (AA) M + 1 591.1/593.1. | AA: m/z = 591.1 (M + H) |
| I-96 | ¹H NMR (400 MHz, DMSO) δ 8.73-8.59 (m, 2H), 8.19 (d, J = 7.4 Hz, 1H), 7.72 (s, 1H), 7.45 (s, 2H), 7.37-7.15 (m, 5H), 4.77-4.63 (m, 1H), 4.09 (dd, J = 9.7, 5.9 Hz, 1H), 4.00-3.90 (m, 4H), 2.35-2.22 (m, 1H), 2.17-2.04 (m, 1H), 2.00-1.89 (m, 1H), 1.83-1.67 (m, 1H), 1.27 (dt, J = 12.9, 9.3 Hz, 1H) | FA: m/z = 523.0 (M + H) |
| I-162 | ¹H NMR (400 MHz, DMSO) δ 8.78 (s, 1H), 8.72 (s, 1H), 8.42 (d, J = 7.9 Hz, 1H), 7.76 (s, 1H), 7.50 (s, 2H), 7.35-7.17 (m, 5H), 4.92-4.61 (m, 2H), 4.10 (dd, J = 9.8, 5.9 Hz, 1H), 4.05-3.85 (m, 4H), 2.37-2.25 (m, 1H), 2.25-2.10 (m, 1H), 1.59-1.40 (m, 1H) | FA: m/z = 541.0 (M + H) |
| I-140 | ¹H NMR (400 MHz, DMSO) δ 8.68 (s, 1H), 8.65 (s, 1H), 8.28 (d, J = 7.5 Hz, 1H), 7.74 (s, 1H), 7.55 (s, 1H), 7.46 (s, 2H), 5.46 (s, 1H), 4.92 (s, 1H), 4.80-4.63 (m, 1H), 4.10 (dd, J = 9.7, 6.0 Hz, 1H), 3.97 (dd, J = 9.4, 7.1 Hz, 2H), 2.41-2.27 (m, 1H), 2.18-2.07 (m, 1H), 1.97 (s, 3H), 1.87 (s, 2H), 1.84-1.72 (m, 1H), 1.64-1.43 (m, 4H), 1.29 (dt, J = 12.6, 9.3 Hz, 1H) | FA: m/z = 493.4 (M + H) |
| I-199 | ¹H NMR (400 MHz, DMSO) δ 8.70 (s, 1H), 8.66 (s, 1H), 8.28 (d, J = 7.4 Hz, 1H), 7.73 (s, 1H), 7.63 (s, 1H), 7.46 (s, 2H), 4.78-4.61 (m, 1H), 4.10 (dd, J = 9.7, 6.0 Hz, 1H), 3.97 (m, 2H), 2.38-2.26 (m, 1H), 2.18-2.04 (m, 1H), 2.03-1.91 (m, 1H), 1.84-1.72 (m, 1H), 1.71-1.47 (m, 6H), 1.35-1.06 (m, 5H), 0.99-0.82 (m, 2H) | FA: m/z = 495.4 (M + H) |
| I-76 | ¹H NMR (400 MHz, DMSO) δ 8.73 (s, 1H), 8.65 (s, 1H), 8.31 (d, J = 7.6 Hz, 1H), 7.82 (s, 1H), 7.54-7.37 (m, 4H), 7.34-7.20 (m, 2H), 4.89 (s, 1H), 4.74 (s, 1H), 4.52-4.41 (m, 1H), 4.11-3.90 (m, 4H), 3.80 (s, 1H), 3.71 (s, 1H), 1.45-1.23 (m, 2H), 1.22-1.06 (m, 1H) | FA: m/z = 619.2 (M + H) |
| I-112 | ¹H NMR (400 MHz, MeOD) δ 8.56 (s, 1H), 8.46 (s, 1H), 7.37 (s, 1H), 7.32-7.24 (m, 2H), 7.15-7.07 (m, 2H), 4.73-4.61 (m, 1H), 4.13-3.97 (m, 3H), 3.90 (s, 2H), 2.43-2.31 (m, 1H), 2.21-2.09 (m, 1H), 2.09-1.96 (m, 1H), 1.82-1.72 (m, 1H), 1.46-1.36 (m, 1H) | FA: m/z = 604.0 (M + H) |
| I-26 | ¹H NMR (400 MHz, DMSO) δ 8.70 (s, 1H), 8.64 (s, 1H), 8.35 (d, J = 7.6 Hz, 1H), 7.83 (d, J = 1.2 Hz, 1H), | FA: m/z = 585.3 (M + H) |

| Compound No. | ¹H NMR | LC/MS |
|---|---|---|
| | 7.72 (d, J = 1.3 Hz, 1H), 7.52 (s, 1H), 7.45 (s, 2H), 7.40 (dt, J = 7.4, 1.7 Hz, 1H), 7.33-7.22 (m, 2H), 4.87 (d, J = 5.9 Hz, 1H), 4.72 (d, J = 4.8 Hz, 1H), 4.51-4.39 (m, 1H), 4.06 (dd, J = 9.7, 6.2 Hz, 1H), 4.03-3.91 (m, 3H), 3.82-3.73 (m, 1H), 3.74-3.65 (m, 1H), 2.34-2.23 (m, 1H), 2.23-2.12 (m, 1H), 1.21-1.06 (m, 1H) | |
| I-135b | ¹H NMR (400 MHz, CDCl₃) δ 8.79 (s, 1H), 8.65 (s, 1H), 8.55 (d, J = 7.3 Hz, 1H), 7.41 (s, 1H), 7.25-7.15 (m, 2H), 7.12 (s, 1H), 7.06-7.01 (m, 1H), 4.85-4.69 (m, 1H), 4.43-4.30 (m, 2H), 4.30-4.22 (m, 1H), 4.18-4.08 (m, 1H), 2.61-2.48 (m, 1H), 2.41-2.28 (m, 4H), 2.16-1.95 (m, 2H), 1.60 (d, J = 7.2 Hz, 3H), 1.53-1.43 (m, 1H) | FA: m/z = 551.4 (M + H) |
| I-135a | ¹H NMR (400 MHz, CDCl₃) δ 8.77 (s, 1H), 8.63 (s, 1H), 8.53 (d, J = 7.2 Hz, 1H), 7.42 (s, 1H), 7.24-7.14 (m, 2H), 7.11 (s, 1H), 7.02 (d, J = 7.5 Hz, 1H), 4.82-4.66 (m, 1H), 4.42-4.27 (m, 2H), 4.23 (dd, J = 10.0, 5.8 Hz, 1H), 4.12 (q, J = 7.2 Hz, 1H), 2.58-2.42 (m, 1H), 2.37 (s, 3H), 2.35-2.26 (m, 1H), 2.20-2.07 (m, 1H), 2.04-1.95 (m, 2H), 1.59 (d, J = 7.2 Hz, 3H), 1.49-1.37 (m, 1H) | FA: m/z = 551.4 (M + H) |
| I-230 | ¹H NMR (400 MHz, DMSO) δ 8.71 (s, 1H), 8.66 (s, 1H), 8.31 (d, J = 7.5 Hz, 1H), 7.87 (d, J = 1.1 Hz, 1H), 7.69 (d, J = 1.2 Hz, 1H), 7.46 (s, 2H), 5.29 (t, J = 5.8 Hz, 1H), 4.91 (d, J = 4.5 Hz, 1H), 4.81-4.63 (m, 1H), 4.50 (d, J = 5.7 Hz, 2H), 4.18-4.04 (m, 1H), 4.03-3.90 (m, 2H), 2.39-2.26 (m, 1H), 2.20-2.05 (m, 1H), 2.01-1.92 (m, 1H), 1.85-1.73 (m, 1H), 1.38-1.20 (m, 1H) | FA: m/z = 429.4 (M + H) |
| I-12a | ¹H NMR (400 MHz, DMSO) δ 8.64 (s, 1H), 8.63 (s, 1H), 8.29 (d, J = 7.5 Hz, 1H), 7.88 (d, J = 1.3 Hz, 1H), 7.73 (d, J = 1.3 Hz, 1H), 7.55 (s, 1H), 7.40-7.16 (m, 3H), 4.76-4.61 (m, 1H), 4.09 (dd, J = 9.7, 6.0 Hz, 1H), 4.02-3.88 (m, 2H), 2.39-2.23 (m, 1H), 2.15-2.03 (m, 1H), 2.02-1.88 (m, 1H), 1.79-1.65 (m, 4H), 1.31-1.17 (m, 1H) | FA: m/z = 552.4 (M + H) |
| I-12b | ¹H NMR (400 MHz, DMSO) δ 8.63 (s, 1H), 8.63 (s, 1H), 8.28 (d, J = 7.5 Hz, 1H), 7.88 (s, 1H), 7.73 (s, 1H), 7.55 (s, 1H), 7.39-7.15 (m, 3H), 4.78-4.61 (m, 1H), 4.17-4.02 (m, 1H), 4.02-3.85 (m, 2H), 2.63 (s, 2H), 2.37-2.22 (m, 1H), 2.16-2.08 (m, 1H), 2.00-1.84 (m, 1H), 1.81-1.66 (m, 4H), 1.35-1.17 (m, 1H) | FA: m/z = 552.4 (M + H) |
| I-217 | ¹H NMR (400 MHz, MeOD) δ 8.78 (s, 1H), 8.61 (s, 1H), 7.83 (s, 1H), 7.66 (s, 1H), 4.84-4.74 (m, 1H), 4.50 (s, 2H), 4.27-4.10 (m, 3H), 3.41 (s, 3H), 2.59-2.47 (m, 1H), 2.35-2.24 (m, 1H), 2.24-2.13 (m, 1H), 2.01-1.86 (m, 1H), 1.53-1.37 (m, 1H) | FA: m/z = 443.5 (M + H) |
| I-15a | ¹H NMR (400 MHz, DMSO) δ 8.72 (s, 1H), 8.68 (s, 1H), 8.23 (d, J = 7.5 Hz, 1H), 7.93 (s, 1H), 7.51 (s, 1H), 7.43 (s, 2H), 7.37-7.26 (m, 3H), 5.14 (s, 1H), 4.89 (d, J = 4.5 Hz, 1H), 4.79-4.61 (m, 1H), 4.09 (dd, J = 9.7, 6.0 Hz, 1H), 3.96 (dd, J = 9.6, 7.0 Hz, 2H), 2.74-2.58 (m, 2H), 2.37-2.24 (m, 1H), 2.17-2.06 (m, 1H), 2.02-1.91 (m, 1H), 1.86-1.71 (m, 1H), 1.34-1.18 (m, 1H) | FA: m/z = 572.4 (M + H) |
| I-15b | ¹H NMR (400 MHz, DMSO) δ 8.72 (s, 1H), 8.68 (s, 1H), 8.22 (d, J = 7.5 Hz, 1H), 7.93 (s, 1H), 7.51 (s, 1H), 7.42 (s, 2H), 7.39-7.21 (m, 3H), 5.14 (s, 1H), 4.89 (d, J = 4.3 Hz, 1H), 4.79-4.63 (m, 1H), 4.10 (dd, J = 9.7, 6.0 Hz, 1H), 4.03-3.88 (m, 2H), 2.39-2.26 (m, 1H), 2.18-2.03 (m, 1H), 2.02-1.87 (m, 1H), 1.84-1.68 (m, 1H), 1.34-1.22 (m, 1H) | FA: m/z = 572.4 (M + H) |
| I-6a | ¹H NMR (400 MHz, DMSO) δ 8.67 (s, 1H), 8.64 (s, 1H), 8.24 (d, J = 7.5 Hz, 1H), 7.75 (s, 1H), 7.49 (s, 1H), 7.43 (s, 2H), 7.36-7.20 (m, 3H), 5.13 (s, 1H), 4.89 (d, J = 4.5 Hz, 1H), 4.77-4.61 (m, 1H), 4.09 (dd, J = 9.8, 6.0 Hz, 1H), 4.01-3.88 (m, 2H), 2.45 (s, 3H), 2.38-2.25 (m, 1H), 2.16-2.04 (m, 1H), 2.03-1.85 (m, 1H), 1.84-1.71 (m, 1H), 1.34-1.18 (m, 1H) | FA: m/z = 552.2 (M + H) |
| I-6b | ¹H NMR (400 MHz, DMSO) δ 8.67 (s, 1H), 8.64 (s, 1H), 8.24 (d, J = 7.3 Hz, 1H), 7.75 (s, 1H), 7.49 (s, 1H), 7.44 (s, 2H), 7.36-7.21 (m, 3H), 5.13 (s, 1H), 4.90 (d, J = 4.4 Hz, 1H), 4.80-4.60 (m, 1H), 4.08 (dd, J = 9.6, 6.0 Hz, 1H), 4.01-3.87 (m, 2H), 2.45 (s, 3H), 2.36-2.23 (m, 1H), 2.16-2.03 (m, 1H), 2.01-1.91 (m, 1H), 1.83-1.69 (m, 1H), 1.34-1.17 (m, 1H) | FA: m/z = 552.2 (M + H) |

| Compound No. | ¹H NMR | LC/MS |
|---|---|---|
| I-251a | (400 MHz, DMSO) δ 8.62 (s, 1H), 8.58 (s, 1H), 8.17 (d, J = 7.5 Hz, 1H), 7.42 (s, 2H), 7.34 (dd, J = 8.2, 1.7 Hz, 1H), 7.13 (d, J = 8.2 Hz, 1H), 6.82 (d, J = 1.2 Hz, 1H), 5.18 (s, 1H), 4.87 (d, J = 4.5 Hz, 1H), 4.77-4.61 (m, 1H), 4.09 (dd, J = 9.7, 6.0 Hz, 1H), 4.01-3.87 (m, 2H), 3.20-3.14 (m, 1H), 3.09 (s, 1H), 2.99-2.81 (m, 2H), 2.76-2.62 (m, 1H), 2.39-2.23 (m, 1H), 2.17-2.05 (m, 1H), 1.96-1.83 (m, 1H), 1.80-1.68 (m, 1H), 1.35-1.21 (m, 1H) | FA: m/z = 644.5 (M + H) |
| I-251b | ¹H NMR (400 MHz, DMSO) δ 8.62 (s, 1H), 8.58 (s, 1H), 8.18 (d, J = 7.5 Hz, 1H), 7.43 (s, 2H), 7.35 (dd, J = 8.2, 1.8 Hz, 1H), 7.14 (d, J = 8.2 Hz, 1H), 6.83 (s, 1H), 5.21 (s, 1H), 4.88 (d, J = 4.6 Hz, 1H), 4.75-4.61 (m, 1H), 4.08 (dd, J = 9.7, 6.0 Hz, 1H), 4.00-3.90 (m, 2H), 3.25-3.11 (m, 1H), 3.00-2.81 (m, 3H), 2.75-2.63 (m, 1H), 2.36-2.21 (m, 1H), 2.16-2.06 (m, 1H), 1.99-1.90 (m, 1H), 1.82-1.69 (m, 1H), 1.31-1.20 (m, 1H) | FA: m/z = 644.5 (M + H) |
| I-259a | ¹H NMR (400 MHz, DMSO) δ 8.61 (s, 2H), 8.26 (d, J = 7.7 Hz, 1H), 7.54-7.38 (m, 3H), 7.33 (d, J = 8.0 Hz, 1H), 7.12 (d, J = 8.2 Hz, 1H), 6.82 (s, 1H), 5.18 (s, 1H), 4.86 (d, J = 5.8 Hz, 1H), 4.70 (d, J = 4.7 Hz, 1H), 4.51-4.39 (m, 1H), 4.14-4.02 (m, 1H), 4.02-3.91 (m, 1H), 3.84-3.74 (m, 1H), 3.74-3.63 (m, 1H), 3.25-3.03 (m, 2H), 3.01-2.79 (m, 2H), 2.67 (d, J = 14.4 Hz, 1H), 2.35-2.11 (m, 2H), 1.22-1.05 (m, 1H) | FA: m/z = 660.4 (M + H) |
| I-259b | ¹H NMR (400 MHz, DMSO) δ 8.61 (s, 1H), 8.59 (s, 1H), 8.25 (d, J = 7.6 Hz, 1H), 7.44 (s, 3H), 7.34 (d, J = 7.9 Hz, 1H), 7.13 (d, J = 8.3 Hz, 1H), 6.82 (s, 1H), 5.20 (s, 1H), 4.90 (d, J = 5.8 Hz, 1H), 4.72 (d, J = 4.7 Hz, 1H), 4.49-4.36 (m, 1H), 4.10-4.00 (m, 1H), 4.00-3.90 (m, 1H), 3.84-3.72 (m, 1H), 3.72-3.64 (m, 1H), 3.25-3.12 (m, 1H), 2.99-2.80 (m, 3H), 2.69 (d, J = 14.7 Hz, 1H), 2.31-2.11 (m, 2H), 1.16-1.06 (m, 1H) | FA: m/z = 660.3 (M + H) |
| I-8a | ¹H NMR (400 MHz, DMSO) δ 8.64 (s, 1H), 8.62 (s, 1H), 8.36 (d, J = 7.6 Hz, 1H), 7.88 (s, 1H), 7.74 (s, 1H), 7.56 (s, 1H), 7.46 (s, 2H), 7.37-7.28 (m, 2H), 7.28-7.21 (m, 1H), 4.89 (s, 1H), 4.73 (d, J = 4.5 Hz, 1H), 4.51-4.39 (m, 1H), 4.05 (dd, J = 9.7, 6.2 Hz, 1H), 4.00-3.92 (m, 1H), 3.78 (s, 1H), 3.74-3.66 (m, 1H), 2.88-2.63 (m, 2H), 2.33-2.22 (m, 1H), 2.22-2.13 (m, 1H), 1.74 (s, 3H), 1.20-1.08 (m, 1H) | FA: m/z = 568.4 (M + H) |
| I-8b | ¹H NMR (400 MHz, DMSO) δ 8.64 (s, 1H), 8.62 (s, 1H), 8.36 (d, J = 7.6 Hz, 1H), 7.88 (d, J = 1.3 Hz, 1H), 7.74 (d, J = 1.3 Hz, 1H), 7.56 (s, 1H), 7.45 (s, 2H), 7.36-7.21 (m, 3H), 4.90 (s, 1H), 4.74 (s, 1H), 4.51-4.40 (m, 1H), 4.06 (dd, J = 9.7, 6.1 Hz, 1H), 3.96 (dd, J = 9.7, 6.7 Hz, 1H), 3.78 (s, 1H), 3.69 (t, J = 4.7 Hz, 1H), 2.67 (s, 2H), 2.34-2.23 (m, 1H), 2.23-2.13 (m, 1H), 1.74 (s, 3H), 1.23-1.09 (m, 1H) | FA: m/z = 568.4 (M + H) |
| I-197 | ¹H NMR (400 MHz, DMSO-d₆) δ 8.87 (s, 1H), 8.65 (s, 1H), 8.49 (d, J = 7.4 Hz, 1H), 7.97 (s, 1H), 7.44 (s, 2H), 7.21 (s, 1H), 5.58 (d, J = 4.5 Hz, 1H), 5.09 (s, 1H), 5.05 (d, J = 3.3 Hz, 1H), 4.90 (d, J = 4.1 Hz, 1H), 4.87 (s, 1H), 4.71 (q, J = 8.2 Hz, 1H), 4.11 (dd, J = 9.7, 6.0 Hz, 1H), 3.97 (dd, J = 9.7, 7.0 Hz, 2H), 2.40-2.24 (m, 1H), 2.19-2.04 (m, 1H), 2.03-1.89 (m, 1H), 1.84-1.70 (m, 1H), 1.63 (s, 3H), 1.33-1.23 (m, 1H) | FA: m/z = 453.5 (M + H) |
| I-139 | ¹H NMR (400 MHz, DMSO-d₆) δ 8.77 (s, 1H), 8.60 (s, 1H), 8.41 (d, J = 7.4 Hz, 1H), 7.43 (s, 2H), 7.34-7.17 (m, 10H), 6.39 (s, 1H), 4.88 (d, J = 4.6 Hz, 1H), 4.73-4.61 (m, 1H), 4.17 (s, 2H), 4.08 (dd, J = 9.7, 5.9 Hz, 1H), 3.95 (dd, J = 9.8, 7.0 Hz, 2H), 3.88 (s, 2H), 2.35-2.26 (m, 1H), 2.16-2.05 (m, 1H), 1.99-1.90 (m, 1H), 1.78-1.68 (m, 1H), 1.29-1.18 (m, 1H) | FA: m/z = 563.3 (M + H) |
| I-234 | ¹H NMR (400 MHz, DMSO-d₆) δ 8.92-8.88 (m, 2H), 8.67 (s, 1H), 8.53 (d, J = 7.5 Hz, 1H), 7.62 (d, J = 0.7 Hz, 1H), 7.45 (s, 2H), 4.92 (s, 1H), 4.78-4.65 (m, 1H), 4.09 (dd, J = 9.7, 6.0 Hz, 1H), 4.00-3.93 (m, 2H), 2.49 (s, 3H), 2.38-2.28 (m, 1H), 2.13 (s, 1H), 1.97 (s, 1H), 1.83-1.73 (m, 1H), 1.34-1.25 (m, 1H) | FA: m/z = 425.4 (M + H) |

-continued

| Compound No. | ¹H NMR | LC/MS |
|---|---|---|
| I-223 | ¹H NMR (400 MHz, DMSO-$d_6$) δ 8.90 (s, 1H), 8.65 (s, 1H), 8.53 (d, J = 7.5 Hz, 1H), 8.11-8.08 (m, 1H), 7.44 (s, 2H), 7.41 (s, 1H), 4.90 (d, J = 4.5 Hz, 1H), 4.77-4.66 (m, 1H), 4.35 (s, 2H), 4.11 (dd, J = 9.7, 6.0 Hz, 1H), 3.98 (dd, J = 9.7, 7.0 Hz, 2H), 3.29 (s, 3H), 2.39-2.30 (m, 1H), 2.18-2.08 (m, 1H), 2.03-1.93 (m, 1H), 1.84-1.73 (m, 1H), 1.34-1.23 (m, 1H) | FA: m/z = 427.5 (M + H) |
| I-18 | ¹H NMR (400 MHz, DMSO-$d_6$) δ 8.71 (s, 1H), 8.67 (s, 1H), 8.23 (d, J = 7.5 Hz, 1H), 7.84 (d, J = 1.5 Hz, 1H), 7.76 (t, J = 7.7 Hz, 1H), 7.60 (d, J = 7.7 Hz, 1H), 7.52 (d, J = 7.8 Hz, 1H), 7.44 (s, 2H), 5.18 (s, 1H), 4.89 (dd, J = 4.5, 2.2 Hz, 1H), 4.77-4.65 (m, 1H), 4.09 (dd, J = 9.7, 6.0 Hz, 1H), 4.00-3.91 (m, 2H), 2.90 (s, 2H), 2.36-2.25 (m, 1H), 2.11 (d, J = 6.1 Hz, 1H), 2.00-1.90 (m, 1H), 1.82-1.72 (m, 1H), 1.34-1.22 (m, 1H). LCMS: (FA) M + 1 617.3 | FA: m/z = 617.3 (M + H) |
| I-18a | ¹H NMR (400 MHz, DMSO-$d_6$) δ 8.71 (s, 1H), 8.67 (s, 1H), 8.23 (d, J = 7.5 Hz, 1H), 7.84 (s, 1H), 7.76 (t, J = 7.7 Hz, 1H), 7.60 (d, J = 7.5 Hz, 1H), 7.52 (d, J = 7.8 Hz, 1H), 7.31 (s, 1H), 5.16 (s, 1H), 4.78-4.65 (m, 1H), 4.08 (dd, J = 9.7, 6.0 Hz, 1H), 3.99-3.91 (m, 1H), 2.69 (s, 1H), 2.35-2.24 (m, 1H), 2.16-2.06 (m, 1H), 2.01-1.92 (m, 1H), 1.82-1.72 (m, 1H), 1.32-1.22 (m, 1H) | FA: m/z = 617.4 (M + H) |
| I-18b | ¹H NMR (400 MHz, DMSO-$d_6$) δ 8.71 (s, 1H), 8.67 (s, 1H), 8.22 (d, J = 7.5 Hz, 1H), 7.84 (s, 1H), 7.76 (t, J = 7.7 Hz, 1H), 7.60 (d, J = 7.5 Hz, 1H), 7.51 (d, J = 7.7 Hz, 1H), 5.16 (s, 1H), 4.77-4.64 (m, 1H), 4.08 (dd, J = 9.7, 6.0 Hz, 1H), 3.99-3.90 (m, 2H), 2.68 (s, 2H), 2.38-2.25 (m, 1H), 2.16-2.06 (m, 1H), 2.00-1.89 (m, 1H), 1.82-1.70 (m, 1H), 1.34-1.21 (m, 1H) | FA: m/z = 617.4 (M + H) |
| I-10 | ¹H NMR (400 MHz, DMSO-$d_6$) δ 8.73 (app d, 1H), 8.66 (s, 1H), 8.32 (t, J = 6.9 Hz, 1H), 7.86 (app d, 1H), 7.80-7.72 (m, 1H), 7.60 (d, J = 7.6 Hz, 1H), 7.53 (d, J = 7.9 Hz, 1H), 7.45 (d, J = 2.0 Hz, 2H), 5.22 (s, 1H), 4.86 (d, J = 5.9 Hz, 1H), 4.71 (t, J = 4.7 Hz, 1H), 4.53-4.42 (m, 1H), 4.13-4.03 (m, 1H), 4.03-3.93 (m, 1H), 3.84-3.75 (m, 1H), 3.75-3.65 (m, 1H), 3.03 (s, 2H), 2.36-2.12 (m, 2H), 1.21-1.11 (m, 1H) | FA: m/z = 633.3 (M + H) |
| I-10a | ¹H NMR (400 MHz, DMSO-$d_6$) δ 8.73 (s, 1H), 8.66 (s, 1H), 8.32 (d, J = 7.5 Hz, 1H), 7.86 (s, 1H), 7.76 (t, J = 7.8 Hz, 1H), 7.60 (d, J = 7.6 Hz, 1H), 7.51 (d, J = 7.8 Hz, 1H), 7.44 (s, 2H), 5.16 (s, 1H), 4.86 (d, J = 5.9 Hz, 1H), 4.70 (d, J = 4.7 Hz, 1H), 4.52-4.41 (m, 1H), 4.07 (dd, J = 9.7, 6.1 Hz, 1H), 3.97 (dd, J = 9.7, 6.7 Hz, 1H), 3.84-3.75 (m, 1H), 3.70 (q, J = 4.6 Hz, 1H), 2.70 (s, 2H), 2.35-2.23 (m, 1H), 2.23-2.13 (m, 1H), 1.21-1.10 (m, 1H) | FA: m/z = 632.9 (M + H) |
| I-10b | ¹H NMR (400 MHz, DMSO-$d_6$) δ 8.72 (s, 1H), 8.66 (s, 1H), 8.30 (d, J = 7.6 Hz, 1H), 7.85 (s, 1H), 7.76 (t, J = 7.7 Hz, 1H), 7.60 (d, J = 7.5 Hz, 1H), 7.52 (d, J = 7.5 Hz, 1H), 7.43 (s, 2H), 5.16 (s, 1H), 4.89 (s, 1H), 4.72 (s, 1H), 4.47 (p, J = 7.7 Hz, 1H), 4.07 (dd, J = 9.7, 6.2 Hz, 1H), 3.96 (dd, J = 9.8, 6.7 Hz, 1H), 3.83-3.74 (m, 1H), 3.71 (d, J = 4.6 Hz, 1H), 2.36-2.12 (m, 2H), 1.20-1.07 (m, 1H) | FA: m/z = 632.9 (M + H) |
| I-280 | ¹H NMR (400 MHz, DMSO-$d_6$) δ 8.60 (s, 1H), 8.57 (s, 1H), 8.18 (d, J = 7.6 Hz, 1H), 7.45 (s, 2H), 7.35 (s, 1H), 7.22 (t, J = 7.4 Hz, 1H), 6.92 (dd, J = 7.6, 5.5 Hz, 2H), 6.79 (d, J = 7.6 Hz, 1H), 6.28 (s, 1H), 5.37 (q, J = 6.1 Hz, 2H), 4.89 (d, J = 3.3 Hz, 1H), 4.75-4.62 (m, 1H), 4.09 (dd, J = 9.8, 6.0 Hz, 1H), 4.00-3.89 (m, 2H), 2.35-2.22 (m, 1H), 2.11 (s, 1H), 1.94 (d, J = 5.0 Hz, 1H), 1.77 (dd, J = 13.5, 6.8 Hz, 1H), 1.32-1.21 (m, 1H) | FA: m/z = 547.2 (M + H) |
| I-280a | ¹H NMR (400 MHz, DMSO-$d_6$) δ 8.71 (s, 1H), 8.67 (s, 1H), 8.23 (d, J = 7.5 Hz, 1H), 7.84 (s, 1H), 7.76 (t, J = 7.7 Hz, 1H), 7.60 (d, J = 7.5 Hz, 1H), 7.52 (d, J = 7.8 Hz, 1H), 7.31 (s, 1H), 5.16 (s, 1H), 4.78-4.65 (m, 1H), 4.08 (dd, J = 9.7, 6.0 Hz, 1H), 3.99-3.91 (m, 1H), 2.69 (s, 1H), 2.35-2.24 (m, 1H), 2.16-2.06 (m, 1H), 2.01-1.92 (m, 1H), 1.82-1.72 (m, 1H), 1.32-1.22 (m, 1H) | FA: m/z = 547.2 (M + H) |
| I-280b | ¹H NMR (400 MHz, DMSO-$d_6$) δ 8.71 (s, 1H), 8.67 (s, 1H), 8.22 (d, J = 7.5 Hz, 1H), 7.84 (s, 1H), 7.76 (t, J = 7.7 Hz, 1H), 7.60 (d, J = 7.5 Hz, 1H), 7.51 (d, J = 7.7 Hz, 1H), 5.16 (s, 1H), 4.77-4.64 (m, 1H), 4.08 (dd, J = 9.7, 6.0 Hz, 1H), 3.99-3.90 (m, 2H), 2.68 (s, 2H), 2.38-2.25 (m, 1H), 2.16-2.06 (m, 1H), 2.00-1.89 (m, 1H), 1.82-1.70 (m, 1H), 1.34-1.21 (m, 1H) | FA: m/z = 547.1 (M + H) |

| Compound No. | $^1$H NMR | LC/MS |
|---|---|---|
| I-272a | $^1$H NMR (400 MHz, DMSO-d$_6$) δ 8.79 (s, 1H), 8.61 (s, 1H), 8.38 (d, J = 7.4 Hz, 1H), 7.45 (s, 2H), 7.20 (d, J = 4.0 Hz, 2H), 7.17-7.09 (m, 1H), 7.06 (s, 1H), 6.80 (d, J = 7.6 Hz, 1H), 5.83 (s, 1H), 4.91 (d, J = 4.5 Hz, 1H), 4.73-4.61 (m, 1H), 4.14-4.02 (m, 2H), 4.00-3.91 (m, 2H), 3.90-3.76 (m, 1H), 3.09-2.96 (m, 1H), 2.81-2.74 (m, 1H), 2.40 (s, 3H), 2.37-2.25 (m, 1H), 2.17-2.08 (m, 1H), 2.01-1.91 (m, 1H), 1.81-1.67 (m, 1H), 1.30-1.19 (m, 1H) | FA: m/z = 529.2 (M + H) |
| I-272b | $^1$H NMR (400 MHz, DMSO-d$_6$) δ 8.80 (s, 1H), 8.61 (s, 1H), 8.38 (d, J = 7.6 Hz, 1H), 7.45 (s, 2H), 7.21 (d, J = 4.0 Hz, 2H), 7.17-7.10 (m, 1H), 7.06 (s, 1H), 6.80 (d, J = 7.5 Hz, 1H), 5.83 (s, 1H), 4.90 (d, J = 3.8 Hz, 1H), 4.73-4.61 (m, 1H), 4.14-4.04 (m, 2H), 3.99-3.91 (m, 2H), 3.90-3.80 (m, 1H), 3.08-2.96 (m, 1H), 2.82-2.72 (m, 1H), 2.40 (s, 3H), 2.37-2.27 (m, 1H), 2.15-2.07 (m, 1H), 1.99-1.90 (m, 1H), 1.79-1.70 (m, 1H), 1.31-1.20 (m, 1H) | FA: m/z = 529.2 (M + H) |
| I-270 | $^1$H NMR (400 MHz, DMSO-d$_6$) δ 8.82 (d, J = 1.1 Hz, 1H), 8.62 (s, 1H), 8.42-8.36 (m, 1H), 7.44 (s, 2H), 7.30-7.22 (m, 2H), 7.11 (s, 1H), 6.84 (s, 1H), 5.82 (s, 1H), 4.89 (dd, J = 4.6, 1.8 Hz, 1H), 4.75-4.61 (m, 1H), 4.13-4.06 (m, 2H), 4.00-3.91 (m, 2H), 3.87-3.79 (m, 1H), 3.05-2.94 (m, 1H), 2.81-2.72 (m, 1H), 2.41 (s, 3H), 2.38-2.26 (m, 1H), 2.17-2.06 (m, 1H), 2.00-1.91 (m, 1H), 1.80-1.69 (m, 1H), 1.36-1.20 (m, 1H) | FA: m/z = 563.2 (M + H) |
| I-270a | $^1$H NMR (400 MHz, DMSO-d$_6$) δ 8.82 (s, 1H), 8.61 (s, 1H), 8.39 (d, J = 7.5 Hz, 1H), 7.42 (s, 2H), 7.32-7.18 (m, 2H), 7.10 (s, 1H), 6.83 (s, 1H), 5.81 (s, 1H), 4.88 (d, J = 4.4 Hz, 1H), 4.74-4.60 (m, 1H), 4.15-4.02 (m, 2H), 4.02-3.88 (m, 2H), 3.87-3.75 (m, 1H), 3.06-2.91 (m, 1H), 2.76 (d, J = 16.5 Hz, 1H), 2.40 (s, 3H), 2.36-2.26 (m, 1H), 2.09 (d, J = 16.0 Hz, 1H), 2.02-1.90 (m, 1H), 1.82-1.68 (m, 1H), 1.32-1.18 (m, 1H) | FA: m/z = 563.2 (M + H) |
| I-270b | $^1$H NMR (400 MHz, DMSO-d$_6$) δ 8.82 (s, 1H), 8.62 (s, 1H), 8.39 (d, J = 7.5 Hz, 1H), 7.44 (s, 2H), 7.30-7.23 (m, 2H), 7.11 (s, 1H), 6.84 (s, 1H), 5.82 (s, 1H), 4.89 (d, J = 4.5 Hz, 1H), 4.73-4.62 (m, 1H), 4.13-4.05 (m, 2H), 4.00-3.92 (m, 2H), 3.88-3.79 (m, 1H), 3.05-2.94 (m, 1H), 2.81-2.73 (m, 1H), 2.41 (s, 3H), 2.37-2.28 (m, 1H), 2.17-2.06 (m, 1H), 2.01-1.91 (m, 1H), 1.80-1.69 (m, 1H), 1.31-1.20 (m, 1H) | FA: m/z = 563.1 (M + H) |
| I-257 | $^1$H NMR (400 MHz, DMSO-d$_6$) δ 8.61 (s, 1H), 8.59 (s, 1H), 8.19 (d, J = 7.5 Hz, 1H), 7.43 (s, 2H), 7.36 (s, 1H), 7.26 (s, 2H), 6.75 (s, 1H), 5.91 (s, 1H), 4.91-4.85 (m, 1H), 4.75-4.63 (m, 1H), 4.16-4.05 (m, 2H), 4.00-3.91 (m, 2H), 3.88-3.78 (m, 1H), 3.09-2.97 (m, 1H), 2.81-2.72 (m, 1H), 2.48 (s, 3H), 2.36-2.25 (m, 1H), 2.17-2.06 (m, 1H), 2.01-1.88 (m, 1H), 1.82-1.70 (m, 1H), 1.32-1.21 (m, 1H) | FA: m/z = 579.2 (M + H) |
| I-257b | $^1$H NMR (400 MHz, DMSO-d$_6$) δ 8.60 (d, J = 9.1 Hz, 2H), 8.19 (d, J = 7.5 Hz, 1H), 7.44 (s, 2H), 7.36 (s, 1H), 7.29-7.22 (m, 2H), 6.75 (s, 1H), 5.91 (s, 1H), 4.88 (d, J = 4.6 Hz, 1H), 4.75-4.63 (m, 1H), 4.16-4.06 (m, 2H), 4.00-3.92 (m, 2H), 3.88-3.79 (m, 1H), 3.08-2.97 (m, 1H), 2.81-2.73 (m, 1H), 2.48 (s, 3H), 2.37-2.26 (m, 1H), 2.16-2.06 (m, 1H), 1.98-1.89 (m, 1H), 1.80-1.70 (m, 1H), 1.32-1.22 (m, 1H) | FA: m/z = 579.2 (M + H) |
| I-261b | $^1$H NMR (400 MHz, DMSO-d$_6$) δ 8.65 (s, 1H), 8.64 (s, 1H), 8.26 (d, J = 7.5 Hz, 1H), 7.95 (s, 1H), 7.64 (d, J = 1.2 Hz, 1H), 7.44 (s, 2H), 7.30-7.22 (m, 2H), 6.91 (s, 1H), 5.91 (s, 1H), 4.89 (d, J = 4.5 Hz, 1H), 4.77-4.65 (m, 1H), 4.13-4.01 (m, 2H), 4.01-3.91 (m, 2H), 3.87-3.78 (m, 1H), 3.01-2.91 (m, 1H), 2.83-2.74 (m, 1H), 2.37-2.28 (m, 1H), 2.18-2.09 (m, 1H), 1.99-1.91 (m, 1H), 1.81-1.72 (m, 1H), 1.34-1.23 (m, 1H) | FA: m/z = 565.1 (M + H) |
| I-259 | $^1$H NMR (400 MHz, DMSO-d$_6$) δ 8.63-8.58 (m, 2H), 8.30-8.22 (m, 1H), 7.49-7.41 (m, 3H), 7.36 (d, J = 8.1 Hz, 1H), 7.15 (d, J = 8.3 Hz, 1H), 6.83 (s, 1H), 5.27 (s, 1H), 4.93-4.82 (m, 1H), 4.75-4.67 (m, 1H), 4.49-4.38 (m, 1H), 4.09-4.00 (m, 1H), 3.99-3.91 (m, 1H), 3.81-3.73 (m, 1H), 3.71-3.65 (m, 1H), 3.27-3.14 (m, 1H), 3.06-2.96 (m, 1H), 2.96-2.83 (m, 1H), 2.78-2.68 (m, 1H), 2.29-2.10 (m, 2H), 1.19-1.07 (m, 1H) | FA: m/z = 658.1 (M + H) |

| Compound No. | ¹H NMR | LC/MS |
|---|---|---|
| I-251 | ¹H NMR (400 MHz, DMSO-$d_6$) δ 8.62 (s, 1H), 8.58 (s, 1H), 8.17 (dd, J = 7.4, 5.0 Hz, 1H), 7.49-7.40 (m, 3H), 7.37-7.31 (m, 1H), 7.13 (d, J = 8.2 Hz, 1H), 6.82 (s, 1H), 5.22 (s, 1H), 4.92-4.86 (m, 1H), 4.73-4.61 (m, 1H), 4.11-4.03 (m, 1H), 3.99-3.88 (m, 2H), 3.17 (d, J = 5.2 Hz, 2H), 3.02-2.82 (m, 2H), 2.69 (d, J = 16.3 Hz, 1H), 2.34-2.21 (m, 1H), 2.15-2.03 (m, 1H), 1.99-1.85 (m, 1H), 1.80-1.67 (m, 1H), 1.31-1.19 (m, 1H) | FA: m/z = 642.1 (M + H) |
| I-333 | ¹H NMR (400 MHz, Methanol-$d_4$) δ 8.71 (s, 1H), 8.59 (s, 1H), 7.82 (s, 1H), 7.62 (d, J = 1.1 Hz, 1H), 7.32 (s, 1H), 6.00 (s, 1H), 4.85-4.76 (m, 1H), 4.28-4.10 (m, 6H), 4.11-4.01 (m, 1H), 2.51 (dt, J = 13.7, 7.6 Hz, 1H), 2.34-2.21 (m, 1H), 2.16 (ddd, J = 12.4, 7.5, 4.4 Hz, 1H), 1.97-1.86 (m, 1H), 1.71 (s, 3H), 1.43 (dt, J = 13.0, 9.1 Hz, 1H) | FA: m/z = 535.1 (M + H) |
| I-332 | ¹H NMR (400 MHz, Methanol-$d_4$) δ 8.73 (s, 1H), 8.59 (s, 1H), 7.92 (s, 1H), 7.67 (s, 1H), 5.94 (s, 1H), 5.79 (s, 1H), 4.82-4.76 (m, 1H), 4.34-4.05 (m, 7H), 2.51 (dt, J = 13.8, 7.7 Hz, 1H), 2.34-2.23 (m, 1H), 2.21 (s, 3H), 2.19-2.11 (m, 1H), 1.91 (dt, J = 14.0, 7.6 Hz, 1H), 1.50-1.38 (m, 1H) | FA: m/z = 535.2 (M + H) |
| I-299 | ¹H NMR (400 MHz, Methanol-$d_4$) δ 8.96 (s, 0.5H), 8.95 (s, 0.5H), 8.58 (s, 1H), 7.26-7.15 (m, 3H), 6.84 (s, 1H), 5.15 (s, 1H), 4.85-4.74 (m, 1H), 4.24-4.10 (m, 3H), 3.28-3.22 (m, 1H), 3.16-2.94 (m, 2H), 2.91-2.78 (m, 1H), 2.56-2.44 (m, 1H), 2.32-2.20 (m, 1H), 2.20-2.09 (m, 1H), 1.96-1.84 (m, 1H), 1.49-1.36 (m, 1H) | FA: m/z = 582.1 (M + H) |
| I-299a | ¹H NMR (400 MHz, Methanol-$d_4$) δ 8.95 (s, 1H), 8.57 (s, 1H), 7.26-7.14 (m, 3H), 6.84 (s, 1H), 5.12 (s, 1H), 4.82-4.74 (m, 1H), 4.24-4.10 (m, 3H), 3.28-3.21 (m, 1H), 3.12-2.91 (m, 2H), 2.89-2.76 (m, 1H), 2.50 (dt, J = 13.9, 7.6 Hz, 1H), 2.32-2.19 (m, 1H), 2.14 (ddd, J = 12.4, 7.4, 4.4 Hz, 1H), 1.89 (dt, J = 13.7, 7.6 Hz, 1H), 1.42 (dt, J = 13.0, 9.1 Hz, 1H) | FA: m/z = 582.1 (M + H) |
| I-299b | ¹H NMR (400 MHz, Methanol-$d_4$) δ 8.96 (s, 1H), 8.57 (s, 1H), 7.25-7.15 (m, 3H), 6.83 (s, 1H), 5.12 (s, 1H), 4.84-4.73 (m, 1H), 4.24-4.10 (m, 3H), 3.28-3.21 (m, 1H), 3.13-2.93 (m, 2H), 2.83 (dt, J = 16.2, 4.4 Hz, 1H), 2.49 (dt, J = 13.4, 7.6 Hz, 1H), 2.33-2.20 (m, 1H), 2.15 (ddd, J = 12.4, 7.3, 4.2 Hz, 1H), 1.96-1.85 (m, 1H), 1.42 (dt, J = 13.1, 9.1 Hz, 1H) | FA: m/z = 582.1 (M + H) |
| I-271a | ¹H NMR (400 MHz, Methanol-$d_4$) δ 8.66 (s, 1H), 8.57 (s, 1H), 7.26 (s, 1H), 7.20-7.16 (m, 2H), 7.15-7.09 (m, 1H), 6.77 (d, J = 7.6 Hz, 1H), 5.93 (s, 1H), 4.85-4.74 (m, 1H), 4.26-4.12 (m, 3H), 4.08 (dd, J = 20.5, 5.1 Hz, 1H), 4.00-3.89 (m, 1H), 3.17-3.04 (m, 2H), 2.88-2.76 (m, 1H), 2.54 (s, 3H), 2.44 (dt, J = 15.0, 7.1 Hz, 1H), 2.33-2.20 (m, 1H), 1.65-1.50 (m, 1H) | FA: m/z = 563.1 (M + H) |
| I-256 | ¹H NMR (400 MHz, Methanol-$d_4$) δ 8.59 (s, 1H), 8.52 (s, 1H), 7.24 (s, 1H), 7.22-7.16 (m, 2H), 7.12 (dt, J = 8.4, 4.2 Hz, 1H), 6.76 (d, J = 7.7 Hz, 1H), 5.93 (s, 1H), 4.81-4.71 (m, 1H), 4.26-4.10 (m, 4H), 4.01-3.88 (m, 1H), 3.17-3.04 (m, 1H), 2.87-2.75 (m, 1H), 2.53 (s, 3H), 2.53-2.42 (m, 1H), 2.32-2.20 (m, 1H), 2.12 (d, J = 6.2 Hz, 1H), 1.95-1.81 (m, 1H), 1.48-1.34 (m, 1H) | FA: m/z = 545.5 (M + H) |
| I-256a | ¹H NMR (400 MHz, Methanol-$d_4$) δ 8.59 (s, 1H), 8.52 (s, 1H), 7.23 (s, 1H), 7.20-7.16 (m, 2H), 7.15-7.08 (m, 1H), 6.76 (d, J = 7.6 Hz, 1H), 5.92 (s, 1H), 4.82-4.70 (m, 1H), 4.24-4.10 (m, 4H), 4.01-3.88 (m, 1H), 3.10 (ddd, J = 15.9, 9.8, 5.5 Hz, 1H), 2.88-2.75 (m, 1H), 2.53 (s, 3H), 2.48 (dt, J = 14.5, 7.8 Hz, 1H), 2.31-2.19 (m, 1H), 2.13 (ddd, J = 12.3, 7.3, 4.1 Hz, 1H), 1.88 (dt, J = 13.6, 7.6 Hz, 1H), 1.39 (dt, J = 13.1, 9.1 Hz, 1H) | FA: m/z = 545.2 (M + H) |
| I-256b | ¹H NMR (400 MHz, Methanol-$d_4$) δ 8.59 (s, 1H), 8.53 (s, 1H), 7.24 (s, 1H), 7.22-7.15 (m, 2H), 7.16-7.07 (m, 1H), 6.76 (d, J = 7.6 Hz, 1H), 5.93 (s, 1H), 4.83-4.70 (m, 1H), 4.24-4.10 (m, 4H), 4.01-3.89 (m, 1H), 3.16-3.03 (m, 1H), 2.87-2.76 (m, 1H), 2.54 (s, 3H), 2.52-2.43 (m, 1H), 2.31-2.19 (m, 1H), 2.13 (ddd, J = 12.7, 7.4, 4.2 Hz, 1H), 1.88 (dt, J = 13.6, 7.2 Hz, 1H), 1.40 (dt, J = 13.1, 9.1 Hz, 1H) | FA: m/z = 545.2 (M + H) |
| I-250 | ¹H NMR (400 MHz, Methanol-$d_4$) δ 8.61 (s, 0.5H), 8.60 (s, 0.5H), 8.53 (s, 1H), 7.24 (s, 1H), 7.21-7.15 (m, 2H), 7.16-7.07 (m, 1H), 6.76 (d, J = 7.7 Hz, 1H), 5.93 | FA: m/z = 561.5 (M + H) |

| Compound No. | ¹H NMR | LC/MS |
|---|---|---|
| | (s, 1H), 4.59-4.49 (m, 1H), 4.24-4.12 (m, 3H), 4.00-3.87 (m, 3H), 3.16-3.04 (m, 1H), 2.86-2.76 (m, 1H), 2.54 (s, 3H), 2.52-2.43 (m, 1H), 2.41-2.29 (m, 1H), 1.40-1.29 (m, 1H) | |
| I-250a | ¹H NMR (400 MHz, Methanol-d₄) δ 8.61 (s, 1H), 8.53 (s, 1H), 7.25 (s, 1H), 7.22-7.16 (m, 2H), 7.17-7.08 (m, 1H), 6.77 (d, J = 7.5 Hz, 1H), 5.93 (s, 1H), 4.59-4.48 (m, 1H), 4.24-4.12 (m, 3H), 4.00-3.86 (m, 3H), 3.12-3.04 (m, 1H), 2.88-2.76 (m, 1H), 2.54 (s, 3H), 2.47 (dt, J = 13.0, 8.4 Hz, 1H), 2.42-2.28 (m, 1H), 1.34 (dt, J = 13.2, 8.7 Hz, 1H) | FA: m/z = 561.2 (M + H) |
| I-250b | ¹H NMR (400 MHz, Methanol-d₄) δ 8.59 (s, 1H), 8.53 (s, 1H), 7.24 (s, 1H), 7.22-7.15 (m, 2H), 7.16-7.07 (m, 1H), 6.76 (d, J = 7.6 Hz, 1H), 5.93 (s, 1H), 4.83-4.70 (m, 1H), 4.24-4.10 (m, 4H), 4.01-3.89 (m, 1H), 3.16-3.03 (m, 1H), 2.87-2.76 (m, 1H), 2.54 (s, 3H), 2.52-2.43 (m, 1H), 2.31-2.19 (m, 1H), 2.13 (ddd, J = 12.7, 7.4, 4.2 Hz, 1H), 1.88 (dt, J = 13.6, 7.2 Hz, 1H), 1.40 (dt, J = 13.1, 9.1 Hz, 1H) | FA: m/z = 561.2 (M + H) |
| I-319 | ¹H NMR (400 MHz, Methanol-d₄) δ 8.85 (s, 1H), 8.59 (s, 1H), 7.70 (s, 1H), 7.24 (d, J = 7.3 Hz, 1H), 7.16 (t, J = 7.3 Hz, 1H), 7.05 (t, J = 7.5 Hz, 1H), 6.56 (d, J = 7.7 Hz, 1H), 5.38 (s, 1H), 4.82-4.76 (m, 1H), 4.28-4.12 (m, 3H), 3.46-3.35 (m, 1H), 3.26-3.18 (m, 1H), 3.05-2.92 (m, 1H), 2.59-2.45 (m, 1H), 2.37-2.22 (m, 1H), 2.22-2.11 (m, 1H), 2.08-1.86 (m, 2H), 1.75-1.57 (m, 1H), 1.53-1.38 (m, 1H) | FA: m/z = 578.4 (M + H) |
| I-283 | ¹H NMR (400 MHz, Methanol-d₄) δ 8.73 (s, 1H), 8.57 (s, 1H), 7.67 (s, 1H), 7.58 (s, 1H), 7.19 (d, J = 3.9 Hz, 2H), 7.17-7.07 (m, 1H), 6.89 (d, J = 7.6 Hz, 1H), 5.32 (s, 1H), 4.83-4.73 (m, 1H), 4.26-4.11 (m, 3H), 3.26-3.16 (m, 1H), 3.15-2.90 (m, 3H), 2.56-2.45 (m, 1H), 2.33-2.21 (m, 1H), 2.22-2.09 (m, 1H), 1.95-1.85 (m, 1H), 1.49-1.36 (m, 1H) | FA: m/z = 530.4 (M + H) |
| I-283a | ¹H NMR (400 MHz, Methanol-d₄) δ 8.73 (s, 1H), 8.56 (s, 1H), 7.64 (s, 1H), 7.57 (s, 1H), 7.21-7.13 (m, 2H), 7.14-7.05 (m, 1H), 6.87 (d, J = 7.7 Hz, 1H), 5.25 (s, 1H), 4.82-4.74 (m, 1H), 4.25-4.10 (m, 3H), 3.23-3.13 (m, 1H), 3.10-2.81 (m, 3H), 2.50 (dt, J = 13.9, 7.7 Hz, 1H), 2.32-2.20 (m, 1H), 2.14 (ddd, J = 12.5, 7.4, 4.4 Hz, 1H), 1.89 (dt, J = 14.9, 7.5 Hz, 1H), 1.42 (dt, J = 13.0, 9.1 Hz, 1H) | FA: m/z = 530.6 (M + H) |
| I-283b | ¹H NMR (400 MHz, Methanol-d₄) δ 8.73 (s, 1H), 8.56 (s, 1H), 7.64 (s, 1H), 7.57 (s, 1H), 7.22-7.13 (m, 2H), 7.15-7.05 (m, 1H), 6.88 (d, J = 7.7 Hz, 1H), 5.25 (s, 1H), 4.82-4.74 (m, 1H), 4.25-4.10 (m, 3H), 3.23-3.14 (m, 1H), 3.10-2.82 (m, 3H), 2.50 (dt, J = 14.0, 7.7 Hz, 1H), 2.32-2.20 (m, 1H), 2.19-2.10 (m, 1H), 1.96-1.85 (m, 1H), 1.42 (dt, J = 12.8, 9.2 Hz, 1H) | FA: m/z = 530.6 (M + H) |
| I-116 | ¹H NMR (400 MHz, Methanol-d₄) δ 8.68 (s, 1H), 8.58 (s, 1H), 7.72 (s, 1H), 7.50 (s, 1H), 5.81 (s, 1H), 4.83-4.74 (m, 1H), 4.24-4.12 (m, 3H), 3.96-3.84 (m, 2H), 2.50 (dt, J = 14.1, 7.7 Hz, 1H), 2.35-2.11 (m, 4H), 2.06 (s, 2H), 2.00-1.84 (m, 5H), 1.56 (s, 4H), 1.48-1.36 (m, 1H) | FA: m/z = 549.2 (M + H) |
| I-166 | ¹H NMR (400 MHz, Methanol-d₄) δ 8.70 (s, 1H), 8.59 (s, 1H), 7.66 (s, 1H), 7.54 (s, 1H), 4.82-4.75 (m, 1H), 4.24-4.12 (m, 3H), 3.93-3.84 (m, 1H), 3.83-3.74 (m, 1H), 2.51 (dt, J = 14.0, 7.7 Hz, 1H), 2.32-2.21 (m, 2H), 2.21-2.11 (m, 1H), 2.11-2.02 (m, 1H), 1.97-1.57 (m, 7H), 1.43 (dt, J = 12.9, 9.1 Hz, 1H), 1.34-1.16 (m, 4H), 1.10-0.96 (m, 2H), 0.87-0.76 (m, 1H) | FA: m/z = 551.2 (M + H) |
| I-238 | ¹H NMR (400 MHz, Methanol-d₄) δ 8.73 (s, 1H), 8.59 (s, 1H), 7.73 (d, J = 1.3 Hz, 1H), 7.62 (d, J = 1.4 Hz, 1H), 4.81-4.75 (m, 1H), 4.23-4.12 (m, 3H), 3.94-3.83 (m, 2H), 2.51 (dt, J = 13.8, 7.7 Hz, 1H), 2.31-2.07 (m, 4H), 2.05-1.79 (m, 3H), 1.43 (dt, J = 13.0, 9.1 Hz, 1H), 1.33-1.24 (m, 1H), 0.52-0.44 (m, 1H), 0.43-0.30 (m, 3H) | FA: m/z = 509.1 (M + H) |
| I-58 | ¹H NMR (400 MHz, MeOD) δ 9.00 (s, 1H), 8.57 (s, 1H), 7.77 (s, 1H), 7.55-7.45 (m, 2H), 7.37-7.29 (m, 2H), 7.29-7.20 (m, 1H), 4.82-4.73 (m, 1H), 4.25-4.13 (m, 3H), 2.50 (dt, J = 12.8, 7.6 Hz, 1H), 2.32-2.20 (m, 1H), 2.20-2.09 (m, 1H), 1.95-1.89 (m, 1H), 1.87 (s, 3H) 1.42 (dt, J = 12.8, 9.2 Hz, 1H) | FA: m/z = 503.3 (M + H) |
| I-58a | ¹H NMR (400 MHz, MeOD) δ 9.03 (s, 1H), 8.56 (s, 1H), 7.77 (d, J = 0.8 Hz, 1H), 7.55-7.44 (m, 2H), 7.36- | FA: m/z = 503.5 (M + H) |

| Compound No. | ¹H NMR | LC/MS |
|---|---|---|
| | 7.30 (m, 2H), 7.30-7.19 (m, 2H), 4.81-4.73 (m, 1H), 4.25-4.09 (m, 3H), 2.50 (dt, J = 13.2, 7.6 Hz, 1H), 2.32-2.21 (m, 1H), 2.20-2.10 (m, 1H), 1.96-1.84 (m, 1H), 1.88 (s, 3H), 1.41 (dt, J = 13.2, 8.8 Hz, 1H) | |
| I-58b | ¹H NMR (400 MHz, MeOD) δ 9.02 (s, 1H), 8.54 (s, 1H), 7.77 (d, J = 0.8 Hz, 1H), 7.53-7.46 (m, 2H), 7.37-7.30 (m, 2H), 7.30-7.21 (m, 2H), 4.82-4.72 (m, 1H), 4.25-4.11 (m, 3H), 2.56-2.45 (m, 1H), 2.32-2.21 (m, 1H), 2.20-2.10 (m, 1H), 1.95-1.84 (m, 1H), 1.88 (s, 3H), 1.41 (dt, J = 13.2, 8.8 Hz, 1H) | FA: m/z = 503.5 (M + H) |
| I-212 | ¹H NMR (400 MHz, MeOD) δ 9.07 (s, 1H), 8.58 (s, 1H), 7.36 (d, J = 3.2 Hz, 1H), 6.67 (d, J = 3.2 Hz, 1H), 4.82-4.72 (m, 1H), 4.52 (s, 2H), 4.27-4.08 (m, 3H), 3.39 (s, 3H), 2.52 (dt, J = 13.6, 7.6 Hz, 1H), 2.33-2.21 (m, 1H), 2.22-2.10 (m, 1H), 1.99-1.82 (m, 1H), 1.44 (dt, J = 12.8, 9.2 Hz, 1H) | FA: m/z = 421.4 (M + H) |
| I-206 | ¹H NMR (400 MHz, MeOD) δ 9.09 (s, 1H), 8.57 (s, 1H), 7.36 (d, J = 3.6 Hz, 1H), 6.60 (d, J = 3.6 Hz, 1H), 4.82-4.75 (m, 1H), 4.64 (s, 2H), 4.26-4.10 (m, 3H), 2.52 (dt, J = 13.2, 7.6 Hz, 1H), 2.33-2.22 (m, 1H), 2.22-2.11 (m, 1H), 1.97-1.86 (m, 1H), 1.44 (dt, J = 12.8, 9.2, 1H) | FA: m/z = 413.2 (M + H) |
| I-220 | ¹H NMR (400 MHz, MeOD) δ 9.07 (s, 1H), 8.58 (s, 1H), 7.80 (s, 1H), 7.39 (s, 1H), 4.82-4.76 (m, 1H), 4.25-4.12 (m, 3H), 2.59-2.45 (m, 1H), 2.34-2.22 (m, 1H), 2.21-2.11 (m, 1H), 1.98-1.87 (m, 1H), 1.54 (s, 6H), 1.48-1.39 (m, 1H) | FA: m/z = 397.3 (M + H) |
| I-216 | ¹H NMR (400 MHz, MeOD) δ 9.04 (s, 1H), 8.58 (s, 1H), 7.84 (s, 1H), 7.39 (s, 1H), 4.81-4.75 (m, 1H), 4.55 (s, 2H), 4.28-4.10 (m, 3H), 2.59-2.45 (m, 1H), 2.34-2.21 (m, 1H), 2.21-2.10 (m, 1H), 1.97-1.84 (m, 1H), 1.43 (dt, J = 12.8, 9.6 Hz, 1H) | FA: m/z = 413.2 (M + H) |
| I-208 | ¹H NMR (400 MHz, MeOD) δ 9.13 (s, 1H), 8.63 (s, 1H), 8.49 (d, J = 0.6 Hz, 1H), 7.97-7.91 (m, 2H), 7.74 (d, J = 0.6 Hz, 1H), 7.72-7.66 (m, 1H), 7.61-7.57 (m, 2H), 4.84-4.77 (m, 1H), 4.28-4.13 (m, 3H), 2.59-2.49 (m, 1H), 2.35-2.23 (m, 1H), 2.23-2.14 (m, 1H), 2.00-1.88 (m, 1H), 1.47 (dt, J = 13.1, 9.1 Hz, 1H) | FA: m/z = 487.4 (M + H) |
| I-189 | ¹H NMR (400 MHz, Methanol-d₄) δ 8.71 (s, 1H), 8.58 (s, 1H), 7.67 (s, 1H), 7.62-7.41 (m, 4H), 4.82-4.74 (m, 1H), 4.28-4.09 (m, 3H), 2.59-2.44 (m, 1H), 2.33-2.19 (m, 1H), 2.22-2.08 (m, 1H), 1.91 (dt, J = 13.5, 7.2 Hz, 1H), 1.43 (dt, J = 13.1, 9.1 Hz, 1H) | FA: m/z = 609.1 (M + H) |
| I-122 | ¹H NMR (400 MHz, Methanol-d₄) δ 8.65 (s, 1H), 8.59 (s, 1H), 8.11 (s, 1H), 8.01 (d, J = 7.5 Hz, 1H), 7.90 (d, J = 7.8 Hz, 1H), 7.81 (t, J = 7.8 Hz, 1H), 7.67 (d, J = 1.5 Hz, 1H), 4.83-4.73 (m, 1H), 4.25-4.09 (m, 3H), 2.56-2.39 (m, 1H), 2.25 (d, J = 5.7 Hz, 1H), 2.20-2.07 (m, 1H), 1.96-1.80 (m, 1H), 1.49-1.34 (m, 1H) | FA: m/z = 625.1 (M + H) |
| I-277b | ¹H NMR (400 MHz, Methanol-d4) δ 8.59 (s, 1H), 8.52 (s, 1H), 7.24 (s, 1H), 7.04 (d, J = 7.9 Hz, 1H), 6.85 (dd, J = 7.9, 1.7 Hz, 1H), 6.47 (s, 1H), 5.86 (s, 1H), 4.80-4.70 (m, 1H), 4.21-4.09 (m, 4H), 3.93-3.84 (m, 1H), 3.07-2.96 (m, 1H), 2.78-2.69 (m, 1H), 2.51 (s, 3H), 2.49-2.42 (m, 1H), 2.29-2.19 (m, 1H), 2.17-2.07 (m, 1H), 1.91-1.83 (m, 1H), 1.78-1.71 (m, 1H), 1.43-1.33 (m, 1H), 0.87-0.82 (m, 2H), 0.56-0.44 (m, 2H). | FA: m/z = 585.3 (M + H) |
| I-277a | ¹H NMR (400 MHz, Methanol-d4) δ 8.60 (s, 1H), 8.53 (s, 1H), 7.25 (s, 1H), 7.05 (d, J = 8.0 Hz, 1H), 6.86 (dd, J = 7.9, 1.7 Hz, 1H), 6.48 (s, 1H), 5.87 (s, 1H), 4.81-4.71 (m, 1H), 4.21-4.10 (m, 4H), 3.93-3.85 (m, 1H), 3.08-2.98 (m, 1H), 2.79-2.71 (m, 1H), 2.52 (s, 3H), 2.50-2.44 (m, 1H), 2.30-2.20 (m, 1H), 2.16-2.08 (m, 1H), 1.93-1.84 (m, 1H), 1.80-1.71 (m, 1H), 1.45-1.35 (m, 1H), 0.89-0.82 (m, 2H), 0.56-0.45 (m, 2H). | FA: m/z = 585.3 (M + H) |
| I-277 | ¹H NMR (400 MHz, Methanol-d4) δ 8.59 (s, 1H), 8.51 (s, 1H), 7.24 (s, 1H), 7.03 (d, J = 8.0 Hz, 1H), 6.83 (dd, J = 7.9, 1.6 Hz, 1H), 6.47 (s, 1H), 5.84 (s, 1H), 4.79-4.68 (m, 1H), 4.22-4.06 (m, 4H), 3.91-3.83 (m, 1H), 3.06-2.96 (m, 1H), 2.76-2.69 (m, 1H), 2.50 (s, 3H), 2.48-2.40 (m, 1H), 2.23 (dt, J = 14.1, 7.2 Hz, 1H), 2.17-2.08 (m, 1H), 1.91-1.82 (m, 1H), 1.76-1.69 (m, 1H), 1.43-1.33 (m, 1H), 0.86-0.79 (m, 2H), 0.55-0.44 (m, 2H). | FA: m/z = 585.5 (M + H) |

| Compound No. | ¹H NMR | LC/MS |
|---|---|---|
| I-329 | ¹H NMR (400 MHz, Methanol-d4) δ 8.60 (s, 1H), 8.53 (s, 1H), 8.43 (s, 1H), 7.31 (s, 2H), 7.23 (d, J = 9.7 Hz, 1H), 6.91 (s, 1H), 5.94 (s, 1H), 4.80-4.69 (m, 1H), 4.22-4.12 (m, 4H), 3.98-3.90 (m, 1H), 3.17-3.08 (m, 1H), 2.86 (d, J = 16.7 Hz, 1H), 2.68 (s, 6H), 2.66 (s, 1H), 2.54 (d, J = 6.2 Hz, 3H), 2.51-2.43 (m, 1H), 2.29-2.19 (m, 1H), 2.16-2.08 (m, 1H), 1.93-1.83 (m, 1H), 1.46-1.36 (m, 1H). | FA: m/z = 602.0 (M + H) |
| I-252a | ¹H NMR (400 MHz, Methanol-d4) δ 8.62 (s, 1H), 8.52 (s, 1H), 7.31-7.24 (m, 2H), 7.17 (d, J = 7.9 Hz, 1H), 6.82 (s, 1H), 5.86 (s, 1H), 4.80-4.71 (m, 1H), 4.23-4.11 (m, 4H), 3.96-3.86 (m, 1H), 3.37 (s, 1H), 3.17-3.02 (m, 1H), 2.81 (d, J = 16.9 Hz, 1H), 2.51 (s, 3H), 2.46 (dd, J = 13.4, 7.2 Hz, 1H), 2.29-2.20 (m, 1H), 2.17-2.10 (m, 1H), 1.92-1.84 (m, 1H), 1.42-1.33 (m, 1H). | FA: m/z = 569.2 (M + H) |
| I-252b | ¹H NMR (400 MHz, Methanol-d4) δ 8.65 (s, 1H), 8.57 (s, 1H), 7.32 (d, J = 14.2 Hz, 2H), 7.22 (d, J = 8.0 Hz, 1H), 6.85 (s, 1H), 5.92 (s, 1H), 4.83-4.77 (m, 1H), 4.21 (dd, J = 9.6, 5.7 Hz, 2H), 4.18-4.11 (m, 2H), 3.99-3.90 (m, 1H), 3.51 (s, 1H), 3.14 (s, 1H), 2.84 (d, J = 16.9 Hz, 1H), 2.55 (s, 3H), 2.49 (dd, J = 14.1, 6.8 Hz, 1H), 2.26 (d, J = 5.7 Hz, 1H), 2.19-2.08 (m, 1H), 1.93-1.84 (m, 1H), 1.42 (dt, J = 13.1, 9.3 Hz, 1H). | FA: m/z = 569.2 (M + H) |
| I-252 | ¹H NMR (400 MHz, Methanol-d4) δ 8.61 (s, 1H), 8.52 (s, 1H), 7.31-7.24 (m, 2H), 7.16 (d, J = 7.9 Hz, 1H), 6.81 (s, 1H), 5.86 (s, 1H), 4.79-4.69 (m, 1H), 4.23-4.11 (m, 4H), 3.96-3.87 (m, 1H), 3.36 (s, 1H), 3.11 (ddd, J = 16.2, 10.1, 5.8 Hz, 1H), 2.80 (d, J = 16.9 Hz, 1H), 2.51 (s, 3H), 2.49-2.40 (m, 1H), 2.28-2.18 (m, 1H), 2.17-2.06 (m, 1H), 1.91-1.80 (m, 1H), 1.55-1.46 (m, 1H). | FA: m/z = 569.4 (M + H) |
| I-288 | ¹H NMR (400 MHz, Methanol-d4) δ 8.68 (s, 1H), 8.56 (s, 1H), 7.76 (dd, J = 8.4, 1.3 Hz, 1H), 7.50 (dd, J = 8.4, 2.0 Hz, 1H), 7.37 (s, 1H), 6.90 (s, 1H), 6.02 (d, J = 3.6 Hz, 1H), 4.84-4.74 (m, 1H), 4.39-4.31 (m, 1H), 4.24-4.11 (m, 4H), 2.51 (s, 3H), 2.50-2.42 (m, 1H), 2.31-2.22 (m, 1H), 2.20-2.10 (m, 1H), 1.96-1.85 (m, 1H), 1.48-1.37 (m, 1H). | FA: m/z = 615.0 (M + H) |
| I-264a | ¹H NMR (400 MHz, Methanol-d4) δ 8.68 (s, 1H), 8.57 (s, 1H), 7.30 (s, 1H), 7.18 (d, J = 1.2 Hz, 2H), 6.73 (s, 1H), 5.88 (s, 1H), 4.84-4.72 (m, 1H), 4.23-4.12 (m, 3H), 4.12-4.02 (m, 1H), 3.91 (ddd, J = 11.5, 10.1, 3.8 Hz, 1H), 3.13-3.01 (m, 1H), 2.82-2.73 (m, 1H), 2.52 (s, 3H), 2.47-2.37 (m, 1H), 2.30-2.18 (m, 1H), 1.61-1.49 (m, 1H). | FA: m/z = 597.4 (M + H) |
| I-264b | ¹H NMR (400 MHz, Methanol-d4) δ 8.71 (s, 1H), 8.59 (s, 1H), 7.32 (s, 1H), 7.20 (d, J = 1.2 Hz, 2H), 6.75 (s, 1H), 5.90 (s, 1H), 4.83-4.75 (m, 1H), 4.25-4.13 (m, 3H), 4.09 (dd, J = 20.4, 5.1 Hz, 1H), 3.93 (ddd, J = 11.5, 10.1, 3.9 Hz, 1H), 3.09 (ddd, J = 15.7, 9.9, 6.2 Hz, 1H), 2.85-2.75 (m, 1H), 2.53 (s, 3H), 2.46 (dt, J = 14.4, 7.1 Hz, 1H), 2.28 (dq, J = 12.8, 5.9 Hz, 1H), 1.59 (q, J = 11.5 Hz, 1H). | FA: m/z = 597.4 (M + H) |
| I-264 | ¹H NMR (400 MHz, Methanol-d4) δ 8.71 (s, 1H), 8.59 (s, 1H), 7.32 (s, 1H), 7.20 (d, J = 1.2 Hz, 2H), 6.76 (s, 1H), 5.91 (s, 1H), 4.84-4.76 (m, 1H), 4.19 (ddd, J = 14.6, 6.0, 3.3 Hz, 3H), 4.09 (dd, J = 20.5, 5.0 Hz, 1H), 3.97-3.89 (m, 1H), 3.14-3.03 (m, 1H), 2.84-2.75 (m, 1H), 2.53 (s, 3H), 2.50-2.39 (m, 1H), 2.34-2.22 (m, 1H), 1.64-1.53 (m, 1H). | FA: m/z = 597.2 (M + H) |
| I-325 | ¹H NMR (400 MHz, Methanol-d4) δ 8.75 (s, 1H), 8.59 (s, 1H), 7.60 (d, J = 3.7 Hz, 1H), 7.36 (d, J = 7.9 Hz, 1H), 7.23-7.12 (m, 2H), 7.03 (d, J = 7.4 Hz, 1H), 6.13 (s, 1H), 4.83-4.74 (m, 1H), 4.23-4.09 (m, 4H), 4.03-3.93 (m, 1H), 2.96-2.89 (m, 2H), 2.55-2.44 (m, 1H), 2.31-2.10 (m, 2H), 1.95-1.84 (m, 1H), 1.46-1.36 (m, 1H). | FA: m/z = 565.2 (M + H) |
| I-282a | ¹H NMR (400 MHz, Methanol-d4) δ 8.60 (s, 1H), 8.54 (s, 1H), 7.29 (s, 1H), 7.20 (d, J = 1.5 Hz, 2H), 6.76 (s, 1H), 5.94 (s, 1H), 4.81-4.72 (m, 1H), 4.25-4.10 (m, 4H), 3.97-3.88 (m, 1H), 3.15-3.07 (m, 1H), 2.82-2.72 (m, 1H), 2.51-2.40 (m, 1H), 2.29-2.18 (m, 1H), 2.17-2.07 (m, 1H), 1.94-1.82 (m, 1H), 1.44-1.33 (m, 1H). | FA: m/z = 599.2 (M + H) |

-continued

| Compound No. | ¹H NMR | LC/MS |
|---|---|---|
| I-282b | ¹H NMR (400 MHz, Methanol-d4) δ 8.61 (s, 1H), 8.55 (s, 1H), 7.30 (s, 1H), 7.21 (d, J = 1.5 Hz, 2H), 6.77 (s, 1H), 5.95 (s, 1H), 4.83-4.73 (m, 1H), 4.27-4.13 (m, 4H), 3.98-3.88 (m, 1H), 3.15-3.06 (m, 1H), 2.83-2.74 (m, 1H), 2.53-2.43 (m, 1H), 2.30-2.21 (m, 1H), 2.17-2.07 (m, 1H), 1.92-1.83 (m, 1H), 1.47-1.36 (m, 1H). | FA: m/z = 599.2 (M + H) |
| I-282 | ¹H NMR (400 MHz, Methanol-d4) δ 8.59 (s, 1H), 8.53 (s, 1H), 7.30 (s, 1H), 7.18 (d, J = 1.1 Hz, 2H), 6.75 (s, 1H), 5.91 (s, 1H), 4.81-4.68 (m, 1H), 4.26-4.10 (m, 4H), 3.96-3.86 (m, 1H), 3.15-3.01 (m, 1H), 2.81-2.71 (m, 1H), 2.52-2.39 (m, 1H), 2.29-2.19 (m, 1H), 2.17-2.06 (m, 1H), 1.92-1.80 (m, 1H), 1.58-1.45 (m, 1H). | FA: m/z = 599.4 (M + H) |
| I-41a | ¹H NMR (400 MHz, MeOD) δ 8.66 (s, 1H), 8.55 (d, J = 3.9 Hz, 1H), 7.40 (s, 1H), 7.28 (t, J = 7.9 Hz, 1H), 7.21 (d, J = 6.9 Hz, 2H), 7.13 (d, J = 7.5 Hz, 1H), 5.22 (t, J = 7.1 Hz, 1H), 4.77 (dd, J = 15.9, 8.1 Hz, 1H), 4.22-4.12 (m, 3H), 4.11-4.05 (m, 1H), 4.04-3.93 (m, 2H), 3.88 (dd, J = 14.6, 7.4 Hz, 1H), 2.53-2.44 (m, 1H), 2.36-2.22 (m, 2H), 2.16-2.05 (m, 2H), 2.04 (s, 1H), 1.93-1.84 (m, 1H), 1.81-1.70 (m, 1H), 1.46-1.36 (m, 1H). | FA: m/z = 593.4 (M + H) |
| I-41b | ¹H NMR (400 MHz, MeOD) δ 8.65 (s, 1H), 8.55 (s, 1H), 7.39 (s, 1H), 7.30-7.24 (m, 1H), 7.20 (d, J = 6.9 Hz, 2H), 7.13 (d, J = 7.4 Hz, 1H), 5.21 (t, J = 7.1 Hz, 1H), 4.77 (dd, J = 7.8 Hz, 1H), 4.22-4.11 (m, 3H), 4.10-4.04 (m, 1H), 4.04-3.92 (m, 2H), 3.88 (dd, J = 14.6, 7.4 Hz, 1H), 2.53-2.44 (m, 1H), 2.36-2.22 (m, 2H), 2.17-2.05 (m, 2H), 2.04 (s, 1H), 1.93-1.84 (m, 1H), 1.80-1.70 (m, 1H), 1.45-1.35 (m, 1H). | FA: m/z = 593.4 (M + H) |
| I-154 | ¹H NMR (400 MHz, MeOD) δ 8.64 (s, 1H), 8.55 (s, 1H), 7.51 (s, 1H), 7.40 (s, 1H), 7.29 (d, J = 6.7 Hz, 2H), 7.25 (dd, J = 5.7, 3.3 Hz, 1H), 5.88 (s, 1H), 4.80-4.74 (m, 1H), 4.19-4.09 (m, 3H), 2.50-2.42 (m, 1H), 2.26-2.19 (m, 1H), 2.14-2.06 (m, 1H), 1.88-1.82 (m, 1H), 1.43-1.34 (m, 1H). | FA: m/z = 593.4 (M + H) |
| I-110 | ¹H NMR (400 MHz, MeOD) δ 8.67 (s, 1H), 8.56 (s, 1H), 7.44 (s, 1H), 7.28 (t, J = 7.7 Hz, 1H), 7.20 (d, J = 12.6 Hz, 2H), 7.12 (d, J = 7.5 Hz, 1H), 4.77 (dd, J = 15.6, 7.7 Hz, 1H), 4.26-4.10 (m, 3H), 4.00 (s, 2H), 3.89 (dd, J = 11.3, 3.0 Hz, 2H), 2.81 (d, J = 7.2 Hz, 2H), 2.48 (dd, J = 13.2, 7.2 Hz, 1H), 2.18 (ddd, J = 17.9, 16.8, 6.2 Hz, 2H), 1.94-1.82 (m, 1H), 1.80-1.68 (m, 1H), 1.61 (d, J = 13.1 Hz, 2H), 1.55-1.16 (m, 4H). | FA: m/z = 623.5 (M + H) |
| I-103 | ¹H NMR (400 MHz, MeOD) δ 8.74 (s, 1H), 8.62 (s, 1H), 7.63 (s, 1H), 6.83 (d, J = 3.8 Hz, 1H), 6.74 (d, J = 3.8 Hz, 1H), 6.04 (s, 1H), 4.80 (dd, J = 16.1, 8.1 Hz, 1H), 4.32-4.01 (m, 3H), 2.55-2.45 (m, 1H), 2.30-2.10 (m, 2H), 1.95-1.84 (m, 1H), 1.43 (dd, J = 21.5, 9.9 Hz, 1H). | FA: m/z = 579.3 (M + H) |
| I-9a | ¹H NMR (400 MHz, MeOD) δ 8.64 (s, 1H), 8.55 (s, 1H), 7.51 (s, 1H), 7.40 (s, 1H), 7.29 (d, J = 6.7 Hz, 2H), 7.25 (dd, J = 5.7, 3.3 Hz, 1H), 5.88 (s, 1H), 4.80-4.74 (m, 1H), 4.19-4.09 (m, 3H), 2.50-2.42 (m, 1H), 2.26-2.19 (m, 1H), 2.14-2.06 (m, 1H), 1.88-1.82 (m, 1H), 1.43-1.34 (m, 1H). | FA: m/z = 573.1 (M + H) |
| I-141 | ¹H NMR (400 MHz, MeOD) δ 8.69 (s, 1H), 8.57 (s, 1H), 7.49 (s, 1H), 5.20 (s, 1H), 5.12 (s, 1H), 4.92 (d, J = 1.0 Hz, 1H), 4.77 (dd, J = 16.0, 8.0 Hz, 1H), 4.20-4.09 (m, 3H), 2.63 (s, 3H), 2.51-2.43 (m, 1H), 2.28-2.18 (m, 1H), 2.16-2.08 (m, 1H), 1.92-1.83 (m, 1H), 1.40 (dd, J = 9.1, 4.1 Hz, 1H). | FA: m/z = 503.3 (M + H) |
| I-9b | ¹H NMR (400 MHz, MeOD) δ 8.68 (s, 1H), 8.58 (s, 1H), 7.56 (s, 1H), 7.45 (s, 1H), 7.37-7.32 (m, 2H), 7.31-7.26 (m, 1H), 5.93 (s, 1H), 4.79 (dd, J = 16.0, 8.1 Hz, 1H), 4.22-4.12 (m, 3H), 2.48 (dd, J = 13.4, 7.3 Hz, 1H), 2.26 (d, J = 5.4 Hz, 1H), 2.19-2.12 (m, 1H), 1.91 (dd, J = 7.2, 4.7 Hz, 1H), 1.45-1.37 (m, 1H). | FA: m/z = 573.1 (M + H) |
| I-207 | ¹H NMR (400 MHz, MeOD) δ 8.81 (s, 1H), 8.59 (s, 1H), 7.85 (t, J = 1.7 Hz, 1H), 7.79-7.71 (m, 2H), 7.68 (dd, J = 8.0, 1.1 Hz, 1H), 7.54 (t, J = 7.9 Hz, 1H), 4.83-4.77 (m, 1H), 4.24-4.11 (m, 3H), 2.54-2.46 (m, 1H), 2.30-2.22 (m, 1H), 2.18-2.10 (m, 1H), 1.95-1.87 (m, 1H), 1.48-1.40 (m, 1H). | FA: m/z = 571.0 (M + H) |
| I-90a | ¹H NMR (400 MHz, MeOD) δ 8.64 (s, 1H), 8.59 (s, 1H), 7.52 (s, 1H), 7.43 (s, 1H), 7.38-7.28 (m, 3H), | FA: m/z = 587.1 (M + H) |

| Compound No. | ¹H NMR | LC/MS |
|---|---|---|
| | 5.50 (s, 1H), 4.83-4.75 (m, 1H), 4.24-4.11 (m, 3H), 3.41 (s, 3H), 2.55-2.44 (m, 1H), 2.30-2.21 (m, 1H), 2.20-2.10 (m, 1H), 1.94-1.85 (m, 1H), 1.46-1.37 (m, 1H). | |
| I-90b | ¹H NMR (400 MHz, MeOD) δ 8.65 (s, 1H), 8.59 (s, 1H), 7.51 (s, 1H), 7.43 (s, 1H), 7.39-7.26 (m, 3H), 5.50 (s, 1H), 4.83-4.74 (m, 1H), 4.25-4.11 (m, 3H), 3.41 (s, 3H), 2.53-2.45 (m, 1H), 2.30-2.20 (m, 1H), 2.19-2.10 (m, 1H), 1.94-1.86 (m, 1H), 1.45-1.37 (m, 1H). | FA: m/z = 587.1 (M + H) |
| I-90 | ¹H NMR (400 MHz, MeOD) δ 8.65 (s, 1H), 8.59 (s, 1H), 7.51 (s, 1H), 7.43 (s, 1H), 7.37-7.25 (m, 3H), 5.49 (s, 1H), 4.82-4.73 (m, 1H), 4.23-4.09 (m, 3H), 3.40 (s, 3H), 2.53-2.44 (m, 1H), 2.30-2.21 (m, 1H), 2.19-2.09 (m, 1H), 1.94-1.83 (m, 1H), 1.47-1.35 (m, 1H). | FA: m/z = 587.1 (M + H) |
| I-11a | ¹H NMR (400 MHz, MeOD) δ 8.66 (s, 1H), 8.56 (s, 1H), 7.47 (s, 1H), 7.41 (s, 1H), 7.35-7.30 (m, 1H), 7.30-7.22 (m, 2H), 5.88 (s, 1H), 4.81-4.72 (m, 1H), 4.23-4.12 (m, 3H), 2.52 (s, 3H), 2.51-2.43 (m, 1H), 2.30-2.22 (m, 1H), 2.18-2.11 (m, 1H), 1.93-1.87 (m, 1H), 1.45-1.37 (m, 1H). | FA: m/z = 553.1 (M + H) |
| I-11b | ¹H NMR (400 MHz, MeOD) δ 8.66 (s, 1H), 8.56 (d, J = 4.3 Hz, 1H), 7.47 (s, 1H), 7.41 (s, 1H), 7.37-7.20 (m, 3H), 5.89 (s, 1H), 4.81-4.73 (m, 1H), 4.23-4.09 (m, 3H), 2.53 (s, 3H), 2.51-2.42 (m, 1H), 2.30-2.22 (m, 1H), 2.18-2.10 (m, 1H), 1.93-1.85 (m, 1H), 1.44-1.37 (m, 1H). | FA: m/z = 553.1 (M + H) |
| I-11 | ¹H NMR (400 MHz, MeOD) δ 8.65 (s, 1H), 8.57 (s, 1H), 7.48 (s, 1H), 7.41 (s, 1H), 7.34-7.23 (m, 3H), 5.87 (s, 1H), 4.81-4.74 (m, 1H), 4.33-4.08 (m, 3H), 2.51 (s, 3H), 2.34-2.20 (m, 1H), 2.19-2.06 (m, 1H), 1.94-1.82 (m, 1H), 1.75-1.56 (m, 1H), 1.54-1.34 (m, 2H). | FA: m/z = 553.1 (M + H) |
| I-100 | ¹H NMR (400 MHz, MeOD) δ 8.70 (s, 1H), 8.53 (s, 1H), 7.37 (s, 1H), 7.35-7.27 (m, 3H), 7.22 (dd, J = 5.9, 2.2 Hz, 1H), 5.82 (s, 1H), 5.38 (s, 1H), 4.81-4.69 (m, 1H), 4.25-4.13 (m, 3H), 2.52-2.45 (m, 1H), 2.34 (s, 3H), 2.30-2.21 (m, 1H), 2.19-2.09 (m, 1H), 1.94-1.85 (m, 1H), 1.45-1.37 (m, 1H). | FA: m/z = 549.1 (M + H) |
| I-102a | ¹H NMR (400 MHz, MeOD) δ 8.64 (s, 1H), 8.55 (s, 1H), 7.51 (s, 1H), 7.40 (s, 1H), 7.29 (d, J = 6.7 Hz, 2H), 7.25 (dd, J = 5.7, 3.3 Hz, 1H), 5.88 (s, 1H), 4.80-4.74 (m, 1H), 4.19-4.09 (m, 3H), 2.50-2.42 (m, 1H), 2.26-2.19 (m, 1H), 2.14-2.06 (m, 1H), 1.88-1.82 (m, 1H), 1.43-1.34 (m, 1H). | FA: m/z = 587.1 (M + H) |
| I-102b | ¹H NMR (400 MHz, MeOD) δ 8.79 (s, 1H), 8.62 (s, 1H), 7.78 (s, 1H), 7.47 (d, J = 1.6 Hz, 1H), 7.35-7.24 (m, 3H), 4.84-4.77 (m, 1H), 4.23-4.11 (m, 3H), 2.55-2.48 (m, 1H), 2.30-2.25 (m, 1H), 2.18-2.13 (m, 1H), 1.97 (s, 3H), 1.94-1.90 (m, 1H), 1.48-1.42 (m, 1H). | FA: m/z = 587.1 (M + H) |
| I-102 | ¹H NMR (400 MHz, MeOD) δ 8.79 (s, 1H), 8.61 (s, 1H), 7.78 (s, 1H), 7.47 (s, 1H), 7.36-7.24 (m, 3H), 4.84-4.78 (m, 1H), 4.24-4.12 (m, 3H), 2.55-2.48 (m, 1H), 2.30-2.23 (m, 1H), 2.20-2.13 (m, 1H), 1.96 (s, 3H), 1.95-1.87 (m, 1H), 1.45-1.38 (m, 1H). | FA: m/z = 587.1 (M + H) |
| I-9 | ¹H NMR (400 MHz, MeOD) δ 8.68 (s, 1H), 8.59 (s, 1H), 7.55 (s, 1H), 7.44 (s, 1H), 7.40-7.20 (m, 3H), 5.92 (s, 1H), 4.84-4.73 (m, 1H), 4.27-4.10 (m, 3H), 2.54-2.42 (m, 1H), 2.32-2.21 (m, 1H), 2.20-2.08 (m, 1H), 1.96-1.83 (m, 1H), 1.47-1.39 (m, 1H). | FA: m/z = 573.0 (M + H) |
| I-168 | ¹H NMR (400 MHz, MeOD) δ 8.83 (s, 1H), 8.61 (s, 1H), 7.91 (s, 1H), 7.78 (s, 1H), 7.21 (d, J = 5.2 Hz, 1H), 6.77 (d, J = 5.2 Hz, 1H), 4.85-4.78 (m, 1H), 4.24-4.13 (m, 3H), 3.93 (s, 2H), 3.72 (s, 2H), 3.03-2.92 (m, 4H), 2.56-2.47 (m, 1H), 2.32-2.23 (m, 1H), 2.20-2.12 (m, 1H), 1.96-1.87 (m, 1H), 1.49-1.41 (m, 1H). | FA: m/z = 550.1 (M + H) |
| I-41 | ¹H NMR (400 MHz, Methanol-d4) δ 8.64 (s, 1H), 8.54 (s, 1H), 7.38 (s, 1H), 7.29-7.22 (m, 1H), 7.21-7.16 (m, 2H), 7.15-7.06 (m, 1H), 5.19 (t, J = 7.0 Hz, 1H), 4.82-4.69 (m, 1H), 4.24-4.11 (m, 1H), 4.11-4.04 (m, 1H), 4.04-3.92 (m, 2H), 3.90-3.81 (m, 1H), 2.54-2.41 (m, 1H), 2.36-2.21 (m, 2H), 2.16-1.98 (m, 3H), 1.93-1.81 (m, 1H), 1.79-1.66 (m, 1H), 1.45-1.33 (m, 1H). | FA: m/z = 593.4 (M + H) |
| I-181 | ¹H NMR (400 MHz, Methanol-d4) δ 8.76 (s, 1H), 8.62 (s, 1H), 8.00 (t, J = 1.9 Hz, 1H), 7.97-7.90 (m, 2H), | FA: m/z = 587.2 (M + H) |

| Compound No. | ¹H NMR | LC/MS |
|---|---|---|
| | 7.74-7.69 (m, 1H), 7.61 (t, J = 8.0 Hz, 1H), 4.82 (q, J = 7.8 Hz, 1H), 4.17 (qd, J = 9.8, 6.0 Hz, 3H), 2.74 (s, 3H), 2.50 (dt, J = 14.3, 7.6 Hz, 1H), 2.32-2.20 (m, 1H), 2.15 (ddd, J = 12.5, 7.6, 4.4 Hz, 1H), 1.90 (dt, J = 13.5, 7.6 Hz, 1H), 1.43 (dt, J = 12.9, 9.1 Hz, 1H). | |
| I-203 | ¹H NMR (400 MHz, Methanol-d4) δ 8.82 (s, 1H), 8.64 (s, 1H), 8.07 (d, J = 1.7 Hz, 1H), 8.00 (d, J = 8.0 Hz, 2H), 7.75 (d, J = 8.0 Hz, 1H), 7.63 (t, J = 8.0 Hz, 1H), 4.85-4.79 (m, 1H), 4.18 (td, J = 10.7, 10.3, 5.8 Hz, 3H), 2.50 (dt, J = 14.2, 7.8 Hz, 1H), 2.32-2.22 (m, 1H), 2.19-2.12 (m, 1H), 1.91 (dt, J = 14.8, 7.6 Hz, 1H), 1.44 (dt, J = 12.8, 9.0 Hz, 1H). | FA: m/z = 607.1 (M + H) |
| I-143 | ¹H NMR (400 MHz, Methanol-d4) δ 8.71 (s, 1H), 8.57 (s, 1H), 7.63 (s, 1H), 7.26 (t, J = 7.9 Hz, 1H), 7.17 (ddd, J = 8.0, 2.0, 1.0 Hz, 1H), 7.09 (t, J = 1.8 Hz, 1H), 7.04 (ddd, J = 7.8, 1.8, 1.0 Hz, 1H), 4.80 (p, J = 8.0 Hz, 1H), 4.23-4.12 (m, 3H), 2.57 (s, 3H), 2.54-2.46 (m, 1H), 2.26 (tq, J = 11.4, 5.7 Hz, 1H), 2.15 (ddd, J = 12.4, 7.3, 4.3 Hz, 1H), 1.96-1.87 (m, 1H), 1.43 (dt, J = 13.0, 9.1 Hz, 1H). | FA: m/z = 555.0 (M + H) |
| I-28 | ¹H NMR (400 MHz, Methanol-d4) δ 8.60 (s, 1H), 8.56 (s, 1H), 7.73 (dd, J = 1.7, 1.0 Hz, 1H), 7.61-7.54 (m, 4H), 4.77 (p, J = 7.9 Hz, 1H), 4.17 (dddt, J = 15.9, 9.7, 7.1, 3.5 Hz, 3H), 2.78 (s, 3H), 2.52-2.43 (m, 1H), 2.24 (dt, J = 13.4, 6.7 Hz, 1H), 2.13 (ddt, J = 12.5, 8.5, 4.6 Hz, 1H), 1.93-1.83 (m, 1H), 1.56-1.42 (m, 1H). | FA: m/z = 571.2 (M + H) |
| I-28b | ¹H NMR (400 MHz, Methanol-d4) δ 8.60 (s, 1H), 8.57 (s, 1H), 7.75-7.72 (m, 1H), 7.60-7.55 (m, 3H), 7.54 (s, 1H), 4.83-4.74 (m, 1H), 4.15 (tt, J = 9.8, 5.2 Hz, 3H), 2.78 (s, 3H), 2.48 (dt, J = 13.3, 7.4 Hz, 1H), 2.29-2.20 (m, 1H), 2.12 (ddd, J = 12.4, 7.6, 4.6 Hz, 1H), 1.91-1.83 (m, 1H), 1.41 (dt, J = 13.1, 9.1 Hz, 1H). | FA: m/z = 571.1 (M + H) |
| I-28a | ¹H NMR (400 MHz, Methanol-d4) δ 8.60 (s, 1H), 8.57 (s, 1H), 7.75-7.73 (m, 1H), 7.61-7.56 (m, 3H), 7.54 (s, 1H), 4.77 (q, J = 7.9 Hz, 1H), 4.24-4.13 (m, 3H), 2.78 (s, 3H), 2.51-2.44 (m, 1H), 2.25 (d, J = 5.9 Hz, 1H), 2.18-2.11 (m, 1H), 1.93-1.85 (m, 1H), 1.46-1.38 (m, 1H). | FA: m/z = 571.0 (M + H) |
| I-68 | ¹H NMR (400 MHz, Methanol-d4) δ 8.56 (d, J = 7.7 Hz, 2H), 7.69 (dt, J = 8.7, 2.4 Hz, 2H), 7.62-7.55 (m, 3H), 7.51 (s, 1H), 4.76 (p, J = 8.1 Hz, 1H), 4.16 (ddtd, J = 13.3, 9.7, 7.1, 6.3, 3.8 Hz, 3H), 2.75 (s, 3H), 2.46 (dq, J = 14.6, 7.4 Hz, 1H), 2.29-2.21 (m, 1H), 2.12 (ddt, J = 12.3, 8.2, 4.4 Hz, 1H), 1.93-1.83 (m, 1H), 1.53-1.48 (m, 1H). | FA: m/z = 537.0 (M + H) |
| I-137 | ¹H NMR (400 MHz, Methanol-d₄) δ 8.66 (s, 1H), 8.55 (s, 1H), 7.52 (s, 1H), 7.26 (t, J = 7.5 Hz, 2H), 7.19-7.11 (m, 3H), 4.77 (p, J = 8.0 Hz, 1H), 4.17 (qd, J = 9.8, 5.8 Hz, 3H), 2.53 (s, 3H), 2.48 (dd, J = 13.2, 7.2 Hz, 1H), 2.25 (dt, J = 14.0, 7.1 Hz, 1H), 2.14 (ddd, J = 12.5, 7.5, 4.4 Hz, 1H), 1.94-1.84 (m, 1H), 1.41 (dt, J = 13.0, 9.1 Hz, 1H). | FA: m/z = 522.2 (M + H) |
| I-69 | ¹H NMR (400 MHz, Methanol-d₄) δ 8.58 (d, J = 12.6 Hz, 2H), 8.05 (s, 1H), 7.89 (dd, J = 12.6, 7.8 Hz, 2H), 7.78 (t, J = 7.8 Hz, 1H), 7.56-7.53 (m, 1H), 4.77 (p, J = 7.8 Hz, 1H), 4.16 (dddt, J = 15.9, 9.7, 7.0, 3.4 Hz, 3H), 2.79 (s, 3H), 2.47 (dq, J = 15.6, 8.0 Hz, 1H), 2.29-2.20 (m, 1H), 2.13 (ddt, J = 12.4, 8.3, 4.8 Hz, 1H), 1.93-1.83 (m, 1H), 1.45-1.35 (m, 1H). | FA: m/z = 606.0 (M + H) |
| I-145 | ¹H NMR (400 MHz, Methanol-d₄) δ 8.70 (s, 1H), 8.56 (s, 1H), 7.65 (s, 1H), 7.49-7.43 (m, 2H), 7.38 (s, 1H), 7.32 (dd, J = 5.1, 3.5 Hz, 1H), 4.83-4.75 (m, 1H), 4.17 (qd, J = 9.8, 5.9 Hz, 3H), 2.56 (s, 3H), 2.50 (dt, J = 13.7, 7.6 Hz, 1H), 2.30-2.21 (m, 1H), 2.14 (ddd, J = 12.3, 7.5, 4.4 Hz, 1H), 1.90 (dt, J = 13.5, 7.2 Hz, 1H), 1.42 (dt, J = 13.0, 9.1 Hz, 1H). | FA: m/z = 589.0 (M + H) |
| I-65 | ¹H NMR (400 MHz, MeOD) δ 9.05 (s, 1H), 8.60 (d, J = 4.1 Hz, 1H), 7.27-7.13 (m, 2H), 7.02 (dd, J = 13.8, 5.9 Hz, 3H), 4.88 (s, 2H), 4.31-4.04 (m, 3H), 3.75 (s, 2H), 2.55-2.36 (m, 4H), 2.35-2.23 (m, 4H), 1.69-1.51 (m, 1H). | FA: m/z = 519.2 (M + H) |

| Compound No. | ¹H NMR | LC/MS |
|---|---|---|
| I-292a | ¹H NMR (400 MHz, MeOD) δ 8.59 (s, 1H), 8.53 (d, J = 10.0 Hz, 1H), 7.25 (s, 1H), 7.16 (d, J = 4.0 Hz, 2H), 7.12-7.04 (m, 1H), 6.74 (d, J = 7.7 Hz, 1H), 5.27 (s, 1H), 4.83-4.69 (m, 1H), 4.29-4.08 (m, 3H), 3.30-3.24 (m, 1H), 3.18-3.00 (m, 2H), 2.94-2.80 (m, 1H), 2.61 (s, 3H), 2.54-2.41 (m, 1H), 2.32-2.20 (m, 1H), 2.18-2.08 (m, 1H), 1.96-1.79 (m, 1H), 1.49-1.35 (m, 1H). | FA: m/z = 544.5 (M + H) |
| I-292b | NMR (400 MHz, MeOD) δ 8.59 (s, 1H), 8.52 (s, 1H), 7.25 (s, 1H), 7.15 (t, J = 6.4 Hz, 2H), 7.13-7.01 (m, 1H), 6.74 (d, J = 7.6 Hz, 1H), 5.27 (s, 1H), 4.84-4.71 (m, 1H), 4.30-4.08 (m, 3H), 3.31-3.22 (m, 1H), 3.18-2.98 (m, 2H), 2.95-2.78 (m, 1H), 2.61 (s, 3H), 2.54-2.40 (m, 1H), 2.33-2.20 (m, 1H), 2.19-2.08 (m, 1H), 1.96-1.79 (m, 1H), 1.49-1.34 (m, 1H). LCMS: (FA) M + 1 544.5 | FA: m/z = 544.5 (M + H) |
| I-247a | ¹H NMR (400 MHz, MeOD) δ 8.66 (s, 1H), 8.55 (s, 1H), 7.37-7.25 (m, 2H), 7.16-7.06 (m, 1H), 6.86 (s, 1H), 5.26 (s, 1H), 4.61-4.50 (m, 1H), 4.26-4.13 (m, 2H), 4.02-3.83 (m, 2H), 3.18-2.95 (m, 2H), 2.90-2.78 (m, 1H), 2.62 (s, 3H), 2.54-2.42 (m, 1H), 2.42-2.31 (m, 1H), 1.44-1.27 (m, 2H). | FA: m/z = 640.4 (M + H) |
| I-247b | ¹H NMR (400 MHz, MeOD) δ 8.70-8.62 (m, 1H), 8.59-8.50 (m, 1H), 7.36-7.26 (m, 2H), 7.11 (d, J = 8.2 Hz, 1H), 6.86 (d, J = 1.2 Hz, 1H), 5.26 (s, 1H), 4.62-4.49 (m, 1H), 4.27-4.13 (m, 2H), 4.00-3.85 (m, 2H), 3.18-2.95 (m, 2H), 2.90-2.77 (m, 1H), 2.61 (s, 3H), 2.55-2.42 (m, 1H), 2.42-2.29 (m, 1H), 1.41-1.26 (m, 2H). | FA: m/z = 640.4 (M + H) |
| I-248a | ¹H NMR (400 MHz, MeOD) δ 8.63 (s, 1H), 8.53 (s, 1H), 7.37-7.24 (m, 2H), 7.15-7.05 (m, 1H), 6.86 (s, 1H), 5.23 (s, 1H), 4.84-4.71 (m, 1H), 4.29-4.08 (m, 3H), 3.31-3.24 (m, 1H), 3.17-2.91 (m, 2H), 2.88-2.74 (m, 1H), 2.61 (s, 3H), 2.55-2.41 (m, 1H), 2.34-2.20 (m, 1H), 2.19-2.08 (m, 1H), 1.95-1.81 (m, 1H), 1.51-1.33 (m, 1H). | FA: m/z = 624.1 (M + H) |
| I-248b | ¹H NMR (400 MHz, MeOD) δ 8.63 (s, 1H), 8.53 (s, 1H), 7.37-7.24 (m, 2H), 7.17-7.07 (m, 1H), 6.86 (s, 1H), 5.24 (s, 1H), 4.84-4.70 (m, 1H), 4.29-4.08 (m, 3H), 3.30-3.23 (m, 1H), 3.16-2.92 (m, 2H), 2.86-2.75 (m, 1H), 2.61 (s, 3H), 2.55-2.41 (m, 1H), 2.34-2.21 (m, 1H), 2.19-2.09 (m, 1H), 1.96-1.83 (m, 1H), 1.49-1.33 (m, 1H). | FA: m/z = 624.1 (M + H) |
| I-261a | ¹H NMR (400 MHz, MeOD) δ 8.72 (s, 1H), 8.59 (s, 1H), 7.80 (d, J = 0.9 Hz, 1H), 7.58 (d, J = 1.3 Hz, 1H), 7.25-7.18 (m, 2H), 6.91 (s, 1H), 5.90 (s, 1H), 4.88-4.75 (m, 1H), 4.27-4.08 (m, 4H), 3.97-3.86 (m, 1H), 3.09-2.95 (m, 1H), 2.90-2.79 (m, 1H), 2.58-2.45 (m, 1H), 2.34-2.22 (m, 1H), 2.22-2.11 (m, 1H), 1.98-1.87 (m, 1H), 1.50-1.36 (m, 1H) | FA: m/z = 565.3 (M + H) |
| I-261b | ¹H NMR (400 MHz, MeOD) δ 8.71 (s, 1H), 8.57 (s, 1H), 7.79 (s, 1H), 7.56 (d, J = 1.0 Hz, 1H), 7.24-7.15 (m, 2H), 6.89 (s, 1H), 5.87 (s, 1H), 4.86-4.72 (m, 1H), 4.27-4.04 (m, 4H), 3.98-3.84 (m, 1H), 3.12-2.94 (m, 1H), 2.89-2.76 (m, 1H), 2.57-2.44 (m, 1H), 2.36-2.22 (m, 1H), 2.20-2.09 (m, 1H), 1.98-1.81 (m, 1H), 1.50-1.37 (m, 1H). | FA: m/z = 565.3 (M + H) |
| I-263a | ¹H NMR (400 MHz, MeOD) δ 8.63 (s, 1H), 8.53 (s, 1H), 7.29 (s, 1H), 7.17 (s, 2H), 6.71 (s, 1H), 5.23 (s, 1H), 4.83-4.69 (m, 1H), 4.32-4.07 (m, 3H), 3.40-3.23 (m, 1H), 3.12-2.94 (m, 2H), 2.90-2.75 (m, 1H), 2.61 (s, 3H), 2.55-2.39 (m, 1H), 2.33-2.19 (m, 1H), 2.18-2.09 (m, 1H), 1.96-1.78 (m, 1H), 1.50-1.34 (m, 1H). | FA: m/z = 578.4 (M + H) |
| I-263b | ¹H NMR (400 MHz, MeOD) δ 8.63 (s, 1H), 8.53 (s, 1H), 7.29 (s, 1H), 7.17 (s, 2H), 6.71 (s, 1H), 5.23 (s, 1H), 4.83-4.70 (m, 1H), 4.27-4.10 (m, 3H), 3.41-3.24 (m, 1H), 3.15-2.95 (m, 2H), 2.87-2.76 (m, 1H), 2.61 (s, 3H), 2.55-2.38 (m, 1H), 2.33-2.20 (m, 1H), 2.18-2.08 (m, 1H), 1.96-1.80 (m, 1H), 1.48-1.33 (m, 1H). | FA: m/z = 578.4 (M + H) |

| Compound No. | ¹H NMR | LC/MS |
|---|---|---|
| I-306 | ¹H NMR (400 MHz, MeOD) δ 8.63 (s, 1H), 8.54 (s, 1H), 7.29 (s, 1H), 7.19 (d, J = 8.2 Hz, 2H), 6.64 (s, 1H), 4.79 (dd, J = 16.0, 7.9 Hz, 1H), 4.66 (s, 1H), 4.29-4.09 (m, 3H), 3.28-3.10 (m, 2H), 2.95-2.85 (m, 1H), 2.83-2.71 (m, 1H), 2.60 (s, 3H), 2.55-2.41 (m, 1H), 2.36 (s, 3H), 2.31-2.21 (m, 1H), 2.19-2.07 (m, 1H), 1.95-1.82 (m, 1H), 1.50-1.32 (m, 1H). | FA: m/z = 592.4 (M + H) |
| I-322 | ¹H NMR (400 MHz, MeOD) δ 8.73 (s, 1H), 8.55 (d, J = 19.2 Hz, 1H), 7.96 (t, J = 7.2 Hz, 1H), 7.55 (d, J = 11.5 Hz, 1H), 7.35 (s, 1H), 7.21 (t, J = 10.6 Hz, 1H), 6.88 (t, J = 7.6 Hz, 1H), 4.85-4.73 (m, 1 H), 4.31 (d, J = 13.6 Hz, 1H), 4.26-4.11 (m, 3H), 3.78 (d, J = 13.5 Hz, 1H), 3.56 (t, J = 6.5 Hz, 1H), 2.63-2.46 (m, 4H), 2.36-2.22 (m, 1H), 2.21-2.10 (m, 1H), 1.98-1.85 (m, 1H), 1.58-1.49 (m, 1H). | FA: m/z = 564.1 (M + H) |
| I-261 | ¹H NMR (400 MHz, MeOD) δ 8.72 (s, 1H), 8.59 (s, 1H), 7.80 (s, 1H), 7.58 (s, 1H), 7.29-7.16 (m, 2H), 6.90 (s, 1H), 5.89 (s, 1H), 4.86-4.75 (m, 1H), 4.28-4.06 (m, 4H), 3.99-3.83 (m, 1H), 3.08-2.92 (m, 1H), 2.92-2.76 (m, 1H), 2.62-2.44 (m, 1H), 2.36-2.24 (m, 1H), 2.23-2.09 (m, 1H), 1.99-1.84 (m, 1H), 1.54-1.34 (m, 1H).). | FA: m/z = 565.3 (M + H) |
| I-149 | ¹H NMR (400 MHz, MeOD) δ 8.59 (s, 1H), 8.56 (s, 1H), 7.77 (d, J = 2.0 Hz, 1H), 7.44-7.34 (m, 1H), 7.33-7.29 (m, 1H), 7.27 (s, 1H), 6.12 (s, 1H), 4.84-4.69 (m, 1H), 4.28-4.07 (m, 3H), 2.57-2.38 (m, 1H), 2.34-2.20 (m, 1H), 2.19-2.08 (m, 1H), 1.94-1.81 (m, 1H), 1.46-1.32 (m, 1H). | FA: m/z = 609.3 (M + H) |
| I-63 | ¹H NMR (400 MHz, MeOD) δ 8.62 (s, 1H), 8.58 (s, 1H), 7.56 (d, J = 2.4 Hz, 1H), 7.35 (s, 1H), 7.26 (dd, J = 8.7, 2.5 Hz, 1H), 6.93 (d, J = 8.8 Hz, 1H), 6.10 (s, 1H), 4.81-4.69 (m, 1H), 4.32-4.07 (m, 3H), 3.78 (s, 3H), 2.58-2.38 (m, 1H), 2.35-2.21 (m, 1H), 2.21-2.08 (m, 1H), 1.95-1.79 (m, 1H), 1.48-1.31 (m, 1H). | FA: m/z = 603.3 (M + H) |
| I-240 | ¹H NMR (400 MHz, MeOD) δ 8.77 (s, 1H), 8.61 (s, 1H), 7.77 (s, 1H), 7.73 (s, 1H), 4.86-4.74 (m, 1H), 4.31-4.08 (m, 3H), 2.61-2.45 (m, 1H), 2.38-2.23 (m, 1H), 2.22-2.11 (m, 1H), 2.00-1.84 (m, 1H), | FA: m/z = 457.3 (M + H) |
| I-142 | ¹H NMR (400 MHz, MeOD) δ 8.75 (s, 1H), 8.58 (s, 1H), 7.61 (s, 1H), 7.39-7.16 (m, 4H), 4.84-4.72 (m, 1H), 4.60 (s, 2H), 4.26 (s, 2H), 4.24-4.11 (m, 3H), 2.60-2.39 (m, 1H), 2.34-2.21 (m, 1H), 2.21-2.08 (m, 1H), 1.97-1.84 (m, 1H), 1.48-1.34 (m, 1H). | FA: m/z = 553.3 (M + H) |
| I-229 | ¹H NMR (400 MHz, MeOD) δ 8.80 (s, 1H), 8.73 (d, J = 1.3 Hz, 1H), 8.62 (d, J = 8.3 Hz, 1H), 8.02 (d, J = 1.3 Hz, 1H), 4.88-4.77 (m, 1H), 4.27-4.13 (m, 3H), 2.58 (s, 3H), 2.56-2.47 (m, 1H), 2.36-2.24 (m, 1H), 2.23-2.12 (m, 1H), 1.99-1.88 (m, 1H), 1.53-1.39 (m, 1H). | FA: m/z = 441.0 (M + H) |
| I-85 | ¹H NMR (400 MHz, MeOD) δ 8.62 (s, 1H), 8.58 (s, 1H), 7.54 (d, J = 7.6 Hz, 1H), 7.38 (s, 1H), 7.29 (td, J = 8.0, 1.7 Hz, 1H), 7.06-6.88 (m, 2H), 6.17 (s, 1H), 4.83-4.72 (m, 1H), 4.27-4.09 (m, 3H), 3.80 (s, 3H), 2.57-2.41 (m, 1H), 2.35-2.21 (m, 1H), 2.19-2.08 (m, 1H), 1.96-1.81 (m, 1H), 1.49-1.34 (m, 1H). | FA: m/z = 569.2 (M + H) |
| I-86 | ¹H NMR (400 MHz, MeOD) δ 8.58 (d, J = 8.7 Hz, 2H), 7.87-7.67 (m, 1H), 7.46-7.37 (m, 2H), 7.34-7.25 (m, 2H), 6.20 (s, 1H), 4.85-4.71 (m, 1H), 4.29-4.07 (m, 3H), 2.59-2.40 (m, 1H), 2.35-2.21 (m, 1H), 2.20-2.09 (m, 1H), 1.95-1.82 (m, 1H), 1.50-1.35 (m, 1H). | FA: m/z = 573.1 (M + H) |
| I-40 | ¹H NMR (400 MHz, MeOD) δ 8.69 (s, 1H), 8.60 (s, 1H), 7.61-7.49 (m, 2H), 7.49-7.37 (m, 1H), 7.21 (t, J = 7.9 Hz, 1H), 6.17 (s, 1H), 4.87-4.71 (m, 1H), 4.27-4.09 (m, 3H), 2.57-2.43 (m, 1H), 2.34-2.22 (m, 1H), 2.20-2.09 (m, 1H), 2.00-1.83 (m, 1H), 1.55-1.35 (m, 1H). | FA: m/z = 591.1 (M + H) |
| I-48 | ¹H NMR (400 MHz, MeOD) δ 8.68 (s, 1H), 8.60 (s, 1H), 7.66-7.59 (m, 1H), 7.52 (s, 1H), 7.40-7.28 (m, 1H), 7.10 (t, J = 9.3 Hz, 1H), 6.12 (s, 1H), 4.85-4.75 (m, 1H), 4.27-4.09 (m, 3H), 2.60-2.44 (m, 1H), 2.36-2.23 (m, 1H), 2.21-2.09 (m, 1H), 1.97-1.83 (m, 1H), 1.52-1.33 (m, 1H). | FA: m/z = 591.1 (M + H) |
| I-136 | ¹H NMR (400 MHz, MeOD) δ 8.61 (s, 1H), 8.55 (s, 1H), 7.48 (s, 1H), 7.30-7.17 (m, 3H), 7.15 (s, 2H), 5.08 (t, J = 6.5 Hz, 1H), 4.87-4.73 (m, 1H), 4.33-4.14 (m, 3H), 3.10 (dd, J = 13.4, 6.5 Hz, 1H), 3.01 (dd, J = | FA: m/z = 553.5 (M + H) |

-continued

| Compound No. | ¹H NMR | LC/MS |
|---|---|---|
| | 13.4, 6.6 Hz, 1H), 2.64-2.42 (m, 1H), 2.36-2.23 (m, 1H), 2.22-2.09 (m, 1H), 1.97-1.83 (m, 1H), 1.52-1.35 (m, 1H). | |
| I-16a | ¹H NMR (400 MHz, MeOD) δ 8.69 (s, 1H), 8.60 (s, 1H), 7.61 (s, 1H), 7.57 (s, 1H), 7.45 (d, J = 7.3 Hz, 1H), 7.38 (d, J = 7.8 Hz, 1H), 7.28 (t, J = 7.8 Hz, 1H), 5.93 (s, 1H), 4.87-4.73 (m, 1H), 4.28-4.09 (m, 3H), 2.59-2.44 (m, 1H), 2.35-2.22 (m, 1H), 2.21-2.09 (m, 1H), 1.98-1.83 (m, 1H), 1.51-1.37 (m, 1H). | FA: m/z = 618.9 (M + H) |
| I-16b | ¹H NMR (400 MHz, MeOD) δ 8.69 (s, 1H), 8.61 (s, 1H), 7.61 (s, 1H), 7.57 (s, 1H), 7.49-7.41 (m, 1H), 7.37 (d, J = 7.8 Hz, 1H), 7.28 (t, J = 7.8 Hz, 1H), 5.93 (s, 1H), 4.87-4.73 (m, 1H), 4.31-4.07 (m, 3H), 2.59-2.41 (m, 1H), 2.35-2.22 (m, 1H), 2.21-2.09 (m, 1H), 1.99-1.83 (m, 1H), 1.52-1.34 (m, 1H). | FA: m/z = 618.9 (M + H) |
| I-138 | ¹H NMR (400 MHz, MeOD) δ 8.70 (s, 1H), 8.58 (s, 1H), 7.62 (d, J = 1.2 Hz, 1H), 7.54 (d, J = 1.3 Hz, 1H), 7.13 (t, J = 8.1 Hz, 1H), 6.80-6.68 (m, 2H), 6.65 (dd, J = 7.9, 1.1 Hz, 1H), 4.84-4.73 (m, 1H), 4.58 (s, 2H), 4.29-4.11 (m, 3H), 3.03 (s, 3H), 2.58-2.43 (m, 1H), 2.37-2.22 (m, 1H), 2.20-2.10 (m, 1H), 1.97-1.82 (m, 1H), | FA: m/z = 552.1 (M + H) |
| I-183 | ¹H NMR (400 MHz, MeOD) δ 8.59 (s, 2H), 7.50 (d, J = 1.2 Hz, 1H), 7.37 (d, J = 1.3 Hz, 1H), 7.19 (td, J = 8.2, 1.7 Hz, 1H), 7.03 (dd, J = 7.4, 1.6 Hz, 1H), 6.93 (d, J = 8.2 Hz, 1H), 6.83 (td, J = 7.4, 1.0 Hz, 1H), 4.86-4.73 (m, 1H), 4.30-4.13 (m, 3H), 3.82 (s, 3H), 2.94 (s, 4 H), 2.60-2.45 (m, 1H), 2.38-2.23 (m, 1H), 2.22-2.11 (m, 1H), 1.98-1.81 (m, 1H), 1.52-1.34 (m, 1H). | FA: m/z = 533.2 (M + H) |
| I-83 | ¹H NMR (400 MHz, MeOD) δ 8.76 (s, 1H), 8.60 (s, 1H), 7.81 (d, J = 1.2 Hz, 1H), 7.68 (d, J = 1.2 Hz, 1H), 6.99 (d, J = 7.7 Hz, 1H), 6.66-6.52 (m, 2H), 4.87-4.76 (m, 1H), 4.33 (s, 2H), 4.27-4.11 (m, 3H), 3.40 (t, J = 8.3 Hz, 2H), 2.93 (t, J = 8.3 Hz, 2H), 2.62-2.43 (m, 1H), 2.35-2.22 (m, 1H), 2.22-2.11 (m, 1H), 1.98-1.86 (m, 1H), 1.58-1.35 (m, 1H). | FA: m/z = 564.2 (M + H) |
| I-114 | ¹H NMR (400 MHz, MeOD) δ 8.61 (d, J = 24.8 Hz, 2H), 7.59 (dd, J = 11.2, 4.5 Hz, 2H), 7.51 (d, J = 1.3 Hz, 1H), 7.40 (dd, J = 8.3, 0.8 Hz, 1H), 7.33 (d, J = 3.2 Hz, 1H), 7.19-7.12 (m, 1H), 7.08-7.01 (m, 1H), 6.51 (dd, J = 3.2, 0.8 Hz, 1H), 5.44 (s, 2H), 4.86-4.73 (m, 1H), 4.26-4.11 (m, 3H), 2.56-2.43 (m, 1H), 2.34-2.21 (m, 1H), 2.21-2.08 (m, 1H), 1.96-1.83 (m, 1H), 1.50-1.36 (m, 1H). | FA: m/z = 528.1 (M + H) |
| I-108 | ¹H NMR (400 MHz, MeOD) δ 8.72-8.42 (m, 2H), 7.59 (dd, J = 42.0, 1.2 Hz, 1H), 7.44 (dd, J = 18.2, 1.3 Hz, 1H), 7.35-7.24 (m, 3H), 7.23-7.14 (m, 2H), 4.85-4.73 (m, 1H), 4.29-4.10 (m, 3H), 3.37-3.27 (m, 2H), 3.06-2.88 (m, 2H), 2.58-2.44 (m, 1H), 2.35-2.23 (m, 1H), 2.21-2.10 (m, 1H), 1.96-1.83 (m, 1H), 1.49-1.34 (m, 1H). | FA: m/z = 503.2 (M + H) |
| I-196 | | FA: m/z = 495.0 (M + H) |
| I-66 | ¹H NMR (400 MHz, MeOD) δ 8.75 (s, 1H), 8.60 (s, 1H), 7.73-7.68 (m, 1H), 7.60 (d, J = 1.4 Hz, 1H), 6.22-6.14 (m, 2H), 4.87-4.76 (m, 1H), 4.28-4.13 (m, 3H), 4.03 (s, 2H), 2.59-2.47 (m, 1H), 2.34-2.23 (m, 1H), 2.23-2.12 (m, 1H), 2.00-1.86 (m, 1H), 1.50-1.37 (m, 1H). | FA: m/z = 513.0 (M + H) |
| I-146 | ¹H NMR (400 MHz, MeOD) δ 8.73-8.55 (m, 2H), 7.70-7.56 (m, 1H), 7.54-7.46 (m, 1H), 7.34-7.10 (m, 4H), 4.87-4.76 (m, 1H), 4.29-4.11 (m, 3H), 3.33 (m, 2 H), 3.04-2.91 (m, 2H), 2.61-2.44 (m, 1H), 2.37-2.24 (m, 1H), 2.22-2.09 (m, 1H), 2.00-1.85 (m, 1H), 1.51-1.35 (m, 1H). | FA: m/z = 537.3 (M + H) |
| I-119 | ¹H NMR (400 MHz, MeOD) δ 8.75 (s, 1H), 8.60 (s, 1H), 7.79-7.70 (m, 1H), 7.63 (d, J = 1.4 Hz, 1H), 6.89 (dd, J = 3.4, 1.3 Hz, 1H), 6.31 (dd, J = 3.4, 0.7 Hz, 1H), 4.88-4.74 (m, 1H), 4.26-4.16 (m, 3H), 4.14 (s, 2H), 2.62-2.43 (m, 1H), 2.35-2.24 (m, 1H), 2.23-2.11 (m, 1H), 1.95-1.88 (m, 1H), 1.53-1.38 (m, 1H). | FA: m/z = 547.1 (M + H) |

| Compound No. | ¹H NMR | LC/MS |
|---|---|---|
| I-43 | ¹H NMR (400 MHz, CDCl3) δ 8.82 (s, 1H), 8.67 (s, 1H), 8.62 (d, J = 7.5 Hz, 1H), 7.42 (d, J = 1.4 Hz, 1H), 7.39 (s, 1H), 7.26-7.23 (m, 1H), 7.18 (s, 1H), 7.09 (d, J = 7.1 Hz, 1H), 5.41 (br, 2H), 4.87-4.68 (m, 1H), 4.43-4.31 (m, 2H), 4.30-4.21 (m, 1H), 3.99 (s, 2H), 2.63-2.49 (m, 1H), 2.42-2.27 (m, 1H), 2.21-2.09 (m, 1H), 2.08-1.97 (m, 1H), 1.54-1.37 (m, 1H). | FA: m/z = 523.2 (M + H) |
| I-253 | ¹H NMR (400 MHz, DMSO-d₆) δ 8.61 (s, 1H), 8.55 (s, 1H), 8.26-8.10 (m, 1H), 7.64 (d, J = 8.1 Hz, 1H), 7.46-7.41 (br s, 2H), 7.40-7.35 (m, 1H), 7.29 (d, J = 8.1 Hz, 1H), 5.20-5.12 (m, 1H), 4.91-4.85 (m, 1H), 4.76-4.59 (m, 1H), 4.09-4.03 (m, 1H), 3.98-3.90 (m, 2H), 3.26-3.18 (m, 1H), 3.15-3.08 (m, 1H), 3.00-2.86 (m, 2H), 2.79-2.65 (m, 1H), 2.34-2.23 (m, 1H), 2.15-2.06 (m, 1H), 1.98-1.86 (m, 1H), 1.80-1.70 (m, 1H), 1.32-1.18 (m, 1H) | FA: m/z = 599.1 (M + H) |
| I-253a | ¹H NMR (400 MHz, Methanol-d₄) δ 8.64 (s, 1H), 8.54 (s, 1H), 7.62 (d, J = 8.1 Hz, 1H), 7.27 (d, J = 8.1 Hz, 1H), 7.23 (s, 1H), 5.33 (s, 1H), 4.85-4.71 (m, 1H), 4.25-4.09 (m, 3H), 3.28-3.21 (m, 1H), 3.19-2.97 (m, 2H), 2.95-2.81 (m, 1H), 2.48 (dt, J = 13.9, 7.8 Hz, 1H), 2.33-2.18 (m, 1H), 2.20-2.07 (m, 1H), 1.88 (dt, J = 13.6, 7.3 Hz, 1H), 1.39 (dt, J = 12.9, 9.2 Hz, 1H) | FA: m/z = 599.1 (M + H) |
| I-253b | ¹H NMR (400 MHz, Methanol-d₄) δ 8.64 (s, 1H), 8.54 (s, 1H), 7.62 (d, J = 8.1 Hz, 1H), 7.27 (d, J = 8.1 Hz, 1H), 7.23 (s, 1H), 5.33 (s, 1H), 4.83-4.71 (m, 1H), 4.25-4.08 (m, 3H), 3.27-3.21 (m, 1H), 3.19-2.96 (m, 2H), 2.95-2.82 (m, 1H), 2.48 (dt, J = 13.9, 7.8 Hz, 1H), 2.32-2.19 (m, 1H), 2.21-2.07 (m, 1H), 1.88 (dt, J = 13.6, 7.3 Hz, 1H), 1.39 (dt, J = 12.9, 9.2 Hz, 1H) | FA: m/z = 599.1 (M + H) |
| I-291 | ¹H NMR (400 MHz, Methanol-d₄) δ 8.58 (s, 1H), 8.52 (s, 1H), 7.54 (d, J = 7.9 Hz, 1H), 7.15 (d, J = 7.9 Hz, 1H), 7.03 (s, 1H), 5.86 (s, 1H), 4.81-4.69 (m, 1H), 4.25-4.10 (m, 3H), 4.11-4.02 (m, 1H), 3.98-3.85 (m, 1H), 3.08-2.95 (m, 1H), 2.94-2.82 (m, 1H), 2.56 (s, 3H), 2.53-2.46 (m, 1H), 2.44 (s, 3H), 2.30-2.19 (m, 1H), 2.17-2.08 (m, 1H), 1.93-1.83 (m, 1H), 1.44-1.35 (m, 1H) | FA: m/z = 560.2 (M + H) |
| I-291a | ¹H NMR (400 MHz, DMSO-d₆) δ 8.58 (s, 1H), 8.48 (s, 1H), 8.16 (d, J = 7.5 Hz, 1H), 7.50 (d, J = 7.9 Hz, 1H), 7.44-7.37 (br s, 2H), 7.16 (s, 1H), 7.09 (d, J = 7.9 Hz, 1H), 5.83 (s, 1H), 4.87 (d, J = 4.5 Hz, 1H), 4.74-4.60 (m, 1H), 4.12-4.00 (m, 2H), 3.98-3.89 (m, 2H), 3.88-3.79 (m, 1H), 3.04-2.91 (m, 1H), 2.82-2.72 (m, 1H), 2.53 (s, 3H), 2.35 (s, 3H), 2.33-2.23 (m, 1H), 2.15-2.08 (m, 1H), 1.93 (ddd, J = 11.7, 7.5, 3.3 Hz, 1H), 1.80-1.67 (m, 1H), 1.25 (dt, J = 12.7, 9.3 Hz, 1H) | FA: m/z = 560.2 (M + H) |
| I-291b | ¹H NMR (400 MHz, DMSO-d₆) δ 8.58 (s, 1H), 8.49 (s, 1H), 8.16 (d, J = 7.5 Hz, 1H), 7.50 (d, J = 7.9 Hz, 1H), 7.44-7.40 (br s, 2H), 7.16 (s, 1H), 7.09 (d, J = 7.8 Hz, 1H), 5.83 (s, 1H), 4.91-4.82 (m, 2H), 4.73-4.60 (m, 1H), 4.12-3.99 (m, 2H), 3.98-3.88 (m, 2H), 3.83 (ddd, J = 11.6, 8.9, 4.0 Hz, 1H), 3.04-2.91 (m, 1H), 2.83-2.71 (m, 1H), 2.53 (s, 3H), 2.35 (s, 3H), 2.33-2.24 (m, 1H), 2.17-2.02 (m, 1H), 1.92 (ddd, J = 12.1, 7.5, 3.7 Hz, 1H), 1.80-1.69 (m, 1H), 1.24 (dt, J = 12.7, 9.3 Hz, 1H) | FA: m/z = 560.2 (M + H) |
| I-317 | ¹H NMR (400 MHz, Methanol-d₄) δ 8.70 (s, 1H), 8.59 (s, 1H), 7.61 (s, 1H), 7.50 (s, 1H), 7.27-7.16 (m, 3H), 4.83-4.76 (m, 1H), 4.24-4.12 (m, 3H), 3.98-3.89 (m, 1H), 3.77-3.67 (m, 1H), 3.02-2.91 (m, 1H), 2.80-2.70 (m, 1H), 2.57-2.45 (m, 1H), 2.33-2.21 (m, 1H), 2.16 (s, 1H), 1.97-1.90 (m, 1H), 1.88 (s, 3H), 1.49-1.37 (m, 1H) | FA: m/z = 579.1 (M + H) |
| I-307 | ¹H NMR (400 MHz, DMSO-d₆) δ 8.62 (s, 1H), 8.59 (s, 1H), 8.22 (d, J = 6.5 Hz, 1H), 7.93 (s, 1H), 7.52-7.47 (m, 1H), 7.46-7.39 (m, 2H), 7.19 (s, 2H), 6.79 (s, 1H), 4.91-4.84 (m, 1H), 4.77-4.61 (m, 1H), 4.57 (s, 1H), 4.13-4.06 (m, 1H), 3.98-3.90 (m, 2H), 3.03-2.93 (m, 2H), 2.84-2.75 (m, 1H), 2.57-2.52 (m, 1H), 2.36-2.24 (m, 1H), 2.21 (s, 3H), 2.16-2.07 (m, 1H), 1.99-1.89 (m, 1H), 1.80-1.71 (m, 1H), 1.32-1.24 (m, 1H) | FA: m/z = 578.4 (M + H) |
| I-307a | ¹H NMR (400 MHz, DMSO-d₆) δ 8.62 (s, 1H), 8.59 (s, 1H), 8.22 (d, J = 7.4 Hz, 1H), 7.92 (d, J = 1.2 Hz, 1H), 7.50 (d, J = 1.2 Hz, 1H), 7.46-7.36 (br s, 2H), 7.19 (s, 2H), 6.79 (s, 1H), 4.88 (d, J = 4.6 Hz, 1H), 4.75-4.61 (m, 1H), 4.57 (s, 1H), 4.08 (dd, J = 9.7, 6.1 Hz, 1H), | FA: m/z = 578.4 (M + H) |

| Compound No. | ¹H NMR | LC/MS |
|---|---|---|
| | 3.99-3.90 (m, 2H), 3.05-2.92 (m, 2H), 2.85-2.74 (m, 1H), 2.57-2.52 (m, 1H), 2.36-2.24 (m, 1H), 2.21 (s, 3H), 2.15-2.05 (m, 1H), 1.96 (ddd, J = 12.0, 7.3, 3.7 Hz, 1H), 1.83-1.70 (m, 1H), 1.32-1.18 (m, 1H) | |
| I-307b | ¹H NMR (400 MHz, DMSO-d₆) δ 8.62 (s, 1H), 8.59 (s, 1H), 8.22 (d, J = 7.5 Hz, 1H), 7.93 (d, J = 1.0 Hz, 1H), 7.50 (d, J = 1.1 Hz, 1H), 7.45-7.36 (br s, 2H), 7.19 (s, 2H), 6.79 (s, 1H), 4.87 (d, J = 4.5 Hz, 1H), 4.75-4.62 (m, 1H), 4.56 (s, 1H), 4.09 (dd, J = 9.7, 6.0 Hz, 1H), 4.00-3.89 (m, 2H), 3.06-2.91 (m, 2H), 2.87-2.73 (m, 1H), 2.56-2.52 (m, 1H), 2.36-2.27 (m, 1H), 2.21 (s, 3H), 2.17-2.06 (m, 1H), 1.98-1.88 (m, 1H), 1.73 (dt, J = 13.3, 6.9 Hz, 1H), 1.27 (dt, J = 12.3, 9.1 Hz, 1H) | FA: m/z = 578.4 (M + H) |
| I-274 | ¹H NMR (400 MHz, DMSO-d₆) δ 8.68 (s, 1H), 8.64 (s, 1H), 8.28 (d, J = 7.6 Hz, 1H), 7.73 (s, 1H), 7.67 (s, 1H), 7.44-7.40 (br s, 2H), 7.24-7.14 (m, 2H), 6.87 (s, 1H), 5.16 (s, 1H), 4.91-4.86 (m, 1H), 4.77-4.63 (m, 1H), 4.13-4.05 (m, 1H), 4.00-3.90 (m, 2H), 3.06-2.98 (m, 1H), 2.93-2.65 (m, 4H), 2.37-2.27 (m, 1H), 2.16-2.06 (m, 1H), 2.01-1.91 (m, 1H), 1.83-1.70 (m, 1H), 1.32-1.26 (m, 1H) | FA: m/z = 564.4 (M + H) |
| I-274a | ¹H NMR (400 MHz, DMSO-d₆) δ 8.68 (s, 1H), 8.64 (s, 1H), 8.27 (d, J = 7.6 Hz, 1H), 7.72 (s, 1H), 7.67 (d, J = 1.1 Hz, 1H), 7.48-7.12 (m, 4H), 6.87 (d, J = 1.6 Hz, 1H), 5.14 (s, 1H), 4.88 (d, J = 4.2 Hz, 1H), 4.77-4.63 (m, 1H), 4.09 (dd, J = 9.8, 6.0 Hz, 1H), 4.02-3.89 (m, 2H), 3.11-2.94 (m, 2H), 2.93-2.64 (m, 3H), 2.37-2.27 (m, 1H), 2.17-2.08 (m, 1H), 1.94 (ddd, J = 11.8, 7.4, 3.7 Hz, 1H), 1.82-1.70 (m, 1H), 1.28 (dt, J = 12.7, 9.2 Hz, 1H) | FA: m/z = 564.4 (M + H) |
| I-274b | ¹H NMR (400 MHz, DMSO-d₆) δ 8.68 (s, 1H), 8.64 (s, 1H), 8.27 (d, J = 7.5 Hz, 1H), 7.72 (s, 1H), 7.67 (d, J = 1.2 Hz, 1H), 7.54-7.08 (m, 4H), 6.87 (d, J = 1.7 Hz, 1H), 5.14 (s, 1H), 4.93-4.84 (m, 1H), 4.76-4.64 (m, 1H), 4.09 (dd, J = 9.8, 6.0 Hz, 1H), 4.00-3.90 (m, 2H), 3.12-2.93 (m, 2H), 2.92-2.65 (m, 3H), 2.37-2.24 (m, 1H), 2.18-2.04 (m, 1H), 1.96 (ddd, J = 11.7, 7.5, 3.7 Hz, 1H), 1.83-1.73 (m, 1H), 1.26 (dt, J = 12.8, 9.2 Hz, 1H) | FA: m/z = 564.4 (M + H) |
| I-334 | ¹H NMR (400 MHz, DMSO-d₆) δ 8.66 (s, 1H), 8.64 (s, 1H), 8.24 (d, J = 7.4 Hz, 1H), 7.64-7.56 (br s, 2H), 7.43 (s, 2H), 7.35 (s, 1H), 7.33-7.25 (m, 2H), 6.31 (s, 1H), 4.88 (d, J = 3.8 Hz, 1H), 4.77-4.63 (m, 1H), 4.09 (dd, J = 9.8, 6.0 Hz, 1H), 4.01-3.79 (m, 3H), 3.19 (s, 1H), 2.89-2.74 (m, 2H), 2.36-2.26 (m, 1H), 2.17-2.05 (m, 1H), 2.00-1.90 (m, 1H), 1.82-1.71 (m, 1H), 1.41 (s, 9H), 1.33-1.19 (m, 1H) | FA: m/z = 664.4 (M + H) |
| I-311b | ¹H NMR (400 MHz, DMSO-d₆) δ 8.60 (s, 1H), 8.52 (s, 1H), 8.11 (d, J = 7.5 Hz, 1H), 7.45-7.40 (br s, 2H), 7.32 (s, 1H), 7.21 (d, J = 1.1 Hz, 2H), 6.66 (s, 1H), 4.86 (d, J = 4.6 Hz, 1H), 4.75-4.60 (m, 1H), 4.57 (s, 1H), 4.08 (dd, J = 9.7, 6.0 Hz, 1H), 4.01-3.85 (m, 2H), 3.14-2.97 (m, 2H), 2.83-2.71 (m, 1H), 2.60-2.52 (m, 1H), 2.38-2.25 (m, 1H), 2.22 (s, 3H), 2.17-2.03 (m, 1H), 1.89 (ddd, J = 11.9, 7.6, 3.8 Hz, 1H), 1.77-1.65 (m, 1H), 1.34-1.26 (m, 1H) | FA: m/z = 612.3(M + H) |
| I-311a | ¹H NMR (400 MHz, DMSO-d₆) δ 8.60 (s, 1H), 8.52 (s, 1H), 8.12 (d, J = 7.5 Hz, 1H), 7.44-7.39 (br s, 2H), 7.32 (s, 1H), 7.21 (d, J = 1.1 Hz, 2H), 6.66 (s, 1H), 4.87 (d, J = 4.6 Hz, 1H), 4.74-4.60 (m, 1H), 4.57 (s, 1H), 4.07 (dd, J = 9.8, 6.0 Hz, 1H), 3.98-3.89 (m, 2H), 3.13-2.97 (m, 2H), 2.82-2.72 (m, 1H), 2.59-2.52 (m, 1H), 2.31-2.23 (m, 1H), 2.22 (s, 3H), 2.15-2.03 (m, 1H), 1.94 (ddd, J = 11.7, 7.4, 3.6 Hz, 1H), 1.82-1.70 (m, 1H), 1.31-1.25 (m, 1H) | FA: m/z = 612.3 (M + H) |
| I-255b | ¹H NMR (400 MHz, DMSO-d₆) δ 8.61 (s, 1H), 8.57 (s, 1H), 8.15 (d, J = 7.0 Hz, 1H), 7.49-7.36 (m, 3H), 7.25-7.12 (m, 2H), 6.67 (s, 1H), 5.17 (s, 1H), 4.86 (d, J = 4.3 Hz, 1H), 4.74-4.60 (m, 1H), 4.13-4.03 (m, 1H), 3.99-3.88 (m, 2H), 3.23-3.02 (m, 2H), 2.98-2.83 (m, 2H), 2.75-2.63 (m, 1H), 2.36-2.23 (m, 1H), 2.15-2.03 (m, 1H), 1.95-1.83 (m, 1H), 1.78-1.65 (m, 1H), 1.33-1.17 (m, 1H) | FA: m/z = 598.3 (M + H) |
| I-255a | ¹H NMR (400 MHz, DMSO-d₆) δ 8.61 (s, 1H), 8.57 (s, 1H), 8.16 (d, J = 7.4 Hz, 1H), 7.47-7.35 (m, 3H), 7.25-7.14 (m, 2H), 6.68 (s, 1H), 5.17 (s, 1H), 4.87 (d, J = | FA: m/z = 598.2 (M + H) |

| Compound No. | ¹H NMR | LC/MS |
|---|---|---|
| | 4.5 Hz, 1H), 4.74-4.60 (m, 1H), 4.07 (dd, J = 9.5, 5.8 Hz, 1H), 4.00-3.88 (m, 2H), 3.23-3.02 (m, 2H), 2.98-2.82 (m, 2H), 2.75-2.64 (m, 1H), 2.35-2.21 (m, 1H), 2.10 (s, 1H), 1.94 (s, 1H), 1.82-1.69 (m, 1H), 1.31-1.16 (m, 1H) | |
| I-349 | ¹H NMR (400 MHz, Methanol-d₄) δ 8.71 (s, 1H), 8.57 (s, 1H), 7.63 (s, 1H), 7.53 (s, 1H), 7.25 (d, J = 8.1 Hz, 1H), 7.17 (dd, J = 8.1, 1.6 Hz, 1H), 6.98 (s, 1H), 4.83-4.75 (m, 1H), 4.51 (t, J = 8.0 Hz, 1H), 4.23-4.12 (m, 3H), 3.08-2.86 (m, 2H), 2.67-2.45 (m, 2H), 2.32-2.07 (m, 3H), 1.96-1.85 (m, 1H), 1.47-1.37 (m, 1H) | FA: m/z = 549.0 (M + H) |
| I-349a | ¹H NMR (400 MHz, Methanol-d₄) δ 8.71 (s, 1H), 8.57 (s, 1H), 7.63 (d, J = 1.0 Hz, 1H), 7.53 (d, J = 1.3 Hz, 1H), 7.25 (d, J = 8.0 Hz, 1H), 7.17 (dd, J = 8.1, 1.5 Hz, 1H), 6.98 (s, 1H), 4.83-4.75 (m, 1H), 4.51 (t, J = 8.0 Hz, 1H), 4.23-4.12 (m, 3H), 3.08-2.87 (m, 2H), 2.65-2.45 (m, 2H), 2.32-2.10 (m, 3H), 1.95-1.85 (m, 1H), 1.47-1.36 (m, 1H). | FA: m/z = 549.2 (M + H) |
| I-349b | ¹H NMR (400 MHz, Methanol-d₄) δ 8.70 (s, 1H), 8.56 (s, 1H), 7.63 (d, J = 1.0 Hz, 1H), 7.53 (d, J = 1.3 Hz, 1H), 7.25 (d, J = 8.1 Hz, 1H), 7.17 (dd, J = 8.0, 1.7 Hz, 1H), 6.98 (s, 1H), 4.83-4.74 (m, 1H), 4.51 (t, J = 8.0 Hz, 1H), 4.24-4.12 (m, 3H), 3.08-2.85 (m, 2H), 2.67-2.45 (m, 2H), 2.32-2.09 (m, 3H), 1.95-1.84 (m, 1H), 1.48-1.36 (m, 1H) | FA: m/z = 548.9 (M + H) |
| I-300a | ¹H NMR (400 MHz, Methanol-d₄) δ 9.86 (s, 1H), 8.56 (s, 1H), 7.21 (s, 2H), 6.76 (s, 1H), 6.12 (s, 1H), 4.30-4.12 (m, 4H), 4.00-3.91 (m, 1H), 3.15-3.03 (m, 1H), 2.90-2.79 (m, 1H), 2.58-2.47 (m, 4H), 2.32-2.13 (m, 2H), 1.98-1.87 (m, 1H), 1.51-1.39 (m, 1H) | FA: m/z = 580.4 (M + H) |
| I-300b | ¹H NMR (400 MHz, Methanol-d₄) δ 9.86 (s, 1H), 8.57 (s, 1H), 7.21 (s, 2H), 6.76 (s, 1H), 6.12 (s, 1H), 4.30-4.13 (m, 4H), 4.00-3.92 (m, 1H), 3.15-3.03 (m, 1H), 2.90-2.80 (m, 1H), 2.58-2.47 (m, 4H), 2.32-2.13 (m, 2H), 2.00-1.88 (m, 1H), 1.52-1.40 (m, 1H) | FA: m/z = 580.4 (M + H) |
| I-268 | ¹H NMR (400 MHz, DMSO-d₆) δ 8.64 (d, J = 3.3 Hz, 2H), 8.26 (d, J = 7.5 Hz, 1H), 7.94 (s, 1H), 7.64 (s, 1H), 7.45-7.36 (m, 3H), 7.18 (d, J = 8.2 Hz, 1H), 7.03 (d, J = 1.6 Hz, 1H), 5.91 (s, 1H), 4.91-4.84 (m, 1H), 4.77-4.62 (m, 1H), 4.14-3.91 (m, 4H), 3.87-3.76 (m, 1H), 2.99-2.87 (m, 1H), 2.82-2.70 (m, 1H), 2.37-2.25 (m, 1H), 2.16-2.06 (m, 1H), 2.01-1.89 (m, 1H), 1.83-1.70 (m, 1H), 1.33-1.21 (m, 1H) | FA: m/z = 611.1 (M + H) |
| I-268a | ¹H NMR (400 MHz, DMSO-d₆) δ 8.64 (d, J = 3.2 Hz, 2H), 8.26 (d, J = 7.4 Hz, 1H), 7.93 (s, 1H), 7.64 (d, J = 1.2 Hz, 1H), 7.46-7.37 (m, 3H), 7.18 (d, J = 8.2 Hz, 1H), 7.03 (d, J = 1.6 Hz, 1H), 5.91 (s, 1H), 4.88 (d, J = 4.6 Hz, 1H), 4.75-4.64 (m, 1H), 4.13-3.90 (m, 4H), 3.87-3.76 (m, 1H), 2.99-2.86 (m, 1H), 2.81-2.70 (m, 1H), 2.35-2.26 (m, 1H), 2.17-2.04 (m, 1H), 2.02-1.90 (m, 1H), 1.83-1.71 (m, 1H), 1.34-1.21 (m, 1H) | FA: m/z = 611.2 (M + H) |
| I-268b | ¹H NMR (400 MHz, DMSO-d₆) δ 8.64 (d, J = 3.3 Hz, 2H), 8.26 (d, J = 7.4 Hz, 1H), 7.94 (s, 1H), 7.63 (d, J = 1.3 Hz, 1H), 7.47-7.36 (m, 3H), 7.18 (d, J = 8.2 Hz, 1H), 7.03 (d, J = 1.7 Hz, 1H), 5.91 (s, 1H), 4.88 (d, J = 4.6 Hz, 1H), 4.76-4.62 (m, 1H), 4.13-3.90 (m, 4H), 3.86-3.76 (m, 1H), 2.99-2.86 (m, 1H), 2.81-2.70 (m, 1H), 2.38-2.26 (m, 1H), 2.17-2.05 (m, 1H), 2.00-1.89 (m, 1H), 1.83-1.72 (m, 1H), 1.34-1.23 (m, 1H) | FA: m/z = 611.2 (M + H) |
| I-286 | ¹H NMR (400 MHz, DMSO-d₆) δ 8.59 (s, 1H), 8.51 (s, 1H), 8.17 (d, J = 7.5 Hz, 1H), 7.72 (d, J = 8.1 Hz, 1H), 7.42 (s, 2H), 7.36 (d, J = 8.1 Hz, 1H), 7.29 (s, 1H), 5.88 (s, 1H), 4.89-4.84 (m, 1H), 4.74-4.61 (m, 1H), 4.15-4.05 (m, 2H), 3.98-3.80 (m, 3H), 3.12-2.99 (m, 1H), 2.87-2.77 (m, 1H), 2.36-2.23 (m, 1H), 2.16-2.04 (m, 1H), 1.98-1.87 (m, 1H), 1.80-1.68 (m, 1H), 1.32-1.19 (m, 1H) | FA: m/z = 582.1 (M + H) |

| Compound No. | ¹H NMR | LC/MS |
|---|---|---|
| I-286a | ¹H NMR (400 MHz, DMSO-$d_6$) δ 8.59 (s, 1H), 8.51 (s, 1H), 8.17 (d, J = 7.4 Hz, 1H), 7.72 (d, J = 8.1 Hz, 1H), 7.49-7.32 (m, 3H), 7.29 (s, 1H), 5.89 (s, 1H), 4.87 (d, J = 4.5 Hz, 1H), 4.73-4.60 (m, 1H), 4.14-4.04 (m, 2H), 3.98-3.81 (m, 3H), 3.11-2.99 (m, 1H), 2.87-2.77 (m, 1H), 2.31-2.23 (m, 1H), 2.16-2.05 (m, 1H), 1.99-1.89 (m, 1H), 1.81-1.69 (m, 1H), 1.30-1.19 (m, 1H) | FA: m/z = 580.1 (M + H) |
| I-286b | ¹H NMR (400 MHz, DMSO-$d_6$) δ 8.59 (s, 1H), 8.51 (s, 1H), 8.17 (d, J = 7.5 Hz, 1H), 7.72 (d, J = 8.1 Hz, 1H), 7.42 (s, 2H), 7.36 (d, J = 8.0 Hz, 1H), 7.29 (s, 1H), 5.88 (s, 1H), 4.87 (d, J = 4.6 Hz, 1H), 4.74-4.61 (m, 1H), 4.14-4.04 (m, 2H), 3.98-3.82 (m, 3H), 3.12-3.00 (m, 1H), 2.86-2.75 (m, 1H), 2.32-2.24 (m, 1H), 2.16-2.05 (m, 1H), 1.97-1.88 (m, 1H), 1.79-1.68 (m, 1H), 1.31-1.20 (m, 1H) | FA: m/z = 580.1 (M + H) |
| I-297 | ¹H NMR (400 MHz, DMSO-$d_6$) δ 8.58 (s, 1H), 8.47 (s, 1H), 8.17 (d, J = 7.4 Hz, 1H), 7.94 (d, J = 8.0 Hz, 1H), 7.75 (d, J = 8.0 Hz, 1H), 7.42 (s, 2H), 7.25 (s, 1H), 6.00 (s, 1H), 4.86 (d, J = 4.5 Hz, 1H), 4.74-4.58 (m, 1H), 4.18-4.03 (m, 2H), 3.99-3.87 (m, 3H), 3.23-3.10 (m, 1H), 3.00-2.88 (m, 1H), 2.54 (s, 3H), 2.35-2.22 (m, 1H), 2.16-2.03 (m, 1H), 1.98-1.87 (m, 1H), 1.79-1.67 (m, 1H), 1.31-1.17 (m, 1H) | FA: m/z = 614.1 (M + 1) |
| I-297a | ¹H NMR (400 MHz, DMSO-$d_6$) δ 8.58 (s, 1H), 8.47 (s, 1H), 8.17 (d, J = 7.4 Hz, 1H), 7.94 (d, J = 7.9 Hz, 1H), 7.75 (d, J = 8.0 Hz, 1H), 7.42 (s, 2H), 7.25 (s, 1H), 6.00 (s, 1H), 4.86 (d, J = 4.5 Hz, 1H), 4.73-4.59 (m, 1H), 4.17-4.04 (m, 2H), 3.98-3.88 (m, 3H), 3.23-3.10 (m, 1H), 2.99-2.88 (m, 1H), 2.54 (s, 3H), 2.31-2.23 (m, 1H), 2.14-2.03 (m, 1H), 1.97-1.87 (m, 1H), 1.79-1.68 (m, 1H), 1.29-1.20 (m, 1H) | FA: m/z = 614.1 (M + H) |
| I-297b | ¹H NMR (400 MHz, DMSO-$d_6$) δ 8.58 (s, 1H), 8.47 (s, 1H), 8.17 (d, J = 7.5 Hz, 1H), 7.94 (d, J = 8.0 Hz, 1H), 7.75 (d, J = 8.0 Hz, 1H), 7.42 (s, 2H), 7.25 (s, 1H), 6.00 (s, 1H), 4.86 (d, J = 4.5 Hz, 1H), 4.73-4.59 (m, 1H), 4.17-3.88 (m, 5H), 3.22-3.10 (m, 1H), 3.00-2.88 (m, 1H), 2.54 (s, 3H), 2.32-2.23 (m, 1H), 2.15-2.03 (m, 1H), 1.97-1.87 (m, 1H), 1.79-1.68 (m, 1H), 1.30-1.20 (m, 1H) | FA: m/z = 615.2 (M + H) |
| I-303 | ¹H NMR (400 MHz, DMSO-$d_6$) δ 8.58 (s, 1H), 8.47 (s, 1H), 8.18 (d, J = 7.5 Hz, 1H), 7.50-7.38 (m, 3H), 7.20-7.11 (m, 2H), 6.09 (s, 1H), 4.87 (d, J = 4.1 Hz, 1H), 4.72-4.58 (m, 1H), 4.12-4.04 (m, 1H), 3.98-3.87 (m, 3H), 3.83-3.74 (m, 1H), 2.99-2.78 (m, 2H), 2.53 (s, 3H), 2.32-2.23 (m, 1H), 2.15-2.04 (m, 1H), 1.97-1.87 (m, 1H), 1.79-1.68 (m, 1H), 1.30-1.20 (m, 1H) | FA: m/z = 597.1 (M + H) |
| I-341 | ¹H NMR (400 MHz, DMSO-$d_6$) δ 8.75 (d, J = 7.5 Hz, 1H), 8.63 (s, 1H), 8.41 (s, 1H), 7.44 (s, 2H), 7.14-7.03 (m, 2H), 6.81 (dd, J = 8.4, 2.6 Hz, 1H), 6.54 (d, J = 2.4 Hz, 1H), 5.99 (s, 1H), 4.91 (d, J = 4.5 Hz, 1H), 4.79-4.65 (m, 1H), 4.15-4.08 (m, 1H), 4.03-3.93 (m, 3H), 3.87-3.77 (m, 1H), 3.67 (s, 3H), 2.87-2.65 (m, 2H), 2.48 (s, 3H), 2.40-2.28 (m, 1H), 2.19-2.08 (m, 1H), 2.04-1.92 (m, 1H), 1.85-1.73 (m, 1H), 1.37-1.24 (m, 1H) | FA: m/z = 575.3 (M + H) |
| I-339 | ¹H NMR (400 MHz, DMSO-$d_6$) δ 8.59 (s, 1H), 8.50 (s, 1H), 8.14 (d, J = 7.5 Hz, 1H), 7.53 (d, J = 8.4 Hz, 1H), 7.42 (s, 2H), 7.27 (s, 1H), 6.66 (d, J = 8.4 Hz, 1H), 5.80 (s, 1H), 4.89-4.82 (m, 1H), 4.72-4.53 (m, 1H), 4.14-4.03 (m, 2H), 3.99-3.76 (m, 3H), 3.65 (s, 3H), 3.02-2.89 (m, 1H), 2.74-2.64 (m, 1H), 2.59 (s, 3H), 2.35-2.22 (m, 1H), 2.16-2.03 (m, 1H), 1.97-1.86 (m, 1H), 1.80-1.67 (m, 1H), 1.31-1.20 (m, 1H) | FA: m/z = 576.3 (M + H) |
| I-339a | ¹H NMR (400 MHz, DMSO-$d_6$) δ 8.59 (s, 1H), 8.50 (s, 1H), 8.13 (d, J = 7.5 Hz, 1H), 7.53 (d, J = 8.4 Hz, 1H), 7.42 (s, 2H), 7.27 (s, 1H), 6.66 (d, J = 8.4 Hz, 1H), 5.80 (s, 1H), 4.86 (d, J = 4.5 Hz, 1H), 4.74-4.59 (m, 1H), 4.15-4.03 (m, 2H), 3.99-3.89 (m, 2H), 3.88-3.79 (m, 1H), 3.65 (s, 3H), 3.01-2.88 (m, 1H), 2.74-2.64 (m, 1H), 2.59 (s, 3H), 2.35-2.23 (m, 1H), 2.15-2.03 (m, 1H), 1.98-1.85 (m, 1H), 1.79-1.67 (m, 1H), 1.31-1.17 (m, 1H) | FA: m/z = 576.3 (M + H) |
| I-339b | ¹H NMR (400 MHz, DMSO-$d_6$) δ 8.59 (s, 1H), 8.50 (s, 1H), 8.14 (d, J = 7.5 Hz, 1H), 7.53 (d, J = 8.4 Hz, 1H), 7.41 (s, 2H), 7.27 (s, 1H), 6.66 (d, J = 8.4 Hz, 1H), 5.80 (s, 1H), 4.87 (d, J = 4.5 Hz, 1H), 4.73-4.59 (m, 1H), 4.13-4.03 (m, 2H), | FA: m/z = 576.3 (M + H) |

| Compound No. | ¹H NMR | LC/MS |
|---|---|---|
| | 3.98-3.78 (m, 3H), 3.65 (s, 3H), 3.01-2.90 (m, 1H), 2.74-2.65 (m, 1H), 2.59 (s, 3H), 2.33-2.21 (m, 1H), 2.07 (m, 1H), 1.98-1.88 (m, 1H), 1.80-1.69 (m, 1H), 1.28-1.17 (m, 1H) | |
| I-79 | ¹H NMR (400 MHz, DMSO) δ 8.86 (s, 1H), 8.63 (s, 1H), 8.47 (d, J = 7.4 Hz, 1H), 7.98 (s, 1H), 7.48-7.39 (m, 2H), 7.37 (s, 2H), 7.33 (d, J = 7.6 Hz, 1H), 7.30-7.22 (m, 2H), 4.88 (d, J = 4.1 Hz, 1H), 4.75-4.61 (m, 1H), 4.09 (dd, J = 9.7, 6.0 Hz, 1H), 4.00-3.90 (m, 2H), 3.84 (s, 2H), 2.39-2.24 (m, 1H), 2.17-2.04 (m, 1H), 2.02-1.91 (m, 1H), 1.81-1.69 (m, 1H), 1.26 (dt, J = 12.6, 9.2 Hz, 1H) | FA: m/z = 507.2 (M + H) |
| I-87 | ¹H NMR (400 MHz, DMSO) δ 8.82 (s, 1H), 8.61 (s, 1H), 8.50 (d, J = 7.5 Hz, 1H), 7.45 (s, 2H), 7.40-7.22 (m, 6H), 6.49 (d, J = 3.6 Hz, 1H), 4.87 (d, J = 6.0 Hz, 1H), 4.72 (d, J = 4.9 Hz, 1H), 4.48-4.36 (m, 1H), 4.15 (s, 2H), 4.06 (dd, J = 9.7, 6.1 Hz, 1H), 3.96 (dd, J = 9.7, 6.7 Hz, 1H), 3.76 (dd, J = 12.8, 5.8 Hz, 1H), 3.69 (dd, J = 9.7, 4.8 Hz, 1H), 2.35-2.23 (m, 1H), 2.23-2.11 (m, 1H), 1.12 (dt, J = 12.9, 8.8 Hz, 1H) | FA: m/z = 489.4 (M + H) |
| I-236 | ¹H NMR (400 MHz, DMSO) δ 8.86 (s, 1H), 8.79 (d, J = 7.8 Hz, 1H), 7.95-7.83 (m, 2H), 7.64 (d, J = 3.8 Hz, 1H), 7.59-7.50 (m, 2H), 7.50-7.41 (m, 3H), 7.33 (d, J = 3.8 Hz, 1H), 4.91 (d, J = 6.1 Hz, 1H), 4.78 (d, J = 4.6 Hz, 1H), 4.48-4.35 (m, 1H), 4.06 (dd, J = 9.7, 6.3 Hz, 1H), 3.97 (dd, J = 9.7, 6.5 Hz, 1H), 3.83 (dd, J = 13.2, 5.9 Hz, 1H), 3.72 (dd, J = 8.9, 4.5 Hz, 1H), 2.35-2.13 (m, 2H), 1.18 (dt, J = 12.1, 8.8 Hz, 1H) | FA: m/z = 508.9 (M + H) |
| I-158 | ¹H NMR (400 MHz, MeOD) δ 9.21 (s, 1H), 8.62 (s, 1H), 7.96 (dd, J = 7.7, 1.7 Hz, 1H), 7.62-7.52 (m, 2H), 7.51-7.38 (m, 2H), 7.36 (d, J = 3.8 Hz, 1H), 4.60 (td, J = 8.2, 6.0 Hz, 1H), 4.27-4.15 (m, 2H), 4.00-3.91 (m, 2H), 2.60-2.47 (m, 1H), 2.45-2.33 (m, 1H), 1.40 (dt, J = 13.3, 8.6 Hz, 1H) | FA: m/z = 509.4 (M + H) |
| I-134 | ¹H NMR (400 MHz, MeOD) δ 9.16 (s, 1H), 8.62 (s, 1H), 7.91-7.84 (m, 2H), 7.54-7.46 (m, 3H), 7.43 (dd, J = 8.4, 6.2 Hz, 1H), 7.10 (d, J = 3.8 Hz, 1H), 4.63-4.55 (m, 1H), 4.25-4.16 (m, 2H), 3.99-3.92 (m, 2H), 2.58-2.47 (m, 1H), 2.43-2.33 (m, 1H), 1.40 (dt, J = 13.3, 8.6 Hz, 1H) | FA: m/z = 475.4 (M + H) |
| I-150 | ¹H NMR (400 MHz, MeOD) δ 8.75 (s, 1H), 8.62 (s, 1H), 7.67 (s, 1H), 5.44 (d, J = 1.7 Hz, 1H), 4.86-4.76 (m, 1H), 4.24-4.11 (m, 3H), 2.56-2.45 (m, 1H), 2.33-2.10 (m, 2H), 1.97-1.86 (m, 1H), 1.48-1.38 (m, 1H), 1.34-1.26 (m, 1H), 0.82-0.76 (m, 2H), 0.67-0.60 (m, 2H) | FA: m/z = 527.1 (M + H) |
| I-144 | ¹H NMR (400 MHz, MeOD) δ 8.62 (s, 1H), 8.53 (s, 1H), 7.38 (s, 1H), 7.33-7.11 (m, 10H), 4.81-4.70 (m, 1H), 4.22-4.10 (m, 5H), 3.99 (s, 2H), 2.54-2.42 (m, 1H), 2.30-2.08 (m, 2H), 1.93-1.81 (m, 1H), 1.46-1.34 (m, 1H) | FA: m/z = 579.4 (M + H) |
| I-218 | ¹H NMR (400 MHz, MeOD) δ 8.76 (s, 1H), 8.60 (s, 1H), 7.61 (s, 1H), 4.86-4.75 (m, 1H), 4.46 (s, 2H), 4.24-4.12 (m, 3H), 3.40 (s, 3H), 2.55-2.46 (m, 1H), 2.32-2.10 (m, 2H), 1.96-1.85 (m, 1H), 1.48-1.38 (m, 1H) | FA: m/z = 479.1 (M + H) |
| I-172 | ¹H NMR (400 MHz, MeOD) δ 8.73 (s, 1H), 8.60 (s, 1H), 7.56 (s, 1H), 4.88-4.75 (m, 1H), 4.53 (d, J = 7.6 Hz, 1H), 4.24-4.11 (m, 3H), 2.57-2.44 (m, 1H), 2.33-2.10 (m, 2H), 2.06-1.86 (m, 2H), 1.83-1.56 (m, 4H), 1.49-1.37 (m, 2H), 1.33-0.96 (m, 5H) | FA: m/z = 545.1 (M + H) |
| I-226 | ¹H NMR (400 MHz, MeOD) δ 8.76 (s, 1H), 8.61 (s, 1H), 7.64 (s, 1H), 4.99 (q, J = 6.6 Hz, 2H), 4.86-4.76 (m, 1H), 4.24-4.12 (m, 3H), 2.56-2.46 (m, 1H), 2.32-2.11 (m, 2H), 1.95-1.86 (m, 1H), 1.48-1.38 (m, 4H) | FA: m/z = 477.1 (M + H) |
| I-242 | ¹H NMR (400 MHz, MeOD) δ 8.82 (s, 1H), 8.62 (s, 1H), 7.95 (s, 1H), 4.87-4.77 (m, 1H), 4.25-4.12 (m, 3H), 2.62 (s, 3H), 2.56-2.45 (m, 1H), 2.32-2.11 (m, 2H), 1.96-1.86 (m, 1H), 1.50-1.39 (m, 1H) | FA: m/z = 475.1 (M + H) |
| I-215 | ¹H NMR (400 MHz, MeOD) δ 8.81 (s, 1H), 8.59 (s, 1H), 7.91-7.84 (m, 2H), 7.74-7.65 (m, 2H), 7.60-7.52 (m, 2H), 4.87-4.76 (m, 1H), 4.24-4.12 (m, 3H), 2.56-2.45 (m, 1H), 2.33-2.10 (m, 2H), 1.98-1.86 (m, 1H), 1.52-1.39 (m, 1H) | FA: m/z = 537.4 (M + H) |
| I-56 | ¹H NMR (400 MHz, MeOD) δ 8.67 (s, 1H), 8.58 (s, 1H), 7.56 (s, 1H), 7.43-7.23 (m, 5H), 5.93 (s, 1H), 4.87-4.73 (m, 1H), 4.25-4.09 (m, 3H), 2.57-2.42 (m, 1H), 2.31-2.09 (m, 2H), 1.95-1.82 (m, 1H), 1.47-1.35 (m, 1H) | FA: m/z = 539.0 (M + H) |
| I-211 | ¹H NMR (400 MHz, MeOD) δ 8.77 (s, 1H), 8.61 (s, 1H), 7.64 (s, 1H), 4.87-4.75 (m, 1H), 4.59 (s, 2H), 4.24-4.12 (m, 3H), 2.56-2.45 (m, 1H), 2.32-2.11 (m, 2H), 1.96-1.85 (m, 1H), 1.49-1.37 (m, 1H) | FA: m/z = 463.2 (M + H) |

| Compound No. | ¹H NMR | LC/MS |
|---|---|---|
| I-228 | ¹H NMR (400 MHz, MeOD) δ 8.78 (s, 1H), 8.60 (s, 1H), 7.81 (s, 1H), 7.69 (s, 1H), 4.86-4.76 (m, 1H), 4.24-4.12 (m, 3H), 3.71 (s, 2H), 2.93 (t, J = 13.1 Hz, 2H), 2.79 (t, J = 7.0 Hz, 2H), 2.58-2.47 (m, 1H), 2.36-2.11 (m, 4H), 1.96-1.87 (m, 1H), 1.49-1.39 (m, 1H) | FA: m/z = 518.1 (M + H) |
| I-224 | ¹H NMR (400 MHz, MeOD) δ 8.78 (s, 1H), 8.60 (s, 1H), 7.79 (s, 1H), 7.70 (s, 1H), 4.86-4.76 (m, 1H), 4.24-4.12 (m, 3H), 3.66 (s, 2H), 2.65 (t, J = 11.4 Hz, 2H), 2.57-2.45 (m, 2H), 2.34-2.12 (m, 2H), 1.96-1.71 (m, 6H), 1.50-1.37 (m, 1H) | FA: m/z = 532.2 (M + H) |
| I-117a | ¹H NMR (400 MHz, MeOD) δ 8.64 (s, 1H), 8.56 (s, 1H), 7.68 (s, 1H), 7.49 (d, J = 1.1 Hz, 1H), 7.33-7.15 (m, 4H), 4.84-4.73 (m, 1H), 4.29-4.10 (m, 4H), 2.54-2.43 (m, 1H), 2.32-2.09 (m, 2H), 1.95-1.84 (m, 1H), 1.65 (d, J = 7.2 Hz, 3H), 1.47-1.35 (m, 1H) | FA: m/z = 539.1 (M + H) |
| I-117b | ¹H NMR (400 MHz, MeOD) δ 8.64 (s, 1H), 8.56 (s, 1H), 7.68 (s, 1H), 7.49 (s, 1H), 7.33-7.15 (m, 4H), 4.84-4.72 (m, 1H), 4.30-4.09 (m, 4H), 2.55-2.43 (m, 1H), 2.31-2.09 (m, 2H), 1.96-1.83 (m, 1H), 1.65 (d, J = 7.2 Hz, 3H), 1.48-1.35 (m, 1H) | FA: m/z = 540.1 (M + H) |
| I-117 | ¹H NMR (400 MHz, MeOD) δ 8.64 (s, 1H), 8.56 (s, 1H), 7.68 (s, 1H), 7.49 (s, 1H), 7.33-7.15 (m, 4H), 4.84-4.72 (m, 1H), 4.30-4.06 (m, 4H), 2.54-2.43 (m, 1H), 2.31-2.09 (m, 2H), 1.95-1.84 (m, 1H), 1.65 (d, J = 7.2 Hz, 3H), 1.47-1.35 (m, 1H) | FA: m/z = 537.4 (M + H) |
| I-106a | ¹H NMR (400 MHz, MeOD) δ 8.62 (s, 1H), 8.56 (s, 1H), 7.64 (s, 1H), 7.46 (s, 1H), 7.36-7.08 (m, 5H), 4.83-4.75 (m, 1H), 4.27-4.10 (m, 4H), 2.54-2.44 (m, 1H), 2.31-2.09 (m, 2H), 1.95-1.84 (m, 1H), 1.65 (d, J = 7.2 Hz, 3H), 1.47-1.36 (m, 1H) | FA: m/z = 503.1 (M + H) |
| I-106b | ¹H NMR (400 MHz, MeOD) δ 8.62 (s, 1H), 8.56 (s, 1H), 7.64 (s, 1H), 7.46 (d, J = 1.2 Hz, 1H), 7.34-7.15 (m, 5H), 4.85-4.73 (m, 1H), 4.28-4.11 (m, 4H), 2.56-2.44 (m, 1H), 2.31-2.10 (m, 2H), 1.94-1.84 (m, 1H), 1.65 (d, J = 7.2 Hz, 3H), 1.49-1.36 (m, 1H) | FA: m/z = 503.4 (M + H) |
| I-106 | ¹H NMR (400 MHz, MeOD) δ 8.62 (s, 1H), 8.56 (s, 1H), 7.64 (s, 1H), 7.46 (s, 1H), 7.34-7.16 (m, 5H), 4.84-4.73 (m, 1H), 4.28-4.10 (m, 4H), 2.54-2.43 (m, 1H), 2.31-2.09 (m, 2H), 1.94-1.84 (m, 1H), 1.65 (d, J = 7.2 Hz, 3H), 1.47-1.35 (m, 1H) | FA: m/z = 503.3 (M + H) |
| I-59 | ¹H NMR (400 MHz, DMSO) δ 8.68 (s, 1H), 8.64 (s, 1H), 8.26 (d, J = 7.4 Hz, 1H), 7.82 (s, 1H), 7.70 (s, 1H), 7.51 (s, 1H), 7.47-7.35 (m, 3H), 7.33-7.21 (m, 2H), 4.88 (d, J = 4.5 Hz, 1H), 4.78-4.63 (m, 1H), 4.09 (dd, J = 9.6, 6.1 Hz, 1H), 4.03-3.88 (m, 4H), 2.36-2.25 (m, 1H), 2.16-2.05 (m, 1H), 2.01-1.90 (m, 1H), 1.82-1.70 (m, 1H), 1.33-1.19 (m, 1H) | FA: m/z = 569.1 (M + H) |
| I-52 | ¹H NMR (400 MHz, DMSO) δ 8.65 (s, 1H), 8.63 (s, 1H), 8.22 (d, J = 7.5 Hz, 1H), 7.61 (s, 1H), 7.47-7.41 (m, 3H), 7.41-7.36 (m, 1H), 7.29-7.20 (m, 2H), 4.89 (d, J = 4.5 Hz, 1H), 4.74-4.63 (m, 1H), 4.12-4.05 (m, 1H), 3.99-3.90 (m, 4H), 2.45 (s, 3H), 2.29 (dd, J = 13.4, 7.3 Hz, 1H), 2.15-2.05 (m, 1H), 1.99-1.91 (m, 1H), 1.80-1.70 (m, 1H), 1.26 (m, 1H) | FA: m/z = 582.9 (M + H) |
| I-20a | ¹H NMR (400 MHz, MeOD) δ 8.66 (s, 1H), 8.59 (s, 1H), 7.82 (s, 1H), 7.59 (s, 1H), 7.51 (s, 1H), 7.40 (d, J = 7.8 Hz, 1H), 7.33 (t, J = 7.8 Hz, 1H), 7.25 (d, J = 7.7 Hz, 1H), 4.85-4.74 (m, 1H), 4.20 (tt, J = 15.9, 7.8 Hz, 2H), 4.07 (t, J = 7.0 Hz, 3H), 2.74-2.62 (m, 1H), 2.57-2.42 (m, 2H), 2.32-2.22 (m, 1H), 2.20-2.11 (m, 1H), 2.11-1.84 (m, 3H), 1.42 (dt, J = 12.6, 9.2 Hz, 1H) | FA: m/z = 579.4 (M + H) |
| I-20b | ¹H NMR (400 MHz, DMSO) δ 8.64 (s, 1H), 8.60 (s, 1H), 8.22 (d, J = 7.5 Hz, 1H), 7.97 (d, J = 1.4 Hz, 1H), 7.67 (d, J = 1.4 Hz, 1H), 7.52 (t, J = 1.8 Hz, 1H), 7.47-7.41 (m, 1H), 7.35 (t, J = 7.8 Hz, 1H), 7.29 (ddd, J = 7.9, 2.0, 1.1 Hz, 1H), 4.69 (dq, J = 16.2, 8.3 Hz, 1H), 4.08 (dd, J = 9.7, 6.0 Hz, 1H), 4.00-3.90 (m, 4H), 3.20-3.12 (m, 1H), 2.74-2.64 (m, 1H), 2.39 (dt, J = 12.6, 7.5 Hz, 1H), 2.35-2.25 (m, 1H), 2.16-2.05 (m, 1H), 1.99-1.82 (m, 3H), 1.79-1.69 (m, 1H), 1.62-1.50 (m, 1H), 1.36-1.19 (m, 2H) | FA: m/z = 579.4 (M + H) |

-continued

| Compound No. | ¹H NMR | LC/MS |
|---|---|---|
| I-49 | ¹H NMR (400 MHz, DMSO) δ 8.78 (s, 1H), 8.69 (s, 1H), 8.23 (d, J = 7.5 Hz, 1H), 7.81 (s, 1H), 7.50-7.41 (m, 3H), 7.41-7.28 (m, 3H), 6.15 (s, 1H), 4.90 (d, J = 4.6 Hz, 1H), 4.80-4.67 (m, 1H), 4.59 (t, J = 4.8 Hz, 1H), 4.10 (dd, J = 9.7, 6.0 Hz, 1H), 4.01-3.92 (m, 2H), 3.47-3.35 (m, 2H), 2.66-2.56 (m, 1H), 2.45 (d, J = 5.4 Hz, 1H), 2.37-2.27 (m, 1H), 2.19-2.07 (m, 1H), 2.02-1.92 (m, 1H), 1.84-1.74 (m, 1H), 1.44-1.35 (m, 1H) | FA: m/z = 619.2 (M + H) |
| I-67 | ¹H NMR (400 MHz, DMSO) δ 8.79 (s, 1H), 8.67 (s, 1H), 8.20 (d, J = 7.6 Hz, 1H), 7.84 (s, 1H), 7.57 (d, J = 1.1 Hz, 1H), 7.49-7.33 (m, 5H), 4.89 (dd, J = 4.5, 0.8 Hz, 1H), 4.78-4.65 (m, 1H), 4.66-4.53 (m, 2H), 4.13-4.04 (m, 1H), 4.01-3.90 (m, 2H), 3.44-3.34 (m, 1H), 3.21-3.10 (m, 1H), 2.37-2.25 (m, 1H), 2.17-2.05 (m, 1H), 2.00-1.90 (m, 1H), 1.83-1.72 (m, 1H), 1.34-1.21 (m, 1H) | FA: m/z = 601.2 (M + H) |
| I-89 | ¹H NMR (400 MHz, DMSO) δ 8.66 (s, 1H), 8.64 (s, 1H), 8.09 (d, J = 7.6 Hz, 1H), 7.66 (d, J = 4.2 Hz, 1H), 7.49-7.39 (br s, 2H), 7.39-7.31 (m, 2H), 7.28 (d, J = 8.1 Hz, 1H), 7.23 (d, J = 7.5 Hz, 1H), 4.88 (d, J = 4.5 Hz, 1H), 4.76-4.61 (m, 1H), 4.08 (dd, J = 9.7, 6.1 Hz, 1H), 3.99-3.88 (m, 4H), 2.32-2.23 (m, 1H), 2.15-2.04 (m, 1H), 1.98-1.87 (m, 1H), 1.81-1.69 (m, 1H), 1.32-1.19 (m, 1H) | FA: m/z = 542.9 (M + H) |
| I-111 | ¹H NMR (400 MHz, DMSO) δ 8.62 (s, 2H), 8.21 (d, J = 7.4 Hz, 2H), 7.54 (s, 1H), 7.48-7.38 (br s, 2H), 7.19 (t, J = 7.6 Hz, 1H), 7.08 (s, 1H), 7.01 (t, J = 8.5 Hz, 2H), 4.88 (d, J = 4.5 Hz, 1H), 4.75-4.62 (m, 1H), 4.08 (dd, J = 9.7, 6.0 Hz, 1H), 3.99-3.86 (m, 4H), 2.56 (q, J = 7.6 Hz, 1H), 2.46 (s, 3H), 2.34-2.25 (m, 1H), 2.15-2.04 (m, 1H), 1.98-1.89 (m, 1H), 1.80-1.70 (m, 1H), 1.31-1.20 (m, 1H), 1.15 (t, J = 7.6 Hz, 3H) | FA: m/z = 531.1 (M + H) |
| I-45 | ¹H NMR (400 MHz, DMSO) δ 8.63 (s, 1H), 8.62 (s, 1H), 8.21 (d, J = 7.5 Hz, 1H), 7.53 (s, 1H), 7.48-7.38 (br s, 2H), 7.16 (t, J = 7.5 Hz, 1H), 7.07-6.96 (m, 3H), 4.88 (d, J = 4.5 Hz, 1H), 4.75-4.62 (m, 1H), 4.08 (dd, J = 9.7, 6.1 Hz, 1H), 3.99-3.91 (m, 2H), 3.89 (s, 2H), 2.46 (s, 3H), 2.35-2.20 (m, 4H), 2.16-2.04 (m, 1H), 1.98-1.89 (m, 1H), 1.80-1.69 (m, 1H), 1.31-1.20 (m, 1H) | FA: m/z = 517.1 (M + H) |
| I-123 | ¹H NMR (400 MHz, DMSO) δ 8.66 (s, 1H), 8.64 (s, 1H), 8.26 (d, J = 7.5 Hz, 1H), 7.78 (s, 1H), 7.66 (s, 1H), 7.49-7.38 (br s, 2H), 7.21 (t, J = 7.9 Hz, 1H), 6.88-6.80 (m, 2H), 6.77 (dd, J = 8.2, 1.8 Hz, 1H), 4.89 (d, J = 4.5 Hz, 1H), 4.76-4.62 (m, 1H), 4.13-4.03 (m, 1H), 4.00-3.88 (m, 4H), 3.72 (s, 2H), 2.29 (dd, J = 12.9, 7.7 Hz, 1H), 2.17-2.04 (m, 1H), 2.00-1.88 (m, 1H), 1.82-1.70 (m, 1H), 1.33-1.19 (m, 1H) | FA: m/z = 519.1 (M + H) |
| I-115 | ¹H NMR (400 MHz, DMSO) δ 8.67 (s, 1H), 8.62 (s, 1H), 8.27 (d, J = 7.6 Hz, 1H), 7.63 (d, J = 3.8 Hz, 1H), 7.54-7.39 (br s, 2H), 7.39-7.29 (m, 4H), 7.29-7.22 (m, 1H), 7.08 (d, J = 3.8 Hz, 1H), 4.86 (d, J = 5.9 Hz, 1H), 4.79-4.62 (br s, 1H), 4.50-4.37 (m, 1H), 4.06 (dd, J = 9.7, 6.2 Hz, 1H), 3.96 (dd, J = 9.7, 6.7 Hz, 1H), 3.77 (dd, J = 12.7, 5.8 Hz, 1H), 3.69 (t, J = 4.6 Hz, 1H), 2.28 (dt, J = 12.6, 8.4 Hz, 1H), 2.22-2.11 (m, 1H), 1.13 (dt, J = 12.6, 8.8 Hz, 1H) | FA: m/z = 505.4 (M + H) |
| I-60 | ¹H NMR (400 MHz, DMSO) δ 8.66 (s, 1H), 8.64 (s, 1H), 8.26 (d, J = 7.6 Hz, 1H), 7.76 (s, 1H), 7.64 (s, 1H), 7.50-7.38 (br s, 2H), 7.18 (t, J = 7.5 Hz, 1H), 7.12-6.96 (m, 3H), 4.89 (d, J = 4.5 Hz, 1H), 4.76-4.62 (m, 1H), 4.08 (dd, J = 9.5, 6.1 Hz, 1H), 4.00-3.87 (m, 3H), 2.36-2.20 (m, 4H), 2.16-2.04 (m, 1H), 2.00-1.88 (m, 1H), 1.81-1.70 (m, 1H), 1.33-1.18 (m, 1H) | FA: m/z = 503.1 (M + H) |
| I-70 | ¹H NMR (400 MHz, DMSO) δ 8.67 (s, 1H), 8.64 (s, 1H), 8.26 (d, J = 7.5 Hz, 1H), 7.81 (s, 1H), 7.69 (s, 1H), 7.46-7.36 (m, 3H), 7.36-7.28 (m, 3H), 4.88 (d, J = 4.5 Hz, 1H), 4.77-4.62 (m, 1H), 4.16 (s, 1H), 4.08 (dd, J = 9.7, 6.1 Hz, 1H), 4.03-3.88 (m, 4H), 2.37-2.25 (m, 1H), 2.18-2.04 (m, 1H), 1.95 (s, 1H), 1.82-1.70 (m, 1H), 1.33-1.19 (m, 1H) | FA: m/z = 513.2 (M + H) |
| I-104 | ¹H NMR (400 MHz, MeOD) δ 8.59 (s, 1H), 8.47 (s, 1H), 7.53 (d, J = 1.3 Hz, 1H), 7.44 (d, J = 1.3 Hz, 1H), 7.33 (m, 2H), 7.09 (dd, J = 8.3, 2.1 Hz, 1H), 4.69 (s, 1H), 4.08 (m, 3H), 3.92 (s, 2H), 2.56 (s, 2H), 2.39 (m, 1H), 2.25-2.11 (m, 1H), 2.10-1.98 (m, 1H), 1.88-1.69 (m, 1H), 1.32 (m, 1H). | FA: m/z = 557.2 (M + H) |
| I-167 | ¹H NMR (400 MHz, MeOD) δ 8.84 (s, 1H), 8.62 (s, 1H), 8.30 (s, 1H), 8.01 (s, 1H), 7.82 (s, 1H), 7.25-7.14 (m, 3H), 7.10 (d, J = 7.0 Hz, 1H), 4.89-4.74 (m, 2H), 4.29-4.12 (m, 4H), 4.08 (s, 2H), 3.97 (s, 2H), 3.15-3.09 (m, 2H), 3.09-3.00 (m, 3H), 2.56-2.46 (m, 1H), 2.34-2.23 (m, 1H), 2.21-2.09 (m, 1H), 1.98-1.84 (m, 1H), 1.53-1.36 (m, 1H). | FA: m/z = 544.3 (M + H) |

-continued

| Compound No. | ¹H NMR | LC/MS |
|---|---|---|
| I-91 | ¹H NMR (400 MHz, MeOD) δ 8.77 (s, 1H), 8.62 (s, 1H), 7.95 (s, 1H), 7.76 (s, 1H), 7.30 (dd, J = 8.8, 7.4 Hz, 2H), 7.01 (d, J = 7.9 Hz, 2H), 6.96 (t, J = 7.4 Hz, 1H), 5.15 (s, 2H), 4.83-4.70 (m, 1H), 4.35-3.99 (m, 4H), 2.57-2.46 (m, 1H), 2.33-2.25 (m, 1H), 2.22-2.11 (m, 1H), 2.00-1.85 (m, 1H), 1.54-1.36 (m, 1H). | FA: m/z = 504.8 (M + H) |
| I-61 | | FA: m/z = 540.8 (M + H) |
| I-193 | | FA: m/z = 480.9 (M + H) |
| I-155 | | FA: m/z = 556.8 (M + H) |
| I-173 | | FA: m/z = 510.9 (M + H) |
| I-210 | | FA: m/z = 523.8 (M + H) |
| I-185 | | FA: m/z = 513.9 (M + H) |
| I-113 | | FA: m/z = 554.8 (M + H) |
| I-84 | | FA: m/z = 540.8 (M + H) |
| I-81 | | FA: m/z = 534.8 (M + H) |
| I-204 | | FA: m/z = 493.9 (M + H) |
| I-192 | | FA: m/z = 529.3 (M + H) |
| I-241 | | FA: m/z = 573.3 (M + H) |
| I-222 | | FA: m/z = 518.3 (M + H) |
| I-219 | | FA: m/z = 480.3 (M + H) |
| I-187 | | FA: m/z = 530.1 (M + H) |
| I-225 | | FA: m/z = 510.3 (M + H) |
| I-168 | | FA: m/z = 550.1 (M + H) |
| I-324 | ¹H NMR (400 MHz, Methanol-$d_4$) δ 8.67 (s, 1H), 8.58 (s, 1H), 7.55 (s, 1H), 7.27-7.11 (m, 3H), 6.86-6.79 (m, 1H), 6.05 (s, 1H), 4.83-4.73 (m, 1H), 4.29-4.12 (m, 4H), 4.00-3.91 (m, 1H), 3.22-3.11 (m, 1H), 2.87-2.76 (m, 1H), 2.56-2.42 (m, 1H), 2.33-2.20 (m, 1H), 2.20-2.08 (m, 1H), 1.98-1.84 (m, 1H), 1.51-1.36 (m, 1H) | AA: m/z = 556.2 (M + H) |
| I-313 | ¹H NMR (400 MHz, Methanol-$d_4$) δ 8.63 (s, 1H), 8.53 (s, 1H), 7.58-7.51 (m, 1H), 7.42-7.36 (m, 1H), 7.31-7.25 (m, 1H), 7.11 (s, 1H), 5.93 (s, 1H), 4.83-4.70 (m, 1H), 4.28-4.09 (m, 4H), 4.02-3.90 (m, 1H), 3.26-3.13 (m, 1H), 2.97-2.84 (m, 1H), 2.57-2.43 (m, 4H), 2.31-2.19 (m, 1H), 2.19-2.07 (m, 1H), 1.96-1.81 (m, 1H), 1.49-1.32 (m, 1H) | AA: m/z = 570.2 (M + H) |
| I-301b | ¹H NMR (400 MHz, Methanol-$d_4$) δ 8.70 (s, 1H), 8.59 (s, 1H), 7.83-7.75 (m, 1H), 7.60-7.52 (m, 1H), 7.38-7.29 (m, 1H), 7.20-7.12 (m, 1H), 6.94-6.85 (m, 1H), 5.92 (s, 1H), 4.85-4.76 (m, 1H), 4.28-4.09 (m, 4H), 3.96 (d, J = 12.1, 7.6, 5.1 Hz, 1H), 3.04-2.84 (m, 2H), 2.61-2.45 (m, 1H), 2.34-2.22 (m, 1H), 2.17 (m, 1H), 1.99-1.85 (m, 1H), 1.53-1.37 (m, 1H) | AA: m/z = 565.1 (M + H) |
| I-301a | ¹H NMR (400 MHz, Methanol-$d_4$) δ 8.70 (s, 1H), 8.59 (s, 1H), 7.86-7.74 (m, 1H), 7.62-7.51 (m, 1H), 7.37-7.29 (m, 1H), 7.23-7.11 (m, 1H), 6.96-6.84 (m, 1H), 5.92 (s, 1H), 4.84-4.73 (m, 1H), 4.30-4.09 (m, 3H), 4.04-3.91 (m, 1H), 3.04-2.83 (m, 2H), 2.59-2.44 (m, 1H), 2.33-2.23 (m, 1H), 2.22-2.12 (m, 1H), 1.98-1.87 (m, 1H), 1.49-1.39 (m, 1H) | AA: m/z = 565.1 (M + H) |
| I-301 | ¹H NMR (400 MHz, Methanol-$d_4$) δ 8.70 (s, 1H), 8.59 (s, 1H), 7.84-7.73 (m, 1H), 7.62-7.50 (m, 1H), 7.38-7.29 (m, 1H), 7.21-7.11 (m, 1H), 6.98-6.81 (m, 1H), 5.92 (s, 1H), 4.86-4.77 (m, 1H), 4.28-4.08 (m, 4H), 4.04-3.91 (m, 1H), 3.04-2.84 (m, 2H), 2.60-2.45 (m, 1H), 2.34-2.23 (m, 1H), 2.23-2.12 (m, 1H), 1.97-1.87 (m, 1H), 1.50-1.39 (m, 1H) | AA: m/z = 565.1 (M + H) |

-continued

| Compound No. | ¹H NMR | LC/MS |
|---|---|---|
| I-289b | ¹H NMR (400 MHz, Methanol-d₄) δ 8.73 (s, 1H), 8.60 (s, 1H), 7.87 (d, J = 1.2 Hz, 1H), 7.79-7.73 (m, 1H), 7.62-7.58 (m, 1H), 7.54-7.48 (m, 1H), 7.12-6.99 (m, 1H), 6.08-5.95 (m, 1H), 4.85-4.76 (m, 1H), 4.34-4.07 (m, 5H), 2.59-2.46 (m, 1H), 2.33-2.23 (m, 1H), 2.21-2.13 (m, 1H), 2.01-1.86 (m, 1H), 1.52-1.39 (m, 1H) | AA: m/z = 601.1 (M + H) |
| I-289a | ¹H NMR (400 MHz, Methanol-d₄) δ 8.74 (s, 1H), 8.60 (s, 1H), 7.90-7.83 (m, 1H), 7.80-7.72 (m, 1H), 7.63-7.57 (m, 1H), 7.57-7.47 (m, 1H), 7.10-7.01 (m, 1H), 6.06-5.97 (m, 1H), 4.85-4.76 (m, 1H), 4.35-4.08 (m, 5H), 2.59-2.46 (m, 1H), 2.34-2.23 (m, 1H), 2.23-2.12 (m, 1H), 2.00-1.87 (m, 1H), 1.52-1.37 (m, 1H) | AA: m/z = 601.1 (M + H) |
| I-289 | ¹H NMR (400 MHz, Methanol-d₄) δ 8.71 (s, 1H), 8.57 (s, 1H), 7.84 (d, J = 1.3 Hz, 1H), 7.78-7.70 (m, 1H), 7.61-7.55 (m, 1H), 7.53-7.45 (m, 1H), 7.03 (s, 1H), 6.03-5.95 (m, 1H), 4.84-4.74 (m, 1H), 4.32-4.05 (m, 5H), 2.58-2.43 (m, 1H), 2.32-2.21 (m, 1H), 2.20-2.10 (m, 1H), 1.97-1.85 (m, 1H), 1.49-1.37 (m, 1H) | AA: m/z = 601.1 (M + H) |
| I-254b | ¹H NMR (400 MHz, Methanol-d₄) δ 8.70 (s, 1H), 8.58 (s, 1H), 7.82-7.74 (m, 1H), 7.59-7.52 (m, 1H), 7.26-7.12 (m, 3H), 6.96-6.87 (m, 1H), 5.92 (s, 1H), 4.85-4.75 (m, 1H), 4.28-4.07 (m, 4H), 4.00-3.89 (m, 1H), 3.10-2.97 (m, 1H), 2.95-2.82 (m, 1H), 2.60-2.47 (m, 1H), 2.34-2.22 (m, 1H), 2.22-2.11 (m, 1H), 1.98-1.84 (m, 1H), 1.51-1.37 (m, 1H) | FA: m/z = 531.6 (M + H) |
| I-254a | ¹H NMR (400 MHz, Methanol-d₄) δ 8.70 (s, 1H), 8.58 (s, 1H), 7.82-7.75 (m, 1H), 7.58-7.52 (m, 1H), 7.25-7.12 (m, 3H), 6.95-6.88 (m, 1H), 5.92 (s, 1H), 4.85-4.75 (m, 1H), 4.28-4.07 (m, 4H), 4.00-3.89 (m, 1H), 3.10-2.98 (m, 1H), 2.94-2.82 (m, 1H), 2.58-2.46 (m, 1H), 2.35-2.23 (m, 1H), 2.22-2.12 (m, 1H), 1.98-1.87 (m, 1H), 1.50-1.37 (m, 1H) | FA: m/z = 531.5 (M + H) |
| I-254 | ¹H NMR (400 MHz, Methanol-d₄) δ 8.69 (s, 1H), 8.57 (s, 1H), 7.80-7.72 (m, 1H), 7.56-7.51 (m, 1H), 7.25-7.09 (m, 3H), 6.93-6.86 (m, 1H), 5.91 (s, 1H), 4.83-4.74 (m, 1H), 4.27-4.05 (m, 4H), 3.98-3.88 (m, 1H), 3.08-2.96 (m, 1H), 2.92-2.80 (m, 1H), 2.56-2.45 (m, 1H), 2.32-2.20 (m, 1H), 2.20-2.09 (m, 1H), 1.97-1.85 (m, 1H), 1.49-1.36 (m, 1H) | FA: m/z = 531.1 (M + H) |
| I-257a | ¹H NMR (400 MHz, Methanol-d₄) δ 8.62 (s, 1H), 8.53 (s, 1H), 7.29 (s, 1H), 7.24-7.14 (m, 2H), 6.77-6.69 (m, 1H), 5.88 (s, 1H), 4.83-4.70 (m, 1H), 4.25-4.09 (m, 4H), 3.98-3.85 (m, 1H), 3.15-2.98 (m, 1H), 2.86-2.71 (m, 1H), 2.56-2.42 (m, 4H), 2.31-2.19 (m, 1H), 2.19-2.08 (m, 1H), 1.95-1.83 (m, 1H), 1.46-1.33 (m, 1H) | AA: m/z = 579.1 (M + H) |
| I-308 | ¹H NMR (400 MHz, Methanol-d₄) δ 8.72 (s, 1H), 8.55 (s, 1H), 8.28-8.17 (m, 1H), 8.04-7.97 (m, 1H), 7.60-7.53 (m, 1H), 7.40-7.24 (m, 3H), 7.01-6.93 (m, 1H), 5.14-5.04 (m, 1H), 4.51-4.40 (m, 1H), 4.19-4.08 (m, 1H), 4.04-3.94 (m, 1H), 3.70-3.55 (m, 2H), 2.67 (s, 3H), 2.53-2.39 (m, 1H), 2.19-2.01 (m, 2H), 1.96-1.82 (m, 1H), 1.44-1.32 (m, 1H) | FA: m/z = 451.5 (M + H) |
| I-304 | ¹H NMR (400 MHz, Methanol-d₄) δ 8.63 (s, 1H), 8.52 (s, 1H), 7.35-7.17 (m, 4H), 6.93-6.85 (m, 1H), 4.99-4.93 (m, 1H), 4.83-4.71 (m, 1H), 4.37-4.28 (m, 1H), 4.25-4.08 (m, 3H), 3.85-3.75 (m, 1H), 2.58-2.41 (m, 4H), 2.30-2.19 (m, 1H), 2.18-2.06 (m, 1H), 1.96-1.81 (m, 1H), 1.48-1.33 (m, 1H) | FA: m/z = 563 (M − H) |
| I-284b | ¹H NMR (400 MHz, Methanol-d₄) δ 8.65 (s, 1H), 8.54 (s, 1H), 7.37 (s, 1H), 7.32-7.24 (m, 2H), 6.88 (s, 1H), 5.00-4.93 (m, 1H), 4.83-4.72 (m, 1H), 4.36-4.26 (m, 1H), 4.26-4.10 (m, 3H), 3.82-3.71 (m, 1H), 2.55-2.44 (m, 4H), 2.32-2.20 (m, 1H), 2.17-2.07 (m, 1H), 1.94-1.83 (m, 1H), 1.49-1.36 (m, 1H) | FA: m/z = 598 (M + H) |
| I-284a | ¹H NMR (400 MHz, Methanol-d₄) δ 8.65 (s, 1H), 8.54 (s, 1H), 7.36 (s, 1H), 7.32-7.23 (m, 2H), 6.87 (s, 1H), 5.01-4.91 (m, 1H), 4.81-4.70 (m, 1H), 4.36-4.27 (m, 1H), 4.25-4.10 (m, 3H), 3.81-3.72 (m, 1H), 2.56-2.42 (m, 4H), 2.32-2.19 (m, 1H), 2.19-2.08 (m, 1H), 1.95-1.83 (m, 1H), 1.48-1.34 (m, 1H) | FA: m/z = 600 (M + H) |
| I-335 | ¹H NMR (400 MHz, Methanol-d4) δ 8.68 (s, 1H), 8.56 (s, 1H), 7.50-7.41 (m, 2H), 7.14-7.08 (m, 2H), 6.93-6.86 (m, 1H), 4.84-4.72 (m, 1H), 4.32-4.24 (m, 1H), | FA: m/z = 563.5 (M + H) |

-continued

| Compound No. | ¹H NMR | LC/MS |
|---|---|---|
| | 4.23-4.12 (m, 3H), 2.93-2.74 (m, 2H), 2.56-2.44 (m, 1H), 2.32-2.21 (m, 1H), 2.21-2.08 (m, 2H), 1.99-1.71 (m, 4H), 1.44-1.36 (m, 1H) | |
| I-335a | ¹H NMR (400 MHz, Methanol-d4) δ 8.70 (s, 1H), 8.58 (s, 1H), 7.52-7.44 (m, 2H), 7.17-7.10 (m, 2H), 6.95-6.90 (m, 1H), 4.85-4.77 (m, 1H), 4.33-4.27 (m, 1H), 4.26-4.14 (m, 3H), 2.92-2.79 (m, 2H), 2.57-2.47 (m, 1H), 2.33-2.23 (m, 1H), 2.22-2.12 (m, 2H), 2.01-1.78 (m, 4H), 1.49-1.39 (m, 1H) | FA: m/z = 563 (M + H) |
| I-335b | ¹H NMR (400 MHz, Methanol-d4) δ 8.70 (s, 1H), 8.58 (s, 1H), 7.51-7.44 (m, 2H), 7.17-7.10 (m, 2H), 6.95-6.89 (m, 1H), 4.85-4.74 (m, 1H), 4.33-4.28 (m, 1H), 4.25-4.14 (m, 3H), 2.95-2.78 (m, 2H), 2.58-2.47 (m, 1H), 2.33-2.24 (m, 1H), 2.21-2.11 (m, 2H), 2.02-1.75 (m, 4H), 1.50-1.39 (m, 1H) | FA: m/z = 563 (M + H) |
| I-309 | ¹H NMR (400 MHz, Methanol-d4) δ 8.73-8.68 (m, 1H), 8.58-8.53 (m, 1H), 7.40-7.34 (m, 1H), 6.85-6.77 (m, 1H), 5.93-5.86 (m, 1H), 4.83-4.72 (m, 1H), 4.26-4.01 (m, 7H), 2.56-2.44 (m, 4H), 2.31-2.22 (m, 1H), 2.19-2.09 (m, 4H), 1.94-1.84 (m, 1H), 1.47-1.35 (m, 1H) | AA: m/z = 549.2 (M + H) |
| I-296 | ¹H NMR (400 MHz, Methanol-d4) δ 8.72-8.66 (m, 1H), 8.58-8.52 (m, 1H), 7.40-7.34 (m, 1H), 6.72-6.65 (m, 1H), 5.89 (s, 1H), 4.83-4.73 (m, 1H), 4.36-4.28 (m, 1H), 4.24-3.90 (m, 6H), 2.56-2.43 (m, 4H), 2.31-2.19 (m, 4H), 2.17-2.10 (m, 1H), 1.94-1.84 (m, 1H), 1.47-1.35 (m, 1H) | AA: m/z = 549.1 (M + H) |
| I-227 | ¹H NMR (400 MHz, Methanol-d4) δ 8.65 (s, 1H), 8.56 (s, 1H), 7.77-7.72 (m, 1H), 7.44-7.39 (m, 1H), 7.37-7.25 (m, 3H), 7.25-7.19 (m, 1H), 4.84-4.74 (m, 1H), 4.27-4.15 (m, 3H), 3.09-2.99 (m, 1H), 2.66-2.46 (m, 3H), 2.32-2.24 (m, 1H), 2.21-2.03 (m, 7H), 1.97-1.87 (m, 1H), 1.52-1.39 (m, 1H) | AA: m/z = 592.1 (M + H) |
| I-38 | ¹H NMR (400 MHz, Methanol-d4) δ 8.64 (s, 1H), 8.59 (s, 1H), 7.87-7.84 (m, 1H), 7.59-7.56 (m, 1H), 7.55-7.51 (m, 1H), 7.43-7.38 (m, 1H), 7.35-7.29 (m, 1H), 7.27-7.22 (m, 1H), 4.82-4.73 (m, 1H), 4.26-4.15 (m, 3H), 3.11-3.01 (m, 2H), 2.64-2.56 (m, 1H), 2.55-2.46 (m, 1H), 2.40-2.32 (m, 1H), 2.31-2.23 (m, 1H), 2.20-2.11 (m, 1H), 1.96-1.85 (m, 3H), 1.46-1.37 (m, 1H) | AA: m/z = 578.1 (M + H) |
| I-27a | ¹H NMR (400 MHz, MeOD) δ 8.68 (s, 1H), 8.59 (s, 1H), 7.84-7.79 (m, 1H), 7.67-7.62 (m, 1H), 7.62-7.57 (m, 1H), 7.44-7.40 (m, 1H), 7.40-7.36 (m, 1H), 7.30-7.23 (m, 1H), 4.64-4.53 (m, 1H), 4.26-4.15 (m, 2H), 4.00-3.89 (m, 2H), 2.56-2.45 (m, 1H), 2.44-2.32 (m, 1H), 1.88 (s, 3H), 1.43-1.32 (m, 1H) | FA: m/z = 614.3 (M + H) |
| I-50 | ¹H NMR (400 MHz, MeOD) δ 8.67 (s, 1H), 8.57 (s, 1H), 7.93-7.88 (m, 1H), 7.53 (s, 2H), 7.40-7.24 (m, 3H), 4.86-4.75 (m, 1H), 4.26-4.15 (m, 3H), 2.57-2.46 (m, 1H), 2.32-2.22 (m, 1H), 2.21-2.12 (m, 1H), 1.97-1.86 (m, 1H), 1.74-1.63 (m, 1H), 1.49-1.38 (m, 1H), 0.68-0.48 (m, 4H) | FA: m/z = 579.1 (M + H) |
| I-99 | ¹H NMR (400 MHz, MeOD) δ 8.83-8.72 (m, 1H), 8.61 (s, 1H), 7.65-7.61 (m, 1H), 7.61-7.52 (m, 3H), 7.29-7.21 (m, 1H), 7.11-7.03 (m, 1H), 4.81-4.70 (m, 1H), 4.25-4.02 (m, 2H), 3.98 (s, 2H), 3.62-3.45 (m, 1H), 2.51-2.39 (m, 1H), 2.32-2.22 (m, 1H), 1.65-1.33 (m, 2H) | FA: m/z = 633.4 (M + H) |
| I-62 | ¹H NMR (400 MHz, MeOD) δ 8.83-8.72 (m, 1H), 8.61 (s, 1H), 7.65-7.61 (m, 1H), 7.61-7.52 (m, 3H), 7.29-7.21 (m, 1H), 7.11-7.03 (m, 1H), 4.81-4.70 (m, 1H), 4.25-4.02 (m, 3H), 3.98 (s, 2H), 3.62-3.45 (m, 1H), 2.51-2.39 (m, 1H), 2.32-2.22 (m, 1H), 1.65-1.33 (m, 2H) | FA: m/z = 615.1 (M + H) |
| I-101 | ¹H NMR (400 MHz, MeOD) δ 8.75 (s, 1H), 8.64-8.59 (m, 1H), 7.60 (s, 1H), 7.54 (s, 1H), 7.42 (s, 1H), 7.40-7.33 (m, 1H), 7.26-7.19 (m, 2H), 4.26-4.12 (m, 2H), 4.12-4.04 (m, 1H), 4.02 (s, 2H), 2.51-2.39 (m, 1H), 2.32-2.22 (m, 1H), 1.65-1.47 (m, 2H), 1.44-1.32 (m, 1H) | FA: m/z = 587.2 (M + H) |
| I-337 | ¹H NMR (400 MHz, Methanol-d₄) δ 8.72 (s, 1H), 8.55 (s, 1H), 7.71-7.61 (s, 1H), 7.46 (s, 1H), 5.97 (s, 1H), 4.77 (m, 1H), 4.38-4.28 (m, 2H), 4.17 (m, 5H), 3.33 (m, 1H), 2.49 (m, 4H), 2.27 (m, 1H), 2.23-2.10 (m, 1H), 1.91-1.84 (m, 1H), 1.41 (m, 1H). | AA: m/z = 603.0 (M + H) |

-continued

| Compound No. | ¹H NMR | LC/MS |
|---|---|---|
| I-320 | ¹H NMR (400 MHz, Chloroform-d) δ 8.85 (s, 1H), 8.68 (s, 1H), 8.63 (d, J = 7.2 Hz, 1H), 7.61 (d, J = 1.1 Hz, 1H), 7.23 (dd, J = 8.2, 2.1 Hz, 1H), 7.20 (s, 1H), 7.15 (d, J = 8.2 Hz, 1H), 7.02 (s, 1H), 5.58 (broad, 2H), 5.14 (s, 1H), 4.80 (m, 1H), 4.37 (m, 2H), 4.27 (m, 1H), 3.12-2.99 (m, 2H), 2.92-2.79 (m, 2H), 2.56 (m, 1H), 2.37 (m, 1H), 2.18 (m, 1H), 2.06-1.97 (m, 1H), 1.53-1.39 (m, 1H). | AA: m/z = 581 (M + H) |
| I-320a | ¹H NMR (400 MHz, Methanol-$d_4$) δ 8.74 (s, 1H), 8.60 (s, 1H), 7.65 (s, 1H), 7.36 (s, 1H), 7.24 (m, 2H), 7.08 (s, 1H), 5.31 (s, 1H), 4.81 (m, 1H), 4.19 (m, 3H), 3.06 (m, 2H), 2.94-2.78 (m, 2H), 2.52 (m, 1H), 2.28 (m, 1H), 2.17 (m, 1H), 1.93 (m, 1H), 1.58-1.38 (m, 1H). | AA: m/z = 581 (M + H) |
| I-320b | ¹H NMR (400 MHz, Methanol-$d_4$) δ 8.74 (s, 1H), 8.60 (s, 1H), 7.64 (s, 1H), 7.36 (s, 1H), 7.28-7.19 (m, 2H), 7.07 (s, 1H), 5.31 (s, 1H), 4.81 (m, 1H), 4.25-4.12 (m, 3H), 3.11-3.03 (m, 2H), 2.93-2.75 (m, 2H), 2.52 (m, 1H), 2.34-2.24 (m, 1H), 2.17 (m, 1H), 1.98-1.88 (m, 1H), 1.45 (m, 1H). | AA: m/z = 581 (M + H) |
| I-278 | ¹H NMR (400 MHz, Chloroform-d) δ 8.90 (s, 1H), 8.68 (d, J = 4.8 Hz, 2H), 7.63 (s, 1H), 7.24 (d, J = 6.6 Hz, 2H), 7.16 (d, J = 8.3 Hz, 1H), 7.02 (s, 1H), 5.14 (s, 1H), 4.44-4.25 (m, 3H), 4.09 (s, 1H), 4.02-3.94 (m, 1H), 3.07 (m, 2H), 2.93-2.76 (m, 2H), 2.59-2.45 (m, 2H), 1.62-1.50 (m, 1H). | AA: m/z = 597 (M + H) |
| I-278a | ¹H NMR (400 MHz, Methanol-$d_4$) δ 8.76 (s, 1H), 8.61 (s, 1H), 7.65 (s, 1H), 7.39 (s, 1H), 7.31-7.20 (m, 2H), 7.08 (s, 1H), 5.32 (s, 1H), 4.69-4.50 (m, 1H), 4.21 (m, 2H), 4.06-3.91 (m, 2H), 3.10 (m, 1H), 2.87 (m, 2H), 2.55-2.45 (m, 1H), 2.45-2.34 (m, 1H), 1.39 (m, 1H). | AA: m/z = 597 (M + H) |
| I-278b | ¹H NMR (400 MHz, Methanol-$d_4$) δ 8.76 (s, 1H), 8.61 (s, 1H), 7.65 (s, 1H), 7.38 (s, 1H), 7.23 (d, J = 8.7 Hz, 2H), 7.08 (s, 1H), 5.32 (s, 1H), 4.61 (m, 1H), 4.20 (m, 2H), 3.96 (m, 2H), 3.17-3.04 (m, 2H), 2.95-2.75 (m, 2H), 2.56-2.47 (m, 1H), 2.38 (s, 1H), 1.45-1.34 (m, 1H). | AA: m/z = 597 (M + H) |
| I-310 | ¹H NMR (400 MHz, Methanol-$d_4$) δ 8.63 (s, 1H), 8.56 (s, 1H), 7.40-7.30 (m, 3H), 7.15 (s, 1H), 6.37 (s, 1H), 5.29 (dd, J = 12.5, 2.6 Hz, 1H), 5.15 (dd, J = 12.5, 1.9 Hz, 1H), 4.77 (q, J = 8.0 Hz, 1H), 4.24-4.14 (m, 3H), 2.56-2.42 (m, 1H), 2.31-2.20 (m, 1H), 2.19-2.09 (m, 1H), 1.96-1.84 (m, 1H), 1.49-1.35 (m, 1H). | AA: m/z = 565 (M + H) |
| I-310a | ¹H NMR (400 MHz, Methanol-$d_4$) δ 8.62 (s, 1H), 8.55 (s, 1H), 7.34 (s, 3H), 7.14 (s, 1H), 6.37 (s, 1H), 5.28 (dd, J = 12.5, 2.3 Hz, 1H), 5.14 (d, J = 12.4 Hz, 1H), 4.84-4.72 (m, 1H), 4.26-4.05 (m, 3H), 2.54-2.41 (m, 1H), 2.30-2.18 (m, 1H), 2.17-2.08 (m, 1H), 1.94-1.81 (m, 1H), 1.45-1.33 (m, 1H). | AA: m/z = 565 (M + H) |
| I-310b | ¹H NMR (400 MHz, Methanol-$d_4$) δ 8.62 (s, 1H), 8.55 (s, 1H), 7.40-7.27 (m, 3H), 7.14 (s, 1H), 6.36 (s, 1H), 5.28 (dd, J = 12.5, 2.2 Hz, 1H), 5.13 (d, J = 12.4 Hz, 1H), 4.81-4.72 (m, 1H), 4.22-4.08 (m, 3H), 2.55-2.36 (m, 1H), 2.31-2.19 (m, 1H), 2.18-2.07 (m, 1H), 1.93-1.81 (m, 1H), 1.48-1.34 (m, 1H). | AA: m/z = 565 (M + H) |
| I-336 | ¹H NMR (400 MHz, Methanol-$d_4$) δ 8.55 (s, 2H), 7.28 (s, 1H), 7.23 (s, 2H), 7.10 (s, 1H), 6.32 (s, 1H), 4.82-4.70 (m, 1H), 4.22-4.05 (m, 4H), 3.46-3.36 (m, 1H), 2.96-2.84 (m, 2H), 2.53-2.40 (m, 1H), 2.28-2.20 (m, 1H), 2.16-2.07 (m, 1H), 1.93-1.83 (m, 1H), 1.46 (s, 9H), 1.41-1.30 (m, 1H). | AA: m/z = 698 (M + H) |
| I-327 | ¹H NMR (400 MHz, Methanol-$d_4$) δ 8.66 (s, 1H), 8.55 (s, 1H), 7.91 (d, J = 8.2 Hz, 1H), 7.72-7.63 (m, 1H), 7.59 (s, 1H), 7.39 (d, J = 1.9 Hz, 1H), 6.76 (s, 1H), 4.84-4.71 (m, 1H), 4.25-4.07 (m, 3H), 2.53-2.38 (m, 1H), 2.30-2.20 (m, 1H), 2.18-2.05 (m, 1H), 1.96-1.84 (m, 1H), 1.49-1.42 (m, 1H). | AA: m/z = 599 (M + H) |
| I-321 | ¹H NMR (400 MHz, Methanol$_4$) δ 8.74 (s, 1H), 8.59 (s, 1H), 7.62 (s, 1H), 7.32 (s, 1H), 7.26-7.12 (m, 3H), 4.84-4.79 (m, 1H), 4.26-4.08 (m, 3H), 3.11-3.02 (m, 1H), 3.01-2.65 (m, 4H), 2.55-2.45 (m, 1H), 2.31-2.23 (m, 1H), 2.20-2.12 (m, 1H), 1.87 (s, 3H), 1.49-1.39 (m, 1H). | AA: m/z = 578 (M + H) |
| I-318 | ¹H NMR (400 MHz, Methanol-$d_4$) δ 8.71 (s, 1H), 8.58 (s, 1H), 8.55-8.46 (m, 2H), 7.56 (s, 1H), 7.42 (s, 1H), 7.23 (s, 3H), 4.84-4.74 (m, 1H), 4.24-4.09 (m, 3H), 3.18-2.91 (m, 4H), 2.56-2.47 (m, 1H), 2.34-2.22 | AA: m/z = 544 (M + H) |

| Compound No. | ¹H NMR | LC/MS |
|---|---|---|
| | (m, 1H), 2.19-2.11 (m, 1H), 1.96 (s, 3H), 1.92-1.85 (m, 1H), 1.44-1.40 (m, 1H). | |
| I-331 | ¹H NMR (400 MHz, Methanol-d₄) δ 8.70-8.60 (m, 2H), 8.55 (s, 1H), 7.52 (dd, J = 7.8, 4.5 Hz, 1H), 7.42 (d, J = 8.0 Hz, 1H), 7.35 (d, J = 3.3 Hz, 1H), 6.11 (d, J = 3.9 Hz, 1H), 4.82-4.71 (m, 1H), 4.54-4.40 (m, 1H), 4.35-4.23 (m, 1H), 4.21-4.11 (m, 3H), 2.52-2.49 (m, 3H), 2.49-2.42 (m, 1H), 2.31-2.19 (m, 1H), 2.17-2.12 (m, 1H), 1.94-1.84 (m, 1H), 1.50-1.36 (m, 1H). | AA: m/z = 574 (M + H) |
| I-287 | ¹H NMR (400 MHz, Methanol-d₄) δ 8.65 (s, 1H), 8.54 (s, 1H), 7.21 (s, 1H), 5.91-5.78 (m, 1H), 4.83-4.71 (m, 1H), 4.22-4.11 (m, 4H), 3.98-3.85 (m, 1H), 3.09-2.98 (m, 1H), 2.90-2.82 (m, 1H), 2.62 (s, 3H), 2.55 (s, 3H), 2.52-2.44 (m, 1H), 2.30-2.20 (m, 1H), 2.19-2.08 (m, 1H), 1.94-1.83 (m, 1H), 1.47-1.35 (m, 1H). | AA: m/z = 566 (M + H) |
| I-287a | ¹H NMR (400 MHz, Methanol-d₄) δ 8.65 (s, 1H), 8.54 (s, 1H), 7.21 (s, 1H), 5.90-5.76 (m, 1H), 4.80-4.69 (m, 1H), 4.25-4.08 (m, 4H), 3.97-3.88 (m, 1H), 3.10-2.99 (m, 1H), 2.91-2.77 (m, 1H), 2.62 (s, 3H), 2.55 (s, 3H), 2.51-2.45 (m, 1H), 2.30-2.21 (m, 1H), 2.19-2.08 (m, 1H), 1.95-1.83 (m, 1H), 1.47-1.35 (m, 1H). | AA: m/z = 566 (M + H) |
| I-287b | ¹H NMR (400 MHz, Methanol-d₄) δ 8.55 (s, 1H), 8.44 (s, 1H), 7.11 (s, 1H), 5.81-5.68 (m, 1H), 4.72-4.60 (m, 1H), 4.13-4.02 (m, 4H), 3.91-3.73 (m, 1H), 3.01-2.85 (m, 1H), 2.83-2.70 (m, 1H), 2.52 (s, 3H), 2.45 (s, 3H), 2.42-2.33 (m, 1H), 2.22-2.10 (m, 1H), 2.10-2.00 (m, 1H), 1.84-1.74 (m, 1H), 1.39-1.26 (m, 1H). | AA: m/z = 566 (M + H) |
| I-305 | ¹H NMR (400 MHz, Methanol-d₄) δ 8.61 (s, 1H), 8.54 (s, 1H), 7.36 (s, 1H), 5.96 (s, 1H), 4.85-4.71 (m, 1H), 4.30-4.22 (m, 1H), 4.22-4.12 (m, 3H), 4.00-3.91 (m, 1H), 3.08-2.93 (m, 1H), 2.84-2.73 (m, 1H), 2.64 (s, 3H), 2.54 (s, 3H), 2.50-2.41 (m, 1H), 2.29-2.20 (m, 1H), 2.17-2.06 (m, 1H), 1.96-1.83 (m, 1H), 1.47-1.33 (m, 1H). | AA: m/z = 566(M + H) |
| I-305a | ¹H NMR (400 MHz, Methanol-d₄) δ 8.63 (s, 1H), 8.56 (s, 1H), 7.38 (s, 1H), 5.98 (s, 1H), 4.83-4.73 (m, 1H), 4.31-4.24 (m, 1H), 4.23-4.14 (m, 3H), 4.04-3.92 (m, 1H), 3.07-2.95 (m, 1H), 2.85-2.75 (m, 1H), 2.66 (s, 3H), 2.57 (s, 3H), 2.53-2.44 (m, 1H), 2.30-2.21 (m, 1H), 2.19-2.10 (m, 1H), 1.94-1.85 (m, 1H), 1.48-1.35 (m, 1H). | AA: m/z = 566 (M + H) |
| I-305b | ¹H NMR (400 MHz, Methanol-d₄) δ 8.63 (s, 1H), 8.56 (s, 1H), 7.38 (s, 1H), 5.98 (s, 1H), 4.83-4.73 (m, 1H), 4.31-4.24 (m, 1H), 4.23-4.14 (m, 3H), 4.04-3.92 (m, 1H), 3.07-2.95 (m, 1H), 2.85-2.75 (m, 1H), 2.66 (s, 3H), 2.57 (s, 3H), 2.53-2.44 (m, 1H), 2.30-2.21 (m, 1H), 2.19-2.10 (m, 1H), 1.94-1.86 (m, 1H), 1.48-1.37 (m, 1H). | AA: m/z = 566 (M + H) |
| I-315 | ¹H NMR (400 MHz, Methanol-d₄) δ 8.63 (s, 1H), 8.55 (s, 1H), 7.37-7.26 (m, 1H), 5.98 (s, 1H), 4.83-4.71 (m, 1H), 4.32-4.24 (m, 1H), 4.23-4.10 (m, 3H), 4.06-3.94 (m, 1H), 3.27-3.17 (m, 1H), 3.08-2.98 (m, 1H), 2.57 (s, 3H), 2.51-2.42 (m, 1H), 2.29-2.22 (m, 1H), 2.19-2.09 (m, 1H), 1.94-1.83 (m, 1H), 1.44-1.35 (m, 1H). | AA: m/z = 620 (M + H) |
| I-275 | ¹H NMR (400 MHz, Methanol-d₄) δ 8.62 (s, 1H), 8.55 (s, 1H), 7.27 (s, 1H), 7.20 (d, J = 5.2 Hz, 1H), 6.53 (d, J = 5.2 Hz, 1H), 5.87 (s, 1H), 4.82-4.70 (m, 1H), 4.24-4.11 (m, 4H), 4.01-3.88 (m, 1H), 3.13-3.03 (m, 1H), 2.92-2.79 (m, 1H), 2.55 (s, 3H), 2.53-2.45 (m, 1H), 2.34-2.24 (m, 1H), 2.19-2.09 (m, 1H), 1.96-1.81 (m, 1H), 1.47-1.35 (m, 1H). | AA: m/z = 551 (M + H) |
| I-285 | ¹H NMR (400 MHz, Methanol-d₄) δ 8.63 (s, 1H), 8.54 (s, 1H), 8.39-8.27 (m, 1H), 7.70 (d, J = 6.4 Hz, 1H), 7.30 (d, J = 7.7, 4.8 Hz, 1H), 7.14 (s, 1H), 5.92 (s, 1H), 4.83-4.70 (m, 1H), 4.25-4.09 (m, 4H), 4.00-3.89 (m, 1H), 3.21-3.08 (m, 1H), 2.98-2.88 (m, 1H), 2.54 (s, 3H), 2.51-2.44 (m, 1H), 2.31-2.20 (m, 1H), 2.19-2.10 (m, 1H), 1.94-1.83 (m, 1H), 1.49-1.34 (m, 1H). | AA: m/z = 546 (M + H) |
| I-285b | ¹H NMR (400 MHz, Methanol-d₄) δ 8.61 (s, 1H), 8.52 (s, 1H), 8.32 (dd, J = 4.8, 1.5 Hz, 1H), 7.68 (dd, J = 7.8, 1.4 Hz, 1H), 7.28 (dd, J = 7.8, 4.8 Hz, 1H), 7.12 (s, 1H), 5.90 (s, 1H), 4.83-4.68 (m, 1H), 4.29-4.09 (m, 4H), 4.03-3.85 (m, 1H), 3.19-3.02 (m, 1H), 2.96-2.86 (m, 1H), 2.53 (s, 3H), 2.52-2.42 (m, 1H), 2.28-2.19 (m, 1H), 2.17-2.06 (m, 1H), 1.95-1.77 (m, 1H), 1.47-1.33 (m, 1H). | AA: m/z = 546 (M + H) |

| Compound No. | $^1$H NMR | LC/MS |
| --- | --- | --- |
| I-285a | $^1$H NMR (400 MHz, Methanol-d$_4$) δ 8.63 (s, 1H), 8.54 (s, 1H), 8.34 (dd, J = 4.8, 1.5 Hz, 1H), 7.70 (d, J = 7.8 Hz, 1H), 7.31 (dd, J = 7.8, 4.8 Hz, 1H), 7.13 (s, 1H), 5.93 (s, 1H), 4.83-4.69 (m, 1H), 4.25-4.11 (m, 4H), 4.02-3.91 (m, 1H), 3.22-3.08 (m, 1H), 2.99-2.88 (m, 1H), 2.55 (s, 3H), 2.52-2.45 (m, 1H), 2.33-2.21 (m, 1H), 2.20-2.09 (m, 1H), 1.93-1.84 (m, 1H), 1.50-1.36 (m, 1H). | AA: m/z = 546 (M + H) |
| I-342 | $^1$H NMR (400 MHz, Methanol-d$_4$) δ 8.73 (s, 1H), 8.60 (s, 1H), 8.05 (dd, J = 7.8, 1.2 Hz, 1H), 7.79 (s, 1H), 7.71-7.57 (m, 2H), 7.51 (t, J = 7.4 Hz, 1H), 7.10 (d, J = 7.7 Hz, 1H), 6.13 (s, 1H), 4.86-4.75 (m, 1H), 4.47-4.38 (m, 2H), 4.26-4.14 (m, 3H), 2.55-2.45 (m, 1H), 2.35-2.23 (m, 1H), 2.21-2.10 (m, 1H), 1.96-1.87 (m, 1H), 1.52-1.38 (m, 1H). | AA: m/z = 545 (M + H) |
| I-269 | $^1$H NMR (400 MHz, Methanol-d$_4$) δ 8.61 (s, 1H), 8.53 (s, 1H), 7.98 (s, 1H), 7.36 (s, 1H), 7.27 (dd, J = 5.1, 0.8 Hz, 1H), 6.87 (d, J = 5.1 Hz, 1H), 5.96 (s, 1H), 4.82-4.67 (m, 1H), 4.28-4.12 (m, 4H), 3.98-3.84 (m, 1H), 2.98-2.88 (m, 1H), 2.76-2.65 (m, 1H), 2.54 (s, 3H), 2.51-2.42 (m, 1H), 2.30-2.21 (m, 1H), 2.18-2.08 (m, 1H), 1.92-1.82 (m, 1H), 1.48-1.32 (m, 1H). | AA: m/z = 551 (M + H) |
| I-269a | $^1$H NMR (400 MHz, Methanol-d$_4$) δ 8.62 (s, 1H), 8.54 (s, 1H), 7.37 (s, 1H), 7.27 (dd, J = 5.1, 0.8 Hz, 1H), 6.87 (d, J = 5.1 Hz, 1H), 5.97 (s, 1H), 4.83-4.70 (m, 1H), 4.26-4.09 (m, 4H), 3.94-3.84 (m, 1H), 2.99-2.85 (m, 2H), 2.75-2.67 (m, 1H), 2.55 (s, 3H), 2.52-2.41 (m, 1H), 2.30-2.19 (m, 1H), 2.21-2.08 (m, 1H), 1.94-1.84 (m, 1H), 1.47-1.32 (m, 1H). | AA: m/z = 551 (M + H) |
| I-269b | $^1$H NMR (400 MHz, Methanol-d$_4$) δ 8.63 (s, 1H), 8.55 (s, 1H), 7.38 (s, 1H), 7.28 (dd, J = 5.1, 0.8 Hz, 1H), 6.88 (d, J = 5.1 Hz, 1H), 5.98 (s, 1H), 4.83-4.72 (m, 1H), 4.28-4.13 (m, 4H), 3.98-3.87 (m, 1H), 3.02-2.89 (m, 2H), 2.78-2.68 (m, 1H), 2.56 (s, 3H), 2.52-2.42 (m, 1H), 2.33-2.20 (m, 1H), 2.21-2.09 (m, 1H), 1.97-1.84 (m, 1H), 1.49-1.36 (m, 1H). | AA: m/z = 551 (M + H) |
| I-2 | $^1$H NMR (400 MHz, Methanol-d$_4$) δ 8.71 (s, 1H), 8.60 (s, 1H), 8.00 (s, 1H), 7.84 (t, J = 7.8 Hz, 1H), 7.61 (d, J = 7.6 Hz, 1H), 7.59 (s, 1H), 7.35 (d, J = 7.8 Hz, 1H), 5.92 (s, 1H), 4.85-4.74 (m, 1H), 4.25-4.15 (m, 3H), 2.56-2.44 (m, 1H), 2.33-2.21 (m, 1H), 2.21-2.10 (m, 1H), 1.96-1.84 (m, 1H), 1.49-1.38 (m, 1H). | AA: m/z = 574 (M + H) |
| I-36 | $^1$H NMR (400 MHz, Methanol-d$_4$) δ 8.73 (s, 1H), 8.61 (s, 1H), 8.54 (broad, 2H), 7.85 (s, 1H), 7.68 (s, 1H), 7.51 (s, 1H), 7.46-7.37 (m, 3H), 5.55 (s, 1H), 4.84-4.77 (m, 1H), 4.25-4.12 (m, 3H), 2.57-2.45 (m, 1H), 2.33-2.23 (m, 1H), 2.20-2.11 (m, 1H), 1.91 (dd, J = 13.7, 7.4 Hz, 1H), 1.51-1.38 (m, 1H). | AA: m/z = 538 (M + H) |
| I-31 | $^1$H NMR (400 MHz, MeOD) δ 8.67 (s, 1H), 8.60 (s, 1H), 8.39 (s, 1H), 7.97 (s, 1H), 7.59 (s, 1H), 7.52 (s, 1H), 7.41 (s, 1H), 7.38 (d, J = 7.7 Hz, 1H), 7.33 (d, J = 6.9 Hz, 1H), 4.58 (dd, J = 14.9, 7.1 Hz, 1H), 4.18 (t, J = 7.9 Hz, 2H), 4.00-3.85 (m, 2H), 3.27 (dd, J = 17.4, 9.7 Hz, 3H), 2.78 (dt, J = 13.3, 6.8 Hz, 1H), 2.50 (dt, J = 22.7, 8.9 Hz, 2H), 2.38 (dd, J = 8.9, 4.6 Hz, 1H), 2.03 (d, J = 19.0 Hz, 2H), 1.44-1.29 (m, 1H). | AA: m/z = 594 (M + H) |
| I-151b | $^1$H NMR (400 MHz, MeOD) δ 8.76 (s, 1H), 8.61 (s, 1H), 7.56 (s, 1H), 7.49 (s, 1H), 7.42-7.29 (m, 3H), 6.10 (s, 1H), 4.87-4.72 (m, 1H), 4.24-4.12 (m, 3H), 2.57-2.46 (m, 1H), 2.31-2.23 (m, 1H), 2.22-2.12 (m, 1H), 1.97-1.87 (m, 1H), 1.44 (dt, J = 13.0, 9.2 Hz, 1H). | AA: m/z = 539.1 (M + H) |
| I-151a | $^1$H NMR (400 MHz, MeOD) δ 8.76 (s, 1H), 8.61 (s, 1H), 7.57 (s, 1H), 7.49 (s, 1H), 7.44-7.30 (m, 3H), 6.10 (s, 1H), 4.88-4.75 (m, 1H), 4.19 (qd, J = 9.8, 6.0 Hz, 3H), 2.58-2.44 (m, 1H), 2.34-2.23 (m, 1H), 2.21-2.12 (m, 1H), 1.97-1.87 (m, 1H), 1.45 (dt, J = 13.0, 9.2 Hz, 1H). | AA: m/z = 539.1 (M + H) |
| I-151 | $^1$H NMR (400 MHz, MeOD) δ 8.76 (s, 1H), 8.61 (s, 1H), 7.57 (s, 1H), 7.49 (s, 1H), 7.44-7.30 (m, 3H), 6.10 (s, 1H), 4.88-4.75 (m, 1H), 4.19 (qd, J = 9.8, 6.0 Hz, 3H), 2.58-2.44 (m, 1H), 2.34-2.23 (m, 1H), 2.21-2.12 (m, 1H), 1.99-1.87 (m, 1H), 1.45 (dt, J = 13.0, 9.2 Hz, 1H). | AA: m/z = 539.1 (M + H) |

-continued

| Compound No. | ¹H NMR | LC/MS |
|---|---|---|
| I-95 | ¹H NMR (400 MHz, MeOD) δ 8.72 (s, 1H), 8.63 (s, 1H), 7.74 (s, 1H), 7.54-7.44 (m, 1H), 7.43-7.31 (m, 3H), 5.11 (s, 1H), 4.81 (dd, J = 7.7 Hz, 1H), 4.30-4.07 (m, 3H), 2.55-2.47 (m, 1H), 2.45 (s, 3H), 2.33-2.08 (m, 2H), 1.91 (ddd, J = 13.4, 7.6, 4.1 Hz, 1H), 1.49-1.32 (m, 1H). | AA: m/z = 586.1 (M + H) |
| I-2a | ¹H NMR (400 MHz, MeOD) δ 8.72 (s, 1H), 8.64 (S, 1H), 7.84 (t, J = 7.8 Hz, 1H), 7.62 (dd, J = 8.0, 3.6 Hz, 2H), 7.35 (d, J = 7.9 Hz, 1H), 5.93 (s, 1H), 4.86-4.70 (m, 1H), 4.28-4.10 (m, 3H), 2.57-2.41 (m, 1H), 2.21 (dd, J = 46.9, 5.5 Hz, 2H), 1.92 (dt, J = 15.2, 7.0 Hz, 1H), 1.53-1.35 (m, 1H). | AA: m/z = 574.0 (M + H) |
| I-2b | ¹H NMR (400 MHz, MeOD) δ 8.72 (s, 1H), 8.64 (S, 1H), 7.84 (t, J = 7.8 Hz, 1H), 7.62 (dd, J = 8.0, 3.6 Hz, 2H), 7.35 (d, J = 7.9 Hz, 1H), 5.93 (s, 1H), 4.86-4.70 (m, 1H), 4.28-4.10 (m, 3H), 2.59-2.41 (m, 1H), 2.21 (dd, J = 46.9, 5.5 Hz, 2H), 1.92 (dt, J = 15.2, 7.0 Hz, 1H), 1.53-1.35 (m, 1H). | AA: m/z = 574.0 (M + H) |
| I-174 | ¹H NMR (400 MHz, MeOD) δ 8.76 (s, 1H), 8.63 (s, 1H), 7.61 (s, 1H), 4.87-4.75 (m, 1H), 4.58 (d, J = 7.6 Hz, 1H), 4.28-4.11 (m, 3H), 4.00 (dd, J = 11.3, 3.7 Hz, 1H), 3.92 (d, J = 11.0 Hz, 1H), 3.45-3.35 (m, 2H), 2.58-2.45 (m, 1H), 2.28 (d, J = 5.4 Hz, 1H), 2.17 (d, J = 6.4 Hz, 1H), 1.92 (t, J = 11.2 Hz, 3H), 1.52-1.34 (m, 3H). | AA: m/z = 547.1 (M + H) |
| I-195 | ¹H NMR (400 MHz, MeOD) δ 8.75 (s, 1H), 8.62 (s, 1H), 7.58 (s, 1H), 4.81 (dd, J = 16.0, 7.9 Hz, 1H), 4.52 (d, J = 7.3 Hz, 1H), 4.27-4.10 (m, 3H), 2.58-2.46 (m, 1H), 2.27 (dt, J = 13.9, 7.1 Hz, 1H), 2.17 (ddd, J = 12.1, 7.5, 4.3 Hz, 1H), 2.01-1.91 (m, 2H), 1.44 (dt, J = 12.8, 9.2 Hz, 1H), 1.01 (dd, J = 27.3, 6.7 Hz, 3H), 0.86 (d, J = 6.8 Hz, 3H). | AA: m/z = 505.1 (M + H) |
| I-54 | ¹H NMR (400 MHz, MeOD) δ 8.73 (s, 1H), 8.60 (s, 1H), 7.85 (s, 1H), 7.73 (d, J = 7.8, 1.1 Hz, 2H), 7.68 (t, J = 7.7 Hz, 1H), 7.44 (d, J = 7.6, 1.0 Hz, 1H), 4.80 (dd, J = 19.9, 12.0 Hz, 1H), 4.27-4.15 (m, 3H), 2.50 (t, J = 15.3 Hz, 1H), 2.28 (s, 1H), 2.17 (s, 1H), 1.93 (s, 4H), 1.45 (s, 1H). | AA: m/z = 598.0 (M + H) |
| I-1a | ¹H NMR (400 MHz, MeOD) δ 8.75 (s, 1H), 8.61 (s, 1H), 7.86 (s, 1H), 7.74 (d, 2H), 7.67 (t, J = 7.7 Hz, 1H), 7.44 (dd, J = 7.7, 1.0 Hz, 1H), 4.59 (dd, J = 14.6, 8.4 Hz, 1H), 4.25-4.14 (m, 2H), 3.98-3.88 (m, 2H), 2.56-2.44 (m, 1H), 2.38 (d, J = 4.9 Hz, 1H), 1.93 (s, 3H), 1.38 (dt, J = 13.1, 8.7 Hz, 1H). | AA: m/z = 614.0 (M + H) |
| I-1b | ¹H NMR (400 MHz, MeOD) δ 8.75 (s, 1H), 8.61 (s, 1H), 7.86 (s, 1H), 7.74 (d, 2H), 7.67 (t, J = 7.7 Hz, 1H), 7.44 (dd, J = 7.7, 1.0 Hz, 1H), 4.59 (dd, J = 14.6, 8.4 Hz, 1H), 4.25-4.14 (m, 2H), 3.98-3.88 (m, 2H), 2.56-2.44 (m, 1H), 2.38 (d, J = 4.9 Hz, 1H), 1.97 (s, 3H), 1.36 (dt, J = 13.1, 8.7 Hz, 1H). | AA: m/z = 614.0 (M + H) |
| I-21 | ¹H NMR (400 MHz, MeOD) δ 8.75 (s, 1H), 8.59 (s, 1H), 7.86 (s, 1H), 7.68 (s, 1H), 6.29 (d, J = 3.3, 0.6 Hz, 1H), 6.22 (d, J = 3.3 Hz, 1H), 5.83 (s, 1H), 4.85-4.75 (m, 1H), 4.27-4.13 (m, 3H), 2.59-2.44 (m, 1H), 2.27 (dt, J = 14.5, 7.2 Hz, 1H), 2.22-2.13 (m, 1H), 1.97-1.85 (m, 1H), 1.44 (dt, J = 12.9, 9.2 Hz, 1H). | AA: m/z = 529.1 (M + H) |
| I-29 | ¹H NMR (400 MHz, MeOD) δ 8.73 (s, 1H), 8.60 (s, 1H), 7.87-7.75 (m, 2H), 7.71 (d, J = 1.3 Hz, 1H), 7.62 (d, J = 7.6 Hz, 1H), 7.35 (d, J = 7.9 Hz, 1H), 5.86 (s, 1H), 4.85-4.74 (m, 1H), 4.18 (tt, J = 8.1, 4.2 Hz, 3H), 2.56-2.46 (m, 1H), 2.34-2.21 (m, 1H), 2.20-2.10 (m, 1H), 1.97-1.86 (m, 1H), 1.43 (dt, J = 13.0, 9.2 Hz, 1H). | AA: m/z = 540.0 (M + H) |
| I-29a | ¹H NMR (400 MHz, MeOD) δ 8.73 (s, 1H), 8.60 (s, 1H), 7.87-7.75 (m, 2H), 7.71 (d, J = 1.3 Hz, 1H), 7.62 (d, J = 7.6 Hz, 1H), 7.35 (d, J = 7.9 Hz, 1H), 5.86 (s, 1H), 4.85-4.74 (m, 1H), 4.18 (tt, J = 8.1, 4.2 Hz, 3H), 2.56-2.46 (m, 1H), 2.34-2.21 (m, 1H), 2.20-2.10 (m, 1H), 1.97-1.84 (m, 1H), 1.45 (dt, J = 13.0, 9.2 Hz, 1H). | AA: m/z = 540.1 (M + H) |
| I-29b | ¹H NMR (400 MHz, MeOD) δ 8.73 (s, 1H), 8.60 (s, 1H), 7.87-7.75 (m, 2H), 7.71 (d, J = 1.3 Hz, 1H), 7.62 (d, J = 7.6 Hz, 1H), 7.35 (d, J = 7.9 Hz, 1H), 5.86 (s, 1H), 4.85-4.74 (m, 1H), 4.18 (tt, J = 8.1, 4.2 Hz, 3H), 2.56-2.46 (m, 1H), 2.34-2.21 (m, 1H), 2.20-2.05 (m, 1H), 1.97-1.84 (m, 1H), 1.41 (dt, J = 13.0, 9.2 Hz, 1H). | AA: m/z = 540.1 (M + H) |
| I-5 | ¹H NMR (400 MHz, MeOD) δ 8.66 (s, 1H), 8.57 (s, 1H), 7.81 (s, 1H), 7.57 (s, 1H), 7.52 (s, 1H), 7.36 (d, J = 7.8 Hz, 1H), 7.31 (t, J = 7.7 Hz, 1H), 7.25 (d, 1H), 4.84-4.73 (m, 1H), 4.19 (tt, J = 15.8, 7.8 Hz, 3H), 2.55-2.42 (m, 1H), 2.27 (td, J = 14.3, 5.7 Hz, 1H), 2.21-2.11 (m, 1H), 1.98-1.83 (m, 4H), 1.43 (ddd, J = 14.5, 9.2, 4.5 Hz, 1H). | AA: m/z = 553.1 (M + H) |
| I-5a | ¹H NMR (400 MHz, MeOD) δ 8.66 (s, 1H), 8.58 (s, 1H), 7.81 (s, 1H), 7.59 (s, 1H), 7.52 (s, 1H), 7.36 (d, J = 7.8 Hz, 1H), 7.31 (t, J = 7.7 Hz, 1H), 7.25 (d, 1H), 4.84-4.73 (m, 1H), 4.19 (tt, J = 15.8, 7.8 Hz, 3H), 2.55-2.42 (m, 1H), 2.27 (td, J = | AA: m/z = 553.1 (M + H) |

| Compound No. | ¹H NMR | LC/MS |
|---|---|---|
| | 14.3, 5.7 Hz, 1H), 2.21-2.11 (m, 1H), 1.98-1.83 (m, 4H), 1.47 (ddd, J = 14.5, 9.2, 4.5 Hz, 1H). | |
| I-5b | ¹H NMR (400 MHz, MeOD) δ 8.68 (s, 1H), 8.58 (s, 1H), 7.81 (s, 1H), 7.59 (s, 1H), 7.52 (s, 1H), 7.36 (d, J = 7.8 Hz, 1H), 7.31 (t, J = 7.7 Hz, 1H), 7.25 (d, 1H), 4.84-4.73 (m, 1H), 4.19 (tt, J = 15.8, 7.8 Hz, 3H), 2.55-2.42 (m, 1H), 2.27 (td, J = 14.3, 5.7 Hz, 1H), 2.21-2.11 (m, 1H), 1.98-1.87 (m, 4H), 1.46 (ddd, J = 14.5, 9.2, 4.5 Hz, 1H). | AA: m/z = 553.1 (M + H) |
| I-47 | ¹H NMR (400 MHz, MeOD) δ 8.58 (s, 1H), 8.48 (s, 1H), 7.70 (d, J = 0.7 Hz, 1H), 7.54 (d, J = 1.3 Hz, 1H), 7.39-7.31 (m, 1H), 7.29-7.22 (m, 2H), 7.22-7.14 (m, 1H), 4.82 (s, 1H), 4.74-4.57 (m, 1H), 4.07 (ddd, J = 21.1, 9.0, 5.1 Hz, 3H), 2.46-2.32 (m, 1H), 2.27 (s, 3H), 2.15 (td, J = 8.6, 5.6 Hz, 1H), 2.08-2.00 (m, 1H), 1.84-1.74 (m, 1H), 1.35-1.29 (m, 1H). | AA: m/z = 552.1 (M + H) |
| I-47a | ¹H NMR (400 MHz, MeOD) δ 8.56 (s, 1H), 8.46 (s, 1H), 7.70 (d, J = 0.7 Hz, 1H), 7.54 (d, J = 1.3 Hz, 1H), 7.39-7.31 (m, 1H), 7.29-7.22 (m, 2H), 7.22-7.14 (m, 1H), 4.82 (s, 1H), 4.74-4.57 (m, 1H), 4.07 (ddd, J = 21.1, 9.0, 5.1 Hz, 3H), 2.46-2.32 (m, 1H), 2.27 (s, 3H), 2.15 (td, J = 8.6, 5.6 Hz, 1H), 2.08-2.00 (m, 1H), 1.84-1.74 (m, 1H), 1.35-1.27 (m, 1H). | AA: m/z = 552.1 (M + H) |
| I-47b | ¹H NMR (400 MHz, MeOD) δ 8.58 (s, 1H), 8.47 (s, 1H), 7.70 (d, J = 0.7 Hz, 1H), 7.54 (d, J = 1.3 Hz, 1H), 7.39-7.31 (m, 1H), 7.29-7.22 (m, 2H), 7.22-7.14 (m, 1H), 4.82 (s, 1H), 4.74-4.57 (m, 1H), 4.07 (ddd, J = 21.1, 9.0, 5.1 Hz, 3H), 2.46-2.32 (m, 1H), 2.27 (s, 3H), 2.15 (td, J = 8.6, 5.6 Hz, 1H), 2.08-2.00 (m, 1H), 1.84-1.74 (m, 1H), 1.35-1.28 (m, 1H). | AA: m/z = 552.1 (M + H) |
| I-15 | ¹H NMR (400 MHz, MeOD) δ 8.75 (s, 1H), 8.62 (s, 1H), 7.77 (s, 1H), 7.45 (s, 1H), 7.39-7.25 (m, 3H), 5.33 (s, 1H), 4.81 (dd, J = 15.9, 7.9 Hz, 1H), 4.19 (qd, J = 9.8, 5.9 Hz, 3H), 2.58-2.45 (m, 1H), 2.31-2.22 (m, 1H), 2.19-2.10 (m, 1H), 1.95-1.84 (m, 1H), 1.47-1.38 (m, 1H). | AA: m/z = 572.1 (M + H) |
| I-3 | ¹H NMR (400 MHz, MeOD) δ 8.67 (s, 1H), 8.58 (s, 1H), 7.82 (s, 1H), 7.67 (t, 1H), 7.57 (s, 1H), 7.40 (d, 2H), 7.25 (t, 1H), 4.85-4.72 (m, 1H), 4.23-4.14 (m, 3H), 2.56-2.43 (m, 1H), 2.33-2.22 (m, 1H), 2.21-2.10 (m, 1H), 1.95-1.85 (m, 4H), 1.42 (dtd, J = 12.8, 9.2, 3.4 Hz, 1H). | AA: m/z = 597.0 (M + H) |
| I-3a | ¹H NMR (400 MHz, CDCl₃) δ 8.65 (s, 1H), 8.55 (s, 1H), 7.80 (s, 1H), 7.66 (s, 1H), 7.55 (s, 1H), 7.38 (dd, J = 8.0, 1.8 Hz, 2H), 7.23 (t, 1H), 4.84-4.71 (m, 1H), 4.24-4.03 (m, 3H), 2.55-2.41 (m, 1H), 2.32-2.21 (m, 1H), 2.19-2.09 (m, 1H), 1.99-1.78 (m, 4H), 1.40 (dt, J = 12.9, 9.2 Hz, 1H). | AA: m/z = 597.0 (M + H) |
| I-3b | ¹H NMR (400 MHz, CDCl₃) δ 8.67 (s, 1H), 8.56 (s, 1H), 7.82 (s, 1H), 7.66 (s, 1H), 7.55 (s, 1H), 7.38 (dd, J = 8.0, 1.8 Hz, 2H), 7.23 (t, 1H), 4.84-4.71 (m, 1H), 4.24-4.03 (m, 3H), 2.55-2.41 (m, 1H), 2.32-2.21 (m, 1H), 2.19-2.09 (m, 1H), 1.98-1.79 (m, 4H), 1.43 (dt, J = 12.9, 9.2 Hz, 1H). | AA: m/z = 597.0 (M + H) |
| I-153 | ¹H NMR (400 MHz, MeOD) δ 8.61 (s, 1H), 8.52 (s, 1H), 7.76 (s, 1H), 7.64 (s, 1H), 7.41 (s, 1H), 7.33 (d, J = 7.7 Hz, 1H), 7.26 (t, J = 7.8 Hz, 1H), 7.18 (d, 1H), 4.78-4.66 (m, 1H), 4.17-4.06 (m, 3H), 2.48-2.33 (m, 1H), 2.24-2.18 (m, 1H), 2.16 (s, 6H), 2.12-2.02 (m, 1H), 1.81 (dd, J = 8.4, 4.8 Hz, 1H), 1.38-1.27 (m, 1H). | AA: m/z = 566.1 (M + H) |
| I-2a | ¹H NMR (400 MHz, MeOD) δ 8.72 (s, 1H), 8.64 (S, 1H), 7.84 (t, J = 7.8 Hz, 1H), 7.62 (dd, J = 8.0, 3.6 Hz, 2H), 7.35 (d, J = 7.9 Hz, 1H), 5.93 (s, 1H), 4.86-4.70 (m, 1H), 4.28-4.10 (m, 3H), 2.57-2.41 (m, 1H), 2.21 (dd, J = 46.9, 5.5 Hz, 2H), 1.92 (dt, J = 15.2, 7.0 Hz, 1H), 1.53-1.35 (m, 1H). | AA: m/z = 574.0 (M + H) |
| I-153a | ¹H NMR (400 MHz, MeOD) δ 8.62 (s, 1H), 8.55 (s, 1H), 7.79 (s, 1H), 7.66 (d, J = 1.3 Hz, 1H), 7.43 (s, 1H), 7.35 (d, 1H), 7.28 (t, J = 7.8 Hz, 1H), 7.21 (d, J = 7.9, 2.0, 1.2 Hz, 1H), 4.80-4.66 (m, 1H), 4.13 (qd, J = 9.8, 5.9 Hz, 3H), 2.51-2.40 (m, 1H), 2.30-2.15 (m, 7H), 2.09 (ddd, J = 19.0, 12.1, 7.4 Hz, 1H), 1.90-1.77 (m, 1H), 1.37 (dt, J = 13.0, 9.1 Hz, 1H). | AA: m/z = 566.1 (M + H) |
| I-153b | ¹H NMR (400 MHz, MeOD) δ 8.64 (s, 1H), 8.57 (s, 1H), 7.79 (s, 1H), 7.66 (d, J = 1.3 Hz, 1H), 7.43 (s, 1H), 7.35 (d, 1H), 7.28 (t, J = 7.8 Hz, 1H), 7.21 (d, J = 7.9, 2.0, 1.2 Hz, 1H), 4.80-4.66 (m, 1H), 4.13 (qd, J = 9.8, 5.9 Hz, 3H), 2.51-2.40 (m, 1H), 2.30-2.15 (m, 7H), 2.09 (ddd, J = 19.0, 12.1, 7.4 Hz, 1H), 1.93-1.79 (m, 1H), 1.39 (dt, J = 13.0, 9.1 Hz, 1H). | AA: m/z = 566.1 (M + H) |
| I-164 | ¹H NMR (400 MHz, MeOD) δ 8.78 (s, 1H), 8.59 (s, 1H), 7.76 (s, 1H), 7.71 (s, 1H), 7.60-7.48 (m, 2H), 7.40-7.27 (m, | AA: m/z = 579.0 (M + H) |

| Compound No. | ¹H NMR | LC/MS |
|---|---|---|
| | 2H), 5.71 (s, 1H), 5.48 (s, 1H), 4.82 (dd, J = 16.2, 8.0 Hz, 1H), 4.20 (qd, J = 9.9, 5.9 Hz, 3H), 2.59-2.47 (m, 1H), 2.33-2.24 (m, 1H), 2.18 (ddd, J = 12.8, 7.9, 4.6 Hz, 1H), 1.92 (dd, J = 10.3, 5.0 Hz, 1H), 1.46 (dt, J = 13.0, 9.1 Hz, 1H). | |
| I-36a | ¹H NMR (400 MHz, MeOD) δ 8.73 (s, 1H), 8.61 (s, 1H), 7.85 (s, 1H), 7.68 (s, 1H), 7.51 (s, 1H), 7.47-7.33 (m, 3H), 5.55 (s, 1H), 4.81 (dd, J = 15.9, 8.0 Hz, 1H), 4.20 (qd, J = 9.9, 5.8 Hz, 3H), 2.57-2.45 (m, 1H), 2.29 (dt, J = 14.0, 7.0 Hz, 1H), 2.17 (ddd, J = 12.6, 11.2, 7.4 Hz, 1H), 1.96-1.82 (m, 1H), 1.50-1.38 (m, 1H). | AA: m/z = 538.1 (M + H) |
| I-36b | ¹H NMR (400 MHz, MeOD) δ 8.70 (s, 1H), 8.59 (s, 1H), 7.83 (s, 1H), 7.68 (s, 1H), 7.51 (s, 1H), 7.47-7.33 (m, 3H), 5.55 (s, 1H), 4.81 (dd, J = 15.9, 8.0 Hz, 1H), 4.20 (qd, J = 9.9, 5.8 Hz, 3H), 2.57-2.45 (m, 1H), 2.29 (dt, J = 14.0, 7.0 Hz, 1H), 2.17 (ddd, J = 12.6, 11.2, 7.4 Hz, 1H), 1.94-1.80 (m, 1H), 1.48-1.39 (m, 1H). | AA: m/z = 538.1 (M + H) |
| I-17 | ¹H NMR (400 MHz, MeOD) δ 8.68 (s, 1H), 8.56 (s, 1H), 7.73 (s, 1H), 7.59 (s, 1H), 7.55 (d, J = 1.2 Hz, 1H), 7.46-7.40 (m, 1H), 7.36 (d, J = 7.8 Hz, 1H), 7.26 (t, J = 7.8 Hz, 1H), 5.84 (s, 1H), 4.84-4.70 (m, 1H), 4.17 (qd, J = 9.8, 5.8 Hz, 3H), 2.56-2.42 (m, 1H), 2.31-2.19 (m, 1H), 2.13 (ddd, J = 14.4, 9.3, 5.6 Hz, 1H), 1.91-1.80 (m, 1H), 1.40 (dt, J = 12.9, 9.1 Hz, 1H). | AA: m/z = 583.0 (M + H) |
| I-4 | ¹H NMR (400 MHz, MeOD) δ 8.67 (s, 1H), 8.56 (s, 1H), 7.72 (s, 1H), 7.54 (s, 1H), 7.43 (s, 1H), 7.34-7.29 (m, 2H), 7.28-7.20 (m, 1H), 5.84 (s, 1H), 4.82-4.70 (m, 1H), 4.22-4.11 (m, 3H), 2.53-2.40 (m, 1H), 2.28-2.18 (m, 1H), 2.17-2.08 (m, 1H), 1.40-1.33 (m, 1H). | AA: m/z = 539.1 (M + H) |
| I-4a | ¹H NMR (400 MHz, MeOD) δ 8.67 (s, 1H), 8.56 (s, 1H), 7.72 (s, 1H), 7.54 (s, 1H), 7.43 (s, 1H), 7.34-7.29 (m, 2H), 7.28-7.20 (m, 1H), 5.84 (s, 1H), 4.82-4.70 (m, 1H), 4.22-4.11 (m, 3H), 2.53-2.40 (m, 2H), 2.28-2.18 (m, 1H), 2.17-2.08 (m, 1H), 1.44-1.36 (m, 1H). | AA: m/z = 539.1 (M + H) |
| I-4b | ¹H NMR (400 MHz, MeOD) δ 8.67 (s, 1H), 8.56 (s, 1H), 7.72 (s, 1H), 7.54 (s, 1H), 7.43 (s, 1H), 7.34-7.29 (m, 2H), 7.28-7.20 (m, 1H), 5.84 (s, 1H), 4.82-4.70 (m, 1H), 4.22-4.11 (m, 3H), 2.53-2.40 (m, 2H), 2.28-2.18 (m, 1H), 2.17-2.08 (m, 1H), 1.42-1.34 (m, 1H). | AA: m/z = 539.1 (M + H) |
| I-237 | ¹H NMR (400 MHz, MeOD) δ 8.87 (s, 1H), 8.65 (s, 1H), 8.09 (s, 1H), 7.91 (s, 1H), 5.96 (d, 1H), 5.84 (d, 1H) 4.90-4.82 (m, 1H), 4.29-4.17 (m, 3H), 2.48 (m, 1H) 2.36 (s, 3H), 2.35-2.28 (m, 1H), 2.25-2.18 (m, 1H), 2.04-1.93 (m, 1H), 1.54-1.46 (m, 1H). | AA: m/z = 493.1 (M + H) |
| I-231 | ¹H NMR (400 MHz, MeOD) δ 8.72 (s, 1H), 8.60 (s, 1H), 7.84-7.79 (m, 2H), 7.65 (s, 1H), 7.20 (s, 1H), 7.01 (s, 1H), 5.30 (s, 2H), 4.86-4.75 (m, 1H), 4.23-4.12 (m, 3H), 2.56-2.44 (m, 1H), 2.31-2.23 (m, 1H), 2.17 (ddd, J = 12.4, 10.9, 7.1 Hz, 1H), 1.94-1.86 (m, 1H), 1.43 (dt, J = 13.0, 9.1 Hz, 1H). | AA: m/z = 479.1 (M + H) |
| I-51 | ¹H NMR (400 MHz, MeOD) δ 8.67 (s, 1H), 8.55 (s, 1H), 7.40 (s, 1H), 7.27 (t, 1H), 7.19 (d, 2H), 7.12 (d, J = 7.8 Hz, 1H), 4.76 (dd, J = 15.9, 7.9 Hz, 1H), 4.26-4.15 (m, 3H), 2.54-2.41 (m, 4H), 2.31-2.21 (m, 1H), 2.18-2.09 (m, 1H), 1.93-1.83 (m, 1H), 1.47-1.37 (m, 1H). | AA: m/z = 537.1 (M + H) |
| I-73a | ¹H NMR (400 MHz, MeOD) δ 8.69 (s, 1H), 8.60 (s, 1H), 7.79 (s, 1H), 7.59 (s, 1H), 7.56 (s, 1H), 7.48 (d, 1H), 7.39 (d, 1H), 7.32 (t, J = 7.8 Hz, 1H), 5.43 (s, 1H), 4.86-4.78 (m, 1H), 4.27-4.08 (m, 3H), 3.40 (s, 3H), 2.56-2.47 (m, 1H), 2.31-2.23 (m, 1H), 2.23-2.16 (m, 1H), 1.97-1.92 (m, 1H), 1.50-1.42 (m, 1H). | AA: m/z = 597.0 (M + H) |
| I-73b | ¹H NMR (400 MHz, MeOD) δ 8.64 (s, 1H), 8.56 (s, 1H), 7.75 (s, 1H), 7.55 (s, 1H), 7.52 (s, 1H), 7.44 (d, 1H), 7.35 (d, 1H), 7.28 (t, J = 7.8 Hz, 1H), 5.39 (s, 1H), 4.82-4.73 (m, 1H), 4.23-4.03 (m, 3H), 3.36 (s, 3H), 2.52-2.42 (m, 1H), 2.27-2.19 (m, 1H), 2.19-2.11 (m, 1H), 1.93-1.88 (m, 1H), 1.46-1.37 (m, 1H). | AA: m/z = 597.0 (M + H) |
| I-314 | | FA: m/z = 579.4 (M + H) |
| I-178 | ¹H NMR (400 MHz, MeOD) δ 8.63 (dd, J = 29.4, 15.7 Hz, 2H), 7.72-7.46 (m, 2H), 7.36-7.24 (m, 3 H), 7.23-7.14 (m, 1H), 4.85-4.75 (m, 1H), 4.34-4.12 (m, 3H), 3.07-2.91 (m, 2H), 2.59-2.44 (m, 1H), 2.37-2.23 (m, 1H), 2.22-2.08 (m, 1H), 1.99-1.84 (m, 1H), 1.66 (d, J = 7.2 Hz, 1H), 1.57-1.34 (m, 2H) | AA: m/z = 537.1 (M + H) |

| Compound No. | ¹H NMR | LC/MS |
|---|---|---|
| I-6 | ¹H NMR (400 MHz, Methanol-$d_4$) δ 8.72 (s, 1H), 8.59 (s, 1H), 7.67 (s, 1H), 7.52-7.37 (m, 3H), 7.32 (d, J = 7.1 Hz, 1H), 5.66 (s, 1H), 4.83-4.74 (m, 1H), 4.25-4.12 (m, 3H), 2.57-2.44 (m, 4H), 2.33-2.21 (m, 1H), 2.21-2.10 (m, 1H), 1.90 (ddd, J = 20.4, 7.5, 4.4 Hz, 1H), 1.49-1.39 (m, 1H) | FA: m/z = 552.2 (M + H) |
| I-8 | ¹H NMR (400 MHz, Chloroform-d) δ 8.67 (d, J = 2.3 Hz, 1H), 8.63 (s, 1H), 8.39 (d, J = 7.1 Hz, 1H), 7.97 (s, 1H), 7.77 (d, J = 1.2 Hz, 1H), 7.56 (s, 1H), 7.44 (s, 2H), 7.41-7.30 (m, 3H), 4.86 (d, J = 5.2 Hz, 1H), 4.72 (t, J = 4.3 Hz, 1H), 4.51-4.39 (m, 1H), 4.13-4.02 (m, 2H), 4.00-3.93 (m, 1H), 3.78 (q, J = 5.8 Hz, 1H), 3.73-3.67 (m, 1H), 3.09-2.98 (m, 2H), 2.31-2.23 (m, 1H), 2.23-2.13 (m, 1H), 1.17-1.11 (m, 1H) | FA: m/z = 568.2 (M + H) |
| I-12 | ¹H NMR (400 MHz, DMSO-$d_6$) δ 8.63 (s, 2H), 8.28 (d, J = 7.5 Hz, 1H), 7.88 (d, J = 1.0 Hz, 1H), 7.72 (d, J = 1.3 Hz, 1H), 7.55 (s, 1H), 7.43 (s, 2H), 7.37-7.28 (m, 2H), 7.25 (dt, J = 6.6, 2.1 Hz, 1H), 4.88 (dd, J = 4.5, 1.2 Hz, 1H), 4.76-4.63 (m, 1H), 4.09 (dd, J = 9.9, 5.8 Hz, 1H), 3.99-3.88 (m, 2H), 3.13-2.70 (m, 2H), 2.36-2.24 (m, 1H), 2.11 (d, J = 5.7 Hz, 1H), 1.95 (td, J = 8.1, 3.7 Hz, 1H), 1.82-1.69 (m, 4H), 1.31-1.22 (m, 1H) | FA: m/z = 552.3 (M + H) |
| I-14a | ¹H NMR (400 MHz, DMSO-$d_6$) δ 8.73 (s, 1H), 8.66 (s, 1H), 8.31 (d, J = 7.7 Hz, 1H), 7.94 (s, 1H), 7.51 (s, 1H), 7.49-7.30 (br s, 2H), 7.37-7.25 (m, 3H), 5.13 (s, 1H), 4.85 (d, J = 5.9 Hz, 1H), 4.70 (d, J = 4.7 Hz, 1H), 4.47 (p, J = 7.8 Hz, 1H), 4.06 (dd, J = 9.8, 6.1 Hz, 1H), 3.96 (dd, J = 9.7, 6.7 Hz, 1H), 3.83-3.74 (m, 1H), 3.70 (q, J = 4.6 Hz, 1H), 2.77-2.54 (br s, 2H), 2.28 (dt, J = 12.7, 8.3 Hz, 1H), 2.23-2.12 (m, 1H), 1.16 (dt, J = 12.7, 8.8 Hz, 1H) | |
| I-14b | ¹H NMR (400 MHz, DMSO-$d_6$) δ 8.75 (s, 1H), 8.67 (s, 1H), 8.59-8.36 (br s, 2H), 8.32 (d, J = 7.6 Hz, 1H), 7.98 (s, 1H), 7.54 (s, 1H), 7.50-7.41 (br s, 2H), 7.41-7.30 (m, 3H), 5.29 (s, 1H), 4.95-4.81 (br s, 1H), 4.74 (d, J = 4.7 Hz, 1H), 4.54-4.41 (m, 1H), 4.07 (dd, J = 9.7, 6.1 Hz, 1H), 3.97 (dd, J = 11.4, 6.7 Hz, 2H), 3.84-3.76 (m, 1H), 3.74-3.67 (m, 1H), 2.28 (dt, J = 12.6, 8.4 Hz, 1H), 2.23-2.14 (m, 1H), 1.19-1.14 (m, 1H) | |
| I-135 | ¹H NMR (400 MHz, DMSO-$d_6$) δ 8.66 (s, 1H), 8.64 (s, 1H), 8.23 (d, J = 7.5 Hz, 1H), 7.71 (s, 1H), 7.43 (s, 2H), 7.37 (s, 1H), 7.32 (t, J = 7.7 Hz, 1H), 7.29-7.20 (m, 2H), 4.88 (dd, J = 4.5, 1.0 Hz, 1H), 4.77-4.63 (m, 1H), 4.26 (q, J = 7.1 Hz, 1H), 4.09 (dd, J = 9.7, 6.0 Hz, 1H), 4.01-3.90 (m, 2H), 2.40 (s, 3H), 2.31 (td, J = 12.2, 7.7 Hz, 1H), 2.17-2.06 (m, 1H), 2.01-1.91 (m, 1H), 1.82-1.70 (m, 1H), 1.58 (d, J = 7.2 Hz, 3H), 1.34-1.21 (m, 1H) | FA: m/z = 551.4 (M + H) |
| I-347 | ¹H NMR (400 MHz, Methanol-$d_4$) δ 8.60 (s, 1H), 8.53 (s, 1H), 7.24 (s, 1H), 7.06 (d, J = 7.8 Hz, 1H), 7.00 (d, J = 7.9 Hz, 1H), 6.56 (s, 1H), 5.88 (s, 1H), 4.82-4.70 (m, 1H), 4.24-4.11 (m, 4H), 3.96-3.85 (m, 1H), 3.10-2.97 (m, 1H), 2.81-2.71 (m, 1H), 2.53 (s, 3H), 2.51-2.43 (m, 1H), 2.31-2.23 (m, 1H), 2.21 (s, 3H), 2.18-2.08 (m, 1H), 1.95-1.83 (m, 1H), 1.47-1.34 (m, 1H) | FA: m/z = 559.2 (M + H) |
| I-346 | ¹H NMR (400 MHz, Methanol-$d_4$) δ 8.59 (s, 1H), 8.52 (s, 1H), 7.24 (s, 1H), 7.09 (d, J = 7.8 Hz, 1H), 7.04 (d, J = 7.9 Hz, 1H), 6.59 (s, 1H), 5.90 (s, 1H), 4.81-4.71 (m, 1H), 4.24-4.09 (m, 4H), 3.96-3.87 (m, 1H), 3.11-2.98 (m, 1H), 2.83-2.72 (m, 1H), 2.59-2.42 (m, 6H), 2.32-2.20 (m, 1H), 2.19-2.07 (m, 1H), 1.95-1.83 (m, 1H), 1.47-1.33 (m, 1H), 1.12 (t, J = 7.6 Hz, 3H) | FA: m/z = 573.2 (M + H) |
| I-1 | ¹H NMR (400 MHz, Methanol-$d_4$) δ 8.74 (s, 1H), 8.60 (s, 1H), 7.85 (s, 1H), 7.79-7.64 (m, 3H), 7.43 (d, J = 7.6 Hz, 1H), 4.64-4.54 (m, 1H), 4.26-4.16 (m, 2H), 4.00-3.91 (m, 2H), 3.37-3.30 (m, 2H), 2.56-2.45 (m, 1H), 2.45-2.34 (m, 1H), 1.93 (s, 3H), 1.42-1.31 (m, 1H) | FA: m/z = 616.0 (M + H) |
| I-29 | ¹H NMR (400 MHz, Methanol-$d_4$) δ 8.73 (s, 1H), 8.60 (s, 1H), 7.89-7.80 (m, 2H), 7.71 (d, J = 1.3 Hz, 1H), 7.62 (d, J = 7.6 Hz, 1H), 7.35 (d, J = 7.9 Hz, 1H), 5.86 (s, 1H), 4.86-4.75 (m, 1H), 4.25-4.14 (m, 3H), 2.52 (m, 1H), 2.28 (m, 1H), 2.22-2.12 (m, 1H), 1.98-1.88 (m, 1H), 1.43 (m, 1H) | |

| Compound No. | ¹H NMR | LC/MS |
|---|---|---|
| I-233 | ¹H NMR (400 MHz, Chloroform-d) δ 8.67 (s, 1H), 8.61 (s, 1H), 8.57 (d, J = 7.3 Hz, 1H), 7.29-7.20 (m, 3H), 7.12 (d, J = 6.6 Hz, 1H), 6.71 (s, 1H), 5.75-5.58 (br s, 2H), 4.81-4.69 (m, 1H), 4.38-4.28 (m, 2H), 4.23 (dd, J = 9.9, 5.8 Hz, 1H), 4.08 (s, 2H), 2.73-2.24 (m, 6H), 2.20-2.09 (m, 1H), 2.03-1.93 (m, 1H), 1.48-1.37 (m, 1H) | FA: m/z = 537.1 (M + H) |
| I-32a | ¹H NMR (400 MHz, DMSO-d₆) δ 8.63 (s, 1H), 8.58 (s, 1H), 8.21 (d, J = 7.5 Hz, 1H), 7.93 (d, J = 1.4 Hz, 1H), 7.61 (d, J = 1.4 Hz, 1H), 7.50-7.44 (m, 2H), 7.42 (s, 2H), 7.36-7.28 (m, 2H), 7.26-7.19 (m, 1H), 4.87 (d, J = 4.4 Hz, 1H), 4.75-4.62 (m, 1H), 4.08 (dd, J = 9.7, 6.0 Hz, 1H), 4.00-3.89 (m, 4H), 2.71-2.61 (m, 1H), 2.44-2.34 (m, 1H), 2.35-2.24 (m, 1H), 2.16-2.06 (m, 1H), 1.98-1.83 (m, 3H), 1.80-1.70 (m, 1H), 1.30-1.20 (m, 1H) | FA: m/z = 545.5 (M + H) |
| I-32b | ¹H NMR (400 MHz, DMSO-d₆) δ 8.63 (s, 1H), 8.58 (s, 1H), 8.21 (d, J = 7.5 Hz, 1H), 7.93 (d, J = 1.4 Hz, 1H), 7.61 (d, J = 1.4 Hz, 1H), 7.50-7.44 (m, 2H), 7.42 (s, 2H), 7.36-7.28 (m, 2H), 7.26-7.19 (m, 1H), 4.87 (d, J = 4.4 Hz, 1H), 4.75-4.62 (m, 1H), 4.08 (dd, J = 9.7, 6.0 Hz, 1H), 4.00-3.89 (m, 4H), 2.71-2.61 (m, 1H), 2.44-2.34 (m, 1H), 2.35-2.24 (m, 1H), 2.16-2.06 (m, 1H), 1.98-1.83 (m, 3H), 1.80-1.70 (m, 1H), 1.30-1.20 (m, 1H) | FA: m/z = 545.5 (M + H) |
| I-344 | ¹H NMR (400 MHz, Methanol-d₄) δ 8.72 (s, 1H), 8.53 (s, 1H), 7.61 (d, J = 7.1, 0.9 Hz, 1H), 7.57 (d, J = 7.3, 1.1 Hz, 1H), 7.50 (s, 1H), 7.38-7.28 (m, 2H), 6.19 (s, 1H), 4.83-4.73 (m, 1H), 4.53-4.44 (m, 1H), 4.43-4.34 (m, 2H), 4.33-4.27 (m, 1H), 4.23-4.13 (m, 3H), 2.55 (s, 3H), 2.53-2.45 (m, 1H), 2.31-2.22 (m, 1H), 2.18-2.10 (m, 1H), 1.94-1.83 (m, 1H), 1.48-1.36 (m, 1H). | AA: m/z = 585.1 (M + H) |
| I-38a | ¹H NMR (400 MHz, Methanol-d₄) δ 8.63 (s, 1H), 8.57 (s, 1H), 7.87 (d, J = 1.4 Hz, 1H), 7.56 (d, J = 1.4 Hz, 1H), 7.52-7.48 (m, 1H), 7.41-7.37 (m, 1H), 7.33 (t, J = 7.8 Hz, 1H), 7.29-7.23 (m, 1H), 4.82-4.73 (m, 1H), 4.24-4.09 (m, 3H), 3.21-3.06 (m, 2H), 2.71-2.60 (m, 1H), 2.55-2.34 (m, 2H), 2.31-2.19 (m, 1H), 2.20-2.08 (m, 1H), 2.00-1.83 (m, 3H), 1.46-1.35 (m, 1H) | FA: m/z = 578.1 (M + H) |
| I-38b | ¹H NMR (400 MHz, Methanol-d₄) δ 8.63 (s, 1H), 8.57 (s, 1H), 7.89 (d, J = 1.4 Hz, 1H), 7.56 (d, J = 1.5 Hz, 1H), 7.53-7.48 (m, 1H), 7.43-7.31 (m, 2H), 7.31-7.25 (m, 1H), 4.82-4.71 (m, 1H), 4.27-4.08 (m, 3H), 3.26-3.10 (m, 2H), 2.75-2.64 (m, 1H), 2.53-2.39 (m, 2H), 2.31-2.20 (m, 1H), 2.19-2.09 (m, 1H), 2.04-1.82 (m, 3H), 1.46-1.38 (m, 1H) | FA: m/z = 578.1 (M + H) |
| I-262 | ¹H NMR (400 MHz, Methanol-d₄) δ 8.65 (s, 1H), 8.54 (s, 1H), 7.31 (m, 3H), 7.07 (s, 1H), 5.73 (s, 1H), 4.81-4.71 (m, 1H), 4.39-4.24 (m, 2H), 4.24-4.08 (m, 3H), 2.55-2.40 (m, 1H), 2.32-2.18 (m, 1H), 2.18-2.07 (m, 1H), 1.94-1.82 (m, 1H), 1.48-1.34 (m, 1H) | AA: m/z = 584.2 (M + H) |
| I-262a | ¹H NMR (400 MHz, DMSO-d₆) δ 8.60 (d, J = 6.2 Hz, 2H), 8.13 (d, J = 7.6 Hz, 1H), 7.49-7.38 (m, 3H), 7.36 (d, J = 8.1 Hz, 1H), 7.30 (dd, J = 8.1, 1.7 Hz, 1H), 7.04 (s, 1H), 5.59 (s, 1H), 4.86 (d, J = 4.5 Hz, 1H), 4.74-4.61 (m, 1H), 4.31-4.14 (m, 2H), 4.08 (dd, J = 9.7, 6.0 Hz, 1H), 4.01-3.88 (m, 2H), 3.73-3.59 (br s, 1H), 2.36-2.23 (m, 1H), 2.16-2.07 (m, 1H), 1.95-1.84 (m, 1H), 1.78-1.66 (m, 1H), 1.33-1.20 (m, 1H) | FA: m/z = 584.2 (M + H) |
| I-262b | ¹H NMR (400 MHz, DMSO-d₆) δ 8.60 (d, J = 6.1 Hz, 2H), 8.14 (d, J = 7.5 Hz, 1H), 7.51-7.38 (m, 3H), 7.36 (d, J = 8.1 Hz, 1H), 7.30 (dd, J = 8.1, 1.6 Hz, 1H), 7.04 (s, 1H), 5.59 (s, 1H), 4.94-4.81 (br s, 1H), 4.74-4.61 (m, 1H), 4.30-4.14 (m, 2H), 4.13-4.03 (m, 1H), 4.00-3.86 (m, 2H), 3.80-3.56 (br s, 1H), 2.36-2.20 (m, 1H), 2.15-2.08 (m, 1H), 2.00-1.86 (m, 1H), 1.80-1.69 (m, 1H), 1.31-1.18 (m, 1H) | FA: m/z = 584.2 (M + H) |
| I-265 | ¹H NMR (400 MHz, Methanol-d₄) δ 8.74 (s, 1H), 8.56 (s, 1H), 7.95 (s, 1H), 7.58 (s, 1H), 7.33-7.22 (m, 2H), 6.86 (s, 1H), 4.83-4.75 (m, 2H), 4.29 (d, J = 13.0 Hz, 1H), 4.24-4.11 (m, 3H), 3.74 (dd, J = 12.9, 2.4 Hz, 1H), 2.55-2.45 (m, 4H), 2.32-2.21 (m, 1H), 2.21-2.10 (m, 1H), 1.90 (dt, J = 15.3, 7.7 Hz, 1H), 1.50-1.37 (m, 1H) | AA: m/z = 564.0 (M + H) |

| Compound No. | ¹H NMR | LC/MS |
|---|---|---|
| I-265a | ¹H NMR (400 MHz, Methanol-d₄) δ 8.74 (s, 1H), 8.56 (s, 1H), 7.96 (d, J = 1.1 Hz, 1H), 7.58 (d, J = 1.3 Hz, 1H), 7.32-7.23 (m, 2H), 6.86 (s, 1H), 4.85-4.74 (m, 2H), 4.29 (d, J = 12.6 Hz, 1H), 4.25-4.11 (m, 3H), 3.74 (dd, J = 13.0, 3.3 Hz, 1H), 2.54-2.50 (m, 4H), 2.32-2.20 (m, 1H), 2.20-2.11 (m, 1H), 1.98-1.86 (m, 1H), 1.43 (dt, J = 12.8, 9.1 Hz, 1H) | AA: m/z = 564.0 (M + H) |
| I-265b | ¹H NMR (400 MHz, Methanol-d₄) δ 8.74 (s, 1H), 8.56 (s, 1H), 7.96 (d, J = 1.2 Hz, 1H), 7.58 (d, J = 1.3 Hz, 1H), 7.32-7.23 (m, 2H), 6.86 (s, 1H), 4.85-4.74 (m, 2H), 4.29 (d, J = 13.5 Hz, 1H), 4.25-4.11 (m, 3H), 3.74 (dd, J = 13.2, 2.6 Hz, 1H), 2.54-2.48 (m, 4H), 2.33-2.22 (m, 1H), 2.22-2.11 (m, 1H), 1.98-1.86 (m, 1H), 1.42 (dt, J = 12.9, 9.1 Hz, 1H) | AA: m/z = 564.0 (M + H) |
| I-345 | ¹H NMR (400 MHz, Methanol-d₄) δ 8.64 (d, J = 3.6 Hz, 2H), 8.09 (s, 1H), 7.97 (d, J = 7.8 Hz, 1H), 7.67 (d, J = 7.6 Hz, 1H), 7.48 (t, J = 7.7 Hz, 1H), 7.36 (s, 1H), 7.18 (d, J = 1.2 Hz, 2H), 6.73 (s, 1H), 5.89 (s, 1H), 5.38-5.28 (m, 1H), 5.02 (d, J = 6.6 Hz, 2H), 4.98-4.88 (m, 1H), 4.37-4.25 (m, 2H), 4.20 (ddd, J = 11.4, 5.6, 3.0 Hz, 1H), 3.92 (td, J = 11.4, 10.8, 3.8 Hz, 1H), 3.15-3.02 (m, 1H), 2.84-2.73 (m, 1H), 2.71-2.62 (m, 1H), 2.60-2.54 (m, 1H), 2.53 (s, 3H), 2.43-2.33 (m, 1H), 2.11 (ddd, J = 14.1, 9.7, 7.1 Hz, 1H), 1.64 (dt, J = 12.5, 9.8 Hz, 1H) | FA: m/z = 792.9 (M + H) |
| I-356 | ¹H NMR (400 MHz, Methanol-d₄) δ ppm 8.71 (s, 1 H) 8.58 (s, 1 H) 8.30 (s, 1 H) 7.42 (d, J = 1.00 Hz, 1 H) 5.94 (s, 1 H) 4.73-4.85 (m, 1 H) 4.31-4.39 (m, 1 H) 3.95-4.23 (m, 6 H) 2.45-2.57 (m, 4 H) 2.24-2.32 (m, 1 H) 2.20 (s, 3 H) 2.13 (s, 3 H) 1.86-1.97 (m, 1 H) 1.43 (m, 1 H) | AA: m/z = 563.1 (M + H) |
| I-356a | ¹H NMR (400 MHz, Methanol-d₄) δ ppm 8.70 (s, 1 H) 8.55 (s, 1 H) 7.37 (s, 1 H) 5.87 (s, 1 H) 4.73-4.84 (m, 1 H) 4.26-4.32 (m, 1 H) 4.13-4.23 (m, 3 H) 3.91-4.12 (m, 4 H) 2.44-2.55 (m, 4 H) 2.26 (m, 1 H) 2.12-2.18 (m, 4 H) 2.08 (s, 3 H) 1.86-1.98 (m, 1 H) 1.41 (m, 1 H) | AA: m/z = 563.1 (M + H) |
| I-356b | ¹H NMR (400 MHz, Methanol-d₄) δ ppm 8.69 (s, 1 H) 8.54 (s, 1 H) 7.35 (s, 1 H) 5.85 (s, 1 H) 4.77 (quin, J = 7.91 Hz, 1 H) 4.23-4.31 (m, 1 H) 4.11-4.20 (m, 3 H) 3.91-4.11 (m, 4 H) 2.45-2.54 (m, 4 H) 2.25 (m, 1 H) 2.10-2.16 (m, 4 H) 2.07 (s, 3 H) 1.84-1.95 (m, 1 H) 1.41 (m, 1 H) | AA: m/z = 563.1 (M + H) |
| I-357 | ¹H NMR (400 MHz, Methanol-d₄) δ ppm 8.70 (s, 1 H) 8.59 (s, 1 H) 7.79 (s, 1 H) 7.56 (s, 1 H) 7.25 (s, 1 H) 7.13-7.18 (m, 1 H) 6.88-6.93 (m, 1 H) 5.89 (s, 1 H) 4.77-4.84 (m, 1 H) 4.07-4.25 (m, 4 H) 3.88-3.97 (m, 1 H) 2.98-3.07 (m, 1 H) 2.81-2.91 (m, 1 H) 2.47-2.57 (m, 1 H) 2.23-2.33 (m, 1 H) 2.12-2.23 (m, 1 H) 1.88-2.04 (m, 1 H) 1.39-1.49 (m, 1 H) | AA: m/z = 565.1 (M + H) |
| I-358 | ¹H NMR (400 MHz, Methanol-d₄) δ ppm 8.88 (s, 1 H) 8.57-8.60 (m, 1 H) 8.57 (s, 1 H) 8.03-8.10 (m, 1 H) 7.89-7.95 (m, 1 H) 7.75-7.84 (m, 3 H) 4.77-4.84 (m, 1 H) 4.15-4.26 (m, 3 H) 2.48-2.58 (m, 1 H) 2.42 (s, 3 H) 2.14-2.37 (m, 2 H) 1.89-2.03 (m, 1 H) 1.40-1.51 (m, 1 H) | AA: m/z = 574.1 (M + H) |
| I-359a | ¹H NMR (400 MHz, DMSO-d₆) δ 8.59 (s, 1H), 8.54 (s, 1H), 8.17 (d, J = 7.3 Hz, 1H), 7.44 (s, 2H), 7.39 (d, J = 8.8 Hz, 1H), 7.36-7.32 (m, 2H), 7.04 (d, J = 1.0 Hz, 1H), 6.06 (s, 1H), 4.90-4.86 (m, 1H), 4.73-4.61 (m, 1H), 4.43 (dd, J = 2.4, 14.7 Hz, 1H), 4.30 (d, J = 14.3 Hz, 1H), 4.10-4.05 (m, 1H), 3.97-3.90 (m, 2H), 2.49 (s, 3H), 2.32-2.23 (m, 1H), 2.13-2.05 (m, 2H), 1.98-1.88 (m, 1H), 1.79-1.69 (m, 1H), 1.29-1.20 (m, 1H); | AA: m/z = 581.1 (M + H) |
| I-359b | ¹H NMR (400 MHz, DMSO-d₆) δ 8.59 (s, 1H), 8.54 (s, 1H), 8.17 (d, J = 7.5 Hz, 1H), 7.47-7.37 (m, 3H), 7.36-7.32 (m, 2H), 7.05-7.02 (m, 1H), 6.06 (s, 1H), 4.88 (d, J = 4.5 Hz, 1H), 4.73-4.61 (m, 1H), 4.43 (dd, J = 2.4, 14.7 Hz, 1H), 4.30 (d, J = 14.3 Hz, 1H), 4.10-4.05 (m, 1H), 3.97-3.90 (m, 2H), 2.49 (s, 3H), 2.32-2.25 (m, 1H), 2.15-2.04 (m, 1H), 1.97-1.88 (m, 1H), 1.78-1.69 (m, 1H), 1.30-1.20 (m, 1H) | FA: m/z = 581.1 (M + H) |

-continued

| Compound No. | ¹H NMR | LC/MS |
|---|---|---|
| I-360 | ¹H NMR (400 MHz, Methanol-d₄) δ ppm 8.82 (s, 1 H) 8.57 (s, 1 H) 7.61 (s, 1 H) 7.46-7.51 (m, 1 H) 7.34-7.40 (m, 1 H) 7.11-7.15 (m, 1 H) 4.76-4.85 (m, 1 H) 4.13-4.26 (m, 3 H) 3.81-3.92 (m, 2 H) 2.81-2.93 (m, 2 H) 2.42-2.56 (m, 4 H) 2.12-2.33 (m, 2 H) 2.00 (s, 1 H) 1.89-1.98 (m, 1 H) 1.35-1.53 (m, 1 H) | FA: m/z = 576.1 (M + H) |
| I-361 | ¹H NMR (400 MHz, Methanol-d₄) δ ppm 8.64 (br s, 1 H) 8.56 (s, 1 H) 7.39 (s, 1 H) 7.22 (s, 1 H) 7.27 (br t, J = 54.59 Hz, 1 H) 7.06-7.19 (m, 1 H) 6.78 (d, J = 8.53 Hz, 1 H) 6.01 (s, 1 H) 4.73-4.83 (m, 1 H) 4.09-4.25 (m, 4 H) 3.87-3.99 (m, 1 H) 3.05-3.27 (m, 1 H) 2.79 (br d, J = 16.81 Hz, 1 H) 2.66 (s, 1 H) 2.39-2.56 (m, 1 H) 2.08-2.31 (m, 2 H) 1.84-1.97 (m, 1 H) 1.34-1.55 (m, 1 H) | FA: m/z = 615 (M + H) |
| I-362 | ¹H NMR (400 MHz, DMSO-d₆) δ 8.72 (s, 1H), 8.63-8.55 (m, 2H), 8.39-8.28 (m, 3H), 7.2 (br s, 2H), 7.46 (s, 1H), 7.29-7.22 (m, 2H), 6.71 (s, 1H), 5.90 (s, 1H), 5.11-5.05 (m, 1H), 4.81-4.71 (m, 1H), 4.20-3.74 (m, 11H, protons overlap with broad acid H2O peak), 3.88-3.79 (m, 2H), 3.08-2.95 (m, 1H), 2.78 (br s, 1H), 2.81-2.71 (m, 1H), 2.48 (m, 5H), 2.38-2.29 (m, 1H), 2.15-2.02 (m, 2H), 1.53-1.43 (m, 1H), 1.41 (d, J = 7.3 Hz, 3H) | FA: m/z = 579.1 (M + H) |
| I-363 | ¹H NMR (400 MHz, DMSO-d₆) δ 8.64-8.55 (m, 2H), 8.19 (d, J = 7.5 Hz, 1H), 7.71-7.38 (m, 2H), 7.35 (s, 1H), 7.29-7.21 (m, 2H), 6.77-6.72 (m, 1H), 5.90 (s, 1H), 4.99-4.93 (m, 1H), 4.73-4.61 (m, 1H), 4.15-4.01 (m, 3H), 3.86-3.78 (m, 1H), 3.16-3.13 (m, 1H), 3.06-2.96 (m, 1H), 2.80-2.72 (m, 1H), 2.47 (s, 3H), 2.42-2.27 (m, 2H), 2.10-1.53 (m, 5H), 1.49-1.36 (m, 2H), 1.15-1.08 (m, 1H), 0.91-0.74 (m, 7H) | AA: m/z = 692.2 (M + H) |
| I-364 | ¹H NMR (400 MHz, Methanol-d₄) δ 8.62 (s, 1 H) 8.57 (s, 1 H) 7.29 (s, 1 H) 7.14-7.23 (m, 6 H) 6.74 (s, 1 H) 5.89 (s, 1 H) 5.05-5.12 (m, 1 H) 4.68-4.79 (m, 1 H) 4.12-4.25 (m, 3 H) 3.92 (td, J = 10.79, 3.76 Hz, 1 H) 3.60 (s, 2 H) 3.01-3.12 (m, 1 H) 2.74-2.84 (m, 1 H) 2.52 (s, 3 H) 2.37-2.49 (m, 2 H) 2.16-2.26 (m, 1 H) 1.89-2.00 (m, 4 H) 1.43-1.56 (m, 1 H) | FA: m/z = 793.1 (M + H) |
| I-365 | ¹H NMR (400 MHz, Methanol-d₄) δ ppm 8.73 (s, 1 H) 8.60 (s, 1 H) 7.57 (s, 1 H) 7.45 (s, 1 H) 7.21-7.33 (m, 3 H) 6.06 (s, 1 H) 4.78-4.85 (m, 1 H) 4.11-4.26 (m, 3 H) 3.75-3.91 (m, 2 H) 3.02-3.16 (m, 1 H) 2.75-2.83 (m, 1 H) 2.48-2.57 (m, 1 H) 2.24-2.33 (m, 1 H) 2.13-2.22 (m, 1 H) 1.88-1.98 (m, 1 H) 1.40-1.50 (m, 1 H) | AA: m/z = 565.1 (M + H) |
| I-366 | ¹H NMR (400 MHz, Methanol-d₄) δ 8.66 (s, 1 H) 8.55 (s, 1 H) 7.37 (d, J = 1.25 Hz, 1 H) 7.19 (s, 2 H) 6.82 (s, 1 H) 5.91 (s, 1 H) 4.90-4.98 (m, 2 H) 4.74-4.85 (m, 1 H) 4.65 (d, J = 15.06 Hz, 1 H) 4.13-4.22 (m, 4 H) 3.87-3.94 (m, 1 H) 3.03-3.14 (m, 1 H) 2.75-2.83 (m, 1 H) 2.45-2.54 (m, 1 H) 2.10-2.30 (m, 2 H) 1.86-1.94 (m, 1 H) 1.41 (m, J = 13.30, 9.00, 9.00, 4.40 Hz, 1 H) | FA: m/z = 596 (M + H) |

Example 215: SAE HTRF Enzyme Assay

The SAE enzymatic reaction totals 50 μl and contains 50 mM HEPES Hemisodium (pH 7.5), 0.05% BSA, 5 mM $MgCl_2$, 0.5 μM ATP, 250 μM GSH, 0.01 μM Ubc9-GST, 0.125 μM Sumo-Flag and 0.11 nM recombinant human SAE enzyme. The enzymatic reaction mixture, with and without inhibitor, Is incubated at 24° C. for 105 min in a 384-well plate before termination with 25 μM of Stop/Detection buffer (0.1M HEPES Hemisodium pH 7.5, 0.05% Tween20, 20 mM EDTA, 410 mM KF, 0.53 nM Europium-Cryptate labeled monoclonal anti-Flag M2 Antibody (CisBio International) and 8.125 g/ml PHYCOLINK goat anti-GST allophycocyanin (XL-APC) antibody (Prozyme)). After incubation for 2 hours at 24° C., quantification of FRET is performed on the Pherostar™ (BMG Labtech). Percentage inhibition values at a single concentration or enzyme inhibition ($IC_{50}$) values are determined from those curves. One skilled in the art will appreciate that the values generated either as percentage inhibition at a single concentration or $IC_{50}$ values are subject to experimental variation.

Example 216: Cell Viability Assay

The cell viability assay is used to measure the effect of various compounds on cancer cell proliferation. Promega's CellTiter-Glo® Luminescent Cell Viability Assay is used to measure ATP concentration present in all metabolically active cells and the concentration declines rapidly when cells undergo necrosis or apoptosis.

The cancer cell lines of interest are propagated in recommended growth medium (Invitrogen) containing 10% Fetal Bovine Serum (Hyclone or ATCC) and 100 I.U.Penicellin/100 μg/mL Streptomycin (Invitrogen) and kept in tissue culture incubator at 37° C. with 5% $CO_2$. On day 1, attached cells are trypsinized with 4.5 mL of 0.25% Trypsin-EDTA (Invitrogen) at 37° C. for 2 minutes or until cells have detached. Suspension cells are collected and washed.

Desired number of cells are cultured in 25 µL of media per well in tissue culture-treated black-walled, clear bottom 384-well plates (BD Biosciences) for 16-24 hours. The exact number of cells per well are optimized for each individual cell line. On day 2, 62.5 nL test compounds in DMSO (ranging from 10 mM to 508 uM in 10 point 3-fold dilution series) are directly added to cells in 384-well plate using Echo liquid handler (Labcyte). This results in a final concentration range of 0.0013 to 25 µM in 3-fold dilutions in the cell plates. On day 5 after 72 hour of incubation in tissue culture incubator, 25 µL CellTiter-Glo®(Promega) are added to the compound treated cell plates. The cell plates are incubated at room temperature for 15 min and then read luminescence on Pherastar plate reader (BMG). The test compound concentration versus cell viability curves are generated using percentage of survival calculated from luminescence readout relative to DMSO and media only controls. The percentage growth inhibition values at a single concentration ($LD_{50}$) values are determined from the curves.

Example 217: In Vivo Tumor Efficacy Model

SAE inhibitors are tested for their ability to inhibit tumor growth in standard xenograft tumor models. For example, HCT-116 cells ($1 \times 10^6$) in 100 µL of phosphate buffered saline are aseptically injected into the subcutaneous space in the right dorsal flank of female CD-1 nude mice (age 5-8 weeks, Charles River) using a 23-ga needle. Beginning at day 7 after inoculation, tumors are measured twice weekly using a vernier caliper. Tumor volumes are calculated using standard procedures ($0.5 \times length \times width^2$). When the tumors reach a volume of approximately 200 mm³, mice are randomized by tumor volume into treatment groups and injected subcutaneously with test compound (300 µL) at various doses and schedules. All control groups receive vehicle alone. Tumor size and body weight are measured twice a week, and the study is terminated when the control tumors reach approximately 2000 mm³. Analogous procedures are followed for colon (colo205 or HCT-116 cells), AML (THP-1 or HL-60 cells), DLBCL (Ly10 or WSU-DLCL2), melanoma (A375 or A2058 cells) and lung (H460 cells) tumor models.

As detailed above, chemical entities of the disclosure inhibit SAE. In certain embodiments, chemical entities of the disclosure inhibit SAE with the percent inhibition at the concentrations shown in the table below. In certain embodiments, chemical entities of the disclosure inhibit SAE with the $IC_{50}$ values shown in the table below.

| Compound No. | Concentration (µM) | Percent Inhibition | IC50 (µM) |
| --- | --- | --- | --- |
| I-1 | 0.111 | 99 | A |
| I-1a | 0.111 | 96 | A |
| I-1b | 0.111 | 100 | A |
| I-2 | 0.111 | 100 | A |
| I-2a | 0.111 | 99 | A |
| I-2b | 0.111 | 61 | B |
| I-3 | 0.111 | 100 | A |
| I-3a | 0.111 | 92 | B |
| I-3b | 0.111 | 100 | A |
| I-4 | 0.111 | 99 | A |
| I-4a | 0.111 | 99 | A |
| I-4b | 0.111 | 100 | A |
| I-5 | 0.111 | 99 | A |
| I-5a | 0.111 | 86 | B |
| I-5b | 0.111 | 100 | A |
| I-6 | 0.111 | 98 | A |
| I-6a | 0.111 | 98 | A |
| I-6b | 0.111 | 98 | A |
| I-7 | 0.111 | 98 | A |
| I-7a | 0.111 | 96 | A |
| I-7b | 0.111 | 98 | A |
| I-8 | 0.111 | 99 | A |
| I-8a | 0.111 | 96 | A |
| I-8b | 0.111 | 99 | A |
| I-9 | 0.111 | 99 | A |
| I-9a | 0.111 | 99 | A |
| I-9b | 0.111 | 97 | A |
| I-10 | 0.111 | 99 | A |
| I-10a | 0.111 | 100 | A |
| I-10b | 0.111 | 97 | A |
| I-11 | 0.111 | 99 | A |
| I-11a | 0.111 | 93 | A |
| I-11b | 0.111 | 99 | A |
| I-12 | 0.111 | 99 | A |
| I-12a | 0.111 | 84 | B |
| I-12b | 0.111 | 100 | A |
| I-13 | 0.111 | 100 | A |
| I-14a | 0.111 | 101 | A |
| I-14b | 0.111 | 95 | A |
| I-15 | 0.111 | 100 | A |
| I-15a | 0.111 | 66 | B |
| I-15b | 0.111 | 100 | A |
| I-16a | 0.111 | 99 | A |
| I-16b | 0.111 | 98 | A |
| I-17 | 0.111 | 99 | A |
| I-18 | 0.111 | 99 | A |
| I-18a | 0.111 | 82 | B |
| I-18b | 0.111 | 99 | A |
| I-19 | 0.111 | 100 | A |
| I-19a | 0.111 | 98 | A |
| I-19b | 0.111 | 99 | A |
| I-20a | 0.111 | 81 | B |
| I-20b | 0.111 | 99 | A |
| I-21 | 0.111 | 100 | A |
| I-22 | 0.111 | 99 | A |
| I-22a | 0.111 | 83 | B |
| I-22b | 0.111 | 99 | A |
| I-24a | 0.111 | 101 | A |
| I-24b | 0.111 | 101 | A |
| I-25 | 0.111 | 98 | A |
| I-25a | 0.111 | 97 | A |
| I-25b | 0.111 | 99 | A |
| I-26 | 0.111 | 100 | A |
| I-27a | 0.111 | 96 | A |
| I-27b | 0.111 | 101 | A |
| I-28 | 0.111 | 98 | A |
| I-28a | 0.111 | 66 | B |
| I-28b | 0.111 | 100 | A |
| I-29 | 0.111 | 100 | A |
| I-29a | 0.111 | 97 | A |
| I-29b | 0.111 | 99 | A |
| I-30 | 0.111 | 98 | A |
| I-30a | 0.111 | 100 | A |
| I-30b | 0.111 | 88 | B |
| I-31 | 0.111 | 98 | A |
| I-32 | 0.111 | 98 | A |
| I-32a | 0.111 | 98 | A |
| I-32b | 0.111 | 90 | B |
| I-33 | 0.111 | 100 | A |
| I-34 | 0.111 | 99 | A |
| I-35 | 0.111 | 98 | A |
| I-36 | 0.111 | 100 | A |
| I-36a | 0.111 | 100 | A |
| I-36b | 0.111 | 99 | A |
| I-37 | 0.111 | 98 | A |
| I-38 | 0.111 | 101 | A |
| I-38a | 0.111 | 75 | B |
| I-38b | 0.111 | 98 | A |
| I-39 | 0.111 | 98 | A |
| I-40 | 0.111 | 96 | A |
| I-41 | 0.111 | 99 | A |
| I-41a | 0.111 | 98 | A |
| I-41b | 0.111 | 98 | A |

| Compound No. | Concentration (μM) | Percent Inhibition | IC50 (μM) |
|---|---|---|---|
| I-42 | 0.111 | 98 | A |
| I-42a | 0.111 | 97 | A |
| I-42b | 0.111 | 99 | A |
| I-43 | 0.111 | 99 | A |
| I-44 | 0.111 | 100 | A |
| I-45 | 0.111 | 99 | A |
| I-46 | 0.111 | 98 | A |
| I-47 | 0.111 | 97 | A |
| I-47a | 0.111 | 99 | A |
| I-47b | 0.111 | 99 | A |
| I-48 | 0.111 | 99 | A |
| I-49 | 0.111 | 98 | A |
| I-50 | 0.111 | 99 | A |
| I-51 | 0.111 | 100 | A |
| I-52 | 0.111 | 99 | A |
| I-53 | 0.111 | 99 | A |
| I-54 | 0.111 | 99 | A |
| I-55 | 0.111 | 97 | A |
| I-56 | 0.111 | 98 | A |
| I-57 | 0.111 | 98 | A |
| I-58 | 0.111 | 96 | A |
| I-58a | 0.111 | 87 | B |
| I-58b | 0.111 | 100 | A |
| I-59 | 0.111 | 99 | A |
| I-60 | 0.111 | 99 | A |
| I-61 | 0.111 | 98 | A |
| I-62 | 0.111 | 98 | A |
| I-63 | 0.111 | 97 | A |
| I-64 | 0.111 | 99 | A |
| I-65 | 0.111 | 99 | A |
| I-66 | 0.111 | 98 | A |
| I-67 | 0.111 | 99 | A |
| I-68 | 0.111 | 98 | A |
| I-69 | 0.111 | 100 | A |
| I-70 | 0.111 | 98 | A |
| I-71 | 0.111 | 98 | A |
| I-72 | 0.111 | 98 | A |
| I-73a | 0.111 | 98 | A |
| I-73b | 0.111 | 98 | A |
| I-74 | 0.111 | 98 | A |
| I-75 | 0.111 | 98 | A |
| I-76 | 0.111 | 99 | A |
| I-77 | 0.111 | 98 | A |
| I-78 | 0.111 | 98 | A |
| I-79 | 0.111 | 97 | A |
| I-80 | 0.111 | 98 | A |
| I-81 | 0.111 | 98 | A |
| I-82 | 0.111 | 99 | A |
| I-83 | 0.111 | 98 | A |
| I-84 | 0.111 | 98 | A |
| I-85 | 0.111 | 97 | A |
| I-86 | 0.111 | 96 | A |
| I-87 | 0.111 | 94 | A |
| I-88 | 0.111 | 98 | A |
| I-89 | 0.111 | 98 | A |
| I-90 | 0.111 | 97 | A |
| I-90a | 0.111 | 98 | A |
| I-90b | 0.111 | 92 | B |
| I-91 | 0.111 | 98 | A |
| I-92 | 0.111 | 98 | A |
| I-93 | 0.111 | 98 | A |
| I-94 | 0.111 | 98 | A |
| I-95 | 0.111 | 97 | A |
| I-96 | 0.111 | 97 | A |
| I-97 | 0.111 | 97 | A |
| I-98 | 0.111 | 97 | A |
| I-99 | 0.111 | 97 | A |
| I-100 | 0.111 | 97 | A |
| I-101 | 0.111 | 96 | A |
| I-102 | 0.111 | 94 | A |
| I-102a | 0.111 | 36 | C |
| I-102b | 0.111 | 97 | A |
| I-103 | 0.111 | 96 | A |
| I-104 | 0.111 | 97 | A |
| I-105 | 0.111 | 96 | A |
| I-106 | 0.111 | 95 | A |
| I-106a | 0.111 | 62 | B |
| I-106b | 0.111 | 98 | A |
| I-107 | 0.111 | 96 | A |
| I-108 | 0.111 | 96 | A |
| I-109 | 0.111 | 96 | A |
| I-110 | 0.111 | 98 | A |
| I-111 | 0.111 | 98 | A |
| I-112 | 0.111 | 97 | A |
| I-113 | 0.111 | 97 | A |
| I-114 | 0.111 | 97 | A |
| I-115 | 0.111 | 90 | A |
| I-116 | 0.111 | 96 | A |
| I-117 | 0.111 | 93 | A |
| I-117a | 0.111 | 73 | B |
| I-117b | 0.111 | 97 | A |
| I-118 | 0.111 | 97 | A |
| I-119 | 0.111 | 96 | A |
| I-120 | 0.111 | 97 | A |
| I-121 | 0.111 | 98 | A |
| I-122 | 0.111 | 98 | A |
| I-123 | 0.111 | 96 | A |
| I-124 | 0.111 | 97 | A |
| I-125 | 0.111 | 97 | A |
| I-126 | 0.111 | 98 | A |
| I-127 | 0.111 | 95 | A |
| I-128 | 0.111 | 95 | A |
| I-129 | 0.111 | 95 | A |
| I-130 | 0.111 | 97 | A |
| I-131 | 0.111 | 96 | A |
| I-132 | 0.111 | 96 | A |
| I-134 | 0.111 | 94 | A |
| I-135 | 0.111 | 94 | B |
| I-135a | 0.111 | 82 | B |
| I-135b | 0.111 | 95 | A |
| I-136 | 0.111 | 96 | A |
| I-137 | 0.111 | 95 | A |
| I-138 | 0.111 | 96 | A |
| I-139 | 0.111 | 94 | A |
| I-140 | 0.111 | 93 | A |
| I-141 | 0.111 | 95 | A |
| I-142 | 0.111 | 94 | A |
| I-143 | 0.111 | 94 | A |
| I-144 | 0.111 | 93 | A |
| I-145 | 0.111 | 93 | A |
| I-146 | 0.111 | 94 | A |
| I-147 | 0.111 | 94 | A |
| I-148 | 0.111 | 91 | A |
| I-149 | 0.111 | 97 | A |
| I-150 | 0.111 | 94 | A |
| I-151 | 0.111 | 88 | B |
| I-151a | 0.111 | 80 | B |
| I-151b | 0.111 | 93 | A |
| I-152 | 0.111 | 93 | A |
| I-153 | 0.111 | 86 | B |
| I-153a | 0.111 | 30 | C |
| I-153b | 0.111 | 92 | A |
| I-154 | 0.111 | 95 | A |
| I-155 | 0.111 | 92 | A |
| I-156 | 0.111 | 92 | A |
| I-157 | 0.111 | 92 | A |
| I-158 | 0.111 | 86 | A |
| I-159 | 0.111 | 91 | A |
| I-160 | 0.111 | 92 | A |
| I-161 | 0.111 | 91 | A |
| I-162 | 0.111 | 91 | B |
| I-163 | 0.111 | 92 | B |
| I-164 | 0.111 | 92 | B |
| I-165 | 0.111 | 91 | B |
| I-166 | 0.111 | 93 | B |
| I-167 | 0.111 | 89 | B |
| I-168 | 0.111 | 90 | B |
| I-169 | 0.111 | 91 | B |
| I-170 | 0.111 | 91 | B |
| I-171 | 0.111 | 90 | B |
| I-172 | 0.111 | 88 | B |
| I-173 | 0.111 | 86 | B |

| Compound No. | Concentration (μM) | Percent Inhibition | IC50 (μM) | | Compound No. | Concentration (μM) | Percent Inhibition | IC50 (μM) |
|---|---|---|---|---|---|---|---|---|
| I-174 | 0.111 | 89 | B | | I-251a | 0.111 | 100 | A |
| I-175 | 0.111 | 90 | B | | I-251b | 0.111 | 97 | A |
| I-176 | 0.111 | 87 | B | | I-252 | 0.111 | 98 | A |
| I-177 | 0.111 | 85 | B | | I-252a | 0.111 | 71 | B |
| I-178 | 0.111 | 87 | B | | I-252b | 0.111 | 98 | A |
| I-179 | 0.111 | 86 | B | | I-253 | 0.111 | 100 | A |
| I-180 | 0.111 | 84 | B | | I-253a | 0.111 | 99 | A |
| I-181 | 0.111 | 82 | B | | I-253b | 0.111 | 83 | B |
| I-182 | 0.111 | 82 | B | | I-254 | 0.111 | 99 | A |
| I-183 | 0.111 | 82 | B | | I-254a | 0.111 | 81 | B |
| I-184 | 0.111 | 85 | B | | I-254b | 0.111 | 99 | A |
| I-185 | 0.111 | 80 | B | | I-255a | 0.111 | 93 | B |
| I-186 | 0.111 | 83 | B | | I-255b | 0.111 | 100 | A |
| I-187 | 0.111 | 76 | B | | I-256 | 0.111 | 100 | A |
| I-188 | 0.111 | 79 | B | | I-256a | 0.111 | 94 | A |
| I-189 | 0.111 | 78 | B | | I-256b | 0.111 | 99 | A |
| I-190 | 0.111 | 77 | B | | I-257a | 0.111 | 74 | B |
| I-191 | 0.111 | 72 | B | | I-257b | 0.111 | 99 | A |
| I-192 | 0.111 | 66 | B | | I-258 | 0.111 | 100 | A |
| I-193 | 0.111 | 72 | B | | I-258a | 0.111 | 98 | A |
| I-194 | 0.111 | 66 | B | | I-258b | 0.111 | 72 | B |
| I-195 | 0.111 | 68 | B | | I-259 | 0.111 | 99 | A |
| I-196 | 0.111 | 63 | B | | I-259a | 0.111 | 100 | A |
| I-197 | 0.111 | 69 | B | | I-259b | 0.111 | 97 | A |
| I-199 | 0.111 | 63 | B | | I-260 | 0.111 | 98 | A |
| I-200 | 0.111 | 62 | B | | I-260a | 0.111 | 99 | A |
| I-201 | 0.111 | 60 | B | | I-260b | 0.111 | 98 | A |
| I-202 | 0.111 | 60 | B | | I-261 | 0.111 | 99 | A |
| I-203 | 0.111 | 58 | B | | I-261a | 0.111 | 76 | B |
| I-204 | 0.111 | 52 | B | | I-261b | 0.111 | 99 | A |
| I-205 | 0.111 | 51 | C | | I-262 | 0.111 | 100 | A |
| I-206 | 0.111 | 49 | C | | I-262a | 0.111 | 98 | A |
| I-207 | 0.111 | 51 | C | | I-262b | 0.111 | 98 | A |
| I-208 | 0.111 | 46 | C | | I-263a | 0.111 | 101 | A |
| I-209 | 0.111 | 45 | C | | I-263b | 0.111 | 89 | B |
| I-210 | 0.111 | 50 | C | | I-264 | 0.111 | 100 | A |
| I-211 | 0.111 | 39 | C | | I-264a | 0.111 | 33 | C |
| I-212 | 0.111 | 43 | C | | I-264b | 0.111 | 98 | A |
| I-215 | 0.111 | 36 | C | | I-265 | 0.111 | 97 | A |
| I-216 | 0.111 | 36 | C | | I-265a | 0.111 | 99 | A |
| I-217 | 0.111 | 36 | C | | I-265b | 0.111 | 72 | B |
| I-218 | 0.111 | 33 | C | | I-266 | 0.111 | 102 | A |
| I-219 | 0.111 | 32 | C | | I-266a | 0.111 | 41 | C |
| I-220 | 0.111 | 36 | C | | I-266b | 0.111 | 100 | A |
| I-221 | 0.111 | 30 | C | | I-267 | 0.111 | 97 | A |
| I-222 | 0.111 | 31 | C | | I-267a | 0.111 | 65 | B |
| I-223 | 0.111 | 28 | C | | I-267b | 0.111 | 100 | A |
| I-224 | 0.111 | 31 | C | | I-268 | 0.111 | 100 | A |
| I-225 | 0.111 | 33 | C | | I-268a | 0.111 | 50 | C |
| I-226 | 0.111 | 33 | C | | I-268b | 0.111 | 102 | A |
| I-227 | 0.111 | 23 | C | | I-269 | 0.111 | 99 | A |
| I-228 | 0.111 | 29 | C | | I-269a | 0.111 | 101 | A |
| I-229 | 0.111 | 25 | C | | I-269b | 0.111 | 95 | B |
| I-230 | 0.111 | 26 | C | | I-270 | 0.111 | 99 | A |
| I-231 | 0.111 | 28 | C | | I-270a | 0.111 | 79 | B |
| I-233 | 0.111 | 22 | C | | I-270b | 0.111 | 99 | A |
| I-234 | 0.111 | 20 | C | | I-271a | 0.111 | 99 | A |
| I-235 | 0.111 | 22 | C | | I-272a | 0.111 | 96 | A |
| I-236 | 0.111 | 19 | C | | I-272b | 0.111 | 97 | A |
| I-237 | 0.111 | 25 | C | | I-273 | 0.111 | 99 | A |
| I-238 | 0.111 | 25 | C | | I-274 | 0.111 | 100 | A |
| I-239 | 0.111 | 14 | C | | I-274a | 0.111 | 98 | A |
| I-240 | 0.111 | 19 | C | | I-274b | 0.111 | 81 | B |
| I-241 | 0.111 | 18 | C | | I-275 | 0.111 | 97 | A |
| I-242 | 0.111 | 25 | C | | I-276 | 0.111 | 98 | A |
| I-243 | 0.111 | 19 | C | | I-276a | 0.111 | 28 | C |
| I-247a | 0.111 | 100 | A | | I-276b | 0.111 | 101 | A |
| I-247b | 0.111 | 98 | A | | I-277 | 0.111 | 99 | A |
| I-248a | 0.111 | 99 | A | | I-277a | 0.111 | 100 | A |
| I-248b | 0.111 | 95 | A | | I-277b | 0.111 | 81 | B |
| I-249a | 0.111 | 100 | A | | I-278 | 0.111 | 98 | A |
| I-249b | 0.111 | 92 | A | | I-278a | 0.111 | 77 | B |
| I-250 | 0.111 | 101 | A | | I-278b | 0.111 | 99 | A |
| I-250a | 0.111 | 97 | A | | I-279 | 0.111 | 99 | A |
| I-250b | 0.111 | 98 | A | | I-279a | 0.111 | 100 | A |
| I-251 | 0.111 | 100 | A | | I-279b | 0.111 | 84 | B |

| Compound No. | Concentration (μM) | Percent Inhibition | IC50 (μM) |
|---|---|---|---|
| I-280 | 0.111 | 98 | A |
| I-280a | 0.111 | 75 | B |
| I-280b | 0.111 | 100 | A |
| I-281 | 0.111 | 98 | A |
| I-281a | 0.111 | 74 | B |
| I-281b | 0.111 | 99 | A |
| I-282 | 0.111 | 100 | A |
| I-282a | 0.111 | 37 | C |
| I-282b | 0.111 | 102 | A |
| I-283 | 0.111 | 97 | A |
| I-283a | 0.111 | 99 | A |
| I-283b | 0.111 | 93 | B |
| I-284a | 0.111 | 49 | C |
| I-284b | 0.111 | 99 | A |
| I-285 | 0.111 | 100 | A |
| I-285a | 0.111 | 101 | A |
| I-285b | 0.111 | 44 | C |
| I-286 | 0.111 | 99 | A |
| I-286a | 0.111 | 39 | C |
| I-286b | 0.111 | 99 | A |
| I-287 | 0.111 | 97 | A |
| I-287a | 0.111 | 9 | C |
| I-287b | 0.111 | 98 | A |
| I-288 | 0.111 | 99 | A |
| I-289 | 0.111 | 98 | A |
| I-289a | 0.111 | 16 | C |
| I-289b | 0.111 | 99 | A |
| I-290a | 0.111 | 62 | B |
| I-290b | 0.111 | 97 | A |
| I-291 | 0.111 | 99 | A |
| I-291a | 0.111 | 17 | C |
| I-291b | 0.111 | 99 | A |
| I-292a | 0.111 | 99 | A |
| I-292b | 0.111 | 87 | B |
| I-293 | 0.111 | 98 | A |
| I-293a | 0.111 | 57 | B |
| I-293b | 0.111 | 98 | A |
| I-294 | 0.111 | 99 | A |
| I-294a | 0.111 | 84 | B |
| I-294b | 0.111 | 98 | A |
| I-295 | 0.111 | 99 | A |
| I-296 | 0.111 | 98 | A |
| I-297 | 0.111 | 96 | A |
| I-297a | 0.111 | 31 | C |
| I-297b | 0.111 | 99 | A |
| I-298 | 0.111 | 96 | A |
| I-298a | 0.111 | 34 | C |
| I-298b | 0.111 | 98 | A |
| I-299 | 0.111 | 98 | A |
| I-299a | 0.111 | 101 | A |
| I-299b | 0.111 | 93 | A |
| I-300a | 0.111 | 26 | C |
| I-300b | 0.111 | 101 | A |
| I-301 | 0.111 | 99 | A |
| I-301a | 0.111 | 40 | C |
| I-301b | 0.111 | 100 | A |
| I-302 | 0.111 | 100 | A |
| I-303 | 0.111 | 99 | A |
| I-304 | 0.111 | 97 | A |
| I-305 | 0.111 | 96 | A |
| I-305a | 0.111 | 28 | C |
| I-305b | 0.111 | 98 | A |
| I-306 | 0.111 | 98 | A |
| I-307 | 0.111 | 95 | A |
| I-307a | 0.111 | 45 | C |
| I-307b | 0.111 | 97 | A |
| I-308 | 0.111 | 98 | A |
| I-309 | 0.111 | 98 | A |
| I-310 | 0.111 | 98 | A |
| I-310a | 0.111 | 27 | C |
| I-310b | 0.111 | 98 | A |
| I-311a | 0.111 | 65 | B |
| I-311b | 0.111 | 96 | A |
| I-313 | 0.111 | 94 | A |
| I-314 | 0.111 | 95 | A |
| I-314a | 0.111 | 49 | C |
| I-314b | 0.111 | 98 | A |
| I-315 | 0.111 | 97 | A |
| I-316 | 0.111 | 94 | A |
| I-317 | 0.111 | 97 | A |
| I-318 | 0.111 | 95 | A |
| I-319 | 0.111 | 94 | A |
| I-320 | 0.111 | 92 | B |
| I-320a | 0.111 | 27 | C |
| I-320b | 0.111 | 93 | A |
| I-321 | 0.111 | 94 | A |
| I-322 | 0.111 | 92 | B |
| I-323 | 0.111 | 90 | B |
| I-324 | 0.111 | 91 | B |
| I-325 | 0.111 | 60 | B |
| I-327 | 0.111 | 51 | C |
| I-329 | 0.111 | 36 | C |
| I-330 | 0.111 | 34 | C |
| I-331 | 0.111 | 28 | C |
| I-332 | 0.111 | 25 | C |
| I-333 | 0.111 | 15 | C |
| I-334 | 0.111 | 10 | C |
| I-335 | 0.111 | 38 | C |
| I-335a | 0.111 | 14 | C |
| I-335b | 0.111 | 41 | C |
| I-336 | 0.111 | 15 | C |
| I-337 | 0.111 | 89 | B |
| I-338 | 0.111 | 56 | B |
| I-339 | 0.111 | 99 | A |
| I-339a | 0.111 | 99 | A |
| I-339b | 0.111 | 94 | A |
| I-341 | 0.111 | 10 | C |
| I-342 | 0.111 | 93 | A |
| I-343a | 0.111 | 57 | B |
| I-343b | 0.111 | 84 | B |
| I-344 | 0.111 | 99 | A |
| I-345 | 0.111 | 5 | C |
| I-346 | 0.111 | 99 | A |
| I-347 | 0.111 | 97 | A |
| I-348 | 0.111 | 97 | A |
| I-349 | 0.111 | 42 | C |
| I-349a | 0.111 | 42 | C |
| I-349b | 0.111 | 58 | B |
| I-350 | 0.111 | 75 | B |
| I-351 | 0.111 | 93 | A |
| I-352 | 0.111 | 100 | A |
| I-353 | 0.111 | 98 | A |
| I-354 | 0.111 | 100 | A |
| I-355 | 0.111 | 96 | A |
| I-355a | 0.111 | 98 | A |
| I-355b | 0.111 | 71 | B |
| I-356 | 0.111 | 97 | A |
| I-356a | 0.111 | 52 | B |
| I-356b | 0.111 | 99 | A |
| I-357 | 0.111 | 97 | A |
| I-358 | 0.111 | 96 | A |
| I-359a | 0.111 | 92 | B |
| I-359b | 0.111 | 95 | A |
| I-360 | 0.111 | 95 | A |
| I-361 | 0.111 | 95 | A |
| I-362 | 0.111 | 91 | B |
| I-363 | 0.111 | 57 | C |
| I-364 | 0.111 | 13 | D |
| I-365 | 0.111 | 62 | B |
| I-366 | 0.111 | 100 | A |

IC50: A) less than 10 nM; B) 10 nM-100 nM, and C) greater than 100 nM and less than 1000 nM

What is claimed is:

1. A chemical entity which is a compound or pharmaceutically acceptable salt of formula (I):

$$\text{(I)}$$

WHEREIN:
stereochemical configurations depicted at asterisked positions indicate absolute stereochemistry;
Y is —O—, —CH$_2$—, or —N(H)—;
R$^a$ is hydrogen, fluoro, —NH$_2$, or hydroxyl;
R$^{a\prime}$ is hydrogen or fluoro, provided that when R$^a$ is —NH$_2$ or hydroxyl, R$^{a\prime}$ is hydrogen;
R$^b$ is hydrogen or, together with the oxygen to which it is attached, forms a prodrug;
R$^c$ is hydrogen or C$_{1-4}$ alkyl;
R$^d$ is hydrogen, halogen, —CF$_3$, or C$_{1-4}$ alkyl;
X$_1$ is C(H) or C(F);
X$_2$ is S or O;
X$_3$ is C(R$^{x3}$) or N;
R$^{x3}$ is hydrogen, methyl, or halogen;
Z$_1$ is hydrogen, halogen, cyano, R$^{z3}$, —S—R$^{z3}$, —S(O)—R$^{z3}$, or —S(O)$_2$—R$^{z3}$;
R$^{z3}$ is an optionally substituted phenyl, an optionally substituted 5- to 7-membered cycloaliphatic, an optionally substituted 5- to 7-membered heterocyclyl, or an optionally substituted C$_{1-4}$ aliphatic;
wherein Z$_1$ is not hydrogen, halogen, methyl, or cyano if Z$_2$ is hydrogen or methyl; and
  (a) Z$_2$ is a ring system having an optionally substituted 5- to 7-membered heterocyclyl with 1-2 heteroatoms or an optionally substituted 5- to 7-membered cycloaliphatic fused to
    (i) an optionally substituted 5-membered heteroaryl or an optionally substituted 6-membered aryl or heteroaryl to form a bicyclic group; or
    (ii) an optionally substituted 9-membered heteroaryl or an optionally substituted 10-membered aryl or heteroaryl to form a tricyclic group;
OR
  (b) Z$_2$ is L-R$^e$ wherein L is -L$_1$-, —V$_1$-L$_2$-, or -L$_1$-V$_1$-L$_2$-;
L$_1$ is a C$_{1-3}$ alkylene chain wherein 1 or 2 saturated carbon atoms are optionally substituted by (R$^f$)(R$^{f\prime}$) and in which there are optionally one or two degrees of unsaturation;
  each R$^f$ is independently hydrogen; hydroxyl; —N(R$^h$)(R$^{h\prime}$); C$_{1-4}$ aliphatic optionally substituted with hydroxyl, —OCH$_3$, or cyclopropyl; —O—C$_{1-4}$ aliphatic optionally substituted with hydroxyl, —OCH$_3$, or cyclopropyl; or, together with R$^{f\prime}$ and the carbon atom to which they are attached, form C=CH$_2$, or a 3- to 6-membered carbocycle or 4- to 6-membered heterocycle comprising a heteroatom chosen from N (which may be protonated or C$_{1-4}$ alkylated), O, or S, the heteroatom optionally located immediately adjacent to the quaternary carbon of the heterocycle;
  each R$^{f\prime}$ is independently hydrogen; C$_{1-4}$ aliphatic optionally substituted with hydroxyl, —OCH$_3$, or cyclopropyl; —O—C$_{1-4}$ aliphatic optionally substituted with hydroxyl, —OCH$_3$, or cyclopropyl; or, together with R$^f$ and the carbon atom to which they are attached, form C=CH$_2$, or a 3- to 6-membered carbocycle or 4- to 6-membered heterocycle comprising a heteroatom chosen from N (which may be protonated or C$_{1-4}$ alkylated), O, or S, the heteroatom optionally located immediately adjacent to the quaternary carbon of the heterocycle; wherein if R$^f$ is hydroxyl, R$^{f\prime}$ is not —O—C$_{1-4}$ aliphatic optionally substituted with hydroxyl, —OCH$_3$, or cyclopropyl;
R$^h$ and R$^{h\prime}$ are each independently hydrogen or C$_{1-4}$ alkyl;
V$_1$ is —S—, —O—, —S(O)—, —S(O)$_2$—, —C(O)— or —N(R$^g$)—;
L$_2$ is a C$_{0-2}$ alkylene chain wherein one saturated carbon atom is optionally substituted by (R$^f$)(R$^{f\prime}$);
R$^g$ is hydrogen or C$_{1-4}$ alkyl; and
  either (i) R$^e$ is hydrogen, hydroxyl, halogen, —CF$_3$, or an optionally substituted C$_{1-4}$ aliphatic, with the proviso that R$^e$ is not hydrogen if R$^f$ and R$^{f\prime}$ are present and form a ring;
  OR (ii) R$^e$ is a ring chosen from optionally substituted 6-membered aryl, optionally substituted 5- to 6-membered heteroaryl, optionally substituted 3- to 7-membered cycloaliphatic, or optionally substituted 4- to 7-membered heterocyclyl, which is optionally fused to a second optionally substituted 6-membered aryl, optionally substituted 5- to 6-membered heteroaryl, optionally substituted 3- to 7-membered cycloaliphatic, or optionally substituted 4- to 7-membered heterocyclyl;
OR
  (c) Z$_2$ is hydrogen.

2. The chemical entity of claim 1, wherein:
  (a) Z$_2$ is a ring system having a 5- to 7-membered heterocyclyl with 1-2 heteroatoms or a 5- to 7-membered cycloaliphatic fused to
    (i) a 5-membered heteroaryl or a 6-membered aryl or heteroaryl to form a bicyclic group; or
    (ii) a 9-membered heteroaryl or a 10-membered aryl or heteroaryl to form a tricyclic group;
wherein the ring system is optionally substituted by 1-3 independent occurrences of halogen, hydroxyl, cyano, C$_{1-4}$ aliphatic, C$_{1-4}$ fluoroaliphatic, C$_{1-4}$ alkoxy, C$_{1-4}$ fluoroalkoxy, —S—C$_{1-4}$ aliphatic, —S—C$_{1-4}$ fluoroaliphatic, —N(R$^{z7}$)$_2$, —C(O)R$^{z8}$, —S(O)R$^{z8}$, —S(O)$_2$R$^{z8}$, —C(O)$_2$R$^{z7}$, —C(O)N(R$^{z7}$)$_2$, —S(O)$_2$N(R$^{z7}$)$_2$, —OC(O)N(R$^{z7}$)$_2$, —N(R$^{z7}$)C(O)R$^{z8}$, —N(R$^{z7}$)SO$_2$R$^{z8}$, —N(R$^{z7}$)C(O)OR$^{z8}$, T$_2$-R$^{z9}$, a 5- to 6-membered heteroaryl, a 6-membered aryl, a 3- to 6-membered cycloaliphatic, or a 4- to 6-membered heterocyclyl; and the ring system is optionally substituted at one saturated carbon with oxo, a spirocyclic 3- to 6-membered carbocycle, or a spirocyclic 4- to 6-membered heterocycle;
each occurrence of R$^{z7}$ is independently hydrogen or C$_{1-4}$ alkyl;
each occurrence of R$^{z8}$ is independently C$_{1-4}$ alkyl;
T$_2$ is a C$_{1-2}$ alkylene chain;

$R^{z9}$ is cyano, $-N(R^{z7})_2$, $-OR^{z7}$, $-C(O)R^{z8}$, $-C(O)_2R^{z7}$, or $-C(O)N(R^{z7})_2$;
OR
(b) $Z_2$ is L-$R^e$ wherein either:
  (i) $R^e$ is hydrogen, hydroxyl, halogen, $-CF_3$, or $C_{1-4}$ aliphatic optionally substituted with one or more hydroxyl, halogen, or $C_{1-4}$ aliphatic,
with the proviso that $R^e$ is not hydrogen if $R^f$ and $R^{f'}$ are present and form a ring;
  OR (ii) $R^e$ is a ring chosen from 6-membered aryl, 5- to 6-membered heteroaryl, 3- to 7-membered cycloaliphatic, or 4- to 7-membered heterocyclyl, which is optionally fused to a second 6-membered aryl, 5- to 6-membered heteroaryl, 3- to 7-membered cycloaliphatic, or 4- to 7-membered heterocyclyl, $R^e$ being optionally substituted by 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, S—$C_{1-4}$ aliphatic, S—$C_{1-4}$ fluoroaliphatic, $-N(R^{z7})_2$, $-C(O)R^{z8}$, $-S(O)R^{z8}$, $-S(O)_2R^{z8}$, $-C(O)_2R^{z7}$, $-C(O)N(R^{z7})_2$, $-S(O)_2N(R^{z7})_2$, $-OC(O)N(R^{z7})_2$, $-N(R^{z7})C(O)R^{z8}$, $-N(R^{z7})SO_2R^{z8}$, $-N(R^{z7})C(O)OR^{z8}$, $T_2$-$R^{z9}$, a 5- to 6-membered heteroaryl, a 6-membered aryl, a 3- to 6-membered cycloaliphatic, or a 4- to 6-membered heterocyclyl; and which is optionally substituted at one saturated carbon with oxo, a spirocyclic 3- to 6-membered carbocycle, or a spirocyclic 4- to 6-membered heterocycle;
each occurrence of $R^{z7}$ is independently hydrogen or $C_{1-4}$ alkyl;
each occurrence of $R^{z8}$ is independently $C_{1-4}$ alkyl;
$T_2$ is a $C_1$-$C_2$ alkylene chain; and
$R^{z9}$ is cyano, $-NO_2$, $-N(R^{z7})_2$, $-OR^{z7}$, $-C(O)R^{z8}$, $-C(O)_2R^{z7}$, or $-C(O)N(R^{z7})_2$.

3. The chemical entity of claim 1, wherein L is $-C(R^f)(R^{f'})-$, $-S-$, $-S(O)-$, $-S(O)_2-$, $-C(O)-$, $-C(=CH_2)-$, $-C(R^f)(R^{f'})-C(=CH_2)-$, $-C(R^f)(R^{f'})-C\equiv C-$, $-C(R^f)(R^{f'})-O-$, $-C(R^f)(R^{f'})-S-$, $-C(R^f)(R^{f'})-N(R^g)-$, $-C(R^f)(R^{f'})-N(R^g)-CH_2-$, $-C(R^f)(R^{f'})-CH_2-$, $-C(R^f)(R^{f'})-CH_2-CH_2-$, or $-C(O)-C(R^f)(R^{f'})-$.

4. The chemical entity of claim 1, wherein:
$Z_1$ is hydrogen, halogen, cyano, $R^{z3}$, $-S-R^{z3}$, $-S(O)-R^{z3}$, or $-S(O)_2-R^{z3}$;
$R^{z3}$ is a phenyl, 5- to 7-membered cycloaliphatic, 5- to 7-membered heterocyclyl, or $C_{1-4}$ aliphatic, any of which may be substituted with one or more independently selected $R^{z4}$;
$R^{z4}$ is hydroxyl, halogen, cyano, $C_{1-4}$ aliphatic, $C_{1-4}$ fluoroaliphatic, $C_{1-4}$ alkoxy, $C_{1-4}$ fluoroalkoxy, $-N(R^{z5})_2$, $-C(O)R^{z6}$, $-C(O)_2R^{z5}$, 5- or 6-membered cycloaliphatic or heterocyclyl, or a phenyl optionally substituted with one or more independently selected halogens;
each occurrence of $R^{z5}$ is independently hydrogen or $C_{1-4}$ alkyl; and
each occurrence of $R^{z6}$ is independently $C_{1-4}$ alkyl.

5. The chemical entity of claim 4, wherein $Z_1$ is hydrogen; halogen; cyano; phenyl optionally substituted with one or more independently selected halogens; 5- to 7-membered cycloaliphatic or heterocyclyl optionally fused to a 6-membered aryl, wherein the 5- to 7-membered cycloaliphatic or heterocyclyl optionally fused to a 6-membered aryl is optionally substituted with one or more independently selected halogens; $C_{1-4}$ fluoroaliphatic; or a $C_{1-4}$ aliphatic group optionally substituted with one or more hydroxyl, $C_{1-4}$ alkoxy, phenyl optionally substituted with one more independently selected halogens, 5- or 6-membered cycloaliphatic, 5- or 6-membered heterocyclyl, or $-N(R^{z5})_2$.

6. The chemical entity of claim 2, wherein:
$Z_2$ is a ring system having a 5- to 7-membered heterocyclyl with 1-2 heteroatoms or a 5- to 7-membered cycloaliphatic fused to
  (i) a 5-membered heteroaryl or 6-membered aryl or heteroaryl to form a bicyclic group; or
  (ii) a 9-membered heteroaryl or 10-membered aryl or heteroaryl to form a tricyclic group;
wherein the ring system is optionally substituted by 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, S—$C_{1-4}$ aliphatic, S—$C_{1-4}$ fluoroaliphatic, $-N(R^{z7})_2$, $-C(O)R^{z8}$, $-S(O)R^{z8}$, $-S(O)_2R^{z8}$, $-C(O)_2R^{z7}$, $-C(O)N(R^{z7})_2$, $-S(O)_2N(R^{z7})_2$, $-OC(O)N(R^{z7})_2$, $-N(R^{z7})C(O)R^{z8}$, $-N(R^{z7})SO_2R^{z8}$, $-N(R^{z7})C(O)OR^{z8}$, $T_2$-$R^{z9}$, 5- to 6-membered heteroaryl, 6-membered aryl, 3- to 6-membered cycloaliphatic or heterocyclyl; and the ring system is optionally substituted at one saturated carbon with oxo, a spirocyclic 3- to 6-membered carbocycle, or a spirocyclic 4- to 6-membered heterocycle;
each occurrence of $R^{z7}$ is independently hydrogen or $C_{1-4}$ alkyl;
each occurrence of $R^{z8}$ is independently $C_{1-4}$ alkyl;
$T_2$ is a $C_{1-2}$ alkylene chain; and
$R^{z9}$ is cyano, $-N(R^{z7})_2$, $-OR^{z7}$, $-C(O)R^{z8}$, $-C(O)_2R^{z7}$, or $-C(O)N(R^{z7})_2$.

7. The chemical entity of claim 6, wherein:
$Z_2$ is a 5- to 7-membered heterocyclyl with 1-2 heteroatoms or a 5- to 7-membered cycloaliphatic fused to a 5-membered heteroaryl or 6-membered aryl or heteroaryl ring to form a bicyclic group, wherein the ring system is optionally substituted as defined in claim 6.

8. The chemical entity of claim 7, wherein:
$Z_2$ is a 6-membered heterocyclyl, the heterocyclyl containing 1 N or O atom, fused to a 6-membered aryl or heteroaryl ring to form a bicyclic group, wherein the ring system is optionally substituted as defined in claim 7.

9. The chemical entity of claim 6, which is a compound or pharmaceutically acceptable salt of formula (V):

(V)

wherein:
m is 0, 1, or 2;
$X_4$ is S, O, or N($R^{n4}$);

$X_5$ is O, C(O), or C(R$^{x5}$)(R$^{x5'}$), wherein $X_5$ is not O if $X_4$ is N(R$^{n4}$) or S;

R$^{n4}$ is hydrogen or C$_{1-4}$ alkyl;

R$^{x5}$ is hydrogen, fluoro, hydroxyl, or C$_{1-4}$ alkyl;

R$^{x5'}$ is hydrogen, fluoro, or C$_{1-4}$ alkyl, wherein R$^{x5'}$ is not fluoro if R$^{x5}$ is hydroxyl;

or R$^{x5}$ and R$^{x5'}$, taken together with the carbon atom to which they are attached, form a spirocyclic 3- to 6-membered carbocycle or a spirocyclic to 4- to 6-membered heterocycle comprising only one heteroatom, the heteroatom being chosen from O, N, or S;

dashed lines indicate single or double bonds;

Ring A is a fused 5-membered heteroaryl or 6-membered aryl or heteroaryl optionally substituted with 1-3 independent occurrences of halogen, hydroxyl, cyano, C$_{1-4}$ aliphatic, C$_{1-4}$ fluoroaliphatic, C$_{1-4}$ alkoxy, C$_{1-4}$ fluoroalkoxy, —S—C$_{1-4}$ aliphatic, —S—C$_{1-4}$ fluoroaliphatic, —N(R$^{z7}$)$_2$, —C(O)R$^{z8}$, —S(O)R$^{z8}$, —S(O)$_2$R$^{z8}$, —C(O)$_2$R$^{z7}$, —C(O)N(R$^{z7}$)$_2$, —S(O)$_2$N(R$^{z7}$)$_2$, —OC(O)N(R$^{z7}$)$_2$, —N(R$^{z7}$)C(O)R$^{z8}$, —N(R$^{z7}$)SO$_2$R$^{z8}$, —N(R$^{z7}$)C(O)OR$^{z8}$, T$_2$-R$^{z9}$, a 5- to 6-membered heteroaryl, a 6-membered aryl, a 3- to 6-membered cycloaliphatic, or a 4- to 6-membered heterocyclyl;

T$_2$ is a C$_1$-C$_2$ alkylene chain;

R$^{z9}$ is cyano, —N(R$^{z7}$)$_2$, —OR$^{z7}$, —C(O)R$^{z8}$, —C(O)$_2$R$^{z7}$, or —C(O)N(R$^{z7}$)$_2$; and R$^k$ is hydrogen or methyl.

10. The chemical entity of claim 9, which is a compound or pharmaceutically acceptable salt of formula (VI):

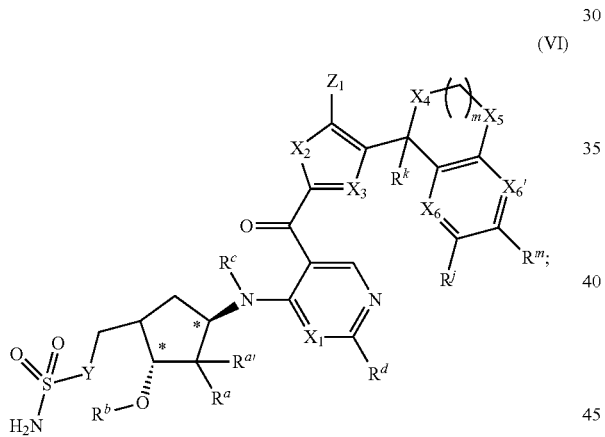

(VI)

wherein:

m is 1 or 2;

X$_6$ is N or C(R$^{x6}$);

X$_6'$ is N or C(R$^{x6'}$); and each of R$^{x6}$, R$^{x6'}$, R$^j$ and R$^m$ is independently hydrogen, halogen, hydroxyl, cyano, C$_{1-4}$ aliphatic, C$_{1-4}$ fluoroaliphatic, C$_{1-4}$ alkoxy, C$_{1-4}$ fluoroalkoxy, —N(R$^{z7}$)$_2$, —C(O)$_2$R$^{z7}$, —C(O)N(R$^{z7}$)$_2$, —S(O)$_2$N(R$^{z7}$)$_2$, —CH$_2$—OR$^{z7}$, —CH$_2$NR$^{z7}$, a 3- to 6-membered cycloaliphatic, or a 4- to 6-membered heterocyclyl;

wherein at least one of R$^{x6}$, R$^{x6'}$, R$^j$ and R$^m$ is hydrogen.

11. The chemical entity of claim 10, wherein:

m is 1;

X$_5$ is CH$_2$;

R$^{n4}$ is hydrogen or methyl; and each of R$^{x6}$, R$^{x6'}$, R$^j$, and R$^m$ is independently hydrogen, chloro, fluoro, bromo, iodo, methyl, ethyl, isopropyl, cyano, cyclopropyl, CF$_3$, —OCH$_3$, —OCH$_2$CH$_3$, or —C≡CH;

wherein at least one of R$^{x6}$, R$^{x7}$, R$^j$ and R$^m$ is hydrogen.

12. The chemical entity of claim 10, wherein:

X$_4$ is O or N(H);

X$_6$ is N or C(H);

X$_6'$ is C(H);

R$^m$ is hydrogen, fluoro or chloro; and

R$^j$ is methyl, ethyl, isopropyl, hydrogen, fluoro, chloro, bromo, cyclopropyl, —C≡CH or —CF$_3$.

13. The chemical entity of claim 10, which is a compound or pharmaceutically acceptable salt of formula (VIa) or (VIb):

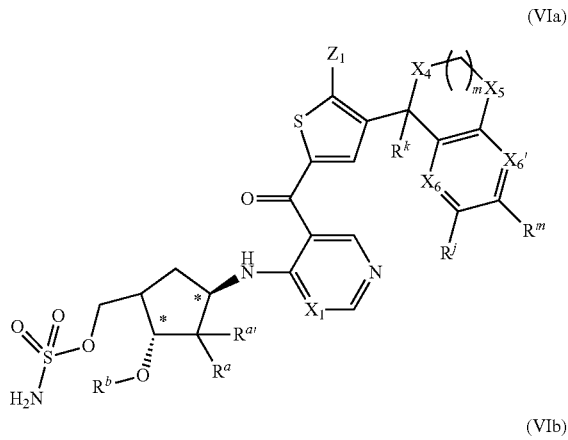

14. The chemical entity of claim 9, wherein Z$_2$ is

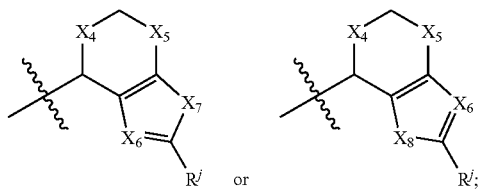

and wherein

X$_4$ is O or N(R$^{n4}$);

X$_5$ is C(R$^{x5}$)(R$^{x5'}$);

X$_6$ is N or C(R$^{x6}$);

X$_7$ is O or S;

X$_8$ is S or N(H); and

R$^{x6}$ and R$^j$ are each independently hydrogen, halogen, hydroxyl, cyano, C$_{1-4}$ aliphatic, C$_{1-4}$ fluoroaliphatic, C$_{1-4}$ alkoxy, C$_{1-4}$ fluoroalkoxy, —N(R$^{z7}$)$_2$, —C(O)$_2$R$^{z7}$, —C(O)N(R$^{z7}$)$_2$, —S(O)$_2$N(R$^{z7}$)$_2$, —CH$_2$—OR$^{z7}$, —CH$_2$N(R$^{z7}$)$_2$, a 3- to 6-membered cycloaliphatic, or a 4- to 6-membered heterocyclyl.

15. The chemical entity of claim 9, wherein Z$_2$ is

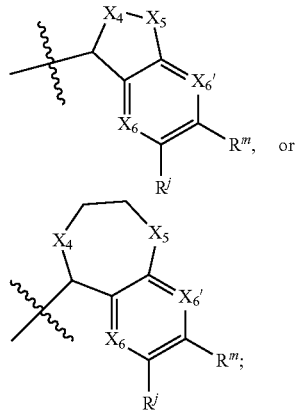

and wherein

X$_4$ is O or N(R$^{n4}$);
X$_5$ is C(R$^{x5}$)(R$^{x5'}$);
X$_6$ is N or C(R$^{x6}$);
X$_6'$ is N or C(R$^{x6}$); and
each R$^{x6}$, R$^j$, and R$^m$ is independently hydrogen, halogen, hydroxyl, cyano, C$_{1-4}$ aliphatic, C$_{1-4}$ fluoroaliphatic, C$_{1-4}$ alkoxy, C$_{1-4}$ fluoroalkoxy, —N(R$^{z7}$)$_2$, —C(O)$_2$R$^{z7}$, —C(O)N(R$^{z7}$)$_2$, —S(O)$_2$N(R$^{z7}$)$_2$, —CH$_2$—OR$^{z7}$, —CH$_2$N(R$^{z7}$)$_2$, a 3- to 6-membered cycloaliphatic, or a 4- to 6-membered heterocyclyl, wherein at least one R$^{x6}$, R$^j$, or R$^m$ is hydrogen.

16. The chemical entity of claim 9, wherein Z$_2$ is

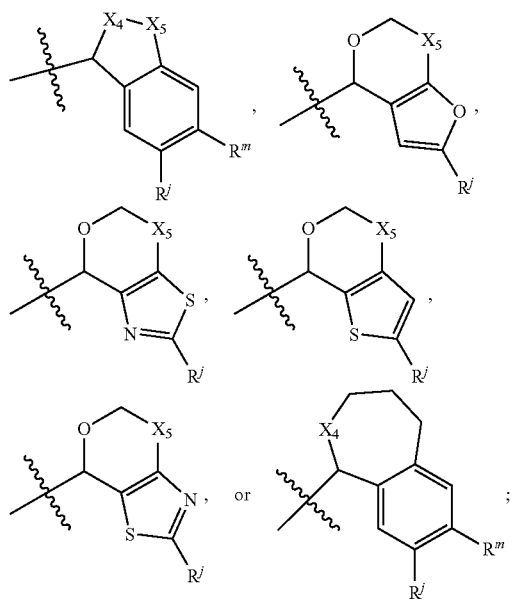

X$_5$ is C(R$^{x5}$)(R$^{x5'}$);
R$^{x5}$ and R$^{x5'}$ are independently hydrogen or fluoro; or, together with the carbon to which they are attached, form a cyclopropyl ring;

R$^j$ is hydrogen, chloro, fluoro, bromo, methyl, ethyl, isopropyl, cyano, cyclopropyl, CF$_3$, —OCH$_3$, —OCH$_2$CH$_3$, or —C≡CH; and
R$^m$ is hydrogen, fluoro, or chloro.

17. The chemical entity of claim 9, wherein Z$_2$ is

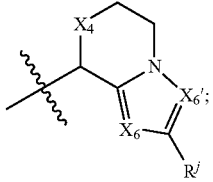

X$_4$ is O or N(R$^{n4}$);
X$_6$ is N or C(R$^{x6}$);
X$_6'$ is N or C(R$^{x6}$);
R$^{n4}$ is hydrogen or C$_{1-4}$ alkyl; and
each of R$^{x6}$, R$^j$ or R$^m$ is independently halogen, hydroxyl, cyano, C$_{1-4}$ aliphatic, C$_{1-4}$ fluoroaliphatic, C$_{1-4}$ alkoxy, C$_{1-4}$ fluoroalkoxy, —N(R$^{z7}$)$_2$, —C(O)$_2$R$^{z7}$, —C(O)N(R$^{z7}$)$_2$, —S(O)$_2$N(R$^{z7}$)$_2$, —CH$_2$—OR$^{z7}$, —CH$_2$NR$^{z7}$, a 3- to 6-membered cycloaliphatic, or a 4- to 6-membered heterocyclyl.

18. The chemical entity of claim 1, wherein Z$_2$ is L-R$^e$.

19. The chemical entity of claim 18, wherein:
L is —C(R$^f$)(R$^{f'}$)—, —S—, —C(=O)—, —C(R$^f$)(R$^{f'}$)—O—, —C(R$^f$)(R$^{f'}$)—S—, —C(R$^f$)(R$^{f'}$)—N(R$^g$)—, —C(R$^f$)(R$^{f'}$)—CH$_2$— or —C(R$^f$)(R$^{f'}$)—C≡C—.

20. The chemical entity of claim 19, which is a compound or pharmaceutically acceptable salt of formula (VIII):

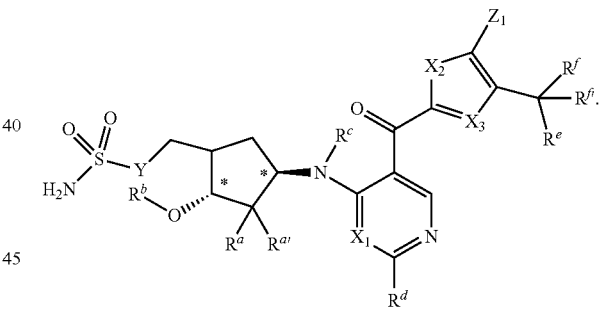

(VIII)

21. The chemical entity of claim 18, wherein:
R$^e$ is a ring chosen from 3- to 7-membered cycloaliphatic or 4- to 7-membered heterocyclyl, which is optionally fused to a second 6-membered aryl, 5- to 6-membered heteroaryl, 3- to 7-membered cycloaliphatic, or 4- to 7-membered heterocyclyl, which is optionally substituted by 1-3 independent occurrences of halogen, hydroxyl, cyano, C$_{1-4}$ aliphatic, C$_{1-4}$ fluoroaliphatic, C$_{1-4}$ alkoxy, C$_{1-4}$ fluoroalkoxy, S—C$_{1-4}$ aliphatic, S—C$_{1-4}$ fluoroaliphatic, —N(R$^{z7}$)$_2$, —C(O)R$^{z8}$, —S(O)R$^{z8}$, —S(O)$_2$R$^{z8}$, —C(O)$_2$R$^{z7}$, —C(O)N(R$^{z7}$)$_2$, —S(O)$_2$N(R$^{z7}$)$_2$, —OC(O)N(R$^{z7}$)$_2$, —N(R$^{z7}$)C(O)R$^{z8}$, —N(R$^{z7}$)SO$_2$R$^{z8}$, —N(R$^{z7}$)C(O)OR$^{z8}$, T$_2$-R$^{z9}$, a 5- to 6-membered heteroaryl, a 6-membered aryl, a 3- to 6-membered cycloaliphatic, or a 4- to 6-membered heterocyclyl; and which is optionally substituted at one saturated carbon with oxo, a spirocyclic 3- to 6-membered carbocycle, or a spirocyclic 4- to 6-membered heterocycle;

each occurrence of $R^{z7}$ is independently hydrogen or $C_{1-4}$ alkyl;

each occurrence of $R^{z8}$ is independently $C_{1-4}$ alkyl;

$T_2$ is a $C_1$-$C_2$ alkylene chain; and $R^{z9}$ is cyano, —N$(R^{z7})_2$, —OR$^{z7}$, —C(O)R$^{z8}$, —C(O)$_2$R$^{z7}$, or —C(O)N$(R^{z7})_2$.

22. The chemical entity of claim 18, wherein:

each $R^f$ is independently hydrogen, hydroxyl, N$(R^{h})(R^{h'})$, $C_{1-4}$ alkoxy, cyclopropyl, or $C_{1-4}$ alkyl optionally substituted with hydroxyl or —OCH$_3$;

each $R^{f'}$ is independently hydrogen, cyclopropyl, or $C_{1-4}$ alkyl optionally substituted with hydroxyl or —OCH$_3$; and $R^e$ is a 5- to 7-membered cycloaliphatic ring or a 5- to 7-membered heterocyclyl having only one heteroatom, wherein the ring is optionally substituted as defined in any one of claims 18 to 21.

23. The chemical entity of claim 18, wherein $R^e$ is

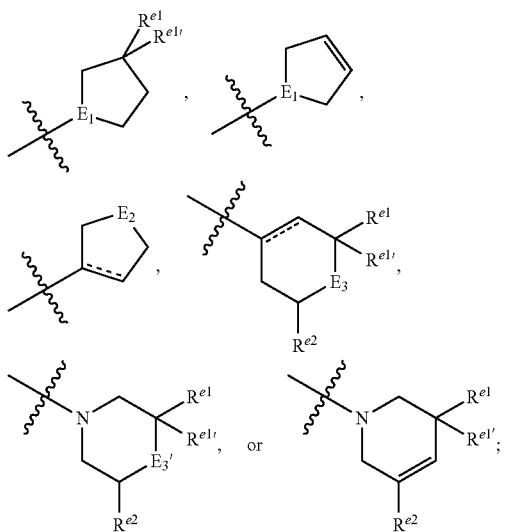

and wherein dashes indicate single or double bonds;

$E_1$ is N or C(H);

$E_2$ is O, S, or CH$_2$;

$E_3$ is O, S, N$(R^{e3})$, or C(H)$(R^{e3})$;

$E_3'$ is O, N$(R^{e3})$ or C(H)$(R^{e3})$;

$R^{e1}$ and $R^{e1'}$ are each independently hydrogen or fluoro;

$R^{e2}$ is hydrogen or methyl; and $R^{e3}$ is hydrogen or methyl.

24. The chemical entity of claim 20, wherein:

$R^f$ and $R^{f'}$ are each independently hydrogen, $C_{1-4}$ alkyl, or cyclopropyl; or are taken together to form =CH$_2$; and $R^e$ is a ring chosen from 6-membered aryl or 5- to 6-membered heteroaryl, which is optionally fused to a second 6-membered aryl, 5- to 6-membered heteroaryl, 3- to 7-membered cycloaliphatic, or 4- to 7-membered heterocyclyl, and is optionally substituted with 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, —N$(R^{z7})_2$, —C(O)$_2$R$^{z7}$, —C(O)N$(R^{z7})_2$, —S(O)$_2$N$(R^{z7})_2$, —CH$_2$—OR$^{z7}$, —CH$_2$NR$^{z7}$ or a 3- to 6-membered cycloaliphatic or 4- to 6-membered heterocyclyl.

25. The chemical entity of claim 20, wherein:

$R^f$ is hydrogen, hydroxyl, N$(R^{h})(R^{h'})$, —OCH$_3$, cyclopropyl, or $C_{1-4}$ aliphatic optionally substituted with hydroxyl or —OCH$_3$;

$R^{f'}$ is hydrogen, cyclopropyl, or $C_{1-4}$ aliphatic optionally substituted with hydroxyl or —OCH$_3$;

or, together with the carbon atom to which they are attached, $R^f$ and $R^{f'}$ form a 4- to 6-membered heterocycle comprising a heteroatom chosen from N (which may be protonated or $C_{1-4}$ alkylated), O, or S, the heteroatom optionally located immediately adjacent to the quaternary carbon of the heterocycle;

wherein at least one of $R^f$ and $R^{f'}$ comprises at least one heteroatom; and $R^e$ is a ring chosen from 6-membered aryl or 5- to 6-membered heteroaryl, which is optionally fused to a second 6-membered aryl, 5- to 6-membered heteroaryl, 3- to 7-membered cycloaliphatic, or 4- to 7-membered heterocyclyl, and is optionally substituted with one or more halogen, $C_{1-4}$ aliphatic optionally substituted with 1-3 independent occurrences of halogen, hydroxyl, cyano, $C_{1-4}$ aliphatic, $C_{1-4}$ fluoroaliphatic, $C_{1-4}$ alkoxy, $C_{1-4}$ fluoroalkoxy, —N$(R^{z7})_2$, —C(O)$_2$R$^{z7}$, —C(O)N$(R^{z7})_2$, —S(O)$_2$N$(R^{z7})_2$, —CH$_2$—OR$^{z7}$, —CH$_2$NR$^{z7}$, a 3- to 6-membered cycloaliphatic, or a 4- to 6-membered heterocyclyl.

26. The chemical entity of claim 18, wherein:

$R^e$ is a ring chosen from 6-membered aryl or 5- to 6-membered heteroaryl, which is optionally substituted with 1-3 independent occurrences of chloro, fluoro, bromo, iodo, methyl, ethyl, cyano, cyclopropyl, CF$_3$, —OCH$_3$, —OCH$_2$CH$_3$, or —C≡CH.

27. The chemical entity of claim 18, wherein $R^e$ is:

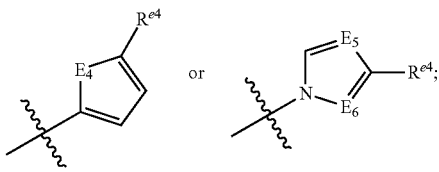

$E_4$ is S or O;

$E_5$ is N or C$(R^{e5})$;

$E_6$ is N or C(H);

$R^{e4}$ is hydrogen, methyl, chloro, fluoro, bromo, iodo, cyano, or —CF$_3$; and $R^{e5}$ is hydrogen or halogen.

28. The chemical entity of claim 18, wherein $R^e$ is

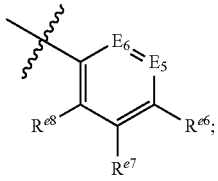

$E_5$ is N or C$(R^{e5})$;

$E_6$ is N or C(H);

each of $R^{e5}$, $R^{e6}$, $R^{e7}$, and $R^{e8}$ is independently hydrogen, halogen, methyl, ethyl, isopropyl, —OCH$_3$, —CF$_3$, or —C≡CH;

and at least two of $R^{e5}$, $R^{e6}$, $R^{e7}$, and $R^{e8}$ are hydrogen.

29. The chemical entity of claim 18, wherein $R^e$ is

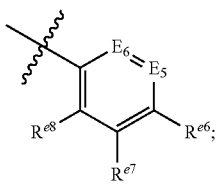

$E_5$ is N or $C(R^{e5})$;
$E_6$ is N or C(H);
$R^{e5}$ is hydrogen, halogen, methyl, —$OCH_3$, —$CF_3$, or —C≡CH;
$R^{e6}$ is hydrogen, fluoro, or chloro;
$R^{e7}$ is hydrogen, fluoro, or chloro; and
$R^{e8}$ is hydrogen, halogen, methyl, —$OCH_3$, or cyano; wherein at least one of $R^{e6}$, $R^{e7}$, and $R^{e8}$ is hydrogen.

30. The chemical entity of claim 28, which is a compound or pharmaceutically acceptable salt of formula (VIIIa) or (VIIIb):

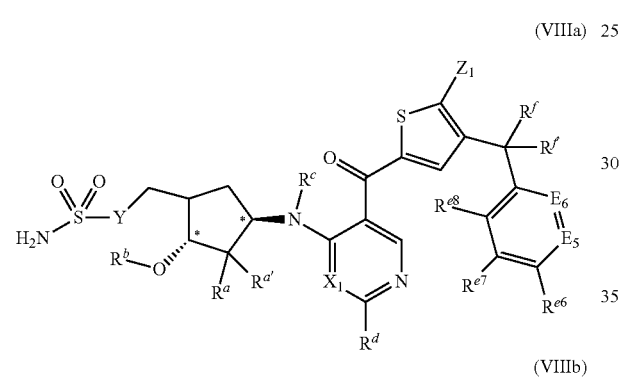
(VIIIa)

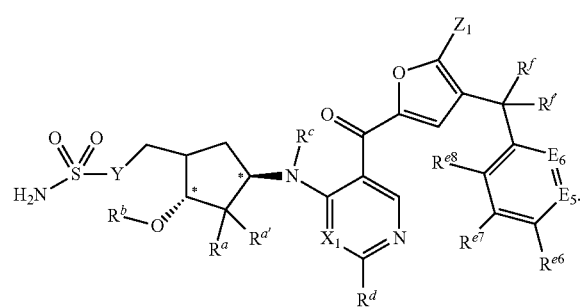
(VIIIb)

31. The chemical entity of claim 18, wherein $R^e$ is hydrogen, hydroxyl, halogen, —$CF_3$, or $C_{1-4}$ alkyl optionally substituted with one or more hydroxyl, halogen, or $C_{1-4}$ alkyl.

32. The chemical entity of claim 1, wherein:
$Z_1$ is hydrogen, halogen, cyano, or $C_{1-4}$ aliphatic optionally substituted with one or more hydroxyl, $C_{1-4}$ alkoxy, —$N(R^{z5})_2$, or phenyl optionally substituted with one more independently selected halogens; and
each occurrence of $R^{z5}$ is independently hydrogen or $C_{1-4}$ alkyl.

33. The chemical entity of claim 1, wherein $Z_1$ is hydrogen, chloro, or methyl.

34. The chemical entity of claim 5, wherein $Z_2$ is hydrogen.

35. The chemical entity of claim 1, wherein $R^b$ is hydrogen.

36. The chemical entity of claim 1, wherein $R^b$ is —C(O)—$R^{bx}$,
$R^{bx}$ is $C_{1-4}$ alkyl, —CH($R^{by}$)—$NH_2$, pyrrolidinyl, or -$L_b$-$OPO_3H_2$,
$R^{by}$ is $C_{1-4}$ alkyl optionally substituted with hydroxyl, phenyl, phenolyl, imidazolyl, carboxyl, amino, guanidino, —$SCH_3$, —C(O)$NH_2$, or indolyl,
$L_b$ is a bivalent linker chosen from $C_{1-4}$ alkylene, —$(CH_2)_{n1}$-phenylene-$(CH_2)_{n2}$— where n1 is 0 or 1 and n2 is 1 or 2.

37. The chemical entity of claim 1, wherein at least one of the following is true:
Y is —O—;
$R^a$ is hydrogen;
$R^{a'}$ is hydrogen;
$R^c$ is hydrogen;
$R^d$ is hydrogen; or
$X_3$ is C(H).

38. A pharmaceutical composition comprising the chemical entity of claim 1 and a pharmaceutically acceptable carrier.

39. A method of treating lung cancer, ovarian cancer, colon cancer, breast cancer, or lymphoma in a subject, comprising administering to a subject having lung cancer, ovarian cancer, colon cancer, breast cancer, or lymphoma a therapeutically effective amount of the chemical entity of claim 1.

* * * * *